US012747203B2

(12) United States Patent
Romero et al.

(10) Patent No.: US 12,747,203 B2
(45) Date of Patent: Sep. 29, 2026

(54) NAMPT MODULATORS

(71) Applicant: Cytokinetics, Inc., South San Francisco, CA (US)

(72) Inventors: Antonio Romero, San Mateo, CA (US); Aroop Chandra, Carmel, IN (US); Christopher Evans, Pacifica, CA (US); Minxing Shen, San Bruno, CA (US)

(73) Assignee: CYTOKINETICS, INC., South San Francisco, CA (US)

( * ) Notice: Subject to any disclaimer, the term of this patent is extended or adjusted under 35 U.S.C. 154(b) by 946 days.

(21) Appl. No.: 17/923,167

(22) PCT Filed: May 5, 2021

(86) PCT No.: PCT/US2021/030950
§ 371 (c)(1),
(2) Date: Nov. 3, 2022

(87) PCT Pub. No.: WO2021/226276
PCT Pub. Date: Nov. 11, 2021

(65) Prior Publication Data
US 2023/0348369 A1 Nov. 2, 2023

Related U.S. Application Data

(60) Provisional application No. 63/020,904, filed on May 6, 2020.

(51) Int. Cl.
*C07D 205/04* (2006.01)
*C07C 275/18* (2006.01)
(Continued)

(52) U.S. Cl.
CPC .......... *C07C 275/26* (2013.01); *C07C 275/18* (2013.01); *C07C 311/13* (2013.01); *C07C 311/20* (2013.01); *C07C 317/30* (2013.01); *C07C 317/32* (2013.01); *C07D 205/04* (2013.01); *C07D 205/12* (2013.01); *C07D 207/06* (2013.01); *C07D 207/08* (2013.01); *C07D 207/267* (2013.01); *C07D 209/08* (2013.01); *C07D 209/44* (2013.01); *C07D 209/54* (2013.01); *C07D 211/26* (2013.01); *C07D 211/58* (2013.01); *C07D 211/78* (2013.01); *C07D 213/38* (2013.01); *C07D 213/40* (2013.01); *C07D 213/56* (2013.01); *C07D 213/65* (2013.01); *C07D 213/68* (2013.01); *C07D 213/71* (2013.01); *C07D 213/74* (2013.01); *C07D 213/75* (2013.01); *C07D 213/81* (2013.01); *C07D 213/82* (2013.01); *C07D 213/87* (2013.01); *C07D 215/06* (2013.01); *C07D 215/08* (2013.01); *C07D 217/04* (2013.01); *C07D 221/20* (2013.01); *C07D 231/12* (2013.01); *C07D 231/14* (2013.01); *C07D 231/56* (2013.01); *C07D 239/26* (2013.01); *C07D 241/04* (2013.01); *C07D 241/08* (2013.01); *C07D 241/12* (2013.01); *C07D 249/06* (2013.01); *C07D 249/08* (2013.01); *C07D 261/08* (2013.01); *C07D 263/56* (2013.01); *C07D 265/36* (2013.01); *C07D 271/10* (2013.01); *C07D 295/16* (2013.01); *C07D 295/182* (2013.01); *C07D 305/08* (2013.01); *C07D 307/22* (2013.01); *C07D 309/08* (2013.01);
(Continued)

(58) Field of Classification Search
CPC .. C07C 275/26; C07D 209/54; C07D 213/40; C07D 221/20; C07D 295/16; C07D 401/04; C07D 401/06; C07D 401/12; C07D 401/14; C07D 403/04; C07D 403/10; C07D 403/12; C07D 405/06
See application file for complete search history.

(56) References Cited

U.S. PATENT DOCUMENTS

| | | | |
|---|---|---|---|
| 5,391,806 | A | 2/1995 | Otsuji et al. |
| 5,846,514 | A | 12/1998 | Foster |

(Continued)

FOREIGN PATENT DOCUMENTS

| | | | |
|---|---|---|---|
| CA | 2477005 | A1 | 9/2003 |
| CL | 2014003560 | A1 | 11/2015 |

(Continued)

OTHER PUBLICATIONS

Cecil Textbook of Medicine, 20th Ed, vol. 1, 1997 (Year: 1997).*
(Continued)

*Primary Examiner* — Alicia L Otton
(74) *Attorney, Agent, or Firm* — MORRISON & FOERSTER LLP

(57) ABSTRACT

Provided are compounds of Formula (II): or a pharmaceutically acceptable salt thereof, wherein R1, n, and Y1 are as defined herein. Also provided is a pharmaceutically acceptable composition comprising a compound of Formula (II), or a pharmaceutically acceptable salt thereof. Also provided are methods of using a compound of Formula (II), or a pharmaceutically acceptable salt thereof.

Formula (II)

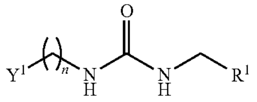

36 Claims, No Drawings

(51) Int. Cl.

| | |
|---|---|
| ***C07C 275/26*** | (2006.01) |
| ***C07C 311/13*** | (2006.01) |
| ***C07C 311/20*** | (2006.01) |
| ***C07C 317/30*** | (2006.01) |
| ***C07C 317/32*** | (2006.01) |
| ***C07D 205/12*** | (2006.01) |
| ***C07D 207/06*** | (2006.01) |
| ***C07D 207/08*** | (2006.01) |
| ***C07D 207/267*** | (2006.01) |
| ***C07D 209/08*** | (2006.01) |
| ***C07D 209/44*** | (2006.01) |
| ***C07D 209/54*** | (2006.01) |
| ***C07D 211/26*** | (2006.01) |
| ***C07D 211/58*** | (2006.01) |
| ***C07D 211/78*** | (2006.01) |
| ***C07D 213/38*** | (2006.01) |
| ***C07D 213/40*** | (2006.01) |
| ***C07D 213/56*** | (2006.01) |
| ***C07D 213/65*** | (2006.01) |
| ***C07D 213/68*** | (2006.01) |
| ***C07D 213/71*** | (2006.01) |
| ***C07D 213/74*** | (2006.01) |
| ***C07D 213/75*** | (2006.01) |
| ***C07D 213/81*** | (2006.01) |
| ***C07D 213/82*** | (2006.01) |
| ***C07D 213/87*** | (2006.01) |
| ***C07D 215/06*** | (2006.01) |
| ***C07D 215/08*** | (2006.01) |
| ***C07D 217/04*** | (2006.01) |
| ***C07D 221/20*** | (2006.01) |
| ***C07D 231/12*** | (2006.01) |
| ***C07D 231/14*** | (2006.01) |
| ***C07D 231/56*** | (2006.01) |
| ***C07D 239/26*** | (2006.01) |
| ***C07D 241/04*** | (2006.01) |
| ***C07D 241/08*** | (2006.01) |
| ***C07D 241/12*** | (2006.01) |
| ***C07D 249/06*** | (2006.01) |
| ***C07D 249/08*** | (2006.01) |
| ***C07D 261/08*** | (2006.01) |
| ***C07D 263/56*** | (2006.01) |
| ***C07D 265/36*** | (2006.01) |
| ***C07D 271/10*** | (2006.01) |
| ***C07D 295/16*** | (2006.01) |
| ***C07D 295/182*** | (2006.01) |
| ***C07D 305/08*** | (2006.01) |
| ***C07D 307/22*** | (2006.01) |
| ***C07D 309/08*** | (2006.01) |
| ***C07D 335/02*** | (2006.01) |
| ***C07D 401/04*** | (2006.01) |
| ***C07D 401/06*** | (2006.01) |
| ***C07D 401/12*** | (2006.01) |
| ***C07D 401/14*** | (2006.01) |
| ***C07D 403/04*** | (2006.01) |
| ***C07D 403/10*** | (2006.01) |
| ***C07D 403/12*** | (2006.01) |
| ***C07D 405/06*** | (2006.01) |
| ***C07D 413/06*** | (2006.01) |
| ***C07D 413/12*** | (2006.01) |
| ***C07D 471/04*** | (2006.01) |

(52) U.S. Cl.

CPC ......... *C07D 335/02* (2013.01); *C07D 401/04* (2013.01); *C07D 401/06* (2013.01); *C07D 401/12* (2013.01); *C07D 401/14* (2013.01); *C07D 403/04* (2013.01); *C07D 403/10* (2013.01); *C07D 403/12* (2013.01); *C07D 405/06* (2013.01); *C07D 413/06* (2013.01); *C07D 413/12* (2013.01); *C07D 471/04* (2013.01); *C07B 2200/05* (2013.01); *C07C 2601/02* (2017.05); *C07C 2601/04* (2017.05); *C07C 2601/14* (2017.05); *C07C 2602/08* (2017.05); *C07C 2602/10* (2017.05); *C07C 2602/50* (2017.05)

(56) References Cited

U.S. PATENT DOCUMENTS

| | | | |
|---|---|---|---|
| 6,334,997 | B1 | 1/2002 | Foster |
| 6,531,506 | B1 | 3/2003 | Kroetz et al. |
| 7,074,785 | B2 | 7/2006 | Seitz et al. |
| 9,132,136 | B2 | 9/2015 | Hoener et al. |
| 10,329,275 | B2 | 6/2019 | Bair et al. |
| 11,007,178 | B2 | 5/2021 | Tipparaju et al. |
| 11,452,717 | B2 | 9/2022 | Gardell et al. |
| 11,485,745 | B2 | 11/2022 | Bair et al. |
| 2006/0205772 | A1 | 9/2006 | Coppola et al. |
| 2007/0287708 | A1 | 12/2007 | Cole et al. |
| 2008/0188561 | A1 | 8/2008 | Vernier et al. |
| 2011/0112080 | A1 | 5/2011 | Galley et al. |
| 2011/0152245 | A1 | 6/2011 | Groebke et al. |
| 2012/0028964 | A1 | 2/2012 | Hoener et al. |
| 2013/0109668 | A1 | 5/2013 | Ceccarelli et al. |
| 2013/0137720 | A1 | 5/2013 | Wang et al. |
| 2013/0317027 | A1 | 11/2013 | Willardsen et al. |
| 2021/0161873 | A1 | 6/2021 | Gardell et al. |
| 2022/0370636 | A1 | 11/2022 | Tipparaju et al. |
| 2023/0116972 | A1 | 4/2023 | Ashcraft et al. |
| 2023/0133132 | A1 | 5/2023 | Romero et al. |
| 2024/0067631 | A1 | 2/2024 | Shen et al. |
| 2024/0279215 | A1 | 8/2024 | Lu et al. |

FOREIGN PATENT DOCUMENTS

| | | | |
|---|---|---|---|
| CN | 1741986 | A | 3/2006 |
| CN | 103709096 | A | 4/2014 |
| CN | 104098556 | A | 10/2014 |
| CN | 106916101 | A | 7/2017 |
| CN | 111848506 | A | 10/2020 |
| CN | 113121518 | A | 7/2021 |
| CN | 115417870 | A | 12/2022 |
| CN | 115521305 | A | 12/2022 |
| CN | 111848506 | B | 1/2023 |
| CN | 116589402 | A | 8/2023 |
| CN | 118108664 | A | 5/2024 |
| EP | 2611777 | B1 | 5/2016 |
| EP | 3568390 | A1 | 11/2019 |
| GB | 760051 | A | 10/1956 |
| JP | 2001-525400 | A | 12/2001 |
| JP | 2005-519079 | A | 6/2005 |
| JP | 2006-517199 | A | 7/2006 |
| JP | 2009-506979 | A | 2/2009 |
| JP | 2009-523812 | A | 6/2009 |
| JP | 2013-522171 | A | 6/2013 |
| JP | 2013-536181 | A | 9/2013 |
| JP | 2013-536868 | A | 9/2013 |
| JP | 2014-534224 | A | 12/2014 |
| JP | 2015-508786 | A | 3/2015 |
| JP | 2015-529224 | A | 10/2015 |
| WO | 1999/29674 | A1 | 6/1999 |
| WO | 0063157 | A1 | 10/2000 |
| WO | 0125190 | A1 | 4/2001 |
| WO | 03024220 | A1 | 3/2003 |
| WO | 2003/72098 | A1 | 9/2003 |
| WO | 2004065351 | A1 | 8/2004 |
| WO | 2004082677 | A1 | 9/2004 |
| WO | 2005/058311 | A1 | 6/2005 |
| WO | 2005073183 | A1 | 8/2005 |
| WO | 2005087754 | A1 | 9/2005 |
| WO | 2007/026920 | A2 | 3/2007 |
| WO | 2007/084667 | A2 | 7/2007 |

(56) References Cited

FOREIGN PATENT DOCUMENTS

| | | | |
|---|---|---|---|
| WO | 2008/082487 | A2 | 7/2008 |
| WO | 2008/103351 | A2 | 8/2008 |
| WO | 2009015667 | A1 | 2/2009 |
| WO | 2010036316 | A1 | 4/2010 |
| WO | 2011/057973 | A1 | 5/2011 |
| WO | 2011109441 | A1 | 9/2011 |
| WO | 2012/016879 | A1 | 2/2012 |
| WO | 2012/031197 | A1 | 3/2012 |
| WO | 2012031196 | A1 | 3/2012 |
| WO | 2012/067965 | A1 | 5/2012 |
| WO | 2012092873 | A1 | 7/2012 |
| WO | 2013/170112 | A1 | 11/2013 |
| WO | 2014/004884 | A1 | 1/2014 |
| WO | 2014/039714 | A2 | 3/2014 |
| WO | 2015105749 | A1 | 7/2015 |
| WO | 2016087975 | A1 | 6/2016 |
| WO | 2018132372 | A1 | 7/2018 |
| WO | 2019101641 | A1 | 5/2019 |
| WO | 2020010252 | A1 | 1/2020 |
| WO | 2020/073031 | A1 | 4/2020 |
| WO | 2021159015 | A1 | 8/2021 |
| WO | 2021207186 | A1 | 10/2021 |
| WO | 2021226276 | A2 | 11/2021 |
| WO | 2022135617 | A1 | 6/2022 |
| WO | 2022140290 | A1 | 6/2022 |
| WO | 2022165114 | A1 | 8/2022 |
| WO | 2023011416 | A1 | 2/2023 |
| WO | 2023/229346 | A1 | 11/2023 |
| WO | 2024/137981 | A1 | 6/2024 |
| WO | 2024/166024 | A1 | 8/2024 |
| WO | 2025/231630 | A1 | 11/2025 |

OTHER PUBLICATIONS

Wu Q, Qian W, Sun X, Jiang S. Small-molecule inhibitors, immune checkpoint inhibitors, and more: FDA-approved novel therapeutic drugs for solid tumors from 1991 to 2021. J Hematol Oncol. Oct. 8, 2022;15(1):143. doi: 10.1186/s13045-022-01362-9. PMID: 36209184; PMCID: PMC9548212. (Year: 2022).*

Blacher, E. et al. (Aug. 2019). "Potential Roles of Gut Microbiome and Metabolites in Modulating ALS in Mice," Nature 570:474-480, 42 pages.

CAS Registry No. 1071363-30-8 (Nov. 7, 2008). "Urea, N-cyclohexyl-N'-[[4-(1-methylethoxy)phenyl]methyl]—," 2 pages.

CAS Registry No. 1111205-27-6 (Feb. 24, 2009). "Urea, N-[(4-methoxyphenyl)methyl]-N'-[4-(5-methyl-1,2,4-oxadiazol-3-yl)phenyl]—," 1 page.

CAS Registry No. 1111205-36-7 (Feb. 24, 2009). "Urea, N-[(4-chlorophenyl)methyl]-N'-[4-(5-cyclobutyl-1,2,4-oxadiazol-3-yl)phenyl]—," 1 page.

CAS Registry No. 1119367-55-3 (Mar. 12, 2009). "2-methyl-N-[4-[[[[(4-methylcyclohexyl)amino]carbonyl]amino] methyl] phenyl]—," 1 page.

CAS Registry No. 1147664-42-3 (May 20, 2009). "Urea, N-[4-(1,1-dioxido-2-isothiazolidinyl)phenyl]-N'-[(4-methoxyphenyl) methyl]—," 1 page.

CAS Registry No. 1170809-16-1 (Jul. 31, 2009). "Urea, N-[(4-methoxyphenyl)methyl]-N'-[4-[[4-(2-pyridinyl)-1-piperazinyl]methyl]phenyl]—," 1 page.

CAS Registry No. 1170972-21-0 (Jul. 31, 2009). "Urea, N-[(4-chlorophenyl)methyl]-N'-[4-[[4-(2-furanylmethyl)-1-piperazinyl]methyl]phenyl]—," 1 page.

CAS Registry No. 1171471-94-5 (Aug. 2, 2009). "Urea, N-[4-[[4-(2-furanylmethyl)-1-piperazinyl]methyl]phenyl]-N'-[(4-methoxyphenyl)methyl]—," 2 pages.

CAS Registry No. 1172336-21-8 (Aug. 4, 2009). "Urea, N-[(4-methoxyphenyl)methyl]-N'-[4-[(4-methyl-1-piperazinyl) methyl]phenyl]—," 1 page.

CAS Registry No. 1172544-60-3 (Aug. 4, 2009). "Urea, N-[(4-flurophenyl)methyl]-N'-[4-{(4-methyl-1-piperazinyl) methyl] phenyl]—," 1 page.

CAS Registry No. 1183542-51-9 (Sep. 13, 2009). "Urea, N-cyclohexyl-N'-(1H-pyrazol-4-ylmethyl)—," 2 pages.

CAS Registry No. 1203067-82-6 (Jan. 24, 2010). "Urea, N-[(4-Chlorophenyl)methyl]-N'-[4-(1,1-dioxido-2-isothiazolidinyl) phenyl]—," 1 page.

CAS Registry No. 1280964-65-9 (Apr. 17, 2011). "Benzamide, 4-[[[(cyclohexylamino)carbonyl]amino]methyl]-N-ethyl—," 1 page.

CAS Registry No. 1303650-36-3 (Jun. 1, 2011). "Urea, N-[(4-bromophenyl) methyl]-N'-cyclohexyl—," 2 pages.

CAS Registry No. 1371486-55-3 (Apr. 30, 2012). "Urea, N-[(4-fluorophenyl)methyl]-N'-[4-(1-piperidinyl)phenyl]—," 1 page.

CAS Registry No. 1385988-48-6 (Aug. 3, 2012). "Urea, N-[3-chloro-4-(1-pyrrolidinyl)phenyl]-N'-[(4-fluorophenyl) methyl]—," 1 page.

CAS Registry No. 1387015-63-5 (Aug. 6, 2012). "Urea, N-[(4-fluorophenyl)methyl]-N'-[4-(4-methyl-2-pyrimidinyl) phenyl]," 1 page.

CAS Registry No. 1387054-86-5 (Aug. 6, 2012). "Urea, N-[(4-chlorophenyl)methyl]-N'-[4-(3,5-dimethyl-1H-pyrazol-1-yl)-3-flurophenyl]—," 2 pages.

CAS Registry No. 1387106-46-8 (Aug. 7, 2012). "Urea, N-cyclohexyl-N'-[[6-(I-methylethoxy)-3-pyridinyl]methyl]—," 1 page.

CAS Registry No. 1387176-98-8 (Aug. 7, 2012). "Urea, N-cyclohexyl-N'-[[4-(2-methylpropoxy)phenyl]methyl]—," 1 page.

CAS Registry No. 1389145-02-1 (Aug. 12, 2012). "Urea, N-[4-(3,5-dimethyl-1H-pyrazol-1-yl)-3-fluorophenyl]-N'-[(4-fluoropheny)methyl]—," 1 page.

CAS registry No. 1389213-95-9 (Aug. 10, 2012). "Urea, N-[(4-chlorophenyl)methyl]-N'-[4-(2-oxo-3-oxazolidinyl) phenyl]—," 2 pages.

CAS Registry No. 1646963-03-2 (Feb. 13, 2015). "Urea, N-[(6-chloro-3-pyridinyl)methyl]-N'-(3-cyclohexylpropyl)—," 1 page.

CAS Registry No. 1713221-96-5 (May 26, 2015). "Urea, N-cyclohexyl-N'-[(6-methoxy-3-pyridinyl)methyl]—," 1 page.

CAS Registry No. 1898739-21-3 (Apr. 27, 2016). "Urea, N-[(4-fluorophenyl)methyl]-N'-[4-(4-methyl-1-piperazinyl) phenyl]—," 1 page.

CAS Registry No. 1899425-35-4 (Apr. 28, 2016). "Urea, N-(cyclohexylmethyl)-N'-[(4-methoxyphenyl)methyl]—," 2 pages.

CAS Registry No. 1902512-90-6 (May 3, 2016). "Urea, N-[(4-methoxyphenyl)methyl]-N'-[4-(4-methyl-1-piperazinyl) phenyl]—," 2 pages.

CAS Registry No. 1902756-28-8 (May 3, 2016). "Urea, N-(2-cyclohexylethyl)-N'-[(4-methoxyphenyl)methyl]—," 1 page.

CAS Registry No. 1902756-85-7 (May 3, 2016). "Urea, N-(2-cyclohexylethyl)-N'-[[4-(hydroxymethyl)phenyl]methyl]—," 2 pages.

CAS Registry No. 1904704-52-4 (May 6, 2016). "Urea, N-[(4-chlorophenyl)methyl]-N'-(cyclohexylmethyl)—," 1 page.

CAS Registry No. 1906033-26-8 (May 8, 2016). "Urea, N-[(4-fluorophenyl) methyl]-N'-[4-(1H-pyrrol-1-yl)phenyl]—," 1 page.

CAS Registry No. 1906636-09-6 (May 9, 2016). "Urea, N-(2-cyclohexylethyl)-N'-(4-pyridinylmethyl)—," 1 page.

CAS Registry No. 1906934-57-3 (May 9, 2016). "Urea, N-(cyclohexylmethyl)-N'-(4-pyridinylmethyl)—," 1 page.

CAS Registry No. 1906939-32-9 (May 9, 2016). "Urea, N-[(4-chlorophenyl)methyl]-N'-[4-(4-methyl-1-piperazinyl) phenyl]—," 2 pages.

CAS Registry No. 1908093-29-7 (May 11, 2016). "Urea, N-[(4-chlorophenyl)methyl]-N'-(2-cyclohexylethyl)—," 1 page.

CAS Registry No. 1908404-55-6 (May 11, 2016). Urea, N-(cyclohexylmethyl)-N'-[(4-fluorophenyl)methyl]—, 2 pages.

CAS Registry No. 1908596-70-2 (May 12, 2016). "Benzamide, 4-[[[(cyclohexylamino)carbonyl]amino]methyl)—," 1 page.

CAS Registry No. 1908872-93-4 (May 12, 2016). "Urea, N-(2-cyclohexylethyl)-N'-[(4-fluorophenyl)methyl]—," 2 pages.

CAS Registry No. 1909101-62-7 (May 12, 2016). "Urea, N-(cyclohexylmethyl)-N'-[[4-(hydroxymethyl)phenyl]methyl]—," 1 page.

CAS Registry No. 1909213-71-3 (May 12, 2016). "Urea, N-cyclohexyl-N'-[[4-(hydroxymethyl)phenyl]methyl]—," 1 Page.

CAS Registry No. 2427208-21-5 (Jun. 17, 2020) "Urea, N-[(4-methoxyphenyl)methyl]-N'-[4-(2-oxo-3-oxazolidinyl) phenyl]—," 1 page.

(56) References Cited

OTHER PUBLICATIONS

CAS Registry No. 313386-80-0 (Jan. 10, 2001). "Urea, N-cyclohexyl-N'-[(4-fluorophenyl)methyl]—," 1 page.
CAS Registry No. 951617-35-9 (Oct. 26, 2007). "Urea, N-[4-(2-benzothiazolyl)-3-chlorophenyl]-N'-[(4-fluorophenyl) methyl]—," 1 page.
European Examination Report mailed on Nov. 21, 2023, for EP Patent Application No. 21710105.4, 13 pages.
Gaina, V. et al. (Jan. 1, 2003). "AB Monomers. I. Synthesis and Polymerization of Furyl-Maleimide Monomers", XP093156487, Database Accession No. 2004:464480, Database CAPLUS [Online] Chemical Abstract Service, Columbus, Ohio, 2 pages.
Goring, S. et al. (Mar. 2014, e-pub. Feb. 10, 2015). "Computer-Guided Design, Synthesis, and Biological Evaluation of Quinoxalinebisarylureas as FLT3 Inhibitors," Chem Med Chem 10(3):511-522.
Harlan, B.A. et al. (May 2020). "Evaluation and the NAD+ Biosynthetic Pathway in ALS Patents and Effect of Modulating NAO+ Levels in hSOD1-Linked ALS Mouse Models," Exp Neural. 327:113219, 25 pages.
International Preliminary Report on Patentability issued on Jun. 13, 2023, for PCT Application No. PCT/US2021/064422, filed on Dec. 20, 2021, 7 pages.
International Preliminary Report on Patentability issued on Jun. 24, 2025, for PCT Application No. PCT/US2023/085420, filed Dec. 21, 2023, 10 pages.
International Search Report and Written Opinion of the International Searching Authority mailed May 8, 2024, for International Application No. PCT/US2023/085420, filed Dec. 21, 2023, 14 pages.
PUBCHEM (Jan. 15, 2016). CID: 108988951. "1-[(4-Chlorophenyl)methyl]-3-(4-phenylmethoxyphenyl)urea," 8 pages.
PUBCHEM (Jan. 15, 2016). CID: 108988965. "1-[(4-Methoxyphenyl)methyl]-3-(4-phenylmethoxyphenyl)urea," 8 pages.
PUBCHEM (May 29, 2009). CID: 38209383. "1-[(4-Fluorophenyl)methyl]-3-(4-phenylmethoxyphenyl)urea," 7 pages.
STN Registry Database Record Report. (Jan. 7, 2025). 124 STN records. 67 pages.
STN Registry No. 1388613-78-2. (Aug. 9, 2012). "N-[(4-Fluorophenyl)methyl]-N'-[4-(2-oxo-3-oxazolidinyl)phenyl] urea", 1 page.
Yin, Y. et al. (Jul. 8, 2010. e-pub Apr. 5, 2010). "Discovery of Potent and Selective Urea-Based ROCK Inhibitors and Their Effects on Intraocular Pressure in Rats," ACS Med Chem Lett. 1(4):175-179.
Akiu, M. et al. (2021). "Discovery of DS68702229 as a Potent, Orally Available NAMPT (Nicotinamide Phosphoribosyltransferase) Activator," Chem Pharm Bull (Tokyo) 69(11):1110-1122.
Akiu, M. et al. (2022). "Optimization NAMPT (Nicotinamide Phosphoribosyltransferase) Activators: Discover of N,N-Diethyl-1,2-Benzoxazole-3-Carboxamide Derivatives As Potent NAMPT Activators With Mitigated Mutagenic Risks," Heterocycles 104(1):94-122, 29 pages.
Akiu, M. et al. (Jul. 1, 2021, e-pub. Apr. 19, 2021). "Discovery of 1-[2-(1-methyl-1H-pyrazol-5-yl)-[1,2,4]triazolo[1,5-a] pyridin-6-yl]-3-(pyridin-4-ylmethyl)Urea as a Potent NAMPT (Nicotinamide Phosphoribosyltransferase) Activator With Attenuated CYP Inhibition," Bioorganic and Medicinal Chemistry Letters 43:128048, 7 pages.
Artursson, P. et al. (Mar. 29, 1991). "Correlation Between Oral Drug Absorption in Humans and Apparent Drug Permeability Coefficients in Human Intestinal Epithelial (CACO-2) Cells," Biochemical and Biophysical Research Communications 175(3): 880-885.
Berge, S.M. et al. (Jan. 1977). "Pharmaceuticals Salts," J. Pharmaceutical Sciences 66(1):1-19.
Braidy, N. et al. (Apr. 2011). "Age Related Changes in NAD+ Metabolism Oxidative Stress and Sirt1 Activity in Wistar Rats," PLoS One 6(4):e19194, 18 pages.
Bu, X-B. et al. (2017). "Rhodium-Catalyzed Oxidative Coupling Reaction of Isocyanides with Alcohols or Amines and Molecular Oxygen as Oxygen Source: Synthesis of Carbamates and Ureas," European Journal of Organic Chemistry 7:1132-1138.
Cerutti, R. et al. (Jun. 3, 2014). "NAD+-Dependent Activation of Sirt1 Corrects the Phenotype in a Mouse Model of Mitochondrial Disease," Cell Metab. 19(6):1042-1049.
Dean, D.C. (2000). "Recent Advances in the Synthesis and Applications of Radiolabeled Compounds for Drug Discovery and Development," Current Pharm. Des. 6(10):113, TOC Only, 2 pages.
Diguet, N. et al. (May 22, 2018). "Nicotinamide Riboside Preserves Cardiac Function in a Mouse Model of Dilated Cardiomyopathy," Circulation 137:2256-2273.
Evans, A.E. (Mar. 1981, e-pub. Jan. 9, 2007). "Synthesis of Radiolabelled Compounds," J Radio Anal. Chem. 64(1-2):9-32.
Fang, E. F. et al. (May 8, 2014). "Defective Mitophagy in XPA via PARP-1 Hyperactivation and NAD(+)/SIRT1 Reduction," Cell 157(4):882-896, 29 pages.
Fang, E.F. et al. (Oct. 2017). "NAD+ In Aging: Molecular Mechanisms and Translational Implications," Trends Mol. Med. 23(10):899-916, 33 pages.
Fulco, M. et al. (May 2008). "Glucose Restriction Inhibits Skeletal Myoblast Differentiation by Activating SIRT1 Through AMPK-Mediated Regulation of Nampt," Dev. Cell. 14(5):661-673.
Galli, U. et al. (May 12, 2020). "Recent Advances in NAMPT Inhibitors: A Novel Immunotherapic Strategy," Frontiers In Pharmacology 11:656, 20 pages.
Gardell, S.J. et al. (2019). "Boosting NAD+ With a Small Molecule That Activated NAMPT," Nature Communications 10:3241, 12 pages.
Ghosh, D. et al. (Apr. 25, 2012). "A Reversible Early Oxidized Redox State That Precedes Macromolecular ROS Damage in Aging Nontransgenic and 3xTg-AD Mouse Neurons," J. Neurosci. 32(17):5821-5832.
Gillig, A. et al. (2012). "Synthesis of a C-Iminoribofuranoside Analog of the Nicotinamide Phosphoribosyltransferase (NAMPT) Inhibitor FK866," HCA 95:34-42.
Greene, T.W. et al. (1999). Protective Groups in Organic Synthesis, 3. Ed., John Wiley & Sons, Cover & Contents pages, 20 pages.
Guarino, M. et al. (Sep. 10, 2019). "Nicotinamide and NAFLD: Is There Nothing New Under the Sun?," Metabolites 9(9):180, 17 pages.
Harlan, B.A. et al. (May 13, 2016). "Enhancing NAD+ Salvage Pathway Reverts the Toxicity of Primary Astrocytes Expressing Amyotrophic Lateral Sclerosis-linked Mutant Superoxide Dismutase 1 (SOD1)," J. Biol. Chem. 291 (20):10836-10846.
Imai, S-I. (2009). "Nicotinamide Phosphoribosyltransferase (Nampt): A Link Between NAD Biology, Metabolism, and Disease," Curr. Pharm. Des. 15(1):20-28, 16 pages.
International Preliminary Report on Patentability issue date of Jul. 28, 2022 for Patent Application No. PCT/US2021/016948, filed Feb. 5, 2021, 12 pages.
International Preliminary Report on Patentability issue date of Nov. 8, 2022 for Patent Application No. PCT/US2021/030950, filed May 5, 2021, 11 pages.
International Search Report and Written Opinion mailed on Mar. 14, 2022, for PCT Application No. PCT/US2021/064422, filed on Dec. 20, 2021, 13 pages.
International Search Report and Written Opinion mailed on Sep. 27, 2021, for PCT Application No. PCT/US2021/030950, filed on May 5, 2021, 15 pages.
International Search Report and Written Opinion of the International Searching Authority mailed Jul. 12, 2021, for International Application No. PCT/US2021/016948, filed Feb. 5, 2021, 18 pages.
Invitation to Pay, ISA form 206 mailed Aug. 2, 2021 for International Patent Application No. PCT/US2021/030950, filed May 5, 2021, 13 pages.
Johnson, S. et al. (2018, e-pub. Nov. 8, 2018). "CA1 Nampt Knockdown Recapitulates Hippocampal Cognitive Phenotypes in Old Mice Which Nicotinamide Mononucleotide Improves," NPJ Aging Mech. Dis. 4:10, 12 pages.
Kabalka, G.W. et al. (1989). "The Synthesis of Radiolabeled Compounds via Organometallic Intermediates," Tetrahedron 45(21):6601-6621.

(56) References Cited

OTHER PUBLICATIONS

Khan, N. A. et al. (Jun. 2014). "Effective Treatment of Mitochondrial Myopathy by Nicotinamide Riboside, A Vitamin B3," EMBO Mol Med. 6(6):721-731.
Massudi, H. et al. (Jul. 2012)."Age-Associated Changes in Oxidative Stress and NAD+ Metabolism in Human Tissue," PLoS One 7(7):e42357, 9 pages.
Mavrodin, A. et al. (1965). "N-Phenylsulfonylphenyl-O-Alkslarylated Urethans. Synthesis of Some New Anticancer Compounds," Revue Roumaine de Chimie 10(10):1025-1033, with English Abstract.
Mehr, A. P. et al. (Sep. 2018, e-pub. Aug. 20, 2018). "De Novo NAD+ Biosynthetic Impairment In Acute Kidney Injury in Humans," Nat Med. 24(9):1351-1359, 27 pages.
Mennie, K. M. et al. (Jan. 17, 2020, e-pub. Jan. 7, 2020). "Reductive sp3-sp2 Coupling Reactions Enable Late-Stage Modification of Pharmaceuticals," Organic Letters 22(2):556-559.
Mohamed, J.S. et al. (Oct. 2014). "Dysregulation of SIRT-1 in Aging Mice Increases Skeletal Muscle Fatigue by a PARP-1-Dependent Mechanism," Aging (Albany NY) 6(10):820-834.
Papageorgiou, E. A. et al. (Apr. 20, 2000, e-pub. Mar. 18, 2000). "Selective Hydrogenolysis of Novel Benzyl Carbamate Protecting Groups," Org Lett. 2(8):1049-1051.
Peek, C.B. et al. (Nov. 1, 2013). "Circadian Clock NAD+ Cycle Drives Mitochondrial Oxidative Metabolism in Mice," Science 342(6158):1243417, 17 pages.
Pi, C. et al. (Jun. 7, 2019). "Nicotinamide Phosphoribosyltransferase Postpones Rat Bone Marrow Mesenchymal Stem Cell Senescence by Mediating NAD+-Sirt1 Signaling," Aging (Albany NY) 11(11):3505-3522.
Pinkerton, A. B. et al. (2021). "Optimization of a Urea-Containing Series of Nicotinamide Phosphoribosyltransferase (NAMPT) Activators," Bioorganic and Medicinal Chemistry Letters 41:128007, 23 pages.
Pinkerton, A. B. et al. (Jun. 1, 2021, e-pub. Mar. 31, 2021). "Optimization of a Urea-Containing Series of Nicotinamide Phosphoribosyltransferase (NAMPT) Activators," Bioorganic and Medicinal Chemistry Letters 41:128007, 5 pages.
PUBCHEM (Jul. 12, 2014). CID: 75363707 "N-[4-(2-methylbutan-2-yl)cyclohexyl]-2-(1,2,4-triazol-1-yl)pyridine-4-carboxamide," 9 pages.
PUBCHEM (Jun. 21, 2010). CID: 45834917 "N-(4-methylcyclohexyl)-2-(1,2,4-triazol-1-yl)pyridine-4-carboxamide," 9 pages.
Ralto, K.M. et al. (Feb. 2020, e-pub. Oct. 31, 2019). "NAD+ Homeostasis in Renal Health and Disease." Nat. Rev. Nephrol. 16(2):99-111.
Revollo, J.R. et al. (Dec. 3, 2004). "The NAD Biosynthesis Pathway Mediated by Nicotinamide Phosphoribosyltransferase Regulates Sir2 Activity in Mammalian Cells," J. Biol. Chem. 279(49):50754-50763.
Revollo, J.R. et al. (Nov. 2007). "Nampt/PBEF/visfatin Regulates Insulin Secretion in β Cells as a Systemic NAD Biosynthetic Enzyme," Cell Matab. 6(5);363-375, 24 pages.
Ryu, D. et al. (Oct. 19, 2016). "NAD+ Repletion Improves Muscle Function in Muscular Dystrophy and Counters Global PARylation," Sci. Transl. Med. 8(361):361ra139, 29 pages.
Smyrnias, I. et al. (Apr. 16, 2019). "Cardioprotective Effect of the Mitochondrial Unfolded Protein Response During Chronic Pressure Overload," J Am Coll Cardiol. 73(14):1795-1806.
Stromland, O. et al. (Feb. 2019). "Keeping the Balance in NAD Metabolism," Biochem.Soc. Trans. 47 (1):119-130, 22 pages.
Takei, H. et al. (Nov. 1965). "The Preparation of Iminosulfonic Acid Derivatives by Means of Sulfinamides and N-Bromosuccinimide," Bulletin of the Chemical Society of Japan 38(11):1989-1993.
U.S. Appl. No. 18/268,569, filed Dec. 20, 2021, for Minxing, Shen et al.
Van Der Veer, E. et al. (Apr. 13, 2007). "Extension of Human Cell Lifespan by Nicotinamide Phosphoribosyltransferase," J. Biol. Chem. 282(15):10841-10845.
Verdin, E. (Dec. 4, 2015). "NAD+ in Aging, Metabolism, and Neurodegeneration," Science 350 (6265):1208-1213.
Williams, P.A. et al. (Apr. 25, 2017). "Nicotinamide and WLDS Act Together to Prevent Neurodegeneration in Glaucoma," Front. Neurosci. 11:232, 10 pages.
Xu, T-Y. et al. (Jun. 4, 2015). "Discovery and Characterization of Novel Small-Molecule Inhibitors Targeting Nicotinamide Phosphoribosyltransferase," Sci Rep. 5:10043, 14 pages.
Yang, H. et al. (Sep. 21, 2007). "Nutrient-Sensitive Mitochondrial NAD+ Levels Dictate Cell Survival," Cell 130 (6):1095-1107.
Yang, Y. et al. (Dec. 2016). "AD+ Metabolism: Bioenergetics, Signaling and Manipulation for Therapy," Biophys. Acta. 1864(12):1787-1800, 31 pages.
Yoshino, J. et al. (Oct. 5, 2011). "Nicotinamide Mononucleotide, a Key NAD+ Intermediate, Treats the Pathophysiology of Diet- and Age-Induced Diabetes in Mice," Cell Metab. 14(4):528-536.
Zak, M. et al. (Sep. 22, 2016, e-pub. Aug. 19, 2016). "Minimizing CYP2C9 Inhibition of Exposed-Pyridine NAMPT (Nicotinamide Phosphoribosyltransferase) Inhibitors," Journal of Medical Chemistry 59(18):8345-8368.
Zhao, Y. et al. (Jul. 2015). "Regenerative Neurogenesis After Ischemic Stroke Promoted by Nicotinamide Phosphoribosyltransferase-Nicotinamide Adenine Dinucleotide Cascade," Stroke 46(7):1966-1974.
Zheng, D. et al. (Jul. 15, 2019). "Nicotinamide Riboside Promotes Auolysosome Clearance in Preventing Doxorubicin-Indued Cardiotoxicity," Clin. Sci. (Lond). 133(13):1505-1521, 27 pages.
Zheng, X. et al. (Jun. 27, 2013, e-pub. Jun. 13, 2013). "Structure-Based Identification of Ureas as Novel Nicotinamide Phosphoribosyltransferase (Nampt) Inhibitors," J Med Chem. 56(12):4921-4937.

* cited by examiner

NAMPT MODULATORS

CROSS-REFERENCE TO RELATED APPLICATIONS

This application is a national stage application under 35 U.S.C. § 371 of International Application No. PCT/US2021/030950, filed internationally on May 5, 2021, which claims the benefit of and priority to U.S. Provisional Application No. 63/020,904, filed on May 6, 2020, the contents of which are hereby incorporated herein by reference in their entirety.

FIELD

Provided herein are alkyl urea compounds, pharmaceutical compositions comprising such compounds, and methods of treating various diseases and conditions mediated by nicotinamide phosphoribosyltransferase (NAMPT) with such compounds.

BACKGROUND

The present disclosure relates to the use of modulators of nicotinamide phosphoribosyltransferase (NAMPT) and derivatives thereof, as well as enhancers or inducers of NAMPT expression, NAMPT activity or NAMPT-mediated signaling for preventing or treating a variety of pathological conditions.

Nicotinamide adenine dinucleotide (NAD+) is an essential coenzyme (enzyme cofactor) involved in fundamental biological processes of both catabolic and anabolic metabolism. As a coenzyme, NAD is associated with many oxidative enzymes (typically dehydrogenases) involved in energy metabolism, serving as a universal electron carrier. NAD exists in cells in the oxidized state (NAD+ and NADP+), and the reduced state (NADH and NADPH), acting as a chemical means to capture and transfer free energy from oxidative processes in catabolism, or to provide small packets of energy to build macromolecules in anabolism. NADH produced from the oxidation of carbohydrates, lipids, and amino acids provides reducing equivalents to the electron transport chain of mitochondria, ultimately driving the synthesis of ATP in oxidative phosphorylation.

More than 200 enzymes use either NAD+ or NADP+ as a coenzyme, and the enzymatic functions are not limited to energy metabolism. It is now appreciated that NAD+ plays a role in regulating diverse functions, including mitochondrial function, respiratory capacity, and biogenesis, mitochondrial-nuclear signaling. Further, it controls cell signaling, gene expression, DNA repair, hematopoiesis, immune function, the unfolded protein response, and autophagy. Furthermore, NAD is anti-inflammatory and is the precursor for NADPH, which is the primary source of reducing power for combating oxidative stress. A large body of literature indicates that boosting NAD levels is an effective strategy to either prevent or ameliorate a wide variety of disease states (Strømland et al., *Biochem Soc Trans.* 2019, 47(1):119-130; Ralto et al., *Nat Rev Nephrol.* 2019; Fang et al., *Trends Mol Med.* 2017, 23(10):899-916; Yoshino et al., *Cell Metab.* 2011, 14(4):528-36; Yang and Sauve, *Biochim Biophys Acta.* 2016, 1864:1787-1800; Verdin, *Science.* 2015, 350(6265):1208-13).

Levels of NAD+ and NADP+-associated enzymes play important roles in normal physiology and are altered under various disease and stress conditions including aging. Cellular NAD+ levels decrease during aging, metabolic disease, inflammatory diseases, during ischemia/reperfusion injury, and in other conditions in humans (Massudi et al., *PLoS ONE.* 2012, 7(7): e42357) and animals (Yang et al., *Cell.* 2007, 130(6):1095-107; Braidy et al. *PLoS One.* 2011, 26; 6(4):e19194; Peek et al. *Science.* 2013, 342(6158):1243417; Ghosh et al., *J Neurosci.* 2012, 32(17):5821-32), suggesting that modulation of cellular NAD+ level affects the speed and severity of the decline and deterioration of bodily functions. Therefore, an increase in cellular NAD+ concentration could be beneficial in the context of aging and age-related diseases.

The cellular NAD+ pool is controlled by a balance between the activity of NAD+-synthesizing and consuming enzymes. In mammals, NAD+ is synthesized from a variety of dietary sources, including one or more of its major precursors that include: tryptophan (Trp), nicotinic acid (NA), nicotinamide riboside (NR), nicotinamide mononucleotide (NMN), and nicotinamide (NAM). Based upon the bioavailability of its precursors, there are three pathways for the synthesis of NAD+ in cells: (i) from Trp by the de novo biosynthesis pathway or kynurenine pathway (ii) from NA in the Preiss-Handler pathway and (iii) from NAM, NR, and NMN in the salvage pathway (Verdin et al., *Science.* 2015, 350(6265):1208-13). Of these, the predominant NAD+ biosynthetic pathway involves the step of synthesis of nicotinamide mononucleotide (NMN) using nicotinamide and 5'-phosphoribosyl-pyrophosphate by the rate-limiting enzyme nicotinamide phosphoribosyl-transferase (NAMPT) that is critical to determination of longevity and responses to a variety of stresses (Fulco et al, *Dev Cell.* 2008, 14(5):661-73; Imai, *Curr Pharm Des.* 2009, 15(1):20-8; Revollo et al., *J Biol Chem.* 2004, 279(49):50754-63; Revollo et al., *Cell Metab.* 2007, November; 6(5):363-75; van der Veer et al., *J Biol Chem.* 2007, 282(15):10841-5; Yang et al., *Cell.* 2007, 130(6):1095-107). Thus, increasing the rate of NAMPT catalysis by a small molecule activator would be an effective strategy to boost NAD levels and thereby address a broad spectrum of disease states. These include cardiac diseases, chemotherapy induced tissue damage, renal diseases, metabolic diseases, muscular diseases, neurological diseases and injuries, diseases caused by impaired stem cell function, DNA damage and primary mitochondrial disorders, and ocular diseases.

SUMMARY

In one aspect, provided herein is a compound of Formula (II):

(II)

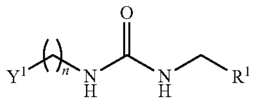

or a pharmaceutically acceptable salt thereof, wherein:

n is 0 to 6;

$Y^1$ is

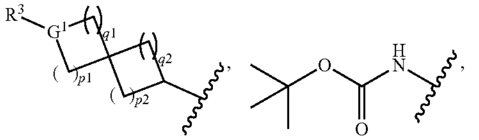 or

-continued

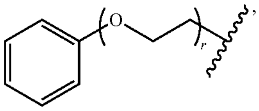

and $R^1$ is selected from the group consisting of

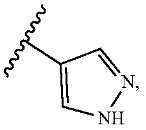
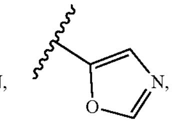
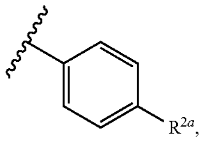
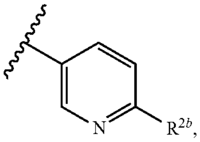
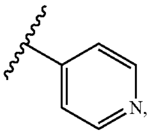

and

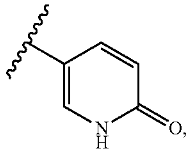

or $Y^1$ is

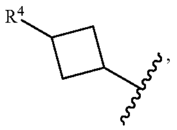
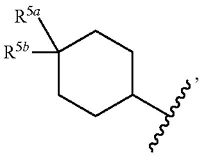

or

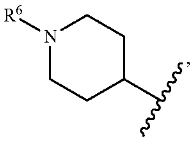

and $R^1$ is selected from the group consisting of

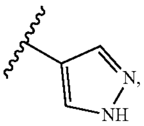
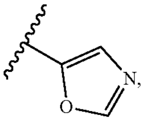
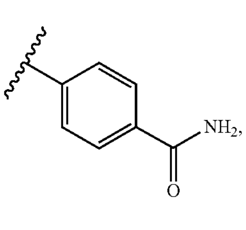
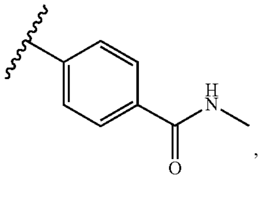
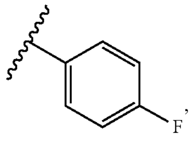

-continued

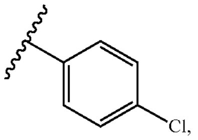
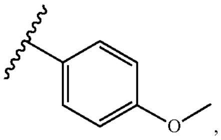
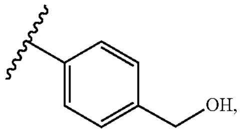
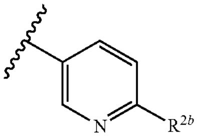
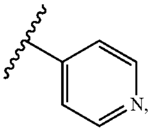

and

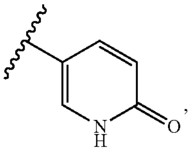

or $Y^1$ is —C(O)—N($R^q$)—($R^s$), wherein $R^q$ is H or $C_1$-$C_6$ alkyl, and $R^s$ is $C_3$-$C_8$ cycloalkyl, optionally substituted $C_6$-$C_{14}$ aryl, optionally substituted 5- to 18-membered heteroaryl, or —($C_1$-$C_6$ alkylene)-(optionally substituted $C_6$-$C_{14}$ aryl), and $R^1$ is selected from the group consisting of

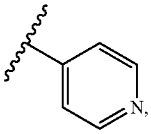
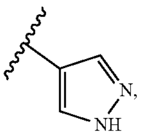
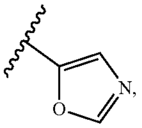
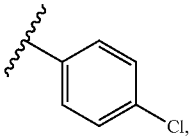

and

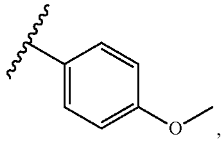

or $Y^1$ is —C(O)—$R^b$, wherein $R^b$ is optionally substituted 3- to 18-membered heterocycloalkyl, and $R^1$ is

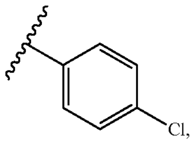 [SMILES: *c1ccc(Cl)cc1]

or $Y^1$ is —N($R^1$)—C(O)$R^u$, wherein $R^t$ is H or $C_1$-$C_6$ alkyl, and $R^u$ is optionally substituted $C_6$-$C_{14}$ aryl, optionally substituted 5- to 18-membered heteroaryl, or —($C_1$-$C_6$ alkylene)-(5- to 18-membered heteroaryl), and $R^1$ is

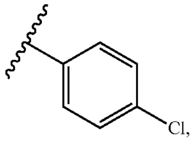 [SMILES: *c1ccc(Cl)cc1]

or $Y^1$ is

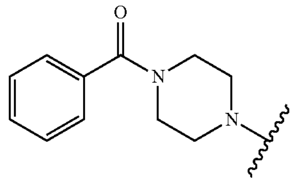 [SMILES: *N1CCN(C(=O)c2ccccc2)CC1]

and $R^1$ is

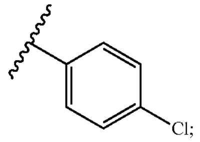

wherein $R^{2a}$ and $R^{2b}$ are each independently halo, —O($C_1$-$C_6$ alkyl), $C_1$-$C_6$ alkyl substituted with —OH, —C(O)$NR^{2c}R^{2d}$, or —N($R^{2e}$)C(O)($C_1$-$C_6$ alkyl); and $R^{2c}$, $R^{2d}$, and $R^{2e}$ are each independently hydrogen or $C_1$-$C_6$ alkyl;

$G^1$ is CH or N;

p1 and p2 are each independently 0, 1, or 2;

q1 and q2 are each independently 1 or 2;

r is 1, 2, or 3;

wherein, when $Y^1$ is

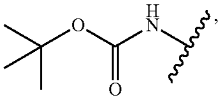 [SMILES: *NC(=O)OC(C)(C)C], then n is 4, 5, or 6;

when $Y^1$ is

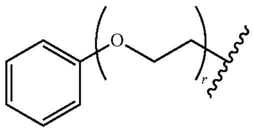

and r is 1, then n is 2, 3, 4, 5, or 6; and when $Y^1$ is —C(O)—N($R^q$)—($R^s$), —C(O)—$R^b$, —N($R^t$)—C(O)$R^u$, or

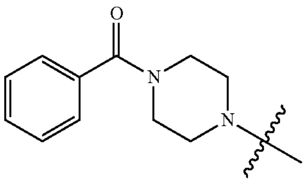, then n is 4 or 5;

$R^3$ is selected from the group consisting of:

i. unsubstituted $C_1$-$C_6$ alkyl;

ii. $C_6$-$C_{14}$ aryl;

iii. optionally substituted 5- to 18-membered heteroaryl;

iv. —$NR^{3a}R^{3b}$, wherein $R^{3a}$ and $R^{3b}$ are each independently selected from the group consisting of hydrogen, $C_6$-$C_{14}$ aryl, 5- to 18-membered heteroaryl, —($C_1$-$C_6$ alkylene)-($C_6$-$C_{14}$ aryl), and —($C_1$-$C_6$ alkylene)-(5- to 18-membered heteroaryl);

v. —$OR^{3c}$, wherein $R^{3c}$, is $C_6$-$C_{14}$ aryl, 5- to 18-membered heteroaryl, or —($C_1$-$C_6$ alkylene)-(5- to 18-membered heteroaryl);

vi. —C(O)$R^{3d}$, wherein $R^{3d}$ is selected from the group consisting of —$NR^{3f}R^{3g}$; $C_3$-$C_8$ cycloalkyl; $C_3$-$C_8$ cycloalkyl substituted with optionally substituted $C_6$-$C_{14}$ aryl; $C_3$-$C_8$ cycloalkenyl; optionally substituted $C_6$-$C_{14}$ aryl; optionally substituted —($C_1$-$C_6$ alkylene)-($C_6$-$C_{14}$ aryl); optionally substituted 3- to 18-membered heterocycloalkyl; and optionally substituted 5- to 18-membered heteroaryl, wherein $R^{3f}$ and $R^{3g}$ are each independently selected from the group consisting of:

(a) hydrogen, (b) optionally substituted $C_1$-$C_6$ alkyl, (c) $C_6$-$C_{14}$ aryl, (d) optionally substituted 3- to 18-membered heterocycloalkyl, (e) optionally substituted 5- to 18-membered heteroaryl, (f) optionally substituted $C_3$-$C_{10}$ cycloalkyl; and (g) optionally substituted $C_3$-$C_{10}$ cycloalkenyl;

vii. $C_1$-$C_6$ alkyl substituted with one or more —OH, —C(O)$NR^{3h}R^{3i}$, optionally substituted $C_6$-$C_{14}$ aryl, optionally substituted 3- to 18-membered heterocycloalkyl, optionally substituted 5- to 18-membered heteroaryl, —N($R^{3P}$)—C(O)$R^{3q}$, —$S(O)_2$—$R^{3r}$, or —C(O)—$R^{3s}$, wherein $R^{3h}$ and $R^{3i}$ are each independently selected from $C_1$-$C_6$ alkyl and —($C_1$-$C_6$ alkylene)-($C_6$-$C_{14}$ aryl), $R^{3p}$ is H or $C_1$-$C_6$ alkyl, $R^{3q}$ is $C_3$-$C_8$ cycloalkyl, optionally substituted 3- to 18-membered heterocycloalkyl, or optionally substituted 5- to 18-membered heteroaryl, $R^{3r}$ is $C_6$-$C_{14}$ aryl or 5- to 18-membered heteroaryl, and $R^{3s}$ is optionally substituted 3- to 18-membered heterocycloalkyl;

viii. —C(O)$OR^{3j}$, wherein $R^{3j}$ is hydrogen or $C_1$-$C_6$ alkyl;

ix. —NHC(O)$R^{3k}$, wherein $R^{3k}$ is optionally substituted $C_6$-$C_{14}$ aryl, optionally substituted —($C_1$-$C_6$ alkylene)-($C_6$-$C_{14}$ aryl), or optionally substituted 5- to 18-membered heteroaryl;

x. —NHC(O)$OR^{3l}$, wherein $R^{3l}$ is hydrogen or $C_1$-$C_6$ alkyl;

xi. —$NHSO_2R^{3m}$, wherein $R^{3m}$ is optionally substituted 5- to 18-membered heteroaryl, optionally substituted $C_6$-$C_{14}$ aryl, or —($C_1$-$C_6$ alkylene)-($C_6$-$C_{14}$ aryl), each of which is optionally substituted; and xii. —$SO_2R^{3a}$; wherein $R^{3n}$ is $C_1$-$C_6$ alkyl, optionally substituted $C_3$-$C_{10}$ cycloalkyl, optionally substituted $C_6$-$C_{14}$ aryl, or optionally substituted —($C_1$-$C_6$ alkylene)-($C_6$-$C_{14}$ aryl);

$R^4$ is phenyl or —C(O)NH—$CH_2$-phenyl;

$R^{5a}$ and $R^{5b}$ are independently selected from the group consisting of hydrogen, methyl, and —NHC(O)O($C_1$-$C_6$ alkyl); and $R^6$ is selected from the group consisting of —C(O)OC$(CH_3)_3$, —NHC(O)O($C_1$-$C_6$ alkyl), —C(O)— (optionally substituted phenyl), —C(O)—($C_1$-$C_6$ alkylene)-(optionally substituted phenyl), —C(O)-(optionally substituted 3- to 18-membered heterocycloalkyl), —C(O)-(optionally substituted 5- to 18-membered heteroaryl), —C(O)—($C_1$-$C_6$ alkylene)-(optionally substituted 5- to 18-membered heteroaryl), and 5- to 18-membered heteroaryl, provided that, when $R^6$ is —C(O)-(substituted phenyl), —C(O)—($C_1$-$C_6$ alkylene)-(optionally substituted phenyl), —C(O)-(optionally substituted 3- to 18-membered heterocycloalkyl), —C(O)-(optionally substituted 5- to 18-membered heteroaryl), —C(O)—($C_1$-$C_6$ alkylene)-(optionally substituted 5- to 18-membered heteroaryl), or 5- to 18-membered heteroaryl, then (1) n is 4 or 5, and (2) $R^1$ is selected from the group consisting of

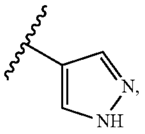
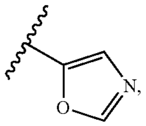
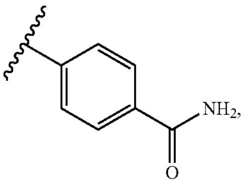
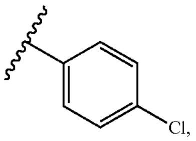
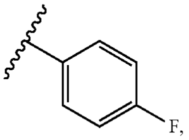
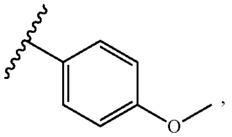
and
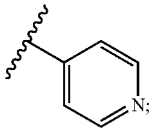

wherein (1) when $Y^1$ is

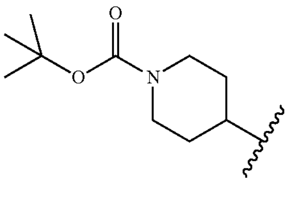 [SMILES: *C1CCN(C(=O)OC(C)(C)C)CC1]

and n is 0 or 1, then $R^1$ is selected from the group consisting of

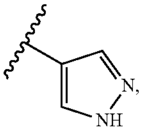
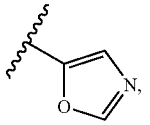
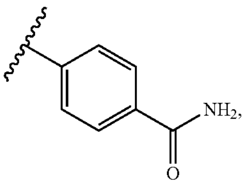
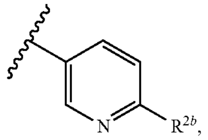
and
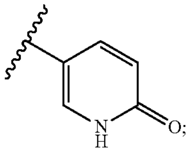

and (2) when $Y^1$ is

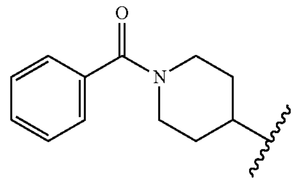 [SMILES: *C1CCN(C(=O)c2ccccc2)CC1]

and n is 0, then $R^1$ is selected from the group consisting of

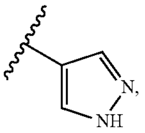
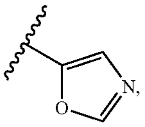
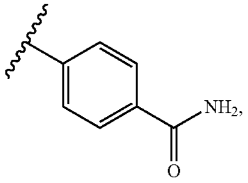
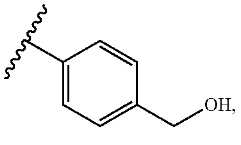
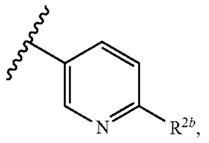
and
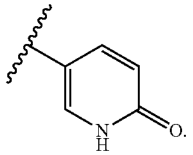

In one aspect, provided herein is a compound of Formula (I):

(I)

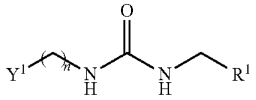

or a pharmaceutically acceptable salt thereof, wherein:

$Y^1$ is

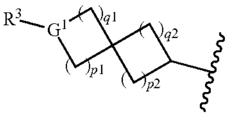 , 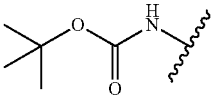 , or

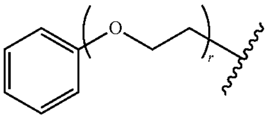 , and $R^1$ is selected from the group consisting of

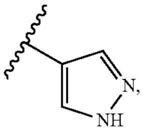 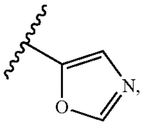

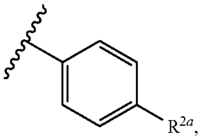 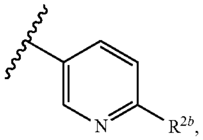

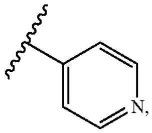 and 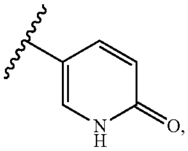

or $Y^1$ is

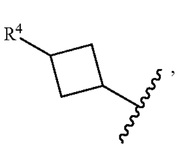 , 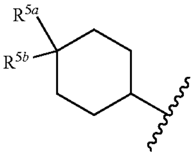 , or

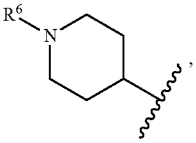 , and $R^1$ is selected from the group consisting of

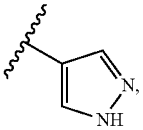 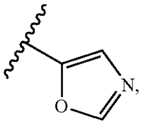

-continued

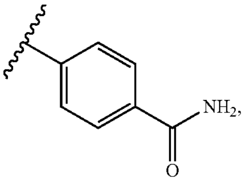 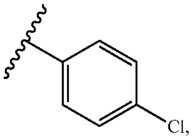

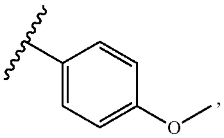 , 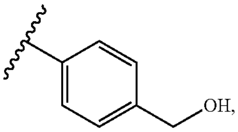

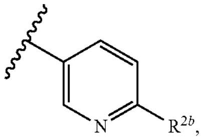 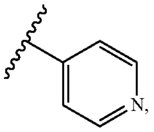 and

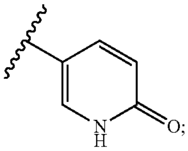

wherein $R^{2a}$ and $R^{2b}$ are each independently halo, —O($C_1$-$C_6$ alkyl), $C_1$-$C_6$ alkyl substituted with —OH, —C(O)$NR^{2c}R^{2d}$, or —N($R^{2e}$)C(O)($C_1$-$C_6$ alkyl); and $R^{2c}$, $R^{2d}$, and $R^{2e}$ are each independently hydrogen or $C_1$-$C_6$ alkyl;

$G^1$ is CH or N;

p1 and p2 are each independently 0, 1, or 2;

q1 and q2 are each independently 1 or 2;

r is 1, 2, or 3;

n is 0 to 6;

wherein when $Y^1$ is

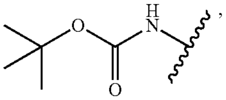 [SMILES: *NC(=O)OC(C)(C)C] , n is 4, 5, or 6; and when $Y^1$ is

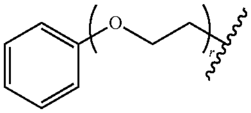

and r is 1, n is 2, 3, 4, 5, or 6;

$R^3$ is selected from the group consisting of:

i. $C_1$-$C_6$ alkyl;

ii. $C_6$-$C_{14}$ aryl;

iii. optionally substituted 5- to 18-membered heteroaryl;

iv. —$NR^{3a}R^{3b}$, wherein $R^{3a}$ and $R^{3b}$ are each independently selected from the group consisting of hydrogen, $C_6$-$C_{14}$ aryl, 5- to 18-membered heteroaryl, —($C_1$-$C_6$ alkylene)-($C_6$-$C_{14}$ aryl), and —($C_1$-$C_6$ alkylene)-(5- to 18-membered heteroaryl);

v. —$OR^{3c}$, wherein $R^{3c}$ is $C_6$-$C_{14}$ aryl;

vi. —$C(O)R^{3d}$, wherein $R^{3d}$ is selected from the group consisting of —$NR^{3f}R^{3g}$; $C_3$-$C_8$ cycloalkyl; $C_3$-$C_8$ cycloalkyl substituted with optionally substituted $C_6$-$C_{14}$ aryl; $C_3$-$C_8$ cycloalkenyl; optionally substituted $C_6$-$C_{14}$ aryl; optionally substituted —($C_1$-$C_6$ alkylene)-($C_6$-$C_{14}$ aryl); optionally substituted 3- to 18-membered heterocycloalkyl; and optionally substituted 5- to 18-membered heteroaryl, wherein $R^{3f}$ and $R^{3g}$ are each independently selected from the group consisting of:

(a) hydrogen, (b) optionally substituted $C_1$-$C_6$ alkyl, (c) $C_6$-$C_{14}$ aryl, (d) optionally substituted 3- to 18-membered heterocycloalkyl, (e) optionally substituted 5- to 18-membered heteroaryl, (f) optionally substituted $C_3$-$C_{10}$ cycloalkyl; and (g) optionally substituted $C_3$-$C_{10}$ cycloalkenyl;

vii. $C_1$-$C_6$ alkyl substituted with $C(O)NR^{3h}R^{3i}$, optionally substituted 3- to 18-membered heterocycloalkyl, or optionally substituted 5- to 18-membered heteroaryl, wherein $R^{3h}$ and $R^{3i}$ are each independently selected from $C_1$-$C_6$ alkyl and —($C_1$-$C_6$ alkylene)-($C_6$-$C_{14}$ aryl);

viii. —$C(O)OR^{3j}$, wherein $R^{3j}$ is hydrogen or $C_1$-$C_6$ alkyl;

ix. —$NHC(O)R^{3k}$, wherein $R^{3k}$ is optionally substituted $C_6$-$C_{14}$ aryl, optionally substituted —($C_1$-$C_6$ alkylene)-($C_6$-$C_{14}$ aryl), or optionally substituted 5- to 18-membered heteroaryl;

x. —$NHC(O)OR^{3l}$, wherein $R^{3l}$ is hydrogen or $C_1$-$C_6$ alkyl;

xi. —$NHSO_2R^{3m}$, wherein $R^{3m}$ is optionally substituted 5- to 18-membered heteroaryl, optionally substituted $C_6$-$C_{14}$ aryl, or —($C_1$-$C_6$ alkylene)-($C_6$-$C_{14}$ aryl), each of which is optionally substituted; and xii. —$SO_2R^{3n}$; wherein $R^{3n}$ is optionally substituted $C_3$-$C_{10}$ cycloalkyl, optionally substituted $C_6$-$C_{14}$ aryl, or optionally substituted —($C_1$-$C_6$ alkylene)-($C_6$-$C_{14}$ aryl);

$R^4$ is phenyl or —C(O)NH—$CH_2$-phenyl;

$R^{5a}$ and $R^{5b}$ are independently selected from the group consisting of hydrogen, methyl, and —NHC(O)O($C_1$-$C_6$ alkyl); and $R^6$ is selected from the group consisting of —C(O)OC$(CH_3)_3$, —NHC(O)O($C_1$-$C_6$ alkyl), and —C(O)-phenyl; and wherein (1) when $Y^1$ is

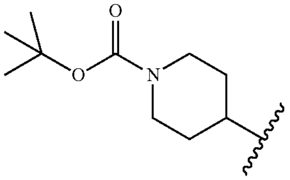 [SMILES: *C1CCN(C(=O)OC(C)(C)C)CC1]

and n is 0 or 1, $R^1$ is selected from the group consisting of

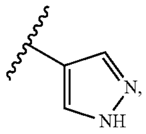

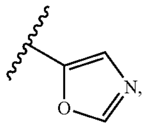

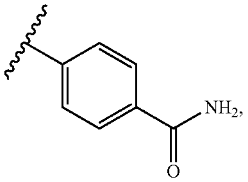

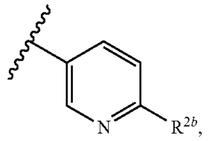

and

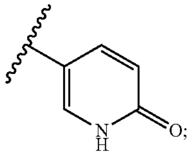

and (2) when $Y^1$ is

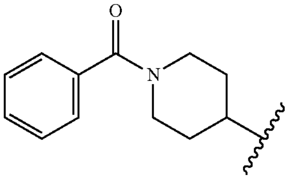 [SMILES: *C1CCN(C(=O)c2ccccc2)CC1]

and n is 0, $R^1$ is selected from the group consisting of

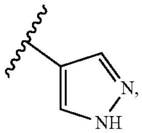

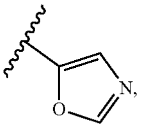

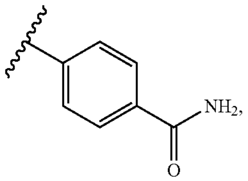

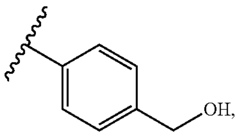

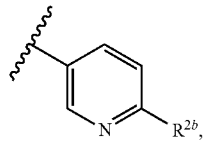

and

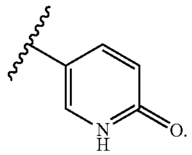

In another aspect, provided herein is a compound of Formula (I-A):

(I-A)

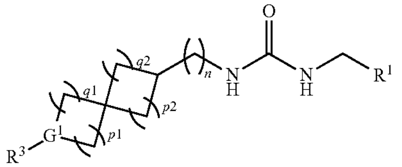

or a salt thereof, wherein $R^1$, $R^3$, $G^1$, p1, p2, q1, q2, and n are as defined for Formula (II) or Formula (I) or any variation or embodiment thereof.

In another aspect, provided herein is a compound of Formula (I-B):

(I-B)

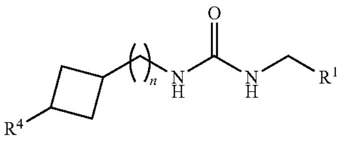

or a salt thereof, wherein $R^1$, $R^4$, and n are as defined for Formula (II) or Formula (I) or any variation or embodiment thereof.

In another aspect, provided herein is a compound of Formula (I-C):

(I-C)

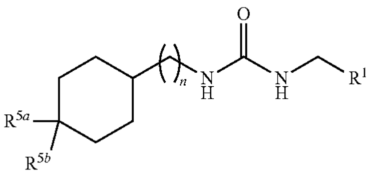

or a salt thereof, wherein $R^1$, $R^{5a}$, $R^{5b}$, and n are as defined for Formula (II) or Formula (I) or any variation or embodiment thereof.

In another aspect, provided herein is a compound of Formula (I-D):

(I-D)

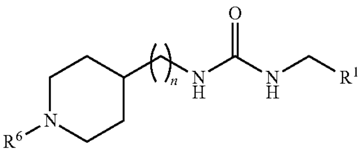

or a salt thereof, wherein $R^1$, $R^6$, and n are as defined for Formula (II) or Formula (I) or any variation or embodiment thereof.

In another aspect, provided herein is a compound of Formula (I-E) or (I-F):

(I-E)

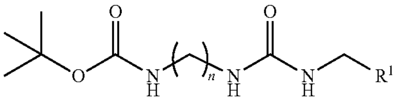

-continued (I-F)

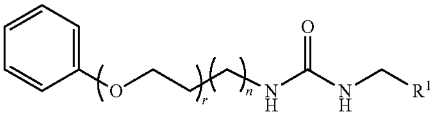

or a salt thereof, wherein $R^1$, n, and r are as defined for Formula (II) or Formula (I) or any variation or embodiment thereof.

In another aspect, provided herein is a compound of Formula (I-G):

(I-G)

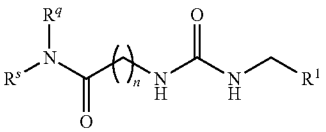

or a salt thereof, wherein $R^1$, $R^q$, $R^s$, and n are as defined for Formula (II), or any variation or embodiment thereof.

In another aspect, provided herein is a compound of Formula (I-H):

(I-H)

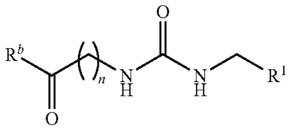

or a salt thereof, wherein $R^1$, $R^b$, and n are as defined for Formula (II), or any variation or embodiment thereof.

In one aspect, provided herein is a compound of Formula (I-J):

(I-J)

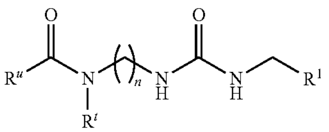

or a salt thereof, wherein $R^1$, $R^t$, $R^u$, and n are as defined herein for Formula (II), or any variation or embodiment thereof.

In one aspect, provided herein is a compound of Formula (I-K):

(I-K)

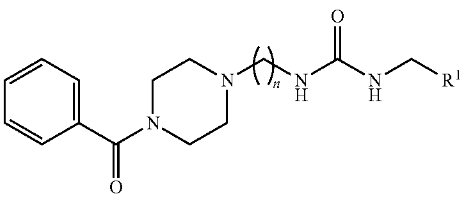

or a salt thereof, wherein $R^1$ and n are as defined herein for Formula (II), or any variation or embodiment thereof.

In a further aspect, provided herein are pharmaceutical compositions comprising at least one compound of Formula (II), (I), (I-A), (I-B), (I-C), (I-D), (I-E), (I-F), (I-G), (I-H), (I-J), or (I-K), such as a compound of Table 1, or a pharmaceutically acceptable salt of any of the foregoing, optionally further comprising a pharmaceutically acceptable excipient.

In another aspect, provided herein is a method of treating a disease or condition mediated by NAMPT activity in a subject in need thereof, comprising administering to the subject an effective amount of at least one compound Formula (II), (I), (I-A), (I-B), (I-C), (I-D), (I-E), (I-F), (I-G), (I-H), (I-J), or (I-K), such as a compound of Table 1, or a pharmaceutically acceptable salt thereof, or a pharmaceutical composition comprising at least one compound of Formula (II), (I), (I-A), (I-B), (I-C), (I-D), (I-E), (I-F), (I-G), (I-H), (I-J), or (I-K). In some embodiments, the disease or condition is selected from the group consisting of cancer, a hyperproliferative disease or condition, an inflammatory disease or condition, a metabolic disorder, a cardiac disease or condition, chemotherapy induced tissue damage, a renal disease, a metabolic disease, a neurological disease or injury, a neurodegenerative disorder or disease, diseases caused by impaired stem cell function, diseases caused by DNA damage, primary mitochondrial disorders, or a muscle disease or muscle wasting disorder. In some embodiments, the disease or condition is selected from the group consisting of obesity, atherosclerosis, insulin resistance, type 2 diabetes, cardiovascular disease, Alzheimer's disease, Huntington's disease, Parkinson's disease, amyotrophic lateral sclerosis, depression, Down syndrome, neonatal nerve injury, aging, axonal degeneration, carpal tunnel syndrome, Guillain-Barre syndrome, nerve damage, polio (poliomyelitis), and spinal cord injury.

Additional embodiments, features, and advantages of the present disclosure will be apparent from the following detailed description and through practice of the present disclosure.

For the sake of brevity, the disclosures of publications cited in this specification, including patents, are herein incorporated by reference.

DETAILED DESCRIPTION

Definitions

As used in the present specification, the following words and phrases are generally intended to have the meanings as set forth below, except to the extent that the context in which they are used indicates otherwise.

Throughout this application, unless the context indicates otherwise, references to a compound of Formula (II) or Formula (I) includes all subgroups of Formula (II) or Formula (I) defined herein, including all substructures, subgenera, preferences, embodiments, examples and particular compounds defined and/or described herein. References to a compound of Formula (II) or Formula (I) and subgroups thereof, include ionic forms, polymorphs, pseudopolymorphs, amorphous forms, solvates, co-crystals, chelates, isomers, tautomers, oxides (e.g., N-oxides, S-oxides), esters, prodrugs, isotopes and/or protected forms thereof. In some embodiments, references to a compound of Formula (II) or Formula (I) and subgroups thereof, include polymorphs, solvates, co-crystals, isomers, tautomers and/or oxides thereof. In some embodiments, references to a compound of Formula (II) or Formula (I) and subgroups thereof, include polymorphs, solvates, and/or co-crystals thereof. In some embodiments, references to a compound of Formula (II) or Formula (I) and subgroups thereof, include isomers, tautomers and/or oxides thereof. In some embodiments, references to a compound of Formula (II) or Formula (I) and subgroups thereof, include solvates thereof. Similarly, the term "salts" includes solvates of salts of compounds.

"Alkyl" encompasses straight and branched carbon chains having the indicated number of carbon atoms, for example, from 1 to 20 carbon atoms, or 1 to 8 carbon atoms, or 1 to 6 carbon atoms. For example, $C_{1-6}$ alkyl encompasses both straight and branched chain alkyl of from 1 to 6 carbon atoms. When an alkyl residue having a specific number of carbons is named, all branched and straight chain versions having that number of carbons are intended to be encompassed; thus, for example, "propyl" includes n-propyl and isopropyl; and "butyl" includes n-butyl, sec-butyl, isobutyl and t-butyl. Examples of alkyl groups include, but are not limited to, methyl, ethyl, propyl, isopropyl, n-butyl, sec-butyl, tert-butyl, pentyl, 2-pentyl, 3-pentyl, isopentyl, neopentyl, hexyl, 2-hexyl, 3-hexyl, and 3-methylpentyl.

As used herein, the term "haloalkyl" refers to an alkyl moiety, as described above, wherein one or more of the hydrogen atoms of the alkyl moiety has been replaced by one or more independently selected halogen atoms. By way of illustration, the term "haloalkyl" includes, but it not limited to, a methyl moiety in which one or more of the hydrogen atoms of the methyl moiety has been replaced by one or more independently selected halogen atoms, e.g., $—CH_2F$, $—CHF_2$, $—CH_2Cl$, $—CCl_3$, —CHClF, $—CCl_2Br$, etc.

As used herein, the term "alkoxy" refers to a —O-alkyl moiety.

As used herein, the term "haloalkoxy" refers to an alkoxy moiety, as described above, wherein one or more of the hydrogen atoms of the alkoxy moiety has been replaced by one or more independently selected halogen atoms. By way of illustration, the term "haloalkoxy" includes, but it not limited to, a methoxy moiety in which one or more of the hydrogen atoms of the methoxy moiety has been replaced by one or more independently selected halogen atoms, e.g., $—O—CH_2F$, $—O—CHF_2$, $—O—CH_2Cl$, $—O—CCl_3$, —O—CHClF, $—O—CCl_2Br$, etc.

As used herein, the term "alkylene" refers to divalent alkyl group as defined herein above having 1 to 20 carbon atoms. Unless otherwise provided, alkylene refers to moieties having 1 to 20 carbon atoms, 1 to 16 carbon atoms, 1 to 10 carbon atoms, 1 to 7 carbon atoms, or 1 to 4 carbon atoms. Alkylene groups include, but are not limited to, methylene, ethylene, n-propylene, iso-propylene, n-butylene, sec-butylene, iso-butylene, tert-butylene, n-pentylene, isopentylene, neopentylene, n-hexylene, 3-methylhexylene, 2,2-dimethylpentylene, 2,3-dimethylpentylene, n-heptylene, n-octylene, n-nonylene, and n-decylene.

When a range of values is given (e.g., $C_{1-6}$ alkyl), each value within the range as well as all intervening ranges are included. For example, "$C_{1-6}$ alkyl" includes $C_1$, $C_2$, $C_3$, $C_4$, $C_5$, $C_6$, $C_{1-6}$, $C_{2-6}$, $C_{3-6}$, $C_{4-6}$, $C_{5-6}$, $C_{1-5}$, $C_{2-5}$, $C_{3-5}$, $C_{4-5}$, $C_{1-4}$, $C_{2-4}$, $C_{3-4}$, $C_{1-3}$, $C_{2-3}$, and $C_{1-2}$ alkyl.

"Alkenyl" refers to an unsaturated branched or straight-chain alkyl group having the indicated number of carbon atoms (e.g., 2 to 8, or 2 to 6 carbon atoms) and at least one carbon-carbon double bond. The group may be in either the cis or trans configuration (Z or E configuration) about the double bond(s). Alkenyl groups include, but are not limited to, ethenyl, propenyl (e.g., prop-1-en-1-yl, prop-1-en-2-yl, prop-2-en-1-yl (allyl), prop-2-en-2-yl), and butenyl (e.g., but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl).

"Alkynyl" refers to an unsaturated branched or straight-chain alkyl group having the indicated number of carbon atoms (e.g., 2 to 8 or 2 to 6 carbon atoms) and at least one carbon-carbon triple bond. Alkynyl groups include, but are not limited to, ethynyl, propynyl (e.g., prop-1-yn-1-yl, prop-2-yn-1-yl) and butynyl (e.g., but-1-yn-1-yl, but-1-yn-3-yl, but-3-yn-1-yl).

"Cycloalkyl" indicates a non-aromatic, fully saturated carbocyclic ring having the indicated number of carbon atoms, for example, 3 to 10, or 3 to 8, or 3 to 6 ring carbon atoms. Cycloalkyl groups may be monocyclic or polycyclic (e.g., bicyclic, tricyclic). Examples of cycloalkyl groups include cyclopropyl, cyclobutyl, cyclopentyl, and cyclohexyl, as well as bridged, caged, and spirocyclic ring groups (e.g., norbornane, bicyclo[2.2.2]octane, spiro[3.3]heptane). In addition, one ring of a polycyclic cycloalkyl group may be aromatic, provided the polycyclic cycloalkyl group is bound to the parent structure via a non-aromatic carbon. For example, a 1,2,3,4-tetrahydronaphthalen-1-yl group (wherein the moiety is bound to the parent structure via a non-aromatic carbon atom) is a cycloalkyl group, while 1,2,3,4-tetrahydronaphthalen-5-yl (wherein the moiety is bound to the parent structure via an aromatic carbon atom) is not considered a cycloalkyl group. Examples of polycyclic cycloalkyl groups consisting of a cycloalkyl group fused to an aromatic ring are described below.

"Cycloalkenyl" indicates a non-aromatic carbocyclic ring, containing the indicated number of carbon atoms (e.g., 3 to 10, or 3 to 8, or 3 to 6 ring carbon atoms) and at least one carbon-carbon double bond. Cycloalkenyl groups may be monocyclic or polycyclic (e.g., bicyclic, tricyclic). Examples of cycloalkenyl groups include cyclopropenyl, cyclobutenyl, cyclopentenyl, cyclopentadienyl, and cyclohexenyl, as well as bridged and caged ring groups (e.g., bicyclo[2.2.2]octene). In addition, one ring of a polycyclic cycloalkenyl group may be aromatic, provided the polycyclic alkenyl group is bound to the parent structure via a non-aromatic carbon atom. For example, inden-1-yl (wherein the moiety is bound to the parent structure via a non-aromatic carbon atom) is considered a cycloalkenyl group, while inden-4-yl (wherein the moiety is bound to the parent structure via an aromatic carbon atom) is not considered a cycloalkenyl group. Examples of polycyclic cycloalkenyl groups consisting of a cycloalkenyl group fused to an aromatic ring are described below.

"Aryl" indicates an aromatic carbocyclic ring having the indicated number of carbon atoms, for example, 6 to 12 or 6 to 10 carbon atoms. Aryl groups may be monocyclic or polycyclic (e.g., bicyclic, tricyclic). In some instances, both rings of a polycyclic aryl group are aromatic (e.g., naphthyl). In other instances, polycyclic aryl groups may include a non-aromatic ring fused to an aromatic ring, provided the polycyclic aryl group is bound to the parent structure via an atom in the aromatic ring. Thus, a 1,2,3,4-tetrahydronaphthalen-5-yl group (wherein the moiety is bound to the parent structure via an aromatic carbon atom) is considered an aryl group, while 1,2,3,4-tetrahydronaphthalen-1-yl (wherein the moiety is bound to the parent structure via a non-aromatic carbon atom) is not considered an aryl group. Similarly, a 1,2,3,4-tetrahydroquinolin-8-yl group (wherein the moiety is bound to the parent structure via an aromatic carbon atom) is considered an aryl group, while 1,2,3,4-tetrahydroquinolin-1-yl group (wherein the moiety is bound to the parent structure via a non-aromatic nitrogen atom) is not considered an aryl group. However, the term "aryl" does not encompass or overlap with "heteroaryl", as defined herein, regardless of the point of attachment (e.g., both quinolin-5-yl and quinolin-2-yl are heteroaryl groups). In some instances, aryl is phenyl or naphthyl. In certain instances, aryl is phenyl. Additional examples of aryl groups comprising an aromatic carbon ring fused to a non-aromatic ring are described below.

"Heteroaryl" indicates an aromatic ring containing the indicated number of atoms (e.g., 5 to 12, or 5 to 10 membered heteroaryl) made up of one or more heteroatoms (e.g., 1, 2, 3 or 4 heteroatoms) selected from N, O and S and with the remaining ring atoms being carbon. Heteroaryl groups do not contain adjacent S and O atoms. In some embodiments, the total number of S and O atoms in the heteroaryl group is not more than 2. In some embodiments, the total number of S and O atoms in the heteroaryl group is not more than 1. Unless otherwise indicated, heteroaryl groups may be bound to the parent structure by a carbon or nitrogen atom, as valency permits. For example, "pyridyl" includes 2-pyridyl, 3-pyridyl and 4-pyridyl groups, and "pyrrolyl" includes 1-pyrrolyl, 2-pyrrolyl and 3-pyrrolyl groups.

In some instances, a heteroaryl group is monocyclic. Examples include pyrrole, pyrazole, imidazole, triazole (e.g., 1,2,3-triazole, 1,2,4-triazole, 1,2,4-triazole), tetrazole, furan, isoxazole, oxazole, oxadiazole (e.g., 1,2,3-oxadiazole, 1,2,4-oxadiazole, 1,3,4-oxadiazole), thiophene, isothiazole, thiazole, thiadiazole (e.g., 1,2,3-thiadiazole, 1,2,4-thiadiazole, 1,3,4-thiadiazole), pyridine, pyridazine, pyrimidine, pyrazine, triazine (e.g., 1,2,4-triazine, 1,3,5-triazine) and tetrazine.

In some instances, both rings of a polycyclic heteroaryl group are aromatic. Examples include indole, isoindole, indazole, benzoimidazole, benzotriazole, benzofuran, benzoxazole, benzoisoxazole, benzoxadiazole, benzothiophene, benzothiazole, benzoisothiazole, benzothiadiazole, 1H-pyrrolo[2,3-b]pyridine, 1H-pyrazolo[3,4-b]pyridine, 3H-imidazo[4,5-b]pyridine, 3H-[1,2,3]triazolo[4,5-b]pyridine, 1H-pyrrolo[3,2-b]pyridine, 1H-pyrazolo[4,3-b]pyridine, 1H-imidazo[4,5-b]pyridine, 1H-[1,2,3]triazolo[4,5-b]pyridine, 1H-pyrrolo[2,3-c]pyridine, 1H-pyrazolo[3,4-c]pyridine, 3H-imidazo[4,5-c]pyridine, 3H-[1,2,3]triazolo[4,5-c]pyridine, 1H-pyrrolo[3,2-c]pyridine, 1H-pyrazolo[4,3-c]pyridine, 1H-imidazo[4,5-c]pyridine, 1H-[1,2,3]triazolo[4,5-c]pyridine, furo[2,3-b]pyridine, oxazolo[5,4-b]pyridine, isoxazolo[5,4-b]pyridine, [1,2,3]oxadiazolo[5,4-b]pyridine, furo[3,2-b]pyridine, oxazolo[4,5-b]pyridine, isoxazolo[4,5-b]pyridine, [1,2,3]oxadiazolo[4,5-b]pyridine, furo[2,3-c]pyridine, oxazolo[5,4-c]pyridine, isoxazolo[5,4-c]pyridine, [1,2,3]oxadiazolo[5,4-c]pyridine, furo[3,2-c]pyridine, oxazolo[4,5-c]pyridine, isoxazolo[4,5-c]pyridine, [1,2,3]oxadiazolo[4,5-c]pyridine, thieno[2,3-b]pyridine, thiazolo[5,4-b]pyridine, isothiazolo[5,4-b]pyridine, [1,2,3]thiadiazolo[5,4-b]pyridine, thieno[3,2-b]pyridine, thiazolo[4,5-b]pyridine, isothiazolo[4,5-b]pyridine, [1,2,3]thiadiazolo[4,5-b]pyridine, thieno[2,3-c]pyridine, thiazolo[5,4-c]pyridine, isothiazolo[5,4-c]pyridine, [1,2,3]thiadiazolo[5,4-c]pyridine, thieno[3,2-c]pyridine, thiazolo[4,5-c]pyridine, isothiazolo[4,5-c]pyridine, [1,2,3]thiadiazolo[4,5-c]pyridine, quinoline, isoquinoline, cinnoline, quinazoline, quinoxaline, phthalazine, naphthyridine (e.g., 1,8-naphthyridine, 1,7-naphthyridine, 1,6-naphthyridine, 1,5-naphthyridine, 2,7-naphthyridine, 2,6-naphthyridine), imidazo[1,2-a]pyridine, 1H-pyrazolo[3,4-d]thiazole, 1H-pyrazolo[4,3-d]thiazole and imidazo[2,1-b]thiazole.

In other instances, polycyclic heteroaryl groups may include a non-aromatic ring (e.g., cycloalkyl, cycloalkenyl, heterocycloalkyl, heterocycloalkenyl) fused to a heteroaryl ring, provided the polycyclic heteroaryl group is bound to the parent structure via an atom in the aromatic ring. For example, a 4,5,6,7-tetrahydrobenzo[d]thiazol-2-yl group (wherein the moiety is bound to the parent structure via an aromatic carbon atom) is considered a heteroaryl group, while 4,5,6,7-tetrahydrobenzo[d]thiazol-5-yl (wherein the moiety is bound to the parent structure via a non-aromatic carbon atom) is not considered a heteroaryl group. Examples of polycyclic heteroaryl groups consisting of a heteroaryl ring fused to a non-aromatic ring are described below.

"Heterocycloalkyl" indicates a non-aromatic, fully saturated ring having the indicated number of atoms (e.g., 3 to 10, or 3 to 7, membered heterocycloalkyl) made up of one or more heteroatoms (e.g., 1, 2, 3 or 4 heteroatoms) selected from N, O and S and with the remaining ring atoms being carbon. Heterocycloalkyl groups may be monocyclic or polycyclic (e.g., bicyclic, tricyclic). Examples of heterocycloalkyl groups include oxiranyl, aziridinyl, azetidinyl, pyrrolidinyl, imidazolidinyl, pyrazolidinyl, piperidinyl, piperazinyl, morpholinyl and thiomorpholinyl. Examples include thiomorpholine S-oxide and thiomorpholine S,S-dioxide. Examples of spirocyclic heterocycloalkyl groups include azaspiro[3.3]heptane, diazaspiro[3.3]heptane, diazaspiro[3.4]octane, and diazaspiro[3.5]nonane. In addition, one ring of a polycyclic heterocycloalkyl group may be aromatic (e.g., aryl or heteroaryl), provided the polycyclic heterocycloalkyl group is bound to the parent structure via a non-aromatic carbon or nitrogen atom. For example, a 1,2,3,4-tetrahydroquinolin-1-yl group (wherein the moiety is bound to the parent structure via a non-aromatic nitrogen atom) is considered a heterocycloalkyl group, while 1,2,3,4-tetrahydroquinolin-8-yl group (wherein the moiety is bound to the parent structure via an aromatic carbon atom) is not considered a heterocycloalkyl group. Examples of polycyclic heterocycloalkyl groups consisting of a heterocycloalkyl group fused to an aromatic ring are described below.

"Heterocycloalkenyl" indicates a non-aromatic ring having the indicated number of atoms (e.g., 3 to 10, or 3 to 7, membered heterocycloalkyl) made up of one or more heteroatoms (e.g., 1, 2, 3 or 4 heteroatoms) selected from N, O and S and with the remaining ring atoms being carbon, and at least one double bond derived by the removal of one molecule of hydrogen from adjacent carbon atoms, adjacent nitrogen atoms, or adjacent carbon and nitrogen atoms of the corresponding heterocycloalkyl. Heterocycloalkenyl groups may be monocyclic or polycyclic (e.g., bicyclic, tricyclic). Examples of heterocycloalkenyl groups include dihydrofuranyl (e.g., 2,3-dihydrofuranyl, 2,5-dihydrofuranyl), dihydrothiophenyl (e.g., 2,3-dihydrothiophenyl, 2,5-dihydrothiophenyl), dihydropyrrolyl (e.g., 2,3-dihydro-1H-pyrrolyl, 2,5-dihydro-1H-pyrrolyl), dihydroimidazolyl (e.g., 2,3-dihydro-1H-imidazolyl, 4,5-dihydro-1H-imidazolyl), pyranyl, dihydropyranyl (e.g., 3,4-dihydro-2H-pyranyl, 3,6-dihydro-2H-pyranyl), tetrahydropyridinyl (e.g., 1,2,3,4-tetrahydropyridinyl, 1,2,3,6-tetrahydropyridinyl) and dihydropyridine (e.g., 1,2-dihydropyridine, 1,4-dihydropyridine). In addition, one ring of a polycyclic heterocycloalkenyl group may be aromatic (e.g., aryl or heteroaryl), provided the polycyclic heterocycloalkenyl group is bound to the parent structure via a non-aromatic carbon or nitrogen atom. For example, a 1,2-dihydroquinolin-1-yl group (wherein the moiety is bound to the parent structure via a non-aromatic nitrogen atom) is considered a heterocycloalkenyl group, while 1,2-dihydroquinolin-8-yl group (wherein the moiety is bound to the parent structure via an aromatic carbon atom) is not considered a heterocycloalkenyl group. Examples of polycyclic heterocycloalkenyl groups consisting of a heterocycloalkenyl group fused to an aromatic ring are described below.

Examples of polycyclic rings consisting of an aromatic ring (e.g., aryl or heteroaryl) fused to a non-aromatic ring (e.g., cycloalkyl, cycloalkenyl, heterocycloalkyl, heterocycloalkenyl) include indenyl, 2,3-dihydro-1H-indenyl, 1,2,3,4-tetrahydronaphthalenyl, benzo[1,3]dioxolyl, tetrahydroquinolinyl, 2,3-dihydrobenzo[1,4]dioxinyl, indolinyl, isoindolinyl, 2,3-dihydro-1H-indazolyl, 2,3-dihydro-1H-benzo[d]imidazolyl, 2,3-dihydrobenzofuranyl, 1,3-dihydroisobenzofuranyl, 1,3-dihydrobenzo[c]isoxazolyl, 2,3-dihydrobenzo[d]isoxazolyl, 2,3-dihydrobenzo[d]oxazolyl, 2,3-dihydrobenzo[b]thiophenyl, 1,3-dihydrobenzo[c]thiophenyl, 1,3-dihydrobenzo[c]isothiazolyl, 2,3-dihydrobenzo[d]isothiazolyl, 2,3-dihydrobenzo[d]thiazolyl, 5,6-dihydro-4H-cyclopenta[d]thiazolyl, 4,5,6,7-tetrahydrobenzo[d]thiazolyl, 5,6-dihydro-4H-pyrrolo[3,4-d]thiazolyl, 4,5,6,7-tetrahydrothiazolo[5,4-c]pyridinyl, indolin-2-one, indolin-3-one, isoindolin-1-one, 1,2-dihydroindazol-3-one, 1H-benzo[d]imidazol-2(3H)-one, benzofuran-2(3H)-one, benzofuran-3(2H)-one, isobenzofuran-1(3H)-one, benzo[c]isoxazol-3(1H)-one, benzo[d]isoxazol-3(2H)-one, benzo[d]oxazol-2(3H)-one, benzo[b]thiophen-2(3H)-one, benzo[b]thiophen-3(2H)-one, benzo[c]thiophen-1(3H)-one, benzo[c]isothiazol-3(1H)-one, benzo[d]isothiazol-3(2H)-one, benzo[d]thiazol-2(3H)-one, 4,5-dihydropyrrolo[3,4-d]thiazol-6-one, 1,2-dihydropyrazolo[3,4-d]thiazol-3-one, quinolin-4(3H)-one, quinazolin-4(3H)-one, quinazoline-2,4(1H,3H)-dione, quinoxalin-2(1H)-one, quinoxaline-2,3(1H,4H)-dione, cinnolin-4(3H)-one, pyridin-2(1H)-one, pyrimidin-2(1H)-one, pyrimidin-4(3H)-one, pyridazin-3(2H)-one, 1H-pyrrolo[3,2-b]pyridin-2(3H)-one, 1H-pyrrolo[3,2-c]pyridin-2(3H)-one, 1H-pyrrolo[2,3-c]pyridin-2(3H)-one, 1H-pyrrolo[2,3-b]pyridin-2(3H)-one, 1,2-dihydropyrazolo[3,4-d]thiazol-3-one and 4,5-dihydropyrrolo[3,4-d]thiazol-6-one. As discussed herein, whether each ring is considered an aryl, heteroaryl, cycloalkyl, cycloalkenyl, heterocycloalkyl or heterocycloalkenyl group is determined by the atom through which the moiety is bound to the parent structure.

"Halogen" or "halo" refers to fluorine, chlorine, bromine or iodine.

Unless otherwise indicated, compounds disclosed and/or described herein include all possible enantiomers, diastereomers, meso isomers and other stereoisomeric forms, including racemic mixtures, optically pure forms and intermediate mixtures thereof. Enantiomers, diastereomers, meso isomers and other stereoisomeric forms can be prepared using chiral synthons or chiral reagents, or resolved using conventional techniques. Unless specified otherwise, when the compounds disclosed and/or described herein contain olefinic double bonds or other centers of geometric asymmetry, it is intended that the compounds include both E and Z isomers. When the compounds described herein contain moieties capable of tautomerization, and unless specified otherwise, it is intended that the compounds include all possible tautomers.

"Protecting group" has the meaning conventionally associated with it in organic synthesis, i.e., a group that selectively blocks one or more reactive sites in a multifunctional compound such that a chemical reaction can be carried out selectively on another unprotected reactive site, and such that the group can readily be removed after the selective reaction is complete. A variety of protecting groups are disclosed, for example, in T. H. Greene and P. G. M. Wuts,

*Protective Groups in Organic Synthesis*, Third Edition, John Wiley & Sons, New York (1999). For example, a "hydroxy protected form" contains at least one hydroxy group protected with a hydroxy protecting group. Likewise, amines and other reactive groups may similarly be protected.

The term "pharmaceutically acceptable salt" refers to a salt of any of the compounds herein which are known to be non-toxic and are commonly used in the pharmaceutical literature. In some embodiments, the pharmaceutically acceptable salt of a compound retains the biological effectiveness of the compounds described herein and are not biologically or otherwise undesirable. Examples of pharmaceutically acceptable salts can be found in Berge et al., Pharmaceutical Salts, *J. Pharmaceutical Sciences*, January 1977, 66(1), 1-19. Pharmaceutically acceptable acid addition salts can be formed with inorganic acids and organic acids. Inorganic acids from which salts can be derived include, for example, hydrochloric acid, hydrobromic acid, sulfuric acid, nitric acid, and phosphoric acid. Organic acids from which salts can be derived include, for example, acetic acid, propionic acid, glycolic acid, pyruvic acid, lactic acid, oxalic acid, malic acid, maleic acid, malonic acid, succinic acid, fumaric acid, tartaric acid, citric acid, benzoic acid, cinnamic acid, mandelic acid, methanesulfonic acid, ethanesulfonic acid, 2-hydroxyethylsulfonic acid, p-toluenesulfonic acid, stearic acid and salicylic acid. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, and aluminum. Organic bases from which salts can be derived include, for example, primary, secondary, and tertiary amines; substituted amines including naturally occurring substituted amines; cyclic amines; and basic ion exchange resins. Examples of organic bases include isopropylamine, trimethylamine, diethylamine, triethylamine, tripropylamine, and ethanolamine. In some embodiments, the pharmaceutically acceptable base addition salt is selected from ammonium, potassium, sodium, calcium, and magnesium salts.

If the compound described herein is obtained as an acid addition salt, the free base can be obtained by basifying a solution of the acid salt. Conversely, if the compound is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds (see, e.g., Berge et al., Pharmaceutical Salts, *J. Pharmaceutical Sciences*, January 1977, 66(1), 1-19). Those skilled in the art will recognize various synthetic methodologies that may be used to prepare pharmaceutically acceptable addition salts.

A "solvate" is formed by the interaction of a solvent and a compound. Suitable solvents include, for example, water and alcohols (e.g., ethanol). Solvates include hydrates having any ratio of compound to water, such as monohydrates, dihydrates and hemi-hydrates.

The term "substituted" means that the specified group or moiety bears one or more substituents including, but not limited to, substituents such as alkoxy, acyl, acyloxy, carbonylalkoxy, acylamino, amino, aminoacyl, aminocarbonylamino, aminocarbonyloxy, cycloalkyl, cycloalkenyl, aryl, heteroaryl, aryloxy, cyano, azido, halo, hydroxyl, nitro, carboxyl, thiol, thioalkyl, cycloalkyl, cycloalkenyl, alkyl, alkenyl, alkynyl, heterocycloalkyl, heterocycloalkenyl, aralkyl, aminosulfonyl, sulfonylamino, sulfonyl, oxo, carbonylalkylenealkoxy and the like. The term "unsubstituted" means that the specified group bears no substituents. Where the term "substituted" is used to describe a structural system, the substitution is meant to occur at any valency-allowed position on the system. When a group or moiety bears more than one substituent, it is understood that the substituents may be the same or different from one another. In some embodiments, a substituted group or moiety bears from one to five substituents. In some embodiments, a substituted group or moiety bears one substituent. In some embodiments, a substituted group or moiety bears two substituents. In some embodiments, a substituted group or moiety bears three substituents. In some embodiments, a substituted group or moiety bears four substituents. In some embodiments, a substituted group or moiety bears five substituents.

By "optional" or "optionally" is meant that the subsequently described event or circumstance may or may not occur, and that the description includes instances where the event or circumstance occurs and instances in which it does not. For example, "optionally substituted alkyl" encompasses both "alkyl" and "substituted alkyl" as defined herein. It will be understood by those skilled in the art, with respect to any group containing one or more substituents, that such groups are not intended to introduce any substitution or substitution patterns that are sterically impractical, synthetically non-feasible, and/or inherently unstable. It will also be understood that where a group or moiety is optionally substituted, the disclosure includes both embodiments in which the group or moiety is substituted and embodiments in which the group or moiety is unsubstituted.

The compounds disclosed and/or described herein can be enriched isotopic forms, e.g., enriched in the content of $^{2}H$, $^{3}H$, $^{11}C$, $^{13}C$ and/or $^{14}C$. In one embodiment, the compound contains at least one deuterium atom. Such deuterated forms can be made, for example, by the procedure described in U.S. Pat. Nos. 5,846,514 and 6,334,997. Such deuterated compounds may improve the efficacy and increase the duration of action of compounds disclosed and/or described herein. Deuterium substituted compounds can be synthesized using various methods, such as those described in: Dean, D., Recent Advances in the Synthesis and Applications of Radiolabeled Compounds for Drug Discovery and Development, *Curr. Pharm. Des.*, 2000; 6(10); Kabalka, G. et al., The Synthesis of Radiolabeled Compounds via Organometallic Intermediates, *Tetrahedron*, 1989, 45(21), 6601-21; and Evans, E., Synthesis of radiolabeled compounds, *J. Radioanal. Chem.*, 1981, 64(1-2), 9-32.

The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in pharmaceutical compositions is contemplated. Supplementary active ingredients can also be incorporated into the pharmaceutical compositions.

The terms "patient," "individual," and "subject" refer to an animal, such as a mammal, bird, or fish. In some embodiments, the patient or subject is a mammal. Mammals include, for example, mice, rats, dogs, cats, pigs, sheep, horses, cows and humans. In some embodiments, the patient or subject is a human, for example a human that has been or will be the object of treatment, observation or experiment.

The compounds, compositions and methods described herein can be useful in both human therapy and veterinary applications.

As used herein, the term "therapeutic" refers to the ability to modulate nicotinamide phosphoribosyltransferase (NAMPT). As used herein, "modulation" refers to a change in activity as a direct or indirect response to the presence of a chemical entity as described herein, relative to the activity of in the absence of the chemical entity. The change may be an increase in activity or a decrease in activity, and may be due to the direct interaction of the chemical entity with the a target or due to the interaction of the chemical entity with one or more other factors that in turn affect the target's activity. For example, the presence of the chemical entity may, for example, increase or decrease the target activity by directly binding to the target, by causing (directly or indirectly) another factor to increase or decrease the target activity, or by (directly or indirectly) increasing or decreasing the amount of target present in the cell or organism.

The term "therapeutically effective amount" or "effective amount" refers to that amount of a compound disclosed and/or described herein that is sufficient to affect treatment, as defined herein, when administered to a patient in need of such treatment. A therapeutically effective amount of a compound may be an amount sufficient to treat a disease responsive to modulation of nicotinamide phosphoribosyltransferase (NAMPT). The therapeutically effective amount will vary depending upon, for example, the subject and disease condition being treated, the weight and age of the subject, the severity of the disease condition, the particular compound, the dosing regimen to be followed, timing of administration, the manner of administration, all of which can readily be determined by one of ordinary skill in the art. The therapeutically effective amount may be ascertained experimentally, for example by assaying blood concentration of the chemical entity, or theoretically, by calculating bioavailability.

"Treatment" (and related terms, such as "treat", "treated", "treating") includes one or more of: preventing a disease or disorder (i.e., causing the clinical symptoms of the disease or disorder not to develop); inhibiting a disease or disorder; slowing or arresting the development of clinical symptoms of a disease or disorder; and/or relieving a disease or disorder (i.e., causing relief from or regression of clinical symptoms). The term encompasses situations where the disease or disorder is already being experienced by a patient, as well as situations where the disease or disorder is not currently being experienced but is expected to arise. The term covers both complete and partial reduction or prevention of the condition or disorder, and complete or partial reduction of clinical symptoms of a disease or disorder. Thus, compounds described and/or disclosed herein may prevent an existing disease or disorder from worsening, assist in the management of the disease or disorder, or reduce or eliminate the disease or disorder. When used in a prophylactic manner, the compounds disclosed and/or described herein may prevent a disease or disorder from developing or lessen the extent of a disease or disorder that may develop.

Compounds

Compounds and salts thereof (such as pharmaceutically acceptable salts) are detailed herein, including in the Brief Summary and in the appended claims. Also provided are the use of all of the compounds described herein, including any and all stereoisomers, including geometric isomers (cis/trans), E/Z isomers, enantiomers, diastereomers, and mixtures thereof in any ratio including racemic mixtures, salts and solvates of the compounds described herein, as well as methods of making such compounds. Any compound described herein may also be referred to as a drug.

In one aspect, provided herein is a compound of Formula (II):

(II)

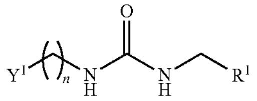

or a pharmaceutically acceptable salt thereof, wherein:

n is 0 to 6;

$Y^1$ is

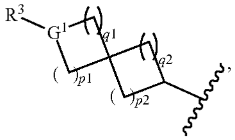,
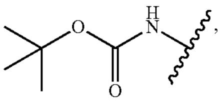, or
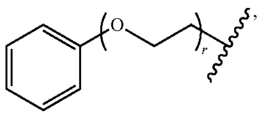, and $R^1$ is selected from the group consisting of

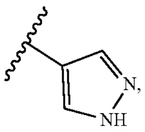,
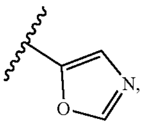,
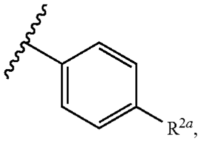,
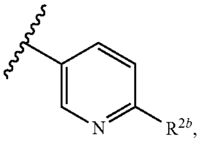,
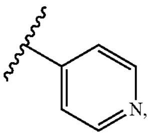, and
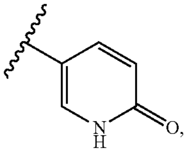, or $Y^1$ is

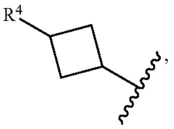,
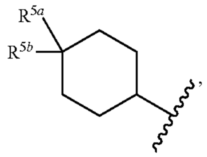, or

-continued

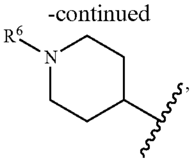

and $R^1$ is selected from the group consisting of

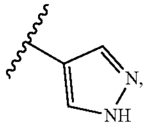 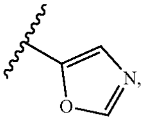 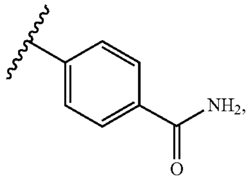

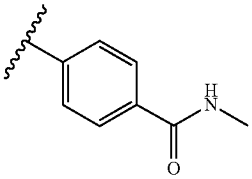 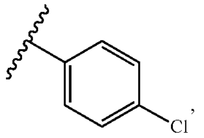

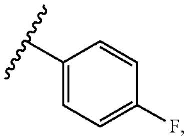 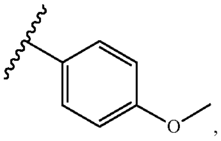

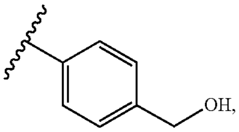 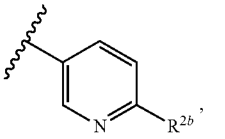

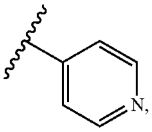 and 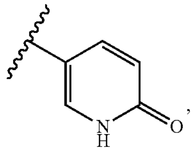

or $Y^1$ is —C(O)—N($R^q$)—($R^s$), wherein $R^q$ is H or $C_1$-$C_6$ alkyl, and $R^s$ is $C_3$-$C_8$ cycloalkyl, optionally substituted $C_6$-$C_{14}$ aryl, optionally substituted 5- to 18-membered heteroaryl, or —($C_1$-$C_6$ alkylene)-(optionally substituted $C_6$-$C_{14}$ aryl), and $R^1$ is selected from the group consisting of

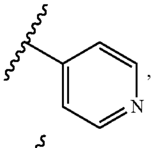 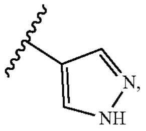 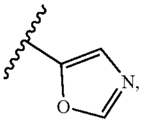

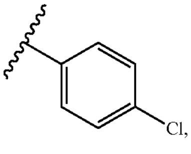 and 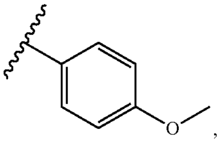

or $Y^1$ is —C(O)—$R^b$, wherein $R^b$ is optionally substituted 3- to 18-membered heterocycloalkyl, and $R^1$ is

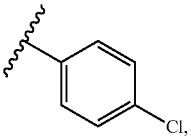 [SMILES: *c1ccc(Cl)cc1]

or $Y^1$ is —N($R^t$)—C(O)$R^u$, wherein $R^t$ is H or $C_1$-$C_6$ alkyl, and $R^u$ is optionally substituted $C_6$-$C_{14}$ aryl, optionally substituted 5- to 18-membered heteroaryl, or —($C_1$-$C_6$ alkylene)-(5- to 18-membered heteroaryl), and $R^1$ is

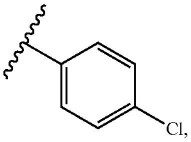 [SMILES: *c1ccc(Cl)cc1]

or $Y^1$ is

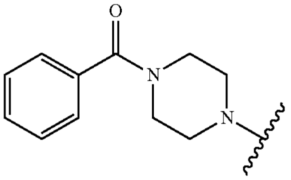 [SMILES: *N1CCN(C(=O)c2ccccc2)CC1]

and $R^1$ is

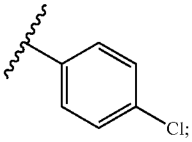

wherein $R^{2a}$ and $R^{2b}$ are each independently halo, —O($C_1$-$C_6$ alkyl), $C_1$-$C_6$ alkyl substituted with —OH, —C(O)$NR^{2c}R^{2d}$, or —N($R^{2e}$)C(O)($C_1$-$C_6$ alkyl); and $R^{2c}$, $R^{2d}$, and $R^{2e}$ are each independently hydrogen or $C_1$-$C_6$ alkyl;

$G^1$ is CH or N;

p1 and p2 are each independently 0, 1, or 2;

q1 and q2 are each independently 1 or 2;

r is 1, 2, or 3;

wherein, when $Y^1$ is

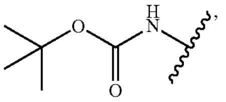 [SMILES: *NC(=O)OC(C)(C)C]

then n is 4, 5, or 6;

when $Y^1$ is

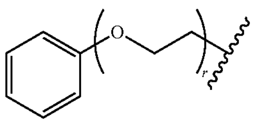

and r is 1, then n is 2, 3, 4, 5, or 6; and when $Y^1$ is —C(O)—N($R^q$)—($R^s$), —C(O)—$R^b$, —N(R)—C(O)$R^u$, or,

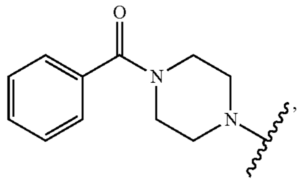 [SMILES: *N1CCN(C(=O)c2ccccc2)CC1]

then n is 4 or 5;

$R^3$ is selected from the group consisting of:

i. unsubstituted $C_1$-$C_6$ alkyl;

ii. $C_6$-$C_{14}$ aryl;

iii. optionally substituted 5- to 18-membered heteroaryl;

iv. —$NR^{3a}R^{3b}$, wherein $R^{3a}$ and $R^{3b}$ are each independently selected from the group consisting of hydrogen, $C_6$-$C_{14}$ aryl, 5- to 18-membered heteroaryl, —($C_1$-$C_6$ alkylene)-($C_6$-$C_{14}$ aryl), and —($C_1$-$C_6$ alkylene)-(5- to 18-membered heteroaryl);

v. —$OR^{3c}$, wherein $R^{3c}$ is $C_6$-$C_{14}$ aryl, 5- to 18-membered heteroaryl, or —($C_1$-$C_6$ alkylene)-(5- to 18-membered heteroaryl);

vi. —C(O)$R^{3d}$, wherein $R^{3d}$ is selected from the group consisting of —$NR^{3f}R^{3g}$; $C_3$-$C_8$ cycloalkyl; $C_3$-$C_8$ cycloalkyl substituted with optionally substituted $C_6$-$C_{14}$ aryl; $C_3$-$C_8$ cycloalkenyl; optionally substituted $C_6$-$C_{14}$ aryl; optionally substituted —($C_1$-$C_6$ alkylene)-($C_6$-$C_{14}$ aryl); optionally substituted 3- to 18-membered heterocycloalkyl; and optionally substituted 5- to 18-membered heteroaryl, wherein $R^{3f}$ and $R^{3g}$ are each independently selected from the group consisting of:

(a) hydrogen, (b) optionally substituted $C_1$-$C_6$ alkyl, (c) $C_6$-$C_{14}$ aryl, (d) optionally substituted 3- to 18-membered heterocycloalkyl, (e) optionally substituted 5- to 18-membered heteroaryl, (f) optionally substituted $C_3$-$C_{10}$ cycloalkyl; and (g) optionally substituted $C_3$-$C_{10}$ cycloalkenyl;

vii. $C_1$-$C_6$ alkyl substituted with one or more —OH, —C(O)$NR^{3h}R^{3i}$, optionally substituted $C_6$-$C_{14}$ aryl, optionally substituted 3- to 18-membered heterocycloalkyl, optionally substituted 5- to 18-membered heteroaryl, —N($R^{3P}$)—C(O)$R^{3q}$, —$S(O)_2$—$R^{3r}$, or —C(O)—$R^{3s}$, wherein $R^{3h}$ and $R^{3i}$ are each independently selected from $C_1$-$C_6$ alkyl and —($C_1$-$C_6$ alkylene)-($C_6$-$C_{14}$ aryl), $R^{3p}$ is H or $C_1$-$C_6$ alkyl, $R^{3q}$ is $C_3$-$C_8$ cycloalkyl, optionally substituted 3- to 18-membered heterocycloalkyl, or optionally substituted 5- to 18-membered heteroaryl, $R^{3r}$ is $C_6$-$C_{14}$ aryl or 5- to 18-membered heteroaryl, and $R^{3s}$ is optionally substituted 3- to 18-membered heterocycloalkyl;

viii. —C(O)$OR^{3j}$, wherein $R^{3j}$ is hydrogen or $C_1$-$C_6$ alkyl;

ix. —NHC(O)$R^{3k}$, wherein $R^{3k}$ is optionally substituted $C_6$-$C_{14}$ aryl, optionally substituted —($C_1$-$C_6$ alkylene)-($C_6$-$C_{14}$ aryl), or optionally substituted 5- to 18-membered heteroaryl;

x. —NHC(O)$OR^{3l}$, wherein $R^{3l}$ is hydrogen or $C_1$-$C_6$ alkyl;

xi. —$NHSO_2R^{3m}$, wherein $R^{3m}$ is optionally substituted 5- to 18-membered heteroaryl, optionally substituted $C_6$-$C_{14}$ aryl, or —($C_1$-$C_6$ alkylene)-($C_6$-$C_{14}$ aryl), each of which is optionally substituted; and xii. —$SO_2R^{3n}$; wherein $R^{3n}$ is $C_1$-$C_6$ alkyl, optionally substituted $C_3$-$C_{10}$ cycloalkyl, optionally substituted $C_6$-$C_{14}$ aryl, or optionally substituted —($C_1$-$C_6$ alkylene)-($C_6$-$C_{14}$ aryl);

$R^4$ is phenyl or —C(O)NH—$CH_2$-phenyl;

$R^{5a}$ and $R^{5b}$ are independently selected from the group consisting of hydrogen, methyl, and —NHC(O)O($C_1$-$C_6$ alkyl); and $R^6$ is selected from the group consisting of —C(O)OC$(CH_3)_3$, —NHC(O)O($C_1$-$C_6$ alkyl), —C(O)-(optionally substituted phenyl), —C(O)—($C_1$-$C_6$ alkylene)-(optionally substituted phenyl), —C(O)-(optionally substituted 3- to 18-membered heterocycloalkyl), —C(O)-(optionally substituted 5- to 18-membered heteroaryl), —C(O)—($C_1$-$C_6$ alkylene)-(optionally substituted 5- to 18-membered heteroaryl), and 5- to 18-membered heteroaryl provided that, when $R^6$ is —C(O)-(substituted phenyl), —C(O)—($C_1$-$C_6$ alkylene)-(optionally substituted phenyl), —C(O)-(optionally substituted 3- to 18-membered heterocycloalkyl), —C(O)-(optionally substituted 5- to 18-membered heteroaryl), —C(O)—($C_1$-$C_6$ alkylene)-(optionally substituted 5- to 18-membered heteroaryl), or 5- to 18-membered heteroaryl, then (1) n is 4 or 5, and (2) $R^1$ is selected from the group consisting of

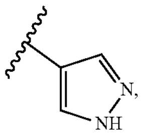

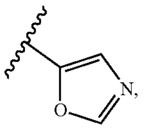

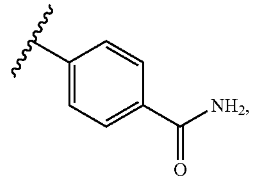

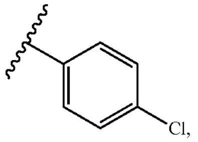

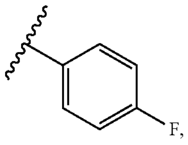

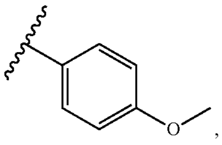

, and

-continued
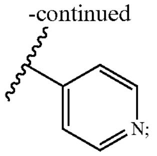
wherein
(1) when $Y^1$ is
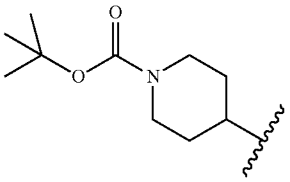 [SMILES: *C1CCN(C(=O)OC(C)(C)C)CC1]
and n is 0 or 1, then $R^1$ is selected from the group consisting of
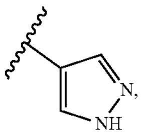
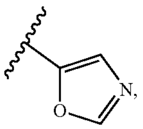
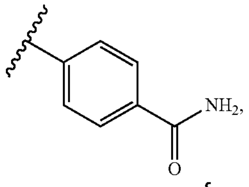
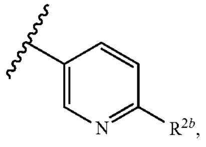
and
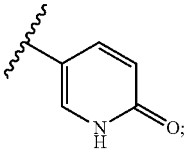
and
(2) when $Y^1$ is
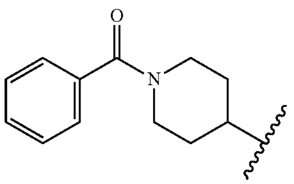 [SMILES: *C1CCN(C(=O)c2ccccc2)CC1]
and n is 0, then $R^1$ is selected from the group consisting of
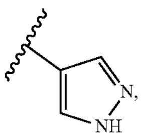
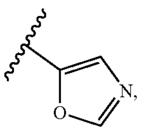
-continued
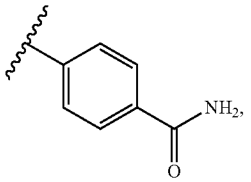
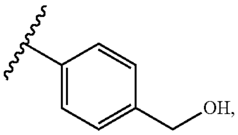
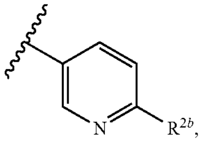
and
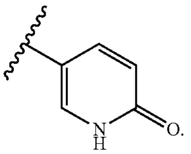
In one aspect, provided are compounds of Formula (I):
(I)
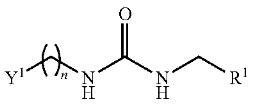
or a pharmaceutically acceptable salt thereof, wherein:
$Y^1$ is
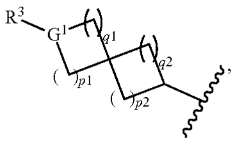
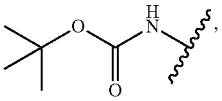
or
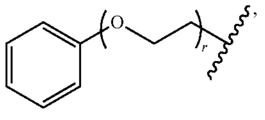
and $R^1$ is selected from the group consisting of
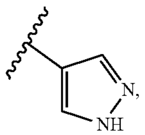
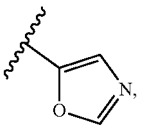
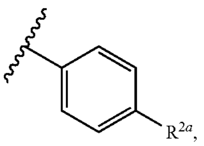
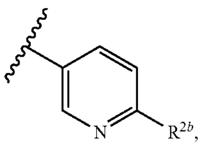
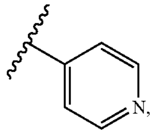
and
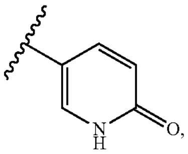

or $Y^1$ is

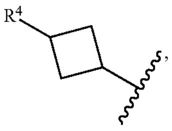

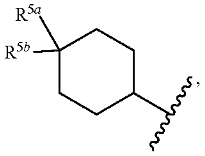

or

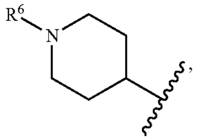

and $R^1$ is selected from the group consisting of

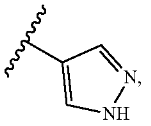

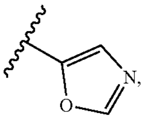

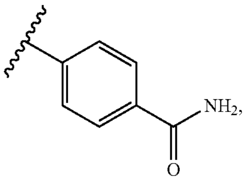

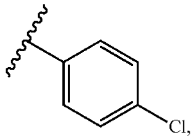

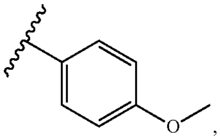

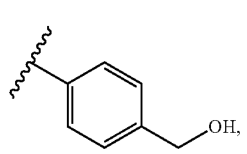

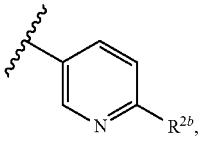

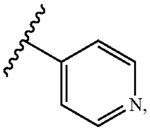

and

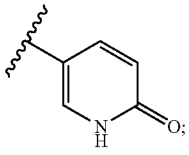

wherein $R^{2a}$ and $R^{2b}$ are each independently halo, —O($C_1$-$C_6$ alkyl), $C_1$-$C_6$ alkyl substituted with —OH, —C(O)$NR^{2c}R^{2d}$, or —N($R^{2e}$)C(O)($C_1$-$C_6$ alkyl); and $R^{2c}$, $R^{2d}$, and $R^{2e}$ are each independently hydrogen or $C_1$-$C_6$ alkyl;

$G^1$ is CH or N;

p1 and p2 are each independently 0, 1, or 2;

q1 and q2 are each independently 1 or 2;

r is 1, 2, or 3;

n is 0 to 6;

wherein when $Y^1$ is

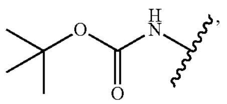 [SMILES: *NC(=O)OC(C)(C)C]

n is 4, 5, or 6; and when $Y^1$ is

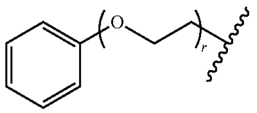

and r is 1, n is 2, 3, 4, 5, or 6;

$R^3$ is selected from the group consisting of:

i. $C_1$-$C_6$ alkyl;

ii. $C_6$-$C_{14}$ aryl;

iii. optionally substituted 5- to 18-membered heteroaryl;

iv. —$NR^{3a}R^{3b}$, wherein $R^{3a}$ and $R^{3b}$ are each independently selected from the group consisting of hydrogen, $C_6$-$C_{14}$ aryl, 5- to 18-membered heteroaryl, —($C_1$-$C_6$ alkylene)-($C_6$-$C_{14}$ aryl), and —($C_1$-$C_6$ alkylene)-(5- to 18-membered heteroaryl);

v. —$OR^{3c}$, wherein $R^{3c}$ is $C_6$-$C_{14}$ aryl;

vi. —C(O)$R^{3d}$, wherein $R^{3d}$ is selected from the group consisting of —$NR^{3f}R^{3g}$; $C_3$-$C_8$ cycloalkyl; $C_3$-$C_8$ cycloalkyl substituted with optionally substituted $C_6$-$C_{14}$ aryl; $C_3$-$C_8$ cycloalkenyl; optionally substituted $C_6$-$C_{14}$ aryl; optionally substituted —($C_1$-$C_6$ alkylene)-($C_6$-$C_{14}$ aryl); optionally substituted 3- to 18-membered heterocycloalkyl; and optionally substituted 5- to 18-membered heteroaryl, wherein $R^{3f}$ and $R^{3g}$ are each independently selected from the group consisting of:

(a) hydrogen, (b) optionally substituted $C_1$-$C_6$ alkyl, (c) $C_6$-$C_{14}$ aryl, (d) optionally substituted 3- to 18-membered heterocycloalkyl, (e) optionally substituted 5- to 18-membered heteroaryl, (f) optionally substituted $C_3$-$C_{10}$ cycloalkyl; and (g) optionally substituted $C_3$-$C_{10}$ cycloalkenyl;

vii. $C_1$-$C_6$ alkyl substituted with C(O)$NR^{3h}R^{3i}$, optionally substituted 3- to 18-membered heterocycloalkyl, or optionally substituted 5- to 18-membered heteroaryl, wherein $R^{3h}$ and $R^{3i}$ are each independently selected from $C_1$-$C_6$ alkyl and —($C_1$-$C_6$ alkylene)-($C_6$-$C_{14}$ aryl);

viii. —C(O)$OR^{3j}$, wherein $R^{3j}$ is hydrogen or $C_1$-$C_6$ alkyl;

ix. —NHC(O)$R^{3k}$, wherein $R^{3k}$ is optionally substituted $C_6$-$C_{14}$ aryl, optionally substituted —($C_1$-$C_6$ alkylene)-($C_6$-$C_{14}$ aryl), or optionally substituted 5- to 18-membered heteroaryl;

x. —NHC(O)$OR^{3l}$, wherein $R^{3l}$ is hydrogen or $C_1$-$C_6$ alkyl;

xi. —$NHSO_2R^{3m}$, wherein $R^{3m}$ is optionally substituted 5- to 18-membered heteroaryl, optionally substituted $C_6$-$C_{14}$ aryl, or —($C_1$-$C_6$ alkylene)-($C_6$-$C_{14}$ aryl), each of which is optionally substituted; and xii. —$SO_2R^{3n}$; wherein $R^{3n}$ is optionally substituted $C_3$-$C_{10}$ cycloalkyl, optionally substituted $C_6$-$C_{14}$ aryl, or optionally substituted —($C_1$-$C_6$ alkylene)-($C_6$-$C_{14}$ aryl);

$R^4$ is phenyl or —C(O)NH—$CH_2$-phenyl;

$R^{5a}$ and $R^{5b}$ are independently selected from the group consisting of hydrogen, methyl, and —NHC(O)O($C_1$-$C_6$ alkyl); and $R^6$ is selected from the group consisting of —C(O)OC$(CH_3)_3$, —NHC(O)O($C_1$-$C_6$ alkyl), and —C(O)-phenyl.

In some embodiments of Formula (II) or Formula (I): (1) when $Y^1$ is

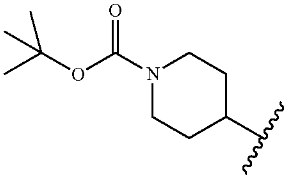 [SMILES: *C1CCN(C(=O)OC(C)(C)C)CC1]

and n is 0 or 1, then $R^1$ is selected from the group consisting of

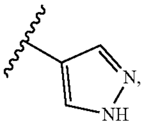, 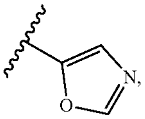, 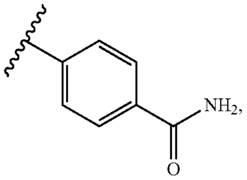,

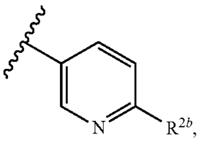, and 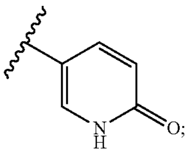;

(2) when $Y^1$ is

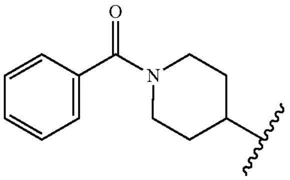 [SMILES: *C1CCN(C(=O)c2ccccc2)CC1]

and n is 0, then $R^1$ is selected from the group consisting of

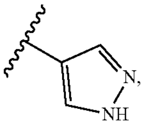, 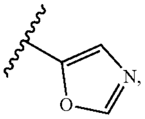, 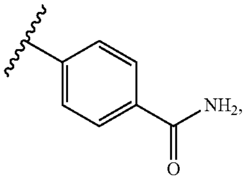,

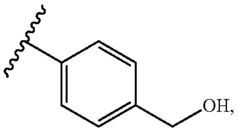, 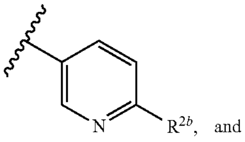, and

-continued

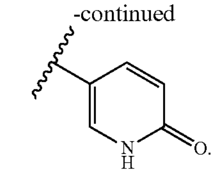.

In some embodiments of Formula (II) or Formula (I), $Y^1$ is

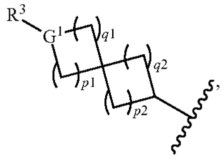, 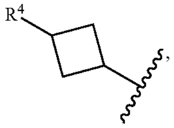,

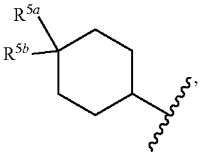, or 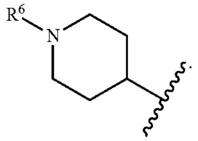.

In some embodiments, $Y^1$ is

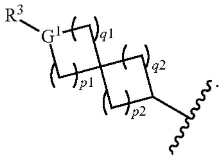.

In some embodiments, $Y^1$ is

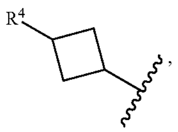, 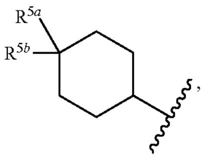, or

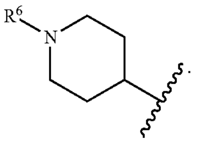.

In other embodiments, $Y^1$ is

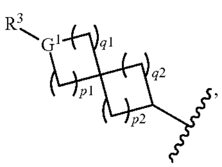, 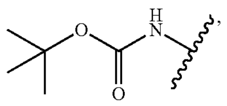, or

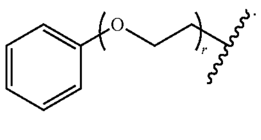.

In some embodiments of Formula (II), $Y^1$ is

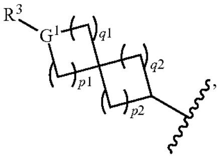,
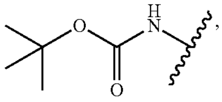,
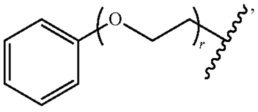,
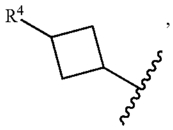,
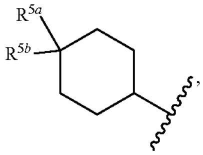,
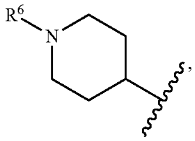,

—C(O)—N($R^q$)—($R^s$), —C(O)—$R^b$, —N($R^t$)—C(O)$R^u$, or

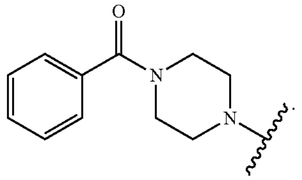 [SMILES: *N1CCN(C(=O)c2ccccc2)CC1].

In some embodiments of Formula (II), $Y^1$ is —C(O)—N($R^q$)—($R^s$), —C(O)—$R^b$, —N($R^t$)—C(O)$R^u$, or

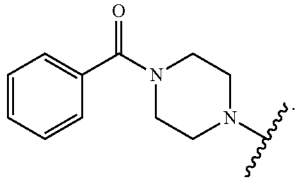 [SMILES: *N1CCN(C(=O)c2ccccc2)CC1].

In another aspect, the compound of Formula (II) or Formula (I) is a compound of Formula (I-A):

(I-A)

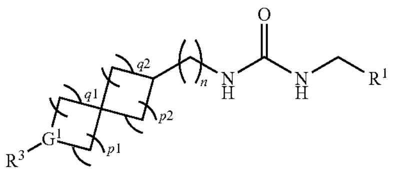

or a salt thereof, wherein $R^1$, $R^3$, $G^1$, p1, p2, q1, q2, and n are as defined for Formula (II) or Formula (I), or any variation or embodiment thereof.

In some embodiments of Formula (II), Formula (I), or Formula (I-A), $R^1$ is

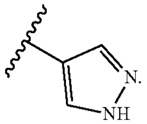

In some embodiments, $R^1$ is

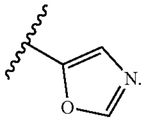 [SMILES: *c1cnco1]

In some embodiments, $R^1$ is

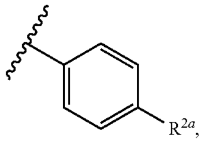

wherein $R^{2a}$ is selected from the group consisting of halo, —O($C_1$-$C_6$ alkyl), $C_1$-$C_6$ alkyl substituted with —OH, —C(O)$NR^{2c}R^{2d}$, and —N($R^{2e}$)C(O)($C_1$-$C_6$ alkyl); and $R^{2c}$, $R^{2d}$ and $R^{2e}$ are each independently hydrogen or $C_1$-$C_6$ alkyl. In some embodiments, $R^{2a}$ is halo or —O($C_1$-$C_6$ alkyl). In some embodiments, $R^{2a}$ is halo. In some embodiments, $R^{2a}$ is methoxy. In some embodiments, $R^1$ is

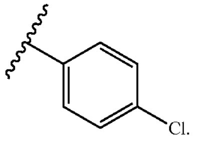 [SMILES: *c1ccc(Cl)cc1]

In some embodiments, $R^1$ is

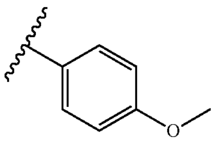 [SMILES: *c1ccc(OC)cc1]

In some embodiments, $R^1$ is

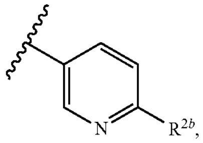

wherein $R^{2b}$ is selected from the group consisting of halo, —O($C_1$-$C_6$ alkyl), $C_1$-$C_6$ alkyl substituted with —OH, —C(O)$NR^{2c}R^{2d}$, and —N($R^{2e}$)C(O)($C_1$-$C_6$ alkyl); and $R^{2c}$, $R^2$, and $R^{2e}$ are each independently hydrogen or $C_1$-$C_6$ alkyl. In some embodiments, $R^1$ is

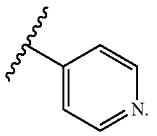

In some embodiments, $R^1$ is H

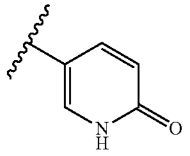 [SMILES: *c1ccc(=O)[nH]c1]

In some embodiments, the compound of Formula (I-A) is a compound of Formula (I-A1) or (I-A2):

(I-A1)

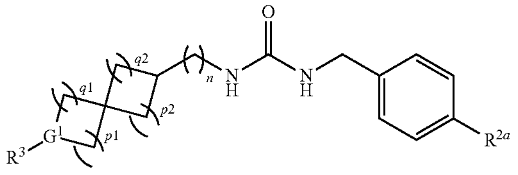

(I-A2)

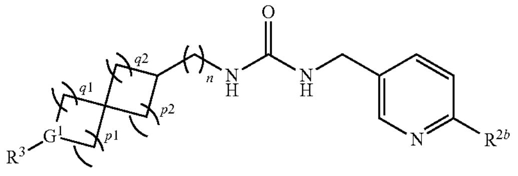

or a salt thereof, wherein $R^{2a}$, $R^{2b}$, $R^3$, $G^1$, p1, p2, q1, q2, and n are as defined for Formula (II) or Formula (I) or any variation or embodiment thereof.

In some embodiments of Formula (II), (I), (I-A), (I-A1), or (I-A2), $G^1$ is CH. In some embodiments, $G^1$ is N.

In some embodiments of Formula (II), (I), (I-A), (I-A1), or (I-A2), p1 is 0, 1, or 2. In some embodiments, p1 is 0. In some embodiments, p1 is 1. In some embodiments, p1 is 2. In some embodiments, p2 is 0, 1, or 2. In some embodiments, p2 is 0. In some embodiments, p2 is 2. In some embodiments, p2 is 2. In some embodiments, q1 is 1 or 2. In some embodiments, q1 is 1. In other embodiments, q1 is 2. In some embodiments, q2 is 1 or 2. In some embodiments, q2 is 1. In other embodiments, q2 is 2.

In some embodiments of Formula (II), (I), (I-A), (I-A1), or (I-A2), p1 is 1 and q1 is 1. In some embodiments, p1 is 2 and q1 is 1. In some embodiments, p1 is 2 and q1 is 2. In some embodiments, p2 is 1 and q2 is 1. In some embodiments, p2 is 0 and q2 is 1. In some embodiments, p2 is 1 and q2 is 2.

In some embodiments of Formula (II), (I), (I-A), (I-A1), or (I-A2), n is 0. In some embodiments, n is 1. In some embodiments, n is 2. In some embodiments, n is 3. In some embodiments, n is 4. In some embodiments, n is 5. In other embodiments, n is 6.

In some embodiments of Formula (II), (I), (I-A), (I-A1), or (I-A2), $R^3$ is $C_1$-$C_6$ alkyl. For instance, in some embodiments, $R^3$ is methyl, ethyl, n-propyl, isopropyl, n-butyl, tert-butyl, sec-butyl, or isobutyl. In some embodiments, $R^3$ is methyl. In some embodiments, $R^3$ is $C_6$-$C_{14}$ aryl. In some embodiments, $R^3$ is phenyl or napthyl. In some embodiments, $R^3$ is phenyl. In some embodiments, $R^3$ is a 5- to 18-membered heteroaryl optionally substituted with $C_1$-$C_6$ alkyl. In some embodiments, $R^3$ is a 5- to 6-membered heteroaryl optionally substituted with $C_1$-$C_6$ alkyl. In some embodiments, $R^3$ is pyridyl or pyrimidyl optionally substituted with $C_1$-$C_6$ alkyl. In certain embodiments, $R^3$ is pyridyl substituted with methyl. In some embodiments, $R^3$ is

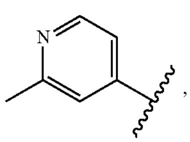,
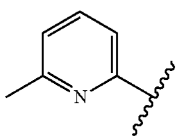, or
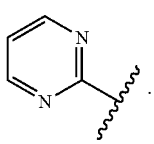.

In some embodiments of Formula (II), (I), (I-A), (I-A1), or (I-A2), $R^3$ is —$NR^{3a}R^{3b}$, wherein $R^{3a}$ and $R^{3b}$ are each independently selected from the group consisting of hydrogen, $C_6$-$C_{14}$ aryl, 5- to 18-membered heteroaryl, —($C_1$-$C_6$ alkylene)-($C_6$-$C_{14}$ aryl), and —($C_1$-$C_6$ alkylene)-(5- to 18-membered heteroaryl). In some embodiments, $R^3$ is —$NR^{3a}R^{3b}$, wherein $R^{3a}$ is hydrogen and $R^{3b}$ is selected from the group consisting of $C_6$-$C_{14}$ aryl, 5- to 18-membered heteroaryl, —($C_1$-$C_6$ alkylene)-($C_6$-$C_{14}$ aryl), and —($C_1$-$C_6$ alkylene)-(5- to 18-membered heteroaryl). In some embodiments, $R^3$ is —$NR^{3a}R^{3b}$, wherein $R^{3a}$ is hydrogen and $R^{3b}$ is selected from the group consisting of 5- to 6-membered heteroaryl, —($C_1$-$C_6$ alkylene)-($C_6$-$C_{14}$ aryl), and —($C_1$-$C_6$ alkylene)-(5- to 6-membered heteroaryl). In some embodiments, $R^3$ is —$NR^{3a}R^{3b}$, wherein $R^{3a}$ and $R^{3b}$ are each —($C_1$-$C_6$ alkylene)-($C_6$-$C_{14}$ aryl). In some embodiments, $R^3$ is

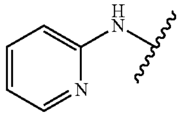,
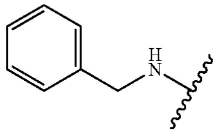,
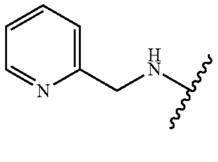, or
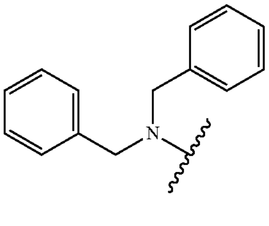.

In some embodiments of Formula (II), (I), (I-A), (I-A1), or (I-A2), $R^3$ is $OR^{3c}$, wherein $R^{3c}$ is $C_6$-$C_{14}$ aryl. In some embodiments, $R^{3c}$ is phenyl or napthyl. In some embodiments, $R^3$ is —O-phenyl. In some embodiments, $R^{3c}$ is $C_6$-$C_{14}$ aryl, 5- to 18-membered heteroaryl, or —($C_1$-$C_6$ alkylene)-(5- to 18-membered heteroaryl).

In some embodiments of Formula (II), (I), (I-A), (I-A1), or (I-A2), $R^3$ is —$C(O)R^{3d}$. In some embodiments, $R^{3d}$ is —$NR^{3f}R^{3g}$ and $R^{3f}$ and $R^{3g}$ are each independently selected from the group consisting of: (a) hydrogen, (b) $C_1$-$C_6$ alkyl optionally substituted with one or more substituents selected from the group consisting of —OH, $C_6$-$C_{14}$ aryl, and 5- to 18-membered heteroaryl, wherein the $C_6$-$C_{14}$ aryl and 5- to 18-membered heteroaryl groups are each independently unsubstituted or substituted with one or more substituents selected from the group consisting of halo, $C_1$-$C_6$ alkyl, hydroxyl, $C_1$-$C_6$ alkoxy, $C_1$-$C_6$ haloalkoxy, and CN, (c) $C_6$-$C_{14}$ aryl, (d) 3- to 18-membered heterocycloalkyl, (e) 5- to 18-membered heteroaryl optionally substituted with methyl or CN, (f) $C_3$-$C_{10}$ cycloalkyl optionally substituted with one or more substituents selected from the group consisting of halo, hydroxyl, $C_1$-$C_6$ alkyl optionally substituted with hydroxyl, $C_6$-$C_{14}$ aryl, and 5- to 18-membered heteroaryl; and (g) $C_3$-$C_{10}$ cycloalkenyl optionally substituted with one or more substituents selected from the group consisting of halo, hydroxyl, $C_1$-$C_6$ alkyl optionally substituted with hydroxyl, $C_6$-$C_{14}$ aryl, and 5- to 18-membered heteroaryl. In some embodiments, $R^{3d}$ is —$NR^{3f}R^{3g}$, $R^{3f}$ is hydrogen or $C_1$-$C_6$ alkyl, and $R^{3g}$ are each independently selected from the group consisting of: (b) $C_1$-$C_6$ alkyl optionally substituted with one or more substituents selected from the group consisting of —OH, $C_6$-$C_{14}$ aryl, and 5- to 18-membered heteroaryl, wherein the $C_6$-$C_{14}$ aryl and 5- to 18-membered heteroaryl groups are each independently unsubstituted or substituted with one or more substituents selected from the group consisting of halo, $C_1$-$C_6$ alkyl, hydroxyl, $C_1$-$C_6$ alkoxy, $C_1$-$C_6$ haloalkoxy, and CN, (c) $C_6$-$C_{14}$ aryl, (d) 3- to 18-membered heterocycloalkyl, (e) 5- to 18-membered heteroaryl optionally substituted with methyl or CN, (f) $C_3$-$C_{10}$ cycloalkyl optionally substituted with one or more substituents selected from the group consisting of halo, hydroxyl, $C_1$-$C_6$ alkyl optionally substituted with hydroxyl, $C_6$-$C_{14}$ aryl, and 5- to 18-membered heteroaryl; and (g) $C_3$-$C_{10}$ cycloalkenyl optionally substituted with one or more substituents selected from the group consisting of halo, hydroxyl, $C_1$-$C_6$ alkyl optionally substituted with hydroxyl, $C_6$-$C_{14}$ aryl, and 5- to 18-membered heteroaryl.

In some embodiments of Formula (II), (I), (I-A), (I-A1), or (I-A2), $R^3$ is —$C(O)R^{3d}$, $R^{3d}$ is —$NR^{3f}R^{3g}$, $R^{3f}$ is hydrogen or $C_1$-$C_6$ alkyl, and $R^{3g}$ is $C_1$-$C_6$ alkyl optionally substituted with one or more substituents selected from the group consisting of hydroxyl, $C_6$-$C_{14}$ aryl, and 5- to 18-membered heteroaryl, wherein the $C_6$-$C_{14}$ aryl and 5- to 18-membered heteroaryl groups are each independently unsubstituted or substituted with one or more substituents selected from the group consisting of halo, $C_1$-$C_6$ alkyl, hydroxyl, $C_1$-$C_6$ alkoxy, $C_1$-$C_6$ haloalkoxy, and CN. In some embodiments, $R^{3f}$ is hydrogen or $C_1$-$C_6$ alkyl, and $R^{3g}$ is $C_1$-$C_6$ alkyl optionally substituted with one or more substituents selected from the group consisting of hydroxyl, phenyl, and 5- to 6-membered heteroaryl, wherein the phenyl and 5- to 6-membered heteroaryl groups are each independently unsubstituted or substituted with one or more substituents selected from the group consisting of halo, $C_1$-$C_6$ alkyl, hydroxyl, $C_1$-$C_6$ alkoxy, $C_1$-$C_6$ haloalkoxy, and CN. In some embodiments, $R^{3f}$ is hydrogen and $R^{3g}$ is $C_1$-$C_6$ alkyl substituted with one or more substituents selected from the group consisting of hydroxyl, phenyl, pyrazolyl, pyridyl, and pyrimidyl, wherein the phenyl, pyrazolyl, pyridyl, and pyrimidyl are each independently unsubstituted or substituted with one or more substituents selected from the group consisting of halo, $C_1$-$C_6$ alkyl, hydroxyl, $C_1$-$C_6$ alkoxy, $C_1$-$C_6$ haloalkoxy, and CN. In some embodiments, $R^3$ is

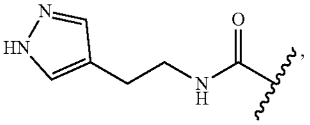

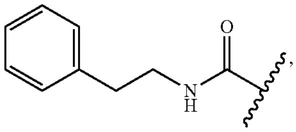

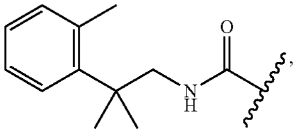

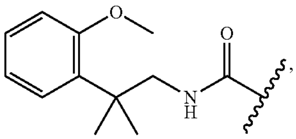

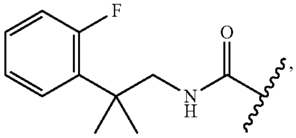

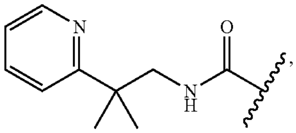

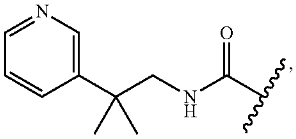

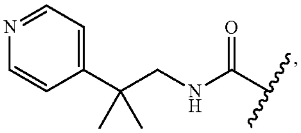

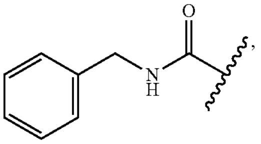

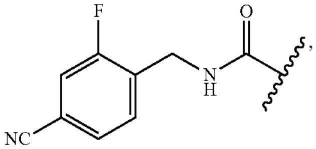

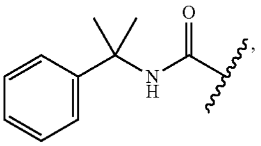

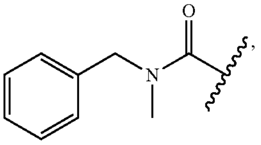

-continued

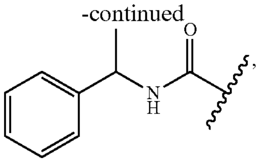
,

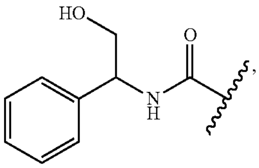
,

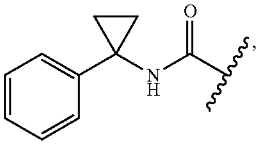
,

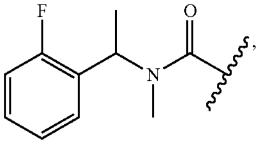
,

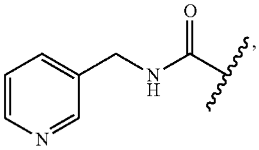
,

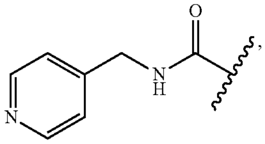
,

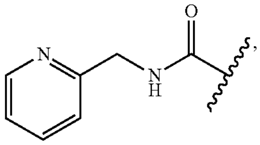
, or

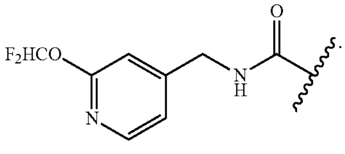
.

In some embodiments of Formula (II), (I), (I-A), (I-A1), or (I-A2), $R^3$ is —C(O)$R^{3d}$, $R^{3d}$ is —$NR^{3f}R^{3g}$, $R^{3f}$ is hydrogen or $C_1$-$C_6$ alkyl, and $R^{38}$ is $C_6$-$C_{14}$ aryl. In some embodiments, $R^{3f}$ is H or $C_1$-$C_6$ alkyl, and $R^{3g}$ is phenyl or napthyl. In some embodiments, $R^3$ is

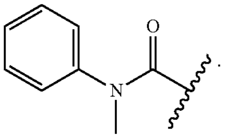 [SMILES: *C(=O)N(C)c1ccccc1]
.

In some embodiments of Formula (II), (I), (I-A), (I-A1), or (I-A2), $R^3$ is —C(O)$R^{3d}$, $R^{3d}$ is —$NR^{3f}R^{3g}$, $R^{3f}$ is hydrogen or $C_1$-$C_6$ alkyl, and $R^{3g}$ is 3- to 18-membered heterocycloalkyl. In some embodiments, $R^{3f}$ is hydrogen or $C_1$-$C_6$ alkyl, and $R^{3g}$ is 3- to 18-membered heterocycloalkyl optionally substituted with halo, hydroxyl, and —($C_1$-$C_6$ alkylene)-OH. In some embodiments, $R^3$ is

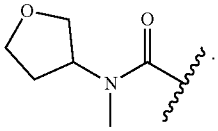 [SMILES: *C(=O)N(C)C1CCOC1]
.

In some embodiments of Formula (II), (I), (I-A), (I-A1), or (I-A2), $R^3$ is —C(O)$R^{3d}$, $R^{3d}$ is —$NR^{3f}R^{3g}$, $R^{3f}$ is hydrogen or $C_1$-$C_6$ alkyl, and $R^{3g}$ is 5- to 10-membered heteroaryl optionally substituted with methyl or CN. In some embodiments, $R^{3f}$ is hydrogen or $C_1$-$C_6$ alkyl, and $R^{3g}$ is pyridyl or pyrimidyl, each optionally substituted with methyl or CN. In some embodiments, $R^3$

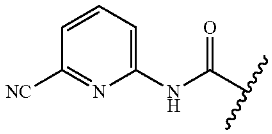
,

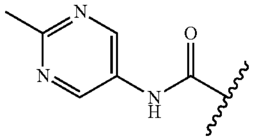
, or

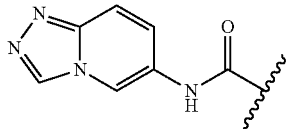
.

In some embodiments of Formula (II), (I), (I-A), (I-A1), or (I-A2), $R^3$ is —C(O)$R^{3d}$, $R^{3d}$ is —$NR^{3f}R^{3g}$, $R^{3f}$ is hydrogen or $C_1$-$C_6$ alkyl, and $R^{3g}$ is $C_3$-$C_{10}$ cycloalkyl optionally substituted with one or more substituents selected from the group consisting of halo, hydroxyl, $C_1$-$C_6$ alkyl optionally substituted with hydroxyl, $C_6$-$C_{14}$ aryl, and 5- to 18-membered heteroaryl. In other embodiments, $R^{3f}$ is hydrogen or $C_1$-$C_6$ alkyl, and $R^{3g}$ is $C_3$-$C_{10}$ cycloalkenyl optionally substituted with one or more substituents selected from the group consisting of halo, hydroxyl, $C_1$-$C_6$ alkyl optionally substituted with hydroxyl, $C_6$-$C_{14}$ aryl, and 5- to 18-membered heteroaryl. In some embodiments, $R^{3f}$ is hydrogen or $C_1$-$C_6$ alkyl, and $R^{3g}$ is $C_3$-$C_{10}$ cycloalkyl optionally substituted with $C_6$-$C_{14}$ aryl or 5- to 18-membered heteroaryl. In some embodiments, $R^{3f}$ is hydrogen or $C_1$-$C_6$ alkyl, and $R^{3g}$ is $C_3$-$C_8$ cycloalkyl optionally substituted with $C_6$-$C_{10}$ aryl or 5- to 6-membered heteroaryl. In some embodiments, $R^{3f}$ is hydrogen or $C_1$-$C_6$ alkyl, and $R^{3g}$ is cyclobutyl optionally substituted with $C_6$-$C_{10}$ aryl or 5- to 6-membered heteroaryl. In some embodiments, $R^{3f}$ is hydrogen or $C_1$-$C_6$ alkyl, and $R^{3g}$ is $C_3$-$C_8$ cycloalkyl optionally substituted with phenyl or pyridyl. In some embodiments, $R^{3f}$ is hydrogen or $C_1$-$C_6$ alkyl, and $R^{3g}$ is $C_3$-$C_{10}$ cycloalkenyl optionally substituted with one or more substituents selected from the group consisting of halo, hydroxyl, $C_1$-$C_6$ alkyl optionally substituted with halo, hydroxyl, and —($C_1$-$C_6$ alkylene)-OH. In some embodiments, In some embodiments, $R^3$ is

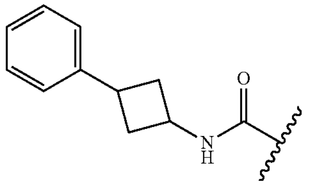

or

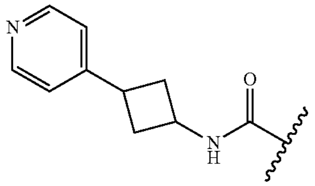

In some embodiments, $R^3$ is

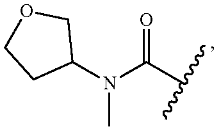,
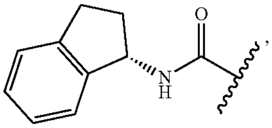,
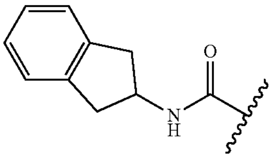,
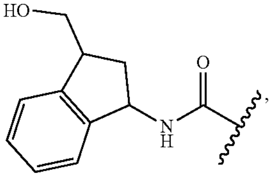,
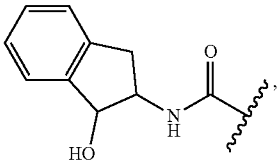,
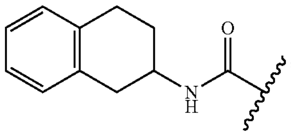,
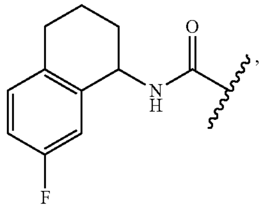, or
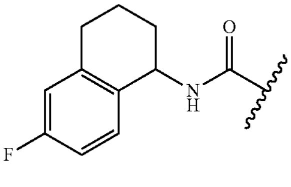.

In some embodiments of Formula (II), (I), (I-A), (I-A1), or (I-A2), $R^3$ is —C(O)$R^{3d}$ and $R^{3d}$ is $C_3$-$C_8$ cycloalkyl. In some embodiments, $R^3$ is —C(O)$R^{3d}$ and $R^{3d}$ is $C_3$-$C_8$ cycloalkyl substituted with $C_6$-$C_{14}$ aryl, wherein the $C_6$-$C_{14}$ aryl is optionally substituted with one or more substituents selected from the group consisting of halo, $C_1$-$C_6$ alkyl, $C_1$-$C_6$ haloalkyl, and $C_1$-$C_6$ alkoxy. In some embodiments, $R^3$ is —C(O)$R^{3d}$ and $R^{3d}$ is $C_3$-$C_8$ cycloalkyl substituted with $C_6$-$C_{10}$ aryl. In some embodiments, $R^3$ is

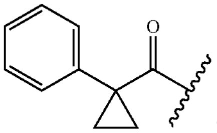.

In some embodiments, $R^3$ is —C(O)$R^{3d}$ and $R^{3d}$ is $C_3$-$C_8$ cycloalkenyl. In some embodiments, $R^3$ is

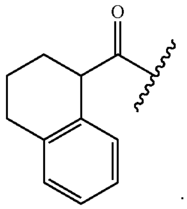 [SMILES: *C(=O)C1CCCc2ccccc21].

In some embodiments of Formula (II), (I), (I-A), (I-A1), or (I-A2), $R^3$ is —C(O)$R^{3d}$ and $R^{3d}$ is $C_6$-$C_{14}$ aryl optionally substituted with one or more substituents selected from the group consisting of hydroxyl, halo, cyano, $C_1$-$C_6$ alkyl, $C_1$-$C_6$ alkoxy, $C_1$-$C_6$ haloalkyl, —($C_1$-$C_6$ alkylene)-OH, —C(O)O($C_1$-$C_6$ alkyl), —$NR^{3e1}R^{3e2}$, —S(O)$_2$($C_1$-$C_6$ alkyl), 5- to 18-membered heteroaryl, and 3- to 18-membered heterocycloalkyl optionally substituted with oxo, wherein $R^{3e1}$ and $R^{3e2}$ are each independently H or $C_1$-$C_6$ alkyl. In some embodiments, $R^3$ is —C(O)$R^{3d}$ and $R^{3d}$ is phenyl optionally substituted with one or more substituents selected from the group consisting of hydroxyl, halo, cyano, $C_1$-$C_6$ alkyl, $C_1$-$C_6$ alkoxy, $C_1$-$C_6$ haloalkyl, —($C_1$-$C_6$ alkylene)-OH, —C(O)O($C_1$-$C_6$ alkyl), —$NR^{3e1}R^{3e2}$, —S(O)$_2$($C_1$-$C_6$ alkyl), 5- to 18-membered heteroaryl, and 3- to 18-membered heterocycloalkyl optionally substituted with oxo, wherein $R^{3e1}$ and $R^{3e2}$ are each independently H or $C_1$-$C_6$ alkyl. In some embodiments, $R^3$ is

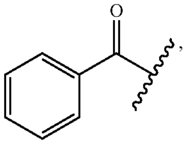,
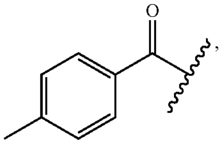,
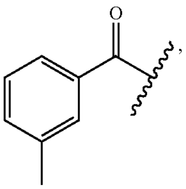,
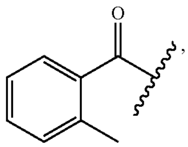,
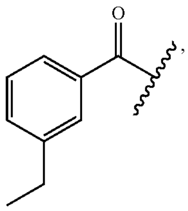,
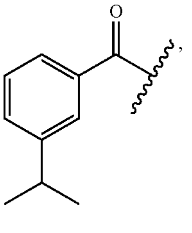,
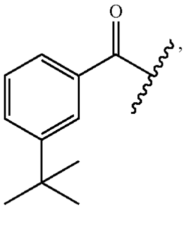, -continued

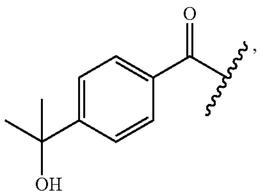,
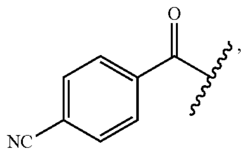,
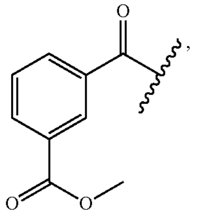,
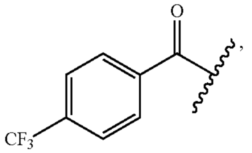,
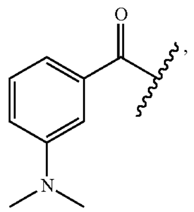,
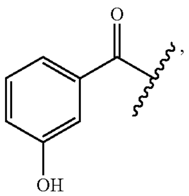,
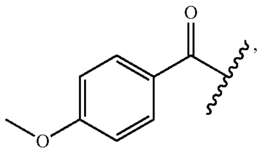,
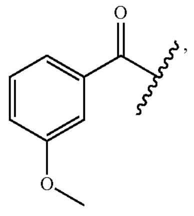,
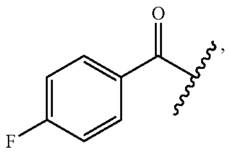,
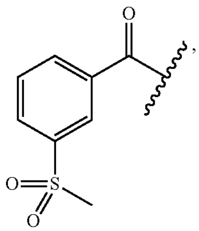,
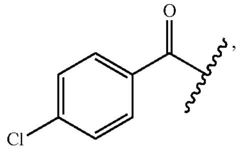,
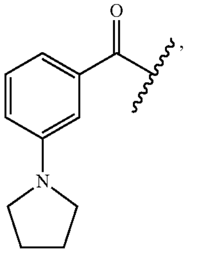,
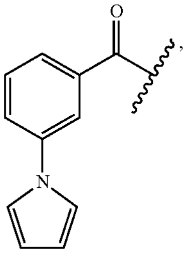,
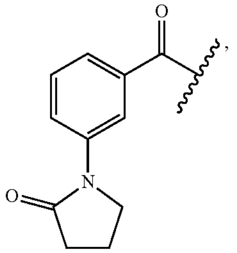, -continued

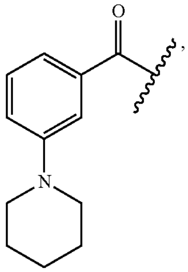, or
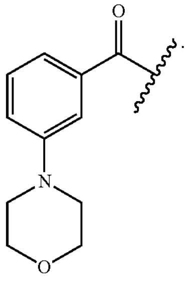.

In some embodiments of Formula (II), (I), (I-A), (I-A1), or (I-A2), $R^3$ is —C(O) $R^{3d}$ and $R^{3d}$ is —($C_1$-$C_6$ alkylene)-($C_6$-$C_{14}$ aryl) optionally substituted with one or more substituents selected from the group consisting of halo, $C_1$-$C_6$ alkyl, $C_1$-$C_6$ haloalkyl, and $C_1$-$C_6$ alkoxy. In some embodiments, $R^3$ is —C(O) $R^{3d}$ and $R^{3d}$ is —($C_1$-$C_6$ alkylene)-phenyl optionally substituted with one or more substituents selected from the group consisting of halo, $C_1$-$C_6$ alkyl, $C_1$-$C_6$ haloalkyl, and $C_1$-$C_6$ alkoxy In some embodiments, $R^3$ is

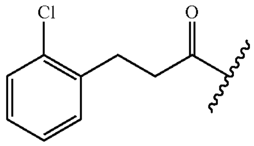,
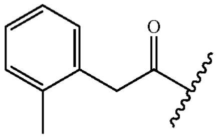,
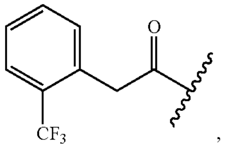,
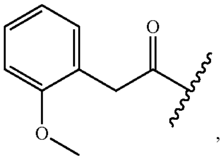,
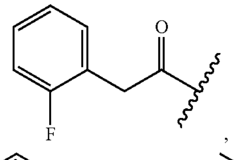,
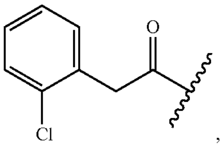,
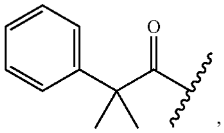,
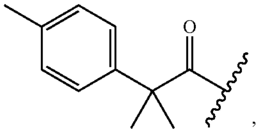, or
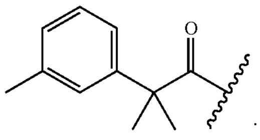.

In some embodiments of Formula (II), (I), (I-A), (I-A1), or (I-A2), $R^3$ is —C(O)$R^{3d}$ and $R^{3d}$ is 3- to 18-membered heterocycloalkyl optionally substituted with one or more substituents selected from the group consisting of (a) $C_1$-$C_6$ alkyl optionally substituted with one or more substituents independently selected from the group consisting of hydroxyl, halo, $C_3$-$C_{10}$ cycloalkyl, and 5- to 18-membered heteroaryl optionally substituted with one or more $C_1$-$C_6$ alkyl substituents; (b) $C_6$-$C_{14}$ aryl; (c) 3- to 18-membered heterocycloalkyl; (d) —C(O)O($C_1$-$C_6$ alkyl); (e) —C(O)($C_6$-$C_{14}$ aryl); (f) halo; (g) $C_1$-$C_6$ alkoxy optionally substituted with one or more halo substituents; and (h) oxo.

In some embodiments of Formula (II), (I), (I-A), (I-A1), or (I-A2), $R^3$ is —C(O)$R^{3d}$ and $R^{3d}$ is 3- to 18-membered heterocycloalkyl optionally substituted with one or more substituents selected from the group consisting of (a) $C_1$-$C_6$ alkyl optionally substituted with one or more substituents selected from the group consisting of hydroxyl, halo, $C_3$-$C_{10}$ cycloalkyl, and 5- to 18-membered heteroaryl optionally substituted with one or more $C_1$-$C_6$ alkyl substituents, (b) $C_6$-$C_{14}$ aryl, (c) 3- to 18-membered heterocycloalkyl, (d) —C(O)O($C_1$-$C_6$ alkyl), (e) —C(O)($C_6$-$C_{14}$ aryl), (f) halo, and (g) $C_1$-$C_6$ alkoxy optionally substituted with one or more halo substituents. In some embodiments, $R^3$ is —C(O)$R^{3d}$ and $R^{3d}$ is 4- to 10-membered heterocycloalkyl optionally substituted with one or more substituents selected from the group consisting of (a) $C_1$-$C_6$ alkyl optionally substituted with one or more substituents selected from the group consisting of hydroxyl, halo, $C_3$-$C_{10}$ cycloalkyl, and 5- to 18-membered heteroaryl optionally substituted with one or more $C_1$-$C_6$ alkyl substituents, (b) $C_6$-$C_{14}$ aryl, (c) 3- to 18-membered heterocycloalkyl, (d) —C(O)O($C_1$-$C_6$ alkyl), (e) —C(O)($C_6$-$C_{14}$ aryl), (f) halo, and (g) $C_1$-$C_6$ alkoxy optionally substituted with one or more halo substituents. In some embodiments, $R^3$ is —C(O)$R^{3d}$ and $R^{3d}$ is azetidinyl, pyrrolidinyl, piperazinyl, piperadinyl, indolinyl, isoindoyl, isoindolinyl, dihydroindenyl, tetrahydroquinolinyl, dihydrobenzooxazinyl, or tetrahydronaphthyridinyl, each optionally substituted with one or more substituents selected from the group consisting of (a) $C_1$-$C_6$ alkyl optionally substituted with one or more substituents selected from the group consisting of hydroxyl, halo, $C_3$-$C_{10}$ cycloalkyl, and 5- to 18-membered heteroaryl optionally substituted with one or more $C_1$-$C_6$ alkyl substituents, (b) $C_6$-$C_{14}$ aryl, (c) 3- to 18-membered heterocycloalkyl, (d) —C(O)O($C_1$-$C_6$ alkyl), (e) —C(O)($C_6$-$C_{14}$ aryl), (f) halo, and (g) $C_1$-$C_6$ alkoxy optionally substituted with one or more halo substituents. In some embodiments, $R^3$ is

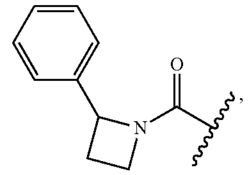
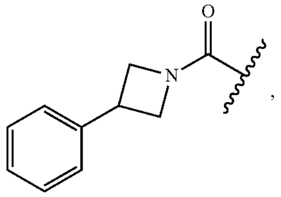
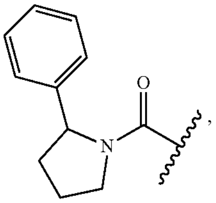
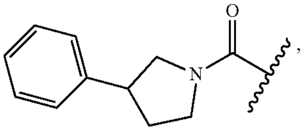
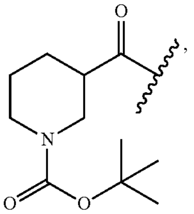
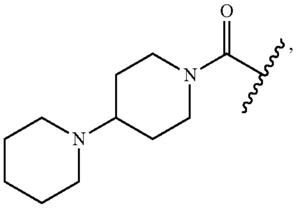
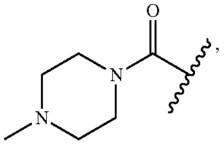
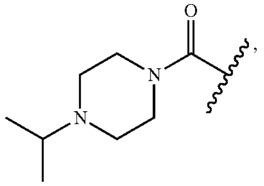

-continued

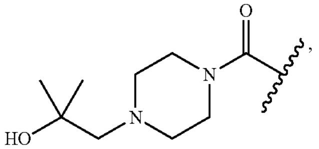
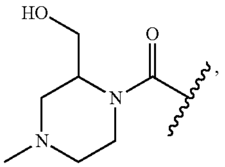
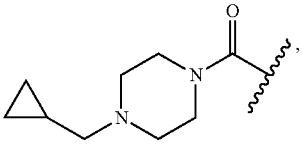
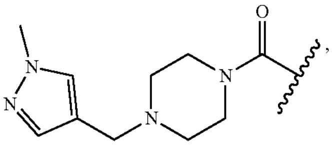
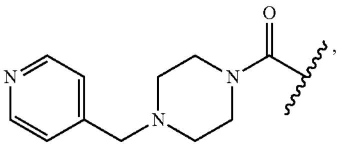
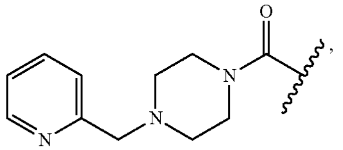
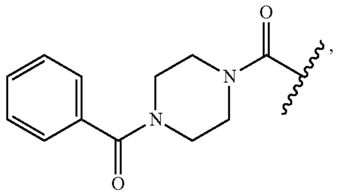
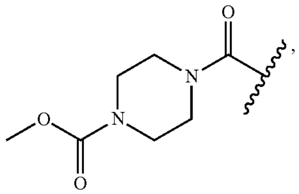
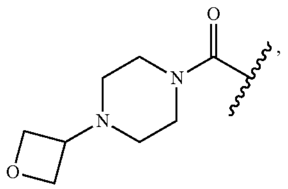
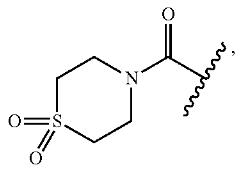
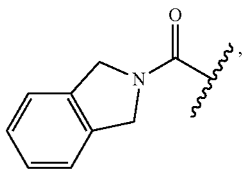
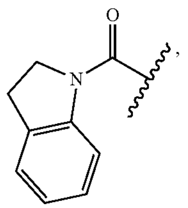

-continued

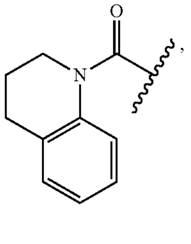 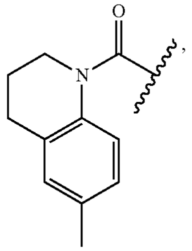 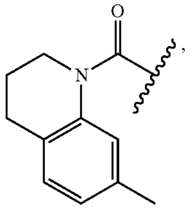

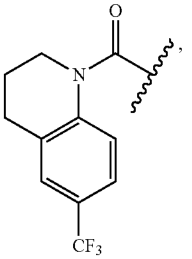 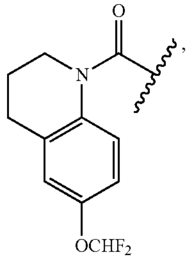 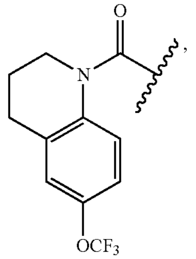

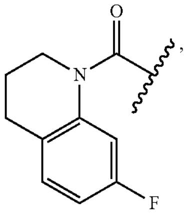 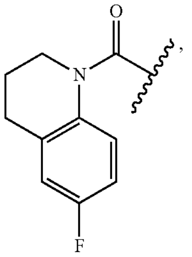 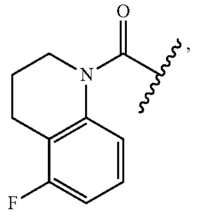

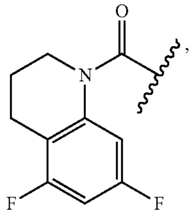 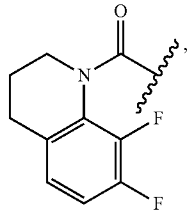 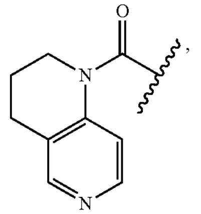

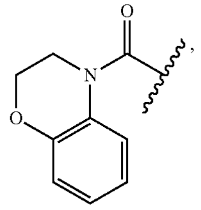 or 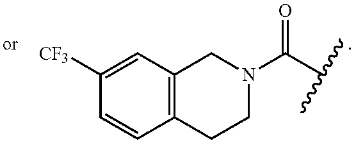

In some embodiments of Formula (II), (I), (I-A), (I-A1), or (I-A2), $R^3$ is —C(O)$R^{3d}$ and $R^{3d}$ is 5- to 18-membered heteroaryl optionally substituted with one or more substituents selected from the group consisting of $C_1$-$C_6$ alkyl, hydroxyl, oxo, and 3- to 18-membered heterocycloalkyl. In some embodiments, $R^3$ is —C(O)$R^{3d}$ and $R^{3d}$ is 5- to 6-membered heteroaryl optionally substituted with one or more substituents selected from the group consisting of $C_1$-$C_6$ alkyl, hydroxyl, oxo, and 3- to 18-membered heterocycloalkyl. In some embodiments, $R^3$ is —C(O)$R^{3d}$ and $R^{3d}$ pyridyl optionally substituted with one or more substituents selected from the group consisting of $C_1$-$C_6$ alkyl, hydroxyl, oxo, and 3- to 18-membered heterocycloalkyl. In some embodiments, $R^3$ is —C(O)$R^{3d}$ and $R^{3d}$ pyridyl substituted with methyl. In some embodiments, $R^3$ is

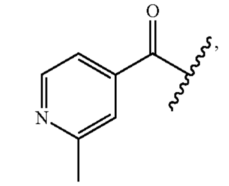 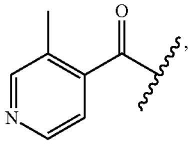

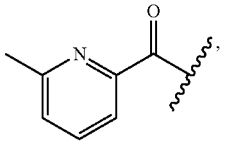 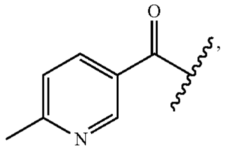

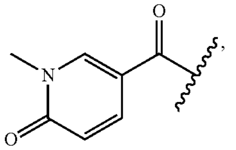 or 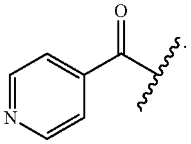

In some embodiments of Formula (II), (I), (I-A), (I-A1), or (I-A2), $R^3$ is $C_1$-$C_6$ alkyl substituted with C(O)N$R^{3h}R^{3i}$, wherein $R^{3h}$ and $R^{3i}$ are each independently selected from $C_1$-$C_6$ alkyl and —($C_1$-$C_6$ alkylene)-($C_6$-$C_{14}$ aryl). In some embodiments, $R^3$ is

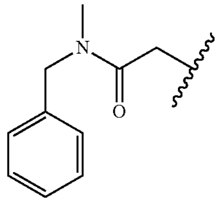 or 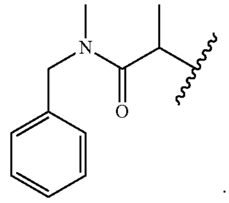

In some embodiments of Formula (II) (I), (I-A), (I-A1), or (I-A2), $R^3$ is $C_1$-$C_6$ alkyl substituted with 3- to 18-membered heterocycloalkyl, wherein the 3- to 18-membered heterocycloalkyl is optionally substituted with one or more substituents independently selected from halo, oxo, $C_1$-$C_6$ alkyl, $C_6$-$C_{14}$ aryl, and 5- to 18-membered heteroaryl. In some embodiments, $R^3$ is $C_1$-$C_6$ alkyl substituted with 3- to 18-membered heterocycloalkyl, wherein the 3- to 18-membered heterocycloalkyl is optionally substituted with one or more substituents selected from halo and $C_6$-$C_{14}$ aryl. In some embodiments, $R^3$ is $C_1$-$C_6$ alkyl substituted with 5- to 10-membered heterocycloalkyl, wherein the 5- to 10-membered heterocycloalkyl is optionally substituted with $C_6$-$C_{14}$ aryl.

In some embodiments, $R^3$ is

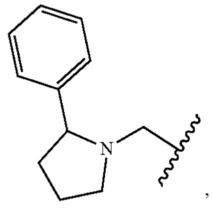, 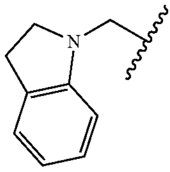, or

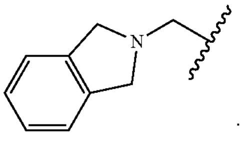.

In some embodiments, $R^3$ is

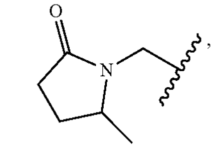, 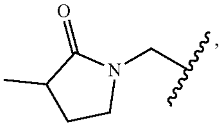, 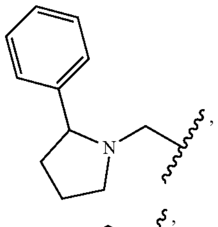, 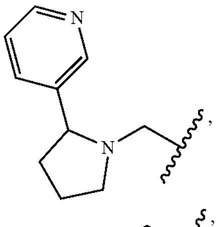, 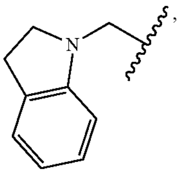, 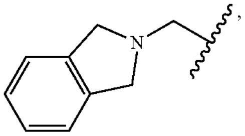, 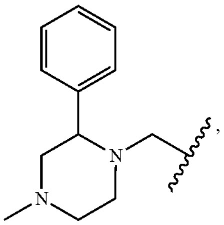, 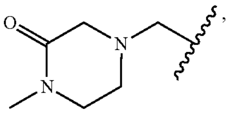, or 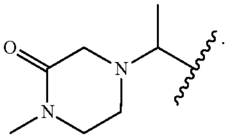.

In some embodiments, $R^3$ is $C_1$-$C_6$ alkyl, wherein the $C_1$-$C_6$ alkyl of $R^3$ is (i) substituted with 5- to 18-membered heteroaryl, wherein the 5- to 18-membered heteroaryl is optionally substituted with one or more $C_1$-$C_6$ alkyl, $C_6$-$C_{14}$ aryl, or cyano, and (ii) optionally substituted with one or more —OH. In some embodiments, $R^3$ is $C_1$-$C_6$ alkyl substituted with 5- to 18-membered heteroaryl. $R^3$ is $C_1$-$C_6$ alkyl substituted with 5- to 10-membered heteroaryl. In some embodiments, $R^3$ is

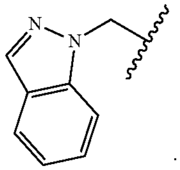.

In some embodiments, $R^3$ is

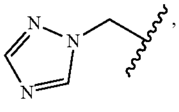, 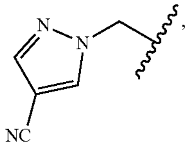, 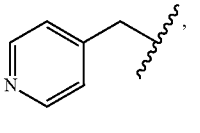,

-continued

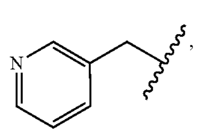, 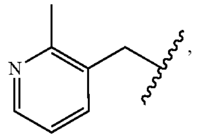, 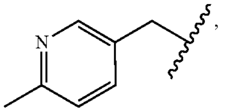, 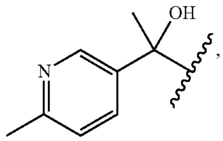, 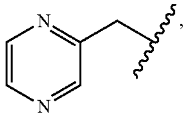, 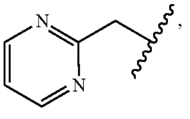, 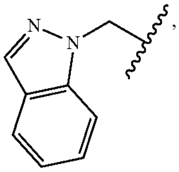, or 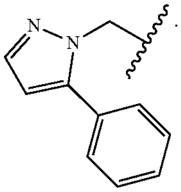.

In some embodiments of Formula (II), (I), (I-A), (I-A1), or (I-A2), $R^3$ is —C(O)OR$^{3j}$, wherein $R^{3j}$ is hydrogen or $C_1$-$C_6$ alkyl. In some embodiments, $R^3$ is

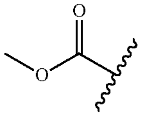 or 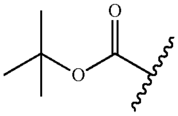.

In some embodiments of Formula (II), (I), (I-A), (I-A1), or (I-A2), $R^3$ is —NHC(O)R$^{3k}$. In some embodiments, $R^{3k}$ is $C_6$-$C_{14}$ aryl optionally substituted with one or more substituents independently selected from the group consisting of $C_1$-$C_6$ alkyl, cyano, —NR$^{3k1}$R$^{3k2}$, hydroxyl, alkoxy, and $S(O)_2$(alkyl), wherein $R^{3k1}$ and $R^{3k2}$ are each independently hydrogen or $C_1$-$C_6$ alkyl. In some embodiments, $R^{3k}$ is phenyl optionally substituted with one or more substituents independently selected from the group consisting of $C_1$-$C_6$ alkyl, cyano, —NR$^{3k1}$R$^{3k2}$, hydroxyl, alkoxy, and $S(O)_2$(alkyl), wherein $R^{3k1}$ and $R^{3k2}$ are each independently hydrogen or $C_1$-$C_6$ alkyl. In some embodiments, $R^3$ is

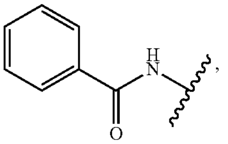, 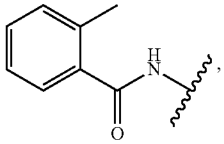, 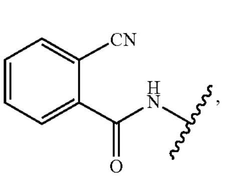, 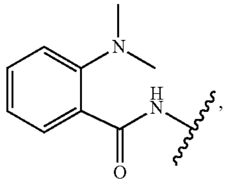,

-continued

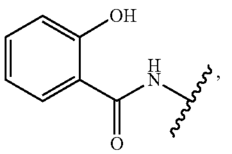,
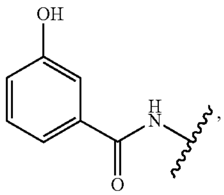,
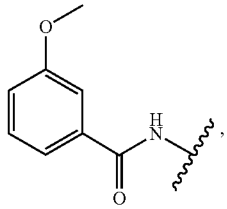, or
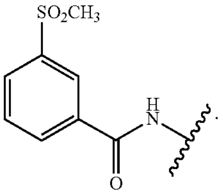.

In some embodiments, $R^{3k}$ is —($C_1$-$C_6$ alkylene)-($C_6$-$C_{14}$ aryl), optionally substituted with one or more substituents independently selected from the group consisting of $C_1$-$C_6$ alkyl, cyano, —$NR^{3k1}R^{3k2}$, hydroxy, alkoxy, and $S(O)_2$(alkyl), wherein $R^{3k1}$ and $R^{3k2}$ are each independently hydrogen or $C_1$-$C_6$ alkyl. In some embodiments, $R^{3k}$ is —($C_1$-$C_6$ alkylene)-phenyl, optionally substituted with one or more substituents independently selected from the group consisting of $C_1$-$C_6$ alkyl, cyano, —$NR^{3k1}R^{3k2}$, hydroxy, alkoxy, and $S(O)_2$(alkyl), wherein $R^{3k1}$ and $R^{3k2}$ are each independently hydrogen or $C_1$-$C_6$ alkyl. In some embodiments, $R^3$ is

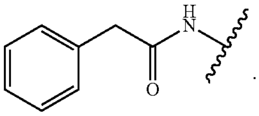 [SMILES: *NC(=O)Cc1ccccc1].

In some embodiments, $R^{3k}$ is 5- to 18-membered heteroaryl optionally substituted with one or more substituents independently selected from the group consisting of $C_1$-$C_6$ alkyl, cyano, —$NR^{3k1}R^{3k2}$, hydroxy, alkoxy, and $S(O)_2$(alkyl), wherein $R^{3k1}$ and $R^{3k2}$ are each independently hydrogen or $C_1$-$C_6$ alkyl. In some embodiments, $R^{3k}$ is 5- to 6-membered heteroaryl optionally substituted with one or more $C_1$-$C_6$ alkyl substituents. In some embodiments, $R^{3k}$ is pyridyl optionally substituted with $C_1$-$C_6$ alkyl. In some embodiments, $R^3$ is

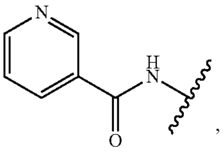,
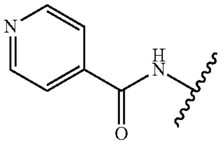,
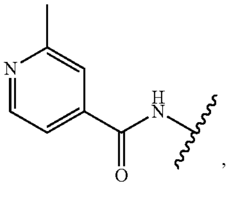,
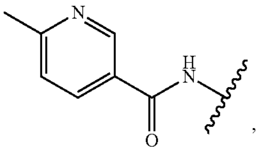,

-continued

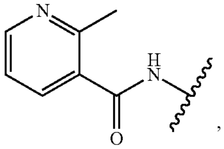, or
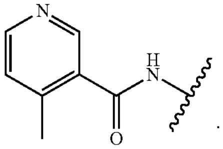.

In some embodiments of Formula (II), (I), (I-A), (I-A1), or (I-A2), $R^3$ is —NHC(O)$OR^{3l}$, wherein $R^{3l}$ is hydrogen or $C_1$-$C_6$ alkyl. In some embodiments, $R^3$ is

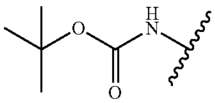.

In some embodiments of Formula (II), (I), (I-A), (I-A1), or (I-A2), $R^3$ is —$NHSO_2R^{3m}$, wherein $R^{3m}$ is 5- to 18-membered heteroaryl, $C_6$-$C_{14}$ aryl, or —($C_1$-$C_6$ alkylene)-($C_6$-$C_{14}$ aryl), wherein the 5- to 18-membered heteroaryl, the $C_6$-$C_{14}$ aryl, and the —($C_1$-$C_6$ alkylene)-($C_6$-$C_{14}$ aryl) are each optionally substituted with one or more substituents selected from halo and $C_1$-$C_6$ alkoxy. In some embodiments, $R^3$ is —$NHSO_2R^{3m}$, wherein $R^{3m}$ is 5- to 18-membered heteroaryl, optionally substituted with one or more substituents selected from halo and $C_1$-$C_6$ alkoxy. In some embodiments, $R^3$ is —$NHSO_2R^{3m}$, wherein $R^{3m}$ is $C_6$-$C_{14}$ aryl, optionally substituted with one or more substituents selected from halo and $C_1$-$C_6$ alkoxy. In some embodiments, $R^3$ is —$NHSO_2R^{3m}$, wherein $R^{3m}$ is —($C_1$-$C_6$ alkylene)-($C_6$-$C_{14}$ aryl), optionally substituted with one or more substituents selected from halo and $C_1$-$C_6$ alkoxy. In some embodiments, $R^3$ is

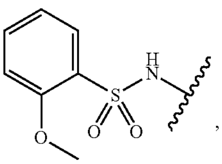,
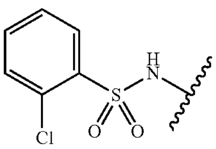,
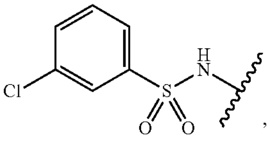, or
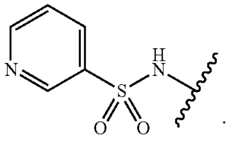.

In some embodiments of Formula (II), (I), (I-A), (I-A1), or (I-A2), $R^3$ is —$SO_2R^{3n}$ and $R^{3n}$ is $C_1$-$C_6$ alkyl, $C_3$-$C_{10}$ cycloalkyl, $C_6$-$C_{14}$ aryl, or —($C_1$-$C_6$ alkylene)-($C_6$-$C_{14}$ aryl), wherein the $C_3$-$C_{10}$ cycloalkyl, the $C_6$-$C_{14}$ aryl, and the —($C_1$-$C_6$ alkylene)-($C_6$-$C_{14}$ aryl) of $R^{3n}$ are each independently optionally substituted with one or more substituents independently selected from halo and —C(O)O($C_1$-$C_6$ alkyl). In some embodiments, $R^3$ is —$SO_2R^{3n}$ and $R^{3n}$ is $C_1$-$C_6$ alkyl. In some embodiments, $R^3$ is —$SO_2R^{3n}$ and $R^{3n}$ is methyl. In some embodiments of Formula (II), (I), (I-A), (I-A1), or (I-A2), $R^3$ is —$SO_2R^{3n}$ and $R^{3n}$ is $C_3$-$C_{10}$cycloalkyl, $C_6$-$C_{14}$ aryl, or —($C_1$-$C_6$ alkylene)-($C_6$-$C_{14}$ aryl), wherein the $C_3$-$C_{10}$ cycloalkyl, the $C_6$-$C_{14}$ aryl, and the —($C_1$-$C_6$ alkylene)-($C_6$-$C_{14}$ aryl) are each optionally substituted with one or more substituents selected from halo and —C(O)O($C_1$-$C_6$ alkyl). In some embodiments, $R^3$ is —$SO_2R^{3n}$ and $R^{3n}$ is $C_3$-$C_{10}$ cycloalkyl optionally substituted with one or more substituents selected from halo and —C(O)O($C_1$-$C_6$ alkyl). In some embodiments, $R^3$ is —$SO_2R^{3n}$ and $R^{3n}$ is $C_6$-$C_{14}$ aryl optionally substituted with one or more substituents selected from halo and —C(O)O ($C_1$-$C_6$ alkyl). In some embodiments, $R^3$ is —$SO_2R^{3n}$ and $R^{3n}$ is —($C_1$-$C_6$ alkylene)-($C_6$-$C_{14}$ aryl) optionally substituted with one or more substituents selected from halo and —C(O)O($C_1$-$C_6$ alkyl). In some embodiments, $R^3$ is

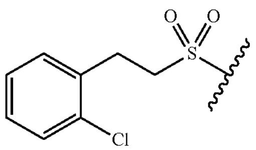,
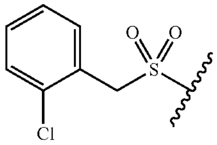,
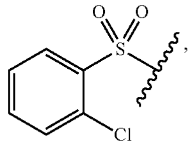,
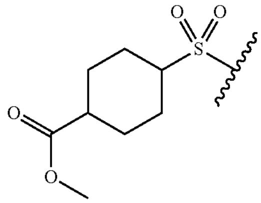, or
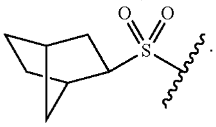.

In some embodiments, $R^3$ is

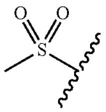,
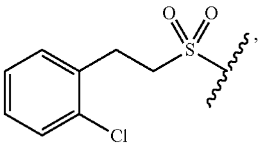,
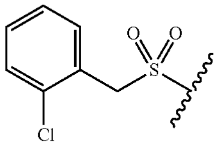,
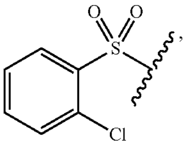,
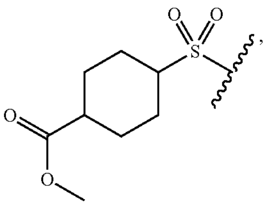, or
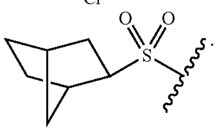.

In some embodiments of Formula (II), (I), (I-A), (I-A1), or (I-A2), $R^3$ is $C_1$-$C_6$ alkyl substituted with one or more —N($R^{3p}$)—C(O)$R^{3q}$, wherein $R^{3p}$ is H or $C_1$-$C_6$ alkyl, and $R^{3q}$ is $C_3$-$C_8$ cycloalkyl, optionally substituted 3- to 18-membered heterocycloalkyl, or optionally substituted 5- to 18-membered heteroaryl. In some embodiments, $R^{3p}$ is H or $C_1$-$C_6$ alkyl, and $R^{3q}$ is (i) $C_3$-$C_8$ cycloalkyl, (ii) 3- to 18-membered heterocycloalkyl optionally substituted with one or more independently selected $C_1$-$C_6$ alkyl or oxo substituents, or (iii) 5- to 18-membered heteroaryl optionally substituted with one or more independently selected $C_1$-$C_6$ alkyl substituents. In some embodiments of the foregoing, $R^{3p}$ is H or methyl. In some embodiments, $R^{3p}$ is H. In some embodiments, $R^{3p}$ is methyl. In some embodiments, $R^{3q}$ is $C_3$-$C_8$ cycloalkyl. In some embodiments, $R^{3q}$ is $C_5$-$C_6$ cycloalkyl. In some embodiments, $R^{3q}$ is cyclopentyl. In some embodiments, $R^3$ is

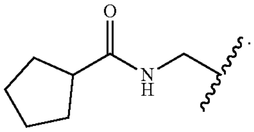.

In some embodiments, $R^{3q}$ is 3- to 18-membered heterocycloalkyl optionally substituted with one or more independently selected oxo substituents. In some embodiments, $R^{3q}$ is 5- to 6-membered heterocycloalkyl optionally substituted with one or more independently selected oxo substituents. In some embodiments, $R^{3q}$ is tetrahydropyranyl, tetrahydrothiopyranyl, or piperidinyl optionally substituted with one or more independently selected oxo substituents. In some embodiments, $R^3$ is

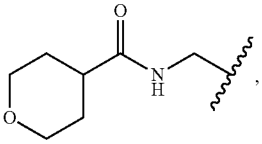,
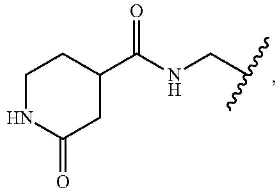, or
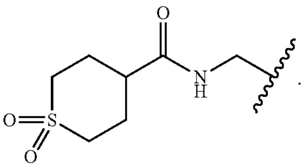.

In some embodiments, $R^{3q}$ is 5- to 18-membered heteroaryl optionally substituted with one or more independently selected $C_1$-$C_6$ alkyl substituents. In some embodiments, $R^{3q}$ is 5- to 6-membered heteroaryl optionally substituted with one or more independently selected $C_1$-$C_6$ alkyl substituents. In some embodiments, $R^{3q}$ is pyridinyl or pyrazolyl optionally substituted with one or more independently selected $C_1$-$C_6$ alkyl substituents. In some embodiments, $R^3$

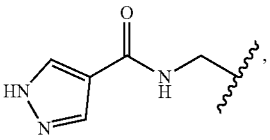,
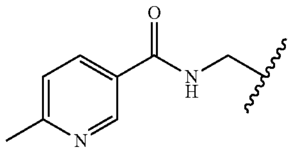,
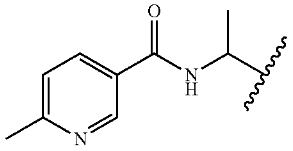,
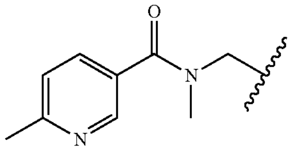,

-continued

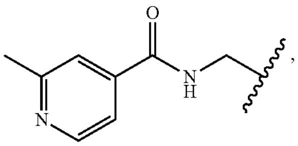

, or

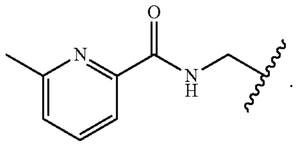

.

In some embodiments, $R^3$ is

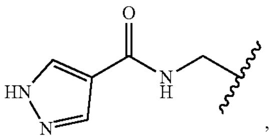

,

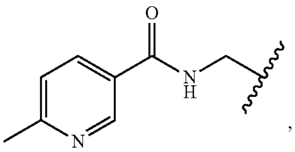

,

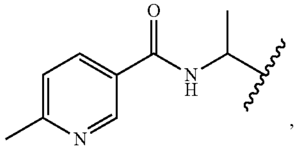

,

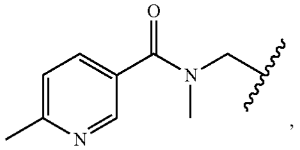

,

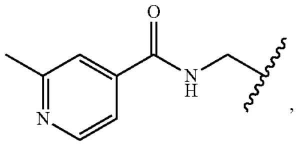

,

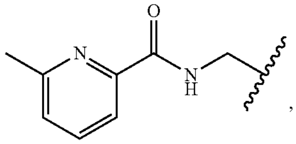

,

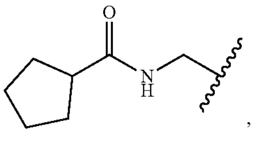 [SMILES: *CNC(=O)C1CCCC1]

,

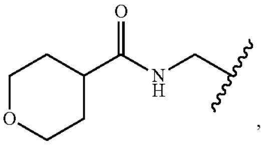

,

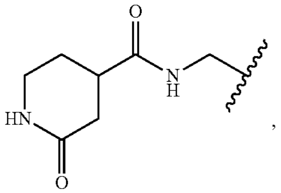

, or

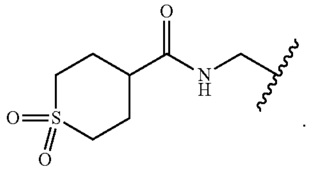

.

In some embodiments of Formula (II), (I), (I-A), (I-A1), or (I-A2), $R^3$ is $C_1$-$C_6$ alkyl substituted with one or more —$S(O)_2$—$R^{3r}$, wherein $R^{3r}$ is $C_6$-$C_{14}$ aryl or 5- to 18-membered heteroaryl. In some embodiments, $R^{3r}$ is $C_6$-$C_{14}$ aryl. In some embodiments, $R^{3r}$ is phenyl. In some embodiments, $R^3$ is

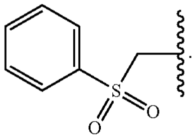 [SMILES: *CS(=O)(=O)c1ccccc1]

In some embodiments, $R^{3r}$ is 5- to 18-membered heteroaryl. In some embodiments, $R^{3r}$ is 5- to 6-membered heteroaryl. In some embodiments, $R^{3r}$ is pridinyl. In some embodiments. $R^3$ is

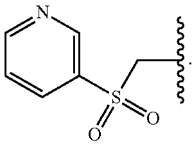

In some embodiments, $R^3$ is

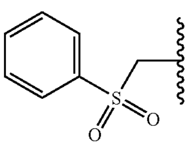

or

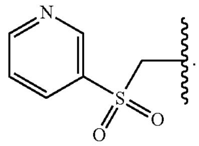 [SMILES: *CS(=O)(=O)c1cccnc1]

In some embodiments of Formula (II), (I), (I-A), (I-A1), or (I-A2), $R^3$ is $C_1$-$C_6$ alkyl substituted with one or more —C(O)—$R^{3s}$, wherein $R^{3s}$ is $R^{3s}$ is optionally substituted 3- to 18-membered heterocycloalkyl. In some embodiments, $R^{3s}$ is 3- to 18-membered heterocycloalkyl optionally substituted with one or more independently selected $C_1$-$C_6$ alkyl substituents, wherein the $C_1$-$C_6$ alkyl is independently optionally substituted with one or more —OH. In some embodiments, $R^{3s}$ is 5- to 6-membered heterocycloalkyl optionally substituted with one or more independently selected $C_1$-$C_6$ alkyl substituents, wherein the $C_1$-$C_6$ alkyl is independently optionally substituted with one or more —OH. In some embodiments, $R^{3s}$ is piperazinyl or pyrrolidinyl optionally substituted with one or more independently selected $C_1$-$C_6$ alkyl substituents, wherein the $C_1$-$C_6$ alkyl is independently optionally substituted with one or more —OH. In some embodiments, $R^3$ is

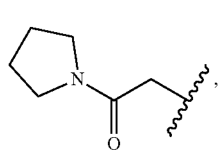

,

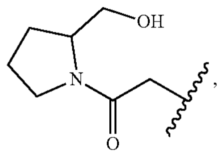

, or

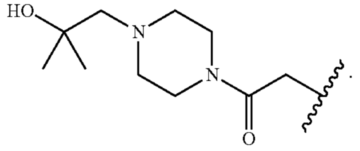

In some embodiments of Formula (II), (I), (I-A), (I-A1), or (I-A2), $R^3$ is $C_1$-$C_6$ alkyl, wherein the $C_1$-$C_6$ alkyl of $R^3$ is substituted with one or more independently selected optionally substituted $C_6$-$C_{14}$ aryl substituents. In some embodiments, $R^3$ is $C_1$-$C_6$ alkyl, wherein the $C_1$-$C_6$ alkyl of $R^3$ is (i) substituted with one or more independently selected $C_6$-$C_{14}$ aryl substituents, wherein the $C_6$-$C_{14}$ aryl is optionally substituted with one or more independently selected $C_1$-$C_6$ alkyl substituents, and (ii) optionally substituted with one or more —OH. In some embodiments, $R^3$ is

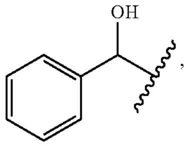, 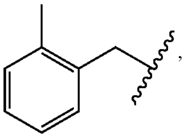, 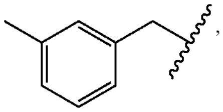, or 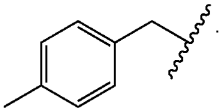.

In another aspect, the compound of Formula (II) or Formula (I) is a compound of Formula (I-B):

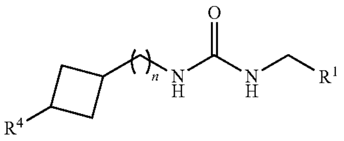 (I-B)

or a salt thereof, wherein $R^1$, $R^4$, and n are as defined for Formula (II) or Formula (I), or any variation or embodiment thereof.

In some embodiments of Formula (I-B), $R^1$ is

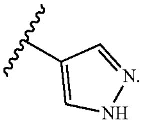 [SMILES: *c1cn[nH]c1]

In some embodiments, $R^1$ is

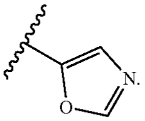 [SMILES: *c1cnco1]

In some embodiments, $R^1$ is

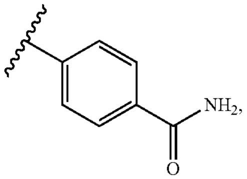, 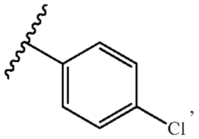, 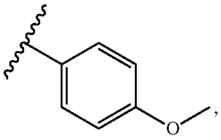, or 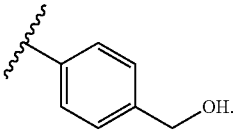

In some embodiments, $R^1$ is

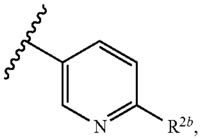

wherein $R^{2b}$ is selected from the group consisting of halo, —O($C_1$-$C_6$ alkyl), $C_1$-$C_6$ alkyl substituted with —OH, —C(O)NR$^{2c}$R$^{2d}$, and —N(R$^{2e}$)C(O)($C_1$-$C_6$ alkyl); and $R^{2c}$, $R^{2d}$, and $R^{2e}$ are each independently hydrogen or $C_1$-$C_6$ alkyl. In some embodiments, $R^1$ is

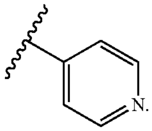 [SMILES: *c1ccncc1]

In some embodiments, $R^1$ is

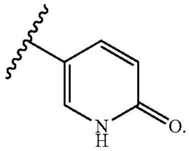 [SMILES: *c1ccc(=O)[nH]c1]

In some embodiments of Formula (I-B), $R^1$ is selected from the group consisting of

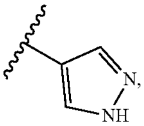, 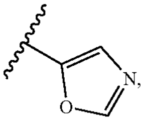, 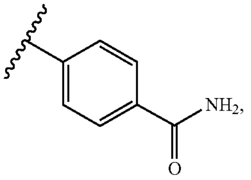, 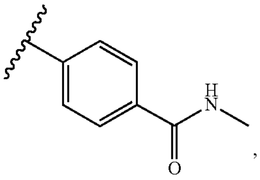, 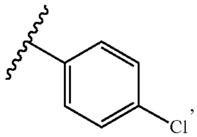, 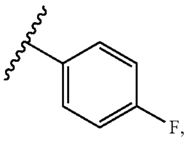, 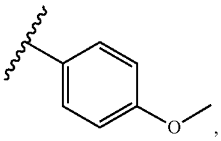, 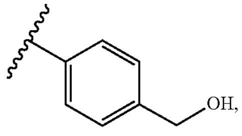, 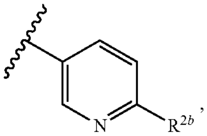, -continued

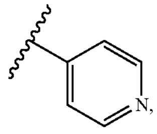, and 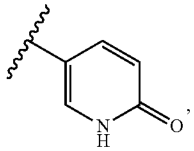,

In some embodiments of Formula (I-B), $R^1$ is selected from the group consisting of

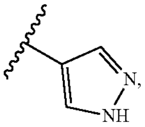, 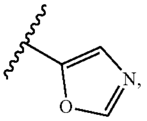, 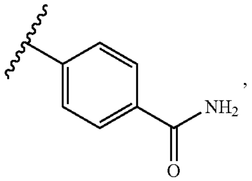,

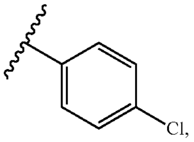, 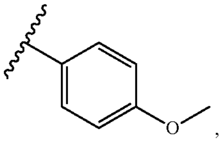,

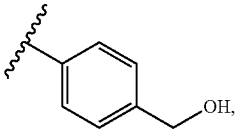, 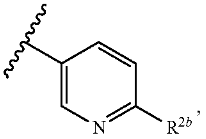,

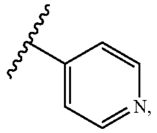, and 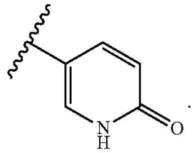.

In some embodiments of Formula (I-B), n is 0. In some embodiments, n is 1. In some embodiments, n is 2. In some embodiments, n is 3. In some embodiments, n is 4. In some embodiments, n is 5. In other embodiments, n is 6.

In some embodiments of Formula (I-B), $R^4$ is phenyl. In other embodiments, $R^4$ is —C(O)NH—$CH_2$-phenyl. In some embodiments of Formula (I-B), when $R^4$ is phenyl and n is 0, $R^1$ is selected from the group consisting of

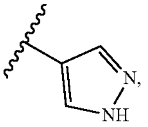, 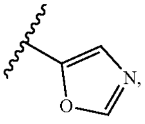, 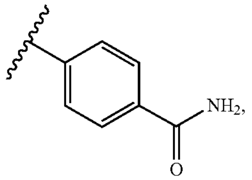,

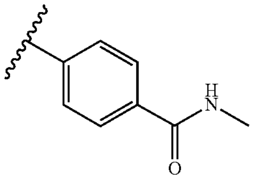, 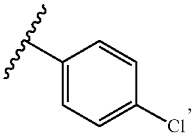,

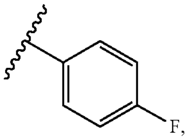, 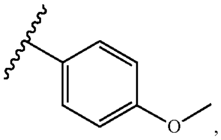,

-continued

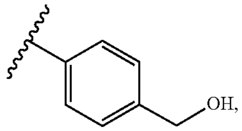, 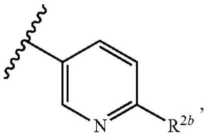,

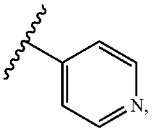, and 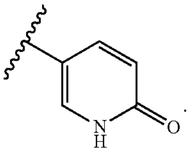.

In some embodiments of Formula (I-B), when $R^4$ is phenyl and n is 0, $R^1$ is selected from the group consisting of

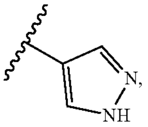, 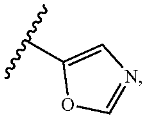, 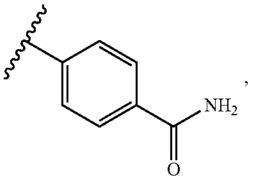,

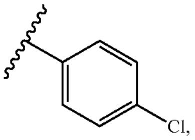, 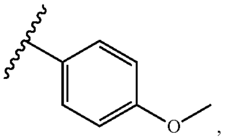,

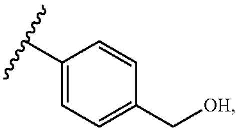, 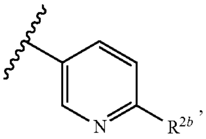, and

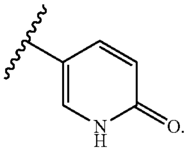

In another aspect, the compound of Formula (II) or Formula (I) is a compound of Formula (I-C):

(I-C)

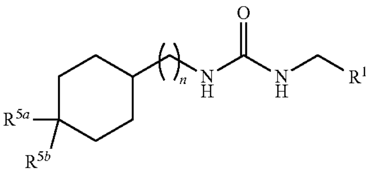

or a salt thereof, wherein $R^1$, $R^{5a}$, $R^{5b}$, and n are as defined for Formula (II) or Formula (I), or any variation or embodiment thereof.

In some embodiments of Formula (I-C), $R^1$ is

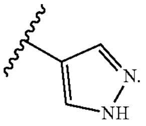 [SMILES: *c1cn[nH]c1]

In some embodiments, $R^1$ is

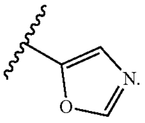 [SMILES: *c1cnco1]

In some embodiments, $R^1$ is

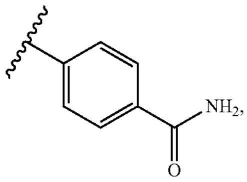

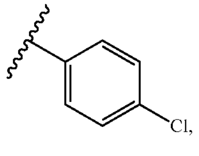

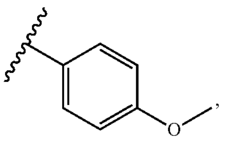

or

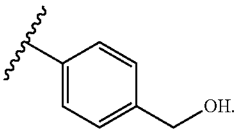

In some embodiments, $R^1$ is

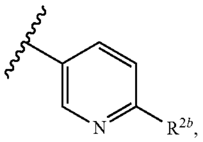

wherein $R^{2b}$ is selected from the group consisting of halo, —O($C_1$-$C_6$ alkyl), $C_1$-$C_6$ alkyl substituted with —OH, —C(O)$NR^{2c}R^{2d}$, and —N($R^{2e}$)C(O)($C_1$-$C_6$ alkyl); and $R^{2c}$, $R^{2d}$, and $R^{2e}$ are each independently hydrogen or $C_1$-$C_6$ alkyl. In some embodiments, $R^1$ is

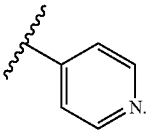 [SMILES: *c1ccncc1]

In some embodiments, $R^1$ is

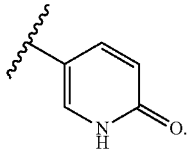

In some embodiments of Formula (I-C), $R^1$ is selected from the group consisting of

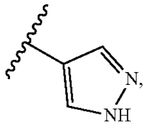

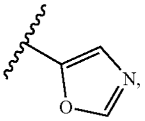

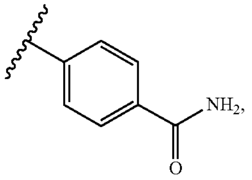

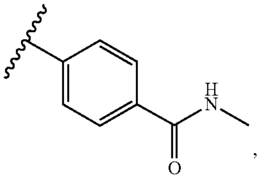

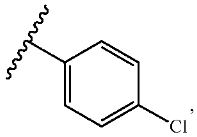

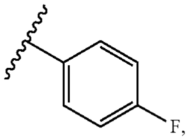

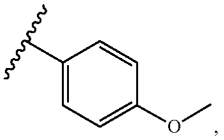

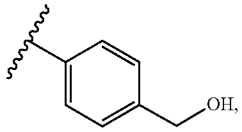

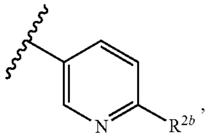

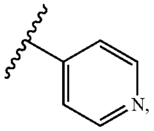

and

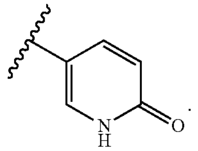

In some embodiments of Formula (I-C), $R^1$ is selected from the group consisting of

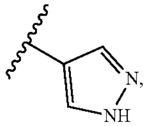

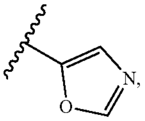

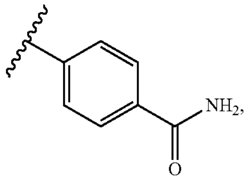

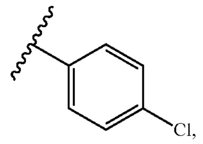

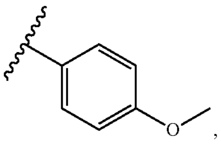

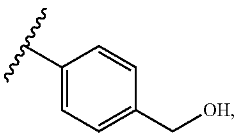

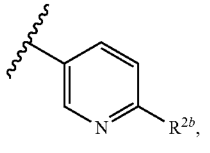

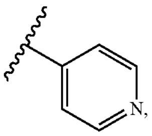

and

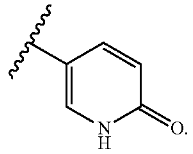 [SMILES: *c1ccc(=O)[nH]c1]

In some embodiments of Formula (I-C), n is 0. In some embodiments, n is 1. In some embodiments, n is 2. In some embodiments, n is 3. In some embodiments, n is 4. In some embodiments, n is 5. In other embodiments, n is 6.

In some embodiments of Formula (I-C), when one of $R^{5a}$ and $R^{5b}$ is H and the other of $R^{5a}$ and $R^{5b}$ is methyl, and n is 0, $R^1$ is selected from the group consisting of

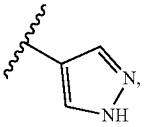 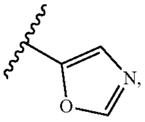 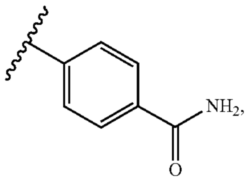

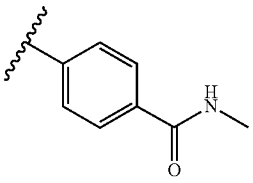 , 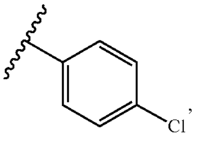 ,

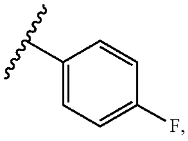 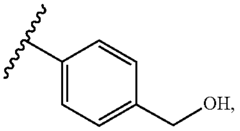

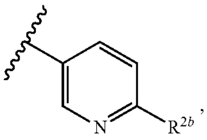 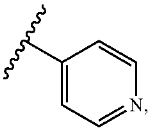 and

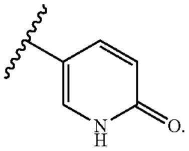

In some embodiments of Formula (I-C), when one of $R^{5a}$ and $R^{5b}$ is H and the other of $R^{5a}$ and $R^{5b}$ is methyl, and n is 0, $R^1$ is selected from the group consisting of

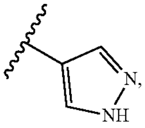 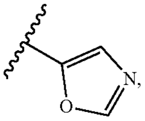 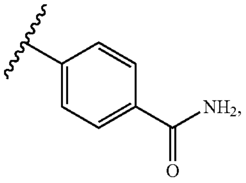

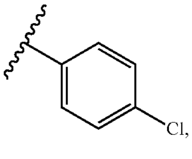 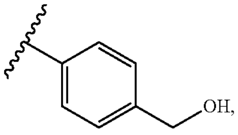

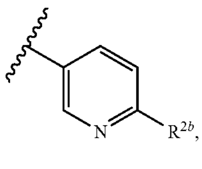 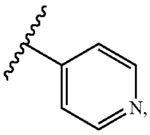 and

-continued

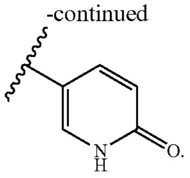

In some embodiments of Formula (I-C), $R^{5a}$ is selected from the group consisting of hydrogen, methyl, and —NHC(O)O($C_1$-$C_6$ alkyl). In some embodiments, $R^{5b}$ is selected from the group consisting of hydrogen, methyl, and —NHC(O)O($C_1$-$C_6$ alkyl). In some embodiments, $R^{5a}$ is hydrogen and $R^{5b}$ is selected from the group consisting of hydrogen, methyl, and —NHC(O)O($C_1$-$C_6$ alkyl). In some embodiments, $R^{5a}$ and $R^{5b}$ are each methyl.

In another aspect, the compound of Formula (II) or Formula (I) is a compound of Formula (I-D):

(I-D)

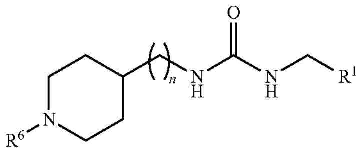

or a salt thereof, wherein $R^1$, $R^6$, and n are as defined for Formula (II) or Formula (I) or any variation or embodiment thereof.

In some embodiments of Formula (I-D), $R^1$ is

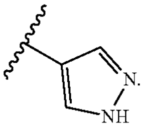 [SMILES: *c1cn[nH]c1]

In some embodiments, $R^1$ is

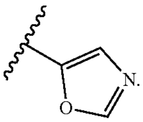 [SMILES: *c1cnco1]

In some embodiments, $R^1$ is

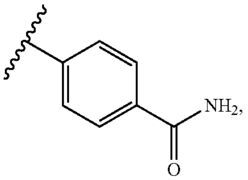 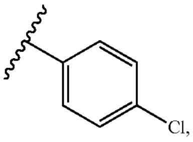

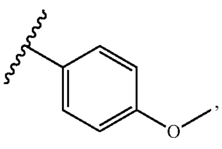 , or 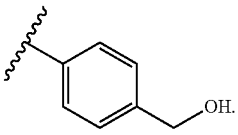

In some embodiments, $R^1$ is

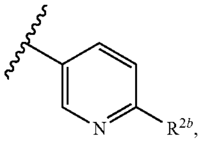

wherein $R^{2b}$ is selected from the group consisting of halo, —O($C_1$-$C_6$ alkyl), $C_1$-$C_6$ alkyl substituted with —OH, —C(O)$NR^{2c}R^{2d}$, and —N($R^{2e}$)C(O)($C_1$-$C_6$ alkyl); and $R^{2c}$, $R^{2d}$, and $R^{2e}$ are each independently hydrogen or $C_1$-$C_6$ alkyl. In some embodiments, $R^1$ is

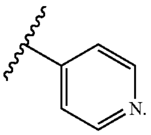 [SMILES: *c1ccncc1]

In some embodiments, $R^1$ is

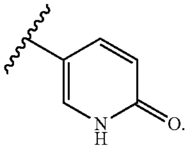

In some embodiments of Formula (I-D), $R^1$ is selected from the group consisting of

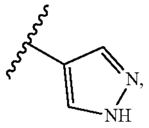 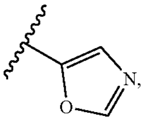 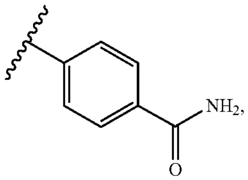

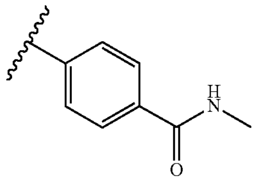 , 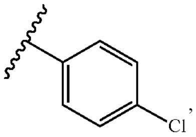 ,

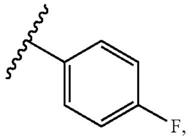 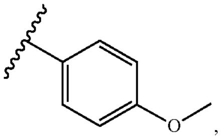 ,

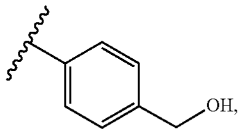 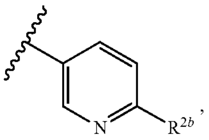 ,

-continued

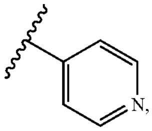 and 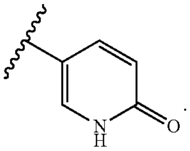 .

In some embodiments of Formula (I-D), $R^1$ is selected from the group consisting of

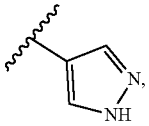 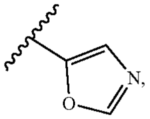 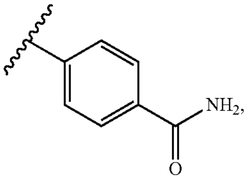

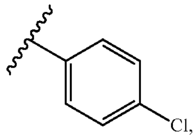 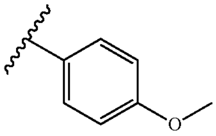 ,

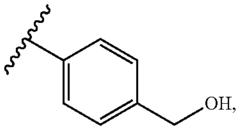 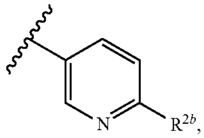

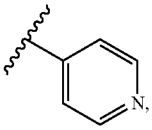 and 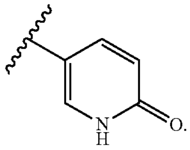 [SMILES: *c1ccc(=O)[nH]c1]

In some embodiments of Formula (I-D), $R^1$ is selected from the group consisting of

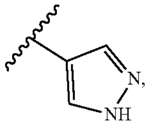 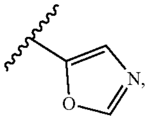 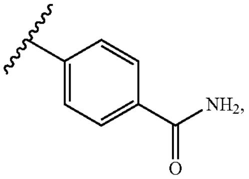

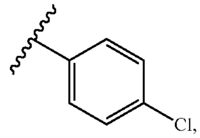 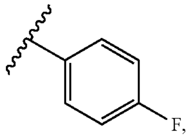

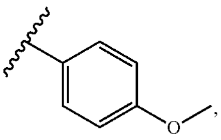 and 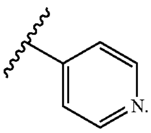

In some embodiments of Formula (I-D), $R^1$ is

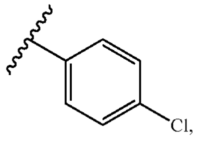

or

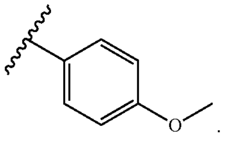

In some embodiments, of Formula (I-D), $R^1$ is

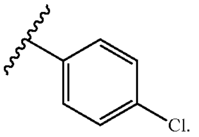

In some embodiments of Formula (I-D), n is 0. In some embodiments, n is 1. In some embodiments, n is 2. In some embodiments, n is 3. In some embodiments, n is 4. In some embodiments, n is 5. In other embodiments, n is 6.

In some embodiments of Formula (I-D), $R^6$ is —C(O)OC$(CH_3)_3$, —NHC(O)O($C_1$-$C_6$ alkyl), —C(O)-(optionally substituted phenyl), —C(O)—($C_1$-$C_6$ alkylene)-(optionally substituted phenyl), —C(O)-(optionally substituted 3- to 18-membered heterocycloalkyl), —C(O)-(optionally substituted 5- to 18-membered heteroaryl), —C(O)—($C_1$-$C_6$ alkylene)-(optionally substituted 5- to 18-membered heteroaryl), and 5- to 18-membered heteroaryl. In some embodiments, $R^6$ is (a) —C(O)OC$(CH_3)_3$; (b) —NHC(O)O($C_1$-$C_6$ alkyl); (c) —C(O)-(phenyl), wherein the phenyl is optionally substituted with one or more substituents independently selected from $C_1$-$C_6$ alkyl, $C_1$-$C_6$ haloalkyl, and 5- to 18-membered heteroaryl; (d) —C(O)—($C_1$-$C_6$ alkylene)-(phenyl), wherein the phenyl is optionally substituted with one or more independently selected $C_1$-$C_6$ alkyl substituents; (e) —C(O)-(3- to 18-membered heterocycloalkyl), wherein the 3- to 18-membered heterocycloalkyl is optionally substituted with one or more independently selected oxo or $C_1$-$C_6$ alkyl substituents; (f) —C(O)-(5- to 18-membered heteroaryl), wherein the 5- to 18-membered heteroaryl is optionally substituted with one or more independently selected $C_1$-$C_6$ alkyl substituents; (g) —C(O)—($C_1$-$C_6$ alkylene)-(5- to 18-membered heteroaryl), wherein the 5- to 18-membered heteroaryl is optionally substituted with one or more independently selected $C_1$-$C_6$ alkyl substituents; or (h) 5- to 18-membered heteroaryl. In some embodiments, $R^6$ is —C(O)-(optionally substituted phenyl). In some embodiments, $R^6$ is —C(O)-(phenyl), wherein the phenyl is optionally substituted with one or more $C_1$-$C_6$ alkyl, $C_1$-$C_6$ haloalkyl, or 5- to 18-membered heteroaryl. In some embodiments, $R^6$ is

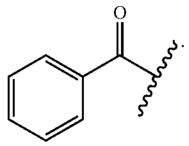 [SMILES: *C(=O)c1ccccc1]

In some embodiments of Formula (I-D), $R^6$ is —C(O)OC$(CH_3)_3$. In some embodiments, $R^6$ is —NHC(O)O($C_1$-$C_6$ alkyl). In some embodiments, $R^6$ is —C(O)—($C_1$-$C_6$ alkylene)-(phenyl), wherein the phenyl is optionally substituted with one or more independently selected $C_1$-$C_6$ alkyl substituents. In some embodiments, $R^6$ is —C(O)-(3- to 18-membered heterocycloalkyl), wherein the 3- to 18-membered heterocycloalkyl is optionally substituted with one or more independently selected oxo or $C_1$-$C_6$ alkyl substituents. In some embodiments, $R^6$ is —C(O)-(5- to 18-membered heteroaryl), wherein the 5- to 18-membered heteroaryl is optionally substituted with one or more independently selected $C_1$-$C_6$ alkyl substituents. In some embodiments, $R^6$ is —C(O)—($C_1$-$C_6$ alkylene)-(5- to 18-membered heteroaryl), wherein the 5- to 18-membered heteroaryl is optionally substituted with one or more independently selected $C_1$-$C_6$ alkyl substituents. In some embodiments, $R^6$ is 5- to 18-membered heteroaryl.

In some embodiments of Formula (I-D), $R^6$ is —C(O)OC$(CH_3)_3$, —NHC(O)O($C_1$-$C_6$ alkyl), or —C(O)-(phenyl), and n is 0-6. In some embodiments of Formula (I-D), $R^6$ is —C(O)-(substituted phenyl), —C(O)—($C_1$-$C_6$ alkylene)-(optionally substituted phenyl), —C(O)-(optionally substituted 3- to 18-membered heterocycloalkyl), —C(O)-(optionally substituted 5- to 18-membered heteroaryl), —C(O)—($C_1$-$C_6$ alkylene)-(optionally substituted 5- to 18-membered heteroaryl), or 5- to 18-membered heteroaryl, and n is 4 or 5. In some embodiments, $R^6$ is

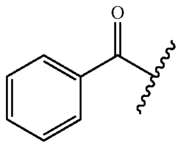 [SMILES: *C(=O)c1ccccc1]

and n is 4 or 5. In some embodiments, $R^6$ is

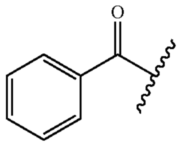 [SMILES: *C(=O)c1ccccc1]

and n is 4. In some embodiments, $R^6$ is

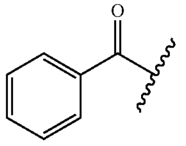 [SMILES: *C(=O)c1ccccc1]

and n is 5.

In some embodiments of Formula (I-D), $R^6$ is —C(O)OC$(CH_3)_3$, —NHC(O)O($C_1$-$C_6$ alkyl), or —C(O)-(phenyl); n is 0-6; and $R^1$ is selected from the group consisting of

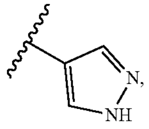

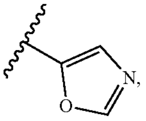

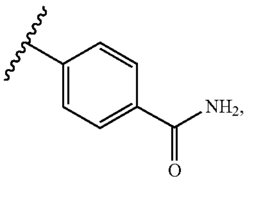

-continued

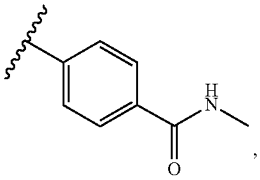, 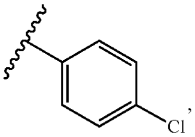, 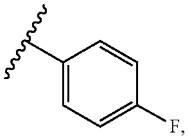 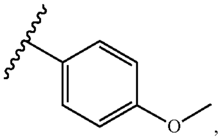, 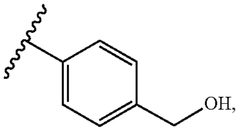 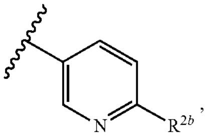, 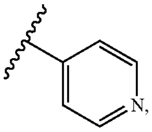 and 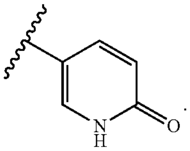.

In some embodiments of Formula (I-D), $R^6$ is —C(O)OC$(CH_3)_3$, —NHC(O)O($C_1$-$C_6$ alkyl), or —C(O)-(phenyl); n is 0-6; and $R^1$ is selected from the group consisting of

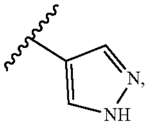 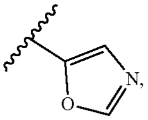 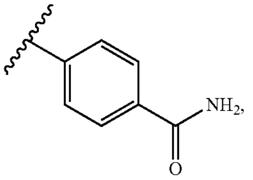 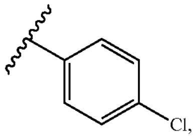 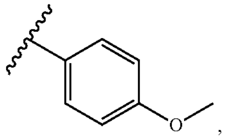, 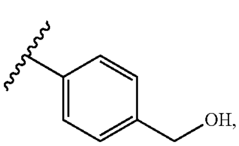 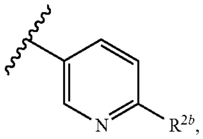 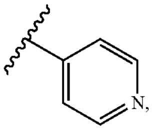 and 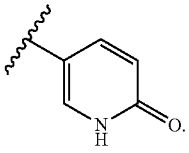

In some embodiments of Formula (I-D), $R^6$ is —C(O)-(substituted phenyl), —C(O)—($C_1$-$C_6$ alkylene)-(optionally substituted phenyl), —C(O)-(optionally substituted 3- to 18-membered heterocycloalkyl), —C(O)-(optionally substituted 5- to 18-membered heteroaryl), —C(O)—($C_1$-$C_6$ alkylene)-(optionally substituted 5- to 18-membered heteroaryl), or 5- to 18-N membered heteroaryl; n is 4 or 5; and $R^1$ is selected from the group consisting of

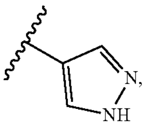 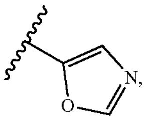 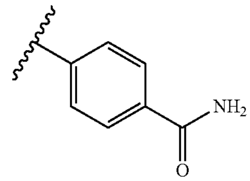, 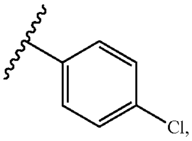 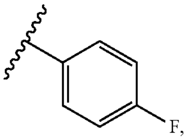 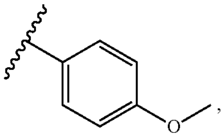, and 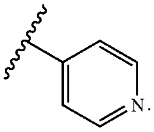

In some embodiments of Formula (I-D), $R^6$ is —C(O)-(substituted phenyl), —C(O)—($C_1$-$C_6$ alkylene)-(optionally substituted phenyl), —C(O)-(optionally substituted 3- to 18-membered heterocycloalkyl), —C(O)-(optionally substituted 5- to 18-membered heteroaryl), —C(O)—($C_1$-$C_6$ alkylene)-(optionally substituted 5- to 18-membered heteroaryl), or 5- to 18-membered heteroaryl; n is 4 or 5; and $R^1$ is selected from the group consisting of

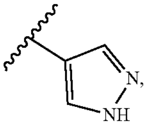 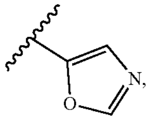 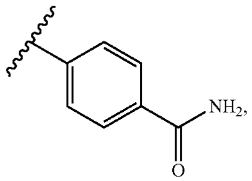 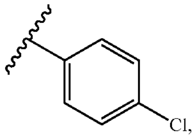 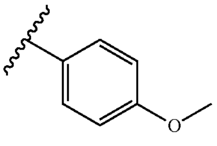, and 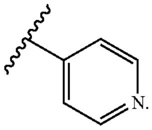

In another aspect, the compound of Formula (II) or Formula (I) is a compound of Formula (I-E):

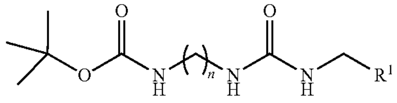 (I-E)

or a salt thereof, wherein $R^1$ and n are as defined for Formula (II) or Formula (I) or any variation or embodiment thereof.

In some embodiments of Formula (I-E), $R^1$ is

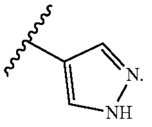 [SMILES: *c1cn[nH]c1]

In some embodiments, $R^1$ is

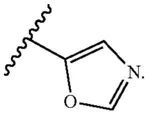 [SMILES: *c1cnco1]

In some embodiments, $R^1$ is

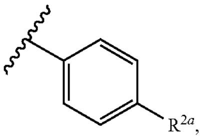

wherein $R^{2a}$ is selected from the group consisting of halo, —O($C_1$-$C_6$ alkyl), $C_1$-$C_6$ alkyl substituted with —OH, —C(O)NR$^{2c}$R$^{2d}$, and —N(R$^{2e}$)C(O)($C_1$-$C_6$ alkyl); and $R^{2c}$, $R^{2d}$, and $R^{2e}$ are each independently hydrogen or $C_1$-$C_6$ alkyl. In some embodiments, $R^1$ is

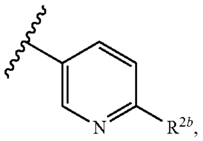

wherein $R^{2b}$ is selected from the group consisting of halo, —O($C_1$-$C_6$ alkyl), $C_1$-$C_6$ alkyl substituted with —OH, —C(O)NR$^{2c}$R$^{2d}$, and —N(R$^{2e}$)C(O)($C_1$-$C_6$ alkyl); and $R^{2c}$, $R^{2d}$, and $R^{2e}$ are each independently hydrogen or $C_1$-$C_6$ alkyl. In some embodiments, $R^1$ is

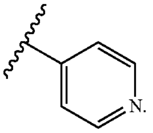 [SMILES: *c1ccncc1]

In some embodiments, $R_1$ is

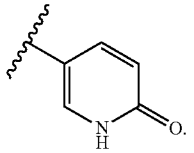 [SMILES: *c1ccc(=O)[nH]c1]

In some embodiments of Formula (I-E), n is 4. In some embodiments, n is 5. In other embodiments, n is 6.

In another aspect, the compound of Formula (II) or Formula (I) is a compound of Formula (I-F):

(I-F)

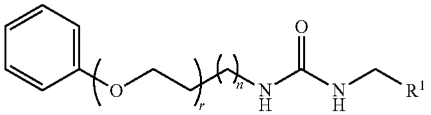

or a salt thereof, wherein $R^1$, n, and r are as defined for Formula (II) or Formula (I) or any variation or embodiment thereof.

In some embodiments of Formula (I-F), $R^1$ is

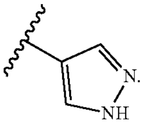 [SMILES: *c1cn[nH]c1]

In some embodiments, $R^1$ is

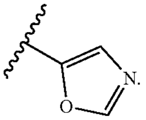 [SMILES: *c1cnco1]

In some embodiments, $R^1$ is

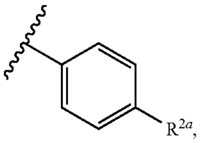

wherein $R^{2a}$ is selected from the group consisting of halo, —O($C_1$-$C_6$ alkyl), $C_1$-$C_6$ alkyl substituted with —OH, —C(O)NR$^{2c}$R$^{2d}$, and —N(R$^{2e}$)C(O)($C_1$-$C_6$ alkyl); and $R^{2c}$, $R^{2d}$, and $R^{2e}$ are each independently hydrogen or $C_1$-$C_6$ alkyl. In some embodiments, $R^1$ is

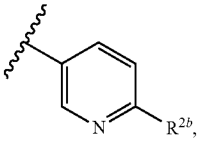

wherein $R^{2b}$ is selected from the group consisting of halo, —O($C_1$-$C_6$ alkyl), $C_1$-$C_6$ alkyl substituted with —OH, —C(O)NR$^{2c}$R$^{2d}$, and —N(R$^{2e}$)C(O)($C_1$-$C_6$ alkyl); and $R^{2c}$, $R^{2d}$, and $R^{2e}$ are each independently hydrogen or $C_1$-$C_6$ alkyl. In some embodiments, $R^1$ is

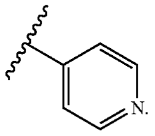 [SMILES: *c1ccncc1]

In some embodiments, $R^1$ is

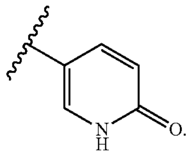 [SMILES: *c1ccc(=O)[nH]c1]

In some embodiments of Formula (I-F), r is 1. In some embodiments, r is 2. In other embodiments, r is 3.

In some embodiments of Formula (I-F), n is 0. In some embodiments, n is 1. In some embodiments, n is 2. In some embodiments, n is 3. In some embodiments, n is 4. In some embodiments, n is 5. In other embodiments, n is 6. n is 4. In some embodiments, n is 5. In other embodiments, n is 6.

In some embodiments of Formula (I-F), r is 1 and n is 2, 3, 4, 5, or 6. In some embodiments, r is 2 and n is 0, 1, 2, 3, 4, 5, or 6. In other embodiments, r is 3 and n is 0, 1, 2, 3, 4, 5, or 6.

In another aspect, the compound of Formula (II) is a compound of Formula (I-G):

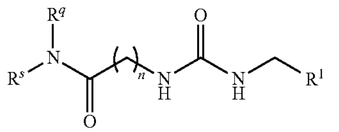
(I-G)

or a salt thereof, wherein $R^1$, $R^q$, $R^s$, and n are as defined for Formula (II) or any variation or embodiment thereof.

In some embodiments of Formula (I-G), $R^q$ is H or $C_1$-$C_6$ alkyl, and $R^s$ is $C_3$-$C_8$ cycloalkyl, optionally substituted $C_6$-$C_{14}$ aryl, optionally substituted 5- to 18-membered heteroaryl, or —($C_1$-$C_6$ alkylene)-(optionally substituted $C_6$-$C_{14}$ aryl). In some embodiments, $R^q$ is H. In some embodiments, $R^q$ is $C_1$-$C_6$ alkyl. In some embodiments, $R^q$ is methyl. In some embodiments, $R^s$ is $C_3$-$C_8$ cycloalkyl. In some embodiments, $R^s$ is cyclopentyl or cyclohexyl. In some embodiments of Formula (II), $Y^1$ is

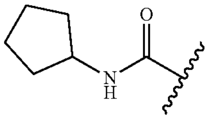 or 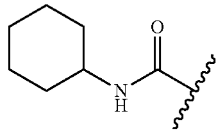

In some embodiments, $R^s$ is optionally substituted $C_6$-$C_{14}$ aryl. In some embodiments, $R^s$ is $C_6$-$C_{14}$ aryl optionally substituted with one or more substituents independently selected from halo, $C_1$-$C_6$ alkyl, and $C_6$-$C_{14}$ aryl. In some embodiments of Formula (II), $Y^1$ is

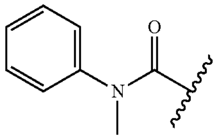, 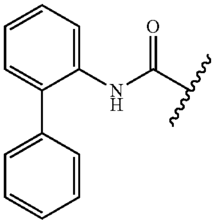,

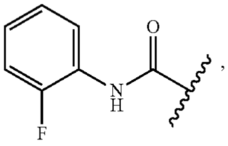, 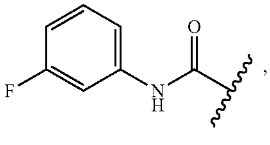,

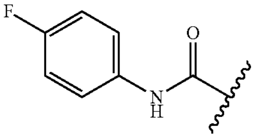, 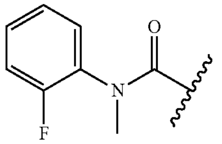,

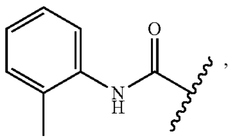, 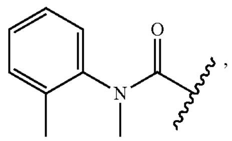, or

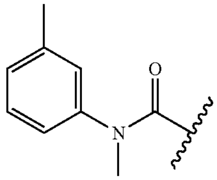

In some embodiments, $R^s$ is optionally substituted 5- to 18-membered heteroaryl. In some embodiments, $R^s$ is 5- to 18-membered heteroaryl optionally substituted with one or more $C_1$-$C_6$ alkyl. In some embodiments, $R^s$ is pyridinyl optionally substituted with one or more $C_1$-$C_6$ alkyl. In some embodiments of Formula (II), $Y^1$ is

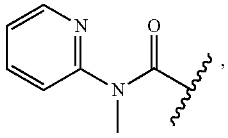, 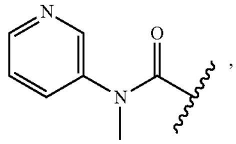,

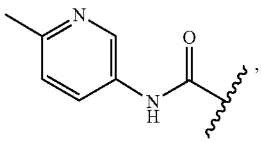, 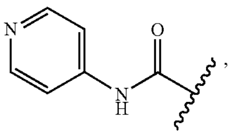, or

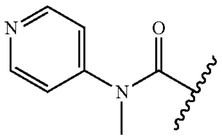

In some embodiments, $R^s$ is —($C_1$-$C_6$ alkylene)-(optionally substituted $C_6$-$C_{14}$ aryl). In some embodiments, —($C_1$-$C_6$ alkylene)-($C_6$-$C_{14}$ aryl), wherein the $C_6$-$C_{14}$ aryl of the —($C_1$-$C_6$ alkylene)-($C_6$-$C_{14}$ aryl) is optionally substituted with one or more $C_1$-$C_6$ alkyl. In some embodiments, $R^s$ is, —($C_1$-$C_6$ alkylene)-(phenyl), wherein the phenyl of the —($C_1$-$C_6$ alkylene)-(phenyl) is optionally substituted with one or more $C_1$-$C_6$ alkyl. In some embodiments of Formula (II), $Y^1$ is

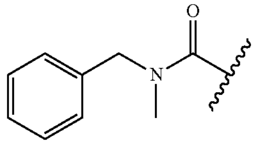

or

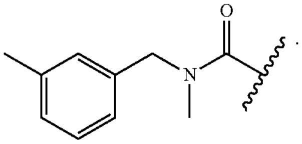

.

In some embodiments of Formula (II), $Y^1$ is

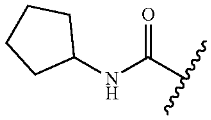

,

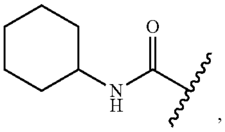

,

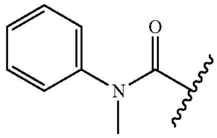

,

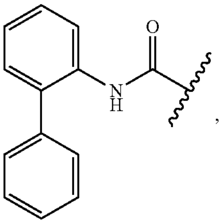

,

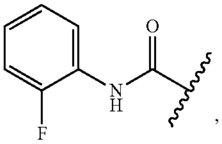

,

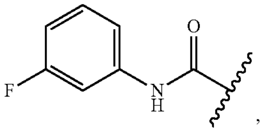

,

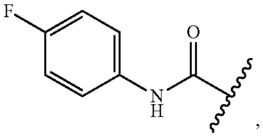

,

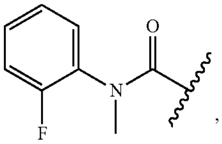

,

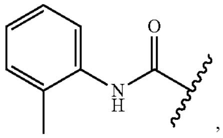

,

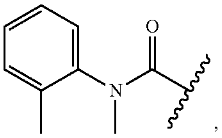

,

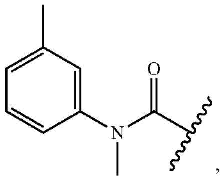

,

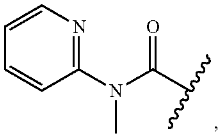

,

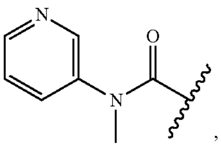

,

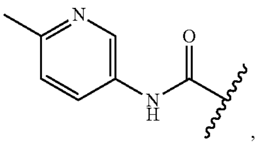

,

-continued

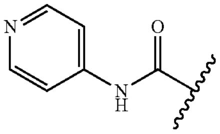

,

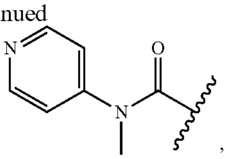

,

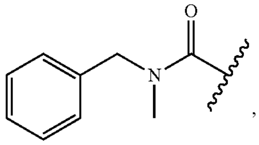

, or

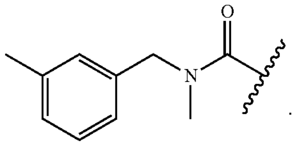

.

In some embodiments of Formula (I-G), $R^1$ is selected from the group consisting of

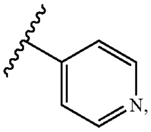

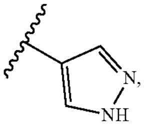

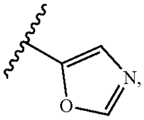

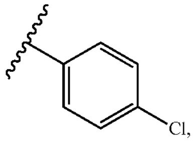

and

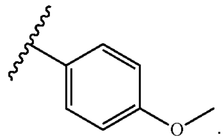 [SMILES: *c1ccc(OC)cc1]

.

In some embodiments, $R^1$ is

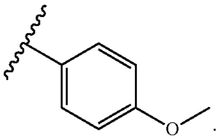

.

In some embodiments of Formula (I-G), n is 4 or 5. In some embodiments, n is 4. In some embodiments, n is 5.

In another aspect, provided herein is a compound of Formula (I-H):

(I-H)

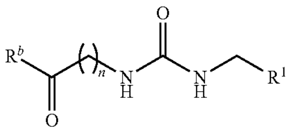

or a salt thereof, wherein $R^1$, $R^b$, and n are as defined for Formula (II), or any variation or embodiment thereof.

In some embodiments of Formula (I-H), $R^b$ is optionally substituted 3- to 18-membered heterocycloalkyl. In some embodiments, $R^b$ is 3- to 18-membered heterocycloalkyl optionally substituted with one or more $C_1$-$C_6$ alkyl, wherein the $C_1$-$C_6$ alkyl is optionally substituted with one or more —OH. In some embodiments, $R^b$ is 6- to 10-membered heterocycloalkyl optionally substituted with one or more $C_1$-$C_6$ alkyl, wherein the $C_1$-$C_6$ alkyl is optionally substituted with one or more —OH. In some embodiments, $R^b$ is 1,2,3,4-tetrahydroquinolinyl, morpholinyl, or piperazinyl, each independently optionally substituted with one or more $C_1$-$C_6$ alkyl, wherein the $C_1$-$C_6$ alkyl is optionally substituted with one or more —OH. In some embodiments of Formula (II), $Y^1$ is

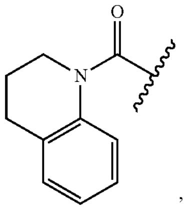
,
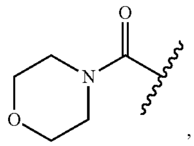
,
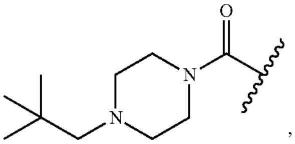
, or
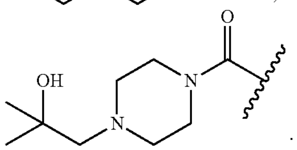
.

In some embodiments of Formula (I-H), $R^1$ is

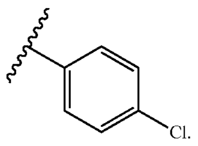 [SMILES: *c1ccc(Cl)cc1]

In some embodiments of Formula (I-H), n is 4 or 5. In some embodiments, n is 4. In some embodiments, n is 5.

In another aspect, provided herein is a compound of Formula (I-J):

(I-J)

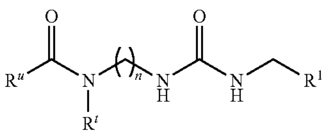

or a salt thereof, wherein $R^1$, $R^t$, $R^u$, and n are as defined herein for Formula (II), or any variation or embodiment thereof.

In some embodiments of Formula (I-J), $R^t$ is H or $C_1$-$C_6$ alkyl. In some embodiments, $R^t$ is H. In some embodiments, $R^t$ is $C_1$-$C_6$ alkyl. In some embodiments, $R^t$ is methyl. In some embodiments, $R^u$ is optionally substituted $C_6$-$C_{14}$ aryl, optionally substituted 5- to 18-membered heteroaryl, or —($C_1$-$C_6$ alkylene)-(5- to 18-membered heteroaryl). In some embodiments, $R^u$ is (a) $C_6$-$C_{14}$ aryl optionally substituted with one or more independently selected $C_1$-$C_6$ alkyl or halo substituents; (b) 5- to 18-membered heteroaryl optionally substituted with one or more independently selected $C_1$-$C_6$ alkyl substituents; or (c) —($C_1$-$C_6$ alkylene)-(5- to 18-membered heteroaryl). In some embodiments, $R^u$ is $C_6$-$C_{14}$ aryl optionally substituted with one or more independently selected halo substituents. In some embodiments, $R^u$ is phenyl optionally substituted with one or more independently selected $C_1$-$C_6$ alkyl or halo substituents. In some embodiments of Formula (II), $Y^1$ is

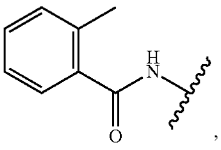
,
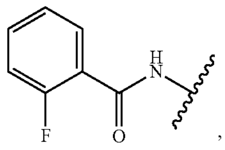
, or
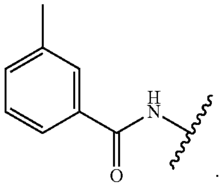
.

In some embodiments, $R^u$ is 5- to 18-membered heteroaryl optionally substituted with one or more independently selected $C_1$-$C_6$ alkyl substituents. In some embodiments, $R^u$ is 5- to 6-membered heteroaryl optionally substituted with one or more independently selected $C_1$-$C_6$ alkyl substituents. In some embodiments, $R^u$ is pyridinyl optionally substituted with one or more independently selected $C_1$-$C_6$ alkyl substituents. In some embodiments of Formula (II), $Y^1$ is

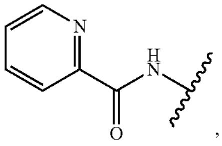
,
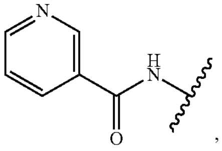
,
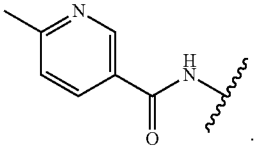
.

In some embodiments, $R^u$ is —($C_1$-$C_6$ alkylene)-(5- to 18-membered heteroaryl). In some embodiments, $R^u$ is —($C_1$-$C_6$ alkylene)-(pyridinyl). In some embodiments of Formula (II), $Y^1$ is

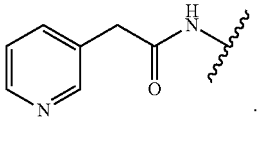
.

In some embodiments of Formula (II), $Y^1$ is

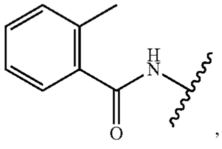
,
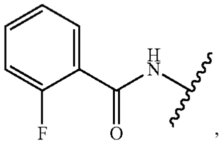
,

-continued

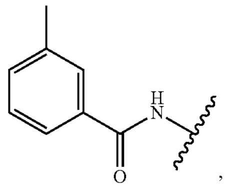
,
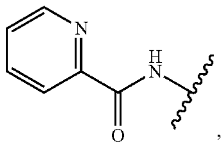
,
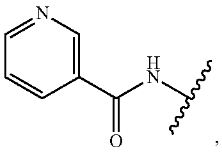
,
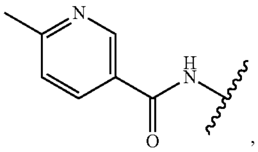
, or
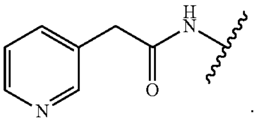 [SMILES: *NC(=O)Cc1cccnc1]
.

In some embodiments of Formula (I-J), $R^1$ is

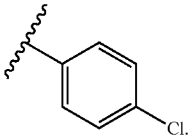 [SMILES: *c1ccc(Cl)cc1]

In some embodiments of Formula (I-J), n is 4 or 5. In some embodiments, n is 4. In some embodiments, n is 5.

In one aspect, provided herein is a compound of Formula (I-K):

(I-K)

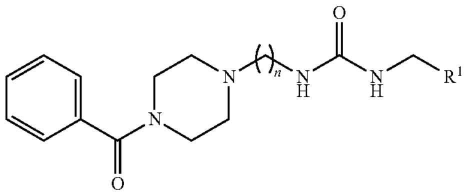

or a salt thereof, wherein $R^1$ and n are as defined herein for Formula (II), or any variation or embodiment thereof.

In some embodiments of Formula (I-K), $R^1$ is

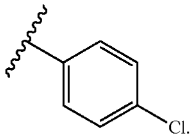 [SMILES: *c1ccc(Cl)cc1]

In some embodiments of Formula (I-K), n is 4 or 5. In some embodiments, n is 4. In some embodiments, n is 5.

In some embodiments, provided herein are compounds, and salts thereof, described in Table 1.

TABLE 1

| Compound No. | Structure | Name |
|---|---|---|
| 1 | 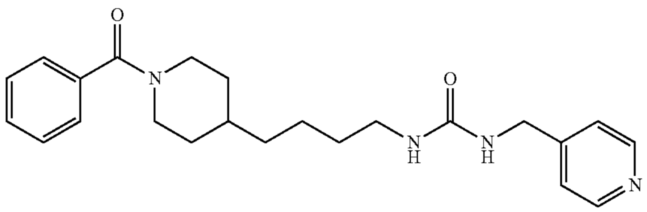 [SMILES: O=C(NCCCCC1CCN(C(=O)c2ccccc2)CC1)NCc1ccncc1] | 1-(4-(1-benzoylpiperidin-4-yl)butyl)-3-(pyridin-4-ylmethyl)urea |
| 2 | 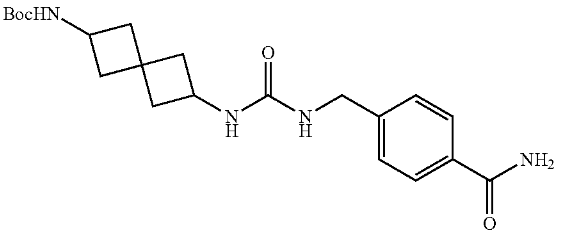 [SMILES: CC(C)(C)OC(=O)NC1CC2(CC(NC(=O)NCc3ccc(C(N)=O)cc3)C2)C1] | tert-butyl (6-(3-(4-carbamoylbenzyl)ureido)spiro[3.3]heptan-2-yl)carbamate |
| 3 | 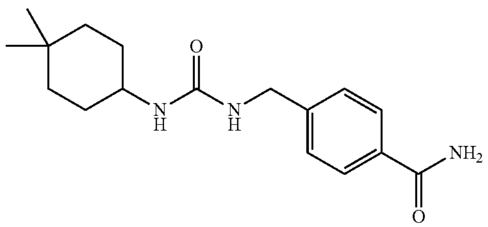 [SMILES: CC1(C)CCC(NC(=O)NCc2ccc(C(N)=O)cc2)CC1] | 4-((3-(4,4-dimethylcyclohexyl)ureido)methyl)benzamide |

TABLE 1-continued

| Compound No. | Structure | Name |
| --- | --- | --- |
| 4 | 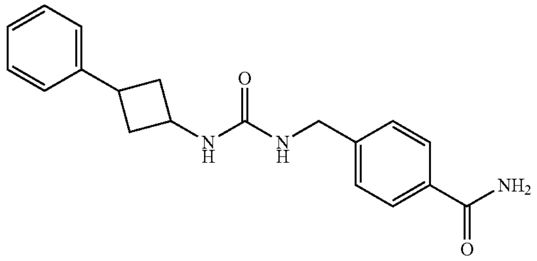 [SMILES: NC(=O)c1ccc(CNC(=O)NC2CC(c3ccccc3)C2)cc1] | 4-((3-(3-phenylcyclobutyl)ureido)methyl)benzamide |
| 5 | 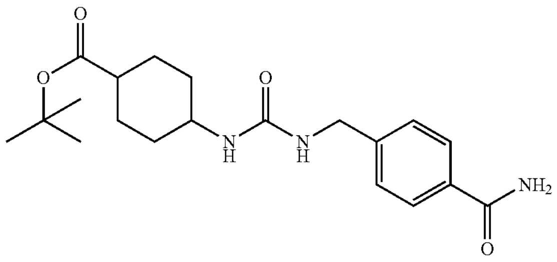 [SMILES: CC(C)(C)OC(=O)C1CCC(NC(=O)NCc2ccc(C(N)=O)cc2)CC1] | tert-butyl 4-(3-(4-carbamoylbenzyl)ureido)piperidine-1-carboxylate |
| 6 | 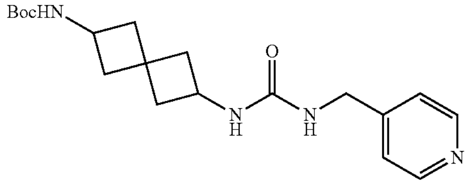 [SMILES: CC(C)(C)OC(=O)NC1CC2(CC(NC(=O)NCc3ccncc3)C2)C1] | tert-butyl (6-(3-(pyridin-4-ylmethyl)ureido)spiro[3.3]heptan-2-yl)carbamate |
| 7 | 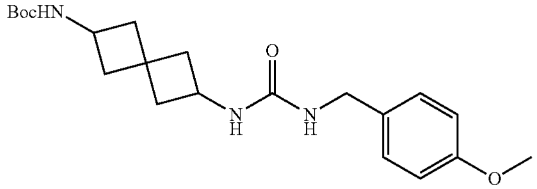 [SMILES: COc1ccc(CNC(=O)NC2CC3(C2)CC(NC(=O)OC(C)(C)C)C3)cc1] | tert-butyl (6-(3-(4-methoxybenzyl)ureido)spiro[3.3]heptan-2-yl)carbamate |
| 8 | 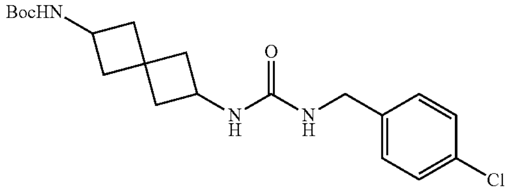 [SMILES: CC(C)(C)OC(=O)NC1CC2(CC(NC(=O)NCc3ccc(Cl)cc3)C2)C1] | tert-butyl (6-(3-(4-chlorobenzyl)ureido)spiro[3.3]heptan-2-yl)carbamate |
| 9 | 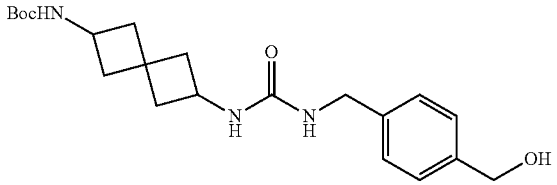 [SMILES: CC(C)(C)OC(=O)NC1CC2(CC(NC(=O)NCc3ccc(CO)cc3)C2)C1] | tert-butyl (6-(3-(4-(hydroxymethyl)benzyl)ureido)spiro[3.3]heptan-2-yl)carbamate |
| 10 | 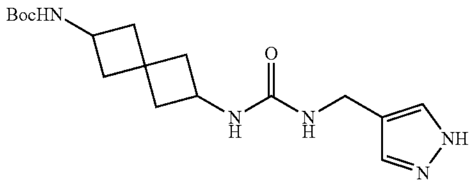 [SMILES: CC(C)(C)OC(=O)NC1CC2(CC(NC(=O)NCc3cn[nH]c3)C2)C1] | terr-butyl (6-(3-((1H-pyrazol-4-yl)methyl)ureido)spiro[3.3]heptan-2-yl)carbamate |

TABLE 1-continued

| Compound No. | Structure | Name |
|---|---|---|
| 11 | 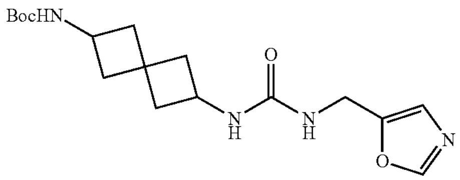 [SMILES: CC(C)(C)OC(=O)NC1CC2(CC(NC(=O)NCc3cnco3)C2)C1] | tert-butyl (6-(3-(oxazol-5-ylmethyl)ureido)spiro[3.3]heptan-2-yl)carbamate |
| 12 | 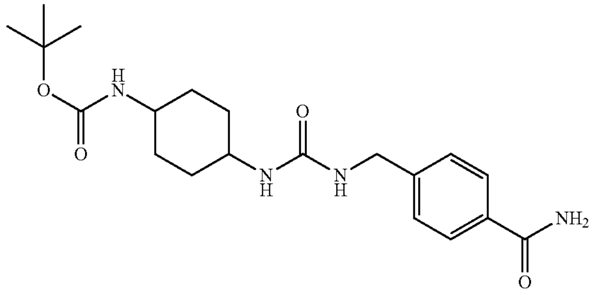 [SMILES: CC(C)(C)OC(=O)NC1CCC(NC(=O)NCc2ccc(C(N)=O)cc2)CC1] | tert-butyl (4-(3-(4-carbamoylbenzyl)ureido)cyclohexyl)carbamate |
| 13 | 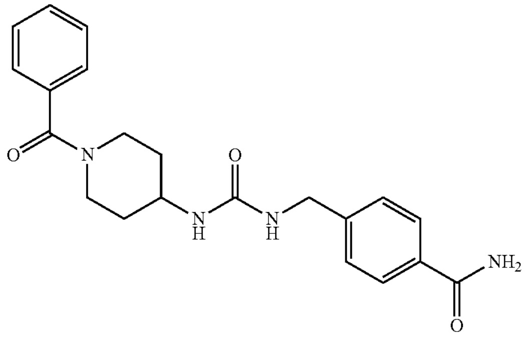 [SMILES: NC(=O)c1ccc(CNC(=O)NC2CCN(C(=O)c3ccccc3)CC2)cc1] | 4-((3-(1-benzoylpiperidin-4-yl)ureido)methyl)benzamide |
| 14 | 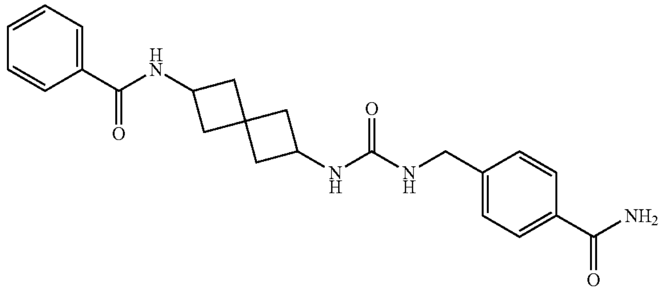 [SMILES: NC(=O)c1ccc(CNC(=O)NC2CC3(C2)CC(NC(=O)c2ccccc2)C3)cc1] | N-(6-(3-(4-carbamoylbenzyl)ureido)spiro[3.3]heptan-2-yl)benzamide |
| 15 | 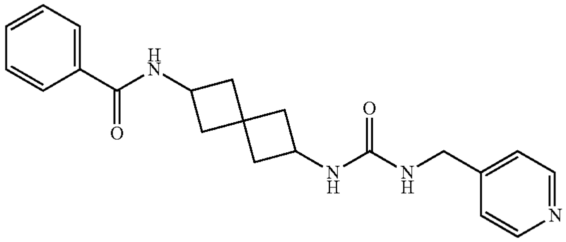 [SMILES: O=C(NCc1ccncc1)NC1CC2(C1)CC(NC(=O)c1ccccc1)C2] | N-(6-(3-(pyridin-4-ylmethyl)ureido)spiro[3.3]heptan-2-yl)benzamide |
| 16 | 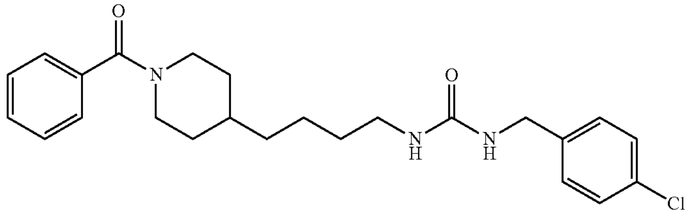 [SMILES: O=C(NCCCCC1CCN(C(=O)c2ccccc2)CC1)NCc1ccc(Cl)cc1] | 1-(4-(1-benzoylpiperidin-4-yl)butyl)-3-(4-chlorobenzyl)urea |

TABLE 1-continued

| Compound No. | Structure | Name |
|---|---|---|
| 17 | 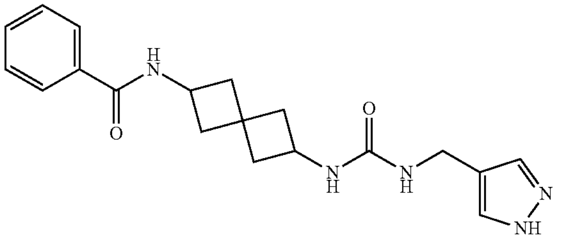 [SMILES: O=C(NCc1cn[nH]c1)NC1CC2(C1)CC(NC(=O)c1ccccc1)C2] | N-(6-(3-((1H-pyrazol-4-yl)methyl)ureido)spiro[3.3]heptan-2-yl)benzamide |
| 18 | 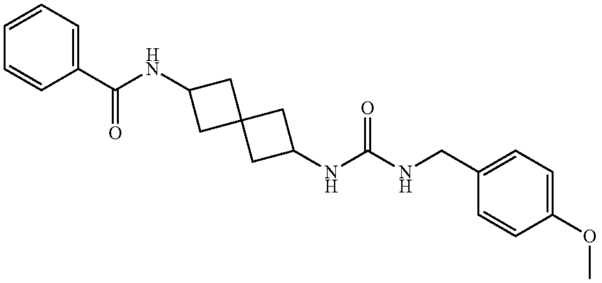 [SMILES: COc1ccc(CNC(=O)NC2CC3(C2)CC(NC(=O)c2ccccc2)C3)cc1] | N-(6-(3-(4-methoxybenzyl)ureido)spiro[3.3]heptan-2-yl)benzamide |
| 19 | 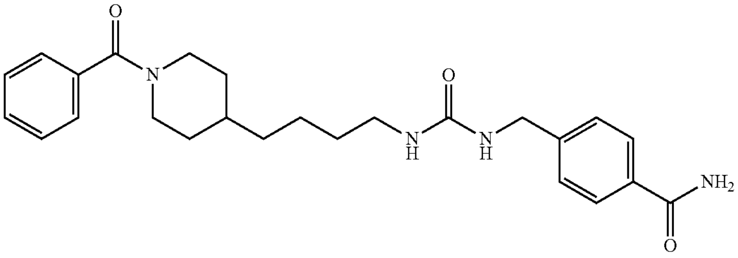 [SMILES: NC(=O)c1ccc(CNC(=O)NCCCCC2CCN(C(=O)c3ccccc3)CC2)cc1] | 4-((3-(4-(1-benzoylpiperidin-4-yl)butyl)ureido)methyl)benzamide |
| 20 | 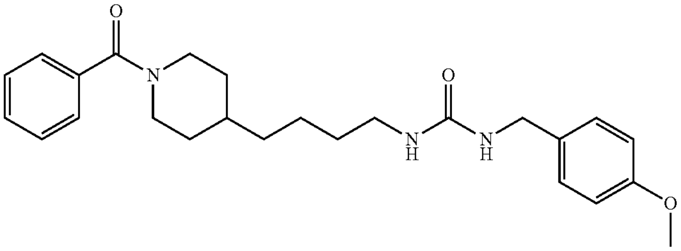 [SMILES: COc1ccc(CNC(=O)NCCCCC2CCN(C(=O)c3ccccc3)CC2)cc1] | 1-(4-(1-benzoylpiperidin-4-yl)butyl)-3-(4-methoxybenzyl)urea |
| 21 | 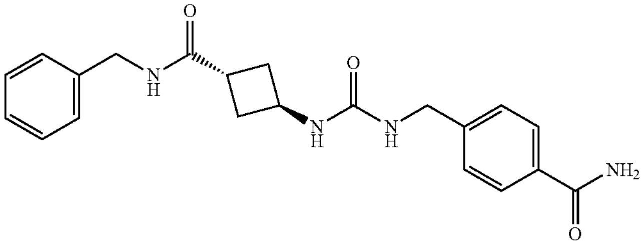 [SMILES: NC(=O)c1ccc(CNC(=O)N[C@H]2C[C@H](C(=O)NCc3ccccc3)C2)cc1] | 4-((3-((1r,3r)-3-(benzylcarbamoyl)cyclobutyl)ureido)methyl)benzamide |
| 22 | 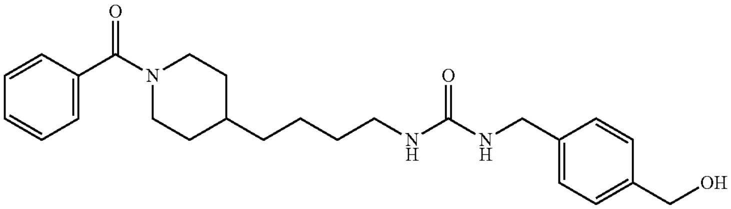 [SMILES: O=C(NCCCCC1CCN(C(=O)c2ccccc2)CC1)NCc1ccc(CO)cc1] | 1-(4-(1-benzylpiperidin-4-yl)butyl)-3-(4-(hydroxymethyl)benzyl)urea |

TABLE 1-continued

| Compound No. | Structure | Name |
|---|---|---|
| 23 | 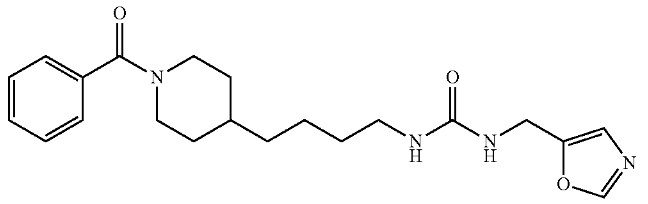 [SMILES: O=C(NCCCCC1CCN(C(=O)c2ccccc2)CC1)NCc1cnco1] | 1-(4-(1-benzoylpiperidin-4-yl)butyl)-3-(oxazol-5-ylmethyl)urea |
| 24 | 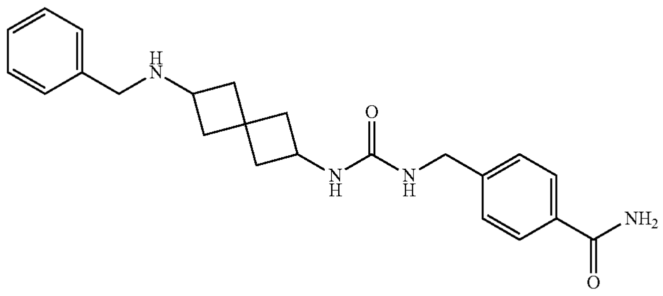 [SMILES: NC(=O)c1ccc(CNC(=O)NC2CC3(CC(NCc4ccccc4)C3)C2)cc1] | 4-((3-(6-(benzylamino)spiro[3.3]heptan-2-yl)ureido)methyl)benzamide |
| 25 | 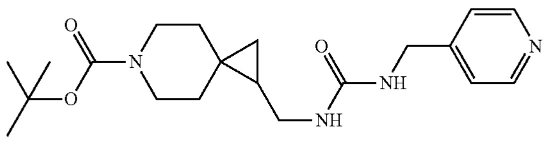 [SMILES: CC(C)(C)OC(=O)N1CCC2(CC1)CC2CNC(=O)NCc1ccncc1] | tert-butyl 1-((3-(pyridin-4-ylmethyl)ureido)methyl)-6-azaspiro[2.5]octane-6-carboxylate |
| 26 | 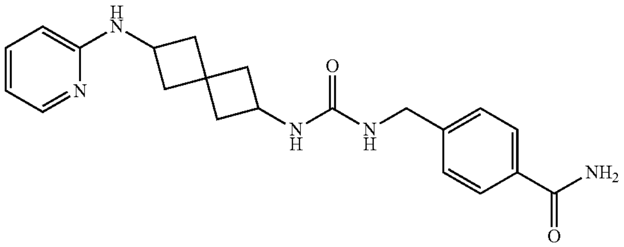 [SMILES: NC(=O)c1ccc(CNC(=O)NC2CC3(C2)CC(Nc2ccccn2)C3)cc1] | 4-((3-(6-(pyridin-2-ylamino)spiro[3.3]heptan-2-yl)ureido)methyl)benzamide |
| 27 | 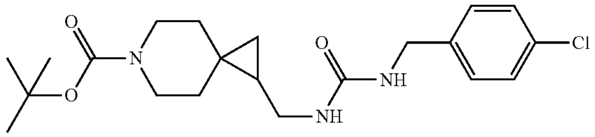 [SMILES: CC(C)(C)OC(=O)N1CCC2(CC1)CC2CNC(=O)NCc1ccc(Cl)cc1] | tert-butyl 1-((3-(4-chlorobenzyl)ureido)methyl)-6-azaspiro[2.5]octane-6-carboxylate |
| 28 | 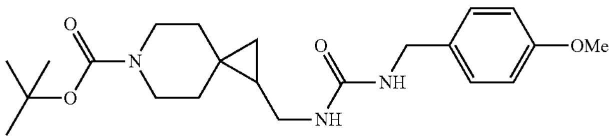 [SMILES: COc1ccc(CNC(=O)NCC2CC23CCN(C(=O)OC(C)(C)C)CC3)cc1] | tert-butyl 1-((3-(4-methoxybenzyl)ureido)methyl)-6-azaspiro[2.5]octane-6-carboxylate |
| 29 | 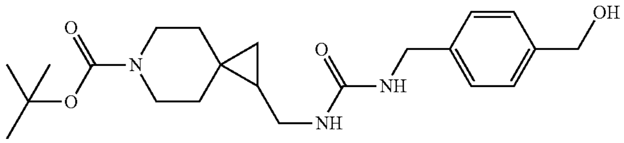 [SMILES: CC(C)(C)OC(=O)N1CCC2(CC1)CC2CNC(=O)NCc1ccc(CO)cc1] | tert-butyl 1-((3-(4-(hydroxymethyl)benzyl)ureido)methyl)-6-azaspiro[2.5]octane-6-carboxylate |
| 30 | 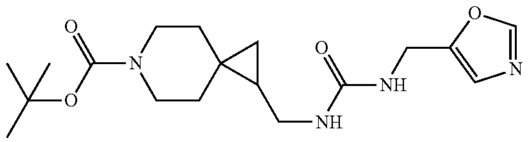 [SMILES: CC(C)(C)OC(=O)N1CCC2(CC1)CC2CNC(=O)NCc1cnco1] | tert-butyl 1-((3-(oxazol-5-ylmethyl)ureido)methyl)-6-azaspiro[2.5]octane-6-carboxylate |

TABLE 1-continued

| Compound No. | Structure | Name |
|---|---|---|
| 31 | 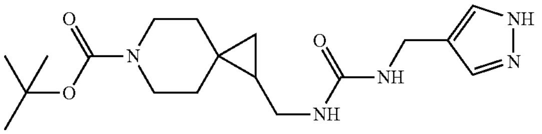 [SMILES: CC(C)(C)OC(=O)N1CCC2(CC1)CC2CNC(=O)NCc1cn[nH]c1] | tert-butyl 1-((3-((1H-pyrazol-4-yl)methyl)ureido)methyl)-6-azaspiro[2.5]octane-6-carboxylate |
| 32 | 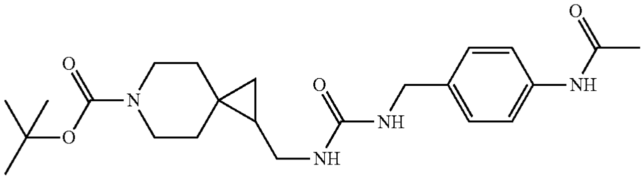 [SMILES: CC(=O)Nc1ccc(CNC(=O)NCC2CC23CCN(C(=O)OC(C)(C)C)CC3)cc1] | tert-butyl 1-((3-(4-acetamidobenzyl)ureido)methyl)-6-azaspiro[2.5]octane-6-carboxylate |
| 33 | 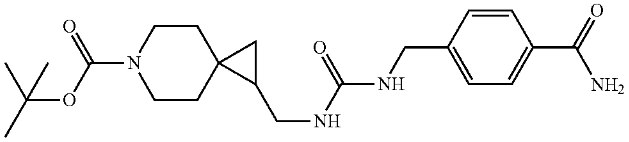 [SMILES: CC(C)(C)OC(=O)N1CCC2(CC1)CC2CNC(=O)NCc1ccc(C(N)=O)cc1] | tert-butyl 1-((3-(4-carbamoylbenzyl)ureido)methyl)-6-azaspiro[2.5]octane-6-carboxylate |
| 34 | 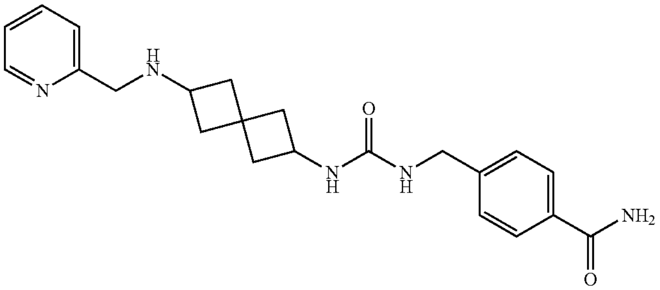 [SMILES: NC(=O)c1ccc(CNC(=O)NC2CC3(CC(NCc4ccccn4)C3)C2)cc1] | 4-((3-(6-((pyridin-2-ylmethyl)amino)spiro[3.3]heptan-2-yl)ureido)methyl)benzamide |
| 35 | 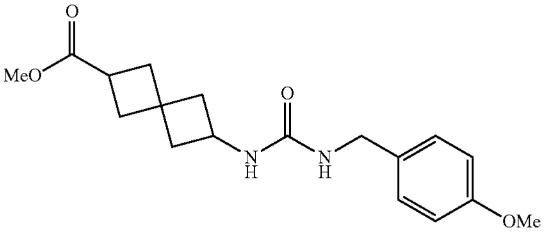 [SMILES: COC(=O)C1CC2(CC(NC(=O)NCc3ccc(OC)cc3)C2)C1] | methyl 6-(3-(4-methoxybenzyl)ureido)spiro[3.3]heptane-2-carboxylate |
| 36 | 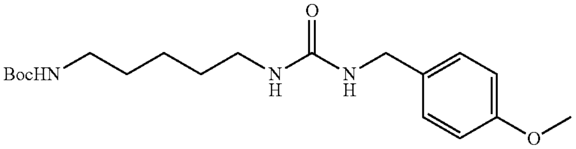 [SMILES: COc1ccc(CNC(=O)NCCCCCNC(=O)OC(C)(C)C)cc1] | tert-butyl (5-(3-(4-methoxybenzyl)ureido)pentyl)carbamate |
| 37 | 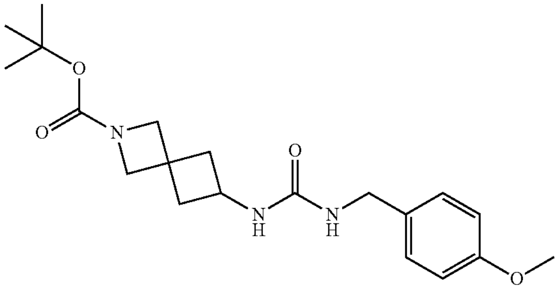 [SMILES: COc1ccc(CNC(=O)NC2CC3(C2)CN(C(=O)OC(C)(C)C)C3)cc1] | tert-butyl 6-(3-(4-methoxybenzyl)ureido)-2-azaspiro[3.3]heptane-2-carboxylate |

TABLE 1-continued

| Compound No. | Structure | Name |
|---|---|---|
| 38 | 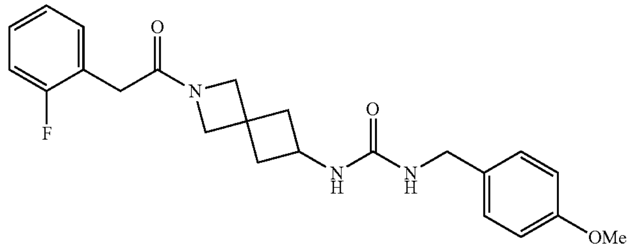 [SMILES: COc1ccc(CNC(=O)NC2CC3(C2)CN(C(=O)Cc2ccccc2F)C3)cc1] | 1-(2-(2-(2-fluorophenyl)acetyl)-2-azaspiro[3.3]heptan-6-yl)-3-(4-methoxybenzyl)urea |
| 39 | 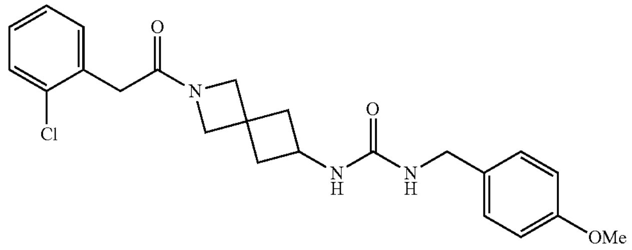 [SMILES: COc1ccc(CNC(=O)NC2CC3(C2)CN(C(=O)Cc2ccccc2Cl)C3)cc1] | 1-(2-(2-(2-chlorophenyl)acetyl)-2-azaspiro[3.3]heptan-6-yl)-3-(4-methoxybenzyl)urea |
| 40 | 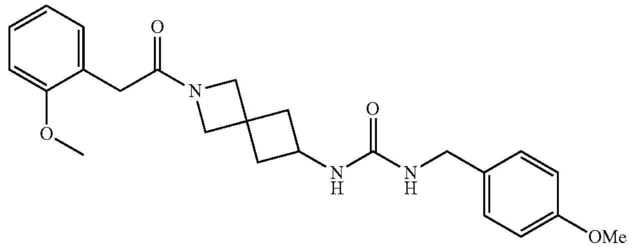 [SMILES: COc1ccc(CNC(=O)NC2CC3(C2)CN(C(=O)Cc2ccccc2OC)C3)cc1] | 1-(4-methoxybenzyl)-3-(2-(2-(2-methoxyphenyl)acetyl)-2-azaspiro[3.3]heptan-6-yl)urea |
| 41 | 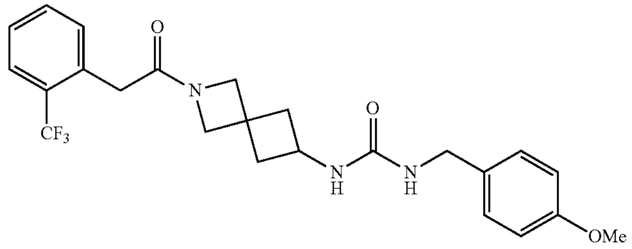 | 1-(4-methoxybenzyl)-3-(2-(2-(2-(trifluoromethyl)phenyl)acetyl)-2-azaspiro[3.3]heptan-6-yl)urea |
| 42 | 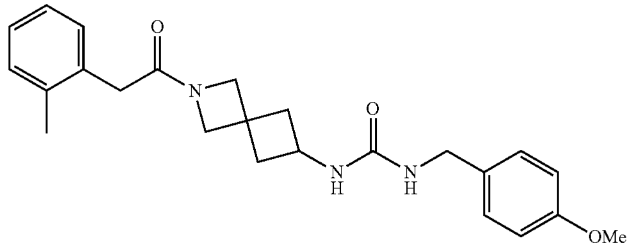 [SMILES: COc1ccc(CNC(=O)NC2CC3(C2)CN(C(=O)Cc2ccccc2C)C3)cc1] | 1-(4-methoxybenzyl)-3-(2-(2-(o-tolyl)acetyl)-2-azaspiro[3.3]heptan-6-yl)urea |
| 43 | 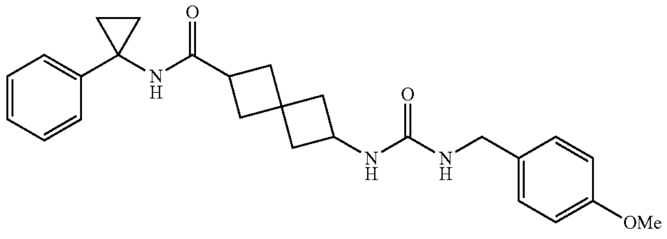 [SMILES: COc1ccc(CNC(=O)NC2CC3(C2)CC(C(=O)NC2(c4ccccc4)CC2)C3)cc1] | 6-(3-(4-methoxybenzyl)ureido)-N-(1-phenylcyclopropyl)spiro[3.3]heptane-2-carboxamide |

TABLE 1-continued

| Compound No. | Structure | Name |
|---|---|---|
| 44 | 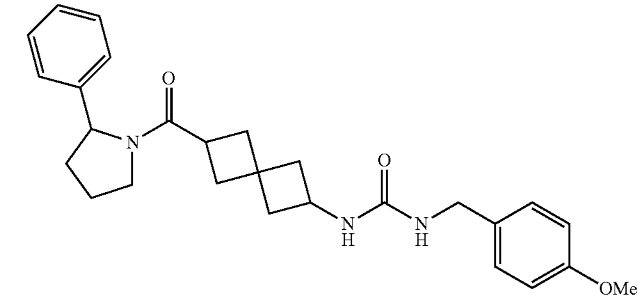 [SMILES: COc1ccc(CNC(=O)NC2CC3(C2)CC(C(=O)N2CCCC2c2ccccc2)C3)cc1] | 1-(4-methoxybenzyl)-3-(6-(2-phenylpyrrolidine-1-carbonyl)spiro[3.3]heptan-2-yl)urea |
| 45 | 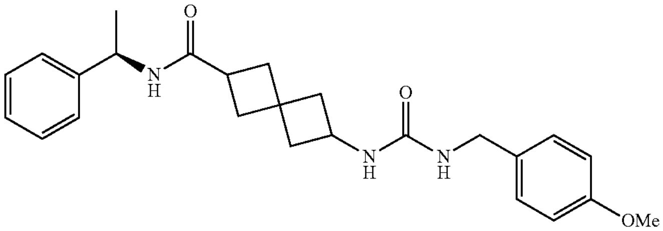 [SMILES: COc1ccc(CNC(=O)NC2CC3(C2)CC(C(=O)N[C@H](C)c2ccccc2)C3)cc1] | (R)-6-(3-(4-methoxybenzyl)ureido)-N-(1-phenylethyl)spiro[3.3]heptane-2-carboxamide |
| 46 | 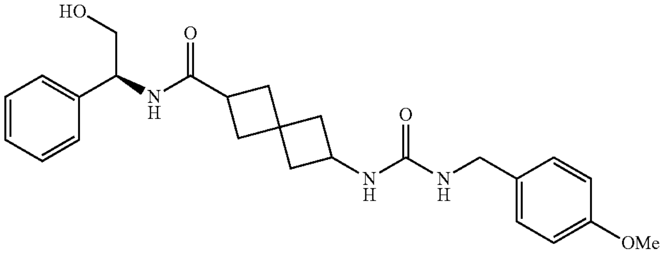 [SMILES: COc1ccc(CNC(=O)NC2CC3(C2)CC(C(=O)N[C@H](CO)c2ccccc2)C3)cc1] | (S)-N-(2-hydroxy-1-phenylethyl)-6-(3-(4-methoxybenzyl)ureido)spiro[3.3]heptane-2-carboxamide |
| 47 | 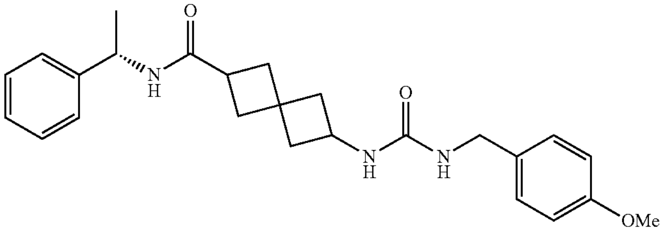 [SMILES: COc1ccc(CNC(=O)NC2CC3(C2)CC(C(=O)N[C@@H](C)c2ccccc2)C3)cc1] | (S)-6-(3-(4-methoxybenzyl)ureido)-N-(1-phenylethyl)spiro[3.3]heptane-2-carboxamide |
| 48 | 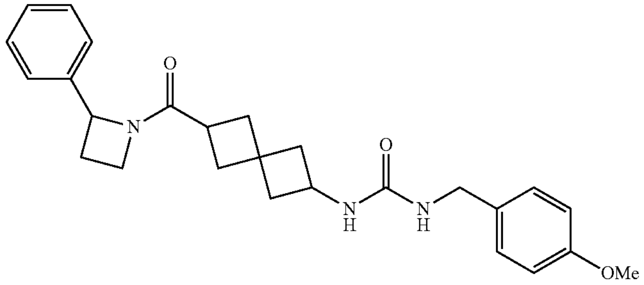 [SMILES: COc1ccc(CNC(=O)NC2CC3(C2)CC(C(=O)N2CCC2c2ccccc2)C3)cc1] | 1-(4-methoxybenzyl)-3-(6-(2-phenylazetidine-1-carbonyl)spiro[3.3]heptan-2-yl)urea |
| 49 | 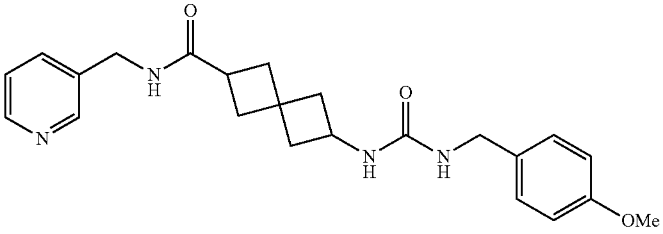 | 6-(3-(4-methoxybenzyl)ureido)-N-(pyridin-3-ylmethyl)spiro[3.3]heptane-2-carboxamide |

TABLE 1-continued

| Compound No. | Structure | Name |
|---|---|---|
| 50 | 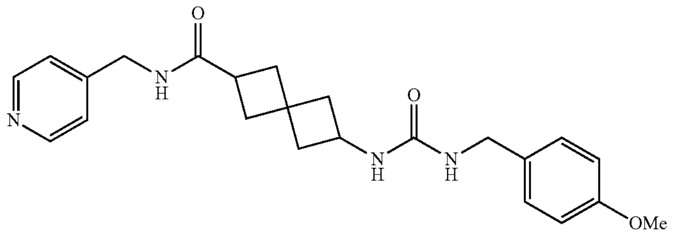 [SMILES: COc1ccc(CNC(=O)NC2CC3(C2)CC(C(=O)NCc2ccncc2)C3)cc1] | 6-(3-(4-methoxybenzyl)ureido)-N-(pyridin-4-ylmethyl)spiro[3.3]heptane-2-carboxamide |
| 51 | 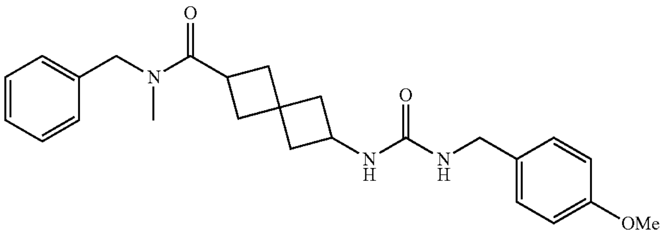 [SMILES: COc1ccc(CNC(=O)NC2CC3(C2)CC(C(=O)N(C)Cc2ccccc2)C3)cc1] | N-benzyl-6-(3-(4-methoxybenzyl)ureido)-N-methylspiro[3.3]heptane-2-carboxamide |
| 52 | 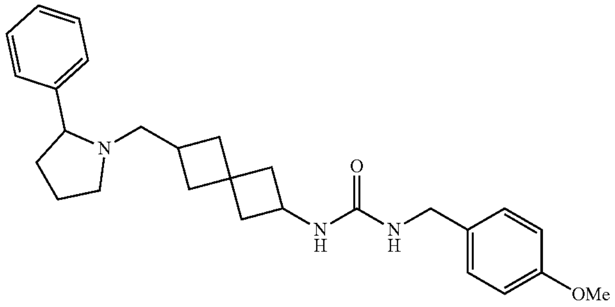 [SMILES: COc1ccc(CNC(=O)NC2CC3(CC(CN4CCCC4c4ccccc4)C3)C2)cc1] | 1-(4-methoxybenzyl)-3-(6-((2-phenylpyrrolidin-1-yl)methyl)spiro[3.3]heptan-2-yl)urea |
| 53 | 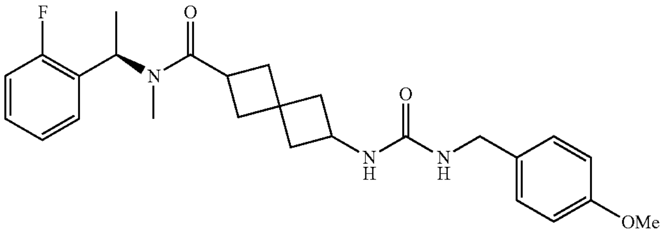 [SMILES: COc1ccc(CNC(=O)NC2CC3(C2)CC(C(=O)N(C)[C@H](C)c2ccccc2F)C3)cc1] | (R)-N-(1-(2-fluorophenyl)ethyl)-6-(3-(4-methoxybenzyl)ureido)-N-methylspiro[3.3]heptane-2-carboxamide |
| 54 | 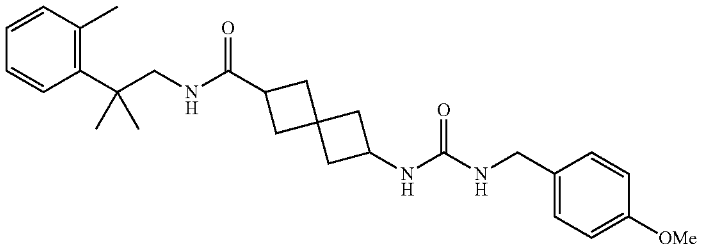 [SMILES: COc1ccc(CNC(=O)NC2CC3(C2)CC(C(=O)NCC(C)(C)c2ccccc2C)C3)cc1] | 6-(3-(4-methoxybenzyl)ureido)-N-(2-methyl-2-(o-tolyl)propyl)spiro[3.3]heptane-2-carboxamide |
| 55 | 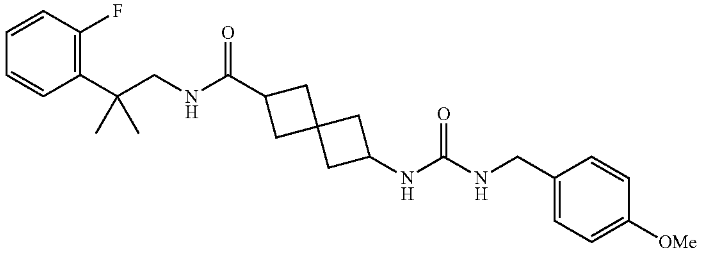 [SMILES: COc1ccc(CNC(=O)NC2CC3(C2)CC(C(=O)NCC(C)(C)c2ccccc2F)C3)cc1] | N-(2-(2-fluorophenyl)-2-methylpropyl)-6-(3-(4-methoxybenzyl)ureido)spiro[3.3]heptane-2-carboxamide |

TABLE 1-continued

| Compound No. | Structure | Name |
|---|---|---|
| 56 | 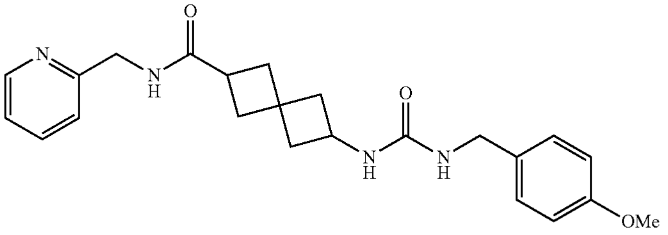 [SMILES: COc1ccc(CNC(=O)NC2CC3(C2)CC(C(=O)NCc2ccccn2)C3)cc1] | 6-(3-(4-methoxybenzyl)ureido)-N-(pyridin-2-ylmethyl)spiro[3.3]heptane-2-carboxamide |
| 57 | 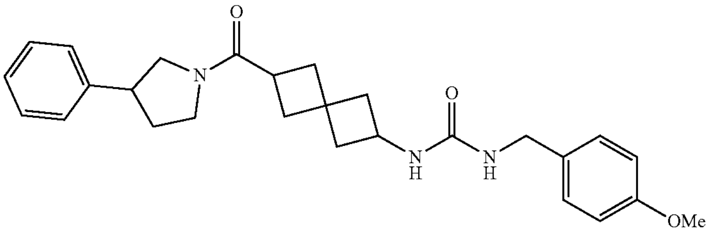 [SMILES: COc1ccc(CNC(=O)NC2CC3(C2)CC(C(=O)N2CCC(c4ccccc4)C2)C3)cc1] | 1-(4-methoxybenzyl)-3-(6-(3-phenylpyrrolidine-1-carbonyl)spiro[3.3]heptan-2-yl)urea |
| 58 | 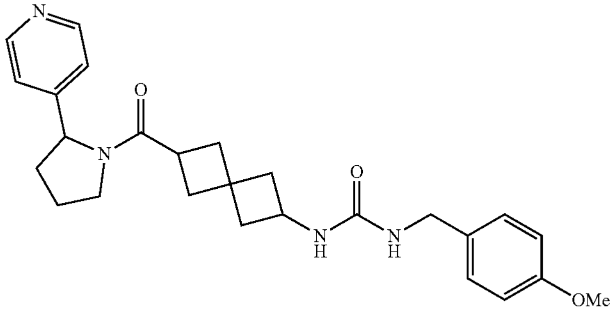 [SMILES: COc1ccc(CNC(=O)NC2CC3(C2)CC(C(=O)N2CCCC2c2ccncc2)C3)cc1] | 1-(4-methoxybenzyl)-3-(6-(2-(pyridin-4-yl)pryrrolidine-1-carbonyl)spiro[3.3]heptan-2-yl)urea |
| 59 | 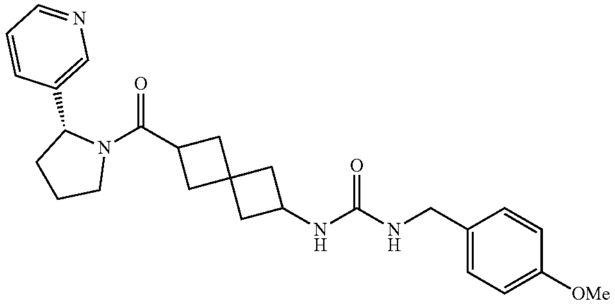 [SMILES: COc1ccc(CNC(=O)NC2CC3(C2)CC(C(=O)N2CCC[C@@H]2c2cccnc2)C3)cc1] | (R)-1-(4-methoxybenzyl)-3-(6-(2-(pyridin-3-yl)pyrrolidine-1-carbonyl)spiro[3.3]heptan-2-yl)urea |
| 60 | 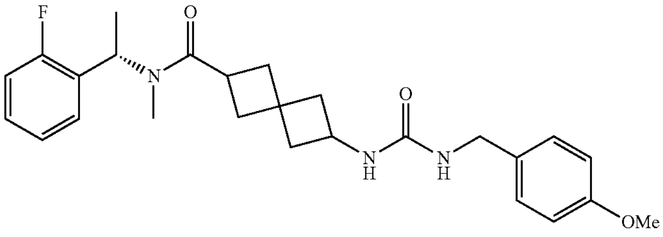 [SMILES: COc1ccc(CNC(=O)NC2CC3(C2)CC(C(=O)N(C)[C@@H](C)c2ccccc2F)C3)cc1] | (S)-N-(1-(2-fluorophenyl)ethyl)-6-(3-(4-methoxybenzyl)ureido)-N-methylspiro[3.3]heptane-2-carboxamide |
| 61 | 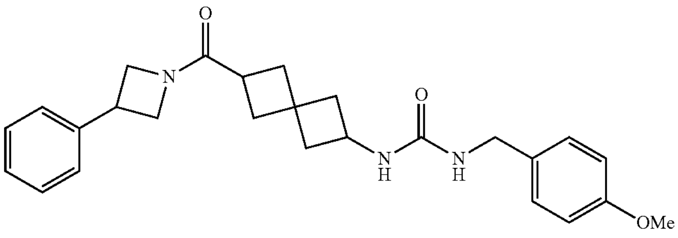 [SMILES: COc1ccc(CNC(=O)NC2CC3(C2)CC(C(=O)N2CC(c4ccccc4)C2)C3)cc1] | 1-(4-methoxybenzyl)-3-(6-(3-phenylazetidine-1-carbonyl)spiro[3.3]heptan-2-yl)urea |

TABLE 1-continued

| Compound No. | Structure | Name |
|---|---|---|
| 62 | 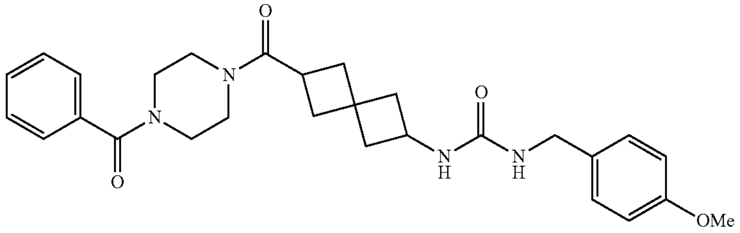 [SMILES: COc1ccc(CNC(=O)NC2CC3(C2)CC(C(=O)N2CCN(C(=O)c4ccccc4)CC2)C3)cc1] | 1-(6-(4-benzoylpiperazine-1-carbonyl)spiro[3.3]heptan-2-yl)-3-(4-methoxybenzyl)urea |
| 63 | 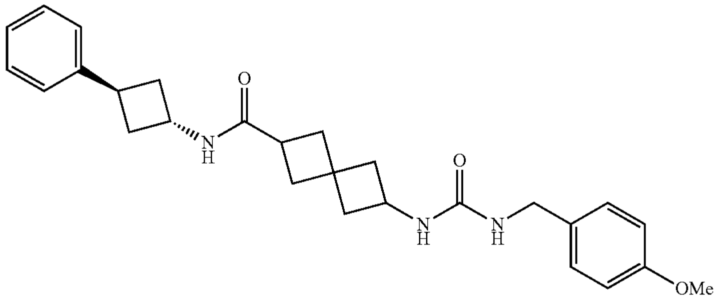 [SMILES: COc1ccc(CNC(=O)NC2CC3(C2)CC(C(=O)N[C@H]2C[C@H](c4ccccc4)C2)C3)cc1] | 6-(3-(4-methoxybenzyl)ureido)-N-((1r,3r)-3-phenylcyclobutyl)spiro[3.3]heptane-2-carboxamide |
| 64 | 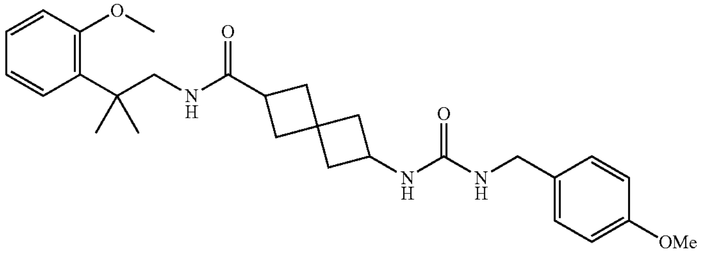 [SMILES: COc1ccc(CNC(=O)NC2CC3(C2)CC(C(=O)NCC(C)(C)c2ccccc2OC)C3)cc1] | 6-(3-(4-methoxybenzyl)ureido)-N-(2-(2-methoxyphenyl)-2-methylpropyl)spiro[3.3]heptane-2-carboxamide |
| 65 | 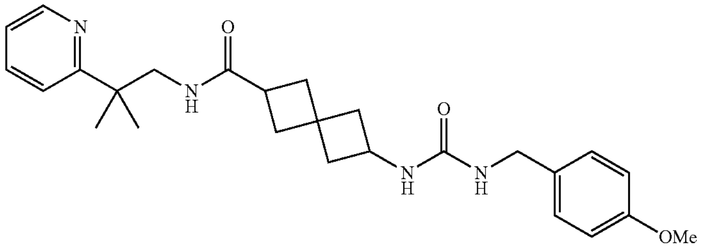 [SMILES: COc1ccc(CNC(=O)NC2CC3(C2)CC(C(=O)NCC(C)(C)c2ccccn2)C3)cc1] | 6-(3-(4-methoxybenzyl)ureido)-N-(2-methyl-2-(pyridin-2-yl)propyl)spiro[3.3]heptane-2-carboxamide |
| 66 | 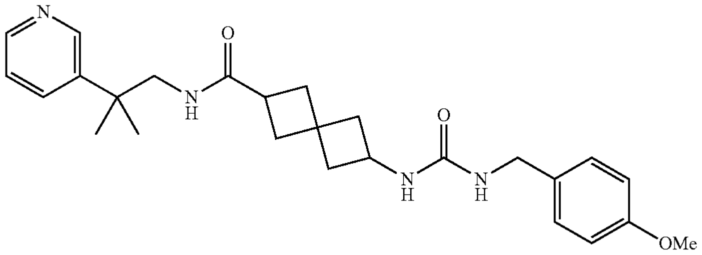 [SMILES: COc1ccc(CNC(=O)NC2CC3(C2)CC(C(=O)NCC(C)(C)c2cccnc2)C3)cc1] | 6-(3-(4-methoxybenzyl)ureido)-N-(2-methyl-2-(pyridin-3-yl)propyl)spiro[3.3]heptane-2-carboxamide |
| 67 | 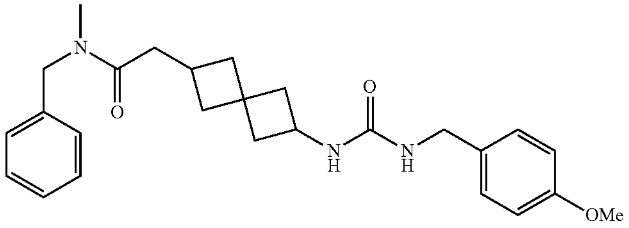 [SMILES: COc1ccc(CNC(=O)NC2CC3(CC(CC(=O)N(C)Cc4ccccc4)C3)C2)cc1] | N-benzyl-2-(6-(3-(4-methoxybenzyl)ureido)spiro[3.3]heptan-2-yl)-N-methylacetamide |

TABLE 1-continued

| Compound No. | Structure | Name |
|---|---|---|
| 68 | 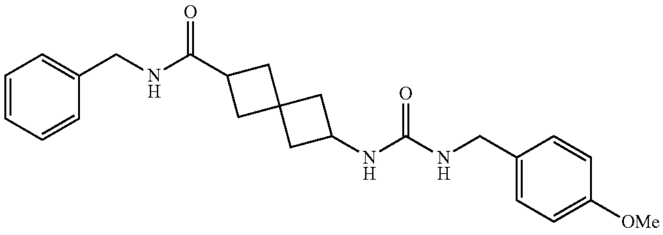 [SMILES: COc1ccc(CNC(=O)NC2CC3(C2)CC(C(=O)NCc2ccccc2)C3)cc1] | N-benzyl-6-(3-(4-methoxybenzyl)ureido)spiro[3.3]heptane-2-carboxamide |
| 69 | 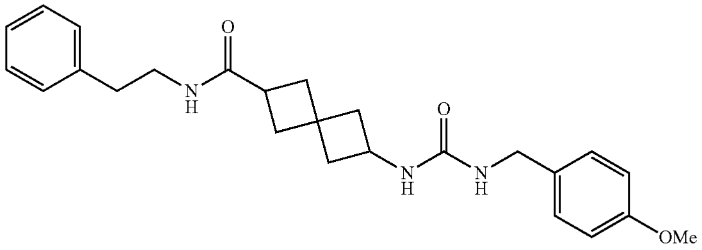 [SMILES: COc1ccc(CNC(=O)NC2CC3(C2)CC(C(=O)NCCc2ccccc2)C3)cc1] | 6-(3-(4-methoxybenzyl)ureido)-N-phenethylspiro[3.3]heptane-2-carboxamide |
| 70 | 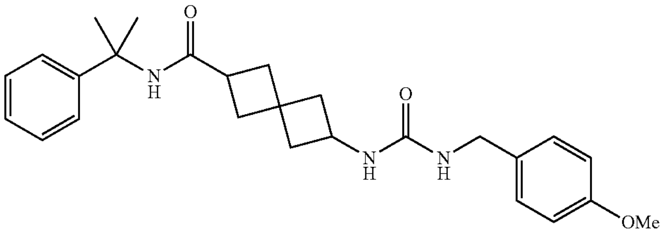 [SMILES: COc1ccc(CNC(=O)NC2CC3(C2)CC(C(=O)NC(C)(C)c2ccccc2)C3)cc1] | 6-(3-(4-methoxybenzyl)ureido)-N-(2-phenylpropan-2-yl)spiro[3.3]heptane-2-carboxamide |
| 71 | 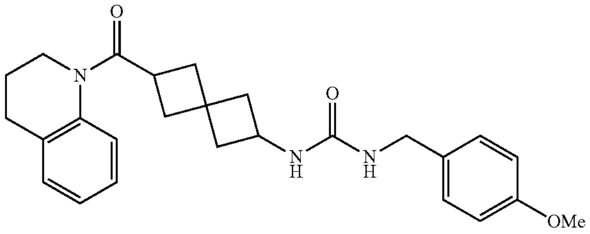 [SMILES: COc1ccc(CNC(=O)NC2CC3(C2)CC(C(=O)N2CCCc4ccccc42)C3)cc1] | 1-(4-methoxybenzyl)-3-(6-(1,2,3,4-tetrahydroquinoline-1-carbonyl)spiro[3.3]heptan-2-yl)urea |
| 72 | 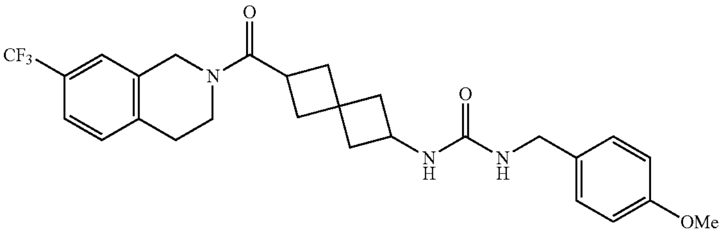 [SMILES: COc1ccc(CNC(=O)NC2CC3(C2)CC(C(=O)N2CCc4ccc(C(F)(F)F)cc4C2)C3)cc1] | 1-(4-methoxybenzyl)-3-(6-(7-(trifluoromethyl)-1,2,3,4-tetrahydroisoquinoline-2-carbonyl)spiro[3.3]heptan-2-y)urea |
| 73 | 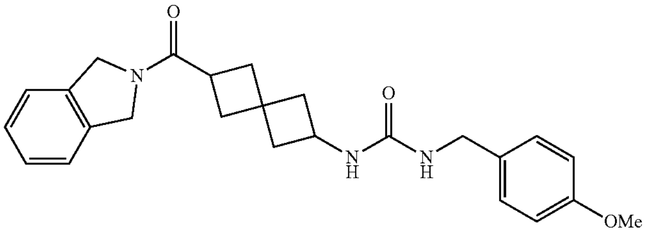 [SMILES: COc1ccc(CNC(=O)NC2CC3(C2)CC(C(=O)N2Cc4ccccc4C2)C3)cc1] | 1-(6-(isoindoline-2-carbonyl)spiro[3.3]heptan-2-yl)-3-(4-methoxybenzyl)urea |

TABLE 1-continued

| Compound No. | Structure | Name |
|---|---|---|
| 74 | 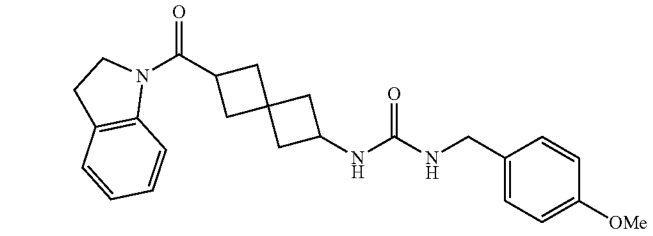 [SMILES: COc1ccc(CNC(=O)NC2CC3(C2)CC(C(=O)N2CCc4ccccc42)C3)cc1] | 1-(6-(indoline-1-carbonyl)spiro[3.3]heptan-2-yl)-3-(4-methoxybenzyl)urea |
| 75 | 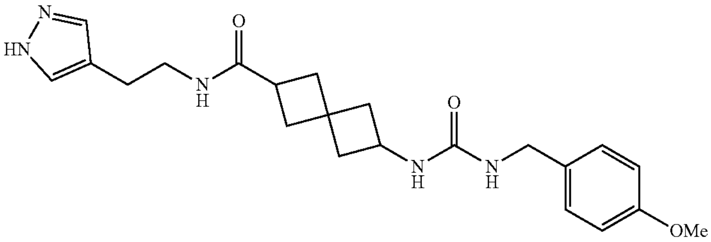 [SMILES: COc1ccc(CNC(=O)NC2CC3(C2)CC(C(=O)NCCc2cn[nH]c2)C3)cc1] | N-(2-(1H-pyrazol-4-yl)ethyl)-6-(3-(4-methoxybenzyl)ureido)spiro[3.3]heptane-2-carboxamide |
| 76 | 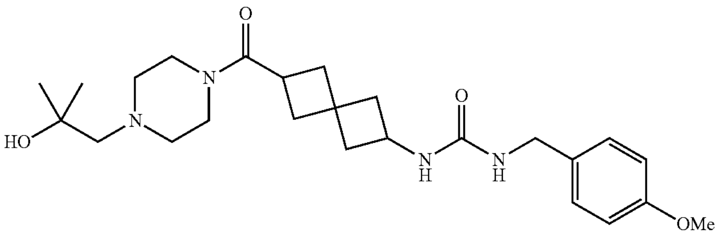 [SMILES: COc1ccc(CNC(=O)NC2CC3(C2)CC(C(=O)N2CCN(CC(C)(C)O)CC2)C3)cc1] | 1-(6-(4-(2-hydroxy-2-methylpropyl)piperazine-1-carbonyl)spiro[3.3]heptan-2-yl)-3-(4-methoxybenzyl)urea |
| 77 | 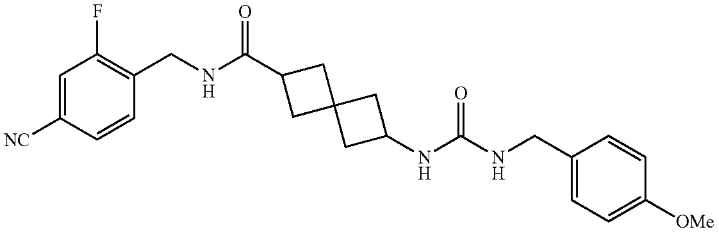 [SMILES: COc1ccc(CNC(=O)NC2CC3(C2)CC(C(=O)NCc2ccc(C#N)cc2F)C3)cc1] | N-(4-cyano-2-fluorobenzyl)-6-(3-(4-methoxybenzyl)ureido)spiro[3.3]heptane-2-carboxamide |
| 78 | 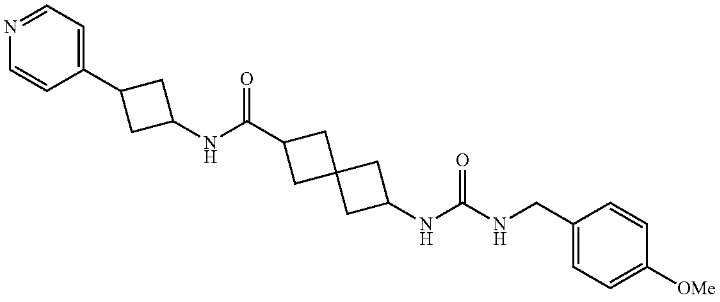 [SMILES: COc1ccc(CNC(=O)NC2CC3(C2)CC(C(=O)NC2CC(c4ccncc4)C2)C3)cc1] | 6-(3-(4-methoxybenzyl)ureido)-N-(3-(pyridin-4-yl)cyclobutyl)spiro[3.3]heptane-2-carboxamide |
| 79 | 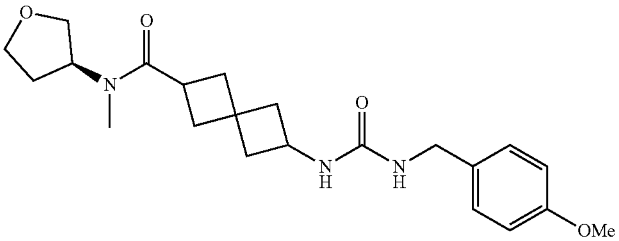 [SMILES: COc1ccc(CNC(=O)NC2CC3(C2)CC(C(=O)N(C)[C@H]2CCOC2)C3)cc1] | (R)-6-(3-(4-methoxybenzyl)ureido)-N-methyl-N-(tetrahydrofuran-3-yl)spiro[3.3]heptane-2-carboxamide |

TABLE 1-continued

| Compound No. | Structure | Name |
|---|---|---|
| 80 | 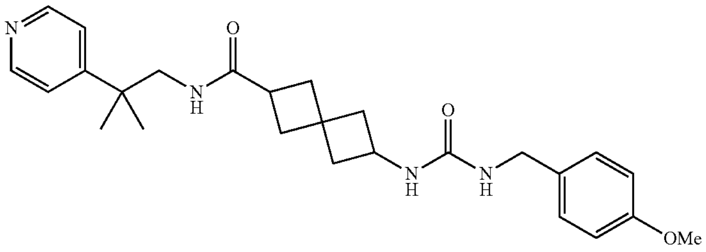 [SMILES: COc1ccc(CNC(=O)NC2CC3(C2)CC(C(=O)NCC(C)(C)c2ccncc2)C3)cc1] | 6-(3-(4-methoxybenzyl)ureido)-N-(2-methyl-2-(pyridin-4-yl)propyl)spiro[3.3]heptane-2-carboxamide |
| 81 | 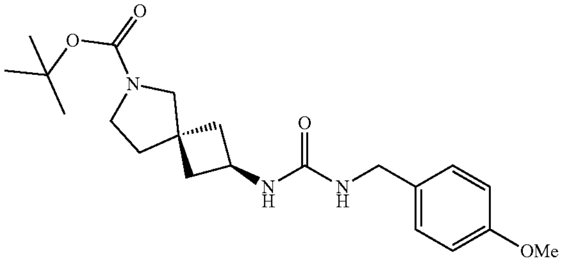 [SMILES: COc1ccc(CNC(=O)N[C@H]2C[C@]3(CCN(C(=O)OC(C)(C)C)C3)C2)cc1] | tert-butyl (2r,4s)-2-(3-(4-methoxybenzyl)ureido)-6-azaspiro[3.4]octane-6-carboxylate |
| 82 | 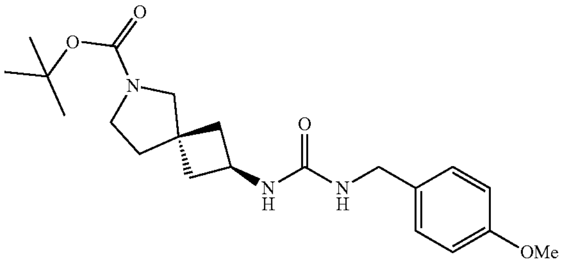 [SMILES: COc1ccc(CNC(=O)N[C@H]2C[C@@]3(CCN(C(=O)OC(C)(C)C)C3)C2)cc1] | tert-butyl (2s4r)-2-(3-(4-methoxybenzyl)ureido)-6-azaspiro[3.4]octane-6-carboxylate |
| 83 | 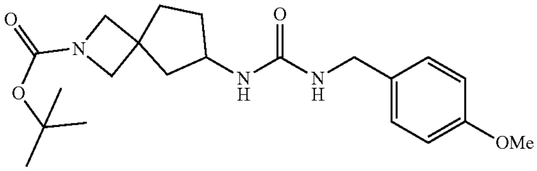 [SMILES: COc1ccc(CNC(=O)NC2CCC3(C2)CN(C(=O)OC(C)(C)C)C3)cc1] | tert-butyl 6-(3-(4-methoxybenzyl)ureido)-2-azaspiro[3.4]octane-2-carboxylate |
| 84 | 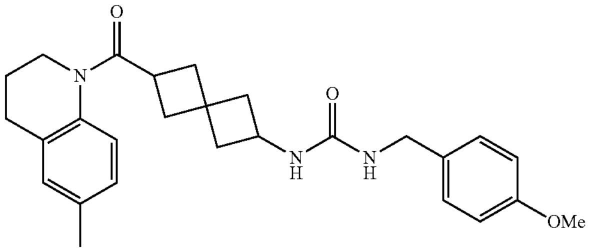 [SMILES: COc1ccc(CNC(=O)NC2CC3(C2)CC(C(=O)N2CCCc4cc(C)ccc42)C3)cc1] | 1-(4-methoxybenzyl)-3-(6-(6-methyl-1,2,3,4-tetrahydroquinoline-1-carbonyl)spiro[3.3]heptan-2-yl)urea |
| 85 | 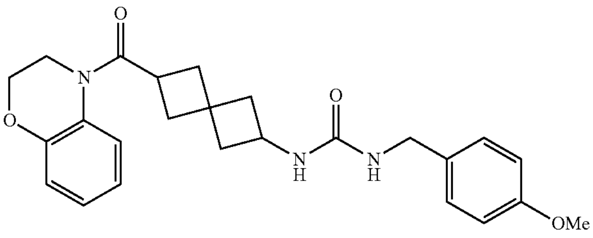 [SMILES: COc1ccc(CNC(=O)NC2CC3(C2)CC(C(=O)N2CCOc4ccccc42)C3)cc1] | 1-(6-(3,4-dihydro-2H-benzo[b][1,4]oxazine-4-carbonyl)spiro[3.3]heptan-2-yl)-3-(4-methoxybenzyl)urea |

TABLE 1-continued

| Compound No. | Structure | Name |
|---|---|---|
| 86 | 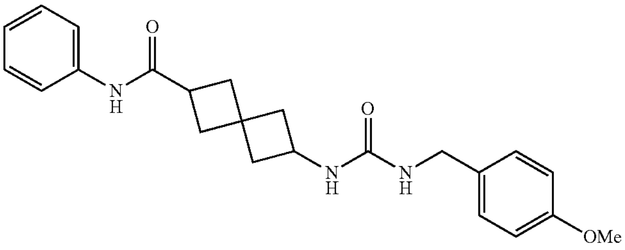 [SMILES: COc1ccc(CNC(=O)NC2CC3(C2)CC(C(=O)Nc2ccccc2)C3)cc1] | 6-(3-(4-methoxybenzyl)ureido)-N-phenylspiro[3.3]heptane-2-carboxamide |
| 87 | 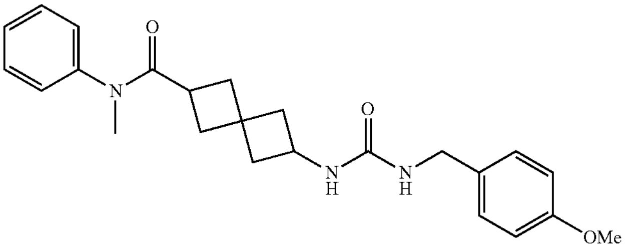 [SMILES: COc1ccc(CNC(=O)NC2CC3(C2)CC(C(=O)N(C)c2ccccc2)C3)cc1] | 6-(3-(4-methoxybenzyl)ureido)-N-methyl-N-phenylspiro[3.3]heptane-2-carboxamide |
| 88 | 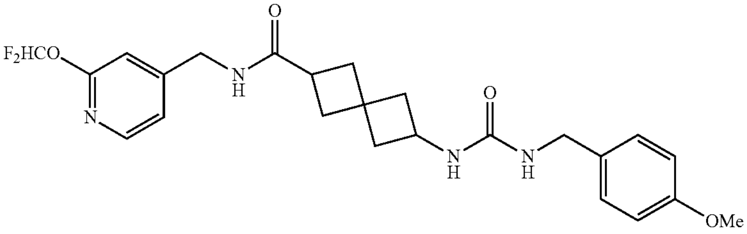 [SMILES: COc1ccc(CNC(=O)NC2CC3(C2)CC(C(=O)NCc2ccnc(OC(F)F)c2)C3)cc1] | N-((2-(difluoromethoxy)pyridin-4-yl)methyl)-6-(3-(4-methoxybenzyl)ureido)spiro[3.3]heptane-2-carboxamide |
| 89 | 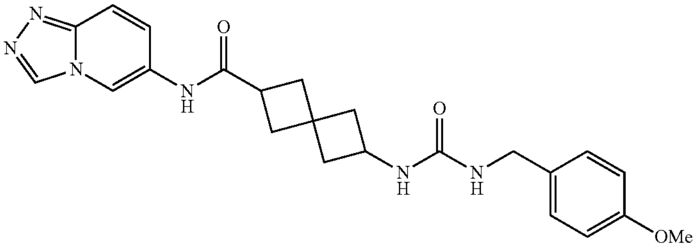 [SMILES: COc1ccc(CNC(=O)NC2CC3(C2)CC(C(=O)Nc2ccc4nncn4c2)C3)cc1] | N-([1,2,4]triazolo[4,3-a]pyridin-6-yl)-6-(3-(4-methoxybenzyl)ureido)spiro[3.3]heptane-2-carboxamide |
| 90 | 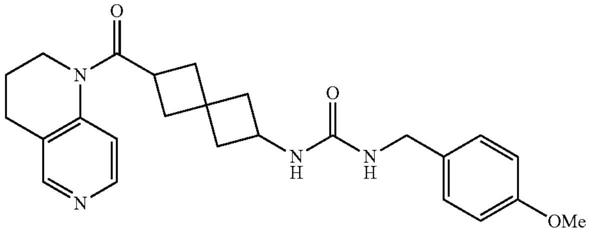 [SMILES: COc1ccc(CNC(=O)NC2CC3(C2)CC(C(=O)N2CCCc4cnccc42)C3)cc1] | 1-(4-methoxybenzyl)-3-(6-(1,2,3,4-tetrahydro-1,6-naphthyridine-1-carbonyl)spiro[3.3]heptan-2-yl)urea |
| 91 | 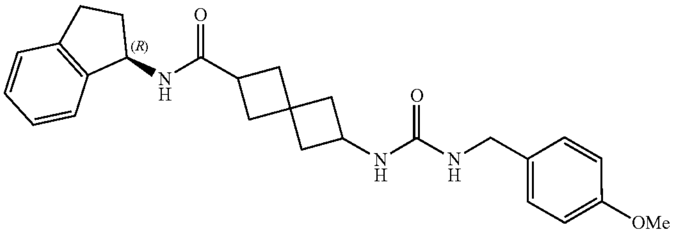 | (R)-N-(2,3-dihydro-1H-inden-1-yl)-6-(3-(4-methoxybenzyl)ureido)spiro[3.3]heptane-2-carboxamide |

TABLE 1-continued

| Compound No. | Structure | Name |
|---|---|---|
| 92 | 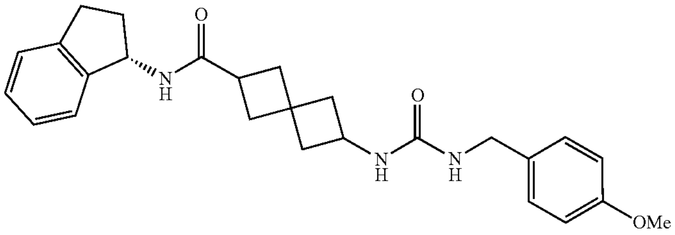 [SMILES: COc1ccc(CNC(=O)NC2CC3(C2)CC(C(=O)N[C@H]2CCc4ccccc42)C3)cc1] | S)-N-(2,3-dihydro-1H-inden-1-yl)-6-(3-(4-methoxybenzyl)ureido)spiro[3.3]heptane-2-carboxamide |
| 93 | 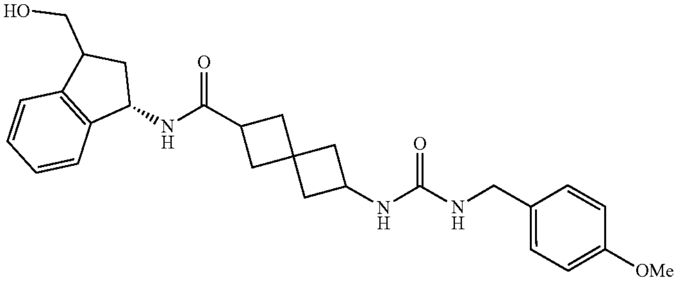 [SMILES: COc1ccc(CNC(=O)NC2CC3(C2)CC(C(=O)N[C@H]2CC(CO)c4ccccc42)C3)cc1] | N-(3-(hydroxymethyl)-2,3-dihydro-1H-inden-1-yl)-6-(3-(4-methoxybenzyl)ureido)spiro[3.3]heptane-2-carboxamide |
| 94 | 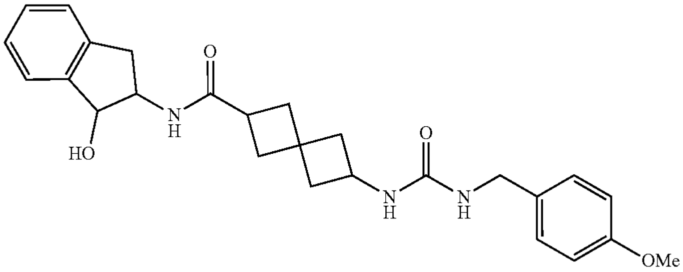 [SMILES: COc1ccc(CNC(=O)NC2CC3(C2)CC(C(=O)NC2Cc4ccccc4C2O)C3)cc1] | N-(1-hydroxy-2,3-dihydro-1H-inden-2-yl)-6-(3-(4-methoxybenzyl)ureido)spiro[3.3]heptane-2-carboxamide |
| 95 | 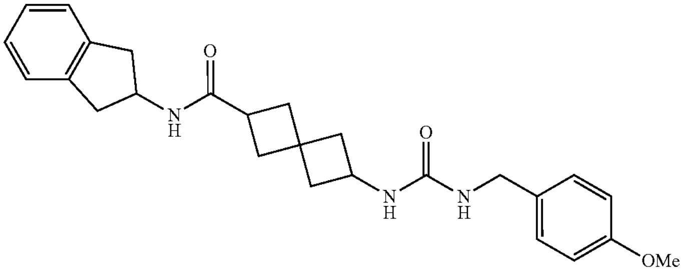 [SMILES: COc1ccc(CNC(=O)NC2CC3(C2)CC(C(=O)NC2Cc4ccccc4C2)C3)cc1] | N-(2,3-dihydro-1H-inden-2-yl)-6-(3-(4-methoxybenzyl)ureido)spiro[3.3]heptane-2-carboxamide |
| 96 | 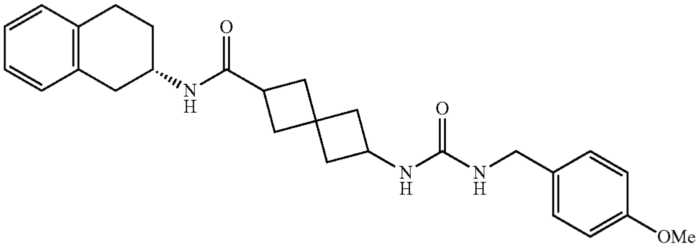 [SMILES: COc1ccc(CNC(=O)NC2CC3(C2)CC(C(=O)N[C@H]2CCc4ccccc4C2)C3)cc1] | (R)-6-(3-(4-methoxybenzyl)ureido)-N-(1,2,3,4-tetrahydronaphthalen-2-yl)spiro[3.3]heptane-2-carboxamide |

TABLE 1-continued

| Compound No. | Structure | Name |
|---|---|---|
| 97 | 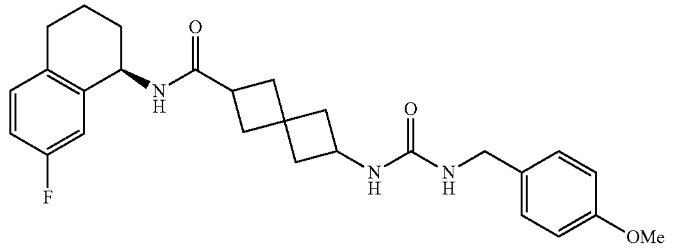 [SMILES: COc1ccc(CNC(=O)NC2CC3(C2)CC(C(=O)N[C@@H]2CCCc4ccc(F)cc42)C3)cc1] | (S)-N-(7-fluoro-1,2,3,4-tetrahydronaphthalen-1-yl)-6-(3-(4-methoxybenzyl)ureido)spiro[3.3]heptane-2-carboxamide |
| 98 | 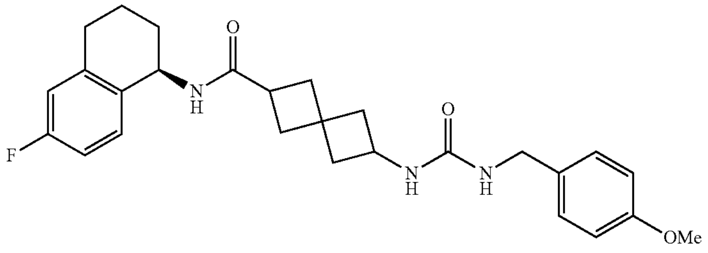 [SMILES: COc1ccc(CNC(=O)NC2CC3(C2)CC(C(=O)N[C@@H]2CCCc4cc(F)ccc42)C3)cc1] | (S)-N-(6-fluoro-1,2,3,4-tetrahydronaphthalen-1-yl)-6-(3-(4-methoxybenzyl)ureido)spiro[3.3]heptane-2-carboxamide |
| 99 | 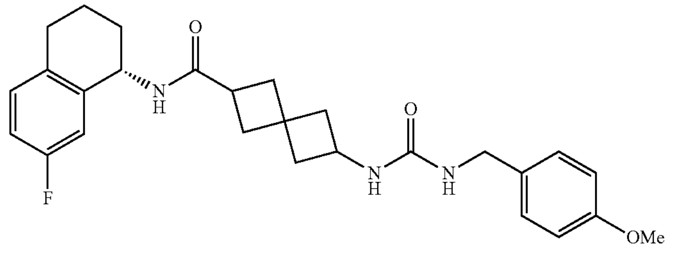 [SMILES: COc1ccc(CNC(=O)NC2CC3(C2)CC(C(=O)N[C@H]2CCCc4ccc(F)cc42)C3)cc1] | (R)-N-(7-fluoro-1,2,3,4-tetrahydronaphthalen-1-yl)-6-(3-(4-methoxybenzyl)ureido)spiro[3.3]heptane-2-carboxamide |
| 100 | 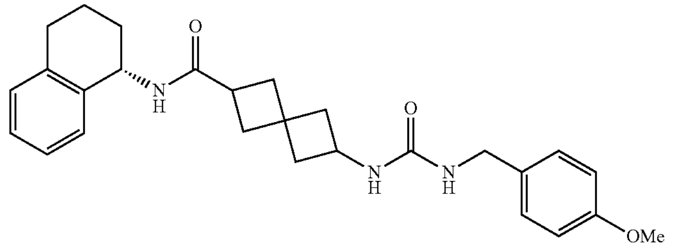 [SMILES: COc1ccc(CNC(=O)NC2CC3(C2)CC(C(=O)N[C@H]2CCCc4ccccc42)C3)cc1] | (R)-6-(3-(4-methoxybenzyl)ureido)-N-(1,2,3,4-tetrahydronaphthalen-1-yl)spiro[3.3]heptane-2-carboxamide |
| 101 | 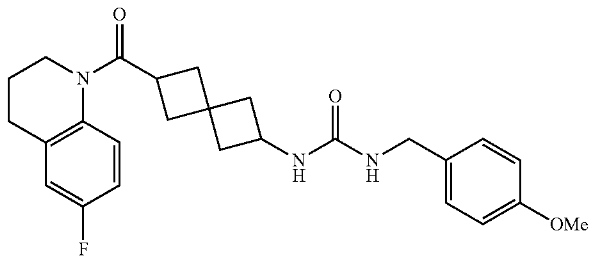 [SMILES: COc1ccc(CNC(=O)NC2CC3(C2)CC(C(=O)N2CCCc4cc(F)ccc42)C3)cc1] | 1-(6-(6-fluoro-1,2,3,4-tetrahydroquinoline-1-carbonyl)spiro[3.3]heptan-2-yl)-3-(4-methoxybenzyl)urea |

TABLE 1-continued

| Compound No. | Structure | Name |
|---|---|---|
| 102 | 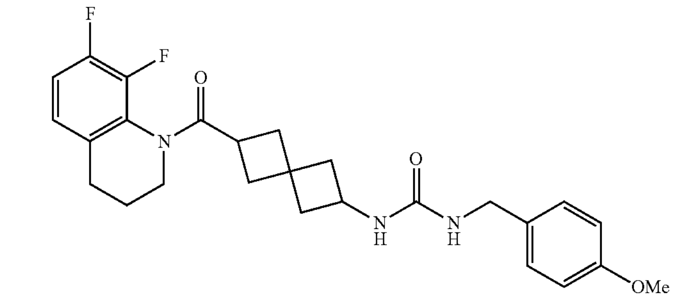 [SMILES: COc1ccc(CNC(=O)NC2CC3(C2)CC(C(=O)N2CCCc4ccc(F)c(F)c42)C3)cc1] | 1-(6-(7,8-difluoro-1,2,3,4-tetrahydroquinoline-1-carbonyl)spiro[3.3]heptan-2-yl)-3-(4-methoxybenzyl)urea |
| 103 | 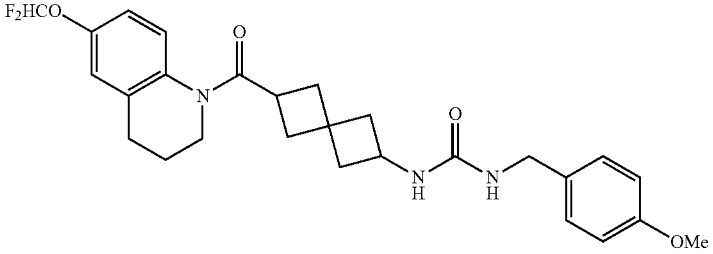 [SMILES: COc1ccc(CNC(=O)NC2CC3(C2)CC(C(=O)N2CCCc4cc(OC(F)F)ccc42)C3)cc1] | 1-(6-(6-(difluoromethoxy)-1,2,3,4-tetrahydroquinoline-1-carbonyl)spiro[3.3]heptan-2-yl)-3-(4-methoxybenzyl)urea |
| 104 | 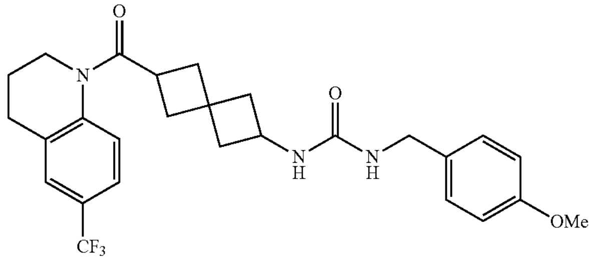 [SMILES: COc1ccc(CNC(=O)NC2CC3(C2)CC(C(=O)N2CCCc4cc(C(F)(F)F)ccc42)C3)cc1] | 1-(4-methoxybenzyl)-3-(6-(6-(trifluoromethyl)-1,2,3,4-tetrahydroquinoline-1-carbonyl)spiro[3.3]heptan-2-yl)urea |
| 105 | 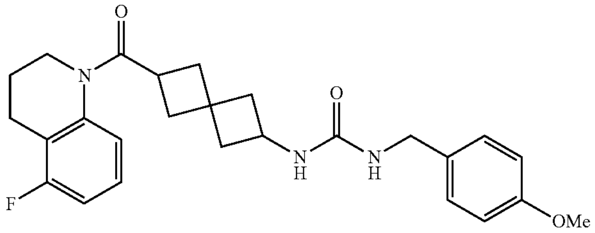 [SMILES: COc1ccc(CNC(=O)NC2CC3(C2)CC(C(=O)N2CCCc4c(F)cccc42)C3)cc1] | 1-(6-(5-fluoro-1,2,3,4-tetrahydroquinoline-1-carbonyl)spiro[3.3]heptan-2-yl)-3-(4-methoxybenzyl)urea |
| 106 | 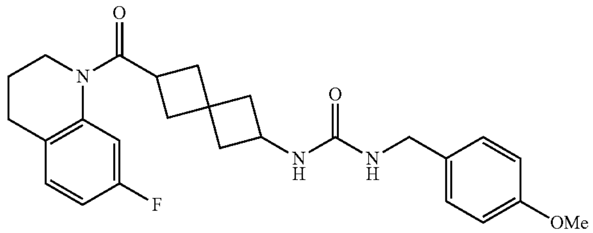 [SMILES: COc1ccc(CNC(=O)NC2CC3(C2)CC(C(=O)N2CCCc4ccc(F)cc42)C3)cc1] | 1-(6-(7-fluoro-1,2,3,4-tetrahydroquinoline-1-carbonyl)spiro[3.3]heptan-2-yl)-3-(4-methoxybenzyl)urea |
| 107 | 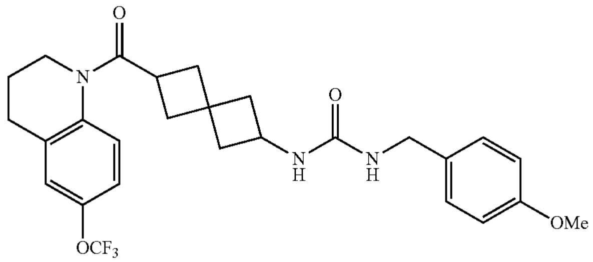 [SMILES: COc1ccc(CNC(=O)NC2CC3(C2)CC(C(=O)N2CCCc4cc(OC(F)(F)F)ccc42)C3)cc1] | 1-(4-methoxybenzyl)-3-(6-(6-(trifluoromethoxy)-1,2,3,4-tetrahydroquinoline-1-carbonyl)spiro[3.3]heptan-2-yl)urea |

TABLE 1-continued

| Compound No. | Structure | Name |
|---|---|---|
| 108 | 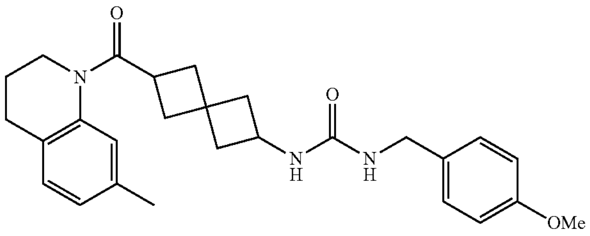 [SMILES: COc1ccc(CNC(=O)NC2CC3(C2)CC(C(=O)N2CCCc4ccc(C)cc42)C3)cc1] | 1-(4-methoxybenzyl)-3-(6-(7-methyl-1,2,3,4-tetrahydroquinoline-1-carbonyl)spiro[3.3]heptan-2-yl)urea |
| 109 | 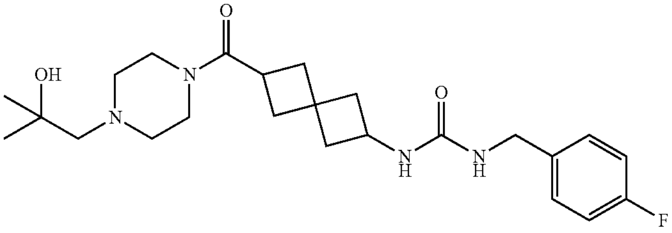 [SMILES: CC(C)(O)CN1CCN(C(=O)C2CC3(CC(NC(=O)NCc4ccc(F)cc4)C3)C2)CC1] | 1-(4-fluorobenzyl)-3-(6-(4-(2-hydroxy-2-methylpropyl)piperazine-1-carbonyl)spiro[3.3]heptan-2-yl)urea |
| 110 | 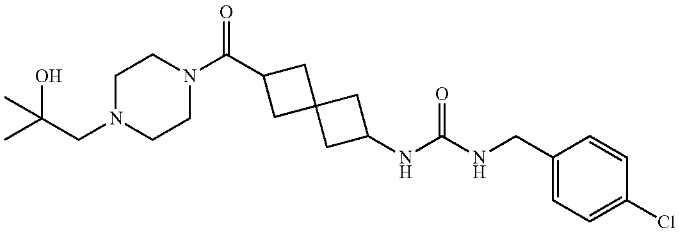 [SMILES: CC(C)(O)CN1CCN(C(=O)C2CC3(CC(NC(=O)NCc4ccc(Cl)cc4)C3)C2)CC1] | 1-(4-chlorobenzyl)-3-(6-(4-(2-hydroxy-2-methylpropyl)piperazine-1-carbonyl)spiro[3.3]heptan-2-yl)urea |
| 111 | 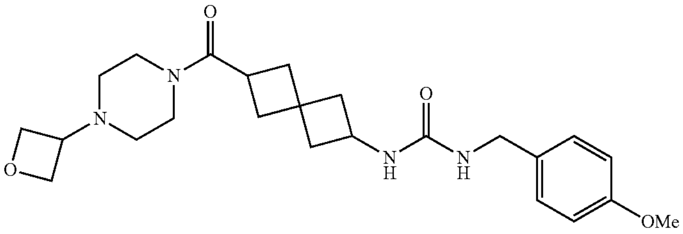 [SMILES: COc1ccc(CNC(=O)NC2CC3(C2)CC(C(=O)N2CCN(C4COC4)CC2)C3)cc1] | 1-(4-methoxybenzyl)-3-(6-(4-(oxetan-3-yl)piperazine-1-carbonyl)spiro[3.3]heptan-2-yl)urea |
| 112 | 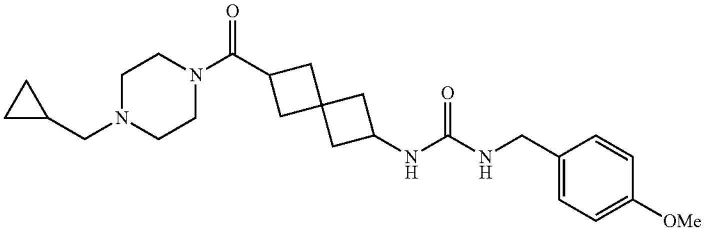 [SMILES: COc1ccc(CNC(=O)NC2CC3(C2)CC(C(=O)N2CCN(CC4CC4)CC2)C3)cc1] | 1-(6-(4-(cyclopropylmethyl)-piperazine-1-carbonyl)spiro[3.3]heptan-2-yl)-3-(4-methoxybenzyl)urea |
| 113 | 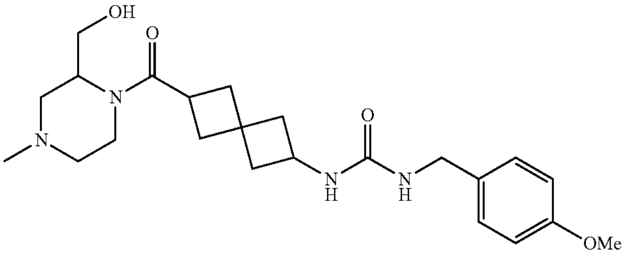 [SMILES: COc1ccc(CNC(=O)NC2CC3(C2)CC(C(=O)N2CCN(C)CC2CO)C3)cc1] | 1-(6-(2-(hydroxymethyl)-4-methylpiperazine-1-carbonyl)spiro[3.3]heptan-2-yl)-3-(4-methoxybenzyl)urea |

TABLE 1-continued

| Compound No. | Structure | Name |
|---|---|---|
| 114 | 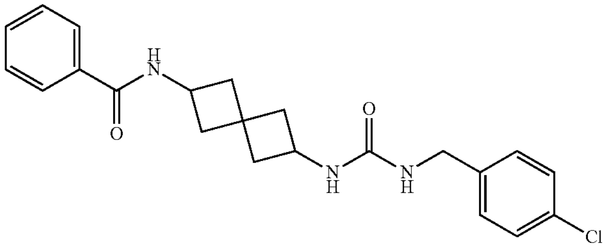 [SMILES: O=C(NCc1ccc(Cl)cc1)NC1CC2(C1)CC(NC(=O)c1ccccc1)C2] | N-(6-(3-(4-chlorobenzyl)ureido) spiro[3.3]heptan-2-y)benzamide |
| 115 | 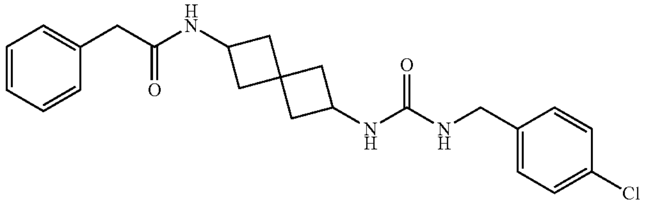 [SMILES: O=C(Cc1ccccc1)NC1CC2(C1)CC(NC(=O)NCc1ccc(Cl)cc1)C2] | N-(6-(3-(4-chlorobenzyl)ureido) spiro[3.3]heptan-2-yl)-2-phenylacetamide |
| 116 | 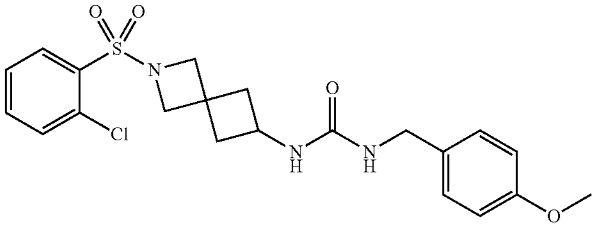 [SMILES: COc1ccc(CNC(=O)NC2CC3(C2)CN(S(=O)(=O)c2ccccc2Cl)C3)cc1] | 1-(2-((2-chlorophenyl)sulfonyl)-2-azaspiro[3.3.]heptan-6-yl)-3-(4-methoxybenzyl)urea |
| 117 | 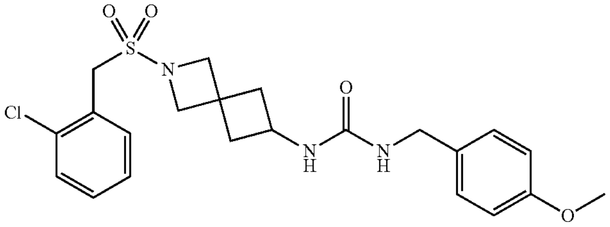 [SMILES: COc1ccc(CNC(=O)NC2CC3(C2)CN(S(=O)(=O)Cc2ccccc2Cl)C3)cc1] | 1-(2-((2-chlorobenzyl)sulfonyl)-2-azaspiro[3.3]heptan-6-yl)-3-(4-methoxybenzyl)urea |
| 118 | 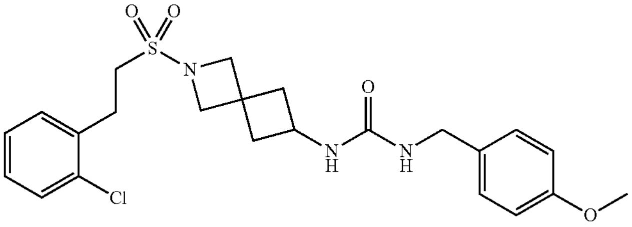 [SMILES: COc1ccc(CNC(=O)NC2CC3(C2)CN(S(=O)(=O)CCc2ccccc2Cl)C3)cc1] | 1-(2-((2-chlorophenethyl)sulfonyl)-2-azaspiro[3.3]heptan-6-yl)-3-(4-methoxybenzyl)urea |
| 119 | 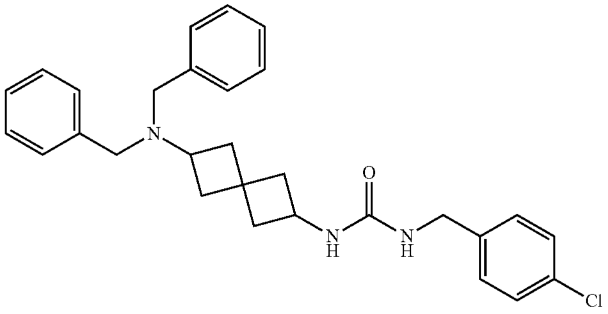 [SMILES: O=C(NCc1ccc(Cl)cc1)NC1CC2(C1)CC(N(Cc1ccccc1)Cc1ccccc1)C2] | 1-(4-chlorobenzyl)-3-(6-(dibenzylamino)spiro [3.3]heptan-2-yl)urea |

TABLE 1-continued

| Compound No. | Structure | Name |
| --- | --- | --- |
| 120 | 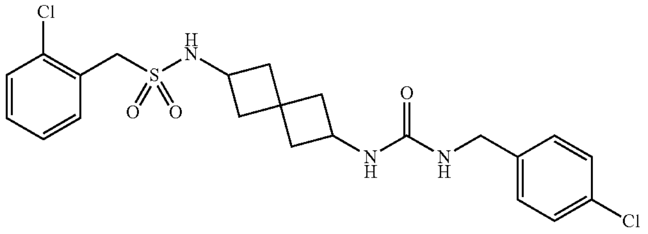 [SMILES: O=C(NCc1ccc(Cl)cc1)NC1CC2(C1)CC(NS(=O)(=O)Cc1ccccc1Cl)C2] | N-(6-(3-(4-chlorobenzyl)ureido) spiro[3.3]heptan-2-yl)-1-(2-chlorophenyl)methane-sulfonamide |
| 121 | 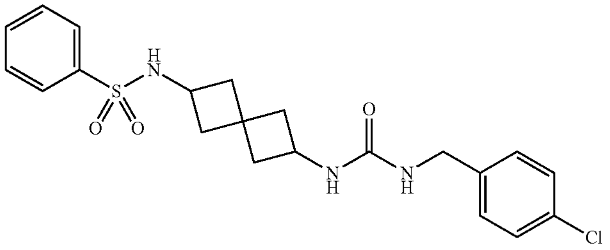 [SMILES: O=C(NCc1ccc(Cl)cc1)NC1CC2(C1)CC(NS(=O)(=O)c1ccccc1)C2] | N-(6-(3-(4-chlorobenzyl)ureido) spiro[3.3]heptan-2-yl)benzenesulfonamide |
| 122 | 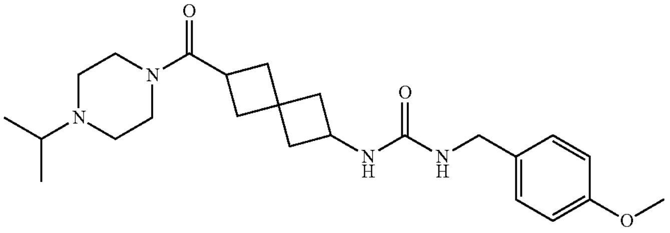 [SMILES: COc1ccc(CNC(=O)NC2CC3(C2)CC(C(=O)N2CCN(C(C)C)CC2)C3)cc1] | 1-(6-(4-isopropylpiperazine-1-carbonyl)spiro[3.3]hep-tan-2-yl)-3-(4-methoxybenzyl)urea |
| 123 | 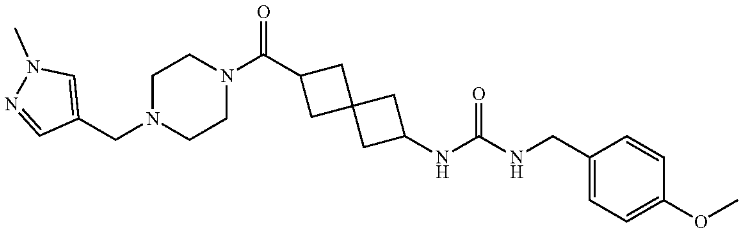 [SMILES: COc1ccc(CNC(=O)NC2CC3(C2)CC(C(=O)N2CCN(Cc4cnn(C)c4)CC2)C3)cc1] | 1-(4-methoxybenzyl)-3-(6-(4-((1-methyl-1H-pyrazol-4-yl)methyl)piperazine-1-carbonyl)spiro[3.3]hep-tan-2-yl)urea |
| 124 | 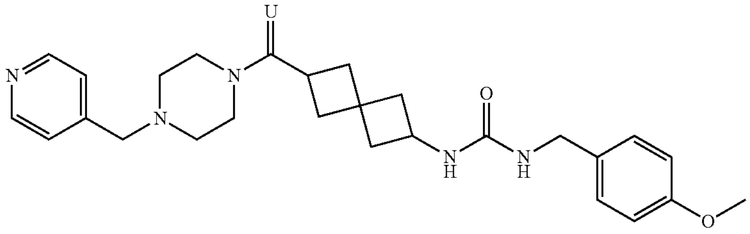 | 1-(4-methoxybenzyl)-3-(6-(4-(pyridin-4-ylmethyl)piperazine-1-carbonyl)spiro[3.3]hep-tan-2-yl)urea |
| 125 | 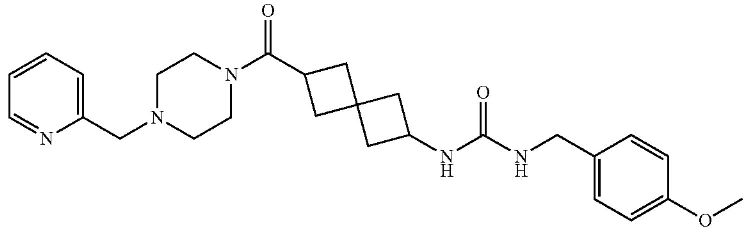 [SMILES: COc1ccc(CNC(=O)NC2CC3(C2)CC(C(=O)N2CCN(Cc4ccccn4)CC2)C3)cc1] | 1-(4-methoxybenzyl)-3-(6-(4-(pyridin-2-ylmethyl)piperazine-1-carbonyl)spiro[3.3]hep-tan-2-yl)urea |

TABLE 1-continued

| Compound No. | Structure | Name |
| --- | --- | --- |
| 126 | 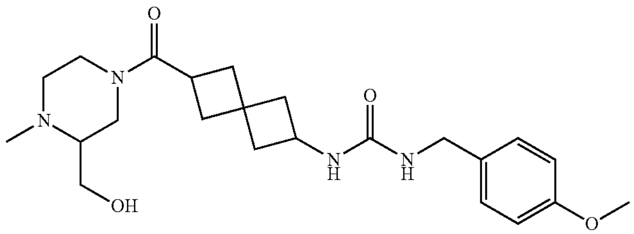 | 1-(6-(3-(hydroxymethyl)-4-methylpiperazine-1-carbonyl)spiro[3.3]heptan-2-yl)-3-(4-methoxybenzyl)urea |
| 127 | 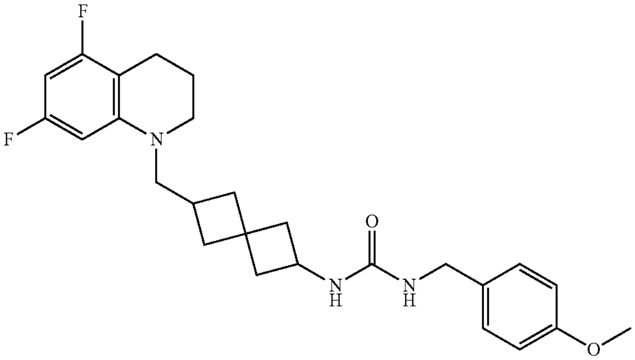 [SMILES: COc1ccc(CNC(=O)NC2CC3(CC(CN4CCCc5c(F)cc(F)cc54)C3)C2)cc1] | 1-(6-((5,7-difluoro-3,4-dihydroquinolin-1(2H)-yl)methyl)spiro[3.3]heptan-2-yl)-3-(4-methoxybenzyl)urea |
| 128 | 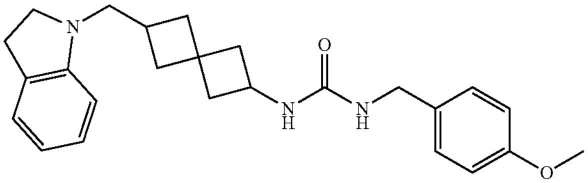 [SMILES: COc1ccc(CNC(=O)NC2CC3(CC(CN4CCc5ccccc54)C3)C2)cc1] | 1-(6-(indolin-1-ylmethyl)spiro[3.3]heptan-2-yl)-3-(4-methoxybenzyl)urea |
| 129 | 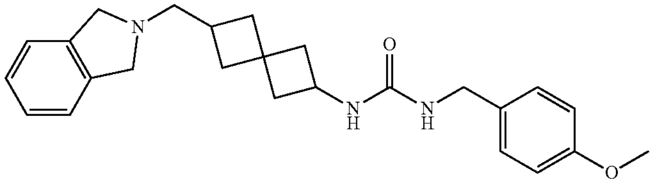 [SMILES: COc1ccc(CNC(=O)NC2CC3(CC(CN4Cc5ccccc5C4)C3)C2)cc1] | 1-(6-(isoindolin-2-ylmethyl)spiro[3.3]heptan-2-yl)-3-(4-methoxybenzyl)urea |
| 130 | 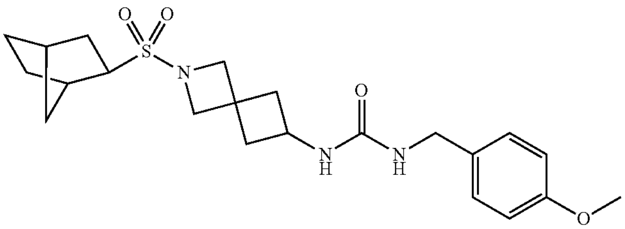 [SMILES: COc1ccc(CNC(=O)NC2CC3(C2)CN(S(=O)(=O)C2CC4CCC2C4)C3)cc1] | 1-(4-(bicyclo[2.2.1]heptan-2-ylsulfonyl)-2-azaspiro[3.3]heptan-6-yl)-3-(4-methoxybenzyl)urea |
| 131 | 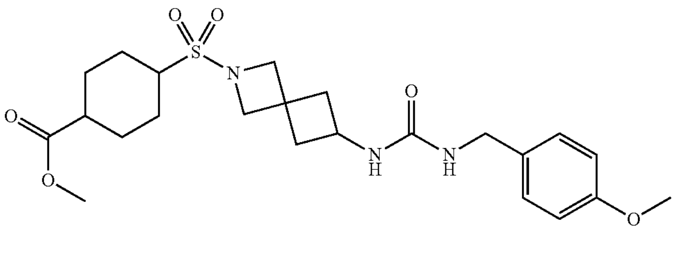 [SMILES: COC(=O)C1CCC(S(=O)(=O)N2CC3(CC(NC(=O)NCc4ccc(OC)cc4)C3)C2)CC1] | methyl 4-((6-(3-(4-methoxybenzyl)ureido)-2-azaspiro[3.3]heptan-2-yl)sulfonyl)cyclohexane-1-carboxylate |

TABLE 1-continued

| Compound No. | Structure | Name |
|---|---|---|
| 132 | 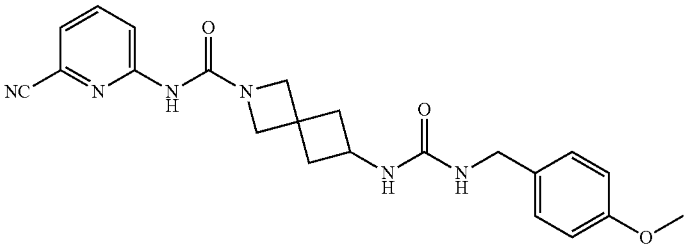 [SMILES: COc1ccc(CNC(=O)NC2CC3(C2)CN(C(=O)Nc2cccc(C#N)n2)C3)cc1] | N-(6-cyanopyridin-2-yl)-6-(3-(4-methoxybenzyl)ureido)-2-azaspiro[3.3]heptane-2-carboxamide |
| 133 | 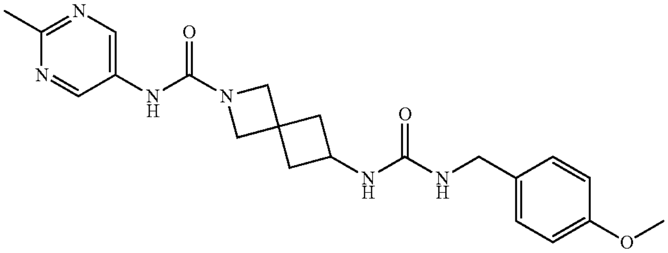 | 6-(3-(4-methoxybenzyl)ureido)-N-(2-methylpyrimidin-5-yl)-2-azaspiro[3.3]heptane-2-carboxamide |
| 134 | 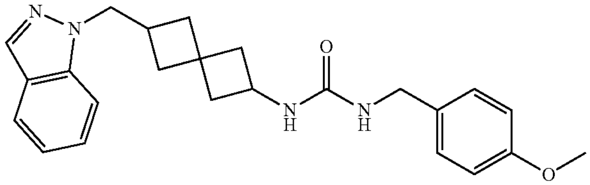 [SMILES: COc1ccc(CNC(=O)NC2CC3(CC(Cn4ncc5ccccc54)C3)C2)cc1] | 1-(6-((1H-indazol-1-yl)methyl)spiro[3.3]heptan-2-yl)-3-(4-methoxybenzyl)urea |
| 135 | 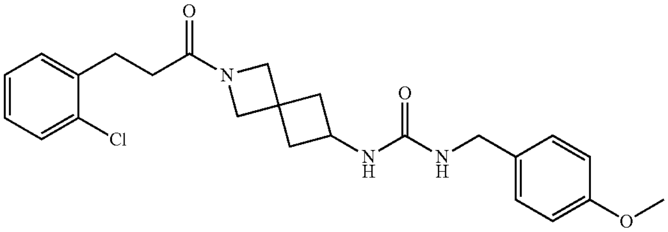 [SMILES: COc1ccc(CNC(=O)NC2CC3(C2)CN(C(=O)CCc2ccccc2Cl)C3)cc1] | 1-(2-(3-(2-chlorophenyl)propanoyl)-2-azaspiro[3.3]heptan-6-yl)-3-(4-methoxybenzyl)urea |
| 136 | 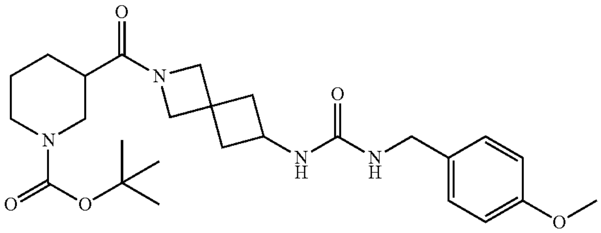 [SMILES: COc1ccc(CNC(=O)NC2CC3(C2)CN(C(=O)C2CCCN(C(=O)OC(C)(C)C)C2)C3)cc1] | tert-butyl 3-(6-(3-(4-methoxybenzyl)ureido)-2-azaspiro[3.3]heptane-2-carbonyl)piperidine-1-carboxylate |
| 137 | 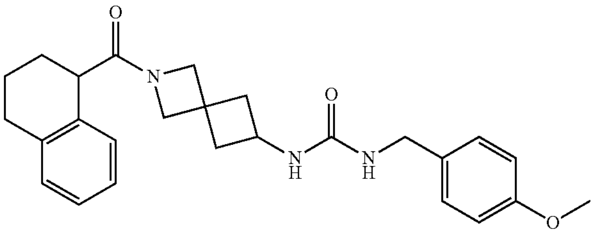 [SMILES: COc1ccc(CNC(=O)NC2CC3(C2)CN(C(=O)C2CCCc4ccccc42)C3)cc1] | 1-(4-methoxybenzyl)-3-(2-(1,2,3,4-tetrahydronaphthalene-1-carbonyl)-2-azaspiro[3.3]heptan-6-yl)urea |

TABLE 1-continued

| Compound No. | Structure | Name |
|---|---|---|
| 138 | 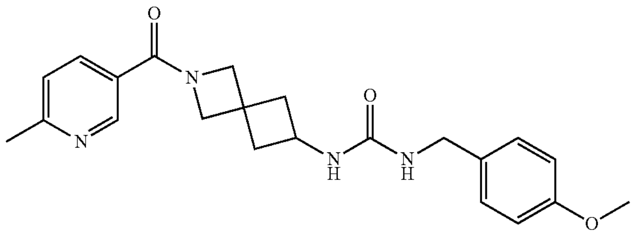 | 1-(4-methoxybenzyl)-3-(2-(6-methylnicotinoyl)-2-azaspiro[3.3]heptan-6-yl)urea |
| 139 | 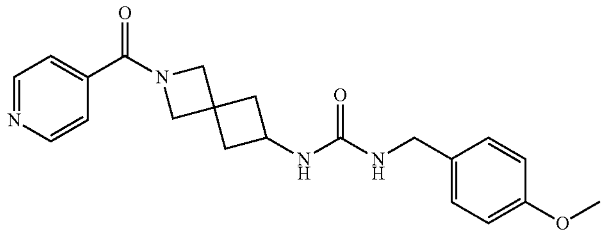 [SMILES: COc1ccc(CNC(=O)NC2CC3(C2)CN(C(=O)c2ccncc2)C3)cc1] | 1-(2-isonicotinoyl-2-azaspiro[3.3]heptan-6-yl)-3-(4-methoxybenzyl)urea |
| 140 | 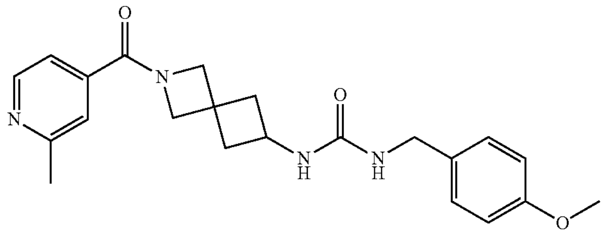 [SMILES: COc1ccc(CNC(=O)NC2CC3(C2)CN(C(=O)c2ccnc(C)c2)C3)cc1] | 1-(4-methoxybenzyl)-3-(2-(2-methylisonicotinyl)-2-azaspiro[3.3]heptan-6-yl)urea |
| 141 | 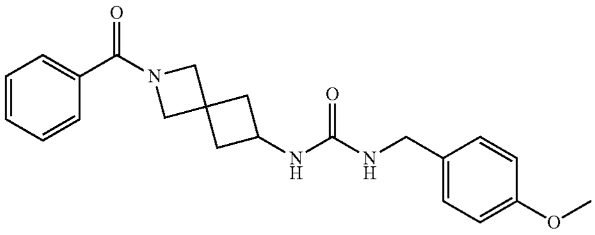 [SMILES: COc1ccc(CNC(=O)NC2CC3(C2)CN(C(=O)c2ccccc2)C3)cc1] | 1-(2-benzoyl-2-azaspiro[3.3]heptan-6-yl)-3-(4-methoxybenzyl)urea |
| 142 | 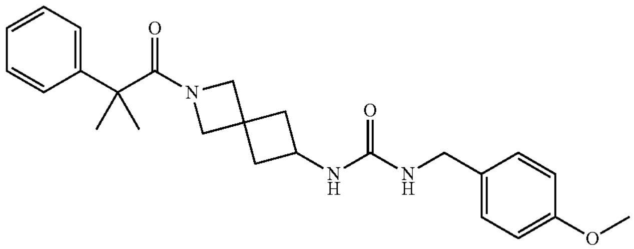 [SMILES: COc1ccc(CNC(=O)NC2CC3(C2)CN(C(=O)C(C)(C)c2ccccc2)C3)cc1] | 1-(4-methoxybenzyl)-3-(2-(2-methyl-2-phenylpropanoyl)-2-azaspiro[3.3]heptan-6-yl)urea |
| 143 | 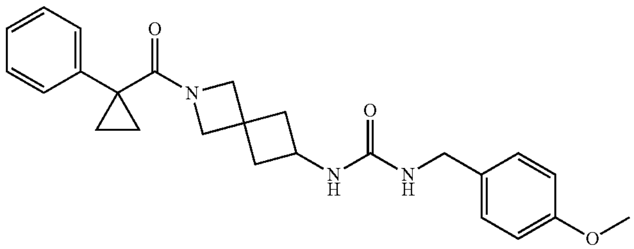 [SMILES: COc1ccc(CNC(=O)NC2CC3(C2)CN(C(=O)C2(c4ccccc4)CC2)C3)cc1] | 1-(4-methoxybenzyl)-3-(2-(1-phenylcyclopropane-1-carbonyl)-2-azaspiro[3.3]heptan-6-yl)urea |

TABLE 1-continued

| Compound No. | Structure | Name |
|---|---|---|
| 144 | 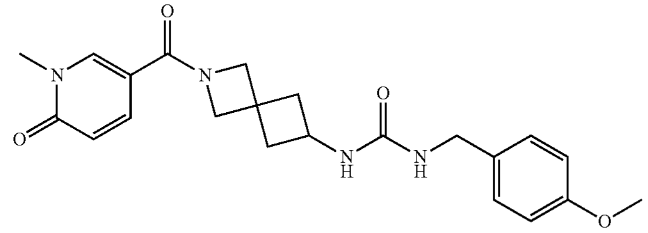 [SMILES: COc1ccc(CNC(=O)NC2CC3(C2)CN(C(=O)c2ccc(=O)n(C)c2)C3)cc1] | 1-(4-methoxybenzyl)-3-(2-(1-methyl-6-oxo-1,6-dihydropyridine-3-carbonyl)-2-azaspiro[3.3]heptan-6-yl)urea |
| 145 | 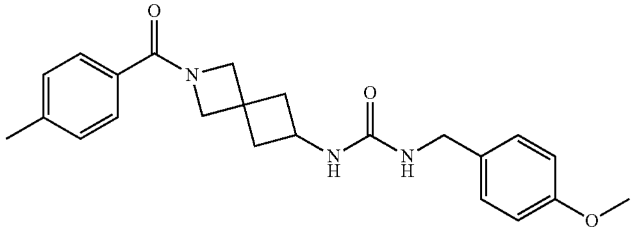 | 1-(4-methoxybenzyl)-3-(2-(4-methylbenzoyl)-2-azaspiro[3.3]heptan-6-yl)urea |
| 146 | 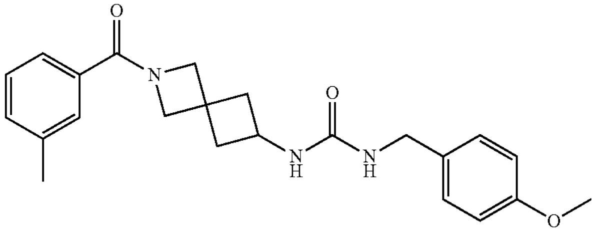 [SMILES: COc1ccc(CNC(=O)NC2CC3(C2)CN(C(=O)c2cccc(C)c2)C3)cc1] | 1-(4-methoxybenzyl)-3-(2-(3-methylbenzoyl)-2-azaspiro[3.3]heptan-6-yl)urea |
| 147 | 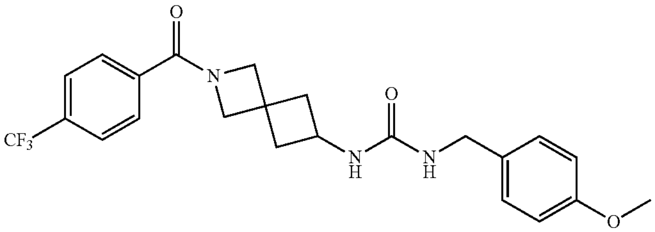 [SMILES: COc1ccc(CNC(=O)NC2CC3(C2)CN(C(=O)c2ccc(C(F)(F)F)cc2)C3)cc1] | 1-(4-methoxybenzyl)-3-(2-(4-(trifluoromethyl)benzoyl)-2-azaspiro[3.3]heptan-6-yl)urea |
| 148 | 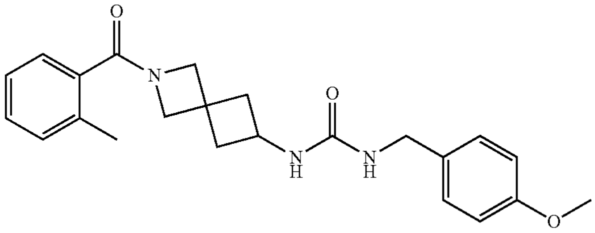 [SMILES: COc1ccc(CNC(=O)NC2CC3(C2)CN(C(=O)c2ccccc2C)C3)cc1] | 1-(4-methoxybenzyl)-3-(2-(2-methylbenzoyl)-2-azaspiro[3.3]heptan-6-yl)urea |
| 149 | 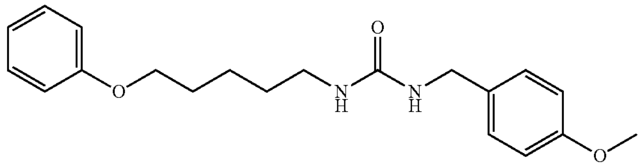 [SMILES: COc1ccc(CNC(=O)NCCCCCOc2ccccc2)cc1] | 1-(4-methoxybenzyl)-3-(5-phenoxypentyl)urea |
| 150 | 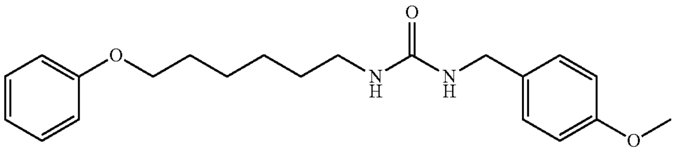 [SMILES: COc1ccc(CNC(=O)NCCCCCCOc2ccccc2)cc1] | 1-(4-methoxybenzyl)-3-(6-phenoxyhexyl)urea |

TABLE 1-continued

| Compound No. | Structure | Name |
|---|---|---|
| 151 | 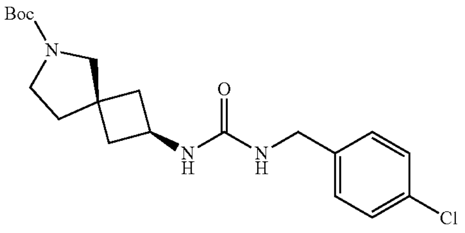 [SMILES: CC(C)(C)OC(=O)N1CC[C@]2(C1)C[C@@H](NC(=O)NCc1ccc(Cl)cc1)C2] | tert-butyl (2r,4s)-2-(3-(4-chlorobenzyl)ureido)-6-azaspiro[3.4]octane-6-carboxylate |
| 152 | 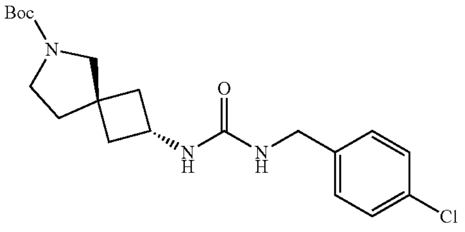 [SMILES: CC(C)(C)OC(=O)N1CC[C@]2(C1)C[C@H](NC(=O)NCc1ccc(Cl)cc1)C2] | tert-butyl (2s,4r)-2-(3-(4-chlorobenzyl)ureido)-6-azaspiro[3.4]octane-6-carboxylate |
| 153 | 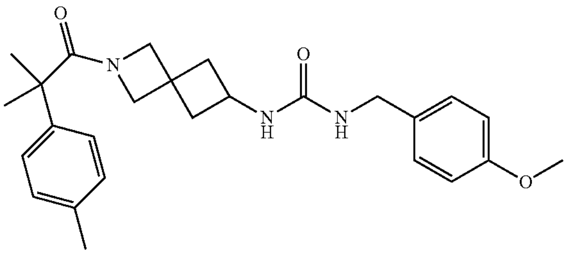 [SMILES: COc1ccc(CNC(=O)NC2CC3(C2)CN(C(=O)C(C)(C)c2ccc(C)cc2)C3)cc1] | 1-(4-methoxybenzyl)-3-(2-(2-methyl-2-(p-tolyl)propanoyl)-2-azaspiro[3.3]heptan-6-yl)urea |
| 154 | 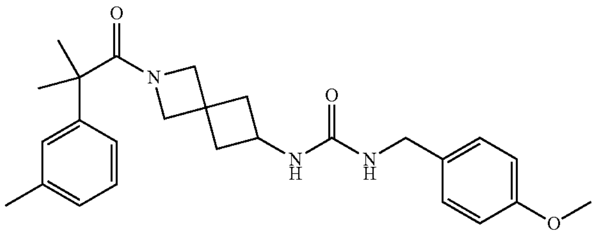 | 1-(4-methoxybenzyl)-3-(2-(2-methyl-2-(m-tolyl)propanoyl)-2-azaspiro[3.3]heptan-6-yl)urea |
| 155 | 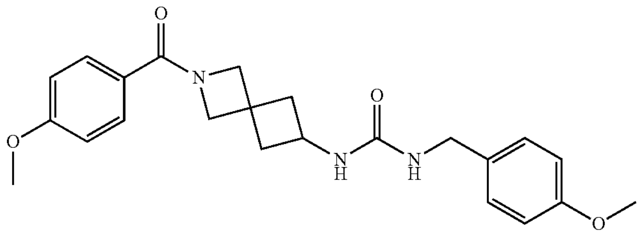 [SMILES: COc1ccc(CNC(=O)NC2CC3(C2)CN(C(=O)c2ccc(OC)cc2)C3)cc1] | 1-(4-(2-methoxybenzoyl)-2-azaspiro[3.3]heptan-6-yl)-3-(4-methoxybenzyl)urea |
| 156 | 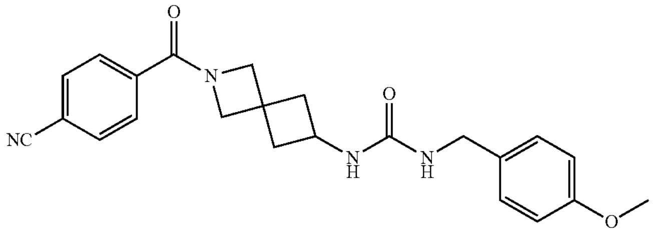 [SMILES: COc1ccc(CNC(=O)NC2CC3(C2)CN(C(=O)c2ccc(C#N)cc2)C3)cc1] | 1-(2-(4-cyanobenzyl)-2-azaspiro[3.3]heptan-6-yl)-3-(4-methoxybenzyl)urea |

TABLE 1-continued
| Compound No. | Structure | Name |
|---|---|---|
| 157 | 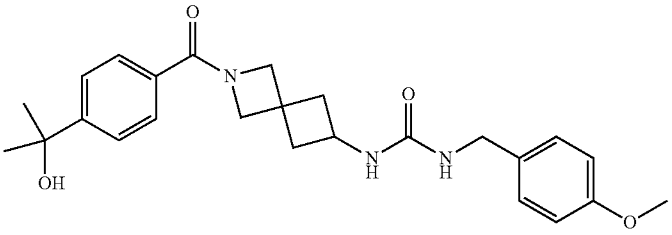 [SMILES: COc1ccc(CNC(=O)NC2CC3(C2)CN(C(=O)c2ccc(C(C)(C)O)cc2)C3)cc1] | 1-(2-(4-(2-hydroxypropan-2-yl)benzoyl)-2-azaspiro[3.3]heptan-6-yl)-3-(4-methoxybenzyl)urea |
| 158 | 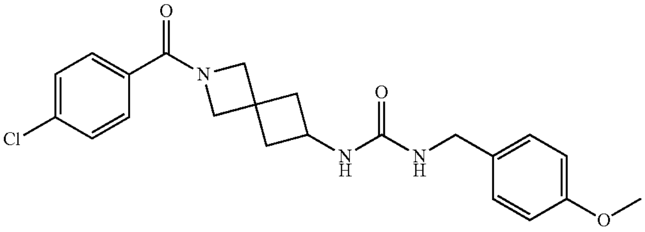 [SMILES: COc1ccc(CNC(=O)NC2CC3(C2)CN(C(=O)c2ccc(Cl)cc2)C3)cc1] | 1-(2-(4-chlorobenzoyl)-2-azaspiro[3.3]heptan-6-yl)-3-(4-methoxybenzyl)urea |
| 159 | 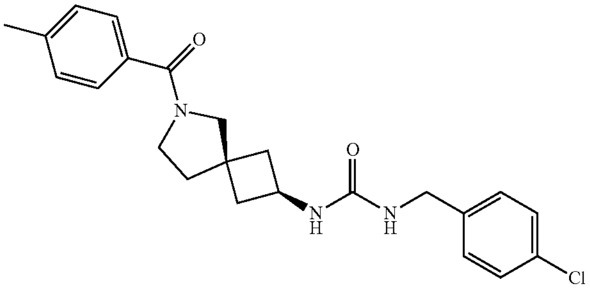 [SMILES: Cc1ccc(C(=O)N2CC[C@]3(C2)C[C@@H](NC(=O)NCc2ccc(Cl)cc2)C3)cc1] | 1-(4-chlorobenzyl)-3-((2r,4s)-6-(4-methylbenzoyl)-6-azaspiro[3.4]octan-2-yl)urea |
| 160 | 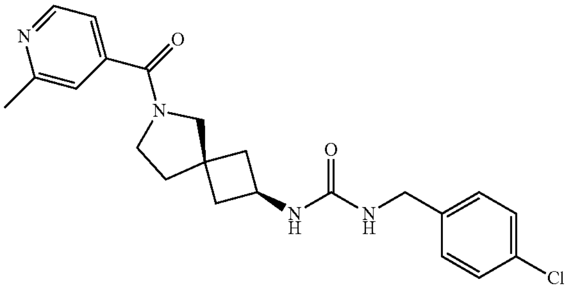 [SMILES: Cc1cc(C(=O)N2CC[C@]3(C2)C[C@@H](NC(=O)NCc2ccc(Cl)cc2)C3)ccn1] | 1-(4-chlorobenzyl)-3-((2r,4s)-6-(2-methylisonicotinyl)-6-azaspiro[3.4]octan-2-yl)urea |
| 161 | 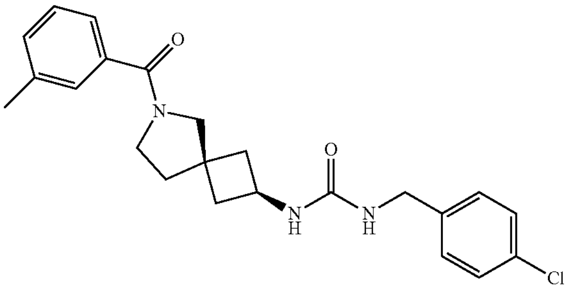 [SMILES: Cc1cccc(C(=O)N2CC[C@]3(C2)C[C@@H](NC(=O)NCc2ccc(Cl)cc2)C3)c1] | 1-(4-chlorobenzyl)-3-((2r,4s)-6-(3-methylbenzoyl)-6-azaspiro[3.4]octan-2-yl)urea |

TABLE 1-continued
| Compound No. | Structure | Name |
| --- | --- | --- |
| 162 | 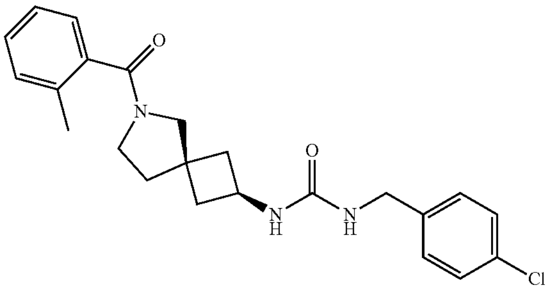 [SMILES: Cc1ccccc1C(=O)N1CC[C@]2(C1)C[C@@H](NC(=O)NCc1ccc(Cl)cc1)C2] | 1-(4-chlorobenzyl)-3-((2r,4s)-6-(2-methylbenzoyl)-6-azaspiro[3.4]octan-2-yl)urea |
| 163 | 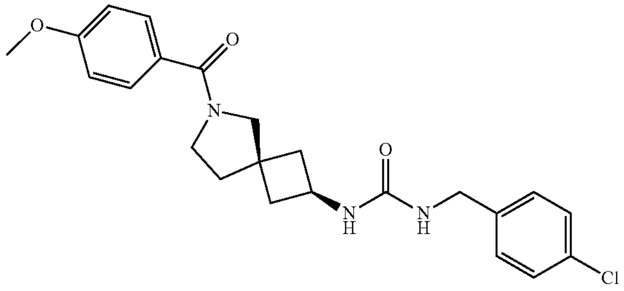 [SMILES: COc1ccc(C(=O)N2CC[C@]3(C2)C[C@@H](NC(=O)NCc2ccc(Cl)cc2)C3)cc1] | 1-(4-chlorobenzyl)-3-((2r,4s)-6-(4-methoxybenzoyl)-6-azaspiro[3.4]octan-2-yl)urea |
| 164 | 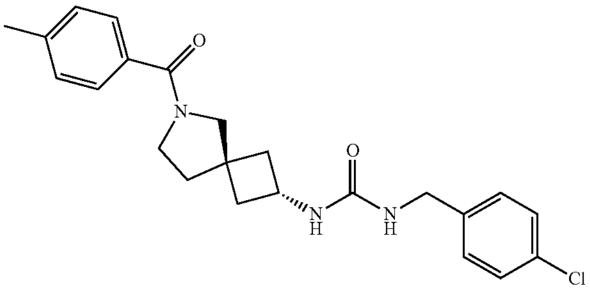 [SMILES: Cc1ccc(C(=O)N2CC[C@]3(C2)C[C@H](NC(=O)NCc2ccc(Cl)cc2)C3)cc1] | 1-(4-chlorobenzyl)-3-((2s,4r)-6-(4-methylbenzoyl)-6-azaspiro[3.4]octan-2-yl)urea |
| 165 | 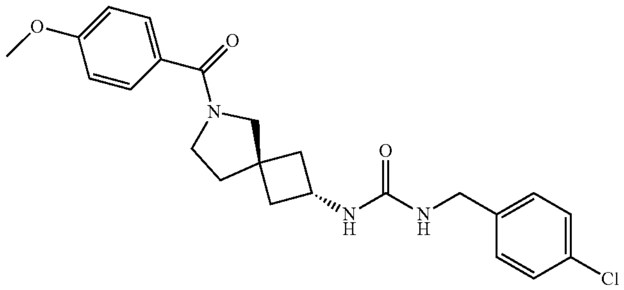 [SMILES: COc1ccc(C(=O)N2CC[C@]3(C2)C[C@H](NC(=O)NCc2ccc(Cl)cc2)C3)cc1] | 1-(4-chlorobenzyl)-3-((2s,4r)-6-(4-methoxybenzoyl)-6-azaspiro[3.4]octan-2-yl)urea |
| 166 | 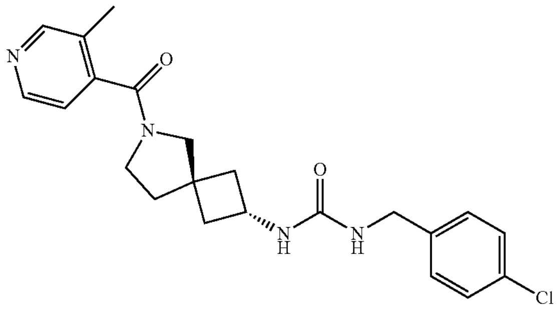 [SMILES: Cc1cnccc1C(=O)N1CC[C@]2(C1)C[C@H](NC(=O)NCc1ccc(Cl)cc1)C2] | 1-(4-chlorobenzyl)-3-((2r,4s)-6-(3-methylisonicotinoyl)-6-azaspiro[3.4]octan-2-yl)urea |

TABLE 1-continued
| Compound No. | Structure | Name |
|---|---|---|
| 167 | 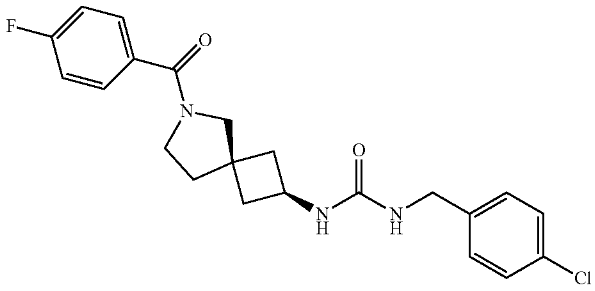 [SMILES: O=C(NCc1ccc(Cl)cc1)N[C@H]1C[C@]2(CCN(C(=O)c3ccc(F)cc3)C2)C1] | 1-(4-chlorobenzyl)-3-((2r,4s)-6-(4-fluorobenzoyl)-6-azaspiro[3.4]octan-2-yl)urea |
| 168 | 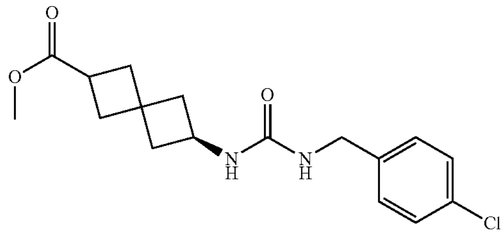 | methyl 6-(3-(4-chlorobenzyl)ureido)spiro[3.3]heptane-2-carboxylate |
| 169 | 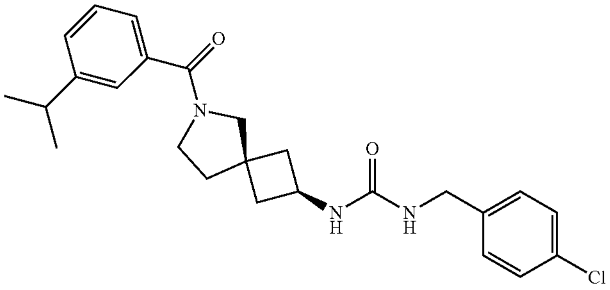 [SMILES: CC(C)c1cccc(C(=O)N2CC[C@]3(C2)C[C@@H](NC(=O)NCc2ccc(Cl)cc2)C3)c1] | 1-(4-chlorobenzyl)-3-((2r,4s)-6-(3-isopropylbenzoyl)-6-azaspiro[3.4]octan-2-yl)urea |
| 170 | 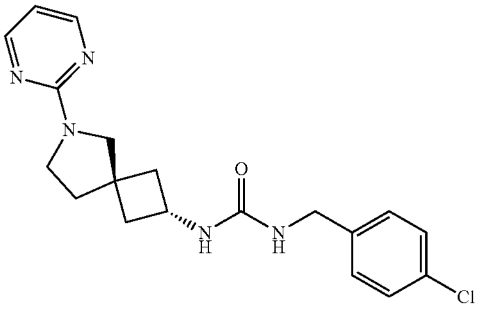 [SMILES: O=C(NCc1ccc(Cl)cc1)N[C@H]1C[C@@]2(CCN(c3ncccn3)C2)C1] | 1-(4-chlorobenzyl)-3-((2s,4r)-6-(pyrimidin-2-yl)-6-azaspiro[3.4]octan-2-yl)urea |
| 171 | 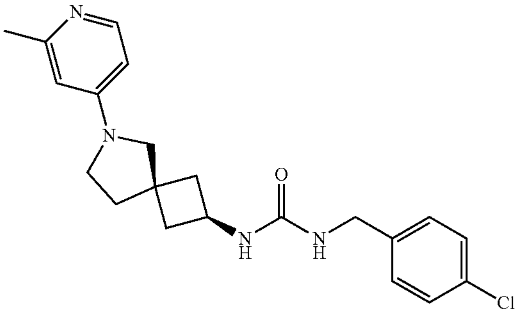 [SMILES: Cc1cc(N2CC[C@]3(C2)C[C@@H](NC(=O)NCc2ccc(Cl)cc2)C3)ccn1] | 1-(4-chlorobenzyl)-3-((2r,5s)-6-(2-methylpyridin-4-yl)-6-azaspiro[3.4]octan-2-yl)urea |

TABLE 1-continued

| Compound No. | Structure | Name |
|---|---|---|
| 172 | 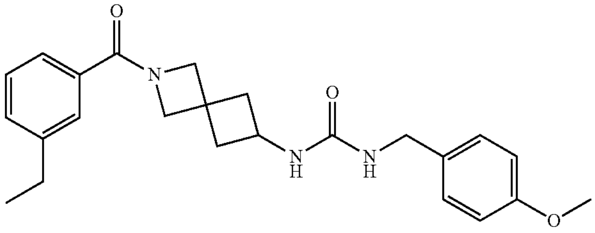 [SMILES: CCc1cccc(C(=O)N2CC3(CC(NC(=O)NCc4ccc(OC)cc4)C3)C2)c1] | 1-(2-(3-ethylbenzoyl)-2-azaspiro[3.3]heptan-6-yl)-3-(4-methoxybenzyl)urea |
| 173 | 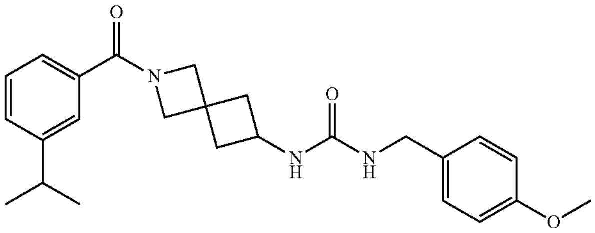 [SMILES: COc1ccc(CNC(=O)NC2CC3(C2)CN(C(=O)c2cccc(C(C)C)c2)C3)cc1] | 1-(2-(3-isopropylbenzoyl)-2-azaspiro[3.3]heptan-6-yl)-3-(4-methoxybenzyl)urea |
| 174 | 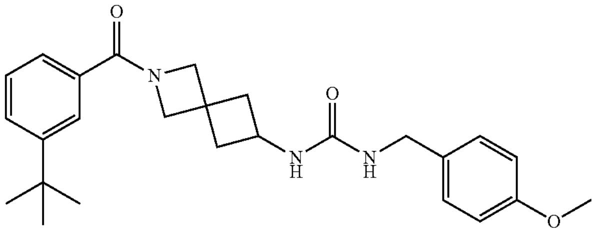 [SMILES: COc1ccc(CNC(=O)NC2CC3(C2)CN(C(=O)c2cccc(C(C)(C)C)c2)C3)cc1] | 1-(2-(3-(tert-butyl)benzoyl)-2-azaspiro[3.3]heptan-6-yl)-3-(4-methoxybenzyl)urea |
| 175 | 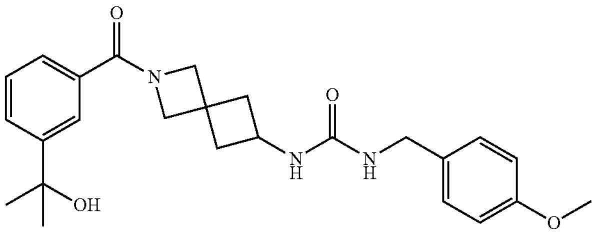 [SMILES: COc1ccc(CNC(=O)NC2CC3(C2)CN(C(=O)c2cccc(C(C)(C)O)c2)C3)cc1] | 1-(2-(3-(2-hydroxypropan-2-yl)benzoyl)-2-azaspiro[3.3]heptan-6-yl)-3-(4-methoxybenzyl)urea |
| 176 | 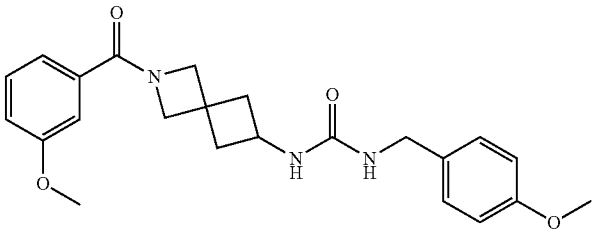 [SMILES: COc1ccc(CNC(=O)NC2CC3(C2)CN(C(=O)c2cccc(OC)c2)C3)cc1] | 1-(2-(3-methoxybenzoyl)-2-azaspiro[3.3]heptan-6-yl)-3-(4-methoxybenzyl)urea |
| 177 | 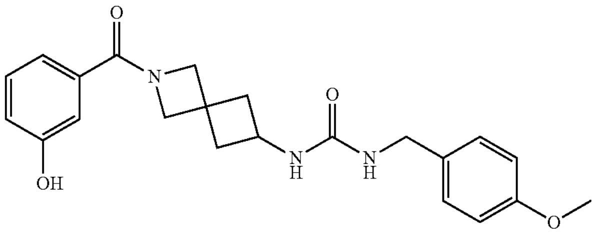 [SMILES: COc1ccc(CNC(=O)NC2CC3(C2)CN(C(=O)c2cccc(O)c2)C3)cc1] | 1-(2-(3-hydroxybenzoyl)-2-azaspiro[3.3]heptan-6-yl)-3-(4-methoxybenzyl)urea |

TABLE 1-continued

| Compound No. | Structure | Name |
|---|---|---|
| 178 | 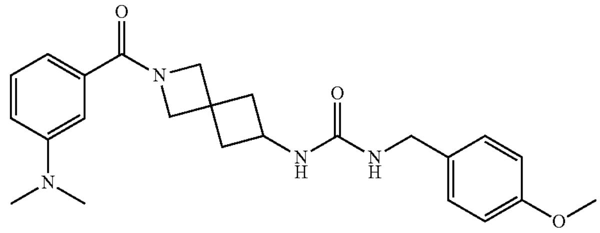 [SMILES: COc1ccc(CNC(=O)NC2CC3(C2)CN(C(=O)c2cccc(N(C)C)c2)C3)cc1] | 1-(2-(3-(dimethylamino)benzoyl)-2-azaspiro[3.3]heptan-6-yl)-3-(4-methoxybenzyl)urea |
| 179 | 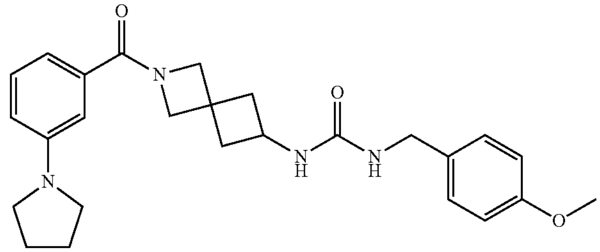 [SMILES: COc1ccc(CNC(=O)NC2CC3(C2)CN(C(=O)c2cccc(N4CCCC4)c2)C3)cc1] | 1-(4-methoxybenzyl)-3-(2-(3-(pyrrolidin-1-yl)benzoyl)-2-azaspiro[3.3]heptan-6-yl)urea |
| 180 | 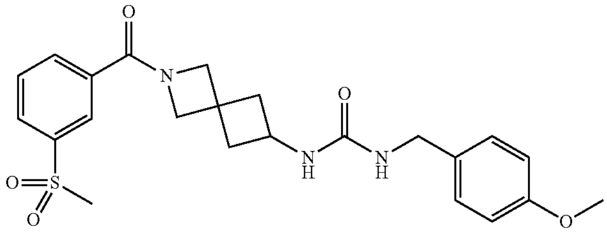 [SMILES: COc1ccc(CNC(=O)NC2CC3(C2)CN(C(=O)c2cccc(S(C)(=O)=O)c2)C3)cc1] | 1-(4-methoxybenzyl)-3-(2-(3-(methylsulfonyl)benzoyl)-2-azaspiro[3.3]heptan-6-yl)urea |
| 181 | 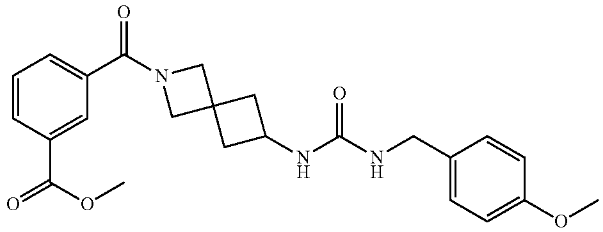 [SMILES: COC(=O)c1cccc(C(=O)N2CC3(CC(NC(=O)NCc4ccc(OC)cc4)C3)C2)c1] | methyl 3-(6-(3-(4-methoxybenzyl)ureido)-2-azaspiro[3.3]heptane-2-carbonyl)benzoate |
| 182 | 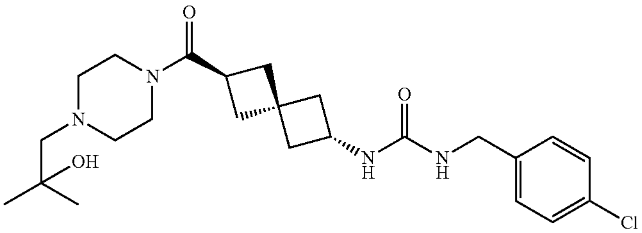 | 1-(4-chlorobenzyl)-3-((2R,4r,6R)-6-(4-(2-hydroxy-2-methylpropyl)piperazine-1-carbonyl)spiro[3.3]heptan-2-yl)urea |
| 183 | 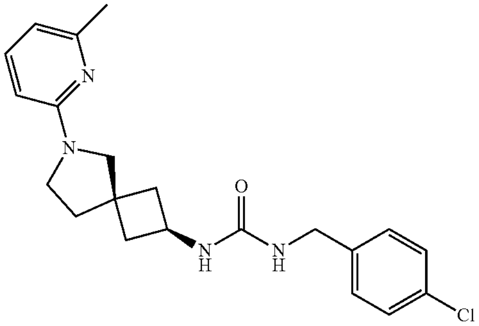 [SMILES: Cc1cccc(N2CC[C@]3(C2)C[C@@H](NC(=O)NCc2ccc(Cl)cc2)C3)n1] | 1-(4-chlorobenzyl)-3-((2r,4s)-6-(6-methylpyridin-2-yl)-6-azaspiro[3.4]octan-2-yl)urea |

TABLE 1-continued

| Compound No. | Structure | Name |
|---|---|---|
| 184 | 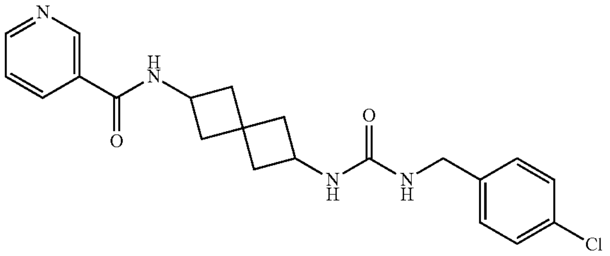 [SMILES: O=C(NCc1ccc(Cl)cc1)NC1CC2(C1)CC(NC(=O)c1cccnc1)C2] | N-(6-(3-(4-chlorobenzyl)ureido)spiro[3.3]heptan-2-yl)nicotinamide |
| 185 | 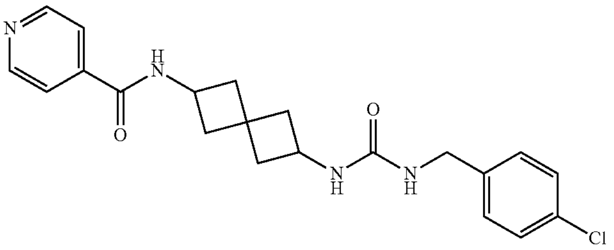 [SMILES: O=C(NCc1ccc(Cl)cc1)NC1CC2(C1)CC(NC(=O)c1ccncc1)C2] | N-(6-(3-(4-chlorobenzyl)ureido)spiro[3.3]heptan-2-yl)isonicotinamide |
| 186 | 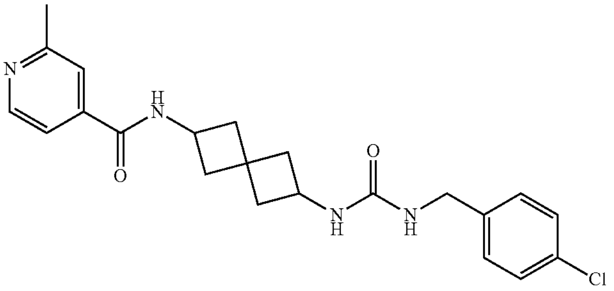 [SMILES: Cc1cc(C(=O)NC2CC3(CC(NC(=O)NCc4ccc(Cl)cc4)C3)C2)ccn1] | N-(6-(3-(4-chlorobenzyl)ureido)spiro[3.3]heptan-2-yl)-2-methylisonicotinamide |
| 187 | 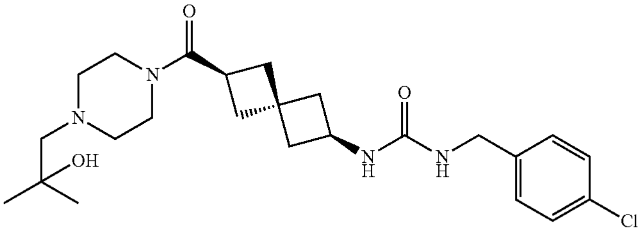 | 1-(4-chlorobenzyl)-3-((2S,4s,6S)-6-(4-(2-hydroxy-2-methylpropyl)piperazine-1-carbonyl)spiro[3.3]heptan-2-yl)urea |
| 188 | 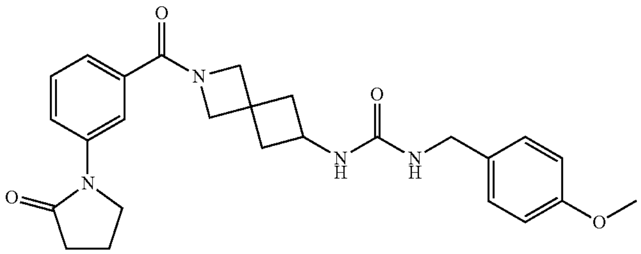 [SMILES: COc1ccc(CNC(=O)NC2CC3(C2)CN(C(=O)c2cccc(N4CCCC4=O)c2)C3)cc1] | 1-(4-methoxybenzyl)-3-(2-(3-(2-oxopyrrolidin-1-yl)benzoyl)-2-azaspiro[3.3]heptan-6-yl)urea |
| 189 | 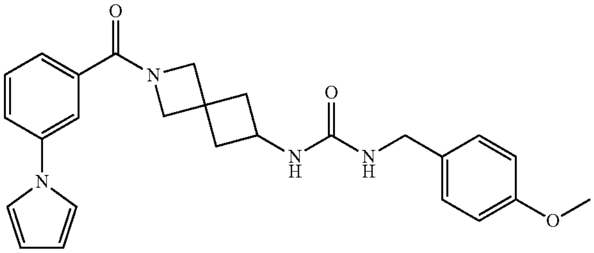 [SMILES: COc1ccc(CNC(=O)NC2CC3(C2)CN(C(=O)c2cccc(-n4cccc4)c2)C3)cc1] | 1-(2-(3-(1H-pyrrol-1-yl)benzoyl)-2-azaspiro[3.3]heptan-6-yl)-3-(4-methoxybenzyl)urea |

TABLE 1-continued
| Compound No. | Structure | Name |
|---|---|---|
| 190 | 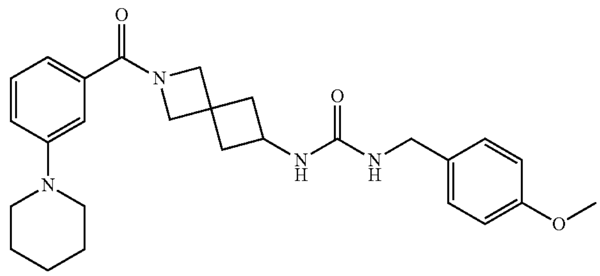 [SMILES: COc1ccc(CNC(=O)NC2CC3(C2)CN(C(=O)c2cccc(N4CCCCC4)c2)C3)cc1] | 1-(4-methoxybenzyl)-3-(2-(3-(piperidin-1-yl)benzoyl)-2-azaspiro[3.3]heptan-6-yl)urea |
| 191 | 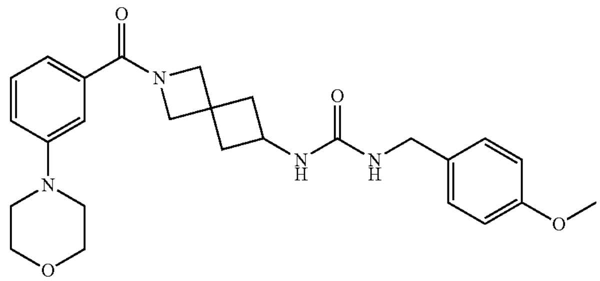 [SMILES: COc1ccc(CNC(=O)NC2CC3(C2)CN(C(=O)c2cccc(N4CCOCC4)c2)C3)cc1] | 1-(4-methoxybenzyl)-3-(2-(3-morpholinobenzyl)-2-azaspiro[3.3]heptan-6-yl)urea |
| 192 | 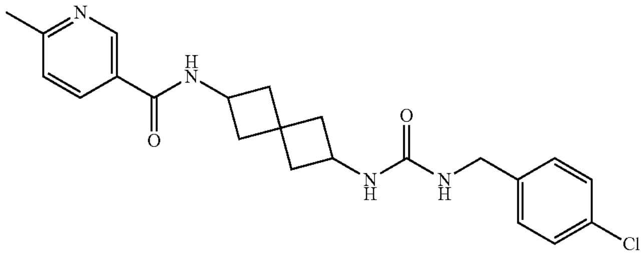 [SMILES: Cc1ccc(C(=O)NC2CC3(CC(NC(=O)NCc4ccc(Cl)cc4)C3)C2)cn1] | N-(6-(3-(4-chlorobenzyl)ureido)spiro[3.3]heptan-2-yl)-6-methylnicotinamide |
| 193 | 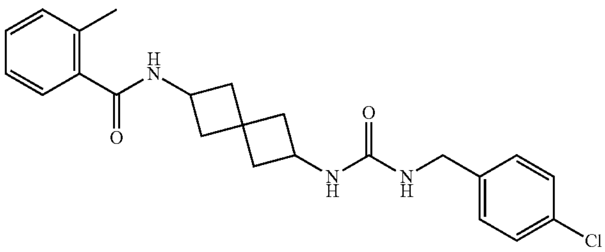 [SMILES: Cc1ccccc1C(=O)NC1CC2(CC(NC(=O)NCc3ccc(Cl)cc3)C2)C1] | N-(6-(3-(4-chlorobenzyl)ureido)spiro[3.3]heptan-2-yl)-2-methylbenzamide |
| 194 | 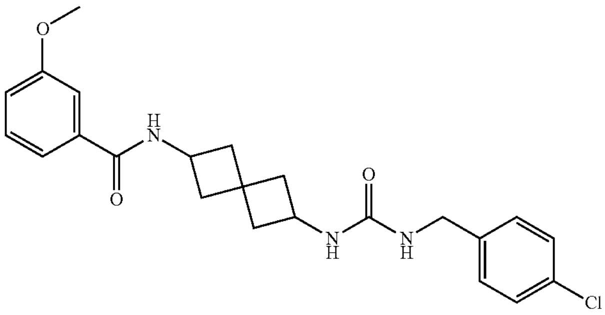 [SMILES: COc1cccc(C(=O)NC2CC3(CC(NC(=O)NCc4ccc(Cl)cc4)C3)C2)c1] | N-(6-(3-(4-chlorobenzyl)ureido)spiro[3.3]heptan-2-yl)-3-methoxybenzamide |

TABLE 1-continued

| Compound No. | Structure | Name |
| --- | --- | --- |
| 195 | 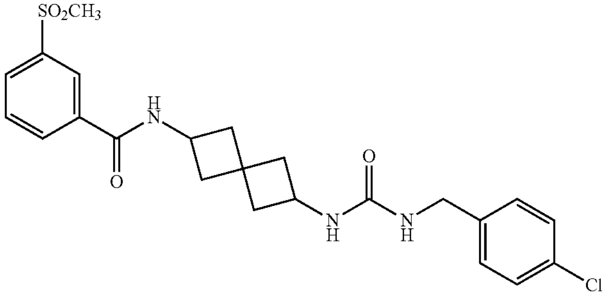 [SMILES: CS(=O)(=O)c1cccc(C(=O)NC2CC3(CC(NC(=O)NCc4ccc(Cl)cc4)C3)C2)c1] | N-(6-(3-(4-chlorobenzyl)ureido) spiro[3.3]heptan-2-yl)-3-(methylsulfonyl)benzamide |
| 196 | 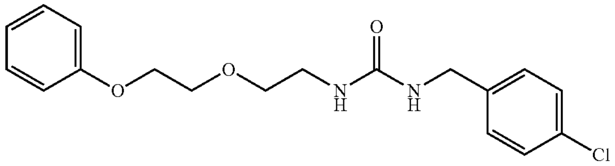 [SMILES: O=C(NCCOCCOc1ccccc1)NCc1ccc(Cl)cc1] | 1-(4-chlorobenzyl)-3-(2-(2-phenoxyethoxy)ethyl) urea |
| 197 | 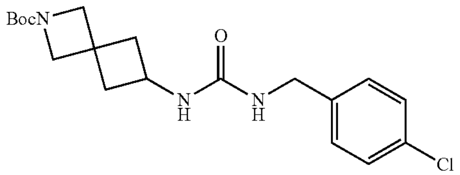 [SMILES: CC(C)(C)OC(=O)N1CC2(CC(NC(=O)NCc3ccc(Cl)cc3)C2)C1] | tert-butyl 6-(3-(4-chlorobenzyl)ureido)-2-azaspiro[3.3]heptane-2-carboxylate |
| 198 | 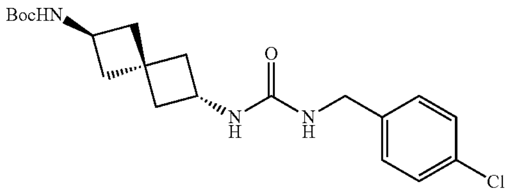 | tert-butyl ((2R,4r,6R)-6-(3-(4-chlorobenzyl)ureido) spiro[3.3]heptan-2-yl)carbamate |
| 199 | 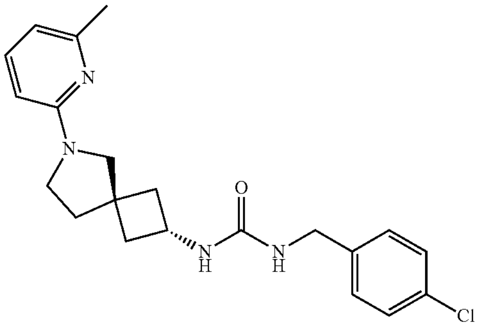 [SMILES: Cc1cccc(N2CC[C@]3(C2)C[C@H](NC(=O)NCc2ccc(Cl)cc2)C3)n1] | 1-(4-chlorobenzyl)-3-((2s,4r)-6-(4-methylpyridin-2-yl)-6-azaspiro[3.4]octan-2-yl)urea |
| 200 | 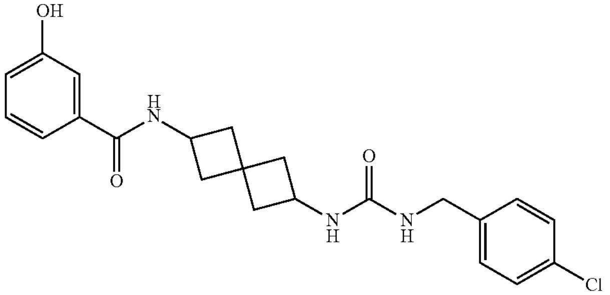 [SMILES: O=C(NCc1ccc(Cl)cc1)NC1CC2(C1)CC(NC(=O)c1cccc(O)c1)C2] | N-(6-(3-(4-chlorobenzyl)ureido) spiro[3.3]heptan-2-yl)-3-hydroxybenzamide |

TABLE 1-continued

| Compound No. | Structure | Name |
|---|---|---|
| 201 | 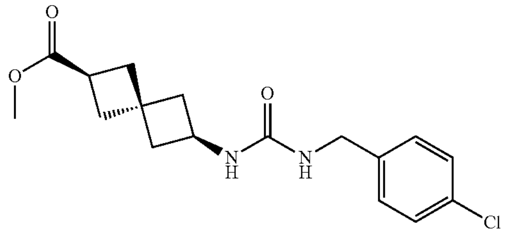 | methyl (2S,4s,6S)-6-(3-(4-chlorobenzyl)ureido) spiro[3.3]heptane-2-carboxylate |
| 202 | 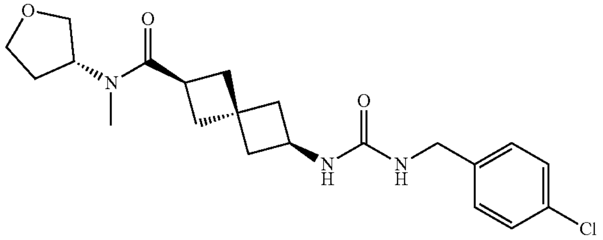 | (2S,4s,6S)-6-(3-(4-chlorobenzyl)ureido)-N-methyl-N-((R)-tetrahydrofuran-3-yl)spiro[3.3]heptane-2-carboxamide |
| 203 | 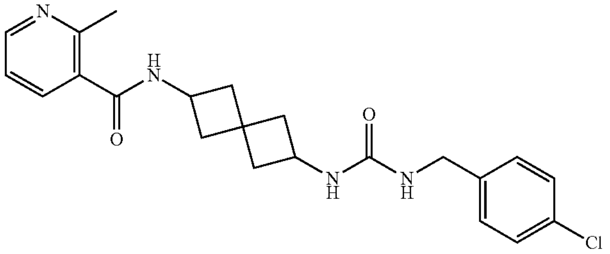 [SMILES: Cc1ncccc1C(=O)NC1CC2(CC(NC(=O)NCc3ccc(Cl)cc3)C2)C1] | N-(6-(3-(4-chlorobenzyl)ureido) spiro[3.3]heptan-2-yl)-2-methylnicotinamide |
| 204 | 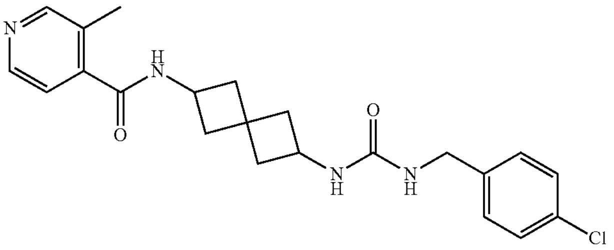 [SMILES: Cc1cnccc1C(=O)NC1CC2(CC(NC(=O)NCc3ccc(Cl)cc3)C2)C1] | N-(6-(3-(4-chlorobenzyl)ureido) spiro[3.3]heptan-2-yl)-3-methylisonicotinamide |
| 205 | 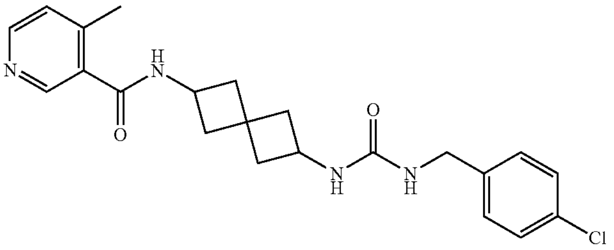 [SMILES: Cc1ccncc1C(=O)NC1CC2(CC(NC(=O)NCc3ccc(Cl)cc3)C2)C1] | N-(6-(3-(4-chlorobenzyl)ureido) spiro[3.3]heptan-2-yl)-4-methylnicotinamide |
| 206 | 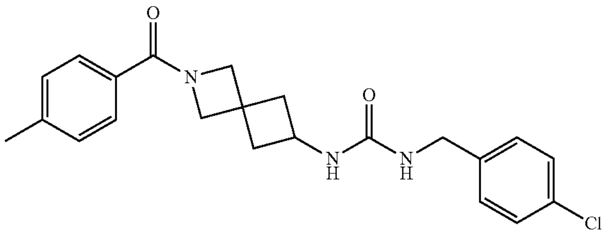 [SMILES: Cc1ccc(C(=O)N2CC3(CC(NC(=O)NCc4ccc(Cl)cc4)C3)C2)cc1] | 1-(4-chlorobenzyl)-3-(2-(4-methylbenzoyl)-2-azaspiro[3.3]heptan-6-yl)urea |

TABLE 1-continued

| Compound No. | Structure | Name |
|---|---|---|
| 207 | 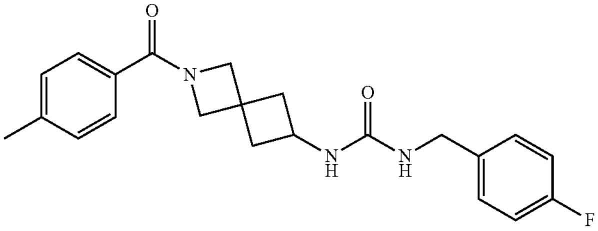 [SMILES: Cc1ccc(C(=O)N2CC3(CC(NC(=O)NCc4ccc(F)cc4)C3)C2)cc1] | 1-(4-fluorobenzyl)-3-(2-(4-methylbenzoyl)-2-azaspiro[3.3]heptan-6-yl)urea |
| 208 | 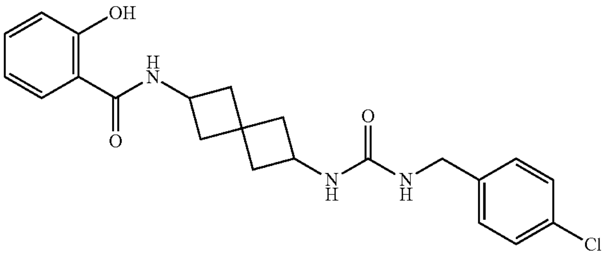 | N-(6-(3-(4-chlorobenzyl)ureido)spiro[3.3]heptan-2-yl)-2-hydroxybenzamide |
| 209 | 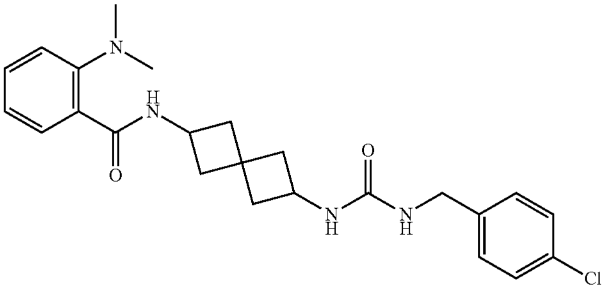 [SMILES: CN(C)c1ccccc1C(=O)NC1CC2(CC(NC(=O)NCc3ccc(Cl)cc3)C2)C1] | N-(6-(3-(4-chlorobenzyl)ureido)spiro[3.3]heptan-2-yl)-2-(dimethylamino)benzamide |
| 210 | 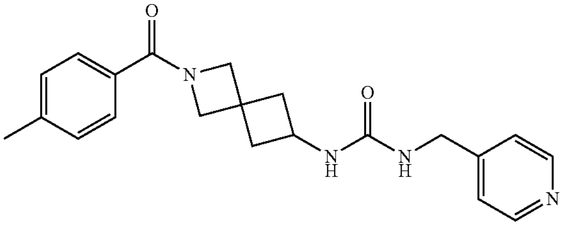 [SMILES: Cc1ccc(C(=O)N2CC3(CC(NC(=O)NCc4ccncc4)C3)C2)cc1] | 1-(2-(4-methylbenzoyl)-2-azaspiro[3.3]heptan-6-yl)-3-(pyridin-4-ylmethyl)urea |
| 211 | 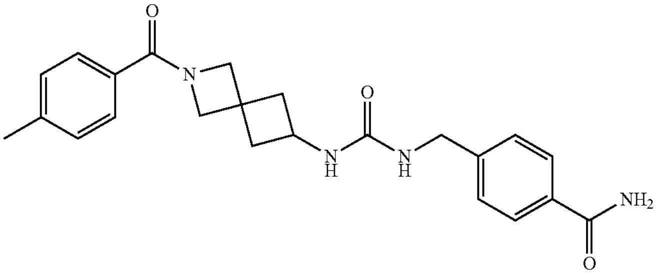 [SMILES: Cc1ccc(C(=O)N2CC3(CC(NC(=O)NCc4ccc(C(N)=O)cc4)C3)C2)cc1] | 4-((3-(2-(4-methylbenzoyl)-2-azaspiro[3.3]heptan-6-yl)ureido)methyl)benzamide |
| 212 | 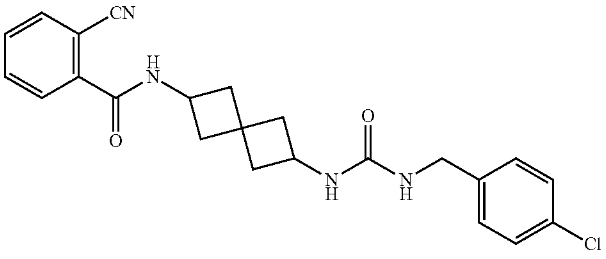 [SMILES: N#Cc1ccccc1C(=O)NC1CC2(CC(NC(=O)NCc3ccc(Cl)cc3)C2)C1] | N-(6-(3-(4-chlorobenzyl)ureido)spiro[3.3]heptan-2-yl)-2-cyanobenzamide |

TABLE 1-continued

| Compound No. | Structure | Name |
|---|---|---|
| 213 | 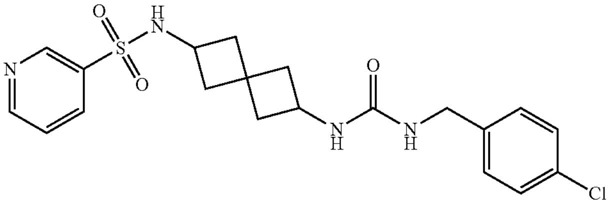 [SMILES: O=C(NCc1ccc(Cl)cc1)NC1CC2(C1)CC(NS(=O)(=O)c1cccnc1)C2] | N-(6-(3-(4-chlorobenzyl)ureido) spiro[3.3]heptan-2-yl)pyridine-3-sulfonamdie |
| 214 | 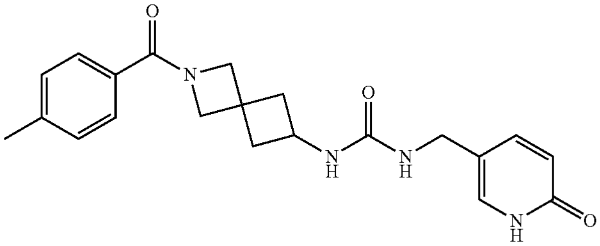 [SMILES: Cc1ccc(C(=O)N2CC3(CC(NC(=O)NCc4ccc(=O)[nH]c4)C3)C2)cc1] | 1-(2-(4-methylbenzoyl)-2-azaspiro[3.3]heptan-6-yl)-3-((6-oxo-1,6-dihydropyridin-3-yl)methyl)urea |
| 215 | 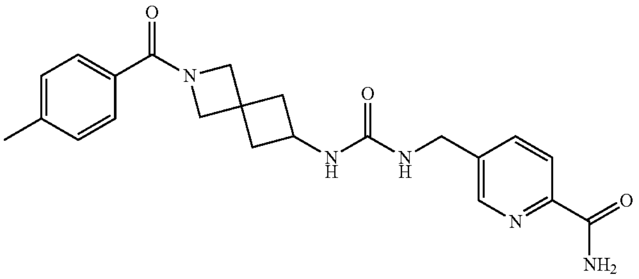 [SMILES: Cc1ccc(C(=O)N2CC3(CC(NC(=O)NCc4ccc(C(N)=O)nc4)C3)C2)cc1] | 5-((3-(2-(4-methylbenzoyl)-2-azaspiro[3.3]heptan-6-yl)ureido)methyl)pic-olinamide |
| 216 | 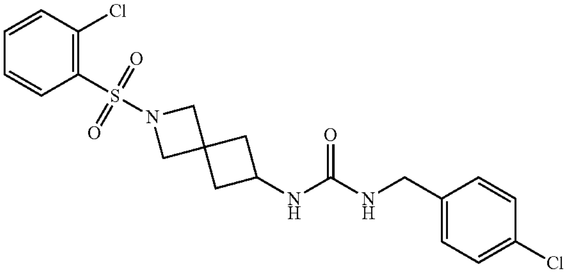 [SMILES: O=C(NCc1ccc(Cl)cc1)NC1CC2(C1)CN(S(=O)(=O)c1ccccc1Cl)C2] | 1-(4-chlorobenzyl)-3-(2-((2-chlorophenyl)sulfonyl)-2-azaspiro[3.3]heptan-6-yl)urea |
| 217 | 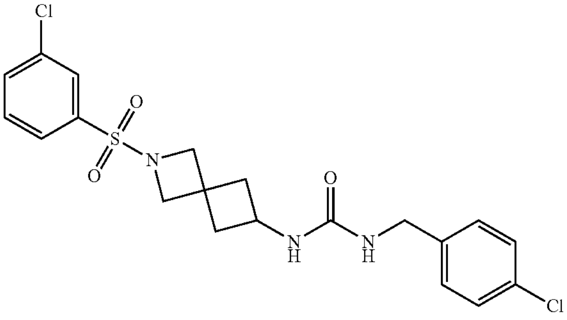 [SMILES: O=C(NCc1ccc(Cl)cc1)NC1CC2(C1)CN(S(=O)(=O)c1cccc(Cl)c1)C2] | 1-(4-chlorobenzyl)-3-(2-((3-chlorophenyl)sulfonyl)-2-azaspiro[3.3]heptan-6-yl)urea |

TABLE 1-continued
| Compound No. | Structure | Name |
|---|---|---|
| 218 | 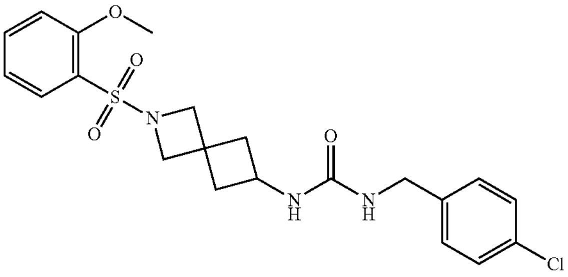 [SMILES: COc1ccccc1S(=O)(=O)N1CC2(CC(NC(=O)NCc3ccc(Cl)cc3)C2)C1] | 1-(4-chlorobenzyl)-3-(2-((2-methoxyphenyl)sulfonyl)-2-azaspiro[3.3]heptan-6-yl)urea |
| 219 | 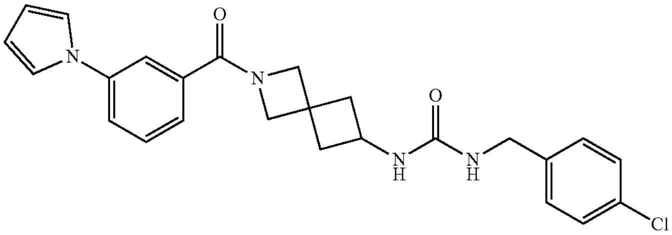 [SMILES: O=C(NCc1ccc(Cl)cc1)NC1CC2(C1)CN(C(=O)c1cccc(-n3cccc3)c1)C2] | 1-(2-(3-(1H-pyrrol-1-yl)benzoyl)-2-azaspiro[3.3]heptan-6-yl)-3-(4-chlorobenzyl)urea |
| 220 | 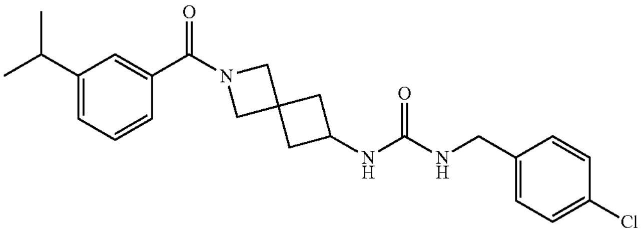 [SMILES: CC(C)c1cccc(C(=O)N2CC3(CC(NC(=O)NCc4ccc(Cl)cc4)C3)C2)c1] | 1-(4-chlorobenzyl)-3-(2-(3-isopropylbenzoyl)-2-azaspiro[3.3]heptan-6-yl)urea |
| 221 | 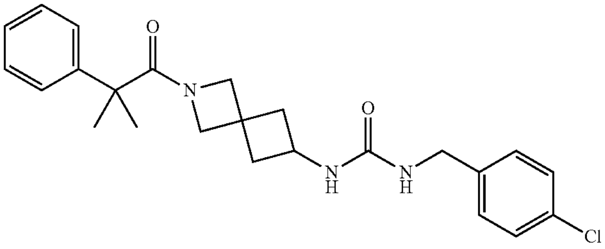 [SMILES: CC(C)(C(=O)N1CC2(CC(NC(=O)NCc3ccc(Cl)cc3)C2)C1)c1ccccc1] | 1-(4-chlorobenzyl)-3-(2-(2-methyl-2-phenylpropanoyl)-2-azaspiro[3.3]heptan-6-yl)urea |
| 222 | 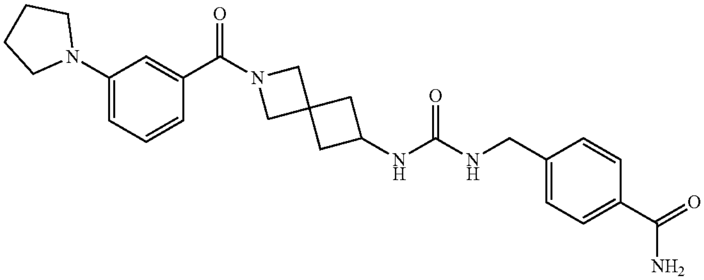 [SMILES: NC(=O)c1ccc(CNC(=O)NC2CC3(C2)CN(C(=O)c2cccc(N4CCCC4)c2)C3)cc1] | 4-((3-(2-(3-(pyrrolidin-1-yl)benzoyl)-2-azaspiro[3.3]heptan-6-yl)ureido)methyl)benzamide |

TABLE 1-continued

| Compound No. | Structure | Name |
|---|---|---|
| 223 | 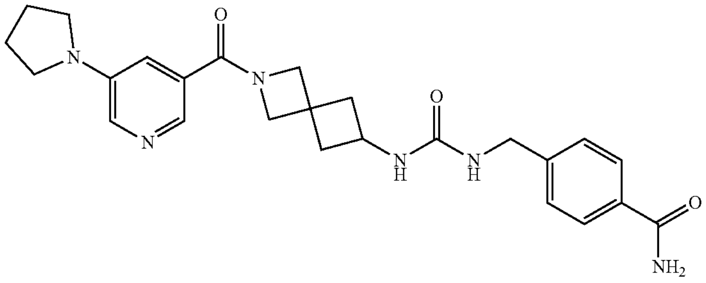 [SMILES: NC(=O)c1ccc(CNC(=O)NC2CC3(C2)CN(C(=O)c2cncc(N4CCCC4)c2)C3)cc1] | 4-((3-(2-(5-(pyrrolidin-1-yl)nicotinoyl)-2-azaspiro[3.3]heptan-6-yl)ureido)methyl)benzamide |
| 224 | 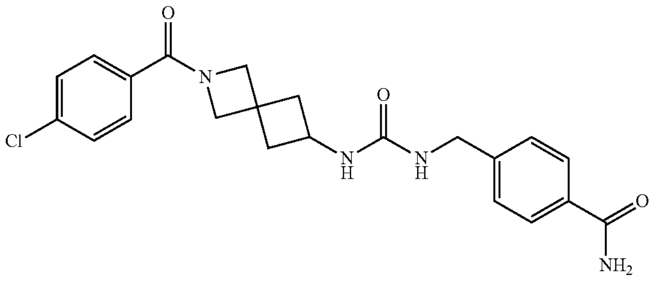 [SMILES: NC(=O)c1ccc(CNC(=O)NC2CC3(C2)CN(C(=O)c2ccc(Cl)cc2)C3)cc1] | 4-((3-(2-(4-chlorobenzoyl)-2-azaspiro[3.3]heptan-6-yl)ureido)methyl)benzamide |
| 225 | 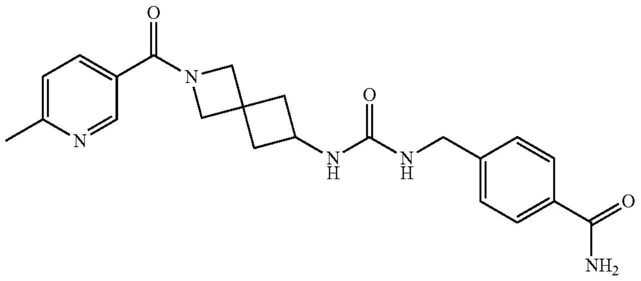 [SMILES: Cc1ccc(C(=O)N2CC3(CC(NC(=O)NCc4ccc(C(N)=O)cc4)C3)C2)cn1] | 4-((3-(2-(6-methylnicotinoyl)-2-azaspiro[3.3]heptan-6-yl)ureido)methyl)benzamide |
| 226 | 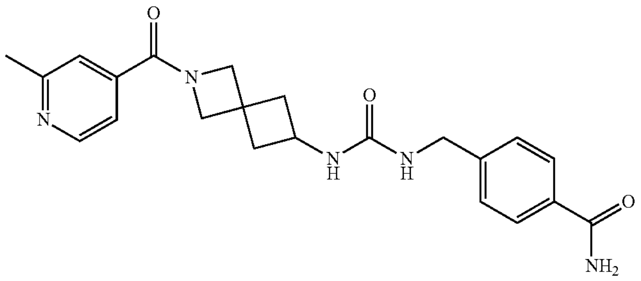 [SMILES: Cc1cc(C(=O)N2CC3(CC(NC(=O)NCc4ccc(C(N)=O)cc4)C3)C2)ccn1] | 4-((3-(2-(2-methylisonicotinoyl)-2-azaspiro[3.3]heptan-6-yl)ureido)methyl)benzamide |
| 227 | 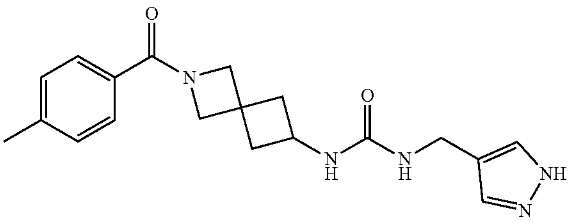 [SMILES: Cc1ccc(C(=O)N2CC3(CC(NC(=O)NCc4cn[nH]c4)C3)C2)cc1] | 1-((1H-pyrazol-4-yl)methyl)-3-(2-(4-methylbenzoyl)-2-azaspiro[3.3]heptan-6-yl)urea |

TABLE 1-continued

| Compound No. | Structure | Name |
|---|---|---|
| 228 | 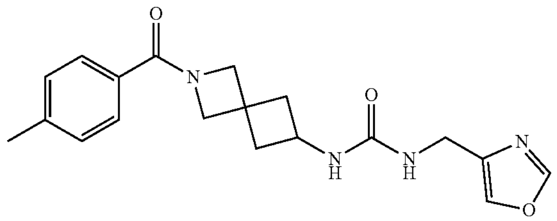 [SMILES: Cc1ccc(C(=O)N2CC3(CC(NC(=O)NCc4cocn4)C3)C2)cc1] | 1-(2-(4-methylbenzoyl)-2-azaspiro[3.3]heptan-6-yl)-3-(oxazol-4-ylmethyl)urea |
| 229 | 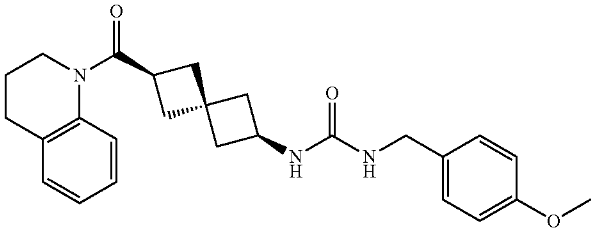 | 1-(4-methoxybenzyl)-3-((2S,4s,6S)-6-(1,2,3,4-tetrahydroquinoline-1-carbonyl)spiro[3.3]heptan-2-yl)urea |
| 230 | 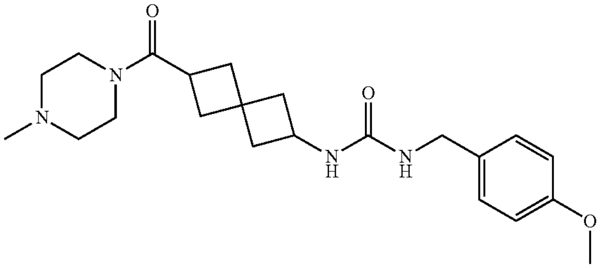 | 1-(4-methoxybenzyl)-3-(6-(4-methylpiperazine-1-carbonyl)spiro[3.3]heptan-2-yl)urea |
| 231 | 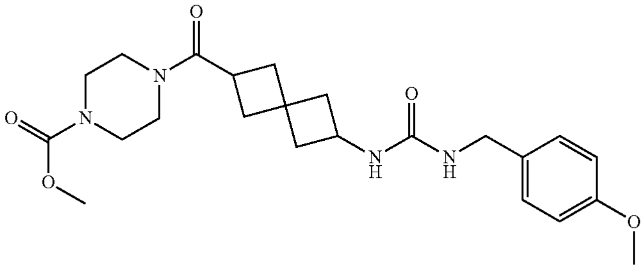 [SMILES: COC(=O)N1CCN(C(=O)C2CC3(CC(NC(=O)NCc4ccc(OC)cc4)C3)C2)CC1] | methyl 4-(6-(3-(4-methoxybenzyl)ureido)spiro[3.3]heptane-2-carbonyl)piperazine-1-carboxylate |
| 232 | 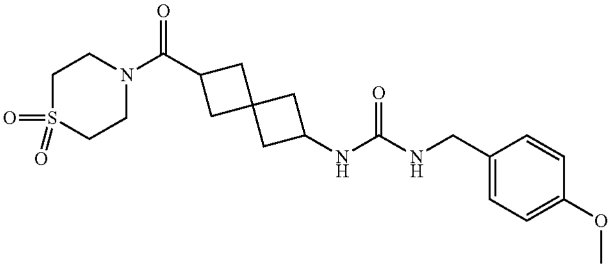 [SMILES: COc1ccc(CNC(=O)NC2CC3(C2)CC(C(=O)N2CCS(=O)(=O)CC2)C3)cc1] | 1-(6-(1,1-dioxidothiomorpholine-4-carbonyl)spiro[3.3]heptan-2-yl)-3-(4-methoxybenzyl)urea |
| 233 | 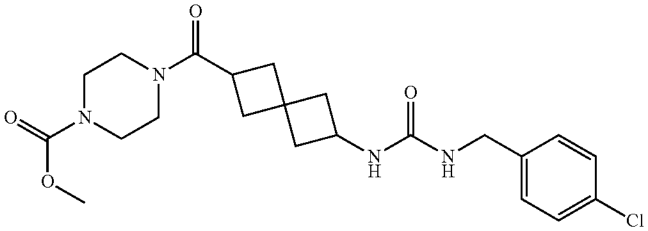 [SMILES: COC(=O)N1CCN(C(=O)C2CC3(CC(NC(=O)NCc4ccc(Cl)cc4)C3)C2)CC1] | methyl 4-(6-(3-(4-chlorobenzyl)ureido)spiro[3.3]heptane-2-carbonyl)piperazine-1-carboxylate |

TABLE 1-continued

| Compound No. | Structure | Name |
|---|---|---|
| 234 | 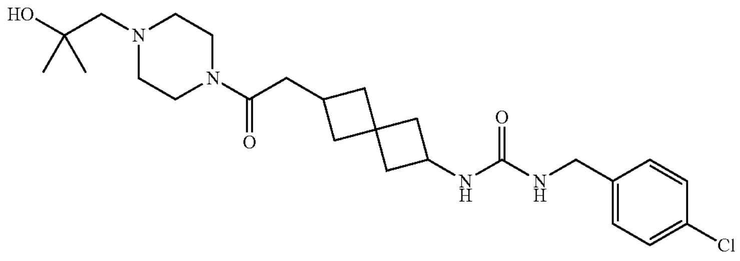 [SMILES: CC(C)(O)CN1CCN(C(=O)CC2CC3(C2)CC(NC(=O)NCc2ccc(Cl)cc2)C3)CC1] | 1-(4-chlorobenzyl)-3-(6-(2-(4-(2-hydroxy-2-methylpropyl)piperazin-1-yl)-2-oxoethyl)spiro[3.3]htan-2-yl)urea |
| 235 | 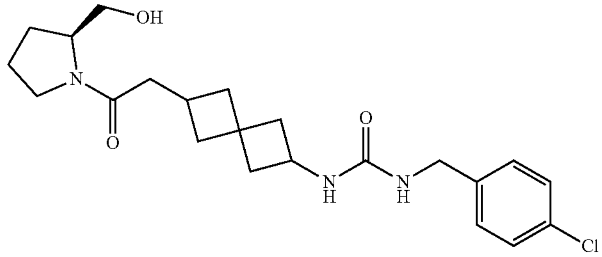 [SMILES: O=C(NCc1ccc(Cl)cc1)NC1CC2(CC(CC(=O)N3CCC[C@H]3CO)C2)C1] | (S)-1-(4-chlorobenzyl)-3-(6-(2-(2-(hydroxymethyl)pyrrolidin-1-yl)-1-oxoethyl)spiro[3.3]heptan-2-yl)urea |
| 236 | 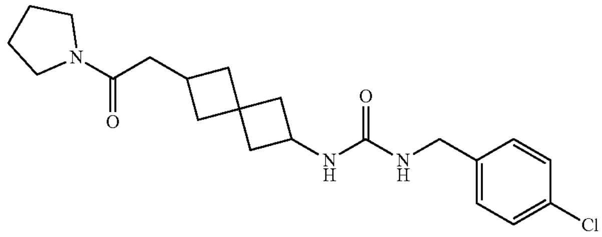 [SMILES: O=C(NCc1ccc(Cl)cc1)NC1CC2(CC(CC(=O)N3CCCC3)C2)C1] | 1-(4-chlorobenzyl)-3-(6-(2-oxo-2-(pyrrolidin-1-yl)ethyl)spiro[3.3]heptan-2-yl)urea |
| 237 | 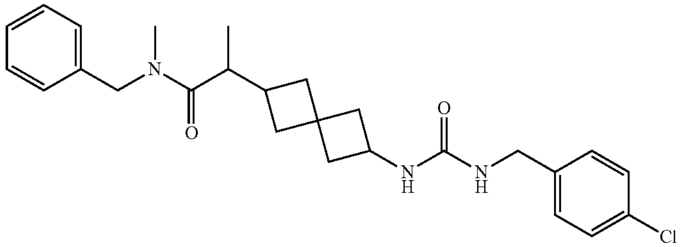 [SMILES: CC(C(=O)N(C)Cc1ccccc1)C1CC2(CC(NC(=O)NCc3ccc(Cl)cc3)C2)C1] | N-benzyl-2-(6-(3-(4-chlorobenzyl)ureido)spiro[3.3]heptan-2-yl)-N-methylpropanamide |
| 238 | 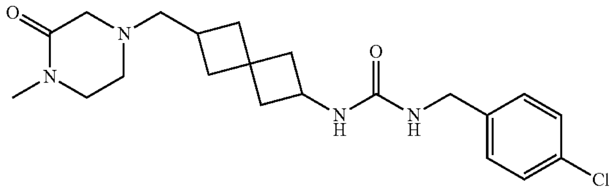 [SMILES: CN1CCN(CC2CC3(C2)CC(NC(=O)NCc2ccc(Cl)cc2)C3)CC1=O] | 1-(4-chlorobenzyl)-3-(6-((4-methyl-3-oxopiperazin-1-yl)methyl)spiro[3.3]heptan-2-yl)urea |
| 239 | 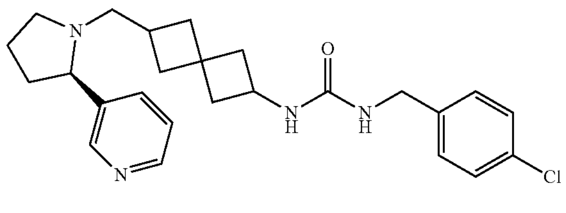 [SMILES: O=C(NCc1ccc(Cl)cc1)NC1CC2(CC(CN3CCC[C@@H]3c3cccnc3)C2)C1] | (R)-1-(4-chlorobenzyl)-3-(6-((2-(pyridin-3-yl)pyrrolidin-1-yl)methyl)spiro[3.3]heptan-2-yl)urea |

TABLE 1-continued

| Compound No. | Structure | Name |
|---|---|---|
| 240 | 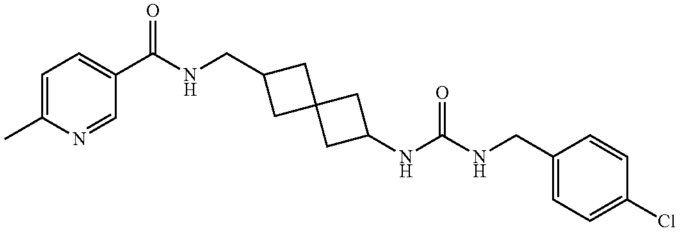 [SMILES: Cc1ccc(C(=O)NCC2CC3(C2)CC(NC(=O)NCc2ccc(Cl)cc2)C3)cn1] | N-((6-(3-(4-chlorobenzyl)ureido) spiro[3.3]heptan-2-yl)methyl)-6-methylnicotinamide |
| 241 | 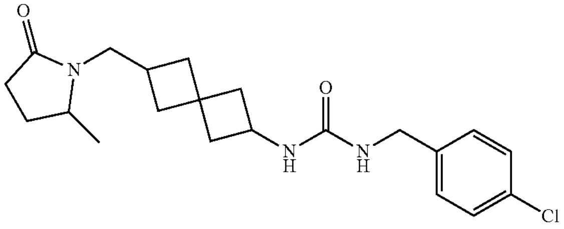 [SMILES: CC1CCC(=O)N1CC1CC2(C1)CC(NC(=O)NCc1ccc(Cl)cc1)C2] | 1-(4-chlorobenzyl)-3-(6-((2-methyl-5-oxopyrrolidin-1-yl)methyl)spiro[3.3] heptan-2-yl)urea |
| 242 | 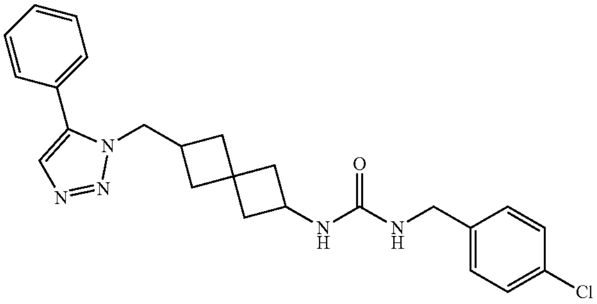 [SMILES: O=C(NCc1ccc(Cl)cc1)NC1CC2(CC(Cn3nncc3-c3ccccc3)C2)C1] | 1-(4-chlorobenzyl)-3-(6-((5-phenyl-1H-1,2,3-triazol-1-yl)methyl)spiro[3.3] heptan-2-yl)urea |
| 243 | 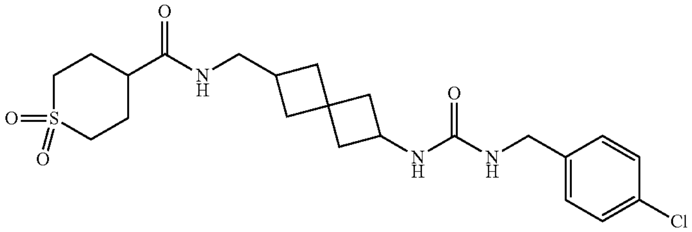 [SMILES: O=C(NCc1ccc(Cl)cc1)NC1CC2(CC(CNC(=O)C3CCS(=O)(=O)CC3)C2)C1] | N-((6-(3-(4-chlorobenzyl)ureido) spiro[3.3]heptan-2-yl)methyl)tetrahydro-2H-thiopyran-4-carboxamide 1,1-dioxide |
| 244 | 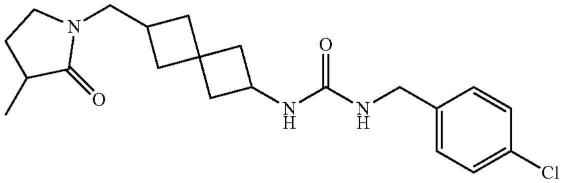 [SMILES: CC1CCN(CC2CC3(C2)CC(NC(=O)NCc2ccc(Cl)cc2)C3)C1=O] | 1-(4-chlorobenzyl)-3-(6-((3-methyl-2-oxopyrrolidin-1-yl)methyl)spiro[3.3] heptan-2-yl)urea |
| 245 | 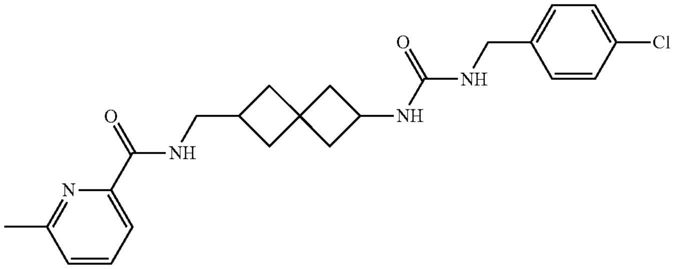 [SMILES: Cc1cccc(C(=O)NCC2CC3(C2)CC(NC(=O)NCc2ccc(Cl)cc2)C3)n1] | N-((6-(3-(4-chlorobenzyl)ureido) spiro[3.3]heptan-2-yl)methyl)-6-methylpicolinamide |

TABLE 1-continued

| Compound No. | Structure | Name |
|---|---|---|
| 246 | 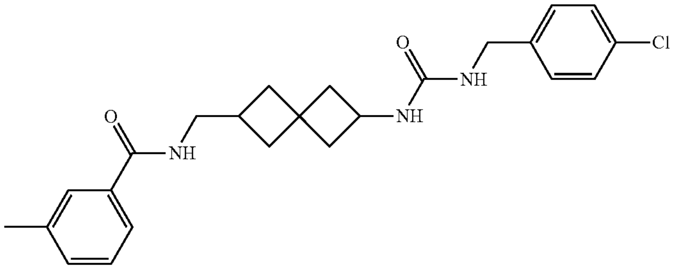 [SMILES: Cc1cccc(C(=O)NCC2CC3(C2)CC(NC(=O)NCc2ccc(Cl)cc2)C3)c1] | N-((6-(3-(4-chlorobenzyl)ureido) spiro[3.3]heptan-2-yl)methyl)-2-methylisonicotinamide |
| 247 | 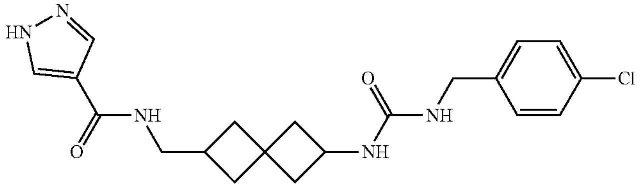 [SMILES: O=C(NCc1ccc(Cl)cc1)NC1CC2(CC(CNC(=O)c3cn[nH]c3)C2)C1] | N-((6-(3-(4-chlorobenzyl)ureido) spiro[3.3]heptan-2-yl)methyl)-1H-pyrazole-4-carboxamide |
| 248 | 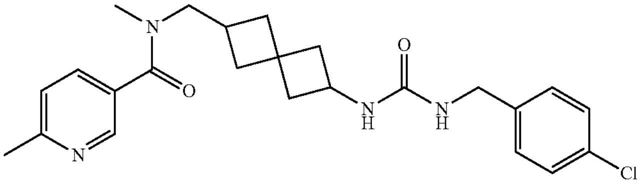 [SMILES: Cc1ccc(C(=O)N(C)CC2CC3(C2)CC(NC(=O)NCc2ccc(Cl)cc2)C3)cn1] | N-((6-(3-(4-chlorobenzyl)ureido) spiro[3.3]heptan-2-yl)methyl)-N,6-dimethylnicotinamide |
| 249 | 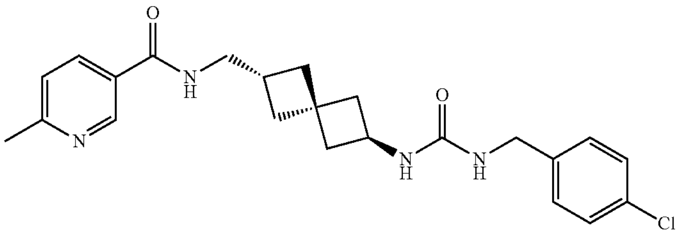 | N-((2R,4r,6R)-6-(3-(4-chlorobenzyl)ureido) spiro[3.3]heptan-2-yl)methyl)-6-methylnicotinamide |
| 250 | 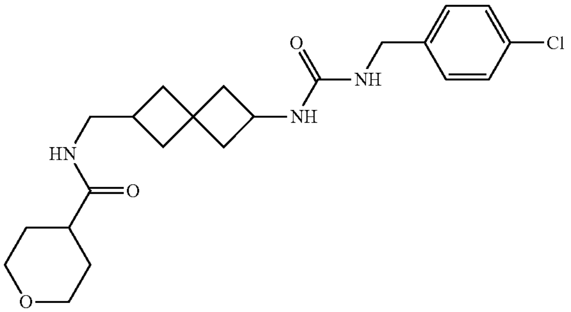 [SMILES: O=C(NCc1ccc(Cl)cc1)NC1CC2(CC(CNC(=O)C3CCOCC3)C2)C1] | N-((6-(3-(4-chlorobenzyl)ureido) spiro[3.3]heptan-2-yl)methyl)tetrahydro-2H-pyran-4-carboxamide |
| 251 | 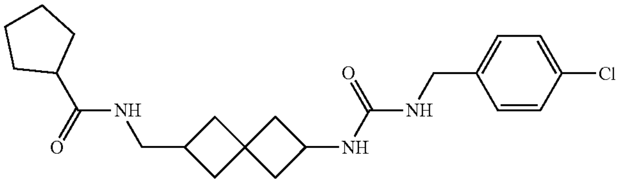 [SMILES: O=C(NCc1ccc(Cl)cc1)NC1CC2(CC(CNC(=O)C3CCCC3)C2)C1] | N-((6-(3-(4-chlorobenzyl)ureido) spiro[3.3]heptan-2-yl)methyl)cyclopentane-carboxamide |

TABLE 1-continued

| Compound No. | Structure | Name |
| --- | --- | --- |
| 252 | 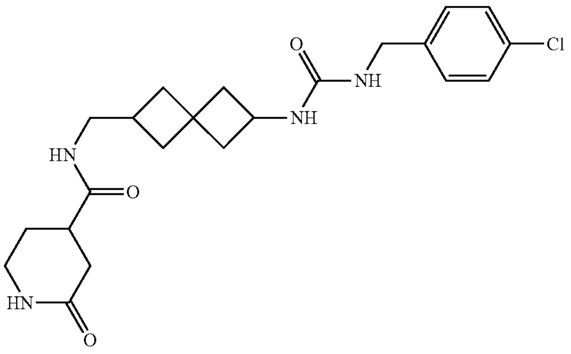 [SMILES: O=C1CC(C(=O)NCC2CC3(C2)CC(NC(=O)NCc2ccc(Cl)cc2)C3)CCN1] | N-((6-(3-(4-chlorobenzyl)ureido)spiro[3.3]heptan-2-yl)methyl)-2-oxopiperidine-4-carboxamide |
| 253 | 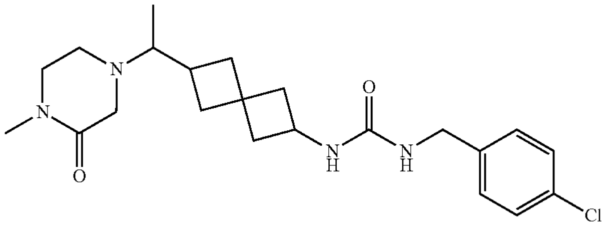 [SMILES: CC(C1CC2(CC(NC(=O)NCc3ccc(Cl)cc3)C2)C1)N1CCN(C)C(=O)C1] | 1-(4-chlorobenzyl)-3-(6-(1-(4-methyl-3-oxopiperazin-1-yl)ethyl)spiro[3.3]heptan-2-yl)urea |
| 254 | 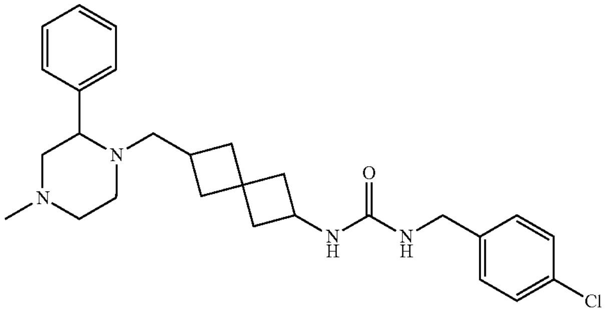 [SMILES: CN1CCN(CC2CC3(C2)CC(NC(=O)NCc2ccc(Cl)cc2)C3)C(c2ccccc2)C1] | 1-(4-chlorobenzyl)-3-(6-((4-methyl-2-phenylpiperazin-1-yl)methyl)spiro[3.3]heptan-2-yl)urea |
| 255 | 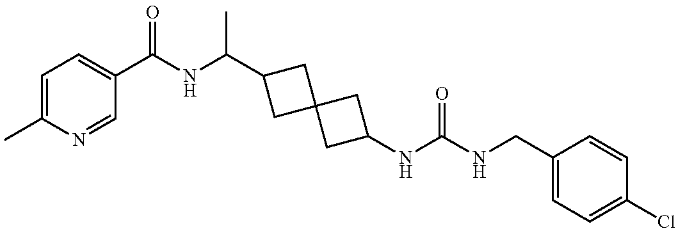 [SMILES: Cc1ccc(C(=O)NC(C)C2CC3(CC(NC(=O)NCc4ccc(Cl)cc4)C3)C2)cn1] | N-(1-(6-(3-(4-chlorobenzyl)ureido)spiro[3.3]heptan-2-yl)ethyl)-6-methylnicotinamide |
| 256 | 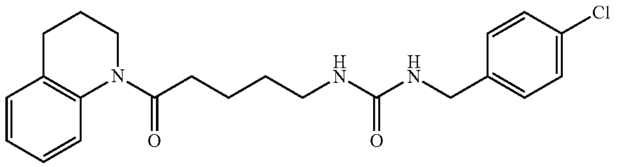 [SMILES: O=C(NCCCCC(=O)N1CCCc2ccccc21)NCc1ccc(Cl)cc1] | 1-(4-chlorobenzyl)-3-(5-(3,4-dihydroquinolin-1(2H)-yl)-5-oxopentyl)urea |
| 257 | 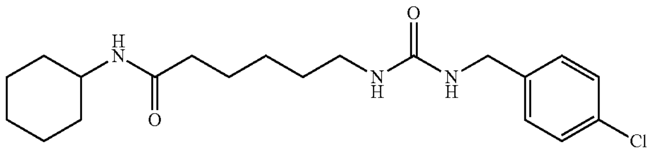 [SMILES: O=C(CCCCCNC(=O)NCc1ccc(Cl)cc1)NC1CCCCC1] | 6-(3-(4-chlorobenzyl)ureido)-N-cyclohexylhexanamide |

TABLE 1-continued

| Compound No. | Structure | Name |
|---|---|---|
| 258 | 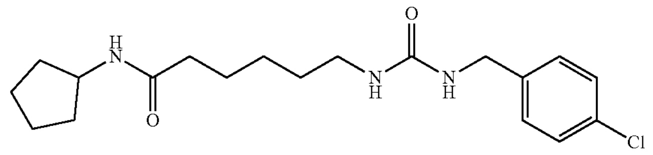 [SMILES: O=C(CCCCCNC(=O)NCc1ccc(Cl)cc1)NC1CCCC1] | 6-(3-(4-chlorobenzyl)ureido)-N-cylcopentylhexanamide |
| 259 | 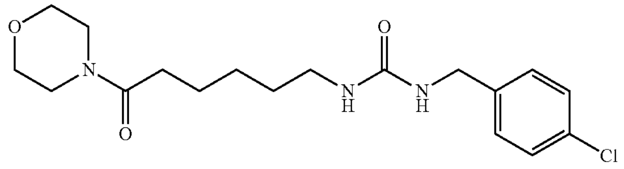 [SMILES: O=C(NCCCCCC(=O)N1CCOCC1)NCc1ccc(Cl)cc1] | 1-(4-chlorobenzyl)-3-(6-morpholino-6-oxohexyl)urea |
| 260 | 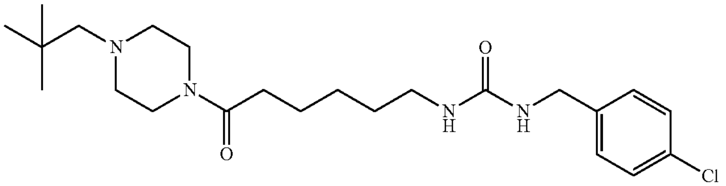 [SMILES: CC(C)(C)CN1CCN(C(=O)CCCCCNC(=O)NCc2ccc(Cl)cc2)CC1] | 1-(4-chlorobenzyl)-3-(6-(4-neopentylpiperazin-1-yl)-6-oxohexyl)urea |
| 261 | 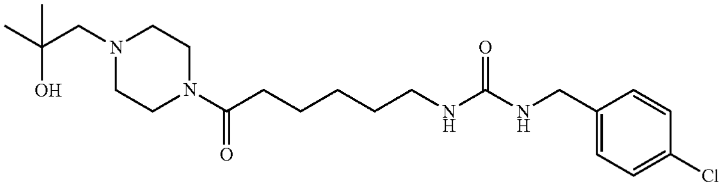 [SMILES: CC(C)(O)CN1CCN(C(=O)CCCCCNC(=O)NCc2ccc(Cl)cc2)CC1] | 1-(4-chlorobenzyl)-3-(6-(4-(2-hydroxy-2-methylpropyl)pipera-zin-1-yl)-6-oxohexyl)urea |
| 262 | 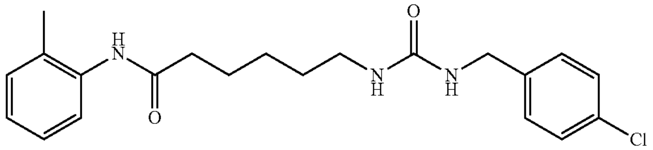 [SMILES: Cc1ccccc1NC(=O)CCCCCNC(=O)NCc1ccc(Cl)cc1] | 6-(3-(4-chlorobenzyl)ureido)-N-(o-tolyl)hexanamide |
| 263 | 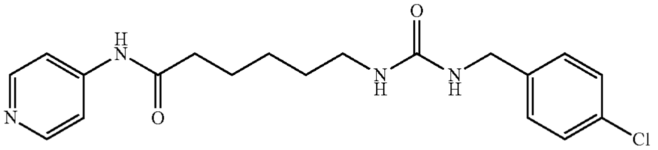 [SMILES: O=C(CCCCCNC(=O)NCc1ccc(Cl)cc1)Nc1ccncc1] | 6-(3-(4-chlorobenzyl)ureido)-N-(pyridin-4-yl)hexanamide |
| 264 | 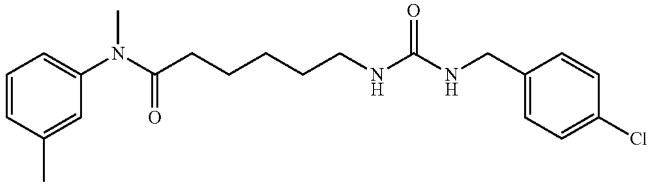 [SMILES: Cc1cccc(N(C)C(=O)CCCCCNC(=O)NCc2ccc(Cl)cc2)c1] | 6-(3-(4-chlorobenzyl)ureido)-N-methyl-N-(m-tolyl)hexanamide |
| 265 | 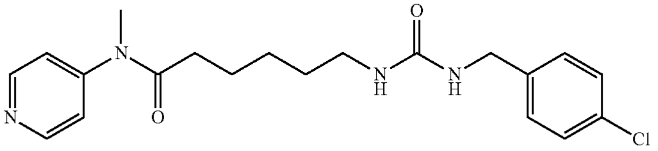 [SMILES: CN(C(=O)CCCCCNC(=O)NCc1ccc(Cl)cc1)c1ccncc1] | 6-(3-(4-chlorobenzyl)ureido)-N-methyl-N-(pyridin-4-yl)hexanamide |
| 266 | 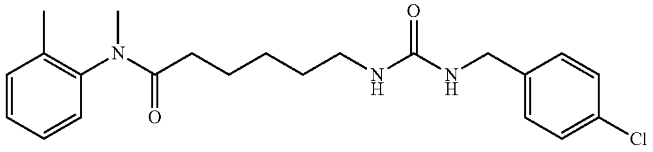 [SMILES: Cc1ccccc1N(C)C(=O)CCCCCNC(=O)NCc1ccc(Cl)cc1] | 6-(3-(4-chlorobenzyl)ureido)-N-methyl-N-(o-tolyl)hexanamide |

TABLE 1-continued

| Compound No. | Structure | Name |
| --- | --- | --- |
| 267 | 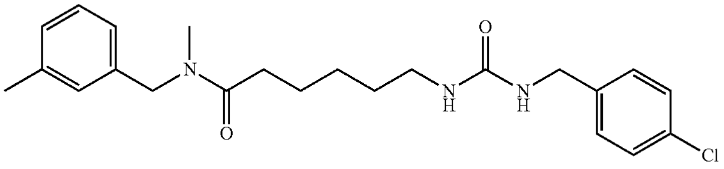 [SMILES: Cc1cccc(CN(C)C(=O)CCCCCNC(=O)NCc2ccc(Cl)cc2)c1] | 6-(3-(4-chlorobenzyl)ureido)-N-methyl-N-(3-methylbenzyl)hexanamide |
| 268 | 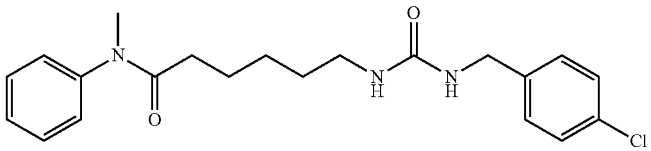 [SMILES: CN(C(=O)CCCCCNC(=O)NCc1ccc(Cl)cc1)c1ccccc1] | 6-(3-(4-chlorobenzyl)ureido)-N-methyl-N-phenylhexanamide |
| 269 | 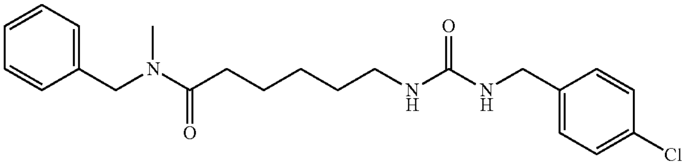 [SMILES: CN(Cc1ccccc1)C(=O)CCCCCNC(=O)NCc1ccc(Cl)cc1] | N-benzyl-6-(3-(4-chlorobenzyl)ureido)-N-methylhexanamide |
| 270 | 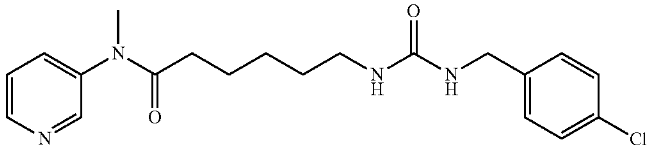 [SMILES: CN(C(=O)CCCCCNC(=O)NCc1ccc(Cl)cc1)c1cccnc1] | 6-(3-(4-chlorobenzyl)ureido)-N-methyl-N-(pyridin-3-yl)hexanamide |
| 271 | 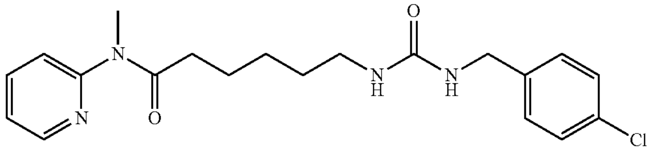 [SMILES: CN(C(=O)CCCCCNC(=O)NCc1ccc(Cl)cc1)c1ccccn1] | 6-(3-(4-chlorobenzyl)ureido)-N-methyl-N-(pyridin-2-yl)hexanamide |
| 272 | 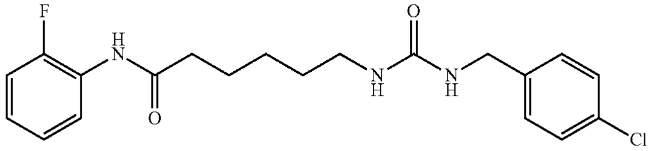 [SMILES: O=C(CCCCCNC(=O)NCc1ccc(Cl)cc1)Nc1ccccc1F] | 6-(3-(4-chlorobenzyl)ureido)-N-(2-fluorophenyl)hexanamide |
| 273 | 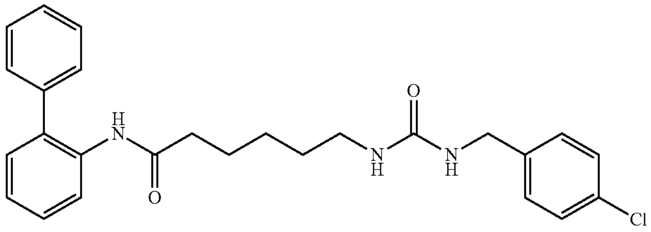 [SMILES: O=C(CCCCCNC(=O)NCc1ccc(Cl)cc1)Nc1ccccc1-c1ccccc1] | N-([1,1'-biphenyl]-2-yl)-6-(3-(4-chlorobenzyl)ureido)hexanamide |
| 274 | 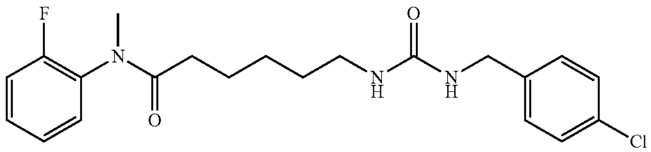 [SMILES: CN(C(=O)CCCCCNC(=O)NCc1ccc(Cl)cc1)c1ccccc1F] | 6-(3-(4-chlorobenzyl)ureido)-N-(2-fluorophenyl)-N-methylhexanamide |

TABLE 1-continued

| Compound No. | Structure | Name |
| --- | --- | --- |
| 275 | 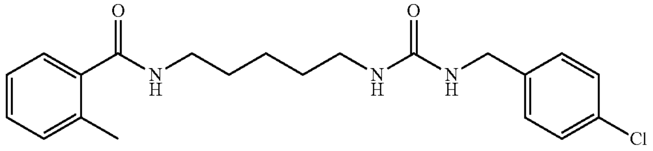 [SMILES: Cc1ccccc1C(=O)NCCCCCNC(=O)NCc1ccc(Cl)cc1] | N-(5-(3-(4-chlorobenzyl)ureido)pentyl)-2-methylbenzamide |
| 276 | 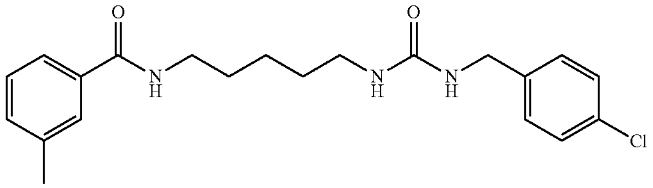 [SMILES: Cc1cccc(C(=O)NCCCCCNC(=O)NCc2ccc(Cl)cc2)c1] | N-(5-(3-(4-chlorobenzyl)ureido)pentyl)-3-methylbenzamide |
| 277 | 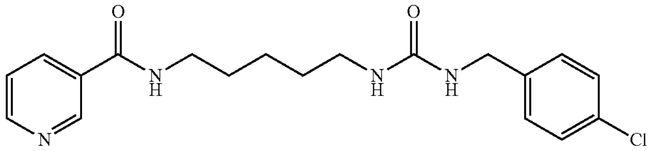 [SMILES: O=C(NCCCCCNC(=O)c1cccnc1)NCc1ccc(Cl)cc1] | N-(5-(3-(4-chlorobenzyl)ureido)pentyl)nicotinamide |
| 278 | 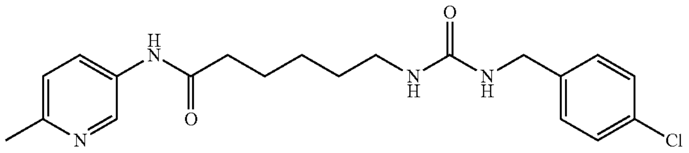 [SMILES: Cc1ccc(NC(=O)CCCCCNC(=O)NCc2ccc(Cl)cc2)cn1] | 6-(3-(4-chlorobenzyl)ureido)-N-(6-methylpyridin-3-yl)hexanamide |
| 279 | 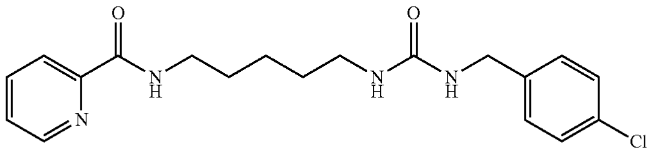 [SMILES: O=C(NCCCCCNC(=O)c1ccccn1)NCc1ccc(Cl)cc1] | N-(5-(3-(4-chlorobenzyl)ureido)pentyl)picolinamide |
| 280 | 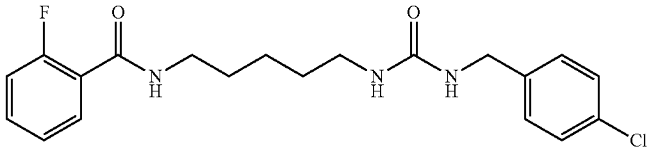 [SMILES: O=C(NCCCCCNC(=O)c1ccccc1F)NCc1ccc(Cl)cc1] | N-(5-(3-(4-chlorobenzyl)ureido)pentyl)-2-fluorobenzamide |
| 281 | 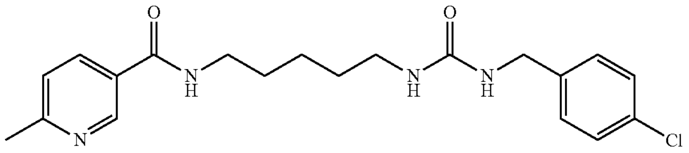 [SMILES: Cc1ccc(C(=O)NCCCCCNC(=O)NCc2ccc(Cl)cc2)cn1] | N-(5-(3-(4-chlorobenzyl)ureido)pentyl)-6-methylnicotinamide |
| 282 | 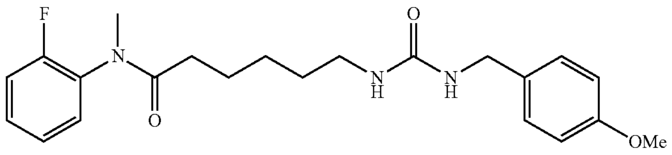 [SMILES: COc1ccc(CNC(=O)NCCCCCC(=O)N(C)c2ccccc2F)cc1] | N-(2-fluorophenyl)-6-(3-(4-methoxybenzyl)ureido)-N-methylhexanamide |
| 283 | 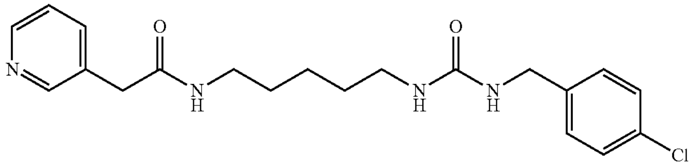 [SMILES: O=C(Cc1cccnc1)NCCCCCNC(=O)NCc1ccc(Cl)cc1] | N-(5-(3-(4-chlorobenzyl)ureido)pentyl)-2-(pyridin-3-yl)acetamide |

TABLE 1-continued

| Compound No. | Structure | Name |
|---|---|---|
| 284 | 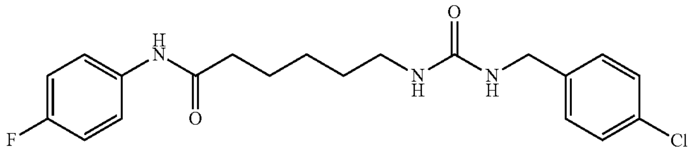 [SMILES: O=C(CCCCCNC(=O)NCc1ccc(Cl)cc1)Nc1ccc(F)cc1] | 6-(3-(4-chlorobenzyl)ureido)-N-(4-fluorophenyl)hexanamide |
| 285 | 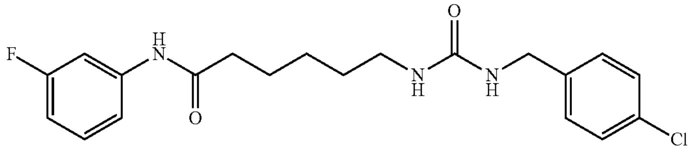 [SMILES: O=C(CCCCCNC(=O)NCc1ccc(Cl)cc1)Nc1cccc(F)c1] | 6-(3-(4-chlorobenzyl)ureido)-N-(3-fluorophenyl)hexanamide |
| 286 | 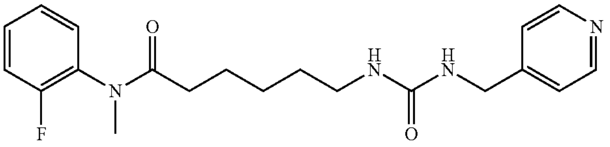 [SMILES: CN(C(=O)CCCCCNC(=O)NCc1ccncc1)c1ccccc1F] | N-(2-fluorophenyl)-N-methyl-6-(3-(pyridin-4-ylmethyl)ureido)hexanamide |
| 287 | 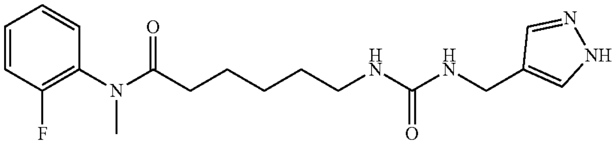 [SMILES: CN(C(=O)CCCCCNC(=O)NCc1cn[nH]c1)c1ccccc1F] | 6-(3-((1H-pyrazol-4-yl)methyl)ureido)-N-(2-fluorophenyl)-N-methylhexanamide |
| 288 | 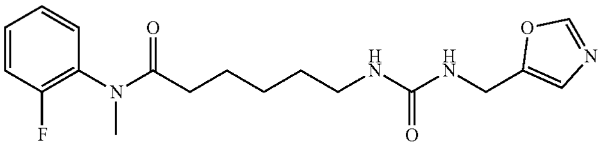 [SMILES: CN(C(=O)CCCCCNC(=O)NCc1cnco1)c1ccccc1F] | N-(2-fluorophenyl)-N-methyl-6-(3-(oxazol-5-ylmethyl)ureido)hexanamide |
| 289 | 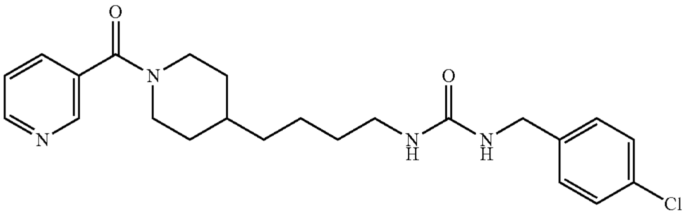 [SMILES: O=C(NCCCCC1CCN(C(=O)c2cccnc2)CC1)NCc1ccc(Cl)cc1] | 1-(4-chlorobenzyl)-3-(4-(1-nicotinoylpiperidin-4-yl)butyl)urea |
| 290 | 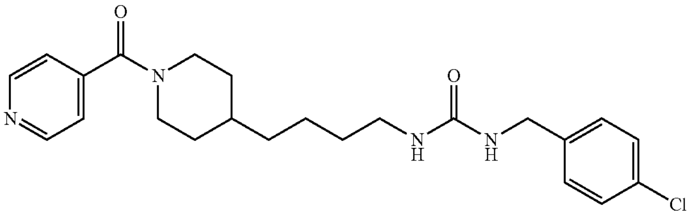 [SMILES: O=C(NCCCCC1CCN(C(=O)c2ccncc2)CC1)NCc1ccc(Cl)cc1] | 1-(4-chlorobenzyl)-3-(4-(1-isonicotinoyl)piperidin-4-yl)butyl)urea |
| 291 | 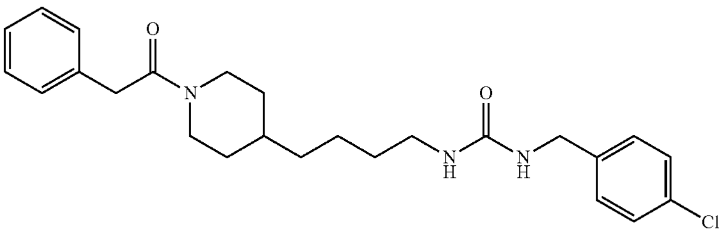 [SMILES: O=C(NCCCCC1CCN(C(=O)Cc2ccccc2)CC1)NCc1ccc(Cl)cc1] | 1-(4-chlorobenzyl)-3-(4-(1-(2-phenylacetyl)piperidin-4-yl)butyl)urea |

TABLE 1-continued

| Compound No. | Structure | Name |
|---|---|---|
| 292 | 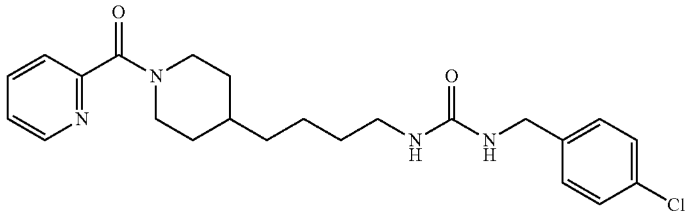 [SMILES: O=C(NCCCCC1CCN(C(=O)c2ccccn2)CC1)NCc1ccc(Cl)cc1] | 1-(4-chlorobenzyl)-3-(4-(1-picolinylpiperidin-4-yl)butyl)urea |
| 293 | 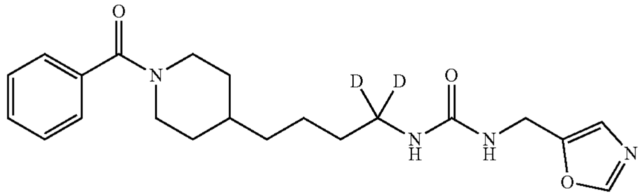 [SMILES: [2H]C([2H])(CCCC1CCN(C(=O)c2ccccc2)CC1)NC(=O)NCc1cnco1] | 1-(4-(1-benzoylpiperidin-4-yl)butyl-1,1-d2)-3-(oxazol-5-ylmethyl)urea |
| 294 | 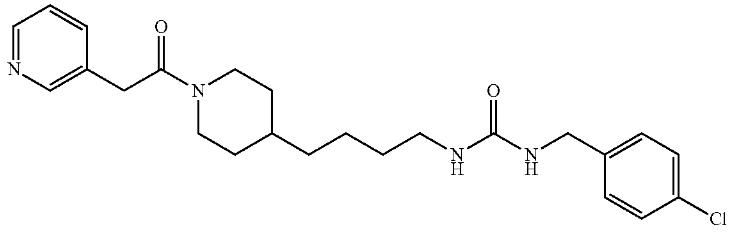 [SMILES: O=C(NCCCCC1CCN(C(=O)Cc2cccnc2)CC1)NCc1ccc(Cl)cc1] | 1-(4-chlorobenzyl)-3-(4-(1-(2-(pyridin-3-yl)acetyl)piperidin-4-yl)butyl)urea |
| 295 | 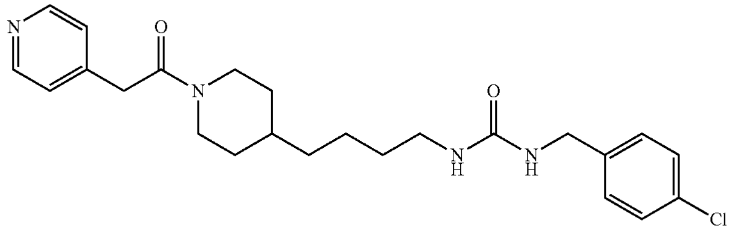 [SMILES: O=C(NCCCCC1CCN(C(=O)Cc2ccncc2)CC1)NCc1ccc(Cl)cc1] | 1-(4-chlorobenzyl)-3-(4-(1-(2-(pyridin-4-yl)acetyl)piperidin-4-yl)butyl)urea |
| 296 | 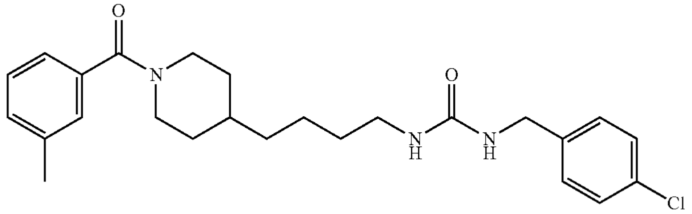 [SMILES: Cc1cccc(C(=O)N2CCC(CCCCNC(=O)NCc3ccc(Cl)cc3)CC2)c1] | 1-(4-chlorobenzyl)-3-(4-(1-(3-methylbenzoyl)piperidin-4-yl)butyl)urea |
| 297 | 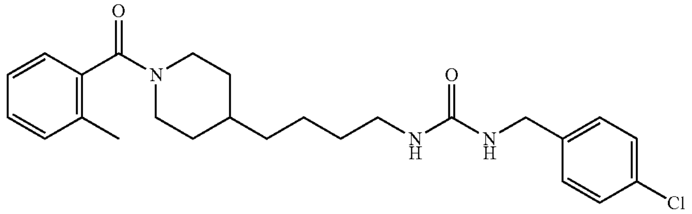 [SMILES: Cc1ccccc1C(=O)N1CCC(CCCCNC(=O)NCc2ccc(Cl)cc2)CC1] | 1-(4-chlorobenzyl)-3-(4-(1-(2-methylbenzoyl)piperidin-4-yl)butyl)urea |
| 298 | 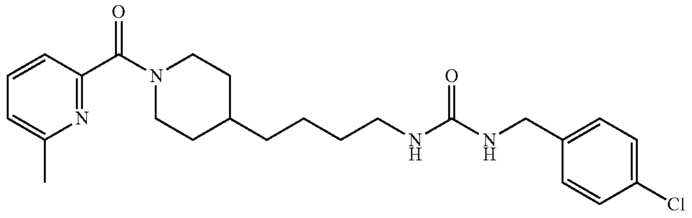 [SMILES: Cc1cccc(C(=O)N2CCC(CCCCNC(=O)NCc3ccc(Cl)cc3)CC2)n1] | 1-(4-chlorobenzyl)-3-(4-(1-(6-methylpicolinyl)piperidin-4-yl)butyl)urea |

TABLE 1-continued

| Compound No. | Structure | Name |
|---|---|---|
| 299 | 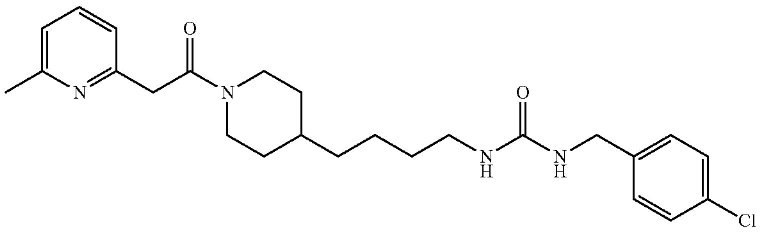 [SMILES: Cc1cccc(CC(=O)N2CCC(CCCCNC(=O)NCc3ccc(Cl)cc3)CC2)n1] | 1-(4-chlorobenzyl)-3-(4-(1-(2-(6-methylpyridin-2-yl)acetyl)piperidin-4-yl)butyl)urea |
| 300 | 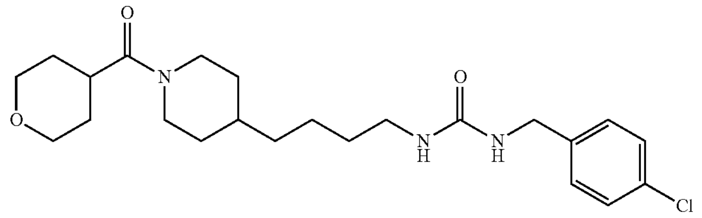 [SMILES: O=C(NCCCCC1CCN(C(=O)C2CCOCC2)CC1)NCc1ccc(Cl)cc1] | 1-(4-chlorobenzyl)-3-(4-(1-(tetrahydro-2H-pyran-4-carbonyl)piperidin-4-yl)butyl)urea |
| 301 | 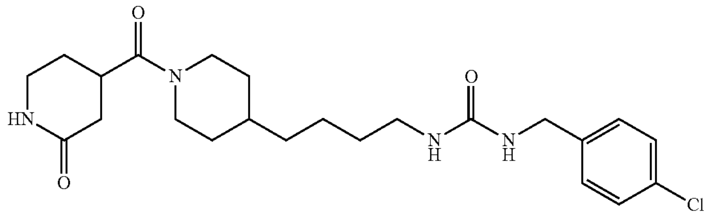 [SMILES: O=C1CC(C(=O)N2CCC(CCCCNC(=O)NCc3ccc(Cl)cc3)CC2)CCN1] | 1-(4-chlorobenzyl)-3-(4-(1-(2-oxopiperidine-4-carbonyl)piperidin-4-yl)butyl)urea |
| 302 | 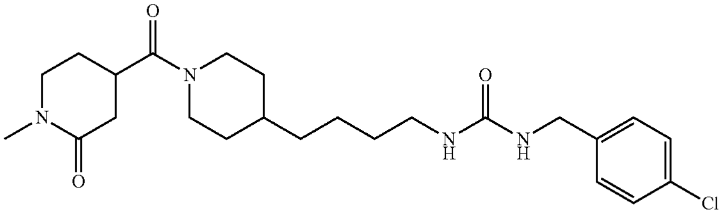 [SMILES: CN1CCC(C(=O)N2CCC(CCCCNC(=O)NCc3ccc(Cl)cc3)CC2)CC1=O] | 1-(4-chlorobenzyl)-3-(4-(1-(1-methyl-2-oxopiperidine-4-carobnyl)piperidin-4-yl)butyl)urea |
| 303 | 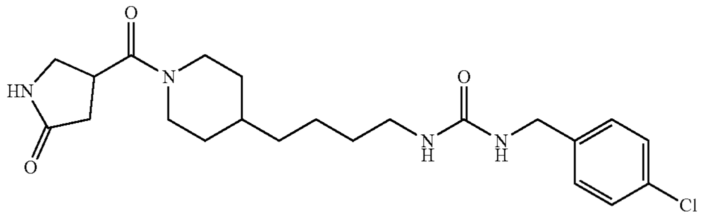 [SMILES: O=C1CC(C(=O)N2CCC(CCCCNC(=O)NCc3ccc(Cl)cc3)CC2)CN1] | 1-(4-chlorobenzyl)-3-(4-(1-(5-oxopyrrolidine-3-carbonyl)piperidin-4-yl)butyl)urea |
| 304 | 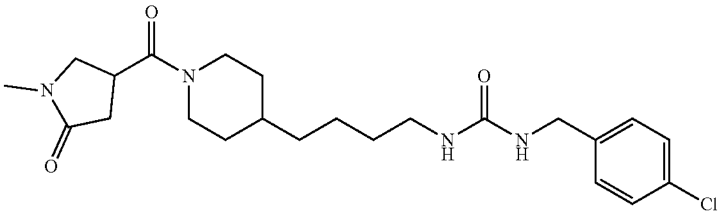 [SMILES: CN1CC(C(=O)N2CCC(CCCCNC(=O)NCc3ccc(Cl)cc3)CC2)CC1=O] | 1-(4-chlorobenzyl)-3-(4-(1-(1-methyl-5-oxopyrrolidine-3-carbonyl)piperidin-4-yl)butyl)urea |

TABLE 1-continued

| Compound No. | Structure | Name |
|---|---|---|
| 305 | 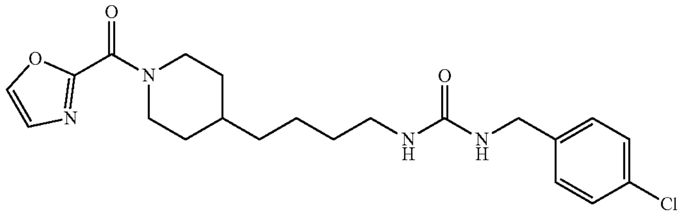 [SMILES: O=C(NCCCCC1CCN(C(=O)c2ncco2)CC1)NCc1ccc(Cl)cc1] | 1-(4-chlorobenzyl)-3-(4-(1-(oxazole-2-carbonyl)piperidin-4-yl)butyl)urea |
| 306 | 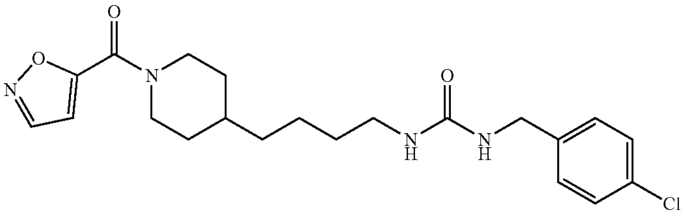 [SMILES: O=C(NCCCCC1CCN(C(=O)c2ccno2)CC1)NCc1ccc(Cl)cc1] | 1-(4-chlorobenzyl)-3-(4-(1-(isoxazole-5-carbonyl)piperidin-4-l)butyl)urea |
| 307 | 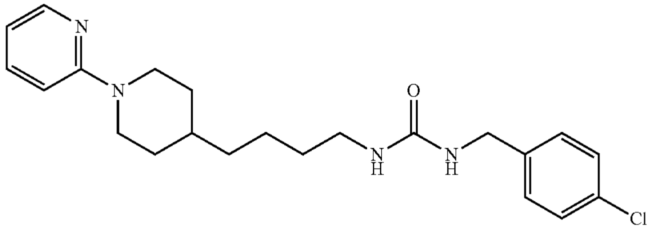 [SMILES: O=C(NCCCCC1CCN(c2ccccn2)CC1)NCc1ccc(Cl)cc1] | 1-(4-chlorobenzyl)-3-(4-(1-(pyridin-2-yl)piperidin-4-yl)butyl)urea |
| 308 | 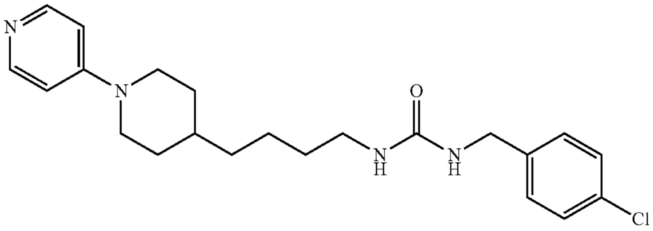 [SMILES: O=C(NCCCCC1CCN(c2ccncc2)CC1)NCc1ccc(Cl)cc1] | 1-(4-chlorobenzyl)-3-(4-(1-(pyridin-4-yl)piperidin-4-yl)butyl)urea |
| 309 | 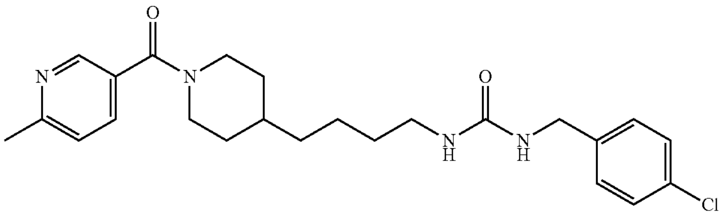 [SMILES: Cc1ccc(C(=O)N2CCC(CCCCNC(=O)NCc3ccc(Cl)cc3)CC2)cn1] | 1-(4-chlorobenzyl)-3-(4-(1-(6-methylnicotinoyl)piper-idin-4-yl)butyl)urea |
| 310 | 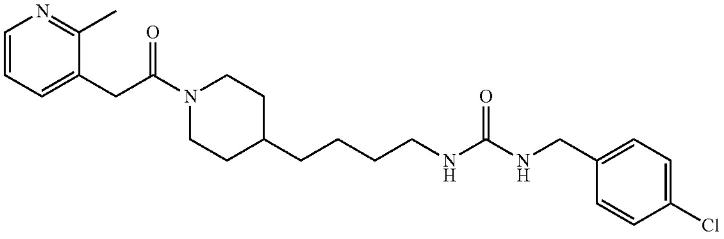 [SMILES: Cc1ncccc1CC(=O)N1CCC(CCCCNC(=O)NCc2ccc(Cl)cc2)CC1] | 1-(4-chlorobenzyl)-3-(4-(1-(2-(2-methylpyridin-3-yl)acetyl)piperidin-4-yl)butyl)urea |

TABLE 1-continued

| Compound No. | Structure | Name |
|---|---|---|
| 311 | 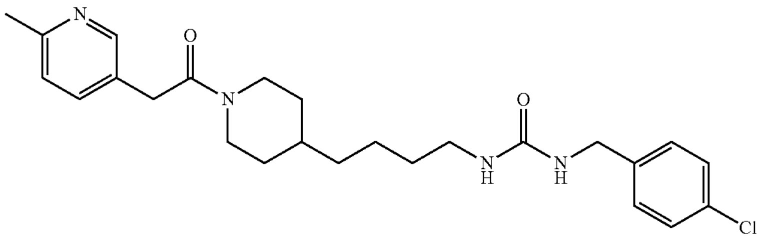 [SMILES: Cc1ccc(CC(=O)N2CCC(CCCCNC(=O)NCc3ccc(Cl)cc3)CC2)cn1] | 1-(4-chlorobenzyl)-3-(4-(1-(2-(6-methylpyridin-3-yl)acetyl)piperidin-4-yl)butyl)urea |
| 312 | 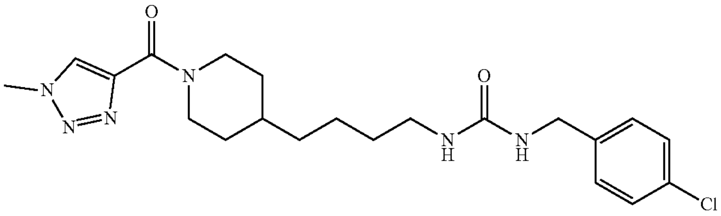 [SMILES: Cn1cc(C(=O)N2CCC(CCCCNC(=O)NCc3ccc(Cl)cc3)CC2)nn1] | 1-(4-chlorobenzyl)-3-(4-(1-(1-methyl-1H-1,2,3-triazole-4-carbonyl)piperidin-4-yl)butyl)urea |
| 313 | 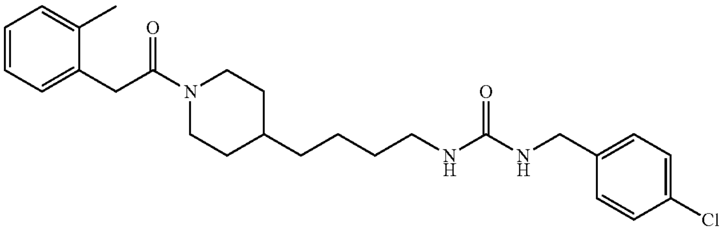 [SMILES: Cc1ccccc1CC(=O)N1CCC(CCCCNC(=O)NCc2ccc(Cl)cc2)CC1] | 1-(4-chlorobenzyl)-3-(4-(1-(2-(o-tolyl)acetyl)piperidin-4-yl)butyl)urea |
| 314 | 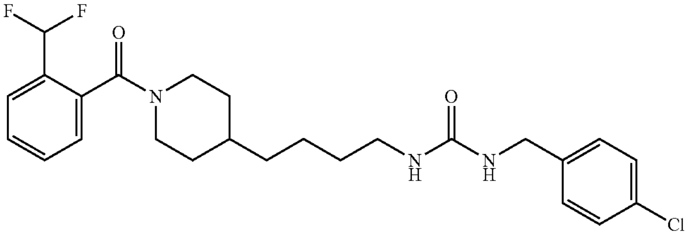 [SMILES: O=C(NCCCCC1CCN(C(=O)c2ccccc2C(F)F)CC1)NCc1ccc(Cl)cc1] | 1-(4-chlorobenzyl)-3-(4-(1-(2-(difluoromethyl)benzoyl)piperidin-4-yl)butyl)urea |
| 315 | 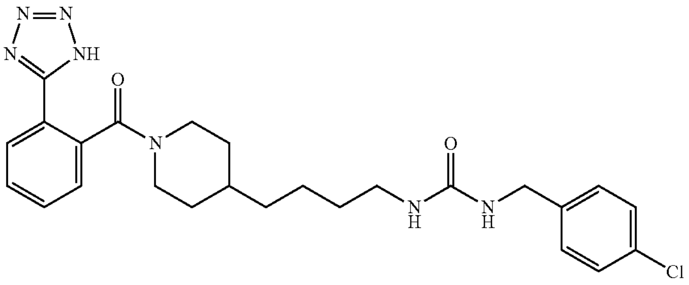 [SMILES: O=C(NCCCCC1CCN(C(=O)c2ccccc2-c2nnn[nH]2)CC1)NCc1ccc(Cl)cc1] | 1-(4-(1-(2-(1H-tetrazol-5-yl)benzoyl)piperidin-4-yl)butyl)-3-(4-chlorobenzyl)urea |
| 316 | 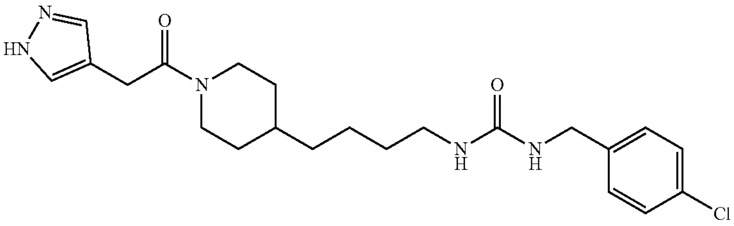 [SMILES: O=C(NCCCCC1CCN(C(=O)Cc2cn[nH]c2)CC1)NCc1ccc(Cl)cc1] | 1-(4-(1-(2-(1H-pyrazol-4-yl)acetyl)piperidin-4-yl)butyl)-3-(4-chlorobenzyl)urea |

TABLE 1-continued

| Compound No. | Structure | Name |
|---|---|---|
| 317 | 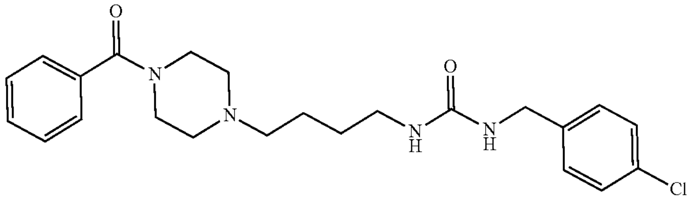 [SMILES: O=C(NCCCCN1CCN(C(=O)c2ccccc2)CC1)NCc1ccc(Cl)cc1] | 1-(4-(4-benzoylpiperazin-1-yl)butyl)-3-(4-chlorobenzyl)urea |
| 318 | 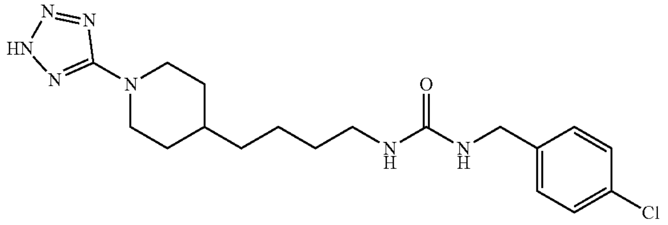 [SMILES: O=C(NCCCCC1CCN(c2nn[nH]n2)CC1)NCc1ccc(Cl)cc1] | 1-(4-(1-(2H-tetrazol-5-yl)piperidin-4-yl)butyl)-3-(4-chlorobenzyl)urea |
| 319 | 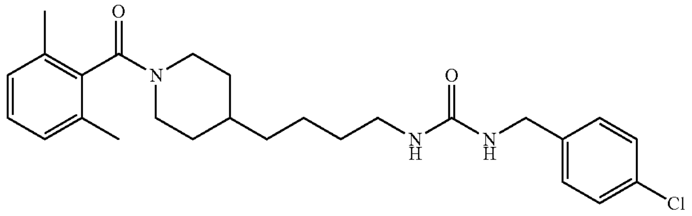 [SMILES: Cc1cccc(C)c1C(=O)N1CCC(CCCCNC(=O)NCc2ccc(Cl)cc2)CC1] | 1-(4-chlorobenzyl)-3-(4-(1-(2,6-dimethylbenzoyl)piper-idin-4-yl)butyl)urea |
| 320 | 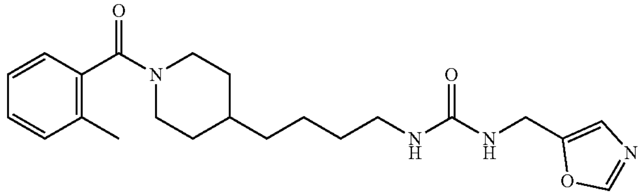 [SMILES: Cc1ccccc1C(=O)N1CCC(CCCCNC(=O)NCc2cnco2)CC1] | 1-(4-(1-(2-methylbenzoyl)piper-idin-4-yl)butyl)-3-(oxazol-5-ylmethyl)urea |
| 321 | 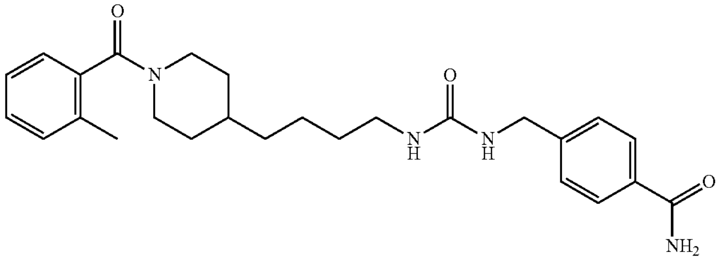 [SMILES: Cc1ccccc1C(=O)N1CCC(CCCCNC(=O)NCc2ccc(C(N)=O)cc2)CC1] | 4-((3-(4-(1-(2-methylbenzoyl)piper-idin-4-yl)butyl)ureido)meth-yl)benzamide |
| 322 | 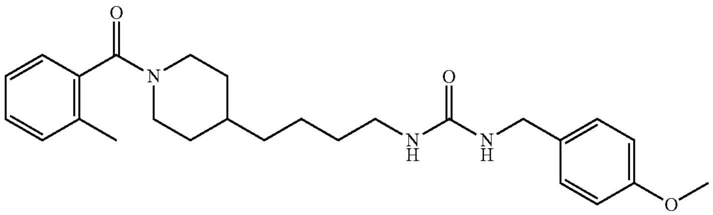 [SMILES: COc1ccc(CNC(=O)NCCCCC2CCN(C(=O)c3ccccc3C)CC2)cc1] | 1-(4-methoxybenzyl)-3-(4-(1-(2-methylbenzoyl)piper-idin-4-yl)butyl)urea |
| 323 | 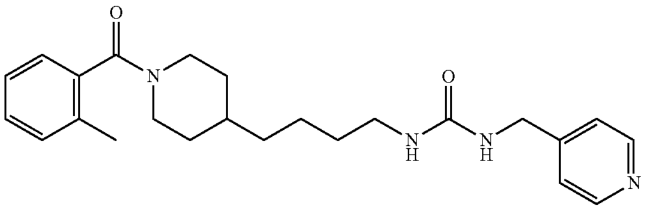 [SMILES: Cc1ccccc1C(=O)N1CCC(CCCCNC(=O)NCc2ccncc2)CC1] | 1-(4-(1-(2-methylbenzoyl)piper-idin-4-yl)butyl)-3-(pyridin-4-ylmethyl)urea |

TABLE 1-continued

| Compound No. | Structure | Name |
|---|---|---|
| 324 | 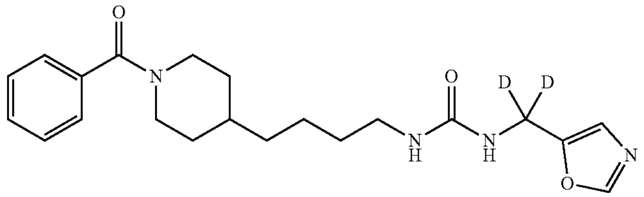 [SMILES: [2H]C([2H])(NC(=O)NCCCCC1CCN(C(=O)c2ccccc2)CC1)c1cnco1] | 1-(4-(1-benzoylpiperidin-4-yl)butyl)-3-(oxazol-5-ylmethyl-d2)urea |
| 325 | 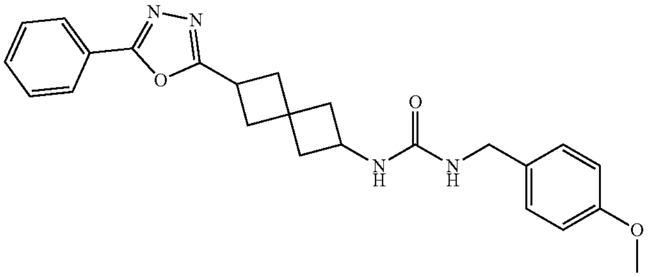 [SMILES: COc1ccc(CNC(=O)NC2CC3(C2)CC(c2nnc(-c4ccccc4)o2)C3)cc1] | 1-(4-methoxybenzyl)-3-(6-(5-phenyl-1,3,4-oxadiazol-2-yl)spiro[3.3]heptan-2-yl)urea |
| 326 | 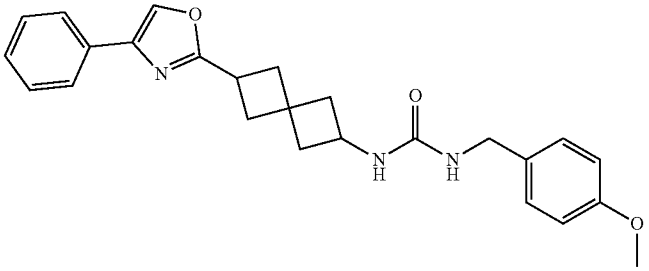 [SMILES: COc1ccc(CNC(=O)NC2CC3(C2)CC(c2nc(-c4ccccc4)co2)C3)cc1] | 1-(4-methoxybenzyl)-3-(6-(4-phenyloxazol-2-yl)spiro[3.3]heptan-2-yl)urea |
| 327 | 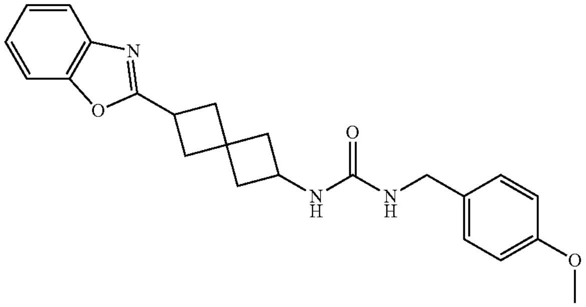 [SMILES: COc1ccc(CNC(=O)NC2CC3(C2)CC(c2nc4ccccc4o2)C3)cc1] | 1-(6-(benzo[d]oxazol-2-yl)spiro[3.3]heptan-2-yl)-3-(4-methoxybenzyl)urea |
| 328 | 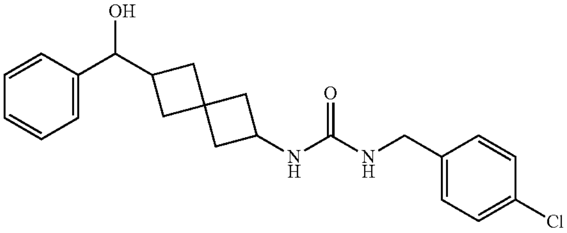 [SMILES: O=C(NCc1ccc(Cl)cc1)NC1CC2(C1)CC(C(O)c1ccccc1)C2] | 1-(4-chlorobenzyl)-3-(6-(hydroxy(phenyl)methyl)spiro[3.3]heptan-2-yl)urea |
| 329 | 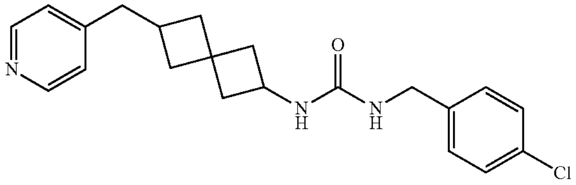 [SMILES: O=C(NCc1ccc(Cl)cc1)NC1CC2(CC(Cc3ccncc3)C2)C1] | 1-(4-chlorobenzyl)-3-(6-(pyridin-4-ylmethyl)spiro[3.3]heptan-2-yl)urea |

TABLE 1-continued

| Compound No. | Structure | Name |
|---|---|---|
| 330 | 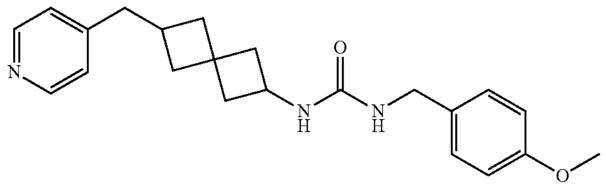 [SMILES: COc1ccc(CNC(=O)NC2CC3(CC(Cc4ccncc4)C3)C2)cc1] | 1-(4-methoxybenzyl)-3-(6-(pyridin-4-ylmethyl)spiro[3.3]heptan-2-yl)urea |
| 331 | 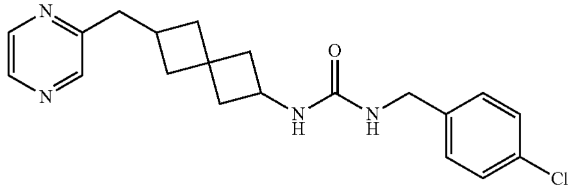 [SMILES: O=C(NCc1ccc(Cl)cc1)NC1CC2(CC(Cc3cnccn3)C2)C1] | 1-(4-chlorobenzyl)-3-(6-(pyrazin-2-ylmethyl)spiro[3.3]heptan-2-yl)urea |
| 332 | 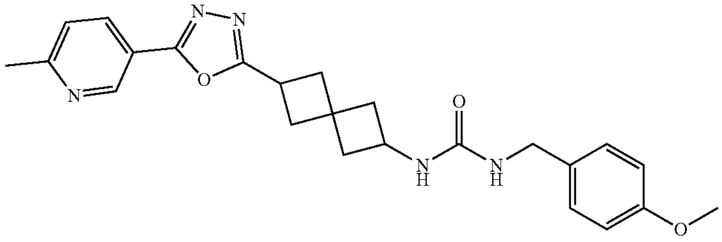 | 1-(4-methoxybenzyl)-3-(6-(5-(6-methylpyridin-3-yl)-1,3,4-oxadiazol-2-yl)spiro[3.3]heptan-2-yl)urea |
| 333 | 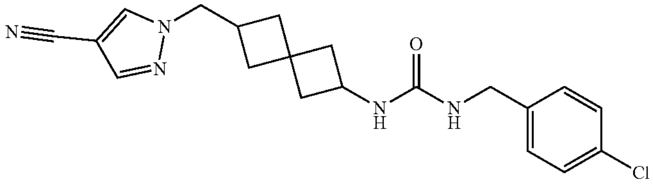 [SMILES: N#Cc1cnn(CC2CC3(C2)CC(NC(=O)NCc2ccc(Cl)cc2)C3)c1] | 1-(4-chlorobenzyl)-3-(6-((4-cyano-1H-pyrazol-1-yl)methyl)spiro[3.3]heptan-2-yl)urea |
| 334 | 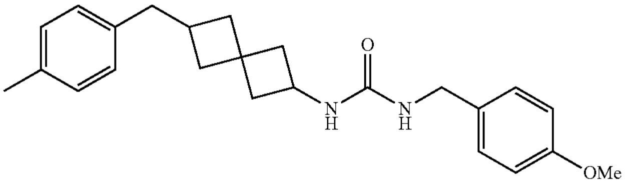 [SMILES: COc1ccc(CNC(=O)NC2CC3(CC(Cc4ccc(C)cc4)C3)C2)cc1] | 1-(4-methoxybenzyl)-3-(6-(4-methylbenzyl)spiro[3.3]heptan-2-yl)urea |
| 335 | 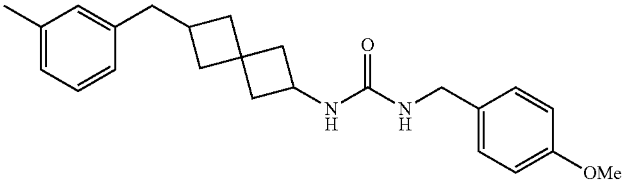 [SMILES: COc1ccc(CNC(=O)NC2CC3(CC(Cc4cccc(C)c4)C3)C2)cc1] | 1-(4-methoxybenzyl)-3-(6-(3-methylbenzoyl)spiro[3.3]heptan-2-y)urea |
| 336 | 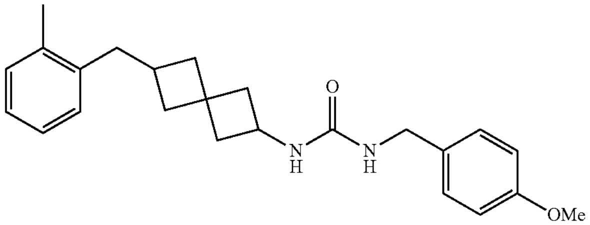 [SMILES: COc1ccc(CNC(=O)NC2CC3(CC(Cc4ccccc4C)C3)C2)cc1] | 1-(4-methoxybenzyl)-3-(6-(2-methylbenzyl)spiro[3.3]heptan-2-yl)urea |

TABLE 1-continued

| Compound No. | Structure | Name |
|---|---|---|
| 337 | 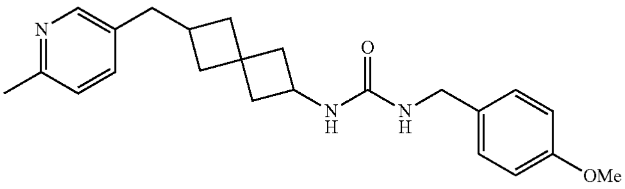 [SMILES: COc1ccc(CNC(=O)NC2CC3(CC(Cc4ccc(C)nc4)C3)C2)cc1] | 1-(4-methoxybenzyl)-3-(6-((6-methylpyridin-3-yl)methyl)spiro[3.3]heptan-2-yl)urea |
| 338 | 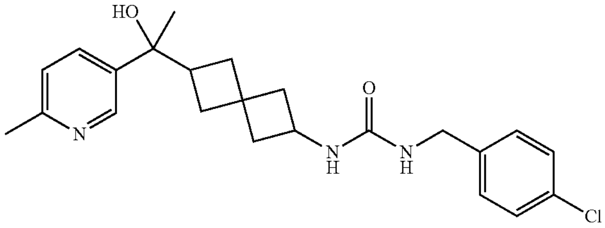 [SMILES: Cc1ccc(C(C)(O)C2CC3(CC(NC(=O)NCc4ccc(Cl)cc4)C3)C2)cn1] | 1-(4-chlorobenzyl)-3-(6-(1-hydroxy-1-(6-methylpyridin-3-yl)ethyl)spiro[3.3]heptan-2-yl)urea |
| 339 | 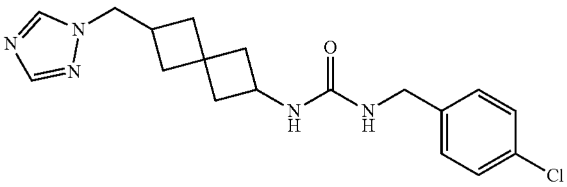 [SMILES: O=C(NCc1ccc(Cl)cc1)NC1CC2(CC(Cn3cncn3)C2)C1] | 1-(6-((1H-1,2,4-triazol-1-yl)methyl)spiro[3.3]heptan-2-yl)-3-(4-chlorobenzyl)urea |
| 340 | 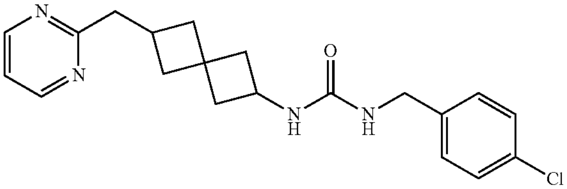 [SMILES: O=C(NCc1ccc(Cl)cc1)NC1CC2(CC(Cc3ncccn3)C2)C1] | 1-(4-chlorobenzyl)-3-(6-(pyrimidin-2-ylmethyl)spiro[3.3]heptan-2-yl)urea |
| 341 | 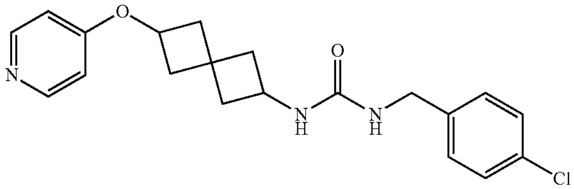 [SMILES: O=C(NCc1ccc(Cl)cc1)NC1CC2(C1)CC(Oc1ccncc1)C2] | 1-(4-chlorobenzyl)-3-(6-(pyridin-4-yloxy)spiro[3.3]heptan-2-yl)urea |
| 342 | 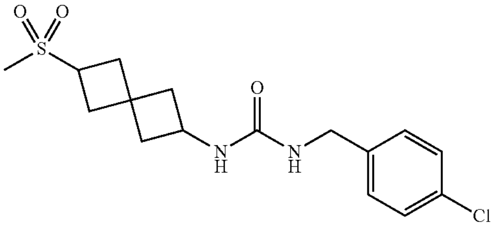 [SMILES: CS(=O)(=O)C1CC2(CC(NC(=O)NCc3ccc(Cl)cc3)C2)C1] | 1-(4-chlorobenzyl)-3-(6-(methylsulfonyl)spiro[3.3]heptan-2-yl)urea |
| 343 | 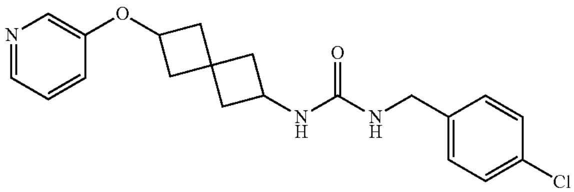 [SMILES: O=C(NCc1ccc(Cl)cc1)NC1CC2(C1)CC(Oc1cccnc1)C2] | 1-(4-chlorobenzyl)-3-(6-(pyridin-3-yloxy)spiro[3.3]heptan-2-yl)urea |

TABLE 1-continued

| Compound No. | Structure | Name |
| --- | --- | --- |
| 344 | 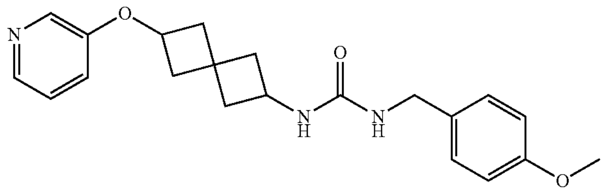 [SMILES: COc1ccc(CNC(=O)NC2CC3(C2)CC(Oc2cccnc2)C3)cc1] | 1-(4-methoxybenzyl)-3-(6-(pyridin-3-yloxy)spiro[3.3]heptan-2-yl)urea |
| 345 | 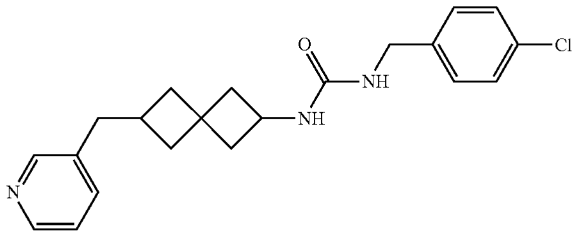 [SMILES: O=C(NCc1ccc(Cl)cc1)NC1CC2(CC(Cc3cccnc3)C2)C1] | 1-(4-chlorobenzyl)-3-(6-(pyiridin-3-ylmethyl)spiro[3.3]heptan-2-yl)urea |
| 346 | 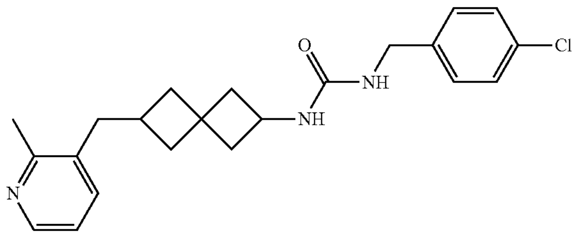 [SMILES: Cc1ncccc1CC1CC2(C1)CC(NC(=O)NCc1ccc(Cl)cc1)C2] | 1-(4-chlorobenzyl)-3-(6-((2-methylpyridin-3-yl)methyl)spiro[3.3]heptan-2-yl)urea |
| 347 | 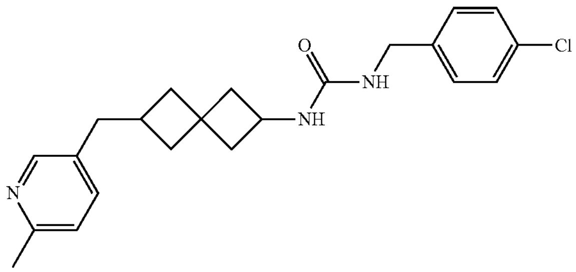 [SMILES: Cc1ccc(CC2CC3(C2)CC(NC(=O)NCc2ccc(Cl)cc2)C3)cn1] | 1-(4-chlorobenzyl)-3-(6-((6-methylpyridin-3-yl)methyl)spiro[3.3]heptan-2-yl)urea |
| 348 | 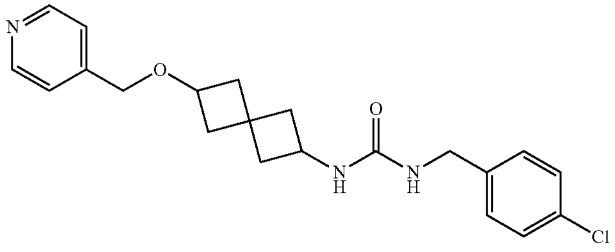 [SMILES: O=C(NCc1ccc(Cl)cc1)NC1CC2(C1)CC(OCc1ccncc1)C2] | 1-(4-chlorobenzyl)-3-(6-(pyridin-4-ylmethoxy)spiro[3.3]heptan-2-yl)urea |
| 349 | 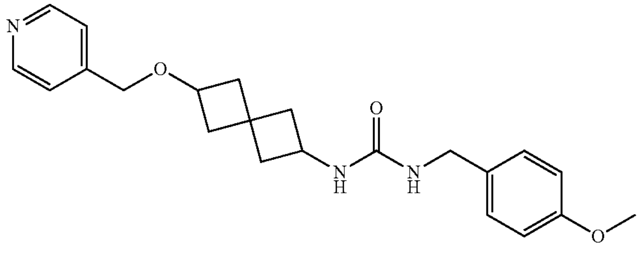 [SMILES: COc1ccc(CNC(=O)NC2CC3(C2)CC(OCc2ccncc2)C3)cc1] | 1-(4-methoxybenzyl)-3-(6-(pyridin-4-ylmethoxy)spiro[3.3]heptan-2-yl)urea |

TABLE 1-continued

| Compound No. | Structure | Name |
|---|---|---|
| 350 | 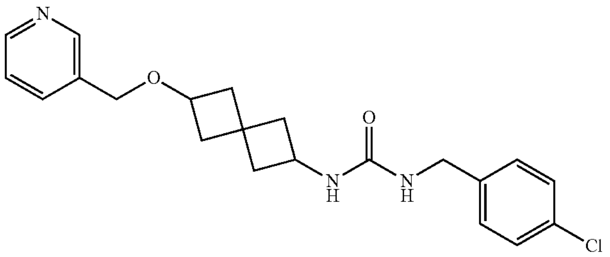 [SMILES: O=C(NCc1ccc(Cl)cc1)NC1CC2(C1)CC(OCc1cccnc1)C2] | 1-(4-chlorobenzyl)-3-(6-(pyridin-3-ylmethoxy)spiro[3.3]heptan-2-yl)urea |
| 351 | 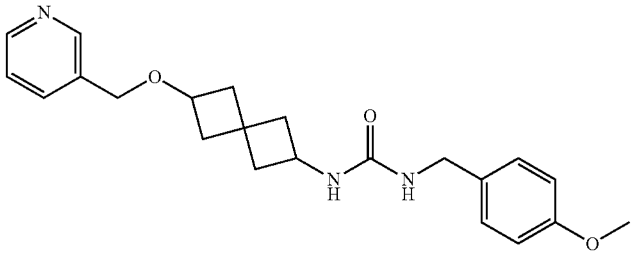 [SMILES: COc1ccc(CNC(=O)NC2CC3(C2)CC(OCc2cccnc2)C3)cc1] | 1-(4-methoxybenzyl)-3-(6-(pyridin-3-ylmethoxy)spiro[3.3]heptan-2-yl)urea |
| 352 | 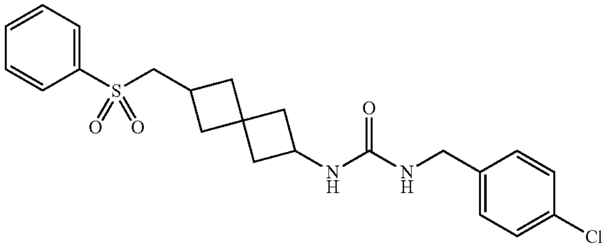 [SMILES: O=C(NCc1ccc(Cl)cc1)NC1CC2(CC(CS(=O)(=O)c3ccccc3)C2)C1] | 1-(4-chlorobenzyl)-3-(6-((phenylsulfonyl)methyl)spiro[3.3]heptan-2-yl)urea |
| 353 | 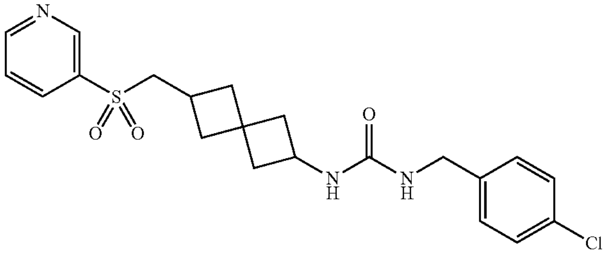 [SMILES: O=C(NCc1ccc(Cl)cc1)NC1CC2(CC(CS(=O)(=O)c3cccnc3)C2)C1] | 1-(4-chlorobenzyl)-3-(6-((pyridin-3-ylsulfonyl)methyl)spiro[3.3]heptan-2-yl)urea |
| 354 | 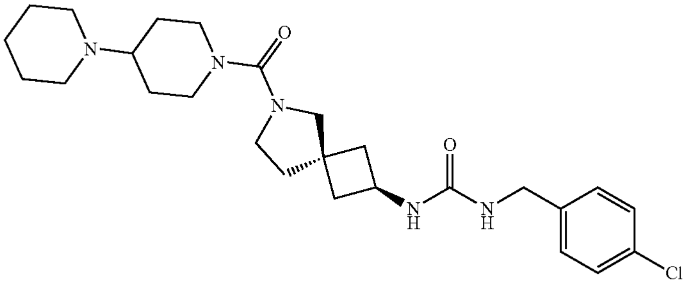 [SMILES: O=C(NCc1ccc(Cl)cc1)N[C@H]1C[C@]2(CCN(C(=O)N3CCC(N4CCCCC4)CC3)C2)C1] | 1-((2r,4s)-6-([1,4'-bipiperidine]-1'-carbonyl)-6-azaspiro[3.4]octan-2-yl)-3-(4-chlorobenzyl)urea |

In some embodiments, provided herein is a compound of Formula (II), or any variation thereof, or a pharmaceutically acceptable salt of any of the foregoing, selected from the group consisting of:

1-(4-(1-benzoylpiperidin-4-yl)butyl)-3-(pyridin-4-ylmethyl)urea;

tert-butyl (6-(3-(4-carbamoylbenzyl)ureido)spiro[3.3]heptan-2-yl)carbamate;

4-((3-(4,4-dimethylcyclohexyl)ureido)methyl)benzamide;

4-((3-(3-phenylcyclobutyl)ureido)methyl)benzamide;

tert-butyl 4-(3-(4-carbamoylbenzyl)ureido)piperidine-1-carboxylate;

tert-butyl (6-(3-(pyridin-4-ylmethyl)ureido)spiro[3.3]heptan-2-yl)carbamate;

tert-butyl (6-(3-(4-methoxybenzyl)ureido)spiro[3.3]heptan-2-yl)carbamate;

tert-butyl (6-(3-(4-(hydroxymethyl)benzyl)ureido)spiro[3.3]heptan-2-yl)carbamate;

tert-butyl (6-(3-((1H-pyrazol-4-yl)methyl)ureido)spiro[3.3]heptan-2-yl)carbamate;
tert-butyl (6-(3-(oxazol-5-ylmethyl)ureido)spiro[3.3]heptan-2-yl)carbamate;
tert-butyl (4-(3-(4-carbamoylbenzyl)ureido)cyclohexyl)carbamate;
4-((3-(1-benzoylpiperidin-4-yl)ureido)methyl)benzamide;
N-(6-(3-(4-carbamoylbenzyl)ureido)spiro[3.3]heptan-2-yl)benzamide;
N-(6-(3-(pyridin-4-ylmethyl)ureido)spiro[3.3]heptan-2-yl)benzamide;
1-(4-(1-benzoylpiperidin-4-yl)butyl)-3-(4-chlorobenzyl)urea;
N-(6-(3-((1H-pyrazol-4-yl)methyl)ureido)spiro[3.3]heptan-2-yl)benzamide;
N-(6-(3-(4-methoxybenzyl)ureido)spiro[3.3]heptan-2-yl)benzamide;
4-((3-(4-(1-benzoylpiperidin-4-yl)butyl)ureido)methyl)benzamide;
1-(4-(1-benzoylpiperidin-4-yl)butyl)-3-(4-methoxybenzyl)urea;
4-((3-(3-(benzylcarbamoyl)cyclobutyl)ureido)methyl)benzamide;
1-(4-(1-benzoylpiperidin-4-yl)butyl)-3-(4-(hydroxymethyl)benzyl)urea;
1-(4-(1-benzoylpiperidin-4-yl)butyl)-3-(oxazol-5-ylmethyl)urea;
4-((3-(6-(benzylamino)spiro[3.3]heptan-2-yl)ureido)methyl)benzamide;
tert-butyl 1-((3-(pyridin-4-ylmethyl)ureido)methyl)-6-azaspiro[2.5]octane-6-carboxylate;
4-((3-(6-(pyridin-2-ylamino)spiro[3.3]heptan-2-yl)ureido)methyl)benzamide;
tert-butyl 1-((3-(4-chlorobenzyl)ureido)methyl)-6-azaspiro[2.5]octane-6-carboxylate;
tert-butyl 1-((3-(4-methoxybenzyl)ureido)methyl)-6-azaspiro[2.5]octane-6-carboxylate;
tert-butyl 1-((3-(4-(hydroxymethyl)benzyl)ureido)methyl)-6-azaspiro[2.5]octane-6-carboxylate;
tert-butyl 1-((3-(oxazol-5-ylmethyl)ureido)methyl)-6-azaspiro[2.5]octane-6-carboxylate;
tert-butyl 1-((3-((1H-pyrazol-4-yl)methyl)ureido)methyl)-6-azaspiro[2.5]octane-6-carboxylate;
tert-butyl 1-((3-(4-acetamidobenzyl)ureido)methyl)-6-azaspiro[2.5]octane-6-carboxylate;
tert-butyl 1-((3-(4-carbamoylbenzyl)ureido)methyl)-6-azaspiro[2.5]octane-6-carboxylate;
4-((3-(6-((pyridin-2-ylmethyl)amino)spiro[3.3]heptan-2-yl)ureido)methyl)benzamide;
methyl 6-(3-(4-methoxybenzyl)ureido)spiro[3.3]heptane-2-carboxylate;
tert-butyl (5-(3-(4-methoxybenzyl)ureido)pentyl)carbamate;
tert-butyl 6-(3-(4-methoxybenzyl)ureido)-2-azaspiro[3.3]heptane-2-carboxylate;
1-(2-(2-(2-fluorophenyl)acetyl)-2-azaspiro[3.3]heptan-6-yl)-3-(4-methoxybenzyl)urea;
1-(2-(2-(2-chlorophenyl)acetyl)-2-azaspiro[3.3]heptan-6-yl)-3-(4-methoxybenzyl)urea;
1-(4-methoxybenzyl)-3-(2-(2-(2-methoxyphenyl)acetyl)-2-azaspiro[3.3]heptan-6-yl)urea;
1-(4-methoxybenzyl)-3-(2-(2-(2-(trifluoromethyl)phenyl)acetyl)-2-azaspiro[3.3]heptan-6-yl)urea;
1-(4-methoxybenzyl)-3-(2-(2-(o-tolyl)acetyl)-2-azaspiro[3.3]heptan-6-yl)urea;
6-(3-(4-methoxybenzyl)ureido)-N-(1-phenylcyclopropyl)spiro[3.3]heptane-2-carboxamide;
1-(4-methoxybenzyl)-3-(6-(2-phenylpyrrolidine-1-carbonyl)spiro[3.3]heptan-2-yl)urea;
6-(3-(4-methoxybenzyl)ureido)-N-(1-phenylethyl)spiro[3.3]heptane-2-carboxamide;
N-(2-hydroxy-1-phenylethyl)-6-(3-(4-methoxybenzyl)ureido)spiro[3.3]heptane-2-carboxamide;
1-(4-methoxybenzyl)-3-(6-(2-phenylazetidine-1-carbonyl)spiro[3.3]heptan-2-yl)urea;
6-(3-(4-methoxybenzyl)ureido)-N-(pyridin-3-ylmethyl)spiro[3.3]heptane-2-carboxamide;
6-(3-(4-methoxybenzyl)ureido)-N-(pyridin-4-ylmethyl)spiro[3.3]heptane-2-carboxamide;
N-benzyl-6-(3-(4-methoxybenzyl)ureido)-N-methylspiro[3.3]heptane-2-carboxamide;
1-(4-methoxybenzyl)-3-(6-((2-phenylpyrrolidin-1-yl)methyl)spiro[3.3]heptan-2-yl)urea;
N-(1-(2-fluorophenyl)ethyl)-6-(3-(4-methoxybenzyl)ureido)-N-methylspiro[3.3]heptane-2-carboxamide;
6-(3-(4-methoxybenzyl)ureido)-N-(2-methyl-2-(o-tolyl)propyl)spiro[3.3]heptane-2-carboxamide;
N-(2-(2-fluorophenyl)-2-methylpropyl)-6-(3-(4-methoxybenzyl)ureido)spiro[3.3]heptane-2-carboxamide;
6-(3-(4-methoxybenzyl)ureido)-N-(pyridin-2-ylmethyl)spiro[3.3]heptane-2-carboxamide;
1-(4-methoxybenzyl)-3-(6-(3-phenylpyrrolidine-1-carbonyl)spiro[3.3]heptan-2-yl)urea;
1-(4-methoxybenzyl)-3-(6-(2-(pyridin-4-yl)pyrrolidine-1-carbonyl)spiro[3.3]heptan-2-yl)urea;
1-(4-methoxybenzyl)-3-(6-(2-(pyridin-3-yl)pyrrolidine-1-carbonyl)spiro[3.3]heptan-2-yl)urea;
1-(4-methoxybenzyl)-3-(6-(3-phenylazetidine-1-carbonyl)spiro[3.3]heptan-2-yl)urea;
1-(6-(4-benzoylpiperazine-1-carbonyl)spiro[3.3]heptan-2-yl)-3-(4-methoxybenzyl)urea;
6-(3-(4-methoxybenzyl)ureido)-N-(3-phenylcyclobutyl)spiro[3.3]heptane-2-carboxamide;
6-(3-(4-methoxybenzyl)ureido)-N-(2-(2-methoxyphenyl)-2-methylpropyl)spiro[3.3]heptane-2-carboxamide;
6-(3-(4-methoxybenzyl)ureido)-N-(2-methyl-2-(pyridin-2-yl)propyl)spiro[3.3]heptane-2-carboxamide;
6-(3-(4-methoxybenzyl)ureido)-N-(2-methyl-2-(pyridin-3-yl)propyl)spiro[3.3]heptane-2-carboxamide;
N-benzyl-2-(6-(3-(4-methoxybenzyl)ureido)spiro[3.3]heptan-2-yl)-N-methylacetamide;
N-benzyl-6-(3-(4-methoxybenzyl)ureido)spiro[3.3]heptane-2-carboxamide;
6-(3-(4-methoxybenzyl)ureido)-N-phenethylspiro[3.3]heptane-2-carboxamide;
6-(3-(4-methoxybenzyl)ureido)-N-(2-phenylpropan-2-yl)spiro[3.3]heptane-2-carboxamide;
1-(4-methoxybenzyl)-3-(6-(1,2,3,4-tetrahydroquinoline-1-carbonyl)spiro[3.3]heptan-2-yl)urea;
1-(4-methoxybenzyl)-3-(6-(7-(trifluoromethyl)-1,2,3,4-tetrahydroisoquinoline-2-carbonyl)spiro[3.3]heptan-2-yl)urea;
1-(6-(isoindoline-2-carbonyl)spiro[3.3]heptan-2-yl)-3-(4-methoxybenzyl)urea;
1-(6-(indoline-1-carbonyl)spiro[3.3]heptan-2-yl)-3-(4-methoxybenzyl)urea;
N-(2-(1H-pyrazol-4-yl)ethyl)-6-(3-(4-methoxybenzyl)ureido)spiro[3.3]heptane-2-carboxamide;
1-(6-(4-(2-hydroxy-2-methylpropyl)piperazine-1-carbonyl)spiro[3.3]heptan-2-yl)-3-(4-methoxybenzyl)urea;
N-(4-cyano-2-fluorobenzyl)-6-(3-(4-methoxybenzyl)ureido)spiro[3.3]heptane-2-carboxamide;
6-(3-(4-methoxybenzyl)ureido)-N-(3-(pyridin-4-yl)cyclobutyl)spiro[3.3]heptane-2-carboxamide;

6-(3-(4-methoxybenzyl)ureido)-N-methyl-N-(tetrahydrofuran-3-yl)spiro[3.3]heptane-2-carboxamide;
6-(3-(4-methoxybenzyl)ureido)-N-(2-methyl-2-(pyridin-4-yl)propyl)spiro[3.3]heptane-2-carboxamide;
tert-butyl 2-(3-(4-methoxybenzyl)ureido)-6-azaspiro[3.4]octane-6-carboxylate;
tert-butyl 6-(3-(4-methoxybenzyl)ureido)-2-azaspiro[3.4]octane-2-carboxylate;
1-(4-methoxybenzyl)-3-(6-(6-methyl-1,2,3,4-tetrahydroquinoline-1-carbonyl)spiro[3.3]heptan-2-yl)urea;
1-(6-(3,4-dihydro-2H-benzo[b][1,4]oxazine-4-carbonyl)spiro[3.3]heptan-2-yl)-3-(4-methoxybenzyl)urea;
6-(3-(4-methoxybenzyl)ureido)-N-phenylspiro[3.3]heptane-2-carboxamide;
6-(3-(4-methoxybenzyl)ureido)-N-methyl-N-phenylspiro[3.3]heptane-2-carboxamide;
N-((2-(difluoromethoxy)pyridin-4-yl)methyl)-6-(3-(4-methoxybenzyl)ureido)spiro[3.3]heptane-2-carboxamide;
N-([1,2,4]triazolo[4,3-a]pyridin-6-yl)-6-(3-(4-methoxybenzyl)ureido)spiro[3.3]heptane-2-carboxamide;
1-(4-methoxybenzyl)-3-(6-(1,2,3,4-tetrahydro-1,6-naphthyridine-1-carbonyl)spiro[3.3]heptan-2-yl)urea;
N-(2,3-dihydro-1H-inden-1-yl)-6-(3-(4-methoxybenzyl)ureido)spiro[3.3]heptane-2-carboxamide;
N-(3-(hydroxymethyl)-2,3-dihydro-1H-inden-1-yl)-6-(3-(4-methoxybenzyl)ureido)spiro[3.3]heptane-2-carboxamide;
N-(1-hydroxy-2,3-dihydro-1H-inden-2-yl)-6-(3-(4-methoxybenzyl)ureido)spiro[3.3]heptane-2-carboxamide;
N-(2,3-dihydro-1H-inden-2-yl)-6-(3-(4-methoxybenzyl)ureido)spiro[3.3]heptane-2-carboxamide;
6-(3-(4-methoxybenzyl)ureido)-N-(1,2,3,4-tetrahydronaphthalen-2-yl)spiro[3.3]heptane-2-carboxamide;
N-(7-fluoro-1,2,3,4-tetrahydronaphthalen-1-yl)-6-(3-(4-methoxybenzyl)ureido)spiro[3.3]heptane-2-carboxamide;
N-(6-fluoro-1,2,3,4-tetrahydronaphthalen-1-yl)-6-(3-(4-methoxybenzyl)ureido)spiro[3.3]heptane-2-carboxamide;
6-(3-(4-methoxybenzyl)ureido)-N-(1,2,3,4-tetrahydronaphthalen-1-yl)spiro[3.3]heptane-2-carboxamide;
1-(6-(6-fluoro-1,2,3,4-tetrahydroquinoline-1-carbonyl)spiro[3.3]heptan-2-yl)-3-(4-methoxybenzyl)urea;
1-(6-(7,8-difluoro-1,2,3,4-tetrahydroquinoline-1-carbonyl)spiro[3.3]heptan-2-yl)-3-(4-methoxybenzyl)urea;
1-(6-(6-(difluoromethoxy)-1,2,3,4-tetrahydroquinoline-1-carbonyl)spiro[3.3]heptan-2-yl)-3-(4-methoxybenzyl)urea;
1-(4-methoxybenzyl)-3-(6-(6-(trifluoromethyl)-1,2,3,4-tetrahydroquinoline-1-carbonyl)spiro[3.3]heptan-2-yl)urea;
1-(6-(5-fluoro-1,2,3,4-tetrahydroquinoline-1-carbonyl)spiro[3.3]heptan-2-yl)-3-(4-methoxybenzyl)urea;
1-(6-(7-fluoro-1,2,3,4-tetrahydroquinoline-1-carbonyl)spiro[3.3]heptan-2-yl)-3-(4-methoxybenzyl)urea;
1-(4-methoxybenzyl)-3-(6-(6-(trifluoromethoxy)-1,2,3,4-tetrahydroquinoline-1-carbonyl)spiro[3.3]heptan-2-yl)urea;
1-(4-methoxybenzyl)-3-(6-(7-methyl-1,2,3,4-tetrahydroquinoline-1-carbonyl)spiro[3.3]heptan-2-yl)urea;
1-(4-fluorobenzyl)-3-(6-(4-(2-hydroxy-2-methylpropyl)piperazine-1-carbonyl)spiro[3.3]heptan-2-yl)urea;
1-(4-methoxybenzyl)-3-(6-(4-(oxetan-3-yl)piperazine-1-carbonyl)spiro[3.3]heptan-2-yl)urea;
1-(6-(4-(cyclopropylmethyl)piperazine-1-carbonyl)spiro[3.3]heptan-2-yl)-3-(4-methoxybenzyl)urea;
1-(6-(2-(hydroxymethyl)-4-methylpiperazine-1-carbonyl)spiro[3.3]heptan-2-yl)-3-(4-methoxybenzyl)urea;
N-(6-(3-(4-chlorobenzyl)ureido)spiro[3.3]heptan-2-yl)benzamide;
N-(6-(3-(4-chlorobenzyl)ureido)spiro[3.3]heptan-2-yl)-2-phenylacetamide;
1-(2-((2-chlorophenyl)sulfonyl)-2-azaspiro[3.3]heptan-6-yl)-3-(4-methoxybenzyl)urea;
1-(2-((2-chlorobenzyl)sulfonyl)-2-azaspiro[3.3]heptan-6-yl)-3-(4-methoxybenzyl)urea;
1-(2-((2-chlorophenethyl)sulfonyl)-2-azaspiro[3.3]heptan-6-yl)-3-(4-methoxybenzyl)urea;
1-(4-chlorobenzyl)-3-(6-(dibenzylamino)spiro[3.3]heptan-2-yl)urea;
N-(6-(3-(4-chlorobenzyl)ureido)spiro[3.3]heptan-2-yl)-1-(2-chlorophenyl)methanesulfonamide;
N-(6-(3-(4-chlorobenzyl)ureido)spiro[3.3]heptan-2-yl)benzenesulfonamide;
1-(6-(4-isopropylpiperazine-1-carbonyl)spiro[3.3]heptan-2-yl)-3-(4-methoxybenzyl)urea;
1-(4-methoxybenzyl)-3-(6-(4-((1-methyl-1H-pyrazol-4-yl)methyl)piperazine-1-carbonyl)spiro[3.3]heptan-2-yl)urea;
1-(4-methoxybenzyl)-3-(6-(4-(pyridin-4-ylmethyl)piperazine-1-carbonyl)spiro[3.3]heptan-2-yl)urea;
1-(4-methoxybenzyl)-3-(6-(4-(pyridin-2-ylmethyl)piperazine-1-carbonyl)spiro[3.3]heptan-2-yl)urea;
1-(6-(3-(hydroxymethyl)-4-methylpiperazine-1-carbonyl)spiro[3.3]heptan-2-yl)-3-(4-methoxybenzyl)urea;
1-(6-((5,7-difluoro-3,4-dihydroquinolin-1(2H)-yl)methyl)spiro[3.3]heptan-2-yl)-3-(4-methoxybenzyl)urea;
1-(6-(indolin-1-ylmethyl)spiro[3.3]heptan-2-yl)-3-(4-methoxybenzyl)urea;
1-(6-(isoindolin-2-ylmethyl)spiro[3.3]heptan-2-yl)-3-(4-methoxybenzyl)urea;
1-(2-(bicyclo[2.2.1]heptan-2-ylsulfonyl)-2-azaspiro[3.3]heptan-6-yl)-3-(4-methoxybenzyl)urea;
methyl 4-((6-(3-(4-methoxybenzyl)ureido)-2-azaspiro[3.3]heptan-2-yl)sulfonyl)cyclohexane-1-carboxylate;
N-(6-cyanopyridin-2-yl)-6-(3-(4-methoxybenzyl)ureido)-2-azaspiro[3.3]heptane-2-carboxamide;
6-(3-(4-methoxybenzyl)ureido)-N-(2-methylpyrimidin-5-yl)-2-azaspiro[3.3]heptane-2-carboxamide;
1-(6-((1H-indazol-1-yl)methyl)spiro[3.3]heptan-2-yl)-3-(4-methoxybenzyl)urea;
1-(2-(3-(2-chlorophenyl)propanoyl)-2-azaspiro[3.3]heptan-6-yl)-3-(4-methoxybenzyl)urea;
tert-butyl 3-(6-(3-(4-methoxybenzyl)ureido)-2-azaspiro[3.3]heptane-2-carbonyl)piperidine-1-carboxylate;
1-(4-methoxybenzyl)-3-(2-(1,2,3,4-tetrahydronaphthalene-1-carbonyl)-2-azaspiro[3.3]heptan-6-yl)urea;
1-(4-methoxybenzyl)-3-(2-(6-methylnicotinoyl)-2-azaspiro[3.3]heptan-6-yl)urea;
1-(2-isonicotinoyl-2-azaspiro[3.3]heptan-6-yl)-3-(4-methoxybenzyl)urea;
1-(4-methoxybenzyl)-3-(2-(2-methylisonicotinoyl)-2-azaspiro[3.3]heptan-6-yl)urea;
1-(2-benzoyl-2-azaspiro[3.3]heptan-6-yl)-3-(4-methoxybenzyl)urea;
1-(4-methoxybenzyl)-3-(2-(2-methyl-2-phenylpropanoyl)-2-azaspiro[3.3]heptan-6-yl)urea;
1-(4-methoxybenzyl)-3-(2-(1-phenylcyclopropane-1-carbonyl)-2-azaspiro[3.3]heptan-6-yl)urea;
1-(4-methoxybenzyl)-3-(2-(1-methyl-6-oxo-1,6-dihydropyridine-3-carbonyl)-2-azaspiro[3.3]heptan-6-yl)urea;
1-(4-methoxybenzyl)-3-(2-(4-methylbenzoyl)-2-azaspiro[3.3]heptan-6-yl)urea;

1-(4-methoxybenzyl)-3-(2-(3-methylbenzoyl)-2-azaspiro[3.3]heptan-6-yl)urea;
1-(4-methoxybenzyl)-3-(2-(4-(trifluoromethyl)benzoyl)-2-azaspiro[3.3]heptan-6-yl)urea;
1-(4-methoxybenzyl)-3-(2-(2-methylbenzoyl)-2-azaspiro[3.3]heptan-6-yl)urea;
1-(4-methoxybenzyl)-3-(5-phenoxypentyl)urea;
1-(4-methoxybenzyl)-3-(6-phenoxyhexyl)urea;
tert-butyl 2-(3-(4-chlorobenzyl)ureido)-6-azaspiro[3.4]octane-6-carboxylate;
1-(4-methoxybenzyl)-3-(2-(2-methyl-2-(p-tolyl)propanoyl)-2-azaspiro[3.3]heptan-6-yl)urea;
1-(4-methoxybenzyl)-3-(2-(2-methyl-2-(m-tolyl)propanoyl)-2-azaspiro[3.3]heptan-6-yl)urea;
1-(2-(4-methoxybenzoyl)-2-azaspiro[3.3]heptan-6-yl)-3-(4-methoxybenzyl)urea;
1-(2-(4-cyanobenzoyl)-2-azaspiro[3.3]heptan-6-yl)-3-(4-methoxybenzyl)urea;
1-(2-(4-(2-hydroxypropan-2-yl)benzoyl)-2-azaspiro[3.3]heptan-6-yl)-3-(4-methoxybenzyl)urea;
1-(2-(4-chlorobenzoyl)-2-azaspiro[3.3]heptan-6-yl)-3-(4-methoxybenzyl)urea;
1-(4-chlorobenzyl)-3-(6-(4-methylbenzoyl)-6-azaspiro[3.4]octan-2-yl)urea;
1-(4-chlorobenzyl)-3-(6-(2-methylisonicotinoyl)-6-azaspiro[3.4]octan-2-yl)urea;
1-(4-chlorobenzyl)-3-(6-(3-methylbenzoyl)-6-azaspiro[3.4]octan-2-yl)urea;
1-(4-chlorobenzyl)-3-(6-(2-methylbenzoyl)-6-azaspiro[3.4]octan-2-yl)urea;
1-(4-chlorobenzyl)-3-(6-(4-methoxybenzoyl)-6-azaspiro[3.4]octan-2-yl)urea;
1-(4-chlorobenzyl)-3-(6-(3-methylisonicotinoyl)-6-azaspiro[3.4]octan-2-yl)urea;
1-(4-chlorobenzyl)-3-(6-(4-fluorobenzoyl)-6-azaspiro[3.4]octan-2-yl)urea;
1-(4-chlorobenzyl)-3-(6-(3-isopropylbenzoyl)-6-azaspiro[3.4]octan-2-yl)urea;
1-(4-chlorobenzyl)-3-(6-(pyrimidin-2-yl)-6-azaspiro[3.4]octan-2-yl)urea;
1-(4-chlorobenzyl)-3-(6-(2-methylpyridin-4-yl)-6-azaspiro[3.4]octan-2-yl)urea;
1-(2-(3-ethylbenzoyl)-2-azaspiro[3.3]heptan-6-yl)-3-(4-methoxybenzyl)urea;
1-(2-(3-isopropylbenzoyl)-2-azaspiro[3.3]heptan-6-yl)-3-(4-methoxybenzyl)urea;
1-(2-(3-(tert-butyl)benzoyl)-2-azaspiro[3.3]heptan-6-yl)-3-(4-methoxybenzyl)urea;
1-(2-(3-(2-hydroxypropan-2-yl)benzoyl)-2-azaspiro[3.3]heptan-6-yl)-3-(4-methoxybenzyl)urea;
1-(2-(3-methoxybenzoyl)-2-azaspiro[3.3]heptan-6-yl)-3-(4-methoxybenzyl)urea;
1-(2-(3-hydroxybenzoyl)-2-azaspiro[3.3]heptan-6-yl)-3-(4-methoxybenzyl)urea;
1-(2-(3-(dimethylamino)benzoyl)-2-azaspiro[3.3]heptan-6-yl)-3-(4-methoxybenzyl)urea;
1-(4-methoxybenzyl)-3-(2-(3-(pyrrolidin-1-yl)benzoyl)-2-azaspiro[3.3]heptan-6-yl)urea;
1-(4-methoxybenzyl)-3-(2-(3-(methylsulfonyl)benzoyl)-2-azaspiro[3.3]heptan-6-yl)urea;
methyl 3-(6-(3-(4-methoxybenzyl)ureido)-2-azaspiro[3.3]heptane-2-carbonyl)benzoate;
1-(4-chlorobenzyl)-3-(6-(4-(2-hydroxy-2-methylpropyl)piperazine-1-carbonyl)spiro[3.3]heptan-2-yl)urea;
N-(6-(3-(4-chlorobenzyl)ureido)spiro[3.3]heptan-2-yl)nicotinamide;
N-(6-(3-(4-chlorobenzyl)ureido)spiro[3.3]heptan-2-yl)isonicotinamide;
N-(6-(3-(4-chlorobenzyl)ureido)spiro[3.3]heptan-2-yl)-2-methylisonicotinamide;
1-(4-methoxybenzyl)-3-(2-(3-(2-oxopyrrolidin-1-yl)benzoyl)-2-azaspiro[3.3]heptan-6-yl)urea;
1-(2-(3-(1H-pyrrol-1-yl)benzoyl)-2-azaspiro[3.3]heptan-6-yl)-3-(4-methoxybenzyl)urea;
1-(4-methoxybenzyl)-3-(2-(3-(piperidin-1-yl)benzoyl)-2-azaspiro[3.3]heptan-6-yl)urea;
1-(4-methoxybenzyl)-3-(2-(3-morpholinobenzoyl)-2-azaspiro[3.3]heptan-6-yl)urea;
N-(6-(3-(4-chlorobenzyl)ureido)spiro[3.3]heptan-2-yl)-6-methylnicotinamide;
N-(6-(3-(4-chlorobenzyl)ureido)spiro[3.3]heptan-2-yl)-2-methylbenzamide;
N-(6-(3-(4-chlorobenzyl)ureido)spiro[3.3]heptan-2-yl)-3-methoxybenzamide;
N-(6-(3-(4-chlorobenzyl)ureido)spiro[3.3]heptan-2-yl)-3-(methylsulfonyl)benzamide;
1-(4-chlorobenzyl)-3-(2-(2-phenoxyethoxy)ethyl)urea;
tert-butyl 6-(3-(4-chlorobenzyl)ureido)-2-azaspiro[3.3]heptane-2-carboxylate;
tert-butyl (6-(3-(4-chlorobenzyl)ureido)spiro[3.3]heptan-2-yl)carbamate;
1-(4-chlorobenzyl)-3-(6-(6-methylpyridin-2-yl)-6-azaspiro[3.4]octan-2-yl)urea;
N-(6-(3-(4-chlorobenzyl)ureido)spiro[3.3]heptan-2-yl)-3-hydroxybenzamide;
methyl 6-(3-(4-chlorobenzyl)ureido)spiro[3.3]heptane-2-carboxylate;
6-(3-(4-chlorobenzyl)ureido)-N-methyl-N-(tetrahydrofuran-3-yl)spiro[3.3]heptane-2-carboxamide;
N-(6-(3-(4-chlorobenzyl)ureido)spiro[3.3]heptan-2-yl)-2-methylnicotinamide;
N-(6-(3-(4-chlorobenzyl)ureido)spiro[3.3]heptan-2-yl)-3-methylisonicotinamide;
N-(6-(3-(4-chlorobenzyl)ureido)spiro[3.3]heptan-2-yl)-4-methylnicotinamide;
1-(4-chlorobenzyl)-3-(2-(4-methylbenzoyl)-2-azaspiro[3.3]heptan-6-yl)urea;
1-(4-fluorobenzyl)-3-(2-(4-methylbenzoyl)-2-azaspiro[3.3]heptan-6-yl)urea;
N-(6-(3-(4-chlorobenzyl)ureido)spiro[3.3]heptan-2-yl)-2-hydroxybenzamide;
N-(6-(3-(4-chlorobenzyl)ureido)spiro[3.3]heptan-2-yl)-2-(dimethylamino)benzamide;
1-(2-(4-methylbenzoyl)-2-azaspiro[3.3]heptan-6-yl)-3-(pyridin-4-ylmethyl)urea;
4-((3-(2-(4-methylbenzoyl)-2-azaspiro[3.3]heptan-6-yl)ureido)methyl)benzamide;
N-(6-(3-(4-chlorobenzyl)ureido)spiro[3.3]heptan-2-yl)-2-cyanobenzamide;
N-(6-(3-(4-chlorobenzyl)ureido)spiro[3.3]heptan-2-yl)pyridine-3-sulfonamide;
1-(2-(4-methylbenzoyl)-2-azaspiro[3.3]heptan-6-yl)-3-((6-oxo-1,6-dihydropyridin-3-yl)methyl)urea;
5-((3-(2-(4-methylbenzoyl)-2-azaspiro[3.3]heptan-6-yl)ureido)methyl)picolinamide;
1-(4-chlorobenzyl)-3-(2-((2-chlorophenyl)sulfonyl)-2-azaspiro[3.3]heptan-6-yl)urea;
1-(4-chlorobenzyl)-3-(2-((3-chlorophenyl)sulfonyl)-2-azaspiro[3.3]heptan-6-yl)urea;
1-(4-chlorobenzyl)-3-(2-((2-methoxyphenyl)sulfonyl)-2-azaspiro[3.3]heptan-6-yl)urea;
1-(2-(3-(1H-pyrrol-1-yl)benzoyl)-2-azaspiro[3.3]heptan-6-yl)-3-(4-chlorobenzyl)urea;

1-(4-chlorobenzyl)-3-(2-(3-isopropylbenzoyl)-2-azaspiro[3.3]heptan-6-yl)urea;

1-(4-chlorobenzyl)-3-(2-(2-methyl-2-phenylpropanoyl)-2-azaspiro[3.3]heptan-6-yl)urea;

4-((3-(2-(3-(pyrrolidin-1-yl)benzoyl)-2-azaspiro[3.3]heptan-6-yl)ureido)methyl)benzamide;

4-((3-(2-(5-(pyrrolidin-1-yl)nicotinoyl)-2-azaspiro[3.3]heptan-6-yl)ureido)methyl)benzamide;

4-((3-(2-(4-chlorobenzoyl)-2-azaspiro[3.3]heptan-6-yl)ureido)methyl)benzamide;

4-((3-(2-(6-methylnicotinoyl)-2-azaspiro[3.3]heptan-6-yl)ureido)methyl)benzamide;

4-((3-(2-(2-methylisonicotinoyl)-2-azaspiro[3.3]heptan-6-yl)ureido)methyl)benzamide;

1-((1H-pyrazol-4-yl)methyl)-3-(2-(4-methylbenzoyl)-2-azaspiro[3.3]heptan-6-yl)urea;

1-(2-(4-methylbenzoyl)-2-azaspiro[3.3]heptan-6-yl)-3-(oxazol-4-ylmethyl)urea;

1-(4-methoxybenzyl)-3-(6-(4-methylpiperazine-1-carbonyl)spiro[3.3]heptan-2-yl)urea;

methyl 4-(6-(3-(4-methoxybenzyl)ureido)spiro[3.3]heptane-2-carbonyl)piperazine-1-carboxylate;

1-(6-(1,1-dioxidothiomorpholine-4-carbonyl)spiro[3.3]heptan-2-yl)-3-(4-methoxybenzyl)urea;

methyl 4-(6-(3-(4-chlorobenzyl)ureido)spiro[3.3]heptane-2-carbonyl)piperazine-1-carboxylate;

1-(4-chlorobenzyl)-3-(6-(2-(4-(2-hydroxy-2-methylpropyl)piperazin-1-yl)-2-oxoethyl)spiro[3.3]heptan-2-yl)urea;

1-(4-chlorobenzyl)-3-(6-(2-(2-(hydroxymethyl)pyrrolidin-1-yl)-2-oxoethyl)spiro[3.3]heptan-2-yl)urea;

1-(4-chlorobenzyl)-3-(6-(2-oxo-2-(pyrrolidin-1-yl)ethyl)spiro[3.3]heptan-2-yl)urea;

N-benzyl-2-(6-(3-(4-chlorobenzyl)ureido)spiro[3.3]heptan-2-yl)-N-methylpropanamide;

1-(4-chlorobenzyl)-3-(6-((4-methyl-3-oxopiperazin-1-yl)methyl)spiro[3.3]heptan-2-yl)urea;

1-(4-chlorobenzyl)-3-(6-((2-(pyridin-3-yl)pyrrolidin-1-yl)methyl)spiro[3.3]heptan-2-yl)urea;

1-(4-chlorobenzyl)-3-(6-((2-methyl-5-oxopyrrolidin-1-yl)methyl)spiro[3.3]heptan-2-yl)urea;

1-(4-chlorobenzyl)-3-(6-((5-phenyl-1H-1,2,3-triazol-1-yl)methyl)spiro[3.3]heptan-2-yl)urea;

N-((6-(3-(4-chlorobenzyl)ureido)spiro[3.3]heptan-2-yl)methyl)tetrahydro-2H-thiopyran-4-carboxamide 1,1-dioxide;

1-(4-chlorobenzyl)-3-(6-((3-methyl-2-oxopyrrolidin-1-yl)methyl)spiro[3.3]heptan-2-yl)urea;

N-((6-(3-(4-chlorobenzyl)ureido)spiro[3.3]heptan-2-yl)methyl)-6-methylpicolinamide;

N-((6-(3-(4-chlorobenzyl)ureido)spiro[3.3]heptan-2-yl)methyl)-2-methylisonicotinamide;

N-((6-(3-(4-chlorobenzyl)ureido)spiro[3.3]heptan-2-yl)methyl)-1H-pyrazole-4-carboxamide;

N-((6-(3-(4-chlorobenzyl)ureido)spiro[3.3]heptan-2-yl)methyl)-N,6-dimethylnicotinamide;

N-((6-(3-(4-chlorobenzyl)ureido)spiro[3.3]heptan-2-yl)methyl)-6-methylnicotinamide;

N-((6-(3-(4-chlorobenzyl)ureido)spiro[3.3]heptan-2-yl)methyl)tetrahydro-2H-pyran-4-carboxamide;

N-((6-(3-(4-chlorobenzyl)ureido)spiro[3.3]heptan-2-yl)methyl)cyclopentanecarboxamide;

N-((6-(3-(4-chlorobenzyl)ureido)spiro[3.3]heptan-2-yl)methyl)-2-oxopiperidine-4-carboxamide;

1-(4-chlorobenzyl)-3-(6-(1-(4-methyl-3-oxopiperazin-1-yl)ethyl)spiro[3.3]heptan-2-yl)urea;

1-(4-chlorobenzyl)-3-(6-((4-methyl-2-phenylpiperazin-1-yl)methyl)spiro[3.3]heptan-2-yl)urea;

N-(1-(6-(3-(4-chlorobenzyl)ureido)spiro[3.3]heptan-2-yl)ethyl)-6-methylnicotinamide;

1-(4-chlorobenzyl)-3-(5-(3,4-dihydroquinolin-1(2H)-yl)-5-oxopentyl)urea;

6-(3-(4-chlorobenzyl)ureido)-N-cyclohexylhexanamide;

6-(3-(4-chlorobenzyl)ureido)-N-cyclopentylhexanamide;

1-(4-chlorobenzyl)-3-(6-morpholino-6-oxohexyl)urea;

1-(4-chlorobenzyl)-3-(6-(4-neopentylpiperazin-1-yl)-6-oxohexyl)urea;

1-(4-chlorobenzyl)-3-(6-(4-(2-hydroxy-2-methylpropyl)piperazin-1-yl)-6-oxohexyl)urea;

6-(3-(4-chlorobenzyl)ureido)-N-(o-tolyl)hexanamide;

6-(3-(4-chlorobenzyl)ureido)-N-(pyridin-4-yl)hexanamide;

6-(3-(4-chlorobenzyl)ureido)-N-methyl-N-(m-tolyl)hexanamide;

6-(3-(4-chlorobenzyl)ureido)-N-methyl-N-(pyridin-4-yl)hexanamide;

6-(3-(4-chlorobenzyl)ureido)-N-methyl-N-(o-tolyl)hexanamide;

6-(3-(4-chlorobenzyl)ureido)-N-methyl-N-(3-methylbenzyl)hexanamide;

6-(3-(4-chlorobenzyl)ureido)-N-methyl-N-phenylhexanamide;

N-benzyl-6-(3-(4-chlorobenzyl)ureido)-N-methylhexanamide;

6-(3-(4-chlorobenzyl)ureido)-N-methyl-N-(pyridin-3-yl)hexanamide;

6-(3-(4-chlorobenzyl)ureido)-N-methyl-N-(pyridin-2-yl)hexanamide;

6-(3-(4-chlorobenzyl)ureido)-N-(2-fluorophenyl)hexanamide;

N-([1,1'-biphenyl]-2-yl)-6-(3-(4-chlorobenzyl)ureido)hexanamide;

6-(3-(4-chlorobenzyl)ureido)-N-(2-fluorophenyl)-N-methylhexanamide;

N-(5-(3-(4-chlorobenzyl)ureido)pentyl)-2-methylbenzamide;

N-(5-(3-(4-chlorobenzyl)ureido)pentyl)-3-methylbenzamide;

N-(5-(3-(4-chlorobenzyl)ureido)pentyl)nicotinamide;

6-(3-(4-chlorobenzyl)ureido)-N-(6-methylpyridin-3-yl)hexanamide;

N-(5-(3-(4-chlorobenzyl)ureido)pentyl)picolinamide;

N-(5-(3-(4-chlorobenzyl)ureido)pentyl)-2-fluorobenzamide;

N-(5-(3-(4-chlorobenzyl)ureido)pentyl)-6-methylnicotinamide;

N-(2-fluorophenyl)-6-(3-(4-methoxybenzyl)ureido)-N-methylhexanamide;

N-(5-(3-(4-chlorobenzyl)ureido)pentyl)-2-(pyridin-3-yl)acetamide;

6-(3-(4-chlorobenzyl)ureido)-N-(4-fluorophenyl)hexanamide;

6-(3-(4-chlorobenzyl)ureido)-N-(3-fluorophenyl)hexanamide;

N-(2-fluorophenyl)-N-methyl-6-(3-(pyridin-4-ylmethyl)ureido)hexanamide;

6-(3-((1H-pyrazol-4-yl)methyl)ureido)-N-(2-fluorophenyl)-N-methylhexanamide;

N-(2-fluorophenyl)-N-methyl-6-(3-(oxazol-5-ylmethyl)ureido)hexanamide;

1-(4-chlorobenzyl)-3-(4-(1-nicotinoylpiperidin-4-yl)butyl)urea;

1-(4-chlorobenzyl)-3-(4-(1-isonicotinoylpiperidin-4-yl)butyl)urea;

1-(4-chlorobenzyl)-3-(4-(1-(2-phenylacetyl)piperidin-4-yl)butyl)urea;

1-(4-chlorobenzyl)-3-(4-(1-picolinoylpiperidin-4-yl)butyl)urea;
1-(4-(1-benzoylpiperidin-4-yl)butyl-1,1-d2)-3-(oxazol-5-ylmethyl)urea;
1-(4-chlorobenzyl)-3-(4-(1-(2-(pyridin-3-yl)acetyl)piperidin-4-yl)butyl)urea;
1-(4-chlorobenzyl)-3-(4-(1-(2-(pyridin-4-yl)acetyl)piperidin-4-yl)butyl)urea;
1-(4-chlorobenzyl)-3-(4-(1-(3-methylbenzoyl)piperidin-4-yl)butyl)urea;
1-(4-chlorobenzyl)-3-(4-(1-(2-methylbenzoyl)piperidin-4-yl)butyl)urea;
1-(4-chlorobenzyl)-3-(4-(1-(6-methylpicolinoyl)piperidin-4-yl)butyl)urea;
1-(4-chlorobenzyl)-3-(4-(1-(2-(6-methylpyridin-2-yl)acetyl)piperidin-4-yl)butyl)urea;
1-(4-chlorobenzyl)-3-(4-(1-(tetrahydro-2H-pyran-4-carbonyl)piperidin-4-yl)butyl)urea;
1-(4-chlorobenzyl)-3-(4-(1-(2-oxopiperidine-4-carbonyl)piperidin-4-yl)butyl)urea;
1-(4-chlorobenzyl)-3-(4-(1-(1-methyl-2-oxopiperidine-4-carbonyl)piperidin-4-yl)butyl)urea;
1-(4-chlorobenzyl)-3-(4-(1-(5-oxopyrrolidine-3-carbonyl)piperidin-4-yl)butyl)urea;
1-(4-chlorobenzyl)-3-(4-(1-(1-methyl-5-oxopyrrolidine-3-carbonyl)piperidin-4-yl)butyl)urea;
1-(4-chlorobenzyl)-3-(4-(1-(oxazole-2-carbonyl)piperidin-4-yl)butyl)urea;
1-(4-chlorobenzyl)-3-(4-(1-(isoxazole-5-carbonyl)piperidin-4-yl)butyl)urea;
1-(4-chlorobenzyl)-3-(4-(1-(pyridin-2-yl)piperidin-4-yl)butyl)urea;
1-(4-chlorobenzyl)-3-(4-(1-(pyridin-4-yl)piperidin-4-yl)butyl)urea;
1-(4-chlorobenzyl)-3-(4-(1-(6-methylnicotinoyl)piperidin-4-yl)butyl)urea;
1-(4-chlorobenzyl)-3-(4-(1-(2-(2-methylpyridin-3-yl)acetyl)piperidin-4-yl)butyl)urea;
1-(4-chlorobenzyl)-3-(4-(1-(2-(6-methylpyridin-3-yl)acetyl)piperidin-4-yl)butyl)urea;
1-(4-chlorobenzyl)-3-(4-(1-(1-methyl-1H-1,2,3-triazole-4-carbonyl)piperidin-4-yl)butyl)urea;
1-(4-chlorobenzyl)-3-(4-(1-(2-(o-tolyl)acetyl)piperidin-4-yl)butyl)urea;
1-(4-chlorobenzyl)-3-(4-(1-(2-(difluoromethyl)benzoyl)piperidin-4-yl)butyl)urea;
1-(4-(1-(2-(1H-tetrazol-5-yl)benzoyl)piperidin-4-yl)butyl)-3-(4-chlorobenzyl)urea;
1-(4-(1-(2-(1H-pyrazol-4-yl)acetyl)piperidin-4-yl)butyl)-3-(4-chlorobenzyl)urea;
1-(4-(4-benzoylpiperazin-1-yl)butyl)-3-(4-chlorobenzyl)urea;
1-(4-(1-(2H-tetrazol-5-yl)piperidin-4-yl)butyl)-3-(4-chlorobenzyl)urea;
1-(4-chlorobenzyl)-3-(4-(1-(2,6-dimethylbenzoyl)piperidin-4-yl)butyl)urea;
1-(4-(1-(2-methylbenzoyl)piperidin-4-yl)butyl)-3-(oxazol-5-ylmethyl)urea;
4-((3-(4-(1-(2-methylbenzoyl)piperidin-4-yl)butyl)ureido)methyl)benzamide;
1-(4-methoxybenzyl)-3-(4-(1-(2-methylbenzoyl)piperidin-4-yl)butyl)urea;
1-(4-(1-(2-methylbenzoyl)piperidin-4-yl)butyl)-3-(pyridin-4-ylmethyl)urea;
1-(4-(1-benzoylpiperidin-4-yl)butyl)-3-(oxazol-5-ylmethyl-d2)urea;
1-(4-methoxybenzyl)-3-(6-(5-phenyl-1,3,4-oxadiazol-2-yl)spiro[3.3]heptan-2-yl)urea;
1-(4-methoxybenzyl)-3-(6-(4-phenyloxazol-2-yl)spiro[3.3]heptan-2-yl)urea;
1-(6-(benzo[d]oxazol-2-yl)spiro[3.3]heptan-2-yl)-3-(4-methoxybenzyl)urea;
1-(4-chlorobenzyl)-3-(6-(hydroxy(phenyl)methyl)spiro[3.3]heptan-2-yl)urea;
1-(4-chlorobenzyl)-3-(6-(pyridin-4-ylmethyl)spiro[3.3]heptan-2-yl)urea;
1-(4-methoxybenzyl)-3-(6-(pyridin-4-ylmethyl)spiro[3.3]heptan-2-yl)urea;
1-(4-chlorobenzyl)-3-(6-(pyrazin-2-ylmethyl)spiro[3.3]heptan-2-yl)urea;
1-(4-methoxybenzyl)-3-(6-(5-(6-methylpyridin-3-yl)-1,3,4-oxadiazol-2-yl)spiro[3.3]heptan-2-yl)urea;
1-(4-chlorobenzyl)-3-(6-((4-cyano-1H-pyrazol-1-yl)methyl)spiro[3.3]heptan-2-yl)urea;
1-(4-methoxybenzyl)-3-(6-(4-methylbenzyl)spiro[3.3]heptan-2-yl)urea;
1-(4-methoxybenzyl)-3-(6-(3-methylbenzyl)spiro[3.3]heptan-2-yl)urea;
1-(4-methoxybenzyl)-3-(6-(2-methylbenzyl)spiro[3.3]heptan-2-yl)urea;
1-(4-methoxybenzyl)-3-(6-((6-methylpyridin-3-yl)methyl)spiro[3.3]heptan-2-yl)urea;
1-(4-chlorobenzyl)-3-(6-(1-hydroxy-1-(6-methylpyridin-3-yl)ethyl)spiro[3.3]heptan-2-yl)urea;
1-(6-((1H-1,2,4-triazol-1-yl)methyl)spiro[3.3]heptan-2-yl)-3-(4-chlorobenzyl)urea;
1-(4-chlorobenzyl)-3-(6-(pyrimidin-2-ylmethyl)spiro[3.3]heptan-2-yl)urea;
1-(4-chlorobenzyl)-3-(6-(pyridin-4-yloxy)spiro[3.3]heptan-2-yl)urea;
1-(4-chlorobenzyl)-3-(6-(methylsulfonyl)spiro[3.3]heptan-2-yl)urea;
1-(4-chlorobenzyl)-3-(6-(pyridin-3-yloxy)spiro[3.3]heptan-2-yl)urea;
1-(4-methoxybenzyl)-3-(6-(pyridin-3-yloxy)spiro[3.3]heptan-2-yl)urea;
1-(4-chlorobenzyl)-3-(6-(pyridin-3-ylmethyl)spiro[3.3]heptan-2-yl)urea;
1-(4-chlorobenzyl)-3-(6-((2-methylpyridin-3-yl)methyl)spiro[3.3]heptan-2-yl)urea;
1-(4-chlorobenzyl)-3-(6-((6-methylpyridin-3-yl)methyl)spiro[3.3]heptan-2-yl)urea;
1-(4-chlorobenzyl)-3-(6-(pyridin-4-ylmethoxy)spiro[3.3]heptan-2-yl)urea;
1-(4-methoxybenzyl)-3-(6-(pyridin-4-ylmethoxy)spiro[3.3]heptan-2-yl)urea;
1-(4-chlorobenzyl)-3-(6-(pyridin-3-ylmethoxy)spiro[3.3]heptan-2-yl)urea;
1-(4-methoxybenzyl)-3-(6-(pyridin-3-ylmethoxy)spiro[3.3]heptan-2-yl)urea;
1-(4-chlorobenzyl)-3-(6-((phenylsulfonyl)methyl)spiro[3.3]heptan-2-yl)urea;
1-(4-chlorobenzyl)-3-(6-((pyridin-3-ylsulfonyl)methyl)spiro[3.3]heptan-2-yl)urea; and
1-(6-([1,4'-bipiperidine]-1'-carbonyl)-6-azaspiro[3.4]octan-2-yl)-3-(4-chlorobenzyl)urea, or a pharmaceutically acceptable salt of any of the foregoing.

In some variations, any of the compounds described herein, such as a compound of Formula (I) or Formula (II), or any variation thereof, or a compound of Table 1 may be deuterated (e.g., a hydrogen atom is replaced by a deuterium atom). In some of these variations, the compound is deuterated at a single site. In other variations, the compound is deuterated at multiple sites. Deuterated compounds can be prepared from deuterated starting materials in a manner similar to the preparation of the corresponding non-deuterated compounds. Hydrogen atoms may also be replaced with deuterium atoms using other method known in the art.

Any formula given herein, such as Formula (II), (I) (I-A), (I-A1), (I-A2), (I-B), (I-C), (I-D), (I-E), (I-F), (I-G), (I-H), (I-J), or (I-K), is intended to represent compounds having structures depicted by the structural formula as well as certain variations or forms. In particular, compounds of any formula given herein may have asymmetric centers and therefore exist in different enantiomeric or diastereomeric forms. All optical isomers and stereoisomers of the compounds of the general formula, and mixtures thereof in any ratio, are considered within the scope of the formula. Thus, any formula given herein is intended to represent a racemate, one or more enantiomeric forms, one or more diastereomeric forms, one or more atropisomeric forms, and mixtures thereof in any ratio. Where a compound of Table 1 is depicted with a particular stereochemical configuration, also provided herein is any alternative stereochemical configuration of the compound, as well as a mixture of stereoisomers of the compound in any ratio. For example, where a compound of Table 1 has a stereocenter that is in an "S" stereochemical configuration, also provided herein is enantiomer of the compound wherein that stereocenter is in an "R" stereochemical configuration. Likewise, when a compound of Table 1 has a stereocenter that is in an "R" configuration, also provided herein is enantiomer of the compound in an "S" stereochemical configuration. Also provided are mixtures of the compound with both the "S" and the "R" stereochemical configuration. Additionally, if a compound of Table 1 has two or more stereocenters, also provided are any enantiomer or diastereomer of the compound. For example, if a compound of Table 1 contains a first stereocenter and a second stereocenter with "R" and "R" stereochemical configurations, respectively, also provided are stereoisomers of the compound having first and second stereocenters with "S" and "S" stereochemical configurations, respectively, "S" and "R" stereochemical configurations, respectively, and "R" and "S" stereochemical configurations, respectively. If a compound of Table 1 contains a first stereocenter and a second stereocenter with "S" and "S" stereochemical configurations, respectively, also provided are stereoisomers of the compound having first and second stereocenters with "R" and "R" stereochemical configurations, respectively, "S" and "R" stereochemical configurations, respectively, and "R" and "S" stereochemical configurations, respectively. If a compound of Table 1 contains a first stereocenter and a second stereocenter with "S" and "R" stereochemical configurations, respectively, also provided are stereoisomers of the compound having first and second stereocenters with "R" and "S" stereochemical configurations, respectively, "R" and "R" stereochemical configurations, respectively, and "S" and "S" stereochemical configurations, respectively. Similarly, if a compound of Table 1 contains a first stereocenter and a second stereocenter with "R" and "S" stereochemical configurations, respectively, also provided are stereoisomers of the compound having first and second stereocenters with "S" and "R" stereochemical configurations, respectively, "R" and "R" stereochemical configurations, respectively, and "S" and "S" stereochemical configurations, respectively. Furthermore, certain structures may exist as geometric isomers (i.e., cis and trans isomers), as tautomers, or as atropisomers. Additionally, any formula given herein is intended to refer also to any one of hydrates, solvates, and amorphous and polymorphic forms of such compounds, and mixtures thereof, even if such forms are not listed explicitly. In some embodiments, the solvent is water and the solvates are hydrates.

Representative examples of compounds detailed herein, including intermediates and final compounds, are depicted in the tables and elsewhere herein. It is understood that in one aspect, any of the compounds may be used in the methods detailed herein, including, where applicable, intermediate compounds that may be isolated and administered to an individual or subject.

The compounds depicted herein may be present as salts even if salts are not depicted, and it is understood that the compositions and methods provided herein embrace all salts and solvates of the compounds depicted here, as well as the non-salt and non-solvate form of the compound, as is well understood by the skilled artisan. In some embodiments, the salts of the compounds provided herein are pharmaceutically acceptable salts.

In one variation, the compounds herein are synthetic compounds prepared for administration to an individual or subject. In another variation, compositions are provided containing a compound in substantially pure form. In another variation, provided are pharmaceutical compositions comprising a compound detailed herein and a pharmaceutically acceptable carrier. In another variation, methods of administering a compound are provided. The purified forms, pharmaceutical compositions and methods of administering the compounds are suitable for any compound or form thereof detailed herein.

Any variation or embodiment of $R^a$, $R^b$, $R^q$, $R^s$, $R^t$, $R^u$, $R^1$, n, $Y^1$, $R^{2a}$, $R^{2b}$, $R^{2c}$, $R^{2d}$, $R^{2e}$, $G^1$, p1, p2, q1, q2, r, $R^3$, $R^{3a}$, $R^{3b}$, $R^{3c}$, $R^{3d}$, $R^{3f}$, $R^{3g}$, $R^{3h}$, $R^{3i}$, $R^{3j}$, $R^{3k}$, $R^{3l}$, $R^{3m}$, $R^{3n}$, $R^{3p}$, $R^{3q}$, $R^{3r}$, $R^3$, $R^4$, $R^5$, and $R^6$ is provided herein can be combined with every other variation or embodiment of $R^a$, $R^b$, $R^q$, $R^s$, $R^t$, $R^u$, $R^1$, n, $Y^1$, $R^{2a}$, $R^{2b}$, $R^{2c}$, $R^{2d}$, $R^{2e}$, $G^1$, p1, p2, q1, q2, r, $R^3$, $R^{3a}$, $R^{3b}$, $R^{3c}$, $R^{3d}$, $R^{3f}$, $R^{3g}$, $R^{3h}$, $R^{3i}$, $R^{3j}$, $R^{3k}$, $R^{3l}$, $R^{3m}$, $R^{3n}$, $R^{3p}$, $R^{3q}$, $R^{3r}$, $R^{3s}$, $R^4$, $R^5$, and $R^6$, the same as if each combination had been individually and specifically described.

Other embodiments will be apparent to those skilled in the art from the following detailed description.

As used herein, when any variable occurs more than one time in a chemical formula, its definition on each occurrence is independent of its definition at every other occurrence.

Formula (II) and/or Formula (I) include all subformulae thereof.

The compound names provided herein, including in Table 1, are provided by ChemBioDraw Professional 15.0. One of skilled in the art would understand that the compounds may be named or identified using various commonly recognized nomenclature systems and symbols. By way of example, the compounds may be named or identified with common names, systematic or non-systematic names. The nomenclature systems and symbols that are commonly recognized in the art of chemistry include, for example, Chemical Abstract Service (CAS), ChemBioDraw Ultra, and International Union of Pure and Applied Chemistry (IUPAC).

Compositions

Also provided are compositions, such as pharmaceutical compositions, that include a compound disclosed and/or described herein and one or more additional medicinal agents, pharmaceutical agents, adjuvants, carriers, excipients, and the like. Suitable medicinal and pharmaceutical agents include those described herein. In some embodiments, the pharmaceutical composition includes a pharmaceutically acceptable excipient or adjuvant and at least one chemical entity as described herein. Examples of pharmaceutically acceptable excipients include, but are not limited to, mannitol, lactose, starch, magnesium stearate, sodium saccharine, talcum, cellulose, sodium crosscarmellose, glucose, gelatin, sucrose, and magnesium carbonate. In some embodiments, provided are compositions, such as pharmaceutical compositions that contain one or more compounds described herein, or a pharmaceutically acceptable salt thereof.

In some embodiments, provided is a pharmaceutically acceptable composition comprising a compound of Formula (II) or Formula (I), such as a compound of Formula (I-A), (I-A1), (I-A2), (I-B), (I-C), (I-D), (I-E), (I-F), (I-G), (I-H), (I-J), or (I-K), or a compound of Table 1, or a pharmaceutically acceptable salt thereof. In some aspects, a composition may contain a synthetic intermediate that may be used in the preparation of a compound described herein. The compositions described herein may contain any other suitable active or inactive agents.

Any of the compositions described herein may be sterile or contain components that are sterile. Sterilization can be achieved by methods known in the art. Any of the compositions described herein may contain one or more compounds or conjugates that are substantially pure.

Also provided are packaged pharmaceutical compositions, comprising a pharmaceutical composition as described herein and instructions for using the composition to treat a patient suffering from a disease or condition described herein.

Methods of Use

Compounds and compositions detailed herein, such as a pharmaceutical composition comprising a compound of any formula provided herein, or a pharmaceutically acceptable salt thereof, and a pharmaceutically acceptable carrier or excipient, may be used in methods of administration and treatment as provided herein.

Without being bound by theory, the compounds and pharmaceutical compositions disclosed herein are believed to act by modulating nicotinamide phosphoribosyltransferase (NAMPT). In some embodiments, the compounds and pharmaceutical compositions disclosed herein are activators of NAMPT. In some embodiments, provided are methods of treating a disease or condition mediated by NAMPT activity in an individual or subject, comprising administering to the individual or subject in need thereof a compound of Formula (II), (I), (I-A), (I-A1), (I-A2), (I-B), (I-C), (I-D), (I-E), (I-F), (I-G), (I-H), (I-J), or (I-K), or a compound of Table 1, or a pharmaceutically acceptable salt thereof. In some embodiments, provided are methods of treating cancer, a hyperproliferative disease or condition, an inflammatory disease or condition, a metabolic disorder, a cardiac disease or condition, chemotherapy induced tissue damage, a renal disease, a metabolic disease, a neurological disease or injury, a neurodegenerative disorder or disease, diseases caused by impaired stem cell function, diseases caused by DNA damage, primary mitochondrial disorders, or a muscle disease or muscle wasting disorder in an individual or subject, comprising administering to the individual or subject in need thereof a compound of Formula (II), (I), (I-A), (I-A1), (I-A2), (I-B), (I-C), (I-D), (I-E), (I-F), (I-G), (I-H), (I-J), or (I-K), or a compound of Table 1, or a pharmaceutically acceptable salt thereof.

Also provided herein is the use of a compound of Formula (II), (I), (I-A), (I-A1), (I-A2), (I-B), (I-C), (I-D), (I-E), (I-F), (I-G), (I-H), (I-J), or (I-K), or a compound of Table 1, or a pharmaceutically acceptable salt thereof in the manufacture of a medicament for treatment of a disease or condition mediated by NAMPT activity in a subject. In some aspects, provided is a compound or composition as described herein for use in a method of treatment of the human or animal body by therapy. In some embodiments, provided herein are compounds of Formula (II), (I), (I-A), (I-A1), (I-A2), (I-B), (I-C), (I-D), (I-E), (I-F), (I-G), (I-H), (I-J), or (I-K), or a compound of Table 1, or a pharmaceutically acceptable salt thereof, for use in a method of treatment of the human or animal body by therapy. In some embodiments, provided herein are compounds of Formula (II), (I), (I-A), (I-A1), (I-A2), (I-B), (I-C), (I-D), (I-E), (I-F), (I-G), (I-H), (I-J), or (I-K), or a compound of Table 1, or a pharmaceutically acceptable salt thereof, for use in treating a disease or condition mediated by NAMPT activity. In some embodiments, the disease or condition is selected from the group consisting of cancer, a hyperproliferative disease or condition, an inflammatory disease or condition, a metabolic disorder, a cardiac disease or condition, chemotherapy induced tissue damage, a renal disease, a metabolic disease, a neurological disease or injury, a neurodegenerative disorder or disease, diseases caused by impaired stem cell function, diseases caused by DNA damage, primary mitochondrial disorders, or a muscle disease or muscle wasting disorder.

Also provided herein are compositions (including pharmaceutical compositions) as described herein for the use in treating, preventing, and/or delaying the onset and/or development of a disease described herein and other methods described herein. In certain embodiments, the composition comprises a pharmaceutical formulation which is present in a unit dosage form.

In some embodiments, the subject is a mammal. In some embodiments, the subject is a mouse, rat, dog, cat, rabbit, pig, sheep, horse, cow, or human. In some embodiments, the subject is a human.

There are numerous conditions in which small molecule-mediated stimulation of NAMPT activity that boosts NAD+ levels would potentially be clinically beneficial (Strsmland et al., *Biochem Soc Trans.* 2019, 47(1):119-130; Ralto et al., *Nat Rev Nephrol.* 2019; Fang et al., *Trends Mol Med.* 2017, 23(10):899-916; Yoshino et al., *Cell Metab.* 2011, 14(4): 528-36; Yang and Sauve, *Biochim Biophys Acta.* 2016, 1864:1787-1800; Verdin, *Science.* 2015, 350(6265):1208-13). These conditions include, but are not limited to, cardiac diseases, chemotherapy induced tissue damage, renal diseases, metabolic diseases, muscular diseases, neurological diseases and injuries, diseases caused by impaired stem cell function, and DNA damage and primary mitochondrial disorders. In some embodiments, the disease or condition mediated by NAMPT activity is a cardiac disease, chemotherapy induced tissue damage, a renal disease, a metabolic disease, a muscular disease, a neurological disease or injury, a disease caused by impaired stem cell function, or DNA damage and primary mitochondrial disorder.

Cardiac Diseases.

In various preclinical models of heart failure NAD as well as NAMPT levels are decreased. In these models, cardiac function can be rescued, either by restoring NAD via oral supplementation or overexpression of NAMPT (Diguet et al, *Circulation.* 2018, 137:2256-2273; Zheng et al., *Clin Sci* (Lond). 2019, 133(13):1505-1521; Smyrnias et al., *J Am Coll Cardiol.* 2019, 73(14):1795-1806). Thus, increasing the catalytic efficiency of NAMPT with a small molecule activator to compensate for the decreased protein levels is a promising strategy to treat various forms of heart failure.

Chemotherapy Induced Tissue Damage.

Use of chemotherapy regimens frequently is limited by toxicity to healthy tissues and severe oxidative stress is thought to play a major role. NAD boosting has been shown to trigger a strong anti-oxidant response. Therefore, NAMPT activators are considered broadly useful in various settings of chemotherapy to prevent reversible and irreversible secondary pathologies. Examples are anthracycline and trastuzumab cardiotoxicity, cisplatin induced kidney injury, peripheral neuropathies induced by cisplatin, paclitaxel, vincristine and other agents. Neuroprotection by NAMPT activation is also useful in treating/preventing chemotherapy associated cognitive ("chemo brain"), which is caused by destruction of healthy nerve tissue, both during active treatment and long after treatment has been halted. For instance, see Zheng et al., *Clin Sci* (Lond). 2019, 133(13):1505-1521.

Renal Diseases.

Renal diseases are highly prevalent and an area of urgent unmet medical need. In approximately 3% of hospitalized patients, acute kidney injury (AKI) is diagnosed. A subset of patients will progress to chronic kidney disease that may require long-term dialysis or kidney transplantation. A key feature of kidney dysfunction is a decrease in the activities of SIRT1 and SIRT3, characterized by a reduction of the sirtuin substrate NAD, primarily due to impairment of de novo NAD+ synthesis. NAMPT is robustly expressed during kidney injury, thus small molecule activation with NAMPT is considered an effective measure to prevent AKI. Similarly, kidney mesangial cell hypertrophy exhibits depletion of NAD+, and restoration of intracellular NAD+ levels is considered efficacious. For instance, see Poyan Mehr et al., *Nat Med.* 2018, September; 24(9): 1351-9.

Metabolic Disease.

NAD+ boosting improves insulin sensitivity, dyslipidemia, mitochondrial function in metabolic disease and protects from/improves non-alcoholic and alcoholic steatohepatitis in preclinical models. More than 3 million people per year in the U.S. alone are diagnosed with non-alcoholic steatohepatitis and it is one of the leading causes of liver transplantation. See Guarino and Dufour, *Metabolites.* 2019, September 10; 9(9), pii: E180; Yoshino et al., *Cell Metab.* 2011, 14(4):528-36.

Muscular Diseases.

Preclinical data has suggested that NAD+ boosting strategies could alleviate skeletal muscle dysfunction in a number of conditions, including Duchenne's muscular dystrophy, and age-related sarcopenia. See Zhang et al., *Clin Sci* (Lond). 2019, 133(13):1505-1521; Mohamed et al., *Aging* (Albany NY). 2014, 6(10):820-34; Ryu et al., *Sci Transl Med.* 2016, 8(361):361ra139.

Neurological Diseases and Injuries.

Repletion of NAD by means of NAMPT activation is neuroprotective and of therapeutic benefit in a wide range of preclinical models of neurological diseases and injuries, including age-related cognitive decline, glaucoma, ischemic stroke, and ALS. See Johnson et al., *NPJ Aging Mech Dis.* 2018, 4:10; Harlan et al., *J Biol Chem.* 2016, 291(20):10836-46; Zhao et al., *Stroke.* 2015, July; 46(7):1966-74; Williams et al., *Front Neurosci.* 2017, Apr. 25; 11:232.

Diseases Caused by Impaired Stem Cell Function.

NAD boosting promotes stem cell activation and hematopoiesis and is useful in accelerating the expansion of stem cell populations following a stem cell transplant. See Pi et al., *Aging* (Albany NY). 2019, 11(11):3505-3522.

DNA Damage Disorders and Primary Mitochondrial Disorders.

NAMPT activators will also be useful in the treatment of DNA damage disorders which are associated with an accelerated aging phenotype, such as Xeroderma pigmentosum, Cockayne syndrome, and Ataxia telangiectasia. Similarly, there are several primary mitochondrial disorders with shared symptoms and manifestations for which NAD boosting via NAMPT activation may be a suitable therapeutic intervention. See Fang et al, *Cell.* 2014, 157(4):882-896; Khan et al, *EMBO Mol Med.* 2014, June; 6(6):721-31; Cerutti et al., *Cell Metab.* 2014, 19(6):1042-9.

Provided in some embodiments are methods of treating a disease or condition mediated by NAMPT activity in a subject in need thereof, comprising administering to the individual or subject in need thereof a compound of Formula (II), (I), (I-A), (I-A1), (I-A2), (I-B), (I-C), (I-D), (I-E), (I-F), (I-G), (I-H), (I-J), or (I-K), or a compound of Table 1, or a pharmaceutically acceptable salt thereof, wherein the disease or condition is selected from the group consisting of cardiac diseases, chemotherapy induced tissue damage, renal diseases, metabolic diseases, muscular diseases, neurological diseases and injuries, diseases caused by impaired stem cell function, and DNA damage and primary mitochondrial disorders.

Additional applications of small molecule NAMPT activators are provided in Table 2.

TABLE 2

| | |
|---|---|
| Cancer and Chemotherapy induced tissue damage | Anthracycline and trastuzumab cardiotoxicity |
| | Proteasome inhibitor cardiotoxicity |
| | Cisplatin induced kidney injury |
| | Prevention/treatment of cognitive dysfunction resulting from chemotherapy ("chemo brain") |
| | Chemotherapy induced impairment of hematopoiesis and myelosuppression |
| | Cachexia of cancer |
| | Chemoprevention of non-melanoma skin cancer in high risk patients |
| | chemoprevention of hepatocellular carcinoma |
| Cardiovascular diseases | Heart failure with reduced ejection fraction |
| | Heart failure with preserved ejection fraction |
| | Hypertrophic cardiomyopathy |
| | Cardiac arrhythmias |
| | Duchenne Muscular Dystrophy-related cardiac dysfunction |
| | Cardiac dysfunction associated with Scleroderma, Lupus, Mitochondrial Disorders, Kawasaki Disease |
| | Hypertension |
| | Myocardial Infarction |
| Renal diseases | Acute kidney injury including nephropathy following major surgeries including cardiac and vascular surgeries |
| | Acute kidney injury following hypotension, hemorrhagic shock, or cardiac arrest |
| | Acute kidney injury following exposure to contrast imaging agents used for MRI, CT scans, or other imaging modalities, particularly in the context of diabetes |
| | Chronic kidney disease |
| | Glomerular nephritis |
| | Kidney mesangial cell hypertrophy |
| | Arterial venous fistula maturation |
| Chronic inflammatory and fibrotic diseases | Chronic obstructive pulmonary disease |
| | Asthma |
| | Scleroderma |
| | Dermatomyositis |
| | Lupus erythematosus |
| | Rheumatoid arthritis and spondyloarthropathy |
| | Juvenile idiopathic arthritis |
| | Crohn's disease |
| | Inflammatory Bowel Disease |
| | Eczema |
| | Psoriasis and psoriatic arthritis |
| | Idiopathic pulmonary fibrosis |

TABLE 2-continued

| | |
|---|---|
| Vascular diseases | Arterial and venous thrombosis<br>Ischemic Stroke<br>Arteriosclerosis |
| Metabolic dysfunction | Obesity<br>Diabetes<br>Metabolic Syndrome<br>Alcoholic steatohepatitis<br>Non-alcoholic steatohepatitis<br>Dyslipidemia<br>Diabetic neuropathy<br>Diabetic gastroparesis |
| Muscular diseases | Muscular dystrophies, including: Duchenne, Becker's, Congenital, Distal, Emery-Dreifuss', Facio-scapulo-humeral, Limb-girdle, myotonic, and oculopharyngeal<br>Sarcopenia<br>Frailty<br>Polymyositis<br>Muscle stem cell senescence developed in the context of nutritional deficiencies<br>Non-mitochondrial myopathies such as inherited myopathies, myotonia, congenital myopathies selected from nemaline myopathy, multi/minicore myopathy, centronuclear myopathy and metabolic myopathies, inflammatory myopathies |
| Neurological diseases and injuries | Depression<br>Frontotemporal dementia<br>Multiple sclerosis<br>Amyotrophic lateral sclerosis<br>Peripheral neuropathy due to diabetes, chemotherapy<br>Alzheimer's disease<br>Parkinson's disease<br>Huntington's Disease<br>Spinal muscular atrophy<br>Spinocerebellar ataxias<br>Spastic paraplegias<br>Glaucoma<br>Age-related macular degeneration<br>Age-related cognitive decline<br>Noise induced and age-related hearing loss<br>Ischemic stroke<br>Traumatic brain injury<br>Neonatal nerve damage<br>Optic nerve injury<br>Spinal cord injuries<br>Peripheral neuropathies or tissue inflammation induced by cisplatin, paclitaxel, vincristine, other chemotherapeutic agents, or radiation.<br>Peripheral neuropathies (length and non-length dependent) affecting motor, sensory, or autonomic nerves, arising from: diabetes, impaired glucose tolerance, hypertension, infection, trauma, autoimmune disorders, vasculitis, arteriosclerosis, vitamin deficiencies (particularly B6 and B12), alcoholism, liver or kidney disease, or exposure to toxins |
| DNA damage disorders and Primary Mitochondrial Disorders | Xeroderma pigmentosum<br>Cockayne syndrome<br>Ataxia telangiectasia<br>MEGDEL syndrome<br>Charcot-Marie-Tooth type 2<br>Primary Mitochondrial Diseases (Disorders) including NARP, MELAS, Chronic Progressive External Ophthalmoplegia, Leigh's disease, Leber's Hereditary Optic Neuropathy, MERRF, Barth Syndrome, Luft Disease, Kearns Sayre Syndrome, Autosomal dominant optic atrophy<br>Friedreich's ataxia<br>Werner syndrome |
| General | Tissue repair following physical trauma, hemorrhagic shock, tissue grafting, organ transplant including heart, lung, liver, and kidney<br>Stem cell therapies, including hematopoietic stem cell transfer, allogenic mesenchymal stem therapy for acute graft-vs-host disease, limbal stem cell deficiency due to genetic or acquired conditions that compromise normal turnover of the corneal epithelium |

In some embodiments, the disease or condition mediated by NAMPT activity is cancer and chemotherapy-induced tissue damage, a cardiovascular disease, a renal disease, chronic inflammatory and fibrotic disease, a vascular disease, metabolic dysfunction, a muscular disease, a neurological disease or injury, or a DNA damage disorder or primary mitochondrial disorder. Provided in some embodiments are methods of treating a disease or condition mediated by NAMPT activity in a subject in need thereof, comprising administering to the individual or subject in need thereof a compound of Formula (II), (I), (I-A), (I-A1), (I-A2), (I-B), (I-C), (I-D), (I-E), (I-F), (I-G), (I-H), (I-J), or (I-K), or a compound of Table 1, or a pharmaceutically acceptable salt thereof. In some embodiments, the disease or condition is cancer or chemotherapy induced tissue damage, a cardiovascular disease, a renal disease, a chronic inflammatory or fibrotic disease, a vascular disease, metabolic dysfunction, a muscular disease, a neurological disease or injury, a DNA damage disorder or Primary Mitochondrial Disorder, including any of the diseases listed in Table 2.

Dosages

The compounds and compositions disclosed and/or described herein are administered at a therapeutically effective dosage, e.g., a dosage sufficient to provide treatment for the disease state. While human dosage levels have yet to be optimized for the chemical entities described herein, generally, a daily dose ranges from about 0.01 to 100 mg/kg of body weight; in some embodiments, from about 0.05 to 10.0 mg/kg of body weight, and in some embodiments, from about 0.10 to 1.4 mg/kg of body weight. Thus, for administration to a 70 kg person, in some embodiments, the dosage range would be about from 0.7 to 7000 mg per day; in some embodiments, about from 3.5 to 700.0 mg per day, and in some embodiments, about from 7 to 100.0 mg per day. The amount of the chemical entity administered will be dependent, for example, on the subject and disease state being treated, the severity of the affliction, the manner and schedule of administration and the judgment of the prescribing physician. For example, an exemplary dosage range for oral administration is from about 5 mg to about 500 mg per day, and an exemplary intravenous administration dosage is from about 5 mg to about 500 mg per day, each depending upon the compound pharmacokinetics.

A daily dose is the total amount administered in a day. A daily dose may be, but is not limited to be, administered each day, every other day, each week, every 2 weeks, every month, or at a varied interval. In some embodiments, the daily dose is administered for a period ranging from a single day to the life of the subject. In some embodiments, the daily dose is administered once a day. In some embodiments, the daily dose is administered in multiple divided doses, such as in 2, 3, or 4 divided doses. In some embodiments, the daily dose is administered in 2 divided doses.

Administration of the compounds and compositions disclosed and/or described herein can be via any accepted mode of administration for therapeutic agents including, but not limited to, oral, sublingual, subcutaneous, parenteral, intravenous, intranasal, topical, transdermal, intraperitoneal, intramuscular, intrapulmonary, vaginal, rectal, or intraocular administration. In some embodiments, the compound or composition is administered orally or intravenously. In some embodiments, the compound or composition disclosed and/or described herein is administered orally.

Pharmaceutically acceptable compositions include solid, semi-solid, liquid and aerosol dosage forms, such as tablet, capsule, powder, liquid, suspension, suppository, and aerosol forms. The compounds disclosed and/or described herein can also be administered in sustained or controlled release dosage forms (e.g., controlled/sustained release pill, depot injection, osmotic pump, or transdermal (including electrotransport) patch forms) for prolonged timed, and/or pulsed administration at a predetermined rate. In some embodiments, the compositions are provided in unit dosage forms suitable for single administration of a precise dose.

The compounds disclosed and/or described herein can be administered either alone or in combination with one or more conventional pharmaceutical carriers or excipients (e.g., mannitol, lactose, starch, magnesium stearate, sodium saccharine, talcum, cellulose, sodium crosscarmellose, glucose, gelatin, sucrose, magnesium carbonate). If desired, the pharmaceutical composition can also contain minor amounts of nontoxic auxiliary substances such as wetting agents, emulsifying agents, solubilizing agents, pH buffering agents and the like (e.g., sodium acetate, sodium citrate, cyclodextrine derivatives, sorbitan monolaurate, triethanolamine acetate, triethanolamine oleate). Generally, depending on the intended mode of administration, the pharmaceutical composition will contain about 0.005% to 95%, or about 0.5% to 50%, by weight of a compound disclosed and/or described herein. Actual methods of preparing such dosage forms are known, or will be apparent, to those skilled in this art; for example, see *Remington's Pharmaceutical Sciences*, Mack Publishing Company, Easton, Pennsylvania.

In some embodiments, the compositions will take the form of a pill or tablet and thus the composition may contain, along with a compounds disclosed and/or described herein, one or more of a diluent (e.g., lactose, sucrose, dicalcium phosphate), a lubricant (e.g., magnesium stearate), and/or a binder (e.g., starch, gum acacia, polyvinylpyrrolidine, gelatin, cellulose, cellulose derivatives). Other solid dosage forms include a powder, marume, solution or suspension (e.g., in propylene carbonate, vegetable oils or triglycerides) encapsulated in a gelatin capsule.

Liquid pharmaceutically administrable compositions can, for example, be prepared by dissolving, dispersing or suspending etc. a compound disclosed and/or described herein and optional pharmaceutical additives in a carrier (e.g., water, saline, aqueous dextrose, glycerol, glycols, ethanol or the like) to form a solution or suspension. Injectables can be prepared in conventional forms, either as liquid solutions or suspensions, as emulsions, or in solid forms suitable for dissolution or suspension in liquid prior to injection. The percentage of the compound contained in such parenteral compositions depends, for example, on the physical nature of the compound, the activity of the compound and the needs of the subject. However, percentages of active ingredient of 0.01% to 10% in solution are employable, and may be higher if the composition is a solid which will be subsequently diluted to another concentration. In some embodiments, the composition will comprise from about 0.2 to 2% of a compound disclosed and/or described herein in solution.

Pharmaceutical compositions of the compounds disclosed and/or described herein may also be administered to the respiratory tract as an aerosol or solution for a nebulizer, or as a microfine powder for insufflation, alone or in combination with an inert carrier such as lactose. In such a case, the particles of the pharmaceutical composition may have diameters of less than 50 microns, or in some embodiments, less than 10 microns.

In addition, pharmaceutical compositions can include a compound disclosed and/or described herein and one or more additional medicinal agents, pharmaceutical agents, adjuvants, and the like. Suitable medicinal and pharmaceutical agents include those described herein.

Kits

Also provided are articles of manufacture and kits containing any of the compounds or pharmaceutical compositions provided herein. The article of manufacture may comprise a container with a label. Suitable containers include, for example, bottles, vials, and test tubes. The containers may be formed from a variety of materials such as glass or plastic. The container may hold a pharmaceutical composition provided herein. The label on the container may indicate that the pharmaceutical composition is used for preventing, treating or suppressing a condition described herein, and may also indicate directions for either in vivo or in vitro use.

In one aspect, provided herein are kits containing a compound or composition described herein and instructions for use. The kits may contain instructions for use in the treatment of a heart disease in an individual or subject in need thereof. A kit may additionally contain any materials or equipment that may be used in the administration of the compound or composition, such as vials, syringes, or IV bags. A kit may also contain sterile packaging.

Combinations

The compounds and compositions described and/or disclosed herein may be administered alone or in combination with other therapies and/or therapeutic agents useful in the treatment of the aforementioned disorders, diseases, or conditions.

ENUMERATED EMBODIMENTS

The following enumerated embodiments are representative of some aspects of the invention.

1. A compound of Formula (I):

(I)

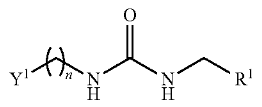

or a pharmaceutically acceptable salt thereof, wherein:

$Y^1$ is

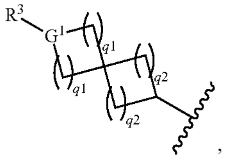

, 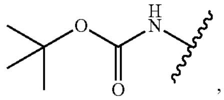

, or 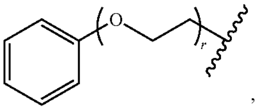

, and $R^1$ is selected from the group consisting of

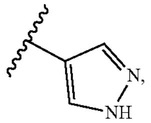

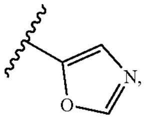

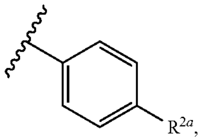

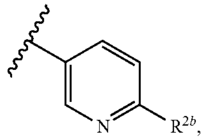

-continued

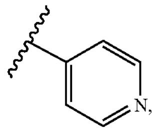, and 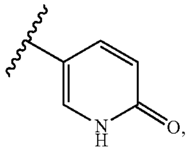, or $Y^1$ is

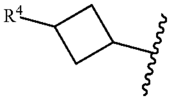, 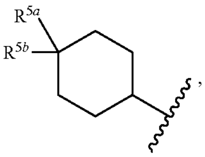, or 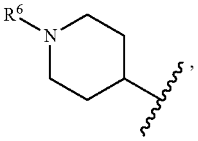, and $R^1$ is selected from the group consisting of

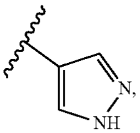, 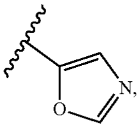, 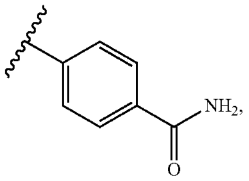, 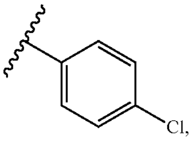, 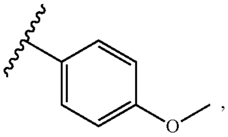, 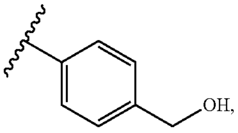, 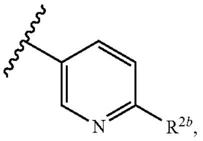, 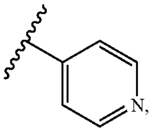, and 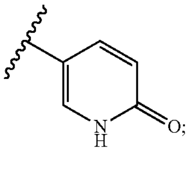;

wherein $R^{2a}$ and $R^{2b}$ are each independently halo, —O($C_1$-$C_6$ alkyl), $C_1$-$C_6$ alkyl substituted with —OH, —C(O)N$R^{2c}R^{2d}$, or —N($R^{2e}$)C(O)($C_1$-$C_6$ alkyl); and $R^{2c}$, $R^{2d}$, and $R^{2e}$ are each independently hydrogen or $C_1$-$C_6$ alkyl;

$G^1$ is CH or N;

p1 and p2 are each independently 0, 1, or 2;

q1 and q2 are each independently 1 or 2;

r is 1, 2, or 3;

n is 0 to 6;

wherein when $Y^1$ is

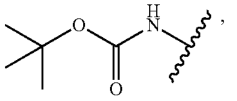 [SMILES: *NC(=O)OC(C)(C)C], n is 4, 5, or 6; and when $Y^1$ is

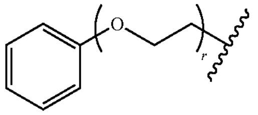

and r is 1, n is 2, 3, 4, 5, or 6;

$R^3$ is selected from the group consisting of:

i. $C_1$-$C_6$ alkyl;

ii. $C_6$-$C_{14}$ aryl;

iii. optionally substituted 5- to 18-membered heteroaryl;

iv. —N$R^{3a}R^{3b}$, wherein $R^{3a}$ and $R^{3b}$ are each independently selected from the group consisting of hydrogen, $C_6$-$C_{14}$ aryl, 5- to 18-membered heteroaryl, —($C_1$-$C_6$ alkylene)-($C_6$-$C_{14}$ aryl), and —($C_1$-$C_6$ alkylene)-(5- to 18-membered heteroaryl);

v. —O$R^{3c}$, wherein $R^{3c}$ is $C_6$-$C_{14}$ aryl;

vi. —C(O)$R^{3d}$, wherein $R^{3d}$ is selected from the group consisting of —N$R^{3f}R^{3g}$; $C_3$-$C_8$ cycloalkyl; $C_3$-$C_8$ cycloalkyl substituted with optionally substituted $C_6$-$C_{14}$ aryl; $C_3$-$C_5$ cycloalkenyl; optionally substituted $C_6$-$C_{14}$ aryl; optionally substituted —($C_1$-$C_6$ alkylene)-($C_6$-$C_{14}$ aryl); optionally substituted 3- to 18-membered heterocycloalkyl; and optionally substituted 5- to 18-membered heteroaryl, wherein $R^{3f}$ and $R^{3g}$ are each independently selected from the group consisting of:

(a) hydrogen, (b) optionally substituted $C_1$-$C_6$ alkyl, (c) $C_6$-$C_{14}$ aryl, (d) optionally substituted 3- to 18-membered heterocycloalkyl, (e) optionally substituted 5- to 18-membered heteroaryl, (f) optionally substituted $C_3$-$C_{10}$ cycloalkyl; and (g) optionally substituted $C_3$-$C_{10}$ cycloalkenyl;

vii. $C_1$-$C_6$ alkyl substituted with C(O)N$R^{3h}R^{3i}$, optionally substituted 3- to 18-membered heterocycloalkyl, or optionally substituted 5- to 18-membered heteroaryl, wherein $R^{3h}$ and $R^{3i}$ are each independently selected from $C_1$-$C_6$ alkyl and —($C_1$-$C_6$ alkylene)-($C_6$-$C_{14}$ aryl);

viii. —C(O)OR$^{3j}$, wherein

R$^{3j}$ is hydrogen or $C_1$-$C_6$ alkyl;

ix. —NHC(O)R$^{3k}$, wherein

R$^{3k}$ is optionally substituted $C_6$-$C_{14}$ aryl, optionally substituted —($C_1$-$C_6$ alkylene)-($C_6$-$C_{14}$ aryl), or optionally substituted 5- to 18-membered heteroaryl;

x. —NHC(O)OR$^{3l}$, wherein

R$^{3l}$ is hydrogen or $C_1$-$C_6$ alkyl;

xi. —NHSO$_2$R$^{3m}$, wherein

R$^{3m}$ is optionally substituted 5- to 18-membered heteroaryl, optionally substituted $C_6$-$C_4$ aryl, or —($C_1$-$C_6$ alkylene)-($C_6$-$C_{14}$ aryl), each of which is optionally substituted; and xii. —SO$_2$R$^{3n}$; wherein R$^{3n}$ is optionally substituted $C_3$-$C_{10}$ cycloalkyl, optionally substituted $C_6$-$C_{14}$ aryl, or optionally substituted —($C_1$-$C_6$ alkylene)-($C_6$-$C_{14}$ aryl);

R$^4$ is phenyl or —C(O)NH—CH$_2$-phenyl;

R$^{5a}$ and R$^{5b}$ are independently selected from the group consisting of hydrogen, methyl, and —NHC(O)O($C_1$-$C_6$ alkyl); and R$^6$ is selected from the group consisting of —C(O)OC(CH$_3$)$_3$, —NHC(O)O($C_1$-$C_6$ alkyl), and —C(O)-phenyl; and wherein (1) when Y$^1$ is

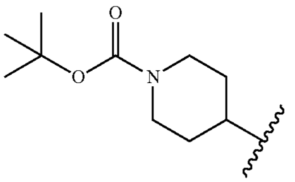 [SMILES: *C1CCN(C(=O)OC(C)(C)C)CC1]

and n is 0 or 1, R$^1$ is selected from the group consisting of

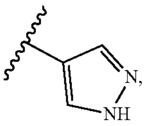

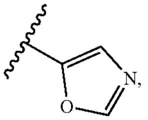

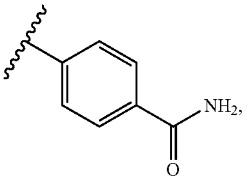

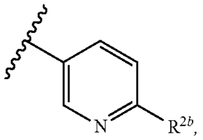

and

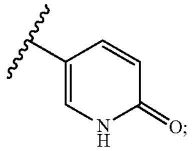

and (2) when Y$^1$ is

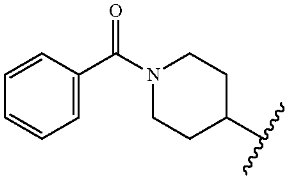 [SMILES: *C1CCN(C(=O)c2ccccc2)CC1]

and n is 0, R$^1$ is selected from the group consisting of

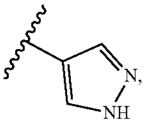

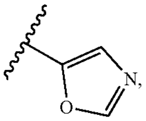

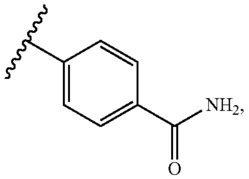

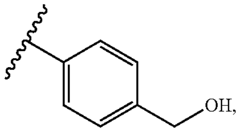

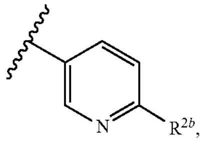

and

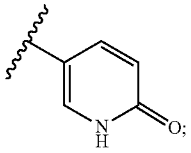

2. The compound of embodiment 1, or a pharmaceutically acceptable salt thereof, wherein Y$^1$ is

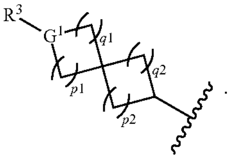

3. The compound of embodiment 1 or embodiment 2, or a pharmaceutically acceptable salt thereof, wherein p1 is 1 and q1 is 1.

4. The compound of embodiment 1 or embodiment 2, or a pharmaceutically acceptable salt thereof, wherein p1 is 2 and q1 is 1.

5. The compound of embodiment 1 or embodiment 2, or a pharmaceutically acceptable salt thereof, wherein p1 is 2 and q1 is 2.

6. The compound of any one of embodiments 1-5, or a pharmaceutically acceptable salt thereof, wherein p2 is 1 and q2 is 1.

7. The compound of any one of embodiments 1-5, or a pharmaceutically acceptable salt thereof, wherein p2 is 0 and q2 is 1.

8. The compound of any one of embodiments 1-5, or a pharmaceutically acceptable salt thereof, wherein p2 is 1 and q2 is 2.

9. The compound of any one of embodiments 1-8, or a pharmaceutically acceptable salt thereof, wherein R$^3$ is $C_1$-$C_6$ alkyl.

10. The compound of any one of embodiments 1-8, or a pharmaceutically acceptable salt thereof, wherein $R^3$ is $C_6$-$C_{14}$ aryl.
11. The compound of any one of embodiments 1-8, or a pharmaceutically acceptable salt thereof, wherein $R^3$ is 5- to 18-membered heteroaryl optionally substituted with $C_1$-$C_6$ alkyl.
12. The compound of embodiment 11, or a pharmaceutically acceptable salt thereof, wherein $R^3$ is pyridyl or pyrimidyl optionally substituted with $C_1$-$C_6$ alkyl.
13. The compound of embodiment 11 or embodiment 12, or a pharmaceutically acceptable salt thereof, wherein $R^3$ is

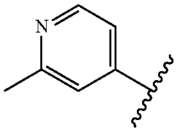, 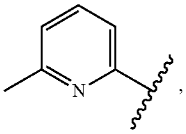, or

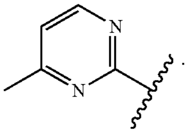.

14. The compound of any one of embodiments 1-8, or a pharmaceutically acceptable salt thereof, wherein $R^3$ is —$NR^{3a}R^{3b}$, wherein $R^{3a}$ and $R^{3b}$ are each independently selected from the group consisting of hydrogen, $C_6$-$C_{14}$ aryl, 5- to 18-membered heteroaryl, —($C_1$-$C_6$ alkylene)-($C_6$-$C_{14}$ aryl), and —($C_1$-$C_6$ alkylene)-(5- to 18-membered heteroaryl).
15. The compound of embodiment 14, or a pharmaceutically acceptable salt thereof, wherein $R^3$ is

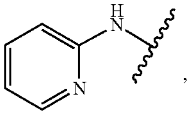, 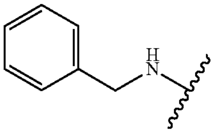,

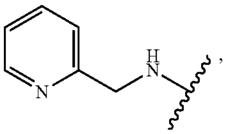, or 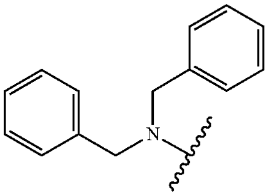.

16. The compound of any one of embodiments 1-8, or a pharmaceutically acceptable salt thereof, wherein $R^3$ is $OR^{3c}$, wherein $R^{3c}$ is $C_6$-$C_{14}$ aryl.
17. The compound of any one of embodiments 1-8, or a pharmaceutically acceptable salt thereof, wherein $R^3$ is —$C(O)R^{3d}$.
18. The compound of embodiment 17, or a pharmaceutically acceptable salt thereof, wherein $R^{3d}$ is —$NR^{3f}R^{3g}$ and $R^{3f}$ and $R^{3g}$ are each independently selected from the group consisting of:
    (a) hydrogen,
    (b) $C_1$-$C_6$ alkyl optionally substituted with one or more substituents selected from the group consisting of —OH, $C_6$-$C_{14}$ aryl, and 5- to 18-membered heteroaryl, wherein the $C_6$-$C_{14}$ aryl and 5- to 18-membered heteroaryl groups are each independently unsubstituted or substituted with one or more substituents selected from the group consisting of halo, $C_1$-$C_6$ alkyl, hydroxyl, $C_1$-$C_6$ alkoxy, $C_1$-$C_6$ haloalkoxy, and CN,
    (c) $C_6$-$C_{14}$ aryl,
    (d) 3- to 18-membered heterocycloalkyl,
    (e) 5- to 18-membered heteroaryl optionally substituted with methyl or CN,
    (f) $C_3$-$C_{10}$ cycloalkyl optionally substituted with one or more substituents selected from the group consisting of halo, hydroxyl, $C_1$-$C_6$ alkyl optionally substituted with hydroxyl, $C_6$-$C_{14}$ aryl, and 5- to 18-membered heteroaryl; and
    (g) $C_3$-$C_{10}$ cycloalkenyl optionally substituted with one or more substituents selected from the group consisting of halo, hydroxyl, $C_1$-$C_6$ alkyl optionally substituted with hydroxyl, $C_6$-$C_{14}$ aryl, and 5- to 18-membered heteroaryl.
19. The compound of embodiment 17 or embodiment 18, or a pharmaceutically acceptable salt thereof, wherein $R^3$ is

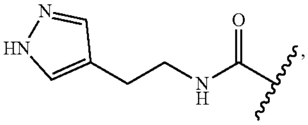,

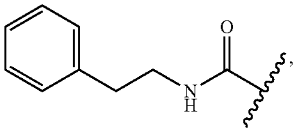,

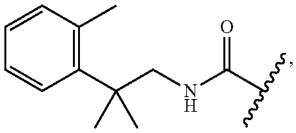,

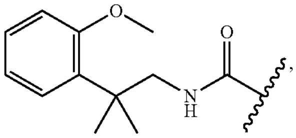,

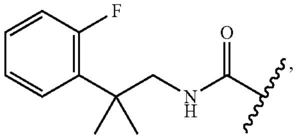,

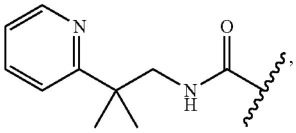,

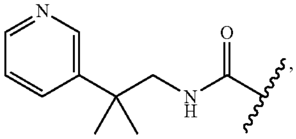,

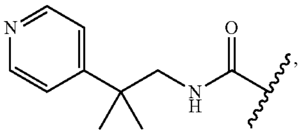,

-continued
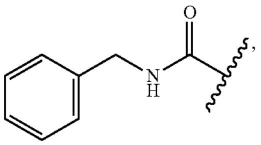
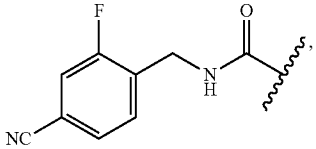
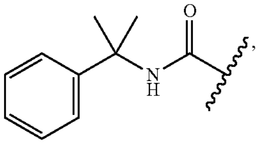
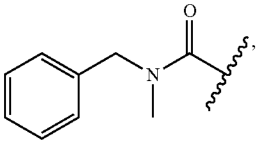
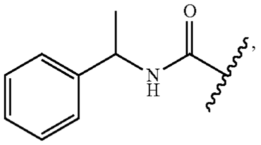
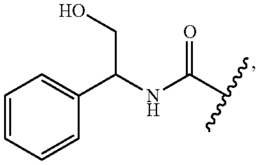
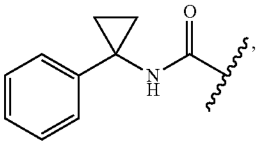
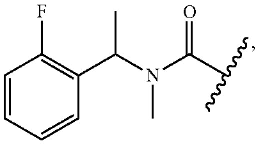
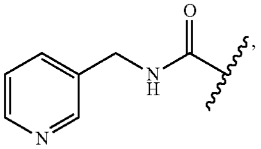
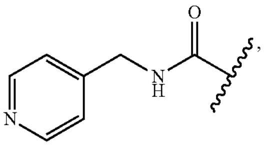
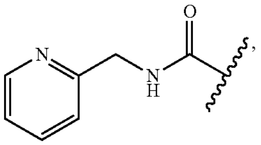
-continued
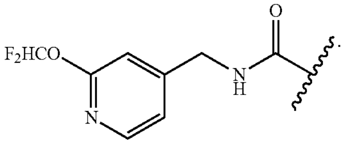
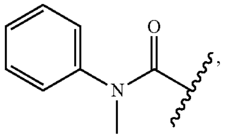
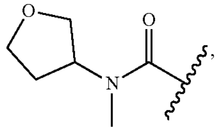
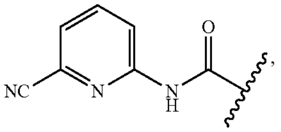
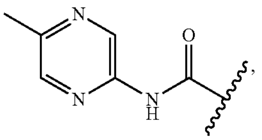
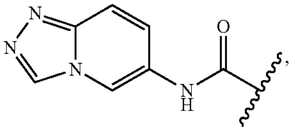
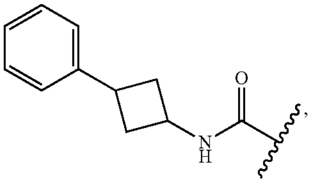
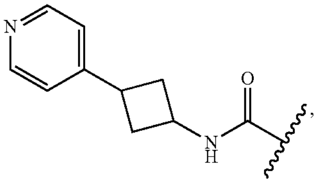
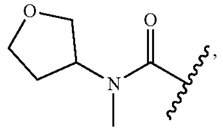
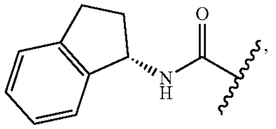
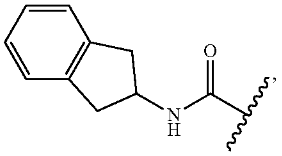
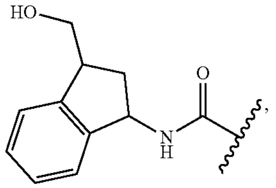
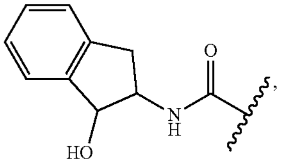
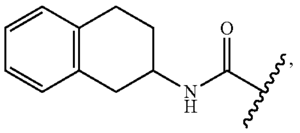
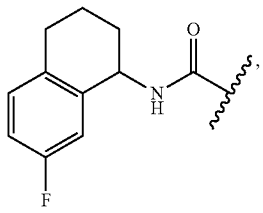
or -continued

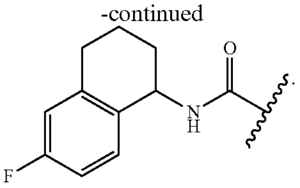.

20. The compound of embodiment 17, or a pharmaceutically acceptable salt thereof, wherein $R^{3d}$ is $C_3$-$C_8$ cycloalkyl.

21. The compound of embodiment 17, or a pharmaceutically acceptable salt thereof, wherein $R^{3d}$ is $C_3$-$C_8$ cycloalkyl substituted with $C_6$-$C_{14}$ aryl, wherein the $C_6$-$C_{14}$ aryl is optionally substituted with one or more substituents selected from the group consisting of halo, $C_1$-$C_6$ alkyl, $C_1$-$C_6$ haloalkyl, and $C_1$-$C_6$ alkoxy.

22. The compound of embodiment 20 or embodiment 21, or a pharmaceutically acceptable salt thereof, wherein $R^3$ is

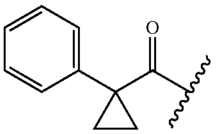.

23. The compound of embodiment 17, or a pharmaceutically acceptable salt thereof, wherein $R^{3d}$ is $C_3$-$C_8$ cycloalkenyl.

24. The compound of embodiment 23, or a pharmaceutically acceptable salt thereof, wherein $R^3$ is

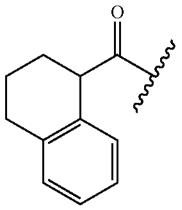.

24. The compound of embodiment 17, or a pharmaceutically acceptable salt thereof, wherein $R^{3d}$ is $C_6$-$C_{14}$ aryl optionally substituted with one or more substituents selected from the group consisting of hydroxyl, halo, cyano, $C_1$-$C_6$ alkyl, $C_1$-$C_6$ alkoxy, $C_1$-$C_6$ haloalkyl, —($C_1$-$C_6$ alkylene)-OH, —C(O)O($C_1$-$C_6$ alkyl), —$NR^{3e1}R^{3e2}$, —$S(O)_2$($C_1$-$C_6$ alkyl), 5- to 18-membered heteroaryl, and 3- to 18-membered heterocycloalkyl optionally substituted with oxo, wherein $R^{3e1}$ and $R^{3e2}$ are each independently H or $C_1$-$C_6$ alkyl.

25. The compound of embodiment 24, or a pharmaceutically acceptable salt thereof, wherein $R^3$ is

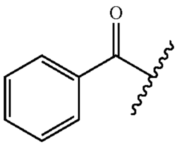, 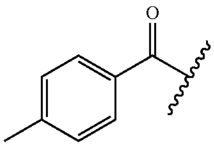,

-continued

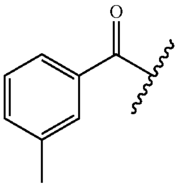, 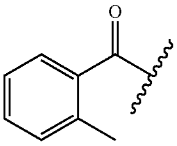, 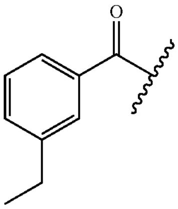,

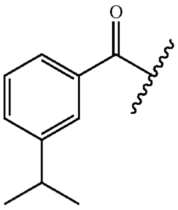, 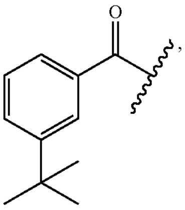,

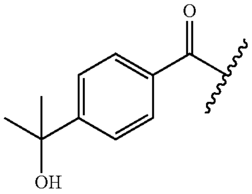, 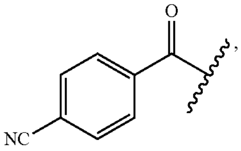,

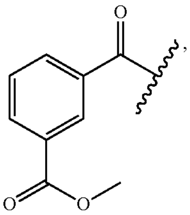, 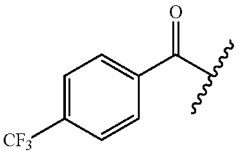,

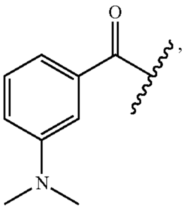, 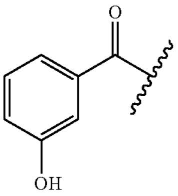,

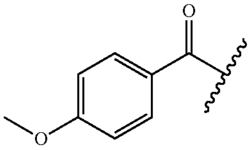, 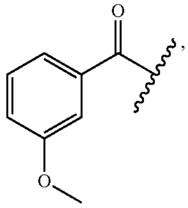,

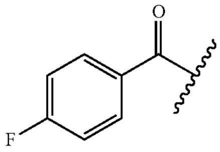, 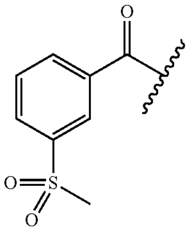,

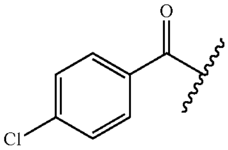, 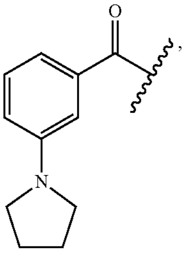,

-continued

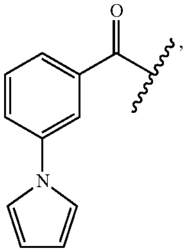,

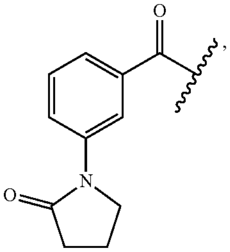,

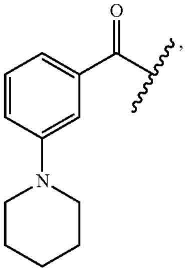, or

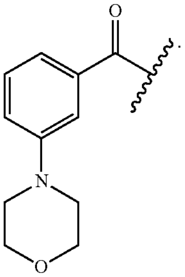.

26. The compound of embodiment 17, or a pharmaceutically acceptable salt thereof, wherein $R^{3d}$ is —($C_1$-$C_6$ alkylene)-($C_6$-$C_{14}$ aryl) optionally substituted with one or more substituents selected from the group consisting of halo, $C_1$-$C_6$ alkyl, $C_1$-$C_6$ haloalkyl, and $C_1$-$C_6$ alkoxy.

27. The compound of embodiment 26, or a pharmaceutically acceptable salt thereof, wherein $R^3$ is

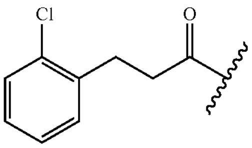,

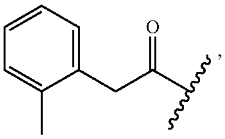,

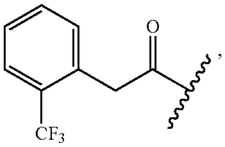,

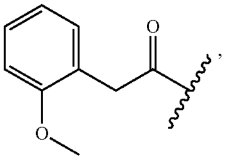,

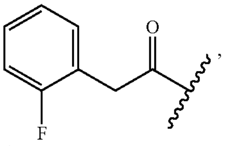,

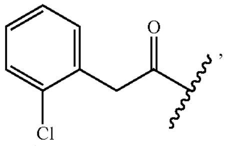,

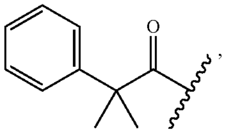 [SMILES: *C(=O)C1(c2ccccc2)CC1],

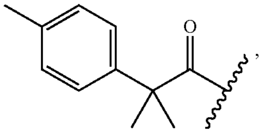, or

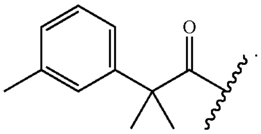.

28. The compound of embodiment 17, or a pharmaceutically acceptable salt thereof, wherein $R^{3d}$ is 3- to 18-membered heterocycloalkyl optionally substituted with one or more substituents selected from the group consisting of (a) $C_1$-$C_6$ alkyl optionally substituted with one or more substituents selected from the group consisting of hydroxyl, halo, $C_3$-$C_{10}$ cycloalkyl, and 5- to 18-membered heteroaryl optionally substituted with one or more $C_1$-$C_6$ alkyl substituents, (b) $C_6$-$C_{14}$ aryl, (c) 3- to 18-membered heterocycloalkyl, (d) —C(O)O($C_1$-$C_6$ alkyl), (e) —C(O)($C_6$-$C_{14}$ aryl), (f) halo, and (g) $C_1$-$C_6$ alkoxy optionally substituted with one or more halo substituents.

29. The compound of embodiment 28, or a pharmaceutically acceptable salt thereof, wherein $R^3$ is

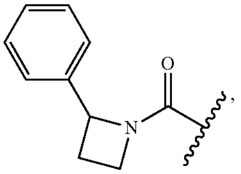,

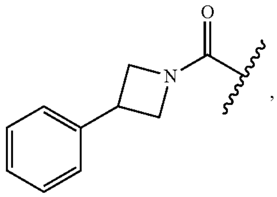,

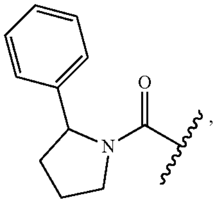,

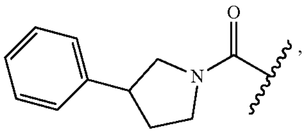,

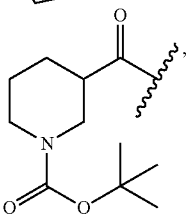,

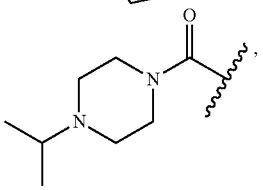,

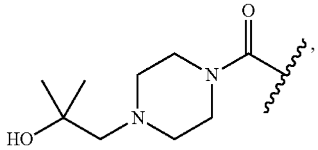,

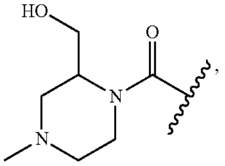,

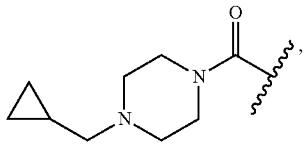,

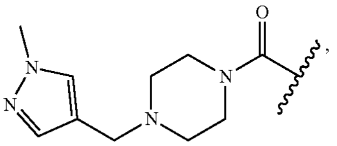,

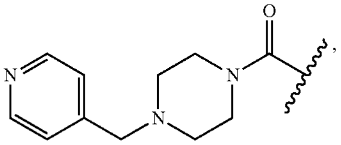,

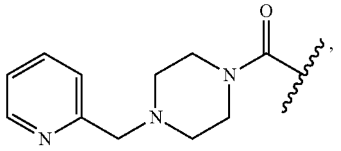,

-continued

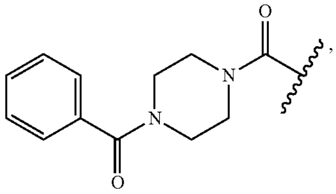,

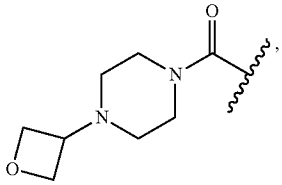, 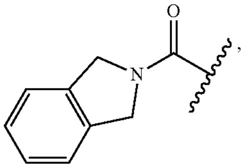,

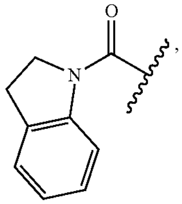, 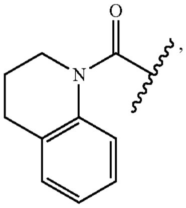 [SMILES: *C(=O)C1CCCc2ccccc21], 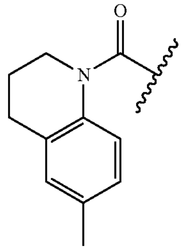,

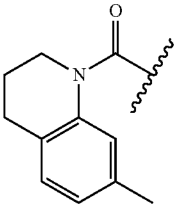, 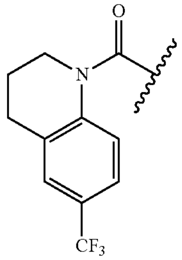, 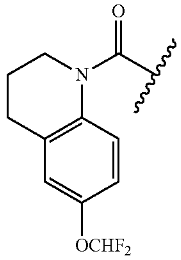,

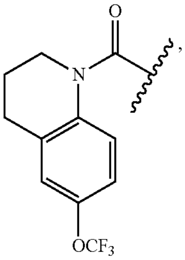, 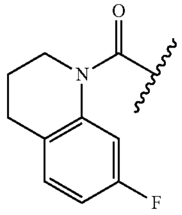, 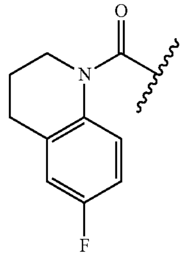,

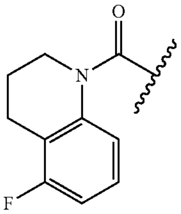, 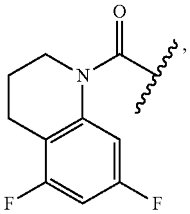,

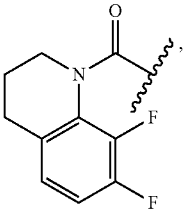, 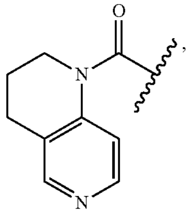,

-continued

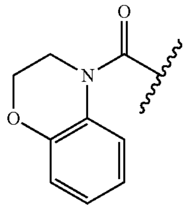, or 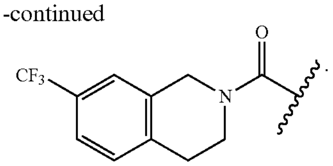.

30. The compound of embodiment 17, or a pharmaceutically acceptable salt thereof, wherein $R^{3d}$ is 5- to 18-membered heteroaryl optionally substituted with one or more substituents selected from the group consisting of $C_1$-$C_6$ alkyl, hydroxyl, oxo, and 3- to 18-membered heterocycloalkyl.

31. The compound of embodiment 30, or a pharmaceutically acceptable salt thereof, wherein $R^3$ is

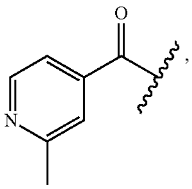, 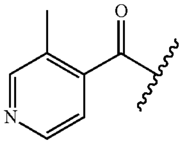,

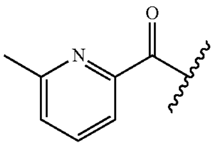, 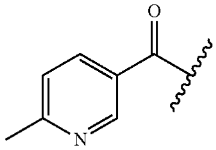,

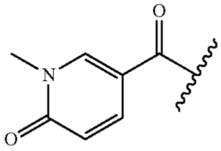, or 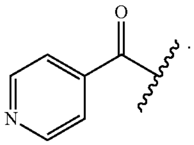.

32. The compound of any one of embodiments 1-8, or a pharmaceutically acceptable salt thereof, wherein $R^3$ is $C_1$-$C_6$ alkyl substituted with $C(O)NR^{3h}R^{3i}$, wherein $R^{3h}$ and $R^{3i}$ are each independently selected from $C_1$-$C_6$ alkyl and —($C_1$-$C_6$ alkylene)-($C_6$-$C_{14}$ aryl).

33. The compound of embodiment 32, or a pharmaceutically acceptable salt thereof, wherein $R^3$ is

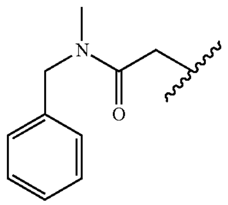 [SMILES: *CC(=O)N(C)Cc1ccccc1]

34. The compound of any one of embodiments 1-8, or a pharmaceutically acceptable salt thereof, wherein $R^3$ is $C_1$-$C_6$ alkyl substituted with 3- to 18-membered heterocycloalkyl, wherein the 3- to 18-membered heterocycloalkyl is optionally substituted with one or more substituents selected from halo and $C_6$-$C_{14}$ aryl.

35. The compound of embodiment 34, or a pharmaceutically acceptable salt thereof, wherein $R^3$ is

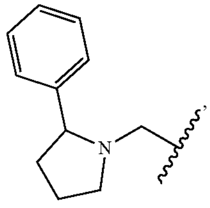
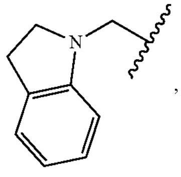

, or

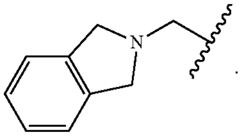

36. The compound of any one of embodiments 1-8, or a pharmaceutically acceptable salt thereof, wherein $R^3$ is $C_1$-$C_6$ alkyl substituted with 5- to 18-membered heteroaryl.

37. The compound of embodiment 36, or a pharmaceutically acceptable salt thereof, wherein $R^3$ is

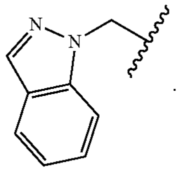 [SMILES: *Cn1ncc2ccccc21]

38. The compound of any one of embodiments 1-8, or a pharmaceutically acceptable salt thereof, wherein $R^3$ is —C(O)$OR^{3j}$, wherein $R^{3j}$ is hydrogen or $C_1$-$C_6$ alkyl.

39. The compound of embodiment 38, or a pharmaceutically acceptable salt thereof, wherein $R^3$ is

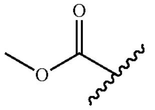

or

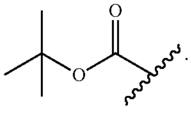

40. The compound of any one of embodiments 1-8, or a pharmaceutically acceptable salt thereof, wherein $R^3$ is —NHC(O)$R^{3k}$.

41. The compound of embodiment 40, or a pharmaceutically acceptable salt thereof, wherein $R^{3k}$ is $C_6$-$C_{14}$ aryl optionally substituted with one or more substituents independently selected from the group consisting of $C_1$-$C_6$ alkyl, cyano, —$NR^{3k1}R^{3k2}$, hydroxy, alkoxy, and $S(O)_2$(alkyl), wherein $R^{3k1}$ and $R^{3k2}$ are each independently hydrogen or $C_1$-$C_6$ alkyl.

42. The compound of embodiment 40 or 41, or a pharmaceutically acceptable salt thereof, wherein $R^3$

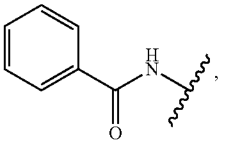
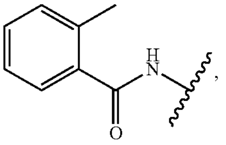

-continued

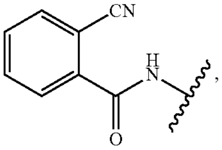
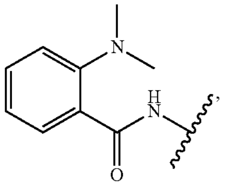
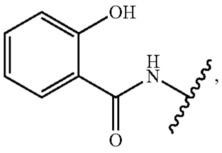
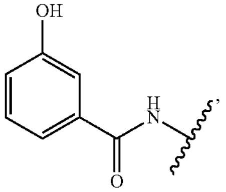
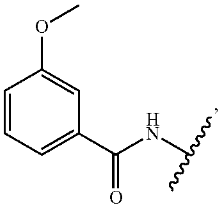

or

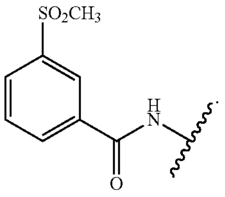

43. The compound of embodiment 40, or a pharmaceutically acceptable salt thereof, wherein $R^{3k}$ is —($C_1$-$C_6$ alkylene)-($C_6$-$C_{14}$ aryl), optionally substituted with one or more substituents independently selected from the group consisting of $C_1$-$C_6$ alkyl, cyano, —$NR^{3k1}R^{3k2}$, hydroxy, alkoxy, and $S(O)_2$(alkyl), wherein $R^{3k1}$ and $R^{3k2}$ are each independently hydrogen or $C_1$-$C_6$ alkyl.

44. The compound of embodiment 40 or 43, or a pharmaceutically acceptable salt thereof, wherein R is

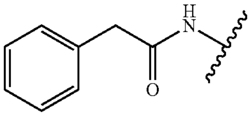 [SMILES: *NC(=O)Cc1ccccc1]

45. The compound of embodiment 40, or a pharmaceutically acceptable salt thereof, wherein $R^{3k}$ is 5- to 18-membered heteroaryl optionally substituted with one or more substituents independently selected from the group consisting of $C_1$-$C_6$ alkyl, cyano, —$NR^{3k1}R^{3k2}$, hydroxy, alkoxy, and $S(O)_2$(alkyl), wherein $R^{3k1}$ and $R^{3k2}$ are each independently hydrogen or $C_1$-$C_6$ alkyl.

46. The compound of embodiment 40 or 45, or a pharmaceutically acceptable salt thereof, wherein $R^3$ is

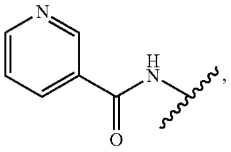
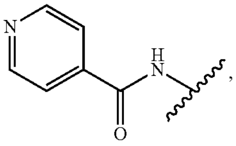
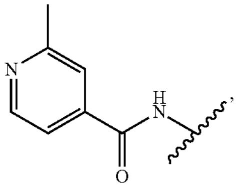
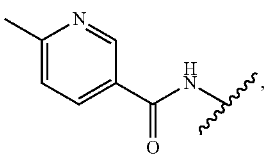

-continued

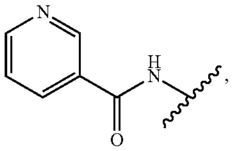, or 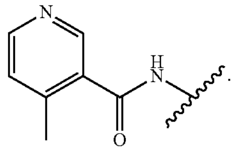.

47. The compound of any one of embodiments 1-8, or a pharmaceutically acceptable salt thereof, wherein $R^3$ is —NHC(O)O$R^{3l}$, wherein $R^{3l}$ is hydrogen or $C_1$-$C_6$ alkyl.

48. The compound of embodiment 47, or a pharmaceutically acceptable salt thereof, wherein $R^3$ is

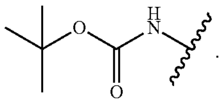 [SMILES: *NC(=O)OC(C)(C)C].

49. The compound of any one of embodiments 1-8, or a pharmaceutically acceptable salt thereof, wherein $R^3$ is —$NHSO_2R^{3m}$, wherein $R^{3m}$ is 5- to 18-membered heteroaryl, $C_6$-$C_{14}$ aryl, or —($C_1$-$C_6$ alkylene)-($C_6$-$C_{14}$ aryl), wherein the 5- to 18-membered heteroaryl, the $C_6$-$C_{14}$ aryl, and the —($C_1$-$C_6$ alkylene)-($C_6$-$C_{14}$ aryl) are each optionally substituted with one or more substituents selected from halo and $C_1$-$C_6$ alkoxy.

50. The compound of embodiment 49, or a pharmaceutically acceptable salt thereof, wherein $R^3$ is

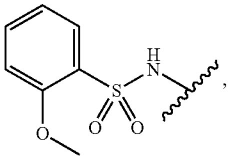, 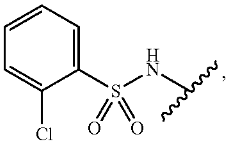,

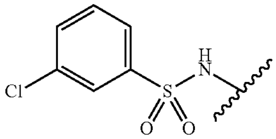, or 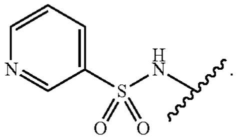.

51. The compound of any one of embodiments 1-8, or a pharmaceutically acceptable salt thereof, wherein $R^3$ is —$SO_2R^{3n}$ and $R^{3n}$ is $C_3$-$C_{10}$ cycloalkyl, $C_6$-$C_{14}$ aryl, or —($C_1$-$C_6$ alkylene)-($C_6$-$C_{14}$ aryl), wherein the $C_3$-$C_{10}$ cycloalkyl, the $C_6$-$C_{14}$ aryl, and the —($C_1$-$C_6$ alkylene)-($C_6$-$C_{14}$ aryl) are each optionally substituted with one or more substituents selected from halo and —C(O)O($C_1$-$C_6$ alkyl).

52. The compound of embodiment 51, or a pharmaceutically acceptable salt thereof, wherein $R^3$ is

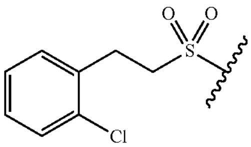, 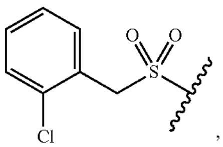,

-continued

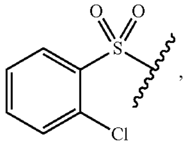, 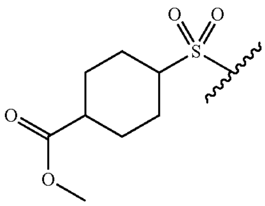, or

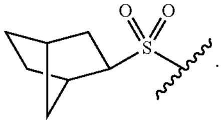.

53. The compound of any one of embodiments 1-52, or a pharmaceutically acceptable salt thereof, wherein $G^1$ is CH.

54. The compound of any one of embodiments 1-52, or a pharmaceutically acceptable salt thereof, wherein $G^1$ is N.

55. The compound of embodiment 1, or a pharmaceutically acceptable salt thereof, wherein $Y^1$ is

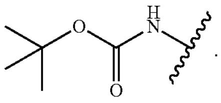 [SMILES: *NC(=O)OC(C)(C)C].

56. The compound of embodiment 1, or a pharmaceutically acceptable salt thereof, wherein $Y^1$ is

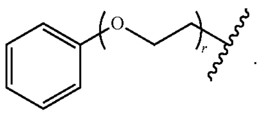.

57. The compound of embodiment 56, or a pharmaceutically acceptable salt thereof, wherein r is 1.

58. The compound of embodiment 56, or a pharmaceutically acceptable salt thereof, wherein r is 2.

59. The compound of embodiment 1, or a pharmaceutically acceptable salt thereof, wherein $Y^1$ is

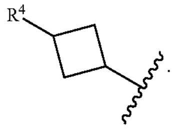.

60. The compound of embodiment 59, or a pharmaceutically acceptable salt thereof, wherein $R^4$ is phenyl.

61. The compound of embodiment 59, or a pharmaceutically acceptable salt thereof, wherein $R^4$ is —C(O)NH—$CH_2$-phenyl.

62. The compound of embodiment 1, or a pharmaceutically acceptable salt thereof, wherein $Y^1$ is

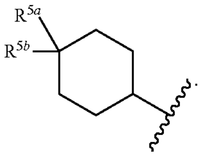

63. The compound of embodiment 62, or a pharmaceutically acceptable salt thereof, wherein $R^{5a}$ is selected from the group consisting of hydrogen, methyl, and —NHC(O)O($C_1$-$C_6$ alkyl).
64. The compound of embodiment 62 or embodiment 63, or a pharmaceutically acceptable salt thereof, wherein $R^{5b}$ is selected from the group consisting of hydrogen, methyl, and —NHC(O)O($C_1$-$C_6$ alkyl).
65. The compound of embodiment 1, or a pharmaceutically acceptable salt thereof, wherein $Y^1$ is

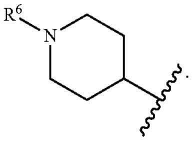

66. The compound of embodiment 65, or a pharmaceutically acceptable salt thereof, wherein $R^6$ is selected from the group consisting of —C(O)OC($CH_3$)$_3$, —NHC(O)O($C_1$-$C_6$ alkyl), and —C(O)-phenyl.
67. The compound of any one of embodiments 1-54, 56, and 58-66, or a pharmaceutically acceptable salt thereof, n is 0.
68. The compound of any one of embodiments 1-54, 56, and 58-66, or a pharmaceutically acceptable salt thereof, wherein n is 1.
69. The compound of any one of embodiments 1-54 and 58-66, or a pharmaceutically acceptable salt thereof, wherein n is 2.
70. The compound of any one of embodiments 1-54 and 56-66, or a pharmaceutically acceptable salt thereof, wherein n is 3.
71. The compound of any one of embodiments 1-66, or a pharmaceutically acceptable salt thereof, wherein n is 4.
72. The compound of any one of embodiments 1-66, or a pharmaceutically acceptable salt thereof, wherein n is 5.
73. The compound of any one of embodiments 1-66, or a pharmaceutically acceptable salt thereof, wherein n is 6.
74. The compound of any one of embodiments 1-73, or a pharmaceutically acceptable salt thereof, wherein $R^1$ is

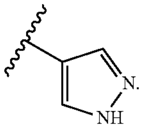 [SMILES: *c1cn[nH]c1]

75. The compound of any one of embodiments 1-73, or a pharmaceutically acceptable salt thereof, wherein $R^1$ is

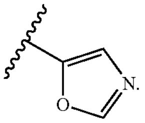

76. The compound of any one of embodiments 1-58 and 67-73, or a pharmaceutically acceptable salt thereof, wherein $R^1$ is

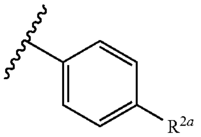

and $R^{2a}$ is selected from the group consisting of halo, —O($C_1$-$C_6$ alkyl), $C_1$-$C_6$ alkyl substituted with —OH, —C(O)$NR^{2c}R^{2d}$, and —N($R^{2e}$)C(O)($C_1$-$C_6$ alkyl), wherein $R^{2c}$, $R^{2d}$, and $R^{2e}$ are each independently hydrogen or $C_1$-$C_6$ alkyl.
77. The compound of any one of embodiments 1-73, or a pharmaceutically acceptable salt thereof, wherein $R^1$ is selected from the group consisting of

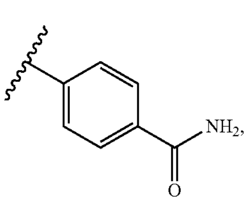

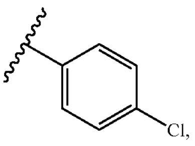

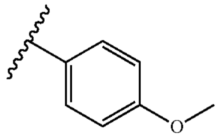

, and

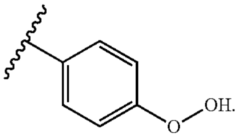

78. The compound of any one of embodiments 1-73, or a pharmaceutically acceptable salt thereof, wherein $R^1$ is

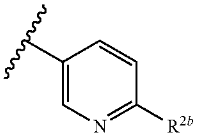

and $R^{2b}$ is selected from the group consisting of halo, —O($C_1$-$C_6$ alkyl), $C_1$-$C_6$ alkyl substituted with —OH, —C(O)$NR^{2c}R^{2d}$, and —N($R^{2e}$)C(O)($C_1$-$C_6$ alkyl), wherein $R^{2c}$, $R^{2d}$, and $R^{2e}$ are each independently hydrogen or $C_1$-$C_6$ alkyl.
79. The compound of any one of embodiments 1-73, or a pharmaceutically acceptable salt thereof, wherein $R^1$ is

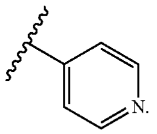

80. The compound of any one of embodiments 1-73, or a pharmaceutically acceptable salt thereof, wherein $R^1$ is

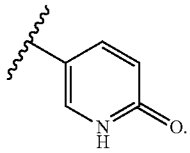

81. A compound selected from the group consisting of compounds of Table 1, or a pharmaceutically acceptable salt thereof.
82. A pharmaceutical composition comprising a compound according to any one of embodiments 1-81, or a pharmaceutically acceptable salt thereof, and a pharmaceutically acceptable excipient.
83. A method of treating a disease or condition mediated by NAMPT activity in a subject in need thereof, comprising administering to the subject a compound of any one of embodiments 1-81, or a pharmaceutically acceptable salt thereof, or a pharmaceutical composition of embodiment 82.
84. The method of embodiment 83, wherein the disease or condition is selected from the group consisting of cancer, a hyperproliferative disease or condition, an inflammatory disease or condition, a metabolic disorder, a cardiac disease or condition, chemotherapy induced tissue damage, a renal disease, a metabolic disease, a neurological disease or injury, a neurodegenerative disorder or disease, diseases caused by impaired stem cell function, diseases caused by DNA damage, primary mitochondrial disorders, or a muscle disease or muscle wasting disorder.
85. The method of embodiment 83, wherein the disease or condition is selected from the group consisting of obesity, atherosclerosis, insulin resistance, type 2 diabetes, cardiovascular disease, Alzheimer's disease, Huntington's disease, Parkinson's disease, amyotrophic lateral sclerosis, depression, Down syndrome, neonatal nerve injury, aging, axonal degeneration, carpal tunnel syndrome, Guillain-Barre syndrome, nerve damage, polio (poliomyelitis), and spinal cord injury.

General Synthetic Methods

Compounds of Formula (II) or Formula (I), or any variation or embodiment thereof, or a salt of any of the foregoing, will now be described by reference to illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. In addition, one of skill in the art will recognize that protecting groups may be used to protect certain functional groups (amino, carboxy, or side chain groups) from reaction conditions, and that such groups are removed under standard conditions when appropriate. Unless otherwise specified, the variables are as defined above in reference to Formula (II) or Formula (I).

Where it is desired to obtain a particular enantiomer of a compound, this may be accomplished from a corresponding mixture of enantiomers using any suitable conventional procedure for separating or resolving enantiomers. Thus, for example, diastereomeric derivatives may be produced by reaction of a mixture of enantiomers, e.g. a racemate, and an appropriate chiral compound. The diastereomers may then be separated by any convenient means, for example by crystallization and the desired enantiomer recovered. In another resolution process, a racemate may be separated using chiral High Performance Liquid Chromatography. Alternatively, if desired a particular enantiomer may be obtained by using an appropriate chiral intermediate in one of the processes described.

Chromatography, recrystallization and other conventional separation procedures may also be used with intermediates or final products where it is desired to obtain a particular isomer of a compound or to otherwise purify a product of a reaction.

Particular non-limiting examples are provided in the Example section below.

EXAMPLES

The following examples are offered to illustrate but not to limit the compositions, uses, and methods provided herein. The compounds are prepared using the general methods described above.

The following abbreviations are used throughout the Examples: TEA (triethylamine), DCM (dichloromethane), $(Boc)_2O$ (di-tert-butyl dicarbonate), EA (Ethyl acetate), PE (Petroleum ether), DMF (N,N-dimethylformamide), DIEA (N-ethyl-N-isopropylpropan-2-amine), HATU (1-[Bis(dimethylamino)methylene]-1H-1,2,3-triazolo[4,5-b]pyridinium 3-oxid hexafluorophosphate), HOAt (1-Hydroxy-7-azabenzotriazole), HOBt (Hydroxybenzotriazole), EDCI (1-Ethyl-3-(3-dimethylaminopropyl)carbodiimide), MeOH (methanol), EtOH (ethanol), iPrOH (propan-2-ol), ACN (acetonitrile), TFA (trifluoroacetic acid), DPPA (Diphenylphosphoryl azide), DBU (1,8-Diazabicyclo(5.4.0)undec-7-ene), THF (tetrahydrofuran), $PPh_3$ (triphenylphosphane), SM (starting material), Hex (hexane), NCS (N-chlorosuccinimide), r.t. (room temperature), DCE (dichloroethane), FA (formic acid), $CHCl_3$ (Chloroform), BnBr (benzyl bromide), HCl (hydrogen chloride), equiv (equivalent), and DSC (bis(2,5-dioxopyrrolidin-1-yl) carbonate), HBTU (O-(benzotriazol-1-yl)-N,N,N',N'-tetramethyluronium hexafluorophosphate).

Example A

Synthesis of Compound 168, Compound 201, and Intermediate 1.15

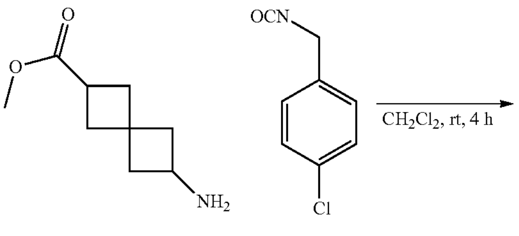

-continued

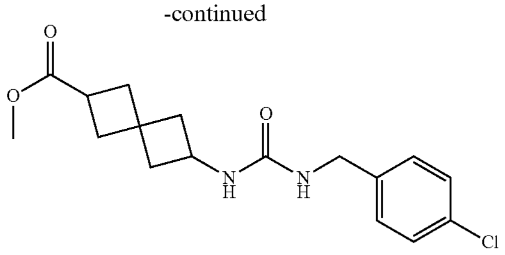

Compound 168

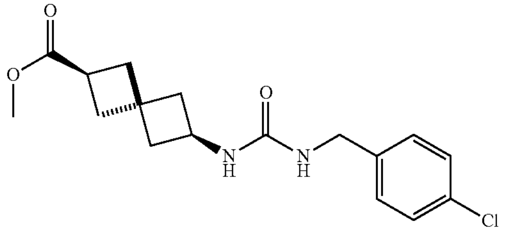

Compound 201

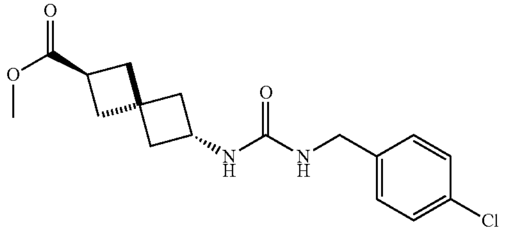

Intermediate 1.15

Preparation of methyl 6-(3-(4-chlorobenzyl)ureido) spiro[3.3]heptane-2-carboxylate (Compound 168)

1-Chloro-4-(isocyanatomethyl)benzene (6.8 g, 40.8 mmol, 1 equiv) was added to a stirring solution of methyl 6-aminospiro[3.3]heptane-2-carboxylate (8.4 g, 40.8 mmol, 1 equiv) in $CH_2Cl_2$ (100 mL) at rt. After 12 h, the solvent was removed by rotary evaporation, the crude material triturated in EtOH (100 mL) for 10 min, filtered, washed with EtOH (2×25 mL), and dried under high vacuum to give the Compound 168 (12 g, 87%) as a white solid. LRMS (APCI) m/z 337.1 (M+H). $^1$H NMR (400 MHz, Methanol-d4) δ 7.31 (d, J=8.6 Hz, 2H), 7.26 (d, J=8.5 Hz, 2H), 4.28 (s, 2H), 4.02 (p, J=8.0 Hz, 1H), 3.66 (s, 3H), 3.37 (s, 3H), 3.06 (p, J=8.6 Hz, 1H), 2.49 (ddd, J=11.8, 7.4, 5.2 Hz, 1H), 2.33 (tq, J=8.5, 3.2, 2.5 Hz, 3H), 2.28-2.07 (m, 2H), 1.87 (ddd, J=25.8, 11.2, 8.6 Hz, 2H).

Chiral Separation of methyl 6-(3-(4-chlorobenzyl) ureido)spiro[3.3]heptane-2-carboxylic acid Five grams of methyl 6-(3-(4-chlorobenzyl)ureido)spiro [3.3]heptane-2-carboxylate were resolved by chiral SFC (Chiralpak AD-H, 30% co-solvent (EtOH w/0.25% isopropylamine) at 70 g/min) affording the two chiral fragments Compound 201 (2.4 g, 48%) and Intermediate 1.15 (2.4 g, 48%) as white solids. The absolute stereochemistry of each fragment was not confirmed. Compound 201 elutes first from SFC using stated conditions, followed by Intermediate 1.15.

Compound 201:

LRMS (APCI) m/z 337.1 (M+H). $^1$H NMR (400 MHz, Methanol-d4) δ 7.32 (d, J=8.5 Hz, 2H), 7.26 (d, J=8.5 Hz, 2H), 4.28 (s, 2H), 4.02 (p, J=8.0 Hz, 1H), 3.66 (s, 3H), 3.06 (p, J=8.5 Hz, 1H), 2.49 (ddd, J=11.7, 7.3, 5.5 Hz, 1H), 2.39-2.28 (m, 3H), 2.28-2.10 (m, 2H), 1.87 (ddd, J=25.9, 11.1, 8.7 Hz, 2H).

Intermediate 1.15:

LRMS (APCI) m/z 337.1 (M+H). $^1$H NMR (400 MHz, Methanol-$d_4$) δ 7.32 (d, J=8.5 Hz, 2H), 7.26 (d, J=8.5 Hz, 2H), 4.28 (s, 2H), 4.02 (p, J=8.0 Hz, 1H), 3.66 (s, 3H), 3.06 (p, J=8.5 Hz, 1H), 2.49 (ddd, J=11.6, 7.2, 5.3 Hz, 1H), 2.39-2.28 (m, 3H), 2.28-2.11 (m, 2H), 1.87 (ddd, J=25.8, 11.0, 8.7 Hz, 2H).

Compounds 35, 8, 197, 37, 151, 152, 83, 81, 82, and 36 as well as Intermediates 1.3 and 1.7 were prepared in a similar manner as Compound 168, using the reagents provided in the table below in place of methyl 6-aminospiro [3.3]heptane-2-carboxylate and 1-chloro-4-(isocyanatomethyl)benzene.

| Compound No. | Amine | Isocyanate | Structure, Name and Data |
|---|---|---|---|
| Compound 35 | methyl 6-aminospiro [3.3]heptane-2-carboxylate | 4-methoxy benzyl isocyanate | 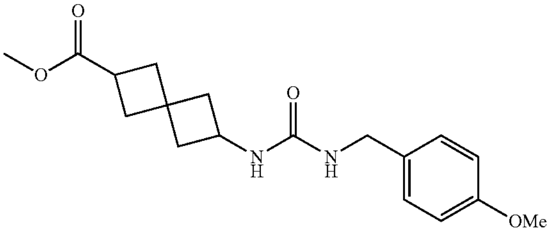 [SMILES: COC(=O)C1CC2(CC(NC(=O)NCc3ccc(OC)cc3)C2)C1] Methyl 6-(3-(4-methoxybenzyl)ureido) spiro[3.3]heptane-2-carboxylate. LCMS-ESI (POS.) m/z: 333 (M + H)+. $^1$H NMR (400 MHz, DMSO-d6) δ 7.15 (d, J = 8.3 Hz, 2H), 6.91-6.78 (m, 2H), 6.16-6.03 (m, 2H), 4.09 (d, J = 5.9 Hz, 2H), 3.91 (q, J = 8.1 Hz, 1H), 3.73 (d, J = 1.8 Hz, 3H), 3.58 (d, J = 1.8 Hz, 3H), 3.03 (p, J = 8.4 Hz, 1H), 2.34 (s, 1H), 2.30-2.22 (m, 1H), 2.14 (dt, J = 26.5, 8.6 Hz, 4H), 1.76 (dt, J = 27.2, 9.8 Hz, 2H). |

-continued

| Compound No. | Amine | Isocyanate | Structure, Name and Data |
|---|---|---|---|
| Intermediate 1.3 | methyl 6-aminospiro[3.3]heptane-2-carboxylate | 4-fluoro benzyl isocyanate | 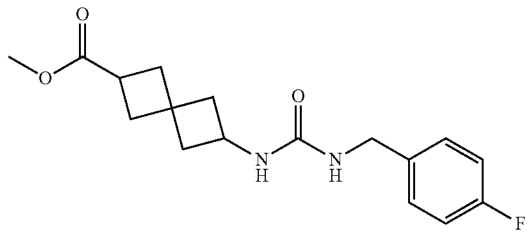 [SMILES: COC(=O)C1CC2(CC(NC(=O)NCc3ccc(F)cc3)C2)C1] 6-(3-(4-fluorobenzyl)ureido)spiro[3.3]heptane-2-carboxylic acid. LCMS-ESI (POS.) m/z: 321 |
| Compound 197 | tert-butyl 6-amino-2-azaspiro[3.3]heptane-2-carboxylate | 4-chloro benzyl isocyanate | 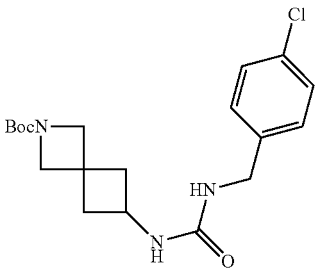 [SMILES: CC(C)(C)OC(=O)N1CC2(CC(NC(=O)NCc3ccc(Cl)cc3)C2)C1] tert-butyl 6-(3-(4-chlorobenzyl)ureido)-2-azaspiro[3.3]heptane-2-carboxylate. LRMS (APCI) m/z 280.1 (M + H− Boc). $^1$H NMR (400 MHz, Methanol-d4) δ 7.32 (d, J = 8.5 Hz, 2H), 7.26 (d, J = 8.4 Hz, 2H), 4.28 (s, 2H), 4.02 (p, J = 8.1 Hz, 1H), 3.98-3.91 (m, 2H), 3.84 (s, 2H), 2.55 (ddd, J = 10.0, 7.6, 2.9 Hz, 2H), 2.06 (td, J = 8.9, 2.9 Hz, 2H), 1.44 (s, 9H). |
| Compound 37 | tert-butyl 6-amino-2-azaspiro[3.3]heptane-2-carboxylate | 4-methoxy benzyl isocyanate | 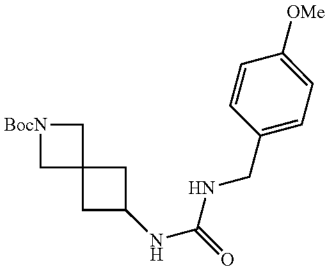 [SMILES: COc1ccc(CNC(=O)NC2CC3(C2)CN(C(=O)OC(C)(C)C)C3)cc1] tert-butyl 6-(3-(4-methoxybenzyl)ureido)-2-azaspiro[3.3]heptane-2-carboxylate. LRMS (APCI) m/z 276.1 (M + H − Boc). $^1$H NMR (400 MHz, DMSO-d6) δ 7.21-7.09 (m, 2H), 6.93-6.75 (m, 2H), 6.24-6.04 (m, 2H), 4.10 (d, J = 5.8 Hz, 2H), 3.93 (p, J = 8.1 Hz, 1H), 3.85 (s, 2H), 3.77-3.64 (m, 5H), 2.41 (ddd, J = 11.7, 6.5, 2.4 Hz, 2H), 2.06-1.86 (m, 2H), 1.37 (d, J = 1.4 Hz, 9H). |

-continued

| Compound No. | Amine | Isocyanate | Structure, Name and Data |
|---|---|---|---|
| Intermediate 1.7 | tert-butyl 6-amino-2-azaspiro[3.3] heptane-2-carboxylate | 4-(isocyanato-methyl)ben-zamide | 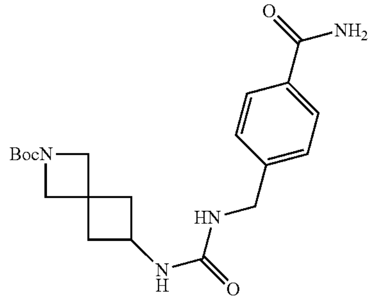 [SMILES: CC(C)(C)OC(=O)N1CC2(CC(NC(=O)NCc3ccc(C(N)=O)cc3)C2)C1] tert-butyl 6-(3-(4-carbamoylbenzyl)ureido)-2-azaspiro[3.3]heptane-2-carboxylate. LRMS (APCI) m/z 289 (M + H– Boc). |
| Compound 151 | tert-butyl (2r,4s)-2-amino-6-azaspiro[3.4] octane-6-carboxylate | 4-chloro benzyl isocyanate | 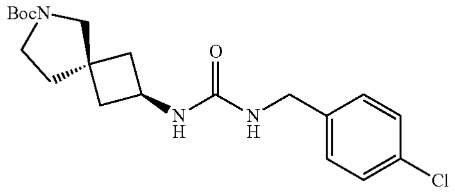 [SMILES: CC(C)(C)OC(=O)N1CC[C@]2(C1)C[C@@H](NC(=O)NCc1ccc(Cl)cc1)C2] tert-butyl (2r,4s)-2-(3-(4-chlorobenzyl)ureido)-6-azaspiro[3.4]octane-6-carboxylate. LRMS (APCI) m/z 394.2 (M + H). $^1$H NMR (400 MHz, DMSO-d6) δ 7.40-7.32 (m, 2H), 7.29-7.22 (m, 2H), 6.36-6.25 (m, 2H), 4.17 (d, J = 4.9 Hz, 2H), 4.03 (d, J = 8.1 Hz, 1H), 3.20 (d, J = 20.8 Hz, 4H), 2.19 (d, J = 9.3 Hz, 2H), 1.84-1.70 (m, 4H), 1.40 (s, 9H). |
| Compound 152 | tert-butyl (2s,4r)-2-amino-6-azaspiro[3.4] octane-6-carboxylate | 4-chloro benzyl isocyanate | 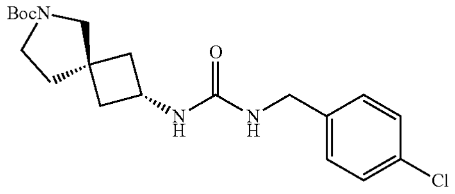 [SMILES: CC(C)(C)OC(=O)N1CC[C@]2(C1)C[C@H](NC(=O)NCc1ccc(Cl)cc1)C2] tert-butyl (2s,4r)-2-(3-(4-chlorobenzyl)ureido)-6-azaspiro[3.4]octane-6-carboxylate. LRMS (APCI) m/z 394.2 (M + H). $^1$H NMR (400 MHz, DMSO-d6) δ 7.40-7.32 (m, 2H), 7.29-7.22 (m, 2H), 6.36-6.25 (m, 2H), 4.17 (d, J = 4.9 Hz, 2H), 4.03 (d, J = 8.1 Hz, 1H), 3.20 (d, J = 20.8 Hz, 4H), 2.19 (d, J = 9.3 Hz, 2H), 1.84-1.70 (m, 4H), 1.40 (s, 9H). |
| Compound 83 | tert-butyl-2-amino-6-azaspiro[3.4] octane-6-carboxylate | 4-methoxy benzyl isocyanate | 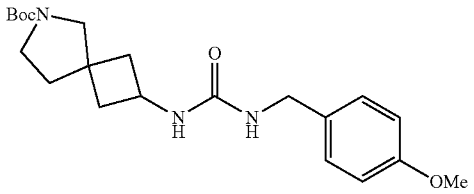 [SMILES: COc1ccc(CNC(=O)NC2CC3(CCN(C(=O)OC(C)(C)C)C3)C2)cc1] tert-butyl 2-(3-(4-methoxybenzyl)ureido)-6-azaspiro[3.4]octane-6-carboxylate. LRMS (APCI) m/z 390.2 (M + H). $^1$H NMR (400 MHz, DMSO-d6) δ 7.16 (d, J = 8.0 Hz, 2H), 6.95-6.78 (m, 2H), 6.08 (t, J = 6.0 Hz, 1H), 5.91 (d, J = 7.3 Hz, 1H), 4.11 (d, J = 5.8 Hz, 2H), 3.87 (q, J = 7.0 Hz, 1H), 3.73 (s, 3H), 3.71-3.61 (m, |

-continued

| Compound No. | Amine | Isocyanate | Structure, Name and Data |
|---|---|---|---|
| | | | 4H), 2.05 (dd, J = 13.2, 7.4 Hz, 1H), 1.86 (dq, J = 12.6, 6.3, 5.7 Hz, 2H), 1.73 (q, J = 8.0, 6.3 Hz, 1H), 1.58 (dd, J = 13.2, 6.6 Hz, 1H), 1.37 (d, J = 1.6 Hz, 9H), 1.35-1.29 (m, 1H). |
| Compound 81 | tert-butyl (2r,4s)-2-amino-6-azaspiro[3.4] octane-6-carboxylate | 4-methoxy benzyl isocyanate | 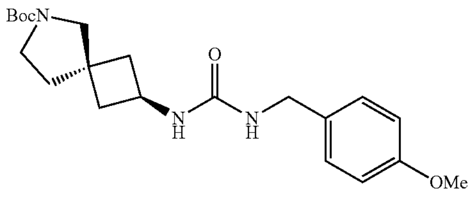 [SMILES: COc1ccc(CNC(=O)N[C@H]2C[C@]3(CCN(C(=O)OC(C)(C)C)C3)C2)cc1] tert-butyl (2r,4s)-2-(3-(4-methoxybenzyl)ureido)-6-azaspiro[3.4]octane-6-carboxylate. LRMS (APCI) m/z 390.2 (M + H). $^{1}$H NMR (400 MHz, DMSO-d6) δ 7.15 (d, J = 8.0 Hz, 2H), 6.91-6.83 (m, 2H), 6.23-6.14 (m, 2H), 4.11 (d, J = 5.8 Hz, 2H), 4.03 (q, J = 8.2 Hz, 1H), 3.72 (s, 3H), 3.23 (d, J = 6.2 Hz, 2H), 3.18 (d, J = 6.9 Hz, 2H), 2.20 (t, J = 9.3 Hz, 2H), 1.78 (t, J = 9.5 Hz, 4H), 1.40 (s, 9H). |
| Compound 82 | tert-butyl (2s,4r)-2-amino-6-azaspiro[3.4] octane-6-carboxylate | 4-methoxy benzyl isocyanate | 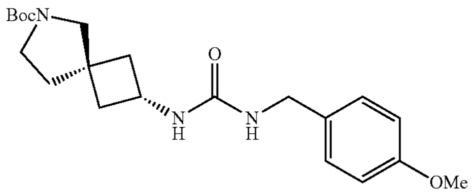 [SMILES: COc1ccc(CNC(=O)N[C@H]2C[C@@]3(CCN(C(=O)OC(C)(C)C)C3)C2)cc1] tert-butyl (2s,4r)-2-(3-(4-methoxybenzyl)ureido)-6-azaspiro[3.4]octane-6-carboxylate. LRMS (APCI) m/z 390.2 (M + H). $^{1}$H NMR (400 MHz, DMSO-d6) δ 7.15 (d, J = 8.0 Hz, 2H), 6.87 (d, J = 8.0 Hz, 2H), 6.25-6.08 (m, 2H), 4.10 (d, J = 6.0 Hz, 2H), 4.08-4.00 (m, 1H), 3.72 (s, 3H), 3.26-3.18 (m, 2H), 3.13 (s, 2H), 2.22-2.09 (m, 2H), 1.81 (t, J = 8.9 Hz, 4H), 1.39 (s, 9H). |
| Compound 36 | tert-butyl (5-aminopentyl) carbamate | 4-methoxy benzyl isocyanate | 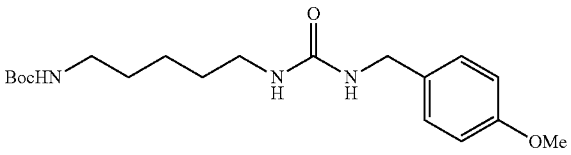 [SMILES: COc1ccc(CNC(=O)NCCCCCNC(=O)OC(C)(C)C)cc1] tert-butyl (5-(3-(4-methoxybenzyl)ureido)pentyl)carbamate. LRMS (APCI) m/z 366 (M + H). $^{1}$H NMR (400 MHz, DMSO-d6) δ 7.16 (d, J = 8.1 Hz, 2H), 6.87 (dd, J = 8.3, 1.5 Hz, 2H), 6.80-6.73 (m, 1H), 6.16 (t, J = 6.1 Hz, 1H), 5.85 (t, J = 5.8 Hz, 1H), 4.12 (d, J = 5.8 Hz, 2H), 3.73 (s, 3H), 2.98 (q, J = 6.6 Hz, 2H), 2.89 (q, J = 6.7 Hz, 2H), 1.41-1.29 (m, 13H), 1.22 (q, J = 8.2 Hz, 2H). |
| Intermediate 1.16 | methyl 5-aminopenta-noate | 4-chloro benzyl isocyanate | 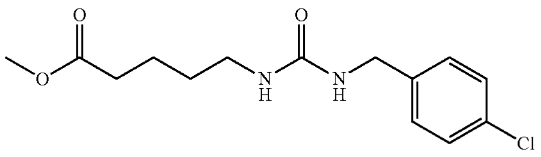 [SMILES: COC(=O)CCCCNC(=O)NCc1ccc(Cl)cc1] Methyl 5-(3-(4-chlorobenzyl)ureido)pentanoate. LRMS (APCI) m/z 299.1 (M + H). $^{1}$H NMR (400 MHz, DMSO-$d_6$) δ 7.36 (d, J = 8.3 Hz, 2H), 7.25 (d, J = 8.3 Hz, 2H), 6.35 (t, J = 6.2 Hz, 1H), 5.99 (t, J = 5.8 Hz, 1H), 4.17 (d, J = 6.1 Hz, 2H), 3.59 (s, 3H), 3.00 (q, J = 6.5 Hz, 2H), 2.31 (t, J = 7.4 Hz, 2H), 1.58-1.44 (m, 2H), 1.44-1.33 (m, 2H). |

-continued

| Compound No. | Amine | Isocyanate | Structure, Name and Data |
|---|---|---|---|
| Intermediate 1.17 | methyl 6-aminohex-anoate | 4-chloro benzyl isocyanate | 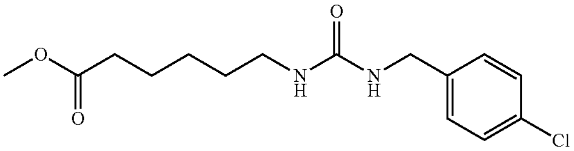 [SMILES: COC(=O)CCCCCNC(=O)NCc1ccc(Cl)cc1] Methyl 6-(3-(4-chlorobenzyl)ureido)hexanoate. LRMS (APCI) m/z 313.1 (M + H). $^1$H NMR (400 MHz, DMSO-$d_6$) δ 7.36 (d, J = 8.4 Hz, 2H), 7.26 (d, J = 8.2 Hz, 2H), 6.45 (t, J = 6.1 Hz, 1H), 6.07 (t, J = 5.8 Hz, 1H), 4.17 (d, J = 6.1 Hz, 2H), 3.58 (s, 3H), 2.98 (q, J = 6.5 Hz, 2H), 2.29 (t, J = 7.4 Hz, 2H), 1.52 (p, J = 7.4 Hz, 2H), 1.42-1.32 (m, 4H). |
| Intermediate 1.18 | tert-butyl (5-aminopentyl) carbamate | 4-chloro benzyl isocyanate | 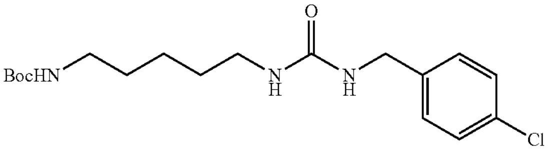 [SMILES: CC(C)(C)OC(=O)NCCCCCNC(=O)NCc1ccc(Cl)cc1] tert-butyl (5-(3-(4-chlorobenzyl)ureido)pentyl)carbamate. LRMS (APCI) m/z 370.1 (M + H). |
| Intermediate 1.19 | tert-butyl 4-(4-aminobutyl) piperidine-1-carboxylate | 4-chloro benzyl isocyanate | 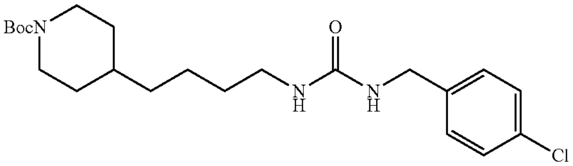 [SMILES: CC(C)(C)OC(=O)N1CCC(CCCCNC(=O)NCc2ccc(Cl)cc2)CC1] tert-butyl 4-(4-(3-(4-chlorobenzyl)ureido)butyl)piperidine-1-carboxylate. LRMS (APCI) m/z 424.1 (M + H). $^1$H NMR (400 MHz, DMSO-$d_6$) δ 7.36 (d, J = 8.1 Hz, 2H), 7.25 (d, J = 8.1 Hz, 2H), 6.31 (t, J = 6.0 Hz, 1H), 5.92 (t, J = 5.7 Hz, 1H), 4.17 (d, J = 6.1 Hz, 2H), 3.91 (d, J = 12.9 Hz, 2H), 2.99 (q, J = 6.4 Hz, 2H), 2.67 (s, 2H), 1.64-1.55 (m, 2H), 1.39 (s, 9H), 1.35 (t, J = 6.9 Hz, 3H), 1.22 (dd, J = 16.4, 7.5 Hz, 4H), 0.93 (qd, J = 12.3, 4.2 Hz, 2H). |
| Intermediate 1.20 | tert-butyl 4-(4-aminobutyl) piperazine-1-carboxylate | 4-chloro benzyl isocyanate | 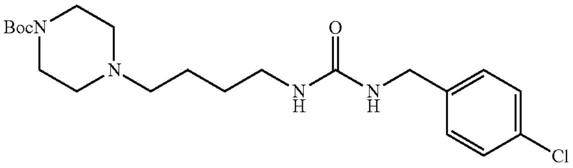 [SMILES: CC(C)(C)OC(=O)N1CCN(CCCCNC(=O)NCc2ccc(Cl)cc2)CC1] tert-butyl 4-(4-(3-(4-chlorobenzyl)ureido)butyl)piperazine-1-carboxylate. LRMS (APCI) m/z 425.2 (M + H ). |
| Intermediate 1.21 | Intermediate 20.1 | 5-(isocyanato-methyl)oxa-zole | 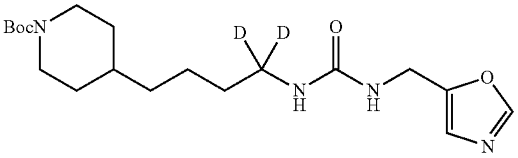 [SMILES: [2H]C([2H])(CCCC1CCN(C(=O)OC(C)(C)C)CC1)NC(=O)NCc1cnco1] tert-butyl 4-(4-(3-(oxazol-5-ylmethyl)ureido)butyl-4,4-d2)piperidine-1-carboxylate. LRMS (APCI) m/z 327 (M + H − tBu). |

Example B

Synthesis of Intermediates 2.1, 2.4, and 2.5

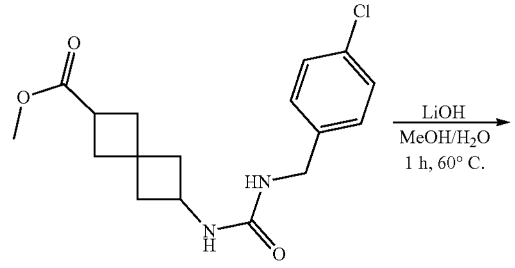

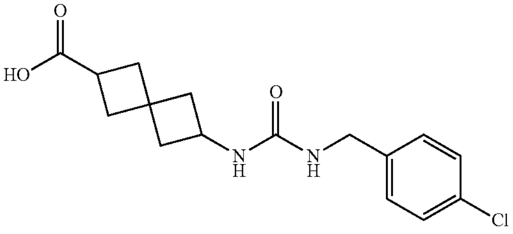

2.1

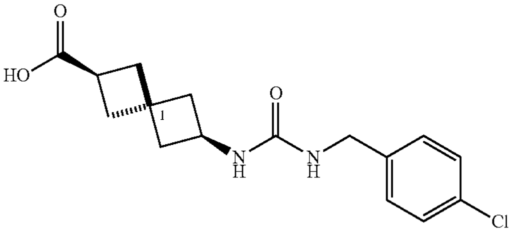

2.4

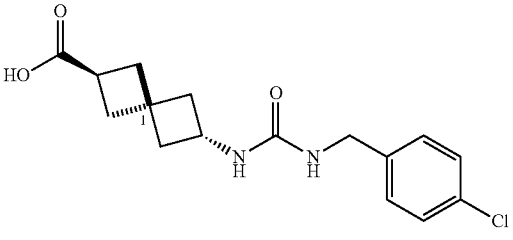

2.5

Preparation of 6-(3-(4-chlorobenzyl)ureido)spiro[3.3]heptane-2-carboxylic acid (Intermediate 2.1)

LiOH (622 mg, 25.98 mmol, 1.25 equiv) and methyl 6-(3-(4-chlorobenzyl)ureido)spiro[3.3]heptane-2-carboxylate (Compound 168) (7 g, 20.78 mmol, 1 equiv) were suspended in MeOH/H2O (50 mL/5 mL) and heated to 60° C. After 1 h, the reaction was cooled to rt and solvent removed by rotary evaporation. The crude material was dissolved in H2O/MeOH (90 mL/10 mL) before being precipitated with 3M HCl, filtered, washed with water (3×20 mL), and dried under high vacuum to give the desired product 2.1 as a white solid (5.2 g, 78%). LRMS (APCI) m/z 323.0 (M+H). $^1$H NMR (400 MHz, Methanol-d4) δ 7.31 (d, J=8.5 Hz, 2H), 7.26 (d, J=8.5 Hz, 2H), 4.28 (s, 2H), 4.02 (p, J=8.1 Hz, 1H), 3.02 (p, J=8.4 Hz, 1H), 2.56-2.43 (m, 1H), 2.33 (td, J=9.8, 8.4, 6.0 Hz, 3H), 2.29-2.11 (m, 2H), 1.87 (ddd, J=24.6, 11.0, 8.7 Hz, 2H).

Chiral Separation of 6-(3-(4-chlorobenzyl)ureido)spiro[3.3]heptane-2-carboxylic acid Five grams of 6-(3-(4-chlorobenzyl)ureido)spiro[3.3]heptane-2-carboxylic acid was resolved by chiral SFC (Chiralpak AD-H, 30% co-solvent [EtOH w/0.25% isopropylamine] at 70 g/min) affording the two chiral fragments 2.4 (2.3 g, 46%) and 2.5 (2.1 g, 42%) as white solids. The absolute stereochemistry of each fragment was not confirmed. Intermediate 2.4 elutes first from SFC using stated conditions, followed by intermediate 2.5.

Intermediate 2.4:

LRMS (APCI) m/z 323.1 (M+H). $^1$H NMR (400 MHz, DMSO-$d_6$) δ 7.36 (d, J=8.4 Hz, 2H), 7.24 (d, J=8.4 Hz, 2H), 6.40 (t, J=6.1 Hz, 1H), 6.29 (d, J=8.0 Hz, 1H), 4.15 (d, J=6.0 Hz, 2H), 3.89 (h, J=8.1 Hz, 1H), 3.09 (p, J=6.4 Hz, 1H), 2.75 (p, J=8.5 Hz, 1H), 2.31 (ddd, J=10.7, 7.3, 5.2 Hz, 1H), 2.20-2.01 (m, 4H), 2.01-1.90 (m, 1H), 1.82-1.63 (m, 2H), 1.06 (d, J=6.3 Hz, 5H). (complexed isopropanol found)

Intermediate 2.5:

LRMS (APCI) m/z 323.1 (M+H). $^1$H NMR (400 MHz, DMSO-$d_6$) δ 7.36 (d, J=8.4 Hz, 2H), 7.24 (d, J=8.2 Hz, 2H), 6.36 (t, J=6.1 Hz, 1H), 6.25 (d, J=8.0 Hz, 1H), 4.15 (d, J=6.0 Hz, 2H), 3.89 (h, J=8.0 Hz, 1H), 3.07 (p, J=6.4 Hz, 1H), 2.78 (p, J=8.5 Hz, 1H), 2.36-2.25 (m, 1H), 2.11 (tdd, J=19.6, 9.3, 6.7 Hz, 4H), 1.97 (ddd, J=11.2, 8.6, 2.4 Hz, 1H), 1.74 (ddd, J=29.1, 10.8, 8.7 Hz, 2H), 1.04 (d, J=6.3 Hz, 5H).

Intermediates 2.2 and 2.3 were prepared in a similar manner as Intermediate 2.1, using the reagents provided in the table below in place of methyl 6-(3-(4-chlorobenzyl)ureido)spiro[3.3]heptane-2-carboxylate (Compound 168).

| Compound | Ester | Structure, Name and Data |
|---|---|---|
| Intermediate 2.2 | Compound 35 | 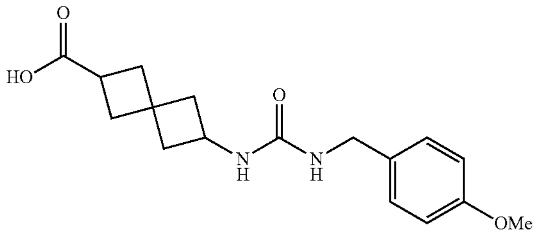 [SMILES: COc1ccc(CNC(=O)NC2CC3(C2)CC(C(=O)O)C3)cc1] 6-(3-(4-methoxybenzyl)ureido)spiro[3.3]heptane-2-carboxylic acid. LCMS-ESI (POS.) m/z: 319.10 (M + H)+. $^1$H NMR (400 MHz, DMSO-$d_6$) δ 12.00 (s, 1H), 7.15 (d, J = 8.1 Hz, 2H), 6.87 (d, J = 8.1 Hz, 2H), 6.12 (s, |

-continued

| Compound | Ester | Structure, Name and Data |
|---|---|---|
| | | 2H), 4.09 (s, 2H), 3.91 (p, J = 8.3 Hz, 1H), 3.73 (s, 3H), 2.92 (p, J = 8.5 Hz, 1H), 2.34 (dt, J = 11.6, 6.3 Hz, 1H), 2.25-2.01 (m, 5H), 1.75 (dt, J = 26.3, 9.8 Hz, 2H). |
| Intermediate 2.3 | Intermediate 1.3 | 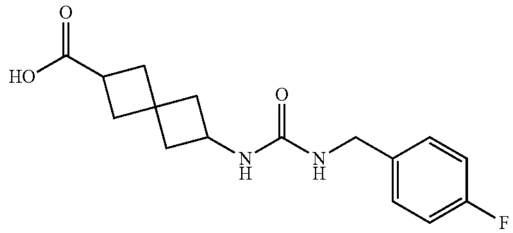 [SMILES: O=C(NCc1ccc(F)cc1)NC1CC2(C1)CC(C(=O)O)C2] 6-(3-(4-fluorobenzyl)ureido)spiro[3.3]heptane-2-carboxylic acid. LCMS-ESI (POS.) m/z: 307.10 (M + H)+. $^1$H NMR (400 MHz, DMSO-$d_6$) δ 11.98 (s, 1H), 7.36 (d, J = 8.4 Hz, 2H), 7.24 (d, J = 8.4 Hz, 2H), 6.26 (t, J = 6.0 Hz, 1H), 6.18 (d, J = 8.0 Hz, 1H), 4.15 (d, J = 6.1 Hz, 2H), 3.91 (q, J = 8.1 Hz, 1H), 3.20 (s, 1H), 2.40 (d, J = 24.9 Hz, 2H), 2.14 (dd, J = 19.9, 9.0 Hz, 4H), 2.01 (t, J = 10.0 Hz, 1H), 1.88-1.77 (m, 1H), 1.71 (t, J = 9.8 Hz, 1H). |
| 2.6 | Intermediate 1.16 | 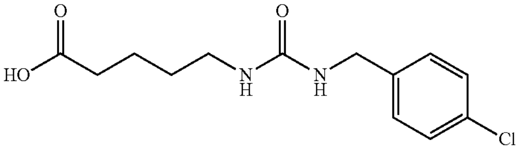 [SMILES: O=C(O)CCCCNC(=O)NCc1ccc(Cl)cc1] 5-(3-(4-chlorobenzyl)ureido)pentanoic acid. LCMS-ESI (POS.) m/z: 285.1 (M + H)+. $^1$H NMR (400 MHz, DMSO-$d_6$) δ 11.96 (s, 1H), 7.36 (d, J = 8.4 Hz, 2H), 7.25 (d, J = 8.3 Hz, 2H), 6.33 (s, 1H), 5.97 (s, 1H), 4.25-4.13 (m, 2H), 3.00 (t, J = 6.8 Hz, 2H), 2.21 (t, J = 7.3 Hz, 2H), 1.58-1.43 (m, 2H), 1.43-1.31 (m, 2H). |
| 2.7 | Intermediate 1.17 | 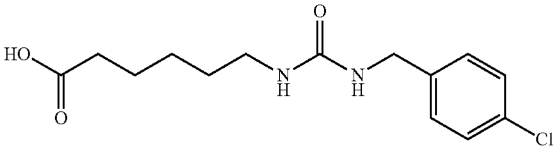 [SMILES: O=C(O)CCCCCNC(=O)NCc1ccc(Cl)cc1] 6-(3-(4-chlorobenzyl)ureido)hexanoic acid. LCMS-ESI (POS.) m/z: 299.1 (M + H)+. $^1$H NMR (400 MHz, DMSO-$d_6$) δ 11.91, 7.37 (d, J = 8.4 Hz, 2H), 7.25 (d, J = 8.4 Hz, 2H), 6.32 (s, 1H), 5.94 (s, 1H), 4.18 (d, J = 4.9 Hz, 2H), 2.98 (d, J = 8.0 Hz, 2H), 2.19 (t, J = 7.3 Hz, 2H), 1.49 (p, J = 7.5 Hz, 2H), 1.37 (p, J = 6.9 Hz, 2H), 1.25 (tt, J = 9.9, 5.8 Hz, 2H). |

Example C

Synthesis of Intermediate 3.1

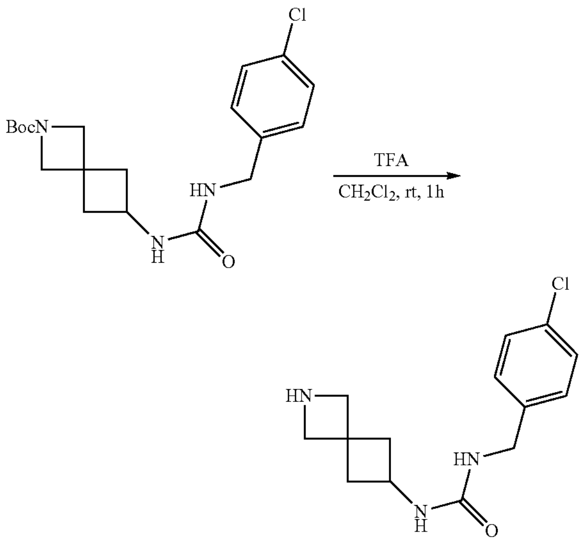

Preparation of 1-(4-Chlorobenzyl)-3-(2-azaspiro [3.3]heptan-6-yl)urea (Intermediate 3.1)

TFA (100 mL) was added to a stirring solution of tert-butyl 6-(3-(4-chlorobenzyl)ureido)-2-azaspiro[3.3]heptane-2-carboxylate (Intermediate 1.5) (17.8 g, 46.9 mmol, 1 equiv) in $CH_2Cl_2$ (200 mL) at rt. After 1 h, solvent was removed by rotary evaporation, the crude oil was azeotroped with toluene (3×100 mL) and dried under high vacuum. The crude oil was suspended in MeOH (250 mL), IONAC Na-38 $OH^-$ resin (50 g) was added, and the reaction stirred gently for 1 h. The reaction was then filtered through a pad of celite and solvent removed by rotary evaporation to give the product as a white solid (12.5 g, 95%). LRMS (APCI) m/z 280.1 (M+H). $^1$H NMR (400 MHz, Methanol-d4) 7.32 (d, J=8.4 Hz, 2H), 7.26 (d, J=8.5 Hz, 2H), 4.75 (s, 1H), 4.64 (s, 1H), 4.29 (d, J=4.3 Hz, 2H), 4.14 (s, 1H), 4.03 (d, J=4.8 Hz, 2H), 2.68 (dddd, J=17.8, 10.3, 7.7, 3.0 Hz, 2H), 2.32-2.24 (m, 2H), 2.22-2.13 (in, 1H).

Intermediates 3.2, 3.3, 3.4, 3.5, and 3.6 were prepared in a similar manner as Intermediate 3.1, using the reagents provided in the table below in place of tert-butyl 6-(3-(4-chlorobenzyl)ureido)-2-azaspiro[13.3]heptane-2-carboxylate (Compound 197).

| Compound | Protected Intermediate | Structure, Name and Data |
|---|---|---|
| Intermediate 3.2 | Compound 37 | 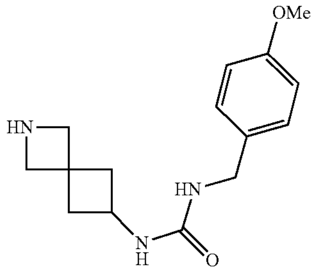 [SMILES: COc1ccc(CNC(=O)NC2CC3(CNC3)C2)cc1] 1-(4-methoxybenzyl)-3-(2-azaspiro[3.3]heptan-6-yl)urea. LRMS (APCI) m/z 276.1 (M + H). |
| Intermediate 3.3 | Intermediate 1.7 | 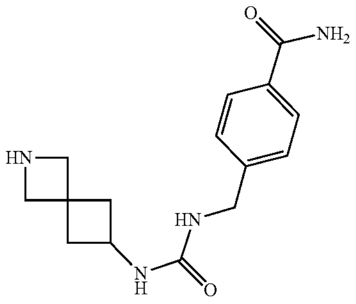 [SMILES: NC(=O)c1ccc(CNC(=O)NC2CC3(CNC3)C2)cc1] 4-((3-(2-azaspiro[3.3]heptan-6-yl)ureido)methyl)benzamide. LRMS (APCI) m/z 289 (M + H). |

-continued

| Compound | Protected Intermediate | Structure, Name and Data |
|---|---|---|
| Intermediate 3.4 | Compound 8 | 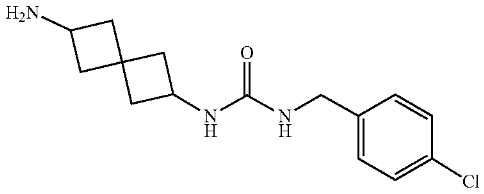 [SMILES: NC1CC2(C1)CC(NC(=O)NCc1ccc(Cl)cc1)C2] tert-butyl (6-(3-(4-methoxybenzyl)ureido) spiro[3.3]heptan-2-yl)carbamate. LCMS-ESI (POS.) m/z: 294.10 (M + H)+. $^1$H NMR (400 MHz, DMSO-d6) δ 8.49-7.95 (m, 3H), 7.36 (d, J = 8.4 Hz, 2H), 7.24 (d, J = 8.4 Hz, 2H), 7.11-6.64 (m, 1H), 4.15 (s, 2H), 3.93 (p, J = 8.2 Hz, 1H), 3.51 (pd, J = 7.9, 2.7 Hz, 1H), 2.33 (dtd, J = 11.7, 7.8, 4.6 Hz, 2H), 2.26-2.03 (m, 4H), 1.82 (ddd, J = 11.1, 8.6, 5.3 Hz, 2H). |
| Intermediate 3.5 | Compound 151 | 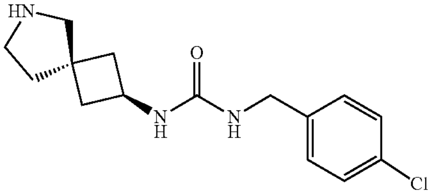 [SMILES: O=C(NCc1ccc(Cl)cc1)N[C@H]1C[C@]2(CCNC2)C1] 1-(4-chlorobenzyl)-3-((2r,4s)-6-azaspiro[3.4]octan-2-yl)urea. LRMS (APCI) m/z 294.1 (M + H). $^1$H NMR (400 MHz, DMSO-d6) δ 7.35 (d, J = 4.3 Hz, 2H), 7.25 (d, J = 4.5 Hz, 2H), 6.41 (d, J = 5.1 Hz, 1H), 6.32 (dd, J = 7.8, 3.6 Hz, 1H), 4.17 (s, 2H), 4.11-3.96 (m, 1H), 3.03-2.93 (m, 2H), 2.88 (d, J = 3.6 Hz, 2H), 2.17 (d, J = 9.1 Hz, 2H), 1.93-1.74 (m, 4H). |
| Intermediate 3.6 | Compound 152 | 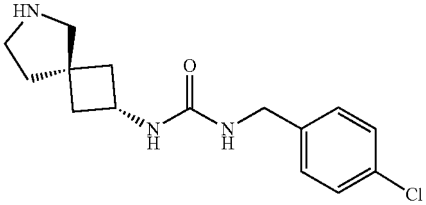 [SMILES: O=C(NCc1ccc(Cl)cc1)N[C@H]1C[C@@]2(CCNC2)C1] 1-(4-chlorobenzyl)-3-((2s,4r)-6-azaspiro[3.4]octan-2-yl)urea. LRMS (APCI) m/z 294.1 (M + H). 1H NMR (400 MHz, DMSO-d6) δ 7.36 (d, J = 8.4 Hz, 2H), 7.25 (d, J = 8.4 Hz, 2H), 6.50-6.34 (m, 2H), 4.17 (d, J = 6.1 Hz, 2H), 4.04 (q, J = 8.1 Hz, 2H), 3.14 (s, 2H), 3.10 (t, J = 7.4 Hz, 2H), 2.37-2.25 (m, 2H), 1.95-1.82 (m, 4H), 1.06 (d, J = 6.6 Hz, 1H). |
| 3.7 | Intermediate 1.18 | 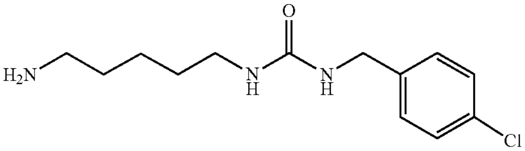 [SMILES: NCCCCCNC(=O)NCc1ccc(Cl)cc1] 1-(5-aminopentyl)-3-(4-chlorobenzyl)urea. LRMS (APCI) m/z 270.1 (M + H). |

-continued

| Compound | Protected Intermediate | Structure, Name and Data |
|---|---|---|
| 3.8 | Intermediate 1.19 | 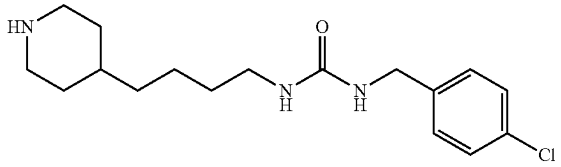 1-(4-chlorobenzyl)-3-(4-(piperidin-4-yl)butyl)urea. LRMS (APCI) m/z 324.1 (M + H). |
| 3.9 | Intermediate 1.20 | 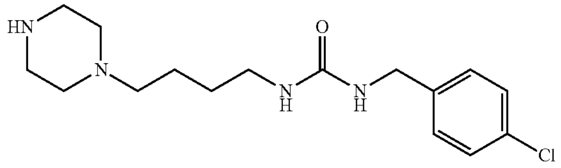 [SMILES: O=C(NCCCCN1CCNCC1)NCc1ccc(Cl)cc1] 1-(4-chlorobenzyl)-3-(4-(piperazin-1-yl)butyl)urea. LRMS (APCI) m/z 325.2 (M + H). |
| 3.10 | Intermediate 18.1 | 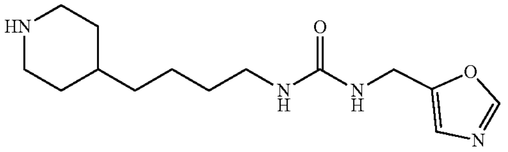 [SMILES: O=C(NCCCCC1CCNCC1)NCc1cnco1] 1-(oxazol-5-ylmethyl)-3-(4-(piperidin-4-yl)butyl)urea. LRMS (APCI) m/z 281.2 (M + H). |
| 3.11 | Intermediate 18.2 | 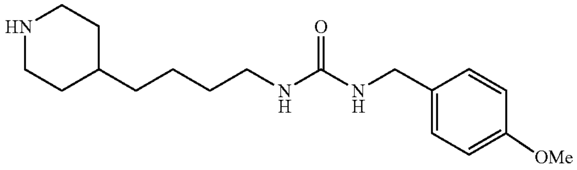 [SMILES: COc1ccc(CNC(=O)NCCCCC2CCNCC2)cc1] 1-(4-methoxybenzyl)-3-(4-(piperidin-4-yl)butyl)urea. LRMS (APCI) m/z 320.2 (M + H). |
| 3.12 | Intermediate 18.3 | 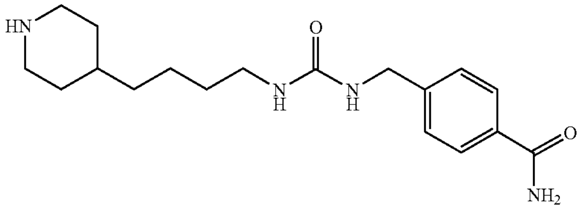 [SMILES: NC(=O)c1ccc(CNC(=O)NCCCCC2CCNCC2)cc1] 4-((3-(4-(piperidin-4-yl)butyl)ureido)methyl)benzamide. LRMS (APCI) m/z 333.2 (M + H). |
| 3.13 | Intermediate 18.4 | 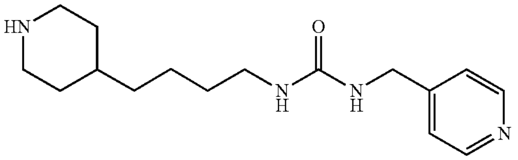 [SMILES: O=C(NCCCCC1CCNCC1)NCc1ccncc1] 1-(4-(piperidin-4-yl)butyl)-3-(pyridin-4-ylmethyl)urea. LRMS (APCI) m/z 291.3 (M + H). |

-continued

| Compound | Protected Intermediate | Structure, Name and Data |
|---|---|---|
| 3.14 | Intermediate 18.5 | 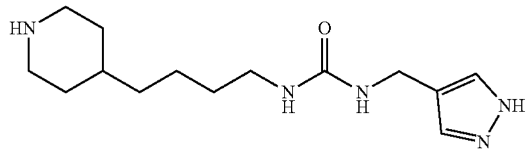 [SMILES: O=C(NCCCCC1CCNCC1)NCc1cn[nH]c1] 1-((1H-pyrazol-4-yl)methyl)-3-(4-(piperidin-4-yl)butyl)urea. LRMS (APCI) m/z 231.7 (M + H). |
| 3.15 | Interemeidate 1.21 | 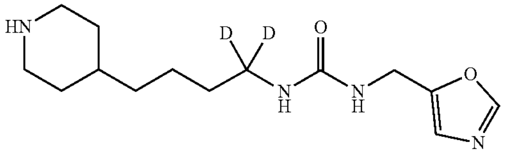 [SMILES: [2H]C([2H])(CCCC1CCNCC1)NC(=O)NCc1cnco1] 1-(oxazol-5-ylmethyl)-3-(4-(piperidin-4-yl)butyl-1,1-d2)urea. LRMS (APCI) m/z 283.1 (M + H). |

Example D

Synthesis of Intermediate 4.1

Preparation of (6-(3-(4-methoxybenzyl)ureido)spiro[3.3]heptan-2-yl)methyl methanesulfonate (Intermediate 4.1)

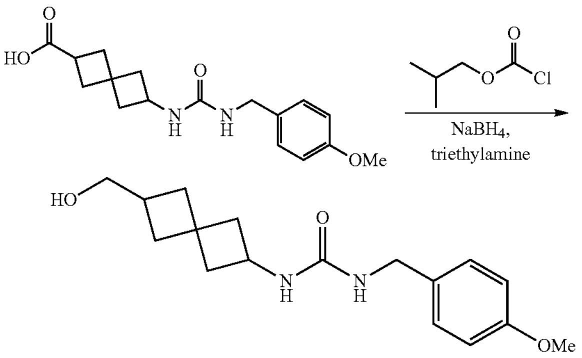

Step 1: Preparation of 3-[6-(hydroxymethyl)spiro[3.3]heptan-2-yl]-1-[(4-methoxyphenyl)methyl]urea To a solution of 6-(3-(4-methoxybenzyl)ureido)spiro[3.3]heptane-2-carboxylic acid (2.0 g, 6.28 mmol, 1.0 equiv) in DCM (20 mL) was added triethylamine (2 equiv) followed by isobutylchloroformate dropwise at 0° C. The solution was stirred at rt and monitored by LCMS. After 1 h, the solution was cooled to 0° C. and the precipitate was filtered and rinsed with DCM. The crude (isobutyl carbonic) 6-(3-(4-methoxybenzyl)ureido)spiro[3.3]heptane-2-carboxylic anhydride was used directly in the next step (99% yield).

The crude anhydride from above was dissolved in THF (20 mL) and sodium borohydride (0.475 g, 12.6 mmol, 2.0 equiv) was added portion wise at rt. The solution was monitored by LCMS analysis. The solution was cooled to 0° C. and satd aqueous sodium carbonate solution (20 mL) was added and the solution was stirred vigorously for 10 mins. The organic layer was separated the aqueous layer was extracted with 30 mL of DCM. The combined organic layer was washed with brine, dried, filtered, and concentrated to provide the product as white foam (1.82 g, 92% yield). LCMS-APCI (POS.) m/z: 315.0 (M+H)+. 1H NMR (400 MHz, DMSO-d6) δ 7.15 (dd, J=8.5, 1.7 Hz, 2H), 6.87 (dt, J=8.6, 2.3 Hz, 2H), 6.18-5.95 (m, 2H), 4.40 (td, J=5.4, 1.3 Hz, 1H), 4.09 (d, J=5.9 Hz, 2H), 3.91 (q, J=8.1 Hz, 1H), 3.82 (td, J=9.3, 7.3, 2.9 Hz, 1H), 3.31 (t, J=5.8 Hz, 3H), 2.83 (q, J=6.9, 4.7 Hz, 1H), 2.79-2.71 (m, 1H), 2.24-2.08 (m, 2H), 2.02 (t, J=9.1 Hz, 1H), 1.87 (t, J=9.9 Hz, 1H), 1.81-1.57 (m, 4H).

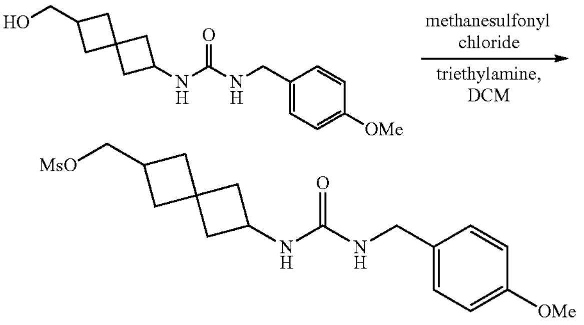

Intermediate 4.1

Step 2: Preparation of (6-(3-(4-methoxybenzyl)ureido)spiro[3.3]heptan-2-yl)methyl methanesulfonate $NEt_3$ (2.0 equiv) was added to a solution of 3-[6-(hydroxymethyl)spiro[3.3]heptan-2-yl]-1-[(4-methoxyphenyl)methyl]urea (1.8 g, 5.71 mmol, 1.0 equiv) in $CH_2Cl_2$ (0.33 M). The reaction was cooled to 0° C. and methanesulfonyl chloride (0.72 g, 0.31 mmol, 1.1 equiv) was added dropwise and stirred for 30 mins. The solution was cooled to 0° C. and satd aqueous ammonium chloride solution was added and the solution stirred vigorously for 10 mins. The organic layer was separated and the aqueous layer extracted with 10 mL of DCM. The combined organic layer was washed with brine, dried, filtered, and concentrated to provide the product as a white foam (1.96 g, 84% yield). LCMS-APCI (POS.) m/z: 384.0 (M+H). 1H NMR (400 MHz, DMSO-d6) δ 7.21 (dd, J=8.2, 1.6 Hz, 2H), 6.94 (dt, J=8.2, 1.6 Hz, 2H), 6.24-6.00 (m, 2H), 5.44 (td, J=5.4 Hz, 1.3 Hz, 2H), 4.59 (td, J=5.2, 1.3 Hz, 1H), 3.91 (q, J=8.1 Hz, 1H), 3.31 (t, J=5.8 Hz, 3H), 2.83 (q, J=6.9, 4.7 Hz, 1H), 2.65 (s, 3H), 2.79-2.71 (m, 1H), 2.24-2.08 (m, 2H), 2.02 (t, J=9.1 Hz, 1H), 1.87 (t, J=9.9 Hz, 1H), 1.81-1.57 (m, 4H).

Example E

Synthesis of Intermediate 5.1

Preparation of N-(6-aminospiro[3.3]heptan-2-yl) benzamide hydrochloride (Intermediate 5.1)

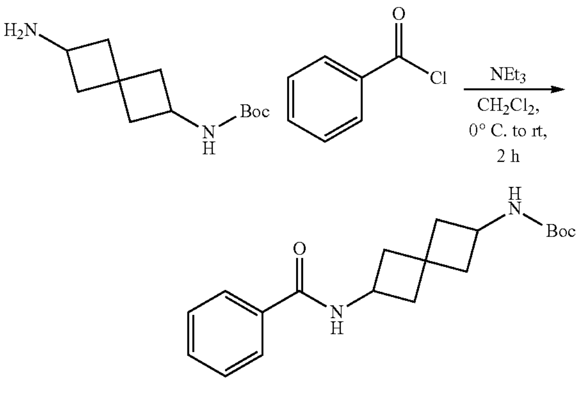

Step 1: Preparation of tert-butyl (6-benzamidospiro [3.3]heptan-2-yl)carbamate $NEt_3$ (670 mg, 6.628 mmol, 3 equiv) and benzoyl chloride (341.61 mg, 2.430 mmol, 1.1 equiv) were added to a stirring solution of tert-butyl N-[6-aminospiro[3.3]heptan-2-yl]carbamate (500.00 mg, 2.209 mmol, 1.0 equiv) in $CH_2Cl_2$ (5 mL) at 0° C. before the reaction was allowed to return to rt. After 2 h, the reaction was then quenched with $H_2O$ (20 mL), extracted with $CH_2Cl_2$ (2×20 mL). Organics were combined, washed with sat sodium chloride (20 mL), dried over sodium sulfate, filtered, and solvent removed by rotary evaporation to give the crude product (850 mg) which was used in the next step without further purification. LRMS (APCI) m/z 275 (M+H−56).

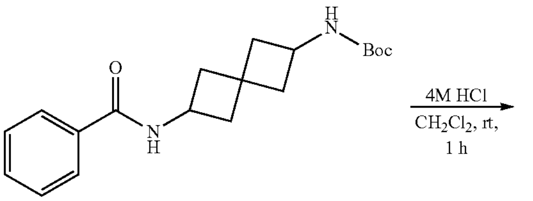

-continued

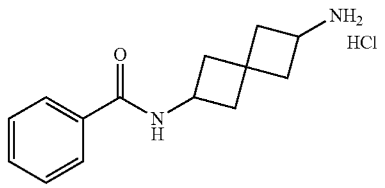

Intermediate 5.1

Step 2: Preparation of N-(6-aminospiro[3.3]heptan-2-yl)benzamide hydrochloride HCl (2.5 mL, 4M in dioxanes) was added to a stirring solution of tert-butyl N-[6-benzamidospiro[3.3]heptan-2-yl] carbamate (830 mg, 2.5 mmol, 1.0 equiv) in $CH_2Cl_2$ (10 mL) at rt. After 1 h, the reaction was concentrated by rotary evaporation to afford the crude product (620 mg) as a white solid which was used without further purification. LRMS (APCI) m/z 231 (M+H).

Example F

Synthesis of Intermediate 6.1

Preparation of N2-(pyridin-2-yl)spiro[3.3]heptane-2,6-diamine hydrochloride (Intermediate 6.1)

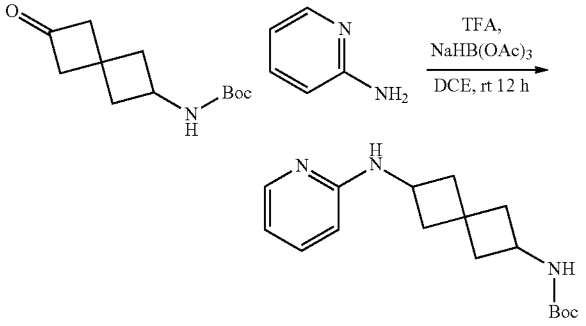

Step 1: Preparation of tert-butyl (6-(pyridin-2-ylamino)spiro[3.3]heptan-2-yl)carbamate 2-Aminopyridine (200 mg, 2.1 mmol, 2.0 equiv) and TFA (243 mg, 2.1 mmol, 2 equiv) were added to a stirring solution of tert-butyl N-[6-oxospiro[3.3]heptan-2-yl]carbamate (240 mg, 1.1 mmol, 1.0 equiv) in DCE (10 mL) at rt. After 30 min, $NaHB(OAc)_3$ (677 mg, 3.2 mmol, 3.0 equiv) was added and the reaction stirred for 12 h. The reaction was quenched with $H_2O$ (20 mL), extracted with $CH_2Cl_2$ (2×20 mL). Organics were combined, washed with sat sodium chloride (20 mL), dried over sodium sulfate, filtered, and solvent removed by rotary evaporation to give the crude product (380 mg) as a yellow solid which was used in the next step without further purification. LRMS (APCI) m/z 248 (M+H−56).

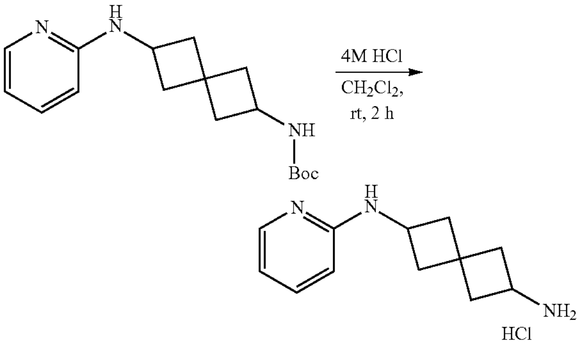

Intermediate 6.1

Step 2: Preparation of N2-(pyridin-2-yl)spiro[3.3] heptane-2,6-diamine hydrochloride HCl (2.5 mL, 4M in dioxanes) was added to a stirring solution of tert-butyl N-[6-(pyridin-2-ylamino)spiro[3.3] heptan-2-yl]carbamate (360 mg, 1.187 mmol, 1.0 equiv) in $CH_2Cl_2$ (5 mL) at rt. After 2 h, the reaction was concentrated by rotary evaporation to afford the crude product (280 mg) as a white solid which was used without further purification. LRMS (APCI) m/z 204 (M+H).

Example G

Synthesis of Intermediate 7.1

Preparation of tert-butyl ((1r,3r)-3-(benzylcarbamoyl)cyclobutyl)carbamate Intermediate

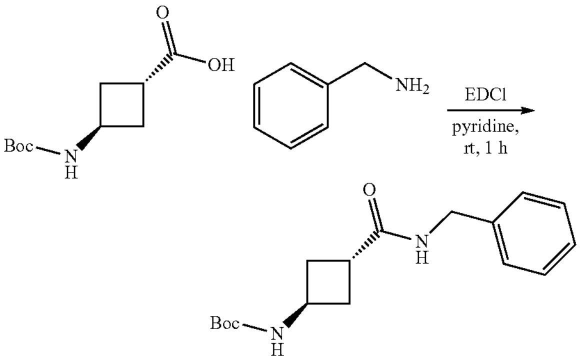

Step 1: Preparation of tert-butyl ((1r,3r)-3-(benzylcarbamoyl)cyclobutyl)carbamate EDCI (670 mg, 3.49 mmol, 1.5 equiv) was added to a stirring solution of (1r,3r)-3-[(tert-butoxycarbonyl)amino] cyclobutane-1-carboxylic acid (500.00 mg, 2.323 mmol, 1.00 equiv) in pyridine (5 mL) at rt. After 5 min, benzylamine (298.50 mg, 2.786 mmol, 1.20 equiv) was added and the reaction stirred for rt for 1 h. The reaction was then quenched with $H_2O$ (20 mL), extracted with EtOAc (2×20 mL). The reaction was then quenched with $H_2O$ (20 mL) and extracted with EtOAc (2×20 mL). The organic layers were combined, washed with sat sodium chloride (20 mL), dried over sodium sulfate, filtered, and solvent removed by rotary evaporation to give the crude product (640 mg) which was used in the next step without further purification. LRMS (APCI) m/z 249 (M+H−56).

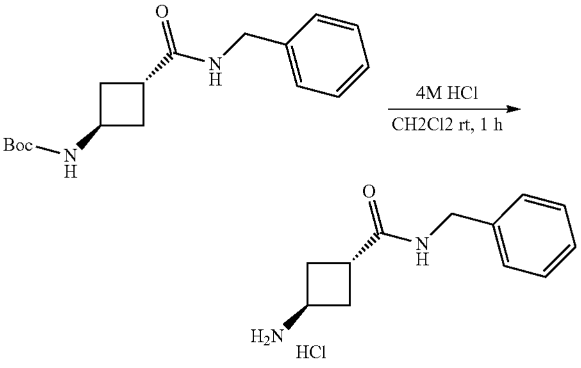

Intermediate 7.1

Step 2: Preparation of (1r,3r)-3-amino-N-benzylcyclobutane-1-carboxamide hydrochloride HCl (2 mL, 4 M in dioxane) was added to a stirring solution of tert-butyl N-[(1r,3r)-3-(benzylcarbamoyl)cyclobutyl]carbamate (827 mg, 1.00 equiv) in $CH_2Cl_2$ (10 mL) at rt. After 1 h, the reaction was concentrated by rotary evaporation to give the crude product as a brown solid (640 mg) which was used in the next step without further purification. LRMS (APCI) m/z 241 (M+H).

Example H

Synthesis of Intermediate 8.1

Preparation of (6-amino-2-azaspiro[3.3]heptan-2-yl) (p-tolyl)methanone (Intermediate 8.1)

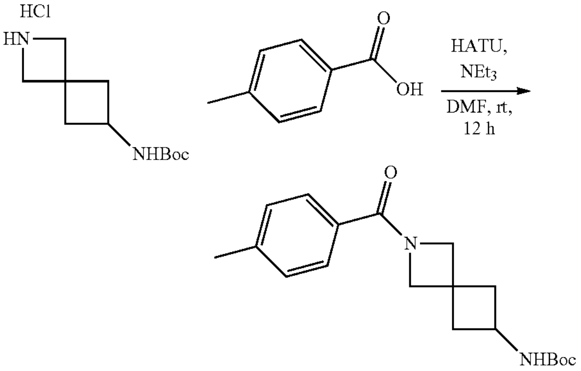

Step 1: Preparation of tert-butyl (2-(4-methylbenzoyl)-2-azaspiro[3.3]heptan-6-yl)carbamate HATU (6.88 g, 18.1 mmol, 1.5 equiv) was added to a stirring solution of tert-butyl (2-azaspiro[3.3]heptan-6-yl)

carbamate hydrochloride (3 g, 12.1 mmol, 1 equiv), 4-methylbenzoic acid (2.46 g, 18.1 mmol, 1.5 equiv) and $NEt_3$ (4.9 mL, 36.2 mmol, 3 equiv) in DMF (100 mL) at rt. After 12 h, the reaction was poured into EtOAc (500 mL), washed with sat sodium bicarbonate (3×250 mL), brine (2×250 mL), dried over sodium sulfate, filtered through a pad of silica, and solvent removed by rotary evaporation to give the crude product as a white solid (3.6 g).

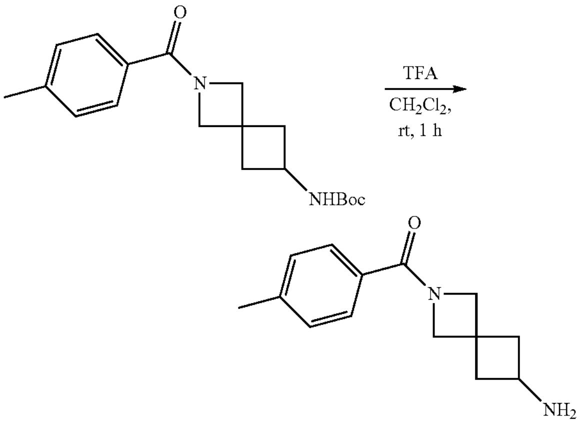

Intermediate 8.1

Step 2: (6-amino-2-azaspiro[3.3]heptan-2-yl)(p-tolyl)methanone

TFA (25 mL) was added to a stirring solution of tert-butyl (2-(4-methylbenzoyl)-2-azaspiro[3.3]heptan-6-yl)carbamate (1 g, 3.03 mmol, 1 equiv) in $CH_2Cl_2$ (50 mL) at rt. After 1 h, the solvent was removed by rotary evaporation, azeotroped with toluene (3×50 mL), and dried under high vacuum to give the crude product as a yellow oil which was used in the next step without further purification. LRMS (APCI) m/z 231.1 (M+H).

Example I

Synthesis of Compound 198 and Intermediate 9.2

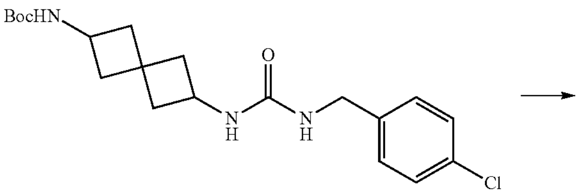

Compound 8

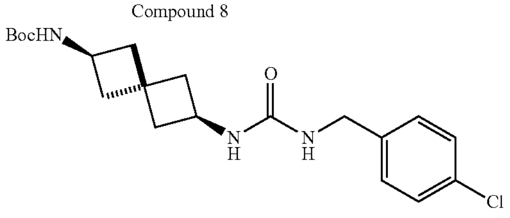

Compound 198

-continued

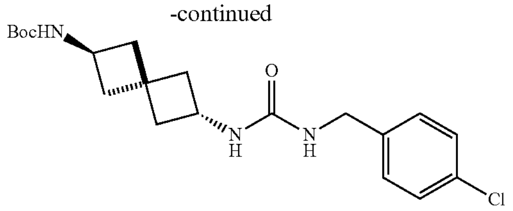

Intermediate 9.2

Chiral resolution of tert-butyl 6-(3-(4-chlorobenzyl)ureido)spiro[3.3]heptan-2-yl)carbamate (Compound 8)

The racemic tert-butyl 6-(3-(4-chlorobenzyl)ureido)spiro[3.3]heptan-2-yl)carbamate (25 g) Compound 8 was resolved by chiral SFC (Chiralpak AD-H, 20% co-solvent [EtOH w/0.25% isopropylamine] at 80 g/min) affording the two chiral fragments Compound 198 (9.4 g, 38%) and Intermediate 9.2 (12 g, 48%) as white solids. The absolute stereochemistry of each fragment was not confirmed. Compound 198 elutes first from SFC using stated conditions, followed by Intermediate 9.2. Absolute stereochemistry was not determined. Compound 8 elutes first from SFC using stated conditions, followed by Intermediate 9.2.

Compound 198:

LRMS (APCI) m/z 294.1 (M+H–Boc). $^1$H NMR (400 MHz, DMSO-$d_6$) δ 7.36 (d, J=8.4 Hz, 2H), 7.24 (d, J=8.4 Hz, 2H), 7.04 (d, J=8.0 Hz, 1H), 6.25 (t, J=6.1 Hz, 1H), 6.17 (d, J=8.0 Hz, 1H), 4.15 (d, J=6.0 Hz, 2H), 3.92 (h, J=8.2 Hz, 1H), 3.79 (q, J=8.3 Hz, 1H), 2.27 (dp, J=18.8, 6.3 Hz, 2H), 2.19-2.00 (m, 2H), 1.93-1.69 (m, 4H), 1.36 (s, 9H).

Intermediate 9.2

LRMS (APCI) m/z 294.1 (M+H–Boc). $^1$H NMR (400 MHz, DMSO-$d_6$) δ 7.36 (d, J=8.4 Hz, 2H), 7.24 (d, J=8.4 Hz, 2H), 7.04 (d, J=7.8 Hz, 1H), 6.25 (t, J=6.1 Hz, 1H), 6.17 (d, J=8.1 Hz, 1H), 4.15 (d, J=6.0 Hz, 2H), 3.92 (h, J=7.9 Hz, 1H), 3.79 (q, J=8.2 Hz, 1H), 2.27 (dp, J=18.9, 7.5, 6.2 Hz, 2H), 2.09 (tq, J=13.3, 6.1 Hz, 2H), 1.93-1.68 (m, 4H), 1.36 (s, 9H).

Example J

Synthesis of Intermediate 10.1

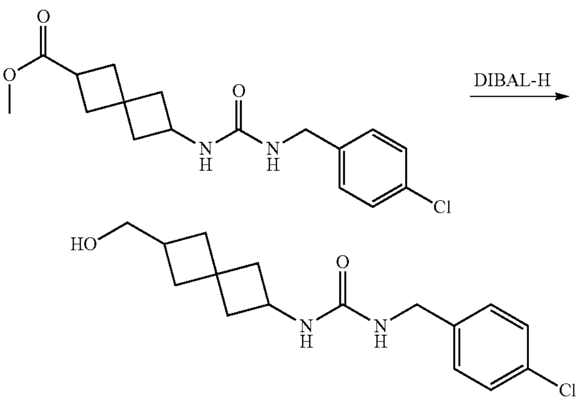

Preparation of 1-(6-(hydroxymethyl)spiro[3.3]heptan-2-yl)-3-(4-methoxybenzyl)urea (Intermediate 10.1)

Diisobutylaluminum hydride (25% in toluene, 10.1 g, 17.8 mmol, 3 equiv.) was added to a stirring solution of methyl 6-(3-(4-chlorobenzyl)ureido)spiro[3.3]heptane-2-carboxylate (2.0 g, 17.8 mmol, 1 equiv) in THF (100 mL) at rt. After 2 h, the reaction was quenched by addition of MeOH (50 mL) and silica before solvent was removed by rotary evaporation. Purification by silica chromatography (0→10% MeOH/$CH_2Cl_2$) as a white solid (1.5 g, 81%). LRMS (APCI) m/z 309.1 (M+H). $^1$H NMR (400 MHz, DMSO-$d_6$) δ 7.14 (d, J=8.6 Hz, 2H), 6.86 (d, J=8.6 Hz, 2H), 6.09 (t, J=5.9 Hz, 1H), 6.06 (d, J=8.1 Hz, 1H), 4.40 (t, J=5.2 Hz, 1H), 4.09 (d, J=5.9 Hz, 2H), 3.91 (h, J=8.2 Hz, 1H), 3.30 (dd, J=6.5, 5.3 Hz, 2H), 2.29 (ddd, J=10.6, 7.4, 5.3 Hz, 1H), 2.21 (dt, J=16.6, 8.2 Hz, 1H), 2.16-2.08 (m, 1H), 2.01 (td, J=9.6, 8.3, 3.0 Hz, 1H), 1.87 (ddd, J=11.2, 8.2, 3.0 Hz, 1H), 1.79-1.60 (m, 4H).

Intermediate 10.2 was prepared in a similar manner as Intermediate 10.1, using the reagents provided in the table below.

| Intermediate | Ester | Structure, Name and Data |
|---|---|---|
| 10.2 | Compound 35 | 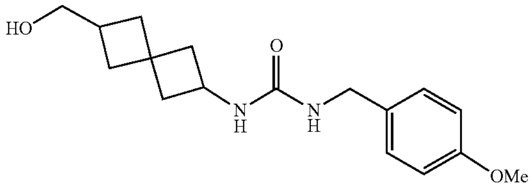 [SMILES: COc1ccc(CNC(=O)NC2CC3(CC(CO)C3)C2)cc1] 1-(6-(hydroxymethyl)spiro[3.3]heptan-2-yl)-3-(4-methoxybenzyl)urea. LRMS (APCI) m/z 305.2 (M + H). |

Example K

Synthesis of Intermediate 11.1

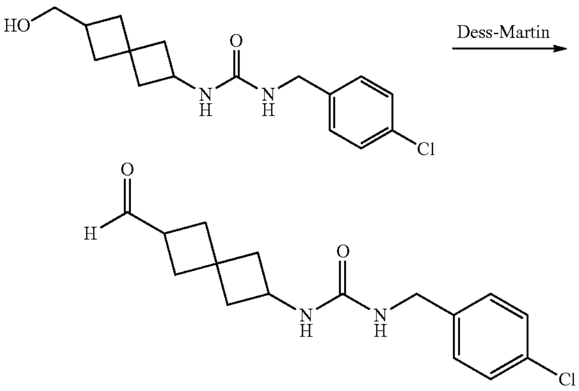

Preparation of 1-(4-chlorobenzyl)-3-(6-formylspiro[3.3]heptan-2-yl)urea (Intermediate 11.1)

Dess-Martin Periodinane (4.1 g, 9.72 mmol, 1 equiv) was added to a stirring solution of 1-(4-chlorobenzyl)-3-(6-(hydroxymethyl)spiro[3.3]heptan-2-yl)urea (3.0 g, 9.72 mmol, 1 equiv) in $CH_2Cl_2$ (100 mL) and acetonitrile (100 mL) at rt. After 2 h, the reaction was quenched with sat sodium thiosulfate (100 mL) and diluted to 700 mL with saturated sodium bicarbonate and stirred vigorously for 10 min. The reaction was then extracted with $CH_2Cl_2$ (3×500 mL), organic layers combined, dried over sodium sulfate, and solvent removed by rotary evaporation to give the crude product as a tan solid (2.5 g, 84%). LRMS (APCI) m/z 307.1 (M+H).

Example L

Synthesis of Intermediates 12.1 and 12.2

Preparation of 1-(6-(aminomethyl)spiro[3.3]heptan-2-yl)-3-(4-methoxybenzyl)urea (Intermediate 12.2)

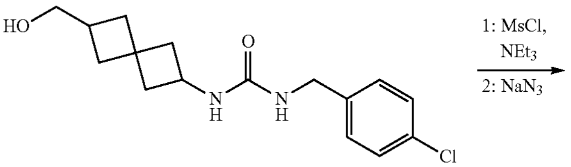

-continued

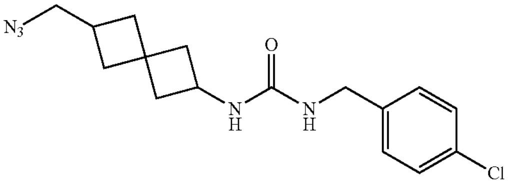

Intermediate 12.1

Step 1: Preparation of 1-(6-(azidomethyl)spiro[3.3]heptan-2-yl)-3-(4-chlorobenzyl)urea Methanesulfonyl chloride (857 mg, 7.5 mmol, 1.1 equiv) was added to a stirring solution of 1-(6-(hydroxymethyl)spiro[3.3]heptan-2-yl)-3-(4-chlorobenzyl)urea (2.1 g, 6.8 mmol, 1 equiv) and $NEt_3$ (2.1 g, 20.4 mmol, 3 equiv) in $CH_2Cl_2$ (50 mL) at rt. After 2 h, the reaction was quenched with saturated sodium bicarbonate (250 mL), extracted with $CH_2Cl_2$ (3×250 mL), organics combined, dried over sodium sulfate, filtered, and solvent removed by rotary evaporation. The crude material was suspended in DMF (8 mL) before $NaN_3$ (0.66 g, 10.2 mmol, 1.5 equiv) added and the reaction heated to 70° C. for 12 h. The reaction was cooled to rt, poured into EtOAc (500 mL), washed with saturated sodium bicarbonate (3×400 mL), the organic layer died over sodium sulfate, filtered, and solvent removed by rotary evaporation to give the desired product as a white solid (1.98 g, 87%). LRMS (APCI) m/z 334.1 (M+H).

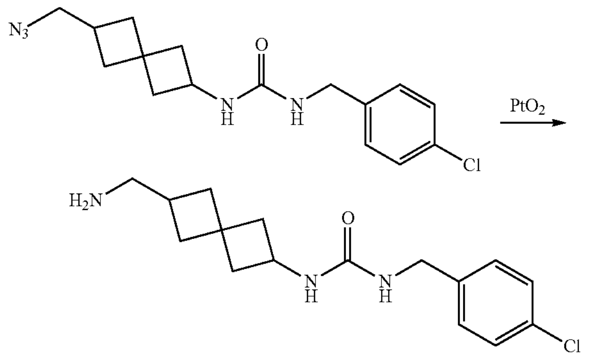

Intermediate 12.2

Step 2: Preparation of 1-(6-(aminomethyl)spiro[3.3]heptan-2-yl)-3-(4-chlorobenzyl)urea $PtO_2$ (0.1 g, 0.449 mmol, 0.1 equiv) and 1-(6-(azidomethyl)spiro[3.3]heptan-2-yl)-3-(4-chlorobenzyl)urea (1.5 g, 4.5 mmol, 1 equiv) were suspended in MeOH (50 mL) at rt before being stirred under $H_2$ (80 psi) for 1 h. The reaction was then filtered through a pad of celite and solvent removed by rotary evaporation to give the desired product as a white semi-solid (1.3 g, 98%). LRMS (APCI) m/z 308.1 (M+H). 1H NMR (400 MHz, Methanol-d4) δ 7.31 (d, J=7.8 Hz, 2H), 7.26 (d, J=7.9 Hz, 2H), 4.29 (d, J=8.7 Hz, 2H), 4.02 (t, J=8.1 Hz, 1H), 2.64 (d, J=7.0 Hz, 2H), 2.46 (t, J=7.8 Hz, 1H), 2.25 (ddd, J=24.0, 11.5, 6.4 Hz, 3H), 2.11-1.99 (m, 1H), 1.92-1.73 (m, 3H), 1.69 (dd, J=11.1, 7.4 Hz, 1H).

Example M

Synthesis of Intermediate 13.1

Preparation of 2-(6-(3-(4-chlorobenzyl)ureido)spiro[3.3]heptan-2-yl)acetic acid (Example 13.1)

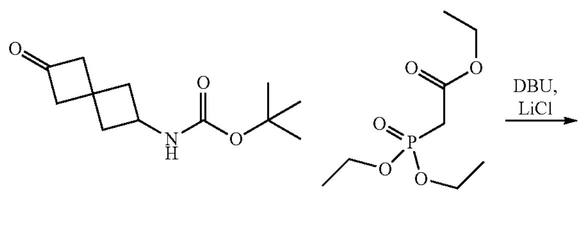

-continued

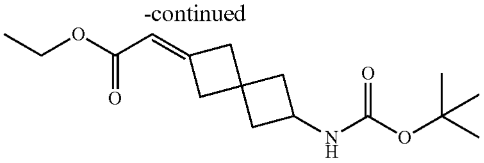

Step 1: Preparation of ethyl 2-(6-((tert-butoxycarbonyl)amino)spiro[3.3]heptan-2-ylidene)acetate Ethyl 2-(diethoxyphosphoryl)acetate (4.9 g, 22.2 mmol, 1 equiv) was added to a stirring solution of LiCl (2.26 g, 53.3 mmol, 2.4 equiv) in THF (25 mL) at rt. After 10 min, DBU (7.43 g, 48.8 mmol, 2.2 equiv) was added and the reaction stirred for an additional 10 min. tert-Butyl (6-oxospiro[3.3]heptan-2-yl)carbamate (5.0 g, 22.2 mmol, 1 equiv) in THF (20 mL) was then added and the reaction stirred for 14 h. The reaction was concentrated by rotary evaporation and product isolated by silica chromotography (0→50% EtOAc/Hex) as a white solid (5.05 g, 77%). LRMS (APCI) m/z 296.1 (M+H). $^1$H NMR (400 MHz, Chloroform-d) δ 5.62 (d, J=6.8 Hz, 1H), 4.66 (s, 1H), 4.22-4.10 (m, 2H), 4.05 (s, 1H), 3.13 (d, J=38.8 Hz, 2H), 2.84 (d, J=38.1 Hz, 2H), 2.57-2.37 (m, 2H), 1.94 (td, J=8.8, 4.2 Hz, 2H), 1.45 (s, 9H), 1.28 (t, J=6.9 Hz, 3H).

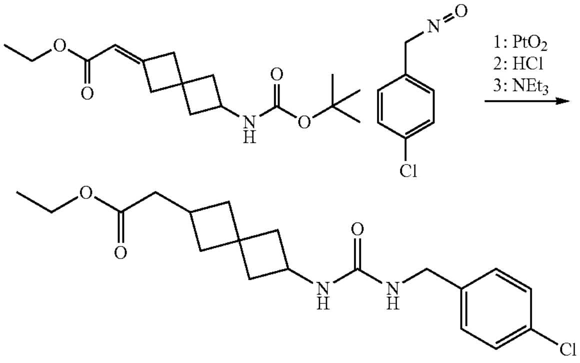

Step 2: Preparation of ethyl 2-(6-(3-(4-chlorobenzyl)ureido)spiro[3.3]heptan-2-yl)acetate Ethyl 2-(6-((tert-butoxycarbonyl)amino)spiro[3.3]heptan-2-ylidene)acetate (5.05 g, 17.1 mmol, 1 equiv) and $PtO_2$ (308 mg, 0.17 mmol, 1 equiv) were suspended in MeOH (150 mL) and stirred under $H_2$ (80 psi) for 1 h. The reaction then filtered through a pad of celite and solvent removed by rotary evaporation. The crude material was suspended in $CH_2Cl_2$ (20 mL) before HCl (4 M in dioxanes, 42 mL, 170.9 mmol, 10 equiv) was added and the reaction stirred at rt for 2 h. The solvent was removed by rotary evaporation and dried under high vacuum before being suspended in $CH_2Cl_2$ (100 mL), $NEt_3$ (3.46 g, 34.2 mmol, 2 equiv) and 1-chloro-4-(isocyanatomethyl)benzene (3 g, 18.0 mmol, 1.05 equiv) were added and the reaction stirred at rt. After 12 h, the reaction was concentrated by rotary evaporation and product isolated by silica chromotography (0→10% MeOH/$CH_2Cl_2$) as a white solid (6.3 g, 98%). LRMS (APCI) m/z 365.1 (M+H). $^1$H NMR (400 MHz, Chloroform-d) δ 7.31 (s, 2H), 7.22 (d, J=8.0 Hz, 2H), 4.67 (t, J=6.0 Hz, 1H), 4.54 (d, J=7.3 Hz, 1H), 4.33 (d, J=5.9 Hz, 2H), 4.11 (q, J=7.1 Hz, 2H), 4.01

(q, J=7.8 Hz, 1H), 3.51 (d, J=5.1 Hz, 3H), 2.62-2.45 (m, 2H), 2.37 (d, J=7.9 Hz, 2H), 2.35-2.21 (m, 2H), 2.10 (ddd, J=11.9, 7.7, 4.1 Hz, 1H), 1.77 (dq, J=19.7, 10.6, 10.1 Hz, 4H), 1.67 (s, 2H), 1.30-1.20 (m, 3H), 1.09 (q, J=5.6 Hz, 1H).

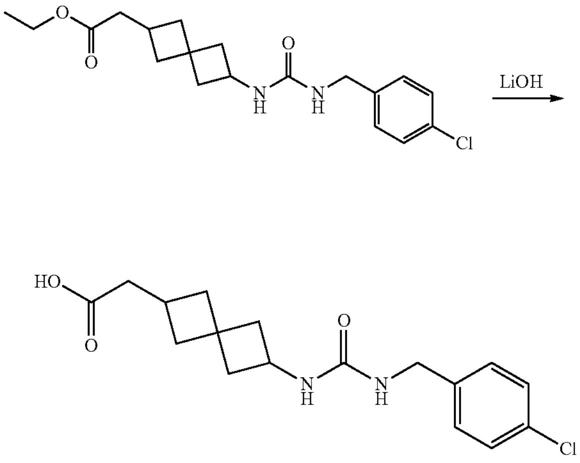

Step 3: Preparation of 2-(6-(3-(4-chlorobenzyl)ureido)spiro[3.3]heptan-2-yl)acetic acid Ethyl 2-(6-(3-(4-chlorobenzyl)ureido)spiro[3.3]heptan-2-yl)acetate (6.3 g, 17.3 mmol, 1 equiv) and LiOH (827 mg, 34.5 mmol, 2 equiv) were suspended in MeOH/water (19 mL/1 mL) at rt. After 4 h, the MeOH was removed by rotary evaporation and the crude diluted with water (~25 mL) before the product was precipitated by addition of 1 M HCl (~20 mL). The resulting precipitate was collected by filtration, washed with water, and dried under high vacuum to give the desired product as a white solid (4.5 g, 77%). LRMS (APCI) m/z 337.1 (M+H). $^{1}$H NMR (400 MHz, Methanol-$d_4$) δ 7.39-7.15 (m, 4H), 4.37-4.18 (m, 2H), 4.01 (d, J=8.9 Hz, 1H), 2.49 (pd, J=11.3, 7.6, 5.9 Hz, 2H), 2.31 (dq, J=36.6, 6.3 Hz, 4H), 2.10 (d, J=10.4 Hz, 1H), 1.77 (ddt, J=36.3, 19.2, 10.0 Hz, 4H).

Intermediate 13.2 was prepared in a similar manner as Intermediate 13.1, using the reagents provided in the table below.

| Intermediate | Phosphonate | Structure, Name and Data |
| --- | --- | --- |
| 13.2 | ethyl 2-(diethoxyphosphoryl)propanoate | 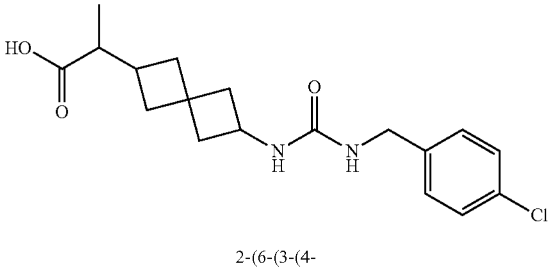 2-(6-(3-(4-chlorobenzyl)ureido)spiro[3.3]heptan-2-yl)propanoic acid. LRMS (APCI) m/z 351.1 (M + H). |

Example N

Synthesis of Intermediate 14.1

Preparation of 1-(6-acetylspiro[3.3]heptan-2-yl)-3-(4-chlorobenzyl)urea (Intermediate 14.1)

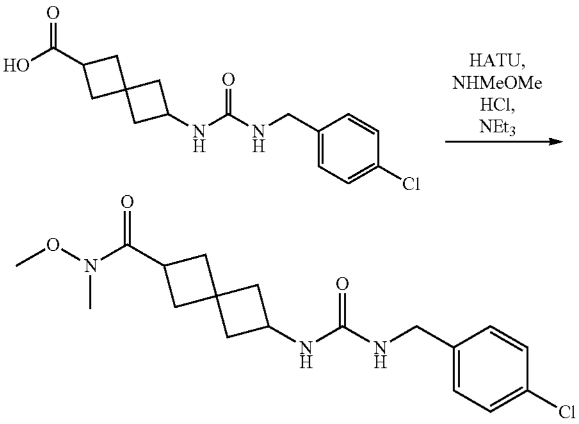

Step 1: Preparation of 6-(3-(4-chlorobenzyl)ureido)-N-methoxy-N-methylspiro[3.3]heptane-2-carboxamide HATU (6.48 g, 17.0 mmol, 1.1 equiv) was added to a stirring solution of 6-(3-(4-chlorobenzyl)ureido)spiro[3.3]heptane-2-carboxylic acid (5.0 g, 15.5 mmol, 1 equiv), N,O-dimethylhydroxylamine (3 g, 31.0 mmol, 2 equiv), and $NEt_3$ (6.3 g, 61.96 mmol, 4 equiv) in EtOAc (30 mL) and iPOH (10 mL) at rt. After 12 h, silica was added and solvent removed by rotary evaporation before the product was isolated by silica chromatography (0→10% MeOH/CH2Cl2) as a glassy solid (5.6 g, 98%). LRMS (APCI) m/z 366.1 (M+H). $^{1}$H NMR (400 MHz, Methanol-$d_4$) δ 7.32 (d, J=8.5 Hz, 2H), 7.26 (d, J=8.5 Hz, 2H), 4.28 (s, 2H), 4.03 (p, J=8.0 Hz, 1H), 3.69 (s, 3H), 3.44 (d, J=14.8 Hz, 1H), 3.18 (s, 3H), 2.54 (ddd, J=11.7, 7.2, 5.2 Hz, 1H), 2.35-2.27 (m, 3H), 2.27-2.20 (m, 1H), 2.11 (t, J=9.8 Hz, 1H), 1.93 (dd, J=11.0, 8.5 Hz, 1H), 1.83 (dd, J=11.4, 8.7 Hz, 1H).

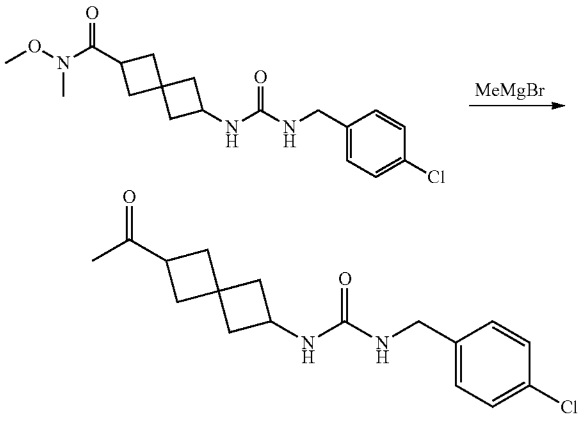

Step 2: Preparation of 1-(6-acetylspiro[3.3]heptan-2-yl)-3-(4-chlorobenzyl)urea

MeMgBr (3 M in THF, 15.4 mL, 46.4 mmol, 3 equiv) was added dropwise to a stirring solution of 6-(3-(4-chlorobenzyl)ureido)-N-methoxy-N-methylspiro[3.3]heptane-2-carboxamide (5.6 g, 15.5 mmol, 1 equiv) in THF (150 mL) at 0° C. After 1 h, the reaction was quenched with saturated sodium bicarbonate (500 mL), extracted with $CH_2Cl_2$ (3×250 mL), organics combined, dried over sodium sulfate, filtered, and solvent removed by rotary evaporation to give the desired compound as a white solid. LRMS (APCI) m/z 321. (M+H). $^1$H NMR (400 MHz, DMSO-$d_6$) δ 7.36 (d, J=8.3 Hz, 2H), 7.24 (d, J=8.2 Hz, 2H), 6.26 (t, J=6.1 Hz, 1H), 6.18 (d, J=8.0 Hz, 1H), 4.15 (d, J=6.0 Hz, 2H), 3.90 (q, J=8.1 Hz, 1H), 3.15 (p, J=8.6 Hz, 1H), 2.34 (ddd, J=10.6, 7.3, 5.3 Hz, 1H), 2.23-1.96 (m, 8H), 1.86-1.64 (m, 2H).

Example O

Synthesis of Intermediate 15.1

Preparation of 1-(6-(1-aminoethyl)spiro[3.3]heptan-2-yl)-3-(4-chlorobenzyl)urea (Intermediate 15.1)

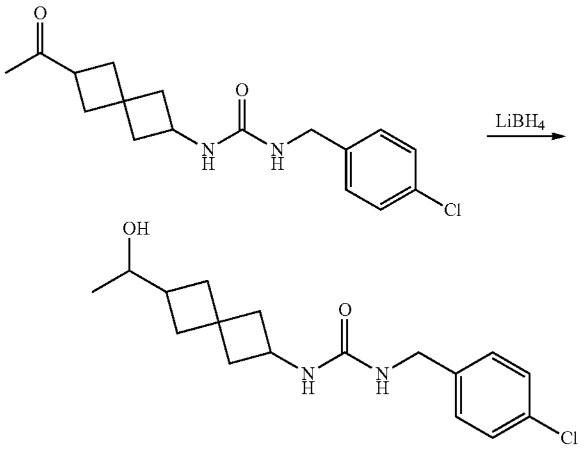

Step 1: Preparation of 1-(4-chlorobenzyl)-3-(6-(1-hydroxyethyl)spiro[3.3]heptan-2-yl)urea $LiBH_4$ (1 M in THF, 468 μL, 0.468 mmol, 0.5 equiv) was added to a stirring solution of 1-(6-acetylspiro[3.3]heptan-2-yl)-3-(4-chlorobenzyl)urea (300 mg, 0.935 mmol, 1 equiv) in THF (10 mL) at rt. After 1 h, the reaction was quenched with MeOH (10 mL) and silica before solvent was removed by rotary evaporation. The product was then isolated by silica chromatography (0→15% MeOH/$CH_2C_2$) as a white solid (300 mg, 99%). LRMS (APCI) m/z 323.1 (M+H). $^1$H NMR (400 MHz, Chloroform-d) δ 7.31 (d, J=8.4 Hz, 2H), 7.23 (d, J=8.3 Hz, 2H), 4.61 (s, 1H), 4.50 (t, J=6.4 Hz, 1H), 4.34 (d, J=5.8 Hz, 2H), 4.02 (q, J=7.9, 7.3 Hz, 1H), 3.65 (d, J=5.8 Hz, 1H), 3.51 (d, J=5.1 Hz, 2H), 2.56-2.43 (m, 1H), 2.31 (td, J=11.6, 4.8 Hz, 1H), 2.21-2.03 (m, 2H), 1.90-1.69 (m, 4H), 1.08 (dd, J=6.2, 3.0 Hz, 3H).

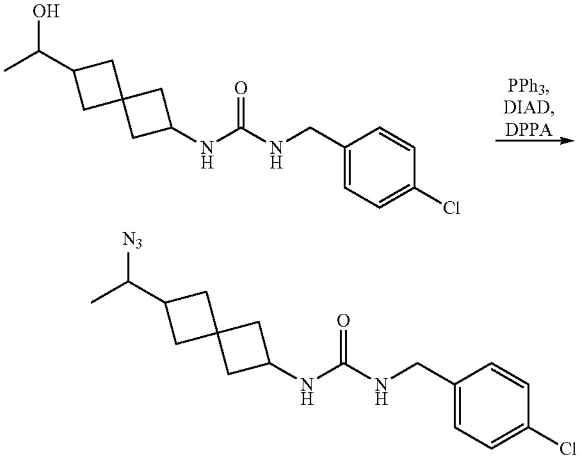

Step 2: Preparation of 1-(6-(1-azidoethyl)spiro[3.3]heptan-2-yl)-3-(4-chlorobenzyl)urea DIAD (376 mg, 1.86 mmol, 1.5 equiv) was added to a stirring solution of triphenylphosphine (1.2 g, 1.86 mmol, 1.5 equiv) in THF at 0° C. After 10 min, DPPA (682 mg, 2.48 mmol, 2 equiv) and 1-(4-chlorobenzyl)-3-(6-(1-hydroxyethyl)spiro[3.3]heptan-2-yl)urea (400 mg, 1.24 mmol, 1 equiv) were added and the reaction stirred for 14 h while returning to rt. Solvent was removed by rotary evaporation and product isolated by silica chromatography (0→100% EtOAc/hexanes) as a white solid (350 mg, 81%). LRMS (APCI) m/z 348.1 (M+H).

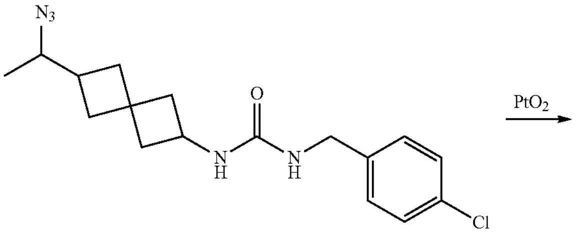

-continued

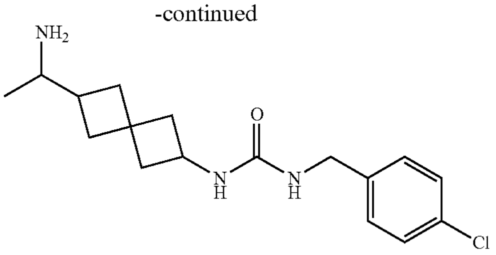

Step 3: Preparation of 1-(6-(1-aminoethyl)spiro[3.3]heptan-2-yl)-3-(4-chlorobenzyl)urea 1-(6-(1-Azidoethyl)spiro[3.3]heptan-2-yl)-3-(4-chlorobenzyl)urea (800 mg, 2.3 mmol, 1 equiv) and $PtO_2$ (52 mg, 0.23 mmol, 0.1 equiv) were suspended in MeOH (25 mL) before being stirred under $H_2$ (80 psi) for 1 h. The reaction was filtered through a pad of celite and solvent removed by rotary evaporation to give the product as a sticky semi-solid (740 mg, 99%). LRMS (APCI) m/z 322.1 (M+H).

Example P

Synthesis of Intermediate 16.1

Preparation of 1-(4-chlorobenzyl)-3-(6-((methylamino)methyl)spiro[3.3]heptan-2-yl)urea (Intermediate 16.1)

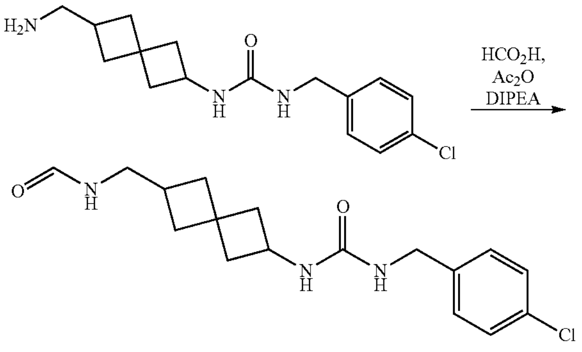

Step 1: Preparation of N-((6-(3-(4-chlorobenzyl)ureido)spiro[3.3]heptan-2-yl)methyl)formamide Formic acid (61 mg, 1.34 mmol, 2.3 equiv) and acetic anhydride (77 mg, 0.755 mmol, 1.3 equiv) were heated to 60° C. for 2 h. The reaction was then cooled to rt before 1-(6-(aminomethyl)spiro[3.3]heptan-2-yl)-3-(4-chlorobenzyl)urea (200 mg, 0.581 mmol, 1 equiv) and DIPEA (300 mg, 2.32 mmol, 4 equiv) were added. After 2 h, the reaction was quenched with MeOH, concentrated by rotary evaporation, and dried under high vaccum. LRMS (APCI) m/z 336.2 (M+H).

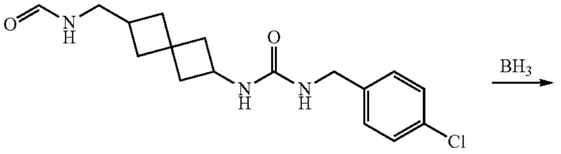

-continued

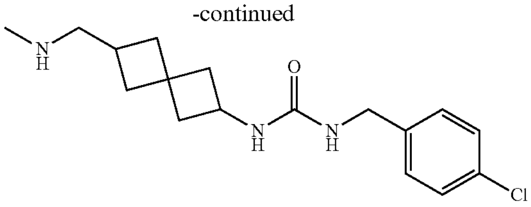

Step 2: Preparation of 1-(4-chlorobenzyl-3-(6-((methylamino)methyl)spiro[3.3]heptan-2-yl)urea N-((6-(3-(4-Chlorobenzyl)ureido)spiro[3.3]heptan-2-yl)methyl)formamide (138 mg, 0.412 mmol, 1 equiv) in THF (500 μL) was added dropwise to a stirring solution of $BH_3$ (dimethylsulfide complex, 2M in THF, 0.791 mL, 1.58 mmol, 4 equiv) at 0° C. before being allowed to return to rt. After 2 h, the reaction was quenched with MeOH and concentrated by rotary evaporation. The resulting oil was suspended in HCl (4 M in dioxanes, 5 mL), concentrated by rotary evaporation. The residue was triturated with EtOAc and resultant solid dried under high vacuum to give the product as a white solid (163 mg, 115%). LRMS (APCI) m/z 322.2 (M+H).

Example Q

Synthesis of Intermediate 17.1

Preparation of 6-((2-fluorophenyl)(methyl)amino)-6-oxohexan-1-aminium chloride (Intermediate 17.1)

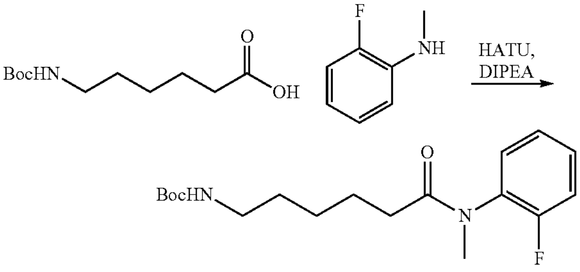

Step 1: tert-butyl (6-((2-fluorophenyl)(methyl)amino)-6-oxohexyl)carbamate

HATU (6.56 g, 17.2 mmol, 2 equiv) was added to a stirring solution of 6-((tert-butoxycarbonyl)amino)hexanoic acid (2 g, 8.6 mmol, 1 equiv), 2-fluoro-N-methylaniline (1.62 g, 12.9 mmol, 1.5 equiv), and DIPEA (3.34 g, 25.9 mmol, 3 equiv) in DMF (15 mL) at rt. After 72 h, the reaction was poured into water (200 mL), extracted with EtOAc (3×75 mL), organics combined, washed with ammonium chloride (3×50 mL), dried over sodium sulfate, filtered, and solvent removed by rotary evaporation. The resultant oil was filtered through a plug of silica to yield the product as an amber oil (2.5 g, 85%). LRMS (APCI) m/z 339.1 (M+H).

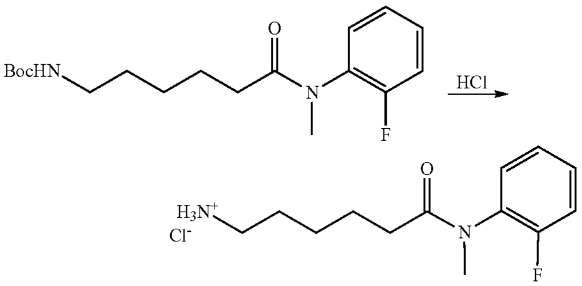

Step 2: 6-((2-fluorophenyl)(methyl)amino)-6-oxo-hexan-1-aminium chloride

HCl (4M in dioxanes, 15 mL, 60 mmol, 10 equiv) was added to a stirring solution of tert-butyl (6-((2-fluorophenyl)(methyl)amino)-6-oxohexyl)carbamate (2.1 g, 6.2 mmol, 1 equiv) in MeOH (100 mL) at rt. After 4 h, solvent was removed by rotary evaporation and dried under high vacuum to give the product as a white solid (1.5 g, 101%). LRMS (APCI) m/z 239.1 (M+H).

Example R

Synthesis of Intermediate 18.1

Preparation of 6-((2-fluorophenyl)(methyl)amino)-6-oxohexan-1-aminium chloride (Intermediate 18.1)

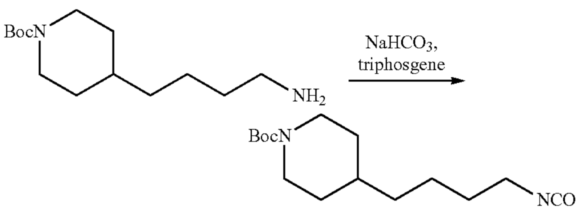

Step 1: tert-butyl 4-(4-isocyanatobutyl)piperidine-1-carboxylate

Triphosgene (926 mg, 3.12 mmol, 0.4 equiv) was added to a vigorously stirring solution of tert-butyl 4-(4-aminobutyl)piperidine-1-carboxylate (2 g, 7.8 mmol, 1 equiv) in saturated sodium bicarbonate (30 mL) and $CH_2C_2$ (30 mL) at 0° C. After 15 min, the organic layer was removed, aqueous later extracted with $CH_2C_2$ (3×30 mL), organic layers combined, dried over sodium sulfate, and filtered. The isocyanate solution was split and used in subsequent steps without further purification.

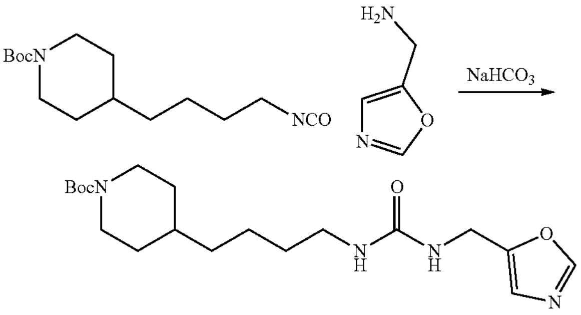

Step 2: tert-butyl 4-(4-(3-(oxazol-5-ylmethyl)ureido)butyl)piperidine-1-carboxylate Oxazol-5-ylmethanamine (152 mg, 1.56 mmol, 1 equiv) was added to a stirring solution of tert-butyl 4-(4-isocyanatobutyl)piperidine-1-carboxylate (441 mg, 1.56 mmol, 1 equiv) in $CH_2Cl_2$ (5 mL) and saturated sodium bicarbonate (3 mL) at rt. After 4 h, the organic layer was separated and filtered through a pad of silica, washed with 5% MeOH/$CH_2C_2$ (20 mL), and solvent removed by rotary evaporation to give the crude product (459 mg, 44%) which was used without further purification. LRMS (APCI) m/z 381.2 (M+H).

Intermediates 18.2-18.5 were prepared in a similar manner as Intermediate 18.1, using the reagents provided in the table below.

| Intermediate | Amine | Structure, Name and Data |
|---|---|---|
| 18.2 | (4-methoxyphenyl)methanamine | 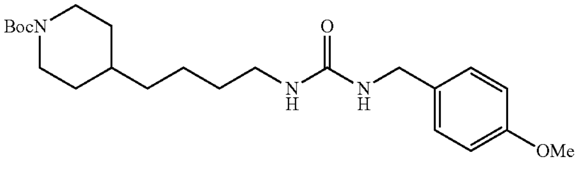 [SMILES: COc1ccc(CNC(=O)NCCCCC2CCN(C(=O)OC(C)(C)C)CC2)cc1] tert-butyl 4-(4-(3-(4-methoxybenzyl)ureido)butyl)piperidine-1-carboxylate. LRMS (APCI) m/z 420.2.1 (M + H). |

-continued

| Intermediate | Amine | Structure, Name and Data |
|---|---|---|
| 18.3 | 4-(aminomethyl)benzamide | 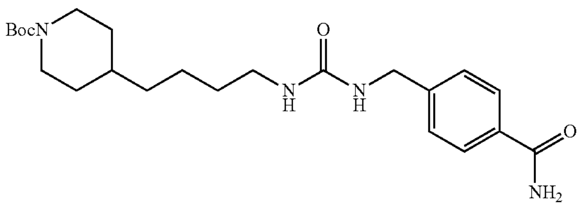 [SMILES: CC(C)(C)OC(=O)N1CCC(CCCCNC(=O)NCc2ccc(C(N)=O)cc2)CC1]<br>tert-butyl 4-(4-(3-(4-carbamoylbenzyl)ureido)butyl)piperidine-1-carboxylate. LRMS (APCI) m/z 433.21 (M + H). |
| 18.4 | pyridin-4-ylmethanamine | 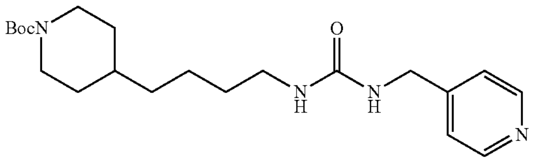 [SMILES: CC(C)(C)OC(=O)N1CCC(CCCCNC(=O)NCc2ccncc2)CC1]<br>tert-butyl 4-(4-(3-(pyridin-4-ylmethyl)ureido)butyl)piperidine-1-carboxylate. LRMS (APCI) m/z 391.3 (M + H). |
| 18.5 | (1H-pyrazol-4-yl)methanamine | 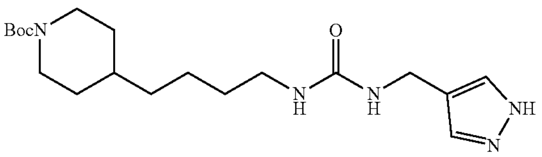 [SMILES: CC(C)(C)OC(=O)N1CCC(CCCCNC(=O)NCc2cn[nH]c2)CC1]<br>tert-butyl 4-(4-(3-((1H-pyrazol-4-yl)methyl)ureido)butyl)piperidine-1-carboxylate. LRMS (APCI) m/z 380.2 (M + H). |

Example S

Synthesis of Intermediate 19.1

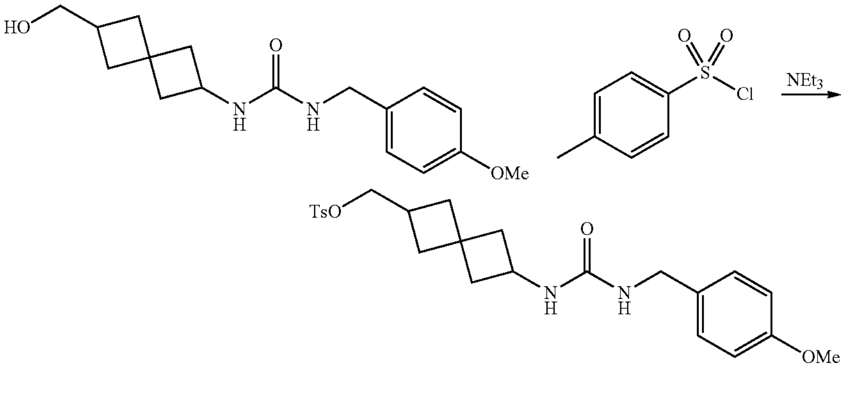

Preparation of (6-(3-(4-methoxybenzyl)ureido)spiro[3.3]heptan-2-yl)methyl 4-methylbenzenesulfonate (Intermediate 19.1)

4-Methylbenzenesulfonyl chloride (532 mg, 2.79 mmol, 1.25 equiv) was added to a stirring solution of 1-(6-(hydroxymethyl)spiro[3.3]heptan-2-yl)-3-(4-methoxybenzyl)urea (Intermediate 10.1, 680 mg, 2.23 mmol, 1 equiv) and triethylamine (452 mg, 4.47 mmol, 2 equiv) in $CH_2C_2$ (25 mL) at rt. After 12 h, the reaction was quenched with saturated sodium bicarbonate (100 mL), extracted with $CH_2C_2$ (3×100 mL), organics combined, dried over sodium sulfate, filtered, and solvent removed by rotary evaporation. LRMS (APCI) m/z 459.1 (M+H). $^1$H NMR (400 MHz, Chloroform-d) δ 7.79 (d, J=8.2 Hz, 2H), 7.36 (d, J=7.8 Hz, 2H), 7.22 (d, J=8.2 Hz, 2H), 6.91-6.81 (m, 2H), 4.57 (t, J=5.6 Hz, 1H), 4.47 (d, J=7.4 Hz, 1H), 4.28 (d, J=5.5 Hz, 2H), 4.00 (d, J=7.0 Hz, 2H), 3.94 (d, J=6.6 Hz, 2H), 3.81 (s, 3H), 2.47 (s, 3H), 2.47-2.40 (m, 1H), 2.27 (dt, J=12.1, 6.3 Hz, 1H), 2.11 (ddd, J=11.7, 8.4, 3.4 Hz, 1H), 1.98 (td, J=10.0, 8.3, 2.8 Hz, 1H), 1.80-1.71 (m, 4H).

Intermediate 19.2 was prepared in a similar manner as Intermediate 19.1, using the reagents provided in the table below.

| Intermediate | Alcohol | Structure, Name and Data |
|---|---|---|
| 19.2 | Intermediate 10.2 | 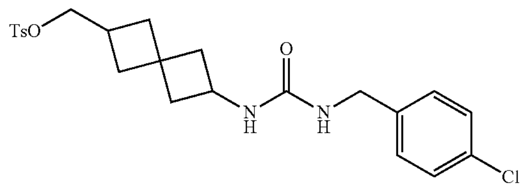 [SMILES: Cc1ccc(S(=O)(=O)OCC2CC3(C2)CC(NC(=O)NCc2ccc(Cl)cc2)C3)cc1] (6-(3-(4-chlorobenzyl)ureido)spiro[3.3]heptan-2-yl)methyl 4-methylbenzenesulfonate. LRMS (APCI) m/z 463.2 (M + H). |

Example T

Synthesis of Intermediate 20.1

Preparation of tert-butyl 4-(4-aminobutyl-4,4-d2) piperidine-1-carboxylate (Intermediate 20.1)

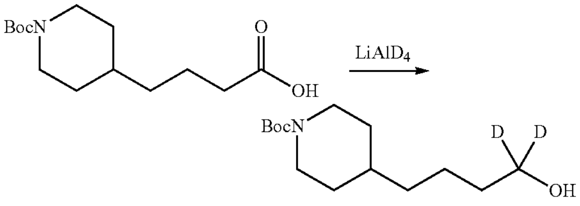

Step 1: tert-butyl 4-(4-hydroxybutyl-4,4-d2)piperidine-1-carboxylate

To a solution of 4-[1-(tert-butoxycarbonyl)piperidin-4-yl] butanoic acid (1 g, 3.685 mmol, 1 equiv) in THF (15 mL) at 0° C. was added $LiAlD_4$ (4.4 mL, 1 mol/L, 1.20 equiv) dropwise under nitrogen atmosphere. After stirred at 0° C. for 2 h under nitrogen atmosphere, the reaction was determined by LCMS. The mixture was adjusted to pH 8 with KOH (aq.) and filtered to remove solids. The filtrate was dried over anhydrous $Na_2SO_4$ and concentrated under reduced pressure to afford the product (860 mg) as a white oil. LRMS (APCI) m/z 204 [M+H−56].

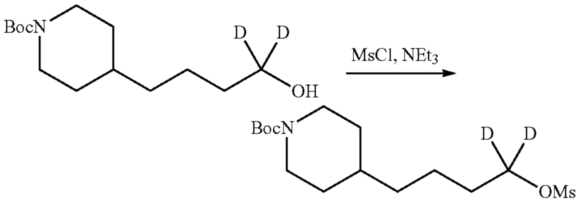

Step 2: tert-butyl 4-(4-((methylsulfonyl)oxy)butyl-4, 4-d2)piperidine-1-carboxylate To a solution of tert-butyl 4-[4-hydroxy(4,4-2H2)butyl] piperidine-1-carboxylate (800 mg, 3.084 mmol, 1 equiv) in DCM (10 mL) at 0° C. were added methanesulfonyl chloride (526 mg, 4.59 mmol, 1.5 equiv) and triethylamine (621 mg, 6.14 mmol, 1.99 equiv). After stirred at r.t. for 2 h, to the resulting mixture was added water (20 mL), extracted with $CH_2Cl_2$ (3×30 mL). The combined organic layers were washed with brine (2×30 mL), dried over anhydrous $Na_2SO_4$, concentrated under reduced pressure to afford the product (1 g) as a yellow oil. LRMS (APCI) m/z 282 [M+H−56].

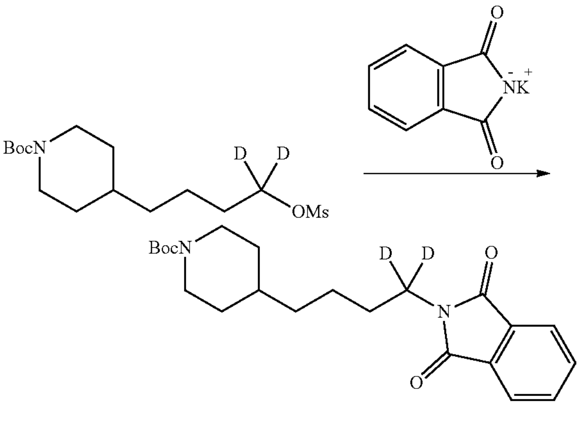

Step 3: tert-butyl 4-(4-(1,3-dioxoisoindolin-2-yl) butyl-4,4-d2)piperidine-1-carboxylate To a solution of tert-butyl 4-[4-(methanesulfonyloxy)(4, 4-2H2)butyl]piperidine-1-carboxylate (1.0 g, 2.96 mmol, 1 equiv) in MeCN (15 mL) at r.t. was added 2-potassioisoindole-1,3-dione (0.83 g, 4.48 mmol, 1.5 equiv). After being stirred at 80° C. overnight, the resulting mixture was cooled to r.t., added water (30 mL), extracted with $CH_2Cl_2$ (3×30 mL). The combined organic layers were washed with brine (2×30 mL), dried over anhydrous $Na_2SO_4$. After filtration, the filtrate was concentrated under reduced pressure to afford the product (1 g) as a yellow oil. LRMS (APCI) m/z 333 [M+H−56].

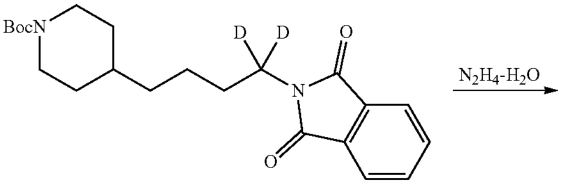

-continued

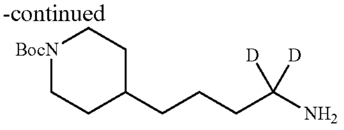

Step 4: tert-butyl 4-(4-aminobutyl-4,4-d2)piperidine-1-carboxylate

To a solution of tert-butyl 4-[4-(1,3-dioxoisoindol-2-yl)(4,4-2H2)butyl]piperidine-1-carboxylate (1.0 g, 2.57 mmol, 1 equiv) in ethyl alcohol (10 mL) at r.t. was added hydrazine monohydrate (642 mg, 13.1 mmol, 5.1 equiv). After being stirred at 80° C. overnight, the mixture was cooled to r.t. and filtered to remove solids. The filtrate was concentrated under reduced pressure to afford the product (630 mg) as a yellow semi-solid. LRMS (ES) m/z 203[M+H−56].

Example U

Synthesis of Intermediate 21.1

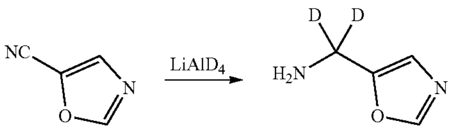

Preparation of oxazol-5-ylmethan-d2-amine (Intermediate 21.1)

To a solution of oxazole-5-carbonitrile (188 mg, 2.00 mmol, 1.0 equiv) in THF (6 mL) was added $LiAlD_4$ (84 mg, 2.00 mmol, 1.0 equiv) as solid. The mixture was vigorously stirred at 23° C. for 3 h. Upon completion, $Na_2SO_4{\cdot}10H_2O$ was added carefully to quench the reaction until gas evolution ceased. The solid was filtered off and the filtrate was concentrated to yield the crude oxazol-5-ylmethan-$d_2$-amine (90 mg, 45%), which was used directly without further purification. LRMS (APCI+) m/z 101.2 (M+H).

Example V

Synthesis of Intermediates 22.1

Preparation of 6-(pyridin-4-ylmethyl)spiro[3.3]heptan-2-amine (Intermediate 22.1)

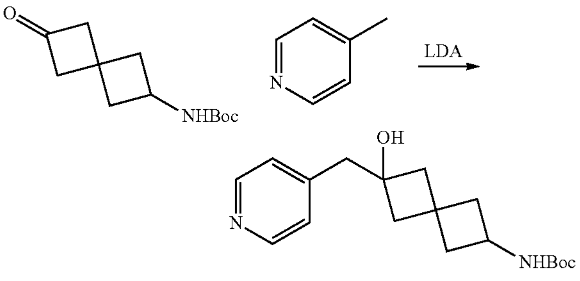

Step 1: tert-butyl (6-hydroxy-6-(pyridin-4-ylmethyl)spiro[3.3]heptan-2-yl)carbamate To a solution of diisopropylamine (303 mg, 3.00 mmol, 2.25 equiv) in THF (5 mL) was added n-BuLi (2.5 M in hexanes, 1.17 mL, 2.93 mmol, 2.2 equiv) at −30° C. The solution was slightly warmed to −10° C. over 20 min. Then the freshly prepared LDA solution was cooled down to −78° C., followed by the dropwise addition of a THF solution (1 mL) of 4-picoline (273 mg, 2.93 mmol, 2.2 equiv). The deprotonation was kept at this temperature for 1 h. Then a solution of tert-butyl (6-oxospiro[3.3]heptan-2-yl)carbamate (300 mg, 1.33 mmol, 1.0 equiv) in THF (2 mL) was added at −78° C. over 1 min. The reaction was then allowed to warm to 23° C. over 2 h and it was further stirred at this temperature for 1 h. Upon completion, half-saturated $NH_4Cl$ solution was added to quench the reaction. The aqueous phase was extracted by EtOAc (5 mL×2). The combined organic phase was washed with brine, dried ($MgSO_4$), filtered, and concentrated to yield the crude tert-butyl (6-hydroxy-6-(pyridin-4-ylmethyl)spiro[3.3]heptan-2-yl)carbamate. LRMS (APCI+) m/z 319.1 (M+H).

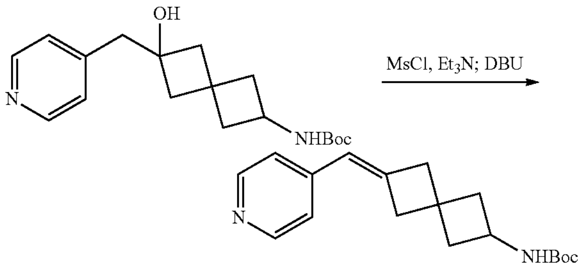

Step 2: tert-butyl (6-(pyridin-4-ylmethylene)spiro[3.3]heptan-2-yl)carbamate

To a solution of the crude tert-butyl (6-hydroxy-6-(pyridin-4-ylmethyl)spiro[3.3]heptan-2-yl)carbamate (up to 1.33 mmol, 1.0 equiv) in $CH_2Cl_2$ (2 mL) was added $Et_3N$ (269 mg, 2.66 mmol, 2.0 equiv) and MsCl (183 mg, 1.60 mmol, 1.2 equiv). The reaction was stirred at 23° C. for 2 h. Upon completion, volatiles were removed in vacuo and PhMe (1.5 mL) was added, followed by DBU (1.01 g, 6.65 mmol, 5.0 equiv). The mixture was heated at 60° C. for 14 h. Upon completion, the reaction was then poured into a mixture of half-saturated brine (10 mL) and EtOAc (10 mL). The aqueous phase was extracted by EtOAc (5 mL×2). The combined organic phase was washed with brine, dried ($MgSO_4$), filtered, concentrated, and purified by flash column chromatography (silica, hexanes/EtOAc) to yield tert-butyl (6-(pyridin-4-ylmethylene)spiro[3.3]heptan-2-yl)carbamate (241 mg, 60% yield over 2 steps) as a colorless oil. LRMS (APCI+) m/z 301.1 (M+H).

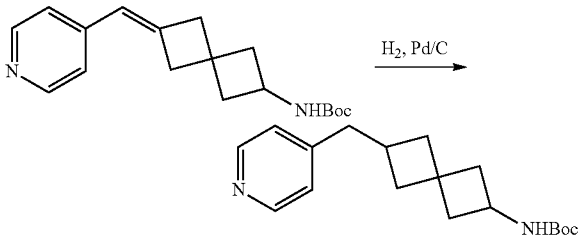

Step 3: tert-butyl (6-(pyridin-4-ylmethyl)spiro[3.3]heptan-2-yl)carbamate

To a solution of tert-butyl (6-(pyridin-4-ylmethylene)spiro[3.3]heptan-2-yl)carbamate (240 mg, 0.80 mmol, 1.0 equiv) in THF/MeOH (6 mL, 2:1) was added Pd/C (10% wt. loading, 30% mass equiv). The mixture was bubbled through $H_2$ gas for 3 min and then stirred under 1 atm $H_2$ atmosphere for 14 h at 23° C. Upon completion, solid was filtered off and the filtrate was concentrated to yield the crude tert-butyl (6-(pyridin-4-ylmethyl)spiro[3.3]heptan-2-yl)carbamate which was directly subjected to next step. LRMS (APCI+) m/z 303.1 (M+H).

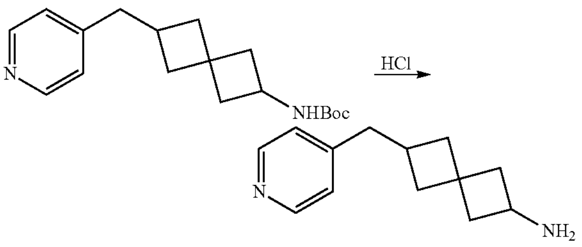

Step 4: 6-(pyridin-4-ylmethyl)spiro[3.3]heptan-2-amine

To a solution of the crude tert-butyl (6-(pyridin-4-ylmethyl)spiro[3.3]heptan-2-yl)carbamate (up to 0.80 mmol) in $CH_2Cl_2$ (3 mL) was added TFA (0.5 mL) at 23° C. The mixture was stirred at this temperature for 3 h. Upon completion, volatiles were removed in vacuo to yield the crude 6-(pyridin-4-ylmethyl)spiro[3.3]heptan-2-amine (Intermediate 22.1, 150 mg, 93%) which was directly used without further purifications. LRMS (APCI+) m/z 203.1 (M+H).

Example W

Synthesis of Intermediate 23.1

Preparation of 6-(5-(6-methylpyridin-3-yl)-1,3,4-oxadiazol-2-yl)spiro[3.3]heptan-2-amine (Intermediate 23.1)

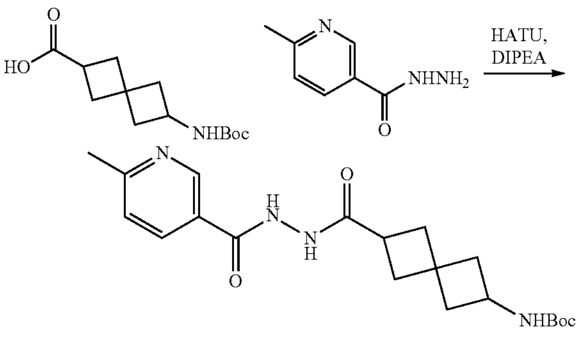

Step 1: tert-butyl (6-(2-(6-methylnicotinoyl)hydrazine-1-carbonyl)spiro[3.3]heptan-2-yl)carbamate To a solution of 6-((tert-butoxycarbonyl)amino)spiro[3.3]heptane-2-carboxylic acid (180 mg, 0.71 mmol, 1.0 equiv)

in DMF (2 mL) was added 6-methylnicotinohydrazide (107 mg, 0.71 mmol, 1.0 equiv) and HATU (280 mg, 0.78 mmol, 1.1 equiv), followed by DIPEA (215 mg, 2.12 mol, 3.0 equiv). The reaction was stirred at 23° C. for 14 h. Upon completion, EtOAc (5 mL) was added. The organic phase was washed by brine, dried ($MgSO_4$), filtered, and concentrated to yield the crude tert-butyl (6-(2-(6-methylnicotinoyl)hydrazine-1-carbonyl)spiro[3.3]heptan-2-yl)carbamate which was directly used in the next step without further purification. LRMS (APCI+) m/z 389.1 (M+H).

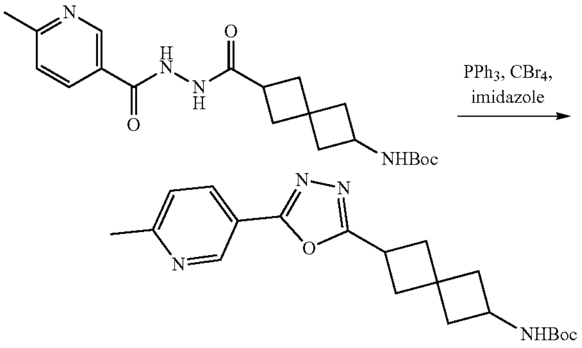

Step 2: tert-butyl (6-(5-(6-methylpyridin-3-yl-1,3,4-oxadiazol-2-yl)spiro[3.3]heptan-2-yl)carbamate To a solution of the crude tert-butyl (6-(2-(6-methylnicotinoyl)hydrazine-1-carbonyl)spiro[3.3]heptan-2-yl)carbamate (0.71 mmol, 1.0 equiv) in THF (2 mL) was added Triphenylphosphine (223 mg, 0.85 mmol, 1.2 equiv), imidazole (145 mg, 2.12 mmol, 3.0 equiv), tetrabromomethane (259 mg, 0.78 mmol, 1.1 equiv) sequentially. The reaction was stirred at 23° C. for 16 h. Upon completion, a mixed solution of $NaHCO_3$ and $Na_2S_2O_3$ was added to quench the reaction. The aqueous phase was extracted by $CH_2Cl_2$ (5 mL×3). The combined organic phase was washed by brine, dried ($MgSO_4$), filtered, concentrated, and purified by flash column chromatography (silica, $CH_2C_2$/MeOH) to yield tert-butyl (6-(5-(6-methylpyridin-3-yl)-1,3,4-oxadiazol-2-yl)spiro[3.3]heptan-2-yl)carbamate (148 mg, 57% over 2 steps) as a white solid. LRMS (APCI+) m/z 371.1 (M+H).

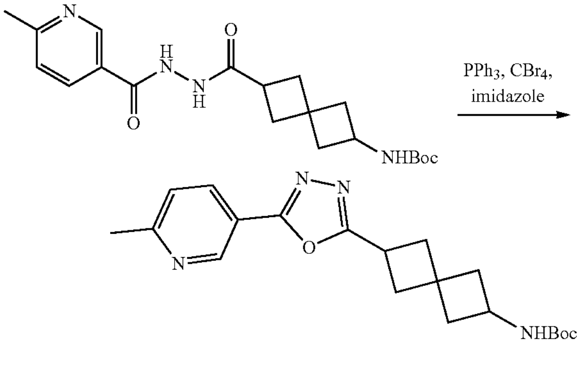

Step 3: 6-(5-(6-methylpyridin-3-yl)-1,3,4-oxadiazol-2-yl)spiro[3.3]heptan-2-amine To a solution of tert-butyl (6-(5-(6-methylpyridin-3-yl)-1,3,4-oxadiazol-2-yl)spiro[3.3]heptan-2-yl)carbamate (74 mg, 0.20 mmol, 1.0 equiv) in $CH_2C_2$ (1 mL) was added HCl (4 M in 1,4-dioxane, 0.40 mL, 1.60 mmol, 8.0 equiv). The mixture was stirred at 23° C. for 20 h. Upon completion, the volatile was removed in vacuo to yield the crude 6-(5-(6-methylpyridin-3-yl)-1,3,4-oxadiazol-2-yl)spiro[3.3]heptan-2-amine (intermediate 23.1, 52 mg, 96%) as a white waxy solid which was directly used without further purifications. LRMS (APCI+) m/z 271.1 (M+H).

Example X

Synthesis of Intermediate 24.1

Preparation of 6-(pyrimidin-2-ylmethyl)spiro[3.3]heptan-2-amine (Intermediate 24.1)

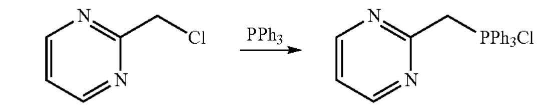

Step 1: tert-butyl (6-(pyrimidin-2-ylmethylene)spiro[3.3]heptan-2-yl)carbamate

To a vial charged with 2-(chloromethyl)pyrimidine HCl salt (495 mg, 3.00 mmol, 1.0 equiv) was added triphenylphosphine (787 mg, 3.00 mmol, 1.0 equiv) and toluene (2 mL). The mixture was stirred at 100° C. for 16 h. Then solvent was decanted and residue was dried to yield the crude triphenyl(pyrimidin-2-yl-methyl)phosphonium chloride. To the crude ylide was added DMSO (2 mL), followed by sodium tert-butoxide (577 mg, 6.00 mmol, 2.0 equiv) at 23° C. The reaction was stirred at this temperature for 1 h, followed by the addition of tert-butyl (6-oxospiro[3.3]heptan-2-yl)carbamate (676 mg, 3.00 mmol, 1.0 equiv). The dark brownish mixture was stirred at 23° C. for 18 h before it was poured into a mixture of half-saturated $NH_4Cl$ solution (10 mL) and $CH_2Cl_2$ (10 mL). The layers were separated and the aqueous phase was extracted by $CH_2Cl_2$ (5 mL×2). The combined organic phase was washed by brine, dried ($MgSO_4$), filtered, concentrated, and purified by flash column chromatography (silica, $CH_2C_2$/MeOH) to yield tert-butyl (6-(pyrimidin-2-ylmethylene)spiro[3.3]heptan-2-yl)carbamate (250 mg, 28% yield) as a yellowish gum. LRMS (APCI+) m/z 302.1 (M+H).

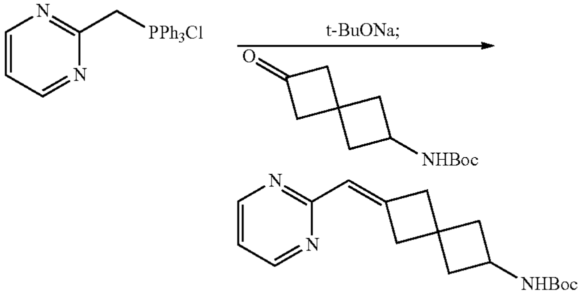

Step 2: tert-butyl (6-(pyrimidin-2-ylmethyl)spiro[3.3]heptan-2-yl)carbamate

To a vial charged with yield tert-butyl (6-(pyrimidin-2-ylmethylene)spiro[3.3]heptan-2-yl)carbamate (250 mg, 0.83 mmol, 1.0 equiv), piperidine (74 mg, 0.87 mmol, 1.05 equiv), formic acid (40 mg, 0.87 mmol, 1.05 equiv), Pd/C (10% wt. loading, 20% mass equiv), and EtOH (3 mL). The mixture was stirred at 75° C. for 6 h. Upon completion, solid was filtered off and the filtrate was concentrated and purified by flash column chromatography (silica, $CH_2C_2$/MeOH) to yield tert-butyl (6-(pyrimidin-2-ylmethyl)spiro[3.3]heptan-2-yl)carbamate (142 mg, 56% yield) as a light yellowish gum. LRMS (APCI+) m/z 304.2 (M+H).

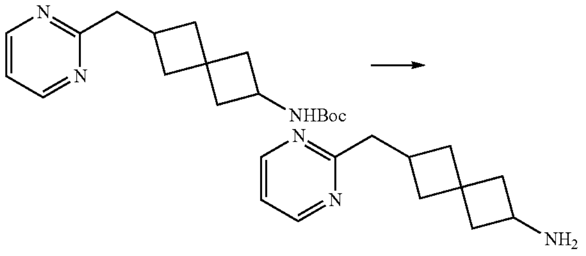

Step 3: 6-(pyrimidin-2-ylmethyl)spiro[3.3]heptan-2-amine

To a solution of tert-butyl (6-(pyrimidin-2-ylmethyl)spiro[3.3]heptan-2-yl)carbamate (142 mg, 0.47 mmol, 1.0 equiv) in $CH_2Cl_2$ (1 mL) was added HCl (4 M in 1,4-dioxane, 0.93 mL, 3.74 mmol, 8.0 equiv). The mixture was stirred at 23° C. for 20 h. Upon completion, the volatile was removed in vacuo to yield the crude 6-(pyrimidin-2-ylmethyl)spiro[3.3]heptan-2-amine (Intermediate 24.1, 95 mg, 99%) as a light yellowish gum which was directly used without further purifications. LRMS (APCI+) m/z 204.1 (M+H).

Example Y

Synthesis of Intermediate 25.1

Preparation of 6-(pyridin-4-yloxy)spiro[3.3]heptan-2-amine (Intermediate 25.1)

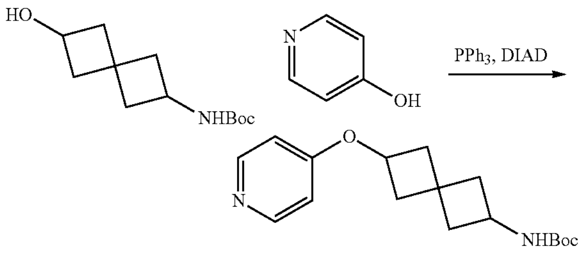

Step 1: tert-butyl (6-(pyridin-4-yloxy)spiro[3.3]heptan-2-yl)carbamate

To a vial charged with tert-butyl N-{6-hydroxyspiro[3.3]heptan-2-yl}carbamate (227 mg, 1.00 mmol, 1.0 equiv), triphenylphosphine (393 mg, 1.50 mmol, 1.5 equiv), 4-hydroxypyridine (142 mg, 1.50 mmol, 1.5 equiv) was added toluene (3 mL), followed by diisopropyl azodicarboxylate (DIAD, 303 mg, 1.50 mmol, 1.5 equiv). The reaction was then stirred at 80° C. for 3 h. Upon completion, the reaction was directly concentrated and purified by reverse-phase column chromatography ($H_2O$ (0.1% $HCO_2H$)/MeCN (0.1% $HCO_2H$)) to yield tert-butyl (6-(pyridin-4-yloxy)spiro[3.3]heptan-2-yl)carbamate (166 mg, 54%) as a colorless oil. LRMS (APCI+) m/z 305.1 (M+H).

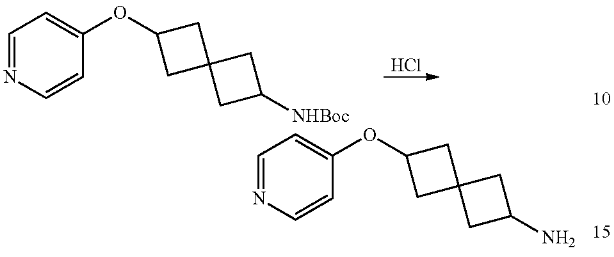

Step 1: 6-(pyridin-4-yloxy)spiro[3.3]heptan-2-amine

To a solution of tert-butyl (6-(pyridin-4-yloxy)spiro[3.3]heptan-2-yl)carbamate (166 mg, 0.545 mmol, 1.0 equiv) in $CH_2Cl_2$ (1 mL) was added HCl (4 M in 1,4-dioxane, 1.09 mL, 4.36 mmol, 8.0 equiv). The mixture was stirred at 23° C. for 20 h. Upon completion, the volatile was removed in vacuo to yield the crude 6-(pyridin-4-yloxy)spiro[3.3]heptan-2-amine (Intermediate 25.1, 110 mg, 98%) as a light yellowish gum which was directly used without further purifications. LRMS (APCI+) m/z 205.1 (M+H).

Intermediate 25.2 was prepared in a similar manner as Intermediate 25.1, using the reagents provided in the table below.

| Intermediate | Phenol | Structure, Name and Data |
|---|---|---|
| 25.2 | 3-hydroxypyridine | 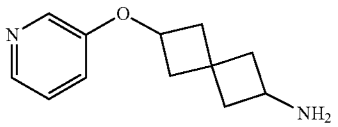 [SMILES: NC1CC2(C1)CC(Oc1cccnc1)C2] 6-(pyridin-3-yloxy)spiro[3.3]heptan-2-amine. LRMS (APCI) m/z 205.1 (M + H). |

Example Z

Synthesis of Intermediates 26.1

Preparation of 6-(methylsulfonyl)spiro[3.3]heptan-2-amine (Intermediate 26.1)

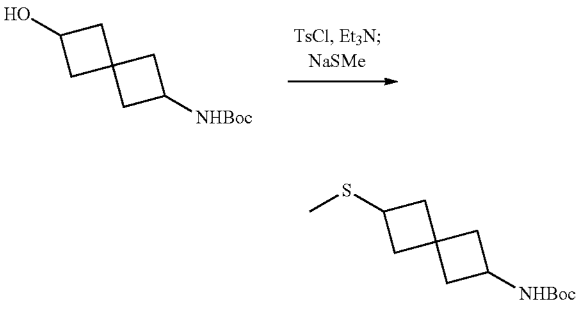

Step 1: tert-butyl (6-(methylthio)spiro[3.3]heptan-2-yl)carbamate

To a solution of tert-butyl N-{6-hydroxyspiro[3.3]heptan-2-yl}carbamate (227 mg, 1.00 mmol, 1.0 equiv) in $CH_2Cl_2$ (3 mL) was added $Et_3N$ (202 mg, 2.00 mmol, 2.0 equiv) and TsCl (229 mg, 1.20 mmol, 1.2 equiv) at 23° C. The mixture was stirred at 23° C. for 3 h before it was poured into a half-saturated $NaHCO_3$ solution. The aqueous phase was extracted by $CH_2Cl_2$ (5 mL×2) and the combined organic phase was washed by brine, dried ($MgSO_4$), filtered, concentrated, and purified by flash column chromatography (silica, hexanes/EtOAc) to yield the desired tosylate. Next, to a suspension of the tosylate obtained above in EtOH (3 mL) was added sodium thiomethoxide (210 mg, 3.00 mmol, 3.0 equiv). The mixture was stirred at 60° C. for 18 h. Upon completion, the reaction was quenched by half-saturated $NH_4Cl$ solution. The aqueous phase was extracted by EtOAc (5 mL×2). The combined organic phase was washed by brine, dried ($MgSO_4$), filtered, and concentrated to yield the crude tert-butyl (6-(methylthio)spiro[3.3]heptan-2-yl)carbamate (183 mg, 71%) as a light yellowish gum. LRMS (APCI+) m/z 258.1 (M+H).

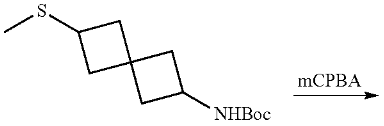

-continued

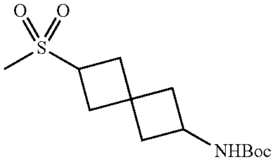

Step 2: tert-butyl (6-(methylsulfonyl)spiro[3.3]heptan-2-yl)carbamate

To a solution of tert-butyl (6-(methylthio)spiro[3.3]heptan-2-yl)carbamate (183 mg, 0.71 mmol, 1.0 equiv) in $CH_2C_2$ (3 mL) was added mCPBA (367 mg, 2.13 mmol, 3.0 equiv) at 0° C. The reaction was then stirred at 23° C. for 3 h. Upon completion, a mixed solution of $NaHCO_3$ and $Na_2S_2O_3$ was added to quench the reaction. The aqueous phase was extracted by $CH_2C_2$ (5 mL×3). The combined organic phase was washed by brine, dried ($MgSO_4$), filtered, and concentrated to yield the crude tert-butyl (6-(methylsulfonyl)spiro[3.3]heptan-2-yl)carbamate (169 mg, 83%) as a white solid, which was directly used without further purifications. LRMS (APCI+) m/z 290.2 (M+H).

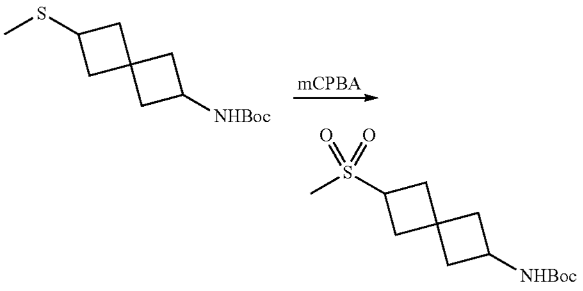

Step 3: 6-(methylsulfonyl)spiro[3.3]heptan-2-amine

To a solution of tert-butyl (6-(methylsulfonyl)spiro[3.3] heptan-2-yl)carbamate (169 mg, 0.584 mmol, 1.0 equiv) in $CH_2Cl_2$ (1 mL) was added HCl (4 M in 1,4-dioxane, 1.17 mL, 4.67 mmol, 8.0 equiv). The mixture was stirred at 23° C. for 20 h. Upon completion, the volatile was removed in vacuo to yield the crude 6-(methylsulfonyl)spiro[3.3]heptan-2-amine (Intermediate 26.1, 109 mg, 98%) as a light yellowish gum which was directly used without further purifications. LRMS (APCI+) m/z 190.1 (M+H).

Example AA

Synthesis of Intermediate 27.1

Preparation of 6-(pyridin-4-ylmethoxy)spiro[3.3] heptan-2-amine (Intermediate 27.1)

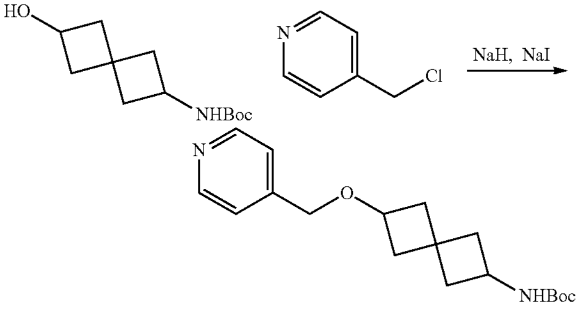

Step 1: tert-butyl (6-(pyridin-4-ylmethoxy)spiro [3.3]heptan-2-yl)carbamate

To a solution of tert-butyl (6-hydroxyspiro[3.3]heptan-2-yl)carbamate (120 mg, 0.53 mmol, 1.0 equiv) in THF (1 mL) was added NaH (44 mg, 60% suspension in mineral oil, 1.11 mmol, 2.1 equiv) at 0° C. The deprotonation was stirred at 23° C. for 1 h. Then potassium iodide (18 mg, 0.11 mmol, 0.2 equiv) and 4-(chloromethyl)pyridine HCl salt (91 mg, 0.55 mmol, 1.05 equiv) was added sequentially. The reaction was stirred at 23° C. for 4 h. Upon completion, half-saturated $NH_4Cl$ solution (5 mL) was added to quench the reaction. The aqueous phase was extracted by $CH_2Cl_2$ (3 mL×2). The combined organic phase was washed by brine, dried ($MgSO_4$), filtered, concentrated, and purified by flash column chromatography (silica, $CH_2Cl_2$/MeOH) to yield tert-butyl (6-(pyridin-4-ylmethoxy)spiro[3.3]heptan-2-yl) carbamate (139 mg, 83% yield) as a colorless gum. LRMS (APCI+) m/z 319.1 (M+H).

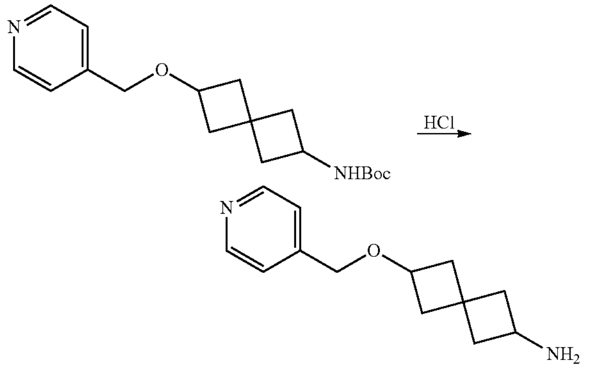

Step 2: 6-(pyridin-4-ylmethoxy)spiro[3.3]heptan-2-amine

To a solution of tert-butyl (6-(pyridin-4-ylmethoxy)spiro [3.3]heptan-2-yl)carbamate (139 mg, 0.436 mmol, 1.0 equiv) in $CH_2Cl_2$ (1 mL) was added HCl (4 M in 1,4-dioxane, 0.87 mL, 3.49 mmol, 8.0 equiv). The mixture was stirred at 23° C. for 20 h. Upon completion, the volatile was removed in vacuo to yield the crude 6-(pyridin-4-ylmethoxy)spiro[3.3]heptan-2-amine (Intermediate 27.1, 95 mg, 99%) as a light yellowish gum which was directly used without further purifications. LRMS (APCI+) m/z 219.1 (M+H).

Intermediate 27.2 was prepared in a similar manner as Intermediate 27.1, using the reagents provided in the table below.

| Intermediate | Phenol | Structure, Name and Data |
|---|---|---|
| 27.2 | 3-(bromomethyl)pyridine | 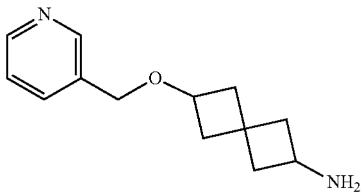 [SMILES: NC1CC2(C1)CC(OCc1cccnc1)C2] Synthesis of 6-(pyridin-3-ylmethoxy)spiro[3.3]heptan-2-amine. LRMS (APCI) m/z 219.1 (M + H). |

Example 1

Preparation of 1-(2-(3-(2-chlorophenyl)propanoyl)-2-azaspiro[3.3]heptan-6-yl)-3-(4-methoxybenzyl) urea (Compound 135)

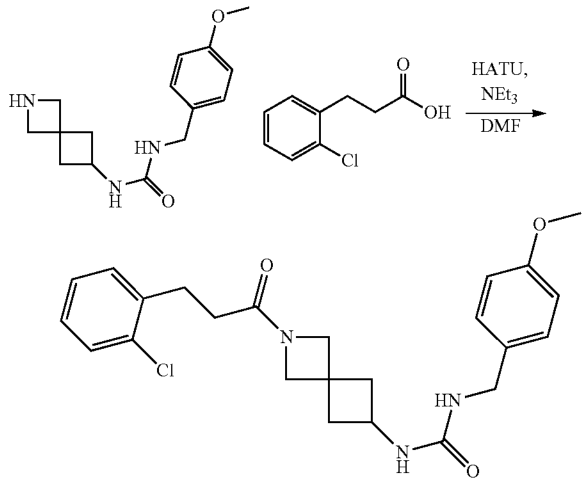

HATU (207 mg, 0.545 mmol, 1.5 equiv) was added to a stirring solution of 3-(2-chlorophenyl)propanoic acid (101 mg, 0.545 mmol, 1.5 equiv), 1-(4-methoxybenzyl)-3-(2-azaspiro[3.3]heptan-6-yl)urea (100 mg, 0.257 mmol, 1 equiv) and $NEt_3$ (147 μL, 0.770 mmol, 3 equiv) in DMF (1 mL) at rt. After 4 h, the reaction was diluted with MeOH to a total volume of 1.8 mL, filtered through a 0.4 μm syringe filter, and product isolated by reverse phase HPLC (0→70% $MeCN/H_2O$ w/0.1% formic acid) as a white solid (42 mg, 26%). LRMS (APCI) m/z 442 (M+H). $^1H$ NMR (400 MHz, DMSO-$d_6$) δ 7.34 (dd, J=7.3, 2.7 Hz, 1H), 7.29-7.23 (m, 1H), 7.23-7.12 (m, 2H), 7.07 (d, J=7.4 Hz, 2H), 6.87-6.69 (m, 2H), 6.08 (dt, J=14.0, 6.1 Hz, 2H), 4.02 (d, J=5.8 Hz, 2H), 3.95 (s, 1H), 3.84 (d, J=12.9 Hz, 2H), 3.77 (s, 1H), 3.65 (s, 4H), 2.80 (t, J=7.9 Hz, 2H), 2.39-2.27 (m, 2H), 2.23 (q, J=7.7 Hz, 2H), 1.86 (ddt, J=12.8, 9.3, 5.6 Hz, 2H).

Compounds in the following table were prepared in a similar manner as Compound 135, using the intermediates and reagents as listed.

| Compound No. | Carboxylic acid | Intermediate | Structure, Name and Data |
|---|---|---|---|
| 136 | 1-(tert-butoxycarbonyl)piperidine-3-carboxylic acid | 3.2 | 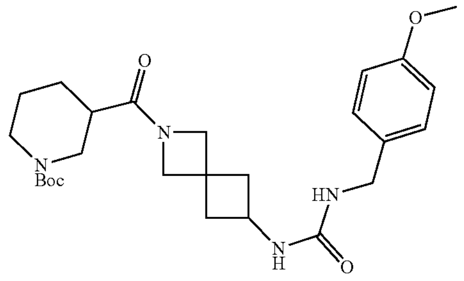 [SMILES: COc1ccc(CNC(=O)NC2CC3(C2)CN(C(=O)C2CCCN(C(=O)OC(C)(C)C)C2)C3)cc1] tert-butyl 3-(6-(3-(4-methoxybenzyl)ureido)-2-azaspiro[3.3]heptane-2-carbonyl)piperidine-1-carboxylate. LRMS (APCI) m/z 487 (M + H). $^1H$ NMR (400 MHz, DMSO-$d_6$) δ 7.15 (d, J = 7.6 Hz, 2H), 6.87 (d, J = 7.6 Hz, 2H), 6.26-6.07 (m, 2H), 4.19 (q, J = 8.3 Hz, 1H), 4.14-4.02 (m, 3H), 3.90 (dt, J = 30.0, 9.6 Hz, 4H), 3.74 (d, J = 9.2 Hz, 3H), 2.78-2.65 (m, 2H), 2.48-2.38 (m, 2H), 2.23 (d, J = 6.4 Hz, 1H), 1.99 (t, J = 9.5 Hz, 2H), 1.75 (d, J = 11.3 Hz, 1H), 1.60 (t, J = 16.2 Hz, 2H), 1.40 (d, J = 2.3 Hz, 9H), 1.14 (t, J = 6.7 Hz, 1H), 1.00 (t, J = 6.9 Hz, 1H). |

-continued

| Compound No. | Carboxylic acid | Intermediate | Structure, Name and Data |
|---|---|---|---|
| 137 | 1,2,3,4-tetrahydro-naphthalene-1-carboxylic acid | 3.2 | 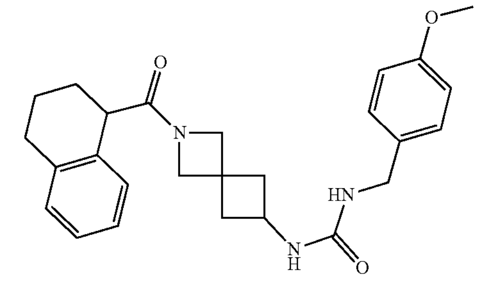 [SMILES: COc1ccc(CNC(=O)NC2CC3(C2)CN(C(=O)C2CCCc4ccccc42)C3)cc1] 1-(4-methoxybenzyl)-3-(2-(1,2,3,4-tetrahydronaphthalene-1-carbonyl)-2-azaspiro[3.3]heptan-6-yl)urea. LRMS (APCI) m/z 434 (M + H). $^1$H NMR (400 MHz, DMSO-$d_6$) δ 7.16 (d, J = 7.5 Hz, 2H), 7.09 (d, J = 6.0 Hz, 3H), 6.92 (d, J = 5.8 Hz, 1H), 6.87 (d, J = 7.4 Hz, 2H), 6.24-6.10 (m, 2H), 4.31 (d, J = 8.2 Hz, 1H), 4.17 (dd, J = 17.3, 8.9 Hz, 1H), 4.11 (d, J = 4.8 Hz, 2H), 4.03 (d, J = 8.8 Hz, 1H), 4.00-3.88 (m, 2H), 3.83 (d, J = 12.2 Hz, 1H), 3.73 (s, 3H), 3.69 (d, J = 6.2 Hz, 1H), 2.73 (d, J = 19.4 Hz, 2H), 2.48-2.40 (m, 1H), 2.11-1.85 (m, 4H), 1.77 (q, J = 11.1, 9.6 Hz, 1H), 1.70-1.54 (m, 1H). |
| 138 | 6-methylnico-tinic acid | 3.2 | 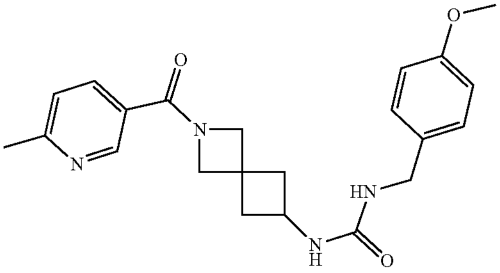 1-(4-methoxybenzyl)-3-(2-(6-methylnicotinoyl)-2-azaspiro[3.3]heptan-6-yl)urea. LRMS (APCI) m/z 395 (M + H). 1H NMR (400 MHz, Methanol-$d_4$) δ 8.64-8.50 (m, 1H), 7.87 (t, J = 5.7 Hz, 1H), 7.29 (d, J = 8.0 Hz, 1H), 7.08 (d, J = 7.7 Hz, 2H), 6.76 (d, J = 7.6 Hz, 2H), 4.35 (s, 1H), 4.22 (s, 1H), 4.11 (s, 3H), 4.00 (s, 1H), 3.94 (dd, J = 14.8, 8.2 Hz, 1H), 3.66 (s, 3H), 2.50 (d, J = 10.5 Hz, 5H), 2.01 (t, J = 9.4 Hz, 2H). |
| 139 | isonicotinic acid | 3.2 | 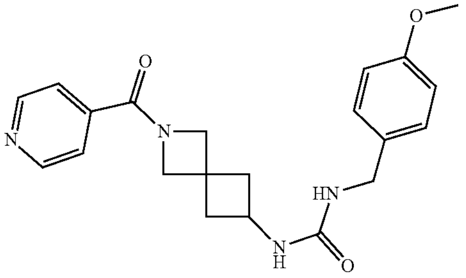 [SMILES: COc1ccc(CNC(=O)NC2CC3(C2)CN(C(=O)c2ccncc2)C3)cc1] 1-(2-isonicotinoyl-2-azaspiro[3.3]heptan-6-yl)-3-(4-methoxybenzyl)urea. LRMS (APCI) m/z 381 (M + H). $^1$H NMR (400 MHz, Methanol-$d_4$) δ 8.63 (s, 2H), 7.61 (d, J = 10.6 Hz, 2H), 7.08 (d, J = 7.7 Hz, 2H), 6.76 (d, J = 7.8 Hz, 2H), 4.33 (s, 1H), 4.20 |

-continued

| Compound No. | Carboxylic acid | Intermediate | Structure, Name and Data |
|---|---|---|---|
| | | | (s, 1H), 4.14 (s, 1H), 4.11 (s, 2H), 4.02 (s, 1H), 3.95 (dt, J = 16.1, 7.9 Hz, 1H), 3.67 (s, 3H), 2.62-2.43 (m, 2H), 2.02 (q, J = 9.4, 8.4 Hz, 2H). |
| 140 | 2-methylisonicotinic acid | 3.2 | 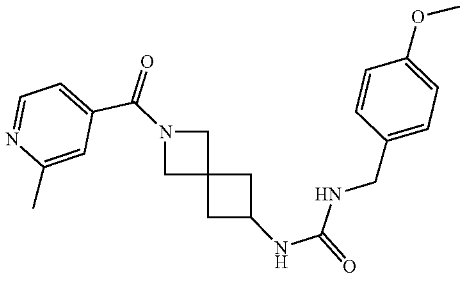 [SMILES: COc1ccc(CNC(=O)NC2CC3(C2)CN(C(=O)c2ccnc(C)c2)C3)cc1] 1-(4-methoxybenzyl)-3-(2-(2-methylisonicotinoyl)-2-azaspiro[3.3]heptan-6-yl)urea. LRMS (APCI) m/z 395 (M + H). $^1$H NMR (400 MHz, Methanol-$d_4$) δ 8.42 (q, J = 4.3 Hz, 1H), 7.38 (s, 1H), 7.31 (d, J = 6.7 Hz, 1H), 7.08 (d, J = 7.7 Hz, 2H), 6.76 (d, J = 7.7 Hz, 2H), 4.30 (s, 1H), 4.17 (s, 1H), 4.12 (s, 3H), 4.00 (s, 1H), 3.93 (dd, J = 17.2, 9.2 Hz, 1H), 3.67 (s, 3H), 2.50 (q, J = 5.0, 3.5 Hz, 5H), 2.01 (q, J = 8.8, 8.0 Hz, 2H). |
| 141 | benzoic acid | 3.2 | 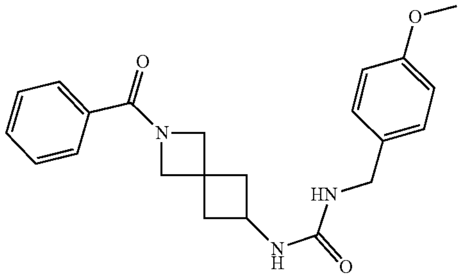 [SMILES: COc1ccc(CNC(=O)NC2CC3(C2)CN(C(=O)c2ccccc2)C3)cc1] 1-(2-benzoyl-2-azaspiro[3.3]heptan-6-yl)-3-(4-methoxybenzyl)urea. LRMS (APCI) m/z 380 (M + H). $^1$H NMR (400 MHz, DMSO-$d_6$) δ 6.88 (s, 2H), 6.73 (dd, J = 16.2, 5.6 Hz, 3H), 6.44 (d, J = 7.9 Hz, 2H), 6.12 (d, J = 7.9 Hz, 2H), 3.57 (d, J = 50.9 Hz, 3H), 3.44 (s, 3H), 3.27 (d, J = 33.3 Hz, 2H), 3.01 (s, 2H), 1.83 (d, J = 11.7 Hz, 4H). 1.35 d, J = 10.7 Hz, 2H). |
| 142 | 2-methyl-2-phenylpropanoic acid | 3.2 | 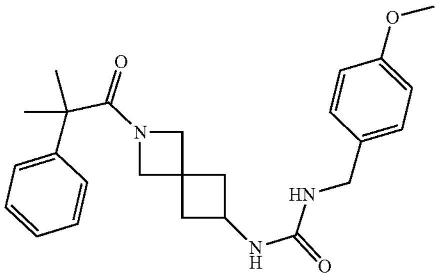 [SMILES: COc1ccc(CNC(=O)NC2CC3(C2)CN(C(=O)C(C)(C)c2ccccc2)C3)cc1] 1-(4-methoxybenzyl)-3-(2-(2-methyl-2-phenylpropanoyl)-2-azaspiro[3.3]heptan-6-yl)urea. LRMS (APCI) m/z 422 (M + H). $^1$H NMR (400 MHz, DMSO-$d_6$) δ 7.28 (d, J = 7.7 Hz, 2H), 7.24-7.12 (m, 3H), 7.04 (d, J = 7.7 Hz, 2H), 6.77 (d, J = 7.8 Hz, 2H), 6.06 (s, 1H), 5.95 (dd, J = 29.4, 6.8 Hz, 1H), 3.98 |

-continued

| Compound No. | Carboxylic acid | Intermediate | Structure, Name and Data |
|---|---|---|---|
| | | | (s, 2H), 3.76 (s, 2H), 3.64 (s, 5H), 3.14 (s, 1H), 2.12 (dt, J = 59.7, 9.2 Hz, 2H), 1.71 (dt, J = 51.5, 9.9 Hz, 2H), 1.31 (s, 6H). |
| 143 | 1-phenylcyclo-propane-1-carboxylic acid | 3.2 | 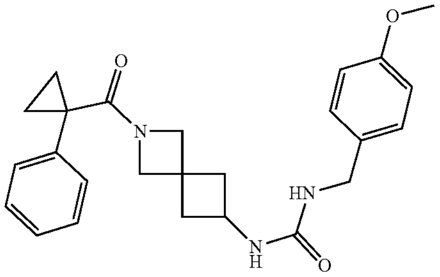 [SMILES: COc1ccc(CNC(=O)NC2CC3(C2)CN(C(=O)C2(c4ccccc4)CC2)C3)cc1] 1-(4-methoxybenzyl)-3-(2-(1-phenylcyclopropane-1-carbonyl)-2-azaspiro[3.3]heptan-6-yl)urea. LRMS (APCI) m/z 420 (M + H). $^1$H NMR (400 MHz, DMSO-$d_6$) δ 7.36 (d, J = 7.5 Hz, 2H), 7.30 (d, J = 7.7 Hz, 3H), 7.05 (d, J = 7.5 Hz, 2H), 6.78 (d, J = 7.5 Hz, 2H), 6.07 (s, 1H), 6.00 (dd, J = 15.7, 7.8 Hz, 1H), 5.01 (s, 2H), 4.63 (s, 2H), 4.00 (s, 2H), 3.89 (s, 1H), 3.86-3.68 (m, 2H), 3.64 (s, 3H), 3.60 (s, 1H), 3.46 (s, 1H), 2.24 (dt, J = 38.4, 9.4 Hz, 2H), 1.80 (dt, J = 34.6, 9.7 Hz, 2H). |
| 144 | 1-methyl-6-oxo-1,6-dihydropyri-dine-3-carboxylic acid | 3.2 | 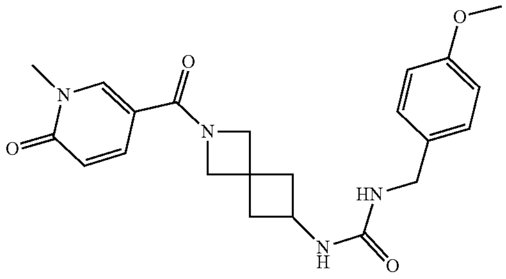 [SMILES: COc1ccc(CNC(=O)NC2CC3(C2)CN(C(=O)c2ccc(=O)n(C)c2)C3)cc1] 1-(4-methoxybenzyl)-3-(2-(1-methyl-6-oxo-1,6-dihydropyridine-3-carbonyl)-2-azaspiro[3.3]heptan-6-yl)urea. LRMS (APCI) m/z 411 (M + H). $^1$H NMR (400 MHz, DMSO-$d_6$) δ 8.06 (s, 1H), 7.56 (d, J = 9.1 Hz, 1H), 7.08 (d, J = 7.5 Hz, 2H), 6.79 (d, J = 7.7 Hz, 2H), 6.31 (d, J = 9.5 Hz, 1H), 6.08 (d, J = 7.9 Hz, 2H), 4.26 (d, J = 50.1 Hz, 2H), 4.02 (s, 2H), 3.99-3.77 (m, 3H), 3.65 (s, 3H), 3.40 (s, 3H), 2.37 (d, J = 8.5 Hz, 2H), 1.92 (t, J = 9.6 Hz, 2H). |
| 145 | 4-methylbenzo-ic acid | 3.2 | 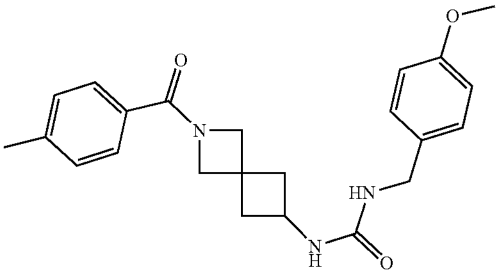 1-(4-methoxybenzyl)-3-(2-(4-methylbenzoyl)-2-azaspiro[3.3]heptan-6-yl)urea. LRMS (APCI) m/z 394 (M + H). $^1$H NMR (400 MHz, DMSO-$d_6$) |

-continued

| Compound No. | Carboxylic acid | Intermediate | Structure, Name and Data |
|---|---|---|---|
| | | | δ 7.44 (d, J = 6.6 Hz, 2H), 7.17 (d, J = 7.8 Hz, 2H), 7.07 (d, J = 8.6 Hz, 2H), 6.79 (d, J = 8.6 Hz, 2H), 6.17-6.00 (m, 2H), 4.25 (s, 1H), 4.13 (s, 1H), 4.02 (d, J = 5.9 Hz, 2H), 3.99 (s, 1H), 3.87 (s, 2H), 3.65 (s, 3H), 2.42-2.32 (m, 2H), 2.27 (s, 3H), 1.93 (d, J = 10.8 Hz, 2H). |
| 146 | 3-methylbenzoic acid | 3.2 | 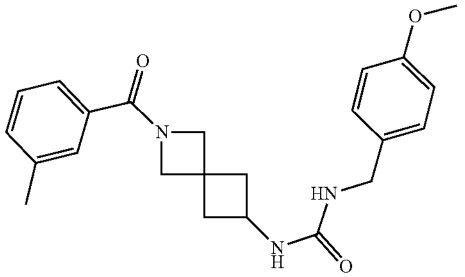 [SMILES: COc1ccc(CNC(=O)NC2CC3(C2)CN(C(=O)c2cccc(C)c2)C3)cc1] 1-(4-methoxybenzyl)-3-(2-(3-methylbenzoyl)-2-azaspiro[3.3]heptan-6-yl)urea. LRMS (APCI) m/z 394 (M + H). $^1$H NMR (400 MHz, DMSO-d6) δ 7.35 (s, 1H), 7.30 (d, J = 5.3 Hz, 1H), 7.28-7.20 (m, 2H), 7.07 (d, J = 8.7 Hz, 2H), 6.79 (d, J = 8.7 Hz, 2H), 6.08 (s, 2H), 4.25 (s, 1H), 4.12 (s, 1H), 4.02 (d, J = 5.1 Hz, 2H), 3.99 (s, 1H), 3.87 (s, 2H), 3.65 (s, 3H), 2.42-2.34 (m, 2H), 2.27 (s, 3H), 1.99-1.83 (m, 2H). |
| 147 | 4-(trifluoromethyl)benzoic acid | 3.2 | 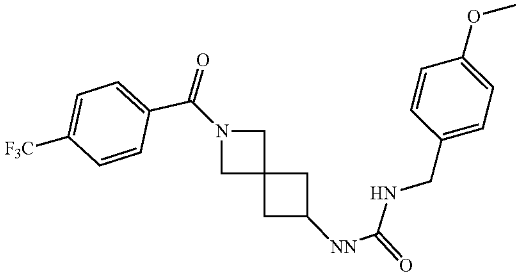 1-(4-methoxybenzyl)-3-(2-(4-(trifluoromethyl)benzoyl)-2-azaspiro[3.3]heptan-6-yl)urea. LRMS (APCI) m/z 448 (M + H). $^1$H NMR (400 MHz, DMSO-$d_6$) δ 7.82 (d, J = 3.9 Hz, 4H), 7.15 (d, J = 8.7 Hz, 2H), 6.86 (d, J = 8.6 Hz, 2H), 6.22-6.08 (m, 2H), 4.35 (s, 1H), 4.22 (s, 1H), 4.16-4.04 (m, 3H), 4.00 (s, 1H), 3.99-3.85 (m, 1H), 3.72 (s, 3H), 2.47 (d, J = 9.8 Hz, 2H), 2.00 (q, J = 10.3 Hz, 2H). |
| 148 | 2-methylbenzoic acid | 3.2 | 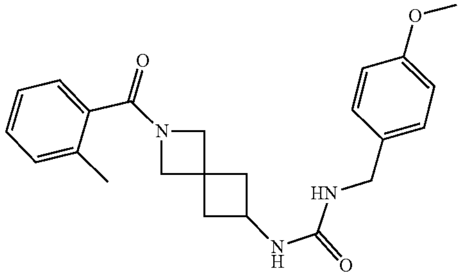 [SMILES: COc1ccc(CNC(=O)NC2CC3(C2)CN(C(=O)c2ccccc2C)C3)cc1] 1-(4-methoxybenzyl)-3-(2-(2-methylbenzoyl)-2-azaspiro[3.3]heptan-6-yl)urea. LRMS (APCI) m/z 394 |

-continued

| Compound No. | Carboxylic acid | Intermediate | Structure, Name and Data |
|---|---|---|---|
| | | | (M + H). $^1$H NMR (400 MHz, DMSO-$d_6$) δ 7.28-7.21 (m, 1H), 7.21-7.10 (m, 3H), 7.07 (d, J = 8.6 Hz, 2H), 6.78 (d, J = 8.4 Hz, 2H), 6.06 (dd, J = 11.5, 7.1 Hz, 2H), 4.01 (d, J = 5.4 Hz, 2H), 3.98 (s, 1H), 3.95-3.76 (m, 3H), 3.70 (s, 1H), 3.65 (s, 3H), 2.42-2.30 (m, 2H), 2.20 (s, 3H), 1.90 (dtd, J = 22.8, 8.9, 2.9 Hz, 2H). |
| 153 | 2-methyl-2-(p-tolyl)propanoic acid | 3.2 | 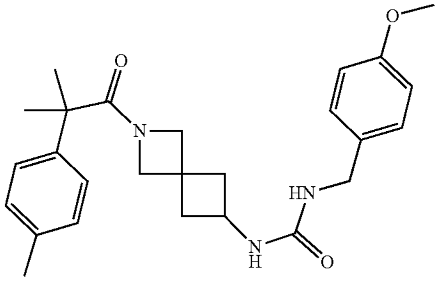 [SMILES: COc1ccc(CNC(=O)NC2CC3(C2)CN(C(=O)C(C)(C)c2ccc(C)cc2)C3)cc1] 1-(4-methoxybenzyl)-3-(2-(2-methyl-2-(p-tolyl)propanoyl)-2-azaspiro[3.3]heptan-6-yl)urea. LRMS (APCI) m/z 436 (M + H). $^1$H NMR (400 MHz, Methanol-$d_4$) δ 7.12-7.01 (m, 6H), 6.78-6.68 (m, 2H), 4.07 (s, 2H), 3.85 (s, 2H), 3.72 (s, 2H), 3.65 (s, 3H), 3.34 (s, 1H), 2.30 (ddd, J = 10.1, 7.5, 3.0 Hz, 1H), 2.23 (d, J = 4.5 Hz, 3H), 2.17 (ddd, J = 12.7, 6.6, 3.0 Hz, 1H), 1.82 (td, J = 8.9, 3.1 Hz, 1H), 1.70 (td, J = 8.9, 3.0 Hz, 1H), 1.34 (d, J = 3.3 Hz, 6H). |
| 154 | 2-methyl-2-(m-tolyl)propanoic acid | 3.2 | 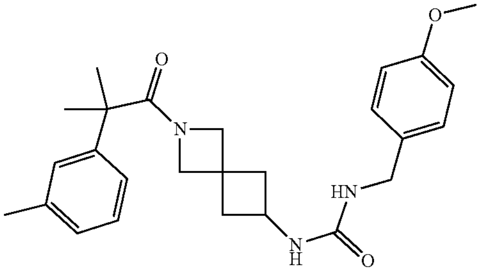 1-(4-methoxybenzyl)-3-(2-(2-methyl-2-(m-tolyl)propanoyl)-2-azaspiro[3.3]heptan-6-yl)urea. LRMS (APCI) m/z 436 (M + H). $^1$H NMR (400 MHz, Methanol-$d_4$) δ 7.14 (q, J = 7.8 Hz, 1H), 7.08-7.02 (m, 2H), 7.02-6.92 (m, 3H), 6.78-6.69 (m, 2H), 4.07 (s, 2H), 3.86 (s, 2H), 3.73 (m, 2H), 3.65 (s, 3H), 3.34 (s, 1H), 2.30 (ddd, J = 10.2, 7.8, 2.8 Hz, 1H), 2.24 (d, J = 5.0 Hz, 3H), 2.16 (ddd, J = 10.0, 7.7, 2.7 Hz, 1H), 1.83 (td, J = 9.0, 2.9 Hz, 1H), 1.70 (td, J = 8.9, 2.8 Hz, 1H), 1.35 (d, J = 3.5 Hz, 6H). |
| 155 | 4-methoxybenzoic acid | 3.2 | 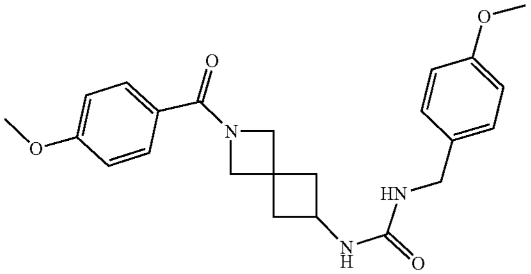 |

-continued

| Compound No. | Carboxylic acid | Intermediate | Structure, Name and Data |
|---|---|---|---|
| | | | 1-(2-(4-methoxybenzoyl)-2-azaspiro[3.3]heptan-6-yl)-3-(4-methoxybenzyl)urea. LRMS (APCI) m/z 410 (M + H). $^1$H NMR (400 MHz, Methanol-$d_4$) δ 7.51 (t, J = 6.6 Hz, 2H), 7.08 (d, J = 8.7 Hz, 2H), 6.88 (d, J = 8.4 Hz, 2H), 6.79-6.72 (m, 2H), 4.33 (s, 1H), 4.20 (s, 1H), 4.11 (s, 2H), 4.09 (s, 1H), 3.97 (s, 2H), 3.74 (s, 3H), 3.66 (s, 3H), 2.50 (ddd, J = 10.1, 7.7, 2.8 Hz, 2H), 2.06-1.91 (m, 2H). |
| 156 | 4-cyanobenzoic acid | 3.2 | 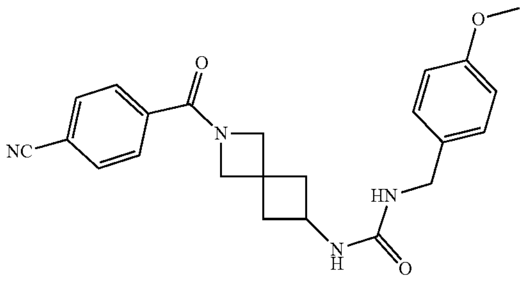 [SMILES: COc1ccc(CNC(=O)NC2CC3(C2)CN(C(=O)c2ccc(C#N)cc2)C3)cc1] 1-(2-(4-cyanobenzoyl)-2-azaspiro[3.3]heptan-6-yl)-3-(4-methoxybenzyl)urea. LRMS (APCI) m/z 405 (M + H). $^1$H NMR (400 MHz, Methanol-$d_4$) δ 7.80-7.64 (m, 4H), 7.08 (d, J = 8.6 Hz, 2H), 6.76 (d, J = 8.6 Hz, 2H), 4.30 (s, 1H), 4.17 (s, 1H), 4.13 (s, 1H), 4.11 (s, 2H), 4.01 (s, 1H), 3.94 (dt, J = 17.0, 8.0 Hz, 1H), 3.67 (s, 3H), 2.57-2.41 (m, 2H), 2.01 (q, J = 9.7 Hz, 2H). |
| 157 | 4-(2-hydroxypropan-2-yl)benzoic acid | 3.2 | 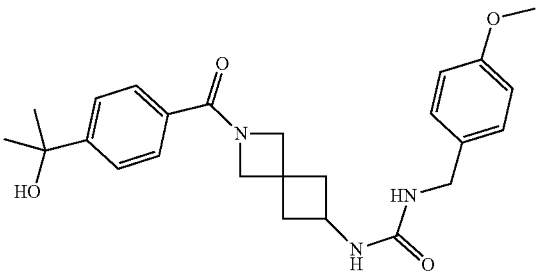 [SMILES: COc1ccc(CNC(=O)NC2CC3(C2)CN(C(=O)c2ccc(C(C)(C)O)cc2)C3)cc1] 1-(2-(4-(2-hydroxypropan-2-yl)benzoyl)-2-azaspiro[3.3]heptan-6-yl)-3-(4-methoxybenzyl)urea. LRMS (APCI) m/z 438 (M + H). $^1$H NMR (400 MHz, Methanol-$d_4$) δ 7.55-7.43 (m, 4H), 7.08 (d, J = 8.7 Hz, 2H), 6.76 (d, J = 8.6 Hz, 2H), 4.32 (s, 1H), 4.19 (s, 1H), 4.11 (d, J = 2.7 Hz, 3H), 3.99 (s, 1H), 3.94 (dd, J = 16.5, 8.2 Hz, 1H), 3.67 (s, 3H), 2.57-2.41 (m, 2H), 2.01 (td, J = 8.8, 3.9 Hz, 2H), 1.44 (s, 6H). |
| 158 | 4-chlorobenzoic acid | 3.2 | 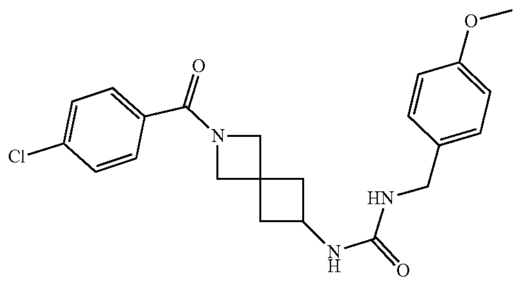 [SMILES: COc1ccc(CNC(=O)NC2CC3(C2)CN(C(=O)c2ccc(Cl)cc2)C3)cc1] |

-continued

| Compound No. | Carboxylic acid | Intermediate | Structure, Name and Data |
|---|---|---|---|
| | | | 1-(2-(4-chlorobenzoyl)-2-azaspiro[3.3]heptan-6-yl)-3-(4-methoxybenzyl)urea. LRMS (APCI) m/z 414 (M + H). $^1$H NMR (400 MHz, Methanol-$d_4$) δ 7.53 (t, J = 7.6 Hz, 2H), 7.37 (dd, J = 8.4, 3.6 Hz, 2H), 7.12-7.02 (m, 2H), 6.80-6.70 (m, 2H), 4.31 (s, 1H), 4.17 (s, 1H), 4.11 (d, J = 2.6 Hz, 3H), 3.98 (s, 1H), 3.97-3.86 (m, 1H), 3.66 (s, 3H), 2.56-2.42 (m, 2H), 2.00 (td, J = 12.0, 10.4, 4.0 Hz, 2H). |
| 172 | 3-ethylbenzoic acid | 3.2 | 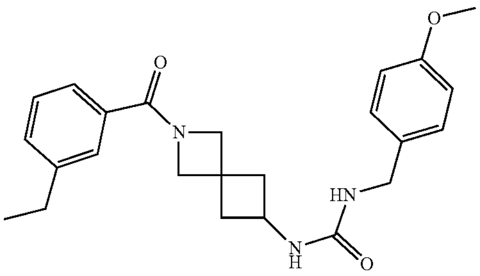 [SMILES: CCc1cccc(C(=O)N2CC3(CC(NC(=O)NCc4ccc(OC)cc4)C3)C2)c1] 1-(2-(3-ethylbenzoyl)-2-azaspiro[3.3]heptan-6-yl)-3-(4-methoxybenzyl)urea. LRMS (APCI) m/z 408 (M + H). $^1$H NMR (400 MHz, Methanol-$d_4$) δ δ 7.48 (d, J = 4.9 Hz, 1H), 7.43 (dd, J = 6.6, 4.2 Hz, 1H), 7.38 (d, J = 4.1 Hz, 2H), 7.20 (d, J = 8.6 Hz, 2H), 6.87 (d, J = 8.5 Hz, 2H), 4.41 (s, 1H), 4.27 (s, 1H), 4.22 (d, J = 2.9 Hz, 3H), 4.07 (d, J = 25.2 Hz, 2H), 3.78 (s, 3H), 2.71 (qd, J = 7.6, 2.8 Hz, 2H), 2.62 (ddt, J = 12.2, 7.4, 3.4 Hz, 2H), 2.12 (ddt, J = 13.1, 8.6, 3.5 Hz, 2H), 1.27 (td, J = 7.6, 2.4 Hz, 3H). |
| 173 | 3-isopropylbenzoic acid | 3.2 | 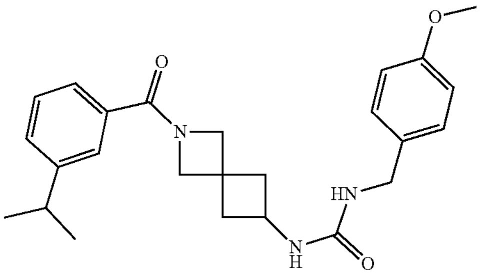 [SMILES: COc1ccc(CNC(=O)NC2CC3(C2)CN(C(=O)c2cccc(C(C)C)c2)C3)cc1] 1-(2-(3-isopropylbenzoyl)-2-azaspiro[3.3]heptan-6-yl)-3-(4-methoxybenzyl)urea. LRMS (APCI) m/z 422 (M + H). $^1$H NMR (400 MHz, Methanol-$d_4$) δ 7.39 (d, J = 4.6 Hz, 1H), 7.36-7.22 (m, 3H), 7.08 (d, J = 8.6 Hz, 2H), 6.75 (d, J = 8.5 Hz, 2H), 4.29 (s, 1H), 4.16 (s, 1H), 4.11 (s, 3H), 3.98 (s, 1H), 3.92 (dt, J = 16.3, 9.2 Hz, 1H), 3.66 (s, 3H), 2.86 (pd, J = 6.9, 3.1 Hz, 1H), 2.50 (ddt, J = 10.2, 6.9, 3.0 Hz, 2H), 1.99 (tt, J = 8.3, 3.6 Hz, 2H), 1.23-1.10 (m, 6H). |

-continued

| Compound No. | Carboxylic acid | Intermediate | Structure, Name and Data |
|---|---|---|---|
| 174 | 3-(tert-butyl)benzoic acid | 3.2 | 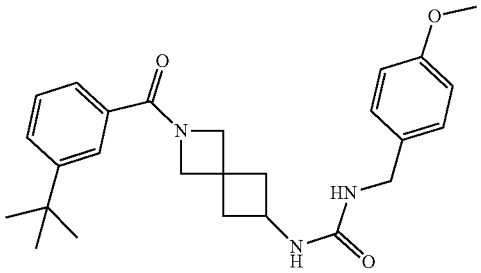 [SMILES: COc1ccc(CNC(=O)NC2CC3(C2)CN(C(=O)c2cccc(C(C)(C)C)c2)C3)cc1] 1-(2-(3-(tert-butyl)benzoyl)-2-azaspiro[3.3]heptan-6-yl)-3-(4-methoxybenzyl)urea. LRMS (APCI) m/z 436 (M + H). $^1$H NMR (400 MHz, Methanol-$d_4$) δ 7.57 (dd, J = 4.5, 2.4 Hz, 1H), 7.47 (ddd, J = 7.3, 3.8, 2.0 Hz, 1H), 7.30 (ddt, J = 10.7, 7.7, 4.5 Hz, 2H), 7.08 (d, J = 8.6 Hz, 2H), 6.75 (d, J = 8.4 Hz, 2H), 4.29 (s, 1H), 4.16 (s, 1H), 4.11 (s, 3H), 3.99 (s, 1H), 3.93 (dd, J = 18.1, 8.8 Hz, 1H), 3.66 (s, 3H), 2.50 (ddt, J = 10.4, 7.3, 3.1 Hz, 2H), 2.09-1.90 (m, 2H), 1.25 (d, J = 2.5 Hz, 9H). |
| 175 | 3-(2-hydroxypropan-2-yl)benzoic acid | 3.2 | 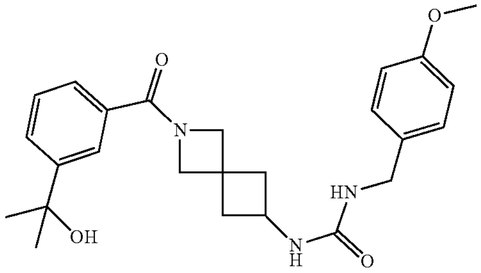 [SMILES: COc1ccc(CNC(=O)NC2CC3(C2)CN(C(=O)c2cccc(C(C)(C)O)c2)C3)cc1] 1-(2-(3-(2-hydroxypropan-2-yl)benzoyl)-2-azaspiro[3.3]heptan-6-yl)-3-(4-methoxybenzyl)urea. LRMS (APCI) m/z 438 (M + H). $^1$H NMR (400 MHz, Methanol-$d_4$) δ 7.66 (d, J = 5.5 Hz, 1H), 7.53 (d, J = 7.8 Hz, 1H), 7.37 (t, J = 7.0 Hz, 1H), 7.31 (td, J = 7.7, 4.0 Hz, 1H), 7.08 (d, J = 8.6 Hz, 2H), 6.75 (d, J = 8.5 Hz, 2H), 4.30 (s, 1H), 4.17 (s, 1H), 4.11 (s, 3H), 3.99 (s, 1H), 3.93 (dd, J = 18.1, 8.2 Hz, 1H), 3.66 (s, 3H), 2.49 (d, J = 12.8 Hz, 2H), 2.00 (q, J = 13.5, 10.4 Hz, 2H), 1.44 (d, J = 1.2 Hz, 6H). |
| 176 | 3-methoxybenzoic acid | 3.2 | 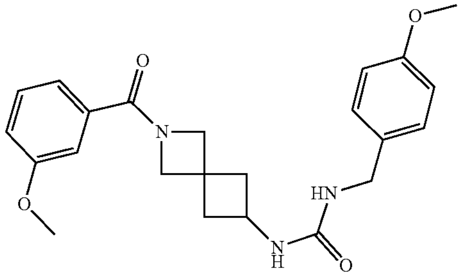 [SMILES: COc1ccc(CNC(=O)NC2CC3(C2)CN(C(=O)c2cccc(OC)c2)C3)cc1] 1-(2-(3-methoxybenzoyl)-2-azaspiro[3.3]heptan-6-yl)-3-(4-methoxybenzoyl)urea. LRMS (APCI) m/z 410 (M + H). $^1$H NMR (400 MHz, Methanol-$d_4$) δ 7.26 (td, J = 7.9, 4.2 Hz, 1H), 7.12-7.03 (m, 4H), 7.01-6.93 (m, 1H), 6.75 (d, J = 8.6 Hz, 2H), 4.29 (s, 1H), |

-continued

| Compound No. | Carboxylic acid | Intermediate | Structure, Name and Data |
|---|---|---|---|
| | | | 4.16 (s, 1H), 4.10 (d, J = 3.9 Hz, 3H), 3.98 (s, 1H), 3.97-3.87 (m, 1H), 3.73 (d, J = 2.5 Hz, 3H), 3.66 (s, 3H), 2.55-2.43 (m, 2H), 2.00 (q, J = 9.5, 6.7 Hz, 2H). |
| 177 | 3-hydroxyben-zoic acid | 3.2 | 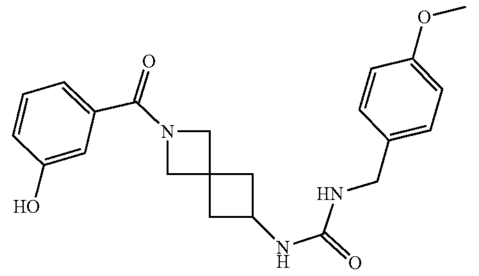 [SMILES: COc1ccc(CNC(=O)NC2CC3(C2)CN(C(=O)c2cccc(O)c2)C3)cc1] 1-(2-(3-hydroxybenzoyl)-2-azaspiro[3.3]heptan-6-yl)-3-(4-methoxybenzyl)urea. LRMS (APCI) m/z 396 (M + H). $^1$H NMR (400 MHz, Methanol-$d_4$) δ 7.16 (td, J = 7.8, 4.2 Hz, 1H), 7.11-7.05 (m, 2H), 6.94 (dd, J = 14.5, 6.0 Hz, 2H), 6.81 (d, J = 8.2 Hz, 1H), 6.78-6.70 (m, 2H), 4.28 (s, 1H), 4.15 (s, 1H), 4.11 (s, 2H), 4.09 (s, 1H), 3.99-3.88 (m, 2H), 3.66 (s, 3H), 2.56-2.41 (m, 2H), 2.06-1.90 (m, 2H). |
| 178 | 3-(dimethyla-mino)benzo-ic acid | 3.2 | 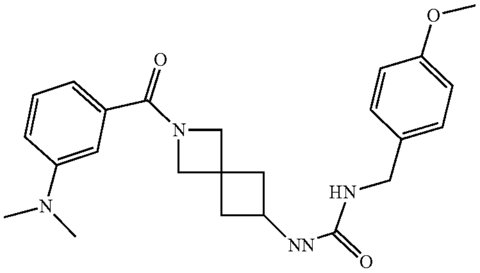 1-(2-(3-(dimethylamino)benzoyl)-2-azaspiro[3.3]heptan-6-yl)-3-(4-methoxybenzyl)urea. LRMS (APCI) m/z 423 (M + H). $^1$H NMR (400 MHz, Methanol-$d_4$) δ 7.16 (td, J = 8.0, 4.5 Hz, 1H), 7.11-7.05 (m, 2H), 6.85 (d, J = 3.9 Hz, 1H), 6.82-6.71 (m, 4H), 4.28 (s, 1H), 4.15 (s, 1H), 4.11 (s, 2H), 4.09 (s, 1H), 3.94 (d, J = 21.2 Hz, 2H), 3.66 (s, 3H), 2.86 (d, J = 2.6 Hz, 6H), 2.49 (ddt, J = 10.1, 7.5, 3.6 Hz, 2H), 2.00 (td, J = 8.8, 3.6 Hz, 2H). |
| 179 | 3-(pyrrolidin-1-yl)benzoic acid | 3.2 | 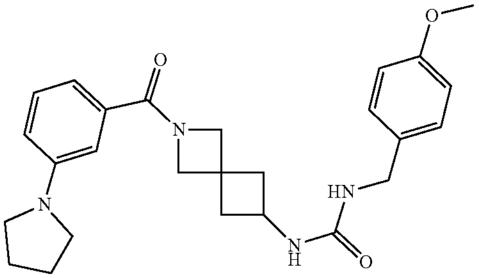 [SMILES: COc1ccc(CNC(=O)NC2CC3(C2)CN(C(=O)c2cccc(N4CCCC4)c2)C3)cc1] 1-(4-methoxybenzyl)-3-(2-(3-(pyrrolidin-1-yl)benzoyl)-2-azaspiro[3.3]heptan-6-yl)urea. LRMS (APCI) m/z 449 (M + H). $^1$H NMR (400 MHz, Methanol-$d_4$) δ 7.12 (ddt, J = 10.1, |

-continued

| Compound No. | Carboxylic acid | Intermediate | Structure, Name and Data |
|---|---|---|---|
| | | | 4.5, 2.3 Hz, 2H), 7.09-7.03 (m, 2H), 6.75 (d, J = 8.3 Hz, 2H), 6.69 (t, J = 7.7 Hz, 1H), 6.65 (p, J = 1.9 Hz, 1H), 6.59 (dt, J = 8.3, 3.0 Hz, 1H), 4.27 (s, 1H), 4.14 (s, 1H), 4.11 (s, 2H), 4.08 (s, 1H), 3.94 (d, J = 19.3 Hz, 2H), 3.66 (s, 3H), 3.19 (d, J = 3.7 Hz, 4H), 2.56-2.42 (m, 2H), 2.03-1.85 (m, 5H). |
| 180 | 3-methylsunfonylbenzoic acid | 3.2 | 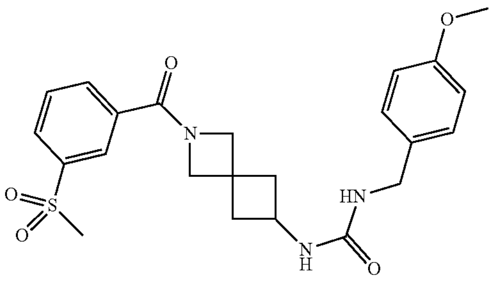 [SMILES: COc1ccc(CNC(=O)NC2CC3(C2)CN(C(=O)c2cccc(S(C)(=O)=O)c2)C3)cc1] 1-(4-methoxybenzyl)-3-(2-(3-(methylsulfonyl)benzoyl)-2-azaspiro[3.3]heptan-6-yl)urea. LRMS (APCI) m/z 458 (M + H). $^1$H NMR (400 MHz, Methanol-$d_4$) δ 8.14-8.07 (m, 1H), 8.00 (d, J = 7.9 Hz, 1H), 7.88 (t, J = 6.5 Hz, 1H), 7.64 (td, J = 7.8, 3.4 Hz, 1H), 7.08 (d, J = 8.6 Hz, 2H), 6.76 (d, J = 8.7 Hz, 2H), 4.35 (s, 1H), 4.22 (s, 1H), 4.15 (s, 1H), 4.12 (s, 2H), 4.03 (s, 1H), 3.94 (dq, J = 16.3, 8.0 Hz, 1H), 3.67 (s, 3H), 3.06 (d, J = 2.4 Hz, 3H), 2.52 (ddd, J = 12.6, 6.3, 2.7 Hz, 2H), 2.02 (qd, J = 8.1, 6.4, 3.3 Hz, 2H). |
| 181 | 3-(methoxycarbonyl)benzoic acid | 3.2 | 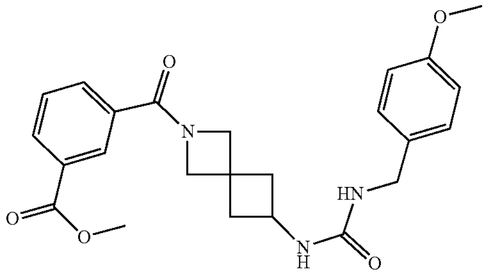 [SMILES: COC(=O)c1cccc(C(=O)N2CC3(CC(NC(=O)NCc4ccc(OC)cc4)C3)C2)c1] methyl 3-(6-(3-(4-methoxybenzyl)ureido)-2-azaspiro[3.3]heptane-2-carbonyl)benzoate. LRMS (APCI) m/z 438 (M + H). $^1$H NMR (400 MHz, Methanol-$d_4$) δ 8.16 (d, J = 5.5 Hz, 1H), 8.05 (d, J = 7.9 Hz, 1H), 7.77 (t, J = 6.4 Hz, 1H), 7.49 (td, J = 7.8, 3.4 Hz, 1H), 7.08 (d, J = 8.6 Hz, 2H), 6.75 (d, J = 8.5 Hz, 2H), 4.33 (s, 1H), 4.20 (s, 1H), 4.13 (s, 1H), 4.11 (s, 2H), 4.01 (s, 1H), 3.94 (dt, J = 16.8, 8.1 Hz, 1H), 3.84 (d, J = 1.4 Hz, 3H), 3.66 (s, 3H), 2.51 (dq, J = 10.1, 3.1 Hz, 2H), 2.01 (td, J = 8.8, 4.2 Hz, 2H). |

-continued

| Compound No. | Carboxylic acid | Intermediate | Structure, Name and Data |
|---|---|---|---|
| 188 | 3-(2-oxypyrrolidin-1-yl)benzoic acid | 3.2 | 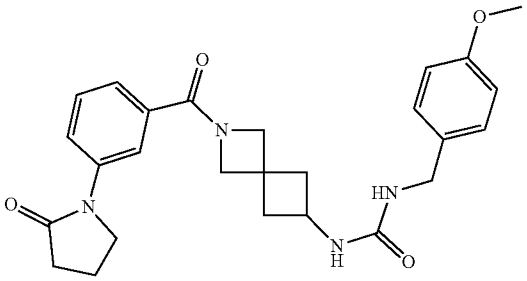 [SMILES: COc1ccc(CNC(=O)NC2CC3(C2)CN(C(=O)c2cccc(N4CCCC4=O)c2)C3)cc1] 1-(4-methoxybenzyl)-3-(2-(3-(2-oxopyrrolidin-1-yl)benzoyl)-2-azaspiro[3.3]heptan-6-yl)urea. LRMS (APCI) m/z 463 (M + H). $^1$H NMR (400 MHz, Methanol-d$_4$) δ 7.89 (s, 1H), 7.61 (t, J = 8.9 Hz, 1H), 7.43-7.30 (m, 2H), 7.08 (d, J = 8.6 Hz, 2H), 6.76 (d, J = 8.4 Hz, 2H), 4.33 (s, 1H), 4.21 (s, 1H), 4.12 (s, 3H), 3.96 (d, J = 27.1 Hz, 2H), 3.86 (td, J = 7.1, 2.7 Hz, 2H), 3.67 (s, 3H), 2.51 (q, J = 6.8, 5.6 Hz 4H), 2.10 (p, J = 7.7 Hz, 2H), 2.05-1.95 (m, 2H). |
| 189 | 3-(1H-pyrrol-1-yl)benzoic acid | 3.2 | 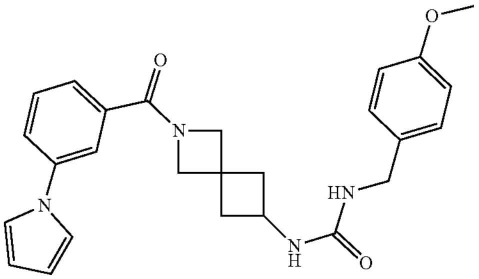 [SMILES: COc1ccc(CNC(=O)NC2CC3(C2)CN(C(=O)c2cccc(-n4cccc4)c2)C3)cc1] 1-(2-(3-(1H-pyrrol-1-yl)benzoyl)-2-azaspiro[3.3]heptan-6-yl)-3-(4-methoxybenzyl)urea. LRMS (APCI) m/z 445 (M + H). $^1$H NMR (400 MHz, Methanol-d$_4$) δ 7.73 (p, J = 1.9 Hz, 1H), 7.65 (d, J = 8.2 Hz, 1H), 7.62-7.52 (m, 1H), 7.50 (dd, J = 4.5, 2.7 Hz, 1H), 7.25 (p, J = 1.6 Hz, 2H), 7.20 (d, J = 8.6 Hz, 2H), 6.87 (d, J = 8.2 Hz, 2H), 6.33 (q, J = 2.1 Hz, 2H), 4.46 (s, 1H), 4.33 (s, 1H), 4.25 (s, 1H), 4.23 (s, 2H), 4.17-4.00 (m, 2H), 3.78 (s, 3H), 2.63 (dd, J = 11.7, 7.8 Hz, 2H), 2.13 (t, J = 9.2 Hz, 2H). |
| 190 | 3-(piperidin-1-yl)benzoic acid | 3.2 | 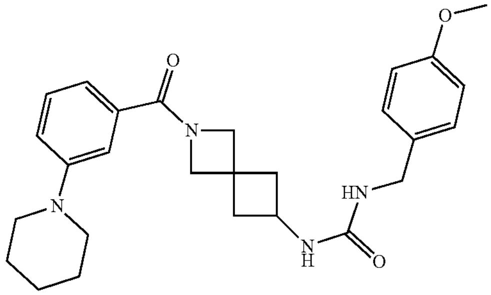 [SMILES: COc1ccc(CNC(=O)NC2CC3(C2)CN(C(=O)c2cccc(N4CCCCC4)c2)C3)cc1] 1-(4-methoxybenzyl)-3-(2-(3-(piperidin-1-yl)benzoyl)-2-azaspiro[3.3]heptan-6-yl)urea. LRMS (APCI) m/z 463 (M + H). $^1$H NMR (400 MHz, Methanol-d$_4$) δ 7.26-7.14 (m, 1H), 7.09 (dq, J = 9.3, 3.1 Hz, 3H), 7.01 (d, J = 8.3 Hz, 1H), 6.91 (t, J = 7.5 Hz, 1H), 6.81-6.71 (m, 2H), 4.28 (s, |

-continued

| Compound No. | Carboxylic acid | Intermediate | Structure, Name and Data |
|---|---|---|---|
| | | | 1H), 4.19-4.06 (m, 4H), 3.96 (d, J = 12.9 Hz, 2H), 3.79 (s, 1H), 3.67 (s, 3H), 3.10 (dq, J = 8.7, 3.7 Hz, 4H), 2.56-2.44 (m, 2H), 2.05-1.94 (m, 1H), 1.63 (q, J = 4.4, 3.9 Hz, 4H), 1.52 (d, J = 5.5 Hz, 2H). |
| 191 | 3-morpholino benzoic acid | 3.2 | 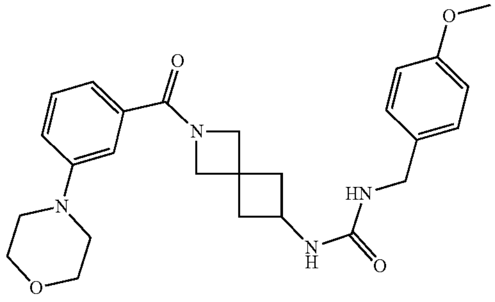 [SMILES: COc1ccc(CNC(=O)NC2CC3(C2)CN(C(=O)c2cccc(N4CCOCC4)c2)C3)cc1] 1-(4-methoxybenzyl)-3-(2-(3-morpholinobenzoyl)-2-azaspiro[3.3]heptan-6-yl)urea. LRMS (APCI) m/z 465 (M + H). $^{1}H$ NMR (400 MHz, Methanol-$d_4$) δ 7.28-7.20 (m, 1H), 7.14-7.05 (m, 3H), 7.04-6.93 (m, 2H), 6.76 (d, J = 8.5 Hz, 2H), 4.29 (s, 1H), 4.16 (s, 1H), 4.12 (s, 2H), 4.10 (s, 1H), 3.95 (d, J = 22.4 Hz, 2H), 3.75 (dq, J = 5.3, 2.8 Hz, 4H), 3.67 (s, 3H), 3.09 (dq, J = 5.3, 2.5 Hz, 4H), 2.55-2.43 (m, 2H), 2.00 (dt, J = 11.2, 6.5 Hz, 2H). |
| 38 | 2-(2-fluorophenyl) acetic acid | 3.2 | 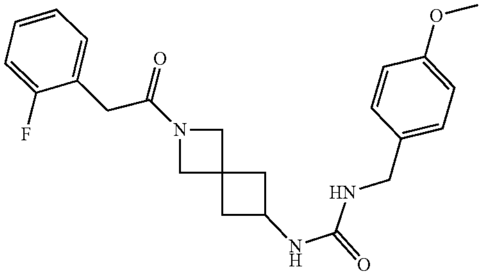 [SMILES: COc1ccc(CNC(=O)NC2CC3(C2)CN(C(=O)Cc2ccccc2F)C3)cc1] 1-(2-(2-(2-fluorophenyl)acetyl)-2-azaspiro[3.3]heptan-6-yl)-3-(4-methoxybenzyl)urea. LRMS (APCI) m/z 412 (M + H). $^{1}H$ NMR (400 MHz, DMSO-$d_6$) δ 7.28 (t, J = 7.1 Hz, 2H), 7.15 (dd, J = 7.7, 4.6 Hz, 4H), 6.87 (d, J = 8.3 Hz, 2H), 6.25-6.09 (m, 2H), 4.22 (s, 1H), 4.11 (d, J = 5.6 Hz, 3H), 3.96 (p, J = 8.0 Hz, 1H), 3.89 (s, 1H), 3.76 (s, 1H), 3.73 (d, J = 0.8 Hz, 3H), 3.44 (d, J = 5.9 Hz, 2H), 2.48-2.36 (m, 2H), 2.00 (tt, J = 9.0, 3.6 Hz, 2H). |
| 39 | 2-(2-chlorophenyl) acetic acid | 3.2 | 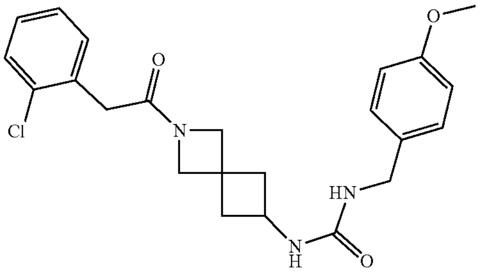 [SMILES: COc1ccc(CNC(=O)NC2CC3(C2)CN(C(=O)Cc2ccccc2Cl)C3)cc1] 1-(2-(2-(2-chlorophenyl)acetyl)-2-azaspiro[3.3]heptan-6-yl)-3-(4- |

-continued

| Compound No. | Carboxylic acid | Intermediate | Structure, Name and Data |
|---|---|---|---|
| | | | methoxybenzyl)urea. LRMS (APCI) m/z 428 (M + H). $^1$H NMR (400 MHz, DMSO-$d_6$) δ 7.47-7.38 (m, 1H), 7.37-7.31 (m, 1H), 7.31-7.21 (m, 2H), 7.16 (d, J = 8.4 Hz, 2H), 6.94-6.77 (m, 2H), 6.27-6.06 (m, 2H), 4.23 (s, 1H), 4.17-4.03 (m, 4H), 3.97 (p, J = 8.0 Hz, 1H), 3.90 (s, 1H), 3.79 (s, 1H), 3.53 (d, J = 5.0 Hz, 2H), 3.18 (d, J = 5.0 Hz, 2H), 2.49-2.36 (m, 1H), 2.01 (td, J = 8.9, 4.4 Hz, 2H). |
| 40 | 2-(2-methoxyphenyl)acetic aicd | 3.2 | 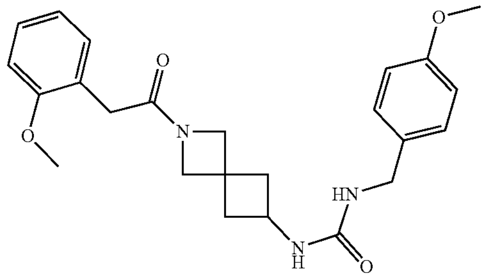 [SMILES: COc1ccc(CNC(=O)NC2CC3(C2)CN(C(=O)Cc2ccccc2OC)C3)cc1] 1-(4-methoxybenzyl)-3-(2-(2-(2-methoxyphenyl)acetyl)-2-azaspiro[3.3]heptan-6-yl)urea. LRMS (APCI) m/z 424 (M + H). $^1$H NMR (400 MHz, DMSO-$d_6$) δ 7.29-7.17 (m, 1H), 7.14 (t, J = 8.6 Hz, 3H), 6.95 (d, J = 8.2 Hz, 1H), 6.88 (dd, J = 8.0, 5.9 Hz, 3H), 6.27-6.05 (m, 2H), 4.10 (d, J = 5.9 Hz, 2H), 4.06 (s, 1H), 3.95 (h, J = 7.1 Hz, 1H), 3.87 (s, 1H), 3.77 (s, 1H), 3.76 (s, 3H), 3.73 (s, 3H), 3.31 (d, J = 4.5 Hz, 2H), 2.44 (ddt, J = 12.1, 7.7, 3.7 Hz, 2H), 2.00 (td, J = 8.8, 4.4 Hz, 2H). |
| 41 | 2-(2-(trifluoromethyl)phenyl) acetic acid | 3.2 | 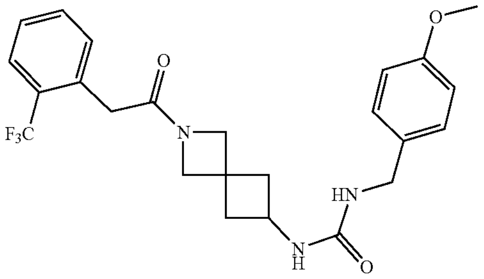 [SMILES: COc1ccc(CNC(=O)NC2CC3(C2)CN(C(=O)Cc2ccccc2C(F)(F)F)C3)cc1] 1-(4-methoxybenzyl)-3-(2-(2-(2-(trifluoromethyl)phenyl)acetyl)-2-azaspiro[3.3]heptan-6-yl)urea. LRMS (APCI) m/z 462 (M + H). $^1$H NMR (400 MHz, DMSO-$d_6$) δ 7.68 (d, J = 7.8 Hz, 1H), 7.62 (t, J = 7.6 Hz, 1H), 7.45 (dd, J = 18.3, 7.8 Hz, 2H), 7.16 (d, J = 8.5 Hz, 2H), 6.93-6.77 (m, 2H), 6.24-6.05 (m, 2H), 4.21 (s, 1H), 4.14-4.02 (m, 3H), 3.96 (q, J = 8.0 Hz, 1H), 3.90 (s, 1H), 3.79 (s, 1H), 3.73 (s, 3H), 3.59 (d, J = 6.3 Hz, 2H), 2.45 (s, 2H), 2.01 (tt, J = 8.4, 3.7 Hz, 2H). |

-continued

| Compound No. | Carboxylic acid | Intermediate | Structure, Name and Data |
|---|---|---|---|
| 42 | 2-(o-tolyl)acetic acid | 3.2 | 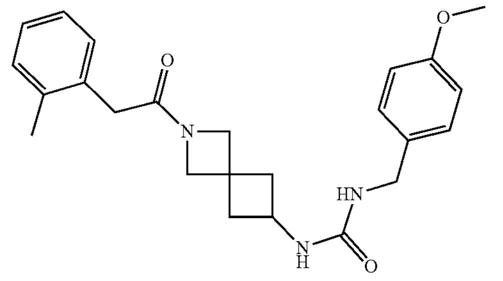 [SMILES: COc1ccc(CNC(=O)NC2CC3(C2)CN(C(=O)Cc2ccccc2C)C3)cc1] 1-(4-methoxybenzyl)-3-(2-(2-(o-tolyl)acetyl)-2-azaspiro[3.3]heptan-6-yl)urea. LRMS (APCI) m/z 408 (M + H). $^{1}$H NMR (400 MHz, DMSO-$d_6$) δ 7.19-7.03 (m, 6H), 6.87 (d, J = 8.2 Hz, 2H), 6.25-6.07 (m, 2H), 4.19 (s, 1H), 4.10 (d, J = 5.7 Hz, 2H), 4.06 (s, 1H), 3.96 (q, J = 8.0 Hz, 1H), 3.90 (s, 1H), 3.78 (s, 1H), 3.73 (s, 3H), 3.40 (d, J = 4.6 Hz, 2H), 2.47-2.36 (m, 2H), 2.21 (t, J = 1.5 Hz, 3H), 1.99 (td, J = 8.9, 2.9 Hz, 2H). |
| 222 | 3-(pyrrolidin-1-yl)benzoic acid | 3.3 | 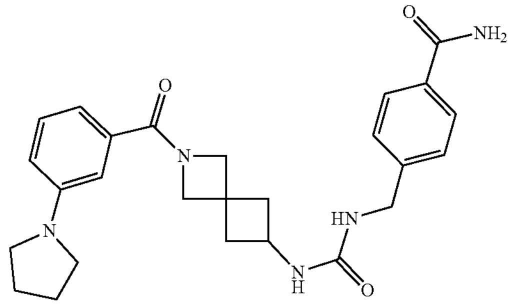 [SMILES: NC(=O)c1ccc(CNC(=O)NC2CC3(C2)CN(C(=O)c2cccc(N4CCCC4)c2)C3)cc1] 4-((3-(2-(3-(pyrrolidin-1-yl)benzoyl)-2-azaspiro[3.3]heptan-6-yl)ureido)methyl)benzamide. LRMS (APCI) m/z 462 (M + H). $^{1}$H NMR (400 MHz, Methanol-$d_4$) δ 7.73 (d, J = 8.0 Hz, 2H), 7.26 (d, J = 8.0 Hz, 2H), 7.13 (td, J = 7.9, 3.5 Hz, 1H), 6.70 (t, J = 7.2 Hz, 1H), 6.66 (s, 1H), 6.60 (d, J = 8.3 Hz, 1H), 4.49 (s, 2H), 4.29 (s, 1H), 4.26 (s, 2H), 4.16 (s, 1H), 4.10 (s, 1H), 3.95 (d, J = 20.2 Hz, 3H), 2.51 (s, 3H), 2.09-1.98 (m, 2H), 1.98-1.86 (m, 4H). |
| 223 | 5-(pyrrolidin-1-yl)nicotinic acid | 3.3 | 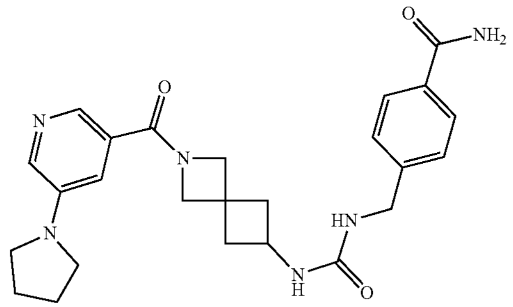 [SMILES: NC(=O)c1ccc(CNC(=O)NC2CC3(C2)CN(C(=O)c2cncc(N4CCCC4)c2)C3)cc1] 4-((3-(2-(5-(pyrrolidin-1-yl)nicotinoyl)-2-azaspiro[3.3]heptan-6-yl)ureido)methyl)benzamide. LRMS (APCI) m/z 463 (M + H). $^{1}$H NMR (400 MHz, Methanol-$d_4$) δ 7.87 (s, 2H), 7.72 (d, J = 8.0 Hz, 2H), 7.26 (d, J = 8.1 Hz, 2H), 7.03 (s, 1H), 4.48 (s, 1H), 4.32 (s, |

-continued

| Compound No. | Carboxylic acid | Intermediate | Structure, Name and Data |
|---|---|---|---|
| | | | 1H), 4.25 (s, 2H), 4.20 (s, 1H), 4.12 (s, 1H), 4.07-3.87 (m, 3H), 3.25 (s, 2H), 2.57 -2.42 (m, 2H), 2.08-1.93 (m, 6H). |
| 224 | 3-chlorobenzoic acid | 3.3 | 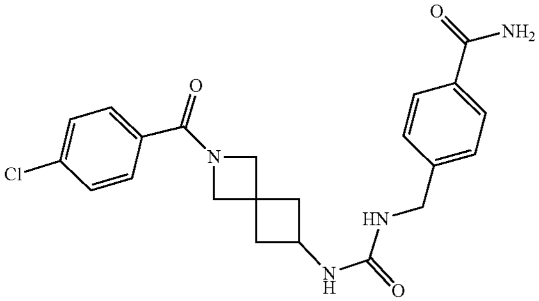 [SMILES: NC(=O)c1ccc(CNC(=O)NC2CC3(C2)CN(C(=O)c2ccc(Cl)cc2)C3)cc1] 4-((3-(2-(4-chlorobenzoyl)-2-azaspiro[3.3]heptan-6-yl)ureido)methyl)benzamide. LRMS (APCI) m/z 427 (M + H). $^{1}H$ NMR (400 MHz, Methanol-$d_4$) δ 7.72 (d, J = 8.0 Hz, 2H), 7.53 (dd, J = 8.1, 5.9 Hz, 2H), 7.37 (dd, J = 8.5, 2.5 Hz, 2H), 7.26 (d, J = 8.1 Hz, 2H), 4.31 (s, 1H), 4.25 (s, 2H), 4.18 (s, 1H), 4.11 (s, 1H), 4.03-3.87 (m, 2H), 2.50 (ddd, J = 10.6, 7.2, 3.5 Hz, 2H), 2.02 (td, J = 8.9, 4.2 Hz, 2H). |
| 225 | 6-methylnicotinic acid | 3.3 | 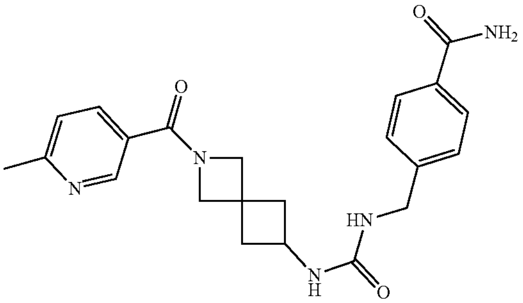 [SMILES: Cc1ccc(C(=O)N2CC3(CC(NC(=O)NCc4ccc(C(N)=O)cc4)C3)C2)cn1] 4-((3-(2-(6-methylnicotinoyl)-2-azaspiro[3.3]heptan-6-yl)ureido)methyl)benzamide. LRMS (APCI) m/z 408 (M + H). $^{1}H$ NMR (400 MHz, Methanol-$d_4$) δ 8.72 (d, J = 6.6 Hz, 1H), 8.19-8.00 (m, 2H), 7.84 (d, J = 8.2 Hz, 2H), 7.47 (dd, J = 8.3, 3.7 Hz, 1H), 7.37 (d, J = 8.2 Hz, 2H), 4.47 (s, 1H), 4.37 (s, 2H), 4.34 (s, 1H), 4.24 (s, 1H), 4.13 (s, 1H), 4.06 (dq, J = 15.5, 7.7 Hz, 1H), 2.94 (d, J = 4.5 Hz, 1H), 2.62 (m, 3H), 2.15 (t, J = 9.4 Hz, 2H). |
| 226 | 2-methylisonicotinic acid | 3.3 | 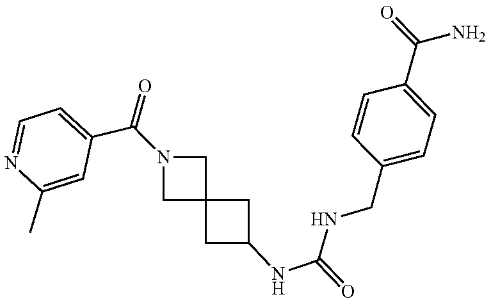 [SMILES: Cc1cc(C(=O)N2CC3(CC(NC(=O)NCc4ccc(C(N)=O)cc4)C3)C2)ccn1] 4-((3-(2-(2-methylisonicotinoyl)-2-azaspiro[3.3]heptan-6- |

-continued

| Compound No. | Carboxylic acid | Intermediate | Structure, Name and Data |
|---|---|---|---|
| | | | yl)ureido)methyl)benzamide. LRMS (APCI) m/z 408 (M + H). $^1$H NMR (400 MHz, Methanol-$d_4$) δ 8.60 (t, J = 6.6 Hz, 1H), 7.79 (d, J = 12.3 Hz, 1H), 7.72 (d, J = 8.2 Hz, 3H), 7.26 (d, J = 8.0 Hz, 2H), 4.33 (s, 1H), 4.25 (s, 2H), 4.20 (s, 1H), 4.16 (s, 1H), 4.04 (s, 1H), 3.95 (dt, J = 15.8, 7.9 Hz, 1H), 2.66 (d, J = 6.0 Hz, 3H), 2.51 (t, J = 8.8 Hz, 2H), 2.05 (dd, J = 11.4, 7.3 Hz, 2H). |
| 219 | 3-(1H-pyrrol-1-yl)benzoic acid | 3.1 | 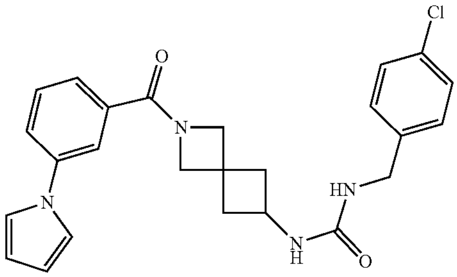 [SMILES: O=C(NCc1ccc(Cl)cc1)NC1CC2(C1)CN(C(=O)c1cccc(-n3cccc3)c1)C2] 1-(2-(3-(1H-pyrrol-1-yl)benzoyl)-2-azaspiro[3.3]heptan-6-yl)-3-(4-chlorobenzyl)urea. LRMS (APCI) m/z 449 (M + H). $^1$H NMR (400 MHz, DMSO-$d_6$) δ 7.75-7.69 (m, 2H), 7.57-7.49 (m, 1H), 7.48-7.41 (m, 3H), 7.36 (d, J = 8.4 Hz, 2H), 7.24 (d, J = 8.4 Hz, 2H), 6.33-6.27 (m, 3H), 6.24 (dd, J = 8.0, 3.7 Hz, 1H), 4.39 (s, 1H), 4.26 (s, 1H), 4.16 (d, J = 6.0 Hz, 2H), 4.10 (s, 1H), 3.96 (d, J = 21.5 Hz, 2H), 2.46 (s, 2H), 2.02 (d, J = 10.3 Hz, 2H). |
| 220 | 3-isopropylbenzoic acid | 3.1 | 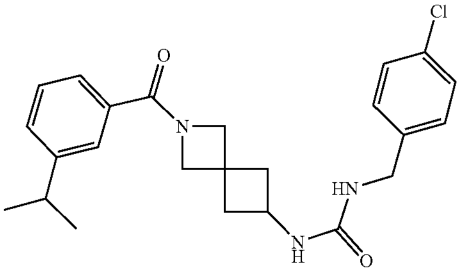 [SMILES: CC(C)c1cccc(C(=O)N2CC3(CC(NC(=O)NCc4ccc(Cl)cc4)C3)C2)c1] 1-(4-chlorobenzyl)-3-(2-(3-isopropylbenzoyl)-2-azaspiro[3.3]heptan-6-yl)urea. LRMS (APCI) m/z 426 (M + H). $^1$H NMR (400 MHz, DMSO-$d_6$) δ 7.47 (s, 1H), 7.43-7.32 (m, 5H), 7.27-7.20 (m, 2H), 6.31 (t, J = 6.1 Hz, 1H), 6.24 (t, J = 7.9 Hz, 1H), 4.33 (s, 1H), 4.21 (s, 1H), 4.16 (d, J = 6.0 Hz, 2H), 4.07 (s, 1H), 3.99-3.88 (m, 3H), 2.94 (hept, J = 6.9 Hz, 1H), 2.47 (s, 1H), 2.00 (dt, J = 9.9, 5.4 Hz, 2H), 1.22 (d, J = 6.9 Hz, 6H). |

-continued

| Compound No. | Carboxylic acid | Intermediate | Structure, Name and Data |
|---|---|---|---|
| 221 | 2-methyl-2-phenylpropanoic acid | 3.1 | 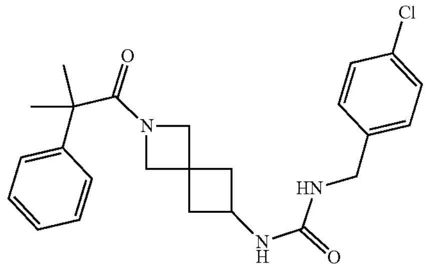 [SMILES: CC(C)(C(=O)N1CC2(CC(NC(=O)NCc3ccc(Cl)cc3)C2)C1)c1ccccc1] 1-(4-chlorobenzyl)-3-(2-(2-methyl-2-phenylpropanoyl)-2-azaspiro[3.3]heptan-6-yl)urea. LRMS (APCI) m/z 426 (M + H). $^1$H NMR (400 MHz, DMSO-$d_6$) δ 7.41-7.29 (m, 4H), 7.29-7.16 (m, 5H), 6.27 (t, J = 6.1 Hz, 1H), 6.12 (dd, J = 30.8, 7.9 Hz, 1H), 4.12 (d, J = 5.9 Hz, 2H), 3.83 (s, 2H), 3.69 (d, J = 26.6 Hz, 2H), 3.21 (s, 1H), 2.27 (s, 1H), 2.10 (d, J = 17.8 Hz, 1H), 1.86 (t, J = 10.1 Hz, 1H), 1.75 (d, J = 10.4 Hz, 1H), 1.38 (s, 6H). |
| 114 | benzoic acid | 3.1 | 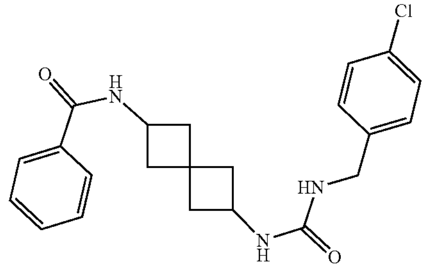 [SMILES: O=C(NCc1ccc(Cl)cc1)NC1CC2(C1)CC(NC(=O)c1ccccc1)C2] N-(6-(3-(4-chlorobenzyl)ureido)spiro[3.3]heptan-2-yl)benzamide. LRMS (APCI) m/z 398 (M + H). $^1$H NMR (400 MHz, DMSO-$d_6$) δ 8.54 (d, J = 7.5 Hz, 1H), 7.87-7.79 (m, 2H), 7.55-7.48 (m, 1H), 7.45 (dd, J = 8.2, 6.5 Hz, 2H), 7.40-7.32 (m, 2H), 7.28-7.22 (m, 2H), 6.28 (t, J = 6.1 Hz, 1H), 6.22 (d, J = 8.1 Hz, 1H), 4.31 (q, J = 8.0 Hz, 1H), 4.17 (d, J = 6.0 Hz, 2H), 3.97 (h, J = 8.3 Hz, 1H), 2.37 (qd, J = 10.2, 9.3, 6.4 Hz, 2H), 2.25-2.15 (m, 2H), 2.15-2.03 (m, 2H), 1.84 (ddd, J = 17.2, 10.5, 8.4 Hz, 2H). |
| 115 | phenylacetic acid | 3.4 | 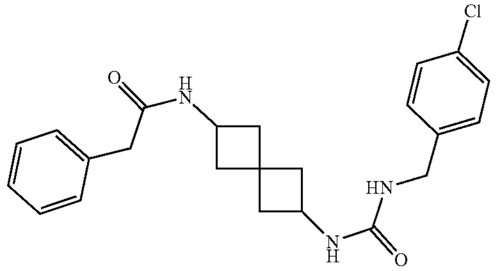 [SMILES: O=C(Cc1ccccc1)NC1CC2(C1)CC(NC(=O)NCc1ccc(Cl)cc1)C2] N-(6-(3-(4-chlorobenzyl)ureido)spiro[3.3]heptan-2-yl)-2-phenylacetamide. LRMS (APCI) m/z 412 (M + H). $^1$H NMR (400 MHz, DMSO-$d_6$) δ 8.24 (d, J = 7.5 Hz, 1H), 7.36 (d, J = 8.4 Hz, 2H), 7.32-7.19 (m, 7H), 6.27 (t, J = 6.1 Hz, 1H), 6.19 (d, J = 8.1 Hz, 1H), 4.15 (d, J = 6.0 Hz, 2H), 4.03 |

-continued

| Compound No. | Carboxylic acid | Intermediate | Structure, Name and Data |
|---|---|---|---|
| | | | (q, J = 8.0 Hz, 1H), 3.93 (q, J = 8.2 Hz, 1H), 2.38-2.26 (m, 3H), 2.15 (dq, J = 12.9, 7.4 Hz, 3H), 1.95-1.70 (m, 4H). |
| 184 | nicotinic acid | 3.4 | 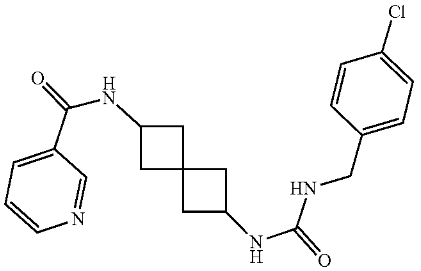 [SMILES: O=C(NCc1ccc(Cl)cc1)NC1CC2(C1)CC(NC(=O)c1cccnc1)C2] N-(6-(3-(4-chlorobenzyl)ureido)spiro[3.3]heptan-2-yl)nicotinamide. LRMS (APCI) m/z 400 (M + H). $^1$H NMR (400 MHz, DMSO-$d_6$) δ 8.98 (d, J = 2.2 Hz, 1H), 8.75 (d, J = 7.3 Hz, 1H), 8.69 (dd, J = 4.8, 1.7 Hz, 1H), 8.21-8.13 (m, 1H), 7.50 (dd, J = 8.0, 4.8 Hz, 1H), 7.41-7.32 (m, 2H), 7.25 (d, J = 8.3 Hz, 2H), 6.27 (d, J = 5.8 Hz, 1H), 6.21 (d, J = 8.0 Hz, 1H), 4.31 (q, J = 8.0 Hz, 1H), 4.17 (d, J = 5.7 Hz, 2H), 3.97 (q, J = 7.9 Hz, 1H), 2.45-2.35 (m, 2H), 2.30-2.16 (m, 2H), 2.16-2.02 (m, 2H), 1.93-1.77 (m, 2H). |
| 185 | isonicotinic acid | 3.4 | 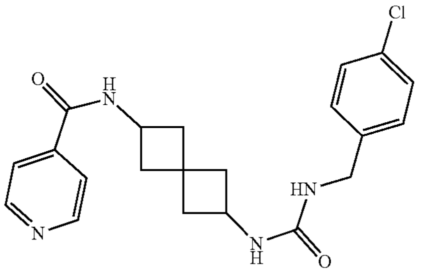 [SMILES: O=C(NCc1ccc(Cl)cc1)NC1CC2(C1)CC(NC(=O)c1ccncc1)C2] N-(6-(3-(4-chlorobenzyl)ureido)spiro[3.3]heptan-2-yl)isonicotinamide. LRMS (APCI) m/z 399 (M + H). $^1$H NMR (400 MHz, DMSO-$d_6$) δ 8.86 (d, J = 7.3 Hz, 1H), 8.77-8.68 (m, 2H), 7.81-7.69 (m, 2H), 7.45-7.31 (m, 2H), 7.25 (d, J = 8.3 Hz, 2H), 6.28 (s, 1H), 6.21 (d, J = 8.1 Hz, 1H), 4.31 (p, J = 8.0 Hz, 1H), 4.16 (d, J = 5.5 Hz, 2H), 3.97 (q, J = 7.8 Hz, 1H), 2.39 (ddt, J = 11.1, 7.8, 4.1 Hz, 2H), 2.27-2.16 (m, 2H), 2.16-2.02 (m, 2H), 1.84 (ddd, J = 16.4, 10.4, 8.4 Hz, 2H). |
| 186 | 2-methylisonicotinic acid | 3.4 | 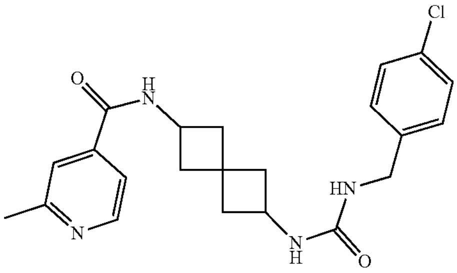 [SMILES: Cc1cc(C(=O)NC2CC3(CC(NC(=O)NCc4ccc(Cl)cc4)C3)C2)ccn1] N-(6-(3-(4-chlorobenzyl)ureido)spiro[3.3]heptan-2-yl)-2-methylisonicotinamide. LRMS |

-continued

| Compound No. | Carboxylic acid | Intermediate | Structure, Name and Data |
|---|---|---|---|
| | | | (APCI) m/z 413 (M + H). $^1$H NMR (400 MHz, DMSO-d6) δ 8.99 (d, J = 7.3 Hz, 1H), 8.72 (d, J = 5.6 Hz, 1H), 7.89 (s, 1H), 7.80 (s, 1H), 7.42-7.31 (m, 2H), 7.25 (d, J = 8.4 Hz, 2H), 6.26 (d, J = 28.7 Hz, 2H), 4.30 (q, J = 8.0 Hz, 1H), 4.17 (s, 2H), 3.97 (s, 1H), 2.64 (s, 3H), 2.40 (dq, J = 12.0, 6.4 Hz, 2H), 2.22 (ddt, J = 17.4, 12.7, 6.4 Hz, 2H), 2.16-2.01 (m, 2H), 1.92-1.69 (m, 2H). |
| 192 | 6-methylnicotinic acid | 3.4 | 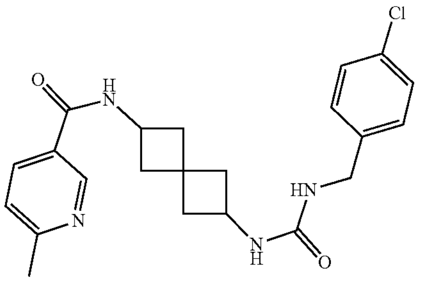 [SMILES: Cc1ccc(C(=O)NC2CC3(CC(NC(=O)NCc4ccc(Cl)cc4)C3)C2)cn1] c. LRMS (APCI) m/z 413 (M + H). $^1$H NMR (400 MHz, DMSO-$d_6$) δ 8.86 (d, J = 2.3 Hz, 1H), 8.65 (d, J = 7.4 Hz, 1H), 8.06 (dd, J = 8.1, 2.4 Hz, 1H), 7.41-7.30 (m, 3H), 7.30-7.17 (m, 2H), 6.28 (t, J = 6.0 Hz, 1H), 6.21 (d, J = 8.0 Hz, 1H), 4.30 (q, J = 8.0 Hz, 1H), 4.16 (d, J = 6.1 Hz, 2H), 3.97 (q, J = 8.1 Hz, 1H), 3.32 (s, 3H), 2.44-2.32 (m, 2H), 2.26-2.16 (m, 2H), 2.08 (ddd, J = 17.1, 12.4, 9.2 Hz, 2H), 1.93-1.76 (m, 2H). |
| 193 | 2-methylbenzoic acid | 3.4 | 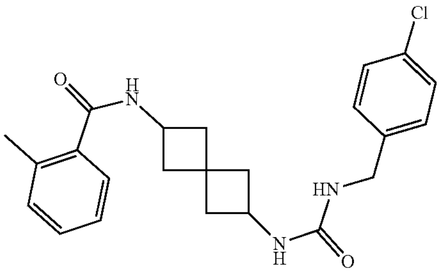 [SMILES: Cc1ccccc1C(=O)NC1CC2(CC(NC(=O)NCc3ccc(Cl)cc3)C2)C1] N-(6-(3-(4-chlorobenzyl)ureido)spiro[3.3]heptan-2-yl)-2-methylbenzamide. LRMS (APCI) m/z 412 (M + H). $^1$H NMR (400 MHz, DMSO-$d_6$) δ 8.40 (d, J = 7.5 Hz, 1H), 7.41-7.33 (m, 2H), 7.34-7.15 (m, 6H), 6.27 (t, J = 6.1 Hz, 1H), 6.20 (d, J = 8.1 Hz, 1H), 4.24 (q, J = 8.0 Hz, 1H), 4.16 (d, J = 6.0 Hz, 2H), 3.95 (q, J = 8.0 Hz, 1H), 2.37 (dt, J = 12.0, 6.3 Hz, 2H), 2.30 (s, 3H), 2.25-2.12 (m, 2H), 2.09-1.95 (m, 2H), 1.82 (dt, J = 19.8, 10.0 Hz, 2H). |

-continued

| Compound No. | Carboxylic acid | Intermediate | Structure, Name and Data |
|---|---|---|---|
| 194 | 3-methoxybenzoic acid | 3.4 | 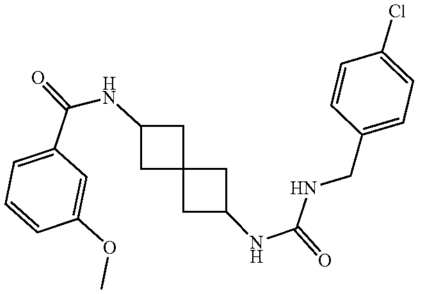 [SMILES: COc1cccc(C(=O)NC2CC3(CC(NC(=O)NCc4ccc(Cl)cc4)C3)C2)c1] N-(6-(3-(4-chlorobenzyl)ureido)spiro[3.3]heptan-2-yl)-3-methoxybenzamide. LRMS (APCI) m/z 428 (M + H). $^1$H NMR (400 MHz, DMSO-$d_6$) δ 8.52 (d, J = 7.5 Hz, 1H), 7.48-7.31 (m, 5H), 7.25 (d, J = 8.1 Hz, 2H), 7.07 (dd, J = 7.9, 2.6 Hz, 1H), 6.27 (t, J = 6.1 Hz, 1H), 6.20 (d, J = 8.1 Hz, 1H), 4.30 (q, J = 8.1 Hz, 1H), 4.16 (d, J = 5.9 Hz, 2H), 3.97 (q, J = 8.0 Hz, 1H), 3.80 (s, 3H), 2.43-2.27 (m, 2H), 2.21 (dt, J = 11.8, 5.6 Hz, 2H), 2.09 (dt, J = 19.4, 10.0 Hz, 2H), 1.84 (dt, J = 18.7, 10.0 Hz, 2H). |
| 195 | 3-(methylsulfonyl)benzoic acid | 3.4 | 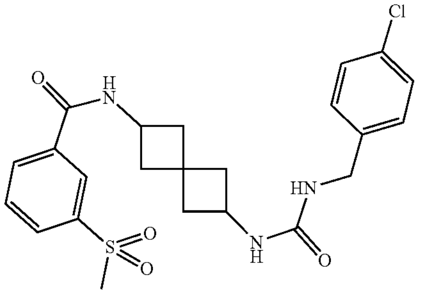 [SMILES: CS(=O)(=O)c1cccc(C(=O)NC2CC3(CC(NC(=O)NCc4ccc(Cl)cc4)C3)C2)c1] N-(6-(3-(4-chlorobenzyl)ureido)spiro[3.3]heptan-2-yl)-3-(methylsulfonyl)benzamide. LRMS (APCI) m/z 476 (M + H). $^1$H NMR (400 MHz, DMSO-$d_6$) δ 8.86 (d, J = 7.4 Hz, 1H), 8.37 (s, 1H), 8.17 (d, J = 7.8 Hz, 1H), 8.07 (d, J = 7.8 Hz, 1H), 7.75 (t, J = 7.8 Hz, 1H), 7.41-7.31 (m, 2H), 7.25 (d, J = 8.1 Hz, 2H), 6.28 (t, J = 6.1 Hz, 1H), 6.21 (d, J = 8.0 Hz, 1H), 4.33 (q, J = 8.0 Hz, 1H), 4.17 (d, J = 6.0 Hz, 2H), 3.97 (q, J = 8.0 Hz, 1H), 3.26 (s, 3H), 2.45-2.35 (m, 2H), 2.29-2.16 (m, 2H), 2.17-2.03 (m, 2H), 1.85 (dt, J = 17.2, 9.9 Hz, 2H). |
| 200 | 3-hydroxybenzoic acid | 3.4 | 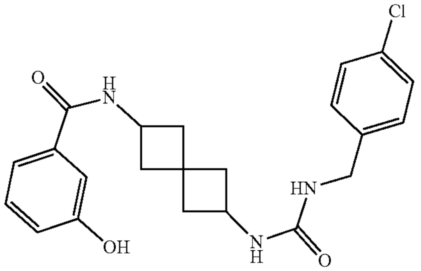 [SMILES: O=C(NCc1ccc(Cl)cc1)NC1CC2(C1)CC(NC(=O)c1cccc(O)c1)C2] N-(6-(3-(4-chlorobenzyl)ureido)spiro[3.3]heptan-2-yl)-3-hydroxybenzamide. LRMS |

-continued

| Compound No. | Carboxylic acid | Intermediate | Structure, Name and Data |
|---|---|---|---|
| | | | (APCI) m/z 414 (M + H). $^1$H NMR (400 MHz, DMSO-$d_6$) δ 9.59 (s, 1H), 8.44 (d, J = 7.5 Hz, 1H), 7.43-7.32 (m, 2H), 7.29-7.18 (m, 5H), 6.88 (dt, J = 6.8, 2.3 Hz, 1H), 6.27 (t, J = 6.3 Hz, 1H), 6.20 (d, J = 8.0 Hz, 1H), 4.27 (q, J = 8.0 Hz, 1H), 4.16 (d, J = 5.9 Hz, 2H), 3.96 (q, J = 8.0 Hz, 1H), 2.36 (ddd, J = 12.8, 10.2, 6.1 Hz, 2H), 2.24-2.13 (m, 2H), 2.07 (ddd, J = 17.0, 11.1, 9.1 Hz, 2H), 1.83 (ddd, J = 16.7, 10.9, 8.9 Hz, 2H). |
| 203 | 2-methylnicotinic acid | 3.4 | 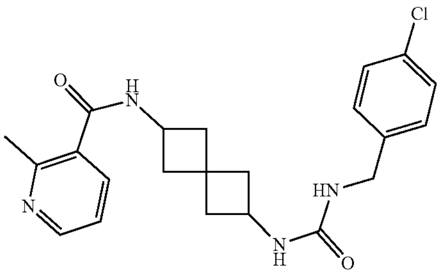 [SMILES: Cc1ncccc1C(=O)NC1CC2(CC(NC(=O)NCc3ccc(Cl)cc3)C2)C1] N-(6-(3-(4-chlorobenzyl)ureido)spiro[3.3]heptan-2-yl)-2-methylnicotinamide. LRMS (APCI) m/z 413 (M + H). $^1$H NMR (400 MHz, DMSO-$d_6$) δ 8.60 (d, J = 7.3 Hz, 1H), 8.50 (dd, J = 4.9, 1.7 Hz, 1H), 7.70 (d, J = 7.6 Hz, 1H), 7.41-7.33 (m, 2H), 7.33-7.20 (m, 3H), 6.27 (t, J = 6.1 Hz, 1H), 6.20 (d, J = 8.1 Hz, 1H), 4.25 (q, J = 7.9 Hz, 1H), 4.16 (d, J = 5.8 Hz, 2H), 3.96 (q, J = 7.9 Hz, 1H), 2.50 (s, 3H), 2.44-2.31 (m, 2H), 2.20 (ddd, J = 19.4, 14.0, 8.7 Hz, 2H), 2.10-1.93 (m, 2H), 1.92-1.75 (m, 2H). |
| 204 | 3-methylisonicotinic acid | 3.4 | 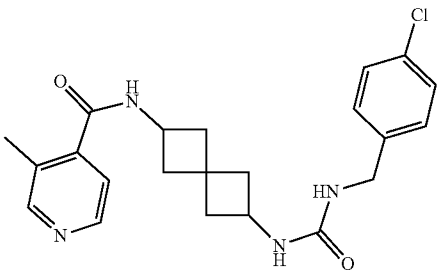 [SMILES: Cc1cnccc1C(=O)NC1CC2(CC(NC(=O)NCc3ccc(Cl)cc3)C2)C1] N-(6-(3-(4-chlorobenzyl)ureido)spiro[3.3]heptan-2-yl)-3-methylisonicotinamide. LRMS (APCI) m/z 413 (M + H). $^1$H NMR (400 MHz, DMSO-$d_6$) δ 8.66 (d, J = 7.4 Hz, 1H), 8.50 (s, 1H), 8.47 (d, J = 5.0 Hz, 1H), 7.40-7.34 (m, 2H), 7.29 (d, J = 5.0 Hz, 1H), 7.25 (d, J = 8.3 Hz, 2H), 6.27 (t, J = 6.0 Hz, 1H), 6.20 (d, J = 8.0 Hz, 1H), 4.24 (q, J = 7.9 Hz, 1H), 4.16 (d, J = 5.8 Hz, 2H), 3.96 (q, J = 8.0 Hz, 1H), 2.38 (d, J = 8.8 Hz, 2H), 2.29 (s, 3H), 2.26-2.12 (m, 2H), 2.09-1.94 (m, 2H), 1.83 (dt, J = 19.1, 9.9 Hz, 2H). |

-continued

| Compound No. | Carboxylic acid | Intermediate | Structure, Name and Data |
|---|---|---|---|
| 205 | 4-methylnicotinic acid | 3.4 | 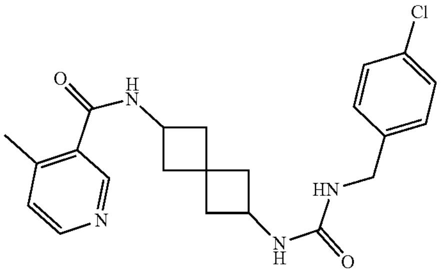 [SMILES: Cc1ccncc1C(=O)NC1CC2(CC(NC(=O)NCc3ccc(Cl)cc3)C2)C1] N-(6-(3-(4-chlorobenzyl)ureido)spiro[3.3]heptan-2-yl)-4-methylnicotinamide. LRMS (APCI) m/z 413 (M + H). $^1$H NMR (400 MHz, DMSO-$d_6$) δ 8.66 (d, J = 7.3 Hz, 1H), 8.48 (d, J = 5.5 Hz, 2H), 7.37 (d, J = 8.4 Hz, 2H), 7.32 (d, J = 5.1 Hz, 1H), 7.25 (d, J = 8.4 Hz, 2H), 6.27 (t, J = 6.0 Hz, 1H), 6.20 (d, J = 8.0 Hz, 1H), 4.25 (q, J = 7.9 Hz, 1H), 4.16 (d, J = 5.9 Hz, 2H), 3.96 (q, J = 8.1 Hz, 1H), 2.34 (s, 5H), 2.31-2.09 (m, 2H), 2.09-1.92 (m, 2H), 1.83 (ddd, J = 19.1, 10.4, 8.4 Hz, 2H). |
| 208 | 2-hydroxybenzoic acid | 3.4 | 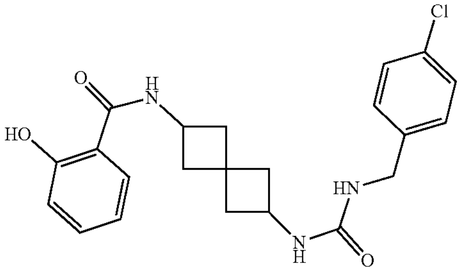 N-(6-(3-(4-chlorobenzyl)ureido)spiro[3.3]heptan-2-yl)-2-hydroxybenzamide. LRMS (APCI) m/z 414 (M + H). $^1$H NMR (400 MHz, DMSO-$d_6$) δ 12.67 (d, J = 2.7 Hz, 1H), 8.86 (d, J = 7.3 Hz, 1H), 7.87 (d, J = 7.9 Hz, 1H), 7.37 (d, J = 8.2 Hz, 3H), 7.25 (t, J = 5.0 Hz, 2H), 6.88 (d, J = 8.1 Hz, 2H), 6.28 (s, 1H), 6.21 (d, J = 8.1 Hz, 1H), 4.31 (d, J = 8.5 Hz, 1H), 4.16 (d, J = 5.8 Hz, 2H), 3.97 (d, J = 8.3 Hz, 1H), 2.40 (s, 2H), 2.22 (s, 2H), 2.12 (p, J = 10.4, 9.5 Hz, 2H), 1.86 (dd, J = 15.5, 8.8 Hz, 2H). |
| 209 | 2-(dimethylamino)benzoic acid | 3.4 | 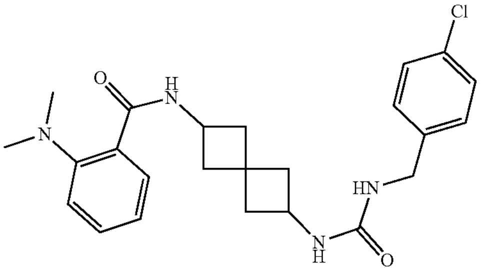 [SMILES: CN(C)c1ccccc1C(=O)NC1CC2(CC(NC(=O)NCc3ccc(Cl)cc3)C2)C1] N-(6-(3-(4-chlorobenzyl)ureido)spiro[3.3]heptan-2-yl)-2-(dimethylamino)benzamide. LRMS (APCI) m/z 441 (M + H). $^1$H NMR (400 MHz, DMSO-$d_6$) δ 9.06 (d, J = 7.5 Hz, 1H), 8.14 (t, J = 2.0 Hz, 1H), 7.60 (d, J = 7.7 Hz, 1H), 7.43 (s, 1H), 7.41-7.33 |

-continued

| Compound No. | Carboxylic acid | Intermediate | Structure, Name and Data |
|---|---|---|---|
| | | | (m, 2H), 7.25 (d, J = 8.2 Hz, 2H), 7.09 (s, 1H), 6.30-6.17 (m, 2H), 4.29 (q, J = 7.7 Hz, 1H), 4.16 (d, J = 4.9 Hz, 2H), 4.03-3.91 (m, 1H), 2.79 (s, 6H), 2.39 (s, 2H), 2.22 (d, J = 9.0 Hz, 2H), 2.03 (q, J = 11.3 Hz, 2H), 1.91-1.78 (m, 2H). |
| 212 | 2-cyanobenzoic acid | 3.4 | 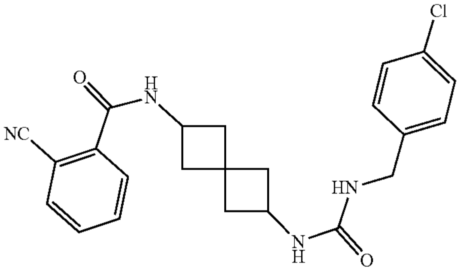 [SMILES: N#Cc1ccccc1C(=O)NC1CC2(CC(NC(=O)NCc3ccc(Cl)cc3)C2)C1] N-(6-(3-(4-chlorobenzyl)ureido)spiro[3.3]heptan-2-yl)-2-cyanobenzamide. LRMS (APCI) m/z 423 (M + H). $^1$H NMR (400 MHz, DMSO-$d_6$) δ 8.85 (d, J = 7.4 Hz, 1H), 7.96-7.84 (m, 1H), 7.82-7.70 (m, 2H), 7.67 (ddd, J = 7.7, 6.2, 2.6 Hz, 1H), 7.42-7.32 (m, 2H), 7.30-7.21 (m, 2H), 6.28 (t, J = 6.0 Hz, 1H), 6.21 (d, J = 8.1 Hz, 1H), 4.29 (p, J = 8.0 Hz, 1H), 4.17 (d, J = 6.0 Hz, 2H), 3.97 (q, J = 8.0 Hz, 1H), 2.45-2.36 (m, 2H), 2.22 (ddt, J = 17.9, 12.0, 6.5 Hz, 2H), 2.07 (ddd, J = 16.3, 10.6, 8.6 Hz, 2H), 1.93-1.77 (m, 2H). |
| 159 | 4-methylbenzoic acid | 3.5 | 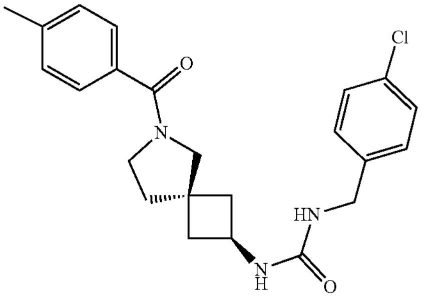 [SMILES: Cc1ccc(C(=O)N2CC[C@]3(C2)C[C@@H](NC(=O)NCc2ccc(Cl)cc2)C3)cc1] 1-(4-chlorobenzyl)-3-((2r,4s)-6-(4-methylbenzoyl)-6-azaspiro[3.4]octan-2-yl)urea. LRMS (APCI) m/z 412 (M + H). $^1$H NMR (400 MHz, Chloroform-d) δ 7.43 (dd, J = 8.0, 3.2 Hz, 1H), 7.40-7.31 (m, 2H), 7.21 (dt, J = 15.1, 7.9 Hz, 3H), 5.05 (t, J = 8.3 Hz, 1H), 4.78 (s, 1H), 4.40 (d, J = 5.7 Hz, 1H), 4.32 (s, 2H), 3.54 (d, J = 24.4 Hz, 5H), 2.44 (s, 3H), 2.26 (s, 2H), 1.99 (s, 5H). |
| 160 | 2-methylisonicotinic acid | 3.5 | 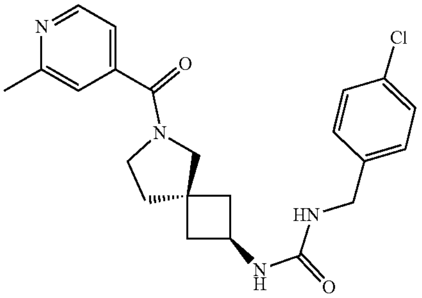 [SMILES: Cc1cc(C(=O)N2CC[C@]3(C2)C[C@@H](NC(=O)NCc2ccc(Cl)cc2)C3)ccn1] |

-continued

| Compound No. | Carboxylic acid | Intermediate | Structure, Name and Data |
|---|---|---|---|
| | | | 1-(4-chlorobenzyl)-3-((2r,4s)-6-(2-methylisonicotinoyl)-6-azaspiro[3.4]octan-2-yl)urea. LRMS (APCI) m/z 413 (M + H). $^1$H NMR (400 MHz, DMSO-$d_6$) δ 8.52 (t, J = 4.6 Hz, 1H), 7.40-7.31 (m, 3H), 7.29-7.20 (m, 3H), 6.35 (d, J = 2.8 Hz, 1H), 6.14 (d, J = 8.1 Hz, 1H), 4.16 (dd, J = 14.2, 6.0 Hz, 2H), 4.12-4.03 (m, 2H), 3.48 (t, J = 6.9 Hz, 1H), 3.43-3.34 (m, 2H), 3.27 (s, 1H), 3.17 (d, J = 5.0 Hz, 2H), 2.29-2.12 (m, 2H), 1.97-1.85 (m, 3H), 1.80 (td, J = 8.7, 2.7 Hz, 1H). |
| 161 | 3-methylbenzoic acid | 3.5 | 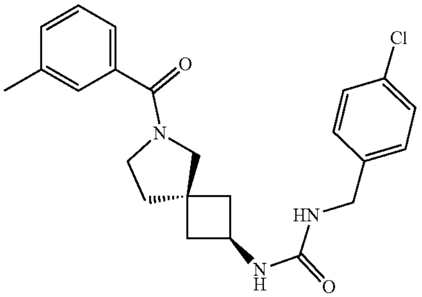 [SMILES: Cc1cccc(C(=O)N2CC[C@]3(C2)C[C@@H](NC(=O)NCc2ccc(Cl)cc2)C3)c1]<br>1-(4-chlorobenzyl)-3-((2r,4s)-6-(3-methylbenzoyl)-6-azaspiro[3.4]octan-2-yl)urea. LRMS (APCI) m/z 412 (M + H). $^1$H NMR (400 MHz, DMSO-$d_6$) δ 7.41-7.32 (m, 4H), 7.32-7.17 (m, 4H), 6.33 (d, J = 7.9 Hz, 1H), 6.14 (d, J = 8.2 Hz, 1H), 4.16 (dd, J = 15.8, 6.0 Hz, 2H), 4.10-4.01 (m, 1H), 3.47 (t, J = 6.9 Hz, 1H), 3.43-3.36 (m, 2H), 2.34 (d, J = 2.1 Hz, 3H), 2.24 (t, J = 9.8 Hz, 1H), 2.16 (t, J = 9.9 Hz, 1H), 1.92 (t, J = 6.6 Hz, 2H), 1.88-1.82 (m, 1H), 1.78 (dd, J = 11.7, 8.7 Hz, 2H). |
| 162 | 2-methylbenzoic acid | 3.5 | 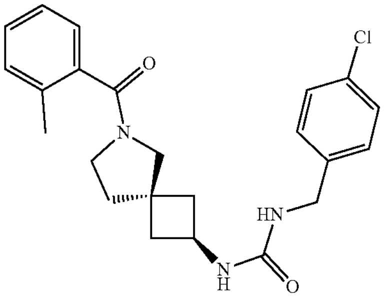 [SMILES: Cc1ccccc1C(=O)N1CC[C@]2(C1)C[C@@H](NC(=O)NCc1ccc(Cl)cc1)C2]<br>1-(4-chlorobenzyl)-3-((2r,4s)-6-(2-methylbenzoyl)-6-azaspiro[3.4]octan-2-yl)urea. LRMS (APCI) m/z 412 (M + H). $^1$H NMR (400 MHz, DMSO-$d_6$) δ 7.40-7.33 (m, 2H), 7.32-7.19 (m, 5H), 7.19-7.14 (m, 1H), 6.33 (dd, J = 10.4, 6.0 Hz, 1H), 6.15 (d, J = 8.1 Hz, 1H), 4.16 (dd, J = 14.5, 6.0 Hz, 2H), 4.12-4.01 (m, 1H), 3.49 (t, J = 7.0 Hz, 1H), 3.42 (s, 1H), 3.17 (d, J = 5.0 Hz, 1H), 3.05 (t, J = 6.7 Hz, 1H), 2.28-2.13 (m, 5H), 1.89 (dt, J = 26.9, 6.8 Hz, 3H), 1.80-1.73 (m, 1H). |

-continued

| Compound No. | Carboxylic acid | Intermediate | Structure, Name and Data |
|---|---|---|---|
| 163 | 4-methoxybenzoic acid | 3.5 | 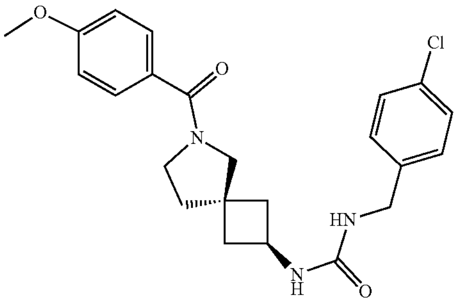 [SMILES: COc1ccc(C(=O)N2CC[C@]3(C2)C[C@@H](NC(=O)NCc2ccc(Cl)cc2)C3)cc1] 1-(4-chlorobenzyl)-3-((2r,4s)-6-(4-methoxybenzoyl)-6-azaspiro[3.4]octan-2-yl)urea. LRMS (APCI) m/z 428 (M + H). $^{1}H$ NMR (400 MHz, DMSO-$d_6$) δ 7.52-7.47 (m, 2H), 7.36 (t, J = 8.3 Hz, 2H), 7.28-7.20 (m, 2H), 6.97 (d, J = 8.1 Hz, 2H), 6.39-6.26 (m, 1H), 6.14 (d, J = 8.1 Hz, 1H), 4.16 (dd, J = 14.8, 6.0 Hz, 2H), 4.12-4.01 (m, 1H), 3.80 (s, 3H), 3.46 (t, J = 6.8 Hz, 2H), 3.38 (s, 2H), 2.24 (s, 1H), 2.16 (t, J = 9.9 Hz, 1H), 1.96-1.83 (m, 3H), 1.78 (t, J = 9.6 Hz, 1H). |
| 166 | 3-methylisonicotinic acid | 3.5 | 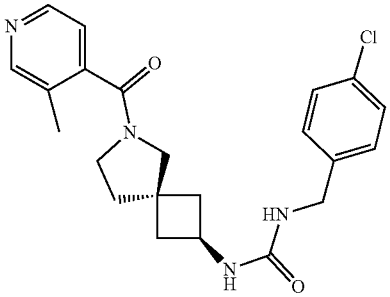 [SMILES: Cc1cnccc1C(=O)N1CC[C@]2(C1)C[C@@H](NC(=O)NCc1ccc(Cl)cc1)C2] 1-(4-chlorobenzyl)-3-((2r,4s)-6-(3-methylisonicotinoyl)-6-azaspiro[3.4]octan-2-yl)urea. LRMS (APCI) m/z 413 (M + H). $^{1}H$ NMR (400 MHz, DMSO-$d_6$) δ 8.57 (s, 1H), 8.51 (d, J = 5.0 Hz, 1H), 7.41-7.29 (m, 3H), 7.29-7.19 (m, 2H), 6.38-6.30 (m, 1H), 6.14 (d, J = 8.1 Hz, 1H), 4.16 (dd, J = 13.2, 5.8 Hz, 2H), 4.07 (q, J = 7.9 Hz, 1H), 3.51 (t, J = 7.0 Hz, 1H), 3.44 (s, 1H), 3.08 (t, J = 6.7 Hz, 1H), 2.99 (s, 1H), 2.29-2.11 (m, 5H), 1.91 (dt, J = 22.0, 7.0 Hz, 3H), 1.78 (dd, J = 11.8, 8.6 Hz, 1H). |
| 167 | 4-fluorobenzoic acid | 3.5 | 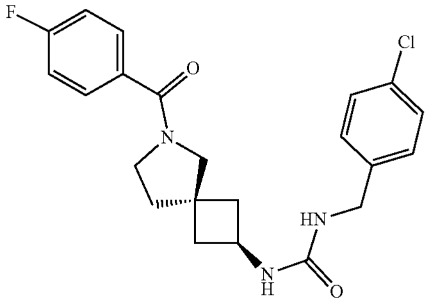 [SMILES: O=C(NCc1ccc(Cl)cc1)N[C@H]1C[C@]2(CCN(C(=O)c3ccc(F)cc3)C2)C1] 1-(4-chlorobenzyl)-3-((2r,4s)-6-(4-fluorobenzoyl)-6-azaspiro[3.4]octan-2-yl)urea. LRMS (APCI) m/z 416 (M + H). $^{1}H$ NMR (400 MHz, DMSO-$d_6$) δ 7.63- |

-continued

| Compound No. | Carboxylic acid | Intermediate | Structure, Name and Data |
|---|---|---|---|
| | | | 7.55 (m, 2H), 7.40-7.33 (m, 2H), 7.25 (dtd, J = 12.6, 6.0, 3.1 Hz, 4H), 6.34 (t, J = 6.8 Hz, 1H), 6.14 (d, J = 8.1 Hz, 1H), 4.16 (dd, J = 14.8, 5.9 Hz, 2H), 4.08 (p, J = 7.9 Hz, 1H), 3.48 (t, J = 6.9 Hz, 1H), 3.45-3.37 (m, 2H), 3.33 (s, 1H), 2.24 (dd, J = 11.4, 8.3 Hz, 1H), 2.21-2.11 (m, 1H), 1.90 (dt, J = 21.9, 6.7 Hz, 3H), 1.79 (dd, J = 11.7, 8.6 Hz, 1H). |
| 169 | 3-isopropylbenzoic acid | 3.5 | 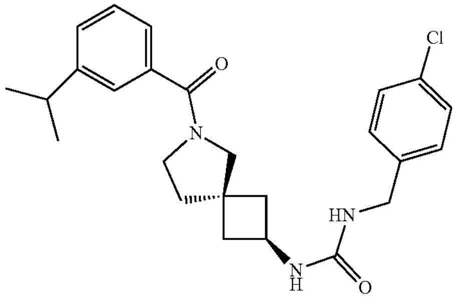 [SMILES: CC(C)c1cccc(C(=O)N2CC[C@]3(C2)C[C@@H](NC(=O)NCc2ccc(Cl)cc2)C3)c1] 1-(4-chlorobenzyl)-3-((2r,4s)-6-(3-isopropylbenzoyl)-6-azaspiro[3.4]octan-2-yl)urea. LRMS (APCI) m/z 440 (M + H). $^1$H NMR (400 MHz, DMSO-$d_6$) δ 7.41-7.28 (m, 5H), 7.24 (dd, J = 14.3, 8.3 Hz, 3H), 6.33 (q, J = 8.6, 7.4 Hz, 1H), 6.14 (d, J = 8.2 Hz, 1H), 4.16 (dd, J = 16.5, 5.9 Hz, 2H), 4.07 (dq, J = 8.6, 5.2 Hz, 1H), 3.48 (t, J = 6.9 Hz, 1H), 3.43-3.28 (m, 4H), 2.93 (p, J = 6.9 Hz, 1H), 2.29-2.20 (m, 1H), 2.20-2.12 (m, 1H), 1.89 (dt, J = 24.7, 6.7 Hz, 2H), 1.78 (dd, J = 11.8, 8.7 Hz, 1H), 1.22 (dd, J = 6.9, 2.2 Hz, 6H). |
| 164 | 4-methylbenzoic acid | 3.6 | 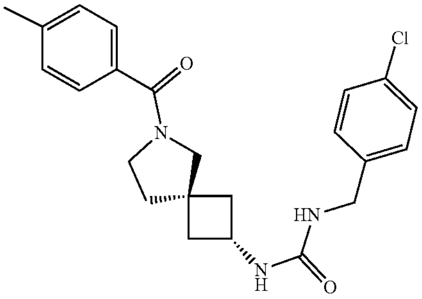 [SMILES: Cc1ccc(C(=O)N2CC[C@]3(C2)C[C@H](NC(=O)NCc2ccc(Cl)cc2)C3)cc1] 1-(4-chlorobenzyl)-3-((2s,4r)-6-(4-methylbenzoyl)-6-azaspiro[3.4]octan-2-yl)urea. LRMS (APCI) m/z 412 (M + H). $^1$H NMR (400 MHz, DMSO-$d_6$) δ 7.41 (d, J = 7.9 Hz, 2H), 7.36 (t, J = 8.6 Hz, 2H), 7.29-7.19 (m, 4H), 6.29 (dd, J = 14.6, 7.8 Hz, 2H), 4.16 (dd, J = 16.3, 5.9 Hz, 2H), 4.09 (d, J = 8.2 Hz, 1H), 3.96-3.84 (m, 1H), 3.45-3.39 (m, 1H), 2.38-2.27 (m, 4H), 2.13 (t, J = 9.8 Hz, 2H), 1.90-1.73 (m, 4H), 1.12 (s, 1H). |

-continued

| Compound No. | Carboxylic acid | Intermediate | Structure, Name and Data |
|---|---|---|---|
| 165 | 4-methoxybenzoic acid | 3.6 | 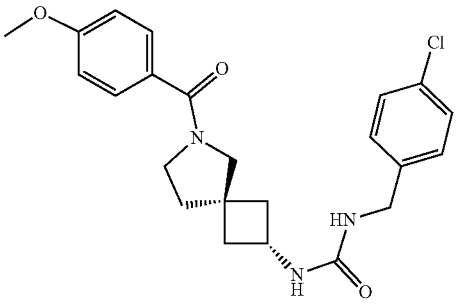 [SMILES: COc1ccc(C(=O)N2CC[C@]3(C2)C[C@H](NC(=O)NCc2ccc(Cl)cc2)C3)cc1] 1-(4-chlorobenzyl)-3-((2s,4r)-6-(4-methoxybenzoyl)-6-azaspiro[3.4]octan-2-yl)urea. LRMS (APCI) m/z 428 (M + H). $^1$H NMR (400 MHz, DMSO-$d_6$) δ 7.54-7.46 (m, 2H), 7.35 (d, J = 8.0 Hz, 2H), 7.24 (t, J = 10.9 Hz, 2H), 6.98 (d, J = 8.1 Hz, 2H), 6.30 (dd, J = 13.5, 7.7 Hz, 2H), 4.23-4.05 (m, 3H), 3.80 (s, 3H), 3.50-3.38 (m, 4H), 2.32 (d, J = 9.3 Hz, 1H), 2.14 (t, J = 9.7 Hz, 1H), 1.84 (dt, J = 16.3, 7.8 Hz, 4H). |
| 354 | [1,4'-bipiperidine]-1'-carboxylic acid | 3.5 | 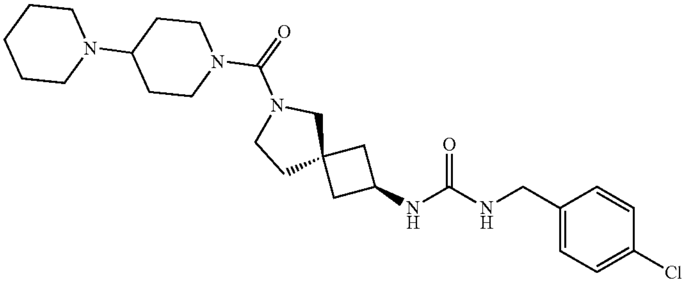 [SMILES: O=C(NCc1ccc(Cl)cc1)N[C@H]1C[C@]2(CCN(C(=O)N3CCC(N4CCCCC4)CC3)C2)C1] 1-((2r,4s)-6-([1,4'-bipiperidine]-1'-carbonyl)-6-azaspiro[3.4]octan-2-yl)-3-(4-chlorobenzyl)urea. LRMS (APCI) m/z 488.1 (M + H). $^1$H NMR (400 MHz, Methanol-$d_4$) δ 7.32 (d, J = 8.2 Hz, 2 H), 7.27 (d, J = 8.2 Hz, 2 H), 4.29 (s, 2 H), 4.17 (p, J = 8.2 Hz, 1 H), 3.93 (d, J = 13.6 Hz, 2 H), 3.43 (t, J = 6.7 Hz, 2 H), 3.34-3.30 (m, 7 H), 2.85 (t, J = 12.8 Hz, 2 H), 2.33 (t, J = 10.2 Hz, 2 H), 2.08 (d, J = 12.1 Hz, 2 H), 1.99-1.81 (m, 8 H), 1.79-1.61 (m, 4 H). |
| 240 | 6-methylnicotinic acid | 12.2 | 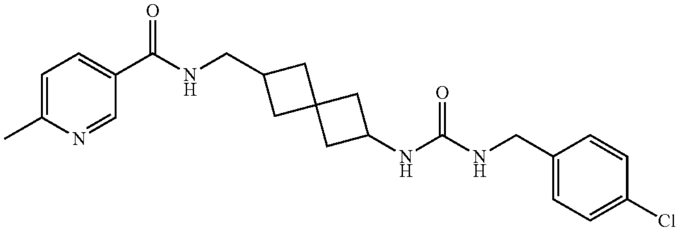 [SMILES: Cc1ccc(C(=O)NCC2CC3(C2)CC(NC(=O)NCc2ccc(Cl)cc2)C3)cn1] N-((6-(3-(4-chlorobenzyl)ureido)spiro[3.3]heptan-2-yl)methyl)-6-methylnicotinamide. LRMS (APCI) m/z 427.1 (M + H). $^1$H NMR (400 MHz, Methanol-$d_4$) δ 8.72 (d, J = 2.2 Hz, 1H), 8.00 (dd, J = 8.2, 2.2 Hz, 1H), 7.29 (d, J = 8.2 Hz, 1H), 7.19 (d, J = 8.2 Hz, 2H), 7.13 (d, J = 8.2 Hz, 2H), 4.16 (s, 2H), 3.91 (p, J = 8.0 Hz, 1H), 3.27 (d, J = 7.2 Hz, 2H), 2.48 (s, 3H), 2.40 (dd, J = |

-continued

| Compound No. | Carboxylic acid | Intermediate | Structure, Name and Data |
|---|---|---|---|
| | | | 15.2, 7.6 Hz, 2H), 2.34 (dd, J = 10.7, 5.7 Hz, 1H), 2.21 (dt, J = 12.1, 6.2 Hz, 1H), 2.11 (td, J = 9.6, 7.9, 3.4 Hz, 1H), 1.72 (ddd, J = 30.9, 11.4, 8.0 Hz, 4H). |
| 243 | tetrahydro-2H-thiopyran-4-carboxylic acid 1,1-dioxide | 12.2 | 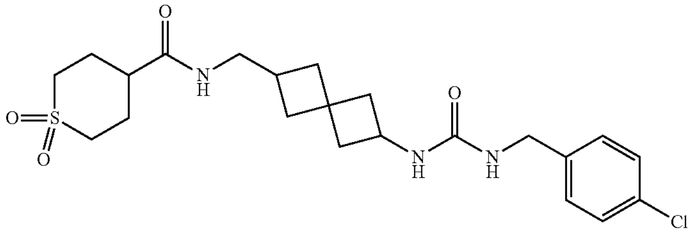 [SMILES: O=C(NCc1ccc(Cl)cc1)NC1CC2(CC(CNC(=O)C3CCS(=O)(=O)CC3)C2)C1] N-((6-(3-(4-chlorobenzyl)ureido)spiro[3.3]heptan-2-yl)methyl)tetrahydro-2H-thiopyran-4-carboxamide 1,1-dioxide. LRMS (APCI) m/z 468.1 (M + H). $^1$H NMR (400 MHz, Methanol-$d_4$) δ 7.31 (d, J = 8.2 Hz, 2H), 7.26 (d, J = 8.2 Hz, 2H), 4.28 (s, 2H), 4.02 (p, J = 8.2 Hz, 1H), 3.23-3.06 (m, 6H), 2.47 (ddq, J = 28.5, 11.7, 5.7 Hz, 2H), 2.40-2.12 (m, 7H), 2.02 (ddd, J = 11.5, 7,9, 3.5 Hz, 1H), 1.90-1.75 (m, 3H), 1.71 (dd, J = 11.0, 8.1 Hz, 1H). |
| 255 | 6-methylnicotinic acid | 15.1 | 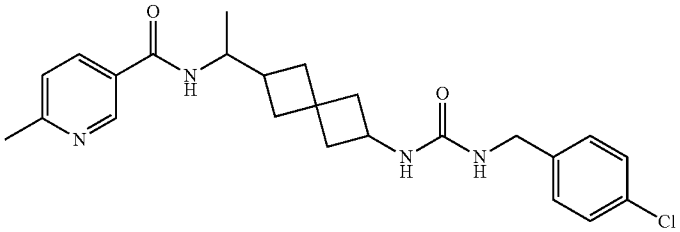 [SMILES: Cc1ccc(C(=O)NC(C)C2CC3(CC(NC(=O)NCc4ccc(Cl)cc4)C3)C2)cn1] N-(1-(6-(3-(4-chlorobenzyl)ureido)spiro[3.3]heptan-2-yl)ethyl)-6-methylnicotinamide LRMS (APCI) m/z 441.1 (M + H). $^1$H NMR (400 MHz, DMSO-$d_6$) δ 8.11 (t, J = 9.2 Hz, 1H), 7.99 (ddd, J = 8.1, 3.8, 2.3 Hz, 1H), 7.32-7.23 (m, 3H), 7.16 (d, J = 8.4 Hz, 2H), 6.22-6.13 (m, 1H), 6.10 (d, J = 8.0 Hz, 1H), 4.07 (d, J = 6.1 Hz, 2H), 3.85 (ddt, J = 23.4, 16.0, 8.9 Hz, 2H), 2.20 (dq, J = 25.0, 8.1 Hz, 2H), 2.09-1.91 (m, 2H), 1.72-1.56 (m, 4H), 1.19-1.04 (m, 5H), 0.95 (dd, J = 6.6, 3.5 Hz, 3H). |
| 245 | 6-methylpicolinic acid | 12.2 | 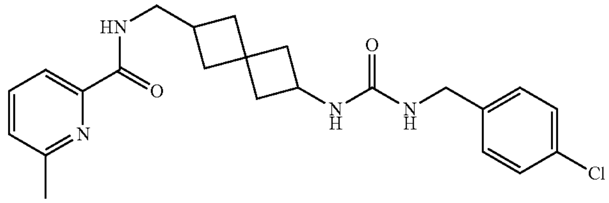 [SMILES: Cc1cccc(C(=O)NCC2CC3(C2)CC(NC(=O)NCc2ccc(Cl)cc2)C3)n1] N-((6-(3-(4-chlorobenzyl)ureido)spiro[3.3]heptan-2-yl)methyl)-6-methylpicolinamide. LRMS (APCI) m/z 427.2 (M + H). $^1$H NMR (400 MHz, DMSO-$d_6$) δ 8.48 (dd, J = 4.8, 1.8 Hz, 1H), 8.40 (t, J = 5.8 Hz, 1H), 7.64 (dd, J = 7.7, 1.8 Hz, 1H), 7.40-7.32 (m, 2H), 7.30-7.21 (m, 3H), 6.26 (t, J = 6.1 Hz, 1H), 6.17 (d, J = 8.1 Hz, 1H), 4.16 (d, J = 6.0 Hz, 2H), 3.92 (h, J = 8.2 Hz, 1H), 3.23 (t, J = 6.5 Hz, 2H), 2.35 |

-continued

| Compound No. | Carboxylic acid | Intermediate | Structure, Name and Data |
|---|---|---|---|
| | | | (ddd, J = 27.2, 13.3, 7.3 Hz, 3H), 2.25-2.05 (m, 3H), 1.97 (ddd, J = 11.4, 7.9, 3.3 Hz, 1H), 1.79 (dd, J = 7.8, 4.3 Hz, 2H), 1.78-1.67 (m, 3H). |
| 246 | 2-methylisonicotinic acid | 12.2 | 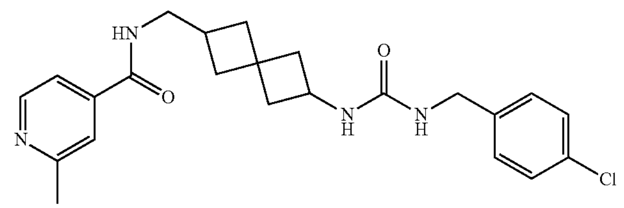 [SMILES: Cc1cc(C(=O)NCC2CC3(C2)CC(NC(=O)NCc2ccc(Cl)cc2)C3)ccn1] N-((6-(3-(4-chlorobenzyl)ureido)spiro[3.3]heptan-2-yl)methyl)-2-methylisonicotinamide. LRMS (APCI) m/z 427.2 (M + H). $^1H$ NMR (400 MHz, DMSO-$d_6$) δ 8.65 (t, J = 5.7 Hz, 1H), 8.56 (d, J = 5.1 Hz, 1H), 7.60 (d, J = 1.6 Hz, 1H), 7.52 (dd, J = 5.2, 1.6 Hz, 1H), 7.40-7.32 (m, 2H), 7.27-7.20 (m, 2H), 6.25 (t, J = 6.1 Hz, 1H), 6.17 (d, J = 8.0 Hz, 1H), 4.15 (d, J = 6.0 Hz, 2H), 4.10 (d, J = 5.5 Hz, 1H), 3.91 (h, J = 8.2 Hz, 1H), 3.26 (t, J = 6.5 Hz, 2H), 3.17 (d, J = 4.1 Hz, 2H), 2.41-2.27 (m, 2H), 2.20 (ddd, J = 12.1, 7.3, 5.1 Hz, 1H), 2.09 (ddd, J = 11.2, 7.9, 3.2 Hz, 1H), 1.96 (ddd, J = 11.3, 7.9, 3.1 Hz, 1H), 1.77 (dd, J = 10.5, 8.5 Hz, 3H), 1.73-1.66 (m, 1H). |
| 247 | 1H-pyrazole-4-carboxylic acid | 12.2 | 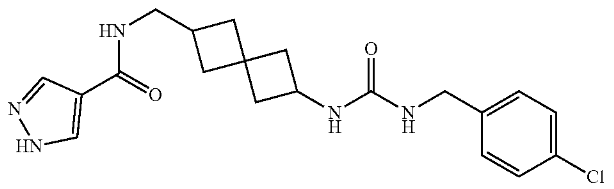 [SMILES: O=C(NCc1ccc(Cl)cc1)NC1CC2(CC(CNC(=O)c3cn[nH]c3)C2)C1] N-((6-(3-(4-chlorobenzyl)ureido)spiro[3.3]heptan-2-yl)methyl)-1H-pyrazole-4-carboxamide. LRMS (APCI) m/z 402.1 (M + H). $^1H$ NMR (400 MHz, DMSO-$d_6$) δ 13.07 (s, 1H), 8.14 (s, 1H), 7.97 (t, J = 5.8 Hz, 1H), 7.86 (s, 1H), 7.36 (d, J = 8.4 Hz, 2H), 7.24 (d, J = 8.2 Hz, 2H), 6.24 (t, J = 6.1 Hz, 1H), 6.16 (d, J = 8.1 Hz, 1H), 4.15 (d, J = 6.0 Hz, 2H), 3.90 (h, J = 8.3 Hz, 1H), 3.18 (dd, J = 8.1, 5.9 Hz, 2H), 2.32 (dq, J = 19.4, 10.8, 9.3 Hz, 2H), 2.23-2.14 (m, 1H), 2.07 (ddd, J = 11.2, 8.0, 3.1 Hz, 1H), 1.94 (ddd, J = 11.3, 7.9, 3.0 Hz, 1H), 1.80-1.70 (m, 3H), 1.67 (dd, J = 11.4, 7.4 Hz, 1H). |
| 248 | 6-methylnicotinic acid | 16.1 | 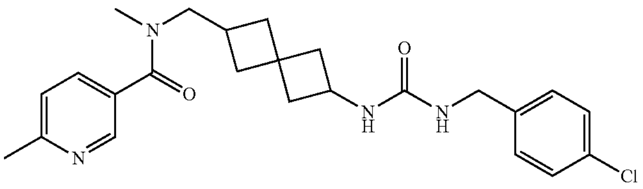 [SMILES: Cc1ccc(C(=O)N(C)CC2CC3(C2)CC(NC(=O)NCc2ccc(Cl)cc2)C3)cn1] N-((6-(3-(4-chlorobenzyl)ureido)spiro[3.3]heptan-2-yl)methyl)-N,6-dimethylnicotinamide. LRMS (APCI) m/z 441.2 (M + H). $^1H$ NMR (400 MHz, DMSO-$d_6$) δ 8.50-8.36 (m, 1H), 7.81-7.64 (m, 1H), 7.32 (dd, J = |

-continued

| Compound No. | Carboxylic acid | Intermediate | Structure, Name and Data |
|---|---|---|---|
| | | | 14.7, 8.1 Hz, 3H), 7.17 (d, J = 8.0 Hz, 2H), 6.28-6.16 (m, 1H), 6.11 (d, J = 20.2 Hz, 1H), 4.15-4.01 (m, 2H), 3.94-3.70 (m, 2H), 3.20-3.15 (m, 1H), 2.85 (s, 1H), 2.80 (s, 1H), 2.47 (s, 3H), 2.37-2.18 (m, 2H), 2.16-2.06 (m, 1H), 1.95 (dd, J = 14.4, 7.5 Hz, 1H), 1.88-1.53 (m, 4H), 1.53-1.29 (m, 2H). |
| 250 | tetrahydro-2H-pyran-4-carboxylic acid | 12.2 | 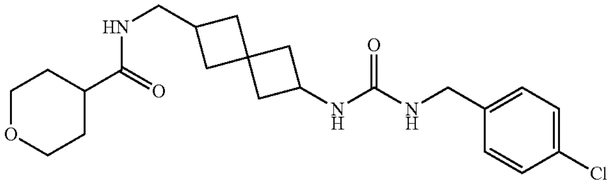 [SMILES: O=C(NCc1ccc(Cl)cc1)NC1CC2(CC(CNC(=O)C3CCOCC3)C2)C1] N-((6-(3-(4-chlorobenzyl)ureido)spiro[3.3]heptan-2-yl)methyl)tetrahydro-2H-pyran-4-carboxamide. LRMS (APCI) m/z 420.2 (M + H). $^1$H NMR (400 MHz, DMSO-$d_6$) δ 7.73 (t, J = 5.8 Hz, 1H), 7.36 (d, J = 8.4 Hz, 2H), 7.23 (d, J = 8.3 Hz, 2H), 6.25 (t, J = 5.9 Hz, 1H), 6.16 (d, J = 8.1 Hz, 1H), 4.15 (d, J = 6.0 Hz, 2H), 3.95-3.87 (m, 1H), 3.84 (dt, J = 11.2, 3.3 Hz, 2H), 3.32-3.24 (m, 2H), 3.02 (t, J = 6.4 Hz, 2H), 2.37-2.27 (m, 2H), 2.23 (dd, J = 15.5, 7.5 Hz, 1H), 2.15 (dt, J = 11.8, 6.3 Hz, 1H), 2.02 (t, J = 9.5 Hz, 1H), 1.93-1.84 (m, 1H), 1.80-1.65 (m, 3H), 1.64-1.56 (m, 2H), 1.54 (dd, J = 8.5, 3.6 Hz, 3H). |
| 251 | cyclopentane-carboxylic acid | 12.2 | 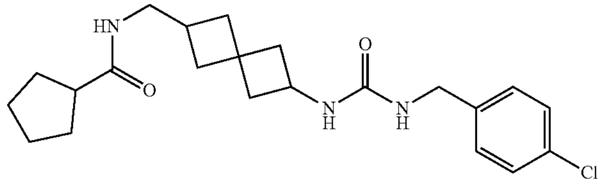 [SMILES: O=C(NCc1ccc(Cl)cc1)NC1CC2(CC(CNC(=O)C3CCCC3)C2)C1] N-((6-(3-(4-chlorobenzyl)ureido)spiro[3.3]heptan-2-yl)methyl)cyclopentanecarboxamide. LRMS (APCI) m/z 404.2 (M + H). $^1$H NMR (400 MHz, DMSO-$d_6$) δ 7.69 (t, J = 5.7 Hz, 1H), 7.40-7.32 (m, 2H), 7.28-7.20 (m, 2H), 6.25 (t, J = 6.1 Hz, 1H), 6.15 (d, J = 8.1 Hz, 1H), 4.15 (d, J = 6.0 Hz, 2H), 3.89 (h, J = 8.2 Hz, 1H), 3.09-2.95 (m, 2H), 2.22 (dddd, J = 29.7, 23.0, 12.1, 5.5 Hz, 4H), 2.03 (ddd, J = 11.1, 8.0, 3.2 Hz, 1H), 1.89 (ddd, J = 11.4, 8.0, 3.2 Hz, 1H), 1.80-1.65 (m, 5H), 1.59 (ttd, J = 11.5, 7.8, 3.5 Hz, 5H), 1.48 (td, J = 5.5, 5.1, 2.4 Hz, 2H). |
| 252 | 2-oxopiperidine-4-carboxylic acid | 12.2 | 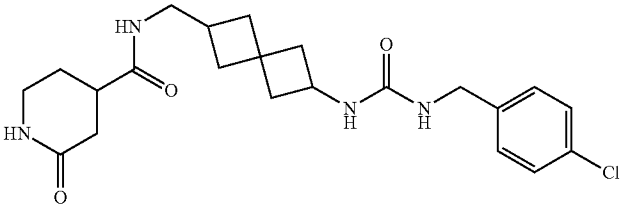 [SMILES: O=C1CC(C(=O)NCC2CC3(C2)CC(NC(=O)NCc2ccc(Cl)cc2)C3)CCN1] N-((6-(3-(4-chlorobenzyl)ureido)spiro[3.3]heptan-2-yl)methyl)-2-oxopiperidine-4-carboxamide. LRMS (APCI) m/z 433.2 (M + H). $^1$H NMR (DMSO-$d_6$) δ: 7.89- |

-continued

| Compound No. | Carboxylic acid | Intermediate | Structure, Name and Data |
|---|---|---|---|
| | | | 7.81 (m, 1H), 7.45 (d, J = 2.7 Hz, 1H), 7.40-7.32 (m, 2H), 7.27-7.20 (m, 2H), 6.26 (t, J = 6.2 Hz, 1H), 6.17 (d, J = 8.1 Hz, 1H), 4.15 (d, J = 6.1 Hz, 2H), 3.90 (h, J = 8.2 Hz, 1H), 3.15-2.94 (m, 5H), 2.59 (tdd, J = 9.6, 6.1, 3.4 Hz, 1H), 2.33-2.10 (m, 5H), 2.04 (ddd, J = 11.1, 7.8, 3.2 Hz, 1H), 1.90 (ddd, J = 11.3, 7.8, 3.2 Hz, 1H), 1.85-1.55 (m, 5H). |
| 275 | 2-methylbenzoic acid | 3.7 | 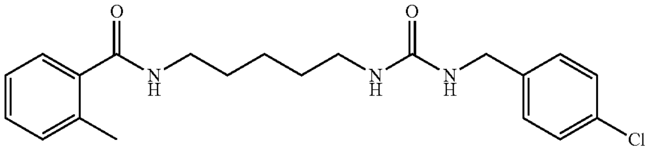 [SMILES: Cc1ccccc1C(=O)NCCCCCNC(=O)NCc1ccc(Cl)cc1] N-(5-(3-(4-chlorobenzyl)ureido)pentyl)-2-methylbenzamide. LRMS (APCI) m/z 388.1 (M + H). $^1$H NMR (400 MHz, DMSO-$d_6$) δ 8.19 (t, J = 5.6 Hz, 1H), 7.37 (d, J = 8.0 Hz, 2H), 7.34-7.17 (m 6H), 6.31 (t, J = 5.7 Hz, 1H), 5.98-5.91 (m, 1H), 4.18 (d, J = 5.7 Hz, 2H), 3.24-3.16 (m, 2H), 3.01 (q, J = 6.3 Hz, 2H), 2.32 (s, 3H), 1.51 (p, J = 7.2 Hz, 2H), 1.41 (p, J = 7.0 Hz, 2H), 1.32 (q, J = 7.1, 6.5 Hz, 2H). |
| 276 | 3-methylbenzoic acid | 3.7 | 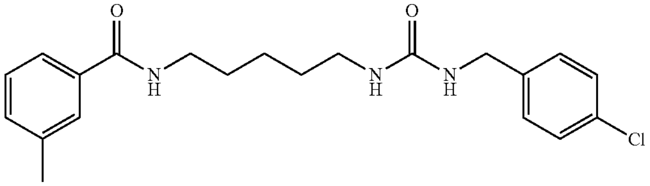 [SMILES: Cc1cccc(C(=O)NCCCCCNC(=O)NCc2ccc(Cl)cc2)c1] N-(5-(3-(4-chlorobenzyl)ureido)pentyl)-3-methylbenzamide. LRMS (APCI) m/z 388.2 (M + H). $^1$H NMR (400 MHz, DMSO-$d_6$) δ 8.37 (t, J = 5.6 Hz, 1H), 7.67-7.59 (m, 2H), 7.34 (dd, J = 13.3, 6.5 Hz, 4H), 7.25 (d, J = 8.1 Hz, 1H), 6.31 (t, J = 6.2 Hz, 1H), 5.95 (d, J = 5.9 Hz, 1H), 4.17 (d, J = 5.9 Hz, 2H), 3.24 (q, J = 6.6 Hz, 2H), 3.01 (q, J = 6.4 Hz, 2H), 2.35 (s, 4H), 1.52 (p, J = 7.1 Hz, 2H), 1.41 (p, J = 7.2 Hz, 2H), 1.30 (q, J = 7.9 Hz, 2H). |
| 277 | nicotinic acid | 3.7 | 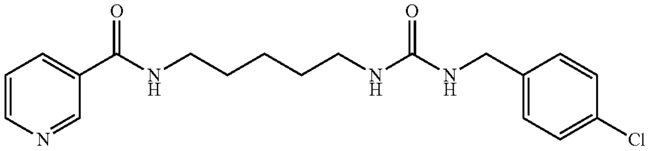 [SMILES: O=C(NCCCCCNC(=O)c1cccnc1)NCc1ccc(Cl)cc1] N-(5-(3-(4-chlorobenzyl)ureido)pentyl)nicotinamide. LRMS (APCI) m/z 375.1 (M + H). $^1$H NMR (400 MHz, DMSO-$d_6$) δ 9.00 (d, J = 2.1 Hz, 1H), 8.71 (d, J = 4.8 Hz, 1H), 8.64 (s, 1H), 8.24-8.16 (m, 1H), 7.52 (dd, J = 8.0, 4.9 Hz, 1H), 7.36 (d, J = 8.1 Hz, 2H), 7.25 (d, J = 8.1 Hz, 2H), 6.31 (s, 1H), 5.95 (s, 1H), 4.17 (d, J = 5.2 Hz, 2H), 3.27 (q, J = 6.6 Hz, 2H), 3.01 (q, J = 6.2, 5.8 Hz, 2H), 1.54 (p, J = 7.2 Hz, 2H), 1.41 (p, J = 6.9 Hz, 2H), 1.31 (q, J = 7.7 Hz, 2H). |

-continued

| Compound No. | Carboxylic acid | Intermediate | Structure, Name and Data |
|---|---|---|---|
| 279 | picolinic acid | 3.7 | 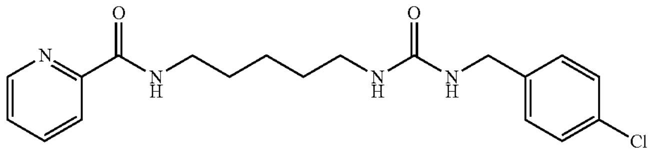 [SMILES: O=C(NCCCCCNC(=O)c1ccccn1)NCc1ccc(Cl)cc1] N-(5-(3-(4-chlorobenzyl)ureido)pentyl)picolinamide. LRMS (APCI) m/z 375.0 (M + H). $^1H$ NMR (400 MHz, DMSO-$d_6$) δ 8.76 (d, J = 6.3 Hz, 1H), 8.64 (d, J = 4.8 Hz, 1H), 8.01 (dt, J = 15.1, 7.7 Hz, 2H), 7.60 (t, J = 6.1 Hz, 1H), 7.36 (d, J = 8.2 Hz, 2H), 7.25 (d, J = 8.1 Hz, 2H), 6.30 (t, J = 6.2 Hz, 1H), 6.01-5.86 (m, 1H), 4.17 (d, J = 5.8 Hz, 2H), 3.29 (d, J = 6.7 Hz, 2H), 3.00 (q, J = 6.5 Hz, 2H), 1.54 (p, J = 7.3 Hz, 2H), 1.40 (p, J = 7.0 Hz, 2H), 1.28 (p, J = 7.7 Hz, 2H). |
| 280 | 2-fluorobenzoic acid | 3.7 | 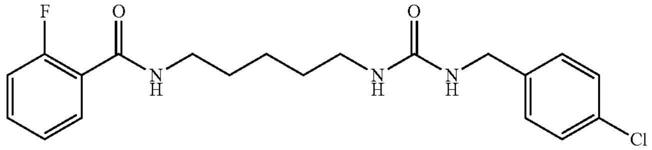 [SMILES: O=C(NCCCCCNC(=O)c1ccccc1F)NCc1ccc(Cl)cc1] N-(5-(3-(4-chlorobenzyl)ureido)pentyl)-2-fluorobenzamide. LRMS (APCI) m/z 392.0 (M + H). $^1H$ NMR (400 MHz, DMSO-$d_6$) δ 8.29 (s, 1H), 7.54 (dt, J = 31.2, 7.3 Hz, 2H), 7.36 (d, J = 8.0 Hz, 2H), 7.25 (d, J = 8.0 Hz, 4H), 6.31 (t, J = 6.2 Hz, 1H), 5.95 (t, J = 5.8 Hz, 1H), 4.17 (d, J = 5.9 Hz, 2H), 3.23 (q, J = 6.6 Hz, 2H), 3.01 (q, J = 6.5 Hz, 2H), 1.51 (p, J = 7.1 Hz, 2H), 1.41 (p, J = 7.0 Hz, 2H), 1.30 (p, J = 7.4 Hz, 2H). |
| 281 | 6-methylnicotinic acid | 3.7 | 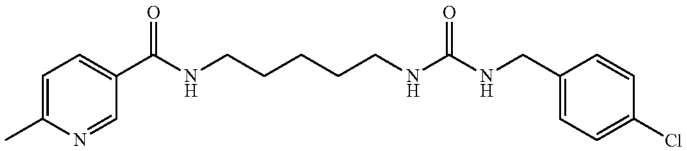 [SMILES: Cc1ccc(C(=O)NCCCCCNC(=O)NCc2ccc(Cl)cc2)cn1] N-(5-(3-(4-chlorobenzyl)ureido)pentyl)-6-methylnicotinamide. LRMS (APCI) m/z 389.0 (M + H). $^1H$ NMR (400 MHz, DMSO-$d_6$) δ 8.89 (d, J = 2.2 Hz, 1H), 8.56 (t, J = 5.6 Hz, 1H), 8.11 (dd, J = 8.1, 2.2 Hz, 1H), 7.42-7.31 (m, 3H), 7.25 (d, J = 8.1 Hz, 2H), 6.32 (d, J = 6.5 Hz, 1H), 5.95 (s, 1H), 4.17 (d, J = 5.7 Hz, 2H), 3.26 (q, J = 6.7 Hz, 2H), 3.01 (q, J = 6.3 Hz, 2H), 2.53 (s, 3H), 1.53 (p, J = 7.3 Hz, 2H), 1.41 (p, J = 7.0 Hz, 2H), 1.31 (q, J = 7.8 Hz, 2H). |
| 283 | 2-(pyridin-3-yl)acetic acid | 3.7 | 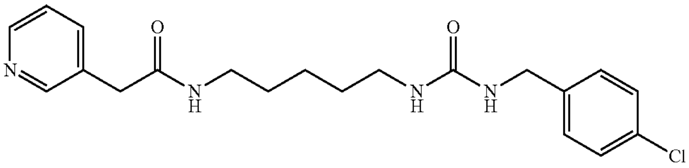 [SMILES: O=C(Cc1cccnc1)NCCCCCNC(=O)NCc1ccc(Cl)cc1] N-(5-(3-(4-chlorobenzyl)ureido)pentyl)-2-(pyridin-3-yl)acetamide. LRMS (APCI) m/z 389.1 (M + H). $^1H$ NMR (400 MHz, DMSO-$d_6$) δ 8.49 (s, 2H), 8.11 (q, J = 6.6, 5.6 Hz, 1H), 7.74 (d, J = 7.9 Hz, |

-continued

| Compound No. | Carboxylic acid | Intermediate | Structure, Name and Data |
|---|---|---|---|
| | | | 1H), 7.46-7.31 (m, 3H), 7.25 (d, J = 8.1 Hz, 2H), 6.31 (t, J = 6.2 Hz, 1H), 5.98-5.88 (m, 1H), 4.18 (d, J = 5.8 Hz, 2H), 3.46 (s, 3H), 3.01 (dq, J = 24.4, 6.6 Hz, 4H), 1.38 (dp, J = 14.7, 7.1 Hz, 4H), 1.24 (q, J = 8.1 Hz, 2H). |
| 289 | nicotinic acid | 3.8 | 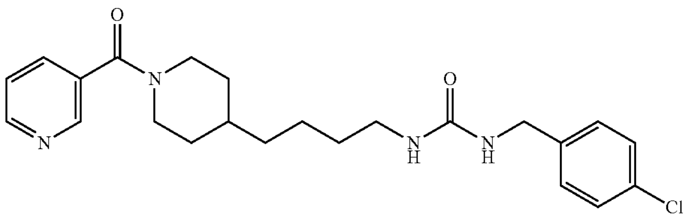 [SMILES: O=C(NCCCCC1CCN(C(=O)c2cccnc2)CC1)NCc1ccc(Cl)cc1] 1-(4-chlorobenzyl)-3-(4-(1-nicotinoylpiperidin-4-yl)butyl)urea. LRMS (APCI) m/z 429.2 (M + H). $^1$H NMR (400 MHz, DMSO-$d_6$) δ 8.63 (d, J = 23.7 Hz, 2H), 7.81 (d, J = 7.8 Hz, 1H), 7.48 (dd, J = 8.0, 4.7 Hz, 1H), 7.36 (d, J = 8.3 Hz, 2H), 7.25 (d, J = 8.2 Hz, 2H), 6.31 (t, J = 6.2 Hz, 1H), 5.93 (t, J = 5.7 Hz, 1H), 4.46 (s, 1H), 4.17 (d, J = 6.1 Hz, 2H), 4.09 (s, 1H), 3.49 (s, 1H), 3.17 (s, 3H), 3.00 (q, J = 6.5 Hz, 2H), 2.76 (s, 1H), 1.74 (s, 1H), 1.60 (s, 1H), 1.49 (s, 1H), 1.41-1.30 (m, 2H), 1.26-1.22 (m, 2H), 1.08 (s, 1H). |
| 290 | isonicotinic acid | 3.8 | 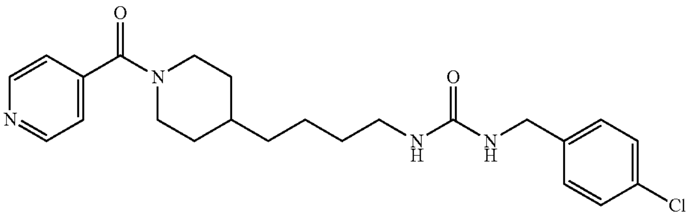 [SMILES: O=C(NCCCCC1CCN(C(=O)c2ccncc2)CC1)NCc1ccc(Cl)cc1] 1-(4-chlorobenzyl)-3-(4-(1-isonicotinoylpiperidin-4-yl)butyl)urea. LRMS (APCI) m/z 429.2 (M + H). $^1$H NMR (400 MHz, DMSO-$d_6$) δ 8.70 (s, 1H), 7.40-7.32 (m, 4H), 7.25 (d, J = 8.1 Hz, 2H), 6.32 (t, J = 6.2 Hz, 1H), 5.93 (t, J = 5.7 Hz, 1H), 4.45 (d, J = 13.0 Hz, 1H), 4.17 (d, J = 6.0 Hz, 2H), 3.40 (d, J = 13.8 Hz, 2H), 3.18 (s, 3H), 2.75 (t, J = 12.4 Hz, 1H), 1.74 (d, J = 13.2 Hz, 1H), 1.58 (d, J = 13.0 Hz, 1H), 1.49 (s, 1H), 1.35 (q, J = 7.0 Hz, 2H), 1.25 (d, J = 10.0 Hz, 4H), 1.08 (ddd, J = 19.5, 12.8, 8.6 Hz, 2H). |
| 292 | picolinic acid | 3.8 | 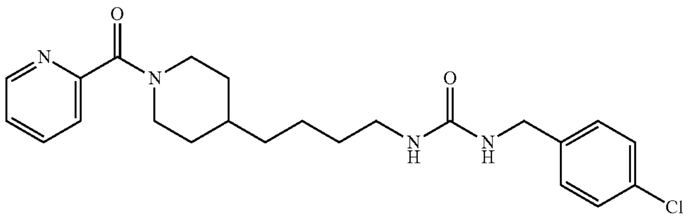 [SMILES: O=C(NCCCCC1CCN(C(=O)c2ccccn2)CC1)NCc1ccc(Cl)cc1] 1-(4-chlorobenzyl)-3-(4-(1-picolinoylpiperidin-4-yl)butyl)urea. LRMS (APCI) m/z 429.2 (M + H). $^1$H NMR (400 MHz, DMSO-$d_6$) δ 8.58 (d, J = 4.9 Hz, 1H), 7.91 (t, J = 7.7 Hz, 1H), 7.55-7.42 (m, 2H), 7.35 (d, J = 8.0 Hz, 2H), 7.25 (d, J = 8.1 Hz, 2H), 6.31 (t, J = |

-continued

| Compound No. | Carboxylic acid | Intermediate | Structure, Name and Data |
|---|---|---|---|
| | | | 6.1 Hz, 1H), 5.93 (t, J = 5.7 Hz, 1H), 4.48 (d, J = 13.2 Hz, 1H), 4.17 (d, J = 5.9 Hz, 2H), 3.60 (d, J = 13.3 Hz, 1H), 3.00 (q, J = 5.5 Hz, 3H), 2.75 (td, J = 12.8, 2.8 Hz, 1H), 1.75 (d, J = 13.3 Hz, 1H), 1.62-1.46 (m, 2H), 1.36 (t, J = 7.1 Hz, 2H), 1.25 (tt, J = 10.3, 6.6, 6.2 Hz, 4H), 1.14-1.00 (m, 2H). |
| 291 | 2-phenylacetic acid | 3.8 | 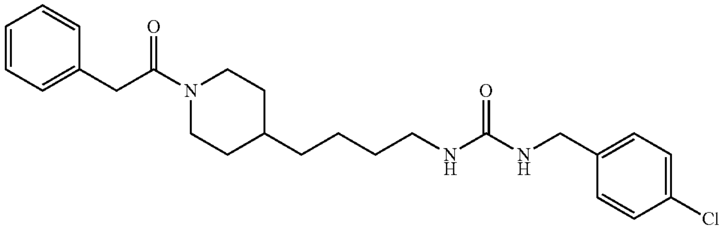 [SMILES: O=C(NCCCCC1CCN(C(=O)Cc2ccccc2)CC1)NCc1ccc(Cl)cc1] 1-(4-chlorobenzyl)-3-(4-(1-(2-phenylacetyl)piperidin-4-yl)butyl)urea. LRMS (APCI) m/z 442.1 (M + H). $^1$H NMR (400 MHz, DMSO-$d_6$) δ 7.36 (d, J = 8.2 Hz, 2H), 7.34-7.15 (m, 7H), 6.30 (t, J = 6.1 Hz, 1H), 5.91 (t, J = 5.7 Hz, 1H), 4.38 (d, J = 13.0 Hz, 1H), 4.17 (d, J = 6.1 Hz, 2H), 3.95-3.82 (m, 1H), 3.69 (s, 2H), 3.18 (s, 2H), 3.03-2.87 (m, 3H), 1.59 (dd, J = 25.2, 13.1 Hz, 2H), 1.38-1.22 (m, 3H), 1.22-1.11 (m, 3H), 0.84 (dtd, J = 28.7, 12.4, 6.3 Hz, 2H). |
| 294 | 2-(pyridin-3-yl)acetic acid | 3.8 | 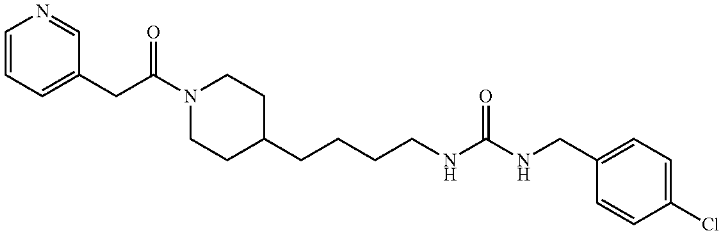 [SMILES: O=C(NCCCCC1CCN(C(=O)Cc2cccnc2)CC1)NCc1ccc(Cl)cc1] 1-(4-chlorobenzyl)-3-(4-(1-(2-(pyridin-3-yl)acetyl)piperidin-4-yl)butyl)urea. LRMS (APCI) m/z 443.2 (M + H). $^1$H NMR (400 MHz, DMSO-$d_6$) δ 8.44 (s, 1H), 7.62 (d, J = 7.8 Hz, 1H), 7.40-7.30 (m, 3H), 7.26 (d, J = 8.0 Hz, 2H), 6.31 (t, J = 6.1 Hz, 1H), 5.93 (t, J = 5.7 Hz, 1H), 5.76 (s, 1H), 4.36 (d, J = 13.2 Hz, 1H), 4.17 (d, J = 6.0 Hz, 2H), 3.97 (d, J = 13.6 Hz, 1H), 3.74 (s, 2H), 2.99 (q, J = 7.4 Hz, 3H), 2.55 (d, J = 13.7 Hz, 1H), 1.69-1.60 (m, 2H), 1.43 (s, 1H), 1.34 (q, J = 7.0 Hz, 2H), 1.26 (q, J = 7.9, 7.2 Hz, 2H), 1.18 (h, J = 6.0, 5.0 Hz, 2H), 0.92 (qt, J = 12.4, 6.2 Hz, 2H). |
| 295 | 2-(pyridin-4-yl)acetic acid | 3.8 | 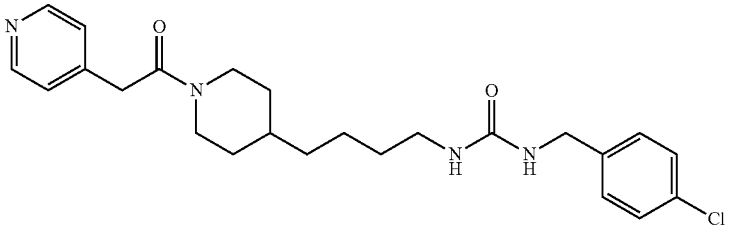 [SMILES: O=C(NCCCCC1CCN(C(=O)Cc2ccncc2)CC1)NCc1ccc(Cl)cc1] 1-(4-chlorobenzyl)-3-(4-(1-(2-(pyridin-4-yl)acetyl)piperidin-4-yl)butyl)urea. LRMS (APCI) m/z 443.2 (M + H). $^1$H |

-continued

| Compound No. | Carboxylic acid | Intermediate | Structure, Name and Data |
|---|---|---|---|
| | | | NMR (400 MHz, DMSO-$d_6$) δ 8.53 (s, 1H), 7.36 (d, J = 8.1 Hz, 2H), 7.27 (t, J = 9.1 Hz, 4H), 6.31 (t, J = 6.1 Hz, 1H), 5.93 (t, J = 5.7 Hz, 1H), 5.76 (s, 1H), 4.36 (d, J = 13.1 Hz, 1H), 4.17 (d, J = 5.9 Hz, 2H), 3.90 (d, J = 13.7 Hz, 1H), 3.77 (s, 2H), 3.04-2.91 (m, 3H), 1.63 (s, 2H), 1.48-1.25 (m, 4H), 1.25-1.12 (m, 4H), 0.90 (q, J = 11.5 Hz, 2H). |
| 296 | 2-(m-tolyl)acetic acid | 3.8 | 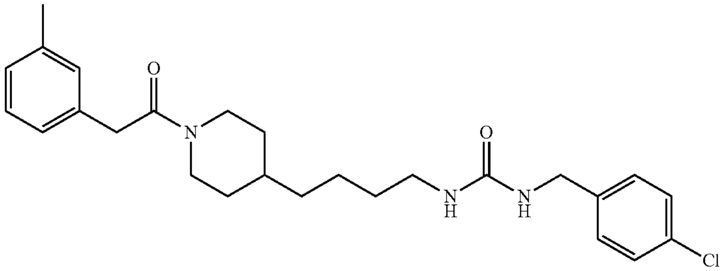 1-(4-chlorobenzyl)-3-(4-(1-(3-methylbenzoyl)piperidin-4-yl)butyl)urea. LRMS (APCI) m/z 442.2 (M + H). $^1$H NMR (400 MHz, DMSO-$d_6$) δ 7.35 (d, J = 8.1 Hz, 2H), 7.33-7.22 (m, 4H), 7.19-7.10 (m, 2H), 6.31 (t, J = 6.2 Hz, 1H), 5.93 (t, J = 5.7 Hz, 1H), 4.45 (s, 1H), 4.17 (d, J = 6.0 Hz, 2H), 3.55 (s, 1H), 3.33 (s, 3H), 3.00 (q, J = 6.5 Hz, 2H), 2.70 (d, J = 17.5 Hz, 1H), 2.33 (s, 3H), 1.81-1.66 (m, 1H), 1.66-1.54 (m, 1H), 1.47 (dt, J = 10.1, 6.5 Hz, 1H), 1.35 (q, J = 6.5 Hz, 2H), 1.23 (s, 4H), 1.14-0.93 (m, 2H). |
| 297 | 2-(o-tolyl)acetic acid | 3.8 | 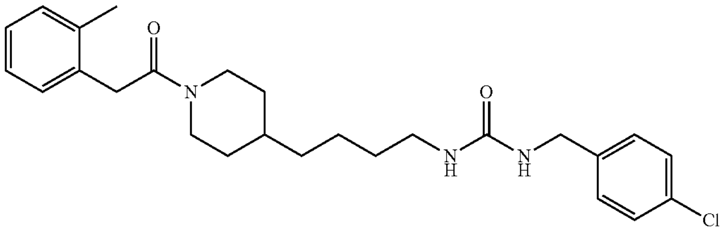 1-(4-chlorobenzyl)-3-(4-(1-(2-methylbenzoyl)piperidin-4-yl)butyl)urea. LRMS (APCI) m/z 442.2 (M + H). $^1$H NMR (400 MHz, DMSO-$d_6$) δ 7.35 (d, J = 8.1 Hz, 2H), 7.32-7.18 (m, 5H), 7.18-7.05 (m, 1H), 6.30 (t, J = 6.3 Hz, 1H), 5.92 (t, J = 5.7 Hz, 1H), 4.52 (d, J = 13.0 Hz, 1H), 4.17 (d, J = 6.0 Hz, 2H), 3.27-3.14 (m, 1H), 3.05-2.85 (m, 3H), 2.72 (t, J = 13.2 Hz, 1H), 2.20 (d, J = 20.0 Hz, 3H), 1.74 (d, J = 12.9 Hz, 1H), 1.65-1.40 (m, 3H), 1.34 (q, J = 6.2, 5.4 Hz, 2H), 1.30-1.14 (m, 4H), 1.14-0.81 (m, 3H). |

-continued

| Compound No. | Carboxylic acid | Intermediate | Structure, Name and Data |
|---|---|---|---|
| 298 | 2-(6-methylpyridin-2-yl)acetic acid | 3.8 | 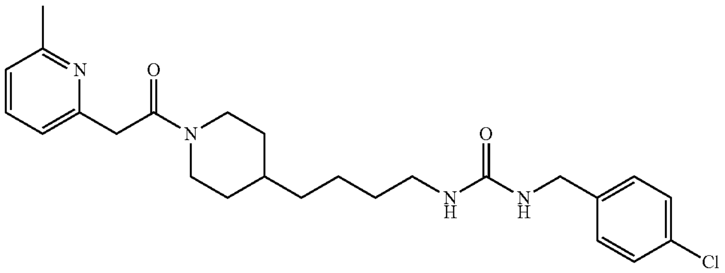 1-(4-chlorobenzyl)-3-(4-(1-(6-methylpicolinoyl)piperidin-4-yl)butyl)urea. LRMS (APCI) m/z 443.3 (M + H). $^1$H NMR (400 MHz, DMSO-$d_6$) δ 7.78 (t, J = 7.6 Hz, 1H), 7.39-7.22 (m, 6H), 6.31 (t, J = 6.1 Hz, 1H), 5.93 (t, J = 5.8 Hz, 1H), 4.47 (d, J = 12.8 Hz, 1H), 4.17 (d, J = 6.0 Hz, 2H), 3.57 (d, J = 13.4 Hz, 1H), 3.05-2.91 (m, 3H), 2.74 (t, J = 12.3 Hz, 1H), 2.48 (s, 3H), 1.75 (d, J = 13.1 Hz, 1H), 1.57 (d, J = 13.4 Hz, 1H), 1.49 (s, 1H), 1.36 (s, 2H), 1.24 (s, 4H), 1.04 (s, 2H). |
| 299 | 2-(6-methylpyridin-2-yl)acetic acid | 3.8 | 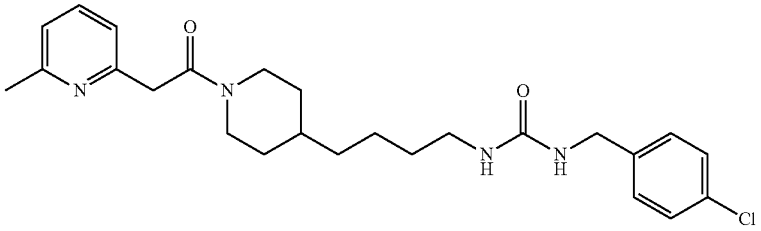 [SMILES: Cc1cccc(CC(=O)N2CCC(CCCCNC(=O)NCc3ccc(Cl)cc3)CC2)n1] 1-(4-chlorobenzyl)-3-(4-(1-(2-(6-methylpyridin-2-yl)acetyl)piperidin-4-yl)butyl)urea. LRMS (APCI) m/z 457.2 (M + H). $^1$H NMR (400 MHz, DMSO-$d_6$) δ 7.62 (t, J = 7.8 Hz, 1H), 7.36 (d, J = 8.1 Hz, 2H), 7.25 (d, J = 8.1 Hz, 2H), 7.09 (dd, J = 18.8, 7.7 Hz, 2H), 6.31 (t, J = 6.1 Hz, 1H), 5.92 (t, J = 5.8 Hz, 1H), 4.35 (s, 1H), 4.17 (d, J = 6.0 Hz, 2H), 3.98 (d, J = 13.6 Hz, 1H), 3.80 (d, J = 4.4 Hz, 2H), 3.17 (s, 1H), 3.04-2.90 (m, 3H), 2.43 (s, 3H), 1.61 (t, J = 14.7 Hz, 2H), 1.42 (s, 1H), 1.35 (t, J = 7.1 Hz, 2H), 1.24 (s, 2H), 1.18 (d, J = 6.5 Hz, 2H), 0.91 (q, J = 9.2, 6.7 Hz, 2H). |
| 300 | tetrahydro-2H-pyran-4-carboxylic acid | 3.8 | 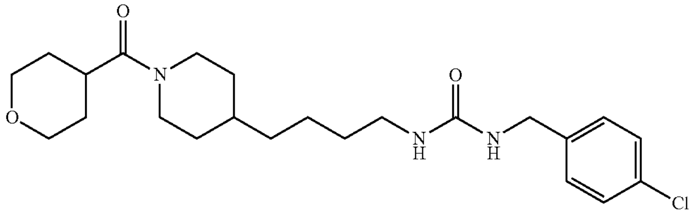 [SMILES: O=C(NCCCCC1CCN(C(=O)C2CCOCC2)CC1)NCc1ccc(Cl)cc1] 1-(4-chlorobenzyl)-3-(4-(1-(tetrahydro-2H-pyran-4-carbonyl)piperidin-4-yl)butyl)urea. LRMS (APCI) m/z 436.2 (M + H). $^1$H NMR (400 MHz, DMSO-$d_6$) δ 7.36 (d, J = 8.1 Hz, 2H), 7.26 (d, J = 8.1 Hz, 2H), 6.31 (t, J = 6.1 Hz, 1H), 5.93 (t, J = 5.8 Hz, 1H), 4.37 (d, J = 13.1 Hz, 1H), 4.17 (d, J = 6.0 Hz, 2H), 3.94 (d, J = 13.7 Hz, 1H), 3.83 (dt, J = 11.6, 3.0 Hz, 2H), 3.39 (d, J = 11.5 Hz, 2H), 2.98 (dd, J = |

-continued

| Compound No. | Carboxylic acid | Intermediate | Structure, Name and Data |
|---|---|---|---|
| | | | 12.3, 5.5 Hz, 3H), 2.90-2.77 (m, 1H), 2.47 (t, J = 11.9 Hz, 1H), 1.73-1.53 (m, 3H), 1.53-1.40 (m, 4H), 1.35 (p, J = 7.2 Hz, 2H), 1.24 (ddd, J = 28.2, 13.9, 6.9 Hz, 3H), 1.05-0.81 (m, 2H). |
| 301 | 2-oxopiperidine-4-carboxylic acid | 3.8 | 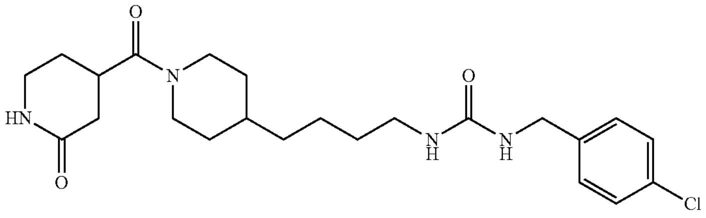 [SMILES: O=C1CC(C(=O)N2CCC(CCCCNC(=O)NCc3ccc(Cl)cc3)CC2)CCN1] 1-(4-chlorobenzyl)-3-(4-(1-(2-oxopiperidine-4-carbonyl)piperidin-4-yl)butyl)urea. LRMS (APCI) m/z 449.2 (M + H). $^1$H NMR (400 MHz, DMSO-$d_6$) δ 7.43 (s, 1H), 7.36 (d, J = 8.1 Hz, 2H), 7.26 (d, J = 8.1 Hz, 2H), 6.32 (t, J = 6.1 Hz, 1H), 5.93 (t, J = 5.8 Hz, 1H), 4.37 (d, J = 13.0 Hz, 1H), 4.17 (d, J = 6.0 Hz, 2H), 3.93 (d, J = 13.4 Hz, 1H), 3.16-3.08 (m, 3H), 3.00 (q, J = 6.3 Hz, 3H), 2.28-2.17 (m, 1H), 2.12 (dd, J = 17.2, 5.5 Hz, 1H), 1.78-1.73 (m, 1H), 1.65 (d, J = 18.6 Hz, 4H), 1.43 (d, J = 11.0 Hz, 1H), 1.35 (q, J = 7.0 Hz, 2H), 1.21 (d, J = 6.8 Hz, 4H), 0.99 (d, J = 12.2 Hz, 1H), 0.91 (d, J = 11.4 Hz, 1H). |
| 302 | 1-methyl-2-oxopiperidine-4-carboxylic acid | 3.8 | 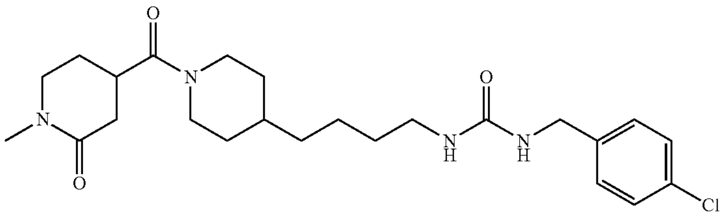 [SMILES: CN1CCC(C(=O)N2CCC(CCCCNC(=O)NCc3ccc(Cl)cc3)CC2)CC1=O] 1-(4-chlorobenzyl)-3-(4-(1-(1-methyl-2-oxopiperidine-4-carbonyl)piperidin-4-yl)butyl)urea. LRMS (APCI) m/z 463.3 (M + H). $^1$H NMR (400 MHz, DMSO-$d_6$) δ 7.36 (d, J = 8.1 Hz, 2H), 7.25 (d, J = 8.1 Hz, 2H), 6.31 (t, J = 6.1 Hz, 1H), 5.93 (t, J = 5.8 Hz, 1H), 4.37 (d, J = 13.1 Hz, 1H), 4.17 (d, J = 6.1 Hz, 2H), 3.92 (d, J = 13.5 Hz, 1H), 3.31-3.23 (m, 1H), 3.18 (q, J = 6.1, 3.5 Hz, 2H), 2.99 (q, J = 6.4 Hz, 3H), 2.79 (s, 3H), 2.46 (s, 1H), 2.25 (dtd, J = 22.8, 17.6, 7.4 Hz, 2H), 1.90-1.80 (m, 1H), 1.64 (d, J = 16.5 Hz, 3H), 1.44 (s, 1H), 1.35 (q, J = 6.6 Hz, 2H), 1.23 (dt, J = 21.5, 8.7 Hz, 4H), 0.96 (dt, J = 41.5, 11.9 Hz, 2H). |
| 303 | 5-oxopyrrolidine-3-carboxylic acid | 3.8 | 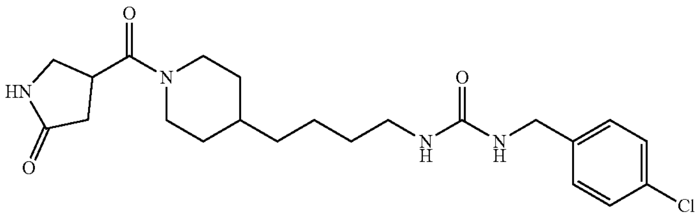 [SMILES: O=C1CC(C(=O)N2CCC(CCCCNC(=O)NCc3ccc(Cl)cc3)CC2)CN1] 1-(4-chlorobenzyl)-3-(4-(1-(5-oxopyrrolidine-3-carbonyl)piperidin-4-yl)butyl)urea. LRMS (APCI) m/z 435.2 (M + H). $^1$H NMR (400 MHz, DMSO-$d_6$) |

-continued

| Compound No. | Carboxylic acid | Intermediate | Structure, Name and Data |
|---|---|---|---|
| | | | δ 7.57 (s, 1H), 7.36 (d, J = 8.1 Hz, 2H), 7.25 (d, J = 8.1 Hz, 2H), 6.31 (t, J = 6.2 Hz, 1H), 5.93 (t, J = 5.7 Hz, 1H), 4.36 (d, J = 12.9 Hz, 1H), 4.17 (d, J = 6.0 Hz, 2H), 3.90-3.82 (m, 1H), 3.64-3.51 (m, 1H), 3.41 (t, J = 9.1 Hz, 1H), 3.30-3.23 (m, 1H), 3.17 (d, J = 4.9 Hz, 1H), 2.99 (q, J = 7.2, 6.8 Hz, 3H), 2.40-2.24 (m, 2H), 1.64 (d, J = 13.0 Hz, 2H), 1.44 (s, 1H), 1.35 (t, J = 7.4 Hz, 2H), 1.24 (dd, J = 22.2, 8.8 Hz, 4H), 0.95 (dt, J = 23.5, 12.5 Hz, 2H). |
| 304 | 1-methyl-5-oxopyrrolidine-3-carboxylic acid | 3.8 | 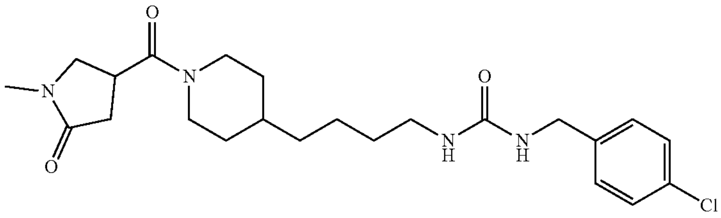 [SMILES: CN1CC(C(=O)N2CCC(CCCCNC(=O)NCc3ccc(Cl)cc3)CC2)CC1=O]<br>1-(4-chlorobenzyl)-3-(4-(1-(1-methyl-5-oxopyrrolidine-3-carbonyl)piperidin-4-yl)butyl)urea. LRMS (APCI) m/z 449.2 (M + H). $^1$H NMR (400 MHz, DMSO-$d_6$) δ 7.36 (d, J = 8.1 Hz, 2H), 7.25 (d, J = 8.1 Hz, 2H), 6.31 (t, J = 6.2 Hz, 1H), 5.93 (t, J = 5.8 Hz, 1H), 4.36 (d, J = 13.1 Hz, 1H), 4.17 (d, J = 6.0 Hz, 2H), 3.86 (d, J = 13.6 Hz, 1H), 3.52 (t, J = 4.8 Hz, 2H), 3.17 (d, J = 4.2 Hz, 2H), 2.99 (q, J = 6.3 Hz, 3H), 2.70 (s, 3H), 2.44 (d, J = 6.7 Hz, 2H), 1.65 (d, J = 13.9 Hz, 2H), 1.45 (s, 1H), 1.35 (q, J = 6.8 Hz, 2H), 1.24 (dq, J = 21.0, 7.4, 6.8 Hz, 4H), 1.05-0.85 (m, 2H). |
| 305 | oxazole-2-carboxylic acid | 3.8 | 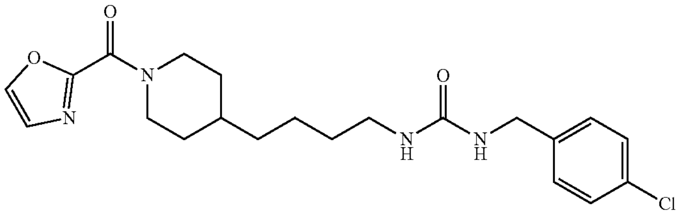 [SMILES: O=C(NCCCCC1CCN(C(=O)c2ncco2)CC1)NCc1ccc(Cl)cc1]<br>1-(4-chlorobenzyl)-3-(4-(1-(oxazole-2-carbonyl)piperidin-4-yl)butyl)urea. LRMS (APCI) m/z 419.1 (M + H). $^1$H NMR (400 MHz, DMSO-$d_6$) δ 8.28 (s, 1H), 7.43 (s, 1H), 7.36 (d, J = 8.2 Hz, 2H), 7.25 (d, J = 8.1 Hz, 2H), 6.31 (t, J = 6.2 Hz, 1H), 5.93 (t, J = 5.8 Hz, 1H), 4.46 (dd, J = 26.1, 13.3 Hz, 2H), 4.17 (d, J = 6.0 Hz, 2H), 3.20-3.07 (m, 1H), 3.00 (q, J = 6.4 Hz, 2H), 2.80 (td, J = 12.8, 2.9 Hz, 1H), 1.73 (t, J = 16.7 Hz, 2H), 1.62-1.44 (m, 1H), 1.35 (q, J = 6.8 Hz, 2H), 1.32-1.17 (m, 4H), 1.08 (dddd, J = 24.4, 20.4, 12.3, 6.1 Hz, 2H). |
| 306 | isoxazole-5-carboxylic acid | 3.8 | 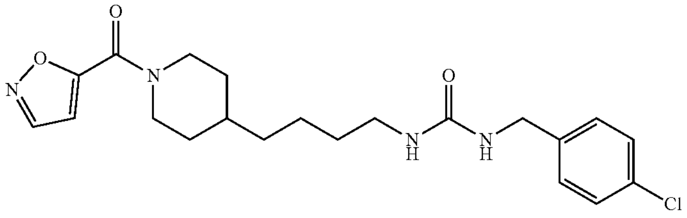 [SMILES: O=C(NCCCCC1CCN(C(=O)c2ccno2)CC1)NCc1ccc(Cl)cc1] |

-continued

| Compound No. | Carboxylic acid | Intermediate | Structure, Name and Data |
|---|---|---|---|
| | | | 1-(4-chlorobenzyl)-3-(4-(1-(isoxazole-5-carbonyl)piperidin-4-yl)butyl)urea. LRMS (APCI) m/z 419.2 (M + H). $^1$H NMR (400 MHz, DMSO-$d_6$) δ 8.73 (s, 1H), 7.36 (d, J = 8.1 Hz, 2H), 7.25 (d, J = 8.1 Hz, 2H), 6.88 (d, J = 1.7 Hz, 1H), 6.30 (d, J = 6.4 Hz, 1H), 5.93 (t, J = 5.7 Hz, 1H), 4.40 (d, J = 13.3 Hz, 1H), 4.17 (d, J = 5.9 Hz, 2H), 3.73 (d, J = 13.6 Hz, 1H), 3.16-3.08 (m, 1H), 3.00 (q, J = 6.5 Hz, 2H), 2.81 (t, J = 12.6 Hz, 1H), 1.73 (dd, J = 25.4, 13.4 Hz, 2H), 1.52 (dd, J = 14.6, 7.2 Hz, 1H), 1.41-1.32 (m, 2H), 1.24 (s, 4H), 1.09 (d, J = 13.7 Hz, 2H). |
| 309 | 6-methylnicotinic acid | 3.8 | 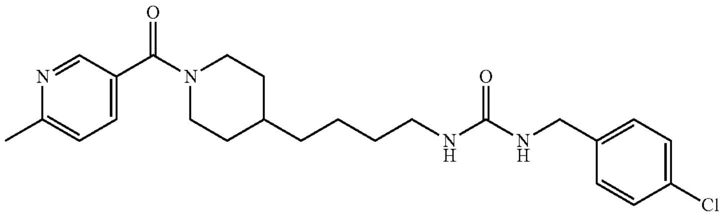 [SMILES: Cc1ccc(C(=O)N2CCC(CCCCNC(=O)NCc3ccc(Cl)cc3)CC2)cn1] 1-(4-chlorobenzyl)-3-(4-(1-(6-methylnicotinoyl)piperidin-4-yl)butyl)urea. LRMS (APCI) m/z 443.2 (M + H). $^1$H NMR (400 MHz, DMSO-$d_6$) δ 8.45 (s, 1H), 7.69 (d, J = 8.0 Hz, 1H), 7.35 (dt, J = 14.8, 5.6 Hz, 2H), 7.25 (t, J = 4.4 Hz, 2H), 6.31 (s, 1H), 5.93 (s, 1H), 4.45 (s, 1H), 4.18 (d, J = 5.9 Hz, 2H), 3.53 (s, 1H), 3.33 (s, 2H), 3.01 (p, J = 7.3, 5.4 Hz, 4H), 2.74 (s, 1H), 1.73 (q, J = 4.9 Hz, 3H), 1.54 (d, J = 50.0 Hz, 2H), 1.30 (d, J = 46.8 Hz, 5H), 1.06 (s, 2H). |
| 310 | 2-(2-methylpyridin-3-yl)acetic acid | 3.8 | 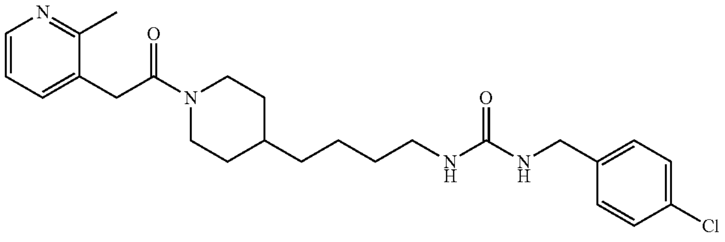 [SMILES: Cc1ncccc1CC(=O)N1CCC(CCCCNC(=O)NCc2ccc(Cl)cc2)CC1] 1-(4-chlorobenzyl)-3-(4-(1-(2-(2-methylpyridin-3-yl)acetyl)piperidin-4-yl)butyl)urea. LRMS (APCI) m/z 457.2 (M + H). $^1$H NMR (400 MHz, DMSO-$d_6$) δ 8.29 (d, J = 4.8 Hz, 1H), 8.15 (s, 1H), 7.43 (d, J = 7.6 Hz, 2H), 7.36 (d, J = 8.1 Hz, 2H), 7.26 (d, J = 8.1 Hz, 2H), 7.14 (dd, J = 7.6, 4.9 Hz, 1H), 6.32 (t, J = 6.2 Hz, 1H), 5.93 (t, J = 5.7 Hz, 1H), 4.38 (d, J = 12.9 Hz, 1H), 4.18 (d, J = 6.0 Hz, 2H), 3.94 (d, J = 13.6 Hz, 1H), 3.72 (d, J = 2.1 Hz, 2H), 3.00 (q, J = 5.9 Hz, 3H), 2.36 (s, 3H), 1.67 (d, J = 13.0 Hz, 2H), 1.47 (d, J = 12.2 Hz, 1H), 1.36 (p, J = 6.9 Hz, 2H), 1.25 (dq, J = 25.9, 8.0, 7.1 Hz, 4H), 1.08-0.85 (m, 2H). |

-continued

| Compound No. | Carboxylic acid | Intermediate | Structure, Name and Data |
|---|---|---|---|
| 311 | 2-(6-methylpyridin-3-yl)acetic acid | 3.8 | 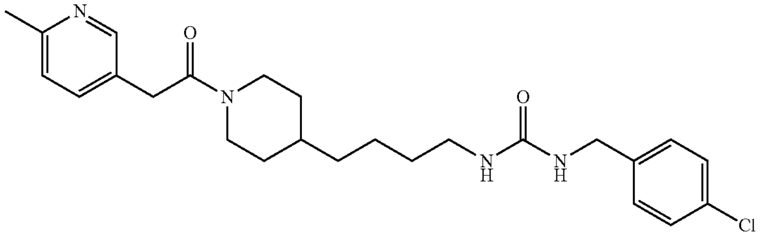 [SMILES: Cc1ccc(CC(=O)N2CCC(CCCCNC(=O)NCc3ccc(Cl)cc3)CC2)cn1] 1-(4-chlorobenzyl)-3-(4-(1-(2-(6-methylpyridin-3-yl)acetyl)piperidin-4-yl)butyl)urea. LRMS (APCI) m/z 457.2 (M + H). $^{1}H$ NMR (400 MHz, DMSO-$d_6$) δ 8.27 (s, 1H), 7.49 (dd, J = 7.7, 2.2 Hz, 1H), 7.36 (d, J = 8.1 Hz, 2H), 7.26 (d, J = 8.1 Hz, 2H), 7.18 (d, J = 7.9 Hz, 1H), 6.31 (t, J = 6.2 Hz, 1H), 5.93 (t, J = 5.8 Hz, 1H), 4.36 (d, J = 13.1 Hz, 1H), 4.17 (d, J = 6.0 Hz, 2H), 3.95 (d, J = 13.5 Hz, 1H), 3.68 (s, 2H), 3.04-2.91 (m, 3H), 2.57 (d, J = 15.4 Hz, 1H), 2.43 (s, 3H), 1.68-1.59 (m, 2H), 1.48-1.40 (m, 1H), 1.35 (p, J = 6.9 Hz, 2H), 1.25 (q, J = 8.1, 7.3 Hz, 2H), 1.18 (h, J = 6.3, 5.3 Hz, 2H), 0.92 (tt, J = 12.0, 6.6 Hz, 2H). |
| 312 | 1-methyl-1H-1,2,3-triazole-4-carboxylic acid | 3.8 | 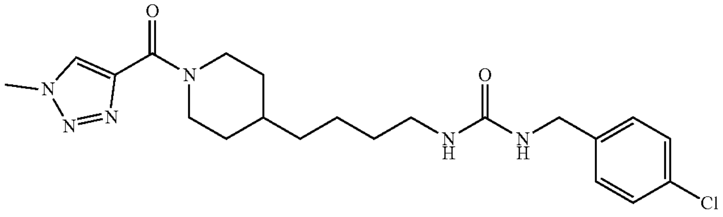 [SMILES: Cn1cc(C(=O)N2CCC(CCCCNC(=O)NCc3ccc(Cl)cc3)CC2)nn1] 1-(4-chlorobenzyl)-3-(4-(1-(1-methyl-1H-1,2,3-triazole-4-carbonyl)piperidin-4-yl)butyl)urea. LRMS (APCI) m/z 433.2 (M + H). $^{1}H$ NMR (400 MHz, DMSO-$d_6$) δ 8.43 (s, 1H), 7.36 (d, J = 8.0 Hz, 2H), 7.26 (d, J = 8.1 Hz, 2H), 6.32 (s, 1H), 5.94 (s, 1H), 4.72 (d, J = 13.1 Hz, 1H), 4.46 (d, J = 12.7 Hz, 1H), 4.17 (d, J = 5.3 Hz, 2H), 4.08 (s, 3H), 3.11 (s, 1H), 3.00 (q, J = 6.2 Hz, 2H), 2.72 (t, J = 13.1 Hz, 1H), 1.78-1.63 (m, 2H), 1.52 (dt, J = 11.0, 5.4 Hz, 1H), 1.36 (q, J = 6.8 Hz, 2H), 1.26 (q, J = 8.8, 6.1 Hz, 4H), 1.15-0.95 (m, 2H). |
| 313 | 2-(o-tolyl)acetic acid | 3.8 | 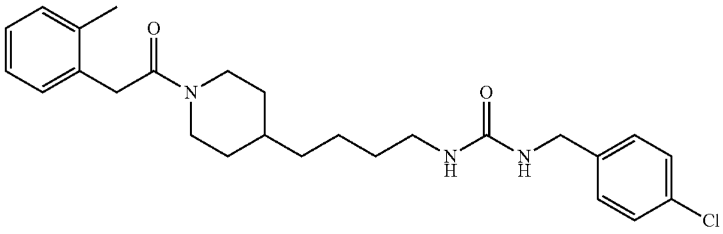 [SMILES: Cc1ccccc1CC(=O)N1CCC(CCCCNC(=O)NCc2ccc(Cl)cc2)CC1] 1-(4-chlorobenzyl)-3-(4-(1-(2-(o-tolyl)acetyl)piperidin-4-yl)butyl)urea. LRMS (APCI) m/z 456.2 (M + H). $^{1}H$ NMR (400 MHz, DMSO-$d_6$) δ 7.36 (d, J = 8.0 Hz, 2H), 7.26 (d, J = 8.0 Hz, 2H), 7.13 (tt, J = 9.0, 5.2 Hz, 3H), 7.08-6.98 (m, 1H), 6.31 (t, J = 6.4 Hz, 1H), 5.93 (t, J = 5.7 Hz, 1H), 4.40 (d, J = 13.0 Hz, 1H), 4.17 (d, J = 6.0 Hz, 2H), 3.87 (d, J = 13.8 Hz, 1H), 3.65 (d, J = 2.8 Hz, 2H), 3.17 (d, |

-continued

| Compound No. | Carboxylic acid | Intermediate | Structure, Name and Data |
|---|---|---|---|
| | | | J = 5.2 Hz, 1H), 3.04-2.90 (m, 3H), 2.54 (t, J = 12.7 Hz, 1H), 2.18 (s, 3H), 1.70-1.58 (m, 2H), 1.34 (q, J = 6.8 Hz, 2H), 1.23 (dq, J = 28.5, 7.8, 7.0 Hz, 4H), 1.04-0.85 (m, 2H). |
| 314 | 2-difluorometh-yl)benzo-ic acid | 3.8 | 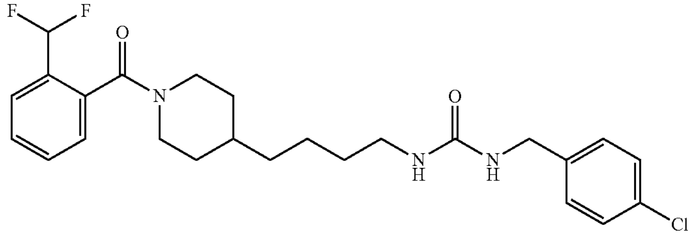 [SMILES: O=C(NCCCCC1CCN(C(=O)c2ccccc2C(F)F)CC1)NCc1ccc(Cl)cc1] 1-(4-chlorobenzyl)-3-(4-(1-(2-(difluoromethyl)benzoyl)piperidin-4-yl)butyl)urea. LRMS (APCI) m/z 478.2 (M + H). $^{1}$H NMR (400 MHz, DMSO-$d_6$) δ 7.65 (dd, J = 26.4, 7.2 Hz, 1H), 7.58 (d, J = 6.3 Hz, 2H), 7.41-7.31 (m, 3H), 7.25 (d, J = 8.1 Hz, 2H), 6.95 (t, J = 55.1 Hz, 1H), 6.31 (t, J = 6.2 Hz, 1H), 5.93 (t, J = 5.7 Hz, 1H), 4.50 (d, J = 12.9 Hz, 1H), 4.17 (d, J = 6.0 Hz, 2H), 3.27 (d, J = 13.5 Hz, 2H), 3.18 (d, J = 5.2 Hz, 1H), 2.99 (q, J = 6.5 Hz, 2H), 2.82-2.70 (m, 1H), 1.74 (d, J = 12.8 Hz, 1H), 1.57-1.44 (m, 2H), 1.35 (q, J = 6.9 Hz, 2H), 1.31-1.16 (m, 4H), 1.09 (d, J = 13.0 Hz, 1H). |
| 315 | 2-(1H-tetrazol-5-yl)benzoic acid | 3.8 | 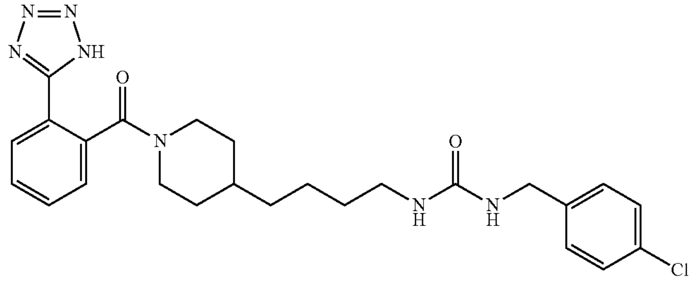 [SMILES: O=C(NCCCCC1CCN(C(=O)c2ccccc2-c2nnn[nH]2)CC1)NCc1ccc(Cl)cc1] 1-(4-(1-(2-(1H-tetrazol-5-yl)benzoyl)piperidin-4-yl)butyl)-3-(4-chlorobenzyl)urea. LRMS (APCI) m/z 496.2 (M + H). $^{1}$H NMR (400 MHz, DMSO-$d_6$) δ 7.86 (s, 1H), 7.66-7.59 (m, 2H), 7.43 (d, J = 6.5 Hz, 1H), 7.35 (d, J = 8.0 Hz, 2H), 7.25 (d, J = 8.1 Hz, 2H), 6.31 (t, J = 6.0 Hz, 1H), 5.93 (t, J = 5.5 Hz, 1H), 4.44 (d, J = 12.9 Hz, 1H), 4.17 (d, J = 5.9 Hz, 2H), 3.27 (dd, J = 6.6, 3.4 Hz, 2H), 2.99 (q, J = 6.5 Hz, 2H), 2.65 (d, J = 15.0 Hz, 1H), 1.81-1.56 (m, 2H), 1.42 (s, 2H), 1.34 (d, J = 7.9 Hz, 2H), 1.22 (s, 4H), 1.07 (d, J = 12.5 Hz, 2H). |
| 316 | 2-(1H-pyrazol-4-yl)acetic acid | 3.8 | 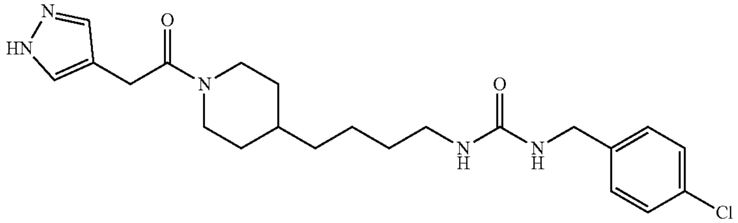 [SMILES: O=C(NCCCCC1CCN(C(=O)Cc2cn[nH]c2)CC1)NCc1ccc(Cl)cc1] 1-(4-(1-(2-(1H-pyrazol-4-yl)acetyl)piperidin-4-yl)butyl)-3-(4- |

-continued

| Compound No. | Carboxylic acid | Intermediate | Structure, Name and Data |
|---|---|---|---|
| | | | chlorobenzyl)urea. LRMS (APCI) m/z 432.2 (M + H). $^1$H NMR (400 MHz, DMSO-$d_6$) δ 7.43 (s, 2H), 7.36 (d, J = 8.0 Hz, 2H), 7.25 (d, J = 8.0 Hz, 2H), 6.31 (t, J = 6.1 Hz, 1H), 5.93 (t, J = 5.7 Hz, 1H), 4.36 (d, J = 13.0 Hz, 1H), 4.17 (d, J = 6.0 Hz, 2H), 4.10 (s, 1H), 3.91 (d, J = 13.5 Hz, 1H), 3.50 (s, 2H), 3.17 (s, 2H), 3.04-2.87 (m, 3H), 1.60 (d, J = 11.0 Hz, 2H), 1.34 (p, J = 6.9 Hz, 2H), 1.23 (dq, J = 10.4, 5.8, 5.3 Hz, 2H), 1.16 (q, J = 7.0 Hz, 2H), 0.87 (q, J = 12.4 Hz, 2H). |
| 317 | benzoic acid | 3.9 | 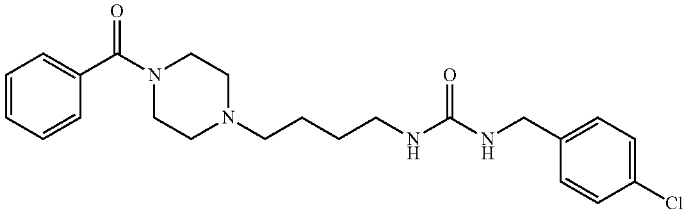 [SMILES: O=C(NCCCCN1CCN(C(=O)c2ccccc2)CC1)NCc1ccc(Cl)cc1] 1-(4-(4-benzoylpiperazin-1-yl)butyl)-3-(4-chlorobenzyl)urea. LRMS (APCI) m/z 429.2 (M + H). $^1$H NMR (400 MHz, DMSO-$d_6$) δ 7.46 (d, J = 5.2 Hz, 3H), 7.42-7.32 (m, 4H), 7.25 (d, J = 8.0 Hz, 2H), 6.35 (t, J = 6.1 Hz, 1H), 5.98 (t, J = 6.0 Hz, 1H), 4.17 (d, J = 6.0 Hz, 2H), 3.50-3.25 (m, 7H), 3.17 (s, 1H), 3.01 (q, J = 6.4 Hz, 2H), 2.48-2.36 (m, 2H), 1.42 (dq, J = 21.1, 8.0, 7.3 Hz, 4H). |
| 319 | 2,6-dimethylbenzoic acid | 3.8 | 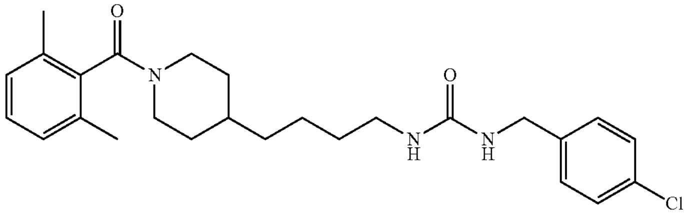 [SMILES: Cc1cccc(C)c1C(=O)N1CCC(CCCCNC(=O)NCc2ccc(Cl)cc2)CC1] 1-(4-chlorobenzyl)-3-(4-(1-(2,6-dimethylbenzoyl)piperidin-4-yl)butyl)urea. LRMS (APCI) m/z 456.2 (M + H). $^1$H NMR (400 MHz, DMSO-$d_6$) δ 8.14 (s, 1H), 7.35 (d, J = 8.1 Hz, 2H), 7.25 (d, J = 8.1 Hz, 2H), 7.16 (t, J = 7.5 Hz, 1H), 7.06 (t, J = 6.5 Hz, 2H), 6.31 (t, J = 6.2 Hz, 1H), 5.92 (t, J = 5.7 Hz, 1H), 4.57 (d, J = 13.1 Hz, 1H), 4.17 (d, J = 6.0 Hz, 2H), 4.03 (q, J = 7.1 Hz, 1H), 3.17 (d, J = 13.3 Hz, 1H), 3.04-2.91 (m, 3H), 2.73 (td, J = 12.7, 2.8 Hz, 1H), 2.14 (d, J = 30.5 Hz, 6H), 1.81-1.73 (m, 1H), 1.56 (d, J = 13.3 Hz, 1H), 1.35 (t, J = 7.0 Hz, 2H), 1.24 (dt, J = 9.4, 4.3 Hz, 3H), 0.96 (dqd, J = 48.4, 12.3, 4.3 Hz, 2H). |
| 320 | 2-methylbenzoic acid | 3.10 | 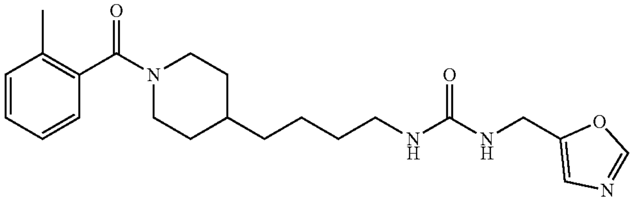 [SMILES: Cc1ccccc1C(=O)N1CCC(CCCCNC(=O)NCc2cnco2)CC1] 1-(4-(1-(2-methylbenzoyl)piperidin-4-yl)butyl)-3-(oxazol-5-ylmethyl)urea. |

-continued

| Compound No. | Carboxylic acid | Intermediate | Structure, Name and Data |
| --- | --- | --- | --- |
| | | | LRMS (APCI) m/z 399.2 (M + H). $^1$H NMR (400 MHz, DMSO-$d_6$) δ 7.26 (tt, J = 15.2, 7.3 Hz, 4H), 7.12 (dd, J = 21.1, 7.5 Hz, 1H), 6.92 (s, 1H), 6.27 (t, J = 5.9 Hz, 1H), 5.94 (t, J = 5.7 Hz, 1H), 4.52 (d, J = 13.0 Hz, 1H), 4.24 (d, J = 5.8 Hz, 2H), 3.05-2.87 (m, 4H), 2.72 (t, J = 12.7 Hz, 1H), 2.20 (d, J = 20.9 Hz, 3H), 1.78-1.68 (m, 1H), 1.49 (dd, J = 29.9, 14.9 Hz, 3H), 1.34 (q, J = 6.8 Hz, 2H), 1.23 (d, J = 7.5 Hz, 5H). |
| 321 | 2-methylbenzoic acid | 3.12 | 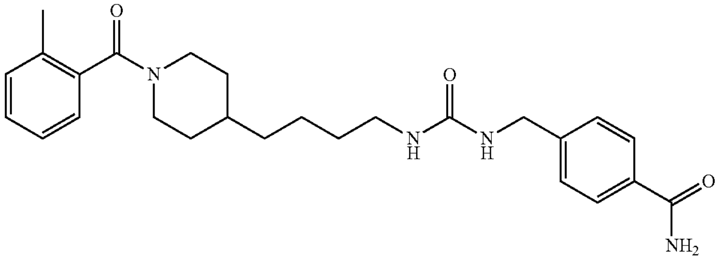 [SMILES: Cc1ccccc1C(=O)N1CCC(CCCCNC(=O)NCc2ccc(C(N)=O)cc2)CC1] 4-((3-(4-(1-(2-methylbenzoyl)piperidin-4-yl)butyl)ureido)methyl)benzamide. LRMS (APCI) m/z 451.3 (M + H). $^1$H NMR (400 MHz, DMSO-$d_6$) δ 7.90 (s, 1H), 7.81 (d, J = 8.0 Hz, 2H), 7.38-7.18 (m, 5H), 7.13 (d, J = 18.6 Hz, 1H), 6.32 (t, J = 6.2 Hz, 1H), 5.94 (t, J = 5.8 Hz, 1H), 4.52 (d, J = 13.1 Hz, 1H), 4.23 (d, J = 6.0 Hz, 2H), 3.07-2.99 (m, 2H), 2.99-2.88 (m, 2H), 2.73 (t, J = 12.2 Hz, 1H), 2.20 (d, J = 19.9 Hz, 3H), 1.74 (q, J = 5.4, 3.1 Hz, 2H), 1.51 (d, J = 34.1 Hz, 2H), 1.35 (d, J = 7.1 Hz, 2H), 1.24 (s, 4H), 1.11-0.92 (m, 2H). |
| 322 | 2-methylbenzo-ic acid | 3.11 | 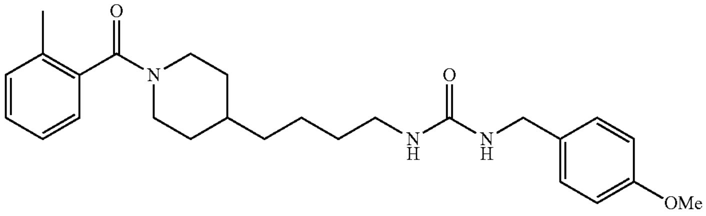 [SMILES: COc1ccc(CNC(=O)NCCCCC2CCN(C(=O)c3ccccc3C)CC2)cc1] 1-(4-methoxybenzyl)-3-(4-(1-(2-methylbenzoyl)piperidin-4-yl)butyl)urea. LRMS (APCI) m/z 438.3 (M + H). $^1$H NMR (400 MHz, DMSO-$d_6$) δ 7.26 (tt, J = 15.4, 7.3 Hz, 3H), 7.15 (d, J = 8.2 Hz, 2H), 7.09 (d, J = 7.7 Hz, 1H), 6.85 (d, J = 8.2 Hz, 2H), 6.16 (t, J = 6.0 Hz, 1H), 5.83 (t, J = 5.7 Hz, 1H), 4.52 (d, J = 12.9 Hz, 1H), 4.11 (d, J = 5.9 Hz, 2H), 3.72 (s, 3H), 3.04-2.87 (m, 3H), 2.72 (t, J = 12.5 Hz, 1H), 2.20 (d, J = 20.2 Hz, 3H), 1.75 (d, J = 13.0 Hz, 1H), 1.64-1.40 (m, 2H), 1.35 (t, J = 7.0 Hz, 2H), 1.21 (dq, J = 14.3, 6.9 Hz, 5H), 1.00 (dt, J = 41.7, 12.9 Hz, 2H). |

-continued

| Compound No. | Carboxylic acid | Intermediate | Structure, Name and Data |
|---|---|---|---|
| 323 | 2-methylbenzoic acid | 3.13 | 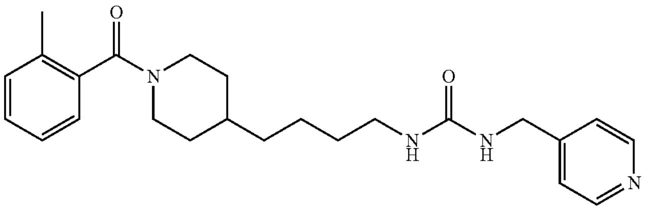 [SMILES: Cc1ccccc1C(=O)N1CCC(CCCCNC(=O)NCc2ccncc2)CC1] 1-(4-(1-(2-methylbenzoyl)piperidin-4-yl)butyl)-3-(pyridin-4-ylmethyl)urea. LRMS (APCI) m/z 409.2 (M + H). $^1$H NMR (400 MHz, DMSO-$d_6$) δ 8.47 (s, 2H), 7.25 (dt, J = 22.2, 6.3 Hz, 5H), 7.18-7.08 (m, 1H), 6.42 (t, J = 6.2 Hz, 1H), 6.05 (t, J = 5.7 Hz, 1H), 4.52 (d, J = 13.1 Hz, 1H), 4.21 (d, J = 6.1 Hz, 2H), 3.05-2.87 (m, 3H), 2.73 (dd, J = 14.5, 10.8 Hz, 1H), 2.20 (d, J = 20.1 Hz, 3H), 1.75 (d, J = 12.9 Hz, 1H), 1.66-1.41 (m, 3H), 1.36 (q, J = 7.0 Hz, 2H), 1.25 (d, J = 10.8 Hz, 4H), 1.10-0.86 (m, 2H). |
| 293 | Benzoic acid | 3.15 | 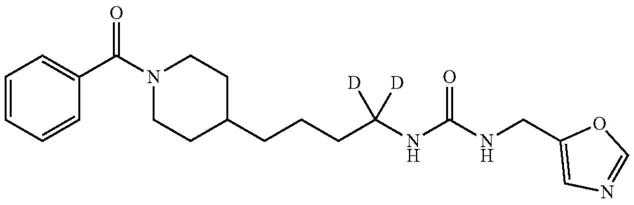 [SMILES: [2H]C([2H])(CCCC1CCN(C(=O)c2ccccc2)CC1)NC(=O)NCc1cnco1] 1-(4-(1-benzoylpiperidin-4-yl)butyl-1,1-d2)-3-(oxazol-5-ylmethyl)urea. LRMS (APCI) m/z 387 (M + H). $^1$H NMR (300 MHz, DMSO) δ 1.07 (s, 2H), 1.21-2.12 (m, 9H), 2.86 (d, J = 69.7 Hz, 2H), 3.55 (s, 1H), 4.26 (dd, J = 5.9, 1.0 Hz, 2H), 4.46 (s, 1H), 5.93 (s, 1H), 6.27 (t, J = 5.9 Hz, 1H), 6.93 (d, J = 0.9 Hz, 1H), 7.33-7.49 (m, 5H), 8.26 (s, 1H). |

Example 2

Preparation of N-benzyl-6-(3-(4-methoxybenzyl)ureido)spiro[3.3]heptane-2-carboxamide (Compound 68)

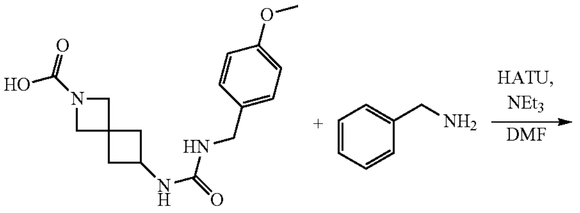

-continued

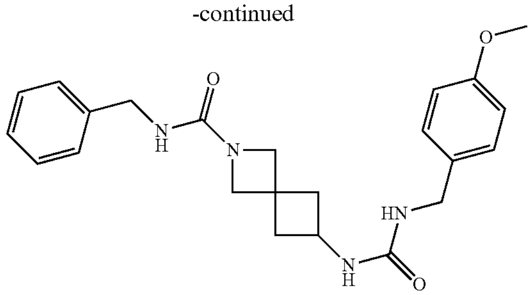

Preparation of N-benzyl-6-(3-(4-methoxybenzyl)ureido)spiro[3.3]heptane-2-carboxamide HATU (201 mg, 0.529 mmol, 2 equiv) was added to a stirring solution of 6-(3-(4-methoxybenzyl)ureido)spiro[3.3]heptane-2-carboxylic acid (80 mg, 0.265 mmol, 1.5 equiv), phenylmethanamide (57 mg, 0.529 mmol, 2 equiv) and $NEt_3$ (134 mg, 1.32 mmol, 5 equiv) in DMF (0.5 mL) at rt. After 3 h, the reaction was quenched with saturated ammonium chloride, extracted with $CH_2Cl_2$, organics combined, dried over sodium sulfate, filtered, and product was isolated by reverse phase HPLC (10→100% MeCN/$H_2O$ w/0.1% formic acid) as a white solid (10 mg, 9%). LRMS (APCI) m/z 408 (M+H). $^{1}$H NMR (400 MHz, DMSO-d6) δ 8.18 (t, J=6.0 Hz, 1H), 7.31 (t, J=7.4 Hz, 2H), 7.21 (d, J=7.7 Hz, 3H), 7.15 (d, J=8.1 Hz, 2H), 6.87 (d, J=8.0 Hz, 2H), 6.20-5.97 (m, 2H), 4.24 (d, J=5.8 Hz, 2H), 4.10 (d, J=5.7 Hz, 2H), 3.92 (h, J=8.2 Hz, 1H), 3.72 (s, 3H), 2.93 (p, J=8.4 Hz, 1H), 2.35 (dt, J=11.9, 6.2 Hz, 1H), 2.15 (p, J=10.1 Hz, 4H), 2.05-1.88 (m, 1H), 1.80 (t, J=9.7 Hz, 1H), 1.71 (t, J=9.9 Hz, 1H).

Compounds in the following table were prepared in a similar manner as Compound 68, using the intermediates and reagents as listed.

| Compound No. | Amine | Intermediate | Structure, Name and Data |
|---|---|---|---|
| 43 | 1-phenylcyclo-propan-1-amine | 2.2 | 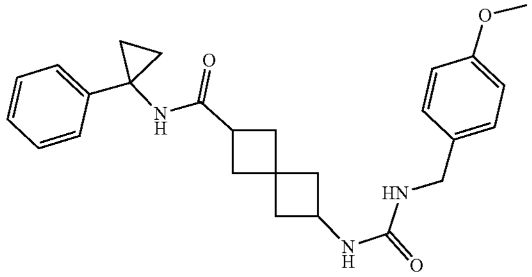 [SMILES: COc1ccc(CNC(=O)NC2CC3(C2)CC(C(=O)NC2(c4ccccc4)CC2)C3)cc1] 6-(3-(4-methoxybenzyl)ureido)-N-(1-phenylcyclopropyl)spiro[3.3]heptane-2-carboxamide. LRMS (APCI) m/z 434 (M + H). $^{1}$H NMR (400 MHz, DMSO-$d_6$) δ 8.38 (s, 1H), 7.25 (t, J = 7.6 Hz, 2H), 7.20-7.02 (m, 5H), 6.87 (d, J = 8.4 Hz, 2H), 6.20-5.98 (m, 2H), 4.10 (d, J = 5.4 Hz, 2H), 3.92 (q, J = 8.0 Hz, 1H), 3.72 (s, 3H), 2.91 (p, J = 8.5 Hz, 1H), 2.35 (ddd, J = 11.4, 7.2, 5.2 Hz, 1H), 2.11 (dd, J = 19.9, 8.4 Hz, 4H), 2.04-1.89 (m, 1H), 1.79 (dd, J = 10.6, 8.7 Hz, 1H), 1.70 (dd, J = 11.1, 8.8 Hz, 1H), 1.13 (t, J = 3.0 Hz, 2H), 1.11-1.00 (m, 2H). |
| 45 | (R)-1-phenylethan-1-amine | 2.2 | 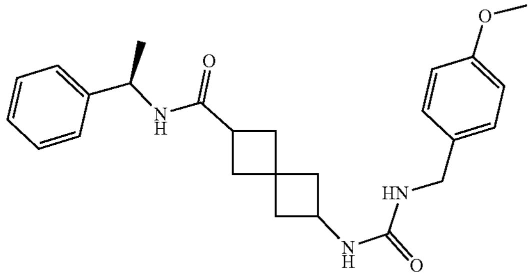 [SMILES: COc1ccc(CNC(=O)NC2CC3(C2)CC(C(=O)N[C@H](C)c2ccccc2)C3)cc1] (R)-6-(3-(4-methoxybenzyl)ureido)-N-(1-phenylethyl)spiro[3.3]heptane-2-carboxamide. LRMS (APCI) m/z 422 (M + H). $^{1}$H NMR (400 MHz, DMSO-$d_6$) δ 8.09 (d, J = 8.2 Hz, 1H), 7.29 (dt, J = 13.5, 4.7 Hz, 4H), 7.21 (t, J = 7.1 Hz, 1H), 7.15 (d, J = 8.3 Hz, 2H), 6.86 (d, J = 8.3 Hz, 2H), 6.17-6.00 (m, 2H), 4.89 (p, J = 7.3 Hz, 1H), 4.10 (d, J = 5.9 Hz, 2H), 3.91 (hd, J = 8.1, 3.9 Hz, 1H), 3.733 (s, 3H), 2.93 (p, J = 8.5 Hz, 1H), 2.34 (dt, J = 11.7, 6.1 Hz, 1H), 2.21-2.00 (m, 4H), 1.93 (dtt, J = 8.3, 5.2, 2.5 Hz, 1H), 1.86-1.73 (m, 1H), 1.68 (ddd, J = 11.5, 8.8, 3.0 Hz, 1H), 1.31 (d, J = 6.9 Hz, 3H). |
| 47 | (S)-1-phenylethan-1-amine | 2.2 | 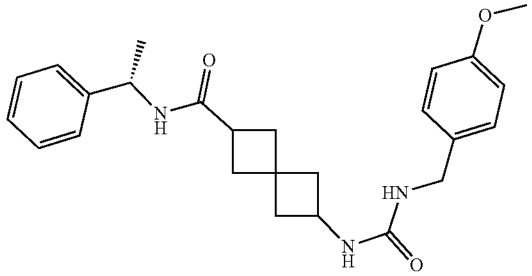 [SMILES: COc1ccc(CNC(=O)NC2CC3(C2)CC(C(=O)N[C@@H](C)c2ccccc2)C3)cc1] |

-continued

| Compound No. | Amine | Intermediate | Structure, Name and Data |
|---|---|---|---|
| | | | (S)-6-(3-(4-methoxybenzyl)ureido)-N-(1-phenylethyl)spiro[3.3]heptane-2-carboxamide. LRMS (APCI) m/z 422 (M + H). $^1$H NMR (400 MHz, DMSO-$d_6$) δ 8.09 (d, J = 8.1 Hz, 1H), 7.41-7.18 (m, 5H), 7.15 (d, J = 8.3 Hz, 2H), 6.86 (d, J = 8.3 Hz, 2H)), 6.21-5.98 (m, 2H), 4.88 (p, J = 7.3 Hz, 1H), 4.09 (d, J = 5.9 Hz, 2H), 3.91 (qd, J = 8.0, 4.2 Hz, 1H), 3.72 (s, 3H), 2.92 (p, J = 8.5 Hz, 1H), 2.34 (dt, J = 11.5, 6.0 Hz, 1H), 2.20-2.01 (m, 4H), 1.93 (ddp, J = 11.4, 8.3, 4.2, 3.7 Hz, 1H), 1.86-1.74 (m, 1H), 1.68 (ddd, J = 11.5, 8.7, 3.0 Hz, 1H), 1.41-1.12 (m, 3H). |
| 44 | 2-phenylpyrrolidine | 2.2 | 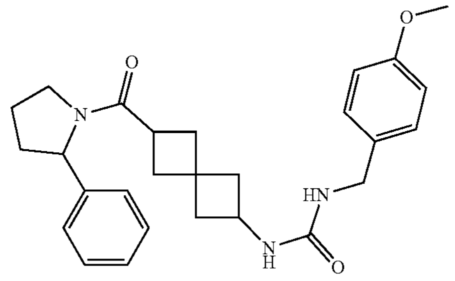 [SMILES: COc1ccc(CNC(=O)NC2CC3(C2)CC(C(=O)N2CCCC2c2ccccc2)C3)cc1]<br>1-(4-methoxybenzyl)-3-(6-(2-phenylpyrrolidine-1-carbonyl)spiro[3.3]heptan-2-yl)urea. LRMS (APCI) m/z 448 (M + H). $^1$H NMR (400 MHz, DMSO-$d_6$) δ 7.35 (td, J = 7.4, 4.9 Hz, 1H), 7.28 (qd, J = 7.5, 2.3 Hz, 3H), 7.23-7.05 (m, 3H), 6.86 (dd, J = 8.5, 6.2 Hz, 2H), 6.24-6.04 (m, 1H), 6.05-5.94 (m, 1H), 5.10-4.79 (m, 1H), 4.10 (d, J = 5.9 Hz, 1H), 4.06 (d, J = 5.9 Hz, 1H), 3.92 (ddp, J = 11.5, 7.8, 4.1, 3.5 Hz, 1H), 3.72 (d, J = 3.0 Hz, 3H), 3.65-3.45 (m, 2H), 3.28-3.15 (m, 1H), 2.75 (p, J = 8.7 Hz, 1H), 2.40 (p, J = 6.2 Hz, 1H), 2.24-1.96 (m, 2H), 1.91-1.51 (m, 6H), 1.19 (dddd, J = 35.6, 11.6, 8.2, 3.7 Hz, 2H). |
| 46 | (S)-amino-2-phenylethan-1-ol | 2.2 | 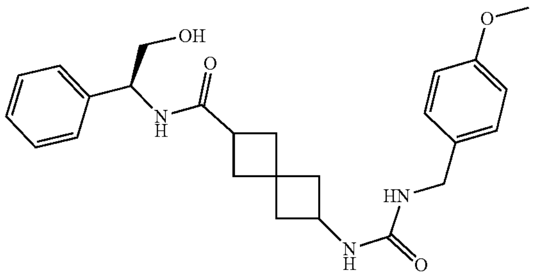<br>(S)-N-(2-hydroxy-1-phenylethyl)-6-(3-(4-methoxybenzyl)ureido)spiro[3.3]heptane-2-carboxamide. LRMS (APCI) m/z 422 (M + H). $^1$H NMR (400 MHz, DMSO-$d_6$) δ 8.03 (dd, J = 8.3, 3.2 Hz, 1H), 7.34-7.25 (m, 4H), 7.25-7.19 (m, 1H), 7.15 (d, J = 8.3 Hz, 2H), 6.86 (d, J = 8.4 Hz, 2H), 6.22-5.97 (m, 2H), 4.81 (q, J = 7.6, 7.1 Hz, 2H), 4.09 (d, J = 5.9 Hz, 2H), 3.91 (qd, J = 8.3, 5.9 Hz, 1H), 3.72 (s, 3H), 3.52 (d, J = 6.4 Hz, 2H), 2.98 (p, J = 8.4 Hz, 1H), 2.35 (ddd, J = 13.6, 7.6, 3.7 Hz, 1H), 2.10 (tdd, J = 22.9, 10.6, 7.5 Hz, 4H), 1.95 (dtd, J = 10.8, 5.2, 2.7 Hz, 1H), 1.79 (ddd, J = 11.4, 8.9, 3.2 Hz, 1H), 1.68 (ddd, J = 11.8, 8.8, 3.9 Hz, 1H). |

-continued

| Compound No. | Amine | Intermediate | Structure, Name and Data |
| --- | --- | --- | --- |
| 48 | 2-phenylazetidine | 2.2 | 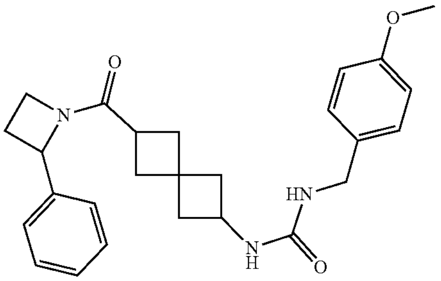 [SMILES: COc1ccc(CNC(=O)NC2CC3(C2)CC(C(=O)N2CCC2c2ccccc2)C3)cc1] 1-(4-methoxybenzyl)-3-(6-(2-phenylazetidine-1-carbonyl)spiro[3.3]heptan-2-yl)urea. LRMS (APCI) m/z 434 (M + H). $^1$H NMR (400 MHz, DMSO-$d_6$); δ 8.32 (s, 1H), 7.64 (t, J = 5.5 Hz, 1H), 7.41 (d, J = 3.5 Hz, 1H), 7.31 (d, J = 4.6 Hz, 2H), 7.22 (p, J = 4.3 Hz, 1H), 7.15 (d, J = 8.4 Hz, 2H), 6.86 (d, J = 8.3 Hz, 1H), 6.22-6.08 (m, 1H), 6.04 (t, J = 8.3 Hz, 1H), 5.19 (t, J = 7.7 Hz, 1H), 4.53 (t, J = 6.5 Hz, 1H), 4.08 (dd, J = 11.9, 5.7 Hz, 1H), 3.91 (q, J = 8.0 Hz, 1H), 3.72 (s, 3H), 3.16-2.99 (m, 2H), 2.83 (p, J = 8.4 Hz, 1H), 2.65 (dt, J = 15.7, 8.0 Hz, 1H), 2.43-2.27 (m, 1H), 2.20-2.04 (m, 2H), 2.01 (dd, J = 9.5, 4.9 Hz, 1H), 1.95-1.86 (m, 1H), 1.78 (t, J = 9.8 Hz, 1H), 1.73-1.64 (m, 2H), 1.28-1.09 (m, 1H). |
| 49 | pyridin-3-ylmethanamine | 2.2 | 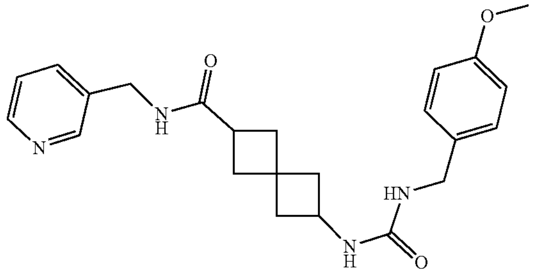 [SMILES: COc1ccc(CNC(=O)NC2CC3(C2)CC(C(=O)NCc2cccnc2)C3)cc1] 6-(3-(4-methoxybenzyl)ureido)-N-(pyridin-3-ylmethyl)spiro[3.3]heptane-2-carboxamide. LRMS (APCI) m/z 409 (M + H). $^1$H NMR (400 MHz, DMSO-$d_6$) δ 8.45 (d, J = 3.4 Hz, 2H), 8.25 (t, J = 6.0 Hz, 1H), 7.62 (dd, J = 7.8, 2.1 Hz, 2H), 7.35 (dd, J = 7.8, 4.7 Hz, 1H), 7.15 (d, J = 8.3 Hz, 2H), 6.86 (d, J = 8.3 Hz, 2H), 6.21-5.95 (m, 1H), 4.26 (d, J = 5.8 Hz, 2H), 4.09 (d, J = 5.9 Hz, 2H), 3.91 (q, J = 8.0 Hz, 1H), 3.72 (s, 3H), 2.92 (p, J = 8.5 Hz, 1H), 2.34 (ddd, J = 11.8, 7.3, 5.2 Hz, 1H), 2.13 (dq, J = 11.4, 8.3 Hz, 4H), 1.96 (ddd, J = 11.3, 8.2, 2.6 Hz, 1H), 1.79 (dd, J = 10.6, 8.7 Hz, 1H), 1.70 (dd, J = 11.1, 8.8 Hz, 1H). |
| 50 | pyridin-4-ylmethanamine | 2.2 | 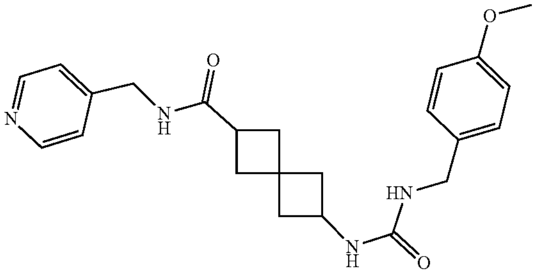 [SMILES: COc1ccc(CNC(=O)NC2CC3(C2)CC(C(=O)NCc2ccncc2)C3)cc1] 6-(3-(4-methoxybenzyl)ureido)-N-(pyridin-4-ylmethyl)spiro[3.3]heptane-2-carboxamide. LRMS (APCI) m/z 409 (M + H). $^1$H NMR (400 MHz, DMSO-$d_6$) δ 8.49 (d, J = 4.9 Hz, 2H), 8.29 (t, J = 6.1 Hz, 1H), 7.21 (d, J = 5.0 Hz, 2H), 7.15 (d, J = 8.3 Hz, 2H), 6.87 (d, J = 8.4 Hz, 2H), 6.27- |

-continued

| Compound No. | Amine | Intermediate | Structure, Name and Data |
|---|---|---|---|
| | | | 5.84 (m, 2H), 4.26 (d, J = 6.0 Hz, 2H), 4.09 (d, J = 5.9 Hz, 2H), 3.92 (q, J = 8.0 Hz, 1H), 3.72 (s, 3H), 2.96 (p, J = 8.5 Hz, 1H), 8.36 (ddd, J = 11.9, 7.2, 5.1 Hz, 1H), 2.16-2.07 (m, 4H), 1.99 (ddd, J = 11.1, 8.4, 2.2 Hz, 1H), 1.80 (dd, J = 10.6, 8.7 Hz, 1H), 1.71 (dd, J = 11.0, 8.8 Hz, 1H). |
| 51 | N-methyl-1-phenylmethanamine | 2.2 | 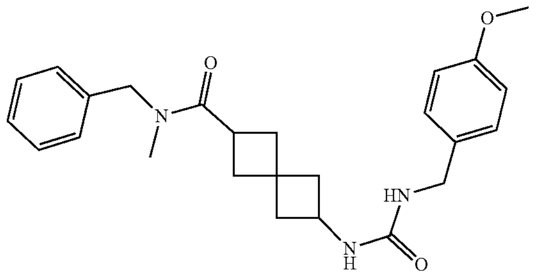 [SMILES: COc1ccc(CNC(=O)NC2CC3(C2)CC(C(=O)N(C)Cc2ccccc2)C3)cc1] N-benzyl-6-(3-(4-methoxybenzyl)ureido)-N-methylspiro[3.3]heptane-2-carboxamide. LRMS (APCI) m/z 422 (M + H). $^1$H NMR (400 MHz, DMSO-$d_6$) δ 7.35 (dt, J = 17.2, 7.4 Hz, 2H), 7.26 (q, J = 7.3, 6.6 Hz, 1H), 7.21-7.06 (m, 4H), 6.86 (dd, J = 8.7, 3.4 Hz, 2H), 6.10 (dq, J = 14.0, 8.0, 7.0 Hz, 2H), 4.47 (d, J = 2.1 Hz, 2H), 4.09 (t, J = 5.9 Hz, 1H), 4.01-3.80 (m, 1H), 3.72 (s, 3H), 3.26 (dt, J = 13.6, 8.5 Hz, 1H), 2.80 (s, 2H), 2.75 (s, 1H), 2.39 (ddd, J = 11.6, 7.3, 5.3 Hz, 1H), 2.35-2.29 (m, 1H), 2.29-2.02 (m, 5H), 1.87-1.77 (m, 1H), 1.71 (ddt, J = 14.5, 11.1, 5.9 Hz, 1H). |
| 53 | (R)-1-(2-fluorophenyl) ethan-1-amine | 2.2 | 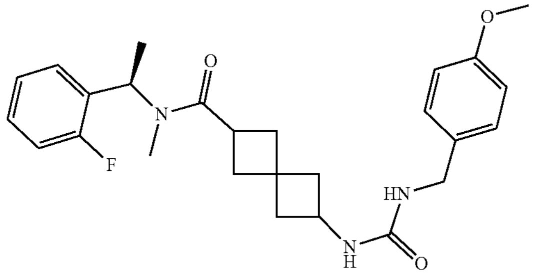 [SMILES: COc1ccc(CNC(=O)NC2CC3(C2)CC(C(=O)N(C)[C@H](C)c2ccccc2F)C3)cc1] (R)-N-(1-(2-fluorophenyl)ethyl)-6-(3-(4-methoxybenzyl)ureido)-N-methylspiro[3.3]heptane-2-carboxamide. LRMS (APCI) m/z 454 (M + H). $^1$H NMR (400 MHz, DMSO-$d_6$) δ 7.39 (ddq, J = 21.0, 13.8, 7.3, 6.8 Hz, 2H), 7.26-7.09 (m, 4H), 6.86 (d, J = 8.4 Hz, 2H), 6.21-6.03 (m, 2H), 5.88 (q, J = 7.1 Hz, 1H), 4.09 (d, J = 5.9 Hz, 2H), 3.91 (p, J = 7.9, 6.8 Hz, 1H), 3.72 (s, 3H), 3.30-3.25 (m, 2H), 3.18 (p, J = 8.5 Hz, 1H), 2.55-2.46 (m, 3H), 2.46-2.28 (m, 1H), 2.29-1.96 (m, 3H), 1.90-1.62 (m, 3H), 1.49 (dd, J = 6.9, 3.9 Hz, 1H), 1.38 (d, J = 7.0 Hz, 2H). |
| 54 | 2-methyl-2-(o-tolyl) propan-1-amine | 2.2 | 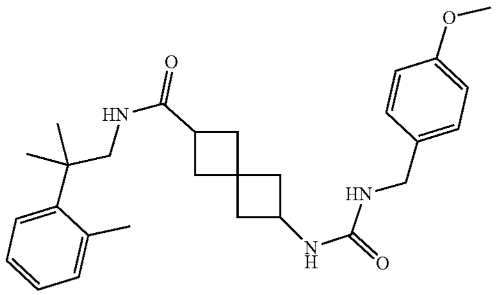 [SMILES: COc1ccc(CNC(=O)NC2CC3(C2)CC(C(=O)NCC(C)(C)c2ccccc2C)C3)cc1] |

-continued

| Compound No. | Amine | Intermediate | Structure, Name and Data |
|---|---|---|---|
| | | | 6-(3-(4-methoxybenzyl)ureido)-N-(2-methyl-2-(o-tolyl)propyl)spiro[3.3]heptane-2-carboxamide. LRMS (APCI) m/z 464 (M + H). $^1$H NMR (400 MHz, DMSO-$d_6$) δ 7.39 (ddq, J = 21.0, 13.8, 7.3, 6.8 Hz, 2H), 7.26-7.09 (m, 4H), 6.86 (d, J = 8.4 Hz, 2H), 6.21-6.03 (m, 2H), 5.88 (q, J = 7.1 Hz, 1H), 4.09 (d, J = 5.9 Hz, 2H), 3.91 (p, J = 7.9, 6.8 Hz, 1H), 3.72 (s, 3H), 3.18 (p, J = 8.5 Hz, 1H), 2.55-2.46 (m, 3H), 2.46-2.28 (m, 1H), 2.29-1.96 (m, 4H), 1.90-1.62 (m, 2H), 1.49 (dd, J = 6.9, 3.9 Hz, 1H), 1.38 (d, J = 7.0 Hz, 2H), 1.21 (d, J = 2.2 Hz, 6H). |
| 55 | 2-(2-fluorophenyl)-2-methylpropan-1-amine | 2.2 | 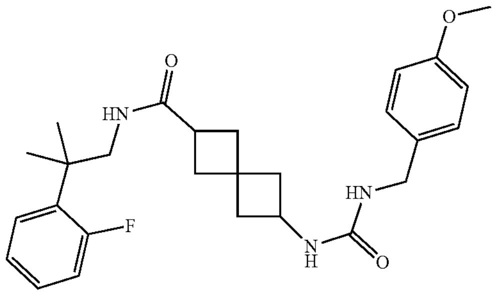 N-(2-(2-fluorophenyl)-2-methylpropyl)-6-(3-(4-methoxybenzyl)ureido)spiro[3.3]heptane-2-carboxamide. LRMS (APCI) m/z 468 (M + H). $^1$H NMR (400 MHz, DMSO-$d_6$) δ 7.45 (t, J = 6.3 Hz, 1H), 7.25 (dd, J = 7.0, 3.1 Hz, 1H), 7.20-7.03 (m, 5H), 6.86 (d, J = 8.5 Hz, 2H), 6.17-5.99 (m, 2H), 4.09 (d, J = 4.9 Hz, 2H), 3.88 (q, J = 7.6 Hz, 1H), 3.72 (s, 3H), 2.87 (p, J = 8.4 Hz, 1H), 2.37-2.24 (m, 3H), 2.11 (ddd, J = 12.0, 7.3, 5.2 Hz, 1H), 1.86 (t, J = 9.8 Hz, 1H), 1.80-1.72 (m, 4H), 1.66 (dd, J = 11.0, 8.8 Hz, 1H), 1.29 (d, J = 7.9 Hz, 6H). |
| 56 | pyridin-2-ylmethanamine | 2.2 | 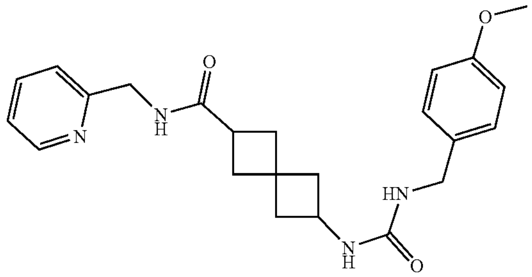 [SMILES: COc1ccc(CNC(=O)NC2CC3(C2)CC(C(=O)NCc2ccccn2)C3)cc1] 6-(3-(4-methoxybenzyl)ureido)-N-(pyridin-2-ylmethyl)spiro[3.3]heptane-2-carboxamide. LRMS (APCI) m/z 409 (M + H). $^1$H NMR (400 MHz, DMSO-$d_6$) δ 8.49 (d, J = 4.8 Hz, 1H), 8.27 (t, J = 6.0 Hz, 1H), 7.77 (t, J = 7.8 Hz, 1H), 7.34-7.21 (m, 2H), 7.19-7.04 (m, 2H), 6.87 (dd, J = 8.5, 1.9 Hz, 2H), 6.21-5.94 (m, 2H), 4.34 (d, J = 5.8 Hz, 2H), 4.10 (d, J = 5.6 Hz, 2H), 3.91 (dt, J = 15.0, 7.6 Hz, 1H), 3.72 (d, J = 1.7 Hz, 3H), 2.98 (p, J = 8.4 Hz, 1H), 2.36 (dt, J = 11.6, 6.2 Hz, 1H), 2.25-2.07 (m, 4H), 2.07-1.93 (m, 1H), 1.80 (t, J = 9.7 Hz, 1H), 1.71 (t, J = 9.9 Hz, 1H). |

-continued

| Compound No. | Amine | Intermediate | Structure, Name and Data |
| --- | --- | --- | --- |
| 57 | 3-phenyl-pyrrolidine | 2.2 | 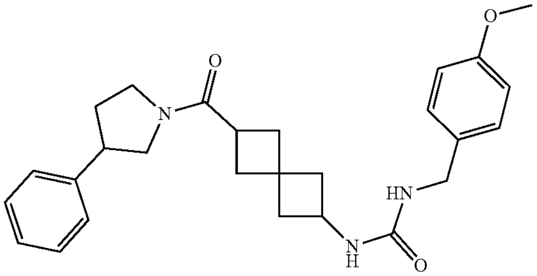 [SMILES: COc1ccc(CNC(=O)NC2CC3(C2)CC(C(=O)N2CCC(c4ccccc4)C2)C3)cc1] 1-(4-methoxybenzyl)-3-(6-(3-phenylpyrrolidine-1-carbonyl)spiro[3.3]heptan-2-yl)urea. LRMS (APCI) m/z 448 (M + H). $^{1}$H NMR (400 MHz, DMSO-$d_6$) δ 7.38-7.27 (m, 4H), 7.27-7.19 (m, 1H), 7.15 (dt, J = 8.7, 2.2 Hz, 2H), 6.86 (dt, J = 8.5, 2.3 Hz, 2H), 6.11 (p, J = 6.9, 6.4 Hz, 2H), 4.09 (d, J = 5.0 Hz, 2H), 3.92 (p, J = 7.8 Hz, 1H), 3.79 (t, J = 7.0 Hz, 1H), 3.72 (s, 3H), 3.55 (q, J = 8.7, 8.0 Hz, 1H), 3.33-3.29 (m, 2H), 3.28 (dt, J = 10.3, 5.1 Hz, 1H), 3.22-3.08 (m, 2H), 2.37 (dq, J = 11.1, 6.3, 5.8 Hz, 1H), 2.16 (dt, J = 19.7, 9.7 Hz, 4H), 1.96 (dq, J = 45.5, 10.6 Hz, 2H), 1.80 (q, J = 10.4 Hz, 1H), 1.70 (dt, J = 10.7, 7.8 Hz, 1H). |
| 58 | 4-(pyrrolidin-2-yl)pyridine | 2.2 | 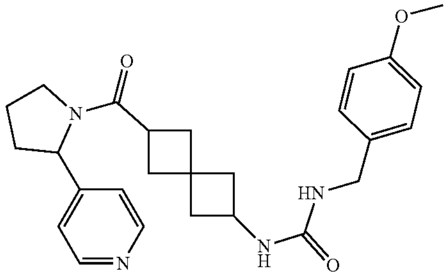 [SMILES: COc1ccc(CNC(=O)NC2CC3(C2)CC(C(=O)N2CCCC2c2ccncc2)C3)cc1] 1-(4-methoxybenzyl)-3-(6-(2-(pyridin-4-yl)pyrrolidine-1-carbonyl)spiro[3.3]heptan-2-yl)urea. LRMS (APCI) m/z 449 (M + H). $^{1}$H NMR (400 MHz, DMSO-$d_6$); ratio or rotamers 4:1. δ 8.52 (s, 3H), 7.20 (d, J = 4.9 Hz, 2H), 7.15 (d, J = 8.2 Hz, 6H), 6.94-6.67 (m, 4H), 6.11 (dd, J = 12.3, 6.9 Hz, 3H), 6.23 (t, J = 8.9 Hz, 1H), 6.01 (t, J = 8.9 Hz, 1H), 5.01 (d, J = 8.0 Hz, 1H), 4.98-4.85 (m, 1H), 4.08 (dd, J = 12.5, 5.8 Hz, 4H), 3.91 (tt, J = 18.1, 7.9 Hz, 2H), 3.72 (s, 6H), 3.68-3.56 (m, 2H), 3.50 (q, J = 9.0, 8.2 Hz, 1H), 3.24 (p, J = 8.8 Hz, 4H), 2.74 (hept, J = 8.2 Hz, 1H), 2.66 (p, J = 8.8 Hz, 2H), 2.61 (hept, J = 8.2 Hz, 1H), 2.45-2.37 (m, 4H), 2.36-2.26 (m, 1H), 2.22 (d, J = 20.0 Hz, 1H), 1.95-1.62 (m, 9H), 1.62-1.50 (m, 2H), 1.40-1.27 (m, 1H), 1.22 (t, J = 9.9 Hz, 1H). |
| 59 | (R)-3-(pyrrolidin-2-yl)pyridine | 2.2 | 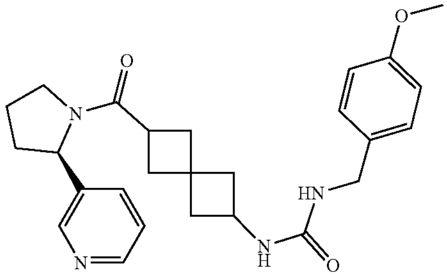 [SMILES: COc1ccc(CNC(=O)NC2CC3(C2)CC(C(=O)N2CCC[C@@H]2c2cccnc2)C3)cc1] (R)-1-(4-methoxybenzyl)-3-(6-(2-(pyridin-3-yl)pyrrolidine-1-carbonyl)spiro[3.3]heptan-2-yl)urea. LRMS (APCI) m/z 449 (M + H). $^{1}$H NMR (400 MHz, DMSO-$d_6$); ratio or rotamers 4:1. δ 8.60-8.25 (m, 3H), 7.58 (d, J = 8.0 Hz, 1H), 7.52 |

-continued

| Compound No. | Amine | Intermediate | Structure, Name and Data |
|---|---|---|---|
| | | | (d, J = 7.9 Hz, 1H), 7.38 (d, J = 6.5 Hz, 1H), 7.32 (dd, J = 8.1, 4.0 Hz, 1H), 7.14 (t, J = 8.8 Hz, 5H), 6.93-6.75 (m, 5H), 6.10 (dd, J = 12.6, 6.8 Hz, 2H), 6.00 (dd, J = 11.2, 8.2 Hz, 1H), 5.06 (d, J = 7.9 Hz, 1H), 5.00 (d, J = 8.0 Hz, 1H), 4.08 (dd, J = 11.8, 5.8 Hz, 4H), 3.99-3.80 (m, 4H), 3.72 (s, 6H), 3.63 (ddq, J = 13.8, 10.2, 4.6 Hz, 1H), 3.50 (q, J = 9.0 Hz, 1H), 3.30-3.29 (m, 5H), 3.23 (p, J = 9.0 Hz, 1H), 2.79 (q, J = 8.5 Hz, 1H), 2.38 (dd, J = 11.5, 6.2 Hz, 1H), 2.32-1.97 (m, 8H), 1.95-1.74 (m, 5H), 1.69 (q, J = 11.6, 8.7 Hz, 2H), 1.57 (t, J = 11.2 Hz, 1H), 1.31-1.19 (m, 1H), 1.19-1.04 (m, 1H). |
| 60 | (S)-1-(2-fluorophenyl)-N-methylethan-1-amine | 2.2 | 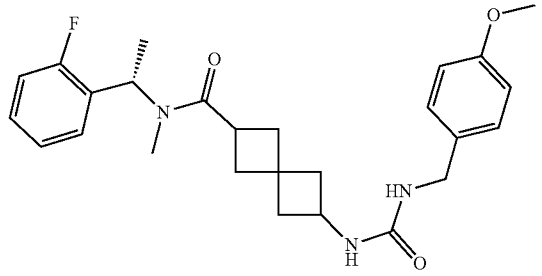 [SMILES: COc1ccc(CNC(=O)NC2CC3(C2)CC(C(=O)N(C)[C@@H](C)c2ccccc2F)C3)cc1] (S)-N-(1-(2-fluorophenyl)ethyl)-6-(3-(4-methoxybenzyl)ureido)-N-methylspiro[3.3]heptane-2-carboxamide. LRMS (APCI) m/z 454 (M + H). $^1$H NMR (400 MHz, DMSO-$d_6$); ratio of rotamers 2:1. δ 7.37 (tt, J = 13.8, 7.8 Hz, 4H), 7.15 (d, J = 8.1 Hz, 5H), 6.86 (d, J = 8.0 Hz, 5H), 6.19-5.96 (m, 4H), 5.88 (q, J = 7.2 Hz, 1H), 5.34-5.17 (m, 1H), 4.10 (d, J = 5.7 Hz, 3H), 3.92 (dd, J = 12.1, 6.3 Hz, 2H), 3.72 (s, 6H), 3.18 (p, J = 8.5 Hz, 2H), 2.50 (d, J = 7.9 Hz, 9H), 2.46-2.30 (m, 1H), 2.20 (d, J = 8.2 Hz, 1H), 2.14 (q, J = 10.5, 9.4 Hz, 1H), 2.06 (dd, J = 8.8, 5.1 Hz, 1H), 1.94 (d, J = 11.4 Hz, 1H), 1.81 (q, J = 9.7, 8.5 Hz, 4H), 1.70 (td, J = 10.2, 4.4 Hz, 4H), 1.49 (dd, J = 6.7, 3.9 Hz, 3H), 1.38 (d, J = 7.1 Hz, 6H). |
| 61 | 3-phenyl-azetidine | 2.2 | 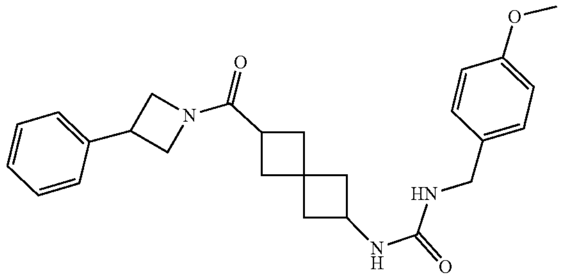 [SMILES: COc1ccc(CNC(=O)NC2CC3(C2)CC(C(=O)N2CC(c4ccccc4)C2)C3)cc1] 1-(4-methoxybenzyl)-3-(6-(3-phenylazetidine-1-carbonyl)spiro[3.3]heptan-2-yl)urea. LRMS (APCI) m/z 434 (M + H). $^1$H NMR (400 MHz, DMSO-$d_6$) δ 7.39 (d, J = 7.5 Hz, 4H), 7.31 (d, J = 7.0 Hz, 1H), 7.18 (d, J = 7.9 Hz, 2H), 6.90 (d, J = 8.0 Hz, 2H), 6.24-6.05 (m, 2H), 4.46 (dt, J = 8.3, 4.3 Hz, 1H), 4.33-4.21 (m, 1H), 4.13 (d, J = 5.5 Hz, 2H), 4.05 (dt, J = 9.9, 5.5 Hz, 1H), 3.95 (q, J = 8.0 Hz, 1H), 3.84 (q, J = 6.9 Hz, 2H), 3.76 (d, J = 1.6 Hz, 3H), 3.21 (d, J = 1.5 Hz, 1H), 3.03 (p, J = 8.5 Hz, 1H), 2.40 (dt, J = 11.7, 6.2 Hz, 1H), 2.29-2.08 (m, 3H), 2.03 (t, J = 10.2 Hz, 1H), 1.83 (t, J = 9.7 Hz, 1H), 1.74 (t, J = 10.0 Hz, 1H). |

-continued

| Compound No. | Amine | Intermediate | Structure, Name and Data |
|---|---|---|---|
| 62 | phenyl (piperazin)-1-yl)methanone | 2.2 | 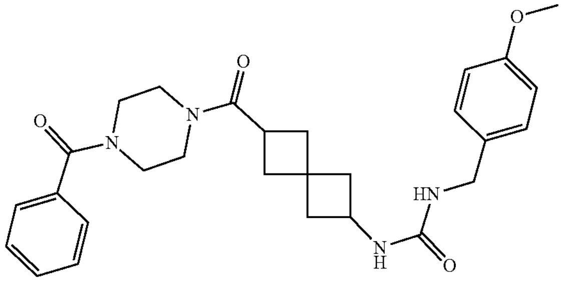 [SMILES: COc1ccc(CNC(=O)NC2CC3(C2)CC(C(=O)N2CCN(C(=O)c4ccccc4)CC2)C3)cc1] 1-(6-(4-benzoylpiperazine-1-carbonyl)spiro[3.3]heptan-2-yl)-3-(4-methoxybenzyl)urea. LRMS (APCI) m/z 491 (M + H). $^1$H NMR (400 MHz, DMSO-$d_6$) δ 7.56-7.43 (m, 3H), 7.41 (d, J = 5.3 Hz, 2H), 7.15 (d, J = 8.0 Hz, 2H), 6.86 (d, J = 7.8 Hz, 2H), 6.10 (q, J = 8.0, 7.0 Hz, 2H), 4.10 (t, J = 7.1 Hz, 6H), 3.91 (q, J = 8.1 Hz, 1H), 3.72 (s, 3H), 3.64-3.40 (m, 5H), 2.37 (s, 1H), 2.27-2.08 (m, 4H), 2.03 (s, 1H), 1.80 (t, J = 9.7 Hz, 1H), 1.70 (t, J = 9.9 Hz, 1H). |
| 63 | (1R,3R)-3-phenyl-cyclobutan-1-amine | 2.2 | 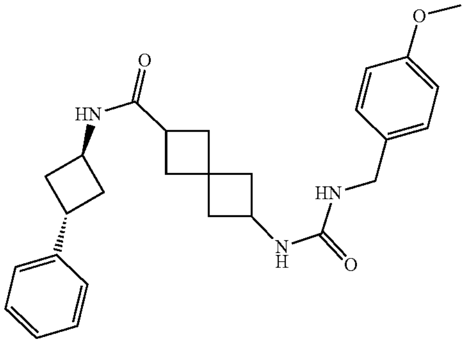 [SMILES: COc1ccc(CNC(=O)NC2CC3(C2)CC(C(=O)N[C@H]2C[C@H](c4ccccc4)C2)C3)cc1] 6-(3-(4-methoxybenzyl)ureido)-N-((1r,3r)-3-phenylcyclobutyl)spiro[3.3]heptane-2-carboxamide. LRMS (APCI) m/z 448 (M + H). $^1$H NMR (400 MHz, DMSO-$d_6$) δ 8.10 (d, J = 7.1 Hz, 1H), 7.30 (dt, J = 12.7, 7.6 Hz, 4H), 7.23-7.06 (m, 3H), 6.95-6.70 (m, 2H), 6.19-5.89 (m, 2H), 4.27 (q, J = 7.1 Hz, 1H), 4.10 (d, J = 5.8 Hz, 2H), 3.92 (h, J = 8.2 Hz, 1H), 3.72 (d, J = 1.5 Hz, 3H), 3.51 (p, J = 7.2 Hz, 1H), 2.86 (p, J = 8.3 Hz, 1H), 2.33 (t, J = 6.3 Hz, 4H), 2.12 (ddd, J = 15.2, 11.8, 7.4 Hz, 5H), 1.94 (td, J = 11.9, 6.2 Hz, 1H), 1.79 (t, J = 9.7 Hz, 1H), 1.70 (t, J = 10.0 Hz, 1H). |
| 64 | 2-(2-methoxy phenyl)-2-methylpropan-1-amine | 2.2 | 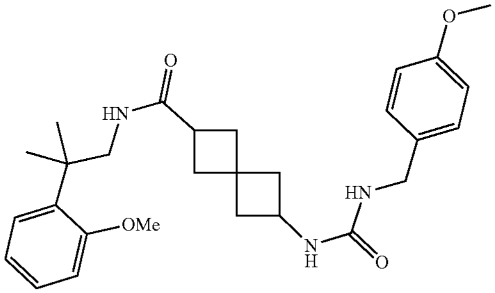 [SMILES: COc1ccc(CNC(=O)NC2CC3(C2)CC(C(=O)NCC(C)(C)c2ccccc2OC)C3)cc1] 6-(3-(4-methoxybenzyl)ureido)-N-(2-(2-methoxyphenyl)-2-methylpropyl)spiro[3.3]heptane-2-carboxamide. LRMS (APCI) m/z 480 (M + H). $^1$H NMR (400 MHz, DMSO-$d_6$) δ 7.27-7.05 (m, 5H), 6.97 (d, J = 8.3 Hz, 1H), 6.86 (d, J = 7.9 Hz, 3H), 6.11 (t, J = 6.2 Hz, 1H), 6.06 (d, J = 8.1 Hz, 1H), 4.09 (d, J = 5.6 Hz, 2H), 3.87 (p, J = 8.1 Hz, |

-continued

| Compound No. | Amine | Intermediate | Structure, Name and Data |
|---|---|---|---|
| | | | 1H), 3.79 (s, 3H), 3.72 (s, 3H), 3.45 (d, J = 6.2 Hz, 2H), 2.84 (p, J = 8.4 Hz, 1H), 2.29 (dt, J = 11.8, 6.1 Hz, 1H), 2.11 (dt, J = 12.1, 6.2 Hz, 1H), 2.06-1.92 (m, 3H), 1.84 (t, J = 9.5 Hz, 1H), 1.74 (t, J = 9.7 Hz, 1H), 1.65 (t, J = 9.9 Hz, 1H), 1.24 (s, 6H). |
| 65 | 2-methyl-2-(pyridin-2-yl)propan-1-amine | 2.2 | 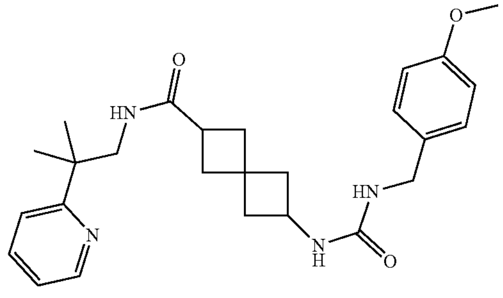 [SMILES: COc1ccc(CNC(=O)NC2CC3(C2)CC(C(=O)NCC(C)(C)c2ccccn2)C3)cc1] 6-(3-(4-methoxybenzyl)ureido)-N-(2-methyl-2-(pyridin-2-yl)propyl)spiro[3.3]heptane-2-carboxamide. LRMS (APCI) m/z 451 (M + H). $^{1}$H NMR (400 MHz, DMSO-$d_6$) δ 8.52 (d, J = 4.8 Hz, 1H), 7.72 (t, J = 7.8 Hz, 1H), 7.37 (d, J = 7.7 Hz, 2H), 7.20 (t, J = 6.2 Hz, 1H), 7.14 (d, J = 8.2 Hz, 2H), 6.86 (d, J = 7.9 Hz, 2H), 6.11 (t, J = 6.3 Hz, 1H), 6.07 (d, J = 8.1 Hz, 1H), 4.09 (d, J = 6.0 Hz, 3H), 3.89 (h, J = 8.2 Hz, 1H), 3.72 (s, 3H), 3.18 (d, J = 4.0 Hz, 1H), 2.88 (p, J = 8.4 Hz, 1H), 2.31 (dt, J = 11.7, 6.3 Hz, 1H), 2.12 (dt, J = 12.1, 6.3 Hz, 1H), 2.03 (dd, J = 15.4, 8.8 Hz, 3H), 1.87 (t, J = 9.8 Hz, 1H), 1.76 (t, J = 9.7 Hz, 1H), 1.67 (t, J = 9.9 Hz, 1H), 1.23 (s, 6H). |
| 66 | 2-methyl-2-(pyridin-3-yl)propan-1-amine | 2.2 | 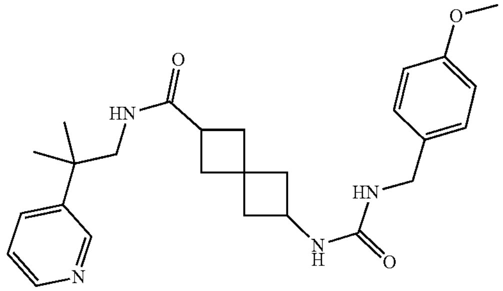 [SMILES: COc1ccc(CNC(=O)NC2CC3(C2)CC(C(=O)NCC(C)(C)c2cccnc2)C3)cc1] 6-(3-(4-methoxybenzyl)ureido)-N-(2-methyl-2-(pyridin-3-yl)propyl)spiro[3.3]heptane-2-carboxamide. LRMS (APCI) m/z 451 (M + H). $^{1}$H NMR (400 MHz, DMSO-$d_6$) δ 8.57 (s, 1H), 8.40 (d, J = 4.5 Hz, 1H), 7.74 (d, J = 8.2 Hz, 1H), 7.48 (t, J = 6.2 Hz, 1H), 7.37-7.26 (m, 1H), 7.14 (d, J = 8.0 Hz, 3H), 6.86 (d, J = 8.0 Hz, 2H), 6.10 (t, J = 6.0 Hz, 1H), 4.09 (d, J = 5.8 Hz, 2H), 3.88 (q, J = 8.0 Hz, 1H), 3.72 (s, 3H), 2.83 (q, J = 8.4 Hz, 1H), 2.36-2.20 (m, 2H), 2.10 (t, J = 8.8 Hz, 1H), 1.98 (dd, J = 19.8, 9.0 Hz, 4H), 1.84 (t, J = 9.8 Hz, 1H), 1.74 (t, J = 9.6 Hz, 1H), 1.65 (t, J = 10.0 Hz, 1H), 1.25 (s, 6H). |
| 69 | 2-phenylethan-1-amine | 2.2 | 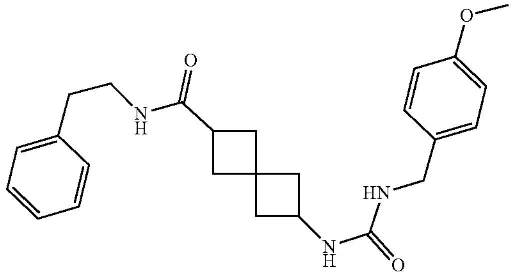 [SMILES: COc1ccc(CNC(=O)NC2CC3(C2)CC(C(=O)NCCc2ccccc2)C3)cc1] |

-continued

| Compound No. | Amine | Intermediate | Structure, Name and Data |
|---|---|---|---|
| | | | 6-(3-(4-methoxybenzyl)ureido)-N-phenethylspiro[3.3]heptane-2-carboxamide. LRMS (APCI) m/z 422 (M + H). $^1$H NMR (400 MHz, DMSO-$d_6$) δ 7.72 (t, J = 5.7 Hz, 1H), 7.27 (d, J = 7.5 Hz, 2H), 7.24-7.09 (m, 5H), 6.94-6.68 (m, 2H), 6.20-5.92 (m, 2H), 4.10 (d, J = 5.8 Hz, 2H), 3.91 (h, J = 8.1 Hz, 1H), 3.72 (d, J = 1.6 Hz, 3H), 3.24 (q, J = 6.9 Hz, 2H), 2.82 (p, J = 8.4 Hz, 1H), 2.68 (t, J = 7.5 Hz, 2H), 2.33 (dt, J = 11.5, 6.3 Hz, 1H), 2.11 (tt, J = 17.6, 8.0 Hz, 4H), 2.00-1.85 (m, 1H), 1.78 (t, J = 9.7 Hz, 1H), 1.69 (t, J = 9.9 Hz, 1H). |
| 70 | 2-phenylpropan-2-amine | 2.2 | 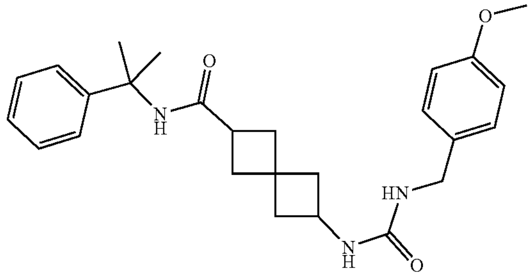 [SMILES: COc1ccc(CNC(=O)NC2CC3(C2)CC(C(=O)NC(C)(C)c2ccccc2)C3)cc1] 6-(3-(4-methoxybenzyl)ureido)-N-(2-phenylpropan-2-yl)spiro[3.3]heptane-2-carboxamide. LRMS (APCI) m/z 436 (M + H). $^1$H NMR (400 MHz, DMSO-$d_6$) δ 7.83 (s, 1H), 7.26 (d, J = 4.2 Hz, 4H), 7.19-7.07 (m, 3H), 6.86 (d, J = 8.0 Hz, 2H), 6.20-5.95 (m, 2H), 4.09 (d, J = 5.8 Hz, 2H), 3.90 (h, J = 8.3 Hz, 1H), 3.72 (d, J = 1.6 Hz, 3H), 2.98 (p, J = 8.4 Hz, 1H), 2.34 (dt, J = 11.6, 6.4 Hz, 1H), 2.18-1.99 (m, 4H), 1.91 (t, J = 9.7 Hz, 1H), 1.78 (t, J = 9.7 Hz, 1H), 1.66 (t, J = 9.9 Hz, 1H), 1.51 (s, 6H). |
| 71 | 1,2,3,4-tetrahydro-quinoline | 2.2 | 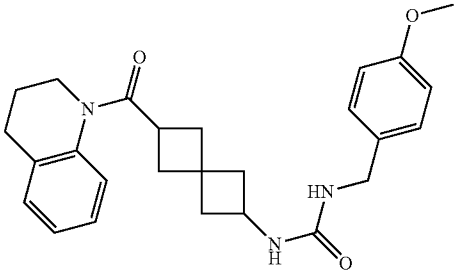 1-(4-methoxybenzyl)-3-(6-(1,2,3,4-tetrahydroquinoline-1-carbonyl)spiro[3.3]heptan-2-yl)urea. LRMS (APCI) m/z 434 (M + H). $^1$H NMR (400 MHz, DMSO-$d_6$) δ 7.34 (d, J = 9.1 Hz, 1H), 7.23-7.02 (m, 5H), 6.86 (d, J = 8.0 Hz, 2H), 6.25-5.94 (m, 2H), 4.09 (d, J = 5.7 Hz, 2H), 3.89 (q, J = 8.2 Hz, 1H), 3.72 (s, 3H), 3.60 (t, J = 6.4 Hz, 2H), 3.39 (s, 1H), 2.68 (t, J = 6.6 Hz, 2H), 2.31 (s, 1H), 2.15 (qd, J = 12.1, 8.1, 6.5 Hz, 3H), 2.02-1.44 (m, 6H). |
| 72 | 7-(trifluoromethyl)-1,2,3,4-tetrahydro-quinoline | 2.2 | 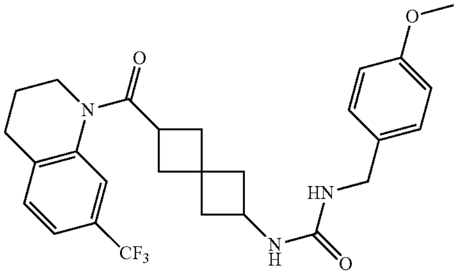 [SMILES: COc1ccc(CNC(=O)NC2CC3(C2)CC(C(=O)N2CCCc4ccc(C(F)(F)F)cc42)C3)cc1] |

-continued

| Compound No. | Amine | Intermediate | Structure, Name and Data |
|---|---|---|---|
| | | | 1-(4-methoxybenzyl)-3-(6-(7-(trifluoromethyl)-1,2,3,4-tetrahydroisoquinoline-2-carbonyl)spiro[3.3]heptan-2-yl)urea. LRMS (APCI) m/z 502 (M + H). $^1$H NMR (400 MHz, DMSO-$d_6$) δ 7.62 (d, J = 6.1 Hz, 1H), 7.51 (t, J = 6.7 Hz, 1H), 7.39 (d, J = 8.0 Hz, 1H), 7.15 (d, J = 8.0 Hz, 2H), 6.86 (d, J = 8.0 Hz, 2H), 6.23-6.02 (m, 2H), 4.67 (s, 1H), 4.62 (s, 1H), 4.10 (d, J = 5.8 Hz, 2H), 3.93 (q, J = 8.2 Hz, 1H), 3.67 (t, J = 6.0 Hz, 1H), 3.72 (s, 3H), 3.58 (t, J = 5.9 Hz, 1H), 3.33-3.25 (m, 1H), 2.89 (d, J = 5.9 Hz, 1H), 2.83 (d, J = 6.1 Hz, 1H), 2.42 (dt, J = 11.9, 6.3 Hz, 1H), 2.16 (dtt, J = 35.0, 12.7, 7.5 Hz, 5H), 1.83 (t, J = 9.7 Hz, 1H), 1.70 (t, J = 9.7 Hz, 1H). |
| 73 | isoindoline | 2.2 | 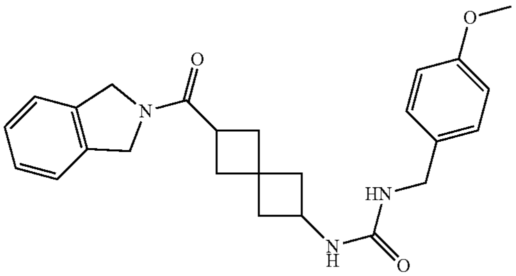 [SMILES: COc1ccc(CNC(=O)NC2CC3(C2)CC(C(=O)N2Cc4ccccc4C2)C3)cc1] 1-(6-(isoindoline-2-carbonyl)spiro[3.3]heptan-2-yl)-3-(4-methoxybenzyl)urea. LRMS (APCI) m/z 420 (M + H). $^1$H NMR (400 MHz, DMSO-$d_6$) δ 7.32 (dt, J = 14.8, 4.6 Hz, 4H), 7.16 (d, J = 8.0 Hz, 2H), 6.87 (d, J = 8.0 Hz, 2H), 6.13 (t, J = 8.3 Hz, 2H), 4.72 (s, 2H), 4.61 (s, 2H), 4.10 (d, J = 5.9 Hz, 2H), 3.95 (h, J = 8.0 Hz, 1H), 3.72 (s, 3H), 3.24 (p, J = 8.7 Hz, 1H), 2.42 (dt, J = 11.7, 6.2 Hz, 1H), 2.35-1.99 (m, 5H), 1.85 (t, J = 9.7 Hz, 1H), 1.73 (t, J = 10.0 Hz, 1H). |
| 74 | indoline | 2.2 | 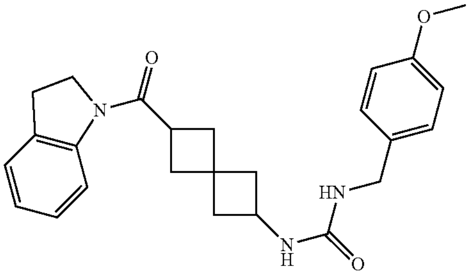 [SMILES: COc1ccc(CNC(=O)NC2CC3(C2)CC(C(=O)N2CCc4ccccc42)C3)cc1] 1-(6-(indoline-1-carbonyl)spiro[3.3]heptan-2-yl)-3-(4-methoxybenzyl)urea. LRMS (APCI) m/z 420 (M + H). $^1$H NMR (400 MHz, DMSO-$d_6$) δ 8.17 (d, J = 8.1 Hz, 1H), 7.32 (d, J = 7.5 Hz, 1H), 7.31-7.18 (m, 3H), 7.08 (t, J = 7.5 Hz, 1H), 7.02-6.75 (m, 2H), 6.22 (d, J = 8.7 Hz, 2H), 4.21 (d, J = 5.8 Hz, 2H), 4.06 (dt, J = 15.1, 8.2 Hz, 3H), 3.83 (d, J = 1.8 Hz, 3H), 3.39 (q, J = 8.7 Hz, 1H), 3.22 (t, J = 8.5 Hz, 2H), 2.52 (dt, J = 11.8, 6.3 Hz, 1H), 2.30 (ddd, J = 47.0, 22.5, 9.6 Hz, 5H), 1.95 (t, J = 9.7 Hz, 1H), 1.85 (t, J = 9.9 Hz, 1H). |

-continued

| Compound No. | Amine | Intermediate | Structure, Name and Data |
|---|---|---|---|
| 75 | 2-(1H-pyrazol-4-yl)ethan-1-amine | 2.2 | 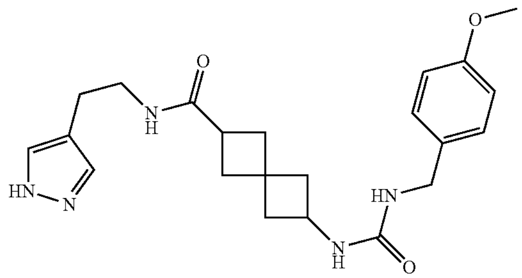 [SMILES: COc1ccc(CNC(=O)NC2CC3(C2)CC(C(=O)NCCc2cn[nH]c2)C3)cc1] N-(2-(1H-pyrazol-4-yl)ethyl)-6-(3-(4-methoxybenzyl)ureido)spiro[3.3]heptane-2-carboxamide. LRMS (APCI) m/z 412 (M + H). $^{1}$H NMR (400 MHz, DMSO-$d_6$) δ 12.55 (s, 1H), 7.71 (t, J = 5.7 Hz, 1H), 7.40 (s, 2H), 7.15 (d, J = 8.0 Hz, 2H), 6.86 (d, J = 8.0 Hz, 2H), 6.29-5.86 (m, 2H), 4.09 (d, J = 5.7 Hz, 2H), 3.91 (q, J = 8.0 Hz, 1H), 3.72 (s, 3H), 3.28 (q, J = 6.8 Hz, 2H), 3.17 (q, J = 6.8 Hz, 2H), 2.84 (p, J = 8.5 Hz, 1H), 2.33 (dt, J = 11.7, 6.1 Hz, 1H), 2.24-2.02 (m, 4H), 1.92 (dt, J = 11.1, 5.5 Hz, 1H), 1.78 (t, J = 9.7 Hz, 1H), 1.69 (t, J = 10.0 Hz, 1H). |
| 76 | 2-methyl-1-(piperazin-1-yl)propan-2-ol | 2.2 | 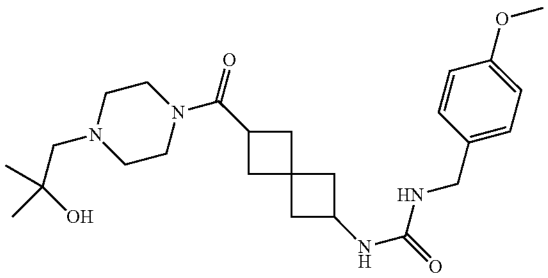 [SMILES: COc1ccc(CNC(=O)NC2CC3(C2)CC(C(=O)N2CCN(CC(C)(C)O)CC2)C3)cc1] 1-(6-(4-(2-hydroxy-2-methylpropyl)piperazine-1-carbonyl)spiro[3.3]heptan-2-yl)-3-(4-methoxybenzyl)urea. LRMS (APCI) m/z 459 (M + H). $^{1}$H NMR (400 MHz, DMSO-$d_6$) δ 7.15 (d, J = 7.9 Hz, 2H), 6.86 (d, J = 7.9 Hz, 2H), 6.19-5.98 (m, 2H), 4.15 (s, 1H), 4.09 (d, J = 5.9 Hz, 2H), 3.90 (h, J = 8.2 Hz, 1H), 3.72 (s, 3H), 3.28 (d, J = 4.9 Hz, 2H), 3.32-3.28 (m, 2H), 3.16 (p, J = 8.9 Hz, 1H), 2.40 (dp, J = 26.3, 6.2, 5.3 Hz, 5H), 2.24-2.06 (m, 6H), 2.00 (t, J = 10.2 Hz, 1H), 1.79 (t, J = 9.7 Hz, 1H), 1.68 (t, J = 9.9 Hz, 1H), 1.09 (s, 6H). |
| 77 | 4-(amino methyl)-3-fluorobenzo-nitrile | 2.2 | 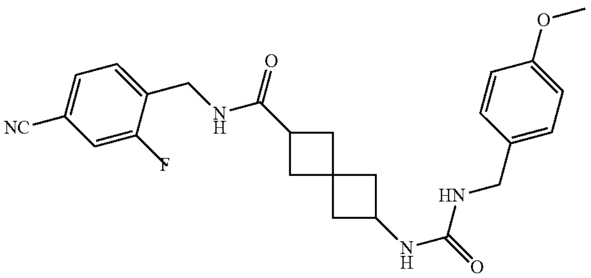 N-(4-cyano-2-fluorobenzyl)-6-(3-(4-methoxybenzyl)ureido)spiro[3.3]heptane-2-carboxamide. LRMS (APCI) m/z 451 (M + H). $^{1}$H NMR (400 MHz, DMSO-$d_6$) δ 8.30 (t, J = 6.0 Hz, 1H), 7.82 (d, J = 9.8 Hz, 1H), 7.68 (d, J = 7.9 Hz, 1H), 7.42 (t, J = 7.7 Hz, 1H), 7.15 (d, J = 7.9 Hz, 2H), 6.93-6.69 (m, 2H), 6.23-5.91 (m, 2H), 4.33 (d, J = 5.7 Hz, 2H), 4.09 (d, J = 5.8 Hz, 2H), 3.92 (h, J = 8.2 Hz, 1H), 3.72 (d, J = 1.6 Hz, 3H), 2.95 (p, J = 8.4 Hz, 1H), 2.35 (dt, J = 11.6 Hz, 6.4 Hz, |

-continued

| Compound No. | Amine | Intermediate | Structure, Name and Data |
|---|---|---|---|
| | | | 1H), 2.13 (dd, J = 19.9, 9.4 Hz, 4H), 1.98 (t, J = 9.9 Hz, 1H), 1.79 (t, J = 9.7 Hz, 1H), 1.70 (t, J = 10.0 Hz, 1H). |
| 78 | 3-(pyridin-4-yl)cyclobutan-1-amine | 2.2 | 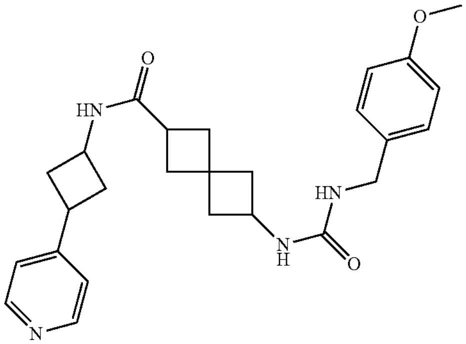 [SMILES: COc1ccc(CNC(=O)NC2CC3(C2)CC(C(=O)NC2CC(c4ccncc4)C2)C3)cc1] 6-(3-(4-methoxybenzyl)ureido)-N-(3-(pyridin-4-yl)cyclobutyl)spiro[3.3]heptane-2-carboxamide. LRMS (APCI) m/z 449 (M + H). $^1$H NMR (400 MHz, DMSO-$d_6$); 1.1 ratio of diastereomers. δ 8.48 (t, J = 4.4 Hz, 4H), 8.12 (d, J = 7.1 Hz, 1H), 7.95 (d, J = 8.0 Hz, 1H), 7.30 (d, J = 4.9 Hz, 1H), 7.26 (d, J = 5.0 Hz, 3H), 7.15 (d, J = 7.9 Hz, 4H), 6.86 (d, J = 7.9 Hz, 4H), 6.21-5.98 (m, 4H), 4.24 (dq, J = 16.8, 8.3, 7.9 Hz, 2H), 4.09 (d, J = 5.8 Hz, 3H), 3.91 (h, J = 8.1 Hz, 2H), 3.72 (d, J = 1.5 Hz, 6H), 3.14 (p, J = 9.3, 8.5 Hz, 2H), 2.82 (dp, J = 25.2, 8.5 Hz, 2H), 2.59 (q, J = 8.7 Hz, 2H), 2.42-2.25 (m, 6H), 2.11 (tt, J = 14.5, 7.2 Hz, 8H), 1.96 (dq, J = 19.9, 10.1 Hz, 4H), 1.79 (t, J = 9.7 Hz, 2H), 1.69 (t, J = 10.0 Hz, 3H). |
| 79 | (R)-N-methyltetra-hydro furan-3-amine | 2.2 | 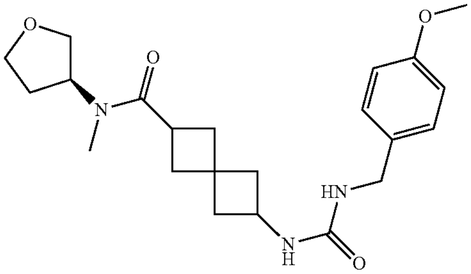 [SMILES: COc1ccc(CNC(=O)NC2CC3(C2)CC(C(=O)N(C)[C@H]2CCOC2)C3)cc1] (R)-6-(3-(4-methoxybenzyl)ureido)-N-methyl-N-(tetrahydrofuran-3-yl)spiro[3.3]heptane-2-carboxamide. LRMS (APCI) m/z 402 (M + H). $^1$H NMR (400 MHz, DMSO-$d_6$) δ 7.23-7.04 (m, 2H), 6.93-6.77 (m, 2H), 6.19-5.96 (m, 1H), 5.14-4.97 (m, 1H), 4.45 (dq, J = 12.2, 5.9 Hz, 1H), 4.09 (d, J = 5.8 Hz, 2H), 3.90 (p, J = 8.1 Hz, 1H), 3.72 (d, J = 1.5 Hz, 3H), 3.59 (s, 3H), 3.27 (q, J = 8.7 Hz, 2H), 3.16 (p, J = 8.6 Hz, 1H), 2.75 (s, 2H), 2.68 (s, 2H), 2.38 (dq, J = 12.6, 6.9 Hz, 1H), 2.13 (ddt, J = 37.2, 25.3, 11.7 Hz, 5H), 1.88-1.51 (m, 2H). |
| 80 | 8-methyl-2-(pyridin-4-yl)propan-1-amine | 2.2 | 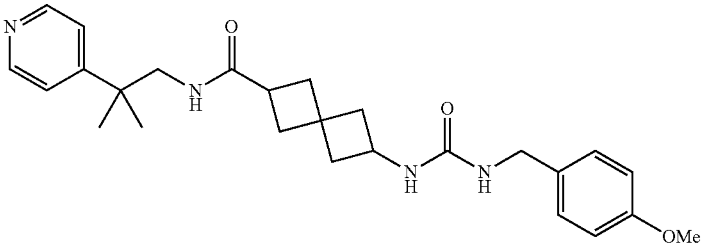 [SMILES: COc1ccc(CNC(=O)NC2CC3(C2)CC(C(=O)NCC(C)(C)c2ccncc2)C3)cc1] |

-continued

| Compound No. | Amine | Intermediate | Structure, Name and Data |
|---|---|---|---|
| | | | 6-(3-(4-methoxybenzyl)ureido)-N-(2-methyl-2-(pyridin-4-yl)propyl)spiro[3.3]heptane-2-carboxamide. LRMS (APCI) m/z 451 (M + H). $^1$H NMR (400 MHz, DMSO-$d_6$) δ 8.46 (d, J = 4.9 Hz, 2H), 7.46 (t, J = 6.4 Hz, 1H), 7.32 (d, J = 4.9 Hz, 2H), 7.14 (d, J = 8.0 Hz, 2H), 6.86 (dd, J = 8.4, 1.7 Hz, 2H), 6.21-5.96 (m, 2H), 4.09 (d, J = 5.8 Hz, 2H), 3.88 (h, J = 7.9 Hz, 1H), 3.72 (d, J = 1.5 Hz, 3H), 3.26 (d, J = 6.1 Hz, 2H), 2.85 (p, J = 8.4 Hz, 1H), 2.30 (dt, J = 11.6, 6.5 Hz, 1H), 2.10 (dt, J = 12.0, 6.3 Hz, 1H), 1.99 (dd, J = 20.8, 9.1 Hz, 3H), 1.85 (t, J = 9.8 Hz, 1H), 1.75 (t, J = 9.7 Hz, 1H), 1.65 (t, J = 10.0 Hz, 1H), 1.21 (s, 6H). |
| 84 | 6-methyl-1,2,3,4-tetrahydro-quinoline | 2.2 | 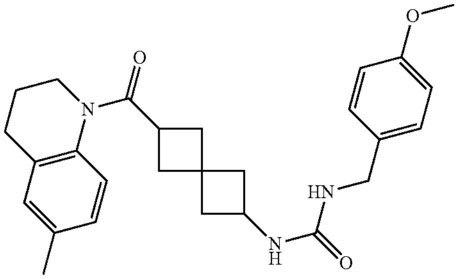 [SMILES: COc1ccc(CNC(=O)NC2CC3(C2)CC(C(=O)N2CCCc4cc(C)ccc42)C3)cc1] 1-(4-methoxybenzyl)-3-(6-(6-methyl-1,2,3,4-tetrahydroquinoline-1-carbonyl)spiro[3.3]heptan-2-yl)urea. LRMS (APCI) m/z 448 (M + H). $^1$H NMR (400 MHz, DMSO-$d_6$) δ 8.05-7.25 (m, 1H), 7.14 (d, J = 8.3 Hz, 2H), 7.10-6.68 (m, 4H), 6.20-5.95 (m, 2H), 4.08 (d, J = 5.8 Hz, 2H), 3.89 (q, J = 8.0 Hz, 1H), 3.72 (s, 3H), 3.57 (t, J = 6.3 Hz, 2H), 3.38-3.20 (m, 3H), 2.63 (s, 3H), 2.38-1.99 (m, 6H), 1.90-1.54 (m, 4H). |
| 85 | 3,4-dihydro-2H-benzo[b][1,4]oxazine | 2.2 | 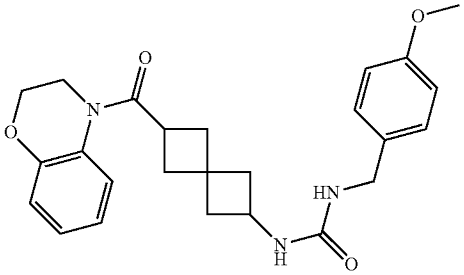 [SMILES: COc1ccc(CNC(=O)NC2CC3(C2)CC(C(=O)N2CCOc4ccccc42)C3)cc1] 1-(6-(3,4-dihydro-2H-benzo[b][1,4]oxazine-4-carbonyl)spiro[3.3]heptan-2-yl)-3-(4-methoxybenzyl)urea. LRMS (APCI) m/z 436 (M + H). $^1$H NMR (400 MHz, DMSO-$d_6$) δ 8.32-7.70 (m, 1H), 7.15 (d, J = 8.2 Hz, 2H), 7.02 (t, J = 7.0 Hz, 1H), 6.87 (d, J = 8.2 Hz, 4H), 6.11 (q, J = 8.3, 7.2 Hz, 2H), 4.22 (t, J = 4.5 Hz, 2H), 4.09 (d, J = 4.8 Hz, 2H), 3.92 (q, J = 6.8, 5.7 Hz, 1H), 3.72 (s, 5H), 3.31 (s, 2H), 2.37 (s, 1H), 2.31-2.11 (m, 3H), 2.07 (s, 1H), 1.81 (t, J = 9.7 Hz, 1H), 1.73 (dd, J = 11.0, 8.8 Hz, 1H). |
| 86 | aniline | 2.2 | 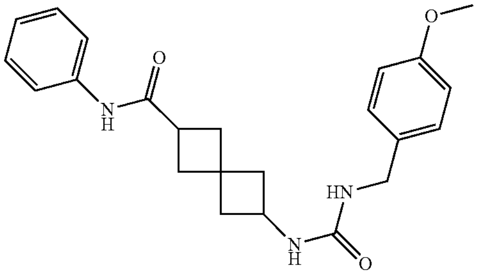 [SMILES: COc1ccc(CNC(=O)NC2CC3(C2)CC(C(=O)Nc2ccccc2)C3)cc1] |

-continued

| Compound No. | Amine | Intermediate | Structure, Name and Data |
|---|---|---|---|
| | | | 6-(3-(4-methoxybenzyl)ureido)-N-phenylspiro[3.3]heptane-2-carboxamide. LRMS (APCI) m/z 394 (M + H). $^1$H NMR (400 MHz, DMSO-$d_6$) δ 9.74 (s, 1H), 7.58 (d, J = 8.1 Hz, 2H), 7.27 (t, J = 7.7 Hz, 2H), 7.15 (d, J = 8.3 Hz, 2H), 7.01 (t, J = 7.4 Hz, 1H), 6.87 (d, J = 8.4 Hz, 2H), 6.27-5.95 (m, 2H), 4.10 (d, J = 5.9 Hz, 2H), 3.94 (h, J = 8.2 Hz, 1H), 3.73 (s, 3H), 3.09 (p, J = 8.4 Hz, 1H), 2.46-2.32 (m, 1H), 2.30-2.09 (m, 4H), 2.02 (ddd, J = 11.5, 8.2, 3.2 Hz, 1H), 1.83 (dd, J = 10.6, 8.7 Hz, 1H), 1.74 (dd, J = 11.1, 8.8 Hz, 1H). |
| 87 | N-Methylaniline | 2.2 | 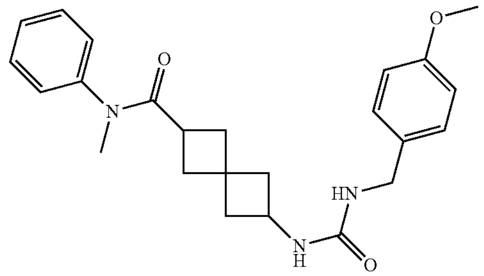 [SMILES: COc1ccc(CNC(=O)NC2CC3(C2)CC(C(=O)N(C)c2ccccc2)C3)cc1] 6-(3-(4-methoxybenzyl)ureido)-N-methyl-N-phenylspiro[3.3]heptane-2-carboxamide. LRMS (APCI) m/z 408 (M + H). $^1$H NMR (400 MHz, DMSO-$d_6$) δ 7.44 (t, J = 7.5 Hz, 2H), 7.36 (t, J = 7.4 Hz, 1H), 7.24 (d, J = 7.7 Hz, 2H), 7.13 (d, J = 8.3 Hz, 2H), 6.85 (d, J = 8.2 Hz, 2H), 6.09 (t, J = 6.0 Hz, 1H), 6.02 (d, J = 8.1 Hz, 1H), 4.07 (d, J = 5.8 Hz, 2H), 3.82 (q, J = 8.1 Hz, 1H), 3.71 (s, 3H), 3.13 (s, 3H), 2.84 (p, J = 8.7 Hz, 1H), 2.30-2.00 (m, 4H), 1.78 (d, J = 10.2 Hz, 1H), 1.63 (q, J = 10.5 Hz, 3H). |
| 88 | (2-difluoro methyl) pyridin-4-yl)methanamine | 2.2 | 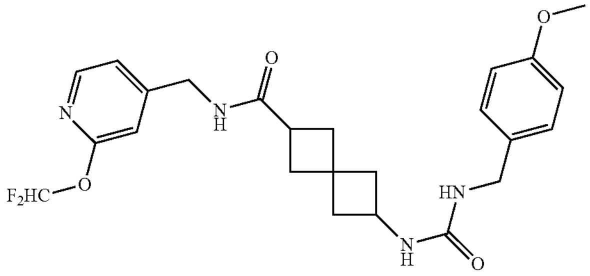 [SMILES: COc1ccc(CNC(=O)NC2CC3(C2)CC(C(=O)NCc2ccnc(OC(F)F)c2)C3)cc1] N-((2-(difluoromethoxy)pyridin-4-yl)methyl)-6-(3-(4-methoxybenzyl)ureido)spiro[3.3]heptane-2-carboxamide. LRMS (APCI); m/z 475 (M + H). $^1$H NMR (400 MHz, DMSO-$d_6$) δ 8.30 (t, J = 6.0 Hz, 1H), 8.18 (d, J = 5.2 Hz, 1H), 7.70 (t, J = 73.0 Hz, 1H), 7.15 (d, J = 8.3 Hz, 2H), 7.10 (d, J = 5.2 Hz, 1H), 6.87 (d, J = 8.6 Hz, 3H), 6.19-5.98 (m, 2H), 4.29 (d, J = 5.9 Hz, 2H), 4.10 (d, J = 5.9 Hz, 2H), 3.92 (h, J = 8.1 Hz, 1H), 3.72 (s, 3H), 2.97 (p, J = 8.4 Hz, 1H), 2.43-2.27 (m, 1H), 2.14 (dd, J = 22.1, 8.8 Hz, 4H), 2.00 (t, J = 9.8 Hz, 1H), 1.80 (dd, J = 10.7, 8.7 Hz, 1H), 1.71 (dd, J = 11.1, 8.8 Hz, 1H). |

-continued

| Compound No. | Amine | Intermediate | Structure, Name and Data |
|---|---|---|---|
| 89 | [1,2,4] triazolo[4,3-a]pyridin-6-amine | 2.2 | 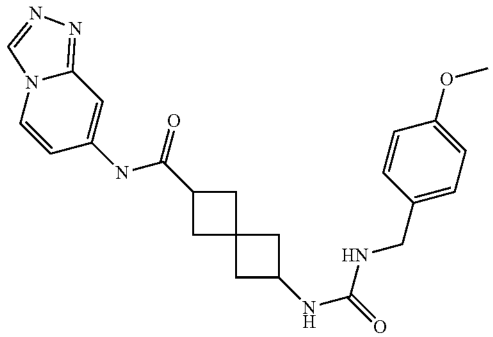 [SMILES: COc1ccc(CNC(=O)NC2CC3(C2)CC(C(=O)Nc2ccn4cnnc4c2)C3)cc1] N-([1,2,4]triazolo[4,3-a]pyridin-6-yl)-6-(3-(4-methoxybenzyl)ureido)spiro[3.3]heptane-2-carboxamide. LRMS (APCI) m/z 435 (M + H). $^1$H NMR (400 MHz, DMSO-$d_6$) δ 10.06 (s, 1H), 9.30 (d, J = 11.5 Hz, 2H), 7.76 (d, J = 9.7 Hz, 1H), 7.28 (dd, J = 9.8, 1.7 Hz, 1H), 7.15 (d, J = 8.4 Hz, 2H), 6.87 (d, J = 8.3 Hz, 2H), 6.22-6.01 (m, 2H), 4.10 (d, J = 5.7 Hz, 2H), 3.95 (h, J = 8.3 Hz, 1H), 3.72 (s, 3H), 3.14 (p, J = 8.0 Hz, 1H), 2.39 (ddd, J = 11.4, 7.3, 5.2 Hz, 1H), 2.33-2.14 (m, 4H), 2.08 (dd, J = 11.3, 8.4 Hz, 1H), 1.84 (dd, J = 10.7, 8.7 Hz, 1H), 1.76 (dd, J = 11.1, 8.8 Hz, 1H). |
| 90 | 1,2,3,4-tetrahydro-1,6-naphthyridine | 2.2 | 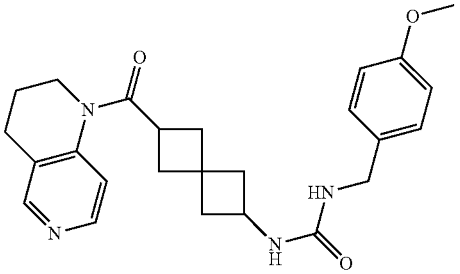 1-(4-methoxybenzyl)-3-(6-(1,2,3,4-tetrahydro-1,6-naphthyridine-1-carbonyl)spiro[3.3]heptan-2-yl)urea. LRMS (APCI) m/z 435 (M + H). $^1$H NMR (400 MHz, DMSO-$d_6$) δ 8.22 (d, J = 4.5 Hz, 1H), 8.16-7.74 (m, 1H), 7.19 (dd, J = 8.3, 4.8 Hz, 1H), 7.15 (d, J = 8.2 Hz, 2H), 6.86 (d, J = 8.3 Hz, 2H), 6.17-6.03 (m, 2H), 4.09 (d, J = 5.9 Hz, 2H), 3.91 (q, J = 8.1 Hz, 1H), 3.72 (s, 3H), 3.68-3.58 (m, 2H), 3.35-3.30 (m, 2H), 2.87 (t, J = 6.7 Hz, 2H), 2.35 (d, J = 14.5 Hz, 1H), 2.29-2.10 (m, 3H), 2.05 (s, 1H), 1.92 (p, J = 6.6 Hz, 2H), 1.80 (t, J = 9.8 Hz, 1H), 1.72 (t, J = 9.9 Hz, 1H). |
| 91 | (R)-2,3-dihydro-1H-inden-1-amine | 2.2 | 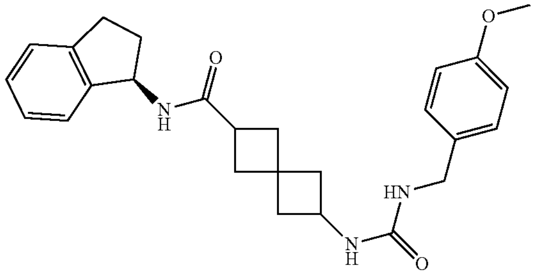 [SMILES: COc1ccc(CNC(=O)NC2CC3(C2)CC(C(=O)N[C@@H]2CCc4ccccc42)C3)cc1] (R)-N-(2,3-dihydro-1H-inden-1-yl)-6-(3-(4-methoxybenzyl)ureido)spiro[3.3]heptane-2-carboxamide. LRMS (APCI) m/z 434 (M + H). $^1$H NMR (400 MHz, DMSO-$d_6$) δ 8.01 (d, J = 8.2 Hz, 1H), 7.27-7.08 (m, 5H), 6.87 (dd, J = 8.5, 3.0 Hz, 2H), 6.15-6.05 (m, 2H), 5.26 (q, J = 8.6 Hz, 1H), 4.10 (t, J = 4.0 Hz, 2H), 3.93 (q, J = 8.2 Hz, 1H), |

-continued

| Compound No. | Amine | Intermediate | Structure, Name and Data |
|---|---|---|---|
| | | | 3.73 (d, J = 3.1 Hz, 3H), 2.96-2.71 (m, 3H), 2.40-2.29 (m, 1H), 2.34 (s, 2H), 2.16 (tt, J = 13.5, 10.1, 8.8 Hz, 4H), 2.03-1.89 (m, 1H), 1.76 (dt, J = 29.6, 10.0 Hz, 3H). |
| 92 | (S)-2,3-dihydro-1H-inden-1-amine | 2.2 | 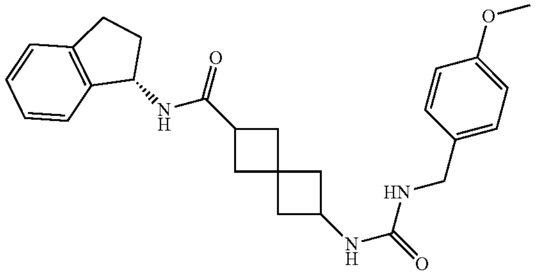 [SMILES: COc1ccc(CNC(=O)NC2CC3(C2)CC(C(=O)N[C@H]2CCc4ccccc42)C3)cc1] (S)-N-(2,3-dihydro-1H-inden-1-yl)-6-(3-(4-methoxybenzyl)ureido)spiro[3.3]heptane-2-carboxamide. LRMS (APCI) m/z 434 (M + H). $^1$H NMR (400 MHz, DMSO-$d_6$) δ 8.00 (d, J = 8.2 Hz, 1H), 7.27-7.12 (m, 6H), 6.87 (dd, J = 8.7, 2.4 Hz, 2H), 6.16-6.04 (m, 2H), 5.25 (d, J = 8.4 Hz, 1H), 4.10 (s, 2H), 3.96-3.87 (m, 1H), 3.73 (d, J = 3.0 Hz, 3H), 2.96-2.86 (m, 2H), 2.78 (dt, J = 16.3, 7.7 Hz, 1H), 2.35 (d, J = 10.0 Hz, 2H), 2.19 (p, J = 10.0 Hz, 4H), 1.98 (s, 1H), 1.76 (dt, J = 29.8, 10.1 Hz, 3H). |
| 93 | (3-amino-2,3-dihydro-1H-inden-1-yl)methanol | 2.2 | 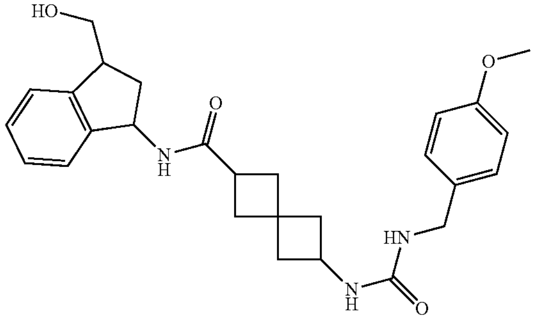 [SMILES: COc1ccc(CNC(=O)NC2CC3(C2)CC(C(=O)NC2CC(CO)c4ccccc42)C3)cc1] N-(3-(hydroxymethyl)-2,3-dihydro-1H-inden-1-yl)-6-(3-(4-methoxybenzyl)ureido)spiro[3.3]heptane-2-carboxamide. LRMS (APCI) m/z 464 (M + H). $^1$H NMR (400 MHz, DMSO-$d_6$) δ 7.98 (d, J = 8.2 Hz, 1H), 7.34 (d, J = 5.6 Hz, 1H), 7.26-7.01 (m, 5H), 6.93-6.81 (m, 2H), 6.12 (dd, J = 13.5, 6.3 Hz, 2H), 5.22 (q, J = 9.1 Hz, 1H), 4.79 (d, J = 4.4 Hz, 1H), 4.10 (t, J = 4.1 Hz, 2H), 3.93 (q, J = 8.8 Hz, 1H), 3.81-3.68 (m, 4H), 3.57 (q, J = 5.4 Hz, 1H), 3.14 (t, J = 7.4 Hz, 1H), 3.02-2.84 (m, 1H), 2.47 (d, J = 11.6 Hz, 1H), 2.35 (q, J = 8.1, 6.8 Hz, 1H), 2.17 (dt, J = 22.2, 9.9 Hz, 4H), 2.06-1.89 (m, 1H), 1.76 (dt, J = 29.4, 9.9 Hz, 2H), 1.53 (q, J = 10.4 Hz, 1H). |
| 94 | 3-amino-2,3-dihydro-1H-inden-1-ol | 2.2 | 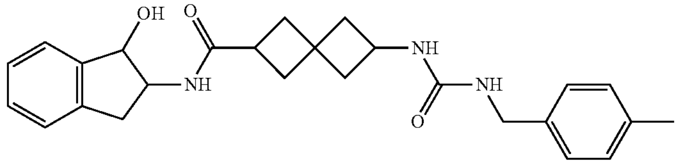 N-(1-hydroxy-2,3-dihydro-1H-inden-2-yl)-6-(3-(4-methoxybenzyl)ureido)spiro[3.3]heptane-2-carboxamide. LRMS (APCI) m/z 450 (M + H). $^1$H NMR (400 MHz, DMSO-$d_6$) δ 8.03 (d, J = 7.2 Hz, 1H), 7.28 (t, J = 4.2 Hz, 1H), 7.18 (ddt, J = 19.6, 8.6, 3.1 Hz, 5H), 6.92-6.72 (m, 2H), 6.18- |

-continued

| Compound No. | Amine | Intermediate | Structure, Name and Data |
|---|---|---|---|
| | | | 5.99 (m, 2H), 5.51 (s, 1H), 4.92-4.80 (m, 1H), 4.10 (d, J = 6.1 Hz, 3H), 3.93 (q, J = 8.0 Hz, 1H), 3.72 (s, 3H), 3.13 (dd, J = 15.8, 8.0 Hz, 1H), 2.90 (qd, J = 9.6, 4.8 Hz, 1H), 2.64-2.53 (m, 1H), 2.41-2.31 (m, 1H), 2.25-2.09 (m, 4H), 1.95 (ddd, J = 11.6, 7.8, 3.5 Hz, 1H), 1.80 (t, J = 9.8 Hz, 1H), 1.70 (dt, J = 29.4, 9.9 Hz, 1H). |
| 95 | 2,3-dihydro-1H-inden-2-amine | 2.2 | 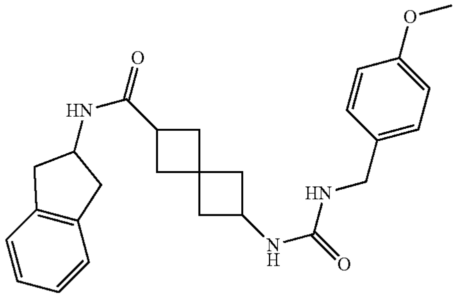 [SMILES: COc1ccc(CNC(=O)NC2CC3(C2)CC(C(=O)NC2Cc4ccccc4C2)C3)cc1] N-(2,3-dihydro-1H-inden-2-yl)-6-(3-(4-methoxybenzyl)ureido)spiro[3.3]heptane-2-carboxamide. LRMS (APCI) m/z 434 (M + H). $^1$H NMR (400 MHz, DMSO-$d_6$) δ 8.04-7.84 (m, 1H), 7.20 (t, J = 4.0 Hz, 2H), 7.15 (q, J = 3.3 Hz, 4H), 6.87 (dd, J = 8.6, 2.7 Hz, 2H), 6.09 (dt, J = 10.3, 6.5 Hz, 2H), 4.42 (q, J = 7.4 Hz, 1H), 4.09 (t, J = 4.3 Hz, 2H), 3.91 (q, J = 8.0 Hz, 1H), 3.73 (d, J = 2.9 Hz, 3H), 3.14 (dd, J = 16.3, 7.5 Hz, 2H), 2.94-2.79 (m, 1H), 2.78-2.61 (m, 2H), 2.33 (q, J = 6.4, 5.7 Hz, 1H), 2.23-2.00 (m, 4H), 1.92 (d, J = 9.9 Hz, 1H), 1.79 (d, J = 9.7 Hz, 1H), 1.70 (t, J = 10.2 Hz, 1H). |
| 96 | (R)-1,2,3,4-tetrahydro-naphthalen-2-amine | 2.2 | 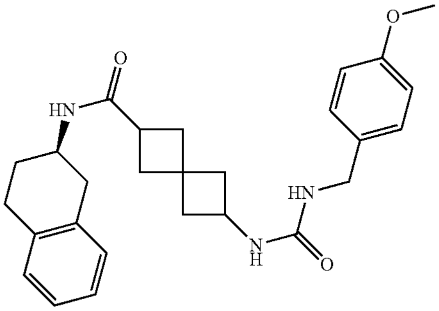 [SMILES: COc1ccc(CNC(=O)NC2CC3(C2)CC(C(=O)N[C@@H]2CCc4ccccc4C2)C3)cc1] (R)-6-(3-(4-methoxybenzyl)ureido)-N-(1,2,3,4-tetrahydronaphthalen-2-yl)spiro[3.3]heptane-2-carboxamide. LRMS (APCI) m/z 448 (M + H). $^1$H NMR (400 MHz, DMSO-$d_6$) δ 7.71 (dd, J = 7.8, 3.1 Hz, 1H), 7.24-7.12 (m, 2H), 7.08 (d, J = 3.7 Hz, 4H), 6.87 (dd, J = 8.5, 3.0 Hz, 2H), 6.23-5.95 (m, 2H), 4.10 (t, J = 4.2 Hz, 2H), 3.91 (t, J = 8.6 Hz, 2H), 3.73 (d, J = 3.3 Hz, 3H), 3.04-2.84 (m, 2H), 2.85-2.69 (m, 2H), 2.57 (dd, J = 16.8, 10.5 Hz, 1H), 2.34 (h, J = 4.2 Hz, 1H), 2.13 (p, J = 10.1, 9.6 Hz, 4H), 2.01-1.85 (m, 2H), 1.84-1.75 (m, 1H), 1.75-1.66 (m, 1H), 1.66-1.50 (m, 1H). |

-continued

| Compound No. | Amine | Intermediate | Structure, Name and Data |
|---|---|---|---|
| 97 | (S)-7-fluoro-1,2,3,4-tetrahydro-naphthalen-1-amine | 2.2 | 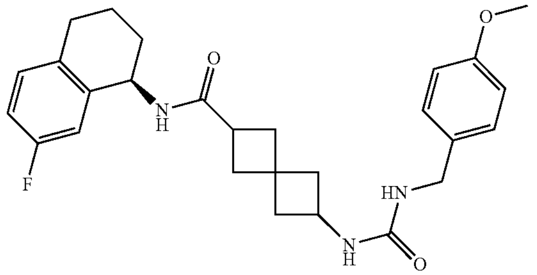 [SMILES: COc1ccc(CNC(=O)NC2CC3(C2)CC(C(=O)N[C@@H]2CCCc4ccc(F)cc42)C3)cc1] (S)-N-(7-fluoro-1,2,3,4-tetrahydronaphthalen-1-yl)-6-(3-(4-methoxybenzyl)ureido)spiro[3.3]heptane-2-carboxamide. LRMS (APCI) m/z 466 (M + H). $^1$H NMR (400 MHz, DMSO-$d_6$) δ 8.06 (d, J = 8.5 Hz, 1H), 7.15 (p, J = 3.3 Hz, 3H), 7.00 (d, J = 8.9 Hz, 1H), 6.92-6.71 (m, 3H), 6.21-5.97 (m, 2H), 4.93 (s, 1H), 4.10 (t, J = 4.5 Hz, 2H), 3.93 (q, J = 8.3 Hz, 1H), 3.72 (d, J = 2.1 Hz, 3H), 3.06-2.83 (m, 1H), 2.69 (s, 2H), 2.34 (s, 1H), 2.18 (p, J = 10.3, 9.9 Hz, 4H), 1.95 (t, J = 9.8 Hz, 1H), 1.90-1.78 (m, 4H), 1.71 (d, J = 9.7 Hz, 1H), 1.60 (q, J = 9.8 Hz, 1H). |
| 98 | (S)-6-fluoro-1,2,3,4-tetrahydro-naphthalen-1-amine | 2.2 | 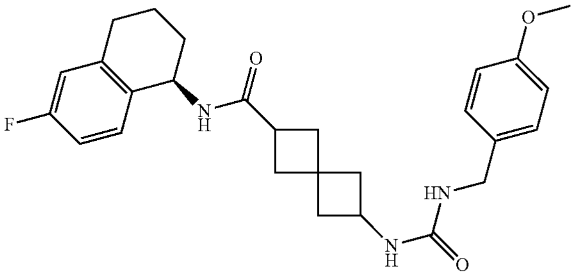 [SMILES: COc1ccc(CNC(=O)NC2CC3(C2)CC(C(=O)N[C@@H]2CCCc4cc(F)ccc42)C3)cc1] (S)-N-(6-fluoro-1,2,3,4-tetrahydronaphthalen-1-yl)-6-(3-(4-methoxybenzyl)ureido)spiro[3.3]heptane-2-carboxamide. LRMS (APCI) m/z 466 (M + H). $^1$H NMR (400 MHz, DMSO-$d_6$) δ 8.00 (dd, J = 8.5, 4.2 Hz, 1H), 7.27-7.04 (m, 3H), 6.94 (dd, J = 18.8, 7.6 Hz, 2H), 6.87 (dd, J = 8.2, 2.7 Hz, 2H), 6.10 (q, J = 8.9, 7.7 Hz, 2H), 4.92 (s, 1H), 4.10 (t, J = 4.2 Hz, 2H), 3.92 (q, J = 8.5 Hz, 1H), 3.73 (t, J = 2.2 Hz, 3H), 2.91 (t, J = 8.3 Hz, 1H), 2.82-2.63 (m, 2H), 2.32 (t, J = 7.7 Hz, 1H), 2.16 (dq, J = 19.8, 9.9, 9.5 Hz, 4H), 1.97 (t, J = 10.9 Hz, 1H), 1.89-1.53 (m, 6H). |
| 99 | (R)-7-fluoro-1,2,3,4-tetrahydro-naphthalen-1-amine | 2.2 | 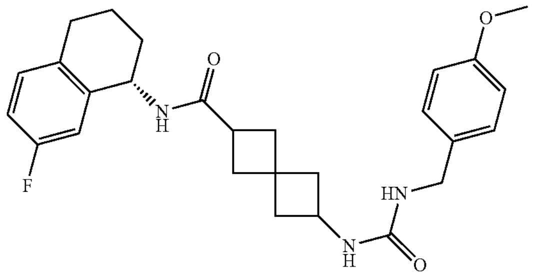 [SMILES: COc1ccc(CNC(=O)NC2CC3(C2)CC(C(=O)N[C@H]2CCCc4ccc(F)cc42)C3)cc1] (R)-N-(7-fluoro-1,2,3,4-tetrahydronaphthalen-1-yl)-6-(3-(4-methoxybenzyl)ureido)spiro[3.3]heptane-2-carboxamide. LRMS (APCI) m/z 466 (M + H). $^1$H NMR (400 MHz, DMSO-$d_6$) δ 8.06 (d, J = 8.5 Hz, 1H), 7.27-7.06 (m, 3H), 6.99 (s, 1H), 6.85 (t, J = 11.7 Hz, 3H), 6.08 (d, J = 11.3 Hz, 2H), 4.92 (d, J = 7.9 Hz, 1H), 4.10 (t, J = 4.2 Hz, 2H), 3.93 |

-continued

| Compound No. | Amine | Intermediate | Structure, Name and Data |
|---|---|---|---|
| | | | (d, J = 9.6 Hz, 1H), 3.73 (d, J = 3.3 Hz, 3H), 2.92 (dd, J = 13.3, 5.8 Hz, 1H), 2.69 (s, 2H), 2.34 (s, 1H), 2.17 (d, J = 10.9 Hz, 4H), 1.97 (d, J = 9.4 Hz, 1H), 1.91-1.51 (m, 6H). |
| 100 | (R)-1,2,3,4-tetrahydro-naphthalen-1-amine | 2.2 | 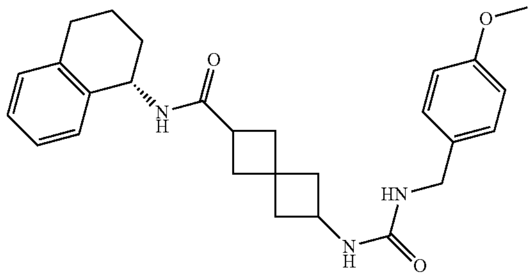 [SMILES: COc1ccc(CNC(=O)NC2CC3(C2)CC(C(=O)N[C@H]2CCCc4ccccc42)C3)cc1] (R)-6-(3-(4-methoxybenzyl)ureido)-N-(1,2,3,4-tetrahydronaphthalen-1-yl)spiro[3.3]heptane-2-carboxamide. LRMS (APCI) m/z 448 (M + H). $^1$H NMR (400 MHz, DMSO-$d_6$) δ 8.00 (dt, J = 8.2, 3.6 Hz, 1H), 7.22-7.01 (m, 6H), 6.87 (dd, J = 7.9, 3.2 Hz, 2H), 6.26-5.86 (m, 2H), 4.94 (d, J = 8.2 Hz, 1H), 4.10 (t, J = 4.3 Hz, 2H), 3.92 (q, J = 8.5 Hz, 1H), 3.73 (d, J = 3.4 Hz, 3H), 2.91 (tt, J = 9.9, 5.0 Hz, 1H), 2.71 (s, 2H), 2.33 (q, J = 7.7, 6.9 Hz, 1H), 2.16 (tt, J = 12.5, 7.0 Hz, 4H), 1.97 (dd, J = 15.1, 9.4 Hz, 1H), 1.91-1.39 (m, 6H). |
| 101 | 6-fluoro-1,2,3,4-tetrahydro-quinoline | 2.2 | 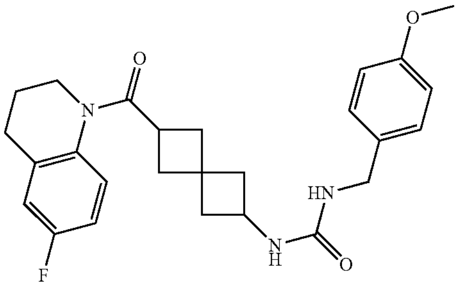 [SMILES: COc1ccc(CNC(=O)NC2CC3(C2)CC(C(=O)N2CCCc4cc(F)ccc42)C3)cc1] 1-(6-(6-fluoro-1,2,3,4-tetrahydroquinoline-1-carbonyl)spiro[3.3]heptan-2-yl)-3-(4-methoxybenzyl)urea. MS (APCI) m/z 452 (M + H). $^1$H NMR (400 MHz, DMSO-$d_6$) δ 7.47 (s, 1H), 7.15 (dt, J = 8.5, 5.1 Hz, 3H), 7.02-6.74 (m, 3H), 6.24-5.86 (m, 2H), 4.09 (t, J = 4.2 Hz, 2H), 3.92 (q, J = 8.5 Hz, 1H), 3.72 (d, J = 3.2 Hz, 3H), 3.59 (dt, J = 7.5, 4.5 Hz, 2H), 3.43 (tt, J = 10.7, 5.5 Hz, 1H), 2.70 (d, J = 7.1 Hz, 2H), 2.36 (s, 1H), 2.18 (dt, J = 14.5, 6.7 Hz, 3H), 2.02 (s, 1H), 1.82 (dq, J = 16.9, 9.4, 7.1 Hz, 4H), 1.76-1.66 (m, 1H). |
| 102 | 7,8-difluoro-1,2,3,4-tetrahydro-quinoline | 2.2 | 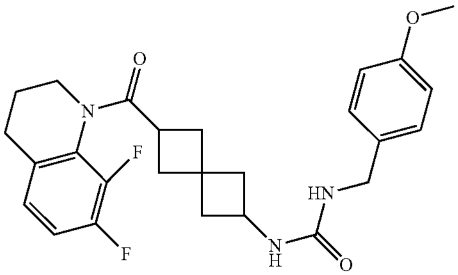 [SMILES: COc1ccc(CNC(=O)NC2CC3(C2)CC(C(=O)N2CCCc4ccc(F)c(F)c42)C3)cc1] 1-(6-(7,8-difluoro-1,2,3,4-tetrahydroquinoline-1-carbonyl)spiro[3.3[heptan-2-yl)-3-(4-methoxybenzyl)urea. LRMS (APCI) m/z 470 (M + H). $^1$H NMR (400 MHz, DMSO-$d_6$) δ 7.15 (d, J = 7.9 Hz, 3H), 6.87 (d, J = 7.8 Hz, 3H), 6.10 |

-continued

| Compound No. | Amine | Intermediate | Structure, Name and Data |
|---|---|---|---|
| | | | (d, J = 9.5 Hz, 2H), 4.09 (s, 2H), 3.73 (d, J = 2.9 Hz, 4H), 3.17 (d, J = 3.1 Hz, 2H), 2.68 (s, 2H), 2.34 (s, 2H), 2.17 (s, 2H), 1.76 (d, J = 35.3 Hz, 3H), 1.25 (s, 4H). |
| 103 | 6-(difluoro methoxy)-1,2,3,4-tetrahydro-quinoline | 2.2 | 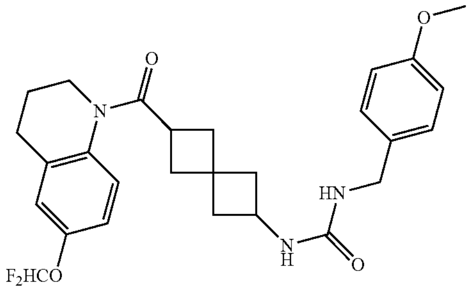 [SMILES: COc1ccc(CNC(=O)NC2CC3(C2)CC(C(=O)N2CCCc4cc(OC(F)F)ccc42)C3)cc1] 1-(6-(6-(difluoromethoxy)-1,2,3,4-tetrahydroquinoline-1-carbonyl)spiro[3.3]heptan-2-yl)-3-(4-methoxybenzyl)urea. LRMS (APCI) m/z 500 (M + H). $^1$H NMR (400 MHz, DMSO-$d_6$) δ 7.34 (br s, 1H), 7.30-7.18 (m, 3H), 6.99 (d, J = 13.8 Hz, 2H), 6.86 (dd, J = 8.5, 2.9 Hz, 2H), 6.08 (d, J = 11.9 Hz, 2H), 4.09 (d, J = 4.6 Hz, 2H), 4.03-3.76 (m, 1H), 3.72 (d, J = 3.0 Hz, 3H), 3.60 (d, J = 7.0 Hz, 2H), 2.70 (d, J = 8.4 Hz, 2H), 2.34 (s, 1H), 2.27-1.91 (m, 6H), 1.90-1.56 (m, 4H). |
| 104 | 6-(trifluoromethyl)-1,2,3,4-tetrahydroquinoline | 2.2 | 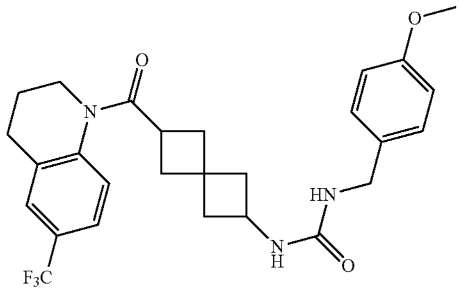 [SMILES: COc1ccc(CNC(=O)NC2CC3(C2)CC(C(=O)N2CCCc4cc(C(F)(F)F)ccc42)C3)cc1] 1-(4-methoxybenzyl)-3-(6-(6-(trifluoromethyl)-1,2,3,4-tetrahydroquinoline-1-carbonyl)spiro[3.3]heptan-2-yl)urea. LRMS (APCI) m/z 502 (M + H). |
| 105 | 5-fluoro-1,2,3,4-tetrahydroquinoline | 2.2 | 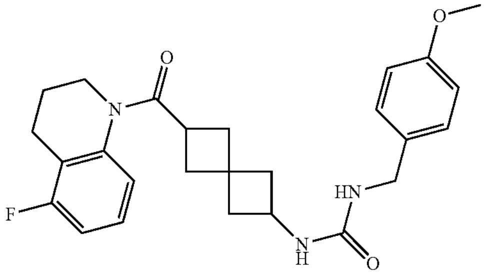 [SMILES: COc1ccc(CNC(=O)NC2CC3(C2)CC(C(=O)N2CCCc4c(F)cccc42)C3)cc1] 1-(6-(5-fluoro-1,2,3,4-tetrahydroquinoline-1-carbonyl)spiro[3.3]heptan-2-yl)-3-(4-methoxybenzyl)urea. LRMS (APCI) m/z 452 (M + H). $^1$H NMR (400 MHz, DMSO-$d_6$) δ 7.34 (s, 1H), 7.25-7.05 (m, 3H), 6.95 (d, J = 9.2 Hz, 1H), 6.90-6.76 (m, 2H), 6.23-5.95 (m, 2H), 4.09 (d, J = 4.6 Hz, 2H), 4.00-3.83 (m, 1H), 3.72 (d, J = 3.1 Hz, 3H), 3.61 (d, J = 5.2 Hz, 2H), 3.42 (q, J = 9.0 Hz, 1H), 2.70 (d, J = 8.2 Hz, 2H), 2.34 (s, 1H), 2.19 (dd, J = 19.3, 9.3 Hz, 4H), 2.01 (s, 1H), 1.91-1.57 (m, 4H). |

-continued

| Compound No. | Amine | Intermediate | Structure, Name and Data |
|---|---|---|---|
| 106 | 7-fluoro-1,2,3,4-tetrahydroquinoline | 2.2 | 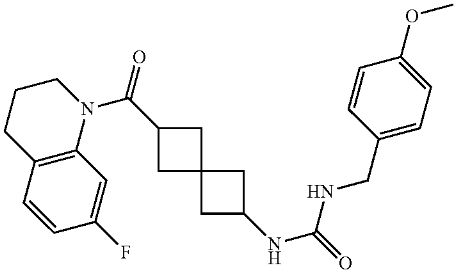 1-(6-(7-fluoro-1,2,3,4-tetrahydroquinoline-1-carbonyl)spiro[3.3]heptan-2-yl)-3-(4-methoxybenzyl)urea. LRMS (APCI) m/z 452 (M + H). $^1$H NMR (400 MHz, DMSO-$d_6$) δ 7.47 (s, 1H), 7.15 (dt, J = 8.5, 5.1 Hz, 3H), 6.98-6.73 (m, 3H), 6.22-5.96 (m, 2H), 4.09 (t, J = 4.2 Hz, 2H), 3.92 (q, J = 8.5 Hz, 1H), 3.72 (d, J = 3.1 Hz, 3H), 3.65-3.52 (m, 2H), 3.45 (tt, J = 9.0, 5.1 Hz, 1H), 2.70 (d, J = 7.1 Hz, 2H), 2.36 (s, 1H), 2.18 (dt, J = 14.5, 6.7 Hz, 4H), 2.02 (s, 1H), 1.82 (dq, J = 16.9, 9.4, 7.1 Hz, 3H), 1.76-1.61 (m, 1H). |
| 107 | 6-(trifluoromethoxy)-1,2,3,4-tetrahydroquinoline | 2.2 | 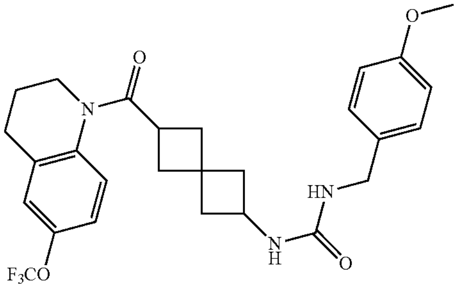 1-(4-methoxybenzyl)-3-(6-(6-(trifluoromethoxy)-1,2,3,4-tetrahydroquinoline-1-carbonyl)spiro[3.3]heptan-2-yl)urea. LRMS (APCI) m/z 518 (M + H). $^1$H NMR (400 MHz, DMSO-$d_6$) δ 7.45 (s, 1H), 7.11 (t, J = 8.5 Hz, 3H), 7.00-6.4 (m, 3H), 6.24-5.99 (m, 2H), 4.13 (t, J = 4.2 Hz, 2H), 3.78 (q, J = 8.5 Hz, 1H), 3.72 (d, J = 3.2 Hz, 3H), 3.45 (dt, J = 7.5, 4.5 Hz, 2H), 3.32 (tt, J = 10.7, 5.5 Hz, 1H), 2.78 (d, J = 7.1 Hz, 2H), 2.36 (s, 1H), 2.18 (dt, J = 14.5, 6.7 Hz, 3H), 2.02 (s, 1H), 1.82 (dq, J = 16.9, 9.4, 7.1 Hz, 4H), 1.76-1.66 (m, 1H). |
| 108 | 7-methyl-1,2,3,4-tetrahydroquinoline | 2.2 | 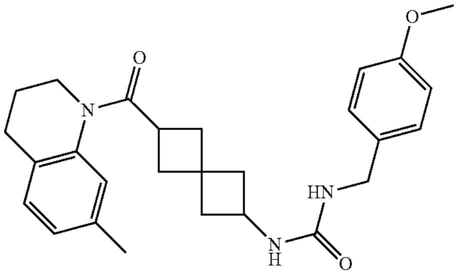 [SMILES: COc1ccc(CNC(=O)NC2CC3(C2)CC(C(=O)N2CCCc4ccc(C)cc42)C3)cc1] 1-(4-methoxybenzyl)-3-(6-(7-methyl-1,2,3,4-tetrahydroquinoline-1-carbonyl)spiro[3.3]heptan-2-yl)urea. LRMS (APCI) m/z 448 (M + H). $^1$H NMR (400 MHz, DMSO-$d_6$) δ 7.45 (s, 1H), 7.20-7.11 (m, 2H), 7.09-7.00 (m, 1H), 6.96-6.80 (m, 3H), 6.18-6.03 (m, 2H), 4.09 (t, J = 4.1 Hz, 2H), 3.90 (q, J = 8.9, 8.4 Hz, 1H), 3.72 (d, J = 3.1 Hz, 3H), 3.58 (d, J = 7.1 Hz, 2H), 2.64 (d, J = 7.5 Hz, 2H), 2.30 (s, 2H), 2.27 (d, J = 3.0 Hz, 3H), 2.23-2.07 (m, 3H), 1.96 (s, 1H), 1.88-1.61 (m, 5H). |

-continued

| Compound No. | Amine | Intermediate | Structure, Name and Data |
|---|---|---|---|
| 109 | 2-methyl-1-(piperazin-1-yl)propan-2-ol | 2.3 | 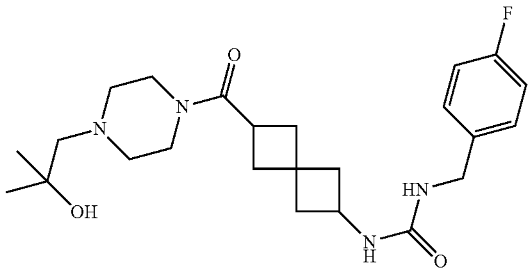<br>1-(4-fluorobenzyl)-3-(6-(4-(2-hydroxy-2-methylpropyl)piperazine-1-carbonyl)spiro[3.3]heptan-2-yl)urea. LRMS (APCI) m/z 447 (M + H). $^1$H NMR (400 MHz, DMSO-$d_6$) δ 7.26 (dd, J = 8.6, 5.7 Hz, 2H), 7.13 (t, J = 8.9 Hz, 2H), 6.23 (t, J = 6.0 Hz, 1H), 6.15 (d, J = 8.0 Hz, 1H), 5.29 (s, 1H), 4.15 (d, J = 6.0 Hz, 2H), 3.91 (q, J = 8.0 Hz, 1H), 3.84-3.64 (m, 1H), 3.48 (s, 1H), 3.12 (s, 1H), 2.47-2.32 (m, 3H), 2.29-2.08 (m, 7H), 2.02 (s, 1H), 1.81 (t, J = 9.7 Hz, 1H), 1.71 (t, J = 10.0 Hz, 1H), 1.25 (s, 3H), 1.09 (s, 6H). |
| 110 | 2-methyl-1-(piperazin-1-yl)propan-2-ol | 2.1 | 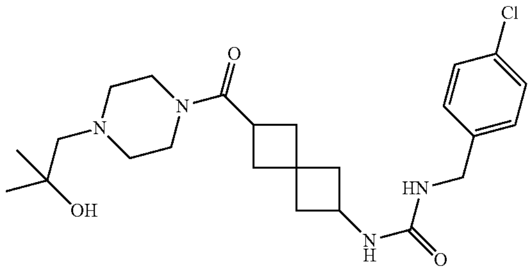 [SMILES: CC(C)(O)CN1CCN(C(=O)C2CC3(CC(NC(=O)NCc4ccc(F)cc4)C3)C2)CC1]<br>1-(4-chlorophenyl)-3-(6-(4-(2-hydroxy-2-methylpropyl)piperazine-1-carbonyl)spiro[3.3]heptan-2-yl)urea. LRMS (APCI) m/z 464 (M + H). $^1$H NMR (400 MHz, DMSO-$d_6$) δ 7.44-7.27 (m, 2H), 7.24 (d, J = 8.4 Hz, 2H), 6.26 (t, J = 6.0 Hz, 1H), 6.18 (d, J = 8.0 Hz, 1H), 4.15 (d, J = 6.1 Hz, 3H), 3.91 (q, J = 8.1 Hz, 1H), 3.20 (br s, 4H), 2.48-2.28 (m, 6H), 2.14 (dd, J = 19.9, 9.0 Hz, 6H), 2.01 (t, J = 10.0 Hz, 1H), 1.89-1.76 (m, 1H), 1.71 (t, J = 9.8 Hz, 1H), 1.17 (d, J = 60.5 Hz, 6H). |
| 111 | 1-(oxetan-3-yl)piperazine | 2.2 | 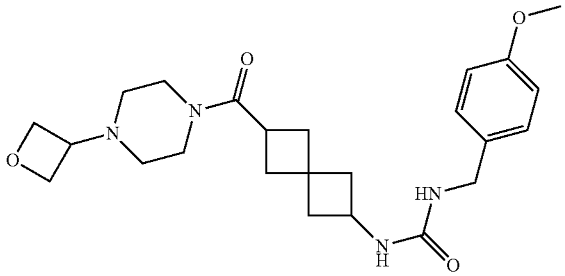 [SMILES: COc1ccc(CNC(=O)NC2CC3(C2)CC(C(=O)N2CCN(C4COC4)CC2)C3)cc1]<br>1-(4-methoxybenzyl)-3-(6-(4-(oxetan-3-yl)piperazine-1-carbonyl)spiro[3.3]heptan-2-yl)urea. LRMS (APCI) m/z 443 (M + H). $^1$H NMR (400 MHz, DMSO-$d_6$) δ 7.15 (d, J = 8.5 Hz, 2H), 6.86 (d, J = 8.6 Hz, 2H), 6.20-5.99 (m, 2H), 4.53 (t, J = 6.5 Hz, 2H), 4.43 (t, J = 6.1 Hz, 2H), 4.09 (d, J = 6.0 Hz, 2H), 3.91 (h, J = 8.2 Hz, 1H), 3.72 (s, 3H), 3.44 (q, J = 3.9 Hz, 2H), 3.31 (d, J = 5.6 Hz, 3H), 3.19 (p, J = 8.6 Hz, 1H), 2.37 (ddd, J = 10.8, 7.5, 5.3 Hz, 1H), 2.15 (dtd, J = 21.8, 8.2, 7.5, |

-continued

| Compound No. | Amine | Intermediate | Structure, Name and Data |
| --- | --- | --- | --- |
| | | | 3.6 Hz, 8H), 2.01 (ddd, J = 11.4, 8.6, 2.8 Hz, 1H), 1.79 (dd, J = 10.8, 8.6 Hz, 1H), 1.69 (dd, J = 11.1, 8.7 Hz, 1H). |
| 112 | 1-(cyclopropyl-methyl) piperazine | 2.2 | 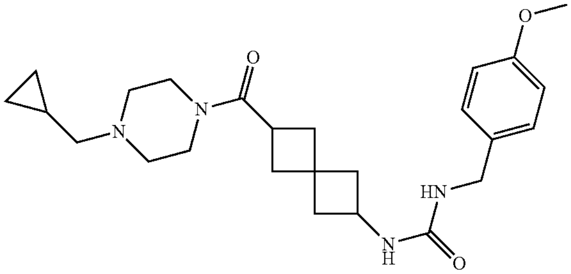 [SMILES: COc1ccc(CNC(=O)NC2CC3(C2)CC(C(=O)N2CCN(CC4CC4)CC2)C3)cc1] 1-(6-(4-(cyclopropylmethyl)piperazine-1-carbonyl)spiro[3.3]heptan-2-yl)-3-(4-methoxybenzyl)urea. LRMS (APCI) m/z 441 (M + H). $^{1}$H NMR (400 MHz, DMSO-$d_6$) δ 7.15 (d, J = 8.6 Hz, 2H), 6.87 (d, J = 8.6 Hz, 2H), 6.26-6.00 (m, 2H), 4.09 (d, J = 5.8 Hz, 2H), 4.00-3.74 (m, 1H), 3.72 (s, 4H), 3.24-3.31 (m, 5H), 3.04 (d, J = 16.1 Hz, 1H), 2.90-2.60 (m, 3H), 2.38 (ddd, J = 10.7, 7.4, 5.3 Hz, 1H), 2.28-2.08 (m, 5H), 2.04 (ddd, J = 11.4, 8.5, 3.0 Hz, 1H), 1.81 (dd, J = 10.7, 8.7 Hz, 1H), 1.71 (dd, J = 11.1, 8.8 Hz, 1H), 0.99 (tq, J = 7.3, 3.7, 2.6 Hz, 1H), 0.73-0.52 (m, 2H), 0.30 (t, J = 4.9 Hz, 2H). |
| 113 | (4-methylpiperazin-2-yl)methanol | 2.2 | 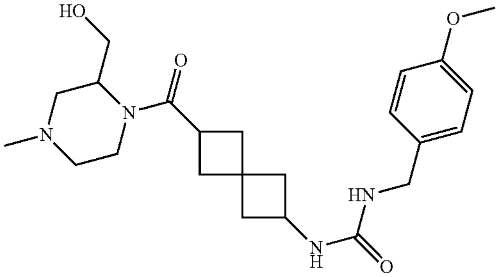 1-(6-(2-(hydroxymethyl)-4-methylpiperazine-1-carbonyl)spiro[3.3]heptan-2-yl)-3-(4-methoxybenzyl)urea. LRMS (APCI) m/z 431 (M + H). $^{1}$H NMR (400 MHz, DMSO-$d_6$) δ 7.63 (d, J = 8.3 Hz, 2H), 7.15 (d, J = 8.6 Hz, 2H), 6.86 (d, J = 8.6 Hz, 1H), 6.23-6.01 (m, 1H), 4.30 (s, 1H), 4.16 (d, J = 13.5 Hz, 2H), 4.09 (d, J = 5.9 Hz, 2H), 4.01-3.85 (m, 1H), 3.72 (s, 3H), 3.67-3.54 (m, 2H), 3.27 (t, J = 8.8 Hz, 1H), 3.04 (ddd, J = 16.2, 7.8, 3.2 Hz, 2H), 2.92 (d, J = 11.4 Hz, 2H), 2.81 (d, J = 11.5 Hz, 1H), 2.75-2.63 (m, 2H), 2.37 (ddt, J = 10.4, 7.6, 4.5 Hz, 1H), 2.17 (s, 1H), 2.16-2.09 (m, 3H), 1.83 (dddd, J = 24.4, 15.5, 12.3, 6.3 Hz, 2H), 1.69 (ddq, J = 12.0, 9.3, 3.6, 3.1 Hz, 2H). |
| 122 | 1-isopropyl-piperazine | 2.2 | 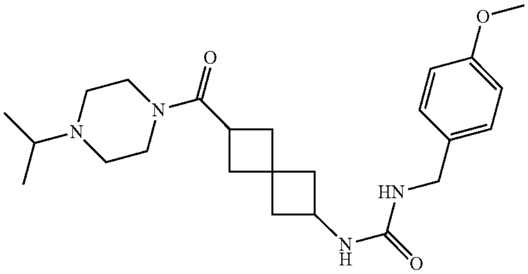 [SMILES: COc1ccc(CNC(=O)NC2CC3(C2)CC(C(=O)N2CCN(C(C)C)CC2)C3)cc1] 1-(6-(4-isopropylpiperazine-1-carbonyl)spiro[3.3]heptan-2-yl)-3-(4- |

-continued

| Compound No. | Amine | Intermediate | Structure, Name and Data |
|---|---|---|---|
| | | | methoxybenzyl)urea. LRMS (APCI) m/z 429 (M + H). $^{1}H$ NMR (400 MHz, DMSO-$d_6$) δ 7.14 (d, J = 8.6 Hz, 2H), 6.86 (d, J = 8.6 Hz, 2H), 6.23-5.92 (m, 2H), 4.09 (d, J = 6.0 Hz, 2H), 3.99-3.84 (m, 1H), 3.72 (s, 3H), 3.34 (t, J = 4.8 Hz, 2H), 3.27 (t, J = 4.8 Hz, 2H), 3.17 (p, J = 8.5 Hz, 1H), 2.67 (dd, J = 9.5, 4.1 Hz, 1H), 2.37 (tt, J = 8.9, 4.0 Hz, 5H), 2.25-2.08 (m, 4H), 2.01 (ddd, J = 11.4, 8.6, 2.8 Hz, 1H), 1.79 (dd, J = 10.8, 8.7 Hz, 1H), 1.68 (dd, J = 11.1, 8.7 Hz, 1H), 0.96 (d, J = 6.5 Hz, 6H). |
| 123 | 1-((1-methyl-1H-pyrazol-4-yl)methyl) yl)piperazine | 2.2 | 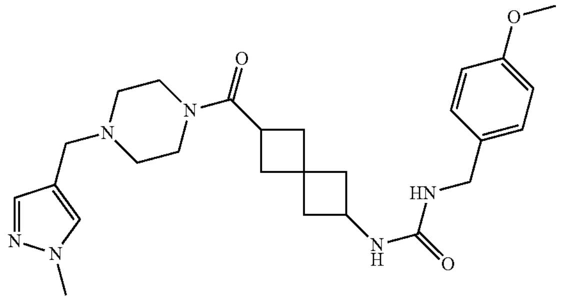 [SMILES: COc1ccc(CNC(=O)NC2CC3(C2)CC(C(=O)N2CCN(Cc4cnn(C)c4)CC2)C3)cc1] 1-(4-methoxybenzyl)-3-(6-(4-((1-methyl-1H-pyrazol-4-yl)methyl)piperazine-1-carbonyl)spiro[3.3]heptan-2-yl)urea. LRMS (APCI) m/z 481 (M + H). $^{1}H$ NMR (400 MHz, DMSO-$d_6$) δ 7.58 (s, 1H), 7.31 (s, 1H), 7.14 (d, J = 8.7 Hz, 2H), 6.86 (d, J = 8.5 Hz, 2H), 6.21-5.94 (m, 2H), 4.09 (d, J = 5.9 Hz, 2H), 3.90 (td, J = 8.8, 7.7, 5.9 Hz, 1H), 3.79 (s, 3H), 3.56 (s, 4H), 3.30 (brs, 8H), 3.17 (p, J = 8.6 Hz, 1H), 2.36 (ddd, J = 12.7, 7.1, 3.5 Hz, 1H), 2.21-2.06 (m, 5H), 2.00 (ddd, J = 11.5, 8.6, 3.0 Hz, 1H), 1.78 (dd, J = 10.7, 8.7 Hz, 1H), 1.68 (dd, J = 11.1, 8.7 Hz, 1H). |
| 124 | 1-(pyridin-4-ylmethyl) piperazine | 2.2 | 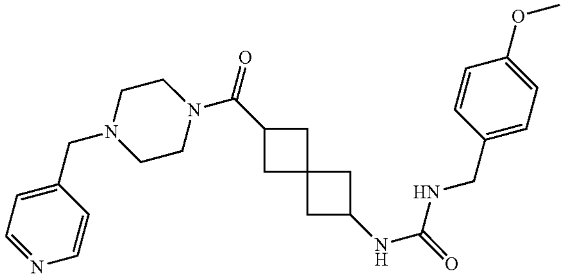 [SMILES: COc1ccc(CNC(=O)NC2CC3(C2)CC(C(=O)N2CCN(Cc4ccncc4)CC2)C3)cc1] 1-(4-methoxybenzyl)-3-(6-(4-(pyridin-4-ylmethyl)piperazine-1-carbonyl)spiro[3.3]heptan-2-yl)urea. LRMS (APCI) m/z 478 (M + H). $^{1}H$ NMR (400 MHz, DMSO-$d_6$) δ 8.58 (d, J = 7.6 Hz, 2H), 7.72 (dd, J = 7.6, 1.8 Hz, 2H), 7.13 (d, J = 8.9 Hz, 2H), 6.90 (d, J = 8.9 Hz, 2H), 6.29-5.99 (m, 2H), 4.11 (d, J = 5.9 Hz, 2H), 3.91-3.82 (m, 1H), 3.73 (s, 3H), 3.64 (s, 3H), 3.41 (d, J = 5.3 Hz, 3H), 3.16 (p, J = 8.6 Hz, 1H), 2.40-2.21 (m, 4H), 2.22-2.1 (m, 5H), 2.09 (ddd, J = 11.5, 8.5, 2.8 Hz, 1H), 1.84 (dd, J = 10.7, 8.6 Hz, 1H), 1.75 (dd, J = 11.0, 8.7 Hz, 1H). |

-continued

| Compound No. | Amine | Intermediate | Structure, Name and Data |
|---|---|---|---|
| 125 | 1-(pyridin-2-ylmethyl) piperazine | 2.2 | 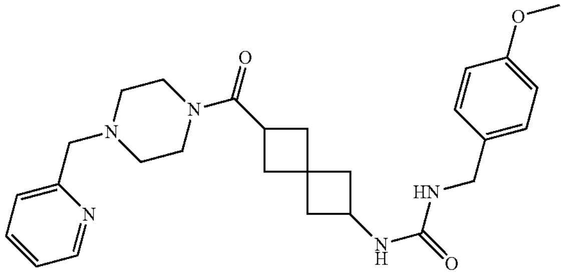 [SMILES: COc1ccc(CNC(=O)NC2CC3(C2)CC(C(=O)N2CCN(Cc4ccccn4)CC2)C3)cc1] 1-(4-methoxybenzyl)-3-(6-(4-(pyridin-2-ylmethyl)piperazine-1-carbonyl)spiro[3.3]heptan-2-yl)urea. LRMS (APCI) m/z 478 (M + H). $^1$H NMR (400 MHz, DMSO-$d_6$) δ 8.51 (d, J = 4.6 Hz, 1H), 7.78 (td, J = 7.6, 1.8 Hz, 1H), 7.45 (d, J = 7.7 Hz, 1H), 7.28 (dd, J = 7.4, 5.0 Hz, 1H), 7.14 (d, J = 8.5 Hz, 2H), 6.86 (d, J = 8.5, 2H), 6.28-5.94 (m, 2H), 4.09 (d, J = 5.9 Hz, 2H), 4.00-3.82 (m, 1H), 3.72 (s, 3H), 3.67 (s, 3H), 3.46 (d, J = 5.3 Hz, 3H), 3.18 (p, J = 8.6 Hz, 1H), 2.48-2.28 (m, 5H), 2.25-2.07 (m, 4H), 2.01 (ddd, J = 11.5, 2.8 Hz, 1H), 1.79 (dd, J = 10.7, 8.6 Hz, 1H), 1.69 (dd, J = 11.0, 8.7 Hz, 1H). |
| 126 | (1-methyl-piperazin-2-yl)methanol | 2.2 | 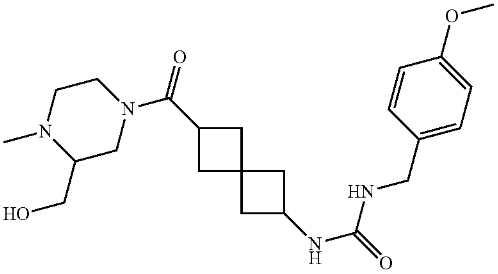 6-(3-(4-methoxybenzyl)ureido)-N-(1-phenylcyclopropyl)spiro[3.3]heptane-2-carboxamide. LRMS (APCI) m/z 431 (M + H). $^1$H NMR (400 MHz, DMSO-$d_6$) δ 7.14 (d, J = 8.5 Hz, 2H), 6.86 (d, J = 8.6 Hz, 2H), 6.21-5.95 (m, 2H), 4.81 (s, 1H), 4.29 (d, J = 13.0 Hz, 1H), 4.09 (d, J = 5.9 Hz, 2H), 4.03-3.85 (m, 1H), 3.72 (s, 3H), 3.68-3.49 (m, 6H), 3.19 (td, J = 8.2, 2.9 Hz, 1H), 3.11-3.01 (m, 1H), 2.96-2.84 (m, 1H), 2.84-2.69 (m, 1H), 2.31 (d, J = 6.9 Hz, 2H), 2.26-1.90 (m, 6H), 1.80 (t, J = 9.6 Hz, 1H), 1.69 (dd, J = 11.0, 8.7 Hz, 1H). |
| 202 | (S)-N-methyl-tetrahydro furan-3-amine | 2.4 | 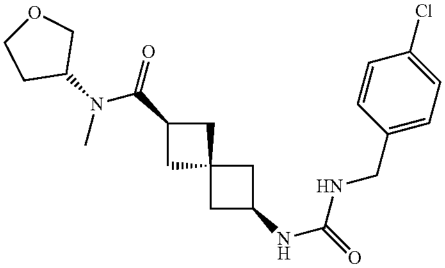 (2S,4s,6S)-6-(3-(4-chlorobenzyl)ureido)-N-methyl-N-((R)-tetrahydrofuran-3-yl)spiro[3.3]heptane-2-carboxamide. LRMS (APCI) m/z 406 (M + H). $^1$H NMR (400 MHz, Methanol-$d_4$) δ 7.20 (d, J = 8.5 Hz, 2H), 7.15 (d, J = 8.5 Hz, 2H), 5.05 (ddd, J = 11.0, 9.2, 4.9 Hz, 1H), 4.53-4.38 (m, 1H), 4.17 (s, 2H), 4.00-3.86 (m, 2H), 3.68-3.60 (m, 2H), 3.56 (tt, J = 8.3, 4.2 |

-continued

| Compound No. | Amine | Intermediate | Structure, Name and Data |
|---|---|---|---|
| | | | Hz, 1H), 2.78 (s, 2H), 2.72 (s, 1H), 2.43 (dq, J = 11.9, 6.2 Hz, 1H), 2.28-1.99 (m, 6H), 1.81 (ddt, J = 13.3, 8.2, 4.3 Hz, 2H), 1.76-1.66 (m, 1H). |
| 230 | 1-methylpiperazine | 2.2 | 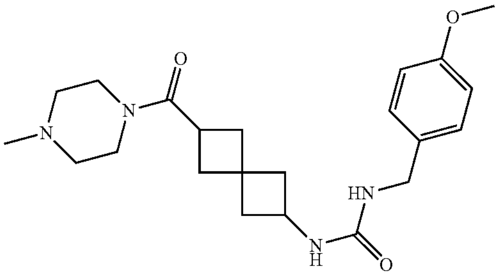 1-(4-methoxybenzyl)-3-(6-(4-methylpiperazine-1-carbonyl)spiro[3.3]heptan-2-yl)urea. LRMS (APCI) m/z 401.1 (M + H). $^1$H NMR (400 MHz, Methanol-$d_4$) δ 7.19 (d, J = 8.3 Hz, 2H), 6.87 (d, J = 8.3 Hz, 2H), 4.23 (s, 2H), 4.04 (p, J = 8.1 Hz, 1H), 3.78 (s, 3H), 3.76-3.62 (m, 2H), 3.57 (t, J = 5.1 Hz, 2H), 3.29 (d, J = 8.6 Hz, 1H), 3.29 (q, J = 5.5 Hz, 4H), 2.58 (s, 3H), 2.53 (dt, J = 11.7, 6.4 Hz, 1H), 2.40-2.22 (m, 4H), 2.14 (ddd, J = 11.7, 8.5, 3.2 Hz, 1H), 1.96-1.87 (m, 1H), 1.87-1.75 (m, 1H). |
| 231 | methyl piperazine-1-carboxylate | 2.2 | 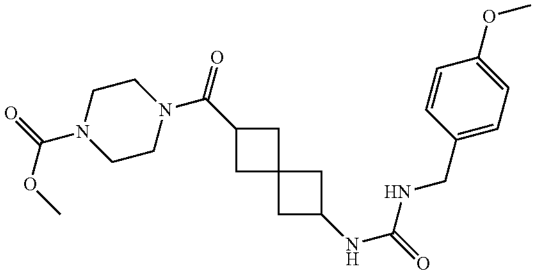 [SMILES: COC(=O)N1CCN(C(=O)C2CC3(CC(NC(=O)NCc4ccc(OC)cc4)C3)C2)CC1] methyl 4-(6-(3-(4-methoxybenzyl)ureido)spiro[3.3]heptane-2-carbonyl)piperazine-1-carboxylate. LRMS (APCI) m/z 445.1 (M + H). $^1$H NMR (400 MHz, Methanol-$d_4$) δ 7.61 (s, 1H), 7.09 (d, J = 8.3 Hz, 2H), 6.76 (d, J = 8.3 Hz, 2H), 4.14 (s, 2H), 3.95 (p, J = 8.2 Hz, 1H), 3.69 (s, 3H), 3.63 (s, 3H), 3.47 (d, J = 4.9 Hz, 2H), 3.35 (dd, J = 20.6, 5.4 Hz, 6H), 3.16 (p, J = 8.6 Hz, 1H), 2.44 (dt, J = 11.6, 6.5 Hz, 1H), 2.29-2.15 (m, 4H), 2.04 (dd, J = 12.0, 8.9 Hz, 1H), 1.85-1.76 (m, 1H), 1.71 (dd, J = 11.1, 9.0 Hz, 1H). |
| 232 | thiomorpholine 1,1-dioxide | 2.2 | 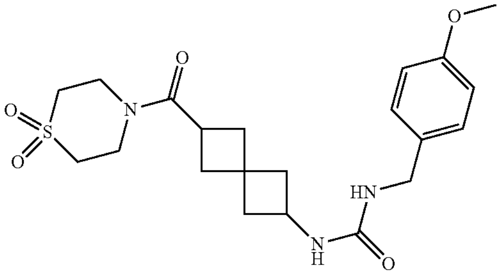 [SMILES: COc1ccc(CNC(=O)NC2CC3(C2)CC(C(=O)N2CCS(=O)(=O)CC2)C3)cc1] 1-(6-(1,1-dioxidothiomorpholine-4-carbonyl)spiro[3.3]heptan-2-yl)-3-(4-methoxybenzyl)urea. LRMS (APCI) m/z 436.2 (M + H). $^1$H NMR (400 MHz, Methanol-$d_4$) δ 7.10 (d, J = 8.3 Hz, 2H), 6.76 (d, J = 8.4 Hz, 2H), 4.14 (s, 2H), 3.95 (q, J = 8.8, 8.0 Hz, 3H), 3.78 (t, J = 5.2 Hz, 2H), 3.69 (s, 3H), 3.18 (q, J = 8.6 Hz, 1H), |

-continued

| Compound No. | Amine | Intermediate | Structure, Name and Data |
|---|---|---|---|
| | | | 3.05-2.93 (m, 4H), 2.45 (dt, J = 11.5, 6.5 Hz, 1H), 2.23 (ddd, J = 18.0, 10.3, 5.1 Hz, 4H), 2.11-2.00 (m, 1H), 1.81 (dd, J = 11.0, 8.6 Hz, 1H), 1.72 (dd, J = 11.1, 9.0 Hz, 1H). |
| 233 | methyl piperazine-1-carboxylate | 2.1 | 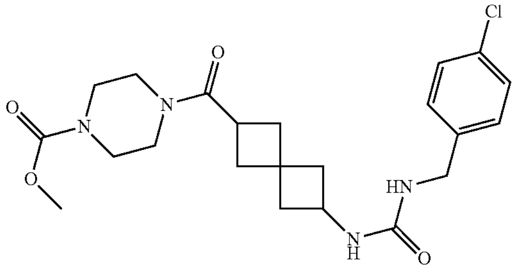 [SMILES: COC(=O)N1CCN(C(=O)C2CC3(CC(NC(=O)NCc4ccc(Cl)cc4)C3)C2)CC1] Methyl 4-(6-(3-(4-chlorobenzyl)ureido)spiro[3.3]heptane-2-carbonyl)piperazine-1-carboxylate. LRMS (APCI) m/z 449.1 (M + H). $^1$H NMR (400 MHz, Methanol-$d_4$) δ 7.32 (d, J = 7.6 Hz, 2H), 7.26 (d, J = 8.2 Hz, 2H), 4.28 (s, 2H), 4.03 (p, J = 7.9 Hz, 1H), 3.72 (s, 3H), 3.57 (t, J = 5.2 Hz, 2H), 3.46 (d, J = 8.9 Hz, 6H), 3.30 (d, J = 9.0 Hz, 1H), 2.54 (dt, J = 11.4, 6.2 Hz, 1H), 2.30 (dt, J = 20.8, 9.9 Hz, 4H), 2.20-2.08 (m, 1H), 1.98-1.88 (m, 1H), 1.88-1.73 (m, 1H). |
| 234 | 2-methyl-1-(piperazin-1-yl)propan-2-ol | 13.1 | 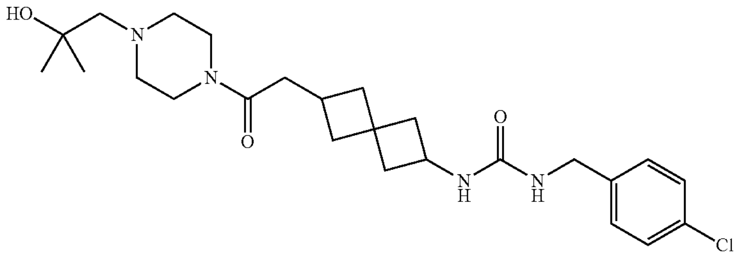 [SMILES: CC(C)(O)CN1CCN(C(=O)CC2CC3(C2)CC(NC(=O)NCc2ccc(Cl)cc2)C3)CC1] 1-(4-chlorobenzyl)-3-(6-(2-(4-(2-hydoxy-2-methylpropyl)piperazin-1-yl)-2-oxoethyl)spiro[3.3]heptan-2-yl)urea. LRMS (APCI) m/z 477.0 (M + H). $^1$H NMR (400 MHz, Methanol-$d_4$) δ 7.31 (d, J = 7.9 Hz, 2H), 7.26 (d, J = 8.1 Hz, 2H), 4.28 (s, 2H), 4.02 (p, J = 7.8 Hz, 1H), 3.67 (p, J = 4.7 Hz, 4H), 2.90 (d, J = 23.7 Hz, 4H), 2.66 (s, 2H), 2.60-2.42 (m, 4H), 2.28 (dt, J = 11.3, 5.9 Hz, 2H), 2.11 (dd, J = 10.6, 6.2 Hz, 1H), 1.94-1.67 (m, 4H), 1.27 (s, 6H). |
| 235 | (S)-pyrrolidin-2-ylmethanol | 13.1 | 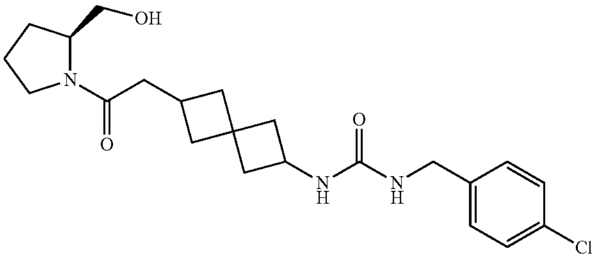 [SMILES: O=C(NCc1ccc(Cl)cc1)NC1CC2(CC(CC(=O)N3CCC[C@H]3CO)C2)C1] (S)-1-(4-chlorobenzyl)-3-(6-(2-(2-(hydroxymethyl) pyrrolidin-1-yl)-2-oxoethyl)spiro[3.3]heptan-2-yl)urea. LRMS (APCI) m/z 420.1 (M + H). $^1$H NMR (400 MHz, Methanol-$d_4$) δ 7.31 (d, J = 7.9 Hz, 2H), 7.26 (d, J = 8.1 Hz, 2H), 4.28 (s, 2H), 4.08 (p, J = 4.7 Hz, 1H), 4.01 (q, J = 7.7 Hz, 1H), 3.63 (dd, J = 10.8, 4.0 Hz, 1H), 3.53 (dt, J = 18.1, |

-continued

| Compound No. | Amine | Intermediate | Structure, Name and Data |
|---|---|---|---|
| | | | 6.3 Hz, 3H), 2.57 (p, J = 7.6 Hz, 1H), 2.52-2.36 (m, 3H), 2.29 (dq, J = 12.1, 5.6, 5.0 Hz, 2H), 2.12 (ddd, J = 11.9, 7.6, 4.0 Hz, 1H), 2.07-1.86 (m, 5H), 1.86-1.70 (m, 3H). |
| 236 | pyrrolidine | 13.1 | 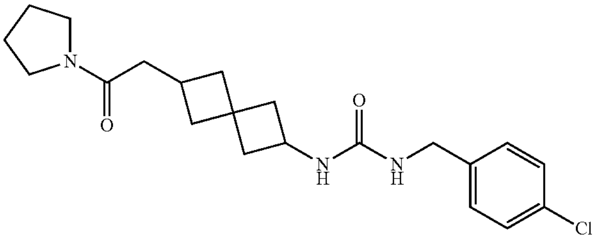 [SMILES: O=C(NCc1ccc(Cl)cc1)NC1CC2(CC(CC(=O)N3CCCC3)C2)C1] 1-(4-chlorobenzyl)-3-(6-(2-oxo-2-(pyrrolidin-1-yl)ethyl)spiro[3.3]heptan-2-yl)urea. LRMS (APCI) m/z 390.2 (M + H). $^1$H NMR (400 MHz, Methanol-$d_4$) δ 7.31 (d, J = 7.9 Hz, 2H), 7.26 (d, J = 8.1 Hz, 2H), 4.28 (s, 2H), 4.08 (p, J = 4.7 Hz, 1H), 4.01 (q, J = 7.7 Hz, 1H), 3.63 (dd, J = 10.8, 4.0 Hz, 1H), 3.53 (dt, J = 18.1, 6.3 Hz, 3H), 2.57 (p, J = 7.6 Hz, 1H), 2.52-2.36 (m, 3H), 2.29 (dq, J = 12.1, 5.6, 5.0 Hz, 2H), 2.12 (ddd, J = 11.9, 7.6, 4.0 Hz, 1H), 2.07-1.86 (m, 5H), 1.86-1.70 (m, 3H). |
| 237 | N-methyl-1-phenyl-methanamine | 13.2 | 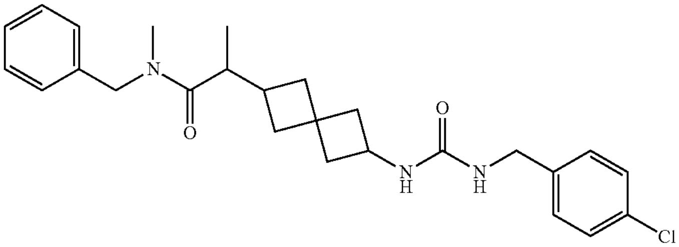 [SMILES: CC(C(=O)N(C)Cc1ccccc1)C1CC2(CC(NC(=O)NCc3ccc(Cl)cc3)C2)C1] N-benzyl-2-(6-(3-(4-chlorobenzyl)ureido)spiro[3.3]heptan-2-yl)-N-methylpropanamide. LRMS (APCI) m/z 454.1 (M + H). $^1$H NMR (400 MHz, Methanol-$d_4$) δ 7.23-7.16 (m, 4H), 7.16-7.06 (m, 5H), 4.66-4.50 (m, 2H), 4.16 (s, 2H), 3.89 (dt, J = 18.2, 8.7 Hz, 1H), 2.88 (dd, J = 31.5, 3.8 Hz, 3H), 2.78-2.55 (m, 1H), 2.42-2.26 (m, 2H), 2.15-1.85 (m, 3H), 1.79-1.52 (m, 4H), 0.96-0.87 (m, 3H). |
| 256 | 1,2,3,4-tetrahydro-quinoline | 2.6 | 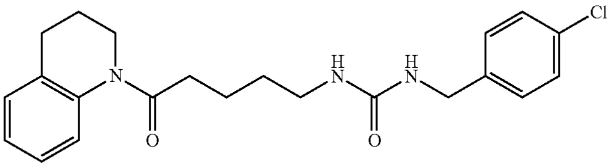 [SMILES: O=C(NCCCCC(=O)N1CCCc2ccccc21)NCc1ccc(Cl)cc1] 1-(4-chlorobenzyl)-3-(5-(3,4-dihydroquinolin-1(2H)-yl)-5-oxopentyl)urea. LRMS (APCI) m/z 400.1 (M + H). $^1$H NMR (400 MHz, DMSO-$d_6$) δ 7.42 (s, 1H), 7.36 (d, J = 8.4 Hz, 2H), 7.25 (d, J = 8.3 Hz, 2H), 7.23-7.12 (m, 2H), 7.08 (t, J = 7.4 Hz, 1H), 6.31 (t, J = 6.1 Hz, 1H), 5.94 (t, J = 5.7 Hz, 1H), 4.17 (d, J = 6.0 Hz, 2H), 3.67 (t, J = 6.4 Hz, 2H), 2.97 (q, J = 6.5 Hz, 2H), 2.69 (t, J = 6.7 Hz, 2H), 2.47 (d, J = 7.3 Hz, 2H), 1.87 (q, J = 6.5 Hz, 2H), 1.58-1.46 (m, 2H), 1.34 (t, J = 7.6 Hz, 2H). |

-continued

| Compound No. | Amine | Intermediate | Structure, Name and Data |
|---|---|---|---|
| 257 | cyclo-hexanamine | 2.7 | 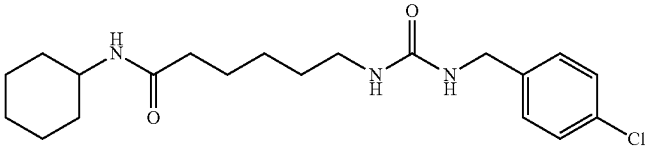 [SMILES: O=C(CCCCCNC(=O)NCc1ccc(Cl)cc1)NC1CCCCC1] 6-(3-(4-chlorobenzyl)ureido)-N-cyclohexylhexanamide. LRMS (APCI) m/z 380.2 (M + H). $^1$H NMR (400 MHz, DMSO-$d_6$) δ 7.59 (d, J = 8.0 Hz, 1H), 7.37 (d, J = 8.4 Hz, 2H), 7.25 (d, J = 8.4 Hz, 2H), 6.30 (t, J = 6.1 Hz, 1H), 5.92 (t, J = 5.6 Hz, 1H), 4.17 (d, J = 6.0 Hz, 2H), 3.56-3.43 (m, 1H), 2.98 (q, J = 6.6 Hz, 2H), 2.02 (t, J = 7.4 Hz, 2H), 1.78-1.61 (m, 4H), 1.59-1.42 (m, 3H), 1.36 (p, J = 7.2 Hz, 2H), 1.28-1.17 (m, 4H), 1.12 (t, J = 11.8 Hz, 3H). |
| 258 | cyclo-pentanamine | 2.7 | 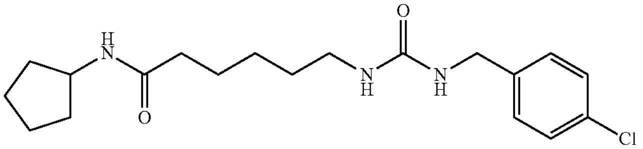 [SMILES: O=C(CCCCCNC(=O)NCc1ccc(Cl)cc1)NC1CCCC1] 6-(3-(4-chlorobenzyl)ureido)-N-cyclopentylhexanamide. LRMS (APCI) m/z 366.2 (M + H). $^1$H NMR (400 MHz, DMSO-$d_6$) δ 7.68 (d, J = 7.2 Hz, 1H), 7.37 (d, J = 8.4 Hz, 2H), 7.25 (d, J = 8.4 Hz, 2H), 6.31 (t, J = 6.1 Hz, 1H), 5.92 (t, J = 5.6 Hz, 1H), 4.18 (d, J = 6.0 Hz, 2H), 3.97 (q, J = 6.9 Hz, 1H), 2.98 (q, J = 6.6 Hz, 2H), 2.01 (t, J = 7.4 Hz, 2H), 1.77 (dq, J = 12.4, 6.5 Hz, 2H), 1.60 (dq, J = 11.0, 6.6, 5.7 Hz, 2H), 1.56-1.40 (m, 4H), 1.40-1.28 (m, 4H), 1.22 (dt, J = 11.8, 6.9 Hz, 2H). |
| 259 | morpholine | 2.7 | 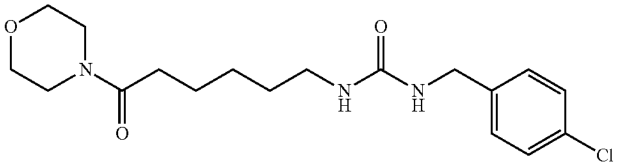 [SMILES: O=C(NCCCCCC(=O)N1CCOCC1)NCc1ccc(Cl)cc1] 1-(4-chlorobenzyl)-3-(6-morpholine-6-oxohexyl)urea. LRMS (APCI) m/z 368.1 (M + H). $^1$H NMR (400 MHz, DMSO-$d_6$) δ 7.37 (d, J = 8.4 Hz, 2H), 7.26 (d, J = 8.4 Hz, 2H), 6.31 (t, J = 6.1 Hz, 1H), 5.93 (t, J = 5.6 Hz, 1H), 4.18 (d, J = 5.9 Hz, 2H), 3.54 (dt, J = 10.1, 4.7 Hz, 4H), 3.42 (dd, J = 5.7, 4.0 Hz, 4H), 2.99 (q, J = 6.5 Hz, 2H), 2.28 (t, J = 7.5 Hz, 2H), 1.49 (p, J = 7.5 Hz, 2H), 1.38 (p, J = 7.0 Hz, 2H), 1.26 (td, J = 8.4, 4.3 Hz, 2H). |
| 260 | 1-neopentyl-piperazine | 2.7 | 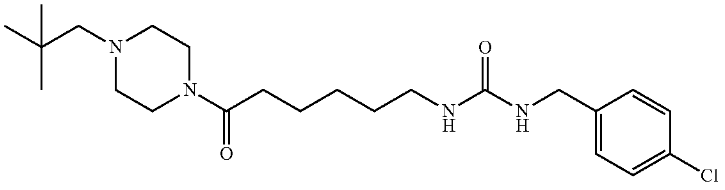 [SMILES: CC(C)(C)CN1CCN(C(=O)CCCCCNC(=O)NCc2ccc(Cl)cc2)CC1] 1-(4-chlorobenzyl)-3-(6-(4-neopentylpiperazin-1-yl)-6-oxohexyl)urea. LRMS (APCI) m/z 437.2 (M + H). $^1$H NMR (400 MHz, DMSO-$d_6$) δ 7.37 (d, J = 8.5 Hz, 2H), 7.25 (d, J = 8.4 Hz, 2H), 6.31 (t, J = 6.1 Hz, 1H), 5.93 (t, J = 5.6 Hz, 1H), 4.18 (d, J = 6.0 Hz, 2H), 3.40 (d, J = 9.2 Hz, 4H), 2.99 (q, J = 6.5 Hz, 2H), 2.47-2.36 (m, 4H), 2.26 (t, J = 7.4 Hz, 2H), 2.05 (s, 2H), 1.47 (p, J = 7.3 Hz, 2H), 1.37 (p, J = 7.0 Hz, 2H), 1.25 (q, J = 7.9 Hz, 3H), 0.86 (s, 9H). |

-continued

| Compound No. | Amine | Intermediate | Structure, Name and Data |
| --- | --- | --- | --- |
| 261 | 2-methyl-1-(piperazin-1-yl)propan-2-ol | 2.7 | 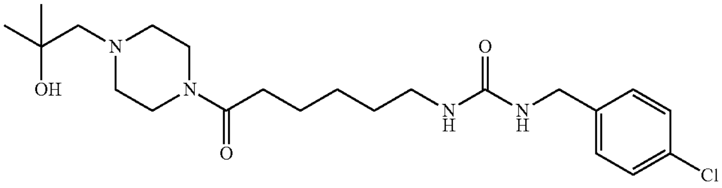 [SMILES: CC(C)(O)CN1CCN(C(=O)CCCCCNC(=O)NCc2ccc(Cl)cc2)CC1] 1-(4-chlorobenzyl)-3-(6-(4-(2-hydroxy-2-methylpropyl)piperazin-1-yl)-6-oxohexyl)urea. LRMS (APCI) m/z 439.2 (M + H). $^1$H NMR (400 MHz, DMSO-$d_6$) δ 9.09 (s, 1H), 7.37 (d, J = 8.4 Hz, 2H), 7.26 (d, J = 8.4 Hz, 2H), 6.33 (s, 1H), 5.94 (s, 1H), 4.21 (dd, J = 24.1, 9.6 Hz, 3H), 3.95 (d, J = 14.5 Hz, 1H), 3.52 (d, J = 13.0 Hz, 4H), 3.24 (t, J = 12.4 Hz, 1H), 3.13 (d, J = 3.8 Hz, 3H), 3.03-2.95 (m, 2H), 2.33 (q, J = 7.2 Hz, 2H), 1.50 (p, J = 7.5 Hz, 2H), 1.39 (p, J = 7.0 Hz, 2H), 1.26 (s, 8H). |
| 262 | o-toluidine | 2.7 | 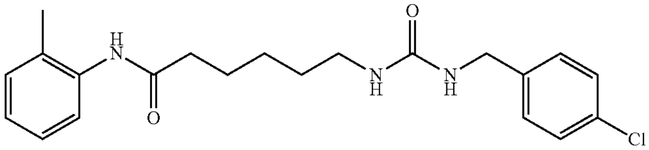 [SMILES: Cc1ccccc1NC(=O)CCCCCNC(=O)NCc1ccc(Cl)cc1] 6-(3-(4-chlorobenzyl)ureido)-N-(o-tolyl)hexanamide. LRMS (APCI) m/z 388.1 (M + H). $^1$H NMR (400 MHz, DMSO-$d_6$) δ 9.21 (s, 1H), 7.36 (d, J = 8.4 Hz, 3H), 7.26 (d, J = 8.4 Hz, 2H), 7.20 (d, J = 7.5 Hz, 1H), 7.14 (t, J = 7.5 Hz, 1H), 7.07 (t, J = 7.3 Hz, 1H), 6.32 (t, J = 6.1 Hz, 1H), 5.95 (t, J = 5.8 Hz, 1H), 4.18 (d, J = 6.0 Hz, 2H), 3.01 (q, J = 6.5 Hz, 2H), 2.32 (t, J = 7.1 Hz, 2H), 2.18 (s, 3H), 1.69-1.53 (m, 2H), 1.41 (q, J = 7.2 Hz, 2H), 1.36-1.25 (m, 2H). |
| 263 | pyridin-4-amine | 2.7 | 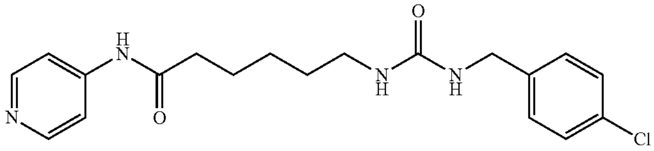 [SMILES: O=C(CCCCCNC(=O)NCc1ccc(Cl)cc1)Nc1ccncc1] 6-(3-(4-chlorobenzyl)ureido)-N-(pyridin-4-yl)hexanamide. LRMS (APCI) m/z 375.0 (M + H). $^1$H NMR (400 MHz, DMSO-$d_6$) δ 8.40 (d, J = 6.4 Hz, 2H), 8.14 (s, 1H), 7.61-7.50 (m, 2H), 7.36 (d, J = 8.5 Hz, 2H), 7.25 (d, J = 8.4 Hz, 2H), 6.31 (t, J = 6.1 Hz, 1H), 5.95 (t, J = 5.7 Hz, 1H), 4.17 (d, J = 6.0 Hz, 2H), 3.17 (d, J = 5.0 Hz, 1H), 3.00 (q, J = 6.5 Hz, 2H), 2.35 (t, J = 7.4 Hz, 2H), 1.59 (p, J = 7.5 Hz, 2H), 1.40 (p, J = 7.0 Hz, 2H), 1.28 (p, J = 7.7 Hz, 2H). |
| 264 | N,3-dimethyl aniline | 2.7 | 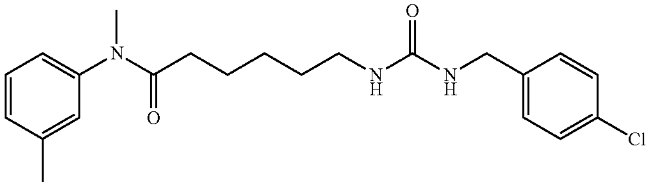 [SMILES: Cc1cccc(N(C)C(=O)CCCCCNC(=O)NCc2ccc(Cl)cc2)c1] 6-(3-(4-chlorobenzyl)ureido)-N-methyl-N-(m-tolyl)hexanamide. LRMS (APCI) m/z 402.2 (M + H). $^1$H NMR (400 MHz, DMSO-$d_6$) δ 7.40-7.29 (m, 3H), 7.24 (d, J = 8.4 Hz, 2H), 7.20-7.06 (m, 3H), 6.28 (t, J = 6.1 Hz, 1H), 5.89 (d, J = 5.5 |

-continued

| Compound No. | Amine | Intermediate | Structure, Name and Data |
|---|---|---|---|
| | | | Hz, 1H), 4.16 (d, J = 5.9 Hz, 2H), 3.13 (s, 3H), 2.93 (q, J = 6.1 Hz, 2H), 2.33 (s, 3H), 2.06-1.93 (m, 2H), 1.50-1.37 (m, 2H), 1.34-1.20 (m, 2H), 1.18-1.01 (m, 2H). |
| 265 | N-methylpyridin-4-amine | 2.7 | 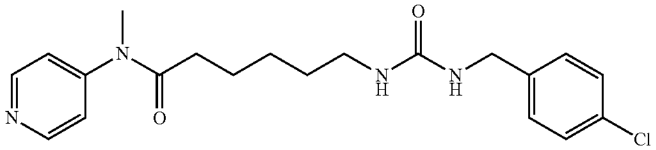 [SMILES: CN(C(=O)CCCCCNC(=O)NCc1ccc(Cl)cc1)c1ccncc1] 6-(3-(4-chlorobenzyl)ureido)-N-methyl-N-(pyridin-4-yl)hexanamide. LRMS (APCI) m/z 389.1 (M + H). $^{1}H$ NMR (400 MHz, DMSO-$d_6$) δ 8.83-8.45 (m, 2H), 7.42 (d, J = 4.7 Hz, 2H), 7.39-7.31 (m, 2H), 7.29-7.20 (m, 2H), 6.30 (t, J = 6.1 Hz, 1H), 5.91 (t, J = 5.8 Hz, 1H), 4.17 (d, J = 6.0 Hz, 2H), 3.24 (s, 3H), 2.96 (q, J = 6.6 Hz, 2H), 2.28 (t, J = 7.4 Hz, 2H), 1.50 (p, J = 7.5 Hz, 2H), 1.31 (p, J = 7.0 Hz, 2H), 1.26-1.13 (m, 2H). |
| 266 | N,2-dimethyl aniline | 2.7 | 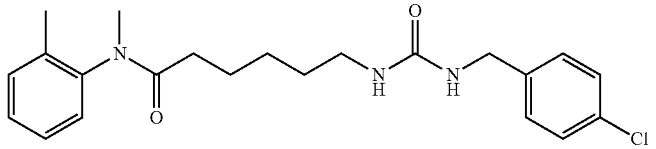 [SMILES: Cc1ccccc1N(C)C(=O)CCCCCNC(=O)NCc1ccc(Cl)cc1] 6-(3-(4-chlorobenzyl)ureido)-N-methyl-N-(o-tolyl)hexanamide. LRMS (APCI) m/z 402.1 (M + H). $^{1}H$ NMR (400 MHz, DMSO-$d_6$) δ 7.39-7.33 (m, 3H), 7.31-7.27 (m, 2H), 7.26-7.20 (m, 3H), 6.28 (t, J = 6.1 Hz, 1H), 5.88 (t, J = 5.7 Hz, 1H), 4.16 (d, J = 6.1 Hz, 2H), 3.05 (s, 3H), 2.92 (q, J = 6.6 Hz, 2H), 2.16 (s, 3H), 1.83 (ddt, J = 55.8, 15.2, 7.3 Hz, 2H), 1.42 (p, J = 7.5 Hz, 2H), 1.24 (dq, J = 14.4, 6.8 Hz, 2H), 1.09 (ddd, J = 12.1, 9.1, 5.3 Hz, 2H). |
| 267 | N-methyl-1-(m-tolyl) methanamine | 2.7 | 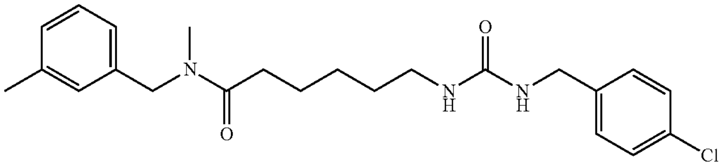 [SMILES: Cc1cccc(CN(C)C(=O)CCCCCNC(=O)NCc2ccc(Cl)cc2)c1] 6-(3-(4-chlorobenzyl)ureido)-N-methyl-N-(3-methylbenzyl)hexanamide. LRMS (APCI) m/z 416.2 (M + H). $^{1}H$ NMR (400 MHz, DMSO-$d_6$) δ 7.41-7.31 (m, 2H), 7.31-7.16 (m, 3H), 7.08 (dd, J = 12.9, 7.5 Hz, 1H), 7.03-6.90 (m, 2H), 6.40-6.24 (m, 1H), 6.00-5.85 (m, 1H), 4.53 (s, 1H), 4.46 (s, 1H), 4.17 (t, J = 4.6 Hz, 2H), 2.99 (dq, J = 13.5, 6.1 Hz, 2H), 2.89 (s, 2H), 2.80 (s, 1H), 2.41-2.32 (m, 2H), 2.29 (d, J = 7.4 Hz, 3H), 1.52 (dp, J = 15.1, 7.4 Hz, 2H), 1.45-1.16 (m, 4H). |
| 268 | N-methylaniline | 2.7 | 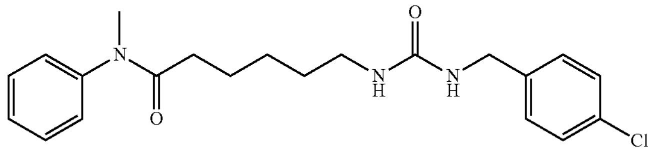 6-(3-(4-chlorobenzyl)ureido)-N-methyl-N-phenylhexanamide. LRMS (APCI) m/z 388.2 (M + H). $^{1}H$ NMR (400 MHz, DMSO-$d_6$) δ 7.45 (t, J = 7.5 Hz, 2H), 7.33 (dd, J = 17.8, 8.0 Hz, 5H), 7.24 (d, J = 8.3 Hz, 2H), 6.28 (t, J = 6.1 Hz, 1H), |

-continued

| Compound No. | Amine | Intermediate | Structure, Name and Data |
|---|---|---|---|
| | | | 5.93-5.79 (m, 1H), 4.16 (d, J = 5.9 Hz, 2H), 3.16 (d, J = 8.2 Hz, 3H), 2.93 (q, J = 6.5 Hz, 2H), 2.10-1.91 (m, 2H), 1.51-1.35 (m, 2H), 1.34-1.18 (m, 2H), 1.18-1.03 (m, 2H). |
| 269 | N-methyl-1-phenylmethanamine | 2.7 | 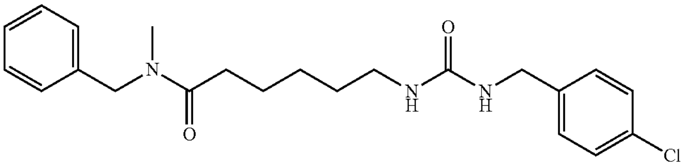 [SMILES: CN(Cc1ccccc1)C(=O)CCCCCNC(=O)NCc1ccc(Cl)cc1] N-benzyl-6-(3-(4-chlorobenzyl)ureido)-N-methylhexanamide. LRMS (APCI) m/z 402.2 (M + H). $^1$H NMR (400 MHz, DMSO-$d_6$) δ 7.43-7.29 (m, 4H), 7.26 (dq, J = 7.5, 4.6, 3.0 Hz, 3H), 7.19 (t, J = 7.1 Hz, 2H), 6.31 (q, J = 6.5 Hz, 1H), 5.93 (dt, J = 13.1, 5.7 Hz, 1H), 4.57 (s, 1H), 4.50 (s, 1H), 4.18 (dd, J = 6.1, 3.7 Hz, 2H), 3.06-2.93 (m, 2H), 2.90 (s, 2H), 2.81 (s, 1H), 2.34 (dt, J = 16.2, 7.4 Hz, 2H), 1.52 (dp, J = 15.2, 7.5 Hz, 2H), 1.33 (dddd, J = 31.9, 28.3, 17.2, 7.0 Hz, 4H). |
| 270 | N-methylpyridin-3-amine | 2.7 | 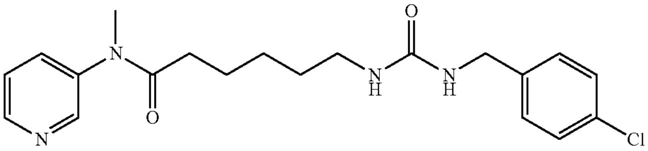 [SMILES: CN(C(=O)CCCCCNC(=O)NCc1ccc(Cl)cc1)c1cccnc1] 6-(3-(4-chlorobenzyl)ureido)-N-methyl-N-(pyridin-3-yl)hexanamide. LRMS (APCI) m/z 389.1 (M + H). $^1$H NMR (400 MHz, DMSO-$d_6$) δ 8.62-8.50 (m, 2H), 7.84 (d, J = 8.3 Hz, 1H), 7.51 (dd, J = 8.1, 4.8 Hz, 1H), 7.36 (d, J = 8.4 Hz, 2H), 7.24 (d, J = 8.3 Hz, 2H), 6.29 (s, 1H), 5.90 (s, 1H), 4.17 (d, J = 5.2 Hz, 2H), 3.19 (d, J = 12.0 Hz, 4H), 2.96 (d, J = 17.7 Hz, 2H), 2.20 (t, J = 7.4 Hz, 1H), 1.49 (dd, J = 15.0, 7.8 Hz, 2H), 1.36 (q, J = 7.2 Hz, 1H), 1.27 (t, J = 7.7 Hz, 2H), 1.15 (dt, J = 13.7, 5.5 Hz, 1H). |
| 271 | N-methylpyridin-2-amine | 2.7 | 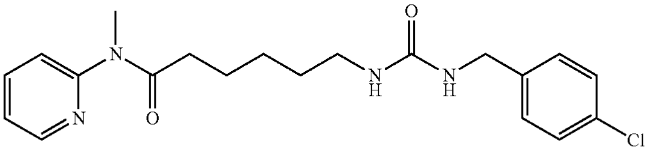 6-(3-(4-chlorobenzyl)ureido)-N-methyl-N-(pyridin-2-yl)hexanamide. LRMS (APCI) m/z 389.1 (M + H). $^1$H NMR (400 MHz, DMSO-$d_6$) δ 8.48 (dd, J = 4.9, 1.8 Hz, 1H), 7.88 (td, J = 7.8, 2.0 Hz, 1H), 7.48 (d, J = 8.1 Hz, 1H), 7.36 (d, J = 8.3 Hz, 2H), 7.30 (dd, J = 7.4, 4.9 Hz, 1H), 7.25 (d, J = 8.2 Hz, 2H), 6.29 (t, J = 6.2 Hz, 1H), 5.90 (t, J = 5.6 Hz, 1H), 4.17 (d, J = 5.8 Hz, 2H), 3.25 (s, 3H), 2.95 (q, J = 6.5 Hz, 2H), 2.26 (t, J = 7.4 Hz, 2H), 1.49 (p, J = 7.4 Hz, 2H), 1.29 (h, J = 8.1, 7.5 Hz, 2H), 1.18 (q, J = 8.0 Hz, 2H). |
| 272 | 2-fluoroaniline | 2.7 | 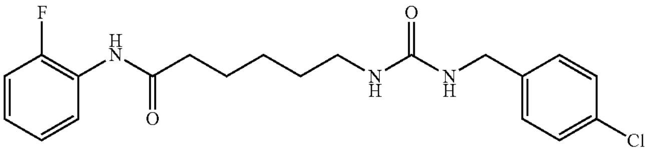 6-(3-(4-chlorobenzyl)ureido)-N-(2-fluorophenyl)hexanamide. LRMS (APCI) m/z 392.1 (M + H). $^1$H NMR (400 MHz, DMSO-$d_6$) δ 9.64 (s, 1H), 7.92-7.80 (m, 1H), 7.36 (d, J = 8.3 Hz, 2H), 7.25 (d, J = 8.4 Hz, 3H), 7.14 (dd, J = |

-continued

| Compound No. | Amine | Intermediate | Structure, Name and Data |
|---|---|---|---|
| | | | 6.6, 3.4 Hz, 2H), 6.32 (t, J = 6.1 Hz, 1H), 5.96 (t, J = 5.7 Hz, 1H), 4.18 (d, J = 6.0 Hz, 2H), 3.01 (q, J = 6.6 Hz, 2H), 2.37 (t, J = 7.4 Hz, 2H), 1.59 (p, J = 7.4 Hz, 2H), 1.41 (p, J = 6.9 Hz, 2H), 1.30 (h, J = 7.5, 6.3 Hz, 2H). |
| 273 | [1,1'-biphenyl]-2-amine | 2.7 | 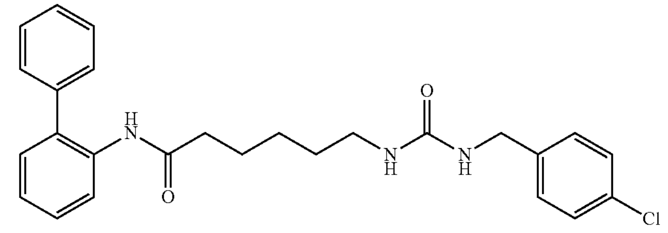 [SMILES: O=C(CCCCCNC(=O)NCc1ccc(Cl)cc1)Nc1ccccc1-c1ccccc1] N-([1,1'-biphenyl]-2-yl)-6-(3-(4-chlorobenzyl)ureido)hexanamide. LRMS (APCI) m/z 450.1 (M + H). $^1$H NMR (400 MHz, DMSO-$d_6$) δ 9.17 (s, 1H), 7.43 (t, J = 8.0 Hz, 3H), 7.40-7.22 (m, 10H), 6.31 (t, J = 6.0 Hz, 1H), 5.93 (t, J = 5.7 Hz, 1H), 4.18 (d, J = 6.0 Hz, 2H), 2.98 (q, J = 6.6 Hz, 2H) 2.14 (t, J = 7.3 Hz, 2H), 1.47 (t, J = 7.6 Hz, 2H), 1.41-1.29 (m, 2H), 1.24-1.14 (m, 2H). |
| 274 | 2-fluoro-N-methylaniline | 2.7 | 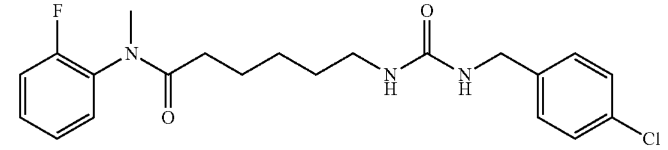 [SMILES: CN(C(=O)CCCCCNC(=O)NCc1ccc(Cl)cc1)c1ccccc1F] 6-(3-(4-chlorobenzyl)ureido)-N-(2-fluorophenyl)-N-methylhexanamide. LRMS (APCI) m/z 406.1 (M + H). $^1$H NMR (400 MHz, DMSO-$d_6$) δ 7.46 (dt, J = 20.7, 10.4 Hz, 2H), 7.35 (d, J = 8.2 Hz, 3H), 7.33-7.18 (m, 3H), 6.28 (s, 1H), 5.89 (d, J = 6.1 Hz, 1H), 4.16 (d, J = 5.7 Hz, 2H), 3.11 (s, 3H), 2.92 (d, J = 6.1 Hz, 2H), 2.06-1.85 (m, 2H), 1.43 (p, J = 7.5 Hz, 2H), 1.24 (q, J = 7.4 Hz, 2H), 1.12 (q, J = 7.8 Hz, 2H). |
| 278 | 6-methylpyridin-3-amine | 2.7 | 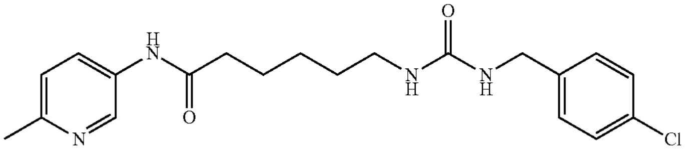 [SMILES: Cc1ccc(NC(=O)CCCCCNC(=O)NCc2ccc(Cl)cc2)cn1] 6-(3-(4-chlorobenzyl)ureido)-N-(6-methylpyridin-3-yl)hexanamide. LRMS (APCI) m/z 389.0 (M + H). $^1$H NMR (400 MHz, DMSO-$d_6$) δ 9.97 (s, 1H), 8.59 (d, J = 2.5 Hz, 1H), 7.91 (dd, J = 8.6, 2.6 Hz, 1H), 7.36 (d, J = 8.1 Hz, 2H), 7.25 (d, J = 8.1 Hz, 2H), 7.17 (d, J = 8.4 Hz, 1H), 6.31 (t, J = 6.1 Hz, 1H), 5.95 (t, J = 5.8 Hz, 1H), 4.17 (d, J = 6.1 Hz, 2H), 3.00 (q, J = 6.5 Hz, 2H), 2.40 (s, 3H), 2.31 (t, J = 7.5 Hz, 2H), 1.59 (p, J = 7.5 Hz, 2H), 1.40 (p, J = 7.0 Hz, 2H), 1.35-1.22 (m, 2H). |
| 284 | 4-fluoroaniline | 2.7 | 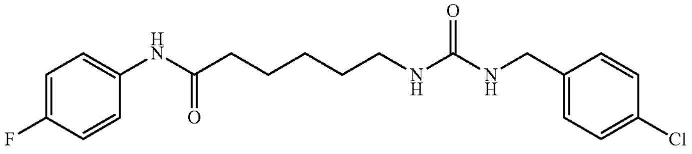 [SMILES: O=C(CCCCCNC(=O)NCc1ccc(Cl)cc1)Nc1ccc(F)cc1] 6-(3-(4-chlorobenzyl)ureido)-N-(4-fluorophenyl)hexanamide. LRMS (APCI) m/z 392.0 (M + H). $^1$H NMR (400 MHz, DMSO-$d_6$) δ 9.91 (s, 1H), 7.60 (t, J = 7.2 Hz, 2H), 7.42-7.30 |

-continued

| Compound No. | Amine | Intermediate | Structure, Name and Data |
| --- | --- | --- | --- |
| | | | (m, 2H), 7.25 (d, J = 7.2 Hz, 2H), 7.12 (t, J = 8.7 Hz, 2H), 6.31 (s, 1H), 5.95 (s, 1H), 4.25-4.09 (m, 2H), 3.00 (d, J = 6.7 Hz, 2H), 2.29 (t, J = 7.5 Hz, 2H), 1.65-1.52 (m, 2H), 1.49-1.34 (m, 2H), 1.34-1.19 (m, 2H). |
| 285 | 3-fluoroaniline | 2.7 | 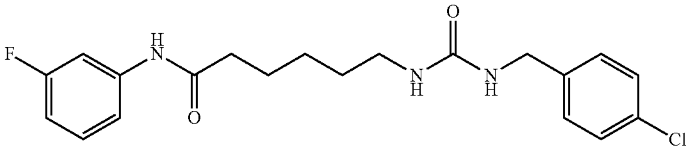 [SMILES: O=C(CCCCCNC(=O)NCc1ccc(Cl)cc1)Nc1cccc(F)c1] 6-(3-(4-chlorobenzyl)ureido)-N-(3-fluorophenyl)hexanamide. LRMS (APCI) m/z 391.9 (M + H). $^1$H NMR (400 MHz, DMSO-$d_6$) δ 10.08 (s, 1H), 7.61 (dd, J = 12.0, 2.3 Hz, 1H), 7.36 (d, J = 7.4 Hz, 2H), 7.34-7.22 (m, 4H), 6.85 (t, J = 8.5 Hz, 1H), 6.31 (d, J = 6.8 Hz, 1H), 5.95 (s, 1H), 4.17 (d, J = 5.8 Hz, 2H), 3.00 (q, J = 5.9 Hz, 2H), 2.31 (t, J = 7.4 Hz, 2H), 1.59 (p, J = 7.6 Hz, 2H), 1.39 (q, J = 7.3 Hz, 2H), 1.29 (q, J = 7.8 Hz, 2H). |

Example 3

Preparation of 1-(2-((2-chlorophenyl)sulfonyl)-2-azaspiro[3.3]heptan-6-yl)-3-(4-methoxybenzyl)urea (Compound 116)

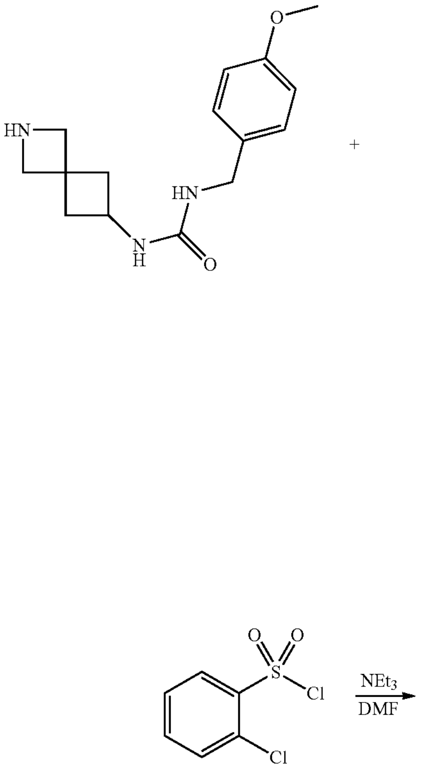

-continued

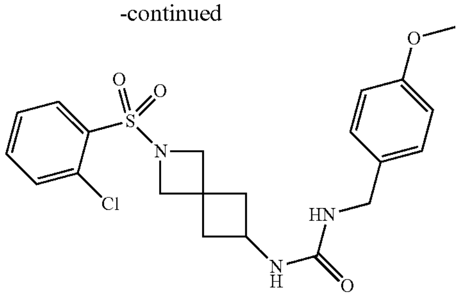

1-(2-((2-chlorophenyl)sulfonyl)-2-azaspiro[3.3]heptan-6-yl)-3-(4-methoxybenzyl)urea 2-Chlorobenzenesulfonyl chloride (114 mg, 0.544 mmol, 1.5 equiv) was added to a stirring solution of 1-(4-methoxybenzyl)-3-(2-azaspiro[3.3]heptan-6-yl)urea (100 mg, 0.363 mmol, 1 equiv) and $NEt_3$ (147 μL, 0.770 mmol, 3 equiv) in DMF (1 mL) at rt. After 2 h, the reaction was diluted with MeOH to a total volume of 1.8 mL, filtered through a 0.4 μm syringe filter, and product isolated by reverse phase HPLC (0→70% MeCN/H2O w/0.1% formic acid) as a white solid (21 mg, 18%). LRMS (APCI) m/z 450 (M+H). $^1$H NMR (400 MHz, DMSO-$d_6$) δ 7.97 (dt, J=8.0, 1.8 Hz, 1H), 7.76-7.68 (m, 2H), 7.59 (t, J=7.4 Hz, 1H), 7.13 (d, J=8.3 Hz, 2H), 6.86 (d, J=8.5 Hz, 2H), 6.17 (t, J=5.9 Hz, 1H), 6.12 (d, J=7.9 Hz, 1H), 4.10 (dd, J=16.2, 6.9 Hz, 2H), 3.97 (s, 1H), 3.94 (s, 2H), 3.87 (s, 1H), 3.83 (s, 1H), 3.72 (s, 2H), 2.48-2.38 (m, 1H), 2.33 (ddd, J=10.2, 7.7, 3.0 Hz, 2H), 2.27-2.15 (m, 1H), 1.93 (td, J=8.9, 3.0 Hz, 1H).

Compounds in the following table were prepared in a similar manner as Compound 116, using the intermediates and reagents as listed.

| Compound No. | Amine | Intermediate | Structure, Name and Data |
|---|---|---|---|
| 117 | (2-chlorophenyl)methanesulfonyl chloride | 3.2 | 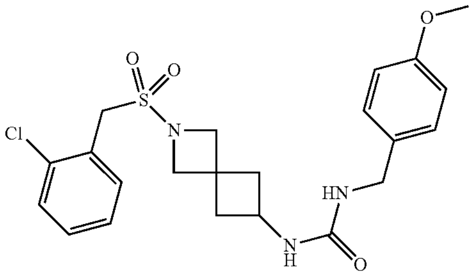 [SMILES: COc1ccc(CNC(=O)NC2CC3(C2)CN(S(=O)(=O)Cc2ccccc2Cl)C3)cc1] 1-(2-((2-chlorobenzyl)sulfonyl)-2-azaspiro[3.3]heptan-6-yl)-3-(4-methoxybenzyl)urea. LRMS (APCI) m/z 464 (M + H). $^1$H NMR (400 MHz, DMSO-$d_6$) δ 7.60 - 7.47 (m, 2H), 7.40 (dd, J = 6.6, 3.2 Hz, 2H), 7.15 (d, J = 8.3 Hz, 2H), 6.87 (d, J = 8.5 Hz, 2H), 6.19 (t, J = 6.0 Hz, 1H), 6.14 (d, J = 7.8 Hz, 1H), 4.59 (s, 2H), 4.10 (d, J = 5.9 Hz, 2H), 4.00 - 3.91 (m, 1H), 3.89 (s, 2H), 3.79 (s, 2H), 3.73 (s, 3H), 2.44 (t, J = 10.0 Hz, 2H), 1.98 (t, J = 10.4 Hz, 2H). |
| 118 | 2-(2-chlorophenyl)ethane-1-sulfonyl chloride | 3.2 | 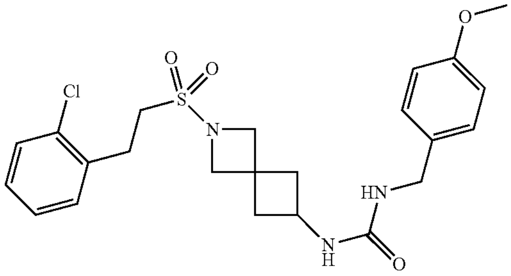 [SMILES: COc1ccc(CNC(=O)NC2CC3(C2)CN(S(=O)(=O)CCc2ccccc2Cl)C3)cc1] 1-(2-((2-chlorophenethyl)sulfonyl)-2-azaspiro[3.3]heptan-6-yl)-3-(4-methoxybenzyl)urea. LRMS (APCI) m/z 478 (M + H). $^1$H NMR (400 MHz, DMSO-$d_6$) δ 7.53 - 7.43 (m, 2H), 7.37 - 7.24 (m, 2H), 7.15 (d, J = 8.3 Hz, 2H), 6.86 (d, J = 8.4 Hz, 2H), 6.16 (dd, J = 16.5, 7.0 Hz, 2H), 4.09 (d, J = 5.9 Hz, 2H), 3.91 (s, 3H), 3.80 (s, 2H), 3.72 (d, J = 0.8 Hz, 3H), 3.37 (d, J = 7.9 Hz, 2H), 3.16 - 3.01 (m, 2H), 2.43 (t, J = 10.1 Hz, 2H), 1.97 (dd, J = 12.0, 8.7 Hz, 2H). |
| 130 | (1S,4R)-bicyclo[2.2.1]heptane-2-sulfonyl chloride | 3.2 | 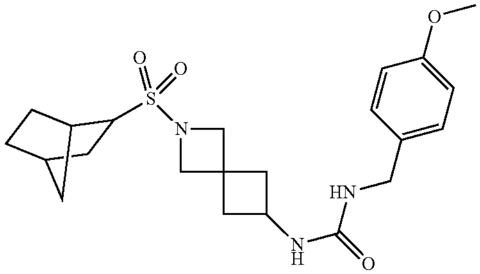 [SMILES: COc1ccc(CNC(=O)NC2CC3(C2)CN(S(=O)(=O)C2CC4CCC2C4)C3)cc1] 1-(2-(bicyclo[2.2.1]heptan-2-ylsulfonyl)-2-azaspiro[3.3]heptan-6-yl)-3-(4-methoxybenzyl)urea. LRMS (APCI) m/z 434 (M + H). $^1$H NMR (400 MHz, DMSO-$d_6$) δ 7.07 (d, J = 8.3 Hz, 2H), 6.79 (d, J = 8.3 Hz, 2H), 6.14 - 6.01 (m, 2H), 4.02 (d, J = 5.9 Hz, 2H), 3.86 (q, J = 8.0 Hz, 1H), 3.78 (s, 2H), 3.67 (d, J = 2.7 Hz, 2H), 3.65 (s, 3H), 3.00 (dd, J = 8.8, 5.9 Hz, 1H), 2.46 (s, 1H), 2.35 (t, J = 10.0 Hz, 2H), 2.23 (s, 1H), 1.90 (dd, J = 12.2, 8.7 Hz, 2H), 1.65 (d, J = 12.7 Hz, 1H), |

-continued

| Compound No. | Amine | Intermediate | Structure, Name and Data |
|---|---|---|---|
| | | | 1.54 (d, J = 9.4 Hz, 2H), 1.44 (d, J = 9.8 Hz, 2H), 1.22 (t, J = 9.3 Hz, 1H), 1.14-0.99 (m, 2H). |
| 131 | methyl 4-(chlorosul-fonyl)cyclo-hexane-1-carboxylate | 3.2 | 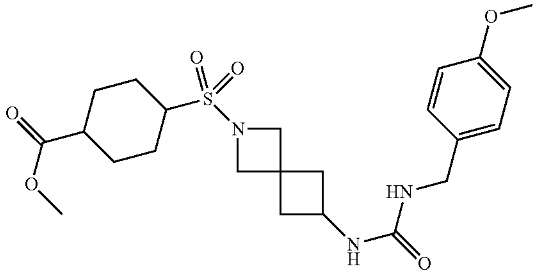 [SMILES: COC(=O)C1CCC(S(=O)(=O)N2CC3(CC(NC(=O)NCc4ccc(OC)cc4)C3)C2)CC1] methyl 4-((6-(3-(4-methoxybenzyl)ureido)-2-azaspiro[3.3]heptan-2-yl)sulfonyl)cyclohexane-1-carboxylate. LRMS (APCI) m/z 480 (M + H). $^1$H NMR (400 MHz, DMSO-$d_6$) δ 7.15 (d, J = 8.3 Hz, 2H), 6.87 (d, J = 8.5 Hz, 2H), 6.24 - 6.05 (m, 2H), 4.09 (d, J = 5.9 Hz, 2H), 3.94 (h, J = 8.1 Hz, 1H), 3.80 (s, 2H), 3.72 (s, 3H), 3.69 (s, 2H), 3.62 (s, 3H), 3.49 (dt, J = 12.6, 3.9 Hz, 2H), 2.84 (td, J = 12.0, 2.7 Hz, 3H), 2.42 (ddd, J = 10.1, 7.7, 3.0 Hz, 2H), 1.97 (td, J = 8.9, 3.0 Hz, 2H), 1.88 (dd, J = 13.7, 3.6 Hz, 2H), 1.52 (qd, J = 11.5, 4.1 Hz, 3H). |
| 120 | phenylmeth-anesulfo-nyl chloride | 3.4 | 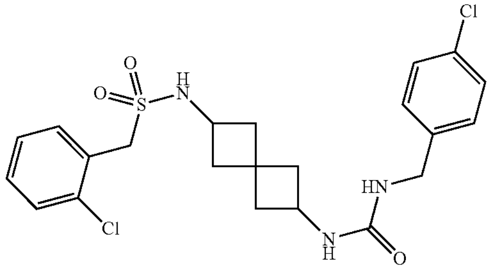 [SMILES: O=C(NCc1ccc(Cl)cc1)NC1CC2(C1)CC(NS(=O)(=O)Cc1ccccc1Cl)C2] N-(6-(3-(4-chlorobenzyl)ureido)spiro[3.3]heptan-2-yl)-1-(2-chlorophenyl)methanesulfonamide. LRMS (APCI) m/z 482 (M + H). $^1$H NMR (400 MHz, Methanol-$d_4$) δ 7.59 - 7.53 (m, 1H), 7.51 - 7.45 (m, 1H), 7.41 -7.34 (m, 2H), 7.34 - 7.23 (m, 4H), 4.48 (s, 2H), 4.28 (s, 2H), 4.01 (p, J = 8.0 Hz, 1H), 3.62 (p, J = 8.3 Hz, 1H), 2.38 (ddd, J = 13.0, 10.9, 5.4 Hz, 2H), 2.22 (dddd, J = 25.0, 12.4, 7.6, 5.5 Hz, 2H), 1.99 (td, J = 11.6, 9.0 Hz, 2H), 1.85 (dd, J = 11.1, 8.6 Hz, 2H). |
| 121 | benzenesul-fonyl chloride | 3.4 | 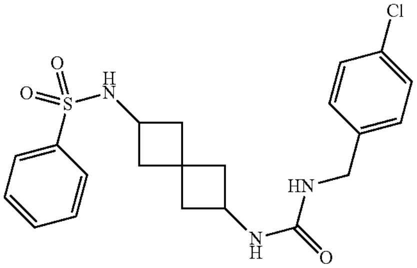 [SMILES: O=C(NCc1ccc(Cl)cc1)NC1CC2(C1)CC(NS(=O)(=O)c1ccccc1)C2] 1-(2-((2-chlorophenyl)sulfonyl)-2-azaspiro[3.3]heptan-6-yl)-3-(4-methoxybenzyl)urea. LRMS (APCI) m/z 434 (M + H). $^1$H NMR (400 MHz, DMSO-$d_6$) |

-continued

| Compound No. | Amine | Intermediate | Structure, Name and Data |
|---|---|---|---|
| | | | δ 7.88 (d, J = 8.6 Hz, 1H), 7.78 (dd, J = 7.0, 1.8 Hz, 2H), 7.65 - 7.55 (m, 3H), 7.38 - 7.28 (m, 3H), 7.24 - 7.18 (m, 2H), 6.23 (s, 1H), 6.12 (s, 1H), 4.13 (s, 2H), 3.50 (q, J = 8.1 Hz, 1H), 2.22 (dt, J = 11.8, 6.1 Hz, 1H), 2.12 - 1.97 (m, 3H), 1.87 (dt, J = 12.2, 6.7 Hz, 1H), 1.79 - 1.63 (m, 3H). LRMS (APCI) m/z 434 (M + H). |
| 213 | pyridine-3-sulfonyl chloride | 3.4 | 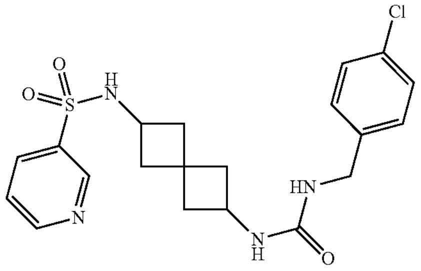 [SMILES: O=C(NCc1ccc(Cl)cc1)NC1CC2(C1)CC(NS(=O)(=O)c1cccnc1)C2] N-(6-(3-(4-chlorobenzyl)ureido)spiro[3.3]heptan-2-yl)pyridine-3-sulfonamide. LRMS (APCI) m/z 435 (M + H). $^1$H NMR (400 MHz, DMSO-$d_6$) δ 8.93 (d, J = 2.3 Hz, 1H), 8.82 (d, J = 4.8 Hz, 1H), 8.14 (t, J = 8.5 Hz, 2H), 7.64 (dd, J = 8.0, 4.9 Hz, 1H), 7.35 (d, J = 8.2 Hz, 2H), 7.22 (d, J = 8.2 Hz, 2H), 6.23 (t, J = 6.1 Hz, 1H), 6.12 (d, J = 8.0 Hz, 1H), 4.13 (d, J = 5.9 Hz, 2H), 3.83 (q, J = 8.0 Hz, 1H), 3.57 (q, J = 8.1 Hz, 1H), 2.31 - 2.19 (m, 1H), 2.16 - 2.00 (m, 2H), 1.91 (dt, J = 12.1, 6.3 Hz, 1H), 1.71 (p, J = 9.5 Hz, 4H). |
| 216 | 2-chlorobenzenesulfonyl chloride | 3.1 | 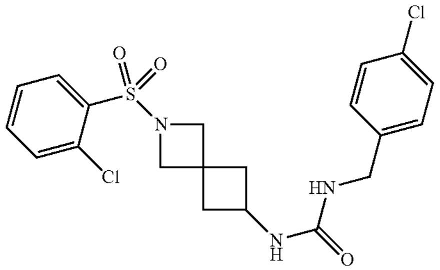 [SMILES: O=C(NCc1ccc(Cl)cc1)NC1CC2(C1)CN(S(=O)(=O)c1ccccc1Cl)C2] 1-(4-chlorobenzyl)-3-(2-((2-chlorophenyl)sulfonyl)-2-azaspiro[3.3]heptan-6-yl)urea. LRMS (APCI) m/z 454 (M + H). $^1$H NMR (400 MHz, DMSO-$d_6$) δ 7.96 (dd, J = 7.9, 1.5 Hz, 1H), 7.77 - 7.66 (m, 2H), 7.58 (ddd, J = 8.5, 6.9, 1.8 Hz, 1H), 7.39 - 7.31 (m, 2H), 7.25- 7.20 (m, 2H), 6.30 (t, J = 6.1 Hz, 1H), 6.21 (d, J = 7.9 Hz, 1H), 4.14 (d, J = 6.0 Hz, 2H), 4.09 (q, J = 5.3 Hz, 1H), 3.93 (s, 2H), 3.83 (s, 2H), 2.33 (ddd, J = 10.1, 7.6, 3.0 Hz, 2H), 1.94 (td, J = 8.9, 3.0 Hz, 2H). |
| 217 | 3-chlorobenzenesulfonyl chloride | 3.1 | 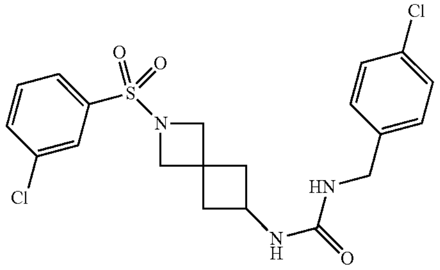 [SMILES: O=C(NCc1ccc(Cl)cc1)NC1CC2(C1)CN(S(=O)(=O)c1cccc(Cl)c1)C2] |

-continued

| Compound No. | Amine | Intermediate | Structure, Name and Data |
|---|---|---|---|
| | | | 1-(4-chlorobenzyl)-3-(2-((3-chlorophenyl)sulfonyl)-2-azaspiro[3.3]heptan-6-yl)urea. LRMS (APCI) m/z 454 (M + H). $^1$H NMR (400 MHz, DMSO-$d_6$) δ 7.87 (dt, J = 8.0, 1.5 Hz, 1H), 7.83 - 7.77 (m, 2H), 7.73 (t, J = 7.8 Hz, 1H), 7.39 - 7.32 (m, 2H), 7.25 - 7.18 (m, 2H), 6.27 (t, J = 6.1 Hz, 1H), 6.15 (d, J = 7.8 Hz, 1H), 4.12 (d, J = 6.0 Hz, 2H), 3.88 - 3.74 (m,3H), 3.67 (s, 2H), 2.13 (ddd, J = 10.1, 7.6, 3.0 Hz, 2H), 1.80 (td, J = 8.9, 3.0 Hz, 2H). |
| 218 | 2-methoxy-benzenesul-fonyl chloride | 3.1 | 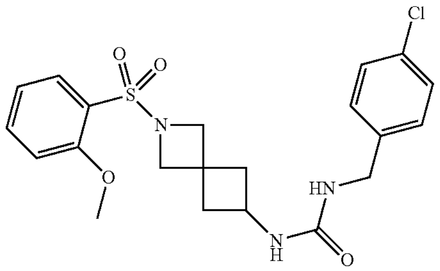 [SMILES: COc1ccccc1S(=O)(=O)N1CC2(CC(NC(=O)NCc3ccc(Cl)cc3)C2)C1] 1-(4-chlorobenzyl)-3-(2-((2-methoxyphenyl)sulfonyl)-2-azaspiro[3.3]heptan-6-yl)urea. LRMS (APCI) m/z 450 (M + H). $^1$H NMR (400 MHz, DMSO-$d_6$) δ 7.72 (dd, J = 7.8, 1.7 Hz, 1H), 7.67 (ddd, J = 8.8, 7.4, 1.8 Hz, 1H), 7.37 - 7.33 (m, 2H), 7.29 (d, J = 8.4 Hz, 1H), 7.25- 7.20 (m, 2H), 7.12 (td, J = 7.6, 1.0Hz,1H), 6.29 (t, J = 6.1 Hz, 1H), 6.19 (d, J = 7.9 Hz, 1H), 4.14 (d, J = 6.0 Hz, 2H), 4.09 (q, J = 5.4 Hz, 1H), 3.91 (s, 3H), 3.86 (s, 2H), 3.76 (s, 2H), 2.28 (ddd, J = 10.1, 7.7, 3.0 Hz, 2H), 1.90 (td, J = 8.9, 3.0 Hz, 2H). |

Example 4

Preparation of tert-butyl 1-((3-(4-chlorobenzyl) ureido)methyl)-6-azaspiro[2.5]octane-6-carboxylate (Compound 27)

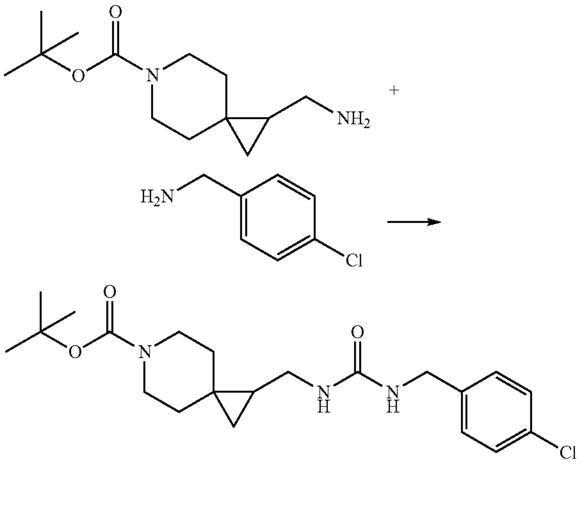

Step 1. tert-butyl 1-((3-(4-chlorobenzyl)ureido) methyl)-6-azaspiro[2.5]octane-6-carboxylate To a room temperature solution of N,N'-disuccinimidyl carbonate (0.160 mg, 0.62 mmol, 1.0 equiv) in acetonitrile (10 mL) was added tert-butyl 1-(aminomethyl)-6-azaspiro [2.5]octane-6-carboxylate (0.15 g, 0.62 mmol, 1.0 equiv) followed by pyridine (0.06 mL, 0.62 mmol, 1.0 equiv) in a dropwise fashion. After 20 minutes, a solution 4-chloro benzyl amine (88 mg, 0.62 mmol, 1.0 equiv) in acetonitrile (2 mL) was added followed by N,N-diisopropylethylamine (0.11 mL, 1.24 mmol, 2.0 equiv). The resulting mixture was stirred at room temperature for approximately one hour then concentrated to dryness. Resultant mixture was diluted with ethyl acetate (50 mL) and extracted with water (2×15 mL) and brine (1×15 mL). The organic phase was dried to a viscous oil which was purified by reverse phase chromatography and afforded the desired product as a white foam (148 mg, 0.36 mmol, 58.1% yield). LCMS-APCI (POS.) m/z: 308 $(M-Boc+H)^+$. 1H NMR (400 MHz, DMSO-$d_6$) δ 7.45-7.32 (m, 2H), 7.25 (d, J=8.5 Hz, 2H), 6.37 (t, J=6.1 Hz, 1H), 5.94 (t, J=5.4 Hz, 1H), 4.18 (d, J=6.0 Hz, 2H), 3.43 (dddd, J=19.2, 12.7, 6.6, 3.8 Hz, 2H), 3.17 (dt, J=13.8, 5.9 Hz, 3H), 2.90 (ddd, J=13.7, 8.5, 5.2 Hz, 1H), 1.51 (ddd, J=12.3, 10.2, 6.2 Hz, 1H), 1.40 (s, 9H), 1.31 (ddd, J=17.2, 7.1, 3.5 Hz, 2H), 1.14 (ddd, J=13.1, 6.5, 3.3 Hz, 1H), 0.79 (tt, J=8.5, 6.2 Hz, 1H), 0.45 (dd, J=8.5, 4.3 Hz, 1H), 0.16 (t, J=4.8 Hz, 1H).

Compounds in the following table were prepared in a similar manner as Compound 27, using the intermediates and reagents as listed.

| Compound No. | Reagent I | Reagent II | Structure, Name and Data |
|---|---|---|---|
| 2 | tert-butyl (6-aminospiro[3.3] heptan-2-yl)carbamate | 4-(aminomethyl) benzamide | 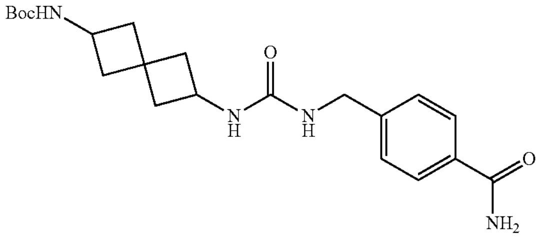 [SMILES: CC(C)(C)OC(=O)NC1CC2(CC(NC(=O)NCc3ccc(C(N)=O)cc3)C2)C1] tert-butyl (6-(3-(4-carbamoylbenzyl)ureido)spiro[3.3]heptan-2-yl)carbamate. LCMS-ESI (POS.) m/z: 303 (M-Boc + H)+. 1H NMR (400 MHz, DMSO-$d_6$) δ 7.90 (s, 1H), 7.85-7.75 (m, 2H), 7.38-7.19 (m, 3H), 7.04 (d, J = 8.1 Hz, 1H), 6.27 (t, J = 6.0 Hz, 1H), 6.18 (d, J = 8.1 Hz, 1H), 4.21 (d, J = 5.9 Hz, 2H), 3.92 (h, J = 8.2 Hz, 1H), 3.79 (h, J = 8.2 Hz, 1H), 2.38-2.18 (m, 2H), 2.18-1.98 (m, 2H), 1.92-1.81 (m, 2H), 1.77 (ddd, J = 13.8, 10.4, 8.6 Hz, 2H), 1.36 (s, 9H). |
| 3 | 4,4-dimethyl-cyclohexan-1-amine | 4-(aminomethyl) benzamide | 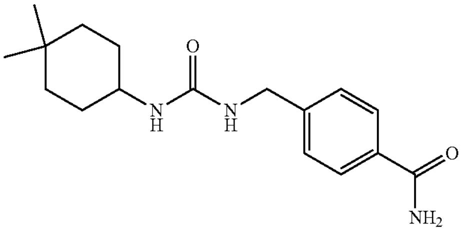 [SMILES: CC1(C)CCC(NC(=O)NCc2ccc(C(N)=O)cc2)CC1] 4-((3-(4,4-dimethylcyclohexyl)ureido)methyl)benzamide. LCMS-ESI (POS.) m/z: 304 (M + H)+. 1H NMR (400 MHz, DMSO-$d_6$) δ 7.92 (s, 1H), 7.86-7.67 (m, 2H), 7.39-7.20 (m, 3H), 6.32 (t, J = 6.1 Hz, 1H), 5.95 (d, J = 8.0 Hz, 1H), 4.23 (d, J = 6.0 Hz, 2H), 1.70-1.56 (m, 2H), 1.39-1.09 (m, 7H), 0.89 (s, 6H). |
| 4 | 3-phenylcyclo-butan-1-amine | 4-(aminomethyl) benzamide | 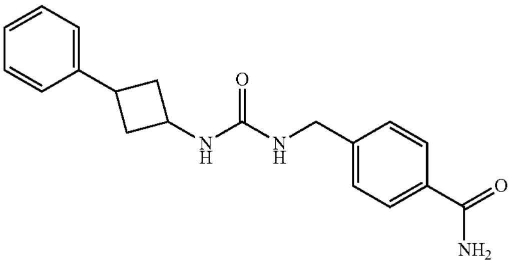 [SMILES: NC(=O)c1ccc(CNC(=O)NC2CC(c3ccccc3)C2)cc1] 4-((3-(3-phenylcyclobutyl)ureido)methyl)benzamide. LCMS-ESI (POS.) m/z: 324 (M + H)+. 1H NMR (400 MHz, DMSO-$d_6$) δ 7.91 (s, 1H), 7.86-7.73 (m, 2H), 7.41-7.25 (m, 7H), 7.23-7.11 (m, 1H), 6.48 (d, J = 7.4 Hz, 1H), 6.37 (t, J = 6.1 Hz, 1H), 4.25 (d, J = 6.0 Hz, 2H), 4.22-4.15 (m, 1H), 3.48 (tt, J = 9.7, 5.5 Hz, 1H), 2.44-2.22 (m, 4H). |

-continued

| Compound No. | Reagent I | Reagent II | Structure, Name and Data |
|---|---|---|---|
| 5 | tert-butyl 4-amino-piperidine-1-carboxylate | 4-(aminomethyl) benzamide | 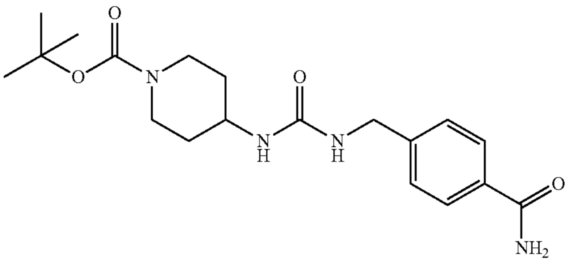 [SMILES: CC(C)(C)OC(=O)N1CCC(NC(=O)NCc2ccc(C(N)=O)cc2)CC1] tert-butyl 4-(3-(4-carbamoylbenzyl)ureido)piperidine-1-carboxylate. LCMS-ESI (POS.) m/z: 277 (M-Boc + H)+. 1H NMR (400 MHz, DMSO-d6) δ 7.91 (s, 1H), 7.86-7.69 (m, 2H), 7.30 (dd, J = 8.6, 2.1 Hz, 3H), 6.30 (t, J = 6.0 Hz, 1H), 6.11-5.93 (m, 1H), 4.24 (d, J = 6.0 Hz, 2H), 3.80 (d, J = 13.3 Hz, 2H), 3.62-3.47 (m, 1H), 2.85 (s, 2H), 1.74 (dd, J = 12.7, 3.8 Hz, 2H), 1.40 (s, 9H), 1.29-1.08 (m, 2H). |
| 6 | tert-butyl (6-aminospiro[3.3] heptan-2-yl)carbamate | pyridin-4-ylmethanamine | 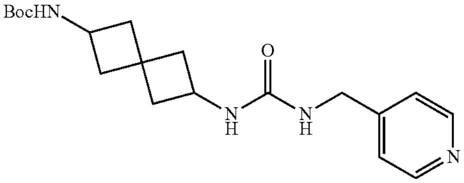 [SMILES: CC(C)(C)OC(=O)NC1CC2(CC(NC(=O)NCc3ccncc3)C2)C1] tert-butyl (6-(3-(pyridin-4-ylmethyl)ureido)spiro[3.3]heptan-2-yl)carbamate. LCMS-ESI (POS.) m/z: 361 (M + H)+. 1H NMR (400 MHz, DMSO-$d_6$) δ 8.47 (d, J = 5.4 Hz, 2H), 7.21 (d, J = 4.9 Hz, 2H), 7.04 (d, J = 8.0 Hz, 1H), 6.37 (t, J = 6.2 Hz, 1H), 6.30 (d, J = 8.0 Hz, 1H), 4.20 (d, J = 6.0 Hz, 2H), 3.92 (h, J = 8.1 Hz, 1H), 3.80 (h, J = 8.1 Hz, 1H), 2.28 (ddq, J = 22.9, 11.0, 6.0, 5.6 Hz, 2H), 2.18-2.00 (m, 2H), 1.95-1.70 (m, 4H), 1.36 (s, 9H). |
| 7 | tert-butyl (6-aminospiro[3.3] heptan-2-yl)carbamate | 4-methoxy benzyl amine | 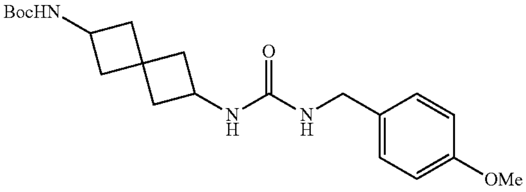 [SMILES: COc1ccc(CNC(=O)NC2CC3(C2)CC(NC(=O)OC(C)(C)C)C3)cc1] tert-butyl (6-(3-(4-methoxybenzyl)ureido)spiro[3.3]heptan-2-yl)carbamate. LCMS-ESI (POS.) m/z: 390 (M + H)+. 1H NMR (400 MHz, DMSO-$d_6$) δ 7.15 (d, J = 8.3 Hz, 2H), 7.04 (d, J = 8.1 Hz, 1H), 6.86 (d, J = 8.4 Hz, 2H), 6.17-5.99 (m, 2H), 4.09 (d, J = 5.8 Hz, 2H), 3.92 (h, J = 8.2 Hz, 1H), 3.79 (q, J = 8.1 Hz, 1H), 3.72 (s, 3H), 2.27 (qd, J = 11.4, 5.2 Hz, 2H), 2.17-2.00 (m, 2H), 1.86 (q, J = 10.1 Hz, 2H), 1.82-1.68 (m, 2H), 1.36 (s, 9H). |

-continued

| Compound No. | Reagent I | Reagent II | Structure, Name and Data |
|---|---|---|---|
| 8 | tert-butyl (6-aminospiro[3.3] heptan-2-yl)carbamate | 4-chloro benzyl amine | 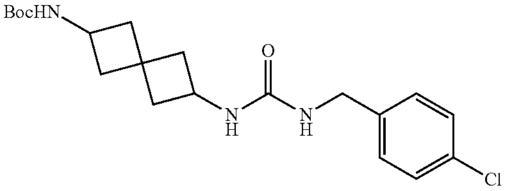 [SMILES: CC(C)(C)OC(=O)NC1CC2(CC(NC(=O)NCc3ccc(Cl)cc3)C2)C1] tert-butyl (6-(3-(4-chlorobenzyl)ureido)spiro[3.3]heptan-2-yl)carbamate. LCMS-ESI (POS.) m/z: 291 (M-Boc + H)+. 1H NMR (400 MHz, DMSO-$d_6$) δ 7.36 (d, J = 8.1 Hz, 2H), 7.24 (d, J = 8.1 Hz, 2H), 7.04 (d, J = 8.3 Hz, 1H), 6.27 (t, J = 6.1 Hz, 1H), 6.19 (d, J = 8.0 Hz, 1H), 4.15 (d, J = 6.0 Hz, 2H), 3.92 (dq, J = 17.8, 9.1, 8.7 Hz, 1H), 3.84-3.70 (m, 1H), 2.28 (ddd, J = 25.2, 14.4, 8.3 Hz, 2H), 2.09 (td, J = 15.1, 13.6, 5.8 Hz, 2H), 1.92-1.65 (m, 4H), 1.36 (s, 9H). |
| 9 | tert-butyl (6-aminospiro[3.3] heptan-2-yl)carbamate | (4-(aminomethyl) phenyl)methanol | 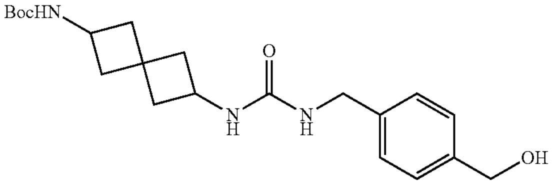 [SMILES: CC(C)(C)OC(=O)NC1CC2(CC(NC(=O)NCc3ccc(CO)cc3)C2)C1] tert-butyl (6-(3-(4-(hydroxymethyl)benzyl)ureido)spiro[3.3] heptan-2-yl)carbamate. LCMS-ESI (POS.) m/z: 390 (M + H)+. 1H NMR (400 MHz, DMSO-$d_6$) δ 7.24 (d, J = 7.8 Hz, 2H), 7.17 (d, J = 7.8 Hz, 2H), 7.04 (d, J = 8.0 Hz, 1H), 6.17 (t, J = 6.0 Hz, 1H), 6.12 (d, J = 8.0 Hz, 1H), 5.12 (t, J = 5.7 Hz, 1H), 4.46 (d, J = 5.0 Hz, 2H), 4.15 (d, J = 5.9 Hz, 2H), 3.93 (h, J = 8.0 Hz, 1H), 3.80 (p, J = 7.9 Hz, 1H), 2.27 (dt, J = 12.5, 5.6 Hz, 2H), 2.18-1.99 (m, 2H), 1.86 (q, J = 9.9 Hz, 2H), 1.80-1.65 (m, 2H), 1.36 (s, 9H). |
| 10 | tert-butyl (6-aminospiro[3.3] heptan-2-yl)carbamate | (1H-pyrazol-4-yl)methanamine | 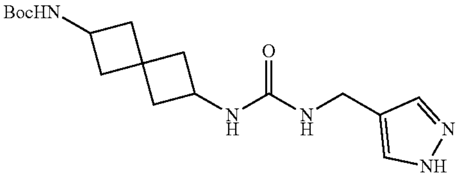 [SMILES: CC(C)(C)OC(=O)NC1CC2(CC(NC(=O)NCc3cn[nH]c3)C2)C1] tert-butyl (6-(3-((1H-pyrazol-4-yl)methyl)ureido)spiro[3.3]heptan-2-yl)carbamate. LCMS-ESI (POS.) m/z: 350 (M + H)+. 1H NMR (400 MHz, DMSO-$d_6$) δ 12.56 (br s, 1H), 7.58-7.34 (m, 2H), 7.04 (d, J = 8.1 Hz, 1H), 6.02 (d, J = 8.1 Hz, 1H), 5.89 (t, J = 5.6 Hz, 1H), 4.01 (d, J = 5.5 Hz, 2H), 3.91 (h, J = 8.1 Hz, 1H), 3.78 (p, J = 8.0 Hz, 1H), 2.27 (qd, J = 11.2, 10.0, 5.5 Hz, 2H), 2.08 (tt, J = 12.6, 5.7 Hz, 2H), 1.85 (q, J = 10.5 Hz, 2H), 1.79-1.66 (m, 2H), 1.36 (s, 9H). |

-continued

| Compound No. | Reagent I | Reagent II | Structure, Name and Data |
|---|---|---|---|
| 11 | tert-butyl (6-aminospiro[3.3] heptan-2-yl)carbamate | oxazol-5-ylmethanamine | 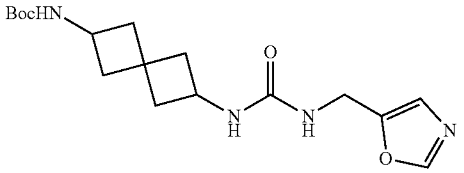 [SMILES: CC(C)(C)OC(=O)NC1CC2(CC(NC(=O)NCc3cnco3)C2)C1] tert-butyl (6-(3-(oxazol-5-ylmethyl)ureido)spiro[3.3]heptan-2-yl)carbamate. LCMS-ESI (POS.) m/z: 351 (M + H)+. 1H NMR (400 MHz, DMSO-$d_6$) δ 8.25 (s, 1H), 7.04 (d, J = 8.0 Hz, 1H), 6.92 (s, 1H), 6.29-6.12 (m, 2H), 4.23 (d, J = 5.8 Hz, 2H), 3.91 (h, J = 8.1 Hz, 1H), 3.79 (q, J = 8.2 Hz, 1H), 2.27 (qt, J = 10.8, 5.6 Hz, 2H), 2.17-2.01 (m, 2H), 1.86 (q, J = 10.0 Hz, 2H), 1.82-1.68 (m, 2H), 1.36 (s, 9H). |
| 12 | tert-butyl (4-aminocyclohexyl) carbamate | 4-(aminomethyl) benzamide | 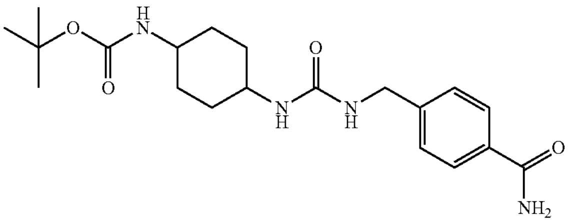 [SMILES: CC(C)(C)OC(=O)NC1CCC(NC(=O)NCc2ccc(C(N)=O)cc2)CC1] tert-butyl (4-(3-(4-carbamoylbenzyl)ureido)cyclohexyl) carbamate. LCMS-ESI (POS.) m/z: 291 (M-Boc + H)+. 1H NMR (400 MHz, DMSO-$d_6$) δ 7.91 (s, 1H), 7.82 (d, J = 8.1 Hz, 2H), 7.30 (d, J = 7.6 Hz, 3H), 6.73 (dd, J = 25.4, 7.3 Hz, 1H), 6.36 (t, J = 6.0 Hz, 1H), 5.89 (d, J = 7.4 Hz, 1H), 4.25 (d, J = 5.9 Hz, 2H), 3.54 (s, 1H), 3.17 (s, 1H), 1.85-1.68 (m, 1H), 1.62-1.43 (m, 6H), 1.39 (s, 9H), 1.25-1.08 (m, 1H). |
| 25 | tert-butyl 1-(aminomethyl)-6-azaspiro[2.5] octane-6-carboxylate | pyridin-4-ylmethanamine | 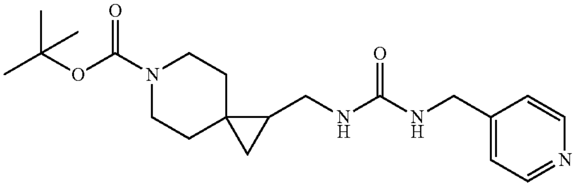 [SMILES: CC(C)(C)OC(=O)N1CCC2(CC1)CC2CNC(=O)NCc1ccncc1] tert-butyl 1-((3-(pyridin-4-ylmethyl)ureido)methyl)-6-azaspiro[2.5]octane-6-carboxylate. LCMS-ESI (POS.) m/z: 375 (M + H)+. 1H NMR (400 MHz, DMSO-$d_6$) δ 7.45-7.32 (m, 2H), 7.25 (d, J = 8.5 Hz, 2H), 6.37 (t, J = 6.1 Hz, 1H), 5.94 (t, J = 5.4 Hz, 1H), 4.18 (d, J = 6.0 Hz, 2H), 3.43 (dddd, J = 19.2, 12.7, 6.6, 3.8 Hz, 2H), 3.17 (dt, J = 13.8, 5.9 Hz, 3H), 2.90 (ddd, J = 13.7, 8.5, 5.2 Hz, 1H), 1.51 (ddd, J = 12.3, 10.2, 6.2 Hz, 1H), 1.40 (s, 9H), 1.31 (ddd, J = 17.2, 7.1, 3.5 Hz, 2H), 1.14 (ddd, J = 13.1, 6.5, 3.3 Hz, 1H), 0.79 (tt, J = 8.5, 6.2 Hz, 1H), 0.45 (dd, J = 8.5, 4.3 Hz, 1H), 0.16 (t, J = 4.8 Hz, 1H). |

-continued

| Compound No. | Reagent I | Reagent II | Structure, Name and Data |
|---|---|---|---|
| 28 | tert-butyl 1-(aminomethyl)-6-azaspiro[2.5] octane-6-carboxylate | 4-methoxy benzyl amine | 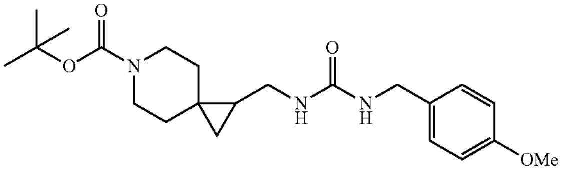 [SMILES: COc1ccc(CNC(=O)NCC2CC23CCN(C(=O)OC(C)(C)C)CC3)cc1] tert-butyl 1-((3-(4-methoxybenzyl)ureido)methyl)-6-azaspiro[2.5]octane-6-carboxylate. LCMS-ESI (POS.) m/z: 304 (M-Boc + H)+. 1H NMR (400 MHz, DMSO-$d_6$) δ 7.23-7.05 (m, 2H), 6.93-6.78 (m, 2H), 6.25 (t, J = 5.9 Hz, 1H), 5.87 (t, J = 5.4 Hz, 1H), 4.12 (d, J = 5.9 Hz, 2H), 3.72 (s, 3H), 3.44 (dddd, J = 19.4, 12.7, 6.6, 3.8 Hz, 2H), 3.19 (tq, J = 13.6, 11.6, 6.1, 4.8 Hz, 3H), 2.88 (ddd, J = 13.7, 8.5, 5.1 Hz, 1H), 1.59-1.44 (m, 1H), 1.39 (s, 9H), 1.31 (ddt, J = 12.8, 8.6, 3.3 Hz, 2H), 1.13 (ddd, J = 13.1, 6.5, 3.5 Hz, 1H), 0.78 (tt, J = 8.4, 5.9 Hz, 1H), 0.45 (dd, J = 8.5, 4.3 Hz, 1H), 0.15 (t, J = 4.8 Hz, 1H). |
| 29 | tert-butyl 1-(aminomethyl)-6-azaspiro[2.5] octane-6-carboxylate | (4-(aminomethyl) phenyl)methanol | 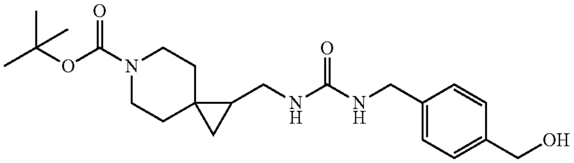 [SMILES: CC(C)(C)OC(=O)N1CCC2(CC1)CC2CNC(=O)NCc1ccc(CO)cc1] tert-butyl 1-((3-(4-(hydroxymethyl)benzyl)ureido)methyl)-6-azaspiro[2.5]octane-6-carboxylate. LCMS-ESI (POS.) m/z: 304 (M-Boc + H)+. 1H NMR (400 MHz, DMSO-$d_6$) δ 7.24 (d, J = 8.0 Hz, 2H), 7.18 (d, J = 8.0 Hz, 2H), 6.30 (t, J = 6.0 Hz, 1H), 5.90 (t, J = 5.4 Hz, 1H), 5.12 (s,1H), 4.45 (s, 2H), 4.17 (d, J = 5.9 Hz, 2H), 3.44 (dddd, J = 19.6, 12.7, 6.6, 3.8 Hz, 2H), 3.26-3.08 (m, 3H), 2.89 (ddd, J = 13.7, 8.5, 5.1 Hz, 1H), 1.57-1.44 (m, 1H), 1.40 (s, 9H), 1.35-1.25 (m, 2H), 1.13 (ddd, J = 13.1, 6.5, 3.4 Hz, 1H), 0.79 (tt, J = 8.4, 5.8 Hz, 1H), 0.45 (dd, J = 8.6, 4.3 Hz, 1H), 0.16 (t, J = 4.8 Hz, 1H). |
| 30 | tert-butyl 1-(aminomethyl)-6-azaspiro[2.5] octane-6-carboxylate | oxazol-5-ylmethanamine | 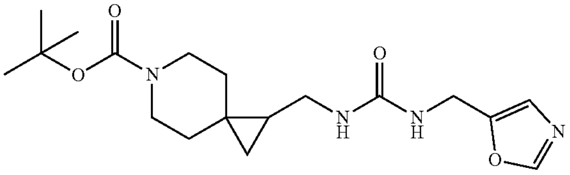 [SMILES: CC(C)(C)OC(=O)N1CCC2(CC1)CC2CNC(=O)NCc1cnco1] tert-butyl 1-((3-(oxazol-5-ylmethyl)ureido)methyl)-6-azaspiro[2.5]octane-6-carboxylate. LCMS-ESI (POS.) m/z: 265 (M-Boc + H)+. 1H NMR (400 MHz, DMSO-$d_6$) δ 8.24 (s, 1H), 6.92 (s, 1H), 6.35 (t, J = 5.9 Hz, 1H), 5.96 (t, J = 5.4 Hz, 1H), 4.26 (dd, J = 5.9, 0.9 Hz, 2H), 3.44 (dddd, J = 15.8, 12.8, 6.6, 3.8 Hz, 2H), 3.28-3.07 (m, 3H), 2.89 (ddd, J = 13.7, 8.4, 5.1 Hz, 1H), 1.59-1.44 (m, 1H), 1.39 (s, 9H), 1.31 (ddd, J = 13.2, 5.6, 3.1 Hz, 2H), 1.12 (ddd, J = 13.1, 6.5, 3.5 Hz, 1H), 0.77 (tt, J = 8.3, 5.8 Hz, 1H), 0.44 (dd, J = 8.5, 4.3 Hz, 1H), 0.15 (t, J = 4.9 Hz, 1H). |

-continued

| Compound No. | Reagent I | Reagent II | Structure, Name and Data |
|---|---|---|---|
| 31 | tert-butyl 1-(aminomethyl)-6-azaspiro[2.5] octane-6-carboxylate | (1H-pyrazol-4-yl)methanamine | 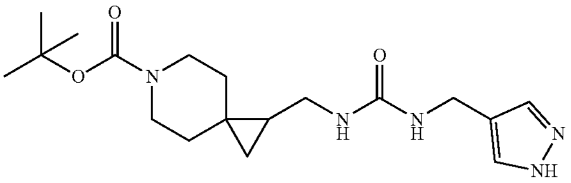 [SMILES: CC(C)(C)OC(=O)N1CCC2(CC1)CC2CNC(=O)NCc1cn[nH]c1] tert-butyl 1-((3-((1H-pyrazol-4-yl)methyl)ureido)methyl)-6-azaspiro[2.5]octane-6-carboxylate. LCMS-ESI (POS.) m/z: 364 (M + H)+. 1H NMR (400 MHz, DMSO-$d_6$) δ 12.55 (s, 1H), 7.47 (s, 2H), 6.01 (t, J = 5.5 Hz, 1H), 5.77 (t, J = 5.4 Hz, 1H), 4.04 (d, J = 5.4 Hz, 2H), 3.45 (tdd, J = 17.5, 6.5, 3.8 Hz, 2H), 3.25-3.10 (m, 3H), 2.87 (ddd, J = 13.6, 8.4, 5.0 Hz, 1H), 1.50 (ddd, J = 12.5, 8.8, 4.2 Hz, 1H), 1.40 (s, 9H), 1.35-1.28 (m, 2H), 1.12 (ddd, J = 12.9, 6.5, 3.4 Hz, 1H), 0.84-0.69 (m, 1H), 0.44 (dd, J = 8.5, 4.3 Hz, 1H), 0.15 (t, J = 4.8 Hz, 1H). |
| 32 | tert-butyl 1-(aminomethyl)-6-azaspiro[2.5] octane-6-carboxylate | N-(4-(aminomethyl) phenyl)acetamide | 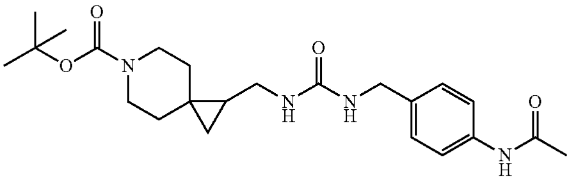 [SMILES: CC(=O)Nc1ccc(CNC(=O)NCC2CC23CCN(C(=O)OC(C)(C)C)CC3)cc1] tert-butyl 1-((3-(4-acetamidobenzyl)ureido)methyl)-6-azaspiro[2.5]octane-6-carboxylate. LCMS-ESI (POS.) m/z: 331 (M-Boc + H)+. 1H NMR (400 MHz, DMSO-$d_6$) δ 9.87 (s, 1H), 7.57-7.36 (m, 2H), 7.22-7.05 (m, 2H), 6.24 (t, J = 5.9 Hz, 1H), 5.85 (t, J = 5.4 Hz, 1H), 4.13 (d, J = 5.8 Hz, 2H), 3.44 (dddd, J = 18.7, 12.6, 6.5, 3.7 Hz, 2H), 3.20 (tdd, J = 13.5, 10.3, 4.9 Hz, 3H), 2.89 (ddd, J = 13.6, 8.4, 5.1 Hz, 1H), 2.02 (s, 3H), 1.50 (ddd, J = 12.5, 8.2, 3.7 Hz, 1H), 1.39 (s, 9H), 1.32 (ddd, J = 12.6, 7.5, 3.7 Hz, 2H), 1.13 (ddd, J = 12.9, 6.4, 3.5 Hz, 1H), 0.79 (tt, J = 8.2, 5.8 Hz, 1H), 0.45 (dd, J = 8.5, 4.3 Hz, 1H), 0.16 (t, J = 4.8 Hz, 1H). |
| 33 | tert-butyl 1-(aminomethyl)-6-azaspiro[2.5] octane-6-carboxylate | 4-(aminomethyl) benzamide | 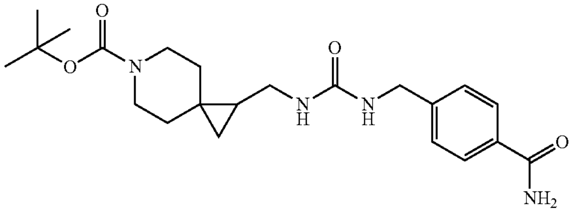 [SMILES: CC(C)(C)OC(=O)N1CCC2(CC1)CC2CNC(=O)NCc1ccc(C(N)=O)cc1] tert-butyl 1-((3-(4-carbamoylbenzyl)ureido)methyl)-6-azaspiro[2.5]octane-6-carboxylate. LCMS-ESI (POS.) m/z: 317 (M-Boc + H)+. 1H NMR (400 MHz, DMSO-$d_6$) δ 7.90 (s, 1H), 7.84-7.73 (m, 2H), 7.39-7.20 (m, 3H), 6.39 (t, J = 6.0 Hz, 1H), 5.95 (t, J = 5.4 Hz, 1H), 4.24 (d, J = 6.0 Hz, 2H), 3.45 (dddd, J = 19.1, 12.6, 5.9, 3.2 Hz, 2H), 3.26-3.09 (m, 3H), 2.91 (ddd, J = 13.6, 8.4, 5.1 Hz, 1H), 1.52 (ddd, J = 17.3, 7.6, 3.6 Hz, 1H), 1.40 (s, 9H), 1.32 (ddd, J = 12.6, 7.5, 3.7 Hz, 2H), 1.14 (ddd, J = 13.0, 6.5, 3.4 Hz, 1H), 0.80 (tt, J = 8.3, 5.8 Hz, 1H), 0.45 (dd, J = 8.5, 4.3 Hz, 1H), 0.16 (q, J = 5.7, 5.3 Hz, 1H). |

-continued

| Compound No. | Reagent I | Reagent II | Structure, Name and Data |
|---|---|---|---|
| 206 | 8.1 | (4-chlorophenyl) methanamine | 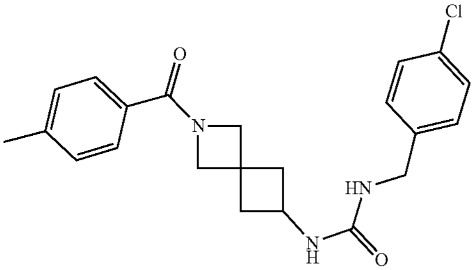 1-(4-chlorobenzyl)-3-(2-(4-methylbenzoyl)-2-azaspiro[3.3]heptan-6-yl)urea. LCMS-ESI (POS.) m/z: 398 $(M + H)^+$. $^1H$ NMR (400 MHz, Methanol-$d_4$) δ 7.43 (t, J = 6.9 Hz, 2H), 7.25-7.09 (m, 6H), 4.49 (s, 2H), 4.30 (s, 1H), 4.17 (s, 3H), 4.10 (s, 1H), 4.03-3.87 (m, 2H), 2.59-2.41 (m, 1H), 2.29 (s, 3H), 2.01 (td, J = 9.4, 8.9, 4.3 Hz, 1H). |
| 207 | 8.1 | (4-fluorophenyl) methanamine | 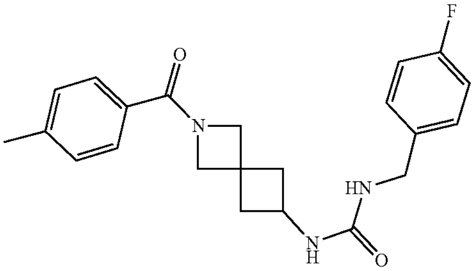 [SMILES: Cc1ccc(C(=O)N2CC3(CC(NC(=O)NCc4ccc(F)cc4)C3)C2)cc1] 1-(4-fluorobenzyl)-3-(2-(4-methylbenzoyl)-2-azaspiro[3.3]heptan-6-yl)urea. LCMS-ESI (POS.) m/z: 382 (M + H). $^1H$ NMR (400 MHz, Methanol-$d_4$) δ 7.42 (t, J = 7.0 Hz, 2H), 7.17 (td, J = 5.5, 2.3 Hz, 4H), 6.92 (t, J = 8.6 Hz, 2H), 4.30 (s, 1H), 4.16 (d, J = 4.0 Hz, 3H), 4.09 (s, 1H), 4.02-3.86 (m, 2H), 2.57-2.43 (m, 2H), 2.28 (s, 3H), 2.00 (td, J = 9.3, 8.8, 4.1 Hz, 2H). |
| 210 | 8.1 | pyridin-4-ylmethanamine | 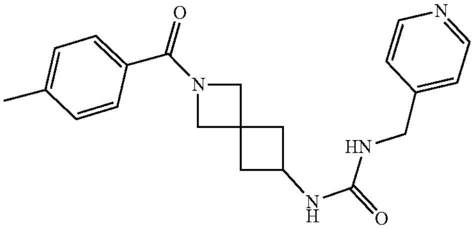 [SMILES: Cc1ccc(C(=O)N2CC3(CC(NC(=O)NCc4ccncc4)C3)C2)cc1] 1-(2-(4-methylbenzoyl)-2-azaspiro[3.3]heptan-6-yl)-3-(pyridin-4-ylmethyl)urea. LCMS-ESI (POS.) m/z: 365 $(M + H)^+$. $^1H$ NMR (400 MHz, Methanol-$d_4$) δ 8.35 (d, J = 5.2 Hz, 2H), 7.42 (dd, J = 7.8, 4.9 Hz, 2H), 7.25 (d, J = 5.9 Hz, 2H), 7.17 (d, J = 7.7 Hz, 2H), 4.30 (s, 1H), 4.26 (s, 2H), 4.18 (s, 1H), 4.10 (s, 1H), 4.04-3.85 (m, 2H), 2.60-2.43 (m, 2H), 2.28 (s, 3H), 2.03 (td, J = 8.8, 4.1 Hz, 2H). |

-continued

| Compound No. | Reagent I | Reagent II | Structure, Name and Data |
|---|---|---|---|
| 211 | 8.1 | 4-(aminomethyl) benzamide | 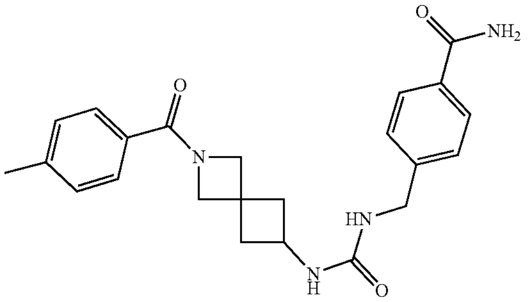 [SMILES: Cc1ccc(C(=O)N2CC3(CC(NC(=O)NCc4ccc(C(N)=O)cc4)C3)C2)cc1] 4-((3-(2-(4-methylbenzoyl)-2-azaspiro[3.3]heptan-6-yl)ureido)methyl)benzamide. LCMS-ESI (POS.) m/z: 407 $(M + H)^+$. $^1H$ NMR (400 MHz, Methanol-$d_4$) δ 7.72 (d, J = 8.3 Hz, 2H), 7.42 (t, J = 6.9 Hz, 2H), 7.26 (d, J = 8.4 Hz, 2H), 7.17 (d, J = 7.4 Hz, 2H), 4.30 (s, 1H), 4.25 (s, 2H), 4.18 (s, 1H), 4.10 (s, 1H), 4.02-3.86 (m, 2H), 2.50 (td, J = 9.7, 7.5, 3.4 Hz, 2H), 2.28 (s, 3H), 2.01 (td, J = 10.5, 3.4 Hz, 2H). |
| 214 | 8.1 | 5-(aminomethyl) pyridin-2(1H)-one | 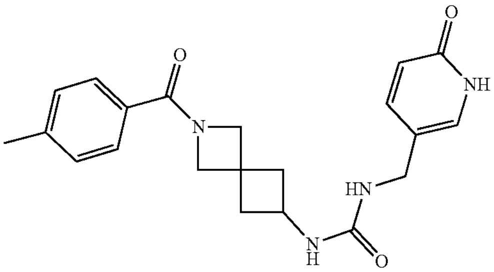 [SMILES: Cc1ccc(C(=O)N2CC3(CC(NC(=O)NCc4ccc(=O)[nH]c4)C3)C2)cc1] 1-(2-(4-methylbenzoyl)-2-azaspiro[3.3]heptan-6-yl)-3-((6-oxo-1,6-dihydropyridin-3-yl)methyl)urea. LCMS-ESI (POS.) m/z: 381 $(M + H)^+$. $^1H$ NMR (400 MHz, Methanol-$d_4$) δ 7.50-7.36 (m, 3H), 7.21 (s, 1H), 7.17 (d, J = 6.6 Hz, 2H), 6.42 (d, J = 9.3 Hz, 1H), 4.30 (s, 1H), 4.17 (s, 1H), 4.09 (s, 1H), 4.02-3.85 (m, 4H), 2.48 (td, J = 8.0, 7.2, 3.5 Hz, 2H), 2.28 (s, 3H), 1.99 (ddd, J = 13.4, 8.1, 3.9 Hz, 2H). |
| 215 | 8.1 | 5-(aminomethyl) picolinamide | 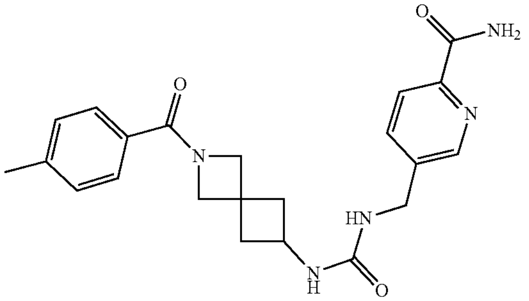 [SMILES: Cc1ccc(C(=O)N2CC3(CC(NC(=O)NCc4ccc(C(N)=O)nc4)C3)C2)cc1] 5-((3-(2-(4-methylbenzoyl)-2-azaspiro[3.3]heptan-6-yl)ureido)methyl)picolinamide. LCMS-ESI (POS.) m/z: 408 $(M + H)^+$. $^1H$ NMR (400 MHz, Methanol-$d_4$) δ 8.44 (d, J = 1.6 Hz, 1H), 7.95 (d, J = 8.0 Hz, 1H), 7.74 (dd, J = 8.0, 2.1 Hz, 1H), 7.43 (t, J = 6.8 Hz, 2H), 7.17 (d, J = 7.2 Hz, 2H), 4.31 (s, 1H), 4.29 (s, 2H), 4.18 (s, 1H), 4.10 (s, 1H), 4.03-3.84 (m, 2H), 2.59-2.42 (m, 2H), 2.29 (s, 3H), 2.02 (ddd, J = 12.7, 8.4, 3.4 Hz, 2H). |

| Compound No. | Reagent I | Reagent II | Structure, Name and Data |
|---|---|---|---|
| 227 | 8.1 | (1H-pyrazol-4-yl)methanamine | 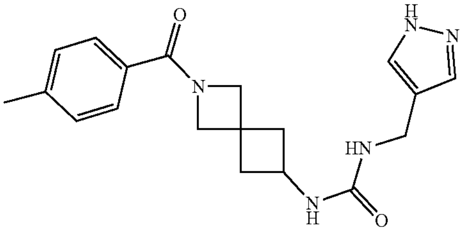 [SMILES: Cc1ccc(C(=O)N2CC3(CC(NC(=O)NCc4cn[nH]c4)C3)C2)cc1] 1-((1H-pyrazol-4-yl)methyl)-3-(2-(4-methylbenzoyl)-2-azaspiro[3.3]heptan-6-yl)urea. LCMS-ESI (POS.) m/z: 354 $(M + H)^+$. $^1H$ NMR (400 MHz, Methanol-$d_4$) δ 8.04 (d, J = 4.2 Hz, 1H), 7.68-7.58 (m, 1H), 7.43 (t, J = 6.9 Hz, 2H), 7.17 (d, J = 6.3 Hz, 2H), 4.30 (s, 1H), 4.18 (s, 1H), 4.12 (d, J = 1.0 Hz, 2H), 4.10 (s, 1H), 3.98 (s, 1H), 3.91 (dt, J = 16.1, 8.1 Hz, 1H), 2.49 (ddt, J = 10.5, 7.5, 3.1 Hz, 2H), 2.29 (s, 3H), 2.00 (tt, J = 8.6, 2.9 Hz, 2H). |
| 228 | 8.1 | oxazol-4-ylmethanamine | 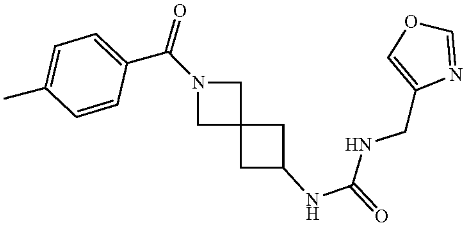 [SMILES: Cc1ccc(C(=O)N2CC3(CC(NC(=O)NCc4cocn4)C3)C2)cc1] 1-(2-(4-methylbenzoyl)-2-azaspiro[3.3]heptan-6-yl)-3-(oxazol-4-ylmethyl)urea. LCMS-ESI (POS.) m/z: 355 $(M + H)^+$. $^1H$ NMR (400 MHz, Methanol-$d_4$) δ 8.04 (d, J = 4.2 Hz, 1H), 7.70-7.59 (m, 1H), 7.43 (t, J = 6.9 Hz, 2H), 7.17 (d, J = 7.4 Hz, 2H), 4.30 (s, 1H), 4.18 (s, 1H), 4.12 (s, 2H), 4.10 (s, 1H), 3.98 (s, 1H), 3.91 (dt, J = 16.1, 8.1 Hz, 1H), 2.49 (ddt, J = 10.5, 7.5, 3.1 Hz, 2H), 2.29 (s, 3H), 2.00 (tt, J = 8.6, 2.9 Hz, 2H). |
| 13 | (4-aminopiperidin-1-yl)(phenyl)methanone | 4-(aminomethyl)benzamide | 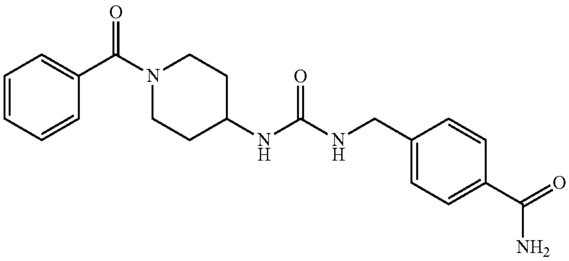 [SMILES: NC(=O)c1ccc(CNC(=O)NC2CCN(C(=O)c3ccccc3)CC2)cc1] 4-((3-(1-benzoylpiperidin-4-yl)ureido)methyl)benzamide. LCMS-ESI (POS.) m/z: 381 $(M + H)^+$. $^1H$ NMR (400 MHz, DMSO-$d_6$) δ 7.90 (s, 1H), 7.85-7.77 (m, 2H), 7.45 (q, J = 2.8 Hz, 3H), 7.41-7.34 (m, 2H), 7.30 (d, J = 7.9 Hz, 3H), 6.35 (t, J = 6.1 Hz, 1H), 6.05 (d, J = 7.7 Hz, 1H), 4.25 (d, J = 6.0 Hz, 2H), 3.73-3.60 (m, 1H), 3.51 (s, 1H), 3.05 (d, J = 41.0 Hz, 2H), 1.81 (d, J = 35.5 Hz, 2H), 1.42-1.19 (m, 3H). |

-continued

| Compound No. | Reagent I | Reagent II | Structure, Name and Data |
| --- | --- | --- | --- |
| 282 | 17.1 | (4-methoxyphenyl) methanamine | 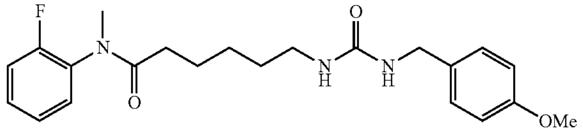 [SMILES: COc1ccc(CNC(=O)NCCCCCC(=O)N(C)c2ccccc2F)cc1] N-(2-fluorophenyl)-6-(3-(4-methoxybenzyl)ureido)-N-methylhexanamide. LCMS-ESI (POS.) m/z: 402.0 $(M + H)^+$. $^1H$ NMR (400 MHz, DMSO-$d_6$) δ 7.43 (dq, J = 30.9, 8.4 Hz, 3H), 7.30 (t, J = 7.6 Hz, 1H), 7.15 (d, J = 8.2 Hz, 2H), 6.86 (d, J = 8.2 Hz, 2H), 6.13 (s, 1H), 5.78 (q, J = 6.1 Hz, 1H), 4.10 (d, J = 5.9 Hz, 2H), 3.72 (s, 3H), 3.17 (d, J = 5.3 Hz, 1H), 3.11 (s, 2H), 2.91 (q, J = 6.5 Hz, 2H), 1.95 (dt, J = 24.5, 7.6 Hz, 2H), 1.43 (p, J = 7.1 Hz, 2H), 1.23 (q, J = 7.2 Hz, 2H), 1.11 (d, J = 7.8 Hz, 2H). |
| 286 | 17.1 | pyridin-4-ylmethanamine | 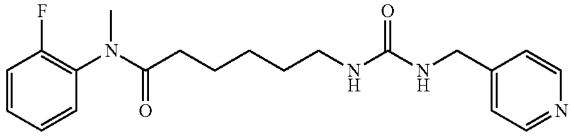 [SMILES: CN(C(=O)CCCCCNC(=O)NCc1ccncc1)c1ccccc1F] N-(2-fluorophenyl)-N-methyl-6-(3-(pyridin-4-ylmethyl)ureido) hexanamide. LCMS-ESI (POS.) m/z: 373.2 $(M + H)^+$. $^1H$ NMR (400 MHz, DMSO-$d_6$) δ 8.52-8.40 (m, 2H), 8.14 (s, 1H), 7.44 (dq, J = 30.4, 9.0, 8.5 Hz, 2H), 7.30 (t, J = 7.6 Hz, 1H), 7.21 (t, J = 5.8 Hz, 2H), 6.38 (q, J = 6.0 Hz, 1H), 6.01 (dt, J = 18.7, 5.7 Hz, 1H), 4.21 (t, J = 6.0 Hz, 2H), 3.11 (s, 3H), 2.96 (dq, J = 27.7, 6.6 Hz, 2H), 2.07-1.83 (m, 2H), 1.42 (qd, J = 15.3, 14.7, 7.1 Hz, 2H), 1.26 (dd, J = 10.4, 7.0 Hz, 2H), 1.13 (d, J = 6.7 Hz, 2H). |
| 287 | 17.1 | (1H-pyrazol-4-yl)methanamine | 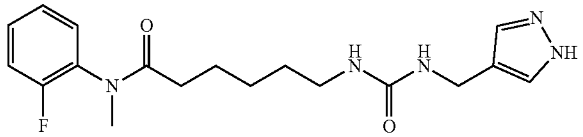 [SMILES: CN(C(=O)CCCCCNC(=O)NCc1cn[nH]c1)c1ccccc1F] 6-(3-((1H-pyrazol-4-yl)methyl)ureido)-N-(2-fluorophenyl)-N-methylhexanamide. LCMS-ESI (POS.) m/z: 362.0 $(M + H)^+$. $^1H$ NMR (400 MHz, DMSO-$d_6$) δ 12.57 (s, 1H), 7.44 (tt, J = 18.4, 8.3 Hz, 5H), 7.30 (t, J = 7.7 Hz, 1H), 5.90 (t, J = 5.6 Hz, 1H), 5.80-5.68 (m, 1H), 4.02 (d, J = 5.5 Hz, 2H), 3.11 (s, 3H), 2.90 (q, J = 6.6 Hz, 2H), 1.95 (dt, J = 23.9, 7.5 Hz, 2H), 1.43 (p, J = 7.4 Hz, 2H), 1.24 (dq, J = 14.4, 7.0 Hz, 2H), 1.16-1.03 (m, 2H). |

-continued

| Compound No. | Reagent I | Reagent II | Structure, Name and Data |
|---|---|---|---|
| 288 | 17.1 | oxazol-5-ylmethanamine | 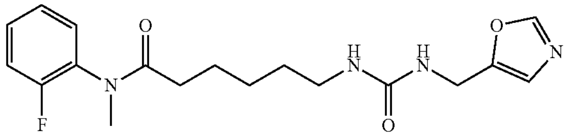 [SMILES: CN(C(=O)CCCCCNC(=O)NCc1cnco1)c1ccccc1F] N-(2-fluorophenyl)-N-methyl-6-(3-(oxazol-5-ylmethyl)ureido) hexanamide. LCMS-ESI (POS.) m/z: 363.0 $(M + H)^+$. $^1H$ NMR (400 MHz, DMSO-$d_6$) δ 8.25 (d, J = 3.3 Hz, 1H), 7.44 (dq, J = 30.7, 8.4 Hz, 2H), 7.30 (t, J = 7.4 Hz, 1H), 6.92 (d, J = 4.4 Hz, 1H), 6.25 (dt, J = 11.2, 5.7 Hz, 1H), 5.92 (dt, J = 18.9, 5.7 Hz, 1H), 4.24 (t, J = 5.7 Hz, 2H), 3.17 (d, J = 5.2 Hz, 2H), 3.11 (s, 2H), 2.94 (dq, J = 28.4, 6.6 Hz, 2H), 1.95 (dt, J = 24.3, 7.5 Hz, 2H), 1.41 (gd, J = 15.3, 14.4, 7.3 Hz, 2H), 1.25 (dd, J = 17.4, 8.9 Hz, 2H), 1.12 (t, J = 7.1 Hz, 2H). |

Example 5

Preparation of N-(6-cyanopyridin-2-yl)-6-(3-(4-methoxybenzyl)ureido)-2-azaspiro[3.3]heptane-2-carboxamide (Compound 132)

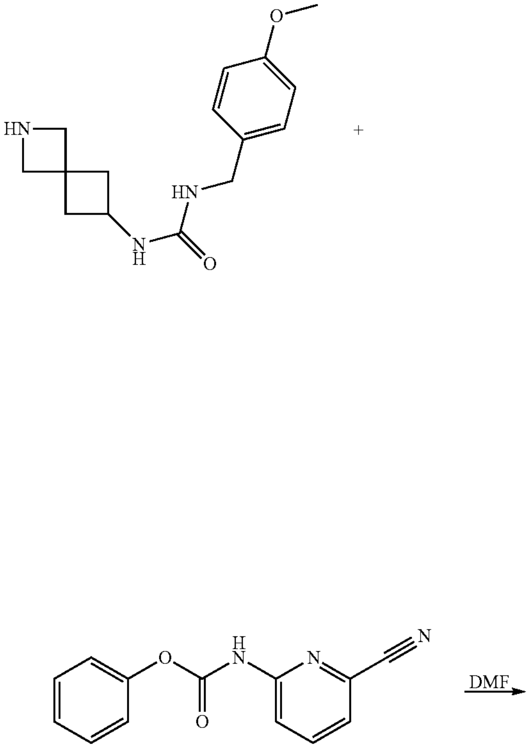

-continued

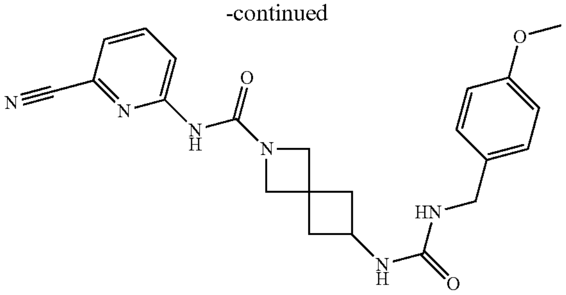

N-(6-cyanopyridin-2-yl)-6-(3-(4-methoxybenzyl) ureido)-2-azaspiro[3.3]heptane-2-carboxamide Phenyl (6-cyanopyridin-2-yl)carbamate (130 mg, 0.54 mmol, 1.5 equiv) was added to a stirring solution of 1-(4-methoxybenzyl)-3-(2-azaspiro[3.3]heptan-6-yl)urea (100 mg, 0.36 mmol, 1 equiv) in DMF (1 mL) at 25° C. After 12 h, the reactions were diluted with MeOH to a total volume of 1.8 mL, filtered through a 0.4 μm syringe filter, and product isolated by reverse phase HPLC (0→70% MeCN/H2O w/0.1% formic acid) as a white solid (39 mg, 26%). $^1H$ NMR (400 MHz, DMSO-$d_6$) 9.56 (s, 1H), 8.14 (dd, J=8.7, 1.8 Hz, 1H), 7.90-7.75 (m, 1H), 7.51 (dd, J=7.3, 1.8 Hz, 1H), 7.08 (d, J=7.9 Hz, 2H), 6.83-6.76 (m, 2H), 6.17-6.10 (m, 1H), 6.08 (d, J=8.1 Hz, 1H), 4.03 (d, J=5.8 Hz, 2H), 3.96 (s, 2H), 3.86 (d, J=10.2 Hz, 3H), 3.65 (s, 3H), 2.36 (t, J=8.8 Hz, 2H), 1.91 (t, J=9.5 Hz, 2H). LRMS (APCI) m/z 421.1 (M+H).

Compounds in the following table were prepared in a similar manner as Compound 132, using the intermediates and reagents as listed.

| Compound No. | Amine | Intermediate | Structure, Name and Data |
|---|---|---|---|
| 133 | phenyl (2-methyl-pyrimidin-5-yl)carbamate | 3.2 | 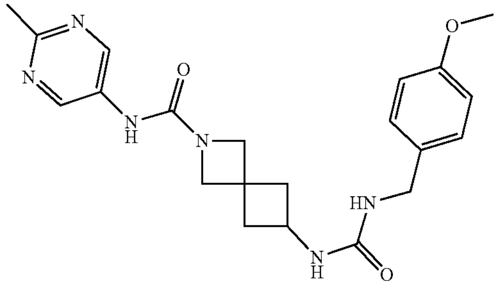 6-(3-(4-methoxybenzyl)ureido)-N-(2-methylpyrimidin-5-yl)-2-azaspiro[3.3]heptane-2-carboxamide. LRMS (APCI) m/z 411 (M + H). $^1$H NMR (400 MHz, DMSO-d6) δ 8.02 (s, 2H), 7.15 (d, J = 7.4 Hz, 2H), 6.87 (d, J = 7.0 Hz, 2H), 6.35-6.18 (m, 2H), 4.10 (d, J = 5.4 Hz, 2H), 4.01 (s, 2H), 3.95 (dd, J = 16.1, 8.2 Hz, 1H), 3.89 (s, 2H), 3.72 (s, 3H), 3.43-3.19 (m, 2H), 3.15 (s, 2H), 2.45 (t, J = 9.1 Hz, 2H), 2.00 (t, J = 9.4 Hz, 2H). |
Example 6
Preparation of 1-(4-chlorobenzyl)-3-((2r,4s)-6-(2-methylpyridin-4-yl)-6-azaspiro[3.4]octan-2-yl)urea (Compound 171)
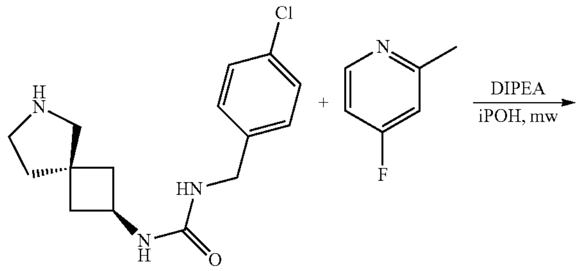
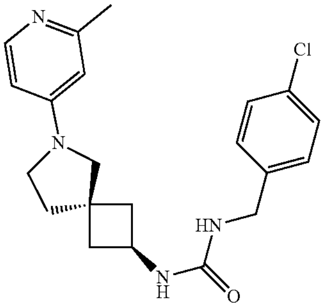

1-(4-chlorobenzyl)-3-((2r,4s)-6-(2-methylpyridin-4-yl)-6-azaspiro[3.4]octan-2-yl)urea 1-(4-chlorobenzyl)-3-((2r,4s)-6-azaspiro[3.4]octan-2-yl)urea (Intermediate 3.5) (100 mg, 0.34 mmol, 1 equiv), 4-fluoro-2-methylpyridine (57 mg, 0.51 mmol, 1.5 equiv), and DIPEA (178 μL, 1.0 mmol, 3 equiv) were suspended in isopropanol (3 mL) before being heated to 150° C. in microwave for 30 m. The solvent was then removed by rotary evaporation and the desired product was isolated by reverse phase HPLC (05→95% MeCN/H2O w/0.1% formic acid) as a white solid (30 mg, 23%). LRMS (APCI) m/z 385 (M+H). $^1$H NMR (400 MHz, DMSO-$d_6$) δ 8.20 (s, 1H), 7.98 (d, J=6.1 Hz, 1H), 7.40-7.32 (m, 2H), 7.30-7.24 (m, 2H), 6.40-6.28 (m, 4H), 4.18 (d, J=6.0 Hz, 2H), 4.12 (q, J=8.1 Hz, 1H), 3.31 (t, J=6.7 Hz, 3H), 2.32 (s, 3H), 2.29-2.20 (m, 2H), 2.01 (t, J=6.7 Hz, 2H), 1.90 (td, J=8.8, 2.7 Hz, 2H).

Compounds in the following table were prepared in a similar manner as Compound 171, using the intermediates and reagents as listed.

| Compound No. | Amine | Intermediate | Structure, Name and Data |
|---|---|---|---|
| 170 | 2-chloro-pyrimidine | 3.5 | 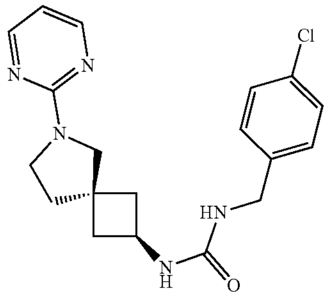 [SMILES: O=C(NCc1ccc(Cl)cc1)N[C@H]1C[C@]2(CCN(c3ncccn3)C2)C1] 1-(4-chlorobenzyl)-3-((2s,4r)-6-(pyrimidin-2-yl)-6-azaspiro[3.4]octan-2-yl)urea. LRMS (APCI) m/z 372 (M + H). $^1$H NMR (400 MHz, DMSO-d6) δ 8.32 (d, J = 4.7 Hz, 2H), 7.41-7.32 (m, 2H), 7.29-7.19 (m, 2H), 6.57 (t, J = 4.8 Hz, 1H), 6.33 (d, J = 7.6 Hz, 2H), 4.18 (d, J = 6.0 Hz, 2H), 4.09 (q, J = 8.1 Hz, 1H), 3.51 (s, 2H), 3.44 (t, J = 6.9 Hz, 2H), 2.31-2.21 (m, 2H), 1.96-1.81 (m, 4H). |
| 183 | 2-fluoro-6-methyl-pyridine | 3.5 | 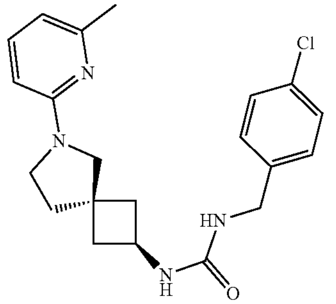 [SMILES: Cc1cccc(N2CC[C@]3(C2)C[C@@H](NC(=O)NCc2ccc(Cl)cc2)C3)n1] 1-(4-chlorobenzyl)-3-((2r,4s)-6-(6-methylpyridin-2-yl)-6-azaspiro[3.4]octan-2-yl)urea. LRMS (APCI) m/z 385 (M + H). $^1$H NMR (400 MHz, DMSO-$d_6$) δ 7.41-7.30 (m, 3H), 7.26 (d, J = 8.4 Hz, 2H), 6.38 (d, J = 7.2 Hz, 1H), 6.34 (t, J = 6.0 Hz, 1H), 6.28 (d, J = 8.0 Hz, 1H), 6.17 (d, J = 8.4 Hz, 1H), 4.18 (d, J = 6.1 Hz, 2H), 4.11 (q, J = 8.2 Hz, 1H), 3.39-3.24 (m, 5H), 2.27 (s, 3H), 2.22 (dd, J = 8.8, 2.9 Hz, 1H), 1.96 (t, J = 6.7 Hz, 2H), 1.89 (td, J = 8.7, 2.7 Hz, 2H). |

-continued

| Compound No. | Amine | Intermediate | Structure, Name and Data |
|---|---|---|---|
| 199 | 2-fluoro-6-methyl-pyridine | 3.6 | 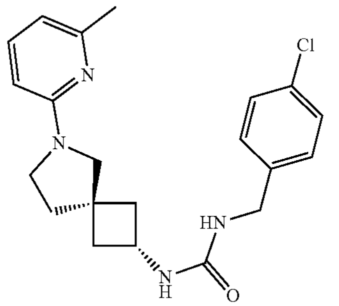 [SMILES: Cc1cccc(N2CC[C@]3(C2)C[C@H](NC(=O)NCc2ccc(Cl)cc2)C3)n1] 1-(4-chlorobenzyl)-3-((2s,4r)-6-(6-methylpyridin-2-yl)-6-azaspiro[3.4]octan-2-yl)urea. LRMS (APCI) m/z 385 (M + H). $^1$H NMR (400 MHz, DMSO-d6) δ 8.14 (s, 1H), 7.41-7.34 (m, 2H), 7.26 (d, J = 8.4 Hz, 2H), 6.39 (d, J = 7.2 Hz, 1H), 6.32 (d, J = 8.2 Hz, 2H), 6.22 (d, J = 8.4 Hz, 1H), 4.18 (d, J = 6.0 Hz, 2H), 4.10 (p, J = 8.2 Hz, 1H), 3.41 (s, 4H), 2.31-2.18 (m, 5H), 1.98-1.77 (m, 4H). |
| 307 | 2-fluoro-pyridine | 3.8 | 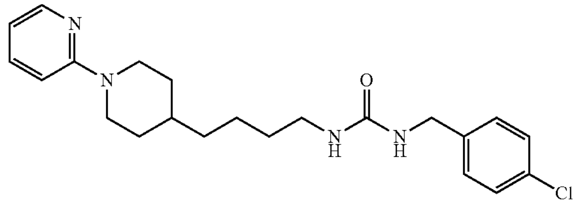 [SMILES: O=C(NCCCCC1CCN(c2ccccn2)CC1)NCc1ccc(Cl)cc1] 1-(4-chlorobenzyl)-3-(4-(1-(pyridin-2-yl)piperidin-4-yl)butyl)urea. LRMS (APCI) m/z 401.2 (M + H). $^1$H NMR (400 MHz, DMSO-$d_6$) δ 8.08 (d, J = 4.9 Hz, 1H), 7.48 (t, J = 8.0 Hz, 1H), 7.37 (d, J = 8.1 Hz, 2H), 7.26 (d, J = 8.1 Hz, 2H), 6.79 (d, J = 8.7 Hz, 1H), 6.57 (dd, J = 7.0, 5.1 Hz, 1H), 6.31 (t, J = 6.2 Hz, 1H), 5.93 (d, J = 6.0 Hz, 1H), 4.27 (d, J = 13.0 Hz, 2H), 4.18 (d, J = 5.9 Hz, 2H), 3.00 (q, J = 6.5 Hz, 2H), 2.73 (t, J = 12.5 Hz, 2H), 1.69 (d, J = 12.9 Hz, 2H), 1.45 (s, 1H), 1.37 (t, J =7.0Hz, 2H), 1.32-1.24 (m, 2H), 1.23 (d, J = 7.0 Hz, 2H), 1.09 (dd, J = 18.1, 8.1 Hz, 2H). |
| 308 | 4-fluoro-pyridine | 3.8 | 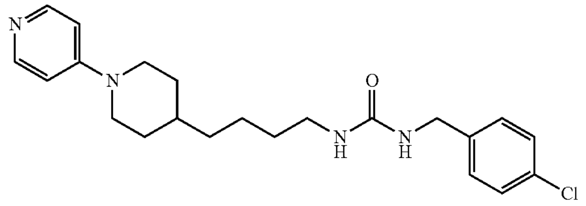 [SMILES: O=C(NCCCCC1CCN(c2ccncc2)CC1)NCc1ccc(Cl)cc1] 1-(4-chlorobenzyl)-3-(4-(1-(pyridin-4-yl)piperidin-4-yl)butyl)urea. LRMS (APCI) m/z 401.2 (M + H). $^1$H NMR (400 MHz, DMSO-$d_6$) δ 8.15 (s, 1H), 7.37 (d, J = 8.1 Hz, 2H), 7.26 (d, J = 8.1 Hz, 2H), 6.99 (s, 1H), 6.35 (t, J = 6.1 Hz, 1H), 5.97 (t, J = 5.7 Hz, 1H), 4.17 (d, J = 6.1 Hz, 2H), 4.05 (d, J = 13.2 Hz, 2H), 3.17 (s, 2H), 3.02 (d, J = 6.4 Hz, 1H), 3.00-2.90 (m, 3H), 1.75 (dd, J = 13.2, 3.2 Hz, 2H), 1.54 (s, 1H), 1.36 (q, J = 6.6, 6.2 Hz, 2H), 1.25 (dq, J = 21.0, 7.7, 6.6 Hz, 4H), 1.09 (qd, J = 12.4, 3.9 Hz, 2H). |

Example 7

Preparation of 1-(6-((5,7-difluoro-3,4-dihydroquinolin-1(2H)-yl)methyl)spiro[3.3]heptan-2-yl)-3-(4-methoxybenzyl)urea (Compound 127)

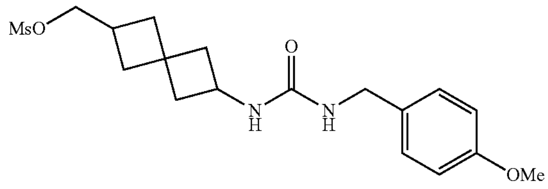

+

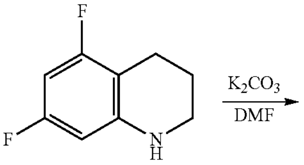

-continued

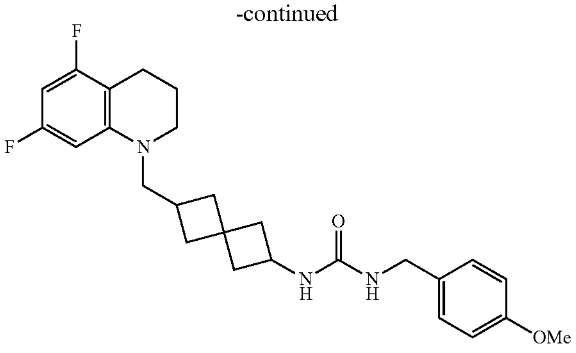

1-(6-((5,7-difluoro-3,4-dihydroquinolin-1(2H)-yl)methyl)spiro[3.3]heptan-2-yl)-3-(4-methoxybenzyl)urea (6-(3-(4-methoxybenzyl)ureido)spiro[3.3]heptan-2-yl)methyl methanesulfonate (Intermediate 4.1) (60 mg, 0.16 mmol, 1.0 equiv) and 5,7-difluoro-1,2,3,4-tetrahydroquinoline (21 mg, 0.19 mmol) were dissolved in DMF (0.5 mL) and potassium carbonate (1.5 equiv) was added. The reaction was stirred at 80° C. for 12 hours. Potassium carbonate was filtered off and the solution was directly purified by reverse phase HPLC with a 10%-100% acetonitrile in water solution that was run over 30 minutes in a Phenomonex Gemini 5u C18 column, providing the desired product (18.0 mg, 24% yield) as a white foam. LCMS-APCI (POS.) m/z: 456.2 (M+H)+. $^1$H NMR (400 MHz, DMSO-$d_6$) δ 7.17 (dd, J=12.2, 2.9 Hz, 2H), 6.99 (d, J=13.8 Hz, 2H), 6.86 (dd, J=8.5, 2.9 Hz, 2H), 6.08 (d, J=11.9 Hz, 2H), 4.09 (d, J=4.6 Hz, 2H), 4.03-3.76 (m, 1H), 3.72 (d, J=3.0 Hz, 3H), 3.60 (d, J=7.0 Hz, 2H), 2.85 (dd, J=7.4, 2.4 Hz, 2H), 2.70 (d, J=8.4 Hz, 2H), 2.34 (s, 2H), 2.27-1.91 (m, 5H), 1.90-1.56 (m, 4H).

Compounds in the following table were prepared in a similar manner as Compound 127, using the intermediates and reagents as listed.

| Compound No. | Amine | Intermediate | Structure, Name and Data |
|---|---|---|---|
| 128 | indoline | 4.1 | 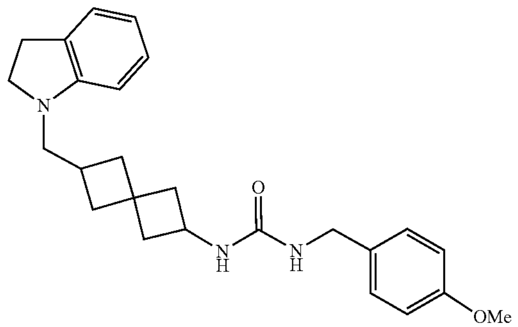 [SMILES: COc1ccc(CNC(=O)NC2CC3(CC(CN4CCc5ccccc54)C3)C2)cc1] 1-(6-(indolin-1-ylmethyl)spiro[3.3]heptan-2-yl)-3-(4-methoxybenzyl)urea. LRMS (APCI) m/z 406 (M + H). $^1$H NMR (400 MHz, DMSO-$d_6$) δ 7.72 (dd, J = 11.2, 3.4 Hz, 2H), 7.55 (dd, J = 11.2, 5.5 Hz, 1H), 7.17 (dd, J = 11.2, 5.5 Hz, 2H), 7.01 (d, J = 13.8 Hz, 2H), 6.84 (dd, J = 8.5, 2.9 Hz, 2H), 6.14 (d, J = 11.9 Hz, 1H), 4.14 (d, J = 4.6 Hz, 2H), 4.05 (s, 1H), 3.76 (d, J = 3.0 Hz, 3H), 3.55 (d, J = 7.0 Hz, 2H), 3.32-3.29 (m, 3H), 2.85 (dd, J = 7.2, 2.6 Hz, 2H), 2.31 (s, 2H), 2.34-1.99 (m, 3H), 1.89-1.51 (m, 3H). |

-continued

| Compound No. | Amine | Intermediate | Structure, Name and Data |
|---|---|---|---|
| 129 | isoindoline | 4.1 | 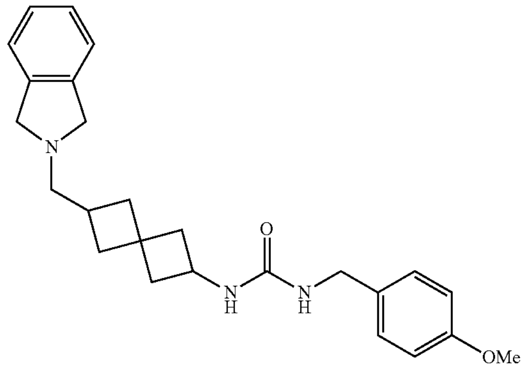 [SMILES: COc1ccc(CNC(=O)NC2CC3(CC(CN4Cc5ccccc5C4)C3)C2)cc1] 1-(6-(isoindolin-2-ylmethyl)spiro[3.3]heptan-2-yl)-3-(4-methoxybenzyl)urea. LRMS (APCI) m/z 406 (M + H). $^1$H NMR (400 MHz, DMSO-$d_6$) δ 7.24 (dd, J = 15.2, 2.9 Hz, 2H), 7.17 (dd, J = 12.2, 2.9 Hz, 2H), 6.99 (d, J = 13.8 Hz, 2H), 6.83 (dd, J = 8.5, 2.9 Hz, 2H), 6.14 (d, J = 11.9 Hz, 2H), 4.09 (d, J = 4.6 Hz, 2H), 4.08-3.89 (m, 1H), 3.74 (d, J = 3.0 Hz, 3H), 3.66 (d, J = 6.8 Hz, 1H), 2.86 (dd, J = 7.4, 2.4 Hz, 4H), 2.79 (d, J = 8.4 Hz, 2H), 2.32 (s, 2H), 2.32-1.99 (m, 3H), 1.91-1.50 (m, 3H). |
| 134 | 1H-indazol | 4.1 | 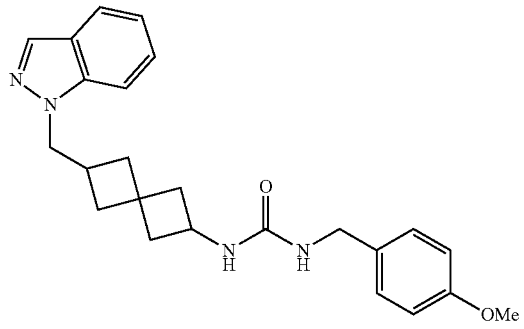 [SMILES: COc1ccc(CNC(=O)NC2CC3(CC(Cn4ncc5ccccc54)C3)C2)cc1] 1-(6-((1H-indazol-1-yl)methyl)spiro[3.3]heptan-2-yl)-3-(4-methoxybenzylurea. LRMS (APCI) m/z 405 (M + H). $^1$H NMR (400 MHz, DMSO-$d_6$) δ 8.51 (d, J = 4.6 Hz, 1H), 7.78 (td, J = 7.7, 1.8 Hz, 1H), 7.45 (d, J = 7.7 Hz, 1H), 7.28 (dd, J = 7.4, 5.0 Hz, 1H), 7.14 (d, J = 8.5 Hz, 3H), 6.86 (d, J = 8.5 Hz, 2H), 6.16-5.92 (m, 2H), 4.09 (d, J = 5.9 Hz, 2H), 3.98-3.84 (m, 1H), 3.72 (s, 3H), 3.67 (s, 1H), 3.46 (d, J = 5.3 Hz, 2H), 3.18 (p, J = 8.6 Hz, 1H), 2.48-2.30 (m, 2H), 2.24-2.06 (m, 2H), 2.01 (ddd, J = 11.5, 8.5, 2.8 Hz, 1H), 1.79 (dd, J = 10.7, 8.6 Hz, 1H), 1.69 (dd, J = 11.0, 8.7 Hz, 1H). |

-continued

| Compound No. | Amine | Intermediate | Structure, Name and Data |
|---|---|---|---|
| 52 | 2-phenyl-pyrrolidine | 4.1 | 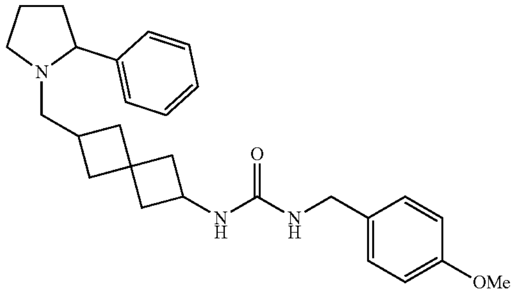 [SMILES: COc1ccc(CNC(=O)NC2CC3(CC(CN4CCCC4c4ccccc4)C3)C2)cc1] 1-(4-methoxybenzyl)-3-(6-((2-phenylpyrrolidin-1-yl)methyl)spiro[3.3]heptan-2-yl)urea. LRMS (APCI) m/z 434 (M + H). $^1$H NMR (400 MHz, DMSO-$d_6$) δ 7.31 (t, J = 4.0 Hz, 4H), 7.23 (q, J = 4.4 Hz, 1H), 7.13 (d, J = 8.3 Hz, 2H), 6.86 (d, J = 8.4 Hz, 2H), 6.16-5.90 (m, 2H), 4.07 (d, J = 5.9 Hz, 2H), 3.85 (q, J = 8.0 Hz, 1H), 3.72 (s, 4H), 3.17 (td, J = 8.4, 2.6 Hz, 2H), 2.37 (ddd, J = 12.5, 8.5, 4.5 Hz, 1H), 2.25 (dq, J = 14.7, 7.3 Hz, 2H), 2.15-1.98 (m, 3H), 1.90 (dtt, J = 12.5, 7.8, 3.8 Hz, 1H), 1.84-1.63 (m, 3H), 1.62-1.33 (m, 5H). |

Example 8

Preparation of 1-(4-chlorobenzyl)-3-((2r,4s)-6-(2-methylpyridin-4-yl)-6-azaspiro[3.4]octan-2-yl)urea (Compound 16)

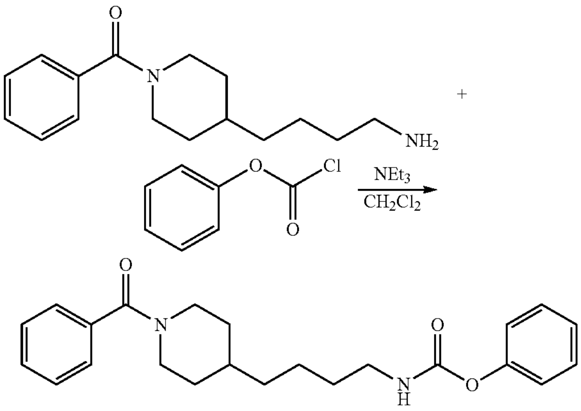

Step 1: Phenyl (4-(1-benzoylpiperidin-4-yl)butyl)carbamate $NEt_3$ (583 mg, 5.76 mmol, 3 equiv) and phenyl chloroformate (360.79 mg, 2.304 mmol, 1.2 equiv) were added to a stirring solution of 4-(1-benzoylpiperidin-4-yl)butan-1-amine (prepared as previously described in "Gillig, A., Majjigapu, S. R., Sordat, B. and Vogel, P. (2012), Synthesis of a C-Iminoribofuranoside Analog of the Nicotinamide Phosphoribosyltransferase (NAMPT) Inhibitor FK866. HCA, 95: 34-42") (500 mg, 1.92 mmol, 1.00 equiv) in $CH_2Cl_2$ (5 mL) at 0° C. before being warmed to rt. After 4 h, the reaction was concentrated by rotary evaporation and the product isolated by prep-TLC (PE/EtOAc 1:1) as a yellow oil (41%). LRMS (ESI) m/z 381 (M+H).

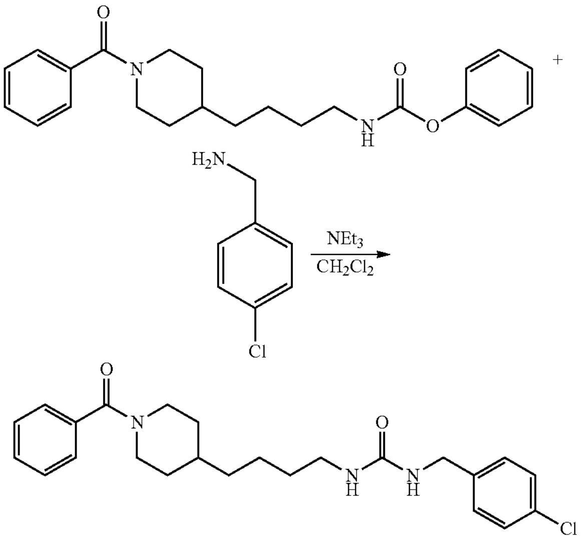

Step 2: 1-(4-(1-benzoylpiperidin-4-yl)butyl)-3-(4-chlorobenzyl)urea $NEt_3$ ((119 mg, 1.2 mmol, 3.00 equiv) was added to a stirring solution of phenyl N-[4-(1-benzoylpiperidin-4-yl)butyl]carbamate (150 mg, 0.4 mmol, 1.00 equiv) and 1-(4-chlorophenyl)methanamine (167 mg, 1.18 mmol, 3.00 equiv) in $CH_2Cl_2$ (2 mL) at rt. After 12 h, the solvent was removed by rotary evaporation and the product isolated by reverse phase HPLC (30%→60% MeCN/H2O w/0.1% ammonium formate) as a white solid (31%). LRMS (ESI) m/z 428 (M+H). $^1$H NMR (300 MHz, DMSO-$d_6$) δ 7.48 (m, 3H), 7.31 (m, 4H), 7.21 (m, 2H), 6.30 (t, J=6.1 Hz, 1H), 5.92

(t, J=5.7 Hz, 1H), 4.46 (s, 1H), 4.17 (d, J=6.0 Hz, 2H), 3.55 (s, 1H), 3.00 (q, J=6.4 Hz, 3H), 2.81 (m, 1H), 1.70 (s, 2H), 1.48 (s, 1H), 1.36 (s, 2H), 1.24 (s, 4H), 1.06 (s, 2H).

Compounds in the following table were prepared in a similar manner as Compound 16, using the intermediates and reagents as listed.

| Compound No. | Amine | Intermediate | Structure, Name and Data |
|---|---|---|---|
| 22 | [4-(amino methyl) phenyl] methanol | 4-(1-benzoylpiperidin-4-yl)butan-1-amine | 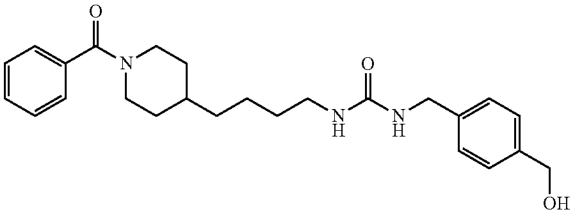 [SMILES: O=C(NCCCCC1CCN(C(=O)c2ccccc2)CC1)NCc1ccc(CO)cc1] 1-(4-(1-benzoylpiperidin-4-yl)butyl)-3-(4-(hydroxymethyl)benzyl)urea. LRMS (ESI) m/z 424 (M + H). $^1$H NMR (400 MHz, Methanol-$d_4$) δ 7.31-7.22 (m, 3H), 7.24-7.16 (m, 2H), 7.09 (q, J = 8.2 Hz, 4H), 4.61 (d, J = 12.3 Hz, 3H), 4.38 (s, 2H), 3.67 (d, J = 13.4 Hz, 1H), 3.14 (m, 2H), 3.06 (m, 1H), 2.96 (t, J = 6.8 Hz, 1H), 1.87 (s, 1H), 1.65 (s, 2H), 1.49 (d, J = 13.0 Hz, 2H), 1.36 (m, 4H), 1.36 (m, 2H). |
| 1 | pyridin-4-ylmethan-amine | 4-(1-benzoylpiperidin-4-yl)butan-1-amine | 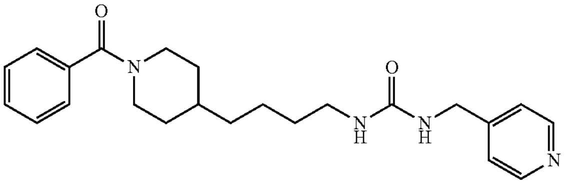 [SMILES: O=C(NCCCCC1CCN(C(=O)c2ccccc2)CC1)NCc1ccncc1] 1-(4-(1-benzoylpiperidin-4-yl)butyl)-3-(pyridin-4-ylmethyl)urea. LRMS (ESI) m/z 395 (M + H). $^1$H NMR (400 MHz, DMSO-$d_6$) δ 8.47 (d, J = 4.6 Hz, 2H), 7.50-7.40 (m, 3H), 7.36 (dd, J = 6.7, 3.0 Hz, 2H), 7.22 (d, J = 5.0 Hz, 2H), 6.40 (t, J = 6.1 Hz, 1H), 6.03 (t, J = 5.8 Hz, 1H), 4.45 (s br, 1H), 4.22 (d, J = 5.8 Hz, 2H), 3.55 (s br, 1H), 3.01 (q, J = 6.1 Hz, 3H), 2.74 (s br, 1H), 1.73 (s br, 1H), 1.60 (s br, 1H), 1.49 (s br, 1H), 1.37 (d, J = 7.0 Hz, 2H), 1.25 (s, 4H), 1.06 (s br, 2H). |
| 17 | (1H-pyrazol-4-yl)methan-amine | 5.1 | 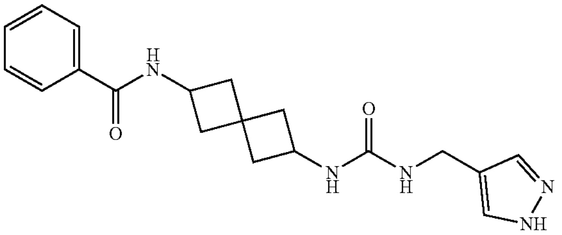 [SMILES: O=C(NCc1cn[nH]c1)NC1CC2(C1)CC(NC(=O)c1ccccc1)C2] N-(6-(3-((1H-pyrazol-4-yl)methyl)ureido)spiro[3.3]heptan-2-yl)benzamide. LRMS (ESI) m/z 354 (M + H). $^1$H NMR (300 MHz, DMSO-$d_6$) δ 12.52 (s, 1H), 8.46 (d, J = 7.5 Hz, 1H), 7.75 (d, J = 7.2 Hz, 2H), 7.44 (t, J = 7.2 Hz, 1H), 7.37 (t, J = 7.4 Hz, 3H), 5.96 (d, J = 8.1 Hz, 1H), 5.83 (t, J = 5.6 Hz, 1H), 4.23 (h, J = 8.4 Hz, 1H), 3.95 (d, J = 5.5 Hz, 2H), 3.88 (dt, J = 16.2, 8.2 Hz, 1H), 2.5 (m, 1H), 2.30 (ddd, J = 12.0, 7.6, 5.1 Hz, 2H), 2.13 (dt, J = 12.3, 6.1 Hz, 2H), 2.01 (dt, J = 19.7, 10.2 Hz, 2H), 1.73 (dt, J = 19.4, 9.9 Hz, 2H). |

-continued

| Compound No. | Amine | Intermediate | Structure, Name and Data |
|---|---|---|---|
| 14 | 4-(amino methyl) benzamide | 5.1 | 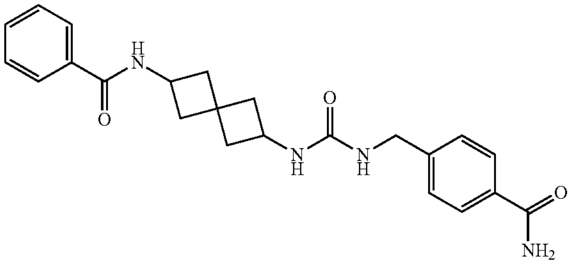 [SMILES: NC(=O)c1ccc(CNC(=O)NC2CC3(C2)CC(NC(=O)c2ccccc2)C3)cc1] N-(6-(3-(4-carbamoylbenzyl)ureido)spiro[3.3]heptan-2-yl)benzamide. LRMS (ESI) m/z 407 (M + H). $^1$H NMR (300 MHz, DMSO-$d_6$) δ 8.54 (d, J = 7.3 Hz, 1H), 7.90 (s, 1H), 7.82 (t, J = 6.7 Hz, 4H), 7.51 (t, J = 7.0 Hz, 1H), 7.45 (t, J = 7.4 Hz, 2H), 7.29 (d, J = 7.8 Hz, 3H), 6.29 (t, J = 5.9 Hz, 1H), 6.21 (d, J = 7.9 Hz, 1H), 4.31 (h, J = 8.2 Hz, 1H), 4.23 (d, J = 5.8 Hz, 2H), 3.98 (h, J = 8.5 Hz, 1H), 2.38 (p, J = 5.4 Hz, 2H), 2.21 (q, J = 6.4 Hz, 2H), 2.09 (dt, J = 19.6, 10.2 Hz, 2H), 1.85 (dt, J = 18.9, 9.6 Hz, 2H). |
| 15 | pyridin-4-ylmethan-amine | 5.1 | 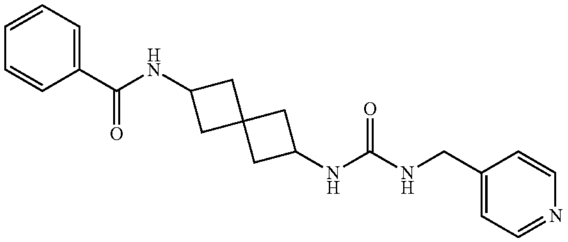 [SMILES: O=C(NCc1ccncc1)NC1CC2(C1)CC(NC(=O)c1ccccc1)C2] N-(6-(3-(pyridin-4-ylmethyl)ureido)spiro[3.3]heptan-2-yl)benzamide. LRMS (ESI) m/z 365 (M + H). $^1$H NMR (300 MHz, DMSO-$d_6$) δ 8.57-8.43 (m, 3H), 7.87-7.77 (m, 2H), 7.56-7.45 (m, 1H), 7.44 (dd, J = 8.1, 6.2 Hz, 2H), 7.25-7.17 (m, 2H), 6.40-6.25 (m, 2H), 4.30 (q, J = 8.0 Hz, 1H), 4.20 (d, J = 5.9 Hz, 2H), 3.96 (q, J = 8.0 Hz, 1H), 2.37 (ddd, J = 10.6, 7.5, 5.0 Hz, 2H), 2.14 (dtd, J = 31.5, 11.5, 7.7 Hz, 4H), 1.94-1.77 (m, 2H). |
| 18 | (4-phenyl) methan-amine methoxy | 5.1 | 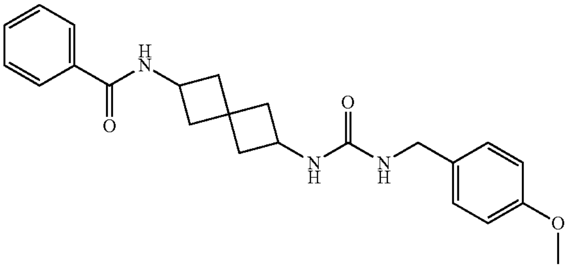 [SMILES: COc1ccc(CNC(=O)NC2CC3(C2)CC(NC(=O)c2ccccc2)C3)cc1] N-(6-(3-(4-methoxybenzyl)ureido)spiro[3.3]heptan-2-yl)benzamide. LRMS (ESI) m/z 394 (M + H). $^1$H NMR (300 MHz, DMSO-$d_6$) δ 8.54 (d, J = 7.5 Hz, 1H), 7.83 (d, J = 7.5 Hz, 2H), 7.51 (t, J = 7.2 Hz, 1H), 7.45 (t, J = 7.4 Hz, 2H), 7.16 (d, J = 8.2 Hz, 2H), 6.87 (d, J = 8.2 Hz, 2H), 6.11 (d, J = 8.6 Hz, 2H), 4.30 (h, J = 8.4 Hz, 1H), 4.10 (d, J = 5.7 Hz, 2H), 3.97 (q, J = 7.5 Hz, 1H), 3.73 (s, 3H), 2.37 (q, J = 6.2 Hz, 2H), 2.19 (p, J = 5.6 Hz, 2H), 2.09 (dt, J = 19.4, 10.0 Hz, 2H), 1.82 (dt, J = 18.8, 9.9 Hz, 2H). |

Example 9

Preparation of 1-(4-(1-benzoylpiperidin-4-yl)butyl)-3-(4-methoxybenzyl)urea (Compound 20)

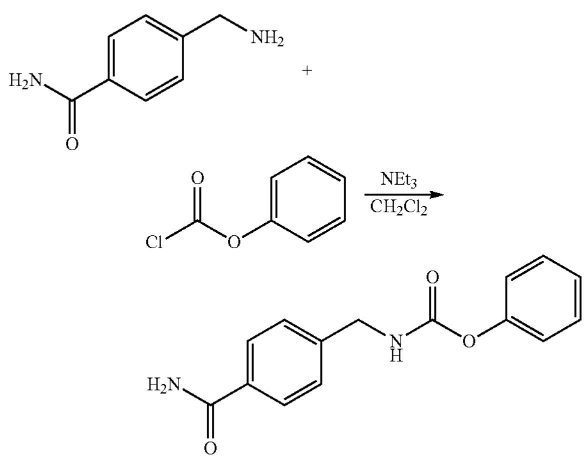

Step 1: Phenyl (4-carbamoylbenzyl)carbamate $NEt_3$ (1.6 g, 16.1 mmol, 3.0 equiv) and phenyl chloroformate (1.0 g, 5.9 mmol, 1.10 equiv) were added to a stirring solution of 4-(aminomethyl)benzamide hydrochloride (1.0 g, 5.4 mmol, 1.0 equiv) in $CH_2Cl_2$ (10 mL) at 0° C. After 2 h, the reaction was quenched with water (20 mL), extracted with $CH_2Cl_2$ (2×20 mL), organics combined, washed with saturated sodium chloride (20 mL), dried over sodium sulfate, filtered, and solvent removed by rotary evaporation to give the crude product (1.2 g) as a white solid which was used in the future steps without further purification. LRMS (ESI) m/z 271 (M+H).

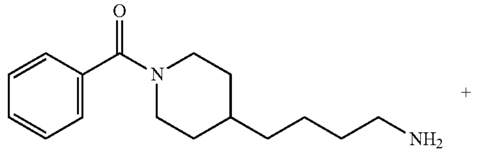

-continued

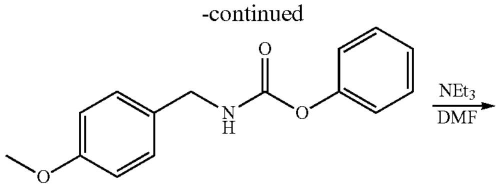

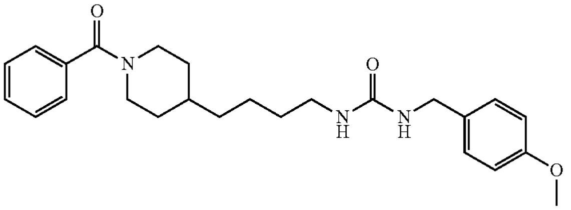

Step 2: 1-(4-(1-benzoylpiperidin-4-yl)butyl)-3-(4-methoxybenzyl)urea $NEt_3$ (291 mg, 2.9 mmol, 5 equiv) was added to a stirring solution of 4-(1-benzoylpiperidin-4-yl)butan-1-amine (150 mg, 0.6 mmol, 1.00 equiv) and phenyl N-[(4-methoxyphenyl)methyl]carbamate (518 mg, 2.0 mmol, 3.5 equiv) in DMF (3 mL) at rt. After 12 h, the reaction was quenched with water (20 mL), extracted with EtOAc (2×20 mL). Organics were combined, washed with saturated sodium chloride (20 mL), dried over sodium sulfate, filtered, and solvent removed by rotary evaporation. The product was then isolated by reverse phase HPLC (30%→60% MeCN/H2O w/0.1% ammonium formate) as yellow tinged solid (82 mg). LRMS (ESI) m/z 424 (M+H). $^1H$ NMR (400 MHz, Methanol-$d_4$) δ 7.49 (m, 3H), 7.42 (m, 2H), 7.23 (m, 2H), 6.88 (m, 2H), 4.60 (d, J=13.1 Hz, 1H), 4.22 (s, 2H), 3.75 (s, 3H), 3.69 (d, J=13.3 Hz, 1H), 3.13 (t, J=6.8 Hz, 3H), 2.84 (d, J=13.1 Hz, 1H), 1.83.

Compounds in the following table were prepared in a similar manner as Compound 20, using the intermediates and reagents as listed.

| Compound No. | Amine - step 1 | Amine - step 2 | Structure, Name and Data |
|---|---|---|---|
| 19 | 4-(aminomethyl)benzamide | 4-(1-benzoylpiperidin-4-yl)butan-1-amine | 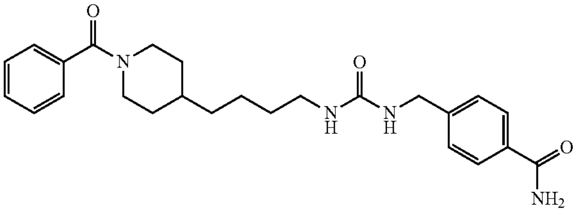 [SMILES: NC(=O)c1ccc(CNC(=O)NCCCCC2CCN(C(=O)c3ccccc3)CC2)cc1] 4-((3-(4-(1-benzoylpiperidin-4-yl)butyl)ureido) methyl)benzamide. LRMS (ESI) m/z 437 (M + H). $^1H$ NMR (400 MHz, Methanol-$d_4$) δ 7.85 (m, 2H), 7.45 (dd, J = 5.0, 2.0 Hz, 3H), 7.41 - 7.33 (m, 4H), 4.60 (d, J = 11.7 Hz, 1H), 4.36 (s, 2H), 3.69 (d, J = 13.5 Hz, |

-continued

| Compound No. | Amine - step 1 | Amine - step 2 | Structure, Name and Data |
|---|---|---|---|
| | | | 1H), 3.14 (t, J = 6.9 Hz, 2H), 3.05 (d, J = 14.2 Hz, 1H), 2.83 (s, 1H), 1.82 (s, 2H), 1.67 (s, 3H), 1.47 (q, J = 7.2 Hz, 4H), 1.33 (t, J = 5.7 Hz, 2H). |
| 23 | oxazol-5-ylmethan-amine | 4-(1-benzoyl-piperidin-4-yl)butan-1-amine | 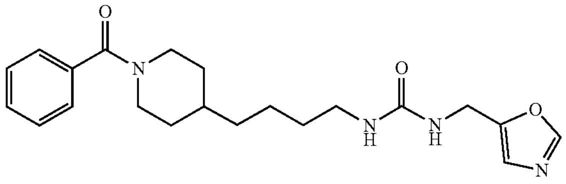 [SMILES: O=C(NCCCCC1CCN(C(=O)c2ccccc2)CC1)NCc1cnco1] 1-(4-(1-benzoylpiperidin-4-yl)butyl)-3-(oxazol-5-ylmethyl)urea. LRMS (ESI) m/z 385 (M + H). $^1$H NMR (300 MHz, DMSO-$d_6$) δ 8.24 (s, 1H), 7.46 - 7.38 (m, 3H), 7.37 - 7.34 (m, 2H), 6.92 (S, 1H), 6.26 (t, J = 5.7 Hz, 1H), 5.94 (t, J = 5.4 Hz, 1H), 4.45 (s, 1H), 4.26 (m, 2H), 3.54 (s, 1H), 2.98 (t, J = 6 Hz, 3H), 2.76 (s, 1H), 1.70 - 1.66 (m, 3H), 1.55 - 1.31 (m, 6H), 1.24-1.03 (m, 2H). |
| 26 | 4-(aminometh-yl)benz-amide | 6.1 | 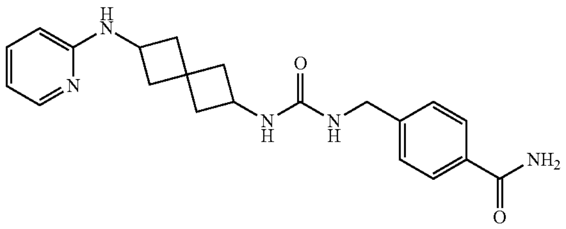 [SMILES: NC(=O)c1ccc(CNC(=O)NC2CC3(C2)CC(Nc2ccccn2)C3)cc1] 4-((3-(6-(pyridin-2-ylamino)spiro[3.3]heptan-2-yl)ureido)methyl)benzamide. LRMS (ESI) m/z 380 (M + H). $^1$H NMR (400 MHz, DMSO-$d_6$) δ 7.97 - 7.86 (m, 2H), 7.81 (d, J = 8.1 Hz, 2H), 7.33 (t, J = 7.7 Hz, 1H), 7.28 (d, J = 8.0 Hz, 3H), 6.62 (d, J = 7.2 Hz, 1H), 6.49 - 6.40 (m, 1H), 6.36 (d, J = 8.4 Hz, 1H), 6.28 (t, J = 5.7 Hz, 1H), 6.21 (d, J = 8.0 Hz, 1H), 4.22 (d, J = 6.0 Hz, 2H), 4.13 (h, J = 7.9 Hz, 1H), 3.97 (h, J = 8.1 Hz, 1H), 2.41 (ddt, J = 24.5, 12.1, 5.7 Hz, 2H), 2.31 - 2.11 (m, 2H), 1.95 - 1.72 (m, 4H). |
| 21 | 4-(amino-methyl)benz-amide | 7.1 | 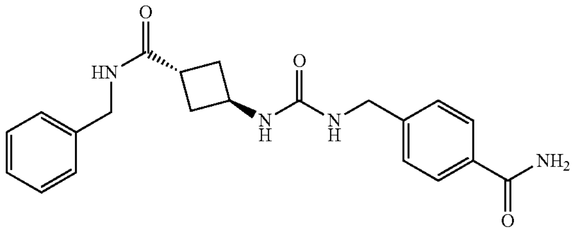 [SMILES: NC(=O)c1ccc(CNC(=O)N[C@H]2C[C@H](C(=O)NCc3ccccc3)C2)cc1] 4-((3-((1r,3r)-3-(benzylcarbamoyl)cyclobutyl)ureido)methyl)benzamide. LRMS (ESI) m/z 381 (M + H). $^1$H NMR (400 MHz, DMSO-$d_6$) δ 8.25 (t, J = 6.0 Hz, 1H), 7.90 (s, 1H), 7.81 (d, J = 7.9 Hz, 2H), 7.30 (t, J = 8.0 Hz, 5H), 7.24 (d, J = 7.1 Hz, 3H), 6.41 - 6.23 (m, 2H), 4.25 (dd, J = 18.9, 6.1 Hz, 5H), 2.95 - 2.78 (m, 1H), 2.36 (t, J = 8.7 Hz, 2H), 2.04 (dt, J = 11.8, 9.3 Hz, 2H). |

Example 10

Preparation of 1-(4-methoxybenzyl)-3-(5-phenoxypentyl)urea (Compound 149)

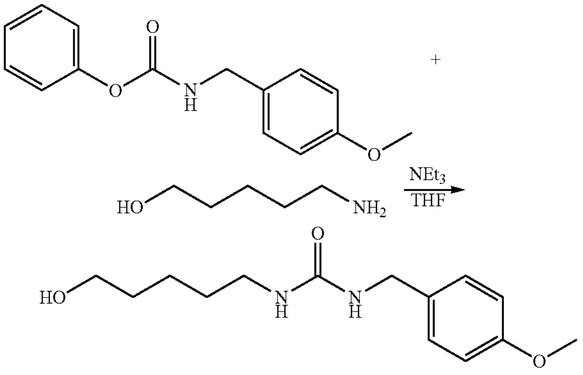

Step 1: 1-(5-hydroxypentyl)-3-(4-methoxybenzyl)urea

Phenyl N-[(4-methoxyphenyl) methyl]carbamate (250 mg, 1.0 mmol, 1.00 equiv), 5-aminopentanol (120 mg, 1.2 mmol, 1.2 equiv), and $NEt_3$ (295 mg, 2.9 mmol, 3 equiv) were dissolved in THF (5 mL) and heated to 65° C. After 1 h, the reaction was cooled to rt, quenched with $H_2O$ (20 mL), extracted with EtOAc (2×20 mL), organics combined and washed with sat sodium chloride (20 mL). The organic layer was then dried over sodium sulfate, filtered, and solvent removed by rotary evaporation to give the crude product as a white solid (250 mg). LRMS (ESI) m/z 267 (M+H).

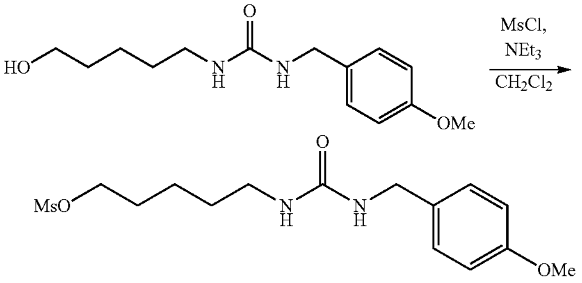

Step 2: 5-(3-(4-methoxybenzyl)ureido)pentyl methanesulfonate

MsCl (226 mg, 1.9 mmol, 2.50 equiv) was added to a stirring solution of 3-(5-hydroxypentyl)-1-[(4-methoxyphenyl)methyl]urea (210 mg, 0.79 mmol, 1.00 equiv) and $NEt_3$ (399 mg, 3.9 mmol, 5 equiv) in $CH_2Cl_2$ (5 mL) at 0° C. before being warmed to rt. After 1 h, the reaction was quenched with $H_2O$ (20 mL), extracted with EtOAc (2×20 mL), organics combined and washed with sat sodium chloride (20 mL). The organic layer was then dried over sodium sulfate, filtered, and solvent removed by rotary evaporation to give the crude product as a white solid (440 mg). LRMS (ESI) m/z 345 (M+H).

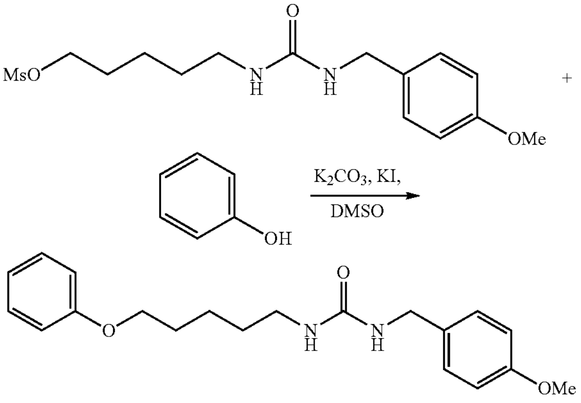

Step 3: 1-(4-methoxybenzyl)-3-(5-phenoxypentyl)urea 5-(carbamoyl]amino)pentyl methanesulfonate (350 mg, 1.0 mmol, 1.00 equiv), $K_2CO_3$ (351 mg, 2.5 mmol, 2.5 equiv), phenol (115 mg, 1.2 mmol, 1.2 equiv) and KI (16.9 mg, 0.10 mmol, 0.1 equiv) were suspended in DMSO (5 mL) before being heated to 80° C. After 2 h, the reaction was cooled to rt and product isolated by reverse phase HPLC (50% MeCN/H2O w/0.5% ammonium formate) as a white solid (15 mg). LRMS (ESI) m/z 343 (M+H). $^1$H NMR (300 MHz, DMSO-d6) δ 7.32-7.21 (m, 2H), 7.15 (d, J=8.6 Hz, 2H), 6.95-6.81 (m, 5H), 6.16 (t, J=6.2 Hz, 1H), 5.86 (s, 1H), 4.11 (d, J=5.8 Hz, 2H), 3.93 (t, J=6.4 Hz, 2H), 3.71 (s, 3H), 3.02 (d, J=6.0 Hz, 2H), 1.70 (t, J=6.8 Hz, 2H), 1.41 (s, 4H).

Compounds in the following table were prepared in a similar manner as Compound 149, using the intermediates and reagents as listed.

| Compound No. | Amine | Carbamate | Structure, Name and Data |
|---|---|---|---|
| 150 | 6-amino-hexanol | Phenyl N-[(4-methoxyphenyl) methyl]carbamate | 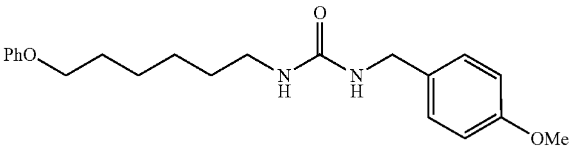 [SMILES: COc1ccc(CNC(=O)NCCCCCCOc2ccccc2)cc1] 1-(4-methoxybenzyl)-3-(6-phenoxyhexyl)urea. LRMS (ESI) m/z 357 (M + H). $^1$H NMR (300 MHz, DMSO-$d_6$) δ 7.26 (dd, J 8.5, 7.3 Hz, 2H), 7.15 (d, J = 8.6 Hz, 2H), 6.95 - 6.81 (m, 5H), 6.14 (t, J = 5.9 Hz, 1H), 5.84 (t, J = 5.7 Hz, 1H), 4.11 (d, J = 5.9 |

-continued

| Compound No. | Amine | Carbamate | Structure, Name and Data |
|---|---|---|---|
| | | | Hz, 2H), 3.94 (t, J = 6.5 Hz, 2H), 3.71 (s, 3H), 3.04 - 2.93 (m, 2H), 1.68 (q, J = 7.0 Hz, 2H), 1.38 (s, 5H), 1.44 - 1.32 (m, 1H). ). |
| 196 | 2-(2-amino-ethoxy) ethan-1-ol | Phenyl N-[(4-chlorophenyl) methyl]carba-mate | 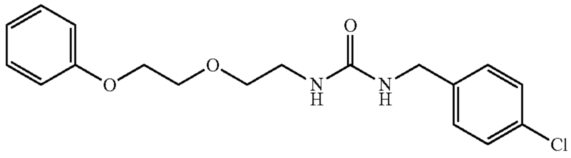 [SMILES: O=C(NCCOCCOc1ccccc1)NCc1ccc(Cl)cc1] 1-(4-chlorobenzyl)-3-(2-(2-phenoxyethoxy)ethyl)urea. LRMS (APCI) m/z 349 (M + H). $^1$H NMR (400 MHz, Methanol-$d_4$) δ 7.16 (td, J = 8.2, 5.4 Hz, 6H), 6.87 - 6.76 (m, 3H), 4.17 (s, 2H), 4.05 - 3.94 (m, 2H), 3.76 - 3.67 (m, 2H), 3.50 (t, J = 5.4 Hz, 2H), 3.24 (t, J = 5.4 Hz, 2H). |

Example 11

Preparation of N-benzyl-2-(6-(3-(4-methoxybenzyl) ureido)spiro[3.3]heptan-2-yl)-N-methylacetamide (Compound 67)

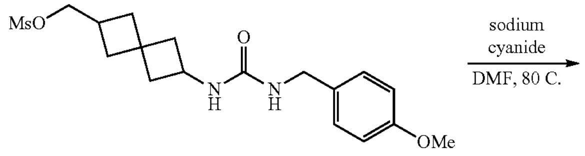

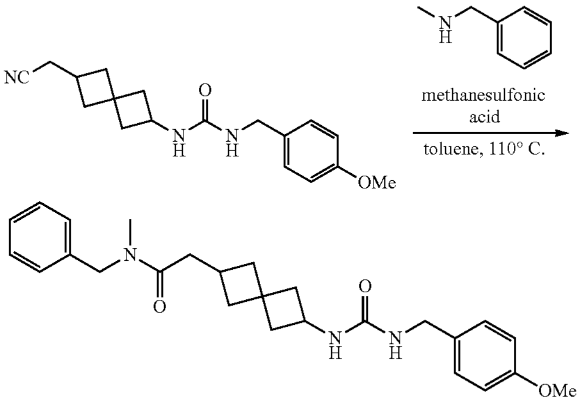

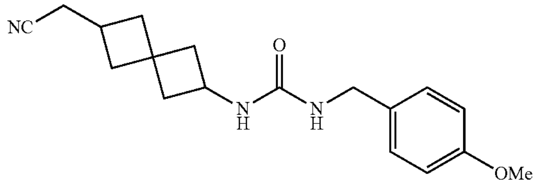

Step 1: Preparation of (6-(3-(4-methoxybenzyl) ureido)spiro[3.3]heptan-2-yl)methyl cyanide (6-(3-(4-methoxybenzyl)ureido)spiro[3.3]heptan-2-yl) methyl methanesulfonate (Intermediate 4.1) (0.1 g, 0.27 mmol, 1.0 equiv) was dissolved in DMF (1 mL) and sodium cyanide (5 eq) was added. The solution was stirred at 80° C. overnight and monitored by LCMS analysis. The solution was cooled to 0° C. and saturated aq. ammonium chloride solution (8 mL) and EtOAc (5 mL) was added and the solution stirred vigorously for 10 mins. The organic layer was separated, and the aq. layer was extracted with 10 mL of EtOAc. The combined organic layers were washed with brine, dried, filtered, and concentrated to provide the product as a white solid 72 mg, 87% yield). LCMS-APCI (POS.) m/z: 314.0 (M+H)+.

Step 2: N-benzyl-2-(6-(3-(4-methoxybenzyl)ureido) spiro[3.3]heptan-2-yl)-N-methylacetamide (6-(3-(4-methoxybenzyl)ureido)spiro[3.3]heptan-2-yl) methyl cyanide (50 mg, 0.17 mmol, 1.0 equiv) and N-methyl benzylamine (19 mg, 0.17 mmol, 1.0 equiv) were dissolved in toluene (0.5 mL) and methanesulfonic acid (16 mg, 0.17 mmol, 1.0 equiv) was added. The reaction was stirred at 110° C. for 24 hours. The solution was cooled to rt and quenched with saturated aq. sodium bicarbonate. The reaction was extracted with DCM and the combined organic layers were dried, filtered and concentrated. The organic phase was dried to a viscous oil which was purified by reverse phase HPLC with a 10%-100% acetonitrile in water solution that was run over 30 minutes in a Phenomonex Gemini 5u C18 column, providing the desired product (51.0 mg, 0.12 mmol, 69% yield) as a white solid. LCMS-APCI (POS.) m/z: 436.0 (M+H)+. 1H NMR (400 MHz, DMSO-$d_6$) δ 7.33 (tt, J=24.0, 7.5 Hz, 3H), 7.16 (dd, J=13.3, 7.3 Hz, 4H), 6.86 (d, J=8.0 Hz, 2H), 6.22-5.97 (m, 2H), 4.55 (s, 1H), 4.47 (s, 1H), 4.09 (t, J=4.3 Hz, 2H), 3.90 (dq, J=15.0, 8.0 Hz, 1H), 3.72 (d, J=1.6 Hz, 3H), 2.88 (s, 2H), 2.78 (s, 2H), 2.45 (d, J=16.9 Hz, 3H), 2.34 (q, J=9.3, 7.5 Hz, 1H), 2.16 (s, 1H), 2.04 (dd, J=15.8, 9.5 Hz, 1H), 1.68 (dh, J=37.2, 9.6 Hz, 4H).

Example 12

Preparation of 1-(4-chlorobenzyl)-3-(6-(dibenzylamino)spiro[3.3]heptan-2-yl)urea (Compound 119)

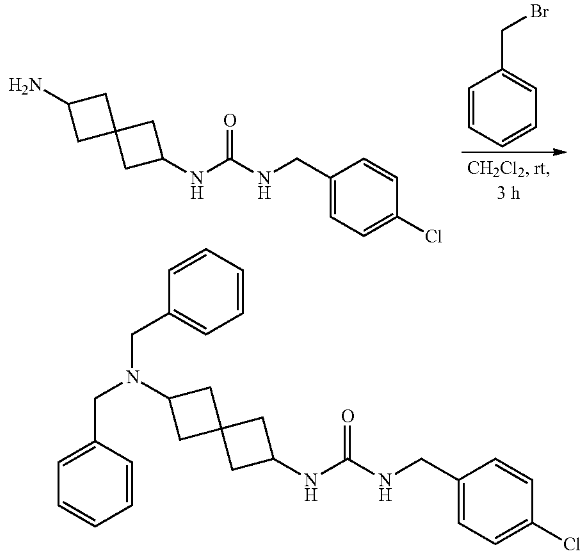

Step 1: Preparation of 1-(4-chlorobenzyl)-3-(6-(dibenzylamino)spiro[3.3]heptan-2-yl)urea Benzyl bromide (18 μL, 0.159 mmol, 1 equiv) was added to a stirring solution of 1-(6-aminospiro[3.3]heptan-2-yl)-3-(4-chlorobenzyl)urea (70 mg, 0.238 mmol, 1.5 equiv) and DIPEA (83 μL, 0.477 mmol, 3 equiv) in $CH_2Cl_2$ (2 mL) at rt. After 3 h, solvent was removed by rotary evaporation and product isolated by reverse phase HPLC (5→95% MeCN/H2O w/0.1% formic acid) as a white solid (28 mg, 40%). LRMS (APCI) m/z 474 (M+H). $^1$H NMR (400 MHz, DMSO-$d_6$) δ 8.14 (s, 1H), 7.41-7.15 (m, 14H), 6.25 (t, J=6.1 Hz, 1H), 6.15 (d, J=8.1 Hz, 1H), 4.14 (d, J=6.0 Hz, 2H), 3.90 (q, J=8.0 Hz, 1H), 3.40 (s, 3H), 3.18 (d, J=3.9 Hz, 1H), 2.99 (q, J=7.9 Hz, 1H), 2.24 (dt, J=11.3, 5.8 Hz, 1H), 2.09 (dq, J=10.0, 5.2, 4.5 Hz, 2H), 1.89 (dt, J=11.5, 5.8 Hz, 1H), 1.75 (qd, J=13.0, 11.8, 9.0 Hz, 3H).

Example 13

Preparation of 4-(4-(6-(benzylamino)spiro[3.3]heptan-2-yl)-3-oxobutyl)benzamide (Compound 24)

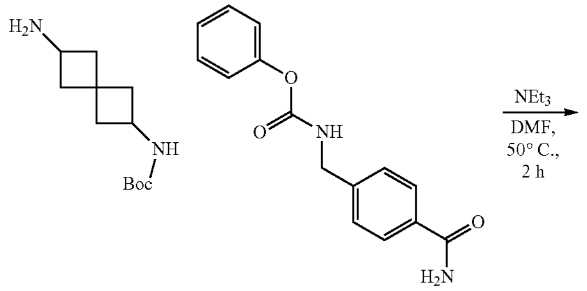

-continued

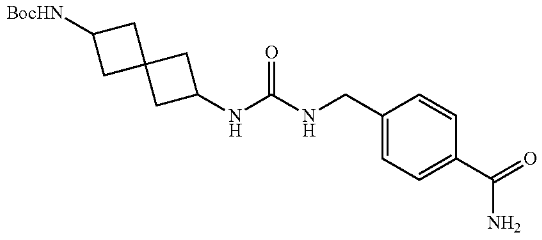

Step 1: Preparation of tert-butyl (6-(4-(4-carbamoylphenyl)-2-oxobutyl)spiro[3.3]heptan-2-yl)carbamate Phenyl N-[(4-carbamoylphenyl)methyl]carbamate (657 mg, 2.4 mmol, 1.1 equiv) and $NEt_3$ (671 mg, 6.6 mmol, 3.00 equiv) were added to a stirring solution of N-[6-aminospiro[3.3]heptan-2-yl]carbamate (500 mg, 2.2 mmol, 1.00 equiv) in DMF (5.00 mL) before being heated to 50° C. After 2 h, the reaction was cooled to rt, and volatiles were removed by rotary evaporation. The product was isolated by reverse phase HPLC (60% MeCN/H2O w/0.1% ammonium formate) as a white solid (45%). LRMS (ESI) m/z 403 (M+H).

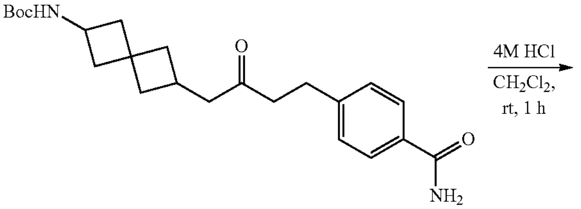

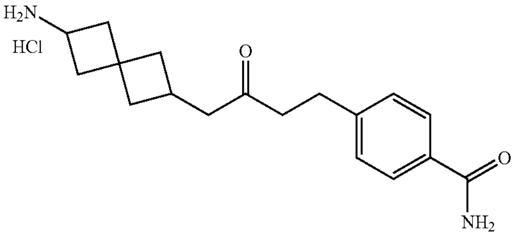

Step 2: Preparation of 4-(4-(6-aminospiro[3.3]heptan-2-yl)-3-oxobutyl)benzamide hydrochloride HCl (10 mL, 4M in dioxanes) was added to a stirring solution of tert-butyl (6-(4-(4-carbamoylphenyl)-2-oxobutyl)spiro[3.3]heptan-2-yl)carbamate carbamate (380 mg, 0.94 mmol, 1.00 equiv) in $CH_2C_2$ (40 mL) at rt. After 1 h, the reaction was concentrated by rotary evaporation to afford the crude product (560 mg) as a white solid which was used without further purification. LRMS (ESI) m/z 303 (M+H).

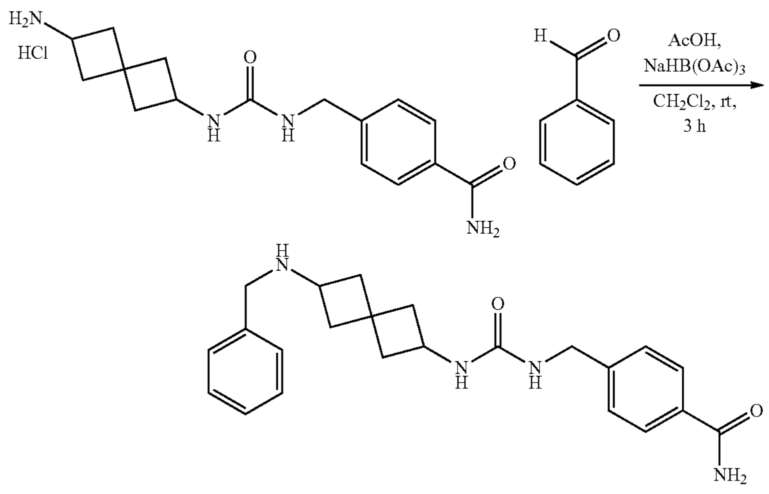

Step 3: Preparation of 4-(4-(6-(benzylamino)spiro[3.3]heptan-2-yl)-3-oxobutyl)benzamide AcOH (29 mg, 0.54 mmol, 2 equiv) and $NaHB(OAc)_3$ (103 mg, 0.54 mmol, 2.00 equiv) were added to a stirring solution of 4-[[([6-aminospiro[3.3]heptan-2-yl]carbamoyl)amino]methyl]benzamide hydrochloride (82 mg, 0.27 mmol, 1.00 equiv) and benzaldehyde (29 mg, 0.27 mmol, 1.00 equiv) in $CH_2Cl_2$ (5 mL) at rt. After 3 h, the solvent was removed by rotary evaporation and product isolated by reverse phase HPLC (15%→45% MeCN/H2O w/0.1% ammonium formate) as a white solid (15%). LRMS (ESI) m/z 393 (M+H). $^1$H NMR (300 MHz, Methanol-$d_4$) δ 7.90 (s, 1H), 7.80 (d, J=7.8 Hz, 2H), 7.28 (s, 6H), 7.23-7.09 (m, 1H), 6.26 (s, 1H), 6.16 (d, J=8.1 Hz, 1H), 4.21 (d, J=4.6 Hz, 2H), 3.92 (d, J=7.9 Hz, 1H), 3.57 (s, 2H), 3.32 (s, 3H), 3.11-2.92 (m, 1H), 2.23 (s, 2H), 2.12 (s, 1H), 2.03 (d, J=7.6 Hz, 1H), 1.73 (dt, J=20.4, 10.2 Hz, 3H).

Example 14

Preparation of 4-((3-(6-((pyridin-2-ylmethyl)amino)spiro[3.3]heptan-2-yl)ureido)methyl)benzamide (Compound 34)

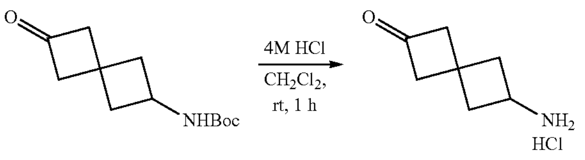 [SMILES: CC(C)(C)OC(=O)NC1CC2(CC(=O)C2)C1 ; NC1CC2(CC(=O)C2)C1 ; Cl]

Step 1: Preparation of 6-aminospiro[3.3]heptan-2-one hydrochloride

HCl (5 mL, 4M in dioxanes) was added to a stirring solution of tert-butyl N-[6-oxospiro[3.3]heptan-2-yl]carbamate (500 mg, 2.2 mmol, 1.00 equiv) in $CH_2C_2$ (5.00 mL). The reaction was then concentrated by rotary evaporation to give the crude product (350 mg) as a white solid. LRMS (ESI) m/z 126 (M+H).

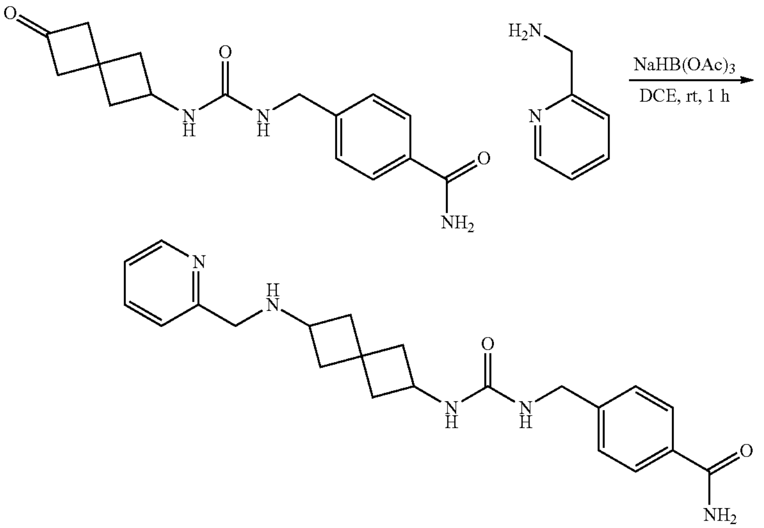

Step 2: Preparation of 4-((3-(6-oxospiro[3.3]heptan-2-yl)ureido)methyl)benzamide N-[(4-carbamoylphenyl) methyl]carbamate (241 mg, 0.90 mmol, 1.2 equiv) and $NEt_3$ (300 mg, 2.97 mmol, 4 equiv) were added to a stirring solution of 6-aminospiro[3.3]heptan-2-one hydrochloride (120 mg, 0.74 mmol, 1.00 equiv) in MeCN (4 mL) and heated to 65° C. After 2 h, the reaction was cooled to rt and concentrated by rotary evaporation to give the crude product (280 mg) as a yellow solid. LRMS (ESI) m/z 302 (M+H).

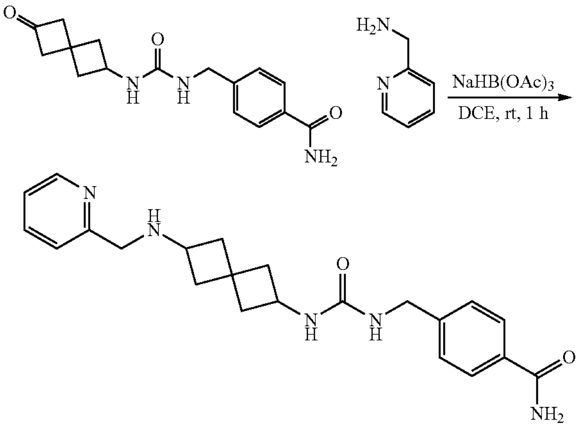

Step 3: Preparation of 4-((3-(6-((pyridin-2-ylmethyl)amino)spiro[3.3]heptan-2-yl)ureido)methyl)benzamide 2-Pyridinemethaneamine (145 mg, 1.34 mmol, 1.5 equiv) and 4-[[([6-oxospiro[3.3]heptan-2-yl]carbamoyl)amino]methyl]benzamide (270 mg, 0.90 mmol, 1.00 equiv) were dissolved in DCE (5 mL) and stirred at rt for 30 min before $NaHB(OAc)_3$ (285 mg, 1.34 mmol, 1.5 equiv) was added. After 1 h, the reaction was concentrated by rotary evaporation and product isolated by reverse phase HPLC (3%→15% MeCN/H2O w/ammonium formate) as a yellow solid (20 mg). LRMS (ESI) m/z 394 (M+H). $^1H$ NMR (400 MHz, DMSO-d6) δ 8.50 (d, J=4.9 Hz, 1H), 8.25 (s, 1H), 7.91 (s, 1H), 7.85-7.71 (m, 3H), 7.42 (d, J=7.9 Hz, 1H), 7.36-7.22 (m, 5H), 6.30 (t, J=6.2 Hz, 1H), 6.21 (d, J=8.0 Hz, 1H), 4.22 (d, J=6.0 Hz, 2H), 3.94 (q, J=7.9 Hz, 1H), 3.16 (p, J=7.7 Hz, 1H), 2.32-2.19 (m, 2H), 2.15 (dt, J=11.9, 6.4 Hz, 1H), 2.06 (dt, J=11.7, 5.9 Hz, 1H), 1.84-1.71 (m, 4H).

Example 15

Preparation of 4-((3-(6-((pyridin-2-ylmethyl)amino)spiro[3.3]heptan-2-yl)ureido)methyl)benzamide (Compound 187 and 182)

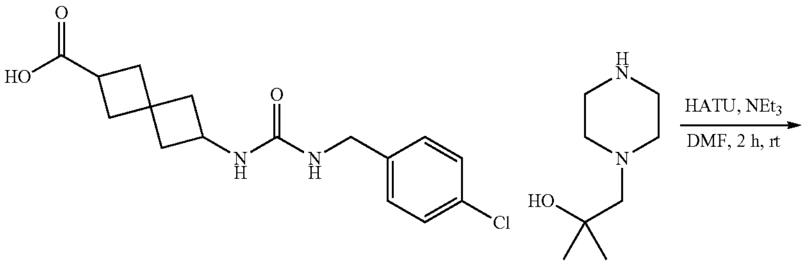

-continued

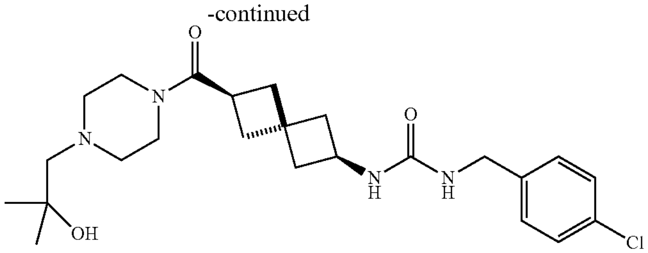

Compound 187

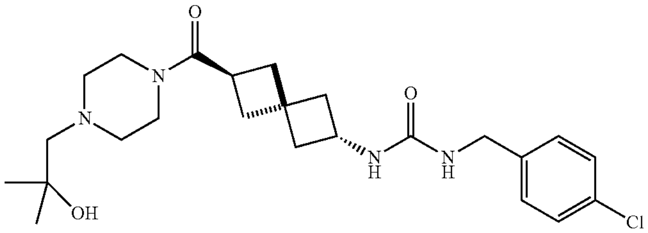

Compound 182

Preparation of 1-(4-chlorobenzyl)-3-(6-(4-(2-hydroxy-2-methylpropyl)piperazine-1-carbonyl)spiro[3.3]heptan-2-yl)urea HATU (1.4 g, 3.7 mmol, 1.5 equiv) was added to a stirring solution of 6-(3-(4-chlorobenzyl)ureido)spiro[3.3]heptane-2-carboxylic acid (intermediate 2.1) (1 g, 0.36 mmol, 1 equiv), 2-methyl-1-(piperazin-1-yl)propan-2-ol (980 mg, 6.2 mmol, 2 equiv) and $NEt_3$ (1.3 mL, 9.3 mmol, 3 equiv) in EtOAc (50 mL) at rt. After 12 h, the reaction was dry loaded onto silica and racemic product isolated by silica chromatography (0→15% MeOH/CH2CL2 w/0.1% formic acid) as a white solid.

Chiral Separation of 1-(4-chlorobenzyl)-3-(6-(4-(2-hydroxy-2-methylpropyl)piperazine-1-carbonyl)spiro[3.3]heptan-2-yl)urea The 1 g mixture of 1-(4-chlorobenzyl)-3-(6-(4-(2-hydroxy-2-methylpropyl)piperazine-1-carbonyl)spiro[3.3]heptan-2-yl)urea was separated by SFC (Chiralcel OX—H column, 50% co-solvent [25% MeOH/MeCN w/0.25% isopropylamine] at 70 g/min) affording the two isomers Compound 187 (0.32 g, 46%) and Compound 182 (0.33 g, 47%) as white solids. The absolute stereochemistry of each isomer was not determined and arbitrarily assigned. Compound 187 elutes first from SFC using stated conditions, followed by Compound 182.

Compound 187:

LRMS (APCI) m/z 464.1 (M+H). $^1$H NMR (400 MHz, Methanol-d4) δ 7.32 (d, J=8.5 Hz, 2H), 7.26 (d, J=8.5 Hz, 2H), 4.28 (s, 2H), 4.03 (p, J=8.0 Hz, 1H), 3.62-3.52 (m, 2H), 3.47-3.39 (m, 2H), 3.27 (q, J=8.6 Hz, 1H), 2.55 (ddt, J=18.0, 11.5, 5.1 Hz, 5H), 2.37-2.22 (m, 6H), 2.12 (ddd, J=11.5, 8.5, 3.2 Hz, 1H), 1.87 (ddd, J=36.9, 11.1, 8.6 Hz, 2H), 1.21 (s, 6H).

Compound 182:

LRMS (APCI) m/z 464.1 (M+H). $^1$H NMR (400 MHz, Methanol-$d_4$) δ 7.31 (d, J=8.5 Hz, 2H), 7.26 (d, J=8.4 Hz, 2H), 4.28 (s, 2H), 4.03 (p, J=8.0 Hz, 1H), 3.57 (q, J=4.6 Hz, 2H), 3.43 (t, J=4.9 Hz, 2H), 3.27 (t, J=8.6 Hz, 1H), 2.54 (ddt, J=18.2, 11.7, 5.0 Hz, 5H), 2.38-2.21 (m, 6H), 2.21-2.07 (m, 1H), 1.87 (ddd, J=37.2, 11.2, 8.6 Hz, 2H), 1.21 (s, 6H).

Compounds in the following table were prepared in a similar manner as Compound 187 and 182, using the intermediates and reagents as listed.

| Compound No. | Racemate | Chiral Column | Structure, Name and Data |
|---|---|---|---|
| 229 | 1-(4-methoxy-benzyl)-3-(6-(1,2,3,4-tetrahydro-quinoline-1-carbonyl) spiro[3.3] heptan-2-yl)urea | Chiralcel OX—H | 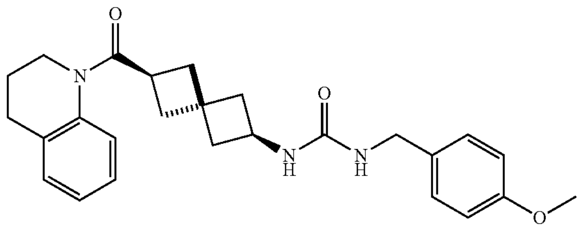 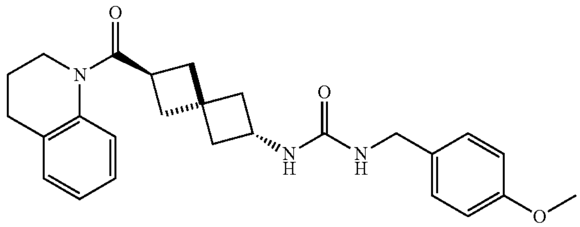 E1: 1-(4-methoxybenzyl)-3-((2S,4s,6S)-6-(1,2,3,4-tetrahydroquinoline-1-carbonyl)spiro[3.3]heptan-2-yl)urea. LRMS (APCI) m/z 434.1 (M + H). $^1$H NMR (400 MHz, Chloroform-d) δ 7.32 - 6.93 (m, 6H), 6.88 - 6.78 (m, 2H), 4.86 (s, 1H), 4.25 (s, 2H), 4.00 (p, J = 7.4 Hz, 1H), 3.79 (s, 3H), 3.71 (s, 2H), 3.36 (p, J = 8.4 Hz, 1H), 2.80 (s, 1H), 2.70 (s, 2H), 2.48 - 2.28 (m, 4H), 2.11 (s, 1H), 1.93 (p, J = 6.6 Hz, 3H), 1.75 (dd, J = 11.5, 8.4 Hz, 2H). E2: 1-(4-methoxybenzyl)-3-((2R,4r,6R)-6-(1,2,3,4-tetrahydroquinoline-1-carbonyl)spiro[3.3]heptan-2-yl)urea. LRMS (APCI) m/z 434.1 (M + H). $^1$H NMR (400 MHz, Chloroform-d) δ 7.34 - 6.96 (m, 6H), 6.87 (d, J = 8.6 Hz, 2H), 4.73 (s, 1H), 4.29 (s, 2H), 4.09 - 3.91 (m, 1H), 3.81 (s, 3H), 3.73 (s, 2H), 3.45-3.28 (m, 1H), 2.79-2.70 (m, 3H), 2.56 -2.30 (m, 4H), 2.08 (d, J = 33.8 Hz, 1H), 1.94 (p, J = 6.6 Hz, 3H), 1.77 (dd, J = 11.5, 8.5 Hz, 2H). n.b. - Stereochemistry assigned randomly and not confirmed by crystallography |
| 249 | N-((6-(3-(4-chlorobenzyl) ureido) spiro[3.3] heptan-2-yl)methyl)-6-methyl-nicotinamide | Chiralpak AD-H | 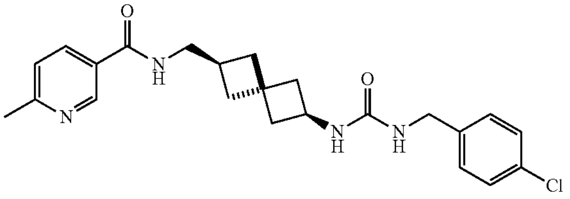 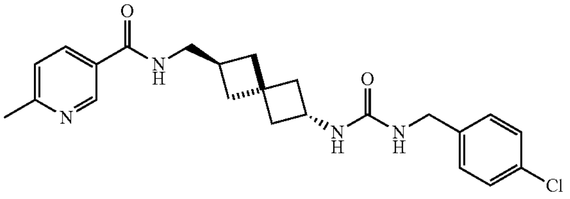 E1: N-(((2S,4s,6S)-6-(3-(4-chlorobenzyl)ureido)spiro[3.3]heptan-2-yl)methyl)-6-methylnicotinamide. LRMS (APCI) m/z 427.1 (M + H). $^1$H NMR (400 MHz, DMSO-$d_6$) δ 8.86 (d, J = 2.4 Hz, 1 H), 8.54 (t, J = 5.7 Hz, 1 H), 8.06 (dd, J = 8.1, 2.3 Hz, 1 H), 7.38-7.32 (m, 3 H), 7.23 (d, J = 8.4 Hz, 2 H), 6.25 (t, J = 6.1 Hz, 1 H), 6.17 (d, J = 8.1 Hz, 1 H), 4.15 (d, J = 6.0 Hz, 2 H), 3.91 (h, J = 8.2 Hz, 1 H), 3.26 (t, J = 6.5 Hz, 2 H), 2.51 (s, 3 H), 2.38 (p, J = 6.7, 5.9 Hz, 1 H), 2.30 (ddd, J = |

-continued

| Compound No. | Racemate | Chiral Column | Structure, Name and Data |
|---|---|---|---|
| | | | 10.8, 7.4, 5.2 Hz, 1 H), 2.19 (ddd, J = 12.3, 7.2, 5.1 Hz, 1 H), 2.09 (ddd, J = 11.2, 8.0, 3.1 Hz, 1 H), 1.95 (ddd, J = 11.3, 8.0, 3.1 Hz, 1 H), 1.82-1.73 (m, 3 H), 1.73-1.66 (m, 1 H).<br>E2: N-(((2R,4r,6R)-6-(3-(4-chlorobenzyl)ureido)spiro[3.3]heptan-2-yl)methyl)-6-methylnicotinamide. LRMS (APCI) m/z 427.1 (M + H). $^1$H NMR (400 MHz, DMSO-$d_6$) δ 8.86 (d, J = 2.3 Hz, 1 H), 8.54 (t, J = 5.7 Hz, 1 H), 8.06 (dd, J = 8.1, 2.3 Hz, 1 H), 7.41-7.30 (m, 3 H), 7.23 (d, J = 8.4 Hz, 2 H), 6.25 (t, J = 6.0 Hz, 1 H), 6.17 (d, J = 8.1 Hz, 1 H), 4.15 (d, J = 6.0 Hz, 2 H), 3.91 (h, J = 8.1 Hz, 1 H), 3.26 (t, J = 6.5 Hz, 2 H), 2.51 (s, 3H), 2.38 (p, J = 7.4 Hz, 1 H), 2.35-2.24 (m, 1 H), 2.19 (dt, J = 12.1, 6.6 Hz, 1 H), 2.09 (ddd, J = 11.1, 8.0, 3.1 Hz, 1 H), 1.95 (ddd, J = 11.2, 8.0, 3.1 Hz, 1 H), 1.83-1.73 (m, 3 H), 1.73-1.66 (m, 1 H).<br>n.b. - Stereochemistry assigned randomly and not confirmed by crystallography |

Example 16

Preparation of 1-(4-chlorobenzyl)-3-(6-((4-methyl-3-oxopiperazin-1-yl)methyl)spiro[3.3]heptan-2-yl) urea (Compound 238)

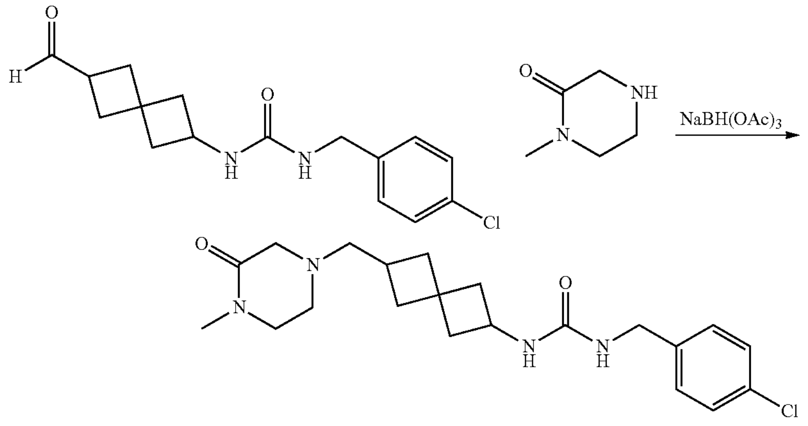

1-(4-Chlorobenzyl)-3-(6-((4-methyl-3-oxopiperazin-1-yl)methyl)spiro[3.3]heptan-2-yl)urea $NaBH(OAc)_3$ (249 mg, 1.17 mmol, 2 equiv) was added to a stirring solution of 1-(4-chlorobenzyl)-3-(6-formylspiro[3.3]heptan-2-yl)urea (Intermediate 11.1, 180 mg, 0.587 mmol, 1 equiv) and 1-methylpiperazin-2-one (134 mg, 1.17 mmol, 2 equiv) in $CH_2C_2$ (2 mL) at rt. After 12 h, solvent was removed by rotary evaporation, the crude suspended in MeOH (3 mL), filtered through a 0.4 μm syringe filter, and product isolated by reverse phase HPLC (0→30% MeCN/water w/0.1% formic acid) as a white solid (60 mg, 25%). LRMS (ESI) m/z 405.1 (M+H). $^1$H NMR (400 MHz, Methanol-$d_4$) δ 7.20 (d, J=8.2 Hz, 2H), 7.14 (d, J=8.2 Hz, 2H), 4.16 (s, 2H), 3.90 (p, J=8.0 Hz, 1H), 3.25 (t, J=5.6 Hz, 2H), 2.97 (s, 2H), 2.83 (s, 3H), 2.60 (t, J=5.7 Hz, 2H), 2.42-2.28 (m, 4H), 2.20-2.08 (m, 2H), 1.96 (ddd, J=11.1, 7.0, 4.1 Hz, 1H), 1.81-1.73 (m, 1H), 1.73-1.57 (m, 3H).

Compounds in the following table were prepared in a similar manner as Compound 238, using the intermediates and reagents as listed.

| Compound No. | Amine | Carbonyl Compound | Structure, Name and Data |
|---|---|---|---|
| 239 | (R)-3-(pyrrolidin-2-yl)pyridine | Intermediate 11.1 | 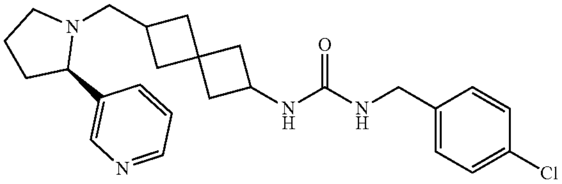 [SMILES: O=C(NCc1ccc(Cl)cc1)NC1CC2(CC(CN3CCC[C@@H]3c3cccnc3)C2)C1] (R)-1-(4-chlorobenzyl)-3-(6-((2-(pyridin-3-yl)pyrrolidin-1-yl)methyl)spiro[3.3]heptan-2-yl)urea. LRMS (ESI) m/z 439.1 (M + H). $^1$H NMR (400 MHz, Methanol-$d_4$) δ 8.44 (s, 1H), 8.40 - 8.30 (m, 1H), 7.78 (t, J = 6.3 Hz, 1H), 7.35 (dt, J = 8.0, 4.1 Hz, 1H), 7.19 (d, J = 8.2 Hz, 2H), 7.13 (d, J = 8.2 Hz, 2H), 4.15 (s, 2H), 3.85 (p, J = 7.2 Hz, 1H), 3.44 (t, J = 8.4 Hz, 1H), 3.26 (t, J = 8.5 Hz, 1H), 2.52 - 2.10 (m, 6H), 2.01 (ddq, J = 17.7, 12.2, 6.1, 5.5 Hz, 2H), 1.95 - 1.78 (m, 3H), 1.69 (q, J = 8.3, 6.8 Hz, 2H), 1.63 - 1.40 (m, 3H). |
| 254 | 1-methyl-3-phenylpiperazine | Intermeidate 11.1 | 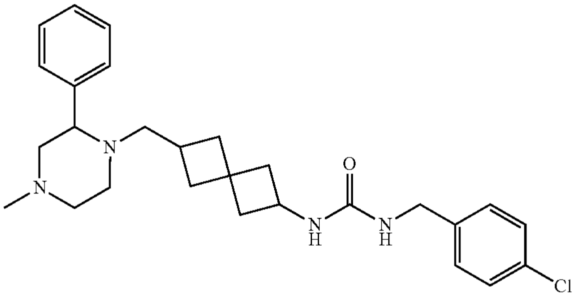 [SMILES: CN1CCN(CC2CC3(C2)CC(NC(=O)NCc2ccc(Cl)cc2)C3)C(c2ccccc2)C1] 1-(4-chlorobenzyl)-3-(6-((4-methyl-2-phenylpiperazin-1-yl)methyl)spiro[3.3]heptan-2-yl)urea. LRMS (ESI) m/z 467.1 (M + H). $^1$H NMR (400 MHz, DMSO-$d_6$) δ 7.32 - 7.21 (m, 6H), 7.21 -7.12 (m, 3H), 6.14 (d, J = 3.4 Hz, 1H), 6.03 (dd, J = 8.1, 2.9 Hz, 1H), 4.06 (d, J = 6.1 Hz, 2H), 3.82-3.67 (m, 1H), 3.08 (dd, J = 10.3, 3.0 Hz, 1H), 2.85 (d, J = 10.9 Hz, 1H), 2.70-2.57 (m, 2H), 2.52 (dt, J = 11.0, 2.6 Hz, 1H), 2.22 (ttd, J = 16.2, 11.1, 10.0, 4.7 Hz, 3H), 2.07 (d, J = 7.9 Hz, 4H), 2.03 - 1.88 (m, 2H), 1.78 (dp, J = 10.4, 5.2, 4.5 Hz, 4H), 1.63 (ddd, J = 11.2, 8.8, 3.3 Hz, 1H), 1.51 - 1.41 (m, 1H), 1.40-1.23 (m, 1H). |
| 241 | Intermediate 12.2 | methyl 4-oxopentanote | 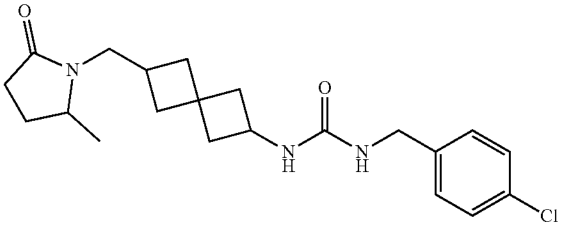 [SMILES: CC1CCC(=O)N1CC1CC2(C1)CC(NC(=O)NCc1ccc(Cl)cc1)C2] 1-(4-chlorobenzyl)-3-(6-((2-methyl-5-oxopyrrolidin-1-yl)methyl)spiro[3.3]heptan-2-yl)urea. LRMS (ESI) m/z 390.1 (M + H). $^1$H NMR (400 MHz, Methanol-$d_4$) δ 7.24 - 7.17 (m, 2H), 7.17 - 7.09 (m, 2H), 4.16 (s, 2H), 3.90 (h, J = 8.1 Hz, 1H), 3.67 - 3.59 (m, 2H), 3.52-3.39 (m, 1H), 2.89 (dd, J = 13.8, 6.8 Hz, 1H), 2.34 (p, J = 6.9 Hz, 2H), 2.21 (td, J = 11.9, 11.4, 6.3 Hz, 2H), 2.15 - 1.98 (m, 2H), 1.80 - 1.73 (m, 3H), 1.70- 1.57 (m, 2H), 1.54-1.41 (m, 1H), 1.11 (d, J = 6.2 Hz, 3H). |

-continued

| Compound No. | Amine | Carbonyl Compound | Structure, Name and Data |
|---|---|---|---|
| 244 | Intermediate 12.2 | methyl 2-methyl-4-oxobutanoate | 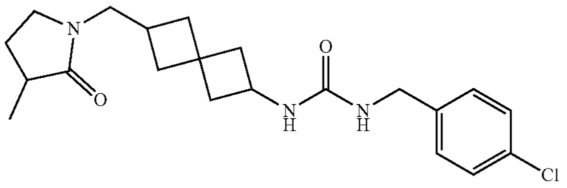 [SMILES: CC1CCN(CC2CC3(C2)CC(NC(=O)NCc2ccc(Cl)cc2)C3)C1=O]<br>1-(4-chlorobenzyl)-3-(6-((3-methyl-2-oxopyrrolidin-1-yl)methyl)spiro[3.3]heptan-2-yl)urea. LRMS (ESI) m/z 390.1 (M + H). $^1$H NMR (400 MHz, Methanol-$d_4$) δ 7.31 (d, J = 7.9 Hz, 2H), 7.26 (d, J = 8.2 Hz, 2H), 4.28 (s, 2H), 4.02 (p, J = 7.7 Hz, 1H), 3.36 (d, J = 3.0 Hz, 1H), 3.32 - 3.19 (m, 3H), 2.46 (dq, J = 15.4, 7.5, 7.1 Hz, 3H), 2.38 - 2.14 (m, 3H), 2.03 (ddd, J = 11.3, 7.8, 3.3 Hz, 1H), 1.84 (dt, J = 17.6, 8.8 Hz, 3H), 1.78 - 1.69 (m, 1H), 1.63 (dq, J = 16.9, 8.3 Hz, 1H), 1.17 (d, J = 7.1 Hz, 3H). |
| 253 | 1-methylpiperazin-2-one | Intermediate 15.1 | 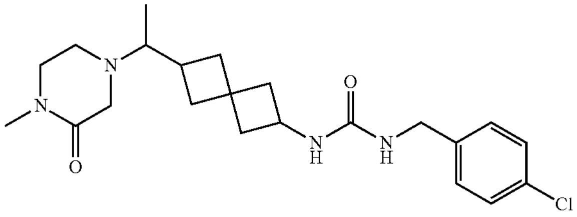 [SMILES: CC(C1CC2(CC(NC(=O)NCc3ccc(Cl)cc3)C2)C1)N1CCN(C)C(=O)C1]<br>1-(4-chlorobenzyl)-3-(6-(1-(4-methyl-3-oxopiperazin-1-yl)ethyl)spiro[3.3]heptan-2-yl)urea. LRMS (ESI) m/z 419.1 (M + H). $^1$H NMR (400 MHz, Methanol-$d_4$) δ 7.31 (d, J = 8.3 Hz, 2H), 7.26 (d, J = 8.3 Hz, 2H), 4.28 (s, 2H), 4.02 (p, J = 7.2 Hz, 1H), 3.47 -3.11 (m, 7H), 2.93 - 2.86 (m, 1H), 2.78 (dq, J = 12.2, 5.8 Hz, 1H), 2.63 (dq, J = 12.6, 6.2 Hz, 1H), 2.50 (dt, J = 11.6, 6.5 Hz, 1H), 2.30 (dd, J = 16.9, 8.4 Hz, 1H), 2.20 (tq, J = 12.0, 4.6, 3.8 Hz, 2H), 2.07 - 1.94 (m, 1H), 1.88 (ddt, J = 12.2, 9.0, 4.8 Hz, 2H), 1.75 (dq, J = 19.5, 10.7 Hz, 2H), 0.95 (t, J = 6.0 Hz, 3H). |

Example 17

Preparation of 1-(4-chlorobenzyl)-3-(6-((5-phenyl-1H-1,2,3-triazol-1-yl)methyl)spiro[3.3]heptan-2-yl) urea (Compound 242)

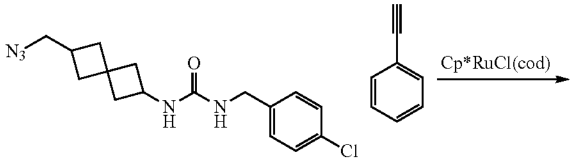

-continued

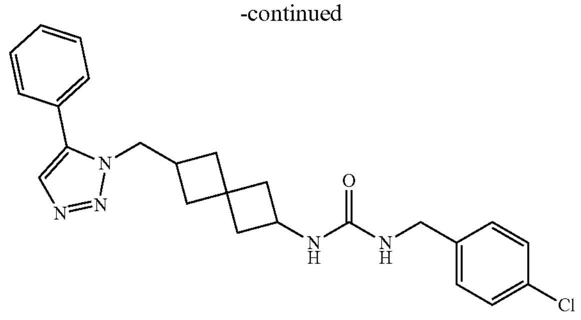

1-(4-Chlorobenzyl)-3-(6-((5-phenyl-1H-1,2,3-triazol-1-yl)methyl)spiro[3.3]heptan-2-yl)urea 1-(6-(Azidomethyl)spiro[3.3]heptan-2-yl)-3-(4-chlorobenzyl)urea (100 mg, 0.30 mmol, 1 equiv), ethynylbenzene (46 mg, 0.449 mmol, 1.5 equiv), and Cp*RuCl(cod) (11 mg, 0.03 mmol, 0.1 equiv) were suspended in THF (5 mL) before being heated to 60° C. After 12 h, the reaction was cooled to rt, solvent removed by rotary evaporation, and product isolated by reverse phase HPLC (5→95% MeCN/water 0.1% formic acid) as a white solid (20 mg, 15%). LRMS (ESI) m/z 436.1 (M+H). $^1$H NMR (400 MHz, Chloroform-d) δ 7.10 (d, J=5.5 Hz, 3H), 6.99-6.92 (m, 2H), 6.88 (d, J=10.0 Hz, 5H), 6.81 (d, J=8.0 Hz, 2H), 4.28 (t, J=5.9 Hz, 1H), 4.19 (d, J=7.4 Hz, 1H), 3.92 (d, J=6.5 Hz, 4H), 3.64-3.50 (m, 1H), 2.24 (dt, J=15.3, 7.5 Hz, 1H), 2.02 (dt, J=11.9, 6.4 Hz, 1H), 1.83 (dt, J=12.1, 6.4 Hz, 1H), 1.74-1.65 (m, 1H), 1.60-1.47 (m, 3H).

Example 18

Preparation of 1-(4-(1-(2H-tetrazol-5-yl)piperidin-4-yl)butyl)-3-(4-chlorobenzyl)urea (Compound 318)

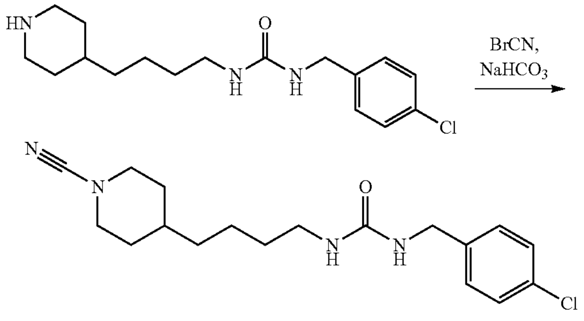

Step 1: 1-(4-Chlorobenzyl)-3-(4-(1-cyanopiperidin-4-yl)butyl)urea

CNBr (154 mg, 1.46 mmol, 1.05 equiv) was added to a stirring solution of 1-(4-chlorobenzyl)-3-(4-(piperidin-4-yl)butyl)urea (Intermediate 3.8, 500 mg, 1.39 mmol, 1 equiv) and saturated sodium bicarbonate (4.2 mL) in $CH_2Cl_2$ (10 mL) at 0° C. After 14 h, the reaction was extracted with $CH_2Cl_2$ (3×5 mL), organics combined, dried over sodium sulfate, filtered through a pad of silica, and solvent removed by rotary evaporation to give the crude product which was used in the next step without further purification (267 mg, 55%). LRMS (ESI) m/z 349.1 (M+H).

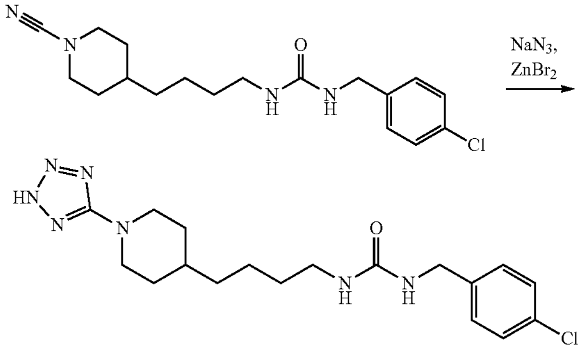

Step 2: 1-(4-(1-(2H-tetrazol-5-yl)piperidin-4-yl)butyl)-3-(4-chlorobenzyl)urea 1-(4-Chlorobenzyl)-3-(4-(1-cyanopiperidin-4-yl)butyl)urea (102 mg, 0.29 mmol, 1 equiv), sodium azide (21 mg, 0.322 mmol, 1.1 equiv), and zinc bromide (66 mg, 0.293 mmol, 1 equiv), were suspended in DMF (2 mL) before being heated to 100° C. for 3 h. The reaction was cooled to rt and product isolated by reverse phase HPLC (10→60% MeCN/water w/0.1% formic acid) as a white solid. LRMS (ESI) m/z 392.1 (M+H). $^1$H NMR (400 MHz, DMSO-$d_6$) δ 7.37 (d, J=8.0 Hz, 2H), 7.26 (d, J=8.0 Hz, 2H), 6.31 (t, J=6.1 Hz, 1H), 5.93 (t, J=5.6 Hz, 1H), 4.18 (d, J=5.9 Hz, 2H), 3.80 (d, J=12.7 Hz, 2H), 3.05-2.90 (m, 4H), 1.71 (d, J=14.1 Hz, 2H), 1.36 (t, J=7.0 Hz, 3H), 1.32-1.07 (m, 7H).

Example 19

Preparation of 1-(4-methoxybenzyl)-3-(6-(5-phenyl-1,3,4-oxadiazol-2-yl)spiro[3.3]heptan-2-yl)urea (Compound 325)

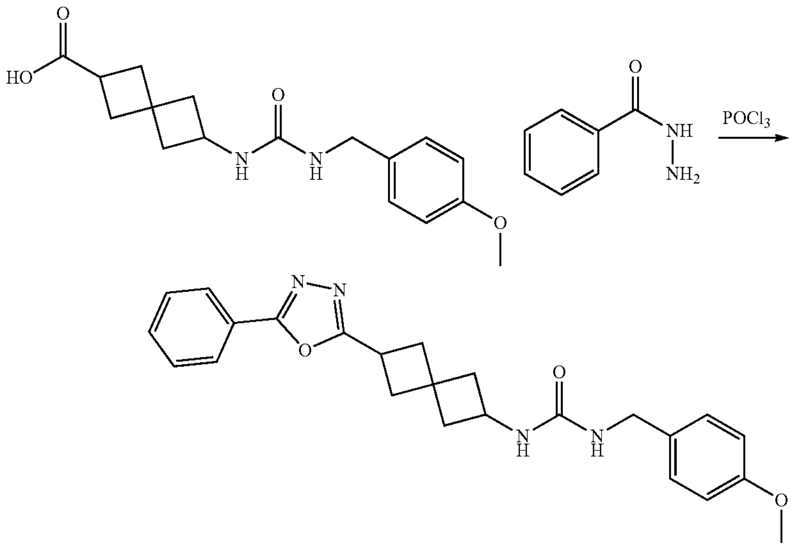

1-(4-Methoxybenzyl)-3-(6-(5-phenyl-1,3,4-oxadiazol-2-yl)spiro[3.3]heptan-2-yl)urea 6-(3-(4-Methoxybenzyl)ureido)spiro[3.3]heptane-2-carboxylic acid (200 mg, 0.628 mmol, 1 equiv) and benzohydrazide (86 mg, 0.628 mmol, 1 equiv) were suspended in phosphorus oxychloride (5 mL) before being stirred at rt for 14 h. The solvent was removed by rotary evaporation and product isolated by reverse phase HPLC (5→95% MeCN/water w/0.1% formic acid) as a white solid (17 mg, 5%). LRMS (ESI) m/z 419.1 (M+H). $^1$H NMR (400 MHz, Methanol-$d_4$) δ 8.04 (d, J=8.3 Hz, 2H), 7.59 (q, J=7.5, 6.5 Hz, 3H), 7.20 (d, J=8.1 Hz, 2H), 6.88 (d, J=7.1 Hz, 2H), 4.24 (s, 2H), 4.10 (p, J=8.0 Hz, 1H), 3.78 (s, 4H), 2.71-2.53 (m, 3H), 2.47 (dd, J=21.5, 7.2 Hz, 3H), 1.98 (dt, J=23.2, 10.0 Hz, 2H).

Example 20

Preparation of 1-(4-methoxybenzyl)-3-(6-(4-phenyloxazol-2-yl)spiro[3.3]heptan-2-yl)urea (Compound 326)

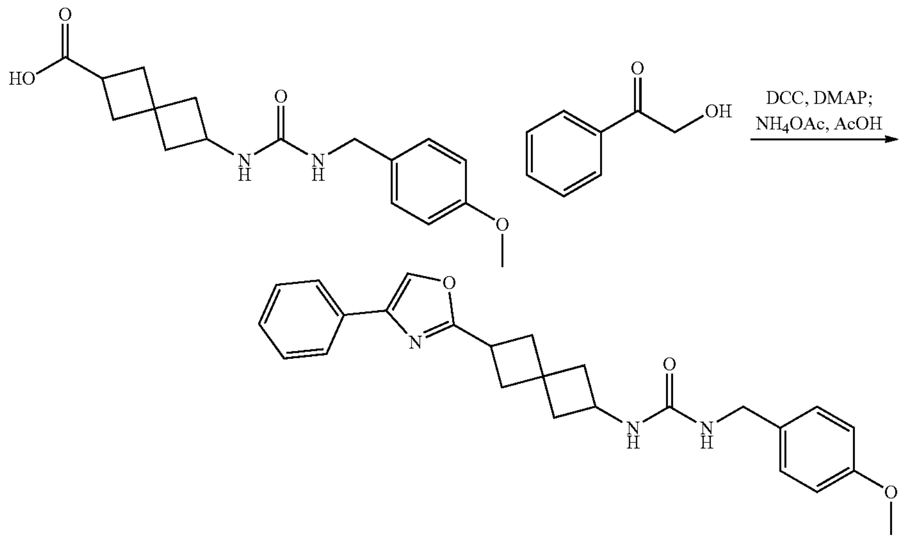

1-(4-Methoxybenzyl)-3-(6-(4-phenyloxazol-2-yl)spiro[3.3]heptan-2-yl)urea

DCC (143 mg, 0.693 mmol, 1.05 equiv) was added to a stirring solution of 6-(3-(4-methoxybenzyl)ureido)spiro[3.3]heptane-2-carboxylic acid (210 mg, 0.660 mmol, 1 equiv), 2-hydroxy-1-phenylethan-1-one (90 mg, 0.660 mmol, 1 equiv), and DMAP (1 mg, 0.007 mmol, 0.01 equiv) in $CH_2Cl_2$ (20 mL) at rt. After 14 h, the reaction was filtered through a pad of celite and solvent removed by rotary evaporation. The crude material was suspended in toluene (50 mL) before ammonium acetate (101 mg, 1.32 mmol, 2 equiv) and AcOH (2 mL) were added and the reaction heated to reflux for 2 h. The reaction was cooled to rt, solvent removed by rotary evaporation, and product isolated by reverse phase HPLC (5→95% MeCN/water w/0.1% formic acid) as a white solid (55 mg, 20%). LRMS (ESI) m/z 418.1 (M+H). $^1$H NMR (400 MHz, Methanol-d4) δ 8.15 (s, 1H), 7.73 (d, J=7.7 Hz, 2H), 7.41 (t, J=7.6 Hz, 2H), 7.32 (t, J=7.4 Hz, 1H), 7.21 (d, J=8.2 Hz, 2H), 6.88 (d, J=8.2 Hz, 2H), 4.24 (s, 2H), 4.09 (p, J=8.1 Hz, 1H), 3.78 (s, 3H), 3.61 (p, J=8.6 Hz, 1H), 2.61 (dt, J=11.5, 5.7 Hz, 1H), 2.57-2.48 (m, 2H), 2.48-2.33 (m, 3H), 2.04-1.95 (m, 1H), 1.95-1.85 (m, 1H).

Example 21

Preparation of 1-(6-(benzo[d]oxazol-2-yl)spiro[3.3]heptan-2-yl)-3-(4-methoxybenzyl)urea (Compound 327)

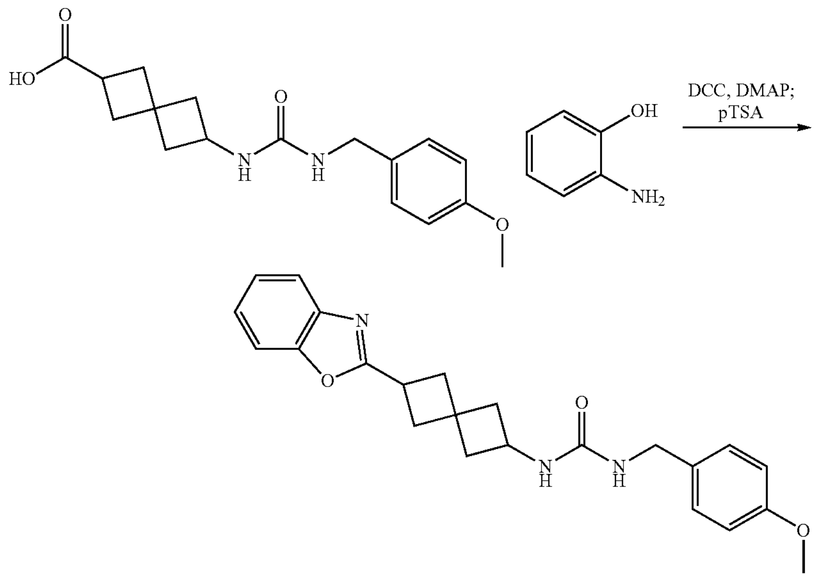

1-(6-(Benzo[d]oxazol-2-yl)spiro[3.3]heptan-2-yl)-3-(4-methoxybenzyl)urea

DCC (136 mg, 0.660 mmol, 1.05 equiv) was added to a stirring solution of 6-(3-(4-methoxybenzyl)ureido)spiro[3.3]heptane-2-carboxylic acid (200 mg, 0.628 mmol, 1 equiv), 2-aminophenol (75 mg, 0.691 mmol, 1 equiv), and DMAP (1 mg, 0.007 mmol, 0.01 equiv) in $CH_2Cl_2$ (20 mL) at rt. After 14 h, the reaction was filtered through a pad of celite and solvent removed by rotary evaporation. The crude material was suspended in toluene (20 mL) before 4-methylbenzenesulfonic acid (11 mg, 0.063 mmol, 0.1 equiv) was added and the reaction heated to reflux for 2 h. The reaction was cooled to rt, solvent removed by rotary evaporation, and product isolated by reverse phase HPLC (5→95% MeCN/water w/0.1% formic acid) as a white solid (35 mg, 14%). LRMS (ESI) m/z 392.1 (M+H). $^1H$ NMR (400 MHz, Methanol-d4) δ 7.68-7.53 (m, 2H), 7.41-7.32 (m, 2H), 7.20 (d, J=7.6 Hz, 2H), 6.88 (d, J=7.5 Hz, 2H), 4.24 (s, 2H), 4.10 (p, J=8.4, 7.7 Hz, 1H), 3.83-3.67 (m, 4H), 2.70-2.35 (m, 6H), 1.97 (dt, J=33.1, 10.0 Hz, 2H).

Example 22

Preparation of 1-(4-chlorobenzyl)-3-(6-(hydroxy(phenyl)methyl)spiro[3.3]heptan-2-yl)urea (Compound 328)

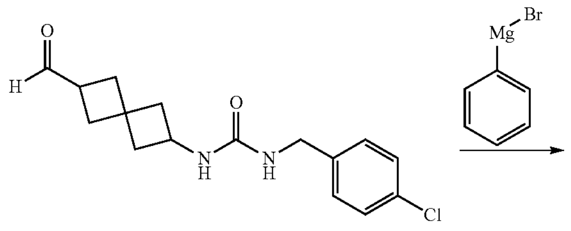

-continued

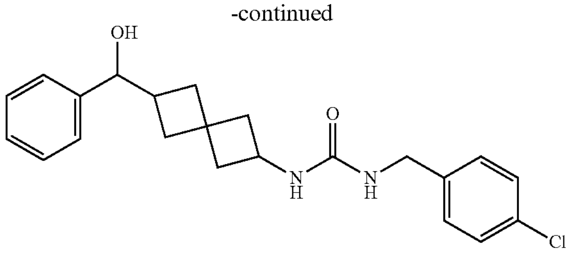

1-(4-Chlorobenzyl)-3-(6-(hydroxy(phenyl)methyl)spiro[3.3]heptan-2-yl)urea

Phenylmagnesium bromide (1 M in THF, 652 mL, 0.652 mmol, 2 equiv) was added to a stirring solution of 1-(4-chlorobenzyl)-3-(6-formylspiro[3.3]heptan-2-yl)urea (Intermediate 11.1, 100 mg, 0.326 mmol, 1 equiv) in THF (5 mL) at 0° C. After 2 h, the reaction was quenched with saturated ammonium chloride (50 mL), extracted with $CH_2Cl_2$ (3×25 mL), organics combined, dried over sodium sulfate, filtered, and solvent removed by rotary evaporation. The product was isolated by reverse phase HPLC (5→95% MeCN/water w/0.1% formic acid) as a white solid (13 mg, 10%). LRMS (ESI) m/z 385.2 (M+H). $^1H$ NMR (400 MHz, Methanol-$d_4$) δ 7.34-6.94 (m, 9H), 4.32 (d, J=8.3 Hz, 1H), 4.16 (s, 2H), 3.88 (dt, J=17.2, 8.3 Hz, 2H), 2.34 (dt, J=15.8, 7.8 Hz, 2H), 2.19-2.05 (m, 2H), 1.99-1.83 (m, 2H), 1.79-1.58 (m, 4H).

Compounds in the following table were prepared in a similar manner as Compound 328, using the intermediates and reagents as listed.

| Compound No. | Intermediate | Grignard | Structure, Name and Data |
| --- | --- | --- | --- |
| 338 | Intermediate 14.1 | (6-methylpyridin-3-yl)magnesium bromide | 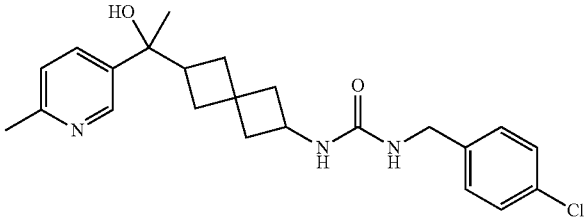 [SMILES: Cc1ccc(C(C)(O)C2CC3(CC(NC(=O)NCc4ccc(Cl)cc4)C3)C2)cn1] 1-(4-chlorobenzyl)-3-(6-(1-hydroxy-1-(6-methylpyridin-3-yl)ethyl)spiro[3.3]heptan-2-yl)urea. LRMS (ESI) m/z 414.1 (M + H). $^1$H NMR (400 MHz, Methanol-$d_4$) δ 8.47 (s, 1H), 7.77 (d, J = 8.2 Hz, 1H), 7.31 (d, J = 8.1 Hz, 2H), 7.25 (d, J = 8.0 Hz, 3H), 4.27 (s, 2H), 3.99 (dt, J = 22.2, 7.9 Hz, 1H), 3.37 (s, 1H), 2.65 - 2.54 (m, 1H), 2.51 (s, 3H), 2.44 (tt, J = 11.4, 5.8 Hz, 1H), 2.19 (dt, J = 11.6, 5.7 Hz, 1H), 2.10 (dd, J = 20.2, 9.7 Hz, 1H), 1.95 (dd, J = 18.3, 8.3 Hz, 1H), 1.85 (dd, J = 19.0, 9.5 Hz, 1H), 1.74 (td, J = 21.3, 19.1, 8.8 Hz, 2H), 1.42 (d, J = 4.1 Hz, 3H). |

Example 23

Preparation of 1-(4-methoxybenzyl)-3-(6-(4-methylbenzyl)spiro[3.3]heptan-2-yl)urea (Compound 334)

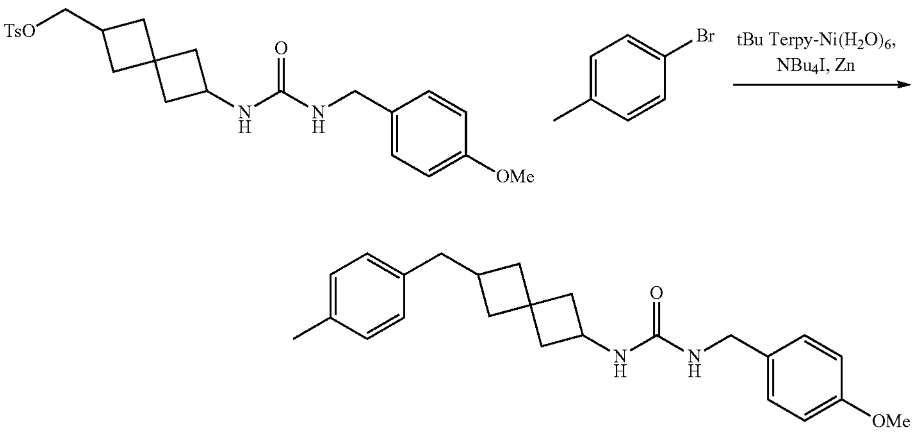

1-(4-Methoxybenzyl)-3-(6-(4-methylbenzyl)spiro[3.3]heptan-2-yl)urea (6-(3-(4-Methoxybenzyl)ureido)spiro[3.3]heptan-2-yl) methyl 4-methylbenzenesulfonate (Intermediate 19.1, 100 mg, 0.218 mmol, 1 equiv), 1-bromo-4-methylbenzene (56 mg, 0.327 mmol, 1.5 equiv), tetrabutylammonium iodide (121 mg, 0.327 mmol, 1.5 equiv), zinc (43 mg, 0.654 mmol, 3 equiv), and Ni precatalyst (as prepared in: Mennie, Katrina; Vara, Brandon; Levi, Samuel. *Reductive sp3-sp2 Coupling Reactions Enable Late-Stage Modification of Pharmaceuticals. Organic Letters.* 2020, 22, 556-559) (6 mg, 0.011 mmol, 0.05 equiv) were placed under cycling $N_2$ for 5 min before MeCN (5 mL) was added, the vial sealed, and the reaction heated to 90° C. After 14 h, the reaction was cooled to rt, solvent removed by rotary evaporation, and product isolated by reverse phase HPLC (5→95% MeCN/water w/0.1% formic acid) as a white solid. LRMS (ESI) m/z 379.2 (M+H). $^1$H NMR (400 MHz, Methanol-$d_4$) δ 7.19 (d, J=8.2 Hz, 2H), 7.06 (d, J=7.7 Hz, 2H), 7.00 (d, J=7.7 Hz, 2H), 6.87 (d, J=8.1 Hz, 2H), 4.22 (s, 2H), 4.01 (p, J=8.1 Hz, 1H), 3.78 (s, 3H), 2.61 (d, J=7.6 Hz, 2H), 2.41 (dq, J=15.4, 7.7, 6.9 Hz, 2H), 2.29 (s, 4H), 2.15 (t, J=10.0 Hz, 1H), 2.02-1.92 (m, 1H), 1.81 (dd, J=16.7, 7.6 Hz, 3H), 1.75-1.66 (m, 1H).

Compounds in the following table were prepared in a similar manner as Compound 334, using the intermediates and reagents as listed.

| Compound No. | Intermediate | Aryl Bromide | Structure, Name and Data |
|---|---|---|---|
| 335 | Intermediate 19.1 | 1-bromo-3-methylbenzene | 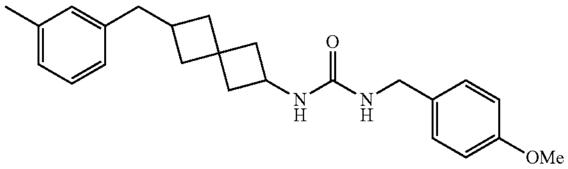 [SMILES: COc1ccc(CNC(=O)NC2CC3(CC(Cc4cccc(C)c4)C3)C2)cc1] 1-(4-Methoxybenzyl)-3-(6-(3-methylbenzyl)spiro[3.3]heptan-2-yl)urea LRMS (ESI) m/z 379.1 (M + H). $^1H$ NMR (400 MHz, Methanol-$d_4$) δ 7.19 (d, J = 8.1 Hz, 2H), 7.12 (t, J = 7.5 Hz, 1H), 7.00 - 6.89 (m, 3H), 6.87 (d, J = 8.1 Hz, 2H), 4.22 (s, 2H), 4.00 (q, J = 8.0 Hz, 1H), 3.78 (s, 3H), 2.62 (d, J = 7.6 Hz, 2H), 2.42 (p, J = 8.8 Hz, 2H), 2.30 (s, 4H), 2.22 - 2.10 (m, 1H), 2.04 - 1.91 (m, 1H), 1.81 (q, J = 10.7 Hz, 3H), 1.76 - 1.66 (m, 1H). |
| 336 | Intermediate 19.1 | 1-bromo-2-methylbenzene | 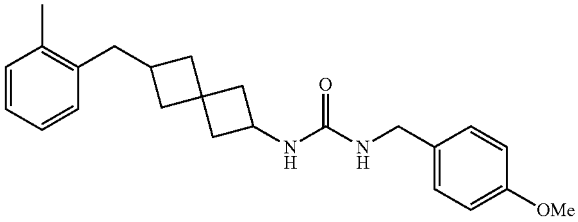 [SMILES: COc1ccc(CNC(=O)NC2CC3(CC(Cc4ccccc4C)C3)C2)cc1] 1-(4-methoxybenzyl)-3-(6-(2-methylbenzyl)spiro[3.3]heptan-2-yl)urea. LRMS (ESI) m/z 379.1 (M + H). $^1H$ NMR (400 MHz, Methanol-$d_4$) δ 7.19 (d, J = 8.1 Hz, 2H), 7.10 (d, J = 7.1 Hz, 1H), 7.06 (s, 3H), 6.90 - 6.83 (m, 2H), 4.22 (s, 2H), 4.01 (d, J = 7.9 Hz, 1H), 3.78 (d, J = 1.3 Hz, 3H), 2.68 (d, J = 7.4 Hz, 2H), 2.46 (dq, J = 13.4, 7.0, 6.3 Hz, 2H), 2.28 (s, 4H), 2.19 (dt, J = 11.2, 5.7 Hz, 1H), 2.06 - 1.95 (m, 1H), 1.82 (q, J = 10.2 Hz, 3H), 1.78 - 1.69 (m, 1H). |
| 331 | Intermeidate 19.2 | 2-bromopyrazine | 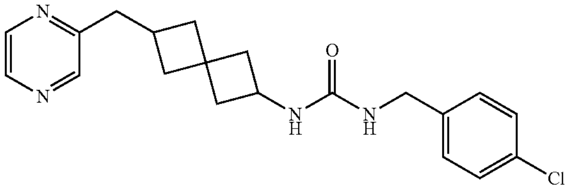 [SMILES: O=C(NCc1ccc(Cl)cc1)NC1CC2(CC(Cc3cnccn3)C2)C1] 1-(4-chlorobenzyl)-3-(6-(pyrazin-2-ylmethyl)spiro[3.3]heptan-2-yl)urea. LRMS (ESI) m/z 371.1 (M + H). $^1H$ NMR (400 MHz, Methanol-$d_4$) δ 8.48 - 8.25 (m, 3H), 7.19 (d, J = 8.5 Hz, 2H), 7.13 (d, J = 8.4 Hz, 2H), 4.16 (s, 2H), 3.90 (p, J = 8.2 Hz, 1H), 2.79 (d, J = 7.8 Hz, 2H), 2.51 (dq, J = 16.0, 8.0 Hz, 1H), 2.34 (dt, J = 11.6, 6.6 Hz, 1H), 2.18 (dt, J = 12.1, 6.7 Hz, 1H), 2.09 (ddd, J = 11.6, 7.8, 4.1 Hz, 1H), 1.91 (ddd, J = 11.8, 7.7, 4.1 Hz, 1H), 1.81 - 1.64 (m, 4H). |

-continued

| Compound No. | Intermediate | Aryl Bromide | Structure, Name and Data |
|---|---|---|---|
| 337 | Intermediate 19.1 | 5-bromo-2-methylpyridine | 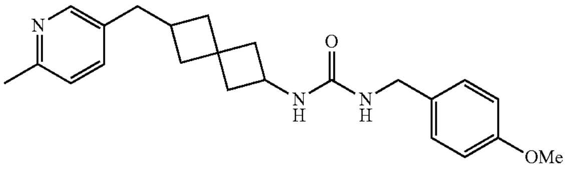 [SMILES: COc1ccc(CNC(=O)NC2CC3(CC(Cc4ccc(C)nc4)C3)C2)cc1] 1-(4-methoxybenzyl)-3-(6-((6-methylpyridin-3-yl)methyl)spiro[3.3]heptan-2-yl)urea. LRMS (ESI) m/z 380.1 (M + H). $^1$H NMR (400 MHz, Methanol-$d_4$) δ 8.20 (s, 1H), 7.55 (d, J = 8.0 Hz, 1H), 7.23 (d, J = 8.0 Hz, 1H), 7.19 (d, J = 8.1 Hz, 2H), 6.91 - 6.81 (m, 2H), 4.22 (s, 2H), 4.02 (p, J = 7.9 Hz, 1H), 3.77 (d, J = 1.5 Hz, 3H), 2.67 (d, J = 7.7 Hz, 2H), 2.50 (s, 3H), 2.42 (d, J = 7.5 Hz, 2H), 2.28 (dt, J = 12.3, 6.3 Hz, 2H), 2.18 (td, J = 9.7, 8.1, 4.0 Hz, 1H), 2.00 (ddd, J = 11.6, 7.6, 4.0 Hz, 1H), 1.82 (q, J = 10.8, 10.3 Hz, 3H), 1.77 - 1.69 (m, 1H). |
| 345 | Intermediate 19.2 | 3-bromopyridine | 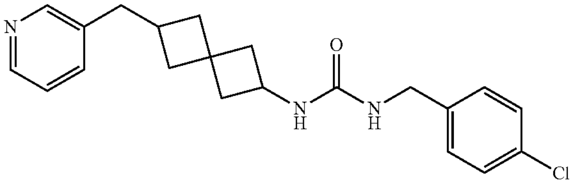 1-(4-chlorobenzyl)-3-(6-(pyridin-3-ylmethyl)spiro[3.3]heptan-2-yl)urea. LRMS (ESI) m/z 370.2 (M + H). $^1$H NMR (400 MHz, DMSO-$d_6$) δ 8.38 (s, 1H), 7.56 (dt, J = 7.8, 2.0 Hz, 1H), 7.41-7.32 (m, 2H), 7.28 (dd, J = 7.8, 4.7 Hz, 1H), 7.23 (d, J = 8.4 Hz, 2H), 6.24 (t, J = 6.1 Hz, 1H), 6.17 (d, J = 8.0 Hz, 1H), 4.14 (d, J = 6.0 Hz, 2H), 3.90 (h, J = 8.1 Hz, 1H), 2.64 (dd, J = 7.6, 1.9 Hz, 2H), 2.43 - 2.24 (m, 3H), 2.16 (dt, J = 12.1, 6.2 Hz, 1H), 2.08 (ddd, J = 11.2, 7.6, 3.9 Hz, 1H), 1.92 (ddd, J = 11.5, 7.7, 3.9 Hz, 1H), 1.81 - 1.70 (m, 3H), 1.68 (dd, J = 11.2, 8.1 Hz, 1H). |
| 346 | Intermediate 19.2 | 3-iodo-2-methylpyridine | 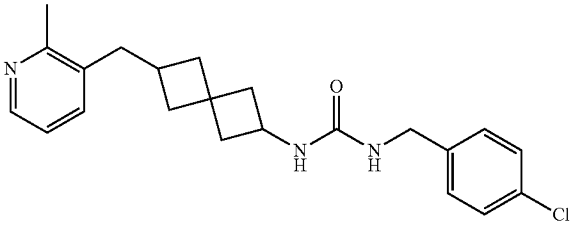 [SMILES: Cc1ncccc1CC1CC2(C1)CC(NC(=O)NCc1ccc(Cl)cc1)C2] 1-(4-chlorobenzyl)-3-(6-((2-methylpyridin-3-yl)methyl)spiro[3.3]heptan-2-yl)urea. LRMS (ESI) m/z 384.2 (M + H). $^1$H NMR (400 MHz, DMSO-$d_6$) δ 8.25 (dd, J = 4.8, 1.7 Hz, 1H), 7.43 (dd, J = 7.7, 1.7 Hz, 1H), 7.36 (d, J = 8.4 Hz, 2H), 7.23 (d, J = 8.4 Hz, 2H), 7.11 (dd, J = 7.6, 4.8 Hz, 1H), 6.24 (t, J = 6.0 Hz, 1H), 6.17 (d, J = 8.0 Hz, 1H), 4.15 (d, J = 6.0 Hz, 2H), 3.91 (h, J = 8.2 Hz, 1H), 2.64 (d, J = 7.5 Hz, 2H), 2.42 (s, 3H), 2.32 (s, 1H), 2.22 - 2.07 (m, 3H), 1.95 (ddd, J = 11.5, 7.7, 4.0 Hz, 1H), 1.76 (q, J = 9.7 Hz, 3H), 1.68 (dd, J = 11.2, 8.2 Hz, 1H). |

-continued

| Compound No. | Intermediate | Aryl Bromide | Structure, Name and Data |
|---|---|---|---|
| 347 | Intermeidate 19.2 | 5-bromo-2-methylpyridine | 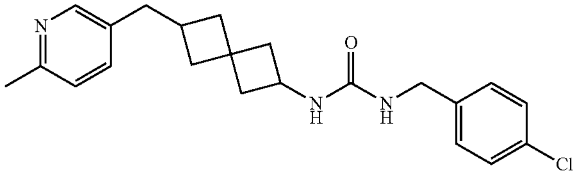 [SMILES: Cc1ccc(CC2CC3(C2)CC(NC(=O)NCc2ccc(Cl)cc2)C3)cn1] 1-(4-chlorobenzyl)-3-(6-((6-methylpyridin-3-yl)methyl)spiro[3.3]heptan-2-yl)urea. LRMS (ESI) m/z 384.2 (M + H). $^1$H NMR (400 MHz, DMSO-$d_6$) δ 8.22 (d, J = 2.2 Hz, 1H), 7.44 (dd, J = 7.9, 2.3 Hz, 1H), 7.41-7.31 (m, 2H), 7.23 (d, J = 8.3 Hz, 2H), 7.13 (d, J = 7.9 Hz, 1H), 6.27 (s, 1H), 6.19 (d, J = 8.1 Hz, 1H), 4.14 (d, J = 5.9 Hz, 2H), 3.90 (td, J = 15.9, 8.0 Hz, 1H), 2.64 - 2.56 (m, 2H), 2.41 (s, 3H), 2.34 - 2.23 (m, 2H), 2.19 - 2.12 (m, 1H), 2.07 (ddd, J = 11.4, 7.8, 3.9 Hz, 1H), 1.91 (ddd, J = 11.5, 7.7, 3.9 Hz, 1H), 1.80 - 1.68 (m, 3H), 1.65 (dd, J = 11.2, 8.1 Hz, 1H). |

Example 24

Preparation of 1-(4-chlorobenzyl)-3-(6-(pyridin-4-ylmethyl)spiro[3.3]heptan-2-yl)urea (Compound 329)

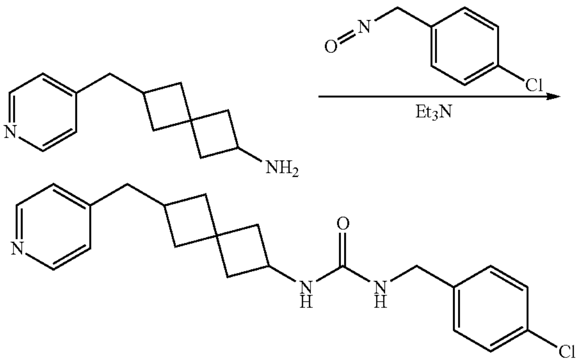

1-(4-Chlorobenzyl)-3-(6-(pyridin-4-ylmethyl)spiro[3.3]heptan-2-yl)urea

To a solution of 6-(pyridin-4-ylmethyl)spiro[3.3]heptan-2-amine (Intermediate 22.1) (75 mg, 0.37 mmol, 1.0 equiv) in $CH_2Cl_2$ (1 mL) was added $Et_3N$ (75 mg, 0.74 mmol, 2.0 equiv) and 1-chloro-4-(isocyanatomethyl)benzene (93 mg, 0.56 mmol, 1.5 equiv) at 23° C. The reaction was stirred at this temperature for 30 min before it was directly concentrated and purified by preparative HPLC ($H_2O$ (0.1% $HCO_2H$)/MeCN (0.1% $HCO_2H$)) to yield 1-(4-chlorobenzyl)-3-(6-(pyridin-4-ylmethyl)spiro[3.3]heptan-2-yl)urea (70 mg, 51%) as a colorless oil. LRMS (APCI+) m/z 370.10 (M+H). $^1$H NMR (400 MHz, DMSO-$d_6$) δ 8.48 (s, 2H), 7.35 (d, J=8.4 Hz, 2H), 7.30-7.17 (m, 4H), 6.25 (t, J=6.1 Hz, 1H), 6.17 (d, J=8.0 Hz, 1H), 4.15 (d, J=6.0 Hz, 2H), 3.90 (h, J=8.1 Hz, 1H), 2.68 (dd, J=7.6, 1.8 Hz, 2H), 2.40 (p, J=7.9 Hz, 1H), 2.30 (ddd, J=10.8, 7.3, 5.2 Hz, 1H), 2.17 (ddd, J=12.1, 7.3, 5.2 Hz, 1H), 2.09 (ddd, J=11.3, 7.7, 3.9 Hz, 1H), 1.93 (ddd, J=11.6, 7.7, 4.0 Hz, 1H), 1.75 (q, J=9.0 Hz, 3H), 1.68 (dd, J=11.2, 8.2 Hz, 1H).

Compounds in the following table were prepared in a similar manner as Compound 329, using the intermediates and reagents as listed.

| Compound No. | Isocyanate | Intermediate | Structure, Name and Data |
|---|---|---|---|
| 330 | 1-methoxy-4-(isocyanato-methyl)benzene | 22.1 | 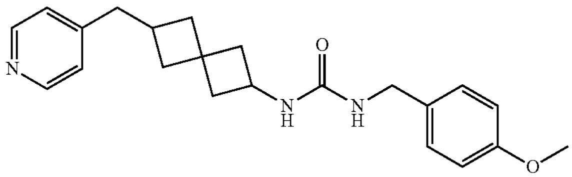 [SMILES: COc1ccc(CNC(=O)NC2CC3(CC(Cc4ccncc4)C3)C2)cc1] 1-(4-methoxybenzyl)-3-(6-(pyridin-4-ylmethyl)spiro[3.3]heptan-2-yl)urea. LRMS (APCI) m/z 366.15 (M + H). $^1$H NMR (400 MHz, DMSO-$d_6$) δ 8.46 (s, 2 H), 7.18 (s, 2 H), 7.14 (d, J = 8.6 Hz, 2 H), 6.86 |

-continued

| Compound No. | Isocyanate | Intermediate | Structure, Name and Data |
|---|---|---|---|
| | | | (d, J = 8.6 Hz, 2 H), 6.15-6.03 (m, 2H), 4.08 (d, J = 5.9 Hz, 2 H), 3.91 (h, J = 8.2 Hz, 1 H), 3.72 (s, 3 H), 2.64 (dd, J = 7.7, 2.4 Hz, 2 H), 2.40 (dq, J = 15.8, 7.8 Hz, 1 H), 2.30 (ddd, J = 10.6, 7.4, 5.2 Hz, 1 H), 2.16 (ddd, J = 12.2, 7.3, 5.2 Hz, 1 H), 2.10 (ddd, J = 11.2, 7.7, 3.9 Hz, 1 H), 1.93 (ddd, J = 11.6, 7.7, 3.9 Hz, 1 H), 1.79-1.63 (m, 4 H). |
| 332 | 1-chloro-4-(isocyanato-methyl)benzene | 23.1 | 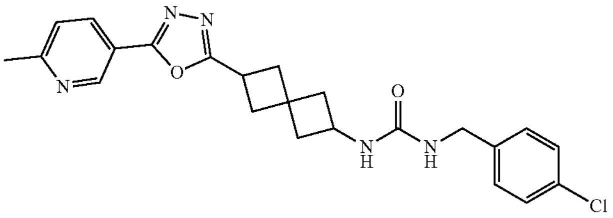 1-(4-chlorobenzyl)-3-(6-(5-(6-methylpyridin-3-yl)-1,3,4-oxadiazol-2-yl)spiro[3.3]heptan-2-yl)urea. LRMS (APCI) m/z 434.2 (M + H). $^1$H NMR (400 MHz, DMSO-$d_6$) δ 9.02 (d, J = 2.2 Hz, 1 H), 8.23 (dd, J = 8.1, 2.3 Hz, 1 H), 7.49 (d, J = 8.1 Hz, 1 H), 7.37 (d, J = 8.5 Hz, 2 H), 7.25 (d, J = 8.4 Hz, 2 H), 6.30 (t, J = 6.1 Hz, 1 H), 6.23 (d, J = 8.0 Hz, 1 H), 4.16 (d, J = 6.0 Hz, 2 H), 3.97 (h, J = 8.2 Hz, 1 H), 3.72 (p, J = 8.3 Hz, 1 H), 2.57 (s, 3 H), 2.53 (d, J = 8.4 Hz, 1 H), 2.49-2.43 (m, 2 H), 2.40 (d, J = 8.4 Hz, 2 H), 2.29 (ddd, J = 12.2, 7.4, 5.2 Hz, 1 H), 1.91 (dd, J = 10.8, 8.7 Hz, 1 H), 1.85 (dd, J = 11.1, 8.8 Hz, 1 H). |
| 340 | 1-chloro-4-(isocyanato-methyl)benzene | 24.1 | 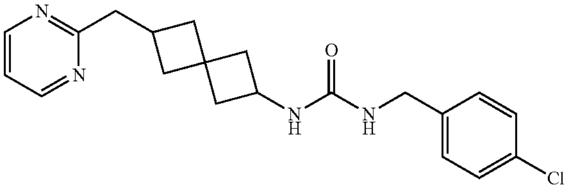 [SMILES: O=C(NCc1ccc(Cl)cc1)NC1CC2(CC(Cc3ncccn3)C2)C1] 1-(4-chlorobenzyl)-3-(6-(pyrimidin-2-ylmethyl)spiro[3.3]heptan-2-yl)urea. LRMS (APCI) m/z 371.10 (M + H). $^1$H NMR (400 MHz, DMSO-$d_6$) δ 8.69 (d, J = 4.8 Hz, 2 H), 7.36 (d, J = 8.1 Hz, 2 H), 7.31 (t, J = 4.9 Hz, 1 H), 7.23 (d, J = 8.1 Hz, 2 H), 6.25 (t, J = 6.1 Hz, 1 H), 6.17 (d, J = 8.0 Hz, 1 H), 4.15 (s, 2 H), 3.90 (h, J = 8.1 Hz, 1 H), 2.92 (d, J = 7.6 Hz, 2 H), 2.64 (hept, J = 7.9 Hz, 1 H), 2.31 (ddd, J = 11.3, 7.2, 5.2 Hz, 1 H), 2.22-2.06 (m, 2 H), 1.97 (ddd, J = 11.5, 7.8, 3.7 Hz, 1 H), 1.83-1.67 (m, 4 H). |
| 341 | 1-chloro-4-(isocyanato-methyl)ben-zene | 25.1 | 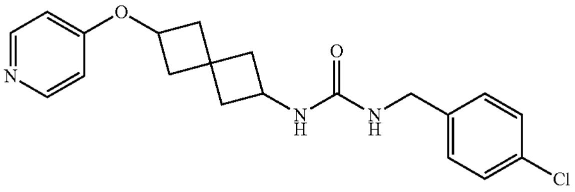 [SMILES: O=C(NCc1ccc(Cl)cc1)NC1CC2(C1)CC(Oc1ccncc1)C2] 1-(4-chlorobenzyl)-3-(6-(pyridin-4-yloxy)spiro[3.3]heptan-2-yl)urea. LRMS (APCI) m/z 372.10 (M + H). $^1$H NMR (400 MHz, DMSO-$d_6$) δ 8.35 (d, J = 5.4 Hz, 2 H), 8.14 (s, 1 H), 7.36 (d, J = 8.4 Hz, 2 H), 7.24 (d, J = 8.4 Hz, 2 H), 6.86 (d, J = 6.5 Hz, 2 H), 6.28 (t, J = 6.1 Hz, 1 H), 4.71 (p, J = 6.9 Hz, 1 H), 4.16 (d, J = 6.0 Hz, 2 H), |

-continued

| Compound No. | Isocyanate | Intermediate | Structure, Name and Data |
|---|---|---|---|
| | | | 3.98 (h, J = 8.0 Hz, 1 H), 2.65 (dt, J = 11.5, 6.0 Hz, 1 H), 2.48 (p, J = 5.7, 5.2 Hz, 1 H), 2.38 (ddd, J = 10.9, 7.4, 5.2 Hz, 1 H), 2.24 (ddd, J = 12.4, 7.5, 5.1 Hz, 1 H), 2.06 (ddd, J = 14.3, 11.6, 7.0 Hz, 2 H), 1.88 (ddd, J = 11.1, 8.8, 5.8 Hz, 2 H). |
| 343 | 1-chloro-4-(isocyanato-methyl)ben-zene | 25.2 | 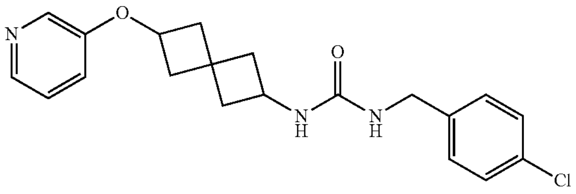 1-(4-chlorobenzyl)-3-(6-(pyridin-3-yloxy)spiro[3.3]heptan-2-yl)urea. LRMS (APCI) m/z 372.10 (M + H). $^1$H NMR (400 MHz, DMSO-$d_6$) δ 8.23-8.11 (m, 2 H), 7.36 (d, J = 8.4 Hz, 2 H), 7.33-7.21 (m, 4 H), 6.28 (t, J = 6.1 Hz, 1 H), 6.23 (d, J = 8.0 Hz, 1 H), 4.68 (p, J = 6.9 Hz, 1 H), 4.16 (d, J = 6.0 Hz, 2 H), 3.98 (h, J = 8.2 Hz, 1 H), 2.64 (dt, J = 11.5, 5.9 Hz, 1 H), 2.46 (p, J = 5.9 Hz, 1 H), 2.38 (ddd, J = 10.8, 7.4, 5.1 Hz, 1 H), 2.24 (ddd, J = 12.1, 7.3, 5.2 Hz, 1 H), 2.05 (td, J = 12.3, 7.0 Hz, 2 H), 1.88 (ddd, J = 11.1, 8.7, 4.3 Hz, 2 H). |
| 342 | 1-chloro-4-(isocyanato-methyl)ben-zene | 26.1 | 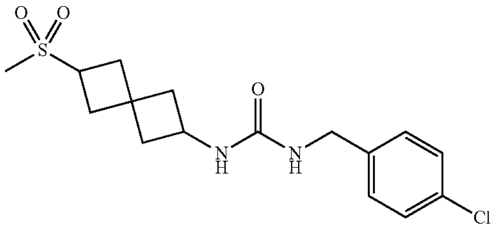 [SMILES: CS(=O)(=O)C1CC2(CC(NC(=O)NCc3ccc(Cl)cc3)C2)C1] 1-(4-chlorobenzyl)-3-(6-(methylsulfonyl)spiro[3.3]heptan-2-yl)urea. LRMS (APCI) m/z 357.10 (M + H). $^1$H NMR (400 MHz, DMSO-$d_6$) δ 7.36 (d, J = 8.4 Hz, 2 H), 7.24 (d, J = 8.4 Hz, 2 H), 6.29 (t, J = 6.2 Hz, 1 H), 6.21 (d, J = 8.0 Hz, 1 H), 4.15 (d, J = 6.0 Hz, 2 H), 3.93 (h, J = 8.0 Hz, 1H), 3.86 (p, J = 8.3 Hz, 1H), 2.82 (s, 3 H), 2.42-2.11 (m, 6 H), 1.86 (dd, J = 10.9, 8.7 Hz, 1 H), 1.80 (dd, J = 11.2, 8.8 Hz, 1 H). |
| 344 | 1-methoxy-4-(isocyanato-methyl)ben-zene | 25.2 | 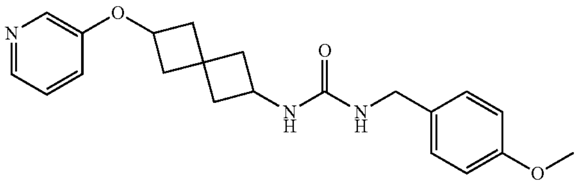 1-(4-methoxybenzyl)-3-(6-(pyridin-3-yloxy)spiro[3.3]heptan-2-yl)urea. LRMS (APCI) m/z 372.10 (M + H). $^1$H NMR (400 MHz, DMSO-$d_6$) δ 8.19 (s, 1 H), 8.15 (d, J = 4.1 Hz, 1 H), 7.36-7.23 (m, 2 H), 7.15 (d, J = 8.6 Hz, 2 H), 6.86 (d, J = 8.6 Hz, 2 H), 6.18-6.08 (m, 2 H), 4.68 (p, J = 6.9 Hz, 1 H), 4.10 (d, J = 5.9 Hz, 2 H), 3.99 (h, J = 8.2 Hz, 1 H), 3.72 (s, 3H), 2.64 (dt, J = 11.5, 5.9 Hz, 1 H), 2.46 (p, J = 5.9 Hz, 1 H), 2.38 (ddd, J = 10.8, 7.4, 5.2 Hz, 1 H), 2.24 (ddd, J = 12.1, 7.4, 5.2 Hz, 1 H), 2.13-1.99 (m, 2 H), 1.92-1.82 (m, 2 H). |

-continued

| Compound No. | Isocyanate | Intermediate | Structure, Name and Data |
|---|---|---|---|
| 348 | 1-chloro-4-(isocyanato-methyl)ben-zene | 27.1 | 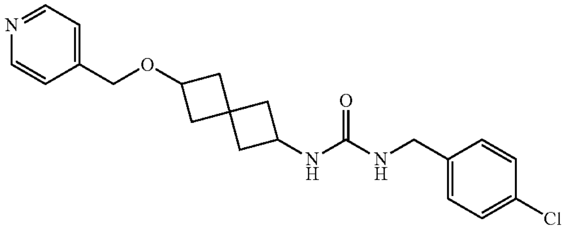 [SMILES: O=C(NCc1ccc(Cl)cc1)NC1CC2(C1)CC(OCc1ccncc1)C2] 1-(4-chlorobenzyl)-3-(6-(pyridin-4-ylmethoxy)spiro[3.3]heptan-2-yl)urea. LRMS (APCI) m/z 386.10 (M + H). $^1$H NMR (400 MHz, DMSO-$d_6$) δ 8.53 (s, 2 H), 7.36 (d, J = 8.4 Hz, 2 H), 7.31 (d, J = 4.9 Hz, 2 H), 7.24 (d, J = 8.4 Hz, 2 H), 6.26 (t, J = 6.1 Hz, 1 H), 6.19 (d, J = 8.0 Hz, 1 H), 4.38 (s, 2 H), 4.15 (d, J = 5.9 Hz, 2 H), 4.01-3.89 (m, 2 H), 2.36 (dt, J = 11.4, 5.9 Hz, 1 H), 2.30-2.12 (m, 3 H), 1.91 (td, J = 11.8, 7.3 Hz, 2 H), 1.81 (q, J = 10.5, 10.0 Hz, 2 H). |
| 349 | 1-methoxy-4-(isocyanato-methyl)ben-zene | 27.1 | 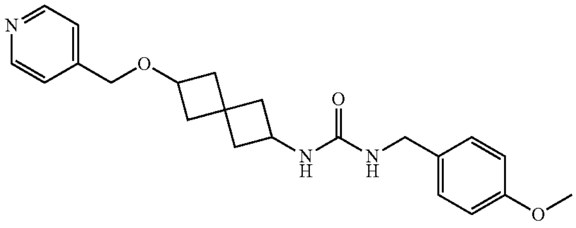 [SMILES: COc1ccc(CNC(=O)NC2CC3(C2)CC(OCc2ccncc2)C3)cc1] 1-(4-methoxybenzyl)-3-(6-(pyridin-4-ylmethoxy)spiro[3.3]heptan-2-yl)urea. LRMS (APCI) m/z 382.20 (M + H). $^1$H NMR (400 MHz, DMSO-$d_6$) δ 8.53 (s, 2 H), 7.31 (d, J = 4.8 Hz, 2 H), 7.14 (d, J = 8.6 Hz, 2 H), 6.86 (d, J = 8.6 Hz, 2 H), 6.18-6.06 (m, 2 H), 4.38 (s, 2 H), 4.09 (d, J = 5.9 Hz, 2 H), 3.94 (dq, J = 13.7, 7.5, 6.8 Hz, 2 H), 3.72 (s, 3 H), 2.36 (dt, J = 11.4, 5.9 Hz, 1 H), 2.29-2.21 (m, 1 H), 2.18 (dt, J = 11.1, 6.0 Hz, 2 H), 1.90 (ddd, J = 13.7, 11.2, 7.3 Hz, 2 H), 1.85-1.74 (m, 2 H). |
| 350 | 1-chloro-4-(isocyanato-methyl)ben-zene | 27.2 | 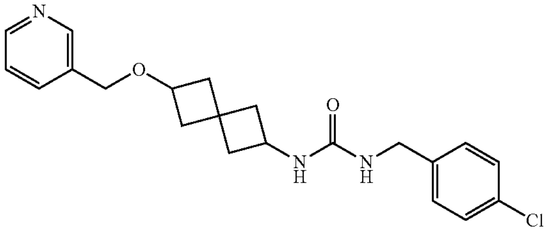 [SMILES: O=C(NCc1ccc(Cl)cc1)NC1CC2(C1)CC(OCc1cccnc1)C2] 1-(4-chlorobenzyl)-3-(6-(pyridin-3-ylmethoxy)spiro[3.3]heptan-2-yl)urea. LRMS (APCI) m/z 386.15 (M + H). $^1$H NMR (400 MHz, DMSO-$d_6$) δ 8.64-8.41 (m, 2 H), 7.72 (d, J = 7.8 Hz, 1 H), 7.43-7.32 (m, 3 H), 7.24 (d, J = 8.4 Hz, 2 H), 6.27 (t, J = 6.1 Hz, 1 H), 6.20 (d, J = 8.0 Hz, 1 H), 4.37 (s, 2 H), 4.15 (d, J = 6.0 Hz, 2 H), 3.93 (dq, J = 14.1, 7.5, 7.0 Hz, 2 H), 2.34 (dt, J = 11.4, 5.8 Hz, 1 H), 2.25 (ddd, J = 10.6, 7.5, 5.2 Hz, 1 H), 2.21-2.11 (m, 2 H), 1.94-1.76 (m, 4 H). |

-continued

| Compound No. | Isocyanate | Intermediate | Structure, Name and Data |
|---|---|---|---|
| 351 | 1-methoxy-4-(isocyanato-methyl)ben-zene | 27.2 | 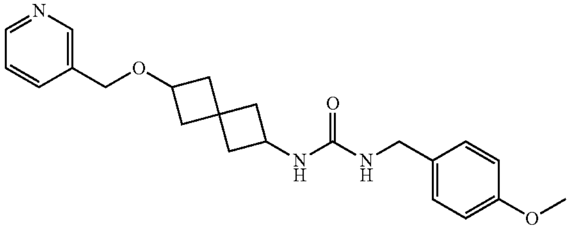 [SMILES: COc1ccc(CNC(=O)NC2CC3(C2)CC(OCc2cccnc2)C3)cc1] 1-(4-methoxybenzyl)-3-(6-(pyridin-3-ylmethoxy)spiro[3.3]heptan-2-yl)urea. LRMS (APCI) m/z 382.20(M + H). $^1$H NMR (400 MHz, DMSO-$d_6$) δ 8.58-8.43 (m, 2 H), 7.72 (dt, J = 7.8, 2.0 Hz, 1 H), 7.37 (dd, J = 7.8, 4.8 Hz, 1 H), 7.14 (d, J = 8.6 Hz, 2 H), 6.86 (d, J = 8.6 Hz, 2 H), 6.14-6.06 (m, 2 H), 4.37 (s, 2 H), 4.09 (d, J = 5.8 Hz, 2 H), 3.93 (h, J = 7.7, 7.1 Hz, 2 H), 3.72 (s, 3 H), 2.34 (dt, J = 11.3, 6.0 Hz, 1 H), 2.29-2.21 (m, 1 H), 2.21-2.11 (m, 2 H), 1.93-1.74 (m, 4 H). |

Example 25

Preparation of 1-(4-chlorobenzyl)-3-(6-((4-cyano-1H-pyrazol-1-yl)methyl)spiro[3.3]heptan-2-yl)urea (Compound 333)

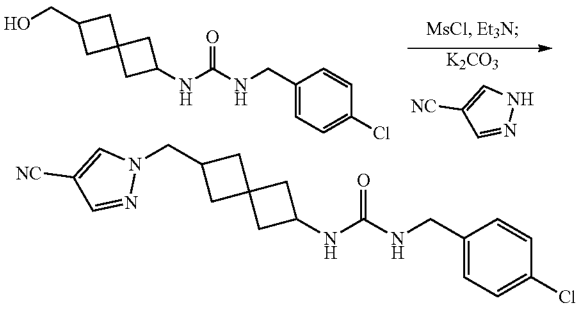

1-(4-chlorobenzyl)-3-(6-((4-cyano-1H-pyrazol-1-yl)methyl)spiro[3.3]heptan-2-yl)urea To a solution of 1-(4-chlorobenzyl)-3-(6-(hydroxymethyl)spiro[3.3]heptan-2-yl)urea (Intermediate 10.1, 120 mg, 0.389 mmol, 1.0 equiv) in $CH_2Cl_2$ (2 mL) was added $Et_3N$ (118 mg, 1.17 mmol, 3.0 equiv) and MsCl (89 mg, 0.777 mmol, 2.0 equiv) sequentially. The mixture was stirred at 23° C. for 3 h before it was poured into a half-saturated $NaHCO_3$ solution. The aqueous phase was extracted by $CH_2Cl_2$ (5 mL×2) and the combined organic phase was washed by brine, dried ($MgSO_4$), filtered, and concentrated to yield the crude mesylate which was used directly without further purifications. Next, to a solution of so-obtained mesylate (up to 0.389 mmol) in DMF (1 mL) was added $K_2CO_3$ (107 mg, 0.777 mmol, 2.0 equiv) and 1H-pyrazole-4-carbonitrile (72 mg, 0.777 mmol, 2.0 equiv). The reaction was heated at 80° C. for 3 h. Upon completion, the reaction was directly subjected to preparative HPLC ($H_2O$(0.1% $HCO_2H$)/MeCN (0.1% $HCO_2H$) to yield 1-(4-chlorobenzyl)-3-(6-((4-cyano-1H-pyrazol-1-yl)methyl)spiro[3.3]heptan-2-yl)urea (61 mg, 40% over 2 steps) as a white solid. LRMS (APCI+) m/z 384.15 (M+H). $^1$H NMR (400 MHz, DMSO-$d_6$) δ 8.55 (s, 1H), 8.04 (s, 1H), 7.36 (d, J=8.4 Hz, 2H), 7.24 (d, J=8.2 Hz, 2H), 6.25 (t, J=6.1 Hz, 1H), 6.17 (d, JJ=8.0 Hz, 1H), 4.15 (d, J=6.7 Hz, 4H), 3.90 (h, J=8.2 Hz, 1H), 2.60 (hept, J=7.7 Hz, 1H), 2.31 (ddd, J=10.7, 7.3, 5.1 Hz, 1H), 2.16 (ddd, J=12.1, 7.4, 5.2 Hz, 1H), 2.07 (ddd, J=11.3, 7.9, 3.5 Hz, 1H), 1.92 (ddd, J=11.5, 7.9, 3.4 Hz, 1H), 1.80 (dd, J=11.73, 8.2 Hz, 2H), 1.74 (dd, J=11.3, 8.4 Hz, 2H).

Compounds in the following table were prepared in a similar manner as Compound 333, using the intermediates and reagents as listed.

| Compound No. | Intermediate | Nucleophile | Structure, Name and Data |
|---|---|---|---|
| 339 | 10.1 | 1,2,4-triazole | 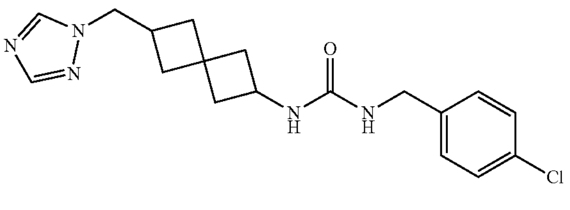 [SMILES: O=C(NCc1ccc(Cl)cc1)NC1CC2(CC(Cn3cncn3)C2)C1] |

-continued

| Compound No. | Intermediate | Nucleophile | Structure, Name and Data |
|---|---|---|---|
| | | | 1-(6-((1H-1,2,4-triazol-1-yl)methyl)spiro[3.3]heptan-2-yl)-3-(4-chlorobenzyl)urea. LRMS (APCI) m/z 360.10 (M + H). $^1$H NMR (400 MHz, DMSO-$d_6$) δ 8.49 (s, 1 H), 7.93 (s, 1 H), 7.36 (d, J = 8.4 Hz, 2 H), 7.23 (d, J = 7.6 Hz, 2 H), 6.26 (t, J = 6.1 Hz, 1 H), 6.18 (d, J = 8.0 Hz, 1 H), 4.15 (d, J = 6.7 Hz, 4 H), 3.90 (h, J = 8.2 Hz, 1 H), 2.59 (p, J = 7.7 Hz, 1 H), 2.31 (dt, J = 11.8, 6.2 Hz, 1 H), 2.16 (dt, J = 12.1, 6.3 Hz, 1 H), 2.07 (td, J = 9.4, 7.9, 3.2 Hz, 1 H), 1.92 (td, J = 9.6, 7.7, 3.3 Hz, 1 H), 1.85-1.69 (m, 4 H). |
| 352 | 10.1 | Sodium benzenesulfinate | 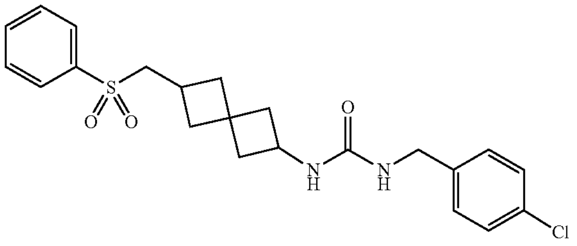 [SMILES: O=C(NCc1ccc(Cl)cc1)NC1CC2(CC(CS(=O)(=O)c3ccccc3)C2)C1] 1-(4-chlorobenzyl)-3-(6-((phenylsulfonyl)methyl)spiro[3.3]heptan-2-yl)urea. LRMS (APCI) m/z 433.10 (M + H). $^1$H NMR (400 MHz, DMSO-$d_6$) δ 7.87 (d, J = 7.9 Hz, 2 H), 7.75 (t, J = 7.3 Hz, 1 H), 7.66 (t, J = 7.6 Hz, 2 H), 7.35 (d, J = 8.1 Hz, 2 H), 7.23 (d, J = 8.1 Hz, 2 H), 6.24 (t, J = 6.1 Hz, 1 H), 6.13 (d, J = 8.1 Hz, 1 H), 4.14 (d, J = 6.0 Hz, 2 H), 3.83 (q, J = 8.0 Hz, 1 H), 3.40 (d, J = 7.3 Hz, 2 H), 2.43-2.24 (m, 3 H), 2.12-1.97 (m, 2 H), 1.89-1.80 (m, 1 H), 1.69 (dq, J = 18.7, 9.8 Hz, 4 H). |
| 353 | 10.1 | Sodium 3-pyridylsulfinate | 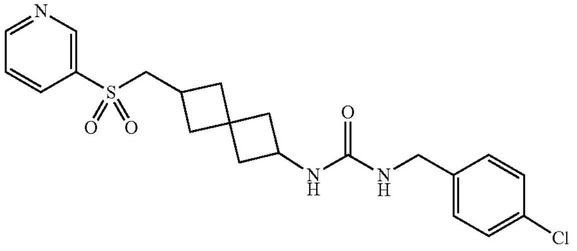 [SMILES: O=C(NCc1ccc(Cl)cc1)NC1CC2(CC(CS(=O)(=O)c3cccnc3)C2)C1] 1-(4-chlorobenzyl)-3-(6-((pyridin-3-ylsulfonyl)methyl)spiro[3.3]heptan-2-yl)urea. LRMS (APCI) m/z 434.10 (M + H). $^1$H NMR (400 MHz, DMSO-$d_6$) δ 9.01 (s, 1 H), 8.92 (d, J = 4.8 Hz, 1 H), 8.27 (dt, J = 8.0, 1.9 Hz, 1 H), 7.70 (dd, J = 8.1, 4.8 Hz, 1 H), 7.35 (d, J = 8.2 Hz, 2 H), 7.22 (d, J = 8.1 Hz, 2 H), 6.25 (t, J = 6.1 Hz, 1 H), 6.13 (d, J = 8.0 Hz, 1 H), 4.14 (d, J = 6.1 Hz, 2 H), 3.84 (h, J = 8.2 Hz, 1 H), 3.53 (d, J = 7.2 Hz, 2 H), 2.41 (p, J = 7.9 Hz, 1 H), 2.34-2.25 (m, 1 H), 2.12-1.99 (m, 2 H), 1.86 (ddd, J = 11.9, 7.8, 4.4 Hz, 1 H), 1.72 (dd, J = 19.9, 10.2 Hz, 2 H), 1.66 (t, J = 11.1 Hz, 1H). |

Biological Example 1

NMN Fluorescence Biochemical and NAD Cellular Assay

A. Human Recombinant Enzyme Assay

Compounds described herein were assayed for their ability to stimulate the synthesis of nicotinamide mononucleotide (NMN) by the enzyme NAMPT. The human recombinant enzyme assay measures the activation of the enzyme activity by compounds using recombinant enzyme and substrates in a buffered cell-free system. The assay conditions closely mimic cellular environments. Dose responses were measured using an assay to detect the formation of nicotinamide mono-nucleotide. All experiments were performed in the 384-well format. Generally, 0.5 μL of DMSO containing varying concentrations of the test compound was mixed with 10 μL of the enzyme reagent solution. Enzyme reactions were initiated with the addition of 10 μL of a solution containing the substrates. The final assay conditions were as follows: 6 nM human NAMPT, 2.5 mM ATP, 20 μM PRPP and 150 μM nicotinamide in 50 mM HEPES, pH 7.2, 1 mM DTT, 1 mM CHAPS 50 mM NaCl, 100 mM $MgCl_2$. Following an incubation of 60 min at ambient temperature, 10 μL of 20% acetophenone in DMSO was added, followed by 10 μL of 2 M KOH and 40 μL of formic acid. The plates were read for fluorescence (Excitation/Emission=355 nm/460 nm) using an EnVision plate reader after 40 mins of incubation at ambient temperature. The potency measurements for compounds, are quantified and represented as $AC_{1.4}$ (the concentration of compounds that generates 40% higher activity over basal) and $EC_{50}$ (concentration of the compound that gives half-maximal activation). Table A shows the $AC_{1.4}$ and $EC_{50}$ data and for the tested compounds.

TABLE A

| Compound No. | $AC_{1.4}$ Human (μM) | $EC_{50}$ Human (μM) |
|---|---|---|
| 1 | 0.1 | 0.8 |
| 2 | 1.0 | 25.9 |
| 3 | 17.5 | 41.4 |
| 4 | 9.9 | 28.5 |
| 5 | 14.5 | 48.6 |
| 6 | 4.5 | 26.8 |
| 7 | 5.1 | 26.3 |
| 8 | 5.4 | 5.1 |
| 9 | 3.4 | 47.0 |
| 10 | 5.8 | 50.7 |
| 11 | 11.5 | N.D. |
| 12 | 12.9 | 40.0 |
| 13 | 17.5 | N.D. |
| 14 | 2.7 | 35.3 |
| 15 | 10.4 | 17.7 |
| 16 | 0.1 | 0.3 |
| 17 | 17.6 | 50.5 |
| 18 | 18.9 | 60.2 |
| 19 | 0.1 | 1.8 |
| 20 | 0.2 | 4.7 |
| 21 | 8.0 | 45.0 |
| 22 | 0.1 | 1.1 |
| 23 | 0.1 | 1.4 |
| 24 | 8.1 | 29.1 |
| 25 | 5.0 | 27.4 |
| 26 | 2.0 | 16.7 |
| 27 | 4.1 | 21.5 |
| 28 | 13.9 | 42.5 |
| 29 | 3.2 | 26.7 |
| 30 | 10.2 | 37.9 |
| 31 | 3.2 | 40.1 |
| 32 | 10.5 | N.D. |
| 33 | 1.6 | 19.8 |
| 34 | 12.1 | 37.7 |
| 35 | 15.4 | 40.2 |
| 36 | 9.8 | 35.4 |
| 37 | 4.2 | 58.9 |
| 38 | 13.7 | 43.7 |
| 39 | 5.6 | 41.9 |
| 40 | 17.2 | 24.0 |
| 41 | 5.0 | 53.5 |
| 42 | 10.7 | 42.2 |
| 43 | 4.9 | 46.4 |
| 44 | 10.1 | 36.5 |
| 45 | 6.6 | 51.7 |
| 46 | 6.8 | 41.3 |
| 47 | 6.5 | 40.6 |
| 48 | 4.7 | 52.1 |

TABLE A-continued

| Compound No. | $AC_{1.4}$ Human (μM) | $EC_{50}$ Human (μM) |
|---|---|---|
| 49 | 6.6 | 46.8 |
| 50 | 17.9 | 32.8 |
| 51 | 1.5 | 53.1 |
| 52 | 4.2 | 43.8 |
| 53 | 0.3 | 8.5 |
| 54 | 1.4 | 29.4 |
| 55 | 1.1 | 40.6 |
| 56 | 9.0 | 47.7 |
| 57 | 1.0 | 25.8 |
| 58 | 11.3 | 39.6 |
| 59 | 11.2 | 40.5 |
| 60 | 0.3 | 6.1 |
| 61 | 2.5 | 34.9 |
| 62 | 1.2 | 23.6 |
| 63 | 4.4 | 4.4 |
| 64 | 1.4 | 50.1 |
| 65 | 2.6 | 50.0 |
| 66 | 3.3 | 37.8 |
| 67 | 2.3 | 35.9 |
| 68 | 5.1 | 45.2 |
| 69 | 4.7 | 38.4 |
| 70 | 3.9 | 38.6 |
| 71 | 0.1 | 1.5 |
| 72 | 0.8 | 10.0 |
| 73 | 1.2 | 7.7 |
| 74 | 0.8 | 13.3 |
| 75 | 11.5 | 42.0 |
| 76 | 0.7 | 17.8 |
| 77 | 7.2 | 35.1 |
| 78 | 4.4 | 45.2 |
| 79 | 1.4 | 39.8 |
| 80 | 2.4 | 45.4 |
| 81 | 12.5 | 37.2 |
| 82 | 10.7 | 52.3 |
| 83 | 19.3 | 30.4 |
| 84 | 0.1 | 2.8 |
| 85 | 0.1 | 1.6 |
| 86 | 4.7 | 49.4 |
| 87 | 0.6 | 27.4 |
| 88 | 16.3 | 48.8 |
| 89 | 10.3 | 33.7 |
| 90 | 0.3 | 5.1 |
| 91 | 3.7 | 13.0 |
| 92 | 2.9 | 13.5 |
| 93 | 6.3 | 34.8 |
| 94 | 11.0 | 38.7 |
| 95 | 4.3 | 13.3 |
| 96 | 2.6 | 4.1 |
| 97 | 1.3 | 2.7 |
| 98 | 3.0 | 7.0 |
| 99 | 5.1 | 3.9 |
| 100 | 8.5 | 10.3 |
| 101 | 0.2 | 2.7 |
| 102 | 8.0 | 33.3 |
| 103 | 0.3 | 7.0 |
| 104 | 0.5 | 10.7 |
| 105 | 0.1 | 2.2 |
| 106 | 0.1 | 1.8 |
| 107 | 2.9 | 48.8 |
| 108 | 0.1 | 1.4 |
| 109 | 3.5 | 10.2 |
| 110 | 0.7 | 3.9 |
| 111 | 1.0 | 26.8 |
| 112 | 3.0 | 46.9 |
| 113 | 3.8 | 51.6 |
| 114 | 11.0 | 33.1 |
| 115 | 10.2 | 14.7 |
| 116 | 8.0 | 51.3 |
| 117 | 3.2 | 33.9 |
| 118 | 3.0 | 14.2 |
| 119 | 3.8 | 16.7 |
| 120 | 0.5 | 2.6 |
| 121 | 1.5 | 5.7 |
| 122 | 5.9 | 47.6 |
| 123 | 2.8 | 51.5 |
| 124 | 1.3 | 24.9 |

TABLE A-continued

| Compound No. | $AC_{1.4}$ Human (μM) | $EC_{50}$ Human (μM) |
|---|---|---|
| 125 | 7.9 | 51.2 |
| 126 | 5.3 | 49.4 |
| 127 | 1.4 | 33.1 |
| 128 | 0.6 | 20.8 |
| 129 | 7.3 | 30.2 |
| 130 | 18.1 | 48.0 |
| 131 | 17.6 | 48.5 |
| 132 | 15.0 | 42.8 |
| 133 | 17.5 | 61.2 |
| 134 | 0.6 | 7.2 |
| 135 | 3.7 | 38.5 |
| 136 | 9.8 | 57.7 |
| 137 | 13.8 | 53.3 |
| 138 | 5.7 | 43.2 |
| 139 | 16.4 | 44.9 |
| 140 | 7.5 | 52.5 |
| 141 | 4.7 | 49.4 |
| 142 | 1.8 | 33.3 |
| 143 | 8.0 | 45.6 |
| 144 | 16.0 | 54.0 |
| 145 | 1.4 | 45.3 |
| 146 | 4.1 | 38.7 |
| 147 | 5.8 | 58.2 |
| 148 | 3.9 | 47.1 |
| 149 | 0.3 | 4.9 |
| 150 | 2.0 | 5.3 |
| 151 | 6.8 | 41.2 |
| 152 | 7.9 | 38.3 |
| 153 | 2.3 | 26.3 |
| 154 | 2.1 | 31.0 |
| 155 | 2.7 | 52.1 |
| 156 | 11.0 | 45.8 |
| 157 | 4.1 | 47.6 |
| 158 | 2.7 | 39.1 |
| 159 | 8.7 | 23.1 |
| 160 | 13.6 | 42.6 |
| 161 | 7.5 | 15.7 |
| 162 | 6.2 | 21.7 |
| 163 | 12.4 | 27.9 |
| 164 | 12.6 | 40.1 |
| 165 | 15.9 | 49.4 |
| 166 | 14.2 | 42.8 |
| 167 | 11.8 | 27.5 |
| 168 | 9.5 | 39.3 |
| 169 | 7.1 | 9.3 |
| 170 | 15.1 | 46.9 |
| 171 | 17.3 | 24.9 |
| 172 | 1.9 | 22.9 |
| 173 | 1.7 | 20.2 |
| 174 | 2.0 | 29.5 |
| 175 | 5.5 | 55.1 |
| 176 | 2.0 | 21.9 |
| 177 | 2.8 | 11.2 |
| 178 | 3.1 | 21.4 |
| 179 | 0.8 | 12.4 |
| 180 | 7.8 | 37.6 |
| 181 | 3.0 | 29.7 |
| 182 | 6.1 | 20.5 |
| 183 | 11.2 | 56.0 |
| 184 | 10.0 | 37.9 |
| 185 | 11.6 | 22.0 |
| 186 | 16.0 | 53.4 |
| 187 | 0.4 | 0.6 |
| 188 | 0.9 | 13.4 |
| 189 | 1.4 | 21.3 |
| 190 | 1.8 | 34.0 |
| 191 | 1.3 | 23.8 |
| 192 | 12.1 | 52.8 |
| 193 | 3.6 | 14.6 |
| 194 | 8.8 | 5.9 |
| 195 | 17.1 | 23.5 |
| 196 | 3.7 | 25.5 |
| 197 | 3.7 | 13.5 |
| 198 | 13.9 | N.D. |
| 199 | 10.6 | 42.2 |
| 200 | 17.1 | 18.2 |

TABLE A-continued

| Compound No. | $AC_{1.4}$ Human (μM) | $EC_{50}$ Human (μM) |
|---|---|---|
| 201 | 6.7 | 22.2 |
| 202 | 0.9 | 2.2 |
| 203 | 8.2 | 34.3 |
| 204 | 13.6 | 26.8 |
| 205 | 10.0 | 23.6 |
| 206 | 2.2 | 4.3 |
| 207 | 13.7 | 6.6 |
| 208 | 9.6 | 11.8 |
| 209 | 10.6 | 38.5 |
| 210 | 1.9 | 49.9 |
| 211 | 0.5 | 27.8 |
| 212 | 7.2 | 6.0 |
| 213 | 6.8 | 6.8 |
| 214 | 10.5 | 36.7 |
| 215 | 3.6 | 30.8 |
| 216 | 4.9 | 20.9 |
| 217 | 19.2 | 20.1 |
| 218 | 13.2 | 22.5 |
| 219 | 2.9 | 5.2 |
| 220 | 3.6 | 4.7 |
| 221 | 1.1 | 4.6 |
| 222 | 0.2 | 28.6 |
| 223 | 0.2 | 38.5 |
| 224 | 0.6 | 47.5 |
| 225 | 2.0 | 50.8 |
| 226 | 2.9 | 31.4 |
| 227 | 2.0 | 33.8 |
| 228 | 1.9 | 39.2 |
| 229 | 0.1 | 1.2 |
| 230 | 1.8 | 30.9 |
| 231 | 0.5 | 7.8 |
| 232 | 3.6 | 37.8 |
| 233 | 0.9 | 1.0 |
| 234 | 3.7 | 8.6 |
| 235 | 4.1 | 7.5 |
| 236 | 3.6 | 5.7 |
| 237 | 2.4 | 2.6 |
| 238 | 3.4 | 20.3 |
| 239 | 2.1 | 22.5 |
| 240 | 0.9 | 3.0 |
| 241 | 2.7 | 5.7 |
| 242 | 3.6 | 0.8 |
| 243 | 1.5 | 4.2 |
| 244 | 3.4 | 7.3 |
| 245 | 3.1 | 4.9 |
| 246 | 2.1 | 4.2 |
| 247 | 2.8 | 7.9 |
| 248 | 5.0 | 6.6 |
| 249 | 1.0 | 2.7 |
| 250 | 1.8 | 7.7 |
| 251 | 2.6 | 6.1 |
| 252 | 2.8 | 9.1 |
| 253 | 3.2 | 5.5 |
| 254 | 1.5 | 2.3 |
| 255 | 2.5 | 6.5 |
| 256 | 1.0 | 2.0 |
| 257 | 2.7 | 17.9 |
| 258 | 3.8 | 23.1 |
| 259 | 8.6 | 59.4 |
| 260 | 2.0 | 17.5 |
| 261 | 2.8 | 42.9 |
| 262 | 0.6 | 4.9 |
| 263 | 1.4 | 10.2 |
| 264 | 1.0 | 6.7 |
| 265 | 0.8 | 1.6 |
| 266 | 0.5 | 1.8 |
| 267 | 2.0 | 7.9 |
| 268 | 0.3 | 0.5 |
| 269 | 0.7 | 5.1 |
| 270 | 1.1 | 3.9 |
| 271 | 0.9 | 3.7 |
| 272 | 0.9 | 2.6 |
| 273 | 0.9 | 0.3 |
| 274 | 1.9 | 0.3 |
| 275 | 1.9 | 11.4 |
| 276 | 1.5 | 9.5 |

TABLE A-continued

| Compound No. | $AC_{1.4}$ Human (μM) | $EC_{50}$ Human (μM) |
|---|---|---|
| 277 | 3.2 | 6.9 |
| 278 | 1.8 | 7.1 |
| 279 | 1.8 | 11.8 |
| 280 | 0.7 | 2.6 |
| 281 | 1.3 | 3.9 |
| 282 | 0.1 | 3.9 |
| 283 | 8.6 | 32.8 |
| 284 | 2.8 | 4.2 |
| 285 | 3.5 | 9.4 |
| 286 | 0.2 | 2.0 |
| 287 | 0.1 | 4.4 |
| 288 | 0.3 | 3.7 |
| 289 | 1.1 | 7.7 |
| 290 | 1.3 | 6.2 |
| 291 | 1.9 | 4.6 |
| 292 | 0.5 | 2.0 |
| 293 | 0.1 | 1.5 |
| 294 | 1.0 | 10.1 |
| 295 | 1.2 | 8.4 |
| 296 | 0.8 | 2.0 |
| 297 | 0.1 | 0.2 |
| 298 | 1.1 | 2.9 |
| 299 | 1.0 | 3.8 |
| 300 | 1.4 | 6.5 |
| 301 | 2.7 | 26.3 |
| 302 | 2.0 | 7.9 |
| 303 | 2.6 | 15.6 |
| 304 | 1.7 | 10.6 |
| 305 | 0.2 | 0.4 |
| 306 | 0.4 | 1.2 |
| 307 | 1.9 | 7.3 |
| 308 | 2.2 | 5.0 |
| 309 | 2.1 | 6.5 |
| 310 | 0.8 | 4.1 |
| 311 | 1.2 | 3.4 |
| 312 | 1.5 | 5.4 |
| 313 | 0.7 | 1.4 |
| 314 | 0.5 | 0.7 |
| 315 | 0.9 | 2.0 |
| 316 | 1.4 | 6.4 |
| 317 | 4.2 | 25.1 |
| 318 | 3.9 | 8.8 |
| 319 | 0.8 | 0.8 |
| 320 | 0.1 | 1.4 |
| 321 | 0.1 | 2.1 |
| 322 | 0.1 | 2.3 |
| 323 | 0.2 | 1.6 |
| 324 | 0.2 | 1.9 |
| 325 | 2.4 | 30.6 |
| 326 | 4.5 | 2.9 |
| 327 | 4.1 | 17.4 |
| 328 | 1.2 | 4.3 |
| 329 | 62.5 | >62.5 |
| 330 | 0.1 | 3.9 |
| 331 | 2.2 | 1.3 |
| 332 | 6.2 | 28.5 |
| 333 | 1.8 | 4.4 |
| 334 | 2.3 | 2.7 |
| 335 | 1.1 | 2.2 |
| 336 | 0.7 | 2.1 |
| 337 | 1.0 | 26.1 |
| 338 | 6.4 | 10.3 |
| 339 | 4.6 | 6.5 |
| 340 | 3.7 | 5.6 |
| 341 | 3.9 | 2.0 |
| 342 | 33.1 | 56.1 |
| 343 | 3.0 | 5.6 |
| 344 | 3.1 | 34.9 |
| 345 | 1.6 | 0.6 |
| 346 | 62.5 | >62.5 |
| 347 | 2.2 | 2.4 |
| 348 | 5.0 | 5.9 |
| 349 | 6.9 | 40.3 |
| 350 | 1.7 | 6.1 |
| 351 | 4.0 | 38.7 |
| 352 | 6.0 | 8.0 |
| 353 | 5.3 | 16.9 |
| 354 | 4.2 | 10.8 |

N.D. = Not Determined

B. Cellular NAD+ Modulation Assay.

The compounds described herein were also assayed for their ability to stimulate the endogenous NAMPT in a native cellular environment in the cellular NAD+ modulation assay, which measures the ability of the compound to modulate cellular NAD levels. Increased levels of NAD are expected by compounds that permeate the cells and activate the catalytic activity of the endogenous NAMPT.

Neuroblastoma SH-SY5Y cells were grown in 1:1 mixture of Eagle's Minimum Essential Medium and F12 Medium, along with 10% fetal bovine serum, in a humidified incubator with an atmosphere of 95% air and 5% $CO_2$ at 37° C. The assays were initiated by plating 20 μL of SH-SY5Y cells in culture medium with 0.1% fetal bovine serum, at a density of 5000 cells per well to a 384-well Corning™ BioCoat™ Poly-D-Lysine Multiwell Plates. The plates were incubated in the 37° C. incubators for a period of 5 hours. Compounds in DMSO were added to the plates in a volume of 120 nL using the Labcyte Echo Liquid Handlers. 5 μL of a 1.5 uM Doxorubicin solution in assay medium is added to each well. The plates are then incubated for 40 hours. 30 μL of a readout-solution containing 0.2 U/mL Diaphorase enzyme, 40 uM resazurin, 10 uM FMN, 0.8 U/mL Alcohol dehydrogenase, 3% ethanol, 0.4 mg/mL bovine serum albumin, 0.2% Triton X-100 in 100 mM Tris-HCl, 30 mM EDTA, pH 8.4. The plates were read for fluorescence (Excitation/Emission=540 nm/590 nm) using an EnVision plate reader after 60 mins of incubation at ambient temperature. Table B shows the $AC_{0.3}$ and $EC_{50}$ data for the tested compounds.

TABLE B

| Compound No. | $AC_{0.3}$ (μM) | $EC_{50}$ (μM) |
|---|---|---|
| 7 | 2.4 | 4.7 |
| 14 | >20.1 | 20.1 |
| 16 | 0.1 | 0.1 |
| 19 | 1.6 | 1.3 |
| 20 | 0.4 | 13.9 |
| 22 | 0.4 | 0.1 |
| 23 | 0.3 | 0.3 |
| 27 | 1.4 | 5.8 |
| 29 | 3.0 | 2.2 |
| 33 | 7.9 | 8.4 |
| 71 | 0.3 | 0.9 |
| 72 | 2.5 | 10.8 |
| 73 | 0.8 | 0.8 |
| 74 | 0.3 | 0.5 |
| 76 | 5.9 | 4.7 |
| 79 | 5.8 | 5.8 |
| 84 | 5.3 | 12.7 |
| 85 | 0.9 | 0.8 |
| 87 | 3.4 | 2.4 |
| 90 | 0.9 | 0.8 |
| 110 | 0.5 | 0.3 |
| 120 | 0.2 | 0.3 |
| 121 | 0.6 | 1.2 |
| 134 | 8.0 | 12.7 |
| 138 | 9.1 | 10.1 |
| 140 | 8.2 | 6.3 |
| 145 | 1.1 | 3.1 |

TABLE B-continued

| Compound No. | $AC_{0.3}$ (μM) | $EC_{50}$ (μM) |
|---|---|---|
| 149 | 0.6 | 1.1 |
| 161 | 0.3 | 0.8 |
| 162 | 0.7 | 1.0 |
| 164 | 11.6 | 12.9 |
| 187 | 0.2 | 0.2 |
| 196 | 1.0 | 3.3 |
| 199 | 2.0 | N.D. |
| 202 | 0.5 | 0.6 |
| 203 | 8.9 | 10.0 |
| 206 | 0.2 | 0.5 |
| 210 | 9.7 | 9.0 |
| 211 | >20.1 | N.D. |
| 212 | 0.3 | 0.1 |
| 214 | >20.1 | N.D. |
| 229 | 0.1 | 0.2 |
| 249 | 0.5 | 0.9 |
| 256 | 0.3 | 0.3 |
| 268 | 0.1 | 0.1 |
| 287 | 0.3 | 1.0 |
| 288 | 0.3 | 0.8 |
| 293 | 0.3 | 0.3 |
| 322 | 0.2 | 0.3 |
| 329 | 0.1 | 0.1 |
| 330 | 0.5 | 8.1 |
| 346 | 0.1 | 0.1 |

N.D. = Not Determined

All publications, patent applications, patents, and other references mentioned herein are expressly incorporated by reference in their entireties, to the same extent as if each were incorporated by reference individually.

It is to be understood that, while the disclosure provided herein has been described in conjunction with the above embodiments, the foregoing description and examples are intended to illustrate and not limit the scope of the disclosure. Other aspects, advantages and modifications within the scope of the disclosure will be apparent to those skilled in the art to which the disclosure pertains.

What is claimed is:

1. A compound of Formula (II):

(II)

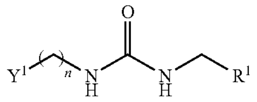

or a pharmaceutically acceptable salt thereof, wherein:

n is 0 to 6;

$Y^1$ is

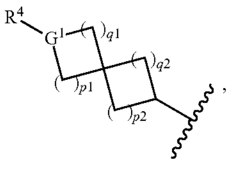

and $R^1$ is selected from the group consisting of

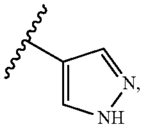

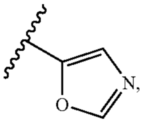

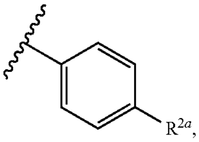

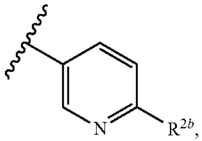

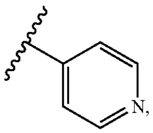

and

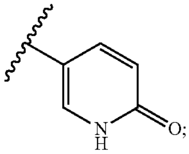

wherein $R^{2a}$ and $R^{2b}$ are each independently halo, —O($C_1$-$C_6$ alkyl), $C_1$-$C_6$ alkyl substituted with —OH, —C(O)$NR^{2c}R^{2d}$, or —N($R^{2e}$)C(O)($C_1$-$C_6$ alkyl); and $R^{2c}$, $R^{2d}$, and $R^{2e}$ are each independently hydrogen or $C_1$-$C_6$ alkyl;

$G^1$ is CH or N;

p1 and p2 are each independently 0, 1, or 2;

q1 and q2 are each independently 1 or 2; and $R^3$ is selected from the group consisting of:

i. unsubstituted $C_1$-$C_6$ alkyl;

ii. $C_6$-$C_{14}$ aryl;

iii. optionally substituted 5- to 18-membered heteroaryl;

iv. —$NR^{3a}R^{3b}$, wherein $R^{3a}$ and $R^{3b}$ are each independently selected from the group consisting of hydrogen, $C_6$-$C_{14}$ aryl, 5- to 18-membered heteroaryl, —($C_1$-$C_6$ alkylene)-($C_6$-$C_{14}$ aryl), and —($C_1$-$C_6$ alkylene)-(5- to 18-membered heteroaryl);

v. —$OR^{3c}$, wherein $R^{3c}$ is $C_6$-$C_{14}$ aryl, 5- to 18-membered heteroaryl, or —($C_1$-$C_6$ alkylene)-(5- to 18-membered heteroaryl);

vi. —C(O)$R^{3d}$, wherein $R^{3d}$ is selected from the group consisting of —$NR^{3f}R^{3g}$; $C_3$-$C_8$ cycloalkyl; $C_3$-$C_8$ cycloalkyl substituted with optionally substituted $C_6$-$C_{14}$ aryl; $C_3$-$C_8$ cycloalkenyl; optionally substituted $C_6$-$C_{14}$ aryl; optionally substituted —($C_1$-$C_6$ alkylene)-($C_6$-$C_{14}$ aryl); optionally substituted 3- to 18-membered heterocycloalkyl; and optionally substituted 5- to 18-membered heteroaryl, wherein $R^{3f}$ and $R^{3g}$ are each independently selected from the group consisting of:

(a) hydrogen, (b) optionally substituted $C_1$-$C_6$ alkyl, (c) $C_6$-$C_{14}$ aryl, (d) optionally substituted 3- to 18-membered heterocycloalkyl, (e) optionally substituted 5- to 18-membered heteroaryl, (f) optionally substituted $C_3$-$C_{10}$ cycloalkyl; and (g) optionally substituted $C_3$-$C_{10}$ cycloalkenyl;

vii. $C_1$-$C_6$ alkyl substituted with one or more —OH, —C(O)$NR^{3h}R^{3i}$, optionally substituted $C_6$-$C_{14}$ aryl, optionally substituted 3- to 18-membered heterocycloalkyl, optionally substituted 5- to 18-membered heteroaryl, —N($R^{3p}$)—C(O)$R^{3q}$, —S(O)$_2$—$R^{3r}$, or —C(O)—$R^{3s}$, wherein $R^{3h}$ and $R^{3i}$ are each independently selected from $C_1$-$C_6$ alkyl and —($C_1$-$C_6$ alkylene)-($C_6$-$C_{14}$ aryl), $R^{3p}$ is H or $C_1$-$C_6$ alkyl, $R^{3q}$ is $C_3$-$C_8$ cycloalkyl, optionally substituted 3- to 18-membered heterocycloalkyl, or optionally substituted 5- to 18-membered heteroaryl, $R^{3r}$ is $C_6$-$C_{14}$ aryl or 5- to 18-membered heteroaryl, and $R^{3s}$ is optionally substituted 3- to 18-membered heterocycloalkyl;

viii. —C(O)$OR^{3j}$, wherein $R^{3j}$ is hydrogen or $C_1$-$C_6$ alkyl;

ix. —NHC(O)$R^{3k}$, wherein $R^{3k}$ is optionally substituted $C_6$-$C_{14}$ aryl, optionally substituted —($C_1$-$C_6$ alkylene)-($C_6$-$C_{14}$ aryl), or optionally substituted 5- to 18-membered heteroaryl;

x. —NHC(O)$OR^{3l}$, wherein $R^{3l}$ is hydrogen or $C_1$-$C_6$ alkyl;

xi. —$NHSO_2R^{3m}$, wherein $R^{3m}$ is optionally substituted 5- to 18-membered heteroaryl, optionally substituted $C_6$-$C_{14}$ aryl, or —($C_1$-$C_6$ alkylene)-($C_6$-$C_{14}$ aryl), each of which is optionally substituted; and xii. —$SO_2R^{3n}$; wherein $R^{3n}$ is $C_1$-$C_6$ alkyl, optionally substituted $C_3$-$C_{10}$ cycloalkyl, optionally substituted $C_6$-$C_{14}$ aryl, or optionally substituted —($C_1$-$C_6$ alkylene)-($C_6$-$C_{14}$ aryl).

2. The compound of claim 1, or a pharmaceutically acceptable salt thereof, wherein p1 is 1 and q1 is 1, or wherein p1 is 2 and q1 is 1, or wherein p1 is 2 and q1 is 2.

3. The compound of claim 1, or a pharmaceutically acceptable salt thereof, wherein p2 is 1 and q2 is 1, or wherein p2 is 0 and q2 is 1, or wherein p2 is 1 and q2 is 2.

4. The compound of claim 1, or a pharmaceutically acceptable salt thereof, wherein $R^3$ is unsubstituted $C_1$-$C_6$ alkyl, or wherein $R^3$ is $C_6$-$C_{14}$ aryl, or wherein $R^3$ is 5- to 18-membered heteroaryl optionally substituted with one or more $R^a$ substituents, wherein $R^a$ is $C_1$-$C_6$ alkyl, $C_6$-$C_{14}$ aryl, or 5- to 18-membered heteroaryl, wherein the 5- to 18-membered heteroaryl of $R^a$ is optionally substituted with one or more $C_1$-$C_6$ alkyl substituents, or wherein $R^3$ is —$NR^{3a}R^{3b}$, wherein $R^{3a}$ and $R^{3b}$ are each independently selected from the group consisting of hydrogen, $C_6$-$C_{14}$ aryl, 5- to 18-membered heteroaryl, —($C_1$-$C_6$ alkylene)-($C_6$-$C_{14}$ aryl), and —($C_1$-$C_6$alkylene)-(5- to 18-membered heteroaryl), or wherein $R^3$ is $OR^{3c}$, wherein $R^{3c}$ is $C_6$-$C_{14}$ aryl, 5- to 18-membered heteroaryl, or —($C_1$-$C_6$ alkylene)-(5- to 18-membered heteroaryl).

5. The compound of claim 1, or a pharmaceutically acceptable salt thereof, wherein $R^3$ is —C(O)$R^{3d}$.

6. The compound of claim 5, or a pharmaceutically acceptable salt thereof, wherein $R^{3d}$ is —$N^{3f}R^{3g}$ and $R^{3f}$ and $R^{3g}$ are each independently selected from the group consisting of:

(a) hydrogen, (b) $C_1$-$C_6$ alkyl optionally substituted with one or more substituents independently selected from the group consisting of —OH, $C_6$-$C_{14}$ aryl, and 5- to 18-membered heteroaryl, wherein the $C_6$-$C_{14}$ aryl and 5- to 18-membered heteroaryl groups are each independently unsubstituted or substituted with one or more substituents independently selected from the group consisting of halo, $C_1$-$C_6$ alkyl, hydroxyl, $C_1$-$C_6$alkoxy, $C_1$-$C_6$ haloalkoxy, and CN, (c) $C_6$-$C_{14}$ aryl, (d) 3- to 18-membered heterocycloalkyl, (e) 5- to 18-membered heteroaryl optionally substituted with methyl or CN, (f) $C_3$-$C_{10}$ cycloalkyl optionally substituted with one or more substituents independently selected from the group consisting of halo, hydroxyl, $C_1$-$C_6$ alkyl optionally substituted with hydroxyl, $C_6$-$C_{14}$ aryl, and 5- to 18-membered heteroaryl; and (g) $C_3$-$C_{10}$ cycloalkenyl optionally substituted with one or more substituents independently selected from the group consisting of halo, hydroxyl, $C_1$-$C_6$ alkyl optionally substituted with hydroxyl, $C_6$-$C_{14}$ aryl, and 5- to 18-membered heteroaryl.

7. The compound of claim 5, or a pharmaceutically acceptable salt thereof, wherein $R^3$ is

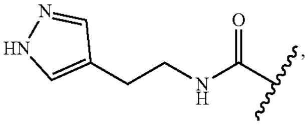,

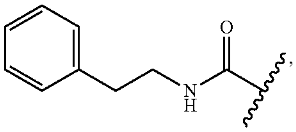,

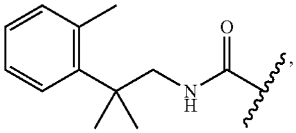,

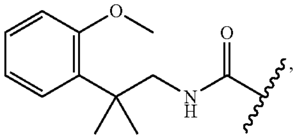,

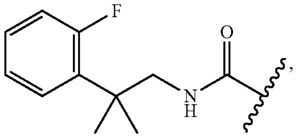,

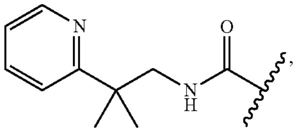,

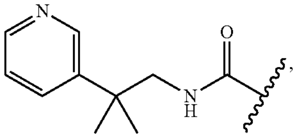,

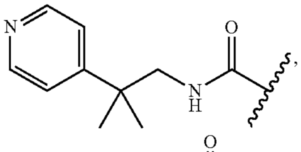,

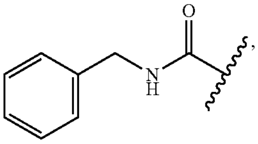,

-continued
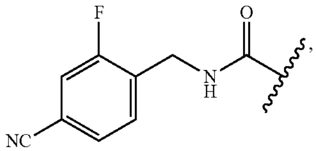
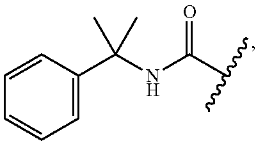
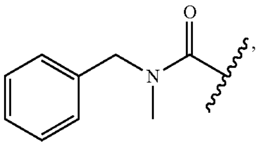
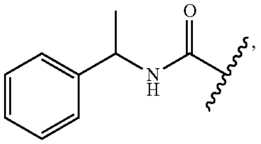
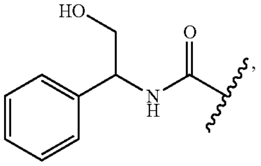
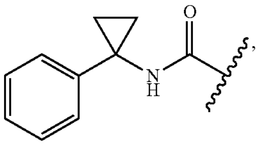
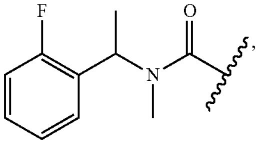
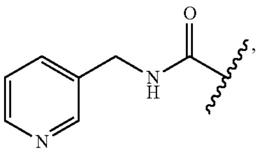
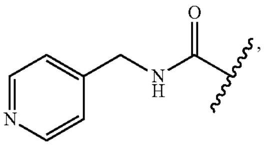
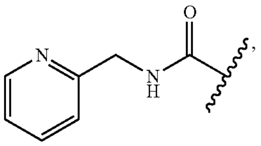
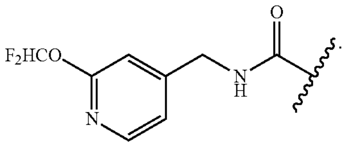
-continued
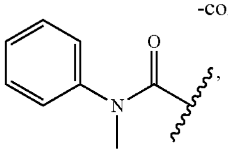 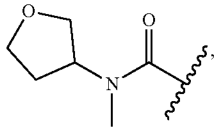
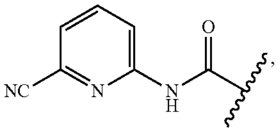
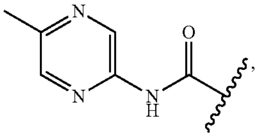 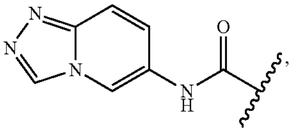
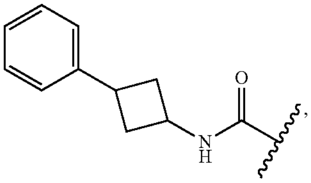
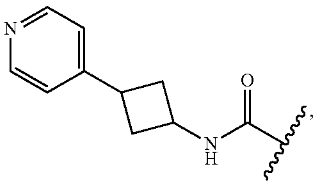 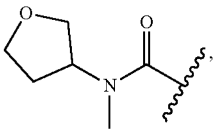
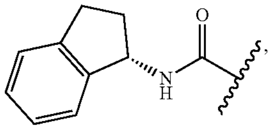 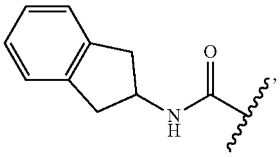
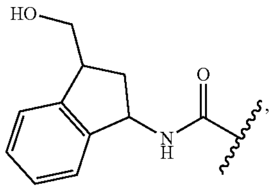 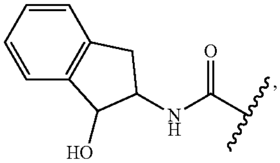
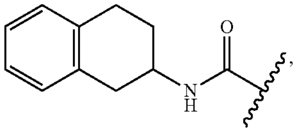
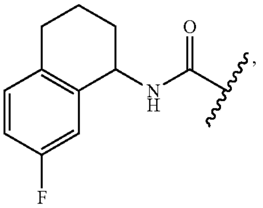 or
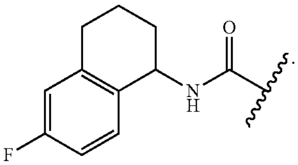
8. The compound of claim 5, or a pharmaceutically acceptable salt thereof, wherein $R^{3d}$ is $C_3$-$C_8$ cycloalkyl, or wherein $R^{3d}$ is $C_3$-$C_8$ cycloalkyl substituted with $C_6$-$C_{14}$ aryl, wherein the $C_6$-$C_{14}$ aryl is optionally substituted with one or more substituents independently selected from the group consisting of halo, $C_1$-$C_6$ alkyl, $C_1$-$C_6$ haloalkyl, and $C_1$-$C_6$ alkoxy.

9. The compound of claim 5, or a pharmaceutically acceptable salt thereof, wherein $R^{3d}$ is $C_3$-$C_8$ cycloalkenyl.

10. The compound of claim 5, or a pharmaceutically acceptable salt thereof, wherein $R^{3d}$ is $C_6$-$C_{14}$ aryl optionally substituted with one or more substituents independently selected from the group consisting of hydroxyl, halo, cyano, $C_1$-$C_6$ alkyl, $C_1$-$C_6$ alkoxy, $C_1$-$C_6$ haloalkyl, —($C_1$-$C_6$ alkylene)-OH, —C(O)O($C_1$-$C_6$ alkyl), —$NR^{3e1}R^{3e2}$, —$S(O)_2$($C_1$-$C_6$ alkyl), 5- to 18-membered heteroaryl, and 3- to 18-membered heterocycloalkyl optionally substituted with oxo, wherein $R^{3e1}$ and $R^{3e2}$ are each independently H or $C_1$-$C_6$ alkyl.

11. The compound of claim 5, or a pharmaceutically acceptable salt thereof, wherein $R^{3d}$ is —($C_1$-$C_6$ alkylene)-($C_6$-$C_{14}$ aryl) optionally substituted with one or more substituents independently selected from the group consisting of halo, $C_1$-$C_6$ alkyl, $C_1$-$C_6$ haloalkyl, and $C_1$-$C_6$ alkoxy.

12. The compound of claim 5, or a pharmaceutically acceptable salt thereof, wherein $R^{3d}$ is 3- to 18-membered heterocycloalkyl optionally substituted with one or more substituents independently selected from the group consisting of:

(a) $C_1$-$C_6$ alkyl optionally substituted with one or more substituents independently selected from the group consisting of hydroxyl, halo, $C_3$-$C_{10}$ cycloalkyl, and 5- to 18-membered heteroaryl optionally substituted with one or more $C_1$-$C_6$ alkyl substituents,
(b) $C_6$-$C_{14}$ aryl,
(c) 3- to 18-membered heterocycloalkyl,
(d) —C(O)O($C_1$-$C_6$ alkyl),
(e) —C(O)($C_6$-$C_{14}$ aryl),
(f) halo,
(g) $C_1$-$C_6$ alkoxy optionally substituted with one or more halo substituents, and
(h) oxo.

13. The compound of claim 12, or a pharmaceutically acceptable salt thereof, wherein $R^3$ is

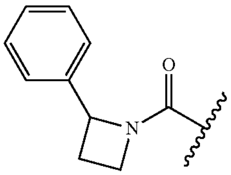,
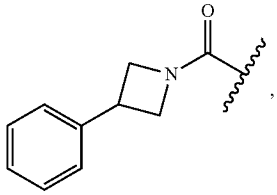,
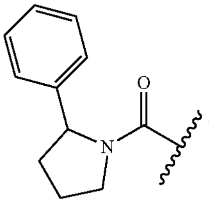,
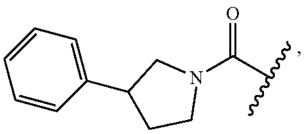,
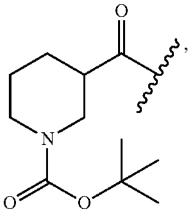,
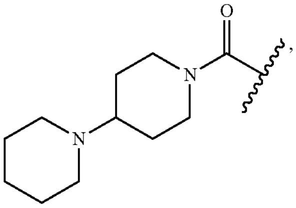, -continued

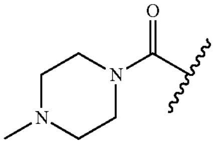,
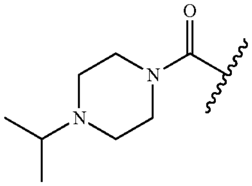,
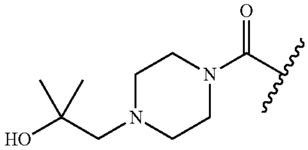,
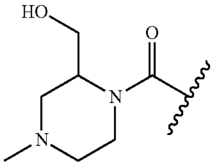,
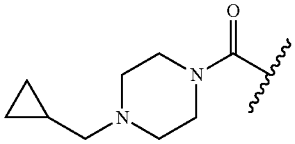,
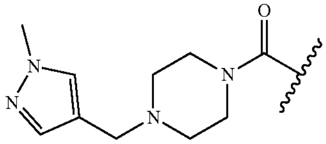,
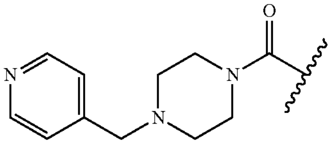,
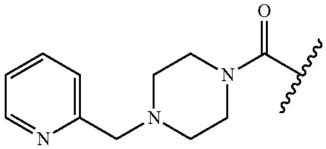,
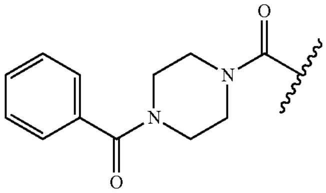,
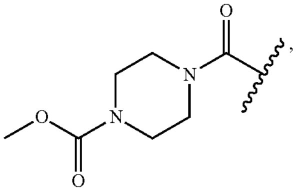,
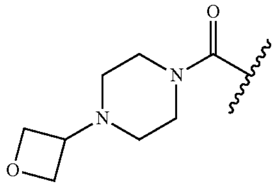,
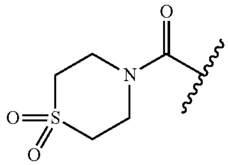,
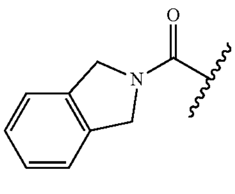,
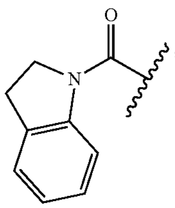, -continued

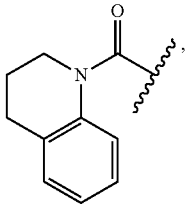, 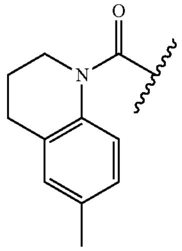, 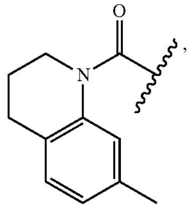,

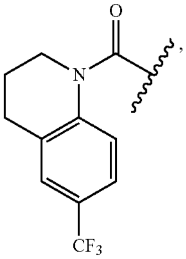, 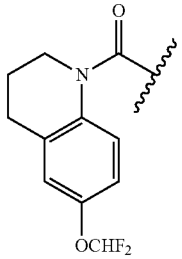, 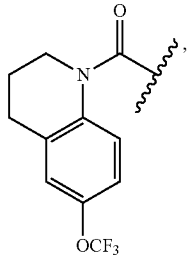,

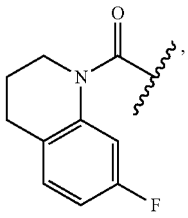, 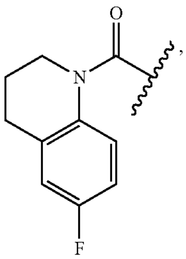, 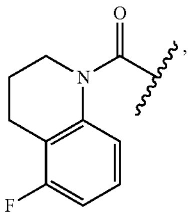,

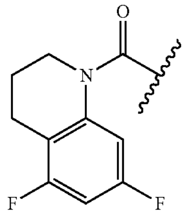, 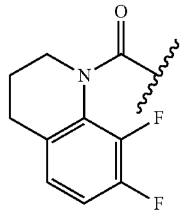, 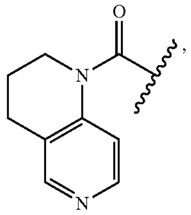,

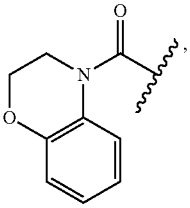, or 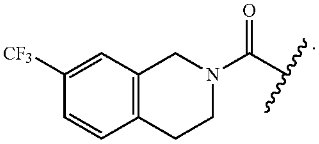.

14. The compound of claim 5, or a pharmaceutically acceptable salt thereof, wherein $R^{3d}$ is 5- to 18-membered heteroaryl optionally substituted with one or more substituents independently selected from the group consisting of $C_1$-$C_6$ alkyl, hydroxyl, oxo, and 3- to 18-membered heterocycloalkyl.

15. The compound of claim 14, or a pharmaceutically acceptable salt thereof, wherein $R^3$ is

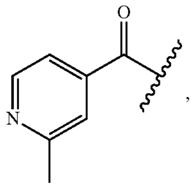, 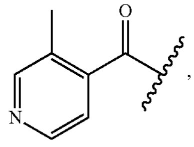,

-continued

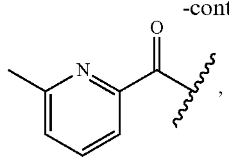, 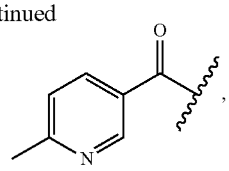,

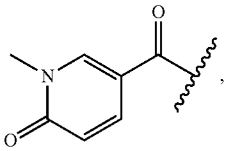, or 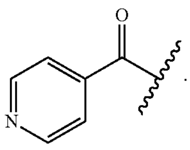.

16. The compound of claim 1, or a pharmaceutically acceptable salt thereof, wherein $R^3$ is $C_1$-$C_6$ alkyl substituted with $C(O)NR^{3h}R^{3i}$, wherein $R^{3h}$ and $R^{3i}$ are each independently selected from $C_1$-$C_6$ alkyl and —($C_1$-$C_6$ alkylene)-($C_6$-$C_{14}$ aryl).

17. The compound of claim 1, or a pharmaceutically acceptable salt thereof, wherein $R^3$ is $C_1$-$C_6$ alkyl substituted with 3- to 18-membered heterocycloalkyl, wherein the 3- to 18-membered heterocycloalkyl is optionally substituted with one or more substituents independently selected from halo, oxo, $C_1$-$C_6$ alkyl, —$C_6$-$C_{14}$ aryl, and 5- to 18-membered heteroaryl.

18. The compound of claim 1, or a pharmaceutically acceptable salt thereof, wherein $R^3$ is $C_1$-$C_6$ alkyl, wherein the $C_1$-$C_6$ alkyl of $R^3$ is (i) substituted with 5- to 18-membered heteroaryl, wherein the 5- to 18-membered heteroaryl is optionally substituted with one or more $C_1$-$C_6$ alkyl, $C_6$-$C_{14}$ aryl, or cyano, and (ii) optionally substituted with one or more —OH.

19. The compound of claim 1, or a pharmaceutically acceptable salt thereof, wherein $R^3$ is —$C(O)OR^{3j}$, wherein $R^{3j}$ is hydrogen or $C_1$-$C_6$ alkyl.

20. The compound of claim 1, or a pharmaceutically acceptable salt thereof, wherein $R^3$ is —$NHC(O)R^{3k}$.

21. The compound of claim 1, or a pharmaceutically acceptable salt thereof, wherein $R^3$ is —$NHSO_2R^{3m}$, wherein $R^{3m}$ is 5- to 18-membered heteroaryl, $C_6$-$C_{14}$ aryl, or —($C_1$-$C_6$ alkylene)-($C_6$-$C_{14}$ aryl), wherein the 5- to 18-membered heteroaryl, the $C_6$-$C_{14}$ aryl, and the —($C_1$-$C_6$ alkylene)-($C_6$-$C_{14}$ aryl) are each optionally substituted with one or more substituents independently selected from halo and $C_1$-$C_6$ alkoxy.

22. The compound of claim 1, or a pharmaceutically acceptable salt thereof, wherein $R^3$ is —$SO_2R^{3n}$ and $R^{3n}$ is $C_1$-$C_6$ alkyl, $C_3$-$C_{10}$ cycloalkyl, $C_6$-$C_{14}$ aryl, or —($C_1$-$C_6$ alkylene)-($C_6$-$C_{14}$ aryl), wherein the $C_3$-$C_{10}$ cycloalkyl, the $C_6$-$C_{14}$ aryl, and the —($C_1$-$C_6$ alkylene)-($C_6$-$C_{14}$ aryl) of $R^{3n}$ are each independently optionally substituted with one or more substituents independently selected from halo and —$C(O)O(C_1$-$C_6$ alkyl).

23. The compound of claim 1, or a pharmaceutically acceptable salt thereof, wherein $R^3$ is $C_1$-$C_6$ alkyl substituted with one or more —$N(R^{3p})$—$C(O)R^{3q}$, wherein $R^{3p}$ is H or $C_1$-$C_6$ alkyl, and $R^{3q}$ is (i) $C_3$-$C_8$ cycloalkyl, (ii) 3- to 18-membered heterocycloalkyl optionally substituted with one or more independently selected oxo substituents, or (iii) 5- to 18-membered heteroaryl optionally substituted with one or more independently selected $C_1$-$C_6$alkyl substituents.

24. The compound of claim 23, or a pharmaceutically acceptable salt thereof, wherein $R^3$ is

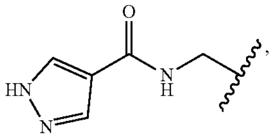,

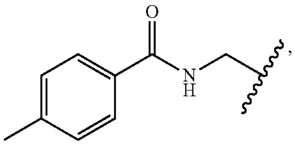,

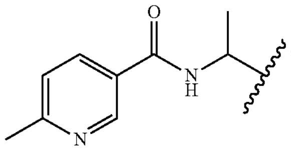,

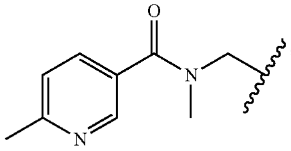,

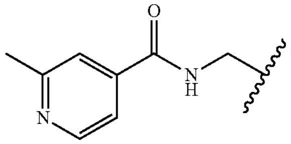,

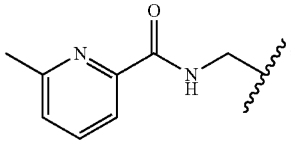,

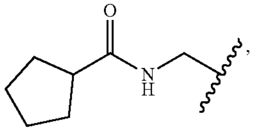,

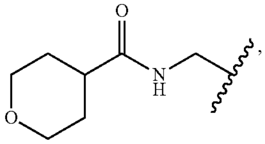,

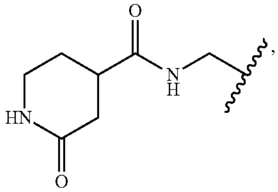, or

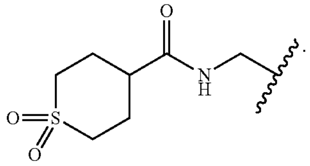.

25. The compound of claim 1, or a pharmaceutically acceptable salt thereof, wherein $R^3$ is $C_1$-$C_6$ alkyl substituted with one or more —$S(O)_2$—$R^{3r}$, wherein $R^{3r}$ is $C_6$-$C_{14}$ aryl or 5- to 18-membered heteroaryl.

26. The compound of claim 1, or a pharmaceutically acceptable salt thereof, wherein $R^3$ is $C_1$-$C_6$ alkyl substituted with one or more —C(O)—$R^{3s}$, wherein $R^{3s}$ is 3- to 18-membered heterocycloalkyl optionally substituted with one or more independently selected $C_1$-$C_6$ alkyl substituents, wherein the $C_1$-$C_6$ alkyl is independently optionally substituted with one or more —OH.

27. The compound of claim 1, or a pharmaceutically acceptable salt thereof, wherein $R^3$ is $C_1$-$C_6$ alkyl, wherein the $C_1$-$C_6$ alkyl of $R^3$ is (i) substituted with one or more independently selected $C_6$-$C_{14}$ aryl substituents, wherein the $C_6$-$C_{14}$ aryl is optionally substituted with one or more independently selected $C_1$-$C_6$ alkyl substituents, and (ii) optionally substituted with one or more —OH.

28. The compound of claim 1, or a pharmaceutically acceptable salt thereof, wherein $G^1$ is CH.

29. The compound of claim 1, or a pharmaceutically acceptable salt thereof, wherein $G^1$ is N.

30. The compound of claim 1, or a pharmaceutically acceptable salt thereof, wherein n is 0, or wherein n is 1, or wherein n is 2, or wherein n is 3.

31. The compound of claim 1, or a pharmaceutically acceptable salt thereof, wherein n is 4, or wherein n is 5, or wherein n is 6.

32. The compound of claim 1, or a pharmaceutically acceptable salt thereof, wherein $R^1$ is

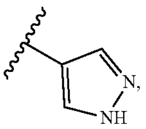 [SMILES: *c1cn[nH]c1]

or wherein $R^1$ is

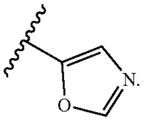 [SMILES: *c1cnco1]

33. The compound of claim 1, or a pharmaceutically acceptable salt thereof, wherein $R^1$ is

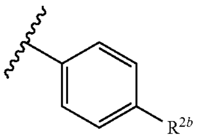

and $R^2$ is selected from the group consisting of halo, —O($C_1$-$C_6$ alkyl), $C_1$-$C_6$ alkyl substituted with —OH, —C(O)$NR^{2c}R^{2d}$, and —N($R^{2e}$)C(O)($C_1$-$C_6$ alkyl), wherein $R^{2c}$, $R^{2d}$, and $R^{2e}$ are each independently hydrogen or $C_1$-$C_6$ alkyl.

34. The compound of claim 1, or a pharmaceutically acceptable salt thereof, wherein $R^1$ is

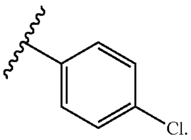 [SMILES: *c1ccc(Cl)cc1]

35. The compound of claim 1, or a pharmaceutically acceptable salt thereof, wherein the compound is selected from the group consisting of:

| Compound No. | Structure |
|---|---|
| 2 | 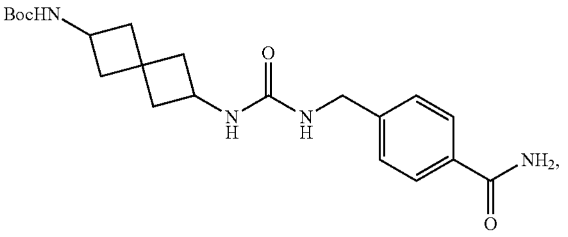 [SMILES: CC(C)(C)OC(=O)NC1CC2(CC(NC(=O)NCc3ccc(C(N)=O)cc3)C2)C1] |
| 6 | 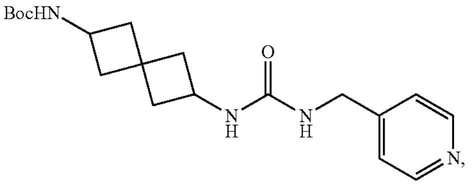 [SMILES: CC(C)(C)OC(=O)NC1CC2(CC(NC(=O)NCc3ccncc3)C2)C1] |
| 7 | 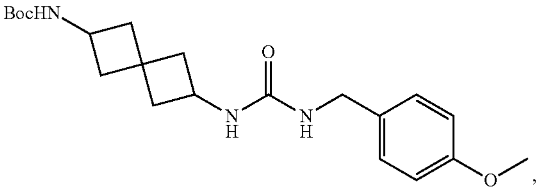 [SMILES: COc1ccc(CNC(=O)NC2CC3(C2)CC(NC(=O)OC(C)(C)C)C3)cc1] |
| 8 | 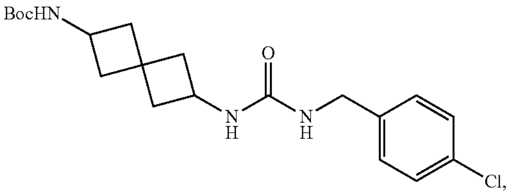 [SMILES: CC(C)(C)OC(=O)NC1CC2(CC(NC(=O)NCc3ccc(Cl)cc3)C2)C1] |
| 9 | 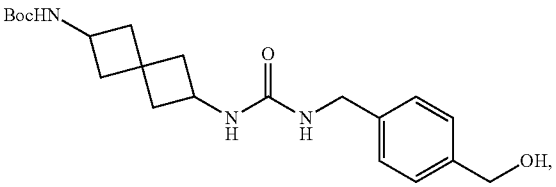 [SMILES: CC(C)(C)OC(=O)NC1CC2(CC(NC(=O)NCc3ccc(CO)cc3)C2)C1] |
| 10 | 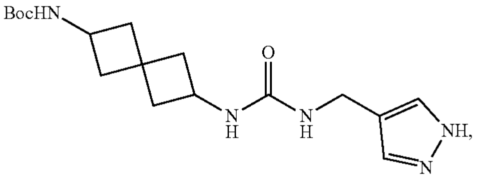 [SMILES: CC(C)(C)OC(=O)NC1CC2(CC(NC(=O)NCc3cn[nH]c3)C2)C1] |
| 11 | 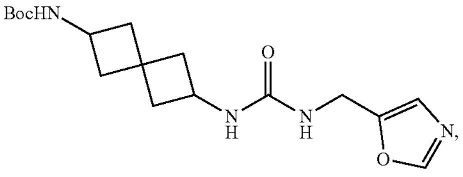 [SMILES: CC(C)(C)OC(=O)NC1CC2(CC(NC(=O)NCc3cnco3)C2)C1] |

-continued
| Compound No. | Structure |
| --- | --- |
| 14 | 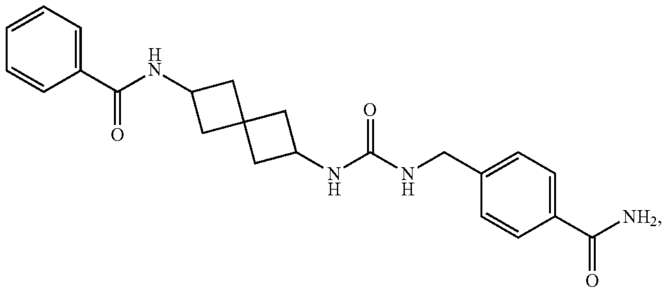 [SMILES: NC(=O)c1ccc(CNC(=O)NC2CC3(C2)CC(NC(=O)c2ccccc2)C3)cc1] |
| 15 | 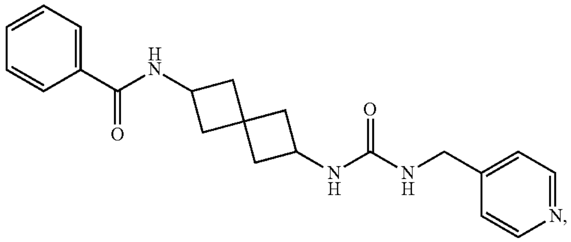 [SMILES: O=C(NCc1ccncc1)NC1CC2(C1)CC(NC(=O)c1ccccc1)C2] |
| 17 | 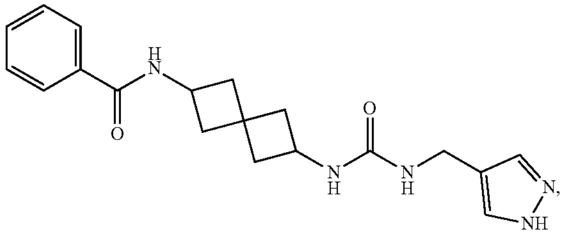 [SMILES: O=C(NCc1cn[nH]c1)NC1CC2(C1)CC(NC(=O)c1ccccc1)C2] |
| 18 | 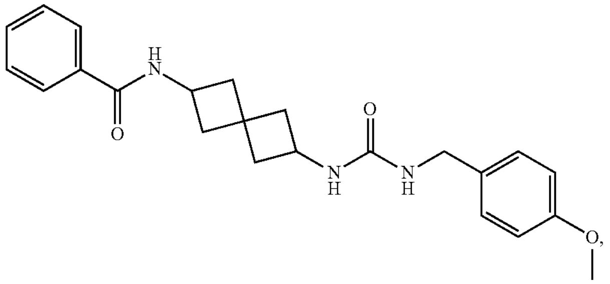 [SMILES: COc1ccc(CNC(=O)NC2CC3(C2)CC(NC(=O)c2ccccc2)C3)cc1] |
| 24 | 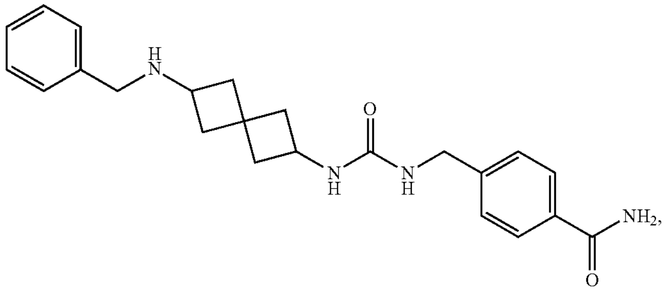 [SMILES: NC(=O)c1ccc(CNC(=O)NC2CC3(CC(NCc4ccccc4)C3)C2)cc1] |
| 25 | 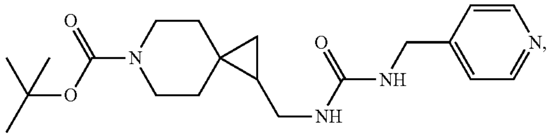 [SMILES: CC(C)(C)OC(=O)N1CCC2(CC1)CC2CNC(=O)NCc1ccncc1] |

-continued
| Compound No. | Structure |
|---|---|
| 26 | 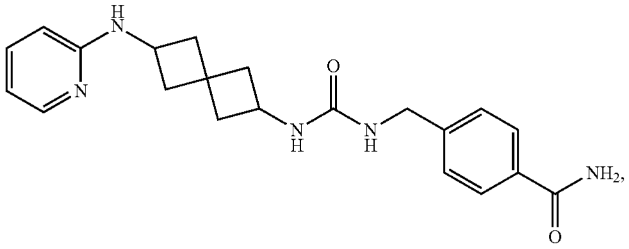 [SMILES: NC(=O)c1ccc(CNC(=O)NC2CC3(C2)CC(Nc2ccccn2)C3)cc1] |
| 27 | 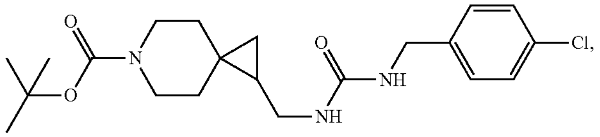 [SMILES: CC(C)(C)OC(=O)N1CCC2(CC1)CC2CNC(=O)NCc1ccc(Cl)cc1] |
| 28 | 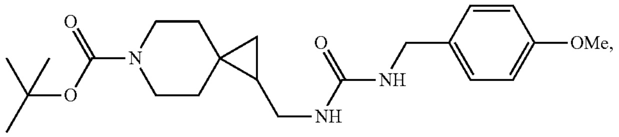 [SMILES: COc1ccc(CNC(=O)NCC2CC23CCN(C(=O)OC(C)(C)C)CC3)cc1] |
| 29 | 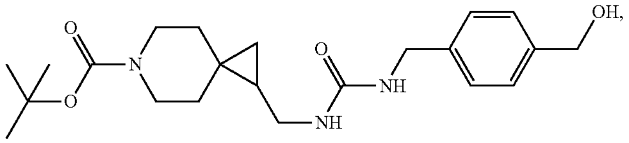 [SMILES: CC(C)(C)OC(=O)N1CCC2(CC1)CC2CNC(=O)NCc1ccc(CO)cc1] |
| 30 | 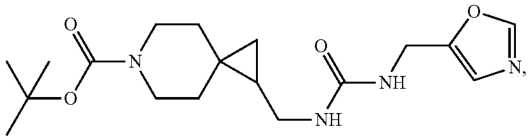 [SMILES: CC(C)(C)OC(=O)N1CCC2(CC1)CC2CNC(=O)NCc1cnco1] |
| 31 | 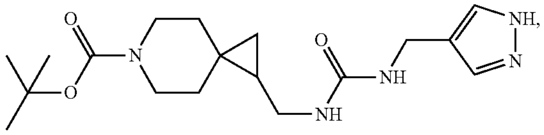 [SMILES: CC(C)(C)OC(=O)N1CCC2(CC1)CC2CNC(=O)NCc1cn[nH]c1] |
| 32 | 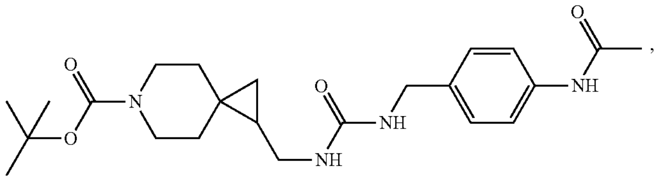 [SMILES: CC(=O)Nc1ccc(CNC(=O)NCC2CC23CCN(C(=O)OC(C)(C)C)CC3)cc1] |
| 33 | 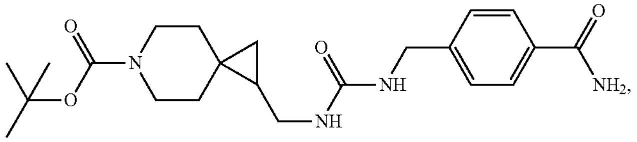 [SMILES: CC(C)(C)OC(=O)N1CCC2(CC1)CC2CNC(=O)NCc1ccc(C(N)=O)cc1] |

-continued
| Compound No. | Structure |
|---|---|
| 34 | 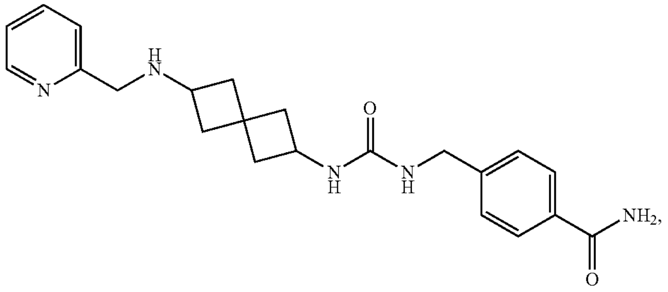 [SMILES: NC(=O)c1ccc(CNC(=O)NC2CC3(CC(NCc4ccccn4)C3)C2)cc1] |
| 35 | 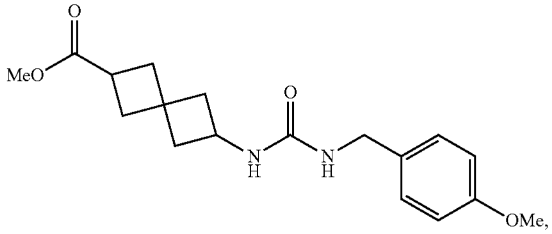 [SMILES: COC(=O)C1CC2(CC(NC(=O)NCc3ccc(OC)cc3)C2)C1] |
| 37 | 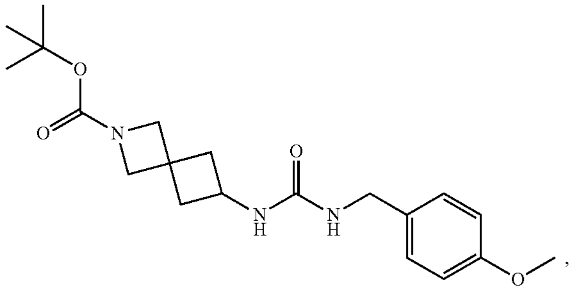 [SMILES: COc1ccc(CNC(=O)NC2CC3(C2)CN(C(=O)OC(C)(C)C)C3)cc1] |
| 38 | 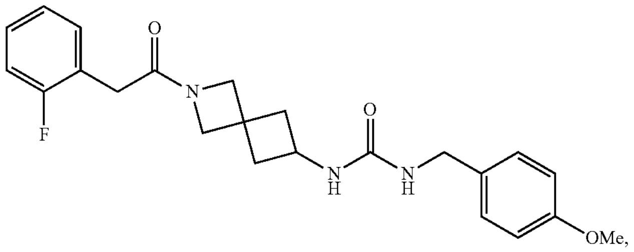 [SMILES: COc1ccc(CNC(=O)NC2CC3(C2)CN(C(=O)Cc2ccccc2F)C3)cc1] |
| 39 | 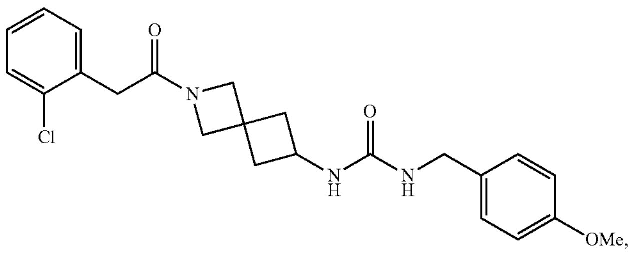 [SMILES: COc1ccc(CNC(=O)NC2CC3(C2)CN(C(=O)Cc2ccccc2Cl)C3)cc1] |

-continued
| Compound No. | Structure |
|---|---|
| 40 | 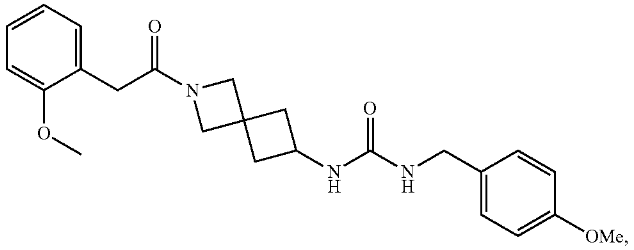 [SMILES: COc1ccc(CNC(=O)NC2CC3(C2)CN(C(=O)Cc2ccccc2OC)C3)cc1] |
| 41 | 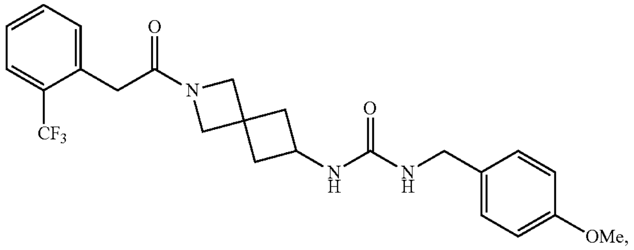 [SMILES: COc1ccc(CNC(=O)NC2CC3(C2)CN(C(=O)Cc2ccccc2C(F)(F)F)C3)cc1] |
| 42 | 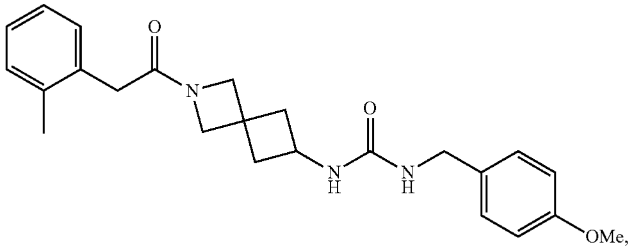 [SMILES: COc1ccc(CNC(=O)NC2CC3(C2)CN(C(=O)Cc2ccccc2C)C3)cc1] |
| 43 | 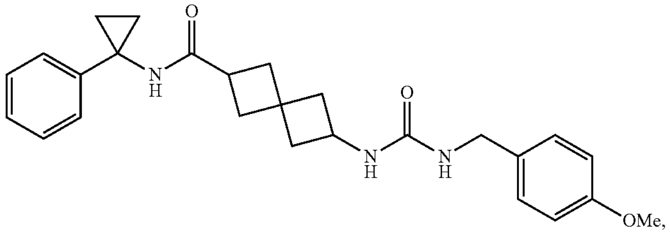 [SMILES: COc1ccc(CNC(=O)NC2CC3(C2)CC(C(=O)NC2(c4ccccc4)CC2)C3)cc1] |
| 44 | 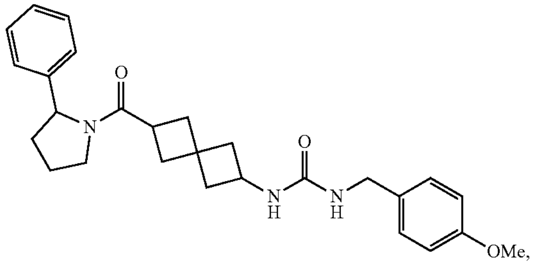 [SMILES: COc1ccc(CNC(=O)NC2CC3(C2)CC(C(=O)N2CCCC2c2ccccc2)C3)cc1] |
| 45 | 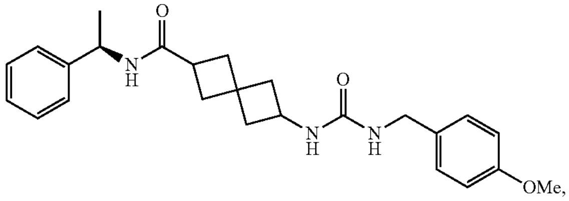 [SMILES: COc1ccc(CNC(=O)NC2CC3(C2)CC(C(=O)N[C@H](C)c2ccccc2)C3)cc1] |

-continued
| Compound No. | Structure |
| --- | --- |
| 46 | 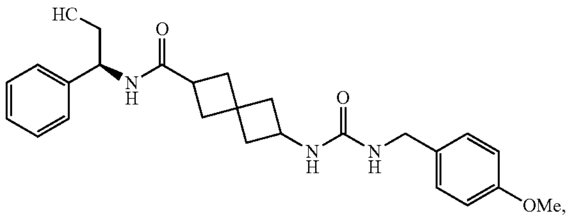 [SMILES: CC[C@@H](NC(=O)C1CC2(CC(NC(=O)NCc3ccc(OC)cc3)C2)C1)c1ccccc1] |
| 47 | 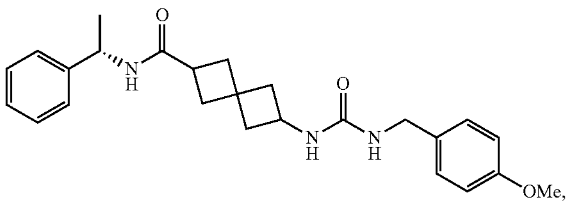 [SMILES: COc1ccc(CNC(=O)NC2CC3(C2)CC(C(=O)N[C@@H](C)c2ccccc2)C3)cc1] |
| 48 | 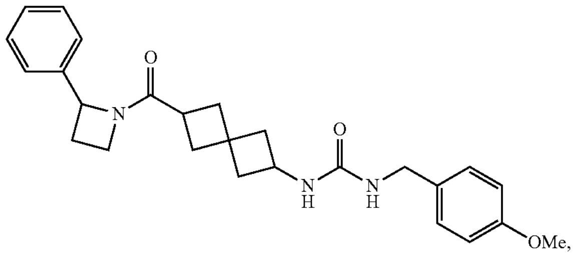 [SMILES: COc1ccc(CNC(=O)NC2CC3(C2)CC(C(=O)N2CCC2c2ccccc2)C3)cc1] |
| 49 | 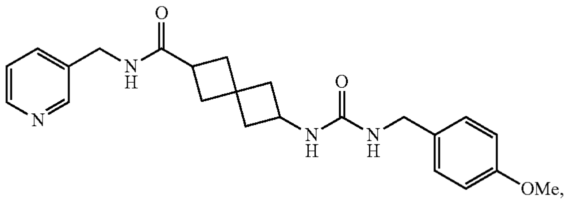 [SMILES: COc1ccc(CNC(=O)NC2CC3(C2)CC(C(=O)NCc2cccnc2)C3)cc1] |
| 50 | 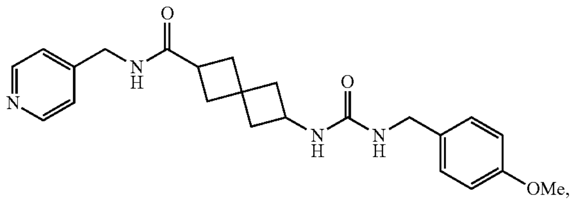 [SMILES: COc1ccc(CNC(=O)NC2CC3(C2)CC(C(=O)NCc2ccncc2)C3)cc1] |
| 51 | 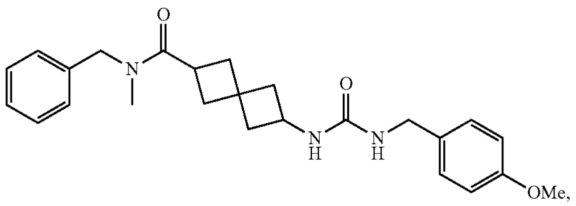 [SMILES: COc1ccc(CNC(=O)NC2CC3(C2)CC(C(=O)N(C)Cc2ccccc2)C3)cc1] |

-continued
| Compound No. | Structure |
|---|---|
| 52 | 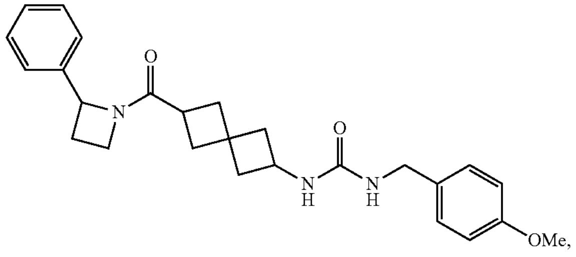 [SMILES: COc1ccc(CNC(=O)NC2CC3(C2)CC(C(=O)N2CCC2c2ccccc2)C3)cc1] |
| 53 | 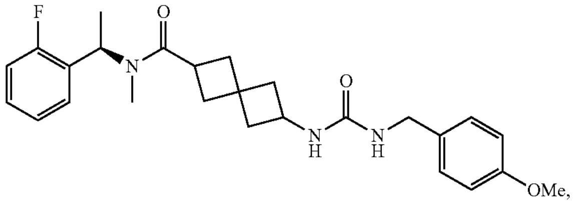 [SMILES: COc1ccc(CNC(=O)NC2CC3(C2)CC(C(=O)N(C)[C@H](C)c2ccccc2F)C3)cc1] |
| 54 | 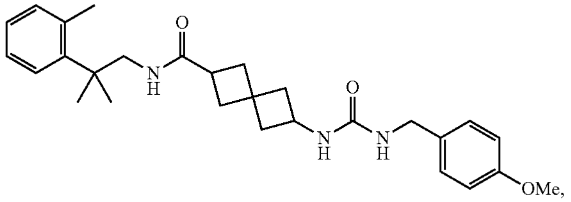 [SMILES: COc1ccc(CNC(=O)NC2CC3(C2)CC(C(=O)NCC(C)(C)c2ccccc2C)C3)cc1] |
| 55 | 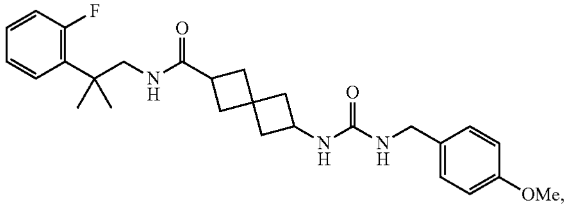 [SMILES: COc1ccc(CNC(=O)NC2CC3(C2)CC(C(=O)NCC(C)(C)c2ccccc2F)C3)cc1] |
| 56 | 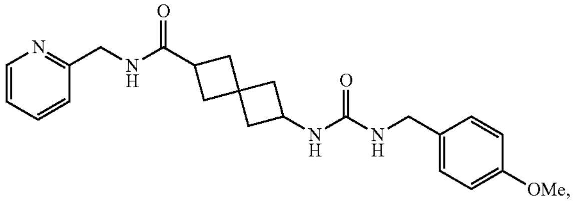 [SMILES: COc1ccc(CNC(=O)NC2CC3(C2)CC(C(=O)NCc2ccccn2)C3)cc1] |
| 57 | 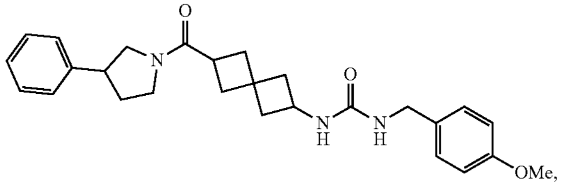 [SMILES: COc1ccc(CNC(=O)NC2CC3(C2)CC(C(=O)N2CCC(c4ccccc4)C2)C3)cc1] |

-continued
| Compound No. | Structure |
|---|---|
| 58 | 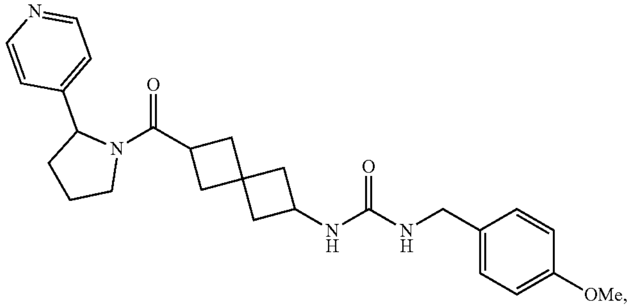 [SMILES: COc1ccc(CNC(=O)NC2CC3(C2)CC(C(=O)N2CCCC2c2ccncc2)C3)cc1] |
| 59 | 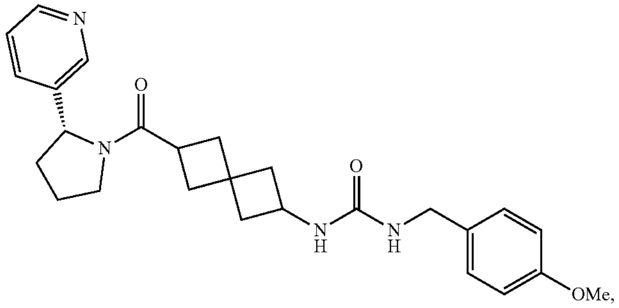 [SMILES: COc1ccc(CNC(=O)NC2CC3(C2)CC(C(=O)N2CCC[C@@H]2c2cccnc2)C3)cc1] |
| 60 | 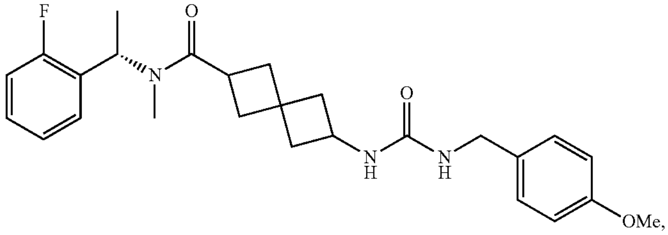 [SMILES: COc1ccc(CNC(=O)NC2CC3(C2)CC(C(=O)N(C)[C@@H](C)c2ccccc2F)C3)cc1] |
| 61 | 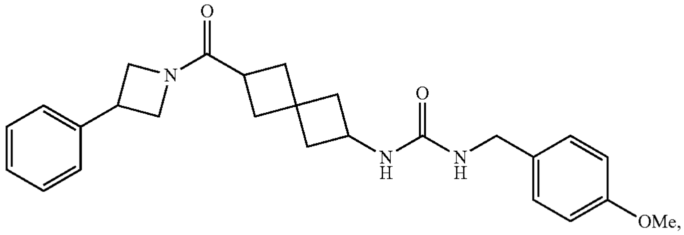 [SMILES: COc1ccc(CNC(=O)NC2CC3(C2)CC(C(=O)N2CC(c4ccccc4)C2)C3)cc1] |
| 62 | 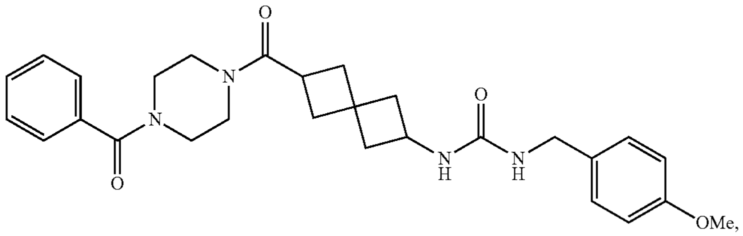 [SMILES: COc1ccc(CNC(=O)NC2CC3(C2)CC(C(=O)N2CCN(C(=O)c4ccccc4)CC2)C3)cc1] |

-continued
| Compound No. | Structure |
|---|---|
| 63 | 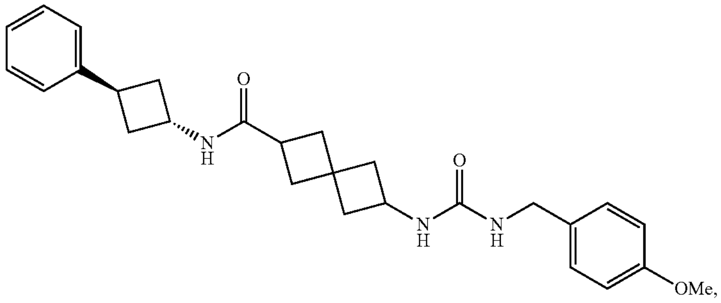 [SMILES: COc1ccc(CNC(=O)NC2CC3(C2)CC(C(=O)N[C@H]2C[C@H](c4ccccc4)C2)C3)cc1] |
| 64 | 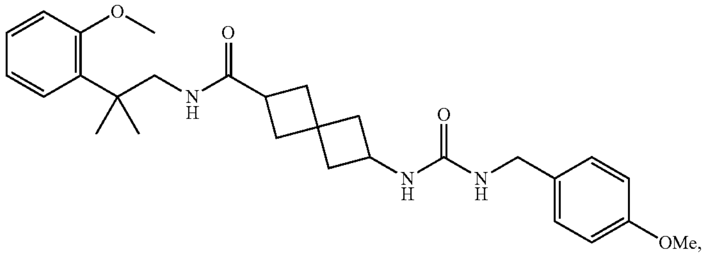 [SMILES: COc1ccc(CNC(=O)NC2CC3(C2)CC(C(=O)NCC(C)(C)c2ccccc2OC)C3)cc1] |
| 65 | 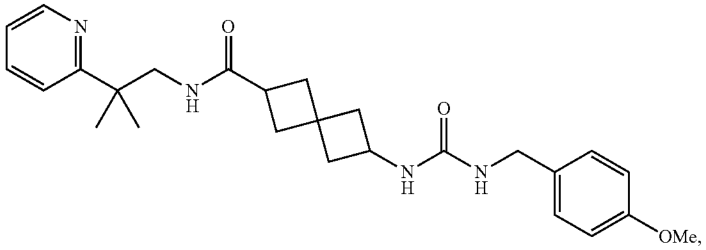 [SMILES: COc1ccc(CNC(=O)NC2CC3(C2)CC(C(=O)NCC(C)(C)c2ccccn2)C3)cc1] |
| 66 | 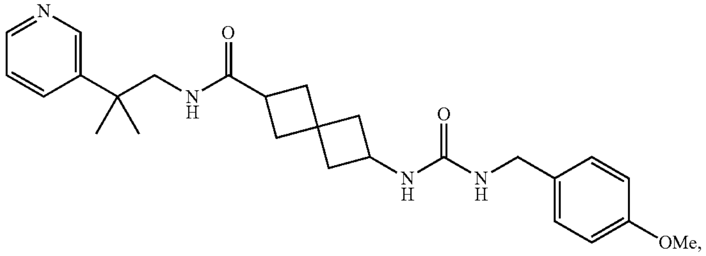 [SMILES: COc1ccc(CNC(=O)NC2CC3(C2)CC(C(=O)NCC(C)(C)c2cccnc2)C3)cc1] |
| 67 | 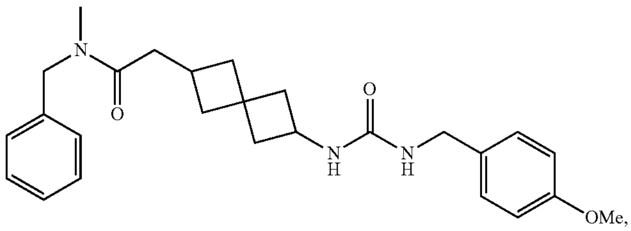 [SMILES: COc1ccc(CNC(=O)NC2CC3(CC(CC(=O)N(C)Cc4ccccc4)C3)C2)cc1] |
| 68 | 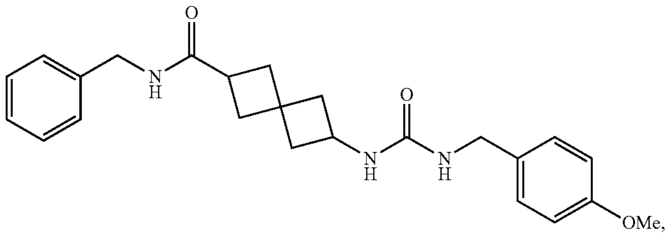 [SMILES: COc1ccc(CNC(=O)NC2CC3(C2)CC(C(=O)NCc2ccccc2)C3)cc1] |

-continued
| Compound No. | Structure |
| --- | --- |
| 69 | 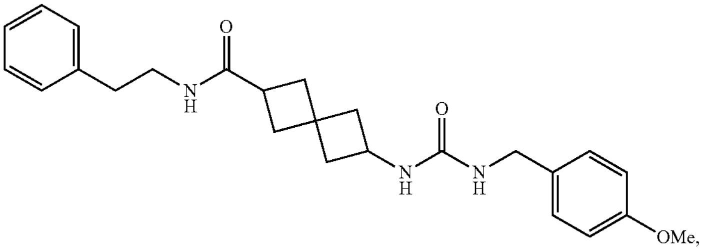 [SMILES: COc1ccc(CNC(=O)NC2CC3(C2)CC(C(=O)NCCc2ccccc2)C3)cc1] |
| 70 | 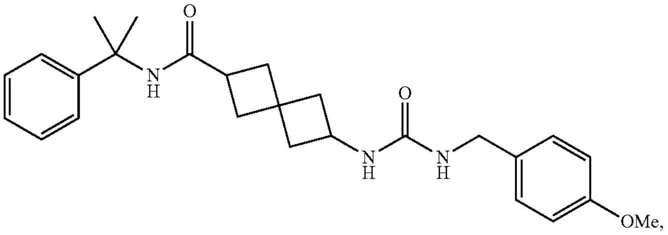 [SMILES: COc1ccc(CNC(=O)NC2CC3(C2)CC(C(=O)NC(C)(C)c2ccccc2)C3)cc1] |
| 71 | 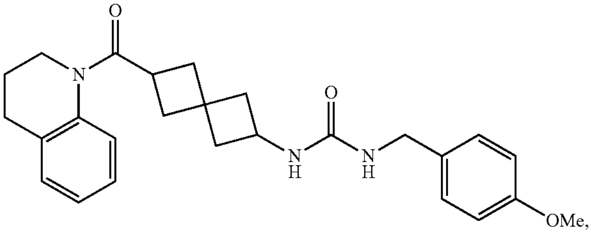 [SMILES: COc1ccc(CNC(=O)NC2CC3(C2)CC(C(=O)N2CCCc4ccccc42)C3)cc1] |
| 72 | 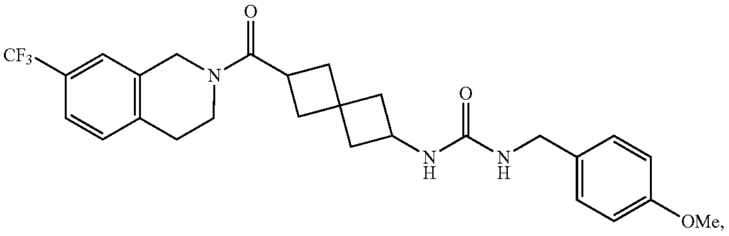 [SMILES: COc1ccc(CNC(=O)NC2CC3(C2)CC(C(=O)N2CCc4ccc(C(F)(F)F)cc4C2)C3)cc1] |
| 73 | 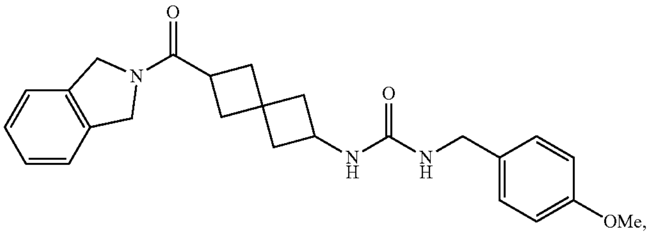 [SMILES: COc1ccc(CNC(=O)NC2CC3(C2)CC(C(=O)N2Cc4ccccc4C2)C3)cc1] |
| 74 | 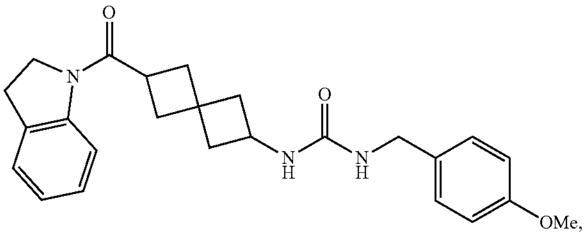 [SMILES: COc1ccc(CNC(=O)NC2CC3(C2)CC(C(=O)N2CCc4ccccc42)C3)cc1] |

-continued
| Compound No. | Structure |
|---|---|
| 75 | 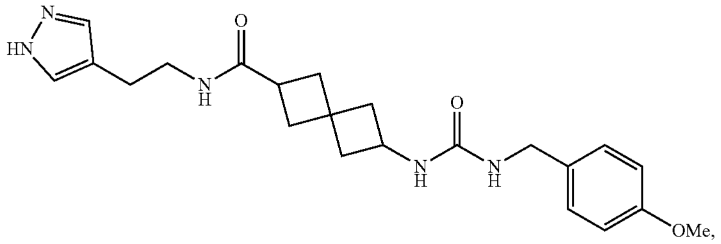 [SMILES: COc1ccc(CNC(=O)NC2CC3(C2)CC(C(=O)NCCc2cn[nH]c2)C3)cc1] |
| 76 | 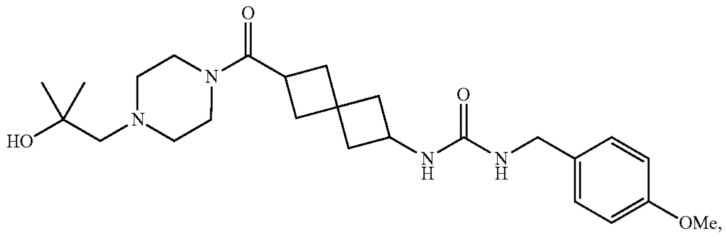 [SMILES: COc1ccc(CNC(=O)NC2CC3(C2)CC(C(=O)N2CCN(CC(C)(C)O)CC2)C3)cc1] |
| 77 | 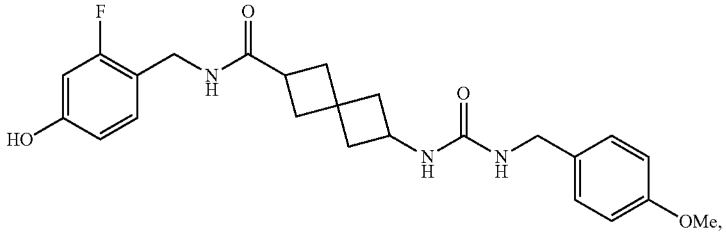 [SMILES: COc1ccc(CNC(=O)NC2CC3(C2)CC(C(=O)NCc2ccc(O)cc2F)C3)cc1] |
| 78 | 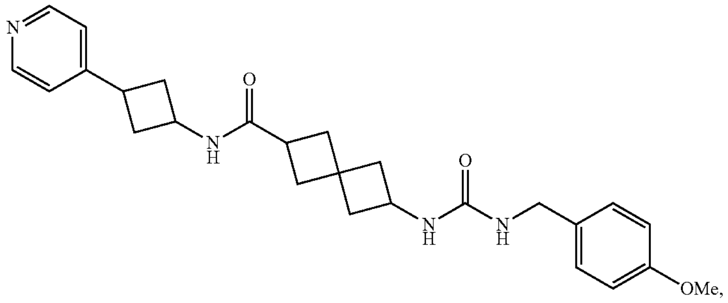 [SMILES: COc1ccc(CNC(=O)NC2CC3(C2)CC(C(=O)NC2CC(c4ccncc4)C2)C3)cc1] |
| 79 | 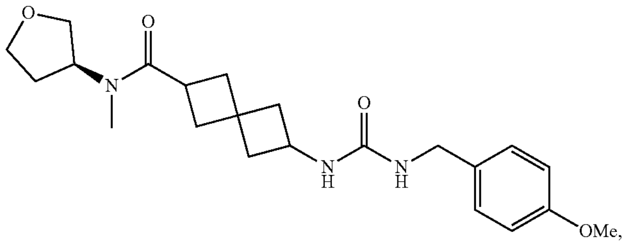 [SMILES: COc1ccc(CNC(=O)NC2CC3(C2)CC(C(=O)N(C)[C@H]2CCOC2)C3)cc1] |
| 80 | 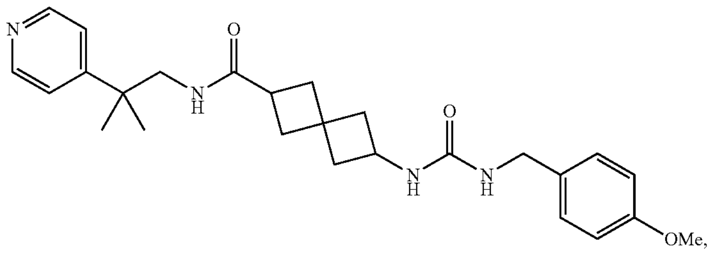 [SMILES: COc1ccc(CNC(=O)NC2CC3(C2)CC(C(=O)NCC(C)(C)c2ccncc2)C3)cc1] |

-continued
| Compound No. | Structure |
|---|---|
| 81 | 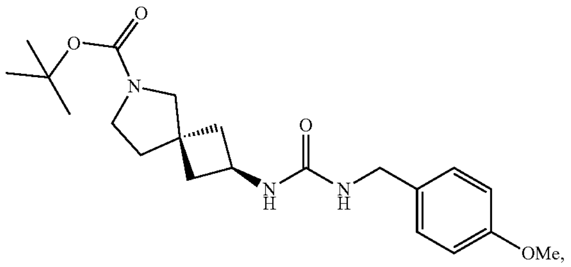 [SMILES: COc1ccc(CNC(=O)N[C@H]2C[C@]3(CCN(C(=O)OC(C)(C)C)C3)C2)cc1] |
| 82 | 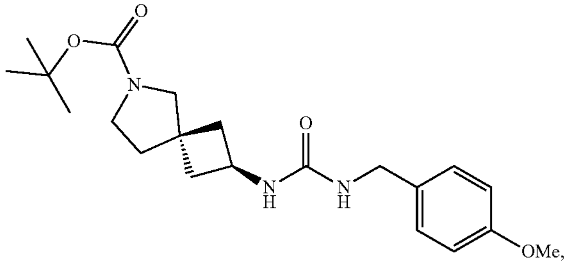 [SMILES: COc1ccc(CNC(=O)N[C@H]2C[C@@]3(CCN(C(=O)OC(C)(C)C)C3)C2)cc1] |
| 83 | 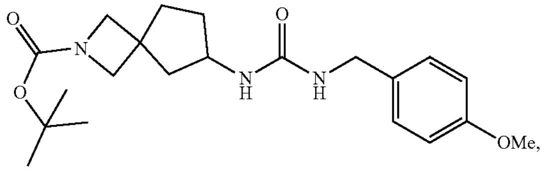 [SMILES: COc1ccc(CNC(=O)NC2CCC3(C2)CN(C(=O)OC(C)(C)C)C3)cc1] |
| 84 | 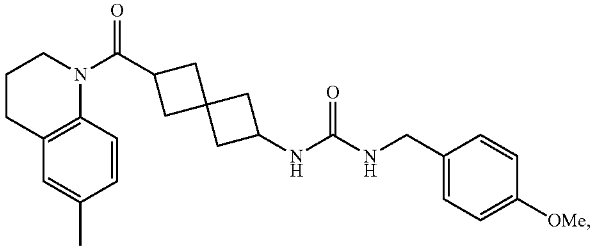 [SMILES: COc1ccc(CNC(=O)NC2CC3(C2)CC(C(=O)N2CCCc4cc(C)ccc42)C3)cc1] |
| 85 | 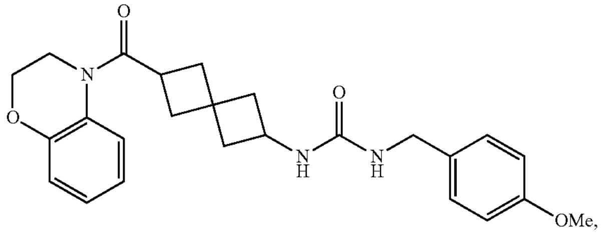 [SMILES: COc1ccc(CNC(=O)NC2CC3(C2)CC(C(=O)N2CCOc4ccccc42)C3)cc1] |
| 86 | 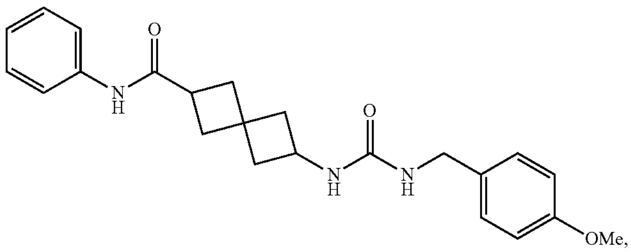 [SMILES: COc1ccc(CNC(=O)NC2CC3(C2)CC(C(=O)Nc2ccccc2)C3)cc1] |

-continued
| Compound No. | Structure |
|---|---|
| 87 | 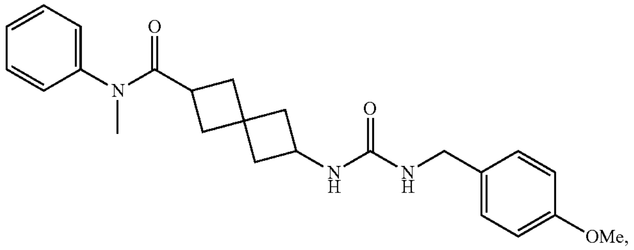 [SMILES: COc1ccc(CNC(=O)NC2CC3(C2)CC(C(=O)N(C)c2ccccc2)C3)cc1] |
| 88 | 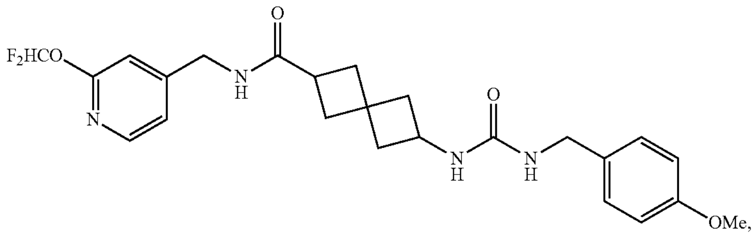 [SMILES: COc1ccc(CNC(=O)NC2CC3(C2)CC(C(=O)NCc2ccnc(OC(F)F)c2)C3)cc1] |
| 89 | 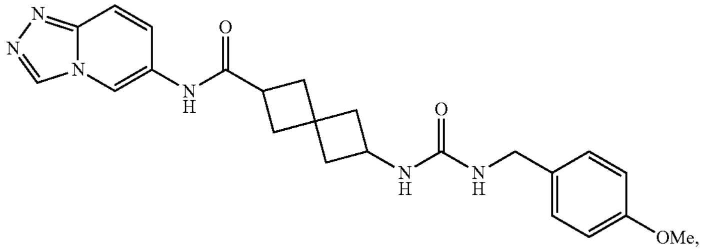 [SMILES: COc1ccc(CNC(=O)NC2CC3(C2)CC(C(=O)Nc2ccc4nncn4c2)C3)cc1] |
| 90 | 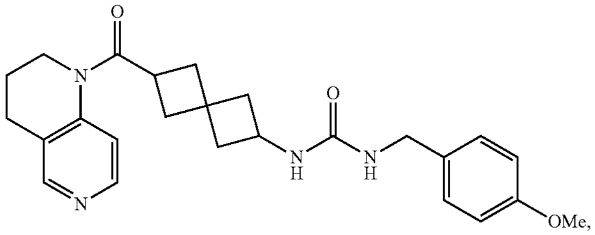 |
| 91 | 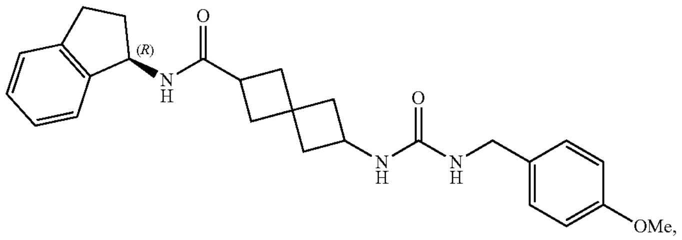 |
| 92 | 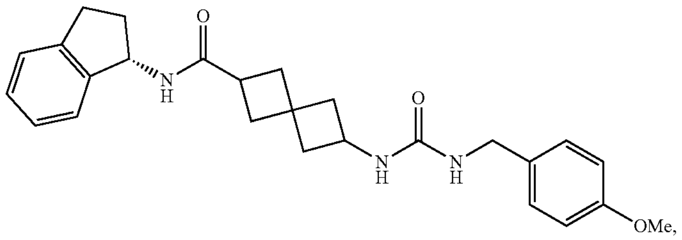 [SMILES: COc1ccc(CNC(=O)NC2CC3(C2)CC(C(=O)N[C@H]2CCc4ccccc42)C3)cc1] |

-continued
| Compound No. | Structure |
| --- | --- |
| 93 | 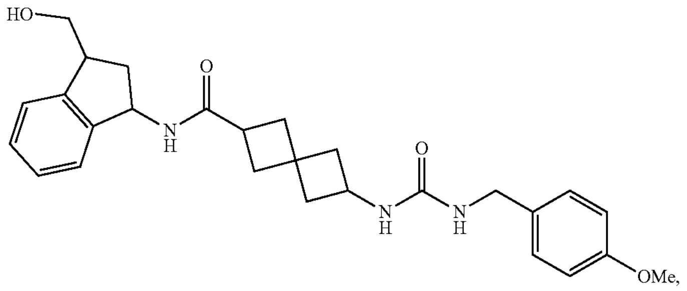 [SMILES: COc1ccc(CNC(=O)NC2CC3(C2)CC(C(=O)NC2CC(CO)c4ccccc42)C3)cc1] |
| 94 | 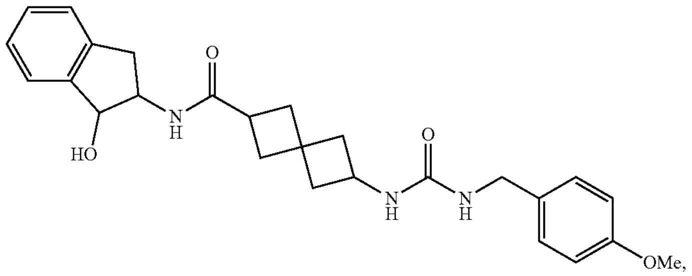 [SMILES: COc1ccc(CNC(=O)NC2CC3(C2)CC(C(=O)NC2Cc4ccccc4C2O)C3)cc1] |
| 95 | 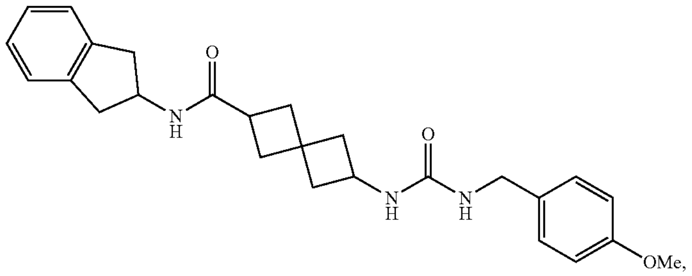 [SMILES: COc1ccc(CNC(=O)NC2CC3(C2)CC(C(=O)NC2Cc4ccccc4C2)C3)cc1] |
| 96 | 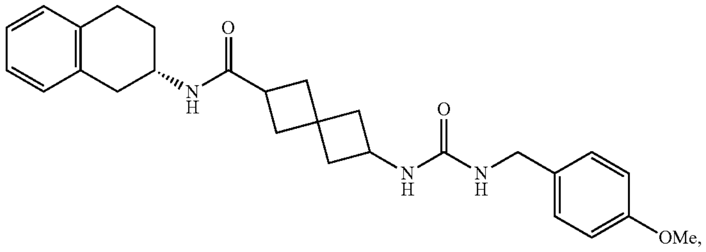 [SMILES: COc1ccc(CNC(=O)NC2CC3(C2)CC(C(=O)N[C@H]2CCc4ccccc4C2)C3)cc1] |
| 97 | 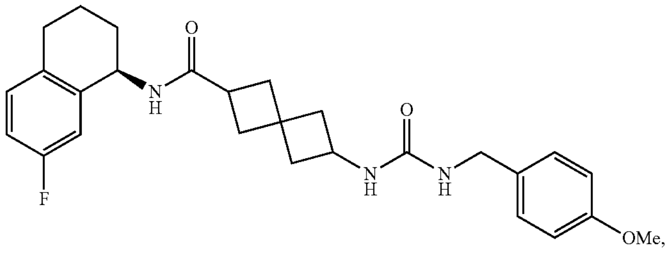 [SMILES: COc1ccc(CNC(=O)NC2CC3(C2)CC(C(=O)N[C@@H]2CCCc4ccc(F)cc42)C3)cc1] |

-continued
| Compound No. | Structure |
|---|---|
| 98 | 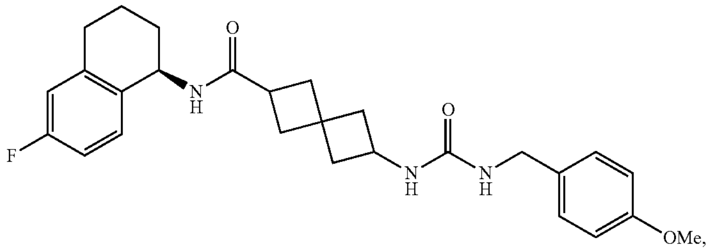 [SMILES: COc1ccc(CNC(=O)NC2CC3(C2)CC(C(=O)N[C@@H]2CCCc4cc(F)ccc42)C3)cc1] |
| 99 | 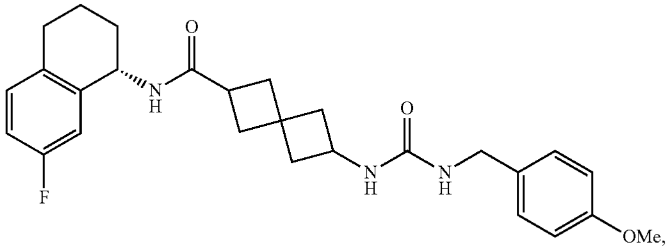 [SMILES: COc1ccc(CNC(=O)NC2CC3(C2)CC(C(=O)N[C@H]2CCCc4ccc(F)cc42)C3)cc1] |
| 100 | 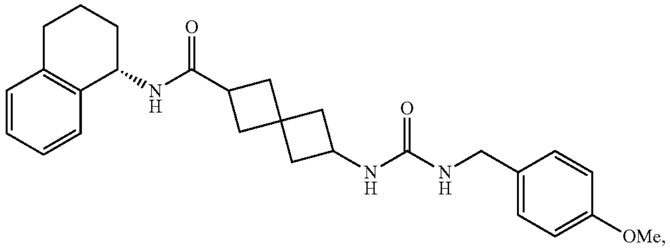 [SMILES: COc1ccc(CNC(=O)NC2CC3(C2)CC(C(=O)N[C@H]2CCCc4ccccc42)C3)cc1] |
| 101 | 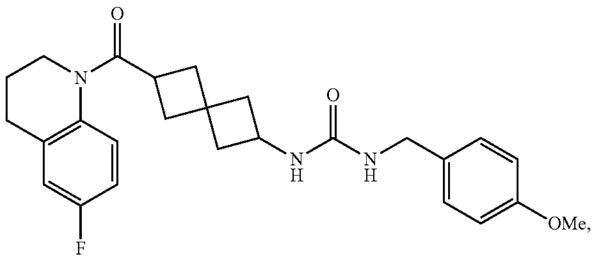 [SMILES: COc1ccc(CNC(=O)NC2CC3(C2)CC(C(=O)N2CCCc4cc(F)ccc42)C3)cc1] |
| 102 | 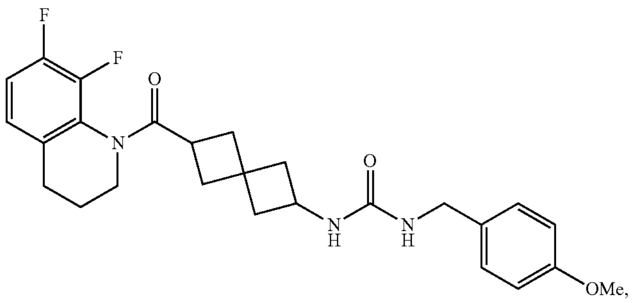 [SMILES: COc1ccc(CNC(=O)NC2CC3(C2)CC(C(=O)N2CCCc4ccc(F)c(F)c42)C3)cc1] |

-continued
| Compound No. | Structure |
|---|---|
| 103 | 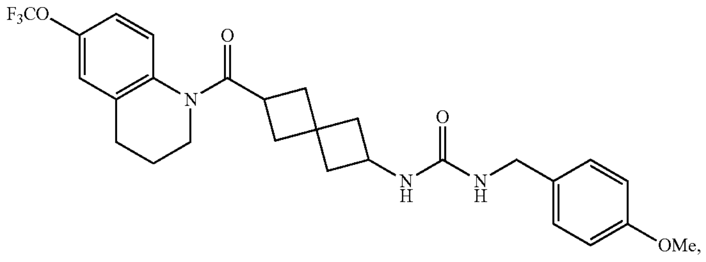 [SMILES: COc1ccc(CNC(=O)NC2CC3(C2)CC(C(=O)N2CCCc4cc(OC(F)(F)F)ccc42)C3)cc1] |
| 104 | 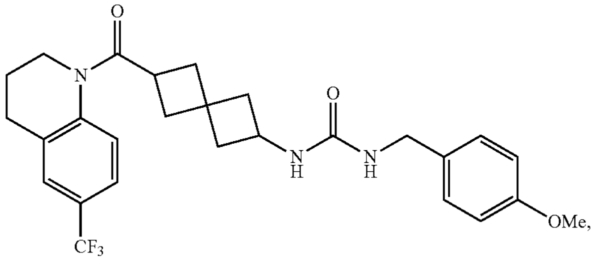 |
| 105 | 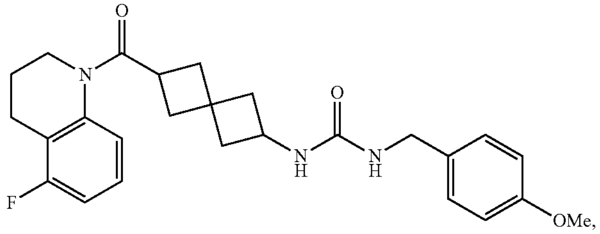 [SMILES: COc1ccc(CNC(=O)NC2CC3(C2)CC(C(=O)N2CCCc4c(F)cccc42)C3)cc1] |
| 106 | 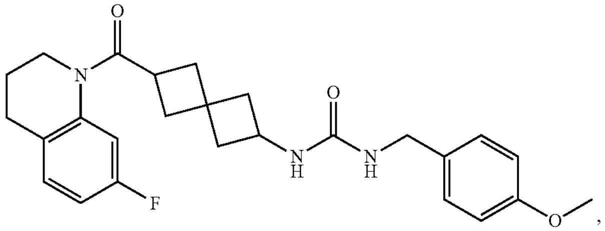 [SMILES: COc1ccc(CNC(=O)NC2CC3(C2)CC(C(=O)N2CCCc4ccc(F)cc42)C3)cc1] |
| 107 | 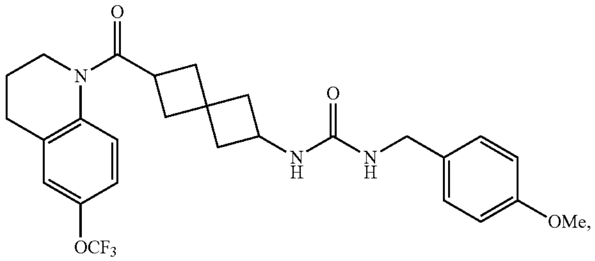 [SMILES: COc1ccc(CNC(=O)NC2CC3(C2)CC(C(=O)N2CCCc4cc(OC(F)(F)F)ccc42)C3)cc1] |
| 108 | 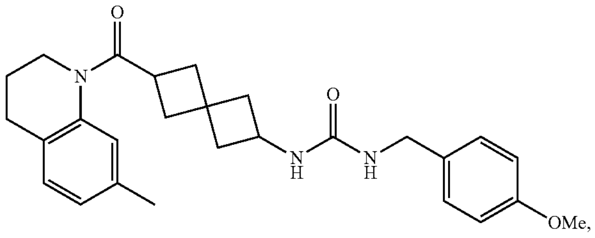 [SMILES: COc1ccc(CNC(=O)NC2CC3(C2)CC(C(=O)N2CCCc4ccc(C)cc42)C3)cc1] |

-continued
| Compound No. | Structure |
|---|---|
| 109 | 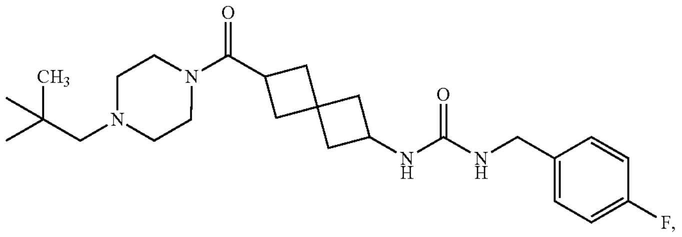 [SMILES: CC(C)(C)CN1CCN(C(=O)C2CC3(CC(NC(=O)NCc4ccc(F)cc4)C3)C2)CC1] |
| 110 | 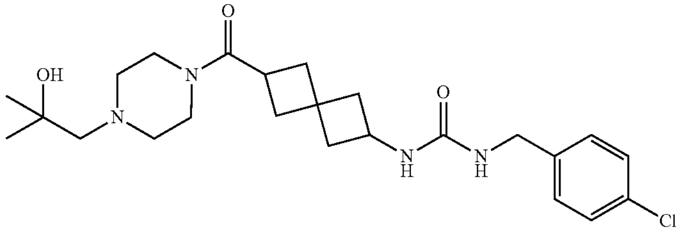 [SMILES: CC(C)(O)CN1CCN(C(=O)C2CC3(CC(NC(=O)NCc4ccc(Cl)cc4)C3)C2)CC1] |
| 111 | 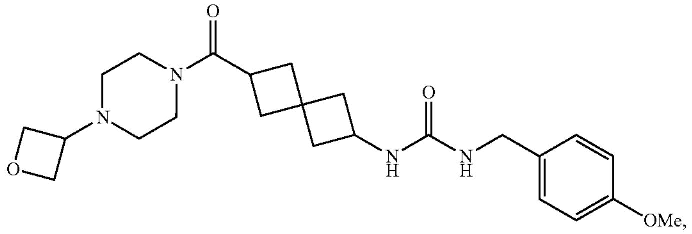 [SMILES: COc1ccc(CNC(=O)NC2CC3(C2)CC(C(=O)N2CCN(C4COC4)CC2)C3)cc1] |
| 112 | 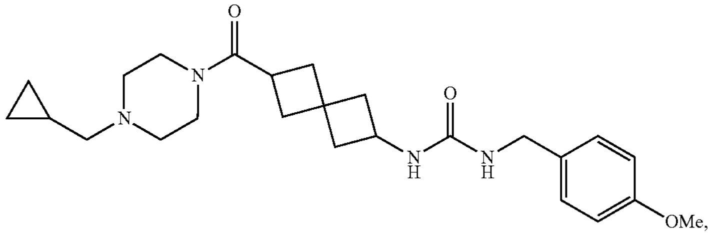 [SMILES: COc1ccc(CNC(=O)NC2CC3(C2)CC(C(=O)N2CCN(CC4CC4)CC2)C3)cc1] |
| 113 | 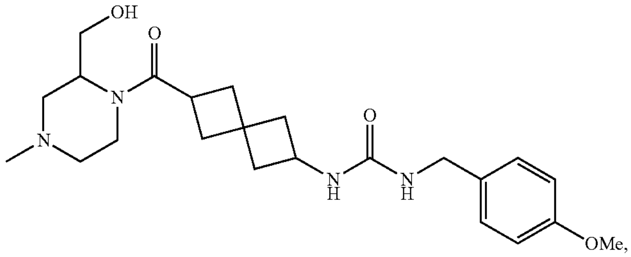 [SMILES: COc1ccc(CNC(=O)NC2CC3(C2)CC(C(=O)N2CCN(C)CC2CO)C3)cc1] |
| 114 | 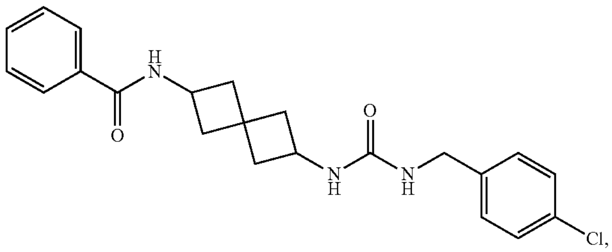 [SMILES: O=C(NCc1ccc(Cl)cc1)NC1CC2(C1)CC(NC(=O)c1ccccc1)C2] |

-continued
| Compound No. | Structure |
|---|---|
| 115 | 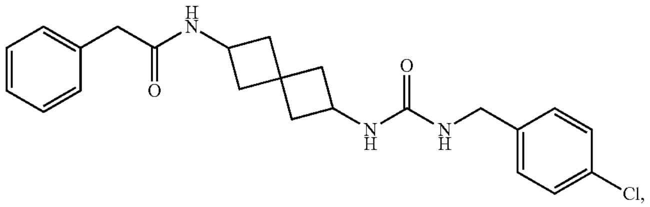 [SMILES: O=C(Cc1ccccc1)NC1CC2(C1)CC(NC(=O)NCc1ccc(Cl)cc1)C2] |
| 116 | 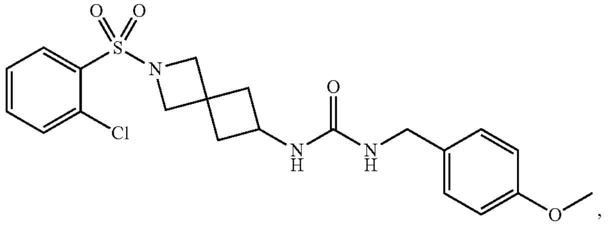 [SMILES: COc1ccc(CNC(=O)NC2CC3(C2)CN(S(=O)(=O)c2ccccc2Cl)C3)cc1] |
| 117 | 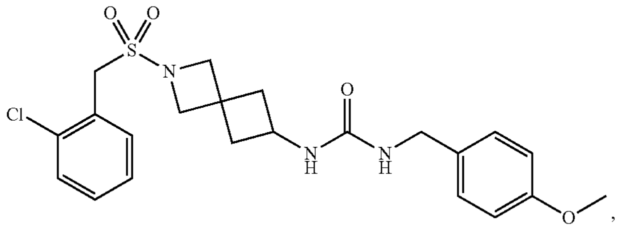 [SMILES: COc1ccc(CNC(=O)NC2CC3(C2)CN(S(=O)(=O)Cc2ccccc2Cl)C3)cc1] |
| 118 | 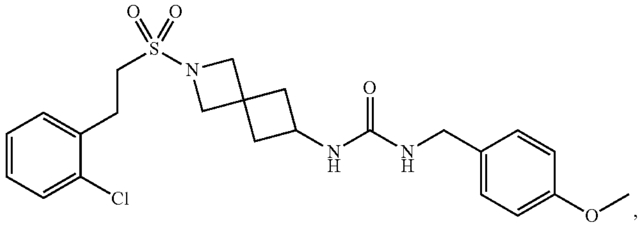 [SMILES: COc1ccc(CNC(=O)NC2CC3(C2)CN(S(=O)(=O)CCc2ccccc2Cl)C3)cc1] |
| 119 | 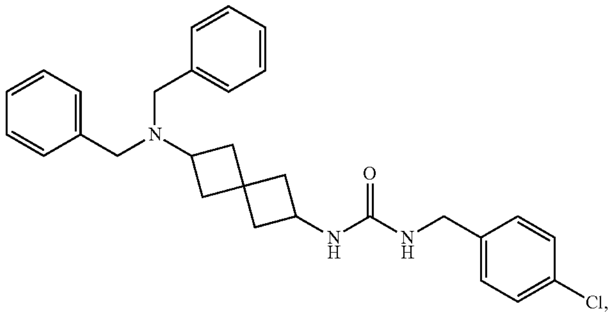 [SMILES: O=C(NCc1ccc(Cl)cc1)NC1CC2(C1)CC(N(Cc1ccccc1)Cc1ccccc1)C2] |
| 120 | 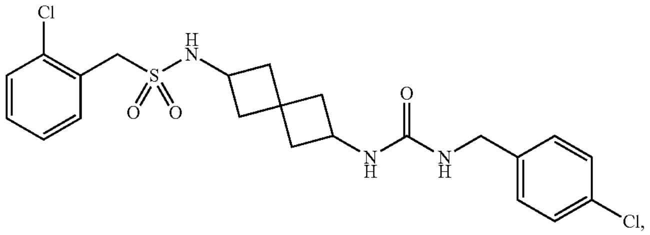 [SMILES: O=C(NCc1ccc(Cl)cc1)NC1CC2(C1)CC(NS(=O)(=O)Cc1ccccc1Cl)C2] |

-continued
| Compound No. | Structure |
|---|---|
| 121 | 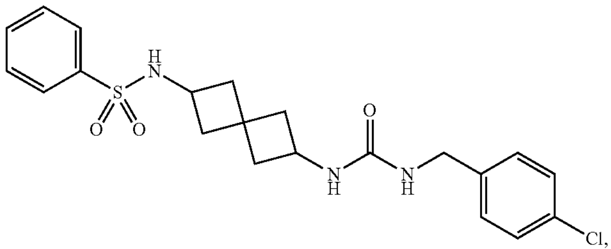 [SMILES: O=C(NCc1ccc(Cl)cc1)NC1CC2(C1)CC(NS(=O)(=O)c1ccccc1)C2] Cl, |
| 122 | 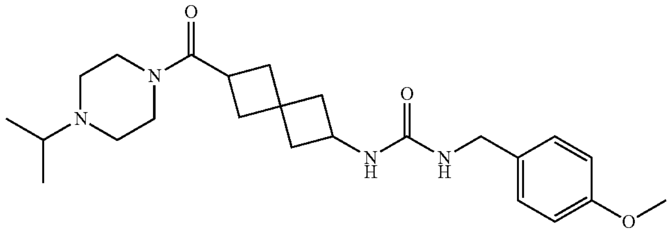 , |
| 123 | 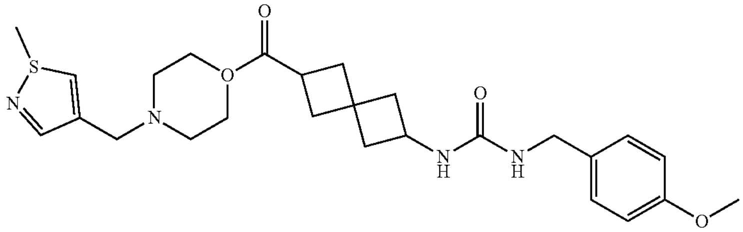 , |
| 124 | 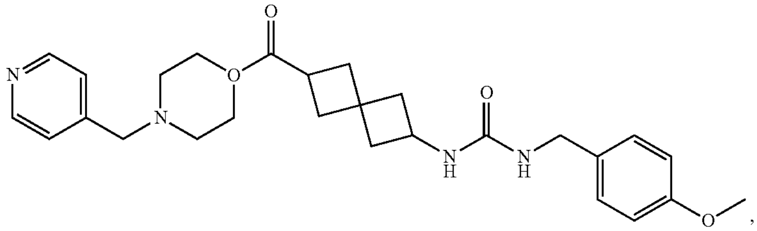 , |
| 125 | 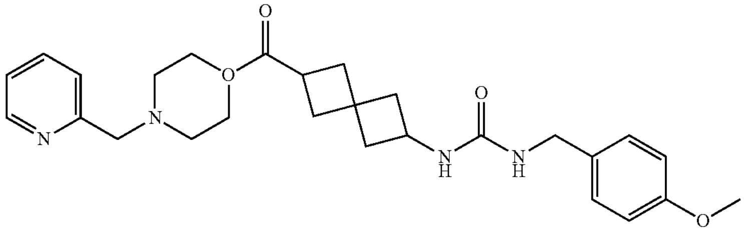 , |
| 126 | 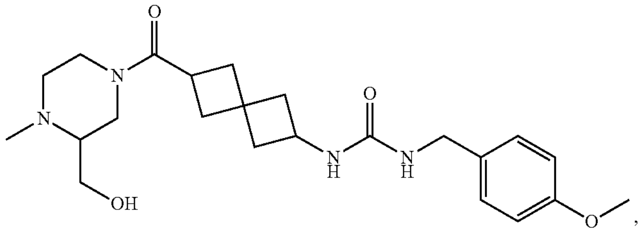 , |

-continued
| Compound No. | Structure |
|---|---|
| 127 | 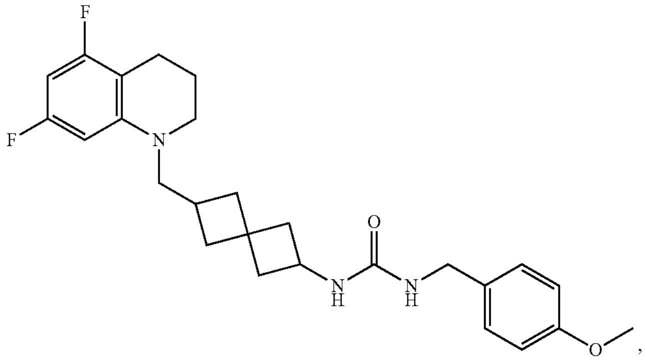 [SMILES: COc1ccc(CNC(=O)NC2CC3(CC(CN4CCCc5c(F)cc(F)cc54)C3)C2)cc1], |
| 128 | 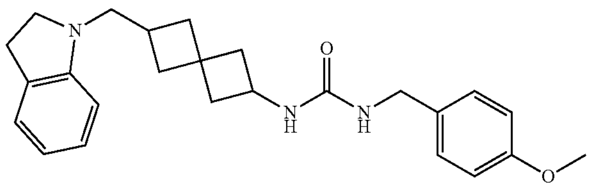, |
| 129 | 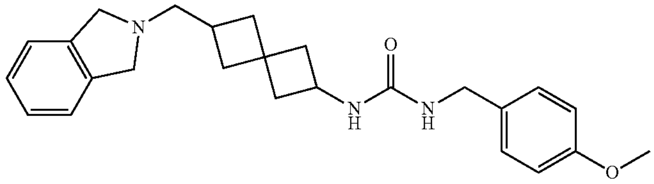, |
| 130 | 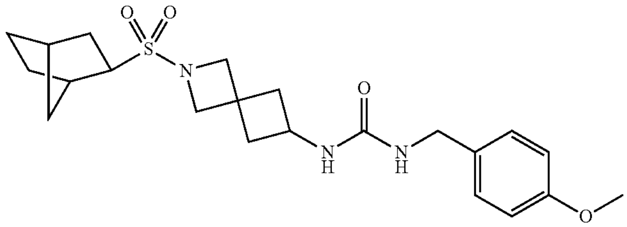, |
| 131 | 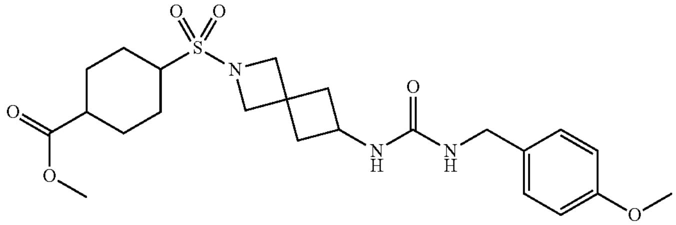, |
| 132 | 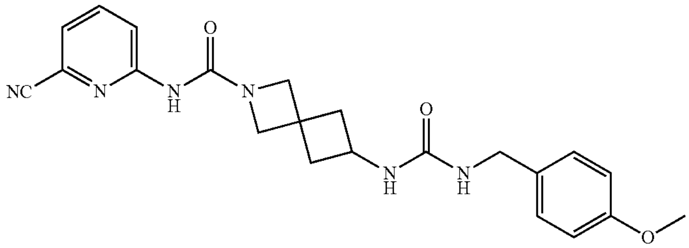 [SMILES: COc1ccc(CNC(=O)NC2CC3(C2)CN(C(=O)Nc2cccc(C#N)n2)C3)cc1], |

-continued
| Compound No. | Structure |
|---|---|
| 133 | 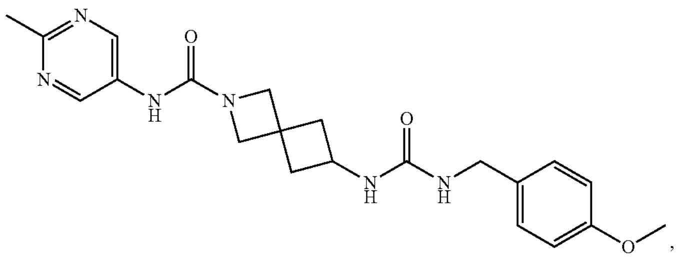, |
| 134 | 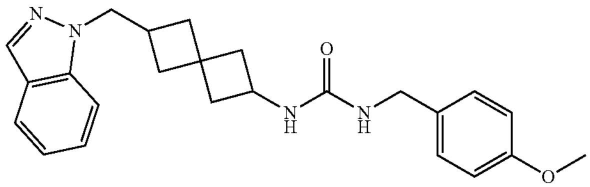, |
| 135 | 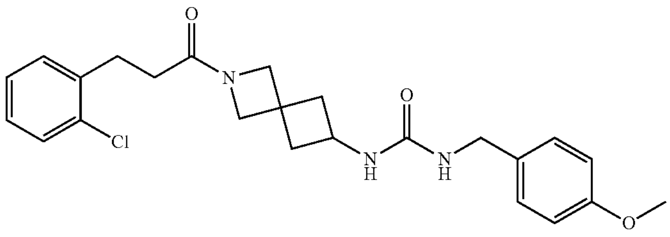, |
| 136 | 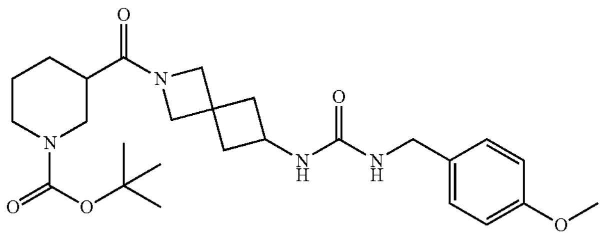, |
| 137 | 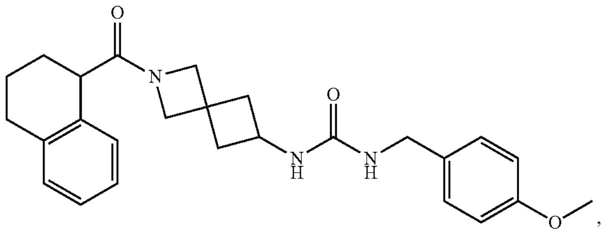 [SMILES: COc1ccc(CNC(=O)NC2CC3(C2)CN(C(=O)C2CCCc4ccccc42)C3)cc1], |
| 138 | 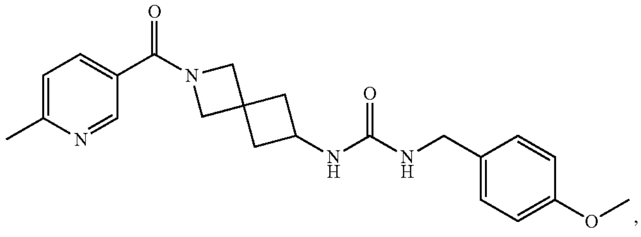, |

-continued
| Compound No. | Structure |
|---|---|
| 139 | 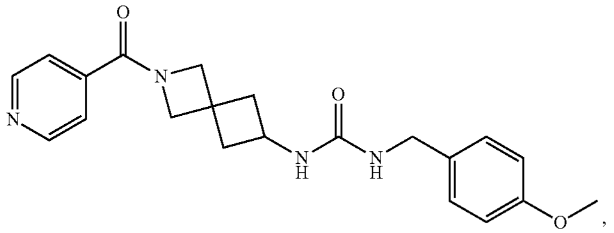 [SMILES: COc1ccc(CNC(=O)NC2CC3(C2)CN(C(=O)c2ccncc2)C3)cc1] |
| 140 | 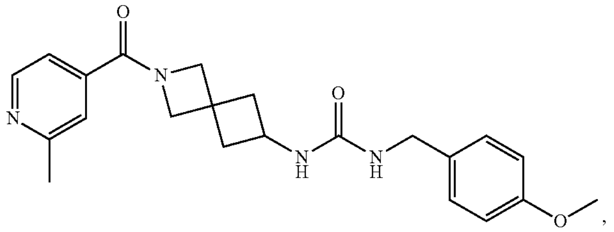 [SMILES: COc1ccc(CNC(=O)NC2CC3(C2)CN(C(=O)c2ccnc(C)c2)C3)cc1] |
| 141 | 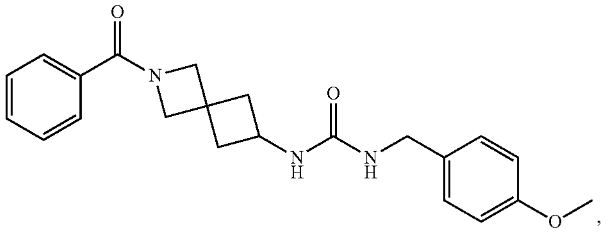 [SMILES: COc1ccc(CNC(=O)NC2CC3(C2)CN(C(=O)c2ccccc2)C3)cc1] |
| 142 | 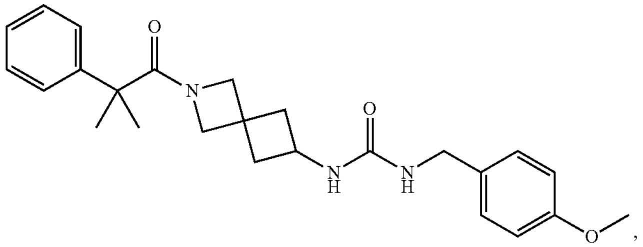 [SMILES: COc1ccc(CNC(=O)NC2CC3(C2)CN(C(=O)C(C)(C)c2ccccc2)C3)cc1] |
| 143 | 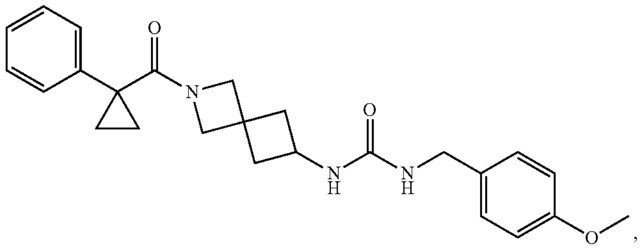 [SMILES: COc1ccc(CNC(=O)NC2CC3(C2)CN(C(=O)C2(c4ccccc4)CC2)C3)cc1] |
| 144 | 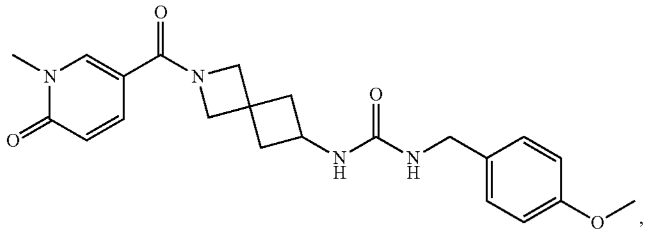 [SMILES: COc1ccc(CNC(=O)NC2CC3(C2)CN(C(=O)c2ccc(=O)n(C)c2)C3)cc1] |

-continued
| Compound No. | Structure |
| --- | --- |
| 145 | 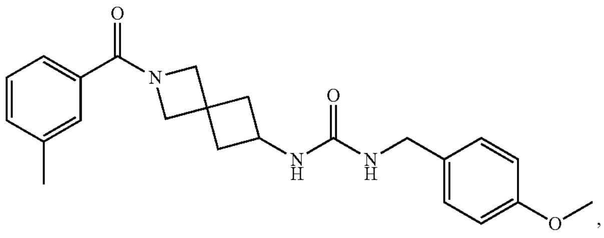 [SMILES: COc1ccc(CNC(=O)NC2CC3(C2)CN(C(=O)c2cccc(C)c2)C3)cc1], |
| 146 | 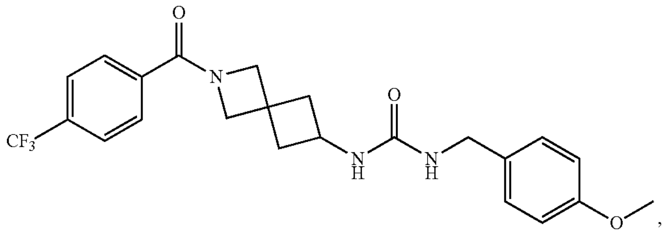 [SMILES: COc1ccc(CNC(=O)NC2CC3(C2)CN(C(=O)c2ccc(C(F)(F)F)cc2)C3)cc1], |
| 147 | 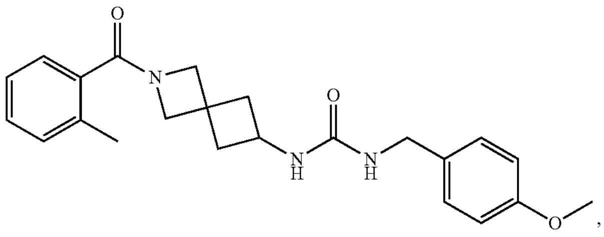 [SMILES: COc1ccc(CNC(=O)NC2CC3(C2)CN(C(=O)c2ccccc2C)C3)cc1], |
| 148 | 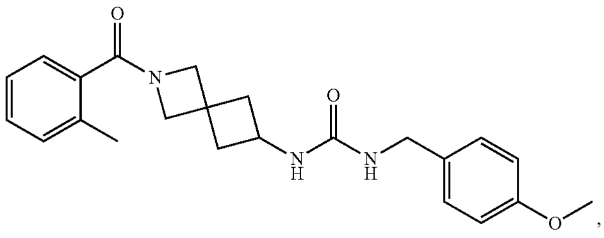 [SMILES: COc1ccc(CNC(=O)NC2CC3(C2)CN(C(=O)c2ccccc2C)C3)cc1], |
| 151 | 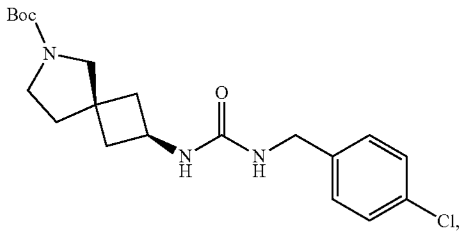 [SMILES: CC(C)(C)OC(=O)N1CC[C@]2(C1)C[C@@H](NC(=O)NCc1ccc(Cl)cc1)C2] |
| 152 | 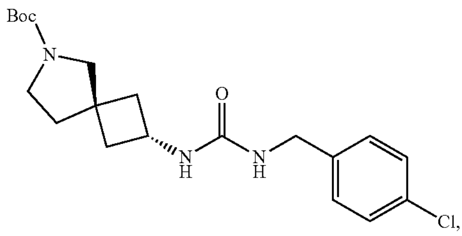 [SMILES: CC(C)(C)OC(=O)N1CC[C@]2(C1)C[C@H](NC(=O)NCc1ccc(Cl)cc1)C2] |

-continued
| Compound No. | Structure |
|---|---|
| 153 | 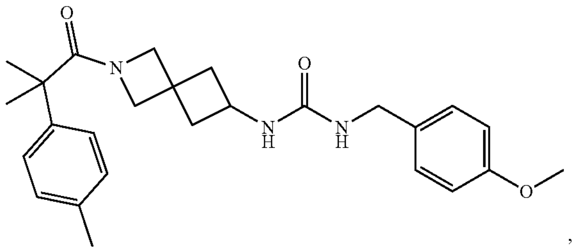 [SMILES: COc1ccc(CNC(=O)NC2CC3(C2)CN(C(=O)C(C)(C)c2ccc(C)cc2)C3)cc1], |
| 154 | 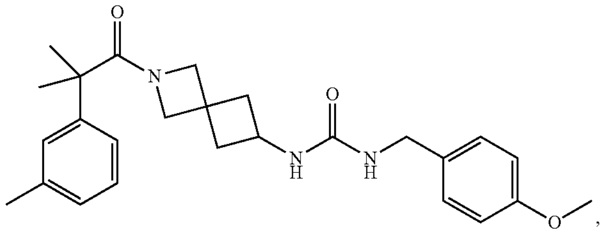, |
| 155 | 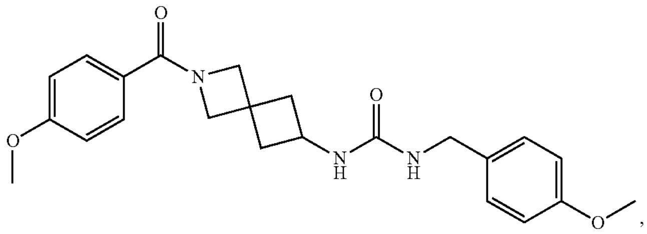 [SMILES: COc1ccc(CNC(=O)NC2CC3(C2)CN(C(=O)c2ccc(OC)cc2)C3)cc1], |
| 156 | 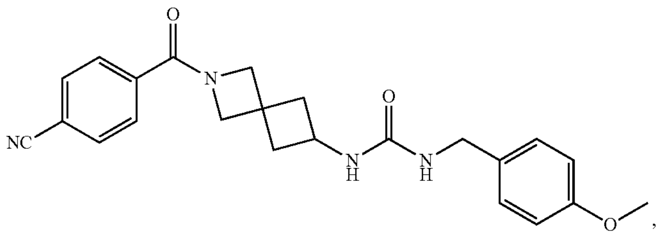 [SMILES: COc1ccc(CNC(=O)NC2CC3(C2)CN(C(=O)c2ccc(C#N)cc2)C3)cc1], |
| 157 | 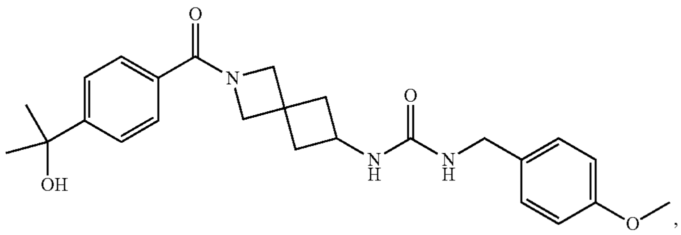 [SMILES: COc1ccc(CNC(=O)NC2CC3(C2)CN(C(=O)c2ccc(C(C)(C)O)cc2)C3)cc1], |
| 158 | 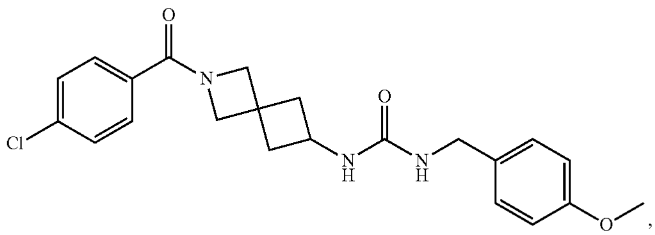 [SMILES: COc1ccc(CNC(=O)NC2CC3(C2)CN(C(=O)c2ccc(Cl)cc2)C3)cc1], |

-continued
| Compound No. | Structure |
|---|---|
| 159 | 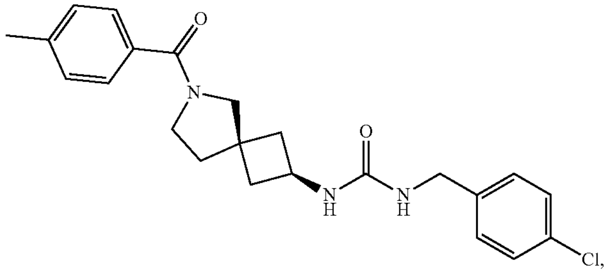 [SMILES: Cc1ccc(C(=O)N2CC[C@]3(C2)C[C@@H](NC(=O)NCc2ccc(Cl)cc2)C3)cc1] |
| 160 | 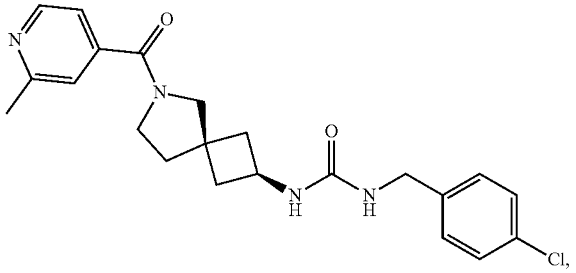 [SMILES: Cc1cc(C(=O)N2CC[C@]3(C2)C[C@@H](NC(=O)NCc2ccc(Cl)cc2)C3)ccn1] |
| 161 | 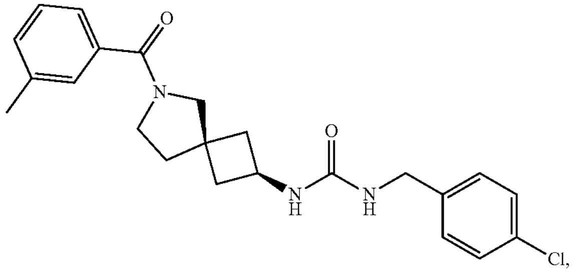 [SMILES: Cc1cccc(C(=O)N2CC[C@]3(C2)C[C@@H](NC(=O)NCc2ccc(Cl)cc2)C3)c1] |
| 162 | 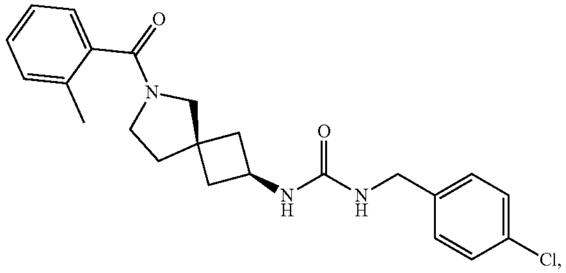 [SMILES: Cc1ccccc1C(=O)N1CC[C@]2(C1)C[C@@H](NC(=O)NCc1ccc(Cl)cc1)C2] |
| 163 | 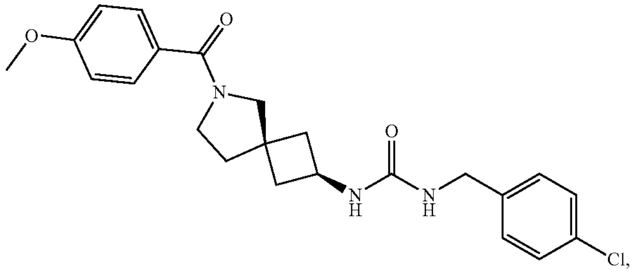 [SMILES: COc1ccc(C(=O)N2CC[C@]3(C2)C[C@@H](NC(=O)NCc2ccc(Cl)cc2)C3)cc1] |

-continued
| Compound No. | Structure |
|---|---|
| 164 | 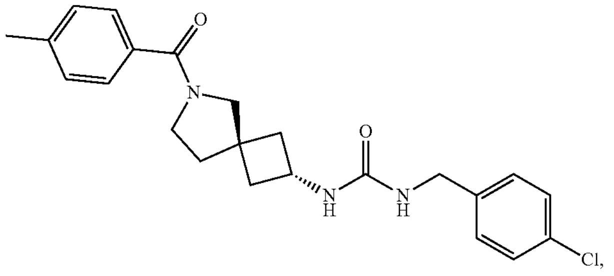 [SMILES: Cc1ccc(C(=O)N2CC[C@]3(C2)C[C@H](NC(=O)NCc2ccc(Cl)cc2)C3)cc1] |
| 165 | 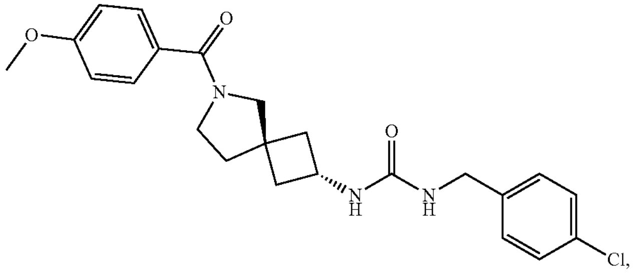 [SMILES: COc1ccc(C(=O)N2CC[C@]3(C2)C[C@H](NC(=O)NCc2ccc(Cl)cc2)C3)cc1] |
| 166 | 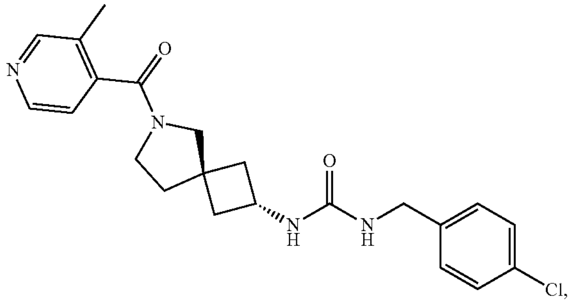 [SMILES: Cc1cnccc1C(=O)N1CC[C@]2(C1)C[C@H](NC(=O)NCc1ccc(Cl)cc1)C2] |
| 167 | 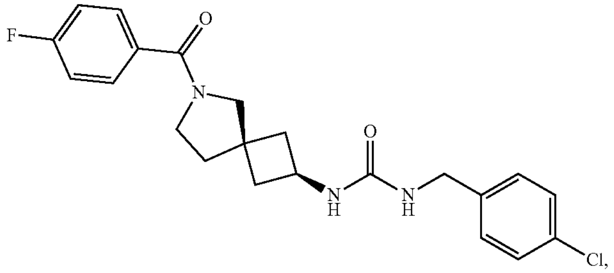 [SMILES: O=C(NCc1ccc(Cl)cc1)N[C@H]1C[C@]2(CCN(C(=O)c3ccc(F)cc3)C2)C1] |
| 168 | 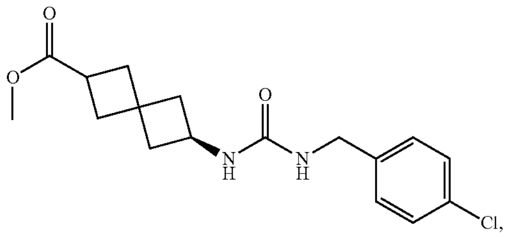 |

-continued
| Compound No. | Structure |
|---|---|
| 169 | 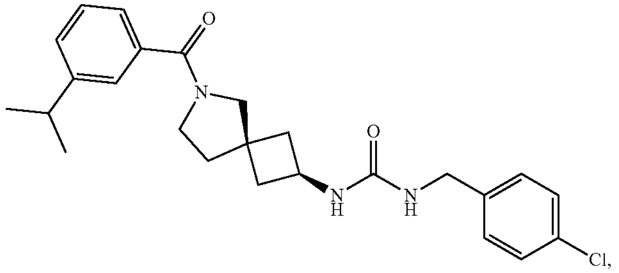 [SMILES: CC(C)c1cccc(C(=O)N2CC[C@]3(C2)C[C@@H](NC(=O)NCc2ccc(Cl)cc2)C3)c1] |
| 170 | 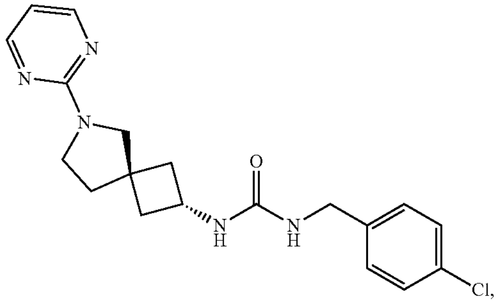 [SMILES: O=C(NCc1ccc(Cl)cc1)N[C@H]1C[C@@]2(CCN(c3ncccn3)C2)C1] |
| 171 | 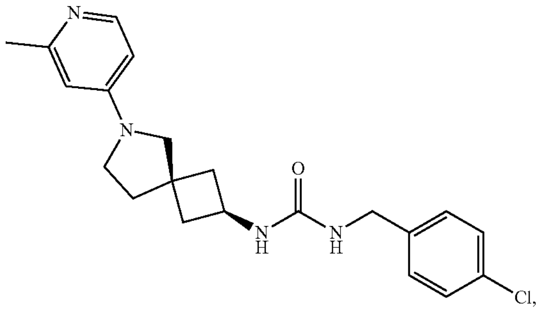 [SMILES: Cc1cc(N2CC[C@]3(C2)C[C@@H](NC(=O)NCc2ccc(Cl)cc2)C3)ccn1] |
| 172 | 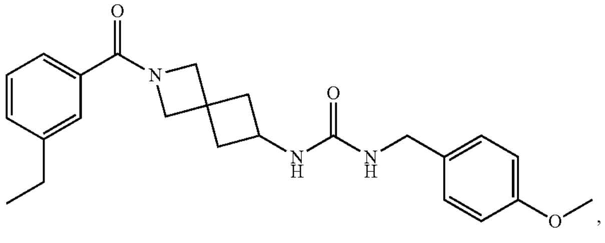 [SMILES: CCc1cccc(C(=O)N2CC3(CC(NC(=O)NCc4ccc(OC)cc4)C3)C2)c1] |
| 173 | 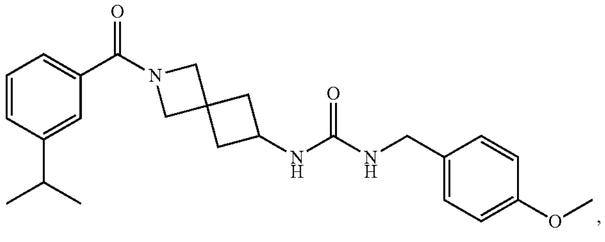 [SMILES: COc1ccc(CNC(=O)NC2CC3(C2)CN(C(=O)c2cccc(C(C)C)c2)C3)cc1] |

-continued
| Compound No. | Structure |
|---|---|
| 174 | 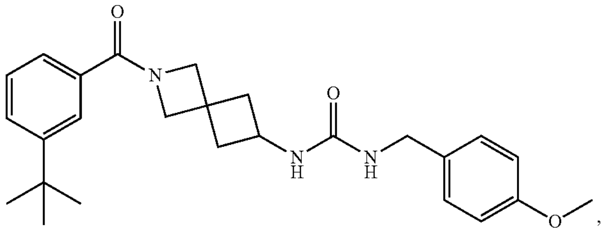 [SMILES: COc1ccc(CNC(=O)NC2CC3(C2)CN(C(=O)c2cccc(C(C)(C)C)c2)C3)cc1] , |
| 175 | 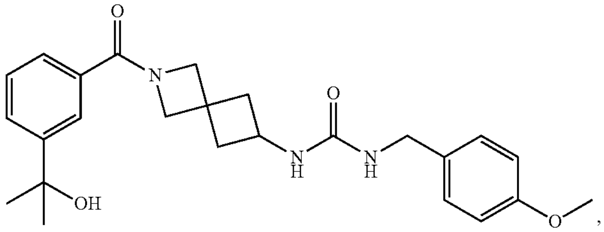 [SMILES: COc1ccc(CNC(=O)NC2CC3(C2)CN(C(=O)c2cccc(C(C)(C)O)c2)C3)cc1] , |
| 176 | 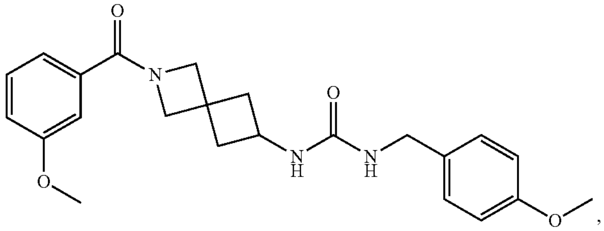 [SMILES: COc1ccc(CNC(=O)NC2CC3(C2)CN(C(=O)c2cccc(OC)c2)C3)cc1] , |
| 177 | 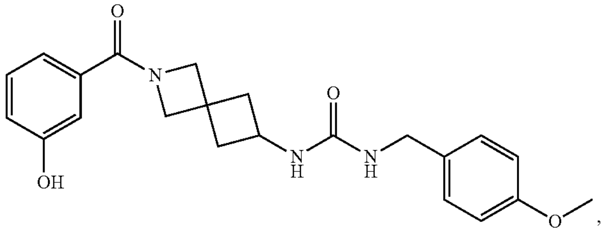 [SMILES: COc1ccc(CNC(=O)NC2CC3(C2)CN(C(=O)c2cccc(O)c2)C3)cc1] , |
| 178 | 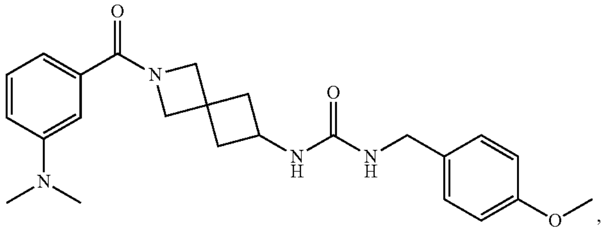 [SMILES: COc1ccc(CNC(=O)NC2CC3(C2)CN(C(=O)c2cccc(N(C)C)c2)C3)cc1] , |
| 179 | 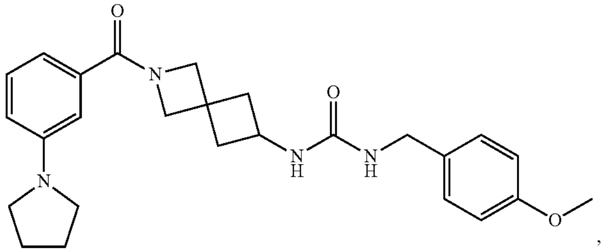 [SMILES: COc1ccc(CNC(=O)NC2CC3(C2)CN(C(=O)c2cccc(N4CCCC4)c2)C3)cc1] , |

-continued
| Compound No. | Structure |
|---|---|
| 180 | 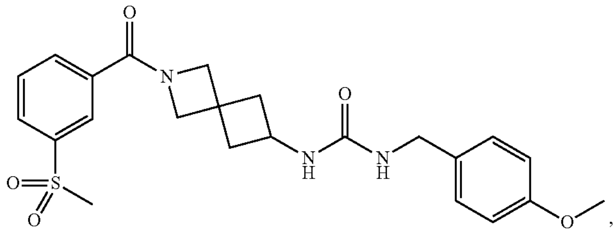 [SMILES: COc1ccc(CNC(=O)NC2CC3(C2)CN(C(=O)c2cccc(S(C)(=O)=O)c2)C3)cc1] , |
| 181 | 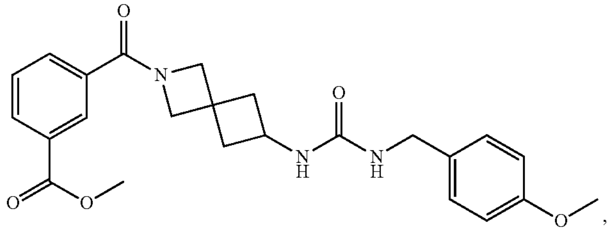 [SMILES: COC(=O)c1cccc(C(=O)N2CC3(CC(NC(=O)NCc4ccc(OC)cc4)C3)C2)c1] , |
| 182 | 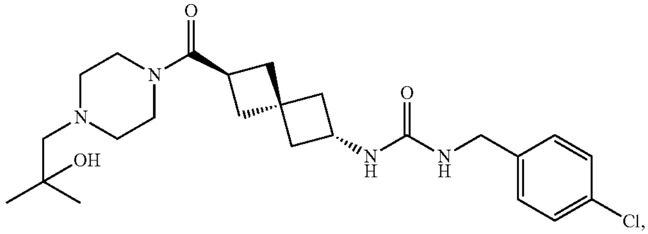 , |
| 183 | 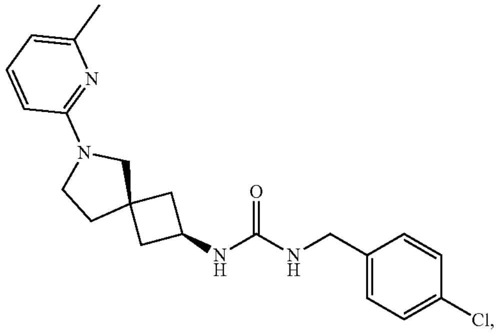 [SMILES: Cc1cccc(N2CC[C@]3(C2)C[C@@H](NC(=O)NCc2ccc(Cl)cc2)C3)n1] , |
| 184 | 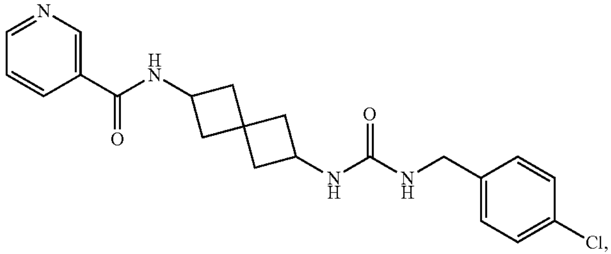 [SMILES: O=C(NCc1ccc(Cl)cc1)NC1CC2(C1)CC(NC(=O)c1cccnc1)C2] , |
| 185 | 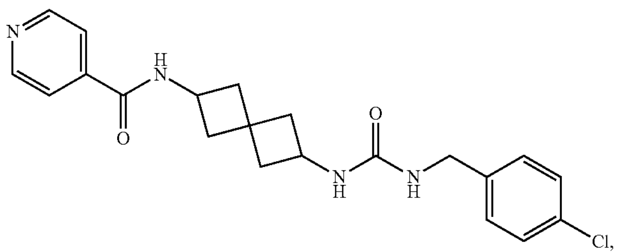 [SMILES: O=C(NCc1ccc(Cl)cc1)NC1CC2(C1)CC(NC(=O)c1ccncc1)C2] , |

-continued
| Compound No. | Structure |
|---|---|
| 186 | 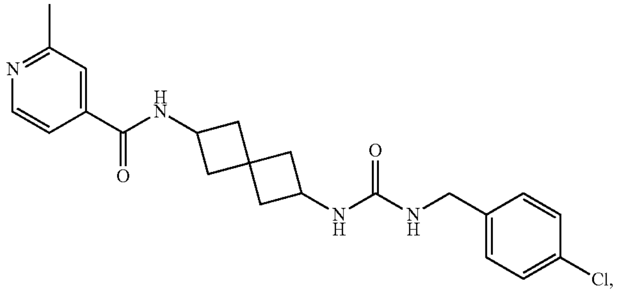 [SMILES: Cc1cc(C(=O)NC2CC3(CC(NC(=O)NCc4ccc(Cl)cc4)C3)C2)ccn1] , |
| 187 | 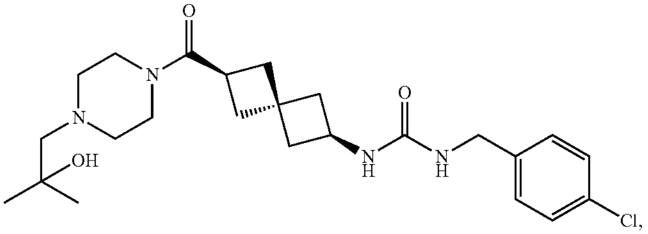 , |
| 188 | 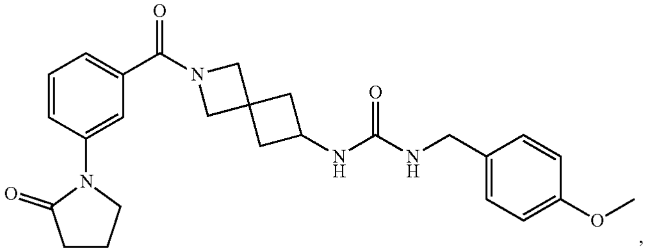 [SMILES: COc1ccc(CNC(=O)NC2CC3(C2)CN(C(=O)c2cccc(N4CCCC4=O)c2)C3)cc1] , |
| 189 | 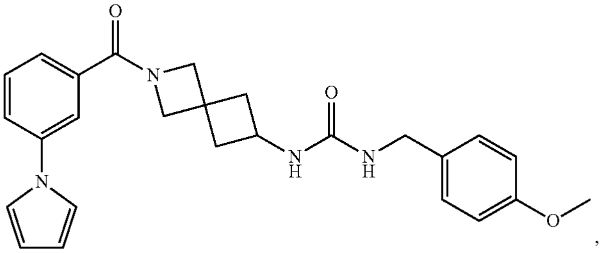 [SMILES: COc1ccc(CNC(=O)NC2CC3(C2)CN(C(=O)c2cccc(-n4cccc4)c2)C3)cc1] , |
| 190 | 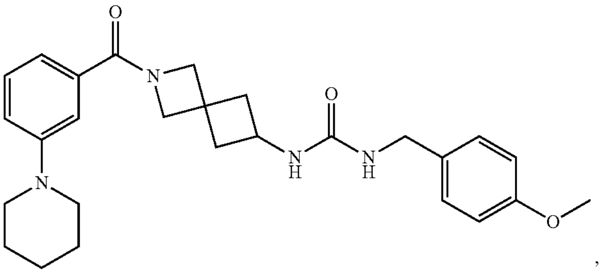 [SMILES: COc1ccc(CNC(=O)NC2CC3(C2)CN(C(=O)c2cccc(N4CCCCC4)c2)C3)cc1] , |

-continued
| Compound No. | Structure |
|---|---|
| 191 | 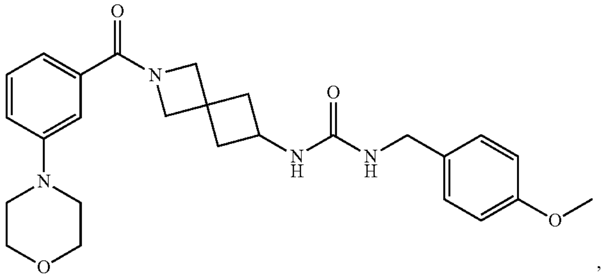 [SMILES: COc1ccc(CNC(=O)NC2CC3(C2)CN(C(=O)c2cccc(N4CCOCC4)c2)C3)cc1] , |
| 192 | 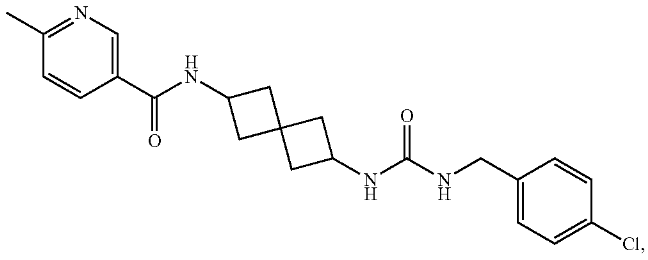 [SMILES: Cc1ccc(C(=O)NC2CC3(CC(NC(=O)NCc4ccc(Cl)cc4)C3)C2)cn1] Cl, |
| 193 | 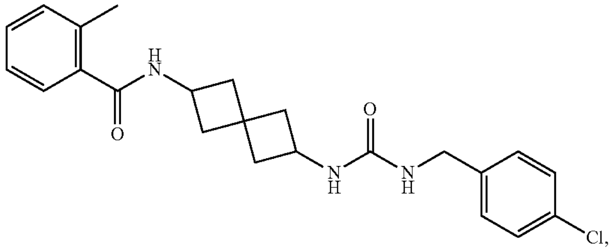 [SMILES: Cc1ccccc1C(=O)NC1CC2(CC(NC(=O)NCc3ccc(Cl)cc3)C2)C1] Cl, |
| 194 | 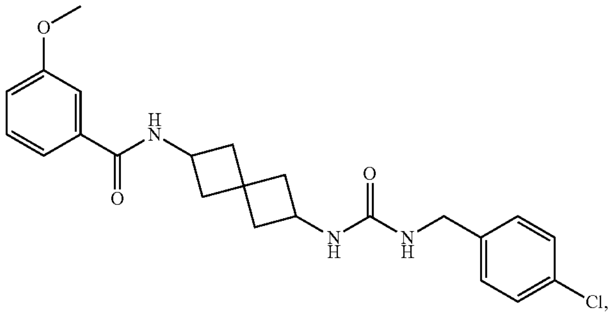 [SMILES: COc1cccc(C(=O)NC2CC3(CC(NC(=O)NCc4ccc(Cl)cc4)C3)C2)c1] Cl, |
| 195 | 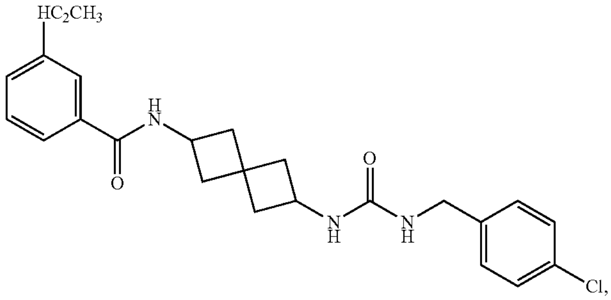 Cl, |

-continued
| Compound No. | Structure |
|---|---|
| 197 | 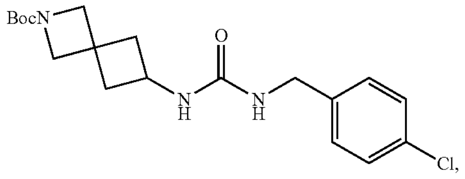 [SMILES: CC(C)(C)OC(=O)N1CC2(CC(NC(=O)NCc3ccc(Cl)cc3)C2)C1] |
| 198 | 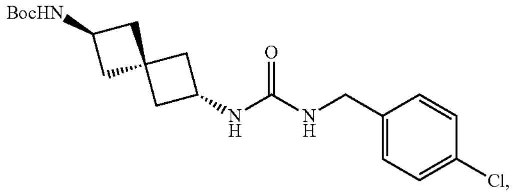 |
| 199 | 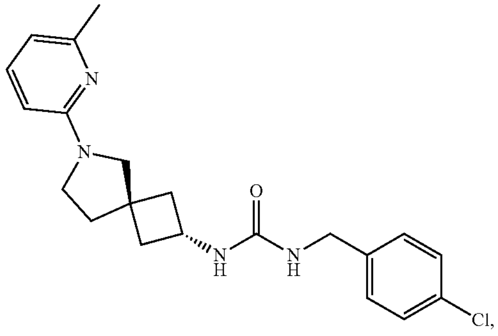 [SMILES: Cc1cccc(N2CC[C@]3(C2)C[C@H](NC(=O)NCc2ccc(Cl)cc2)C3)n1] |
| 200 | 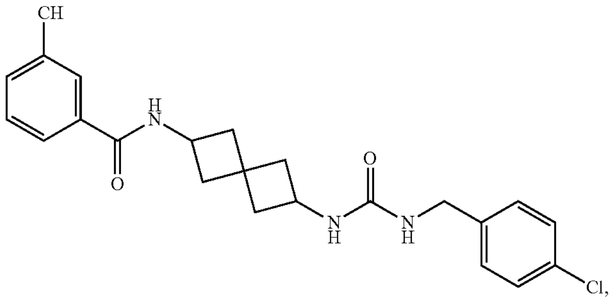 [SMILES: Cc1cccc(C(=O)NC2CC3(CC(NC(=O)NCc4ccc(Cl)cc4)C3)C2)c1] |
| 201 | 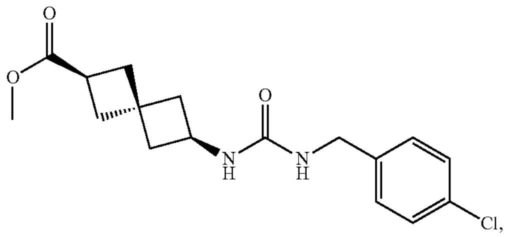 |
| 202 | 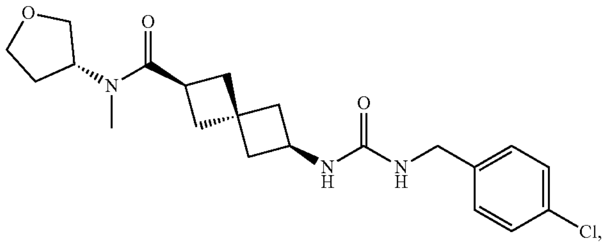 |

-continued
| Compound No. | Structure |
|---|---|
| 203 | 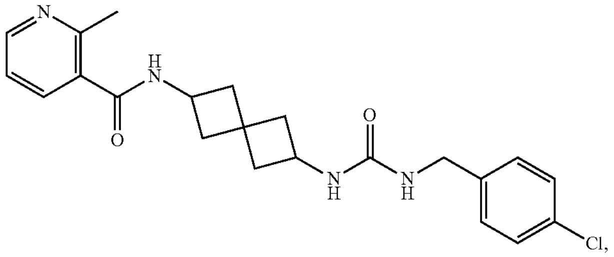 [SMILES: Cc1ncccc1C(=O)NC1CC2(CC(NC(=O)NCc3ccc(Cl)cc3)C2)C1] |
| 204 | 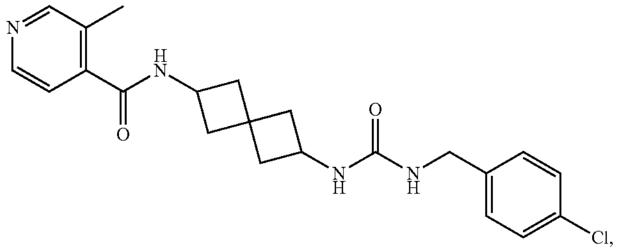 [SMILES: Cc1cnccc1C(=O)NC1CC2(CC(NC(=O)NCc3ccc(Cl)cc3)C2)C1] |
| 205 | 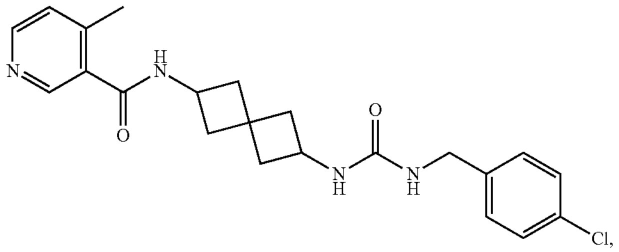 [SMILES: Cc1ccncc1C(=O)NC1CC2(CC(NC(=O)NCc3ccc(Cl)cc3)C2)C1] |
| 206 | 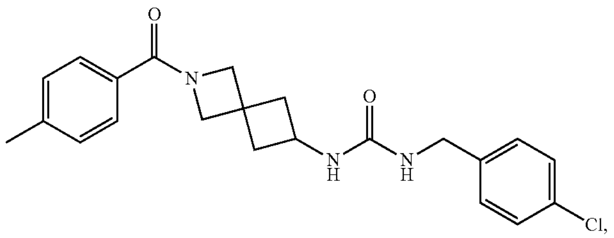 [SMILES: Cc1ccc(C(=O)N2CC3(CC(NC(=O)NCc4ccc(Cl)cc4)C3)C2)cc1] |
| 207 | 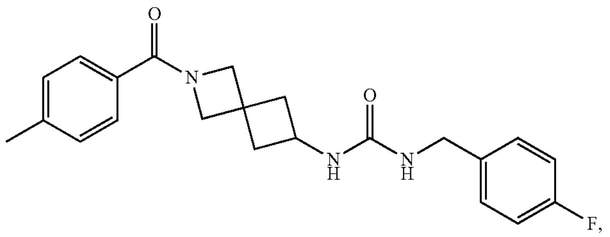 [SMILES: Cc1ccc(C(=O)N2CC3(CC(NC(=O)NCc4ccc(F)cc4)C3)C2)cc1] |
| 208 | 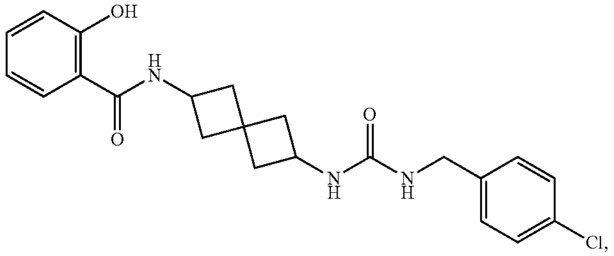 [SMILES: O=C(NCc1ccc(Cl)cc1)NC1CC2(C1)CC(NC(=O)c1ccccc1O)C2] |

-continued
| Compound No. | Structure |
|---|---|
| 209 | 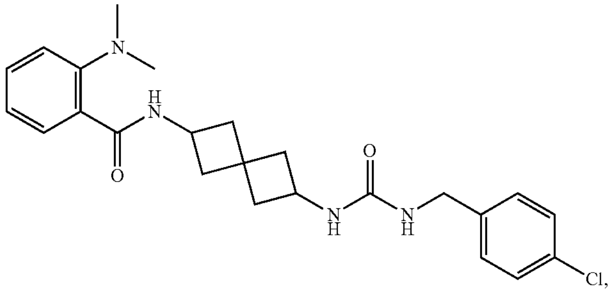 [SMILES: CN(C)c1ccccc1C(=O)NC1CC2(CC(NC(=O)NCc3ccc(Cl)cc3)C2)C1] |
| 210 | 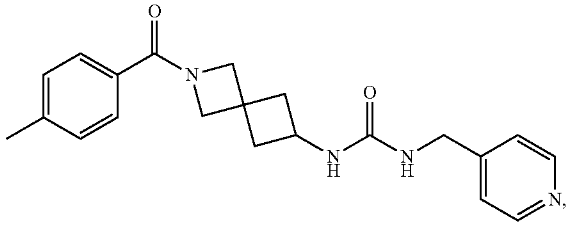 [SMILES: Cc1ccc(C(=O)N2CC3(CC(NC(=O)NCc4ccncc4)C3)C2)cc1] |
| 211 | 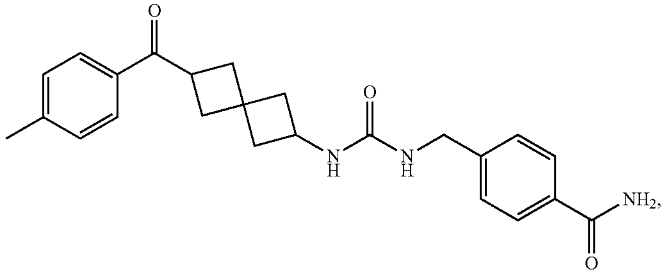 [SMILES: Cc1ccc(C(=O)C2CC3(CC(NC(=O)NCc4ccc(C(N)=O)cc4)C3)C2)cc1] |
| 212 | 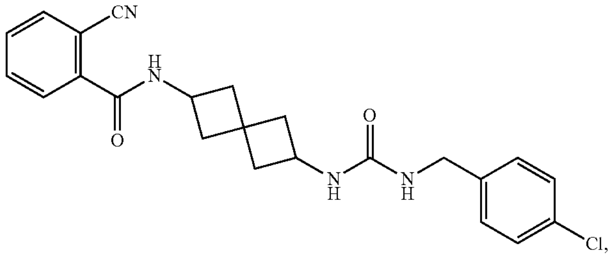 [SMILES: N#Cc1ccccc1C(=O)NC1CC2(CC(NC(=O)NCc3ccc(Cl)cc3)C2)C1] |
| 213 | 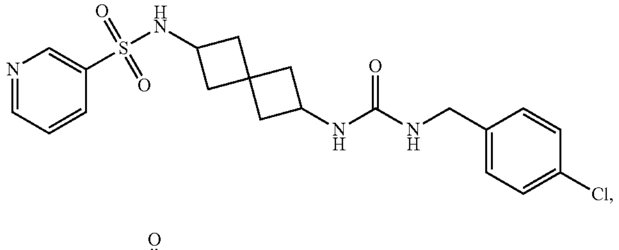 |
| 214 | 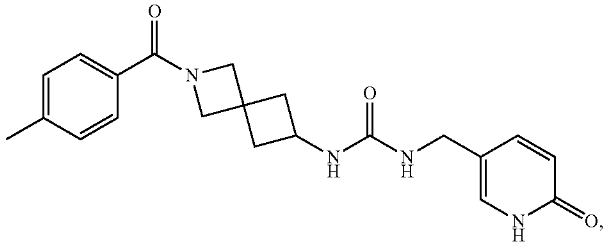 [SMILES: Cc1ccc(C(=O)N2CC3(CC(NC(=O)NCc4ccc(=O)[nH]c4)C3)C2)cc1] |

-continued
| Compound No. | Structure |
|---|---|
| 215 | 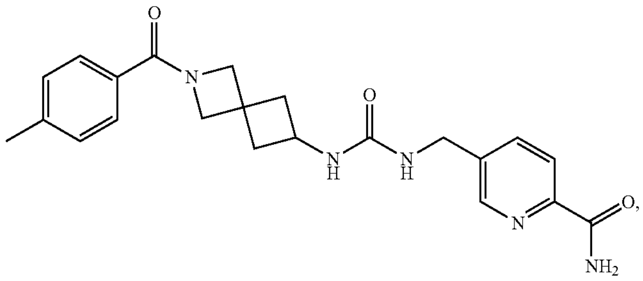 [SMILES: Cc1ccc(C(=O)N2CC3(CC(NC(=O)NCc4ccc(C(N)=O)nc4)C3)C2)cc1] |
| 216 | 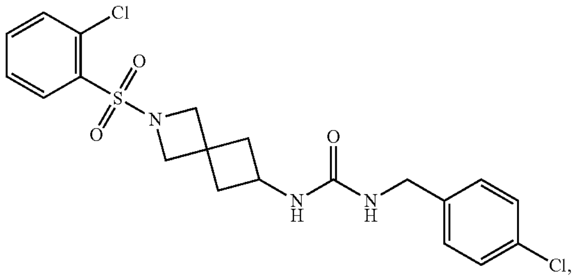 [SMILES: O=C(NCc1ccc(Cl)cc1)NC1CC2(C1)CN(S(=O)(=O)c1ccccc1Cl)C2] |
| 217 | 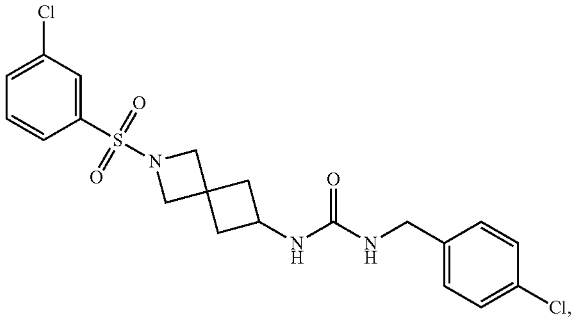 [SMILES: O=C(NCc1ccc(Cl)cc1)NC1CC2(C1)CN(S(=O)(=O)c1cccc(Cl)c1)C2] |
| 218 | 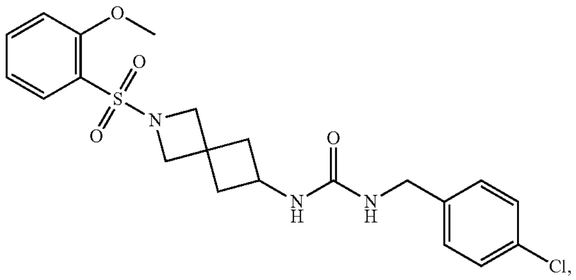 [SMILES: COc1ccccc1S(=O)(=O)N1CC2(CC(NC(=O)NCc3ccc(Cl)cc3)C2)C1] |
| 219 | 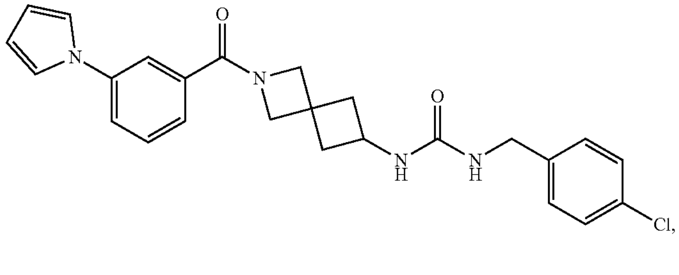 [SMILES: O=C(NCc1ccc(Cl)cc1)NC1CC2(C1)CN(C(=O)c1cccc(-n3cccc3)c1)C2] |

-continued
| Compound No. | Structure |
|---|---|
| 220 | 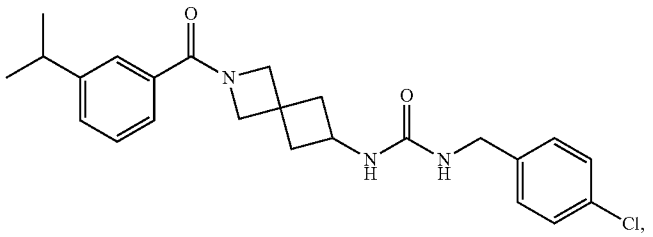 [SMILES: CC(C)c1cccc(C(=O)N2CC3(CC(NC(=O)NCc4ccc(Cl)cc4)C3)C2)c1] |
| 221 | 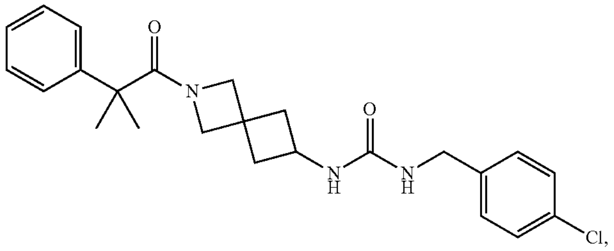 [SMILES: CC(C)(C(=O)N1CC2(CC(NC(=O)NCc3ccc(Cl)cc3)C2)C1)c1ccccc1] |
| 222 | 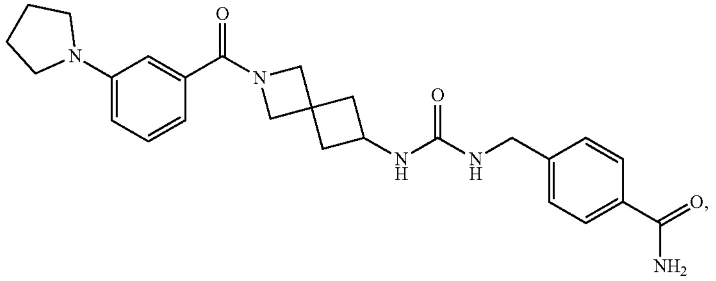 [SMILES: NC(=O)c1ccc(CNC(=O)NC2CC3(C2)CN(C(=O)c2cccc(N4CCCC4)c2)C3)cc1] |
| 223 | 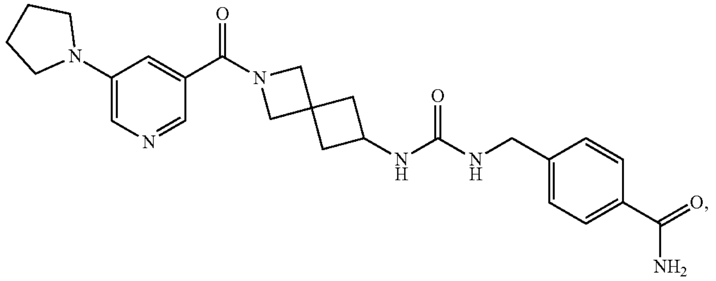 [SMILES: NC(=O)c1ccc(CNC(=O)NC2CC3(C2)CN(C(=O)c2cncc(N4CCCC4)c2)C3)cc1] |
| 224 | 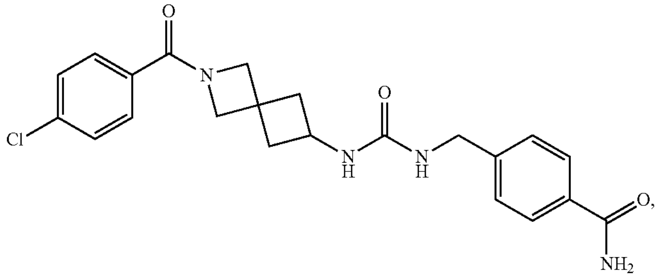 [SMILES: NC(=O)c1ccc(CNC(=O)NC2CC3(C2)CN(C(=O)c2ccc(Cl)cc2)C3)cc1] |

-continued
| Compound No. | Structure |
|---|---|
| 225 | 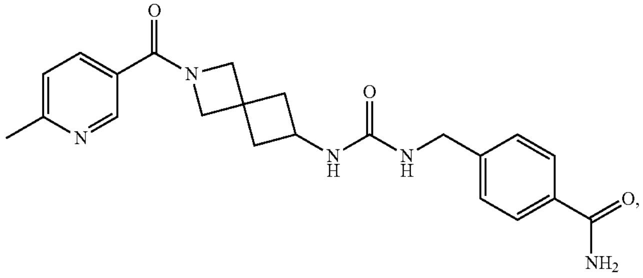 [SMILES: Cc1ccc(C(=O)N2CC3(CC(NC(=O)NCc4ccc(C(N)=O)cc4)C3)C2)cn1] |
| 226 | 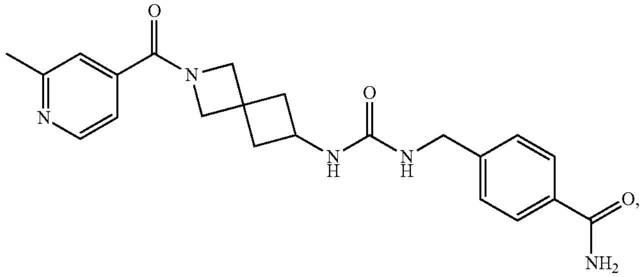 [SMILES: Cc1cc(C(=O)N2CC3(CC(NC(=O)NCc4ccc(C(N)=O)cc4)C3)C2)ccn1] |
| 227 | 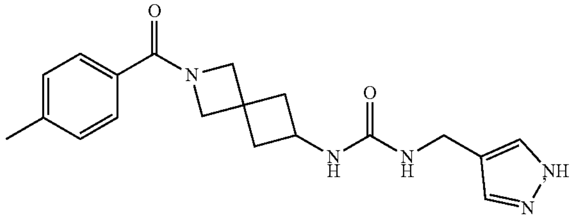 [SMILES: Cc1ccc(C(=O)N2CC3(CC(NC(=O)NCc4cn[nH]c4)C3)C2)cc1] |
| 228 | 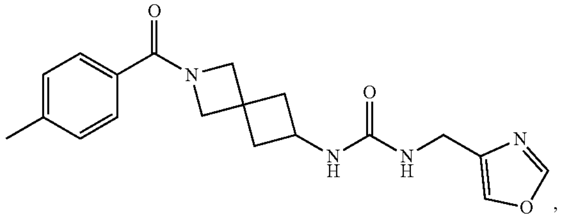 [SMILES: Cc1ccc(C(=O)N2CC3(CC(NC(=O)NCc4cocn4)C3)C2)cc1] |
| 229 | 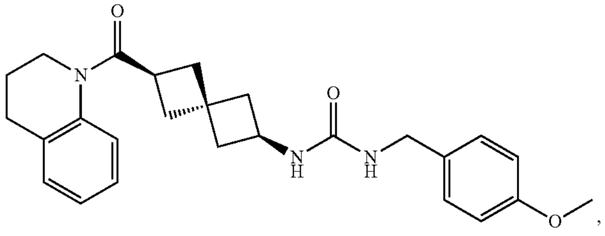 |
| 230 | 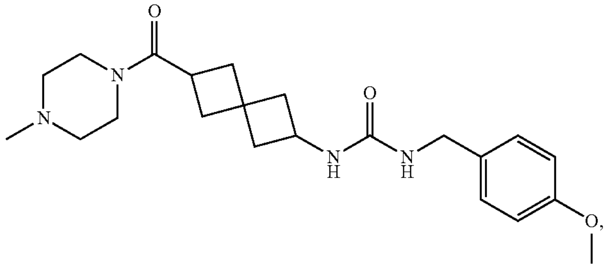 |

-continued
| Compound No. | Structure |
|---|---|
| 231 | 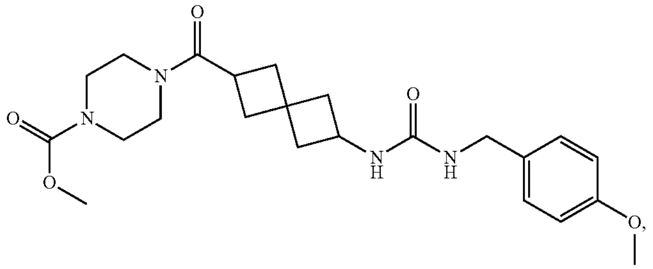 [SMILES: COC(=O)N1CCN(C(=O)C2CC3(CC(NC(=O)NCc4ccc(OC)cc4)C3)C2)CC1] |
| 232 | 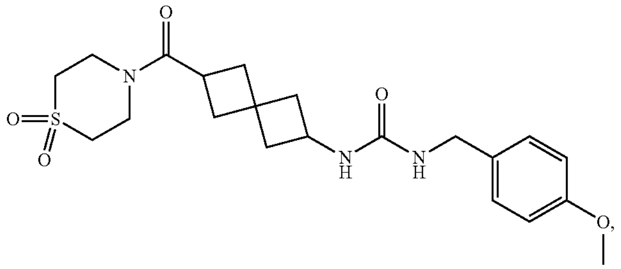 [SMILES: COc1ccc(CNC(=O)NC2CC3(C2)CC(C(=O)N2CCS(=O)(=O)CC2)C3)cc1] |
| 233 | 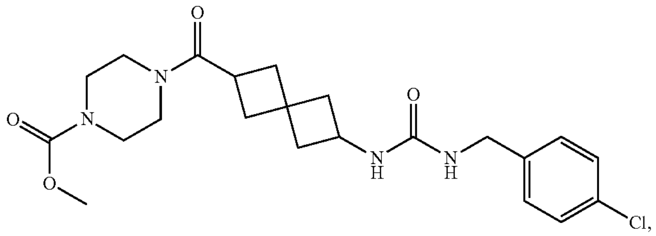 [SMILES: COC(=O)N1CCN(C(=O)C2CC3(CC(NC(=O)NCc4ccc(Cl)cc4)C3)C2)CC1] |
| 234 | 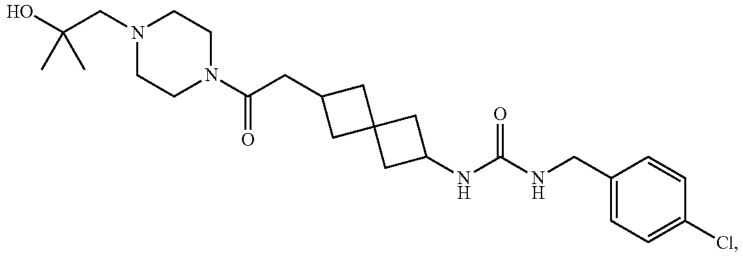 [SMILES: CC(C)(O)CN1CCN(C(=O)CC2CC3(C2)CC(NC(=O)NCc2ccc(Cl)cc2)C3)CC1] |
| 235 | 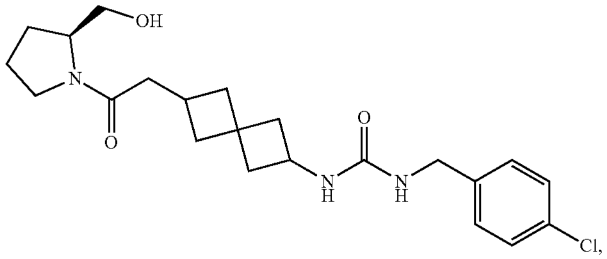 [SMILES: O=C(NCc1ccc(Cl)cc1)NC1CC2(CC(CC(=O)N3CCC[C@H]3CO)C2)C1] |
| 236 | 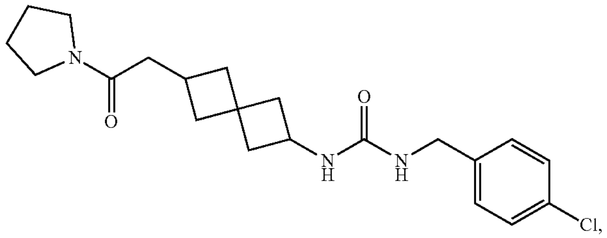 [SMILES: O=C(NCc1ccc(Cl)cc1)NC1CC2(CC(CC(=O)N3CCCC3)C2)C1] |

-continued
| Compound No. | Structure |
|---|---|
| 237 | 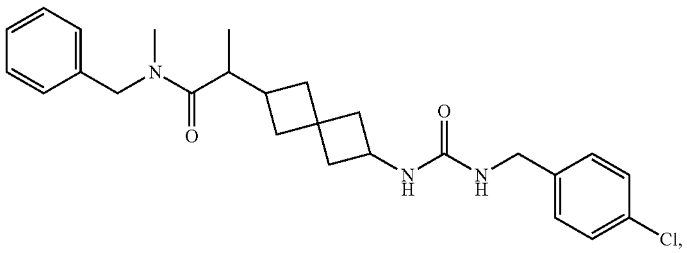 [SMILES: CC(C(=O)N(C)Cc1ccccc1)C1CC2(CC(NC(=O)NCc3ccc(Cl)cc3)C2)C1] |
| 238 | 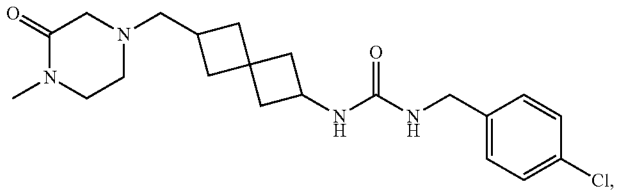 [SMILES: CN1CCN(CC2CC3(C2)CC(NC(=O)NCc2ccc(Cl)cc2)C3)CC1=O] |
| 239 | 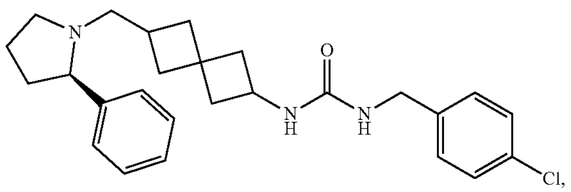 [SMILES: O=C(NCc1ccc(Cl)cc1)NC1CC2(CC(CN3CCC[C@@H]3c3ccccc3)C2)C1] |
| 240 | 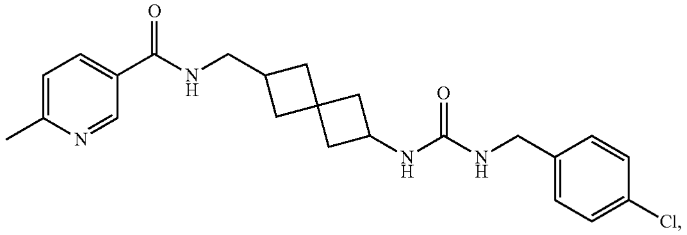 [SMILES: Cc1ccc(C(=O)NCC2CC3(C2)CC(NC(=O)NCc2ccc(Cl)cc2)C3)cn1] |
| 241 | 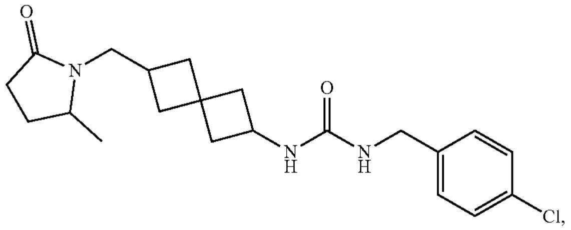 [SMILES: CC1CCC(=O)N1CC1CC2(C1)CC(NC(=O)NCc1ccc(Cl)cc1)C2] |
| 242 | 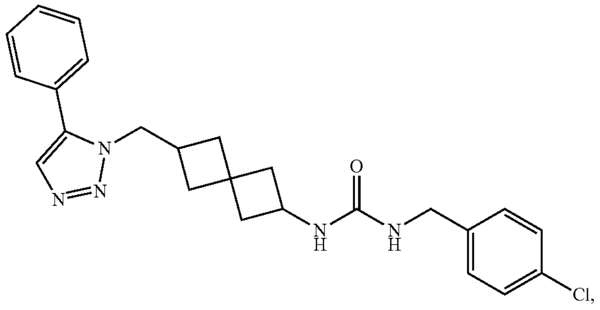 [SMILES: O=C(NCc1ccc(Cl)cc1)NC1CC2(CC(Cn3nncc3-c3ccccc3)C2)C1] |

-continued
| Compound No. | Structure |
|---|---|
| 243 | 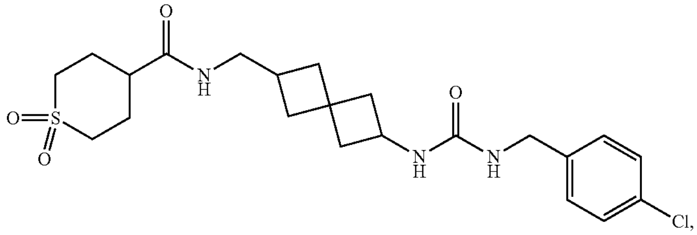 [SMILES: O=C(NCc1ccc(Cl)cc1)NC1CC2(CC(CNC(=O)C3CCS(=O)(=O)CC3)C2)C1] |
| 244 | 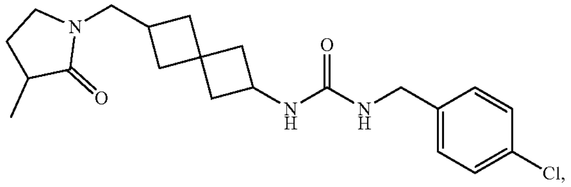 [SMILES: CC1CCN(CC2CC3(C2)CC(NC(=O)NCc2ccc(Cl)cc2)C3)C1=O] |
| 245 | 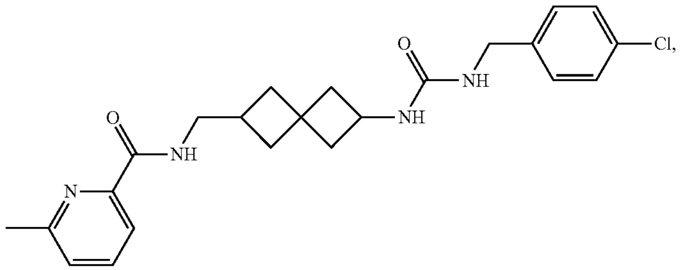 [SMILES: Cc1cccc(C(=O)NCC2CC3(C2)CC(NC(=O)NCc2ccc(Cl)cc2)C3)n1] |
| 246 | 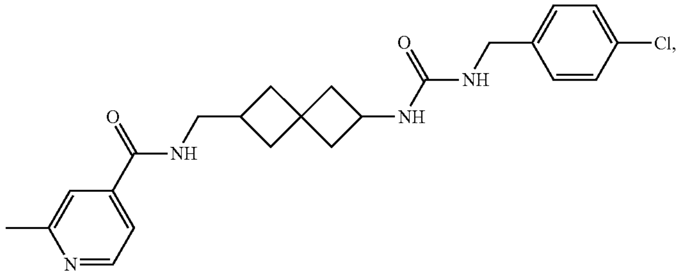 [SMILES: Cc1cc(C(=O)NCC2CC3(C2)CC(NC(=O)NCc2ccc(Cl)cc2)C3)ccn1] |
| 247 | 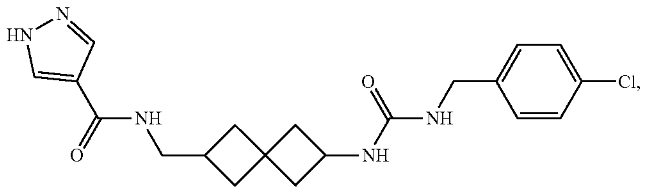 [SMILES: O=C(NCc1ccc(Cl)cc1)NC1CC2(CC(CNC(=O)c3cn[nH]c3)C2)C1] |
| 248 | 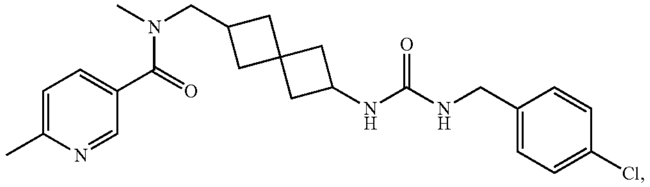 [SMILES: Cc1ccc(C(=O)N(C)CC2CC3(C2)CC(NC(=O)NCc2ccc(Cl)cc2)C3)cn1] |

-continued
| Compound No. | Structure |
|---|---|
| 249 | 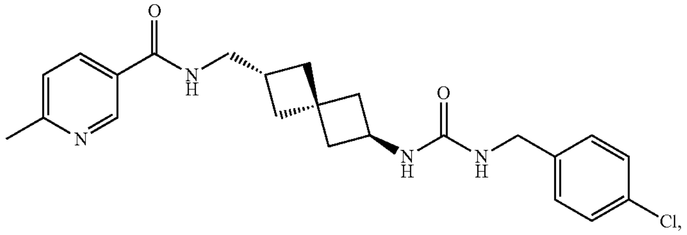 |
| 250 | 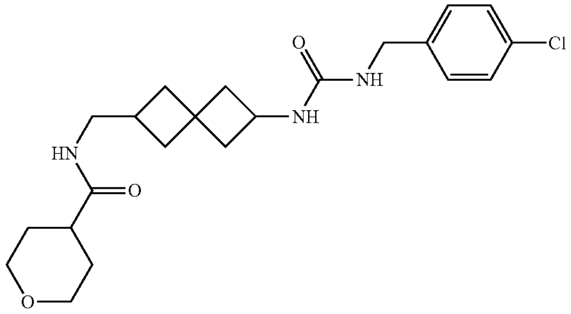 [SMILES: O=C(NCc1ccc(Cl)cc1)NC1CC2(CC(CNC(=O)C3CCOCC3)C2)C1] |
| 251 | 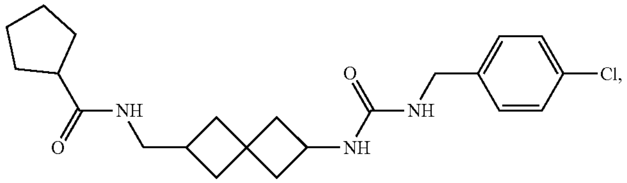 [SMILES: O=C(NCc1ccc(Cl)cc1)NC1CC2(CC(CNC(=O)C3CCCC3)C2)C1] |
| 252 | 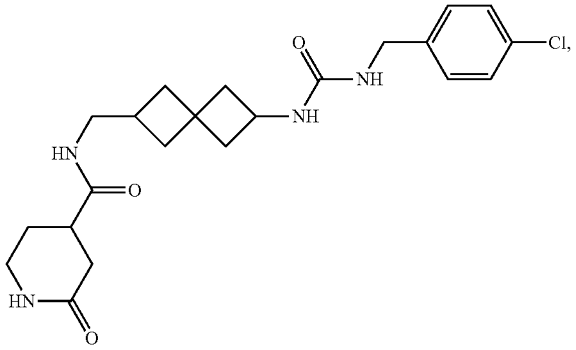 [SMILES: O=C1CC(C(=O)NCC2CC3(C2)CC(NC(=O)NCc2ccc(Cl)cc2)C3)CCN1] |
| 253 | 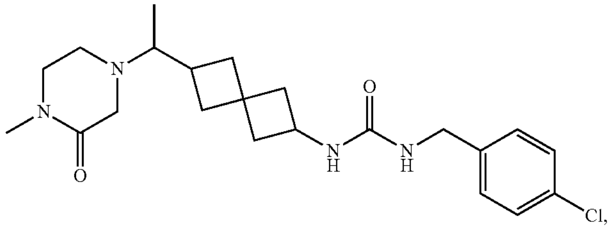 [SMILES: CC(C1CC2(CC(NC(=O)NCc3ccc(Cl)cc3)C2)C1)N1CCN(C)C(=O)C1] |

-continued
| Compound No. | Structure |
|---|---|
| 254 | 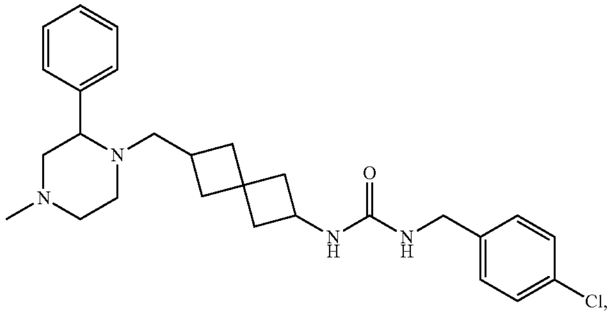 [SMILES: CN1CCN(CC2CC3(C2)CC(NC(=O)NCc2ccc(Cl)cc2)C3)C(c2ccccc2)C1] |
| 255 | 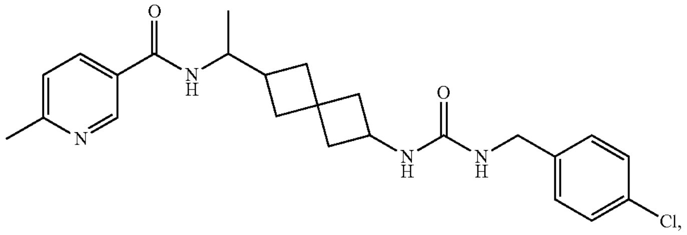 [SMILES: Cc1ccc(C(=O)NC(C)C2CC3(CC(NC(=O)NCc4ccc(Cl)cc4)C3)C2)cn1] |
| 325 | 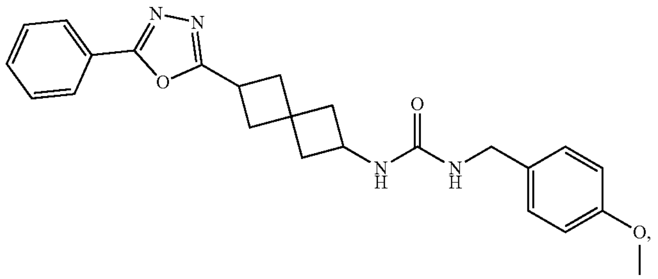 [SMILES: COc1ccc(CNC(=O)NC2CC3(C2)CC(c2nnc(-c4ccccc4)o2)C3)cc1] |
| 326 | 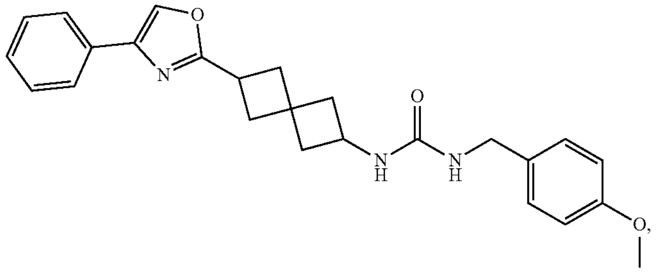 [SMILES: COc1ccc(CNC(=O)NC2CC3(C2)CC(c2nc(-c4ccccc4)co2)C3)cc1] |
| 327 | 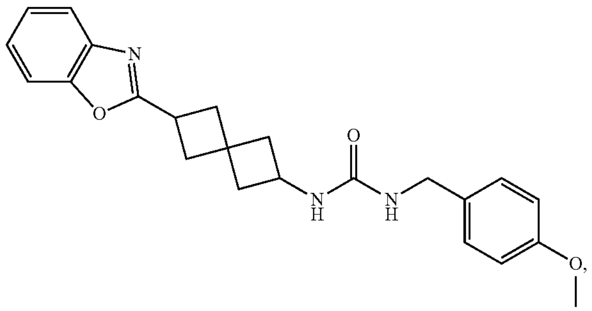 [SMILES: COc1ccc(CNC(=O)NC2CC3(C2)CC(c2nc4ccccc4o2)C3)cc1] |

-continued
| Compound No. | Structure |
|---|---|
| 328 | 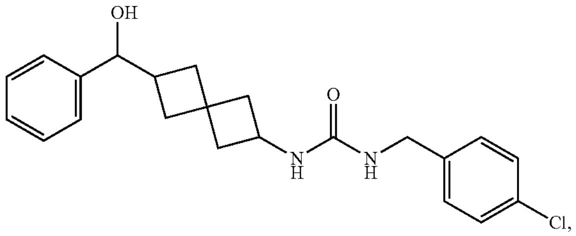 [SMILES: O=C(NCc1ccc(Cl)cc1)NC1CC2(C1)CC(C(O)c1ccccc1)C2] |
| 329 | 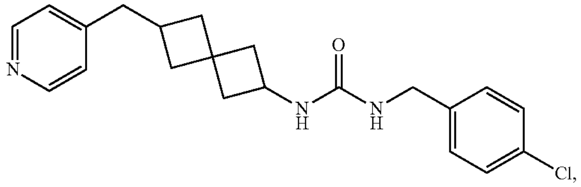 [SMILES: O=C(NCc1ccc(Cl)cc1)NC1CC2(CC(Cc3ccncc3)C2)C1] |
| 330 | 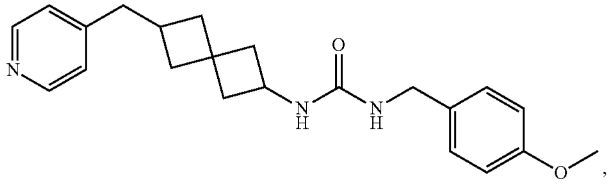 [SMILES: COc1ccc(CNC(=O)NC2CC3(CC(Cc4ccncc4)C3)C2)cc1] |
| 331 | 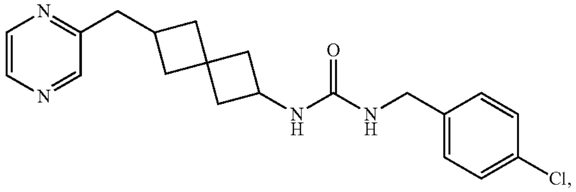 [SMILES: O=C(NCc1ccc(Cl)cc1)NC1CC2(CC(Cc3cnccn3)C2)C1] |
| 332 | 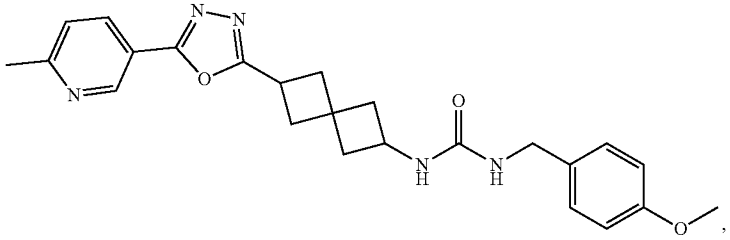 |
| 333 | 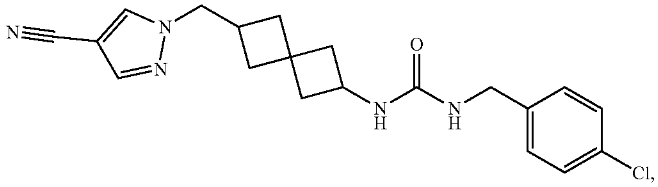 [SMILES: N#Cc1cnn(CC2CC3(C2)CC(NC(=O)NCc2ccc(Cl)cc2)C3)c1] |
| 334 | 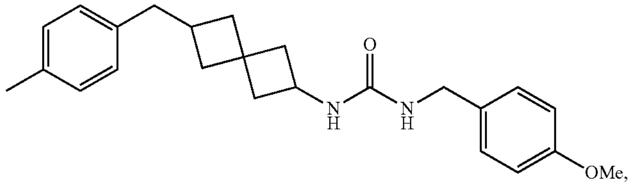 |

-continued
| Compound No. | Structure |
| --- | --- |
| 335 | 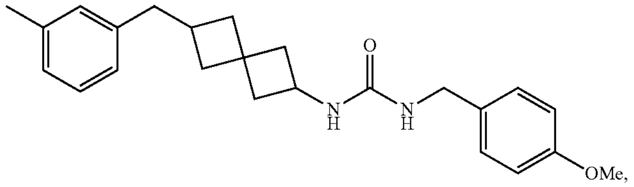 [SMILES: COc1ccc(CNC(=O)NC2CC3(CC(Cc4cccc(C)c4)C3)C2)cc1] |
| 336 | 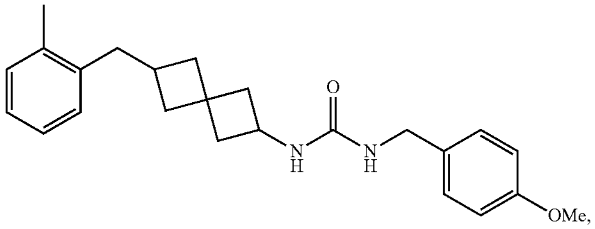 [SMILES: COc1ccc(CNC(=O)NC2CC3(CC(Cc4ccccc4C)C3)C2)cc1] |
| 337 | 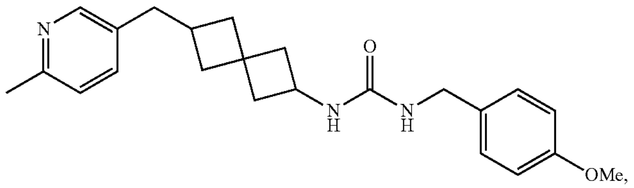 [SMILES: COc1ccc(CNC(=O)NC2CC3(CC(Cc4ccc(C)nc4)C3)C2)cc1] |
| 338 | 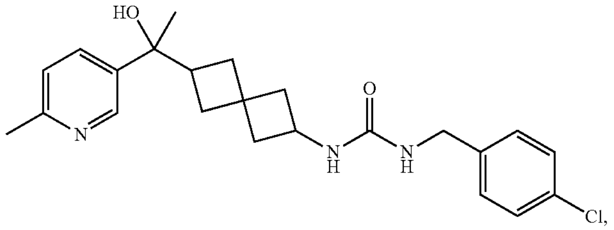 [SMILES: Cc1ccc(C(C)(O)C2CC3(CC(NC(=O)NCc4ccc(Cl)cc4)C3)C2)cn1] |
| 339 | 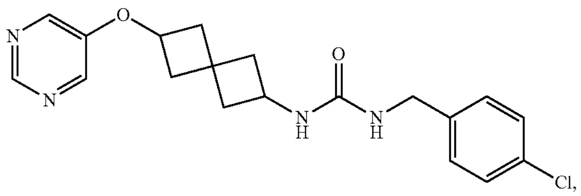 [SMILES: O=C(NCc1ccc(Cl)cc1)NC1CC2(C1)CC(Oc1cncnc1)C2] |
| 340 | 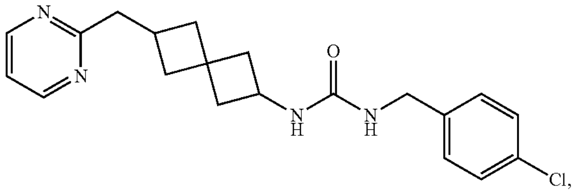 [SMILES: O=C(NCc1ccc(Cl)cc1)NC1CC2(CC(Cc3ncccn3)C2)C1] |
| 341 | 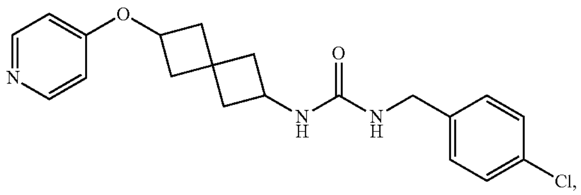 [SMILES: O=C(NCc1ccc(Cl)cc1)NC1CC2(C1)CC(Oc1ccncc1)C2] |

-continued
| Compound No. | Structure |
|---|---|
| 342 | 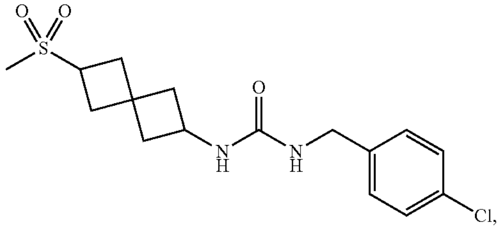 [SMILES: CS(=O)(=O)C1CC2(CC(NC(=O)NCc3ccc(Cl)cc3)C2)C1], |
| 343 | 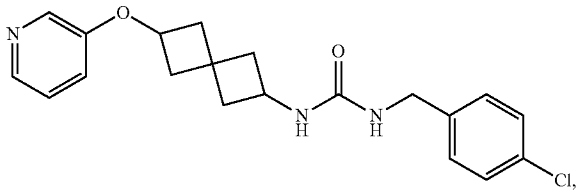, |
| 344 | 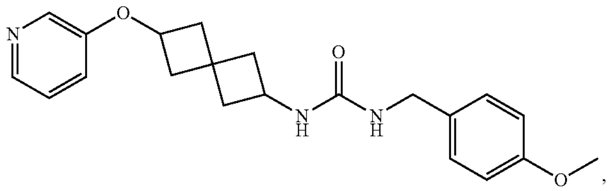 [SMILES: COc1ccc(CNC(=O)NC2CC3(C2)CC(Oc2cccnc2)C3)cc1], |
| 345 | 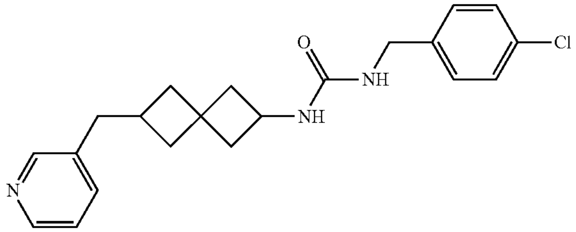 [SMILES: O=C(NCc1ccc(Cl)cc1)NC1CC2(CC(Cc3cccnc3)C2)C1] |
| 346 | 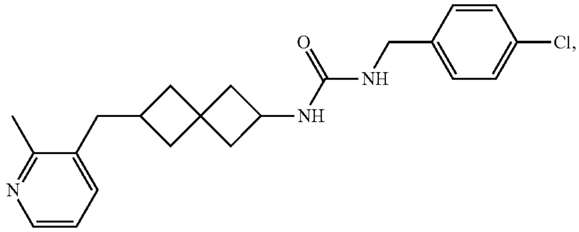 [SMILES: Cc1ncccc1CC1CC2(C1)CC(NC(=O)NCc1ccc(Cl)cc1)C2], |
| 347 | 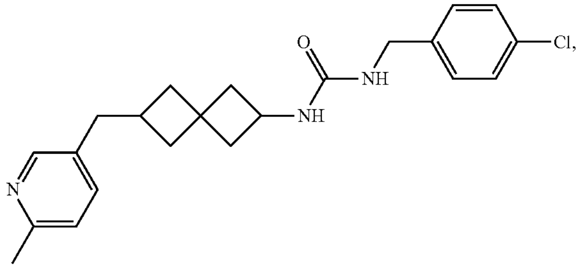 [SMILES: Cc1ccc(CC2CC3(C2)CC(NC(=O)NCc2ccc(Cl)cc2)C3)cn1], |

-continued
| Compound No. | Structure |
|---|---|
| 348 | 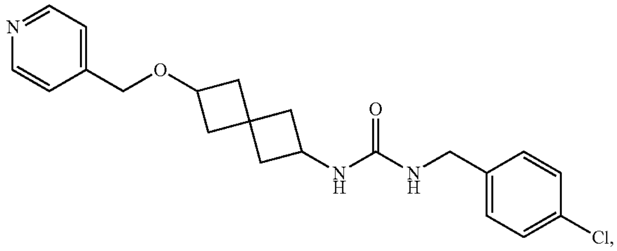 [SMILES: O=C(NCc1ccc(Cl)cc1)NC1CC2(C1)CC(OCc1ccncc1)C2], |
| 349 | 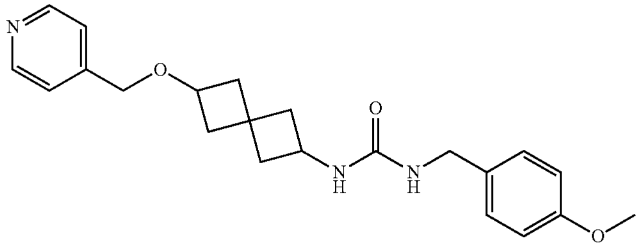, |
| 350 | 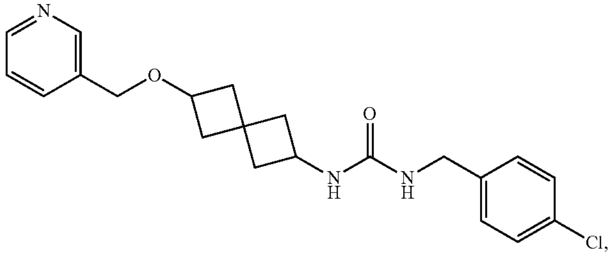 [SMILES: O=C(NCc1ccc(Cl)cc1)NC1CC2(C1)CC(OCc1cccnc1)C2], |
| 351 | 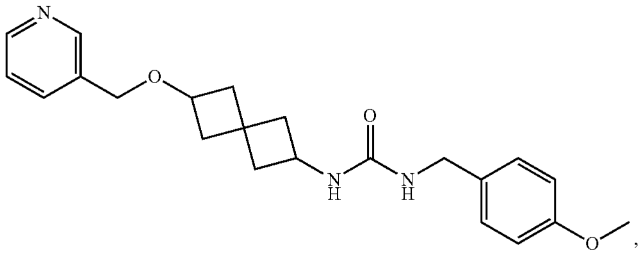 [SMILES: COc1ccc(CNC(=O)NC2CC3(C2)CC(OCc2cccnc2)C3)cc1], |
| 352 | 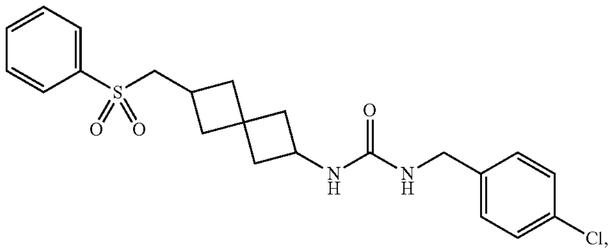 [SMILES: O=C(NCc1ccc(Cl)cc1)NC1CC2(CC(CS(=O)(=O)c3ccccc3)C2)C1], |
| 353 | 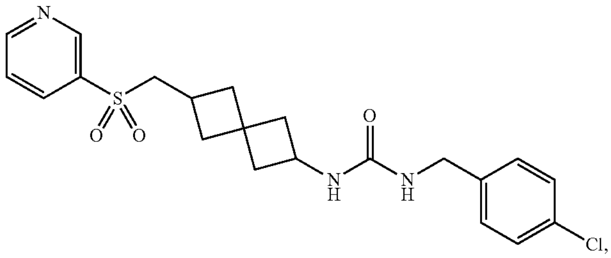, and |

-continued
| Compound No. | Structure |
| --- | --- |
| 354 | 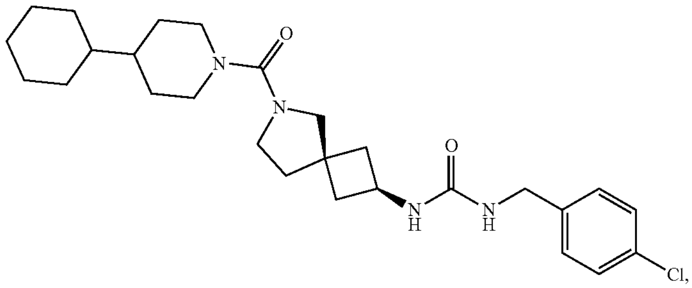 [SMILES: O=C(NCc1ccc(Cl)cc1)N[C@H]1C[C@]2(CCN(C(=O)N3CCC(C4CCCCC4)CC3)C2)C1] |
or a pharmaceutically acceptable salt thereof.
36. A pharmaceutical composition comprising a compound according to claim 1, or a pharmaceutically acceptable salt thereof, and one or more pharmaceutically acceptable excipients.
* * * * *